US012649751B2

(12) United States Patent
Corbin et al.

(10) Patent No.: US 12,649,751 B2
(45) Date of Patent: Jun. 9, 2026

(54) INHIBITORS OF HPK1 AND METHODS OF USE THEREOF

(71) Applicant: Arcus Biosciences, Inc., Hayward, CA (US)

(72) Inventors: Joshua R. Corbin, Hayward, CA (US); Sandeep Dhanju, Fremont, CA (US); Corinne Nicole Foley, San Carlos, CA (US); Jeremy Fournier, Fremont, CA (US); Padmanabha V. Kattamuri, Fremont, CA (US); Manmohan Reddy Leleti, Dublin, CA (US); Pradeep Nareddy, Fremont, CA (US); Jay Patrick Powers, Sisters, OR (US); Ehesan Ul Sharif, Fremont, CA (US); Joice Thomas, San Ramon, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 420 days.

(21) Appl. No.: 18/219,046

(22) Filed: Jul. 6, 2023

(65) Prior Publication Data

US 2024/0124490 A1 Apr. 18, 2024

Related U.S. Application Data

(60) Provisional application No. 63/446,747, filed on Feb. 17, 2023, provisional application No. 63/389,777, filed on Jul. 15, 2022.

(51) Int. Cl.
*C07D 519/00* (2006.01)
*C07D 513/04* (2006.01)

(52) U.S. Cl.
CPC ......... *C07D 519/00* (2013.01); *C07D 513/04* (2013.01)

(58) Field of Classification Search
CPC .. C07D 519/00; C07D 513/04; C07D 513/02; A61P 35/00
See application file for complete search history.

(56) References Cited

U.S. PATENT DOCUMENTS

| | | | |
|---|---|---|---|
| 2019/0315717 A1 | 10/2019 | Hummel et al. | |
| 2020/0253978 A1 | 8/2020 | Wang et al. | |

FOREIGN PATENT DOCUMENTS

| | | | |
|---|---|---|---|
| WO | WO2015061247 A2 * | 4/2015 | ........... C07D 213/81 |
| WO | WO-2019/238067 A1 | 12/2019 | |
| WO | WO-2020/023551 A1 | 1/2020 | |
| WO | WO-2020/023560 A1 | 1/2020 | |
| WO | WO-2020/061377 A1 | 3/2020 | |
| WO | WO-2020/072627 A1 | 4/2020 | |
| WO | WO-2020/072695 A1 | 4/2020 | |
| WO | WO-2020/120257 A1 | 6/2020 | |
| WO | WO-2021/050964 A1 | 3/2021 | |

OTHER PUBLICATIONS

Yongling Xu et al, Discovery of a highly potent small-molecule pd-1/pd-l1 inhibitors with a novel scaffold for cancer immunotherapy, J Med Chem, 2024, 67, 4083-4099 (Year: 2024).*

Q. Ding et al., Pd(PPh3)4-catalyzed direct ortho-fluorination of 2-arylbenzothiazoles with an electrophile fluoride N-fluorobenzenesulfonimide, Tetrahedron 2014, 70, 409-416. (Year: 2014).*

Degnan et al., "Discovery of Orally Active Isofuranones as Potent, Selective Inhibitors of Hematopoetic Progenitor Kinase 1", ACS Med Chem Lett. 12(3):443-450 (Feb. 19, 2021).

Ge et al., "Discovery of Novel HPK1 Inhibitors Through Structure-Based Virtual Screening", Frontiers in Pharmacology, 13:1-10 (Mar. 14, 2022).

International Search Report and Written Opinion on PCT/US2023/027051 dated Sep. 6, 2023, 11 pages.

Wang et al., "Pharmacological Inhibition of Hematopoietic Progenitor Kinase 1 Positively Regulates T-Cell Function," PLoS One, 15(12):e0243145, 19 pages (Dec. 3, 2020).

Wu et al., "Hematopoietic Progenitor Kinanse-1 Structure in a Domain-Swapped Dimer", Structure, 27(1):125-133 (Jan. 2, 2019).

You et al., "Enhanced Antitumor Immunity by a Novel Small Molecule HPK1 Inhibitor," Journal for Immunotherapy of Cancer, 9(1):e001402, 12 pages (Oct. 27, 2020).

Yu et al., "Identification of Potent Reverse Indazole Inhibitors for HPK1", ACS Med Chem Lett, 12(3):459-466 (Mar. 1, 2021).

* cited by examiner

*Primary Examiner* — James H Alstrum-Acevedo
*Assistant Examiner* — Allen Chao
(74) *Attorney, Agent, or Firm* — Foley & Lardner LLP; Zhengzheng Yao

(57) ABSTRACT

Disclosed herein are compounds that are Hematopoietic Progenitor Kinase 1 (HPK1) inhibitors having a structure according to Formula I, and compositions containing those compounds. Methods of preparing the compounds, and methods of using the compounds for the treatment of diseases, disorders, or conditions are also described.

(Formula I)

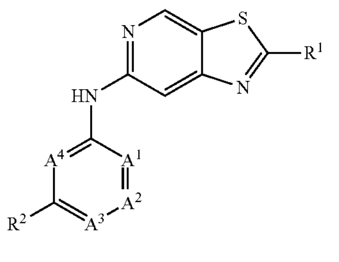

28 Claims, No Drawings

INHIBITORS OF HPK1 AND METHODS OF USE THEREOF

CROSS-REFERENCE TO RELATED APPLICATIONS

This application claims the benefit of priority to U.S. Provisional Patent Application No. 63/389,777, filed on Jul. 15, 2022, and U.S. Provisional Patent Application No. 63/446,747, filed on Feb. 17, 2023, the entire content of each of which is incorporated by reference herein.

BACKGROUND

The following discussion is provided to aid the reader in understanding the disclosure and is not admitted to describe or constitute prior art thereto.

Hematopoietic Progenitor Kinase 1 (HPK1) is a serine/threonine protein kinase in the MAP4K family and is highly expressed in hematopoietic cells and across T cells, B cells, and dendritic cells. HPK1 is a negative regulator of T cell and B cell signaling. For example, HPK1 activity has been demonstrated to restrain T cell activation through phosphorylation of SLP-76 at Serine 376, leading to T cell receptor (TCR) disassembly, thereby reducing T cell activity.

Mediators generated in the tumor microenvironment (TME) such as adenosine, PGE2 and TGFβ can dampen immune cell activity and present a significant barrier to cancer therapy. HPK1 inhibition reduces TCR disassembly and can aid in restoring T cell activity in the suppressive conditions of the TME. Accordingly, inhibition of HPK1 is a promising approach for cancer therapy.

SUMMARY

In one aspect, the present disclosure relates to compounds represented by Formula I:

(Formula I)

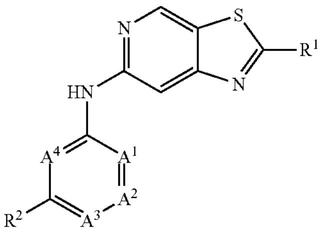

or pharmaceutically acceptable salts thereof, as described further herein.

In another aspect, this disclosure is directed to methods of inhibiting HPK1 in a subject comprising administering to the subject an effective amount of a compound described herein.

In yet another aspect, this disclosure provides methods for treating a disease, disorder, or condition mediated at least in part by HPK1 activity in a subject, comprising administering to the subject an effective amount of a compound described herein. Diseases, disorders, and conditions mediated by HPK1 include cancer and viral infections. Certain aspects of the present disclosure further comprise the administration of one or more additional therapeutic agents as set forth herein below.

DETAILED DESCRIPTION OF THE DISCLOSURE

Before the present disclosure is further described, it is to be understood that the disclosure is not limited to the particular embodiments set forth herein, and it is also to be understood that the terminology used herein is for the purpose of describing particular embodiments only, and is not intended to be limiting.

Definitions

Unless otherwise defined, all terms of art, notations and other scientific terms or terminology used herein are intended to have the meanings commonly understood by those of skill in the art to which this disclosure pertains.

The term "about" as used herein has its original meaning of approximately and is to provide literal support for the exact number that it precedes, as well as a number that is near to or approximately the number that the term precedes. In general, the term "about" refers to the usual error range for the respective value readily known to the skilled person in this technical field. If the degree of approximation is not otherwise clear from the context, "about" means either within plus or minus 10% of the provided value, or rounded to the nearest significant FIGURE, in all cases inclusive of the provided value. Where ranges are provided, they are inclusive of the boundary values.

The term "alkyl", by itself or as part of another substituent, means, unless otherwise stated, a saturated monovalent hydrocarbon radical, having, in some embodiments, one to eight (e.g., $C_1$-$C_8$ alkyl), or one to six (e.g., $C_1$-$C_6$ alkyl), or one to three carbon atoms (e.g., $C_1$-$C_3$ alkyl), respectively. The term "alkyl" encompasses straight and branched-chain hydrocarbon groups. Examples of alkyl groups include, but are not limited to, methyl (Me), ethyl (Et), n-propyl, isopropyl, n-butyl, t-butyl, isobutyl, sec-butyl, isopentyl, tert-pentyl, n-pentyl, isohexyl, n-hexyl, n-heptyl, 4-isopropylheptane, n-octyl, and the like. In some embodiments, the alkyl groups are $C_1$-$C_6$ alkyl groups (e.g., methyl, ethyl, isopropyl, n-butyl, isobutyl, sec-butyl, or t-butyl).

The term "alkylene" refers to a straight or branched, saturated, hydrocarbon radical having, in some embodiments, one to six (e.g., $C_1$-$C_6$ alkylene), or one to four (e.g., $C_1$-$C_4$ alkylene), or one to three (e.g., $C_1$-$C_3$ alkylene), or one to two (e.g., $C_1$-$C_2$ alkylene) carbon atoms, and linking at least two other groups, i.e., a divalent hydrocarbon radical. When two moieties are linked to the alkylene they can be linked to the same carbon atom (i.e., geminal), or different carbon atoms of the alkylene group. For instance, a straight chain alkylene can be the bivalent radical of $-(CH_2)_n-$, where n is 1, 2, 3, 4, 5 or 6 (i.e., a $C_1$-$C_6$ alkylene). Representative alkylene groups include, but are not limited to, methylene, ethylene, propylene, isopropylene, butylene, isobutylene, secbutylene, pentylene, hexylene and the like. In some embodiments, the alkylene groups are $C_1$-$C_2$ alkylene groups (e.g., methylene or ethylene) or $C_1$-$C_3$ alkylene groups (e.g., methylene, ethylene, or propylene).

As used herein, the term "alkoxy" refers to an alkyl group, as defined herein, that is attached to the remainder of the molecule via an oxygen atom (e.g., $-O-C_1$-$C_{12}$ alkyl, $-O-C_1$-$C_8$ alkyl, $-O-C_1$-$C_6$ alkyl, or $-O-C_1$-$C_3$ alkyl). Non-limiting examples of alkoxy groups include methoxy, ethoxy, n-propoxy, iso-propoxy, n-butoxy, sec-butoxy, n-pentoxy, n-hexoxy, and the like. In some embodiments, the alkoxy groups are $C_1$-$C_3$-alkoxy groups (e.g., methoxy, ethoxy, propoxy, or iso-propoxy).

The term "cycloalkyl" refers to a monocyclic, bicyclic or polycyclic hydrocarbon ring system having, in some embodiments, 3 to 14 carbon atoms (e.g., $C_3$-$C_{14}$ cycloalkyl), or 3 to 10 carbon atoms (e.g., $C_3$-$C_{10}$ cycloalkyl), or 3 to 8 carbon atoms (e.g., $C_3$-$C_8$ cycloalkyl), or 3 to 6 carbon atoms (e.g., $C_3$-$C_6$ cycloalkyl) or 5 to 6 carbon atoms (e.g., $C_5$-$C_6$ cycloalkyl). Cycloalkyl groups can be saturated or characterized by one or more points of unsaturation (i.e., carbon-carbon double and/or triple bonds), provided that the points of unsaturation do not result in an aromatic system. Examples of monocyclic cycloalkyl groups include, but are not limited to, cyclopropyl, cyclobutyl, cyclopentyl, cyclohexyl, cyclohexenyl, cycloheptyl, cycloheptenyl, cycloheptadienyl, cyclooctyl, cyclooctenyl, cyclooctadienyl and the like. The rings of bicyclic and polycyclic cycloalkyl groups can be fused, bridged, or spirocyclic. Non-limiting examples of bicyclic, spirocyclic and polycyclic hydrocarbon groups include bicyclo[2.2.1]heptane, bicyclo[2.2.2]octane, adamantyl, indanyl, spiro[5.5]undecane, spiro[2.2]pentane, spiro[2.2]pentadiene, spiro[2.5]octane, spiro[2.2]pentadiene, and the like. In some embodiments, the cycloalkyl groups of the present disclosure are monocyclic $C_3$-$C_7$ cycloalkyl moieties (e.g., cyclopropyl, cyclobutyl, cyclopentyl, cyclohexyl, or cycloheptyl). In some embodiments, the cycloalkyl groups of the present disclosure are monocyclic $C_3$-$C_5$ cycloalkyl moieties (e.g., cyclopropyl, cyclobutyl, or cyclopentyl).

The term "heterocycloalkyl" refers to a non-aromatic monocyclic, bicyclic or polycyclic cycloalkyl ring having, in some embodiments, 3 to 14 members (e.g., 3- to 14-membered heterocycle), or 3 to 10 members (e.g., 3- to 10-membered heterocycle), or 3 to 8 members (e.g., 3- to 8-membered heterocycle), or 3 to 6 members (e.g., 3- to 6-membered heterocycle), or 5 to 6 members (e.g., 5- to 6-membered heterocycle), and having from one to five, one to four, one to three, one to two or one heteroatom selected from nitrogen (N), oxygen (O), and sulfur (S). In some embodiments, the nitrogen and sulfur atom(s) of the heterocycloalkyl group are optionally oxidized (e.g., N-oxide ($N^+$—$O^-$), sulfoxide (S═O), or sulfone (S(═O)$_2$)), and the nitrogen atom(s) are optionally quaternized. Heterocycloalkyl groups are saturated or characterized by one or more points of unsaturation (e.g., one or more carbon-carbon double bonds, carbon-carbon triple bonds, carbon-nitrogen double bonds, and/or nitrogen-nitrogen double bonds), provided that the points of unsaturation do not result in an aromatic system. The rings of bicyclic and polycyclic heterocycloalkyl groups can be fused, bridged, or spirocyclic. Non-limiting examples of heterocycloalkyl groups include aziridine, oxirane, thiirane, pyrrolidine, imidazolidine, pyrazolidine, dioxolane, phthalimide, piperidine, 1,4-dioxane, morpholine, thiomorpholine, thiomorpholine-S-oxide, thiomorpholine-S,S-oxide, piperazine, 3,4,5,6-tetrahydropyridazine, pyran, decahydroisoquinoline, 3-pyrroline, thiopyran, tetrahydrofuran, tetrahydrothiophene, quinuclidine, 2,6-diazaspiro[3.3]heptane, 2-azaspiro[3.3]heptane, 1-oxaspiro[3.3]heptane, 6-azaspiro[3.4]octane, and the like. A heterocycloalkyl group can be attached to the remainder of the molecule through a ring carbon atom, or a ring heteroatom, when chemically permissible. In some embodiments, the heterocycloalkyl groups of the present disclosure are monocyclic or bicyclic 3- to 9-membered heterocycloalkyl moieties having one or two heteroatom or heteroatom groups selected from N, O, S, S═O and S(═O)$_2$ (e.g., aziridine, azetidine, piperidine, piperazine, morpholine, thiomorpholine, thiomorpholine 1,1-dioxide, pyrrolidine, imidazolidine, pyrazolidine, oxazolidine, isoxazolidine, thiazolidine, isothiazolidine, tetrahydrofuran, tetrahydropyran, isothiazolidine 1,1-dioxide, diazepine, oxazepine, hexahydrofuro[3,4-c]pyrrole, hexahydro-5H-1,4-dioxino[2,3-c]pyrrole, octahydropyrrolo[3,2-b]pyrrole, octahydropyrrolo[3,4-b]pyrrole, 2,5-diazabicyclo[2.2.1]heptane, 3,8-diazabicyclo[3.2.1]octane, 3-azabicyclo[3.2.1]octane, 3-oxa-6-azabicyclo[3.1.1]heptane, 3-oxa-8-azabicyclo[3.2.1]octane, 8-oxa-3-azabicyclo[3.2.1]octane, 8-oxa-7-azaspiro[4.4]nonane, 2-oxa-5-azabicyclo[2.2.1]heptane, octahydropyrrolo[1,2-a]pyrazine, or 2,5-diazabicyclo[4.1.0]heptane).

The term "aryl" refers to an aromatic ring system containing one ring, or two or three rings fused together, and having, in some embodiments, six to fourteen (i.e., $C_{6-14}$ aryl), or six to ten (i.e., $C_{6-10}$ aryl), or six (i.e., $C_6$ aryl) carbon atoms. The aromatic ring system contains a cyclic, delocalized (4n+2) π-electron system in accordance with Hückel's Rule. Non-limiting examples of aryl groups include phenyl, naphthyl and anthracenyl. In some embodiments, aryl groups are phenyl.

The term "heteroaryl" refers to monocyclic or fused bicyclic aromatic groups (or rings) having, in some embodiments, from 5 to 14 (i.e., 5- to 14-membered heteroaryl), or from 5 to 10 (i.e., 5- to 10-membered heteroaryl), or from 5 to 6 (i.e., 5- to 6-membered heteroaryl) members (i.e., ring vertices), and containing from one to five, one to four, one to three, one to two or one heteroatom selected from nitrogen (N), oxygen (O), and sulfur (S). In some embodiments, the nitrogen atom(s) are optionally oxidized (e.g., N-oxide ($N^+$—$O^-$)), and the nitrogen atom(s) are optionally quaternized. The heteroaromatic group or ring may be substituted with one or more oxo substituents provided the ring contains a cyclic, delocalized (4n+2) π-electron system in accordance with Wicker s Rule (e.g., pyridinone, pyridazinone, 2,4-(1H,3H)-pyrimidinedione, and the like). A heteroaryl group can be attached to the remainder of the molecule through a carbon atom or a heteroatom of the heteroaryl group, when chemically permissible. Non-limiting examples of heteroaryl groups include pyridyl, pyridazinyl, pyrazinyl, pyrimindinyl, triazinyl, purinyl, thienopyridinyl, thienopyrimidinyl, pyrazolopyrimidinyl, pyrazolopyridinyl, imidazopyridines, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. In some embodiments, the heteroaryl group is fused to an aryl group (i.e., a phenyl group). In certain such embodiments, the heteroaryl group is attached to the remainder of the molecule through a carbon atom in the aryl portion, or a carbon or heteroatom in the heteroaryl portion, when chemically permissible. Exemplary heteroaryl groups fused to an aryl group include, but are not limited to, benzimidazolyl, benzopyrazolyl, benzotriazolyl, benzotriazinyl, benzisoxazolyl, isobenzofuryl, indolyl, isoindolyl, indolizinyl, benzotriazinyl, benzothiaxolyl, benzofuranyl, benzothienyl, quinolyl, isoquinolyl, quinoxalinyl, quinazolinyl, cinnolinyl, phthalazinyl, and the like. In some embodiments, the heteroaryl groups of the present disclosure are monocyclic or bicyclic 5- to 9-membered heteroaryl moieties (e.g., pyridinyl, pyrimidinyl, pyridazinyl, pyrazinyl, triazolyl, imidazolyl, pyrazolyl, oxazolyl, oxadiazole, thiazolyl, pyrazolopyrazine, or pyrazolopyridine). In some embodiments, the heteroaryl groups of the present disclosure are monocyclic 5- to 6-membered heteroaryl moieties (e.g., pyridinyl, pyrimidinyl, pyridazinyl, pyrazinyl, triazolyl, imidazolyl, pyrazolyl, oxazolyl, oxadiazole, or thiazolyl).

As used herein, a wavy line,  , that intersects a single, double or triple bond in any chemical structure depicted herein, represents that the point of attachment of the single, double, or triple bond to the remainder of the molecule is through either one of the atoms that make up the single, double or triple bond. Additionally, a bond extending from a substituent to the center of a ring (e.g., a phenyl ring) is meant to indicate attachment of that substituent to the ring at any of the available ring vertices, i.e., such that attachment of the substituent to the ring results in a chemically stable arrangement.

The terms “halo” or “halogen,” by themselves or as part of another substituent, mean, unless otherwise stated, a fluorine, chlorine, bromine, or iodine atom. Additionally, terms such as “haloalkyl,” refer to alkyl groups, as defined herein, that are substituted with one or more halogen(s) (e.g., 1-3 halo). For example, the term “$C_1$-$C_4$ haloalkyl” is meant to include difluoromethyl, trifluoromethyl, 2,2,2-trifluoroethyl, 4-chlorobutyl, 3-bromopropyl, and the like.

The term “hydroxyalkyl” refers to an alkyl group, as defined herein, that is substituted with one or more hydroxyl groups (e.g., 1-3 hydroxyl groups). Exemplary hydroxyalkyl groups include methanol, ethanol, 1,2-propanediol, 1,2-hexanediol, isopropanol, glycerol, and the like.

The compounds of the present disclosure can be present in their neutral form, or as a pharmaceutically acceptable salt, isomer, polymorph or solvate thereof, and may be present in a crystalline form, amorphous form or mixtures thereof.

As referred to herein, “pharmaceutically acceptable salt” is meant to include salts of the compounds according to this disclosure that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, “Pharmaceutical Salts”, *Journal of Pharmaceutical Science,* 1977, 66, 1-19). Certain specific compounds of the present disclosure may contain both basic and acidic functionalities that allow the compounds to be converted into either base or acid addition salts.

The neutral forms of the compounds may be regenerated by contacting the salt with a base or acid and isolating the parent compound in the conventional manner.

This disclosure also contemplates isomers of the compounds described herein (e.g., stereoisomers and atropisomers). For example, certain compounds of the present disclosure possess asymmetric carbon atoms (chiral centers), or hindered rotation about a single bond; the racemates, diastereomers, enantiomers, and atropisomers (e.g., $R_a$, $S_a$, P and M isomers) of which are all intended to be encompassed within the scope of the present disclosure. Stereoisomeric forms may be defined, in terms of absolute stereochemistry, as (R) or (S), and/or depicted uses dashes and/or wedges. When a stereochemical depiction (e.g., using dashes,  , and/or wedges,  ) is shown in a chemical structure, or a stereochemical assignment (e.g., using (R) and (S) notation) is made in a chemical name, it is meant to indicate that the depicted isomer is present and substantially free of one or more other isomer(s) (e.g., enantiomers and diastereomers, when present). “Substantially free of” other isomer(s) indicates at least an 70/30 ratio of the indicated isomer to the other isomer(s), more preferably 80/20, 90/10, or 95/5 or more. In some embodiments, the indicated isomer will be present in an amount of at least 99%. A chemical bond to an asymmetric carbon that is depicted as a solid line (  ) indicates that all possible stereoisomers (e.g., enantiomers, diastereomers, racemic mixtures, etc.) at that carbon atom are included. In such instances, the compound may be present as a racemic mixture, scalemic mixture, or a mixture of diastereomers.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere herein. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. In some embodiments, the compounds according to this disclosure are characterized by one or more deuterium atoms.

The terms “patient” or “subject” are used interchangeably to refer to a human or a non human animal (e.g., a mammal).

The terms “treat”, “treating”, treatment” and the like refer to a course of action that eliminates, reduces, suppresses, mitigates, ameliorates, or prevents the worsening of, either temporarily or permanently, a disease, disorder or condition to which the term applies, or at least one of the symptoms associated therewith. Treatment includes alleviation of symptoms, diminishment of extent of disease, inhibiting (e.g., arresting the development or further development of the disease, disorder or condition or clinical symptoms association therewith) an active disease, delaying or slowing of disease progression, improving the quality of life, and/or prolonging survival of a subject as compared to expected survival if not receiving treatment or as compared to a published standard of care therapy for a particular disease.

The term "in need of treatment" as used herein refers to a judgment made by a physician or similar professional that a subject requires or will benefit from treatment. This judgment is made based on a variety of factors that are in the realm of the physician's expertise, which may include a positive diagnosis of a disease, disorder or condition.

The terms "prevent", "preventing", "prevention", "prophylaxis" and the like refer to a course of action initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state. Prevention also refers to a course of action initiated in a subject after the subject has been treated for a disease, disorder, condition or a symptom associated therewith in order to prevent relapse of that disease, disorder, condition or symptom.

The term "in need of prevention" as used herein refers to a judgment made by a physician or other caregiver that a subject requires or will benefit from preventative care. This judgment is made based on a variety of factors that are in the realm of a physician's or caregiver's expertise.

"Substantially pure" indicates that a component (e.g., a compound according to this disclosure) makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

Compounds that are selective may be particularly useful in the treatment of certain disorders or may offer a reduced likelihood of undesired side effects. In one embodiment, compounds of the present disclosure are selective over other MAP4K isoforms (e.g., MAP4K2, MAP4K3, MAP4K4, MAP4K5, MAPK6, and MAPK7). In another embodiment, compounds of the present disclosure are selective over other kinases (e.g., LCK and/or ZAP70). Selectivity may be determined, for example, by comparing the inhibition of a compound as described herein against HPK1 against the inhibition of a compound as described herein against another isoform (e.g., MAP4K2, MAP4K3, MAP4K4, and/or MAP4K5), or another kinase (e.g. LCK and/or ZAP70). In one embodiment, the selective inhibition of HPK1 is at least 1000 times greater, 500 times greater, or 100 times greater, or 20 times greater than inhibition of another protein or isoform.

Compounds provided herein may have advantageous pharmacokinetic profiles including, for example, e.g., potency against HPK1 in whole blood, inhibition against the human Ether-a-go-go Related Gene potassium ion channel (hERG), hepatocyte stability, clearance, and inhibition against CYP.

Compounds of the Disclosure

The present disclosure relates to compounds that inhibit the activity of HPK1.

In one aspect, this disclosure is directed to a compound, or a pharmaceutically acceptable salt or solvate thereof, having a structure according to Formula I:

(Formula I)

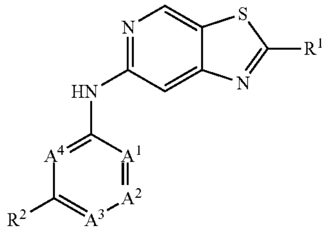

or a pharmaceutically acceptable salt thereof, wherein:

$R^1$ is —NH—C(O)-phenyl, phenyl, 5- to 10-membered heteroaryl, or 5- to 8-membered heterocycloalkyl, wherein said 5- to 10 membered heteroaryl and 5- to 8-membered heterocycloalkyl have from 1-3 ring heteroatoms independently selected from N, O, and S, and wherein said —NH—C(O)-phenyl, phenyl, 5- to 10-membered heteroaryl and 5- to 8-membered heterocycloalkyl are optionally substituted with 1-3 $R^{1a}$, and said 5- to 8-membered heterocycloalkyl is further optionally substituted with one oxo;

each $R^{1a}$, when present, is independently halo, —CN, —OH, —$C_1$-$C_6$-alkyl, —$C_1$-$C_6$-hydroxyalkyl, —$C_1$-$C_6$-haloalkyl, —O—$C_1$-$C_6$-alkyl, —$NR^aR^b$, —C(O)$NR^aR^b$, —$C_1$-$C_3$-alkylene-C(O)$NR^aR^b$, —$S(O)_2$—($C_1$-$C_6$-alkyl), —$NR^aS(O)_2$—($C_1$-$C_6$-alkyl), —$S(O)_2NR^aR^b$, —$C_3$-$C_7$-cycloalkyl, 5- to 8-membered heterocycloalkyl, or 5- to 6-membered heteroaryl, wherein said 5- to 8-membered heterocycloalkyl and 5- to 6-membered heteroaryl have 1-3 ring heteroatoms independently selected from N, O, and S; said 5- to 8-membered heterocycloalkyl is optionally substituted with one oxo, —OH, or halo; said 5- to 6-membered heteroaryl is optionally substituted with one —OH or halo; and said —$C_3$-$C_7$-cycloalkyl is optionally substituted with 1-3 substituents independently selected from group consisting of halo, —OH, and —$C_1$-$C_6$-alkoxy; or two adjacent $R^{1a}$ are taken together with the atoms to which they are attached to form a 5- to 7-membered heterocycloalkyl having 1-2 ring heteroatoms independently selected from N, O, and S, wherein said 5- to 7-membered heterocycloalkyl is optionally substituted with 1-2 substituents independently selected from oxo, and —$C_1$-$C_6$-alkyl;

each $R^a$ and $R^b$, when present, are independently selected from —H, —$C_1$-$C_6$-alkyl, and —$C_3$-$C_7$-cycloalkyl; or $R^a$ and $R^b$ are taken together with the N atom to which they are attached to form a 5- to 7-membered heterocycloalkyl optionally having 1-2 additional ring heteroatoms independently selected from N, O, and S;

$A^1$ is N, or $CR^{A1}$;

$A^2$ is N, or $CR^{A2}$;

$A^3$ is N, or $CR^{A3}$;

$A^4$ is N, or CH;

$R^2$ is —$X^1$—$NR^{2a}R^{2b}$, or —$X^1$-(5- to 10-membered heterocycloalkyl) having 1-4 ring heteroatom or heteroatom groups independently selected from N, O, S(O), and $S(O)_2$, wherein said 5- to 10-membered heterocycloalkyl is optionally substituted with 1-3 substituents independently selected from the group consisting of halo, —OH, —CN, —$NH_2$, $C_1$-$C_6$-alkyl, $C_1$-$C_6$-hydroxyalkyl, —$C_1$-$C_2$-alkylene-$NH_2$, and 5- to 6-membered heterocycloalkyl having 1-2 ring heteroatoms independently selected from N, O, and S; wherein:

$X^1$ is —O—, —$(CR^oR^o)_n$—, or —O—$C_1$-$C_6$-alkylene-;

n is 0, 1 or 2;

each $R^o$ is independently —H or —$C_1$-$C_6$-alkyl; or two $R^o$ attached to the same C atom taken together form —$C_3$-$C_5$-cycloalkyl; and $R^{2a}$ and $R^{2b}$ are independently selected from the group consisting of —H, —$C_1$-$C_6$-alkyl, —$S(O)_2(C_1$-$C_6$-alkyl), —$C_1$-$C_2$-alkylene-(5- to 6-membered heteroaryl), and 5- to 6-membered heterocycloalkyl, wherein said 5- to 6-membered heteroaryl and 5- to 6-membered heterocycloalkyl have from 1-2 ring heteroatoms independently selected from N, O, and S, and wherein said 5- to 6-membered heteroaryl is optionally substituted with one $C_1$-$C_3$-alkyl;

$R^{A1}$ and $R^{A2}$ are independently selected from —H, -halo, —$C_1$-$C_6$-alkyl, —O—$C_1$-$C_6$-alkyl, and 5- to 6-membered heterocycloalkyl having 1-2 ring heteroatoms independently selected from N and O; and $R^{A3}$ is —H, -halo, —$C_1$-$C_6$-alkyl, —$C_1$-$C_6$-haloalkyl, —$C_3$-$C_6$-cycloalkyl, or 5- to 6-membered heterocycloalkyl having 1-2 ring heteroatoms independently selected from N, O, and S, wherein said 5- to 6-membered heterocycloalkyl is optionally substituted with 1-2 substituents independently selected from -halo and —OH.

In another aspect, this disclosure is directed to a compound, or a pharmaceutically acceptable salt or solvate thereof, having a structure according to Formula I:

(Formula I)

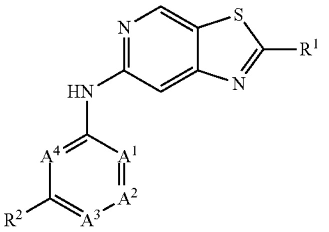

wherein:

$R^1$ is —NH—C(O)-phenyl, —NH—($C_1$-$C_3$-alkylene)-phenyl, —O—($C_1$-$C_3$-alkylene)-phenyl, —O-(5- to 10-membered heteroaryl), phenyl, 5- to 10-membered heteroaryl, or 5- to 8-membered heterocycloalkyl; wherein said 5- to 10-membered heteroaryl and 5- to 8-membered heterocycloalkyl have from 1-3 ring heteroatoms independently selected from N, O, and S; and wherein said —NH—C(O)-phenyl, phenyl, —O—($C_1$-$C_3$-alkylene)-phenyl, 5- to 10-membered heteroaryl and 5- to 8-membered heterocycloalkyl are substituted with 0-3 $R^{1a}$;

each $R^{1a}$, when present, is independently selected from:

a) halo, oxo, —CN, —OH, —$C_1$-$C_6$-alkyl, —O—$C_1$-$C_6$-alkyl, —O—$C_1$-$C_6$-haloalkyl, —O—($C_1$-$C_3$-alkylene)-($C_3$-$C_6$-cycloalkyl), —$S(O)_2$—$R^{1b}$, —$S(O)_2NR^aR^b$, —$NR^aS(O)_2$—($C_1$-$C_6$-alkyl), —$NR^aR^b$, —$C(O)NR^aR^b$, and phenyl;

b) —$C_1$-$C_6$-alkyl substituted with 1-4 substituents independently selected from —OH, halo, —CN, —O—$C_1$-$C_3$-alkyl, —$C_3$-$C_6$-cycloalkyl, —O—($C_3$-$C_6$-cycloalkyl), —$S(O)_2$—($C_1$-$C_3$-alkyl), —C(O)$NR^aR^b$, phenyl, and -5- to 6-membered heterocycloalkyl; wherein said 5- to 6-membered heterocycloalkyl has 1-3 ring heteroatoms independently selected from N, O, and S; wherein said 5- to 6-membered heterocycloalkyl is substituted with 0-1 oxo; and wherein said —$C_3$-$C_6$-cycloalkyl is substituted with 0-2 substituents independently selected from halo;

c) —$C_3$-$C_7$-cycloalkyl substituted with 0-3 substituents independently selected from the group consisting of halo, —OH, —$C_1$-$C_6$-alkoxy, and —$C(O)NR^aR^b$;

d) 4- to 8-membered heterocycloalkyl and —O-(4- to 8-membered heterocycloalkyl); wherein said 4- to 8-membered heterocycloalkyl has 1-3 ring heteroatoms independently selected from N, O, and S; and said 4- to 8-membered heterocycloalkyl is substituted with 0-3 substituents independently selected from the group consisting of oxo, —OH, halo, —$C_1$-$C_6$ alkyl, —$C_1$-$C_3$-alkoxy, —C(O)($C_1$-$C_3$-alkyl), and —$S(O)_2(C_1$-$C_3$-alkyl); and e) 5- to 6-membered heteroaryl, —O-(5- to 6-membered heteroaryl), and —C≡C-(5- to 6-membered heteroaryl), wherein said 5- to 6-membered heteroaryl has 1-3 ring heteroatoms independently selected from N, O, and S; and wherein said 5- to 6-membered heteroaryl is substituted with 0-2 substituents independently selected from —OH, halo, and —$C_1$-$C_6$-alkyl; and f) two adjacent $R^{1a}$ are taken together with the atoms to which they are attached to form a 5- to 7-membered heterocycloalkyl, or a 5- to 6-membered heteroaryl; wherein said 5- to 7-membered heterocycloalkyl and 5- to 6-membered heteroaryl each have 1-2 ring heteroatoms independently selected from N, O, and S; and wherein said 5- to 7-membered heterocycloalkyl is substituted with 0-3 substituents independently selected from oxo, —$C_1$-$C_6$-alkyl, —C(O)($C_1$-$C_3$-alkyl), and —$S(O)_2(C_1$-$C_3$-alkyl);

$R^{1b}$ is —$C_1$-$C_6$-alkyl, —$C_3$-$C_6$-cycloalkyl, or —($C_1$-$C_3$-alkylene)-($C_3$-$C_6$-cycloalkyl);

each $R^a$ and $R^b$, when present, are independently selected from —H; —$C_1$-$C_6$-alkyl; —$C_3$-$C_7$-cycloalkyl; —$C_1$-$C_6$-hydroxyalkyl; —C(O)($C_1$-$C_3$-alkyl); —C(O)($C_3$-$C_6$-cycloalkyl); phenyl; 5- to 10-membered heterocycloalkyl; and $C_1$-$C_3$-alkyl substituted with —$C_3$-$C_6$-cycloalkyl, —O—$C_1$-$C_3$-alkyl, phenyl, or 5- to 6-membered heterocycloalkyl having 1-3 ring heteroatoms independently selected from N, O, and S; wherein each 5- to 10-membered heterocycloalkyl has 1-3 ring heteroatoms independently selected from N, O, and S; and said 5- to 10-membered heterocycloalkyl is substituted with 0-1 substituents selected from —$S(O)_2$ ($C_1$-$C_3$ alkyl), and —C(O)($C_1$-$C_3$-alkyl); or $R^a$ and $R^b$ are taken together with the N atom to which they are attached to form a 5- to 10-membered heterocycloalkyl having 0-2 additional ring heteroatoms independently selected from N, O, and S; and said 5- to 10-membered heterocycloalkyl is substituted with 0-2 substituents independently selected from the group consisting of halo, —OH, —$C_1$-$C_3$-alkyl, —$C_1$-$C_3$-alkoxy, and —$C_1$-$C_3$-alkylene-O—($C_1$-$C_3$-alkyl);

$A^1$ is N, or $CR^{A1}$;

$A^2$ is N, or $CR^{A2}$;

$A^3$ is N, or $CR^{A3}$;

$A^4$ is N, or CH;

$R^2$ is —$X^1$—$NR^{2a}R^{2b}$, or —$X^1$-(5- to 10-membered heterocycloalkyl) having 1-4 ring heteroatom or heteroatom groups independently selected from N, O, S(O), and $S(O)_2$; wherein said 5- to 10-membered heterocycloalkyl is substituted with 0-3 substituents independently selected from the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—O—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl); wherein:

$X^1$ is —O—, —$(CR^oR^o)_n$—, or —O—$C_1$-$C_6$-alkylene-;

n is 0, 1 or 2;

each $R^o$ is independently —H or —$C_1$-$C_6$-alkyl; or two $R^o$ attached to the same C atom taken together form —$C_3$-$C_5$-cycloalkyl;

$R^{2a}$ and $R^{2b}$ are independently selected from the group consisting of —H, —$C_1$-$C_6$-alkyl, —$S(O)_2$($C_1$-$C_6$-alkyl), —$C_1$-$C_2$-alkylene-(5- to 6-membered heteroaryl), and 5- to 6-membered heterocycloalkyl; wherein said 5- to 6-membered heteroaryl and 5- to 6-membered heterocycloalkyl have 1-2 ring heteroatoms independently selected from N, O, and S; and wherein said 5- to 6-membered heteroaryl is optionally substituted with one —$C_1$-$C_3$-alkyl;

$Y^1$ is —$C_1$-$C_3$-alkylene; and $R^{2c}$ and $R^{2d}$ are independently —H, —$C_1$-$C_3$-alkyl, —C(O)($C_1$-$C_3$-alkyl), or —$S(O)_2$($C_1$-$C_3$-alkyl);

$R^{A1}$ is selected from —H, -halo, —$C_1$-$C_6$-alkyl, —O—$C_1$-$C_6$-alkyl, and 5- to 6-membered heterocycloalkyl having 1-2 ring heteroatoms independently selected from N and O;

$R^{A2}$ is selected from —H, -halo, —$C_1$-$C_6$-alkyl, —$C_1$-$C_6$-haloalkyl, —$C_1$-$C_6$-hydroxyalkyl, —O—$C_1$-$C_6$-alkyl, —$C_3$-$C_6$-cycloalkyl, 5- to 6-membered heterocycloalkyl, and 5- to 6-membered heteroaryl; wherein said 5- to 6-membered heterocycloalkyl and 5- to 6-membered heteroaryl have 1-2 ring heteroatoms independently selected from N and O; and wherein said —$C_3$-$C_6$-cycloalkyl, 5- to 6-membered heterocycloalkyl, and 5- to 6-membered heteroaryl are each substituted with 0-2 substituents independently selected from halo, —CN, and —OH; and $R^{A3}$ is —H, -halo, —$C_1$-$C_6$-alkyl, —$C_1$-$C_6$-haloalkyl, —$C_3$-$C_6$-cycloalkyl, or 5- to 6-membered heterocycloalkyl having 1-2 ring heteroatoms independently selected from N, O, and S; wherein said 5- to 6-membered heterocycloalkyl is optionally substituted with 1-2 substituents independently selected from -halo and —OH; or $R^2$ and $R^{A3}$ taken together with the atoms to which they are attached to form phenyl, —$C_5$-$C_7$-cycloalkyl, or 5- to 8-membered heterocycloalkyl having 1-3 ring heteroatoms selected from N, O, and S; wherein said phenyl, —$C_5$-$C_7$-cycloalkyl and 5- to 8-membered heterocycloalkyl are substituted with 0-3 substituents independently selected from —$C_1$-$C_3$-alkyl, —$NH_2$, —$C_1$-$C_3$-alkylene-$NH_2$, and 5- to 8-membered heterocycloalkyl having 1-2 ring heteroatoms independently selected from N and O.

In some embodiments, $R^2$ is —$X^1$-(5- to 10-membered heterocycloalkyl) having 1-4 ring heteroatoms independently selected from N, O and S, wherein said 5- to 10-membered heterocycloalkyl is substituted with 0-3 substituents independently selected from the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl); $X^1$ is —$(CR^oR^o)_n$—; n is 0; and $Y^1$ is —$C_1$-$C_3$-alkylene.

In some embodiments, $R^2$ is —$X^1$-(5- to 10-membered heterocycloalkyl) having 1-4 ring heteroatom or heteroatom groups independently selected from N, O, and $S(O)_2$, wherein said 5- to 10-membered heterocycloalkyl is optionally substituted with 1-3 substituents independently selected from the group consisting of -halo, —OH, —CN, —$NH_2$, —$C_1$-$C_6$-alkyl, —$C_1$-$C_6$-hydroxyalkyl, —$C_1$-$C_2$-alkylene-$NH_2$, and 5- to 6-membered heterocycloalkyl having 1-2 ring heteroatoms selected from N and O; $X^1$ is —$(CR^oR^o)_n$—; and n is 0.

In some embodiments, $R^2$ is selected from the group consisting of

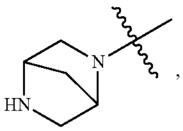, 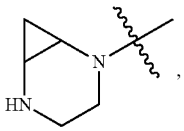,

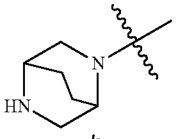, 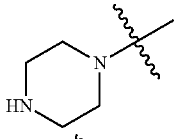,

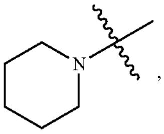, 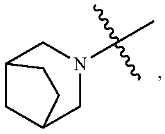,

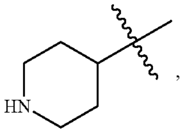, 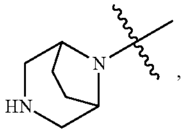,

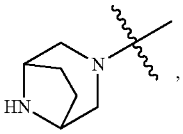, 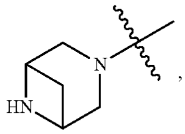,

-continued

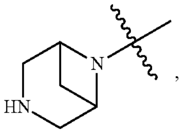, 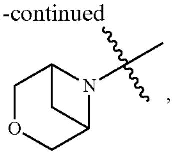,

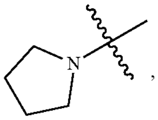, 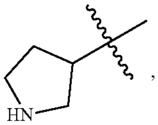,

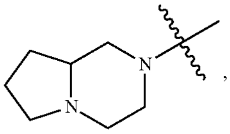, 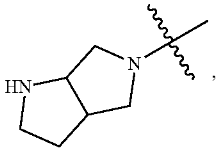,

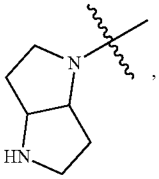, 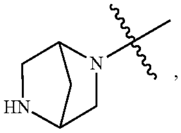, and

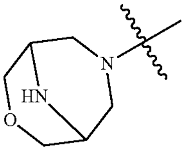

each of which is substituted with 0-3 substituents independently selected from the group consisting of the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—O—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl).

In some embodiments, $R^2$ is

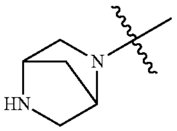

which is substituted with 0-3 substituents independently selected from the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl).

In some embodiments, $R^2$ is substituted with 0-2 substituents independently selected from the group consisting of —F, —$CH_3$, —$CH_2CH_3$, —$CH(CH_3)_2$, —OH, —$NH_2$, —$CH_2OH$, —$CH_2NH_2$, —$(CH_2)_2$—OH, —$(CH_2)_2$—O—$CH_3$, —$(CH_2)_2$—O—$CH_2CH_3$, —$(CH_2)_2$—O—$(CH_2)_2$—OH, —$(CH_2)_2$—O—$CH(CH_3)_2$, —$(CH_2)_2$—$NH_2$,

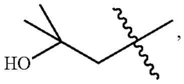, 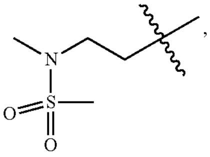,

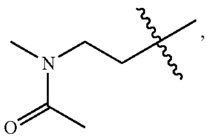, 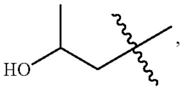,

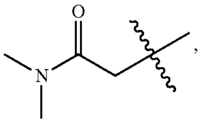, 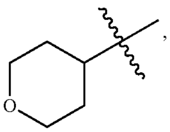 [SMILES: *C1CCOCC1],

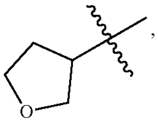, 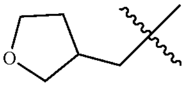,

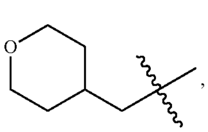, 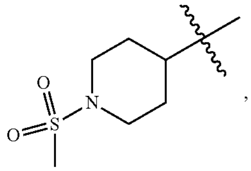,

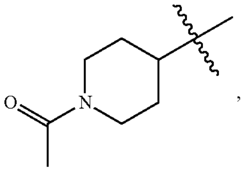, 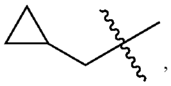,

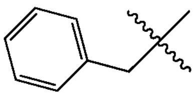, 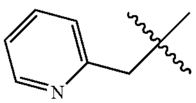,

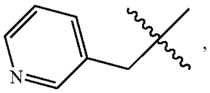, and 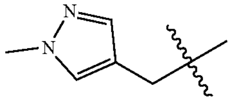.

In some embodiments, $R^2$ and $R^{A3}$ taken together with the atoms to which they are attached form phenyl, —$C_5$-$C_7$-cycloalkyl, or 5- to 8-membered heterocycloalkyl having 1-3 ring heteroatoms selected from N, O, and S; wherein said phenyl, —$C_5$-$C_7$-cycloalkyl and 5- to 8-membered heterocycloalkyl are substituted with 0-3 substituents independently selected from —$C_1$-$C_3$-alkyl, —$NH_2$, —$C_1$-$C_3$-alkylene-$NH_2$, and 5- to 8-membered heterocycloalkyl having 1-2 ring heteroatoms independently selected from N and O.

In some embodiments, $R^2$ and $R^{A3}$ taken together with the atoms to which they are attached form

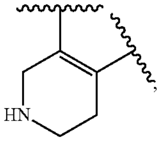,
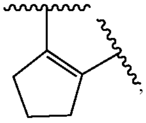,
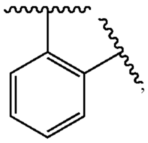,
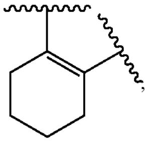,
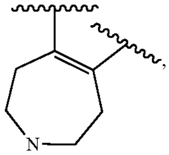, or
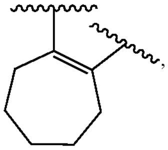, each of which is substituted with 0-2 substituents independently selected from —$C_1$-$C_3$-alkyl, —$NH_2$, —$C_1$-$C_3$-alkylene-$NH_2$, and 5- to 8-membered heterocycloalkyl having 1-2 ring heteroatoms independently selected from N and O.

In some embodiments, $R^2$ and $R^{A3}$ taken together with the atoms to which they are attached form

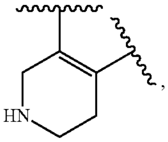,
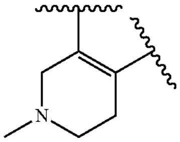,
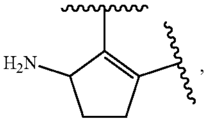,
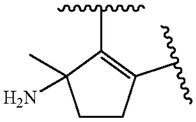,
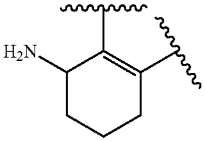,
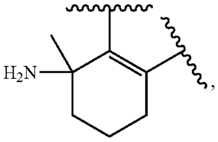,
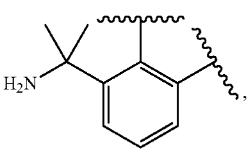,
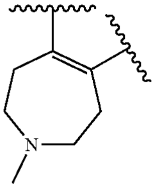,
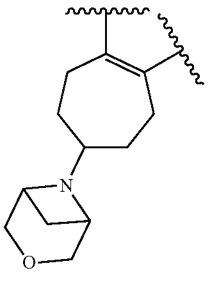, or
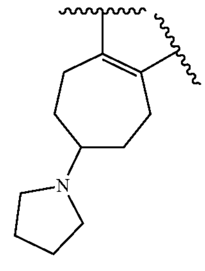.

In some embodiments, $R^2$ is selected from the group consisting of:

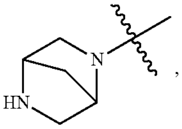 [SMILES: *N1CC2CC1CN2],
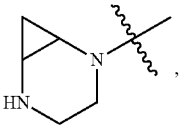,
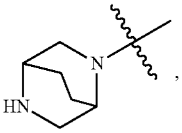,
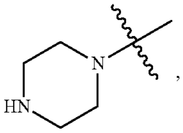,
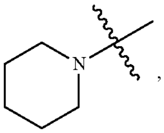,
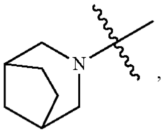,
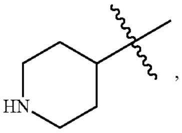,
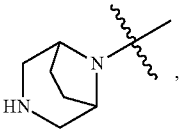,
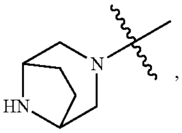,
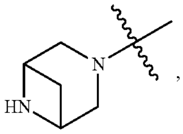,
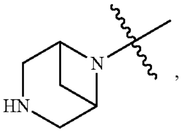,
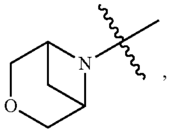,
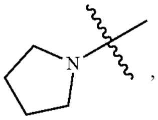,
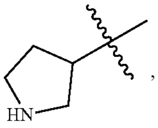,
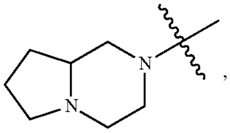,
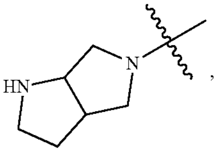, and
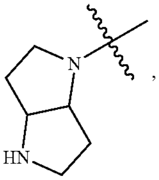, each of which is optionally substituted with 1-3 substituents independently selected from the group consisting of halo, —OH, —CN, —$NH_2$, —$C_1$-$C_6$-alkyl, —$C_1$-$C_6$-hydroxyalkyl, —$C_1$-$C_2$-alkylene-$NH_2$, and 5- to 6-membered heterocycloalkyl having 1-2 ring heteroatoms independently selected from N and O. In some embodiments, each $R^2$ is substituted with 1-3 substituents independently selected from the group consisting of —$CH_3$, —$CH(CH_3)_2$, —OH, —$NH_2$, —$CH_2OH$, —$CH_2NH_2$, —$(CH_2)_2$—OH, —$(CH_2)_2$—$NH_2$, and

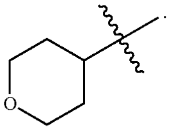
In some embodiments, $R^2$ is selected from the group consisting of:
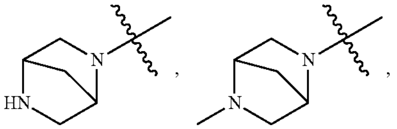
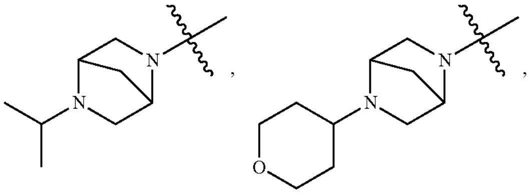
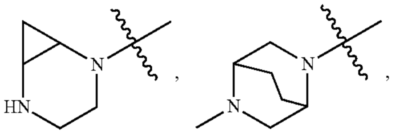
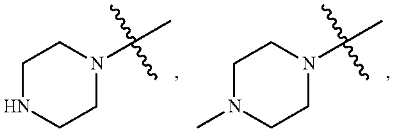
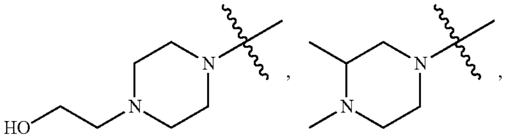
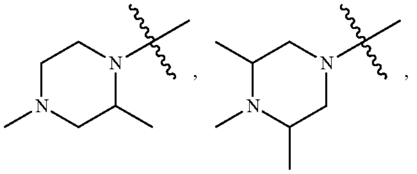
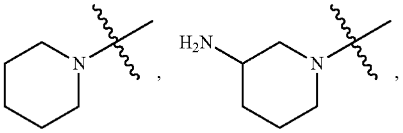
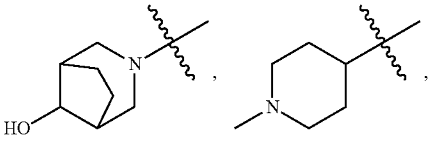
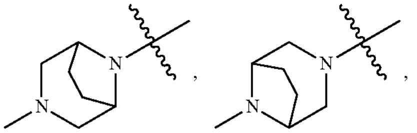
-continued
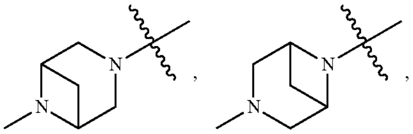
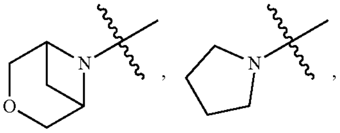
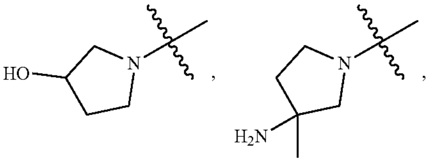
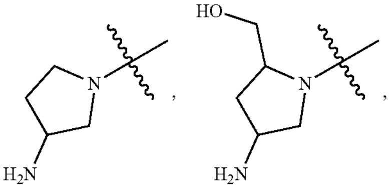
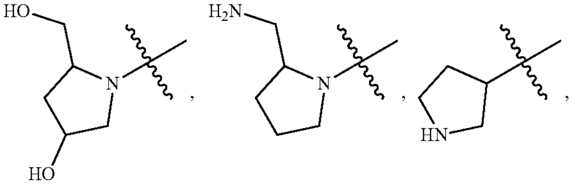
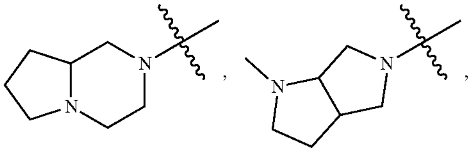 and
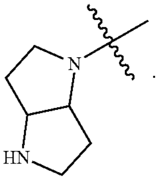
In some embodiments, $R^2$ is selected from the group consisting of:
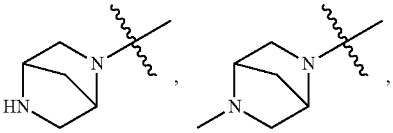
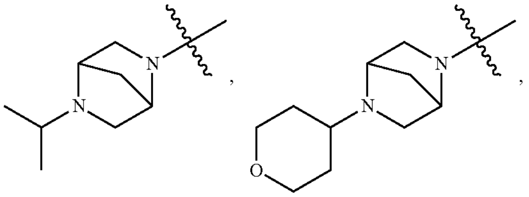

-continued
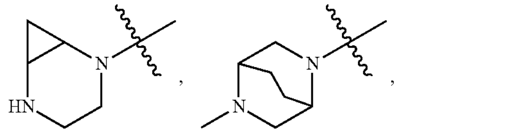
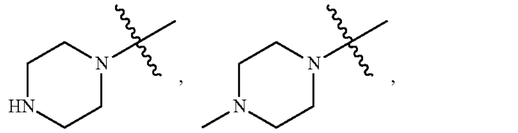
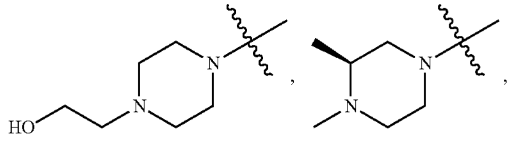
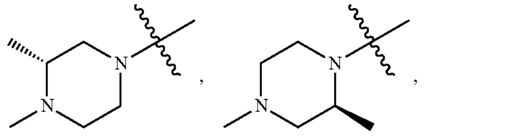
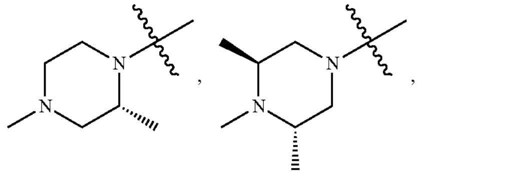
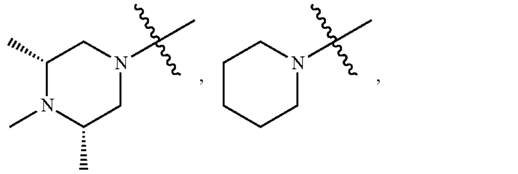
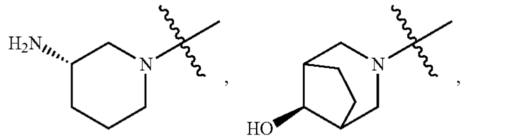
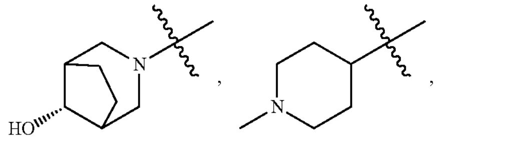
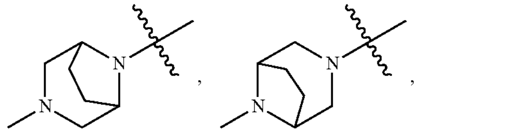
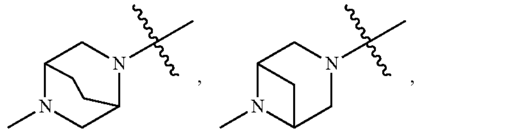
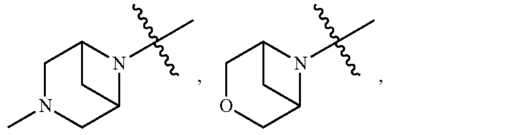
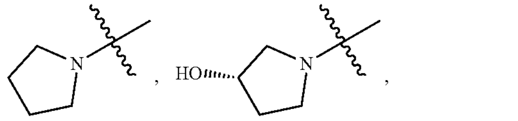
-continued
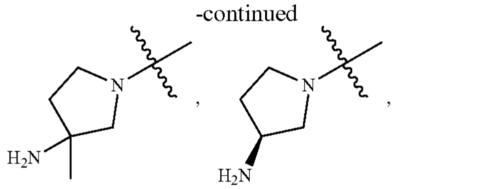
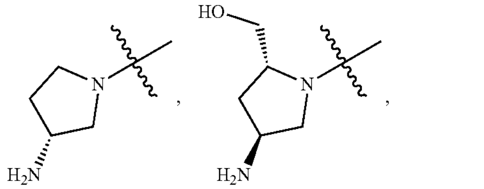
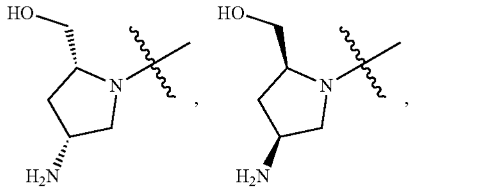
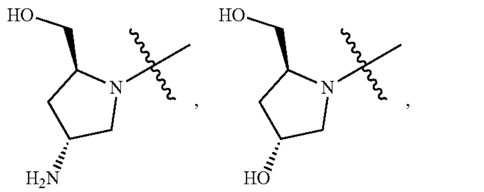
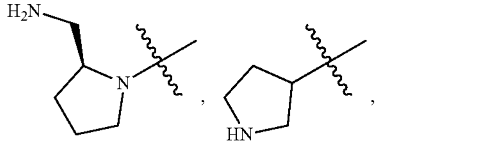
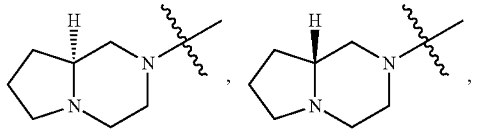
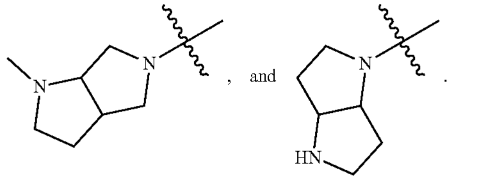
In some embodiments, $R^2$ is
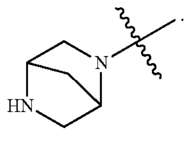
In some embodiments, $R^2$ is
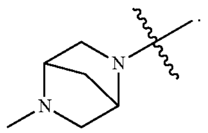 [SMILES: *N1CC2CC1CN2C]

In some embodiments, $R^2$ is —$X^1$-(5- to 6-membered heterocycloalkyl) having 1-3 ring heteroatom or heteroatom groups selected from N, O, and $S(O)_2$, wherein said 5- to 6-membered heterocycloalkyl is optionally substituted with 1-3 substituents independently selected from the group consisting of halo, —OH, —CN, —$NH_2$, —$C_1$-$C_6$-alkyl, —$C_1$-$C_6$-hydroxyalkyl, —$C_1$-$C_2$-alkylene-$NH_2$, and 5- to 6-membered heterocycloalkyl having 1-2 ring heteroatoms independently selected from N and O; $X^1$ is —$(CR^oR^o)_n$—; each $R^o$ is —H; and n is 1 or 2. In some embodiments, $R^2$ is selected from the group consisting of:

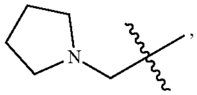,
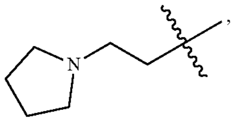,
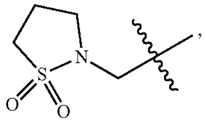,
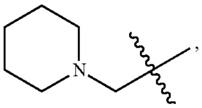, and
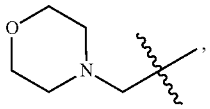, each heterocycloalkyl of which is optionally substituted with 1-3 substituents independently selected from the group consisting of halo, —OH, —CN, —$NH_2$, —$C_1$-$C_6$-alkyl, —$C_1$-$C_6$-hydroxyalkyl, —$C_1$-$C_2$-alkylene-$NH_2$, and 5- to 6-membered heterocycloalkyl having 1-2 ring heteroatoms independently selected from N and O. In some embodiments, $R^2$ is

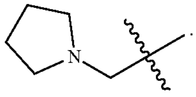 [SMILES: *CN1CCCC1].

In some embodiments, each heterocycloalkyl of $R^2$ is optionally substituted with 1-3 substituents independently selected from the group consisting of halo, —CN, —$NH_2$, —$C_1$-$C_6$-alkyl, and —$C_1$-$C_6$-hydroxyalkyl.

In some embodiments, $R^2$ is —$X^1$—$NR^{2a}R^{2b}$, $X^1$ is —$(CR^oR^o)_n$—, n is 0 or 1; each $R^o$ is independently H or —$C_1$-$C_6$-alkyl; or two $R^o$ attached to the same C atom taken together form $C_3$-$C_5$-cycloalkyl; and $R^{2a}$ and $R^{2b}$ are independently selected from the group consisting of —H, $C_1$-$C_6$-alkyl, —$S(O)_2(C_1$-$C_6$-alkyl), —$C_1$-$C_2$-alkylene-(5- to 6-membered heteroaryl), and 5- to 6-membered heterocycloalkyl, wherein said 5- to 6-membered heteroaryl and 5- to 6-membered heterocycloalkyl have from 1-2 ring heteroatoms independently selected from N and O, and wherein said 5- to 6-membered heteroaryl is optionally substituted with one $C_1$-$C_3$-alkyl. In some embodiments, $R^2$ is

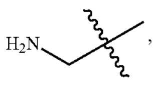,
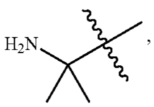,
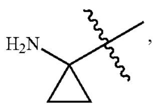,

-continued

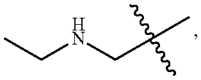,
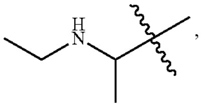,
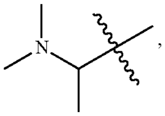,
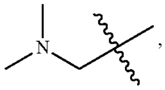,
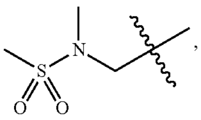,
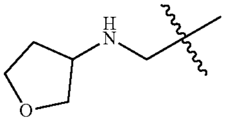, or
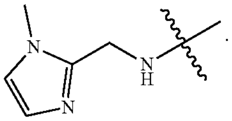.

In some embodiments, $R^2$ is —$X^1$-(5- to 6-membered heterocycloalkyl) having one ring N heteroatom, wherein said 5- to 6-membered heterocycloalkyl is optionally substituted with 1-2 substituents independently selected from halo, and $C_1$-$C_3$-alkyl; and $X^1$ is —O—. In some embodiments, $R^2$ is —O-piperidine, or —O-pyrrolidine, each of which is optionally substituted with 1-2 halo. In some embodiments, $R^2$ is

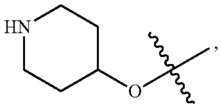,
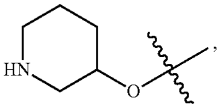,
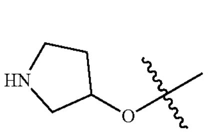, or
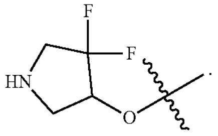.

In some embodiments, $R^2$ is

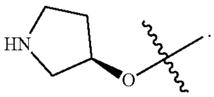 [SMILES: *O[C@@H]1CCNC1].

In some embodiments, $R^1$ is pyridyl, pyridinonyl, phenyl, pyrazolyl, imidazolyl, oxazolyl, 1,2,4-triazolyl, pyrazinyl, pyridazinyl, pyrimidinyl, 6-oxa-3-azabicyclo[3.1.1]heptanyl, 2-oxa-5-azabicyclo[2.2.1]heptanyl, piperidinyl, morpholinyl, pyrrolidinyl, pyrrolidonyl, tetrahydropyranyl, tetrahydrofuranyl, pyrazolo[3,4-b]pyridinyl, pyrazolo[1,5-a]pyrazinyl, pyrazolo[1,5-a]pyridinyl, —NH—C(O)-phenyl, —NH—$CH(CH_3)$-phenyl, —O—$CH(CH_3)$-phenyl, or —O— pyridyl, each of which is substituted with 0-3 $R^{1a}$.

In some embodiments, $R^1$ is pyridyl, phenyl, pyrazolyl, imidazolyl, oxazolyl, 1,2,4-triazolyl, pyrazinyl, pyridazinyl, pyrimidinyl, 6-oxa-3-azabicyclo[3.1.1]heptanyl, 2-oxa-5-azabicyclo[2.2.1]heptanyl, piperidinyl, morpholinyl, pyrrolidinyl, pyrrolidonyl, tetrahydropyranyl, tetrahydrofuranyl, pyrazolo[3,4-b]pyridinyl, pyrazolo[1,5-a]pyrazinyl, pyrazolo[1,5-a]pyridinyl, —NH—C(O)-phenyl, —NH—$CH(CH_3)$-phenyl, —O—$CH(CH_3)$-phenyl, or —O— pyridyl, each of which is substituted with 0-3 $R^{1a}$.

In some embodiments, $R^1$ is pyridinyl, phenyl, pyrazolyl, imidazolyl, pyrazinyl, pyridazinyl, pyrimidinyl, oxazolyl, 6-oxa-3-azabicyclo[3.1.1]heptanyl, 2-oxa-5-azabicyclo [2.2.1]heptanyl, piperidinyl, morpholinyl, pyrrolidinyl, pyrrolidonyl, tetrahydropyranyl, tetrahydrofuranyl, pyrazolo[3,4-b]pyridinyl, or —NH—C(O)-phenyl, each of which is optionally substituted with 1-3 $R^{1a}$.

In some embodiments, $R^1$ is pyridinyl, phenyl, pyrazolyl, imidazolyl, pyrazinyl, pyridazinyl, pyrimidinyl, oxazolyl, 6-oxa-3-azabicyclo[3.1.1]heptanyl, 2-oxa-5-azabicyclo [2.2.1]heptanyl, piperidinyl, morpholinyl, pyrrolidinyl, pyrrolidonyl, tetrahydropyranyl, pyrazolo[3,4-b]pyridinyl, or —NH—C(O)-phenyl, each of which is optionally substituted with 1-3 $R^{1a}$. In some embodiments, $R^1$ is phenyl. In some embodiments, $R^1$ is pyridinyl.

In some embodiments, when present, at least one $R^{1a}$ is selected from halo, oxo, —CN, —OH, —$C_1$-$C_6$-alkyl, —O—$C_1$-$C_6$-alkyl, —O—$C_1$-$C_6$-haloalkyl, —O—($C_1$-$C_3$-alkylene)-($C_3$-$C_6$-cycloalkyl), —$S(O)_2$—$R^{1b}$, —$S(O)_2NR^aR^b$, —$NR^aS(O)_2$—($C_1$-$C_6$-alkyl), —$NR^aR^b$, —C(O)$NR^aR^b$, and phenyl.

In some embodiments, when present, at least one $R^{1a}$ is selected from halo, oxo, —CN, —OH, —$C_1$-$C_6$-alkyl, —O—$C_1$-$C_6$-alkyl, —O—$C_1$-$C_6$-haloalkyl, —$S(O)_2$—$R^{1b}$, —$S(O)_2NR^aR^b$, —$NR^aS(O)_2$—($C_1$-$C_6$-alkyl), —$NR^aR^b$, —C(O)$NR^aR^b$, and phenyl.

In some embodiments, at least one $R^{1a}$ is selected from —F, —Cl, oxo, —CN, —OH, —$NH_2$, —$CH_3$, —$CH_2CH_3$, —$CH(CH_3)_2$, —$OCF_2H$, —$OCH_3$, phenyl,

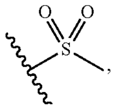, 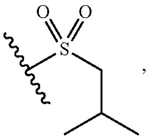, 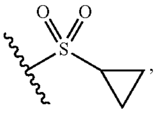,

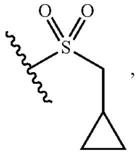, 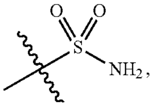, 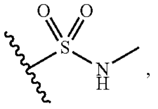,

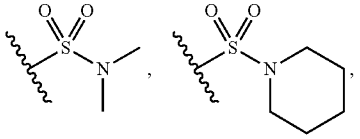,

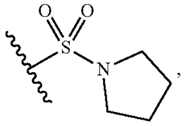, 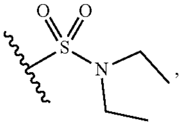,

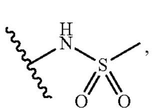, 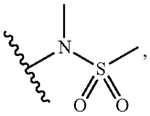, 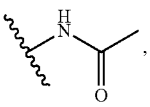,

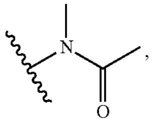, 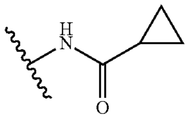, 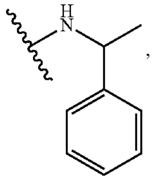,

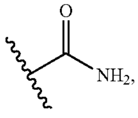, 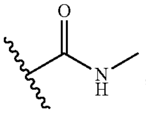, 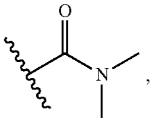,

-continued

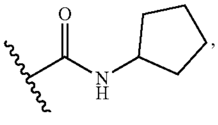, 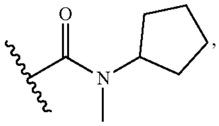,

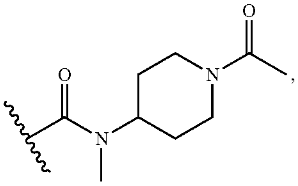, 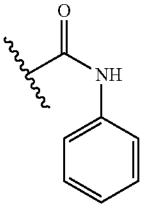,

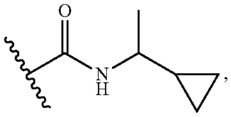,

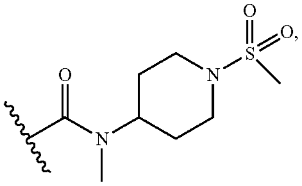

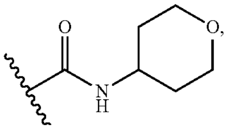 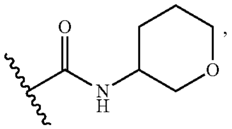,

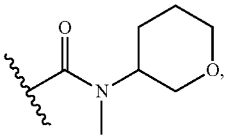 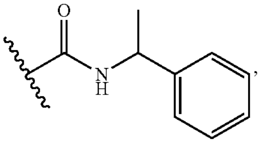,

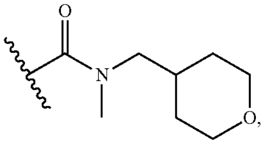 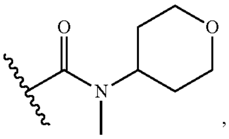,

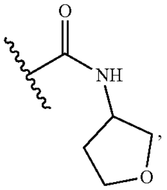, 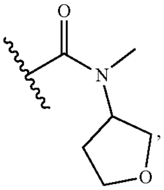, 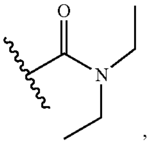,

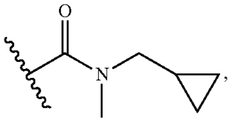, 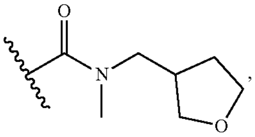,

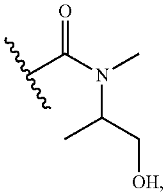 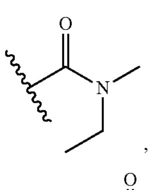, 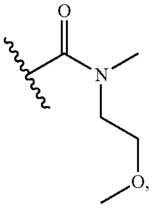

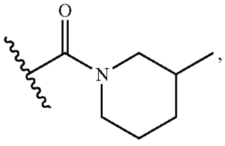, 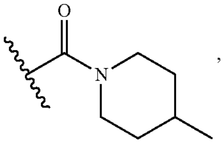,

-continued

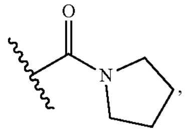, 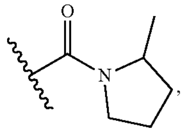,

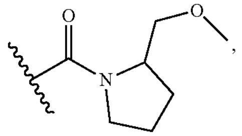, 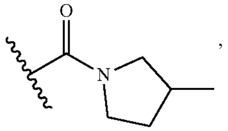,

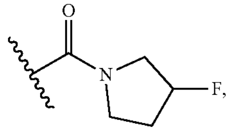, 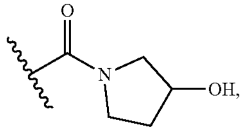,

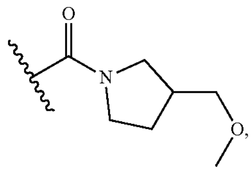, 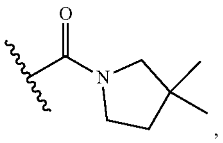,

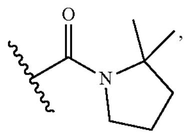, 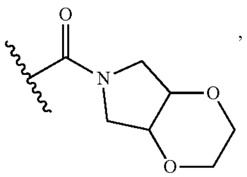,

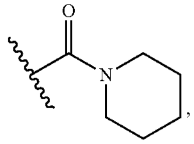, 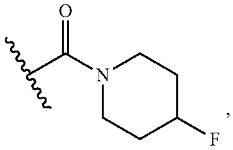,

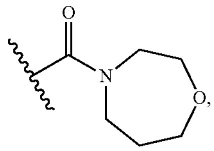, 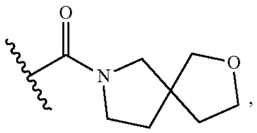,

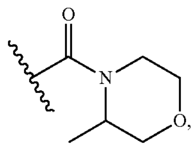, 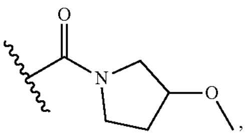,

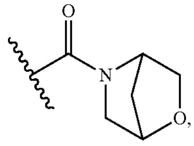 and 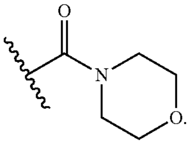.

In some embodiments, when present, at least one $R^{1a}$ is —$C_1$-$C_6$-alkyl substituted with 1-4 substituents independently selected from —OH, halo, —CN, —O—$C_1$-$C_3$-alkyl, —$C_3$-$C_6$-cycloalkyl, —O—($C_3$-$C_6$-cycloalkyl), —$S(O)_2$—($C_1$-$C_3$-alkyl), —C(O)$NR^aR^b$, phenyl, and -5- to 6-membered heterocycloalkyl; wherein said 5- to 6-membered heterocycloalkyl has 1-3 ring heteroatoms independently selected from N, O, and S; wherein said 5- to 6-membered heterocycloalkyl is substituted with 0-1 oxo; and wherein said —$C_3$-$C_6$-cycloalkyl is substituted with 0-2 substituents independently selected from halo.

In some embodiments, at least one $R^{1a}$ is —$CF_3$, —$CF_2H$,

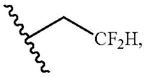, 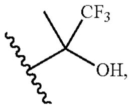, 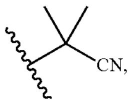,

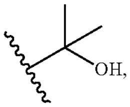, 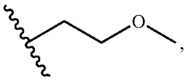, 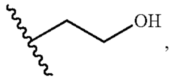,

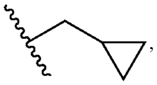, 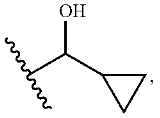, 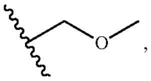,

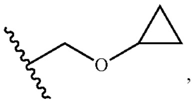, 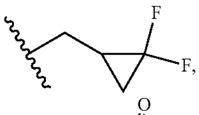,

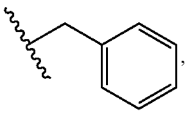, 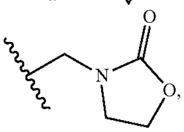,

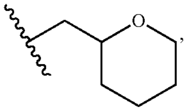, 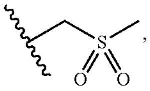, 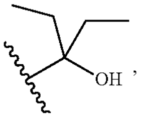,

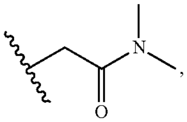, 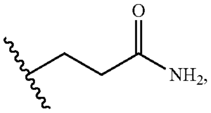, or

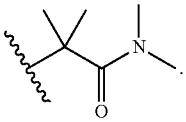.

In some embodiments, when present, at least one $R^{1a}$ is —$C_3$-$C_7$-cycloalkyl substituted with 0-3 substituents independently selected from the group consisting of halo, —OH, —$C_1$-$C_6$-alkoxy, and —C(O)$NR^aR^b$. In some embodiments, at least one $R^{1a}$ is

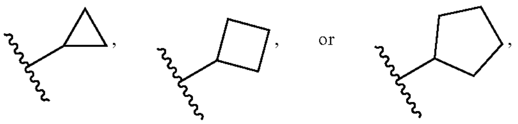

each of which is unsubstituted or substituted with a substituent selected from —OH and —C(O)$NR^aR^b$. In some embodiments, $R^{1a}$ is

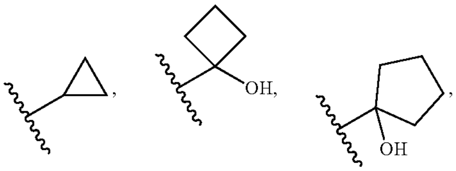

-continued

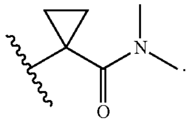

In some embodiments, when present, at least one $R^{1a}$ is 4- to 8-membered heterocycloalkyl or —O-(4- to 8-membered heterocycloalkyl); wherein said 4- to 8-membered heterocycloalkyl has 1-3 ring heteroatoms independently selected from N, O, and S; and said 4- to 8-membered heterocycloalkyl is substituted with 0-3 substituents independently selected from the group consisting of oxo, —OH, halo, —$C_1$-$C_6$ alkyl, —$C_1$-$C_3$-alkoxy, —C(O)($C_1$-$C_3$-alkyl), and —$S(O)_2$($C_1$-$C_3$-alkyl). In some embodiments, at least one $R^{1a}$ is

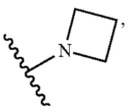, 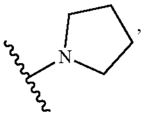, 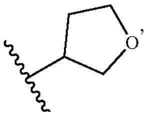,

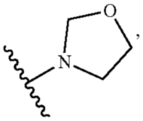, 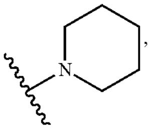, 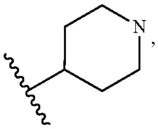,

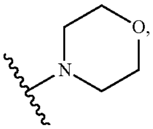, 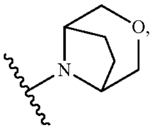, 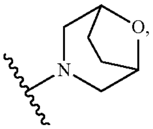,

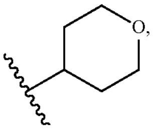, 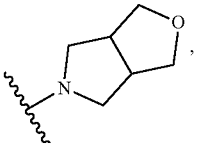,

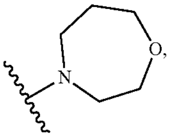, 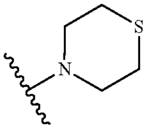, or

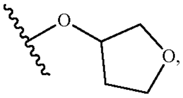, each of which is substituted with 0-2 substituents independently selected from oxo, —OH, halo, —$C_1$-$C_3$ alkyl, —$C_1$-$C_3$-alkoxy, —$C(O)CH_3$, and —$S(O)_2CH_3$. In some embodiments, at least one $R^{1a}$ is

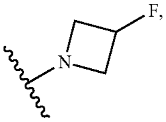, 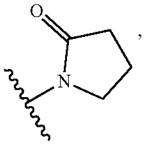, 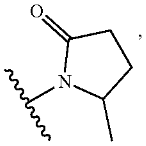,

-continued

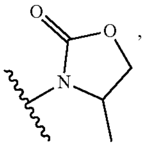, 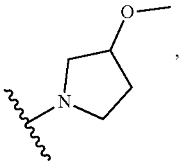, 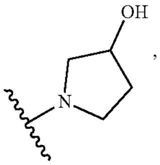,

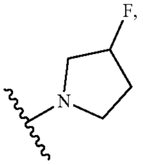, 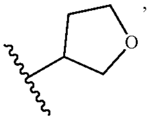,

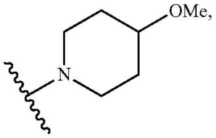, 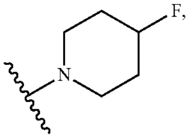,

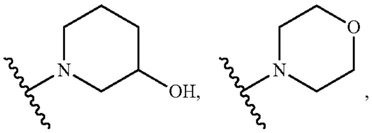,

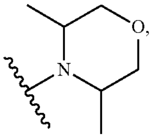, 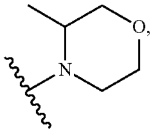, 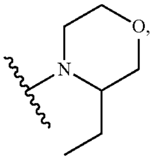,

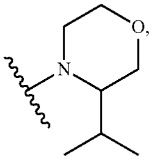, 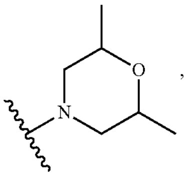,

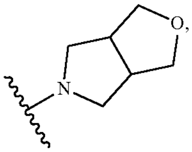, 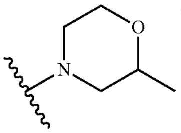,

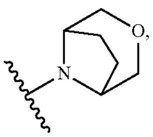, 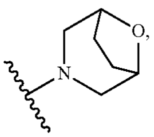, 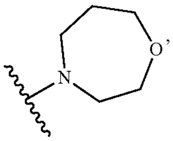,

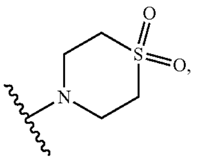, 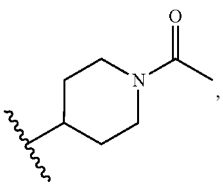,

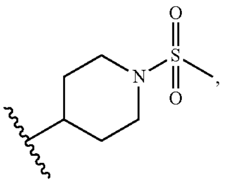, 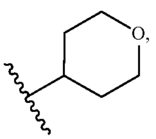, or

-continued

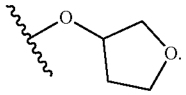

In some embodiments, each $R^{1a}$, when present, is independently —F, —Cl, —$CH_3$, —$CH(CH_3)_2$, —$CF_3$, —$CF_2H$, —CN, —OH, —$OCH_3$, —$NH_2$,

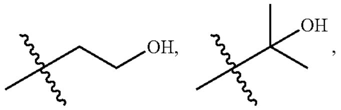

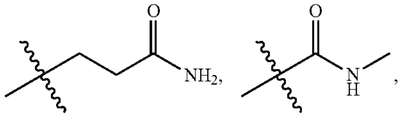

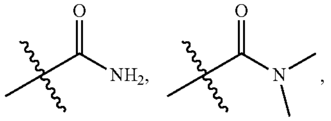

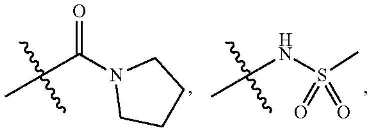

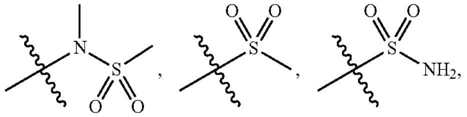

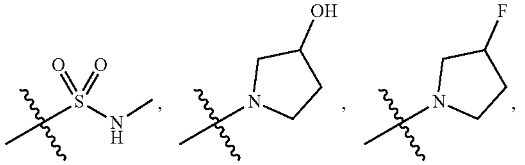

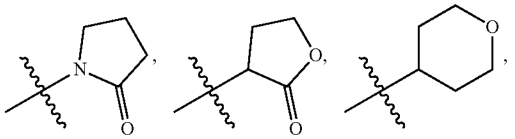

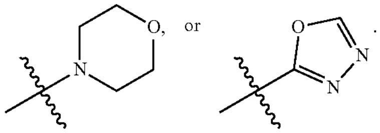

In some embodiments, when present, at least one $R^{1a}$ is 5- to 6-membered heteroaryl, —O—(5- to 6-membered heteroaryl), or —C≡C-(5- to 6-membered heteroaryl), wherein said 5- to 6-membered heteroaryl has 1-3 ring heteroatoms independently selected from N, O, and S; and wherein said 5- to 6-membered heteroaryl is substituted with 0-2 substituents independently selected from —OH, halo, and —$C_1$-$C_6$-alkyl. In some embodiments, at least one $R^{1a}$ is

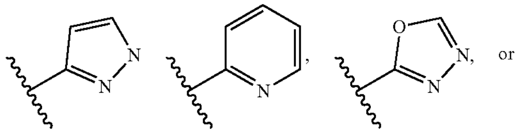

-continued

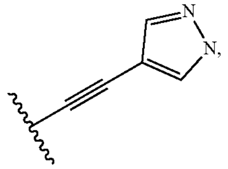

each of which is substituted with 0-2 substituents independently selected from halo and $C_1$-$C_3$-alkyl. In some embodiments, at least one $R^{1a}$ is

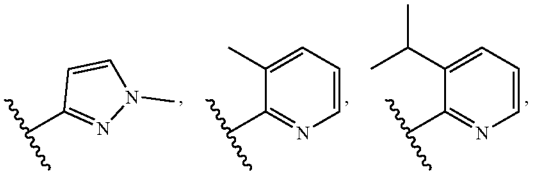

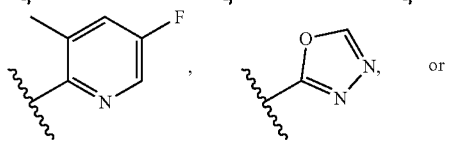

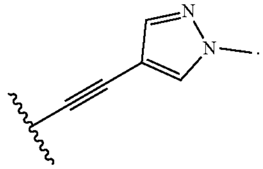

In some embodiments, two adjacent $R^{1a}$ are taken together with the atoms to which they are attached to form a 5- to 7-membered heterocycloalkyl, or a 5- to 6-membered heteroaryl; wherein said 5- to 7-membered heterocycloalkyl and 5- to 6-membered heteroaryl each have 1-2 ring heteroatoms independently selected from N, O, and S; and wherein said 5- to 7-membered heterocycloalkyl is substituted with 0-3 substituents independently selected from oxo, —$C_1$-$C_6$-alkyl, —C(O)($C_1$-$C_3$-alkyl), and —$S(O)_2$($C_1$-$C_3$-alkyl). In some embodiments, $R^1$ is

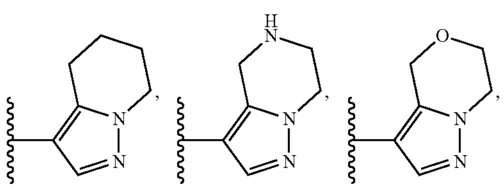

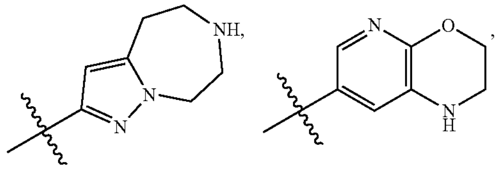

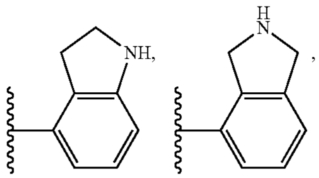

-continued

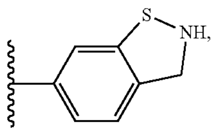 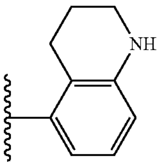,

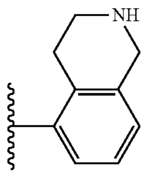, or 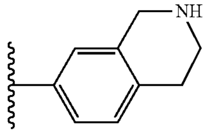, each of which is substituted with 0-3 substituents independently selected from oxo, —$C_1$-$C_6$-alkyl, —C(O)($C_1$-$C_3$-alkyl), and —$S(O)_2$($C_1$-$C_3$-alkyl). In some embodiments, $R^1$ is

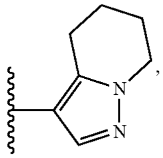, 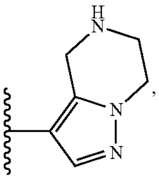, 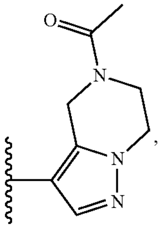,

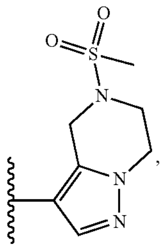, 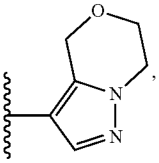,

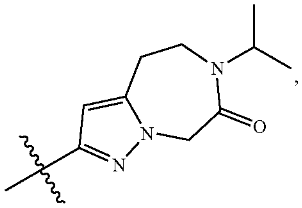,

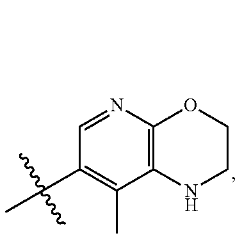, 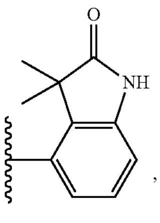,

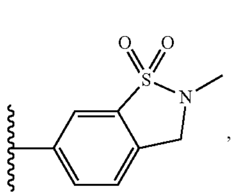, 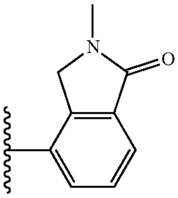,

-continued

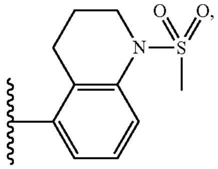 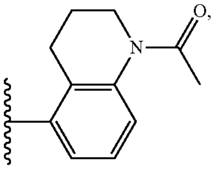

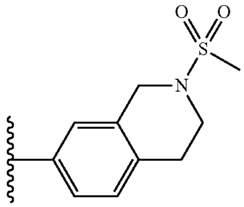, 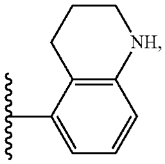

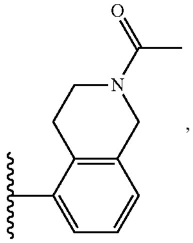, or 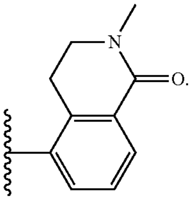

In some embodiments, $R^1$ is

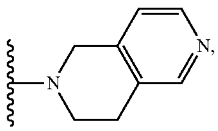 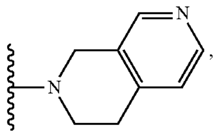,

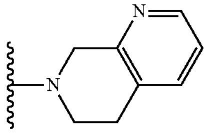, 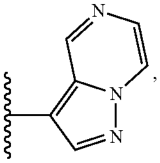,

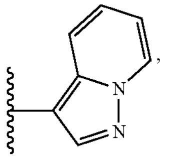, 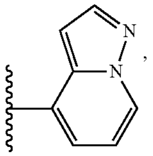,

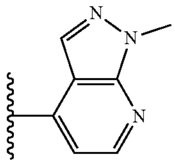, or 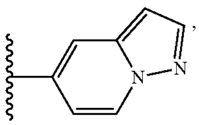,

In some embodiments, two adjacent $R^{1a}$ together with the atoms to which they are attached form morpholine, diazepane, or diazepanone, each of which is optionally substituted with one $C_1$-$C_3$-alkyl. In some embodiments, $R^1$ is,

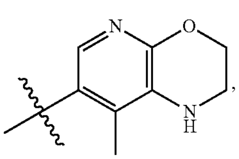, or

-continued
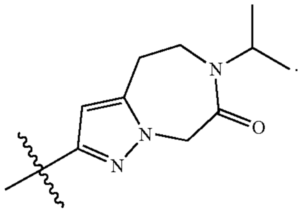.
In some embodiments, $R^1$ is
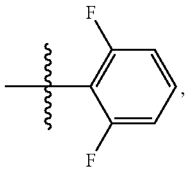, 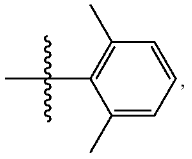, 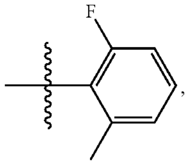, 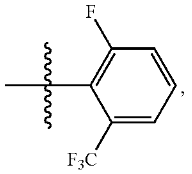, 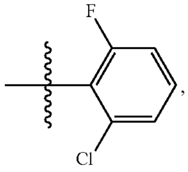, 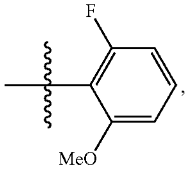, 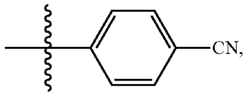, 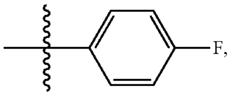, 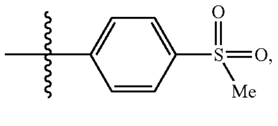, 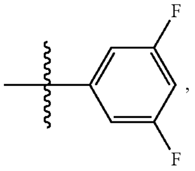, 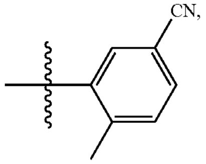, 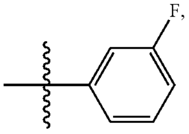, 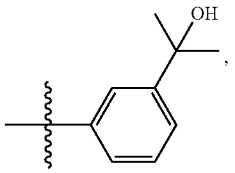, 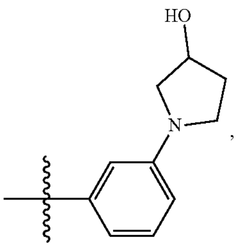, 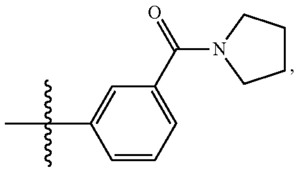,
-continued
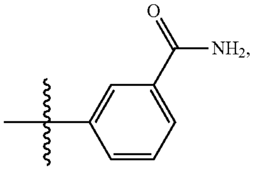, 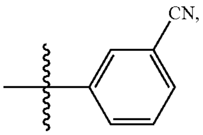, 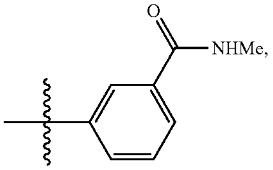, 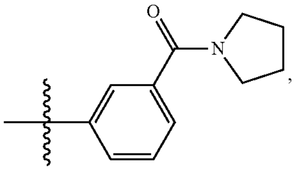, 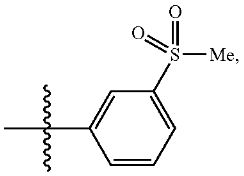, 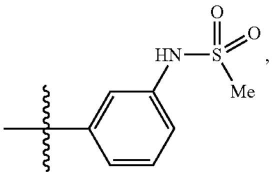, 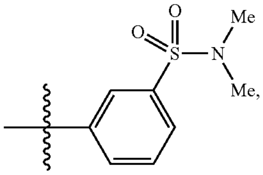, 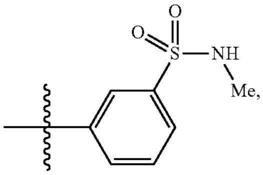, 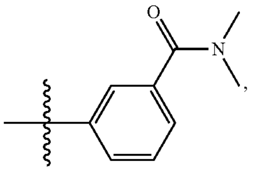, 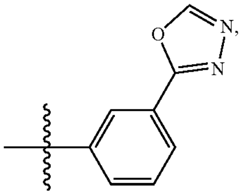, or 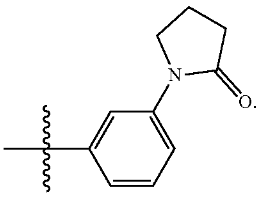.
In some embodiments, $R^1$ is
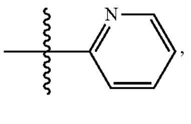, 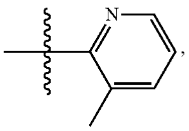 [SMILES: *c1ncccc1C], -continued
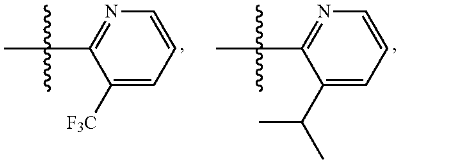
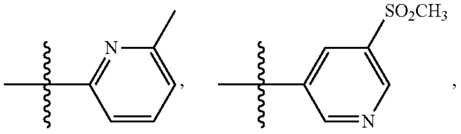
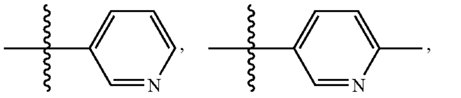
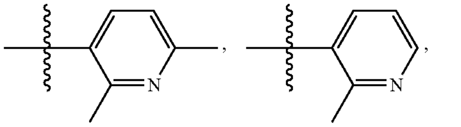
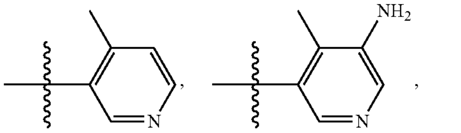
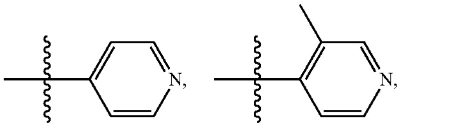
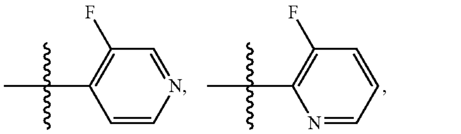
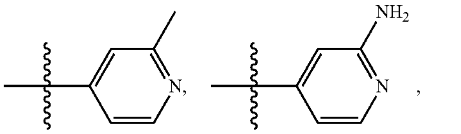
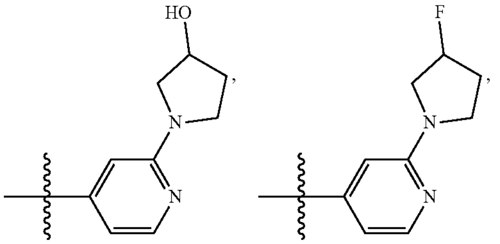
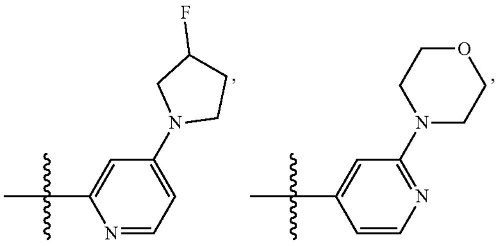
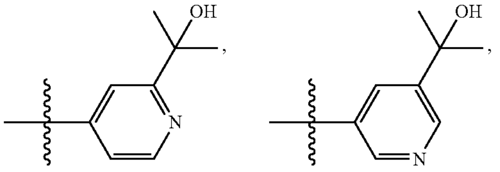
-continued
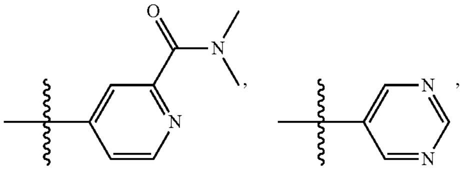
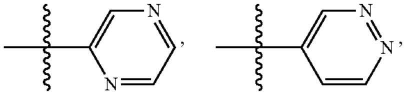
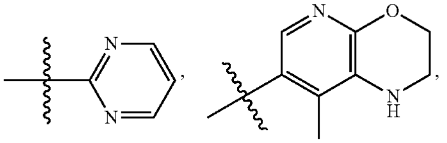
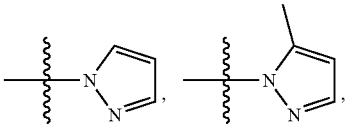
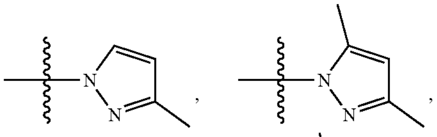
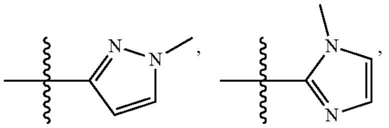
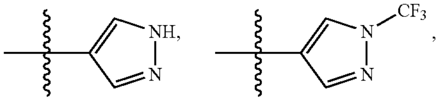
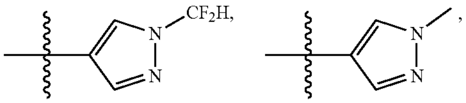
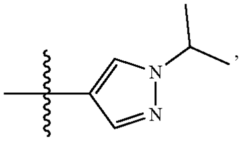
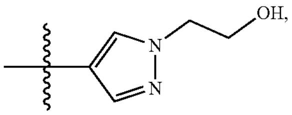
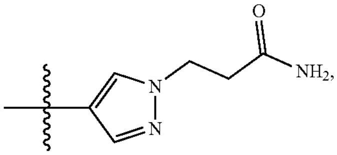
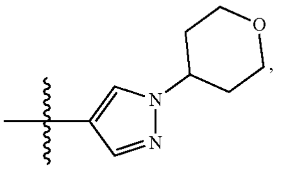
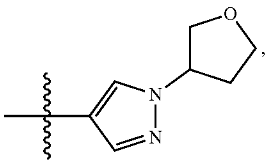

-continued
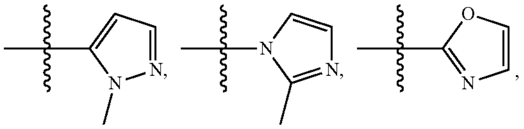
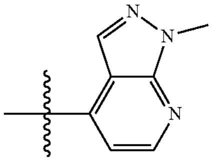
or
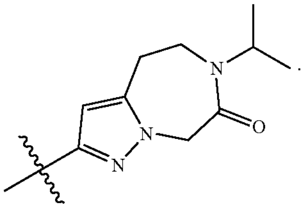
In some embodiments, $R^1$ is
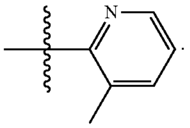
In some embodiments, $R^1$ is
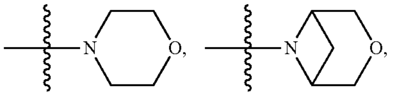
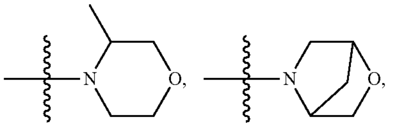
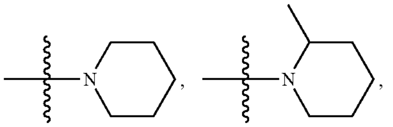
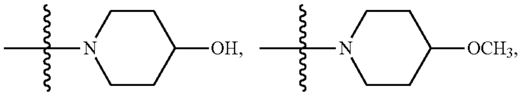
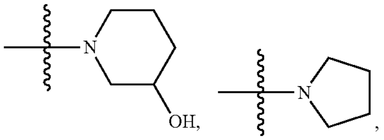
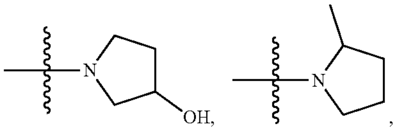
-continued
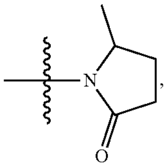
or
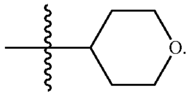
In some embodiments, $R^1$ is
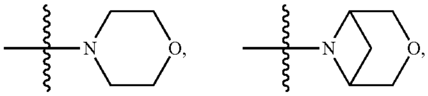
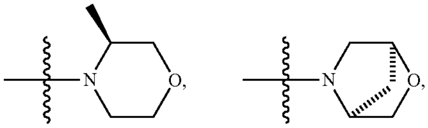
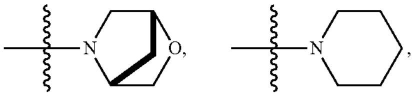
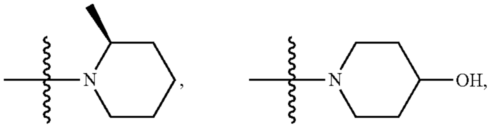
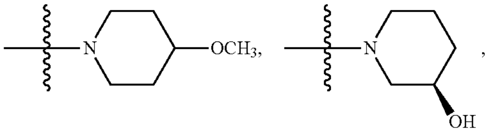
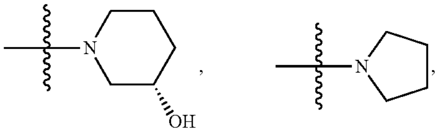
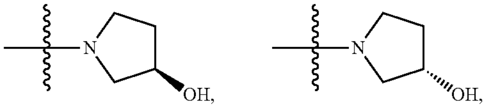
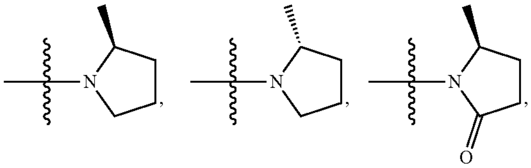
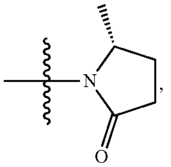
or
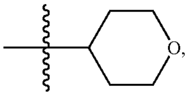
In some embodiments, the compound has a structure selected from the group consisting of:

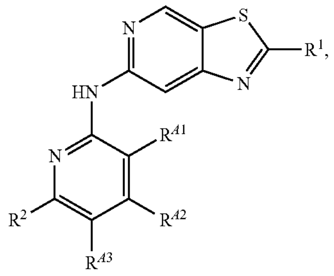

(i)

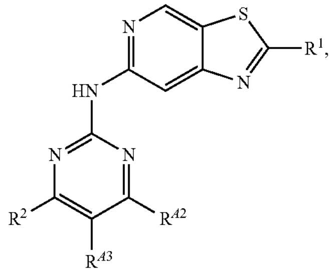

(ii)

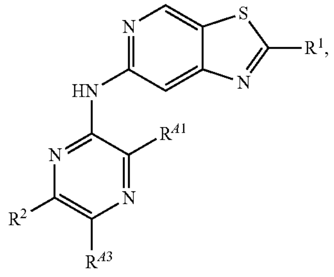

(iii)

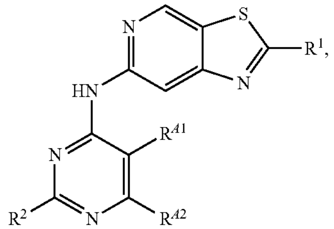

(iv)

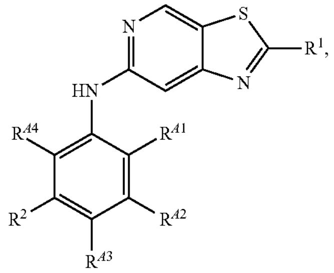

(v)

and

-continued

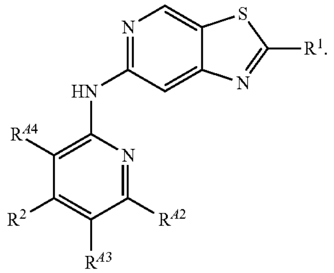

(vi)

In some embodiments, $R^{A1}$, when present, is —H, halo, $C_1$-$C_6$-alkyl, —O—$C_1$-$C_6$-alkyl, or 5- to 6-membered heterocycloalkyl having 1-2 ring heteroatoms independently selected from N and O; $R^{A2}$, when present, is H, halo, $C_1$-$C_6$-alkyl, or 5- to 6-membered heterocycloalkyl having 1-2 ring heteroatoms independently selected from N and O; and $R^{A3}$, when present, is —H, halo, $C_1$-$C_6$-alkyl, $C_1$-$C_6$-haloalkyl, $C_3$-$C_6$-cycloalkyl, or 5- to 6-membered heterocycloalkyl having 1-2 ring heteroatoms independently selected from N and O, wherein said 5- to 6-membered heterocycloalkyl is optionally substituted with 1-2 substituents independently selected from halo and —OH.

In some embodiments, $R^{A1}$, when present, is —H, —F, —$CH_3$, —$OCH_3$, or morpholinyl. In some embodiments, $R^{A1}$, when present, is —H. In some embodiments, $R^{A1}$, when present, is —F. In some embodiments, $R^{A1}$, when present, is —$CH_3$. In some embodiments, $R^{A1}$, when present, is —$OCH_3$. In some embodiments, $R^{A1}$, when present, is morpholinyl.

In some embodiments, $R^{A2}$, when present, is —H, -halo, —$C_1$-$C_3$-alkyl, —$C_1$-$C_3$-haloalkyl, —$C_1$-$C_3$-hydroxyalkyl, cyclopropyl, cyclohexyl, tetrahydropyranyl, pyrrolidinyl, morpholinyl, or pyridinyl, wherein said tetrahydropyranyl, pyrrolidinyl, morpholinyl, and pyridinyl are optionally substituted with 1-2 substituents independently selected from —F, —CN, and —OH. In some embodiments, $R^{A2}$, when present, is —H, —Cl, —F, —$CH_3$, —$CF_3$,

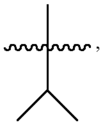,
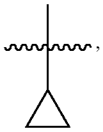,
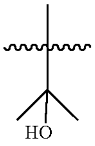,
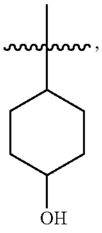,
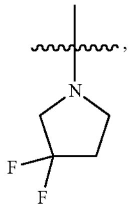,
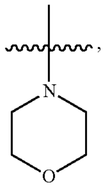,
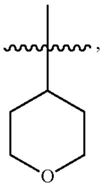,
or
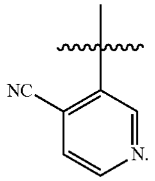

In some embodiments, $R^{A2}$, when present, is —H, —F, —$CH_3$, —$CH_2NMe_2$, tetrahydropyranyl, or morpholinyl. In some embodiments, $R^{A2}$, when present, is —H. In some embodiments, $R^{A2}$, when present, is —F. In some embodiments, $R^{A2}$, when present, is —$CH_3$. In some embodiments, $R^{A2}$, when present, is tetrahydropyranyl. In some embodiments, $R^{A2}$, when present, is morpholinyl.

In some embodiments, $R^{A3}$, when present, is —H, -halo, —$C_1$-$C_3$-alkyl, —$C_1$-haloalkyl, cyclopropyl, tetrahydrofuranyl, tetrahydropyranyl, morpholinyl, pyrrolidinyl, or piperidinyl, wherein said tetrahydrofuranyl, tetrahydropyranyl, morpholinyl, pyrrolidinyl, and piperidinyl are optionally substituted with 1-2 substituents independently selected from —F and —OH. In some embodiments, $R^{A3}$, when present, is —H, —Cl, —F, —$CH_3$, $CF_3$,

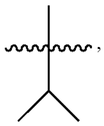,
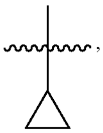,
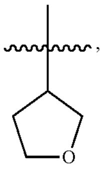,
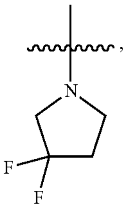,

-continued

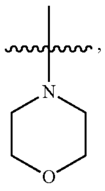,
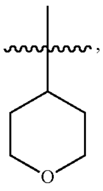, or
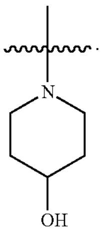.

In one or more embodiments, the compound, or pharmaceutically acceptable salt or solvate thereof, according to this disclosure is selected from the compounds provided in Tables 1 and 2. In further embodiments, the compound, or pharmaceutically acceptable salt thereof, according to this disclosure is selected from the compounds provided in Tables 1 and 2.

TABLE 1

| Ex. No. | Structure |
|---|---|
| 1 | 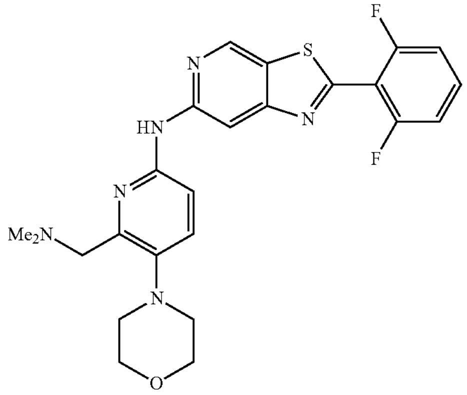 [SMILES: CN(C)Cc1nc(Nc2cc3nc(-c4c(F)cccc4F)sc3cn2)ccc1N1CCOCC1] |
| 2 | 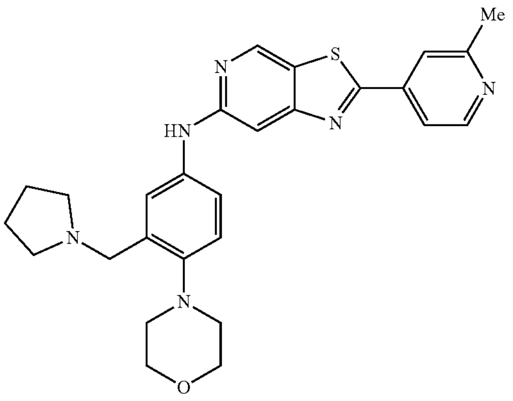 [SMILES: Cc1cc(-c2nc3cc(Nc4ccc(N5CCOCC5)c(CN5CCCC5)c4)ncc3s2)ccn1] |

TABLE 1-continued
| Ex. No. | Structure |
| --- | --- |
| 3 | 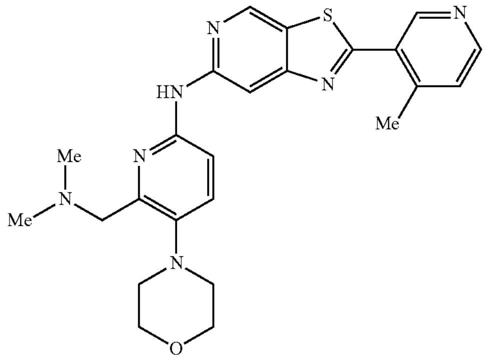 [SMILES: Cc1ccncc1-c1nc2cc(Nc3ccc(N4CCOCC4)c(CN(C)C)n3)ncc2s1] |
| 4 | 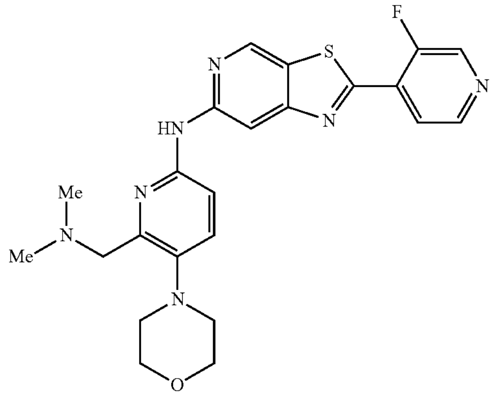 [SMILES: CN(C)Cc1nc(Nc2cc3nc(-c4ccncc4F)sc3cn2)ccc1N1CCOCC1] |
| 5 | 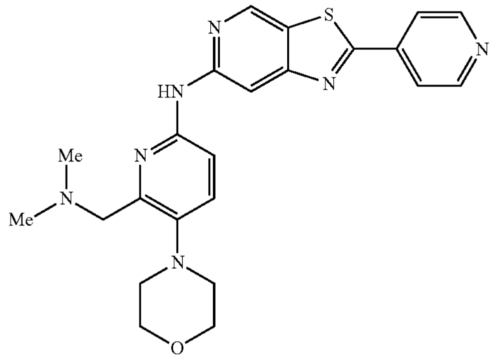 [SMILES: CN(C)Cc1nc(Nc2cc3nc(-c4ccncc4)sc3cn2)ccc1N1CCOCC1] |
| 6 | 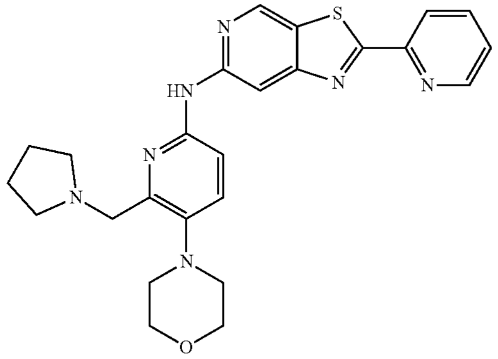 [SMILES: c1ccc(-c2nc3cc(Nc4ccc(N5CCOCC5)c(CN5CCCC5)n4)ncc3s2)nc1] |

TABLE 1-continued
| Ex. No. | Structure |
| --- | --- |
| 7 | 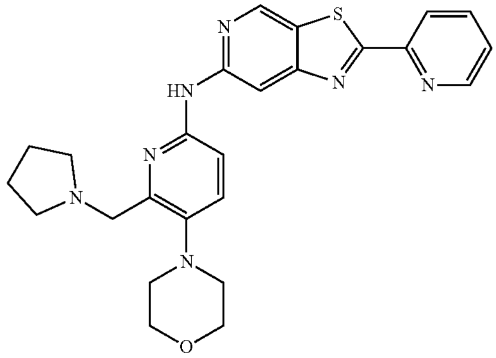 [SMILES: c1ccc(-c2nc3cc(Nc4ccc(N5CCOCC5)c(CN5CCCC5)n4)ncc3s2)nc1] |
| 8 | 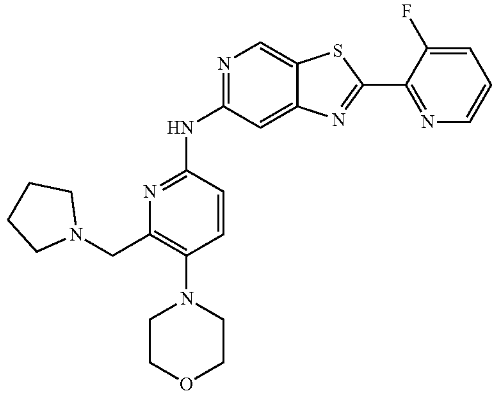 [SMILES: Fc1cccnc1-c1nc2cc(Nc3ccc(N4CCOCC4)c(CN4CCCC4)n3)ncc2s1] |
| 9 | 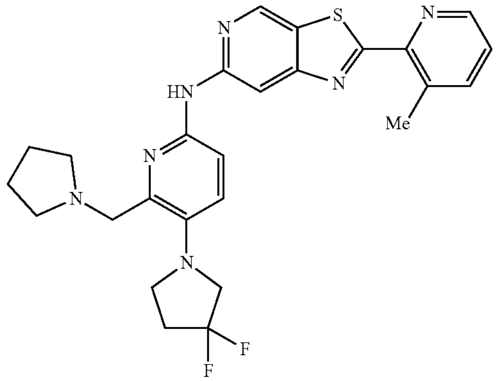 [SMILES: Cc1cccnc1-c1nc2cc(Nc3ccc(N4CCC(F)(F)C4)c(CN4CCCC4)n3)ncc2s1] |
| 10 | 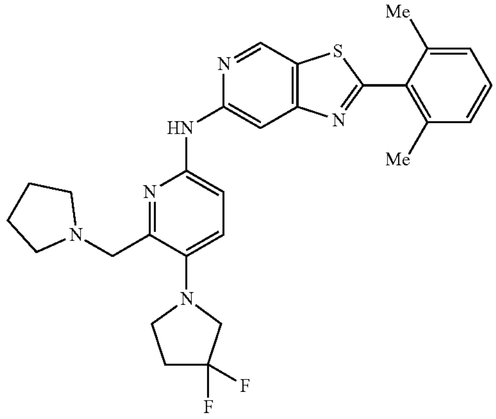 [SMILES: Cc1cccc(C)c1-c1nc2cc(Nc3ccc(N4CCC(F)(F)C4)c(CN4CCCC4)n3)ncc2s1] |

TABLE 1-continued
| Ex. No. | Structure |
|---|---|
| 11 | 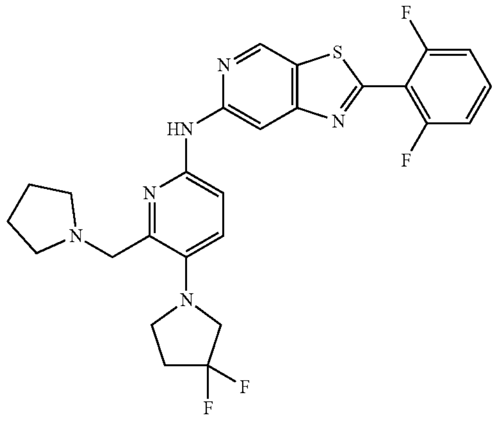 [SMILES: Fc1cccc(F)c1-c1nc2cc(Nc3ccc(N4CCC(F)(F)C4)c(CN4CCCC4)n3)ncc2s1] |
| 12 | 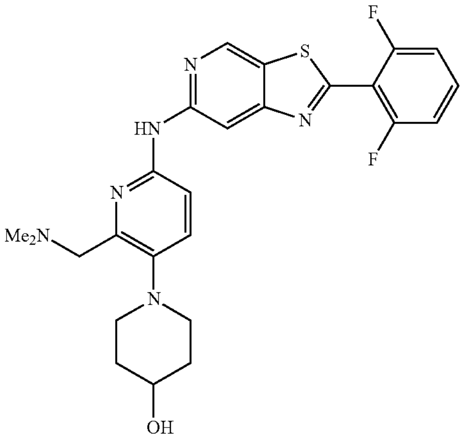 [SMILES: CN(C)Cc1nc(Nc2cc3nc(-c4c(F)cccc4F)sc3cn2)ccc1N1CCC(O)CC1] |
| 13 | 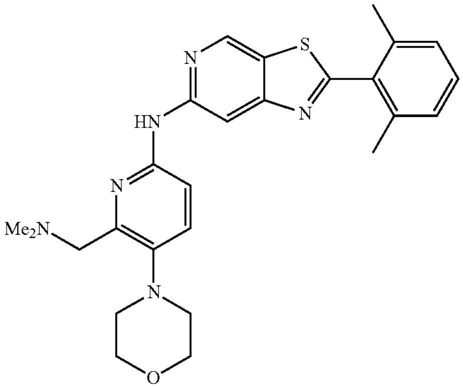 [SMILES: Cc1cccc(C)c1-c1nc2cc(Nc3ccc(N4CCOCC4)c(CN(C)C)n3)ncc2s1] |

TABLE 1-continued
| Ex. No. | Structure |
|---|---|
| 14 | 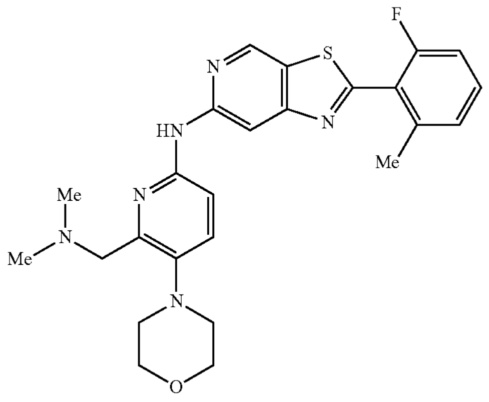 [SMILES: Cc1cccc(F)c1-c1nc2cc(Nc3ccc(N4CCOCC4)c(CN(C)C)n3)ncc2s1] |
| 15 | 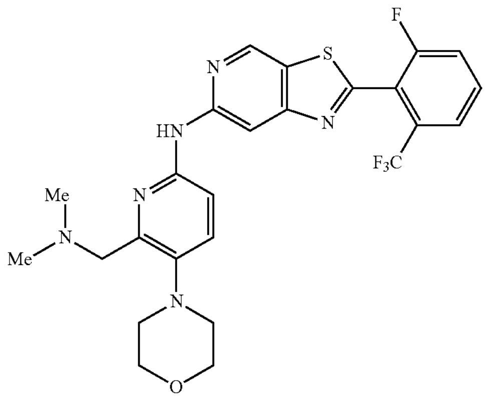 [SMILES: CN(C)Cc1nc(Nc2cc3nc(-c4c(F)cccc4C(F)(F)F)sc3cn2)ccc1N1CCOCC1] |
| 16 | 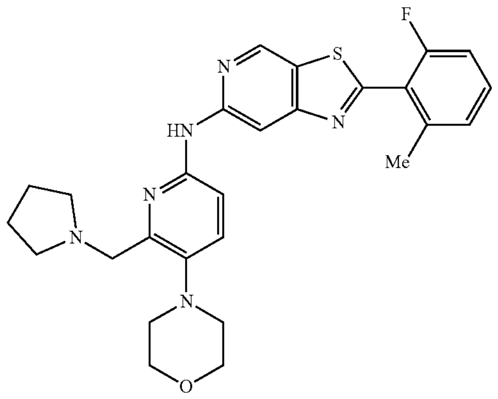 [SMILES: Cc1cccc(F)c1-c1nc2cc(Nc3ccc(N4CCOCC4)c(CN4CCCC4)n3)ncc2s1] |
| 17 | 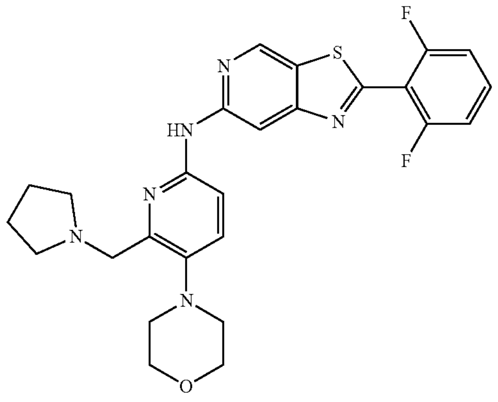 [SMILES: Fc1cccc(F)c1-c1nc2cc(Nc3ccc(N4CCOCC4)c(CN4CCCC4)n3)ncc2s1] |

TABLE 1-continued
| Ex. No. | Structure |
|---|---|
| 18 | 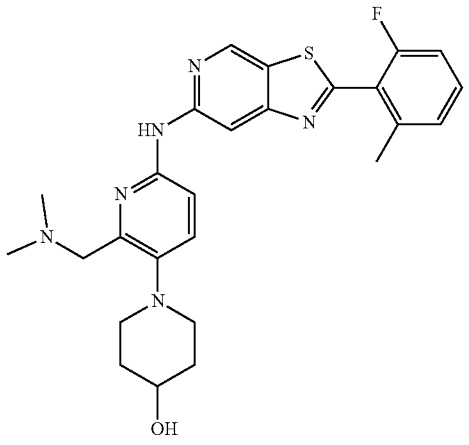 [SMILES: Cc1cccc(F)c1-c1nc2cc(Nc3ccc(N4CCC(O)CC4)c(CN(C)C)n3)ncc2s1] |
| 19 | 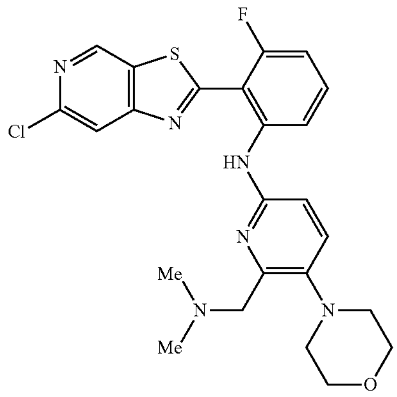 [SMILES: CN(C)Cc1nc(Nc2cccc(F)c2-c2nc3cc(Cl)ncc3s2)ccc1N1CCOCC1] |
| 20 | 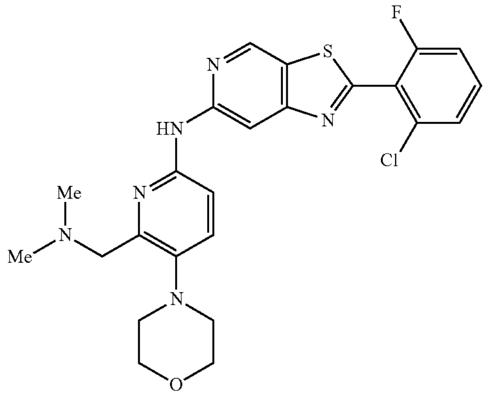 [SMILES: CN(C)Cc1nc(Nc2cc3nc(-c4c(F)cccc4Cl)sc3cn2)ccc1N1CCOCC1] |
| 21 | 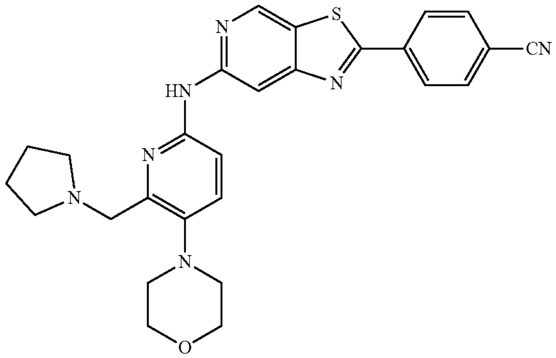 [SMILES: N#Cc1ccc(-c2nc3cc(Nc4ccc(N5CCOCC5)c(CN5CCCC5)n4)ncc3s2)cc1] |

TABLE 1-continued
| Ex. No. | Structure |
|---|---|
| 22 | 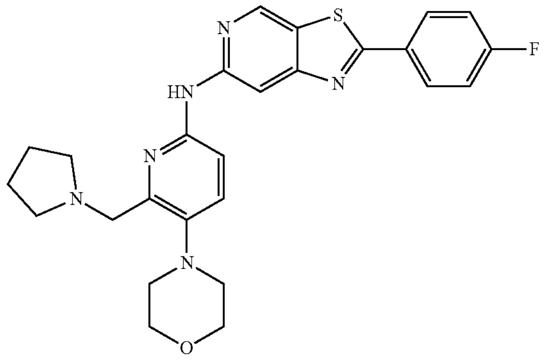 |
| 23 | 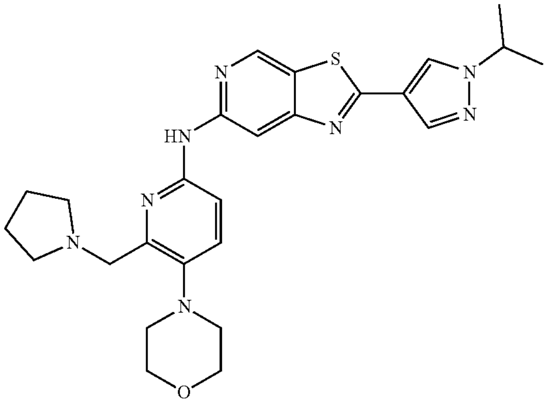 [SMILES: CC(C)n1cc(-c2nc3cc(Nc4ccc(N5CCOCC5)c(CN5CCCC5)n4)ncc3s2)cn1] |
| 24 | 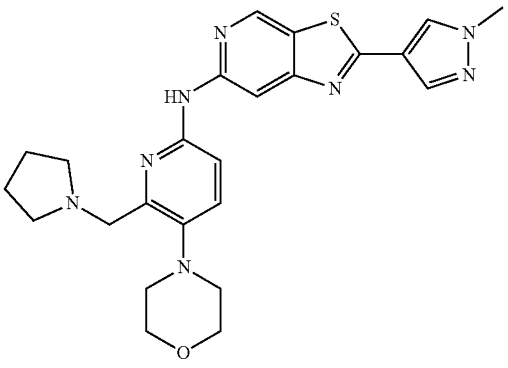 [SMILES: Cn1cc(-c2nc3cc(Nc4ccc(N5CCOCC5)c(CN5CCCC5)n4)ncc3s2)cn1] |
| 25 | 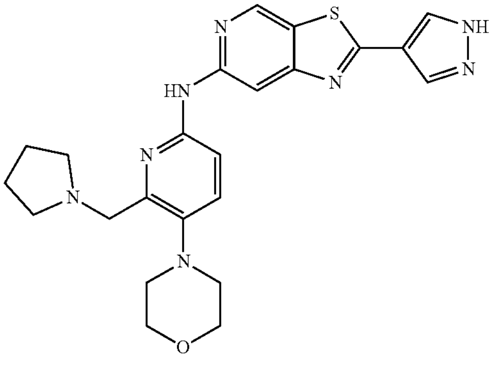 [SMILES: c1n[nH]cc1-c1nc2cc(Nc3ccc(N4CCOCC4)c(CN4CCCC4)n3)ncc2s1] |

TABLE 1-continued
| Ex. No. | Structure |
|---|---|
| 26 | 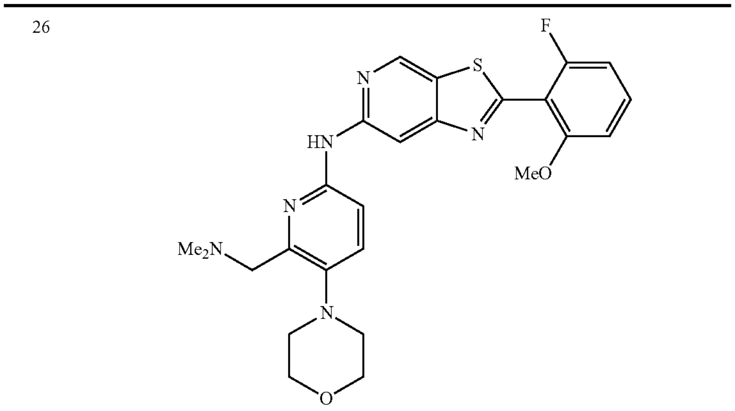 |
| 27 | 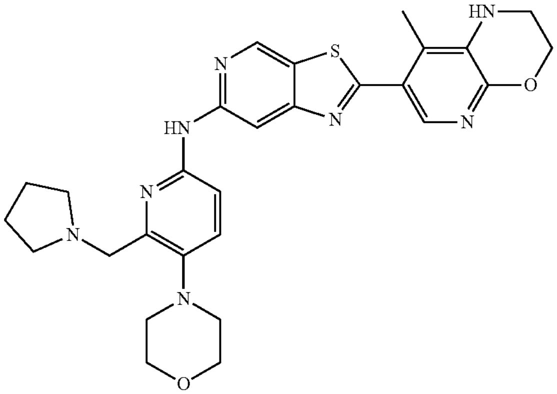 [SMILES: Cc1c(-c2nc3cc(Nc4ccc(N5CCOCC5)c(CN5CCCC5)n4)ncc3s2)cnc2c1NCCO2] |
| 28 | 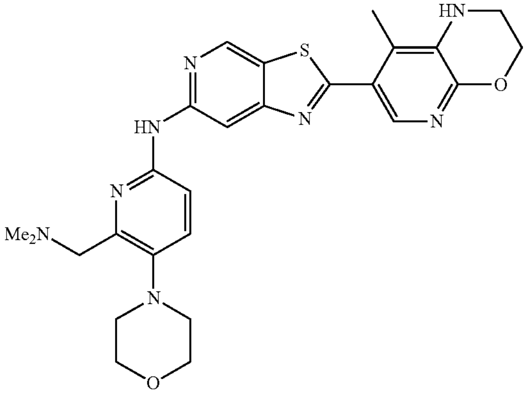 [SMILES: Cc1c(-c2nc3cc(Nc4ccc(N5CCOCC5)c(CN(C)C)n4)ncc3s2)cnc2c1NCCO2] |
| 29 | 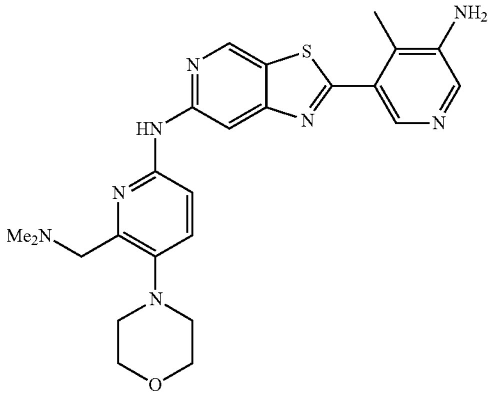 [SMILES: Cc1c(N)cncc1-c1nc2cc(Nc3ccc(N4CCOCC4)c(CN(C)C)n3)ncc2s1] |

TABLE 1-continued
| Ex. No. | Structure |
|---|---|
| 30 | 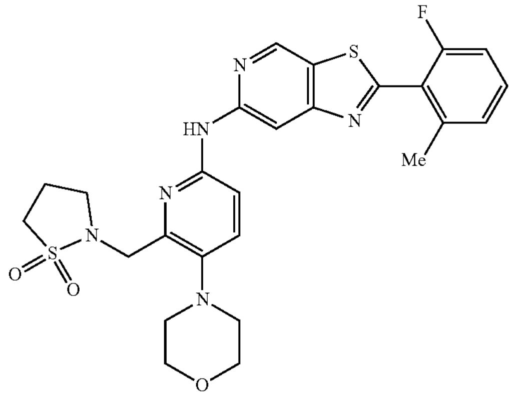 [SMILES: Cc1cccc(F)c1-c1nc2cc(Nc3ccc(N4CCOCC4)c(CN4CCCS4(=O)=O)n3)ncc2s1] |
| 31 | 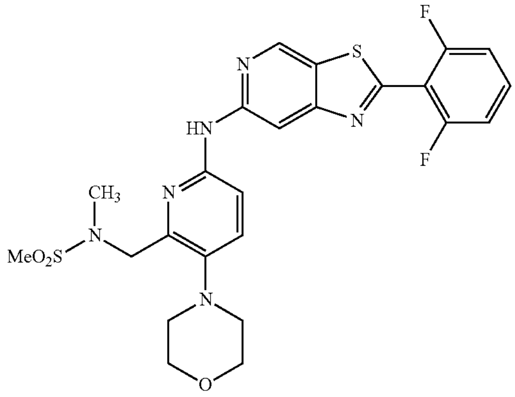 [SMILES: CN(Cc1nc(Nc2cc3nc(-c4c(F)cccc4F)sc3cn2)ccc1N1CCOCC1)S(C)(=O)=O] |
| 32 | 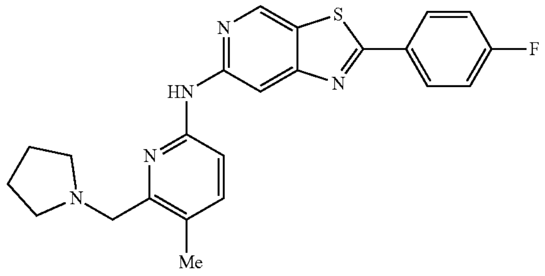 [SMILES: Cc1ccc(Nc2cc3nc(-c4ccc(F)cc4)sc3cn2)nc1CN1CCCC1] |
| 33 | 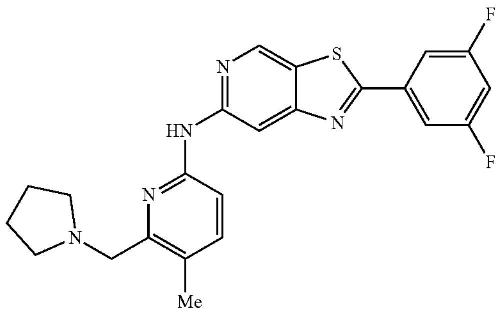 [SMILES: Cc1ccc(Nc2cc3nc(-c4cc(F)cc(F)c4)sc3cn2)nc1CN1CCCC1] |

TABLE 1-continued
| Ex. No. | Structure |
|---|---|
| 34 | 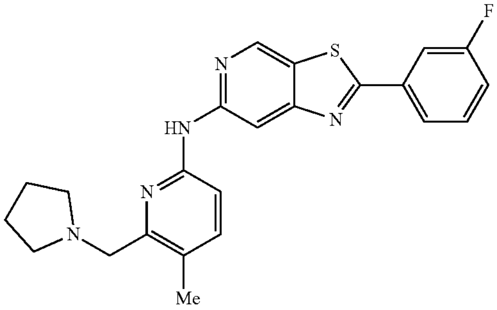 [SMILES: Cc1ccc(Nc2cc3nc(-c4cccc(F)c4)sc3cn2)nc1CN1CCCC1] |
| 35 | 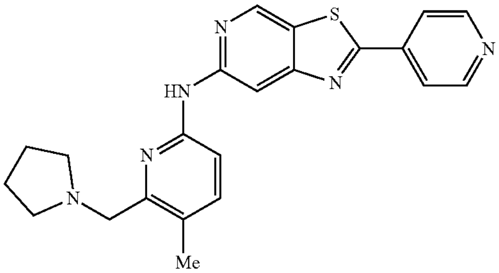 [SMILES: Cc1ccc(Nc2cc3nc(-c4ccncc4)sc3cn2)nc1CN1CCCC1] |
| 36 | 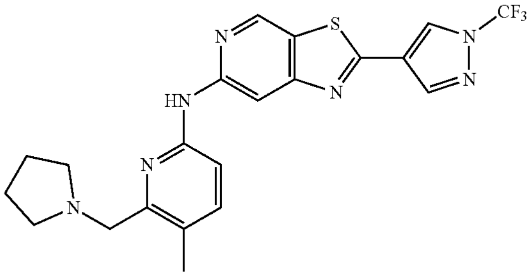 [SMILES: Cc1ccc(Nc2cc3nc(-c4cnn(C(F)(F)F)c4)sc3cn2)nc1CN1CCCC1] |
| 37 | 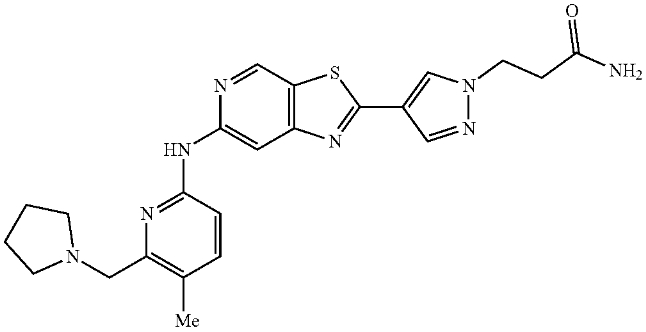 [SMILES: Cc1ccc(Nc2cc3nc(-c4cnn(CCC(N)=O)c4)sc3cn2)nc1CN1CCCC1] |
| 38 | 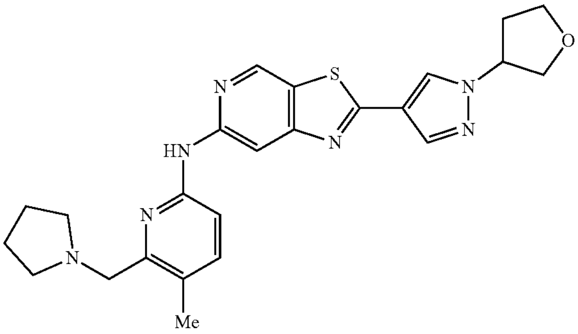 [SMILES: Cc1ccc(Nc2cc3nc(-c4cnn(C5CCOC5)c4)sc3cn2)nc1CN1CCCC1] |

TABLE 1-continued
| Ex. No. | Structure |
|---|---|
| 39 | 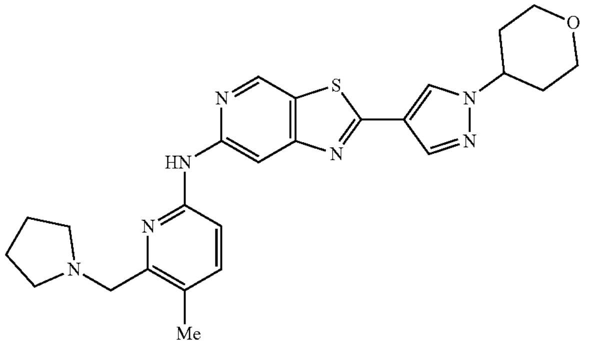 [SMILES: Cc1ccc(Nc2cc3nc(-c4cnn(C5CCOCC5)c4)sc3cn2)nc1CN1CCCC1] |
| 40 | 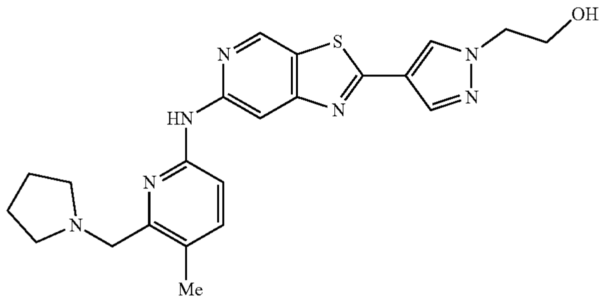 [SMILES: Cc1ccc(Nc2cc3nc(-c4cnn(CCO)c4)sc3cn2)nc1CN1CCCC1] |
| 41 | 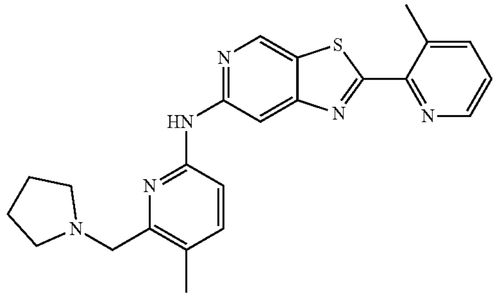 [SMILES: Cc1ccc(Nc2cc3nc(-c4ncccc4C)sc3cn2)nc1CN1CCCC1] |
| 42 | 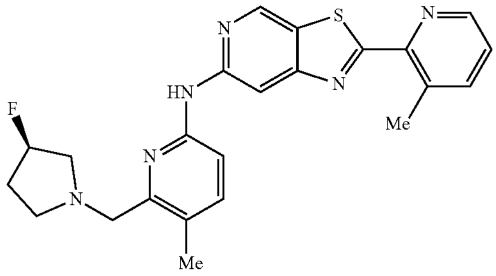 [SMILES: Cc1ccc(Nc2cc3nc(-c4ncccc4C)sc3cn2)nc1CN1CC[C@@H](F)C1] |
| 43 | 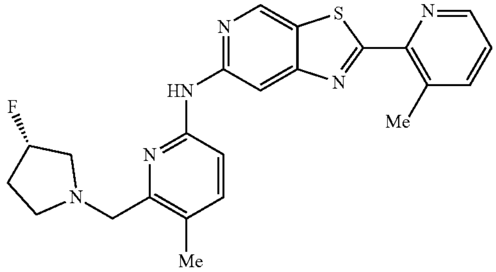 [SMILES: Cc1ccc(Nc2cc3nc(-c4ncccc4C)sc3cn2)nc1CN1CC[C@H](F)C1] |

TABLE 1-continued
| Ex. No. | Structure |
| --- | --- |
| 44 | 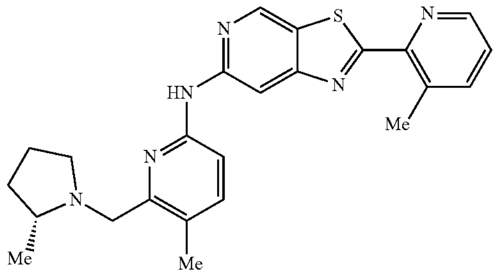 [SMILES: Cc1ccc(Nc2cc3nc(-c4ncccc4C)sc3cn2)nc1CN1CCC[C@H]1C] |
| 45 | 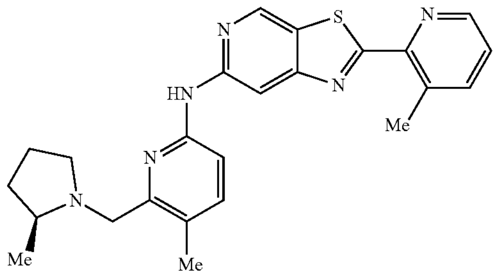 [SMILES: Cc1ccc(Nc2cc3nc(-c4ncccc4C)sc3cn2)nc1CN1CCC[C@@H]1C] |
| 46 | 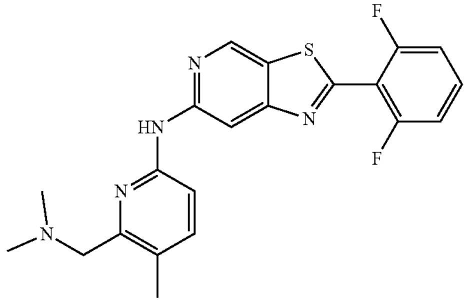 [SMILES: Cc1ccc(Nc2cc3nc(-c4c(F)cccc4F)sc3cn2)nc1CN(C)C] |
| 47 | 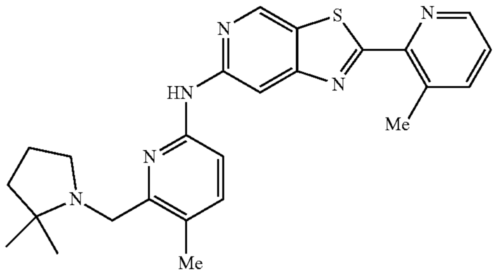 [SMILES: Cc1ccc(Nc2cc3nc(-c4ncccc4C)sc3cn2)nc1CN1CCCC1(C)C] |
| 48 | 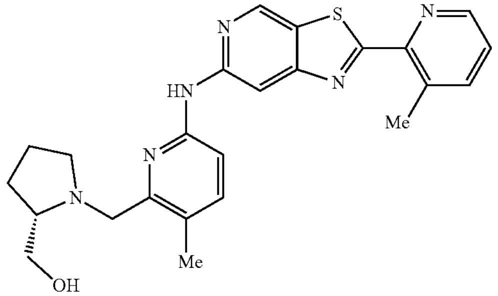 [SMILES: Cc1ccc(Nc2cc3nc(-c4ncccc4C)sc3cn2)nc1CN1CCC[C@H]1CO] |

TABLE 1-continued
| Ex. No. | Structure |
| --- | --- |
| 49 | 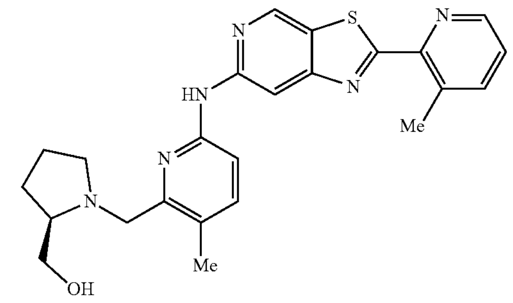 [SMILES: Cc1ccc(Nc2cc3nc(-c4ncccc4C)sc3cn2)nc1CN1CCC[C@@H]1CO] |
| 50 | 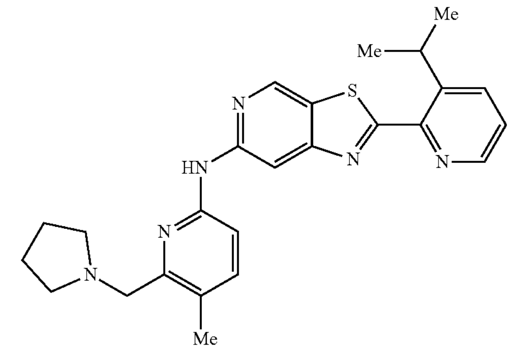 [SMILES: Cc1ccc(Nc2cc3nc(-c4ncccc4C(C)C)sc3cn2)nc1CN1CCCC1] |
| 51 | 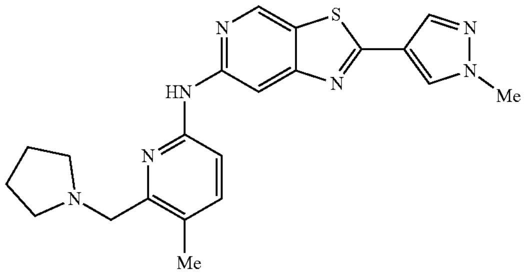 [SMILES: Cc1ccc(Nc2cc3nc(-c4cnn(C)c4)sc3cn2)nc1CN1CCCC1] |
| 52 | 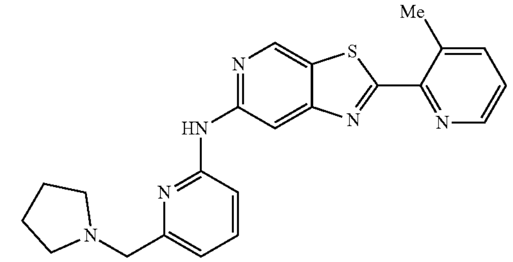 [SMILES: Cc1cccnc1-c1nc2cc(Nc3cccc(CN4CCCC4)n3)ncc2s1] |
| 53 | 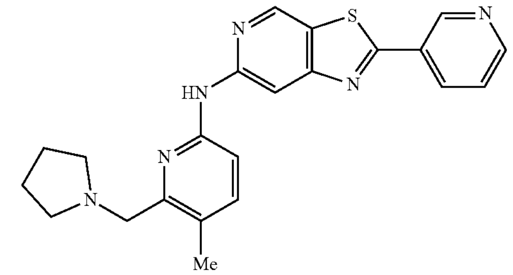 [SMILES: Cc1ccc(Nc2cc3nc(-c4cccnc4)sc3cn2)nc1CN1CCCC1] |

TABLE 1-continued
| Ex. No. | Structure |
| --- | --- |
| 54 | 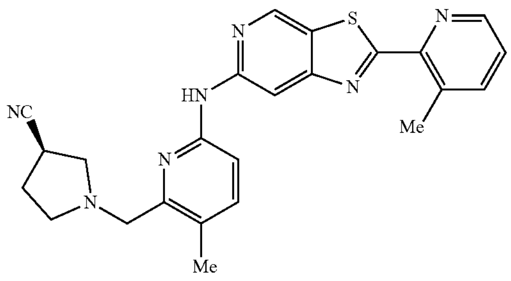 [SMILES: Cc1ccc(Nc2cc3nc(-c4ncccc4C)sc3cn2)nc1CN1CC[C@@H](C#N)C1] |
| 55 | 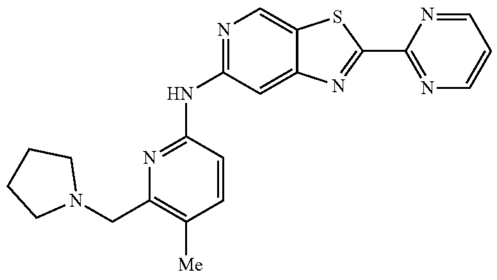 [SMILES: Cc1ccc(Nc2cc3nc(-c4ncccn4)sc3cn2)nc1CN1CCCC1] |
| 56 | 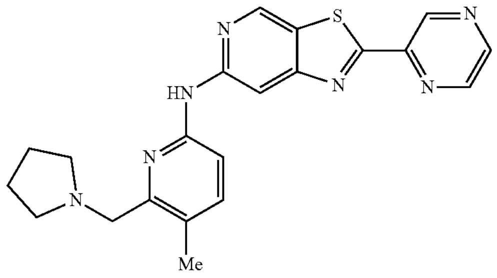 [SMILES: Cc1ccc(Nc2cc3nc(-c4cnccn4)sc3cn2)nc1CN1CCCC1] |
| 57 | 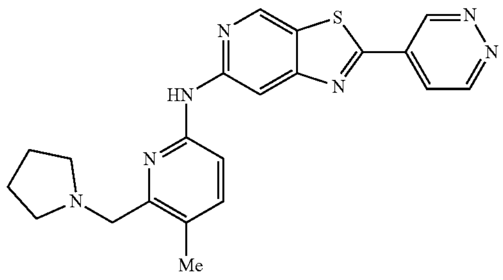 |
| 58 | 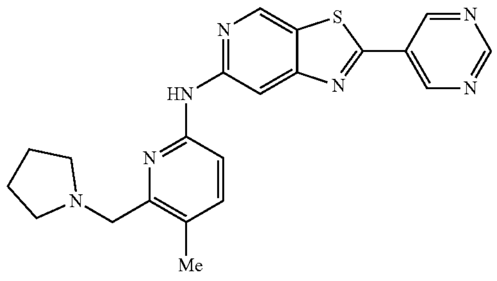 [SMILES: Cc1ccc(Nc2cc3nc(-c4cncnc4)sc3cn2)nc1CN1CCCC1] |

TABLE 1-continued
| Ex. No. | Structure |
|---|---|
| 59 | 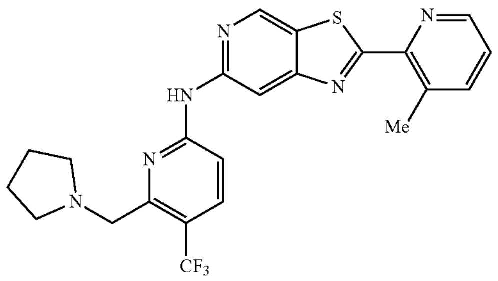 [SMILES: Cc1cccnc1-c1nc2cc(Nc3ccc(C(F)(F)F)c(CN4CCCC4)n3)ncc2s1] |
| 60 | 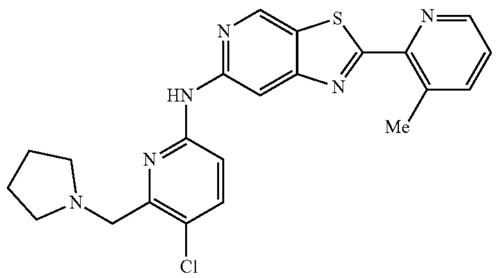 |
| 61 | 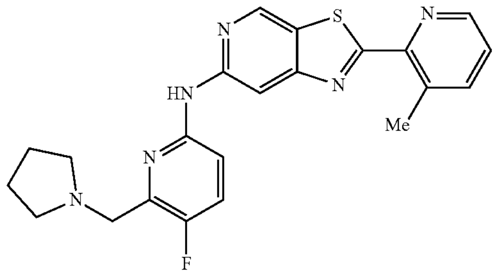 [SMILES: Cc1cccnc1-c1nc2cc(Nc3ccc(F)c(CN4CCCC4)n3)ncc2s1] |
| 62 | 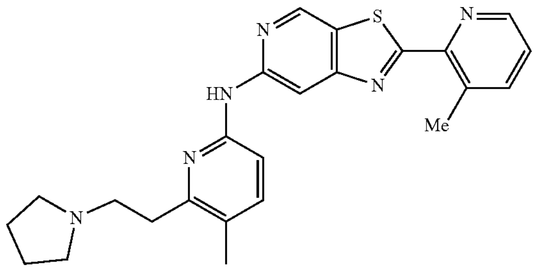 [SMILES: Cc1ccc(Nc2cc3nc(-c4ncccc4C)sc3cn2)nc1CCN1CCCC1] |
| 63 | 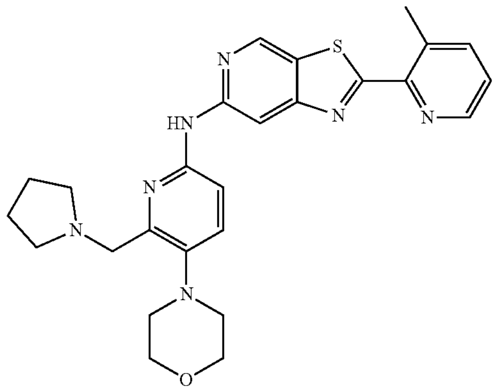 [SMILES: Cc1cccnc1-c1nc2cc(Nc3ccc(N4CCOCC4)c(CN4CCCC4)n3)ncc2s1] |

TABLE 1-continued
| Ex. No. | Structure |
|---|---|
| 64 | 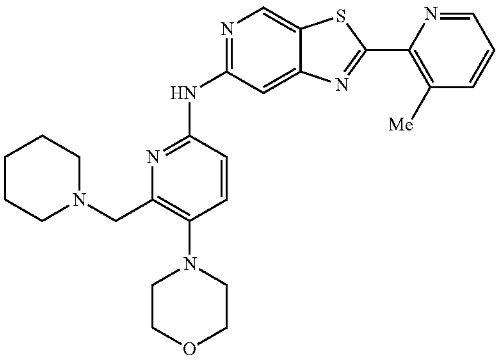 [SMILES: Cc1cccnc1-c1nc2cc(Nc3ccc(N4CCOCC4)c(CN4CCCCC4)n3)ncc2s1] |
| 65 | 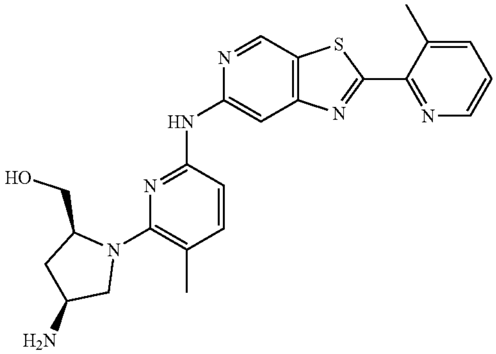 [SMILES: Cc1cccnc1-c1nc2cc(Nc3ccc(C)c(N4C[C@@H](N)C[C@H]4CO)n3)ncc2s1] |
| 66 | 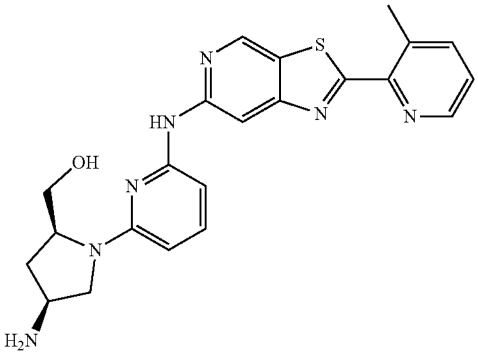 [SMILES: Cc1cccnc1-c1nc2cc(Nc3cccc(N4C[C@@H](N)C[C@H]4CO)n3)ncc2s1] |
| 67 | 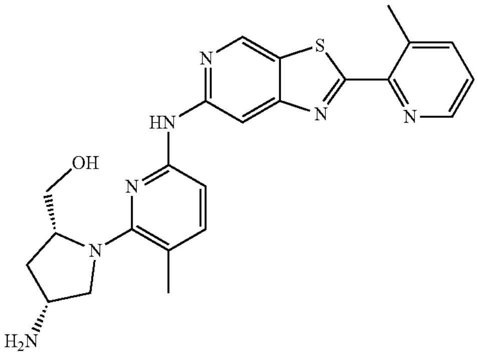 [SMILES: Cc1cccnc1-c1nc2cc(Nc3ccc(C)c(N4C[C@H](N)C[C@@H]4CO)n3)ncc2s1] |

TABLE 1-continued
| Ex. No. | Structure |
| --- | --- |
| 68 | 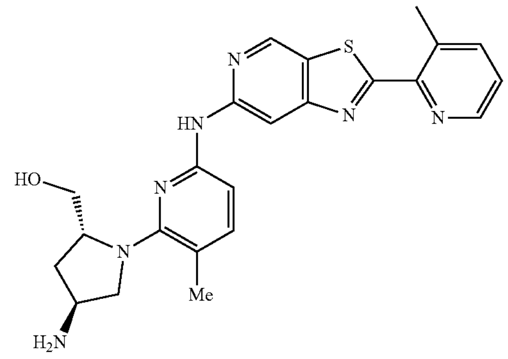 [SMILES: Cc1cccnc1-c1nc2cc(Nc3ccc(C)c(N4C[C@@H](N)C[C@@H]4CO)n3)ncc2s1] |
| 69 | 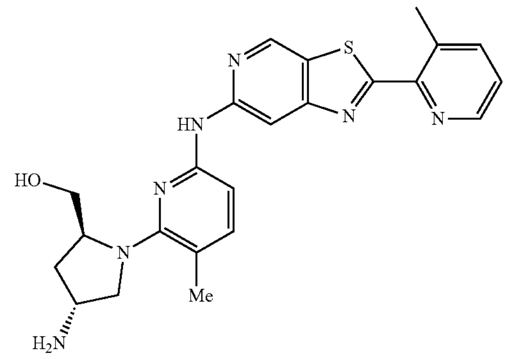 [SMILES: Cc1cccnc1-c1nc2cc(Nc3ccc(C)c(N4C[C@H](N)C[C@H]4CO)n3)ncc2s1] |
| 70 | 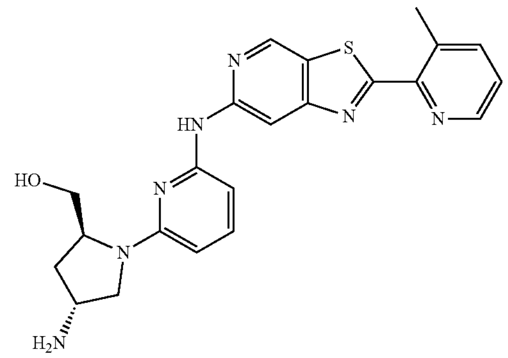 [SMILES: Cc1cccnc1-c1nc2cc(Nc3cccc(N4C[C@H](N)C[C@H]4CO)n3)ncc2s1] |
| 71 | 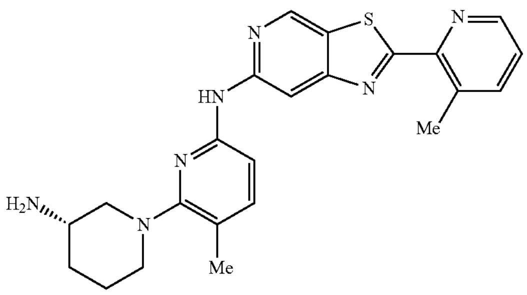 [SMILES: Cc1cccnc1-c1nc2cc(Nc3ccc(C)c(N4CCC[C@H](N)C4)n3)ncc2s1] |

TABLE 1-continued
| Ex. No. | Structure |
|---|---|
| 72 | 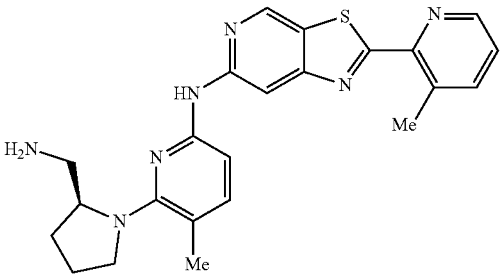 [SMILES: Cc1cccnc1-c1nc2cc(Nc3ccc(C)c(N4CCC[C@H]4CN)n3)ncc2s1] |
| 73 | 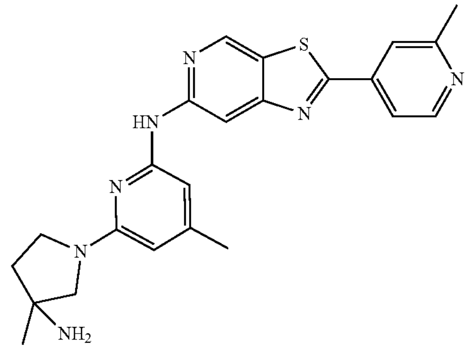 [SMILES: Cc1cc(Nc2cc3nc(-c4ccnc(C)c4)sc3cn2)nc(N2CCC(C)(N)C2)c1] |
| 74 | 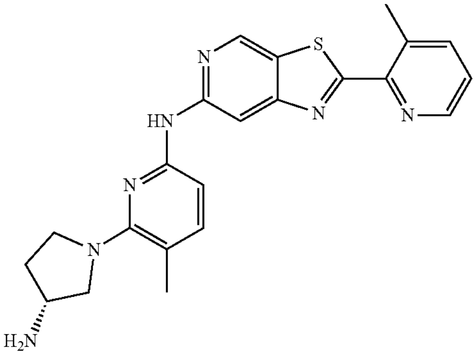 [SMILES: Cc1cccnc1-c1nc2cc(Nc3ccc(C)c(N4CC[C@@H](N)C4)n3)ncc2s1] |
| 75 | 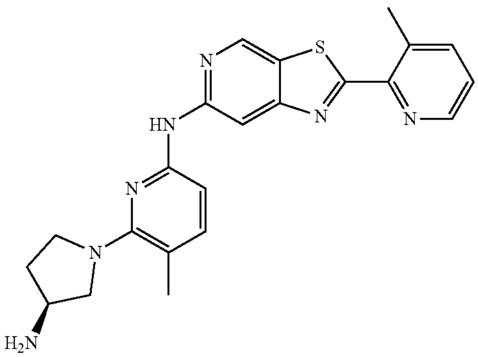 [SMILES: Cc1cccnc1-c1nc2cc(Nc3ccc(C)c(N4CC[C@H](N)C4)n3)ncc2s1] |

TABLE 1-continued
| Ex. No. | Structure |
| --- | --- |
| 76 | 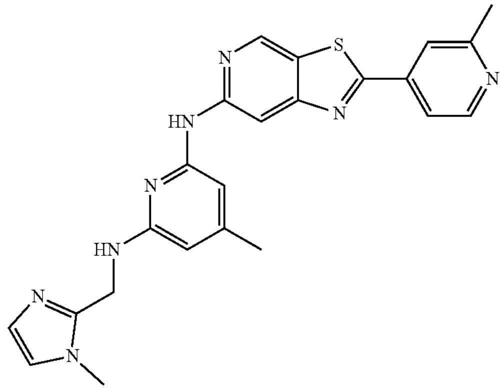 [SMILES: Cc1cc(NCc2nccn2C)nc(Nc2cc3nc(-c4ccnc(C)c4)sc3cn2)c1] |
| 77 | 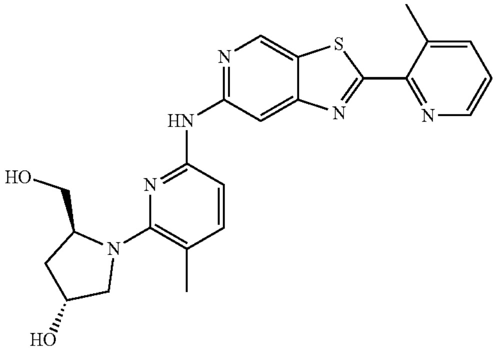 [SMILES: Cc1cccnc1-c1nc2cc(Nc3ccc(C)c(N4C[C@H](O)C[C@H]4CO)n3)ncc2s1] |
| 78 | 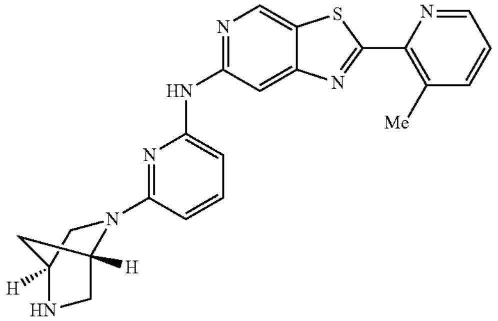 [SMILES: Cc1cccnc1-c1nc2cc(Nc3cccc(N4C[C@@H]5C[C@H]4CN5)n3)ncc2s1] |
| 79 | 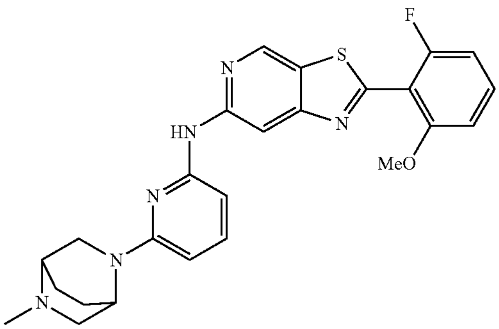 [SMILES: COc1cccc(F)c1-c1nc2cc(Nc3cccc(N4CC5CCC4CN5C)n3)ncc2s1] |

TABLE 1-continued
| Ex. No. | Structure |
|---|---|
| 80 | 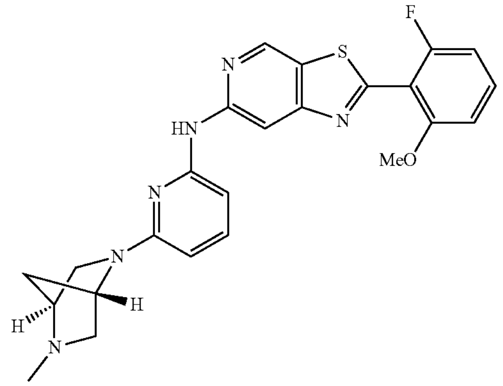 [SMILES: COc1cccc(F)c1-c1nc2cc(Nc3cccc(N4C[C@@H]5C[C@H]4CN5C)n3)ncc2s1] |
| 81 | 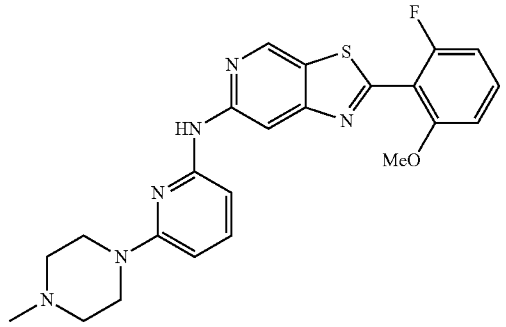 [SMILES: COc1cccc(F)c1-c1nc2cc(Nc3cccc(N4CCN(C)CC4)n3)ncc2s1] |
| 82 | 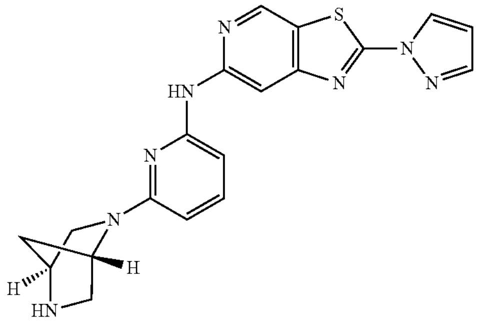 [SMILES: c1cc(Nc2cc3nc(-n4cccn4)sc3cn2)nc(N2C[C@@H]3C[C@H]2CN3)c1] |
| 83 | 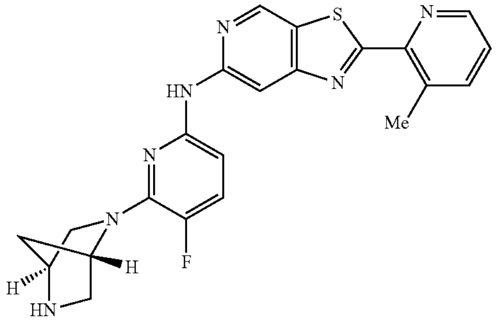 [SMILES: Cc1cccnc1-c1nc2cc(Nc3ccc(F)c(N4C[C@@H]5C[C@H]4CN5)n3)ncc2s1] |

TABLE 1-continued
| Ex. No. | Structure |
|---|---|
| 84 | 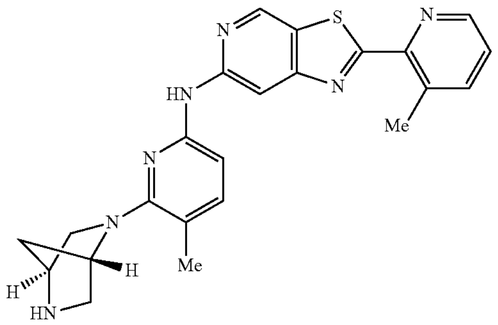 |
| 85 | 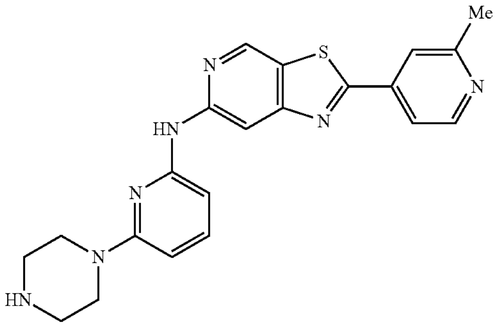 [SMILES: Cc1cc(-c2nc3cc(Nc4cccc(N5CCNCC5)n4)ncc3s2)ccn1] |
| 86 | 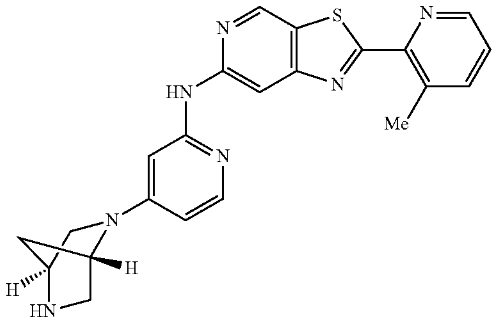 [SMILES: Cc1cccnc1-c1nc2cc(Nc3cc(N4C[C@@H]5C[C@H]4CN5)ccn3)ncc2s1] |
| 87 | 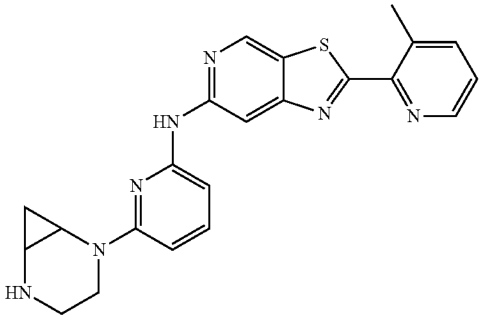 |

TABLE 1-continued
| Ex. No. | Structure |
| --- | --- |
| 88 | 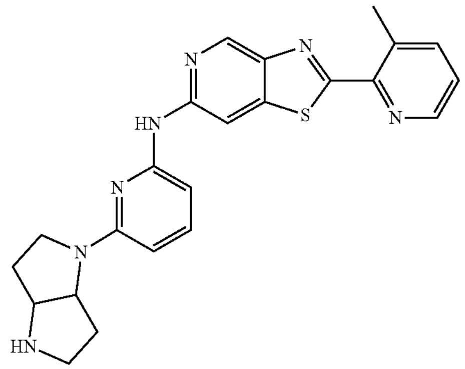 [SMILES: Cc1cccnc1-c1nc2cnc(Nc3cccc(N4CCC5NCCC54)n3)cc2s1] |
| 89 | 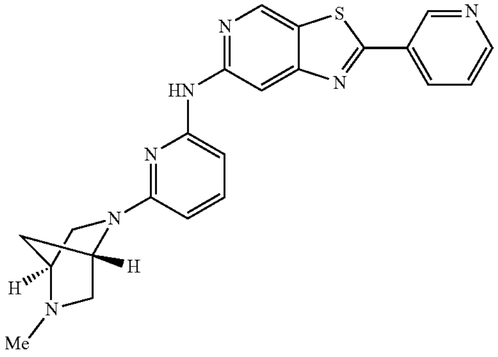 [SMILES: CN1C[C@@H]2C[C@H]1CN2c1cccc(Nc2cc3nc(-c4cccnc4)sc3cn2)n1] |
| 90 | 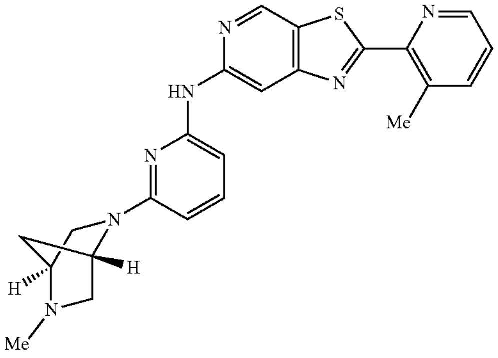 [SMILES: Cc1cccnc1-c1nc2cc(Nc3cccc(N4C[C@@H]5C[C@H]4CN5C)n3)ncc2s1] |
| 91 | 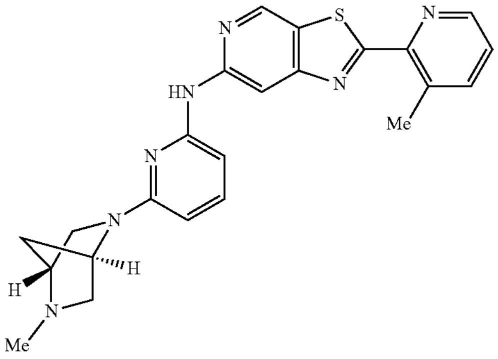 [SMILES: Cc1cccnc1-c1nc2cc(Nc3cccc(N4C[C@H]5C[C@@H]4CN5C)n3)ncc2s1] |

TABLE 1-continued
| Ex. No. | Structure |
| --- | --- |
| 92 | 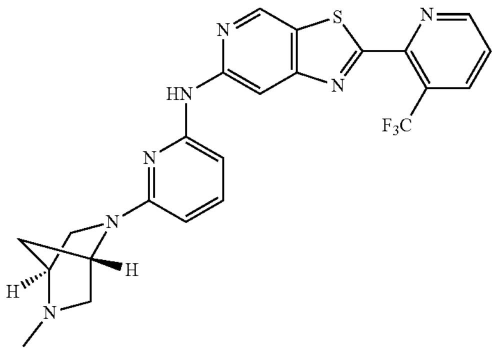 [SMILES: CN1C[C@@H]2C[C@H]1CN2c1cccc(Nc2cc3nc(-c4ncccc4C(F)(F)F)sc3cn2)n1] |
| 93 | 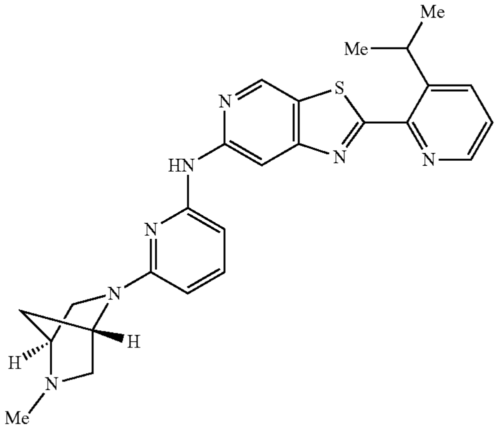 [SMILES: CC(C)c1cccnc1-c1nc2cc(Nc3cccc(N4C[C@@H]5C[C@H]4CN5C)n3)ncc2s1] |
| 94 | 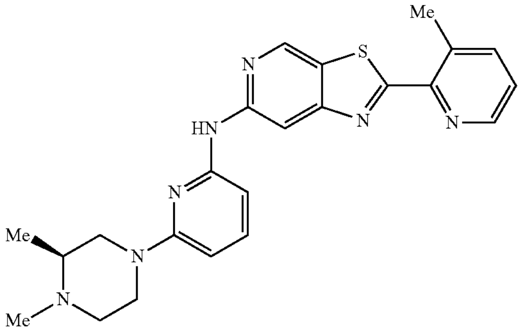 [SMILES: Cc1cccnc1-c1nc2cc(Nc3cccc(N4CCN(C)[C@@H](C)C4)n3)ncc2s1] |
| 95 | 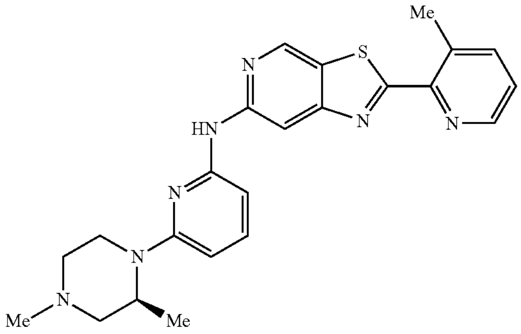 [SMILES: Cc1cccnc1-c1nc2cc(Nc3cccc(N4CCN(C)C[C@@H]4C)n3)ncc2s1] |

TABLE 1-continued
| Ex. No. | Structure |
| --- | --- |
| 96 | 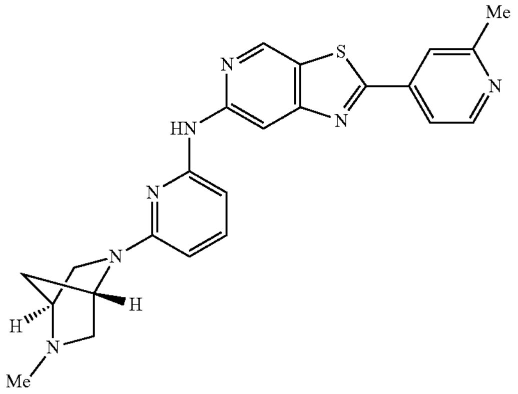 [SMILES: Cc1cc(-c2nc3cc(Nc4cccc(N5C[C@@H]6C[C@H]5CN6C)n4)ncc3s2)ccn1] |
| 97 | 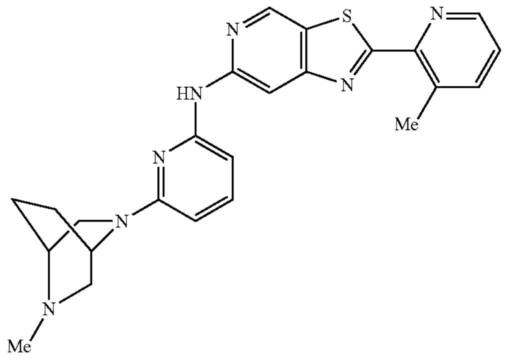 [SMILES: Cc1cccnc1-c1nc2cc(Nc3cccc(N4CC5CCC4CN5C)n3)ncc2s1] |
| 98 | 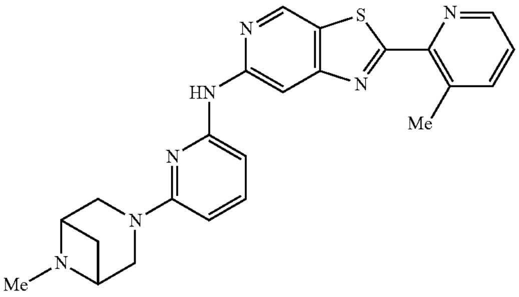 [SMILES: Cc1cccnc1-c1nc2cc(Nc3cccc(N4CC5CC(C4)N5C)n3)ncc2s1] |
| 99 | 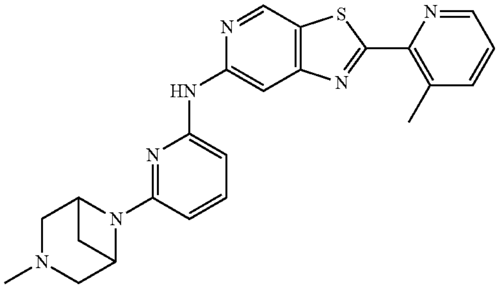 [SMILES: Cc1cccnc1-c1nc2cc(Nc3cccc(N4C5CC4CN(C)C5)n3)ncc2s1] |

TABLE 1-continued
| Ex. No. | Structure |
|---|---|
| 100 | 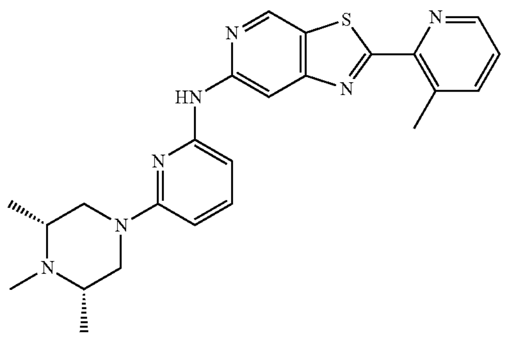 [SMILES: Cc1cccnc1-c1nc2cc(Nc3cccc(N4C[C@@H](C)N(C)[C@@H](C)C4)n3)ncc2s1] |
| 101 | 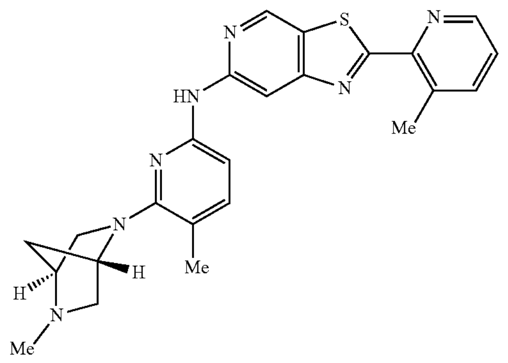 [SMILES: Cc1cccnc1-c1nc2cc(Nc3ccc(C)c(N4C[C@@H]5C[C@H]4CN5C)n3)ncc2s1] |
| 102 | 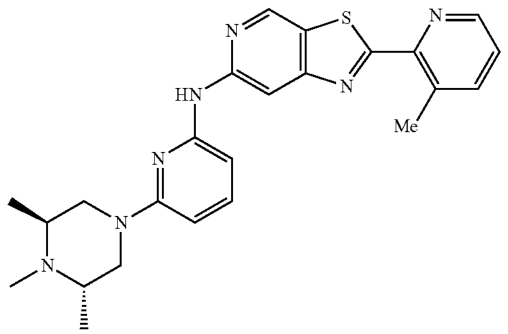 [SMILES: Cc1cccnc1-c1nc2cc(Nc3cccc(N4C[C@H](C)N(C)[C@@H](C)C4)n3)ncc2s1] |
| 103 | 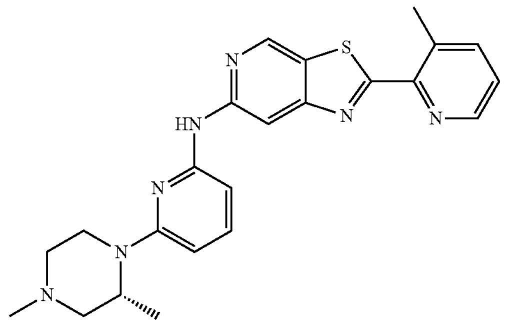 [SMILES: Cc1cccnc1-c1nc2cc(Nc3cccc(N4CCN(C)C[C@H]4C)n3)ncc2s1] |

TABLE 1-continued
| Ex. No. | Structure |
| --- | --- |
| 104 | 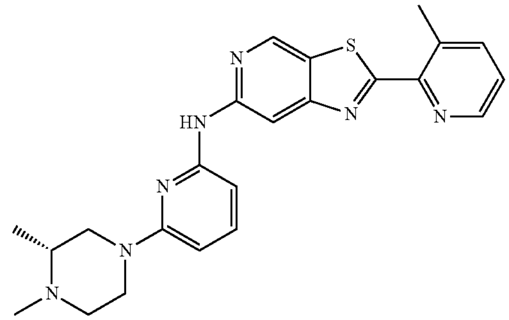 [SMILES: Cc1cccnc1-c1nc2cc(Nc3cccc(N4CCN(C)[C@H](C)C4)n3)ncc2s1] |
| 105 | 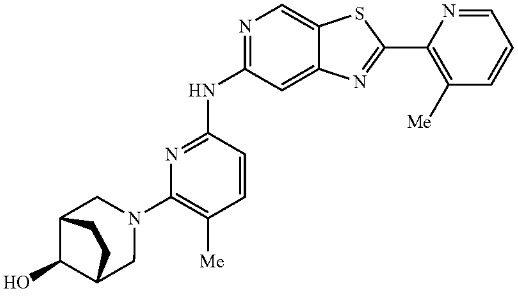 |
| 106 | 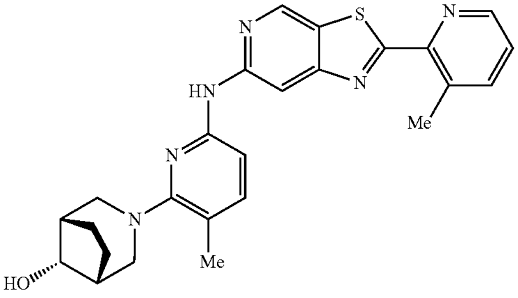 |
| 107 | 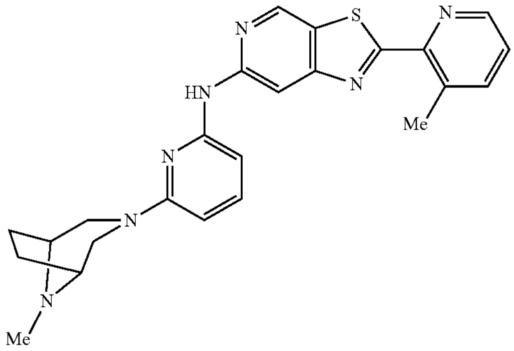 [SMILES: Cc1cccnc1-c1nc2cc(Nc3cccc(N4CC5CCC(C4)N5C)n3)ncc2s1] |

TABLE 1-continued
| Ex. No. | Structure |
| --- | --- |
| 108 | 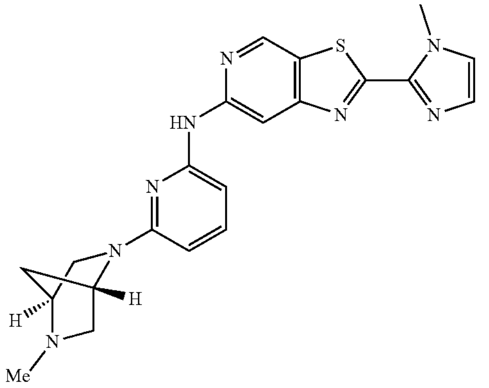 [SMILES: CN1C[C@@H]2C[C@H]1CN2c1cccc(Nc2cc3nc(-c4nccn4C)sc3cn2)n1] |
| 109 | 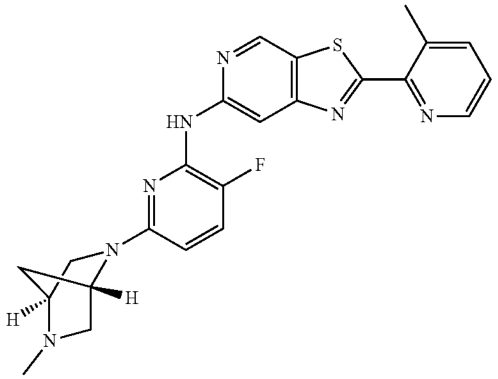 [SMILES: Cc1cccnc1-c1nc2cc(Nc3nc(N4C[C@@H]5C[C@H]4CN5C)ccc3F)ncc2s1] |
| 110 | 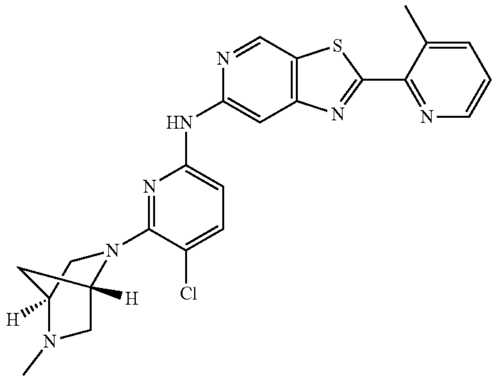 [SMILES: Cc1cccnc1-c1nc2cc(Nc3ccc(Cl)c(N4C[C@@H]5C[C@H]4CN5C)n3)ncc2s1] |
| 111 | 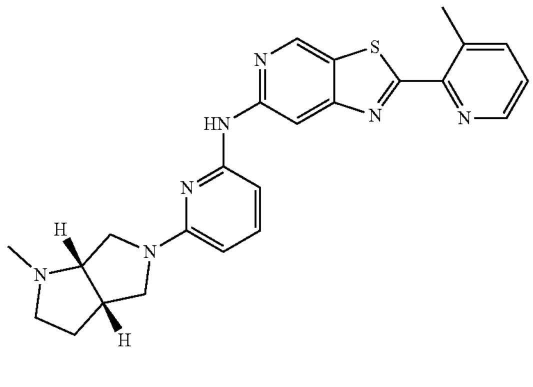 [SMILES: Cc1cccnc1-c1nc2cc(Nc3cccc(N4C[C@@H]5CCN(C)[C@@H]5C4)n3)ncc2s1] |

TABLE 1-continued
| Ex. No. | Structure |
| --- | --- |
| 112 | 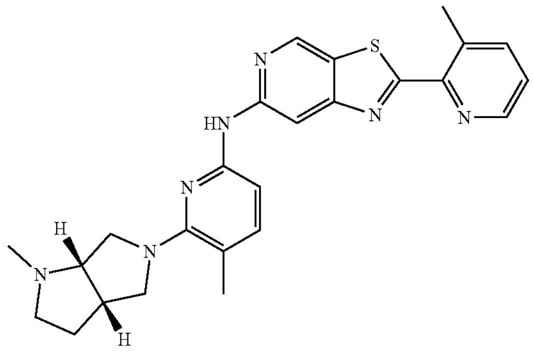 [SMILES: Cc1cccnc1-c1nc2cc(Nc3ccc(C)c(N4C[C@@H]5CCN(C)[C@@H]5C4)n3)ncc2s1] |
| 113 | 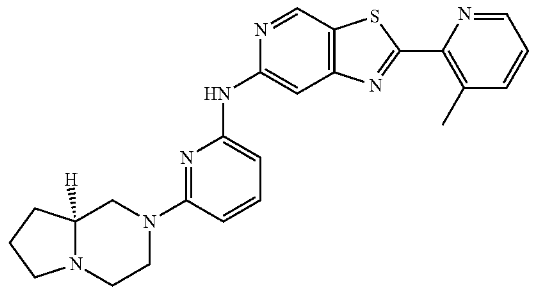 [SMILES: Cc1cccnc1-c1nc2cc(Nc3cccc(N4CCN5CCC[C@H]5C4)n3)ncc2s1] |
| 114 | 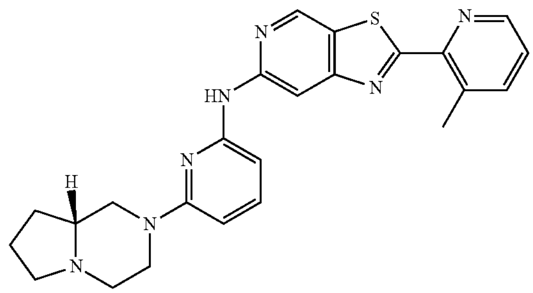 [SMILES: Cc1cccnc1-c1nc2cc(Nc3cccc(N4CCN5CCC[C@@H]5C4)n3)ncc2s1] |
| 115 | 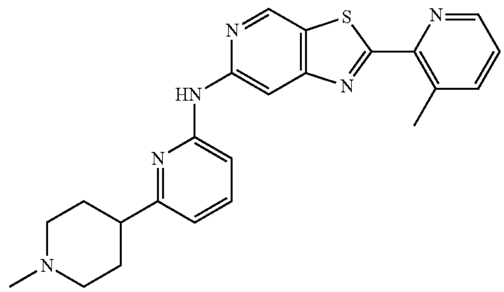 [SMILES: Cc1cccnc1-c1nc2cc(Nc3cccc(C4CCN(C)CC4)n3)ncc2s1] |

TABLE 1-continued
| Ex. No. | Structure |
| --- | --- |
| 116 | 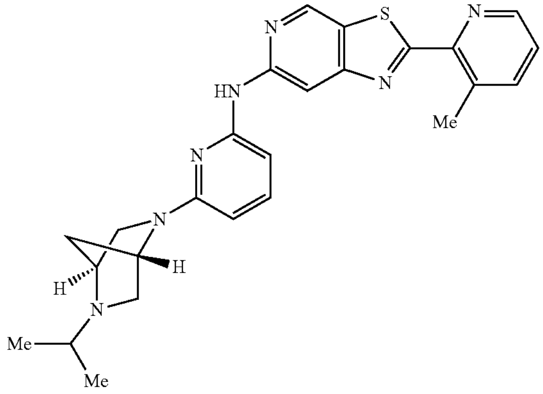 [SMILES: Cc1cccnc1-c1nc2cc(Nc3cccc(N4C[C@@H]5C[C@H]4CN5C(C)C)n3)ncc2s1] |
| 117 | 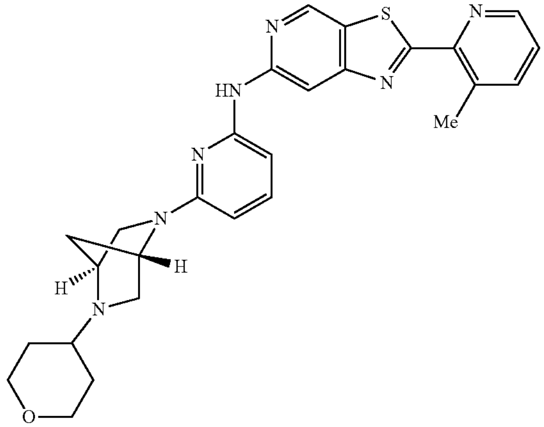 [SMILES: Cc1cccnc1-c1nc2cc(Nc3cccc(N4C[C@@H]5C[C@H]4CN5C4CCOCC4)n3)ncc2s1] |
| 118 | 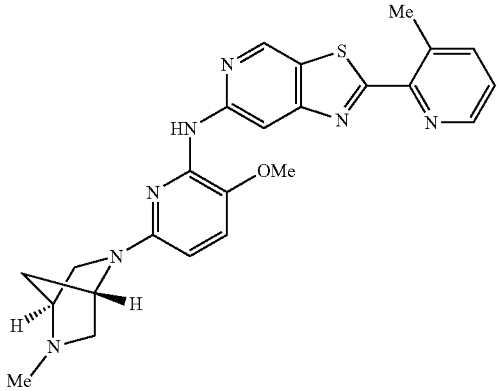 [SMILES: COc1ccc(N2C[C@@H]3C[C@H]2CN3C)nc1Nc1cc2nc(-c3ncccc3C)sc2cn1] |
| 119 | 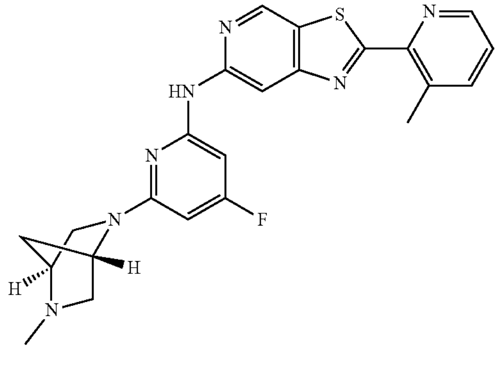 [SMILES: Cc1cccnc1-c1nc2cc(Nc3cc(F)cc(N4C[C@@H]5C[C@H]4CN5C)n3)ncc2s1] |

TABLE 1-continued
| Ex. No. | Structure |
| --- | --- |
| 120 | 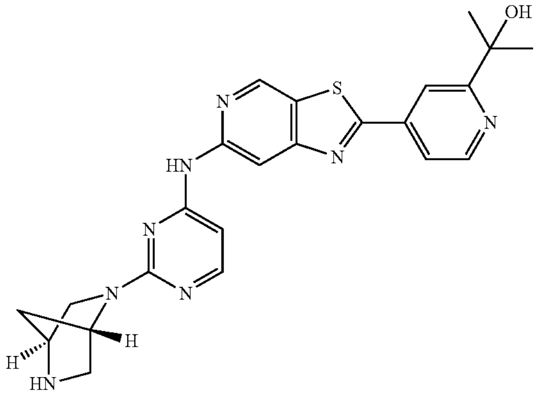 [SMILES: CC(C)(O)c1cc(-c2nc3cc(Nc4ccnc(N5C[C@@H]6C[C@H]5CN6)n4)ncc3s2)ccn1] |
| 121 | 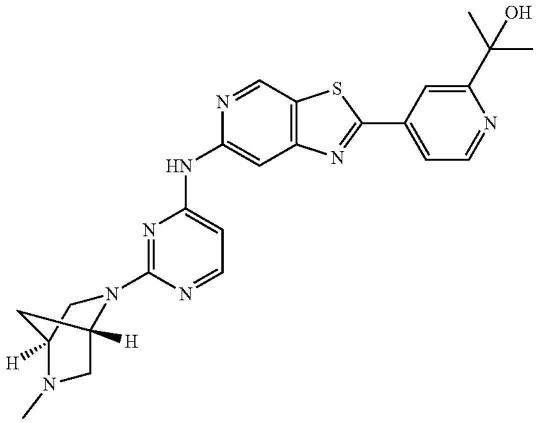 [SMILES: CN1C[C@@H]2C[C@H]1CN2c1nccc(Nc2cc3nc(-c4ccnc(C(C)(C)O)c4)sc3cn2)n1] |
| 122 | 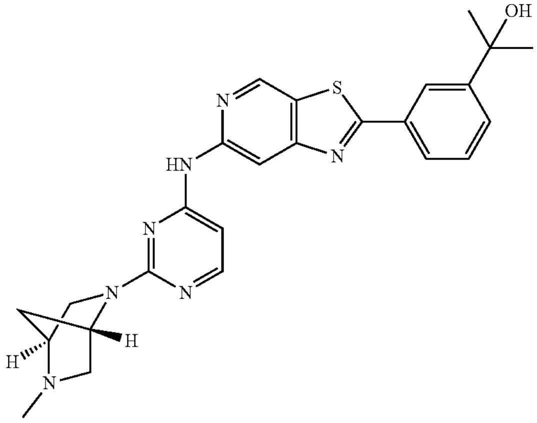 [SMILES: CN1C[C@@H]2C[C@H]1CN2c1nccc(Nc2cc3nc(-c4cccc(C(C)(C)O)c4)sc3cn2)n1] |

TABLE 1-continued
| Ex. No. | Structure |
|---|---|
| 123 | 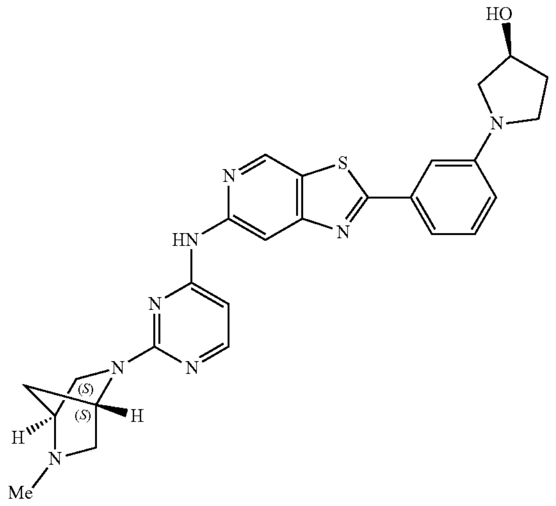 |
| 124 | 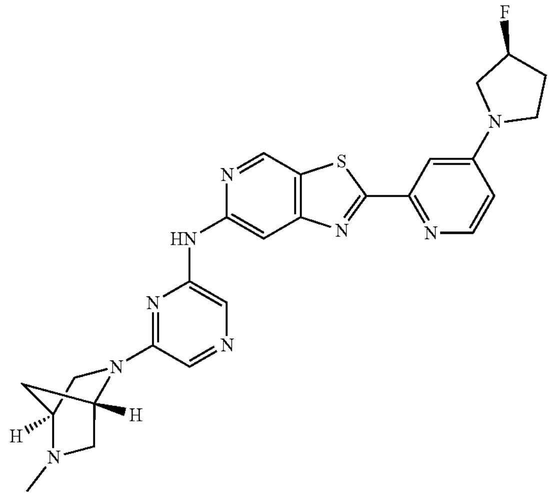 [SMILES: CN1C[C@@H]2C[C@H]1CN2c1cncc(Nc2cc3nc(-c4cc(N5CC[C@H](F)C5)ccn4)sc3cn2)n1] |
| 125 | 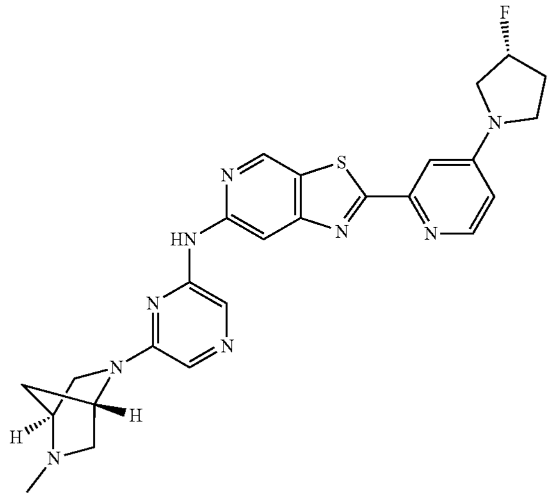 [SMILES: CN1C[C@@H]2C[C@H]1CN2c1cncc(Nc2cc3nc(-c4cc(N5CC[C@@H](F)C5)ccn4)sc3cn2)n1] |

TABLE 1-continued
| Ex. No. | Structure |
| --- | --- |
| 126 | 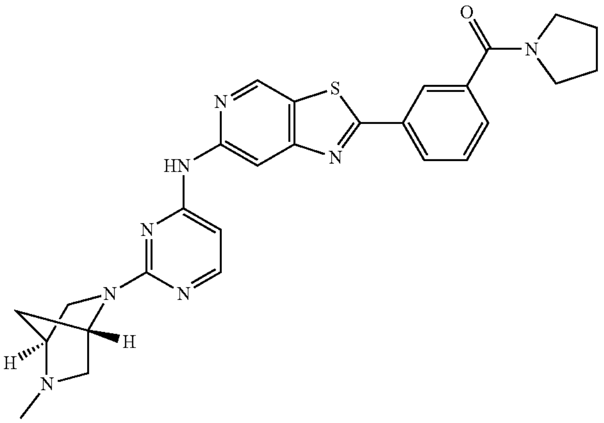 [SMILES: CN1C[C@@H]2C[C@H]1CN2c1nccc(Nc2cc3nc(-c4cccc(C(=O)N5CCCC5)c4)sc3cn2)n1] |
| 127 | 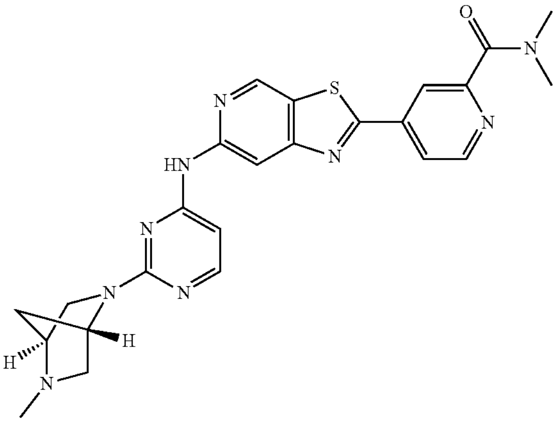 |
| 128 | 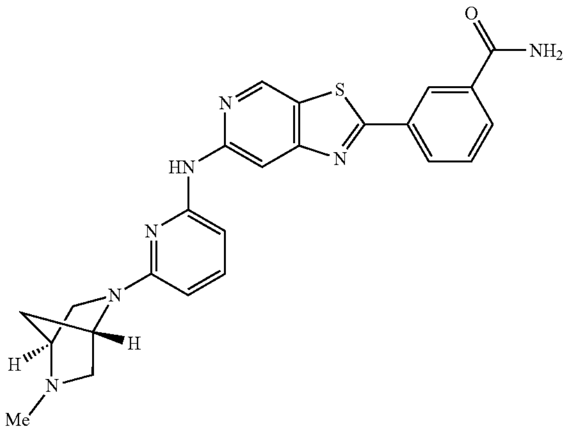 [SMILES: CN1C[C@@H]2C[C@H]1CN2c1cccc(Nc2cc3nc(-c4cccc(C(N)=O)c4)sc3cn2)n1] |

TABLE 1-continued
| Ex. No. | Structure |
|---|---|
| 129 | 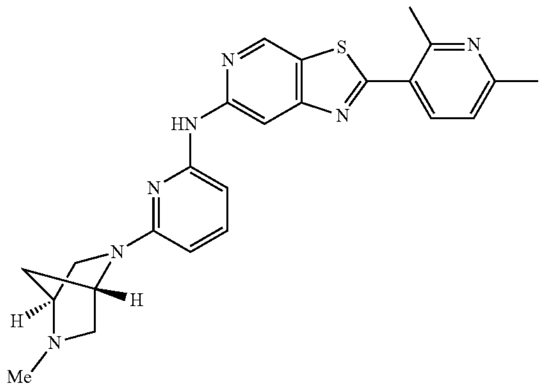 [SMILES: Cc1ccc(-c2nc3cc(Nc4cccc(N5C[C@@H]6C[C@H]5CN6C)n4)ncc3s2)c(C)n1] |
| 130 | 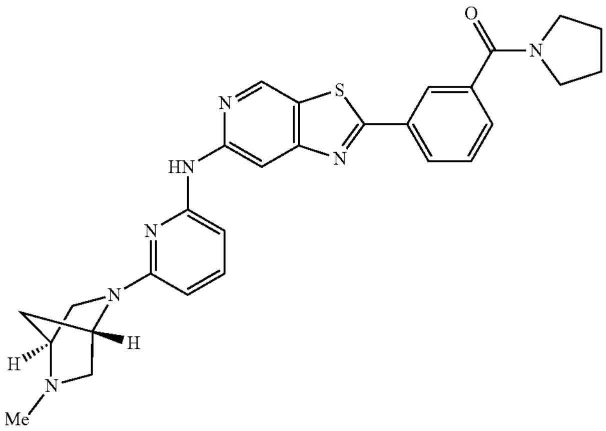 [SMILES: CN1C[C@@H]2C[C@H]1CN2c1cccc(Nc2cc3nc(-c4cccc(C(=O)N5CCCC5)c4)sc3cn2)n1] |
| 131 | 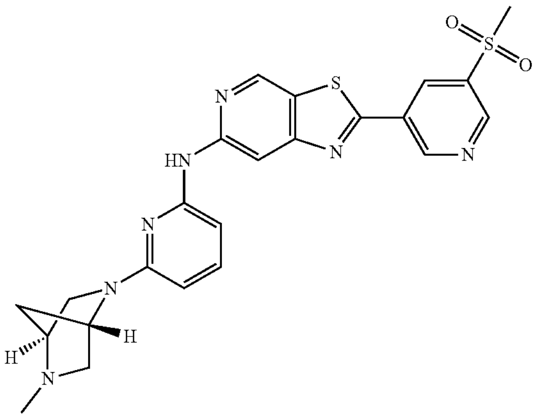 [SMILES: CN1C[C@@H]2C[C@H]1CN2c1cccc(Nc2cc3nc(-c4cncc(S(C)(=O)=O)c4)sc3cn2)n1] |

TABLE 1-continued
| Ex. No. | Structure |
| --- | --- |
| 132 | 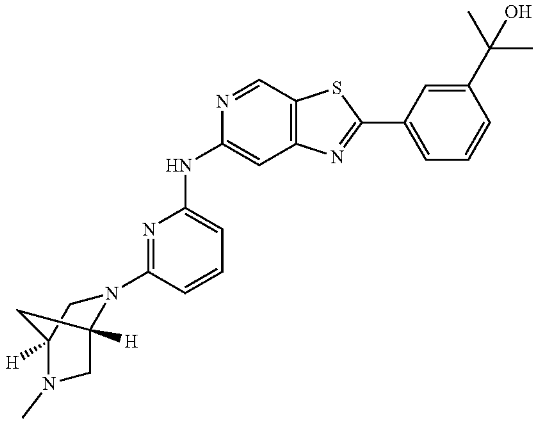 [SMILES: CN1C[C@@H]2C[C@H]1CN2c1cccc(Nc2cc3nc(-c4cccc(C(C)(C)O)c4)sc3cn2)n1] |
| 133 | 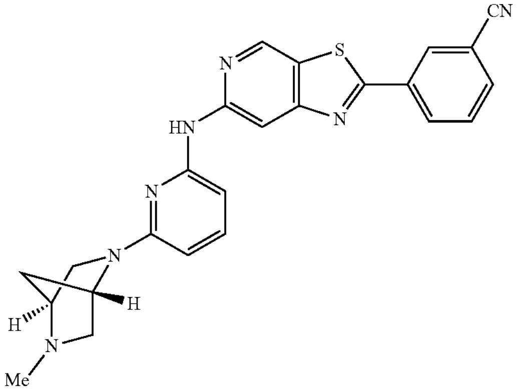 [SMILES: CN1C[C@@H]2C[C@H]1CN2c1cccc(Nc2cc3nc(-c4cccc(C#N)c4)sc3cn2)n1] |
| 134 | 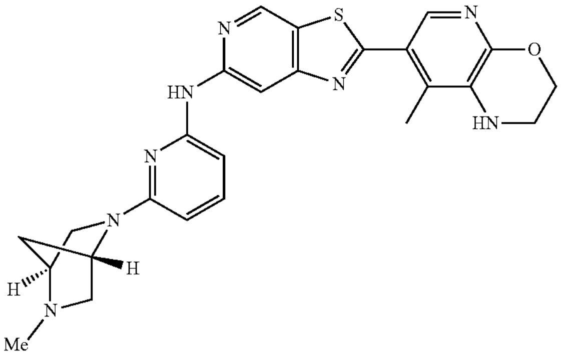 [SMILES: Cc1c(-c2nc3cc(Nc4cccc(N5C[C@@H]6C[C@H]5CN6C)n4)ncc3s2)cnc2c1NCCO2] |
| 135 | 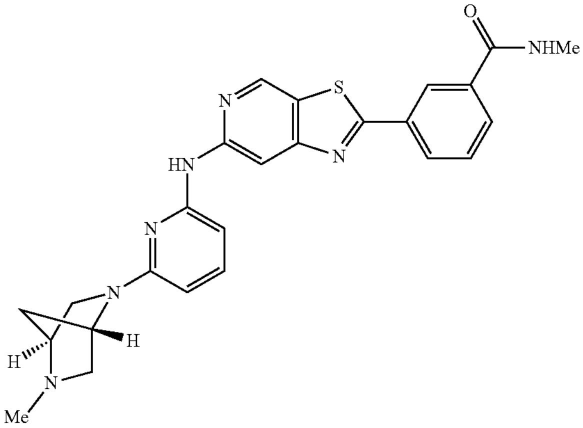 [SMILES: CNC(=O)c1cccc(-c2nc3cc(Nc4cccc(N5C[C@@H]6C[C@H]5CN6C)n4)ncc3s2)c1] |

TABLE 1-continued
| Ex. No. | Structure |
| --- | --- |
| 136 | 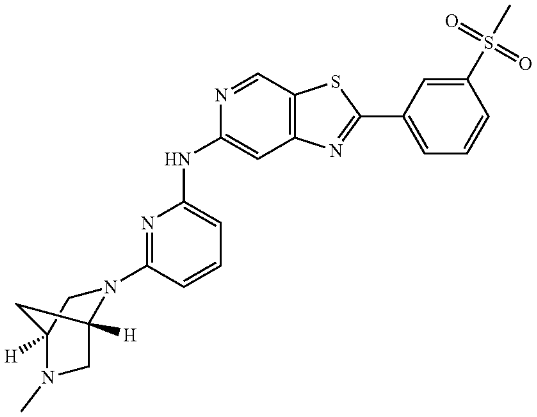 [SMILES: CN1C[C@@H]2C[C@H]1CN2c1cccc(Nc2cc3nc(-c4cccc(S(C)(=O)=O)c4)sc3cn2)n1] |
| 137 | 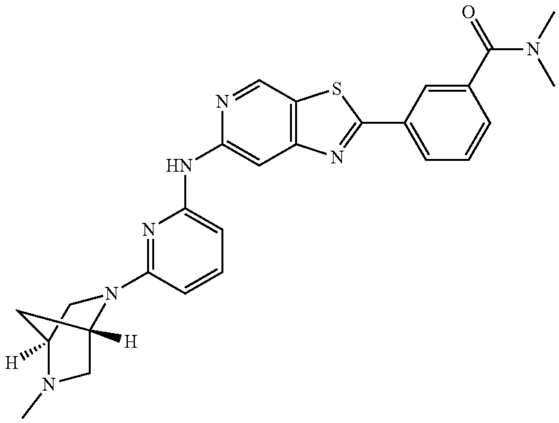 [SMILES: CN(C)C(=O)c1cccc(-c2nc3cc(Nc4cccc(N5C[C@@H]6C[C@H]5CN6C)n4)ncc3s2)c1] |
| 138 | 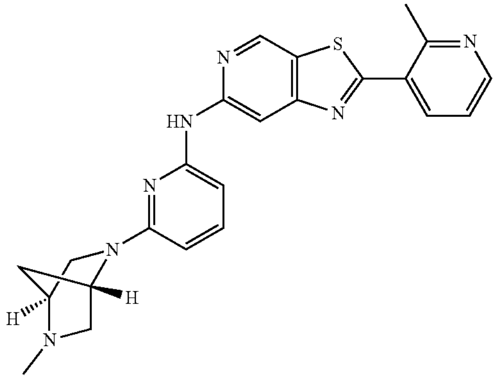 [SMILES: Cc1ncccc1-c1nc2cc(Nc3cccc(N4C[C@@H]5C[C@H]4CN5C)n3)ncc2s1] |
| 139 | 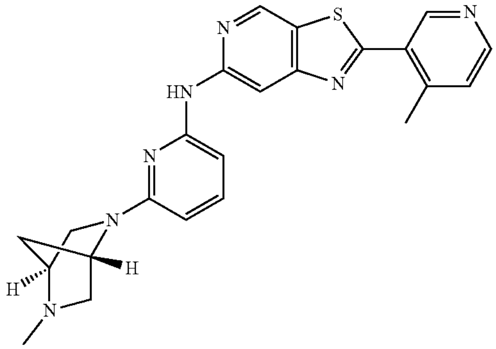 [SMILES: Cc1ccncc1-c1nc2cc(Nc3cccc(N4C[C@@H]5C[C@H]4CN5C)n3)ncc2s1] |

TABLE 1-continued
| Ex. No. | Structure |
|---|---|
| 140 | 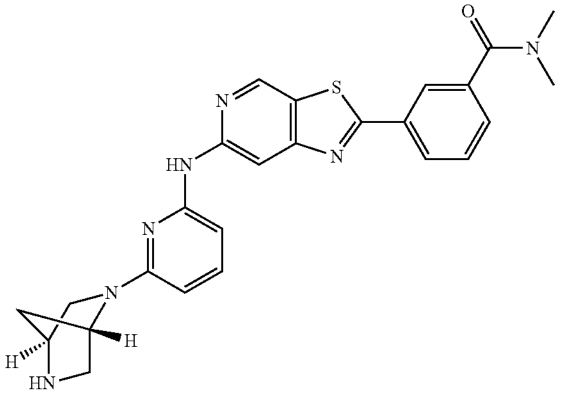 [SMILES: CN(C)C(=O)c1cccc(-c2nc3cc(Nc4cccc(N5C[C@@H]6C[C@H]5CN6)n4)ncc3s2)c1] |
| 141 | 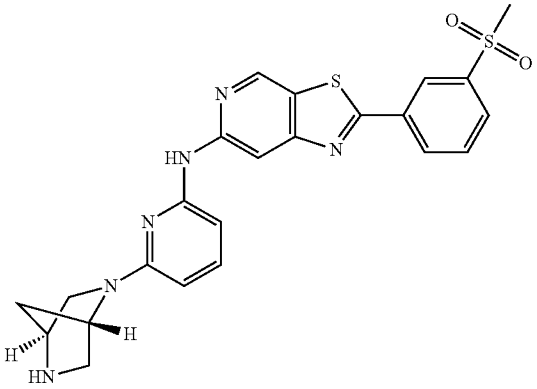 [SMILES: CS(=O)(=O)c1cccc(-c2nc3cc(Nc4cccc(N5C[C@@H]6C[C@H]5CN6)n4)ncc3s2)c1] |
| 142 | 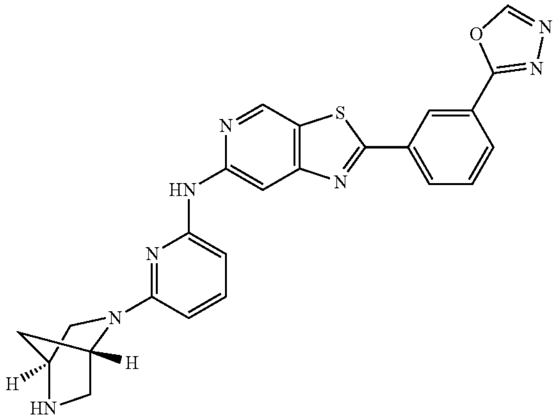 [SMILES: c1cc(-c2nnco2)cc(-c2nc3cc(Nc4cccc(N5C[C@@H]6C[C@H]5CN6)n4)ncc3s2)c1] |

TABLE 1-continued
| Ex. No. | Structure |
|---|---|
| 143 | 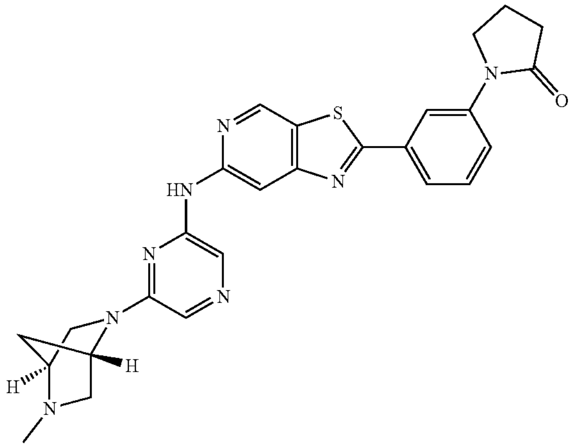 [SMILES: CN1C[C@@H]2C[C@H]1CN2c1cncc(Nc2cc3nc(-c4cccc(N5CCCC5=O)c4)sc3cn2)n1] |
| 144 | 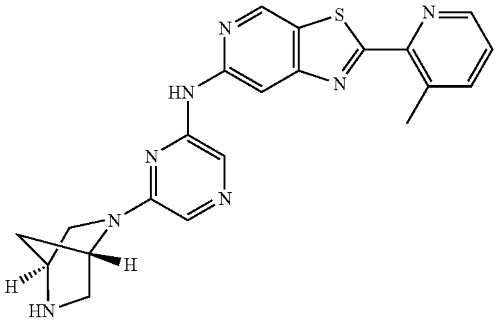 [SMILES: Cc1cccnc1-c1nc2cc(Nc3cncc(N4C[C@@H]5C[C@H]4CN5)n3)ncc2s1] |
| 145 | 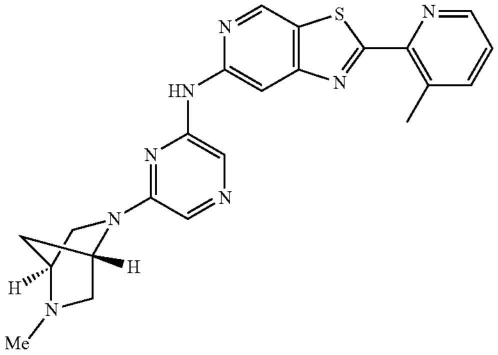 [SMILES: Cc1cccnc1-c1nc2cc(Nc3cncc(N4C[C@@H]5C[C@H]4CN5C)n3)ncc2s1] |
| 146 | 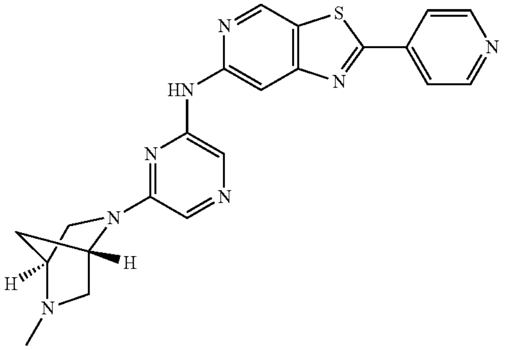 [SMILES: CN1C[C@@H]2C[C@H]1CN2c1cncc(Nc2cc3nc(-c4ccncc4)sc3cn2)n1] |

TABLE 1-continued
| Ex. No. | Structure |
| --- | --- |
| 147 | 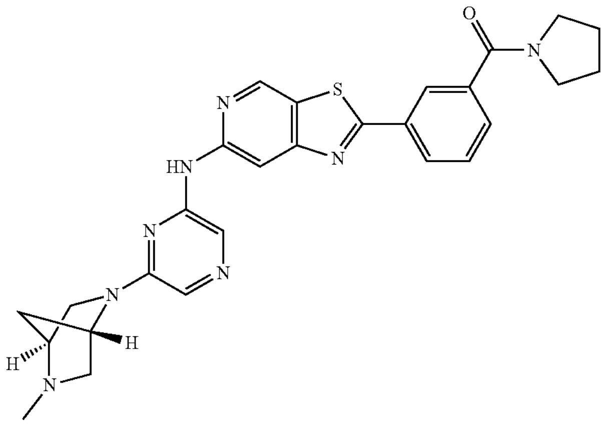 [SMILES: CN1C[C@@H]2C[C@H]1CN2c1cncc(Nc2cc3nc(-c4cccc(C(=O)N5CCCC5)c4)sc3cn2)n1] |
| 148 | 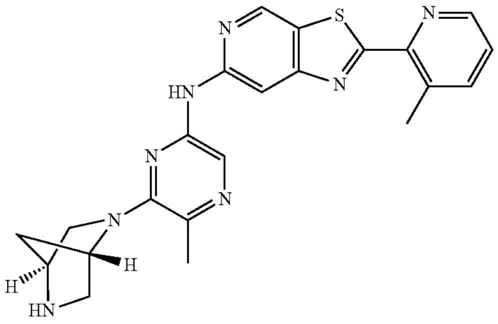 [SMILES: Cc1cccnc1-c1nc2cc(Nc3cnc(C)c(N4C[C@@H]5C[C@H]4CN5)n3)ncc2s1] |
| 149 | 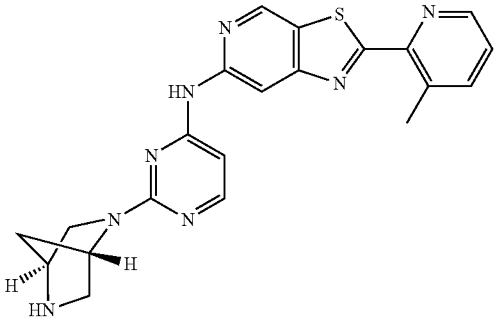 [SMILES: Cc1cccnc1-c1nc2cc(Nc3ccnc(N4C[C@@H]5C[C@H]4CN5)n3)ncc2s1] |
| 150 | 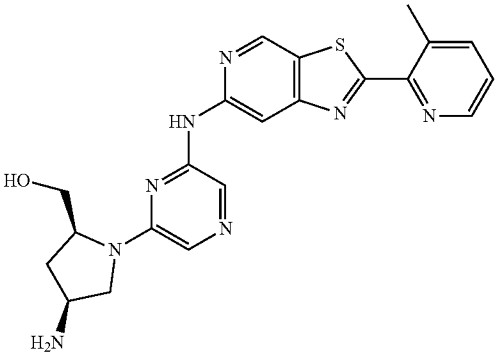 |

TABLE 1-continued
| Ex. No. | Structure |
|---|---|
| 151 | 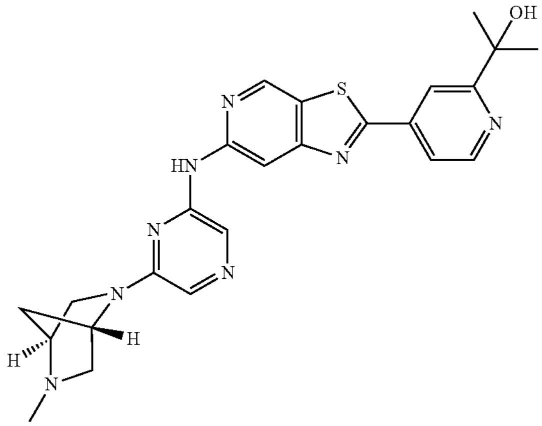 [SMILES: CN1C[C@@H]2C[C@H]1CN2c1cncc(Nc2cc3nc(-c4ccnc(C(C)(C)O)c4)sc3cn2)n1] |
| 152 | 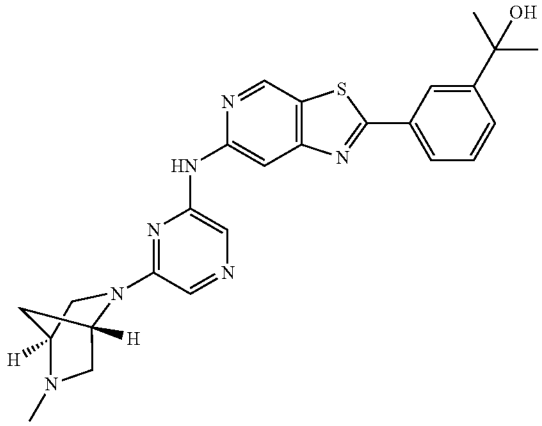 [SMILES: CN1C[C@@H]2C[C@H]1CN2c1cncc(Nc2cc3nc(-c4cccc(C(C)(C)O)c4)sc3cn2)n1] |
| 153 | 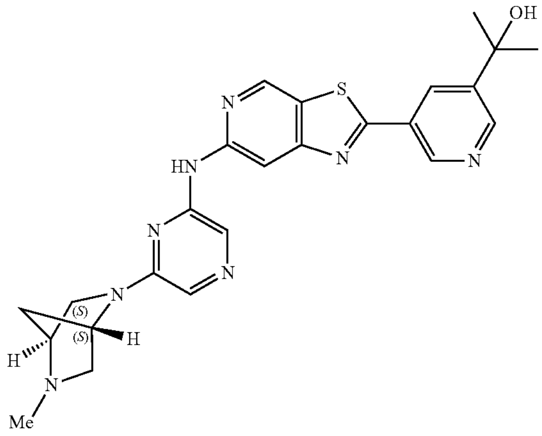 |

TABLE 1-continued
| Ex. No. | Structure |
| --- | --- |
| 154 | 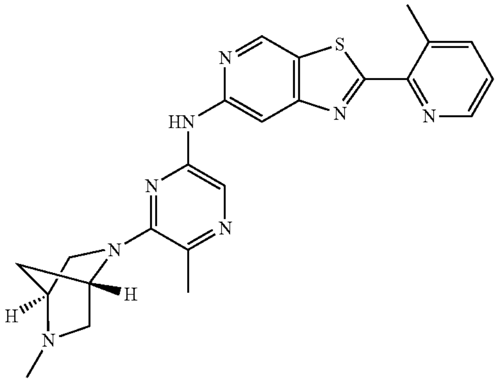 [SMILES: Cc1cccnc1-c1nc2cc(Nc3cnc(C)c(N4C[C@@H]5C[C@H]4CN5C)n3)ncc2s1] |
| 155 | 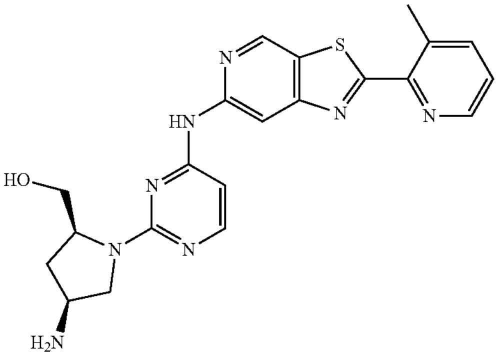 [SMILES: Cc1cccnc1-c1nc2cc(Nc3ccnc(N4C[C@@H](N)C[C@H]4CO)n3)ncc2s1] |
| 156 | 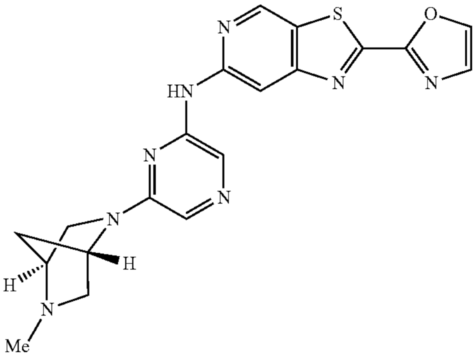 [SMILES: CN1C[C@@H]2C[C@H]1CN2c1cncc(Nc2cc3nc(-c4ncco4)sc3cn2)n1] |
| 157 | 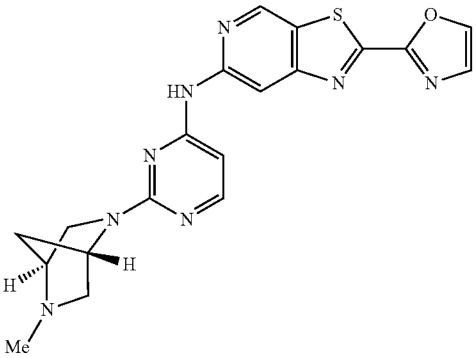 [SMILES: CN1C[C@@H]2C[C@H]1CN2c1nccc(Nc2cc3nc(-c4ncco4)sc3cn2)n1] |

TABLE 1-continued
| Ex. No. | Structure |
| --- | --- |
| 158 | 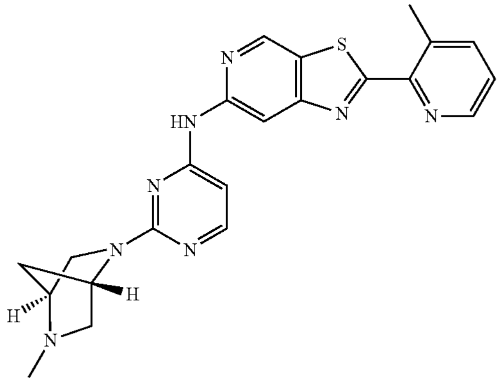 [SMILES: Cc1cccnc1-c1nc2cc(Nc3ccnc(N4C[C@@H]5C[C@H]4CN5C)n3)ncc2s1] |
| 159 | 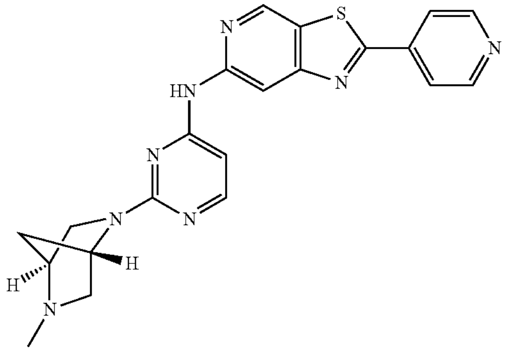 [SMILES: CN1C[C@@H]2C[C@H]1CN2c1nccc(Nc2cc3nc(-c4ccncc4)sc3cn2)n1] |
| 160 | 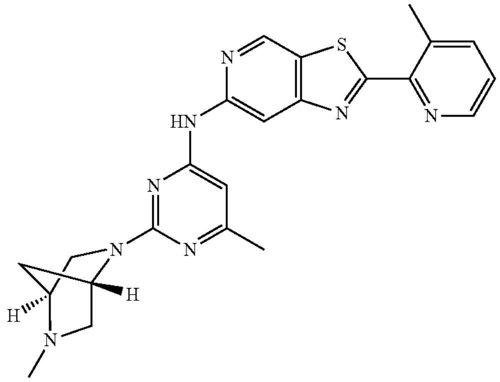 [SMILES: Cc1cc(Nc2cc3nc(-c4ncccc4C)sc3cn2)nc(N2C[C@@H]3C[C@H]2CN3C)n1] |
| 161 | 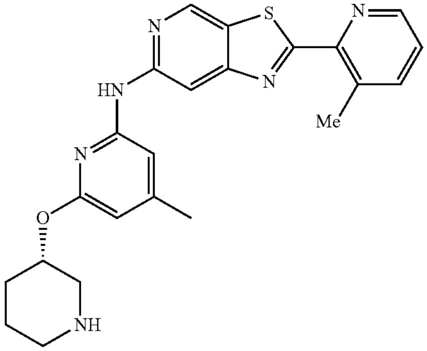 [SMILES: Cc1cc(Nc2cc3nc(-c4ncccc4C)sc3cn2)nc(O[C@H]2CCCNC2)c1] |

TABLE 1-continued
| Ex. No. | Structure |
|---|---|
| 162 | 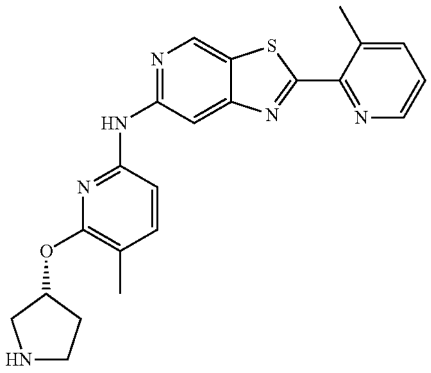 |
| 163 | 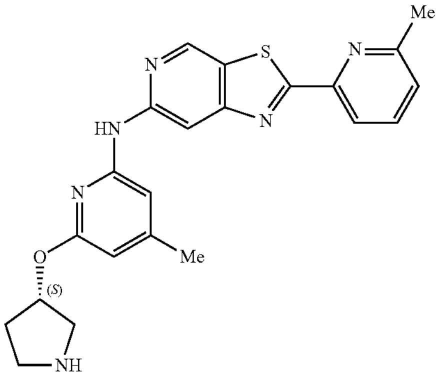 |
| 164 | 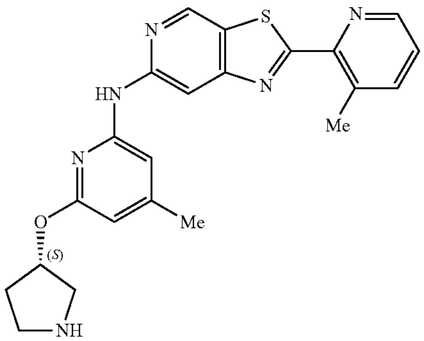 |
| 165 | 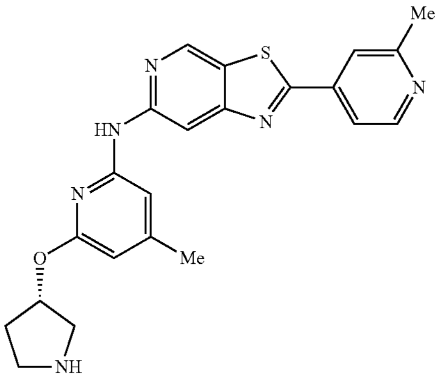 [SMILES: Cc1cc(Nc2cc3nc(-c4ccnc(C)c4)sc3cn2)nc(O[C@H]2CCNC2)c1] |

TABLE 1-continued
| Ex. No. | Structure |
| --- | --- |
| 166 | 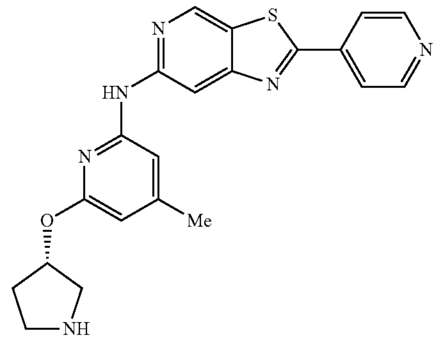 [SMILES: Cc1cc(Nc2cc3nc(-c4ccncc4)sc3cn2)nc(O[C@H]2CCNC2)c1] |
| 167 | 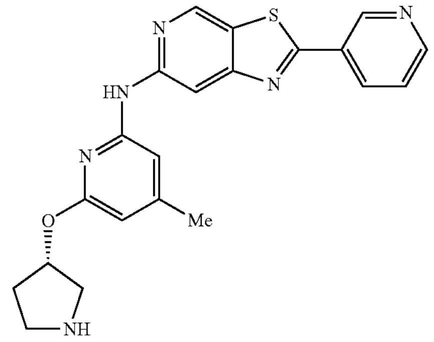 [SMILES: Cc1cc(Nc2cc3nc(-c4cccnc4)sc3cn2)nc(O[C@H]2CCNC2)c1] |
| 168 | 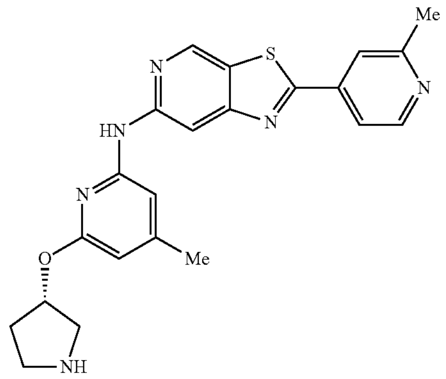 [SMILES: Cc1cc(Nc2cc3nc(-c4ccnc(C)c4)sc3cn2)nc(O[C@H]2CCNC2)c1] |
| 169 | 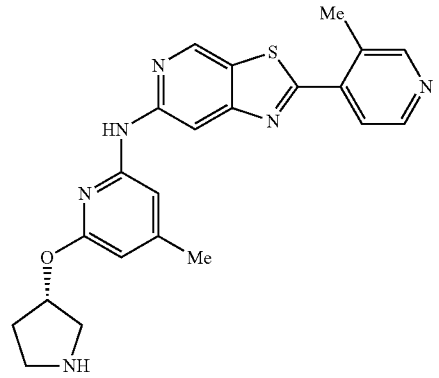 [SMILES: Cc1cc(Nc2cc3nc(-c4ccncc4C)sc3cn2)nc(O[C@H]2CCNC2)c1] |

TABLE 1-continued
| Ex. No. | Structure |
| --- | --- |
| 170 | 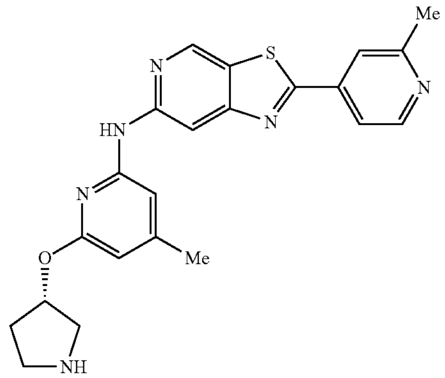 [SMILES: Cc1cc(Nc2cc3nc(-c4ccnc(C)c4)sc3cn2)nc(O[C@H]2CCNC2)c1] |
| 171 | 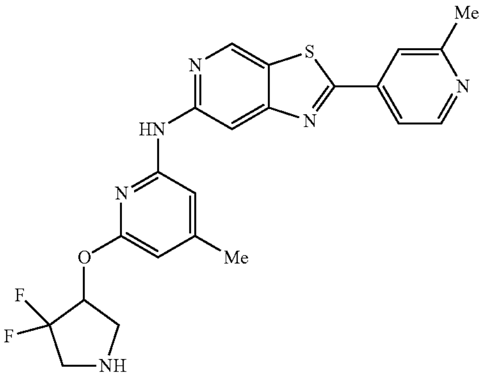 [SMILES: Cc1cc(Nc2cc3nc(-c4ccnc(C)c4)sc3cn2)nc(OC2CNCC2(F)F)c1] |
| 172 | 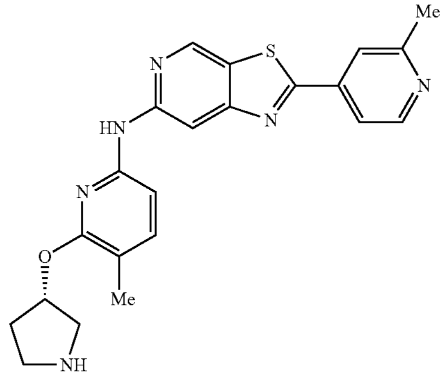 [SMILES: Cc1cc(-c2nc3cc(Nc4ccc(C)c(O[C@H]5CCNC5)n4)ncc3s2)ccn1] |
| 173 | 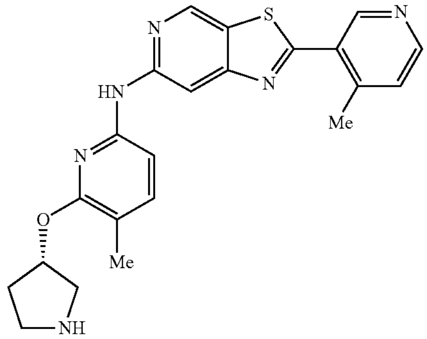 [SMILES: Cc1ccncc1-c1nc2cc(Nc3ccc(C)c(O[C@H]4CCNC4)n3)ncc2s1] |

TABLE 1-continued
| Ex. No. | Structure |
|---|---|
| 174 | 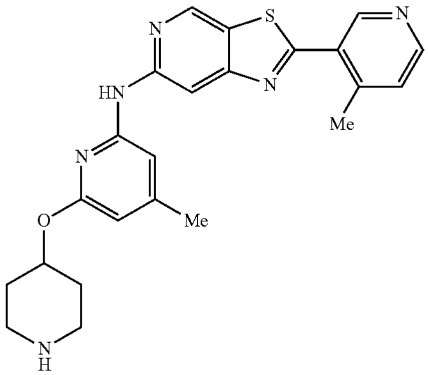 [SMILES: Cc1cc(Nc2cc3nc(-c4cnccc4C)sc3cn2)nc(OC2CCNCC2)c1] |
| 175 | 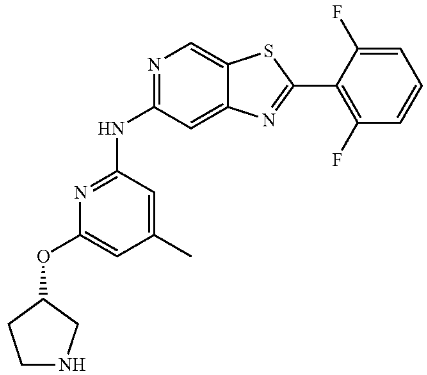 |
| 176 | 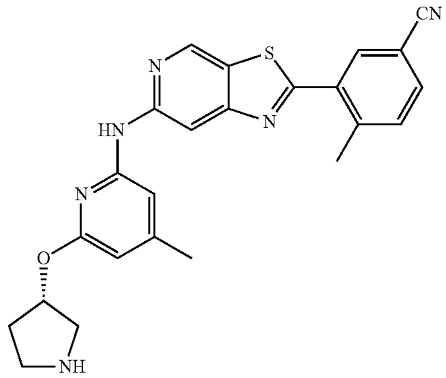 [SMILES: Cc1cc(Nc2cc3nc(-c4cc(C#N)ccc4C)sc3cn2)nc(O[C@H]2CCNC2)c1] |
| 177 | 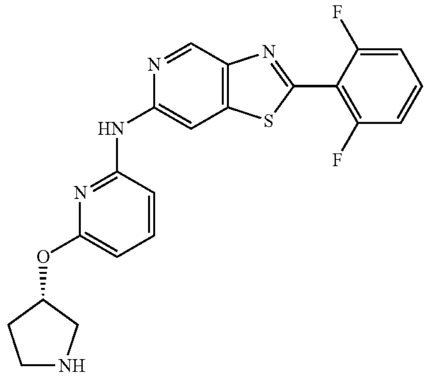 |

TABLE 1-continued
| Ex. No. | Structure |
|---|---|
| 178 | 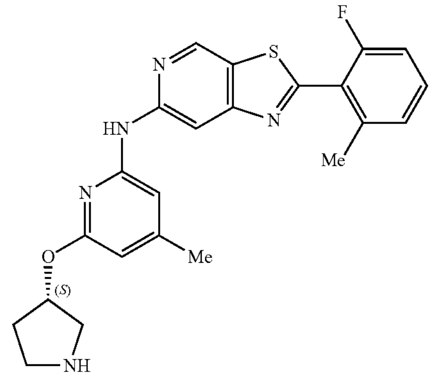 |
| 179 | 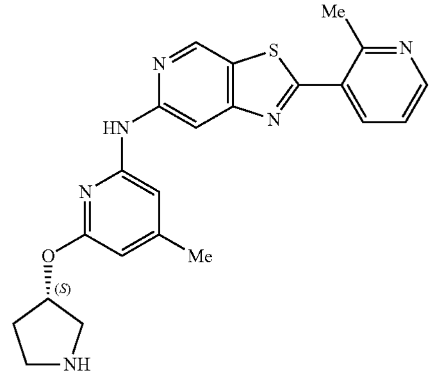 |
| 180 | 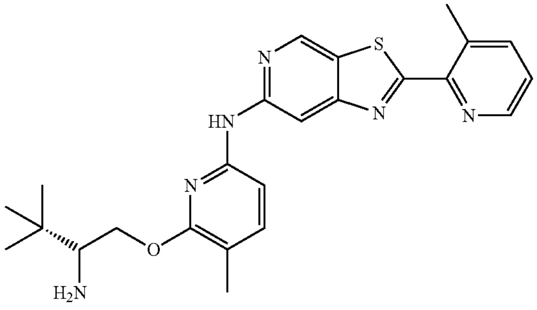 |
| 181 | 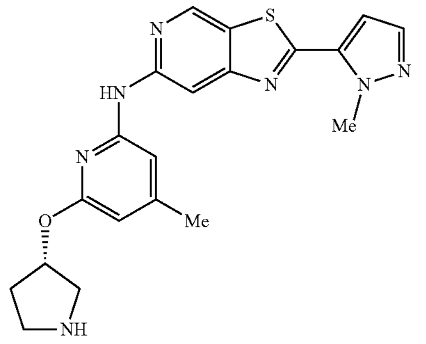 [SMILES: Cc1cc(Nc2cc3nc(-c4ccnn4C)sc3cn2)nc(O[C@H]2CCNC2)c1] |

TABLE 1-continued
| Ex. No. | Structure |
| --- | --- |
| 182 | 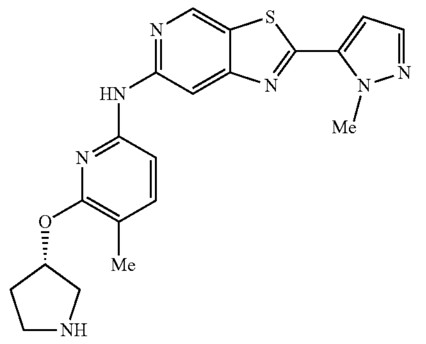 [SMILES: Cc1ccc(Nc2cc3nc(-c4ccnn4C)sc3cn2)nc1O[C@H]1CCNC1] |
| 183 | 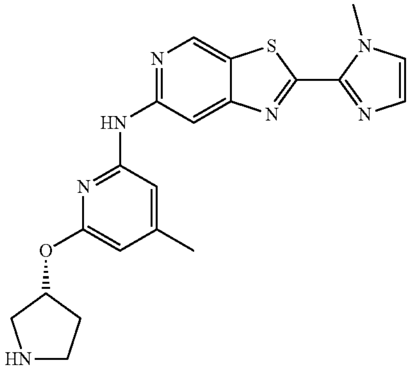 |
| 184 | 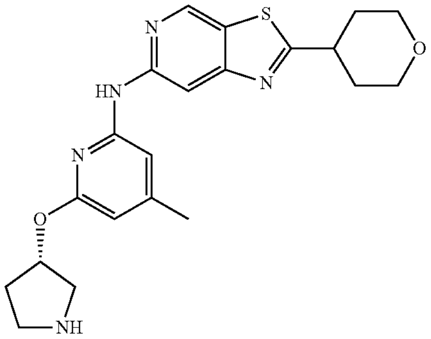 [SMILES: Cc1cc(Nc2cc3nc(C4CCOCC4)sc3cn2)nc(O[C@H]2CCNC2)c1] |
| 185 | 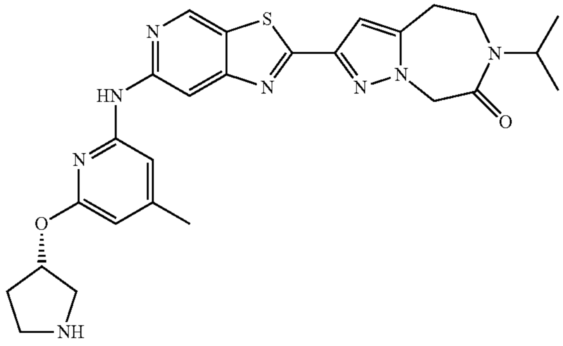 |

TABLE 1-continued
| Ex. No. | Structure |
|---|---|
| 186 | 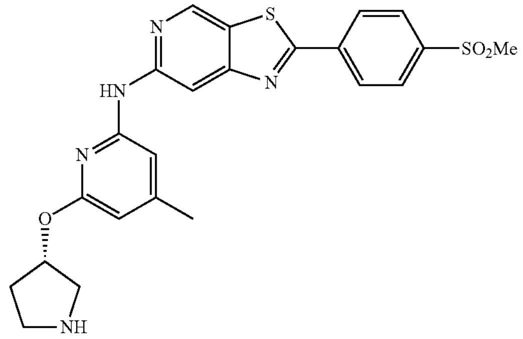 [SMILES: Cc1cc(Nc2cc3nc(-c4ccc(S(C)(=O)=O)cc4)sc3cn2)nc(O[C@H]2CCNC2)c1] |
| 187 | 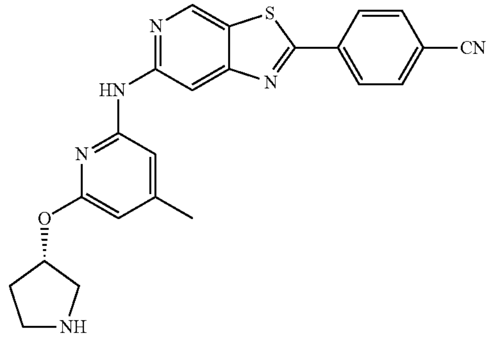 [SMILES: Cc1cc(Nc2cc3nc(-c4ccc(C#N)cc4)sc3cn2)nc(O[C@H]2CCNC2)c1] |
| 188 | 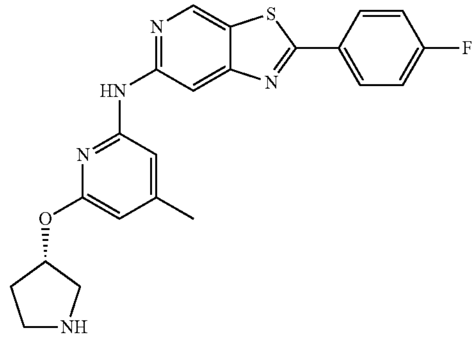 [SMILES: Cc1cc(Nc2cc3nc(-c4ccc(F)cc4)sc3cn2)nc(O[C@H]2CCNC2)c1] |
| 189 | 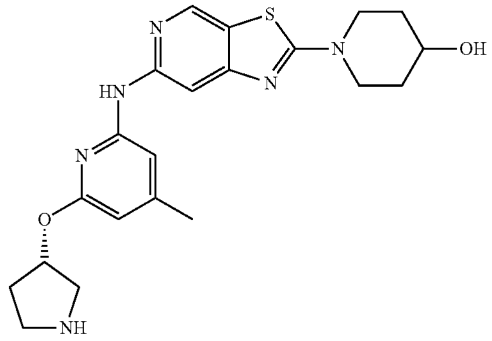 |

TABLE 1-continued
| Ex. No. | Structure |
| --- | --- |
| 190 | 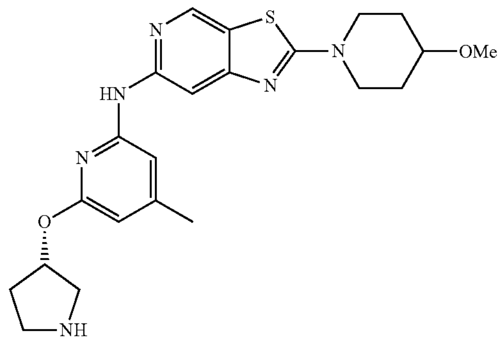 |
| 191 | 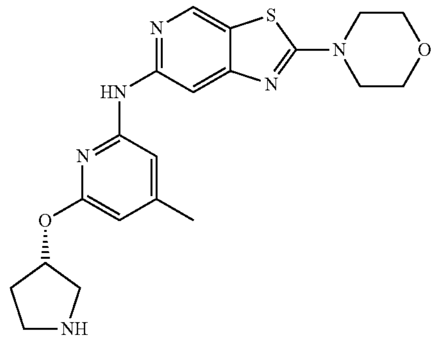 |
| 192 | 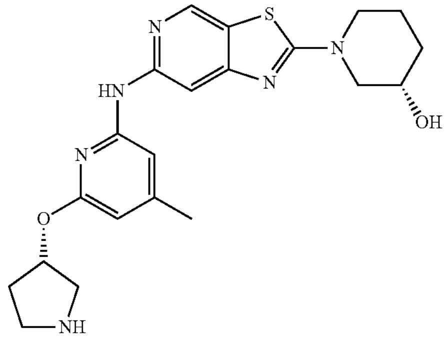 |
| 193 | 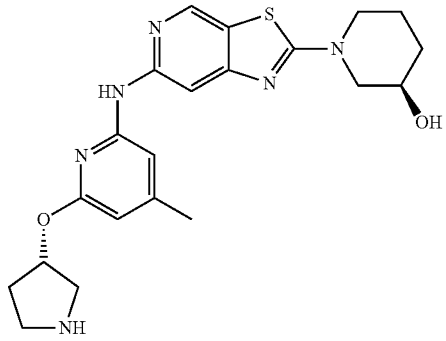 |

TABLE 1-continued
| Ex. No. | Structure |
|---|---|
| 194 | 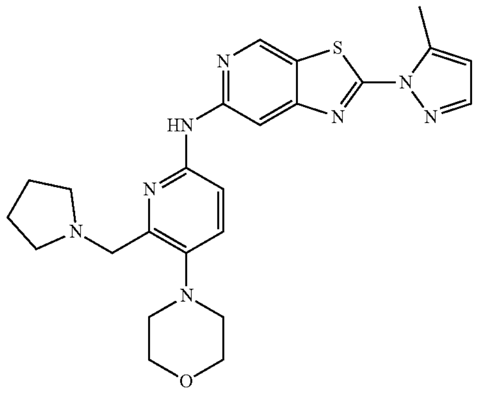 [SMILES: Cc1ccnn1-c1nc2cc(Nc3ccc(N4CCOCC4)c(CN4CCCC4)n3)ncc2s1] |
| 195 | 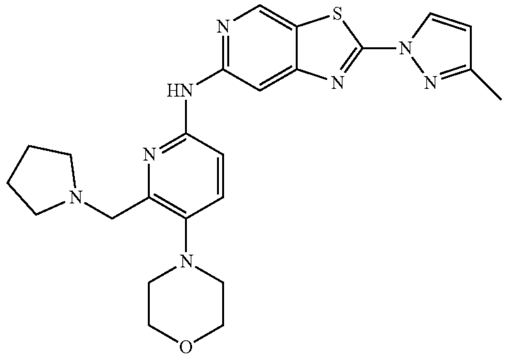 [SMILES: Cc1ccn(-c2nc3cc(Nc4ccc(N5CCOCC5)c(CN5CCCC5)n4)ncc3s2)n1] |
| 196 | 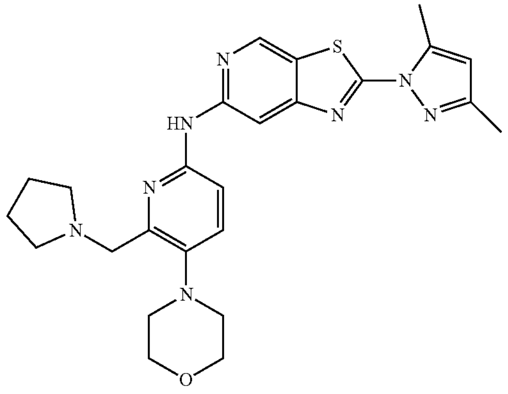 [SMILES: Cc1cc(C)n(-c2nc3cc(Nc4ccc(N5CCOCC5)c(CN5CCCC5)n4)ncc3s2)n1] |
| 197 | 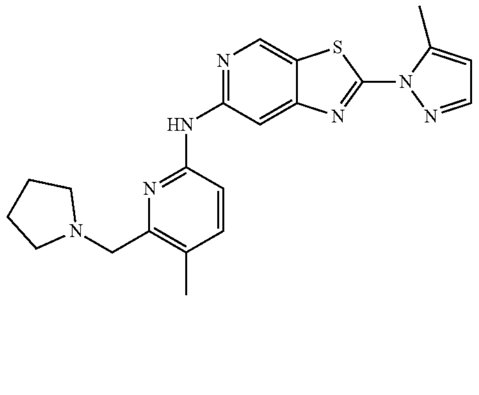 [SMILES: Cc1ccc(Nc2cc3nc(-n4nccc4C)sc3cn2)nc1CN1CCCC1] |

TABLE 1-continued
| Ex. No. | Structure |
| --- | --- |
| 198 | 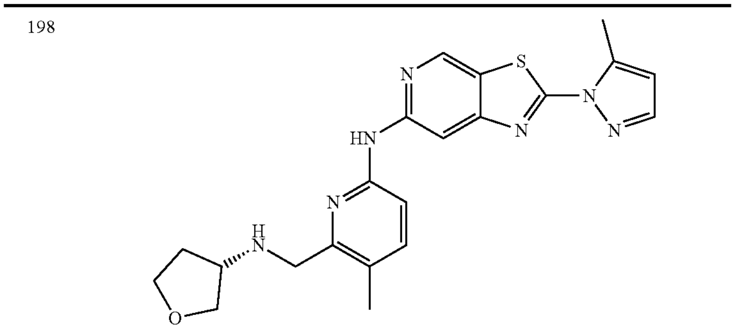 |
| 199 | 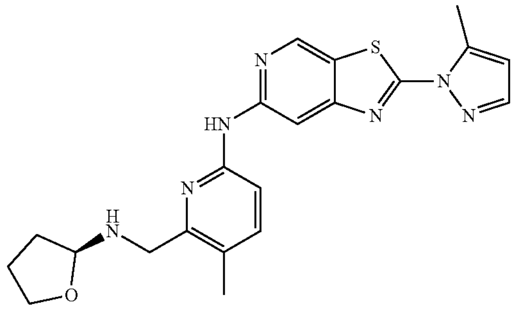 [SMILES: Cc1ccc(Nc2cc3nc(-n4nccc4C)sc3cn2)nc1CN[C@@H]1CCCO1] |
| 200 | 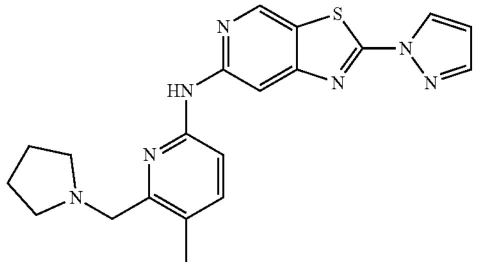 [SMILES: Cc1ccc(Nc2cc3nc(-n4cccn4)sc3cn2)nc1CN1CCCC1] |
| 201 | 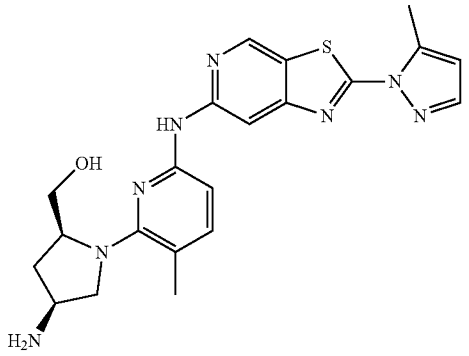 [SMILES: Cc1ccc(Nc2cc3nc(-n4nccc4C)sc3cn2)nc1N1C[C@@H](N)C[C@H]1CO] |
| 202 | 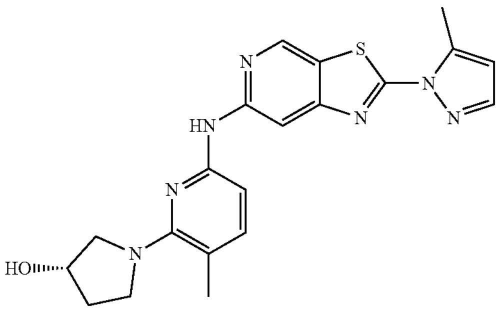 [SMILES: Cc1ccc(Nc2cc3nc(-n4nccc4C)sc3cn2)nc1N1CC[C@H](O)C1] |

TABLE 1-continued
| Ex. No. | Structure |
|---|---|
| 203 | 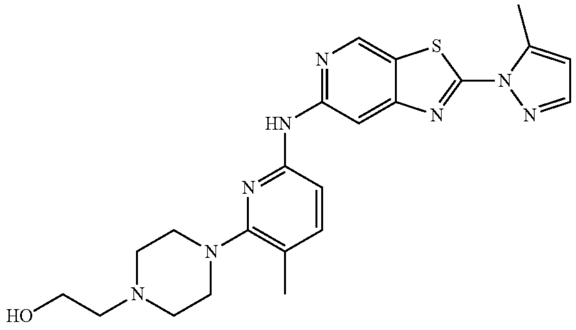 [SMILES: Cc1ccc(Nc2cc3nc(-n4nccc4C)sc3cn2)nc1N1CCN(CCO)CC1] |
| 204 | 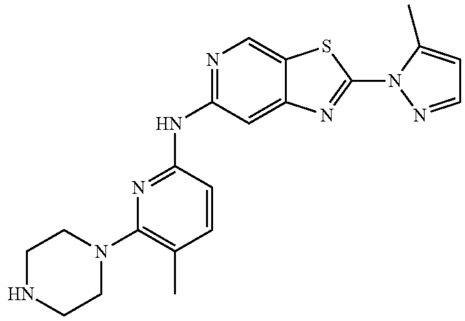 [SMILES: Cc1ccc(Nc2cc3nc(-n4nccc4C)sc3cn2)nc1N1CCNCC1] |
| 205 | 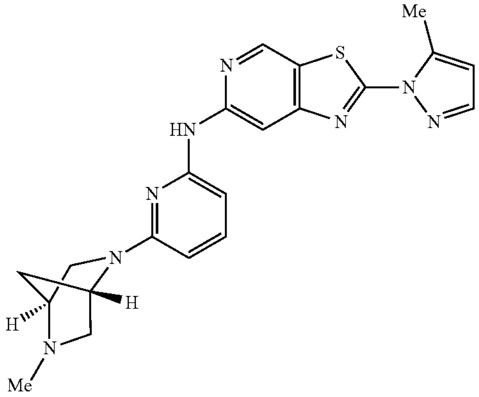 [SMILES: Cc1ccnn1-c1nc2cc(Nc3cccc(N4C[C@@H]5C[C@H]4CN5C)n3)ncc2s1] |
| 206 | 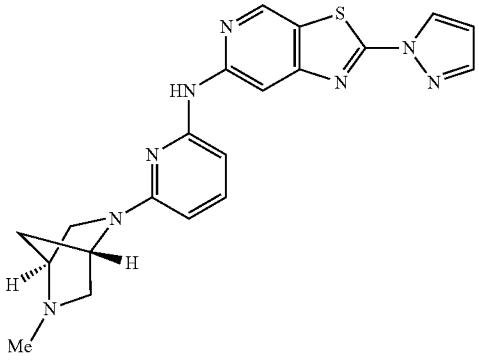 [SMILES: CN1C[C@@H]2C[C@H]1CN2c1cccc(Nc2cc3nc(-n4cccn4)sc3cn2)n1] |

TABLE 1-continued
| Ex. No. | Structure |
|---|---|
| 207 | 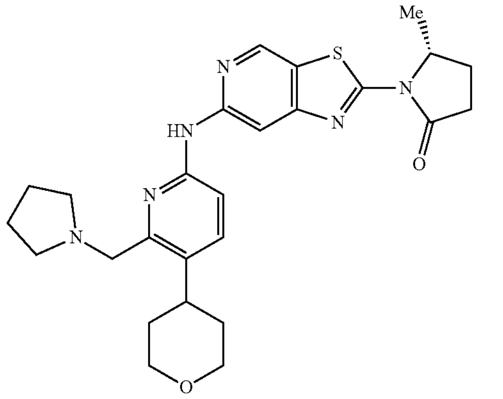 [SMILES: C[C@@H]1CCC(=O)N1c1nc2cc(Nc3ccc(C4CCOCC4)c(CN4CCCC4)n3)ncc2s1] |
| 208 | 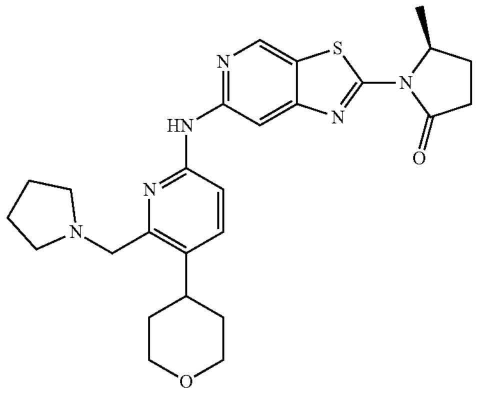 [SMILES: C[C@H]1CCC(=O)N1c1nc2cc(Nc3ccc(C4CCOCC4)c(CN4CCCC4)n3)ncc2s1] |
| 209 | 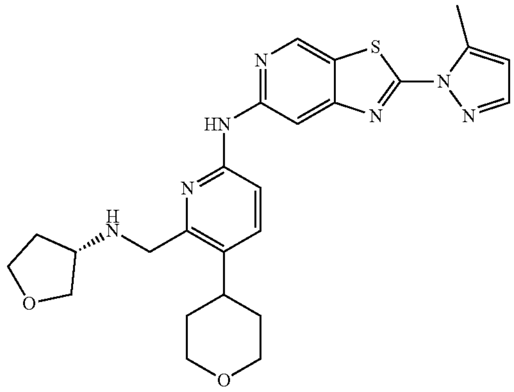 [SMILES: Cc1ccnn1-c1nc2cc(Nc3ccc(C4CCOCC4)c(CN[C@H]4CCOC4)n3)ncc2s1] |
| 210 | 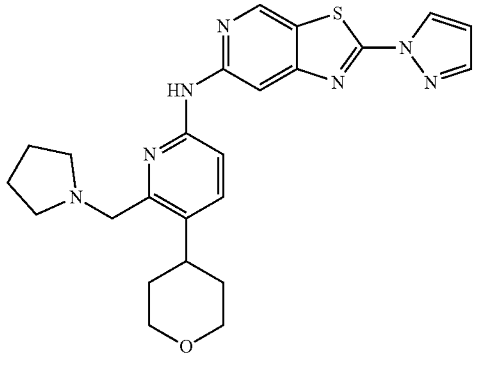 [SMILES: c1cnn(-c2nc3cc(Nc4ccc(C5CCOCC5)c(CN5CCCC5)n4)ncc3s2)c1] |

TABLE 1-continued
| Ex. No. | Structure |
| --- | --- |
| 211 | 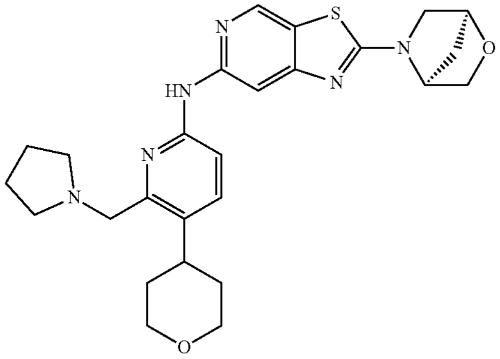 [SMILES: c1cc(C2CCOCC2)c(CN2CCCC2)nc1Nc1cc2nc(N3C[C@@H]4C[C@H]3CO4)sc2cn1] |
| 212 | 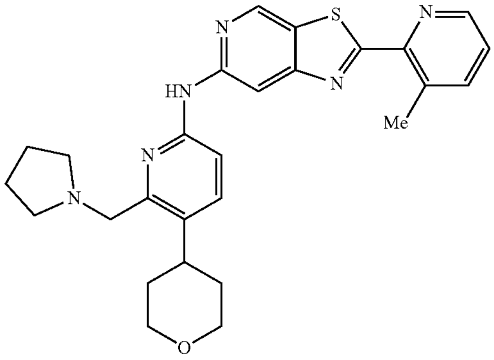 [SMILES: Cc1cccnc1-c1nc2cc(Nc3ccc(C4CCOCC4)c(CN4CCCC4)n3)ncc2s1] |
| 213 | 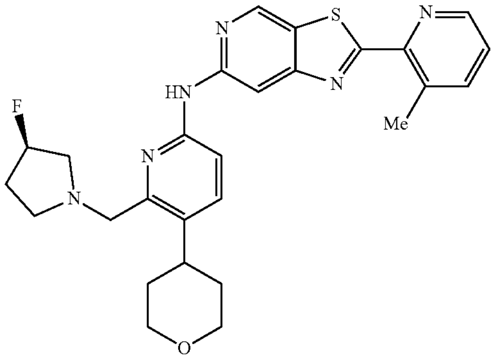 [SMILES: Cc1cccnc1-c1nc2cc(Nc3ccc(C4CCOCC4)c(CN4CC[C@@H](F)C4)n3)ncc2s1] |
| 214 | 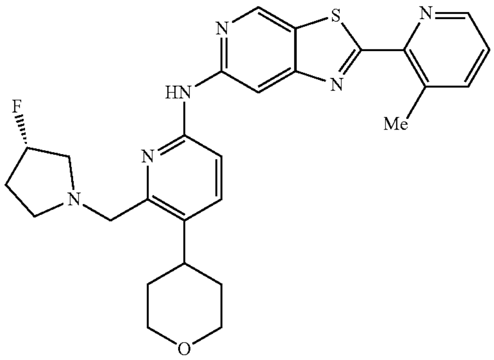 [SMILES: Cc1cccnc1-c1nc2cc(Nc3ccc(C4CCOCC4)c(CN4CC[C@H](F)C4)n3)ncc2s1] |

TABLE 1-continued
| Ex. No. | Structure |
|---|---|
| 215 | 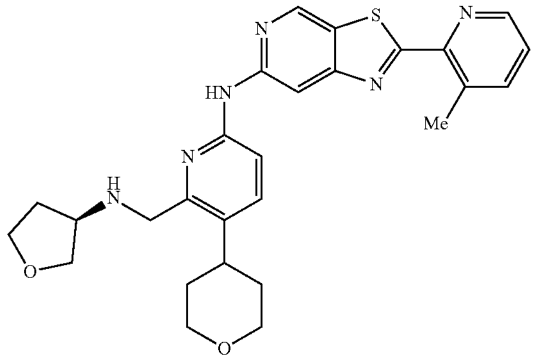 [SMILES: Cc1cccnc1-c1nc2cc(Nc3ccc(C4CCOCC4)c(CN[C@@H]4CCOC4)n3)ncc2s1] |
| 216 | 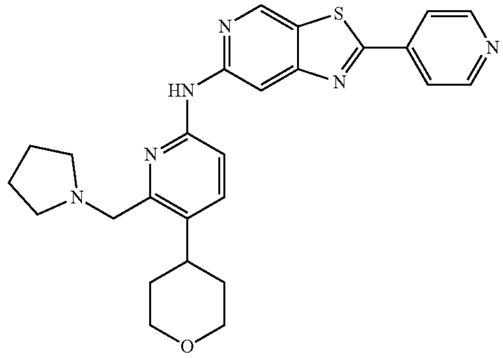 [SMILES: c1cc(-c2nc3cc(Nc4ccc(C5CCOCC5)c(CN5CCCC5)n4)ncc3s2)ccn1] |
| 217 | 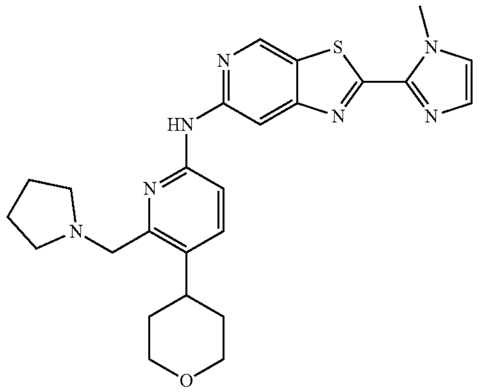 [SMILES: Cn1ccnc1-c1nc2cc(Nc3ccc(C4CCOCC4)c(CN4CCCC4)n3)ncc2s1] |
| 218 | 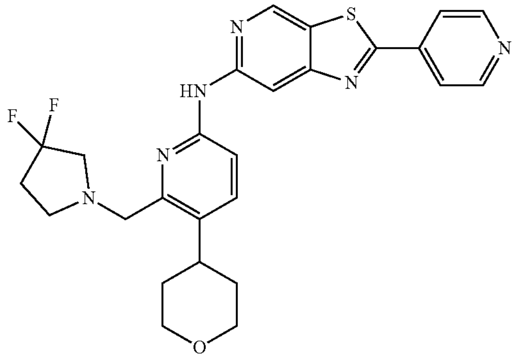 [SMILES: FC1(F)CCN(Cc2nc(Nc3cc4nc(-c5ccncc5)sc4cn3)ccc2C2CCOCC2)C1] |

TABLE 1-continued
| Ex. No. | Structure |
| --- | --- |
| 219 | 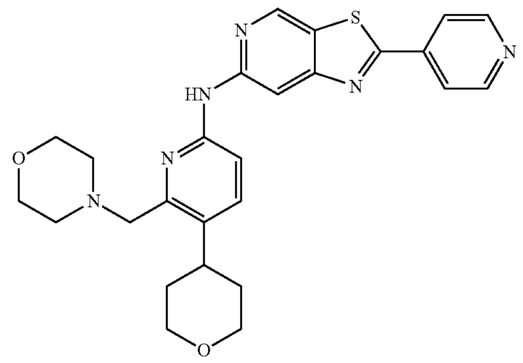 [SMILES: c1cc(-c2nc3cc(Nc4ccc(C5CCOCC5)c(CN5CCOCC5)n4)ncc3s2)ccn1] |
| 220 | 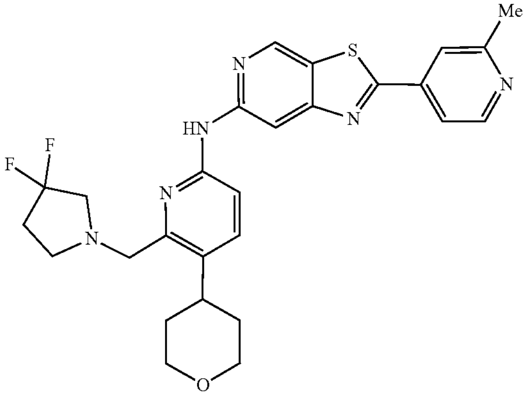 [SMILES: Cc1cc(-c2nc3cc(Nc4ccc(C5CCOCC5)c(CN5CCC(F)(F)C5)n4)ncc3s2)ccn1] |
| 221 | 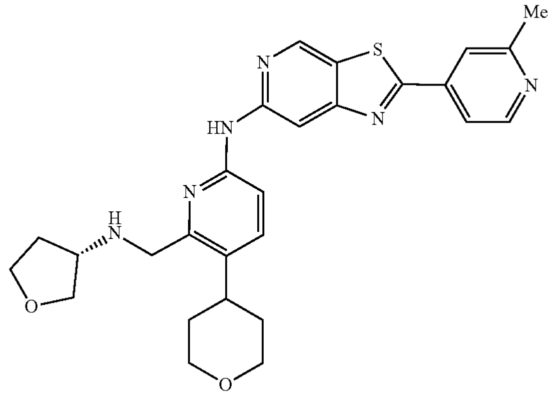 [SMILES: Cc1cc(-c2nc3cc(Nc4ccc(C5CCOCC5)c(CN[C@H]5CCOC5)n4)ncc3s2)ccn1] |
| 222 | 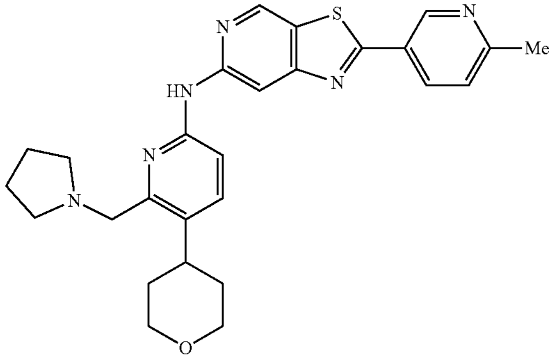 [SMILES: Cc1ccc(-c2nc3cc(Nc4ccc(C5CCOCC5)c(CN5CCCC5)n4)ncc3s2)cn1] |

TABLE 1-continued
| Ex. No. | Structure |
| --- | --- |
| 223 | 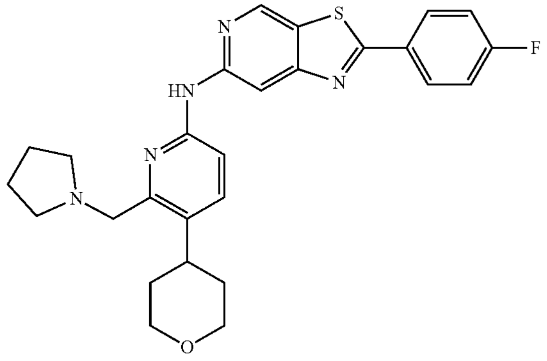 |
| 224 | 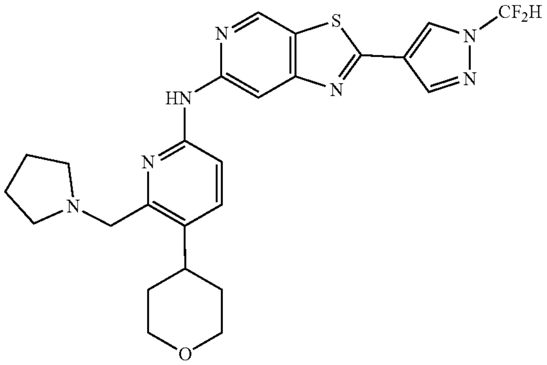 [SMILES: FC(F)n1cc(-c2nc3cc(Nc4ccc(C5CCOCC5)c(CN5CCCC5)n4)ncc3s2)cn1] |
| 225 | 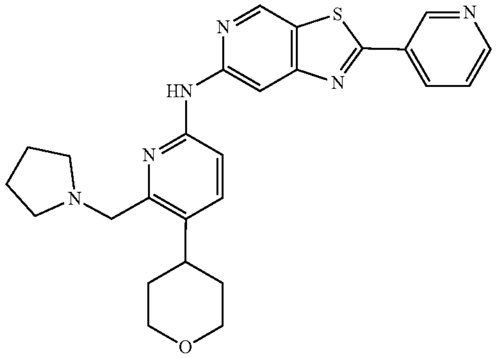 [SMILES: c1cncc(-c2nc3cc(Nc4ccc(C5CCOCC5)c(CN5CCCC5)n4)ncc3s2)c1] |
| 226 | 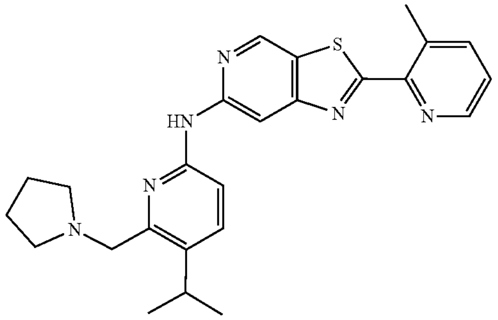 [SMILES: Cc1cccnc1-c1nc2cc(Nc3ccc(C(C)C)c(CN4CCCC4)n3)ncc2s1] |

TABLE 1-continued
| Ex. No. | Structure |
|---|---|
| 227 | 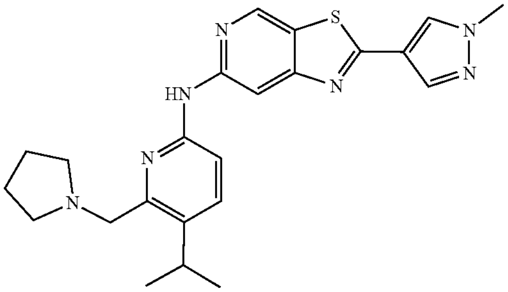 [SMILES: CC(C)c1ccc(Nc2cc3nc(-c4cnn(C)c4)sc3cn2)nc1CN1CCCC1] |
| 228 | 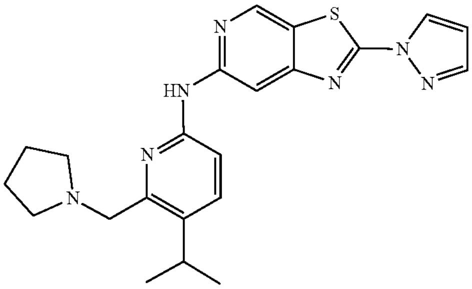 [SMILES: CC(C)c1ccc(Nc2cc3nc(-n4cccn4)sc3cn2)nc1CN1CCCC1] |
| 229 | 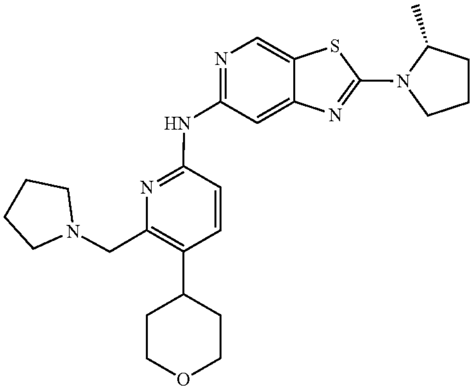 [SMILES: C[C@@H]1CCCN1c1nc2cc(Nc3ccc(C4CCOCC4)c(CN4CCCC4)n3)ncc2s1] |
| 230 | 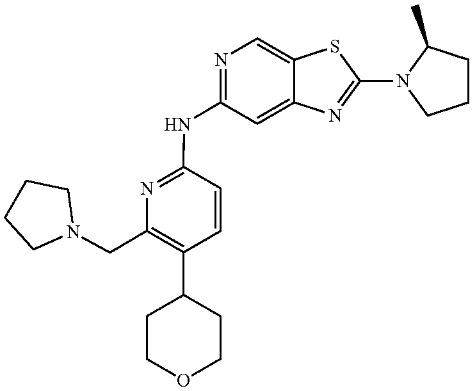 [SMILES: C[C@H]1CCCN1c1nc2cc(Nc3ccc(C4CCOCC4)c(CN4CCCC4)n3)ncc2s1] |

TABLE 1-continued
| Ex. No. | Structure |
| --- | --- |
| 231 | 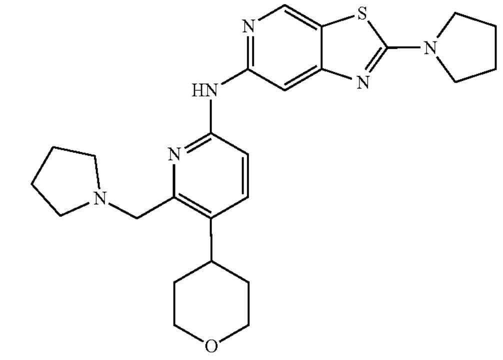 [SMILES: c1cc(C2CCOCC2)c(CN2CCCC2)nc1Nc1cc2nc(N3CCCC3)sc2cn1] |
| 232 | 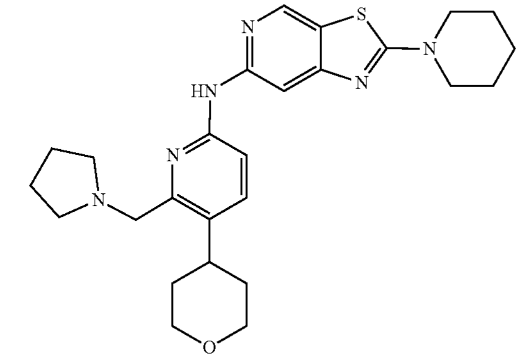 [SMILES: c1cc(C2CCOCC2)c(CN2CCCC2)nc1Nc1cc2nc(N3CCCCC3)sc2cn1] |
| 233 | 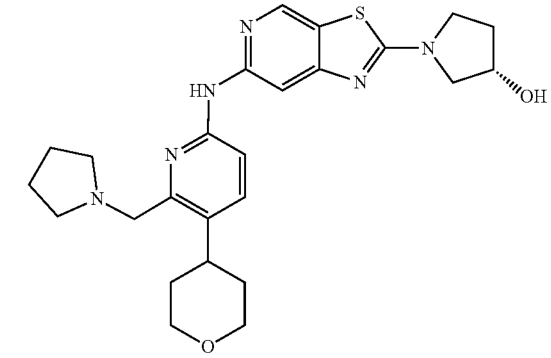 [SMILES: O[C@H]1CCN(c2nc3cc(Nc4ccc(C5CCOCC5)c(CN5CCCC5)n4)ncc3s2)C1] |
| 234 | 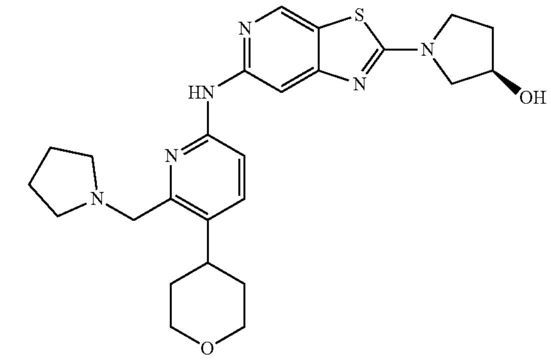 [SMILES: O[C@@H]1CCN(c2nc3cc(Nc4ccc(C5CCOCC5)c(CN5CCCC5)n4)ncc3s2)C1] |

TABLE 1-continued
| Ex. No. | Structure |
|---|---|
| 235 | 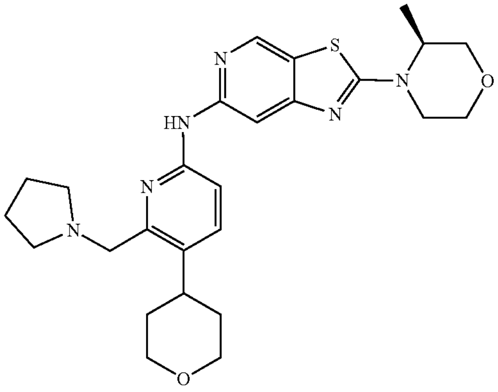 [SMILES: C[C@H]1COCCN1c1nc2cc(Nc3ccc(C4CCOCC4)c(CN4CCCC4)n3)ncc2s1] |
| 236 | 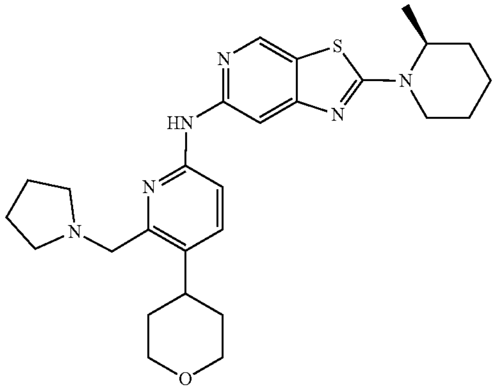 [SMILES: C[C@H]1CCCCN1c1nc2cc(Nc3ccc(C4CCOCC4)c(CN4CCCC4)n3)ncc2s1] |
| 237 | 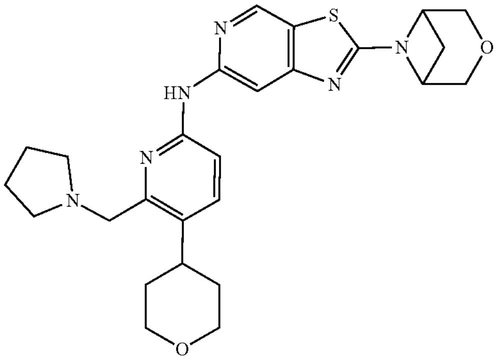 [SMILES: c1cc(C2CCOCC2)c(CN2CCCC2)nc1Nc1cc2nc(N3C4COCC3C4)sc2cn1] |
| 238 | 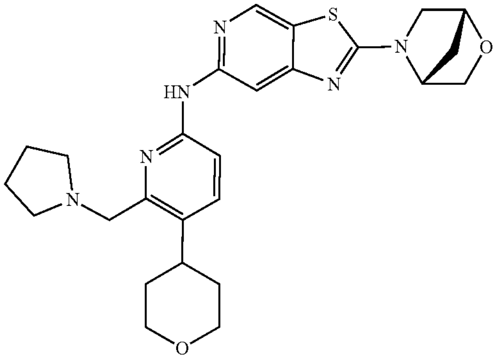 [SMILES: c1cc(C2CCOCC2)c(CN2CCCC2)nc1Nc1cc2nc(N3C[C@H]4C[C@@H]3CO4)sc2cn1] |

TABLE 1-continued
| Ex. No. | Structure |
|---|---|
| 239 | 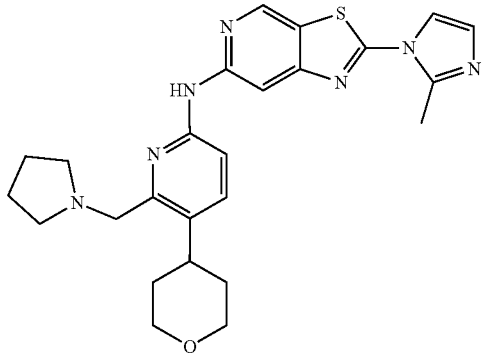 [SMILES: Cc1nccn1-c1nc2cc(Nc3ccc(C4CCOCC4)c(CN4CCCC4)n3)ncc2s1] |
| 240 | 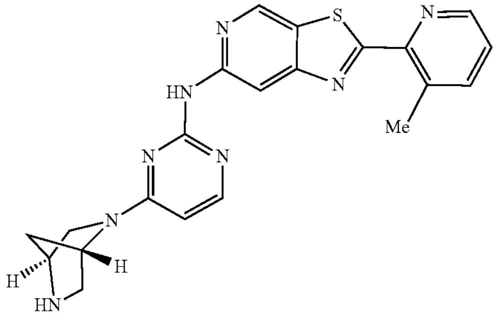 [SMILES: Cc1cccnc1-c1nc2cc(Nc3nccc(N4C[C@@H]5C[C@H]4CN5)n3)ncc2s1] |
| 241 | 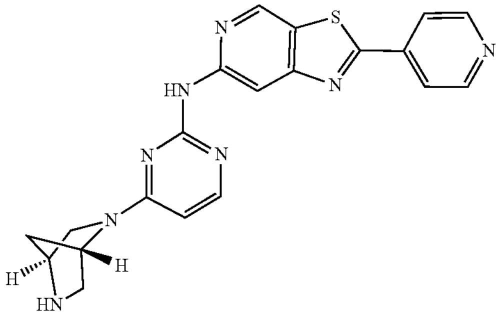 [SMILES: c1cc(-c2nc3cc(Nc4nccc(N5C[C@@H]6C[C@H]5CN6)n4)ncc3s2)ccn1] |
| 242 | 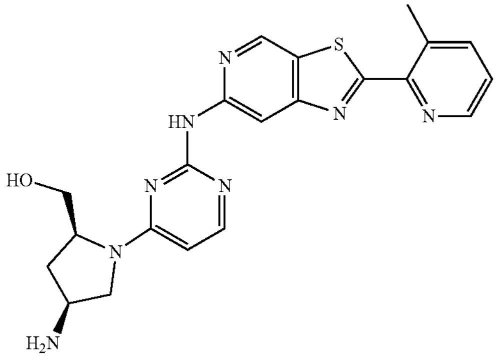 [SMILES: Cc1cccnc1-c1nc2cc(Nc3nccc(N4C[C@@H](N)C[C@H]4CO)n3)ncc2s1] |

TABLE 1-continued
| Ex. No. | Structure |
| --- | --- |
| 243 | 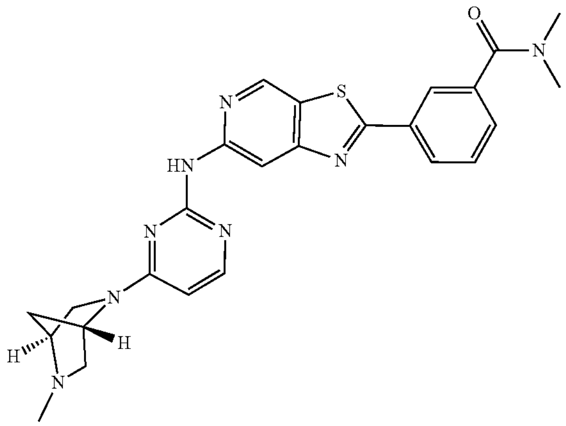 [SMILES: CN(C)C(=O)c1cccc(-c2nc3cc(Nc4nccc(N5C[C@@H]6C[C@H]5CN6C)n4)ncc3s2)c1] |
| 244 | 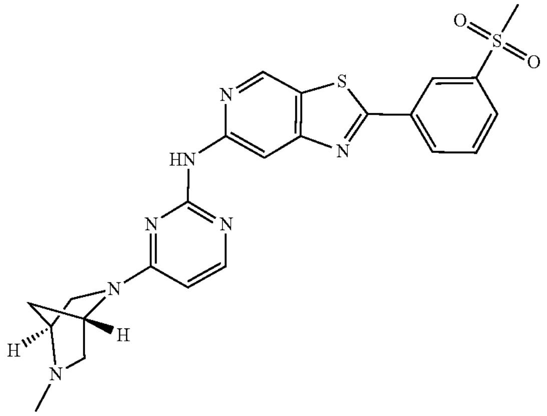 [SMILES: CN1C[C@@H]2C[C@H]1CN2c1ccnc(Nc2cc3nc(-c4cccc(S(C)(=O)=O)c4)sc3cn2)n1] |
| 245 | 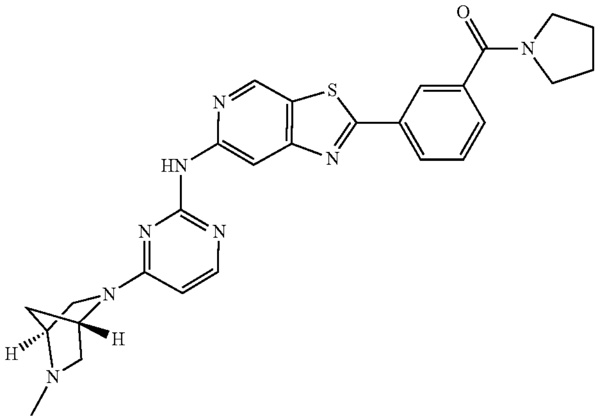 [SMILES: CN1C[C@@H]2C[C@H]1CN2c1ccnc(Nc2cc3nc(-c4cccc(C(=O)N5CCCC5)c4)sc3cn2)n1] |

TABLE 1-continued
| Ex. No. | Structure |
|---|---|
| 246 | 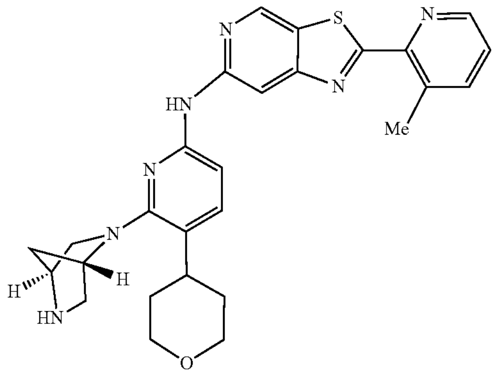 [SMILES: Cc1cccnc1-c1nc2cc(Nc3ccc(C4CCOCC4)c(N4C[C@@H]5C[C@H]4CN5)n3)ncc2s1] |
| 247 | 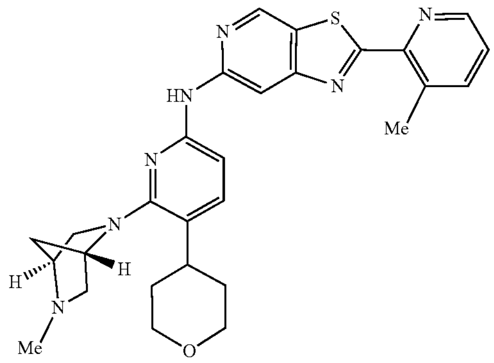 [SMILES: Cc1cccnc1-c1nc2cc(Nc3ccc(C4CCOCC4)c(N4C[C@@H]5C[C@H]4CN5C)n3)ncc2s1] |
| 248 | 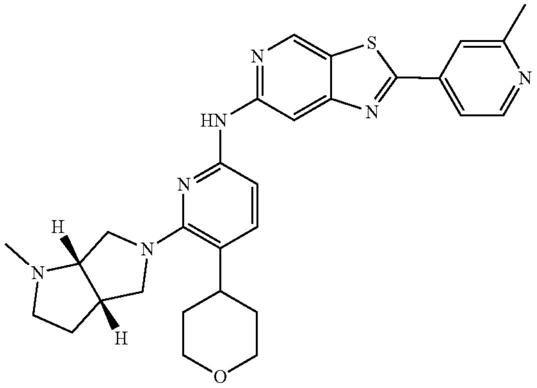 |
| 249 | 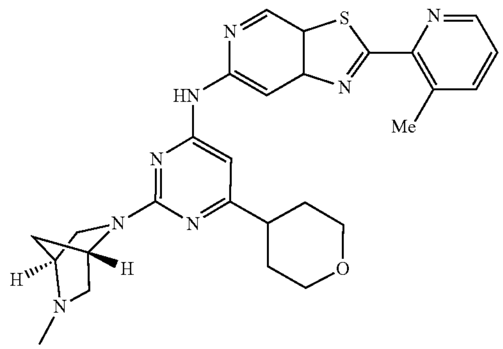 [SMILES: Cc1cccnc1C1=NC2C=C(Nc3cc(C4CCOCC4)nc(N4C[C@@H]5C[C@H]4CN5C)n3)N=CC2S1] |

TABLE 1-continued
| Ex. No. | Structure |
|---|---|
| 250 | 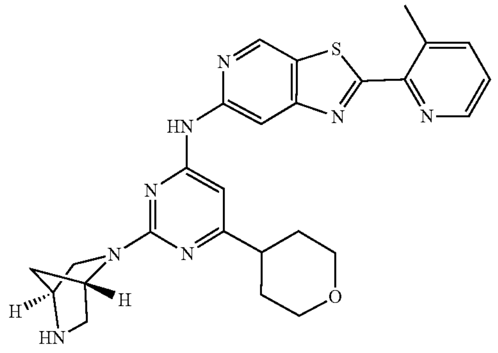 [SMILES: Cc1cccnc1-c1nc2cc(Nc3cc(C4CCOCC4)nc(N4C[C@@H]5C[C@H]4CN5)n3)ncc2s1] |
| 251 | 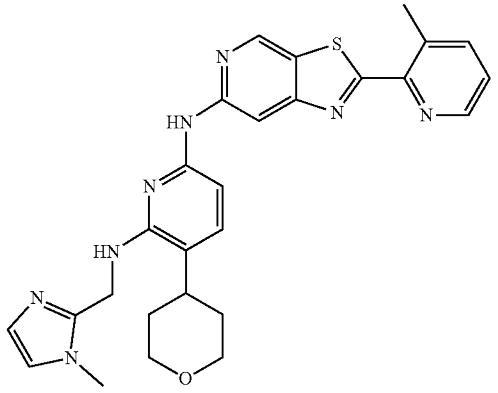 [SMILES: Cc1cccnc1-c1nc2cc(Nc3ccc(C4CCOCC4)c(NCc4nccn4C)n3)ncc2s1] |
| 252 | 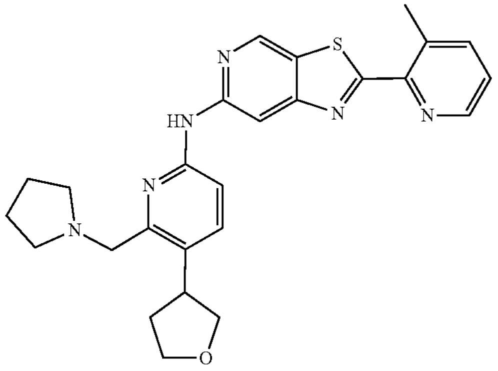 [SMILES: Cc1cccnc1-c1nc2cc(Nc3ccc(C4CCOC4)c(CN4CCCC4)n3)ncc2s1] |
| 253 | 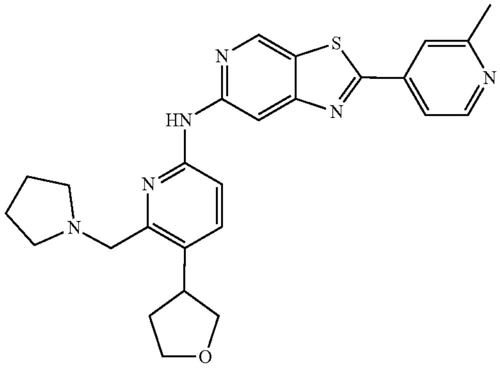 [SMILES: Cc1cc(-c2nc3cc(Nc4ccc(C5CCOC5)c(CN5CCCC5)n4)ncc3s2)ccn1] |

TABLE 1-continued
| Ex. No. | Structure |
| --- | --- |
| 254 | 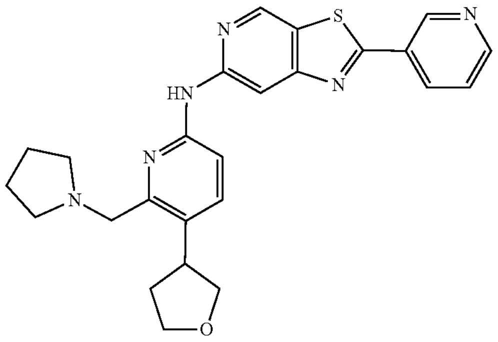 [SMILES: c1cncc(-c2nc3cc(Nc4ccc(C5CCOC5)c(CN5CCCC5)n4)ncc3s2)c1] |
| 255 | 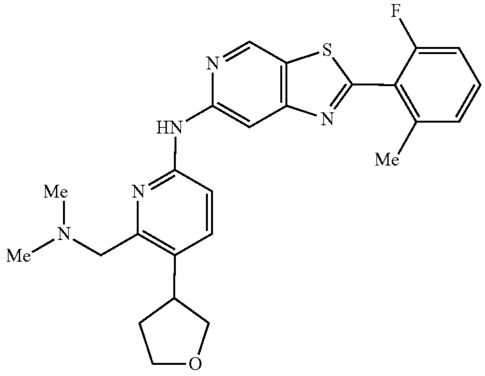 [SMILES: Cc1cccc(F)c1-c1nc2cc(Nc3ccc(C4CCOC4)c(CN(C)C)n3)ncc2s1] |
| 256 | 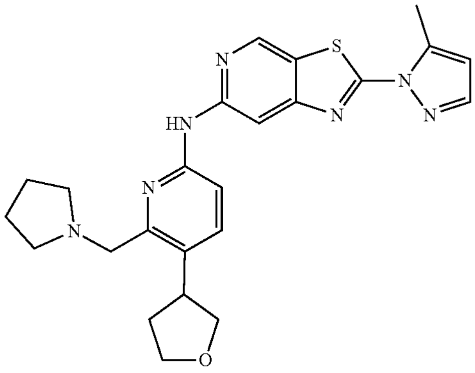 [SMILES: Cc1ccnn1-c1nc2cc(Nc3ccc(C4CCOC4)c(CN4CCCC4)n3)ncc2s1] |
| 257 | 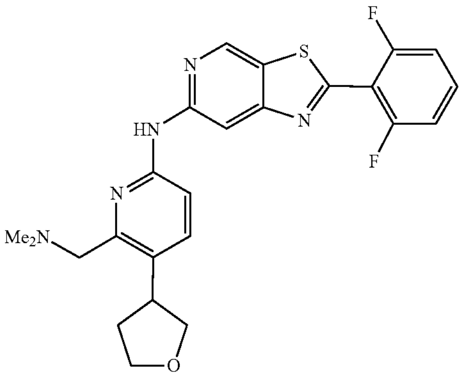 [SMILES: CN(C)Cc1nc(Nc2cc3nc(-c4c(F)cccc4F)sc3cn2)ccc1C1CCOC1] |

TABLE 1-continued
| Ex. No. | Structure |
| --- | --- |
| 258 | 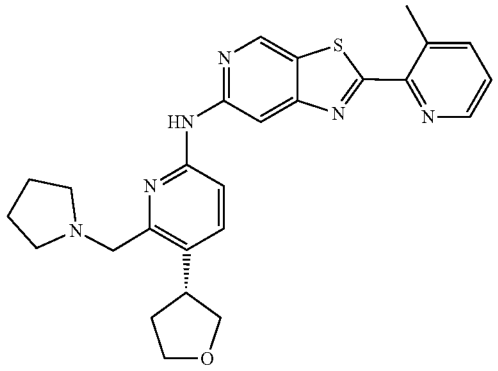 [SMILES: Cc1cccnc1-c1nc2cc(Nc3ccc([C@H]4CCOC4)c(CN4CCCC4)n3)ncc2s1] |
| 259 | 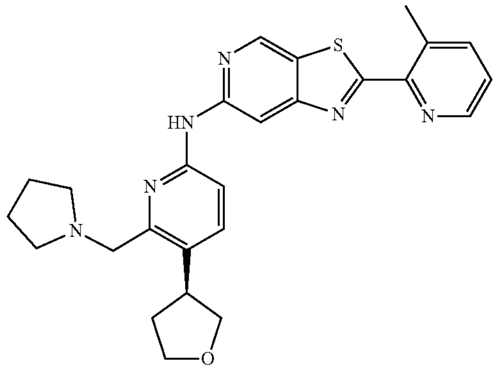 [SMILES: Cc1cccnc1-c1nc2cc(Nc3ccc([C@@H]4CCOC4)c(CN4CCCC4)n3)ncc2s1] |
| 260 | 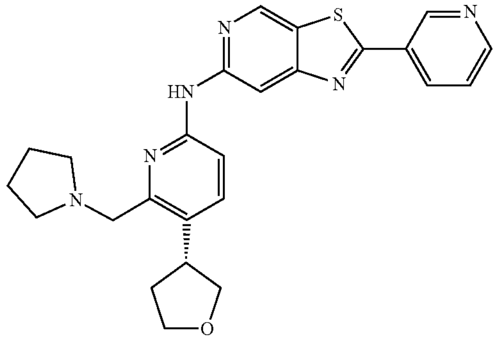 [SMILES: c1cncc(-c2nc3cc(Nc4ccc([C@H]5CCOC5)c(CN5CCCC5)n4)ncc3s2)c1] |
| 261 | 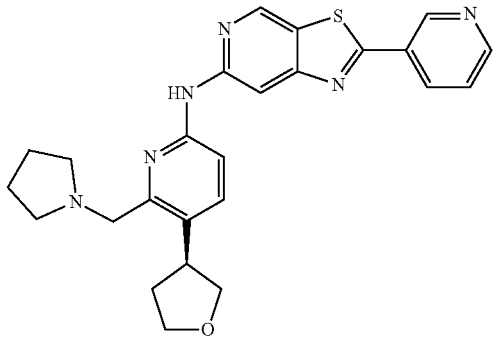 [SMILES: c1cncc(-c2nc3cc(Nc4ccc([C@@H]5CCOC5)c(CN5CCCC5)n4)ncc3s2)c1] |

TABLE 1-continued
| Ex. No. | Structure |
|---|---|
| 262 | 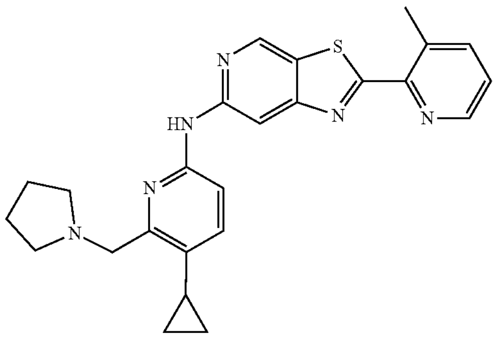 [SMILES: Cc1cccnc1-c1nc2cc(Nc3ccc(C4CC4)c(CN4CCCC4)n3)ncc2s1] |
| 263 | 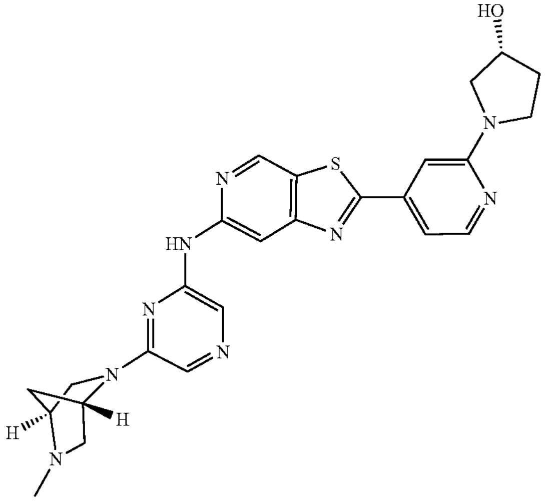 [SMILES: CN1C[C@@H]2C[C@H]1CN2c1cncc(Nc2cc3nc(-c4ccnc(N5CC[C@@H](O)C5)c4)sc3cn2)n1] |
| 264 | 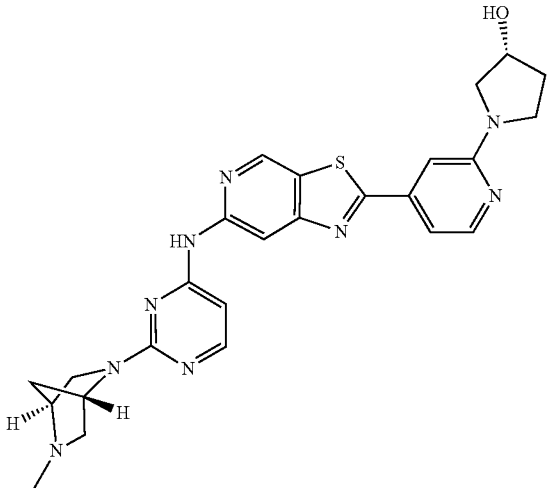 [SMILES: CN1C[C@@H]2C[C@H]1CN2c1nccc(Nc2cc3nc(-c4ccnc(N5CC[C@@H](O)C5)c4)sc3cn2)n1] |

TABLE 1-continued
| Ex. No. | Structure |
|---|---|
| 265 | 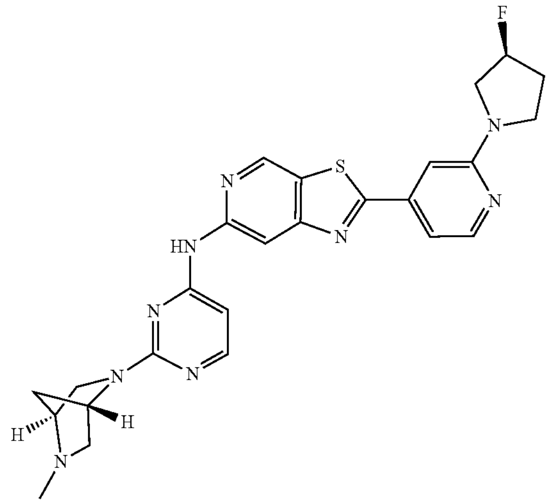 [SMILES: CN1C[C@@H]2C[C@H]1CN2c1nccc(Nc2cc3nc(-c4ccnc(N5CC[C@H](F)C5)c4)sc3cn2)n1] |
| 266 | 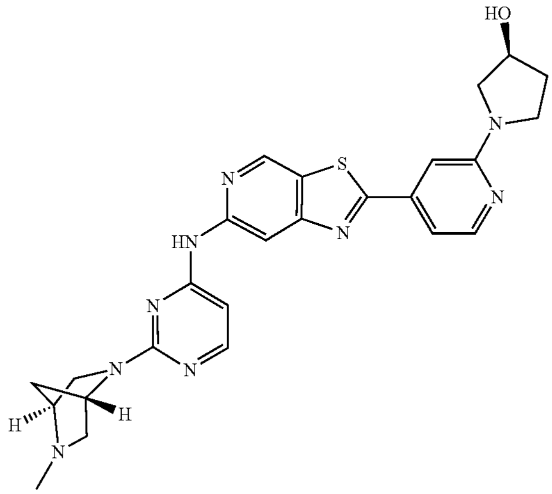 [SMILES: CN1C[C@@H]2C[C@H]1CN2c1nccc(Nc2cc3nc(-c4ccnc(N5CC[C@H](O)C5)c4)sc3cn2)n1] |
| 267 | 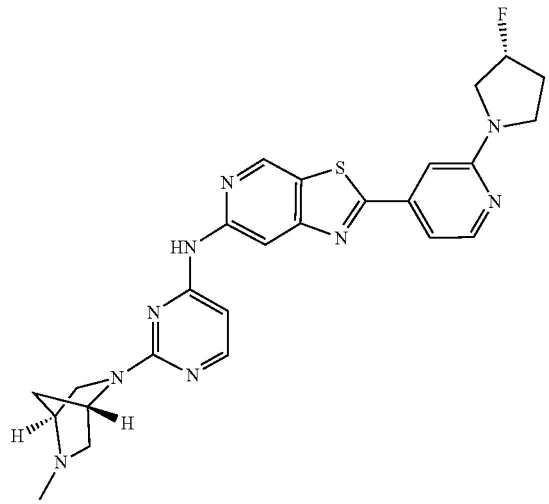 [SMILES: CN1C[C@@H]2C[C@H]1CN2c1nccc(Nc2cc3nc(-c4ccnc(N5CC[C@@H](F)C5)c4)sc3cn2)n1] |

TABLE 1-continued
| Ex. No. | Structure |
|---|---|
| 268 | 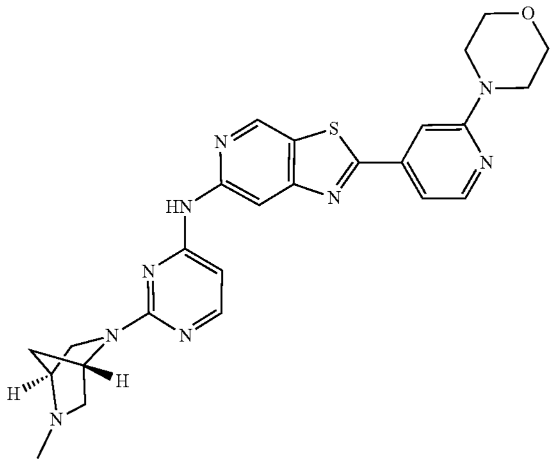 [SMILES: CN1C[C@@H]2C[C@H]1CN2c1nccc(Nc2cc3nc(-c4ccnc(N5CCOCC5)c4)sc3cn2)n1] |
| 269 | 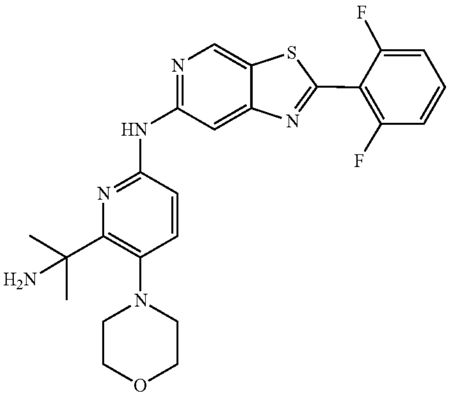 [SMILES: CC(C)(N)c1nc(Nc2cc3nc(-c4c(F)cccc4F)sc3cn2)ccc1N1CCOCC1] |
| 270 | 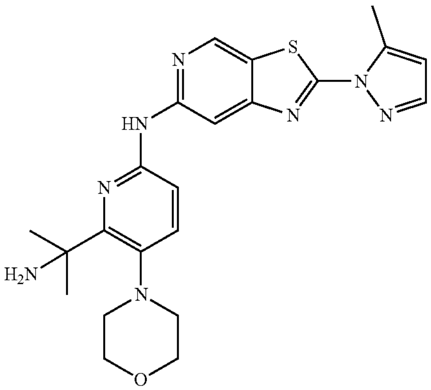 [SMILES: Cc1ccnn1-c1nc2cc(Nc3ccc(N4CCOCC4)c(C(C)(C)N)n3)ncc2s1] |

TABLE 1-continued
| Ex. No. | Structure |
|---|---|
| 271 | 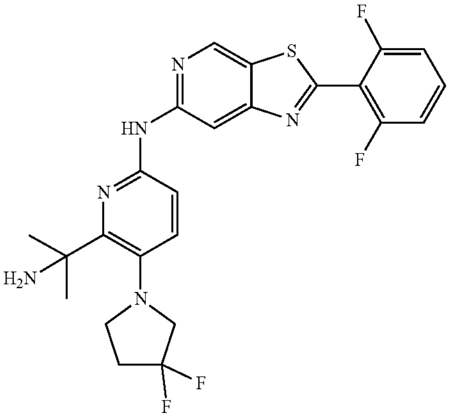 [SMILES: CC(C)(N)c1nc(Nc2cc3nc(-c4c(F)cccc4F)sc3cn2)ccc1N1CCC(F)(F)C1] |
| 272 | 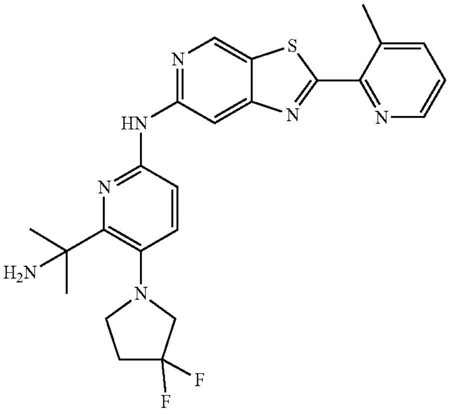 [SMILES: Cc1cccnc1-c1nc2cc(Nc3ccc(N4CCC(F)(F)C4)c(C(C)(C)N)n3)ncc2s1] |
| 273 | 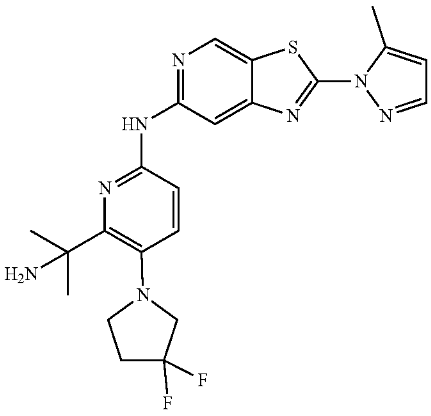 [SMILES: Cc1ccnn1-c1nc2cc(Nc3ccc(N4CCC(F)(F)C4)c(C(C)(C)N)n3)ncc2s1] |

TABLE 1-continued
| Ex. No. | Structure |
|---|---|
| 274 | 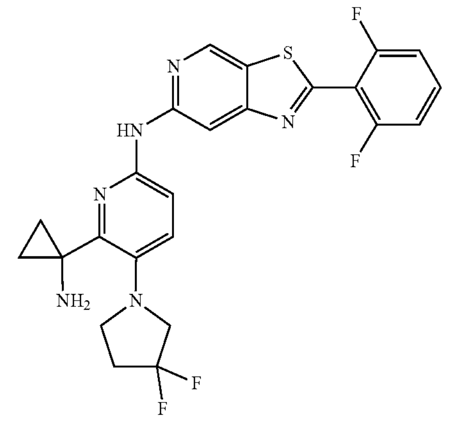 [SMILES: NC1(c2nc(Nc3cc4nc(-c5c(F)cccc5F)sc4cn3)ccc2N2CCC(F)(F)C2)CC1] |
| 275 | 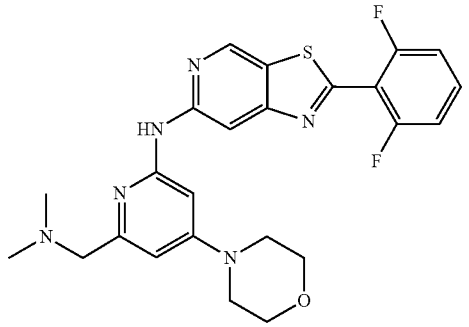 [SMILES: CN(C)Cc1cc(N2CCOCC2)cc(Nc2cc3nc(-c4c(F)cccc4F)sc3cn2)n1] |
| 276 | 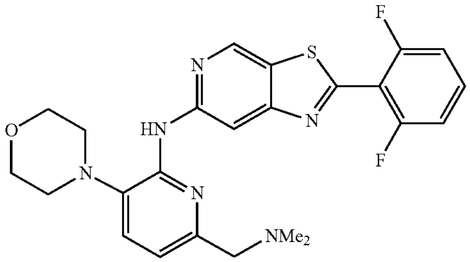 [SMILES: CN(C)Cc1ccc(N2CCOCC2)c(Nc2cc3nc(-c4c(F)cccc4F)sc3cn2)n1] |
| 277 | 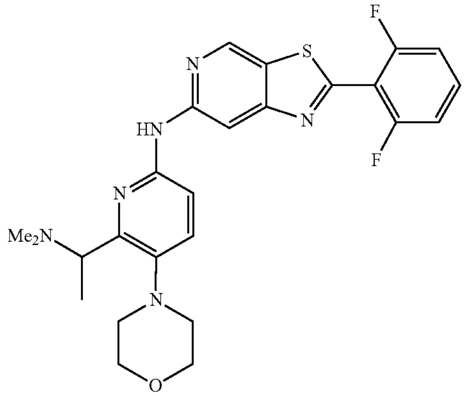 [SMILES: CC(c1nc(Nc2cc3nc(-c4c(F)cccc4F)sc3cn2)ccc1N1CCOCC1)N(C)C] |

TABLE 1-continued
| Ex. No. | Structure |
| --- | --- |
| 278 | 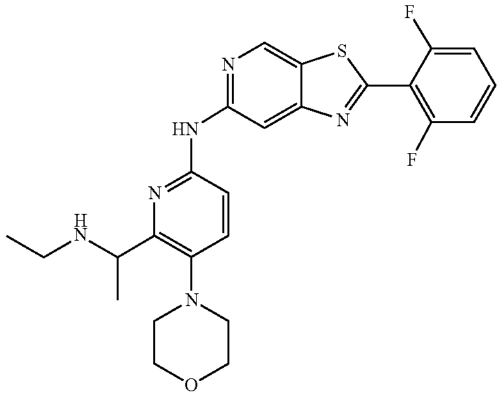 [SMILES: CCNC(C)c1nc(Nc2cc3nc(-c4c(F)cccc4F)sc3cn2)ccc1N1CCOCC1] |
| 279 | 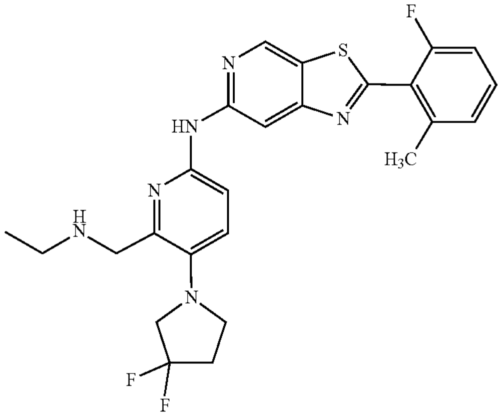 [SMILES: CCNCc1nc(Nc2cc3nc(-c4c(C)cccc4F)sc3cn2)ccc1N1CCC(F)(F)C1] |
| 280 | 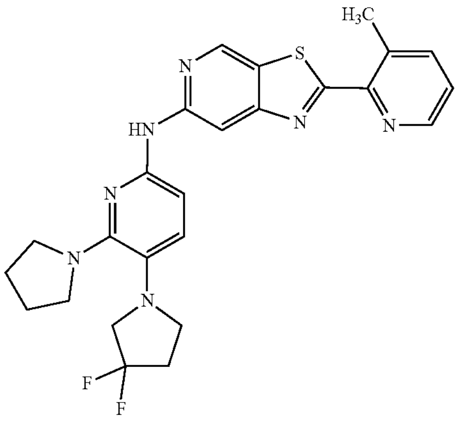 [SMILES: Cc1cccnc1-c1nc2cc(Nc3ccc(N4CCC(F)(F)C4)c(N4CCCC4)n3)ncc2s1] |

TABLE 1-continued
| Ex. No. | Structure |
| --- | --- |
| 281 | 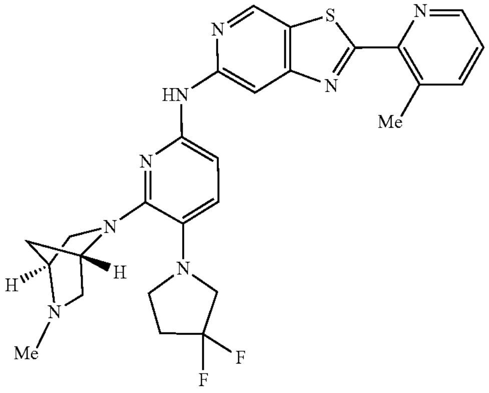 [SMILES: Cc1cccnc1-c1nc2cc(Nc3ccc(N4CCC(F)(F)C4)c(N4C[C@@H]5C[C@H]4CN5C)n3)ncc2s1] |
| 282 | 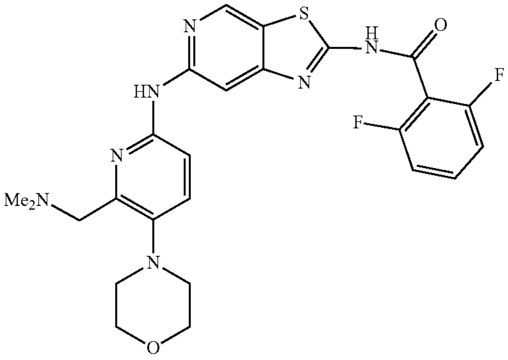 [SMILES: CN(C)Cc1nc(Nc2cc3nc(NC(=O)c4c(F)cccc4F)sc3cn2)ccc1N1CCOCC1] |
| 283 | 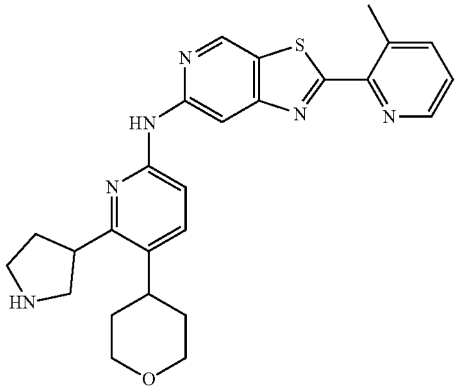 [SMILES: Cc1cccnc1-c1nc2cc(Nc3ccc(C4CCOCC4)c(C4CCNC4)n3)ncc2s1] |
| 284 | 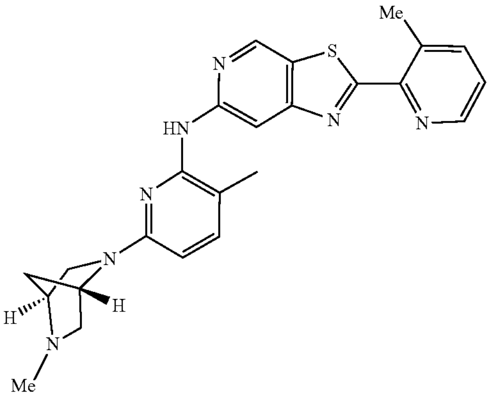 [SMILES: Cc1ccc(N2C[C@@H]3C[C@H]2CN3C)nc1Nc1cc2nc(-c3ncccc3C)sc2cn1] |

TABLE 1-continued
| Ex. No. | Structure |
|---|---|
| 285 | 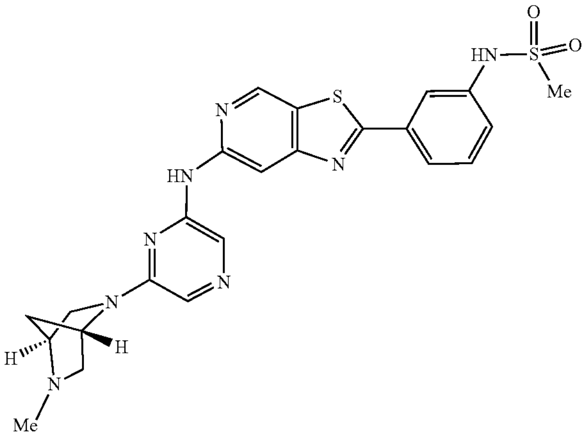 [SMILES: CN1C[C@@H]2C[C@H]1CN2c1cncc(Nc2cc3nc(-c4cccc(NS(C)(=O)=O)c4)sc3cn2)n1] |
| 286 | 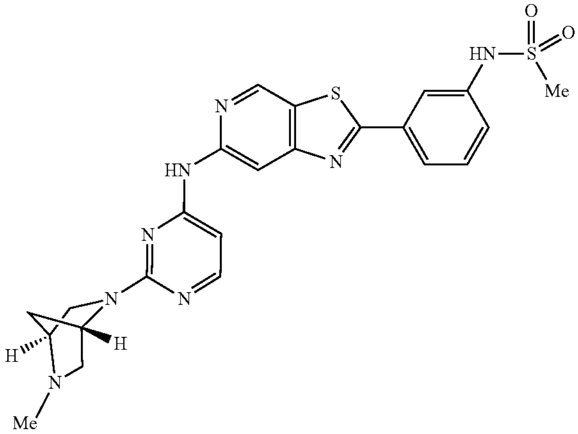 [SMILES: CN1C[C@@H]2C[C@H]1CN2c1nccc(Nc2cc3nc(-c4cccc(NS(C)(=O)=O)c4)sc3cn2)n1] |
| 287 | 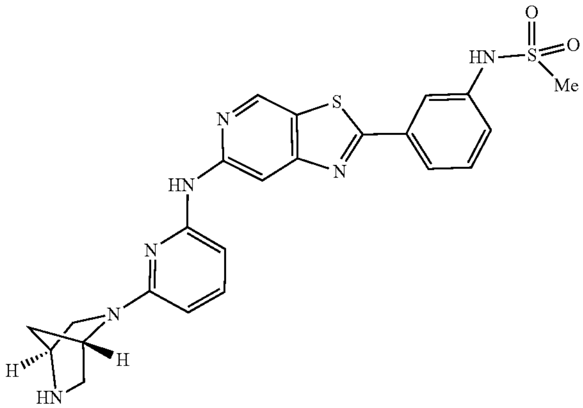 |

TABLE 1-continued
| Ex. No. | Structure |
|---|---|
| 288 | 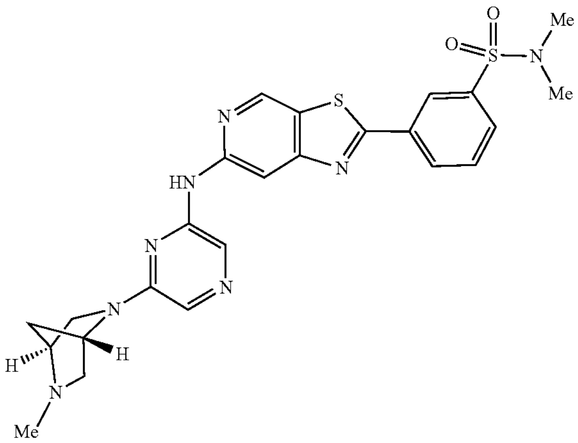 [SMILES: CN1C[C@@H]2C[C@H]1CN2c1cncc(Nc2cc3nc(-c4cccc(S(=O)(=O)N(C)C)c4)sc3cn2)n1] |
| 289 | 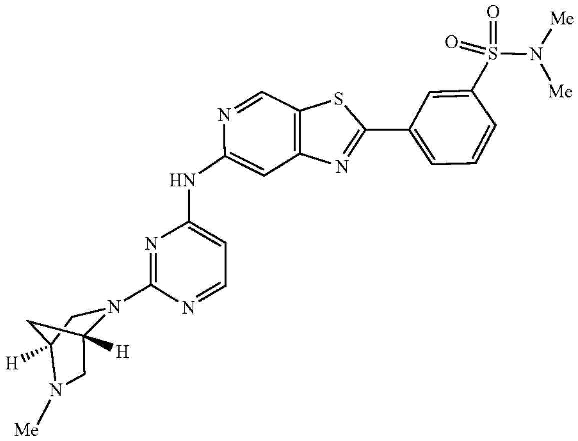 [SMILES: CN1C[C@@H]2C[C@H]1CN2c1nccc(Nc2cc3nc(-c4cccc(S(=O)(=O)N(C)C)c4)sc3cn2)n1] |
| 290 | 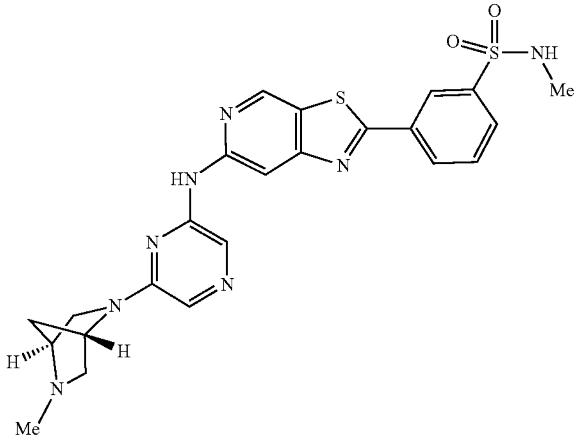 [SMILES: CNS(=O)(=O)c1cccc(-c2nc3cc(Nc4cncc(N5C[C@@H]6C[C@H]5CN6C)n4)ncc3s2)c1] |

TABLE 1-continued
| Ex. No. | Structure |
| --- | --- |
| 291 | 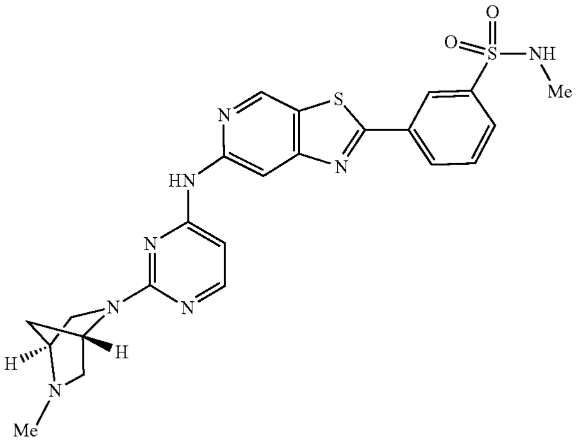 [SMILES: CNS(=O)(=O)c1cccc(-c2nc3cc(Nc4ccnc(N5C[C@@H]6C[C@H]5CN6C)n4)ncc3s2)c1] |
| 292 | 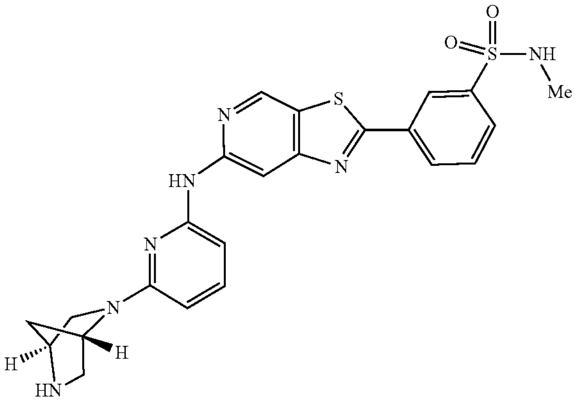 [SMILES: CNS(=O)(=O)c1cccc(-c2nc3cc(Nc4cccc(N5C[C@@H]6C[C@H]5CN6)n4)ncc3s2)c1] |
| 293 | 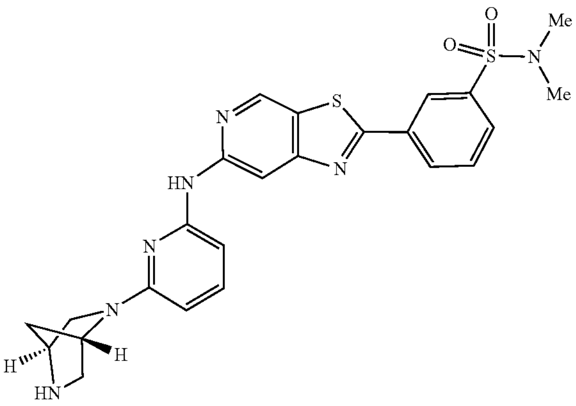 [SMILES: CN(C)S(=O)(=O)c1cccc(-c2nc3cc(Nc4cccc(N5C[C@@H]6C[C@H]5CN6)n4)ncc3s2)c1] |

TABLE 1-continued
| Ex. No. | Structure |
| --- | --- |
| 294 | 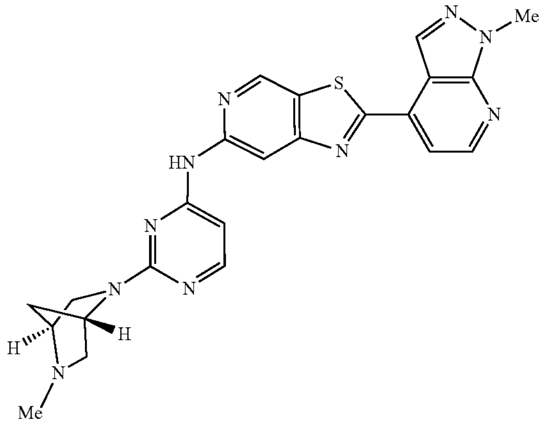 [SMILES: CN1C[C@@H]2C[C@H]1CN2c1nccc(Nc2cc3nc(-c4ccnc5c4cnn5C)sc3cn2)n1] |
TABLE 2
| Ex. No. | Structure |
| --- | --- |
| 295 | 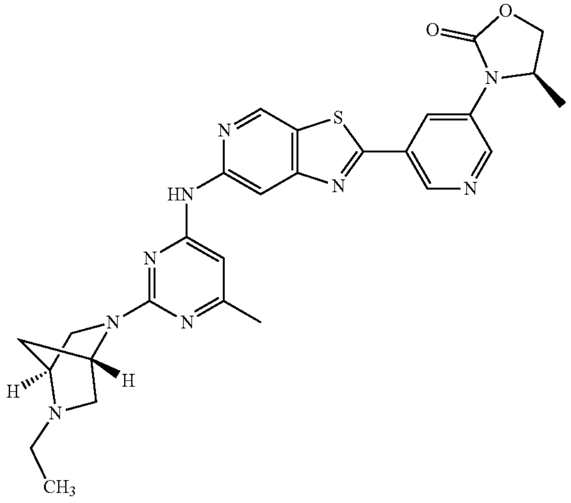 [SMILES: CCN1C[C@@H]2C[C@H]1CN2c1nc(C)cc(Nc2cc3nc(-c4cncc(N5C(=O)OC[C@H]5C)c4)sc3cn2)n1] |
| 296 | 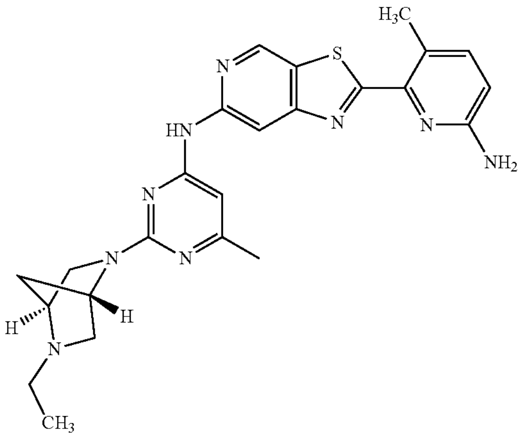 [SMILES: CCN1C[C@@H]2C[C@H]1CN2c1nc(C)cc(Nc2cc3nc(-c4nc(N)ccc4C)sc3cn2)n1] |

TABLE 2-continued
| Ex. No. | Structure |
| --- | --- |
| 297 | 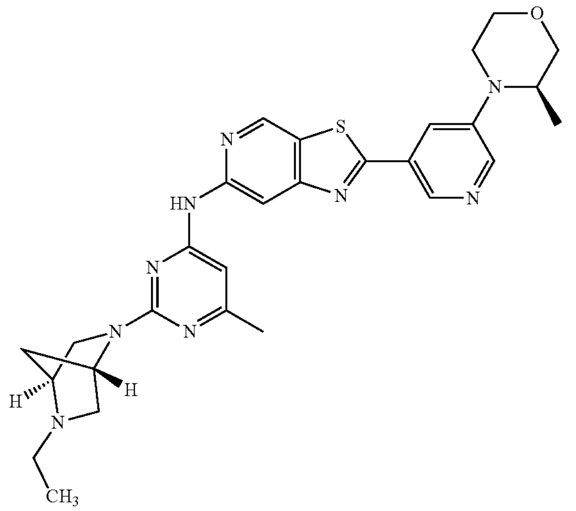 [SMILES: CCN1C[C@@H]2C[C@H]1CN2c1nc(C)cc(Nc2cc3nc(-c4cncc(N5CCOC[C@H]5C)c4)sc3cn2)n1] |
| 298 | 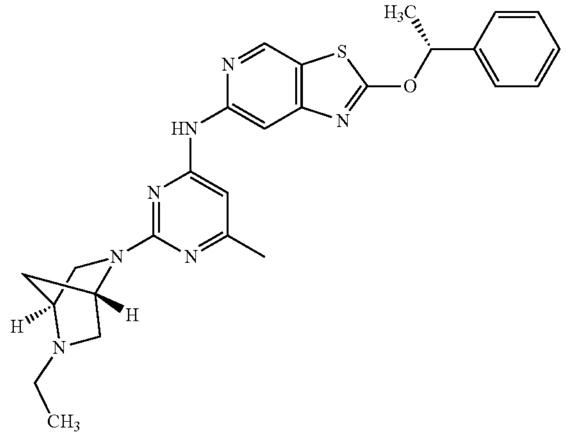 [SMILES: CCN1C[C@@H]2C[C@H]1CN2c1nc(C)cc(Nc2cc3nc(O[C@H](C)c4ccccc4)sc3cn2)n1] |
| 299 | 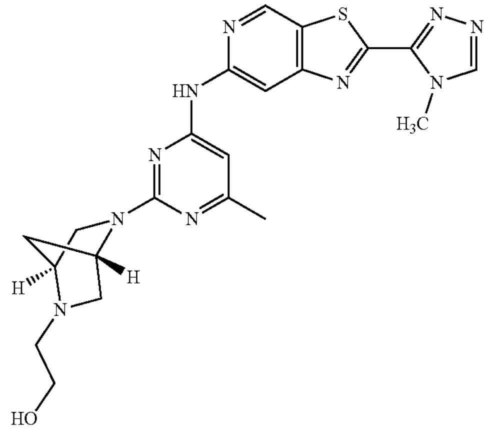 [SMILES: Cc1cc(Nc2cc3nc(-c4nncn4C)sc3cn2)nc(N2C[C@@H]3C[C@H]2CN3CCO)n1] |

TABLE 2-continued
| Ex. No. | Structure |
|---|---|
| 300 | 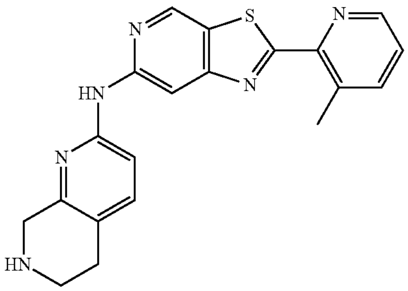 [SMILES: Cc1cccnc1-c1nc2cc(Nc3ccc4c(n3)CNCC4)ncc2s1] |
| 301 | 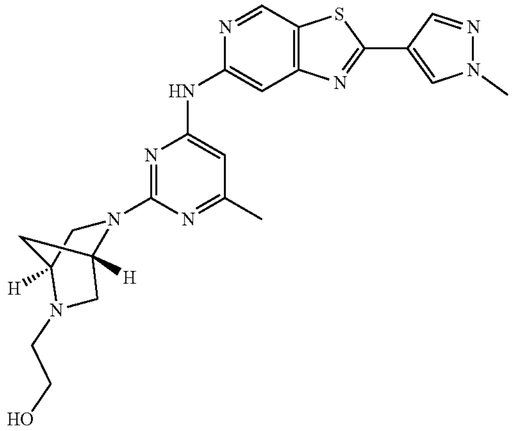 [SMILES: Cc1cc(Nc2cc3nc(-c4cnn(C)c4)sc3cn2)nc(N2C[C@@H]3C[C@H]2CN3CCO)n1] |
| 302 | 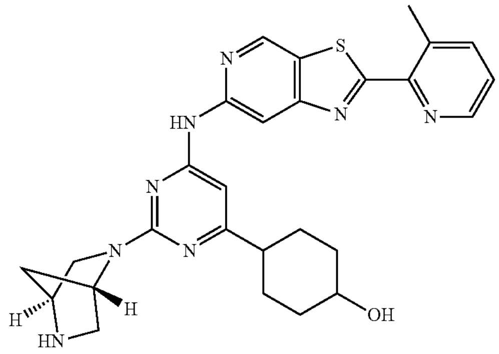 [SMILES: Cc1cccnc1-c1nc2cc(Nc3cc(C4CCC(O)CC4)nc(N4C[C@@H]5C[C@H]4CN5)n3)ncc2s1] |
| 303 | 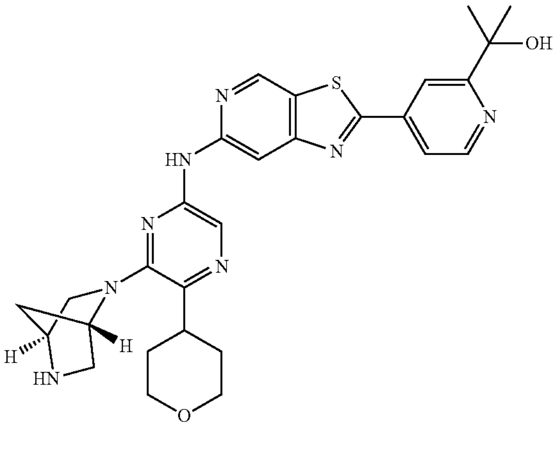 [SMILES: CC(C)(O)c1cc(-c2nc3cc(Nc4cnc(C5CCOCC5)c(N5C[C@@H]6C[C@H]5CN6)n4)ncc3s2)ccn1] |

TABLE 2-continued
| Ex. No. | Structure |
| --- | --- |
| 304 | 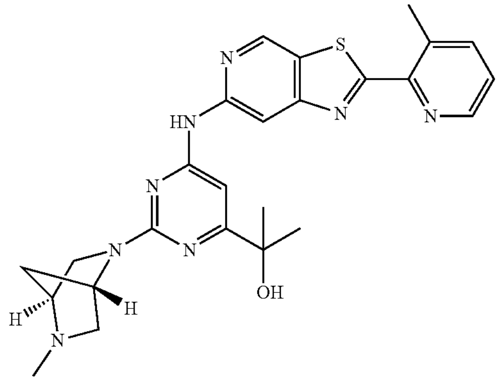 [SMILES: Cc1cccnc1-c1nc2cc(Nc3cc(C(C)(C)O)nc(N4C[C@@H]5C[C@H]4CN5C)n3)ncc2s1] |
| 305 | 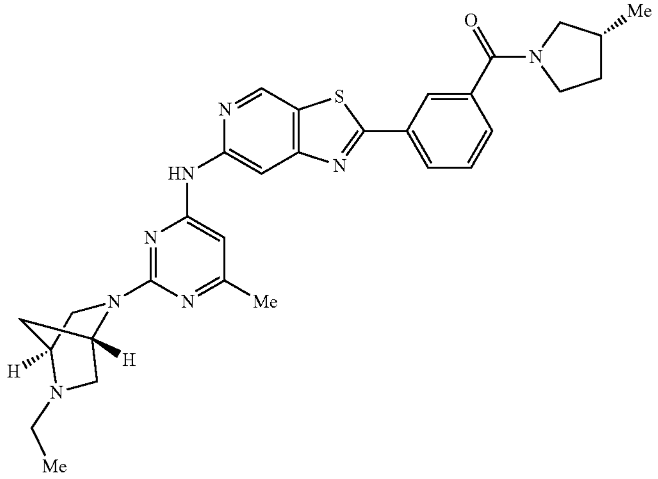 [SMILES: CCN1C[C@@H]2C[C@H]1CN2c1nc(C)cc(Nc2cc3nc(-c4cccc(C(=O)N5CC[C@@H](C)C5)c4)sc3cn2)n1] |
| 306 | 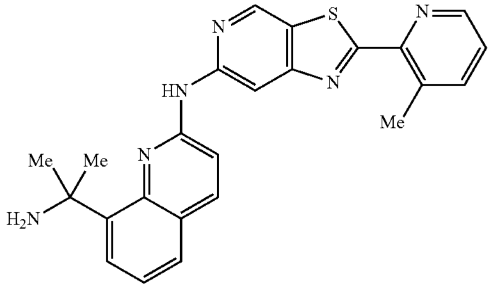 [SMILES: Cc1cccnc1-c1nc2cc(Nc3ccc4cccc(C(C)(C)N)c4n3)ncc2s1] |
| 307 | 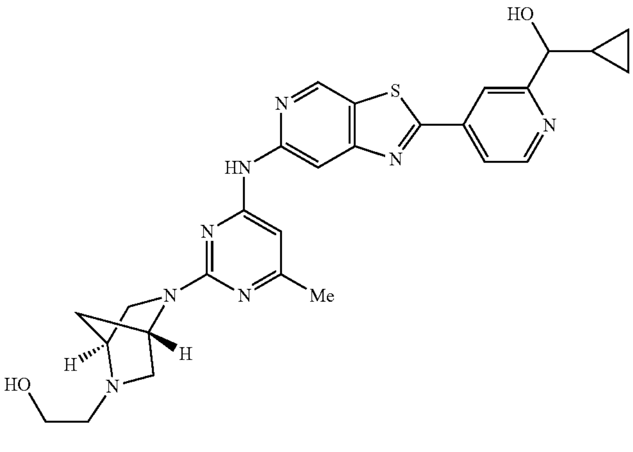 [SMILES: Cc1cc(Nc2cc3nc(-c4ccnc(C(O)C5CC5)c4)sc3cn2)nc(N2C[C@@H]3C[C@H]2CN3CCO)n1] |

TABLE 2-continued
| Ex. No. | Structure |
|---|---|
| 308 | 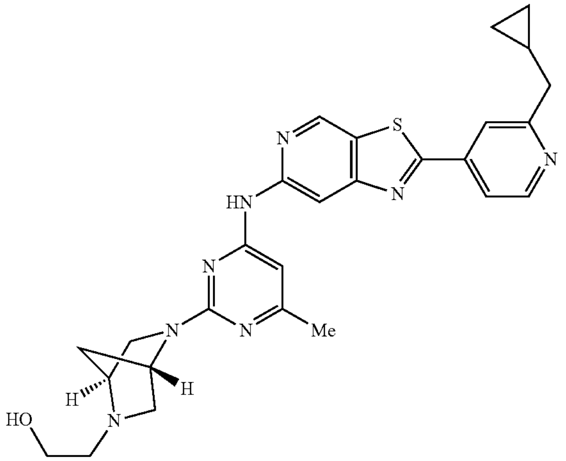 [SMILES: Cc1cc(Nc2cc3nc(-c4ccnc(CC5CC5)c4)sc3cn2)nc(N2C[C@@H]3C[C@H]2CN3CCO)n1] |
| 309 | 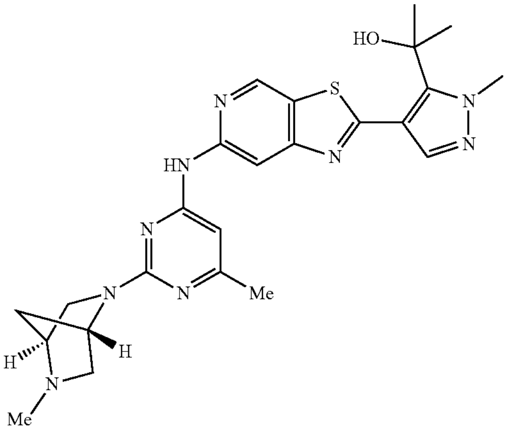 [SMILES: Cc1cc(Nc2cc3nc(-c4cnn(C)c4C(C)(C)O)sc3cn2)nc(N2C[C@@H]3C[C@H]2CN3C)n1] |
| 310 | 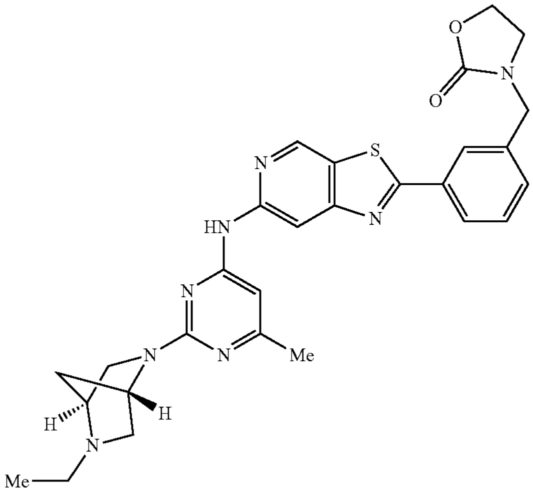 [SMILES: CCN1C[C@@H]2C[C@H]1CN2c1nc(C)cc(Nc2cc3nc(-c4cccc(CN5CCOC5=O)c4)sc3cn2)n1] |

TABLE 2-continued
| Ex. No. | Structure |
|---|---|
| 311 | 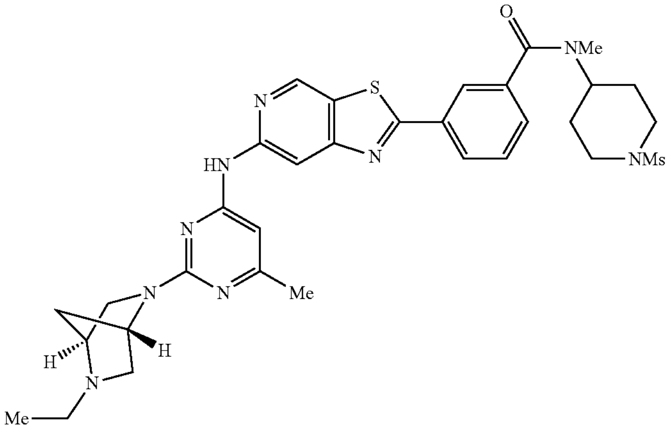 |
| 312 | 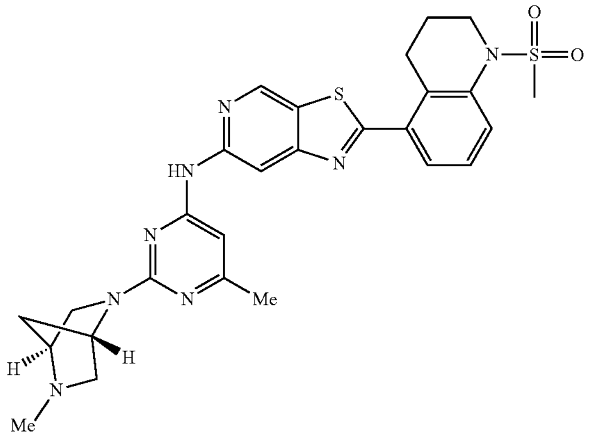 [SMILES: Cc1cc(Nc2cc3nc(-c4cccc5c4CCCN5S(C)(=O)=O)sc3cn2)nc(N2C[C@@H]3C[C@H]2CN3C)n1] |
| 313 | 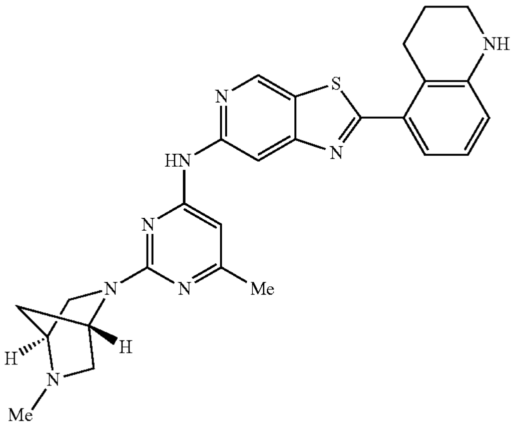 [SMILES: Cc1cc(Nc2cc3nc(-c4cccc5c4CCCN5)sc3cn2)nc(N2C[C@@H]3C[C@H]2CN3C)n1] |

TABLE 2-continued
| Ex. No. | Structure |
| --- | --- |
| 314 | 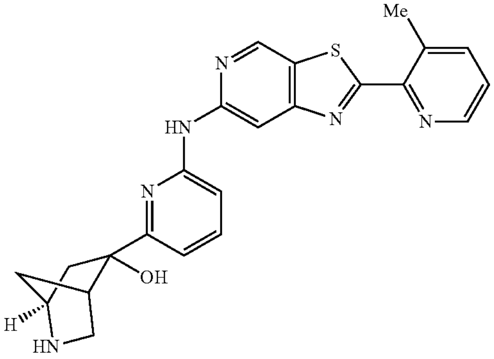 [SMILES: Cc1cccnc1-c1nc2cc(Nc3cccc(C4(O)C[C@@H]5CC4CN5)n3)ncc2s1] |
| 315 | 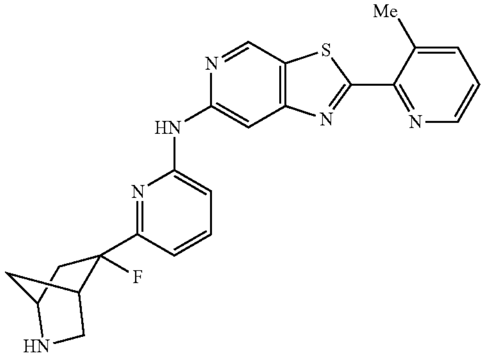 [SMILES: Cc1cccnc1-c1nc2cc(Nc3cccc(C4(F)CC5CC4CN5)n3)ncc2s1] |
| 316 | 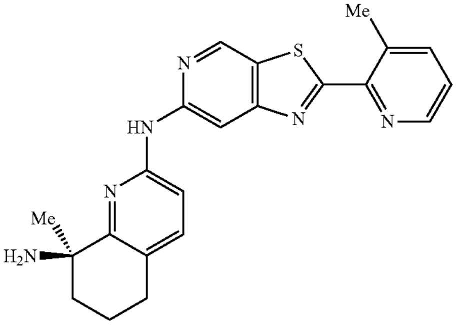 [SMILES: Cc1cccnc1-c1nc2cc(Nc3ccc4c(n3)[C@](C)(N)CCC4)ncc2s1] |
| 317 | 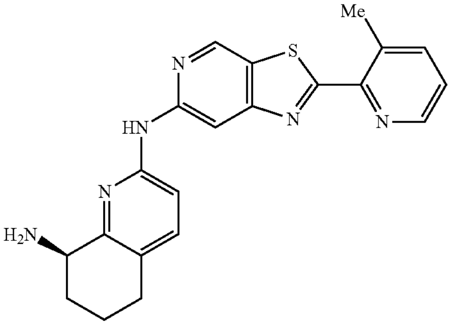 [SMILES: Cc1cccnc1-c1nc2cc(Nc3ccc4c(n3)[C@H](N)CCC4)ncc2s1] |

TABLE 2-continued
| Ex. No. | Structure |
| --- | --- |
| 318 | 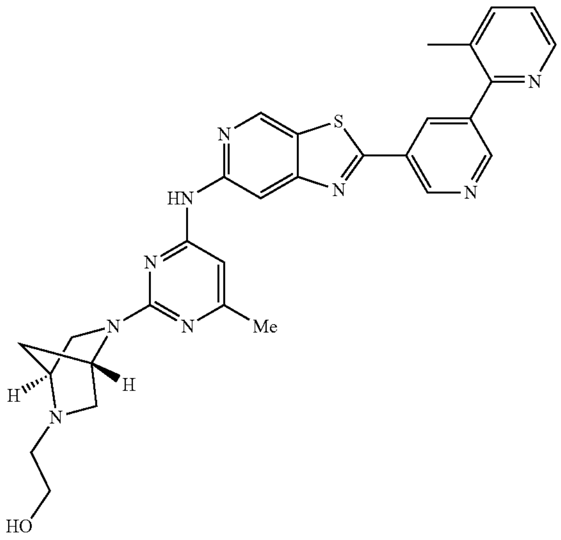 [SMILES: Cc1cc(Nc2cc3nc(-c4cncc(-c5ncccc5C)c4)sc3cn2)nc(N2C[C@@H]3C[C@H]2CN3CCO)n1] |
| 319 | 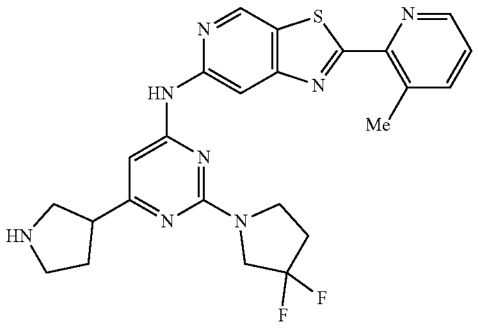 [SMILES: Cc1cccnc1-c1nc2cc(Nc3cc(C4CCNC4)nc(N4CCC(F)(F)C4)n3)ncc2s1] |
| 320 | 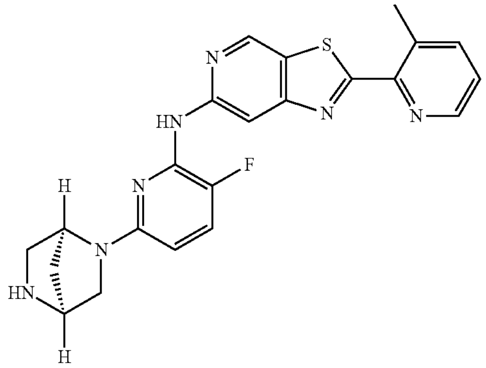 [SMILES: Cc1cccnc1-c1nc2cc(Nc3nc(N4C[C@@H]5C[C@H]4CN5)ccc3F)ncc2s1] |

TABLE 2-continued
| Ex. No. | Structure |
| --- | --- |
| 321 | 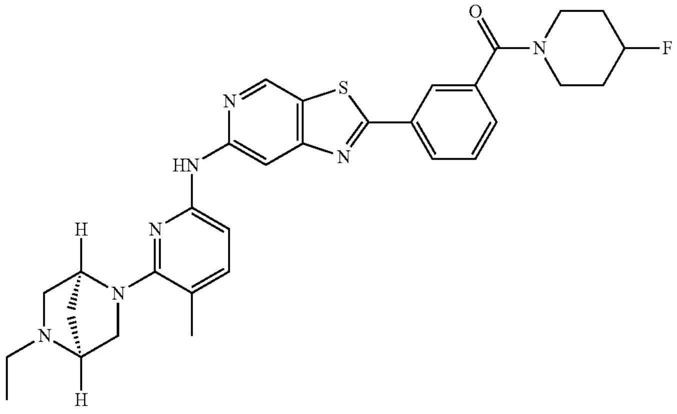 [SMILES: CCN1C[C@@H]2C[C@H]1CN2c1nc(Nc2cc3nc(-c4cccc(C(=O)N5CCC(F)CC5)c4)sc3cn2)ccc1C] |
| 322 | 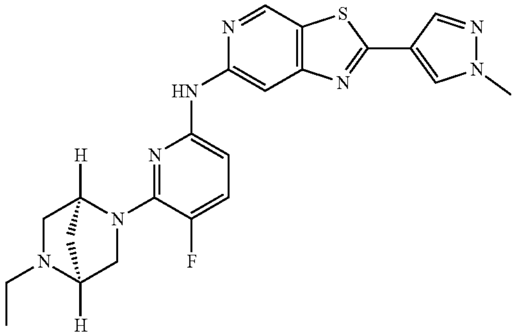 [SMILES: CCN1C[C@@H]2C[C@H]1CN2c1nc(Nc2cc3nc(-c4cnn(C)c4)sc3cn2)ccc1F] |
| 323 | 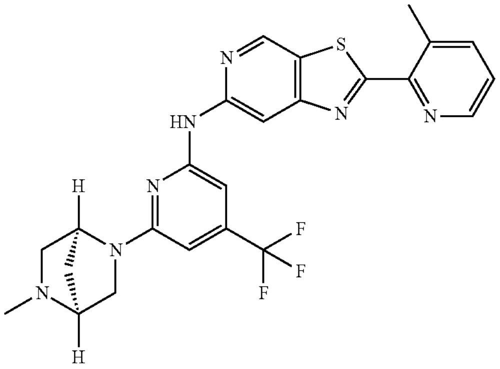 [SMILES: Cc1cccnc1-c1nc2cc(Nc3cc(C(F)(F)F)cc(N4C[C@@H]5C[C@H]4CN5C)n3)ncc2s1] |
| 324 | 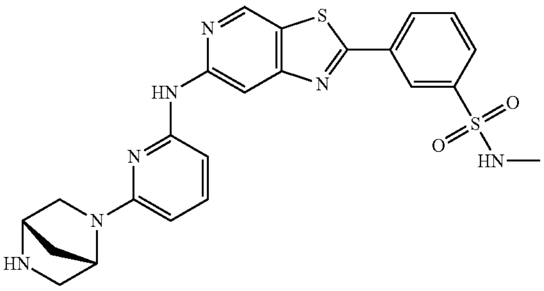 [SMILES: CNS(=O)(=O)c1cccc(-c2nc3cc(Nc4cccc(N5C[C@@H]6C[C@H]5CN6)n4)ncc3s2)c1] |

TABLE 2-continued
| Ex. No. | Structure |
|---|---|
| 325 | 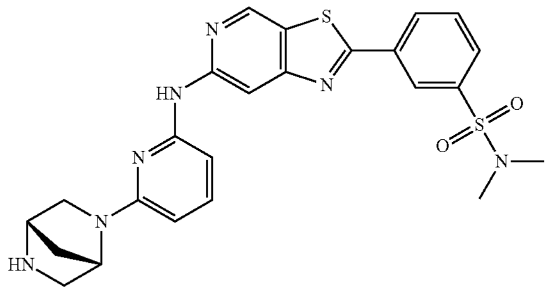 [SMILES: CN(C)S(=O)(=O)c1cccc(-c2nc3cc(Nc4cccc(N5C[C@@H]6C[C@H]5CN6)n4)ncc3s2)c1] |
| 326 | 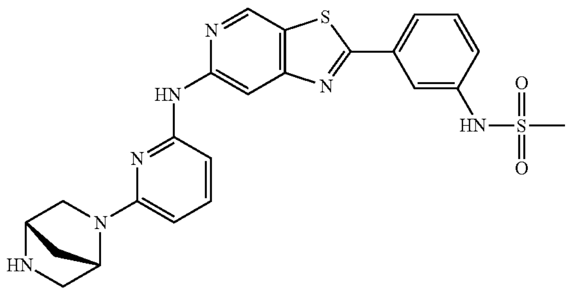 [SMILES: CS(=O)(=O)Nc1cccc(-c2nc3cc(Nc4cccc(N5C[C@@H]6C[C@H]5CN6)n4)ncc3s2)c1] |
| 327 | 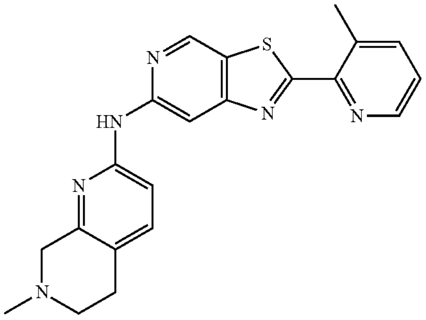 [SMILES: Cc1cccnc1-c1nc2cc(Nc3ccc4c(n3)CN(C)CC4)ncc2s1] |
| 328 | 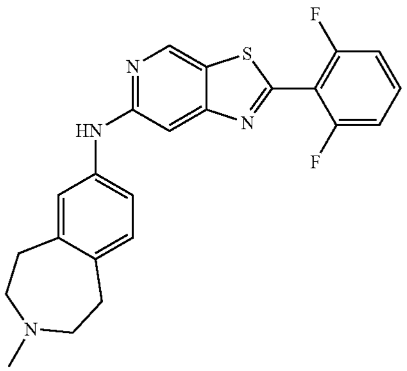 [SMILES: CN1CCc2ccc(Nc3cc4nc(-c5c(F)cccc5F)sc4cn3)cc2CC1] |

TABLE 2-continued
| Ex. No. | Structure |
|---|---|
| 329 | 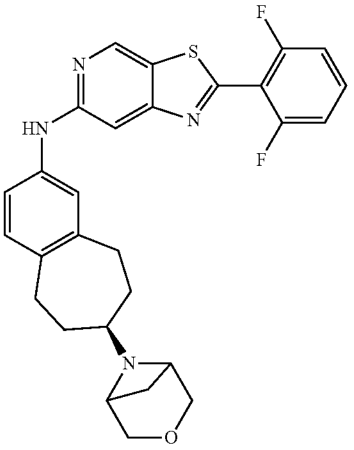 [SMILES: Fc1cccc(F)c1-c1nc2cc(Nc3ccc4c(c3)CC[C@@H](N3C5COCC3C5)CC4)ncc2s1] |
| 330 | 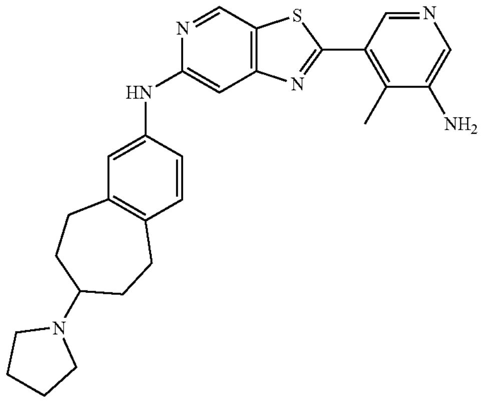 [SMILES: Cc1c(N)cncc1-c1nc2cc(Nc3ccc4c(c3)CCC(N3CCCC3)CC4)ncc2s1] |
| 331 | 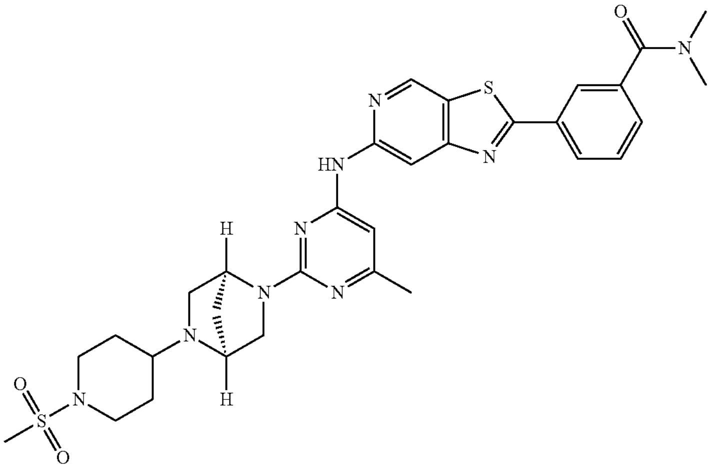 |

TABLE 2-continued
| Ex. No. | Structure |
| --- | --- |
| 332 | 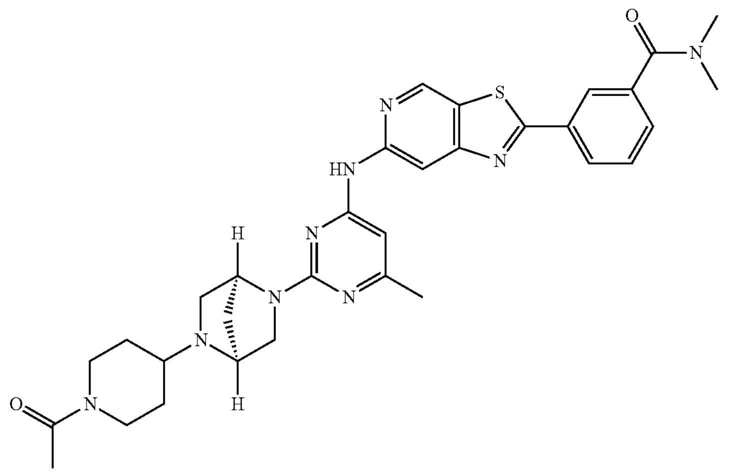 [SMILES: CC(=O)N1CCC(N2C[C@@H]3C[C@H]2CN3c2nc(C)cc(Nc3cc4nc(-c5cccc(C(=O)N(C)C)c5)sc4cn3)n2)CC1] |
| 333 | 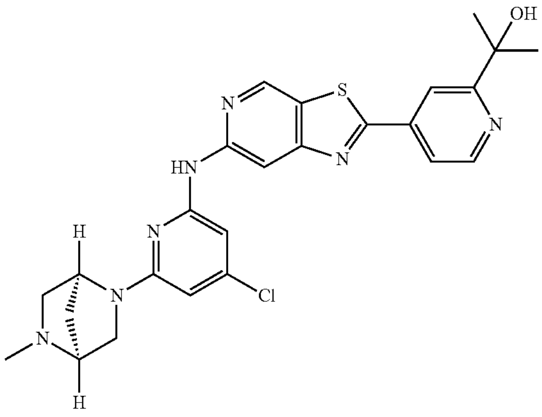 [SMILES: CN1C[C@@H]2C[C@H]1CN2c1cc(Cl)cc(Nc2cc3nc(-c4ccnc(C(C)(C)O)c4)sc3cn2)n1] |
| 334 | 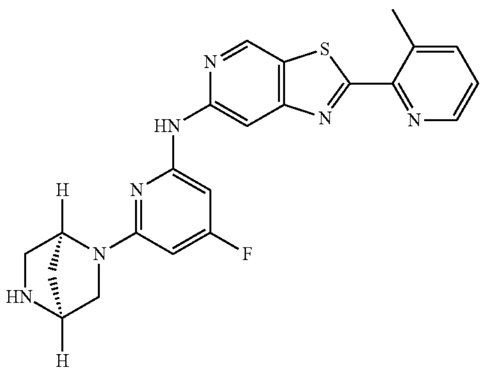 [SMILES: Cc1cccnc1-c1nc2cc(Nc3cc(F)cc(N4C[C@@H]5C[C@H]4CN5)n3)ncc2s1] |
| 335 | 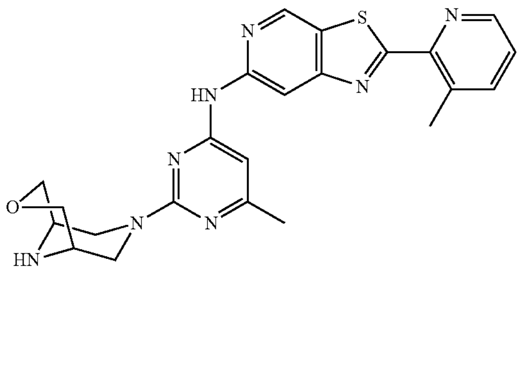 [SMILES: Cc1cc(Nc2cc3nc(-c4ncccc4C)sc3cn2)nc(N2CC3COCC(C2)N3)n1] |

TABLE 2-continued
| Ex. No. | Structure |
| --- | --- |
| 336 | 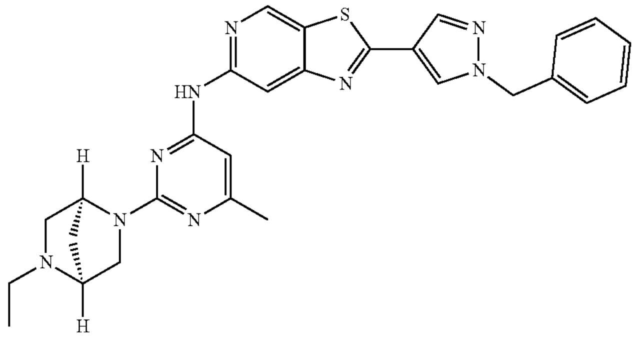 [SMILES: CCN1C[C@@H]2C[C@H]1CN2c1nc(C)cc(Nc2cc3nc(-c4cnn(Cc5ccccc5)c4)sc3cn2)n1] |
| 337 | 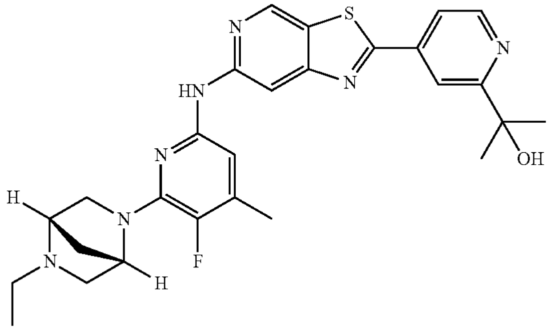 [SMILES: CCN1C[C@@H]2C[C@H]1CN2c1nc(Nc2cc3nc(-c4ccnc(C(C)(C)O)c4)sc3cn2)cc(C)c1F] |
| 338 | 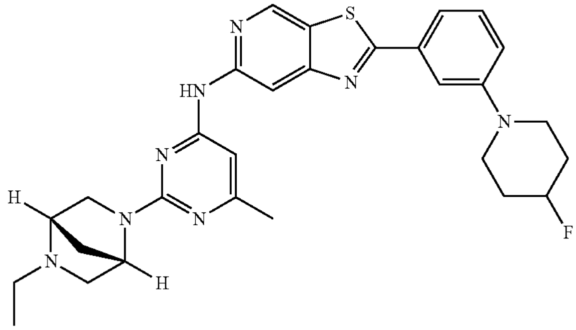 [SMILES: CCN1C[C@@H]2C[C@H]1CN2c1nc(C)cc(Nc2cc3nc(-c4cccc(N5CCC(F)CC5)c4)sc3cn2)n1] |
| 339 | 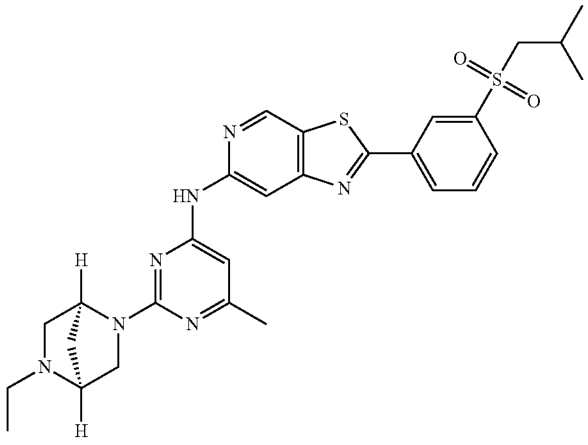 [SMILES: CCN1C[C@@H]2C[C@H]1CN2c1nc(C)cc(Nc2cc3nc(-c4cccc(S(=O)(=O)CC(C)C)c4)sc3cn2)n1] |

TABLE 2-continued
| Ex. No. | Structure |
|---|---|
| 340 | 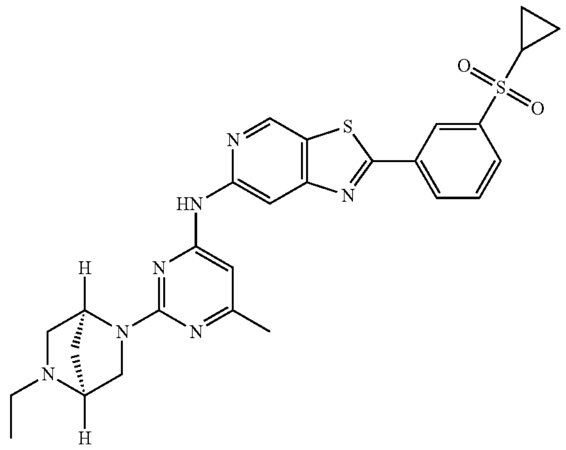 [SMILES: CCN1C[C@@H]2C[C@H]1CN2c1nc(C)cc(Nc2cc3nc(-c4cccc(S(=O)(=O)C5CC5)c4)sc3cn2)n1] |
| 341 | 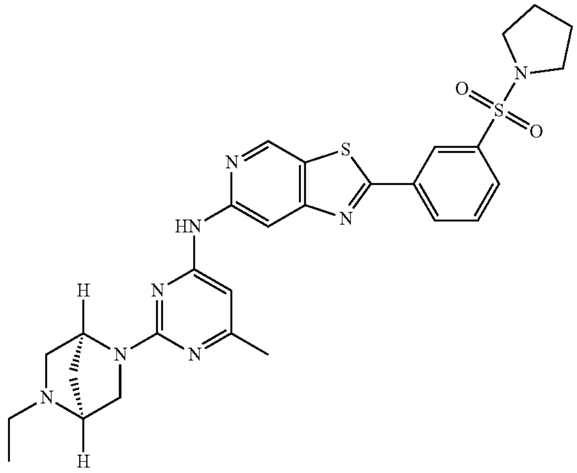 [SMILES: CCN1C[C@@H]2C[C@H]1CN2c1nc(C)cc(Nc2cc3nc(-c4cccc(S(=O)(=O)N5CCCC5)c4)sc3cn2)n1] |
| 342 | 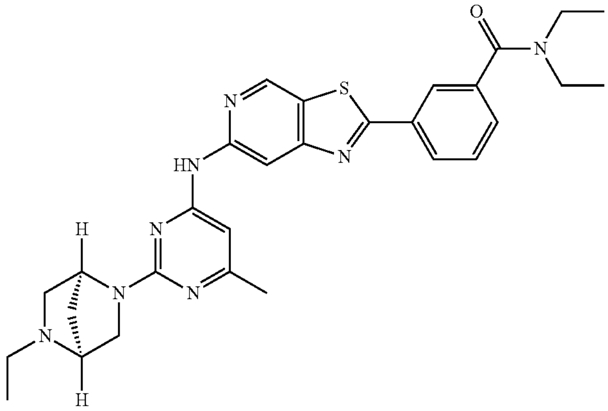 [SMILES: CCN(CC)C(=O)c1cccc(-c2nc3cc(Nc4cc(C)nc(N5C[C@@H]6C[C@H]5CN6CC)n4)ncc3s2)c1] |

TABLE 2-continued
| Ex. No. | Structure |
|---|---|
| 343 | 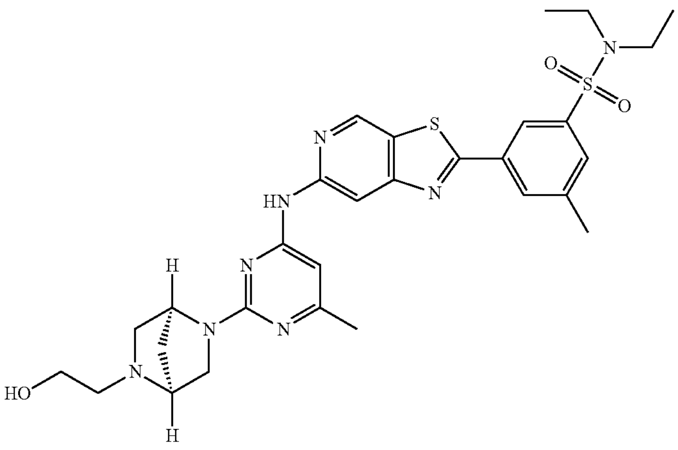 [SMILES: CCN(CC)S(=O)(=O)c1cc(C)cc(-c2nc3cc(Nc4cc(C)nc(N5C[C@@H]6C[C@H]5CN6CCO)n4)ncc3s2)c1] |
| 344 | 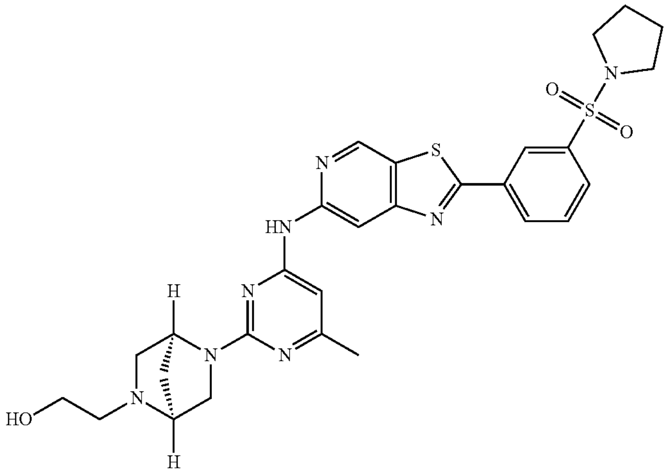 [SMILES: Cc1cc(Nc2cc3nc(-c4cccc(S(=O)(=O)N5CCCC5)c4)sc3cn2)nc(N2C[C@@H]3C[C@H]2CN3CCO)n1] |
| 345 | 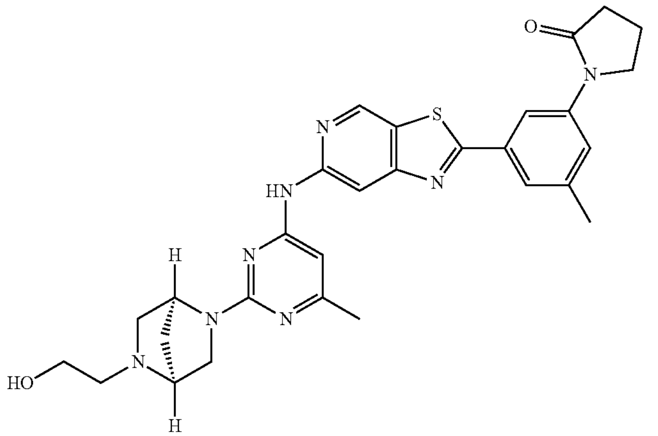 [SMILES: Cc1cc(-c2nc3cc(Nc4cc(C)nc(N5C[C@@H]6C[C@H]5CN6CCO)n4)ncc3s2)cc(N2CCCC2=O)c1] |

TABLE 2-continued
| Ex. No. | Structure |
| --- | --- |
| 346 | 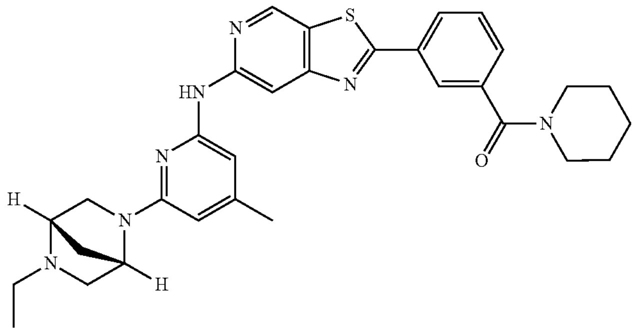 [SMILES: CCN1C[C@@H]2C[C@H]1CN2c1cc(C)cc(Nc2cc3nc(-c4cccc(C(=O)N5CCCCC5)c4)sc3cn2)n1] |
| 347 | 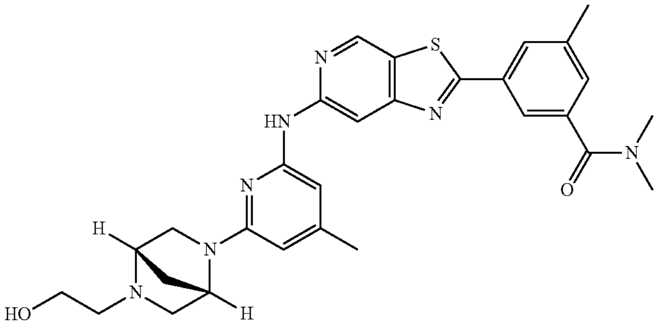 [SMILES: Cc1cc(C(=O)N(C)C)cc(-c2nc3cc(Nc4cc(C)cc(N5C[C@@H]6C[C@H]5CN6CCO)n4)ncc3s2)c1] |
| 348 | 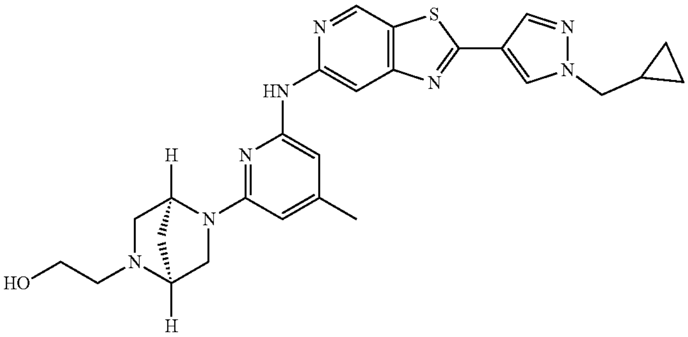 [SMILES: Cc1cc(Nc2cc3nc(-c4cnn(CC5CC5)c4)sc3cn2)nc(N2C[C@@H]3C[C@H]2CN3CCO)c1] |
| 349 | 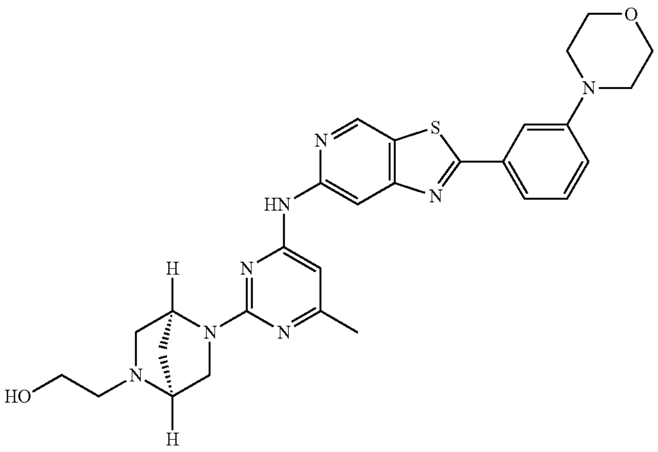 |

TABLE 2-continued
| Ex. No. | Structure |
| --- | --- |
| 350 | 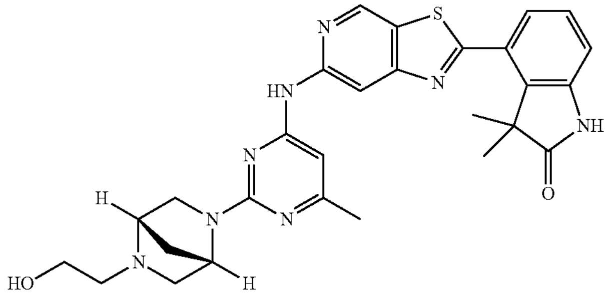 [SMILES: Cc1cc(Nc2cc3nc(-c4cccc5c4C(C)(C)C(=O)N5)sc3cn2)nc(N2C[C@@H]3C[C@H]2CN3CCO)n1] |
| 351 | 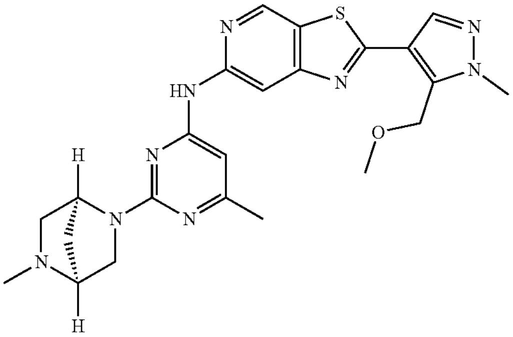 |
| 352 | 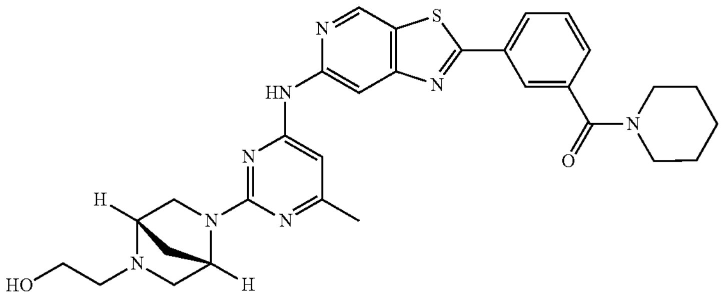 [SMILES: Cc1cc(Nc2cc3nc(-c4cccc(C(=O)N5CCCCC5)c4)sc3cn2)nc(N2C[C@@H]3C[C@H]2CN3CCO)n1] |
| 353 | 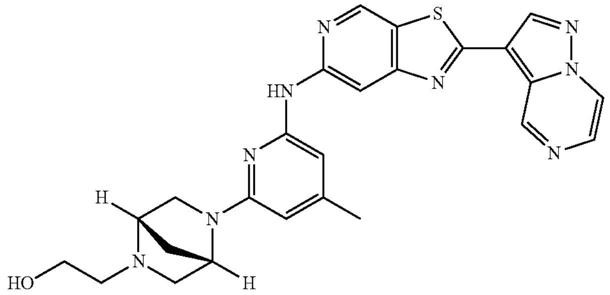 [SMILES: Cc1cc(Nc2cc3nc(-c4cnn5ccncc45)sc3cn2)nc(N2C[C@@H]3C[C@H]2CN3CCO)c1] |
| 354 | 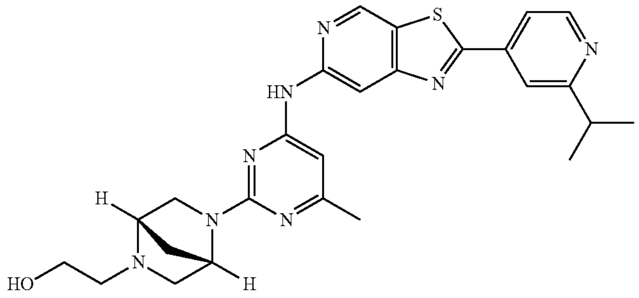 [SMILES: Cc1cc(Nc2cc3nc(-c4ccnc(C(C)C)c4)sc3cn2)nc(N2C[C@@H]3C[C@H]2CN3CCO)n1] |

TABLE 2-continued
| Ex. No. | Structure |
|---|---|
| 355 | 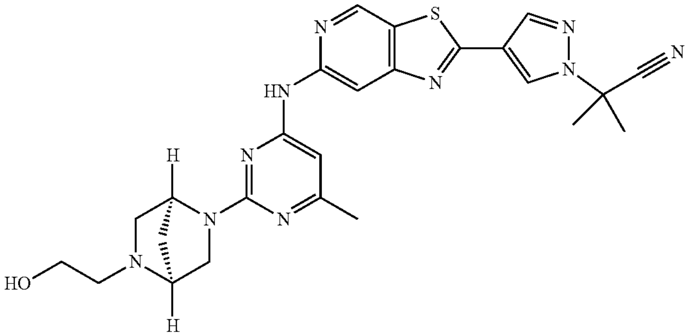 [SMILES: Cc1cc(Nc2cc3nc(-c4cnn(C(C)(C)C#N)c4)sc3cn2)nc(N2C[C@@H]3C[C@H]2CN3CCO)n1] |
| 356 | 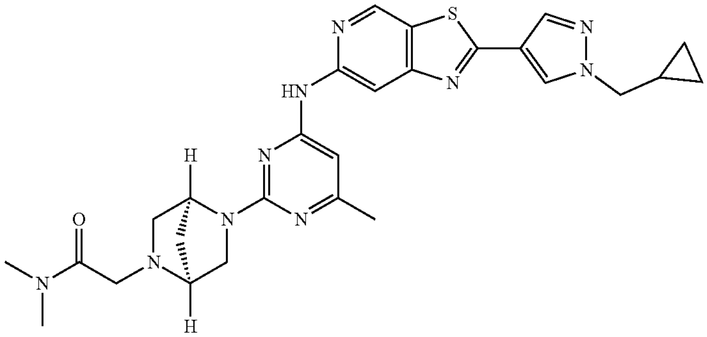 [SMILES: Cc1cc(Nc2cc3nc(-c4cnn(CC5CC5)c4)sc3cn2)nc(N2C[C@@H]3C[C@H]2CN3CC(=O)N(C)C)n1] |
| 357 | 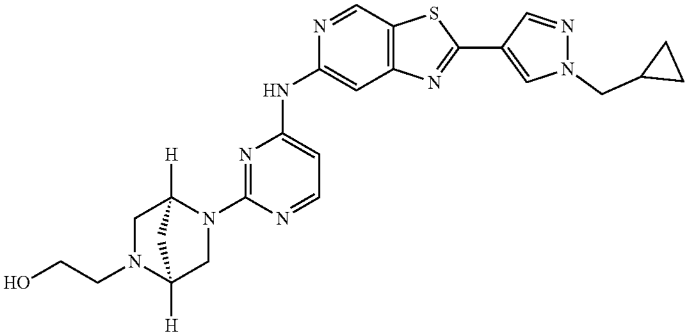 [SMILES: OCCN1C[C@@H]2C[C@H]1CN2c1nccc(Nc2cc3nc(-c4cnn(CC5CC5)c4)sc3cn2)n1] |
| 358 | 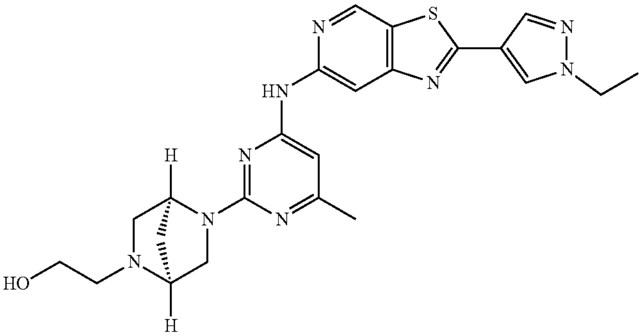 [SMILES: CCn1cc(-c2nc3cc(Nc4cc(C)nc(N5C[C@@H]6C[C@H]5CN6CCO)n4)ncc3s2)cn1] |

TABLE 2-continued
| Ex. No. | Structure |
|---|---|
| 359 | 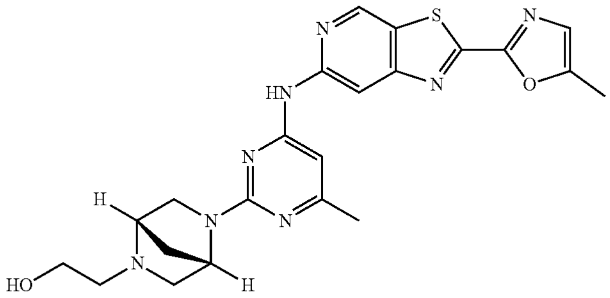 [SMILES: Cc1cc(Nc2cc3nc(-c4ncc(C)o4)sc3cn2)nc(N2C[C@@H]3C[C@H]2CN3CCO)n1] |
| 360 | 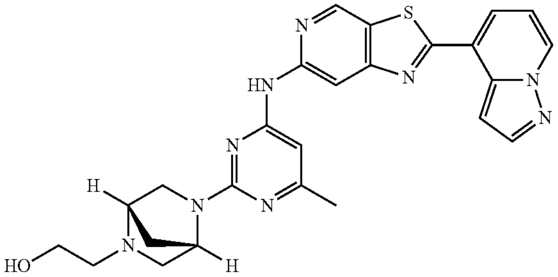 [SMILES: Cc1cc(Nc2cc3nc(-c4cccn5nccc45)sc3cn2)nc(N2C[C@@H]3C[C@H]2CN3CCO)n1] |
| 361 | 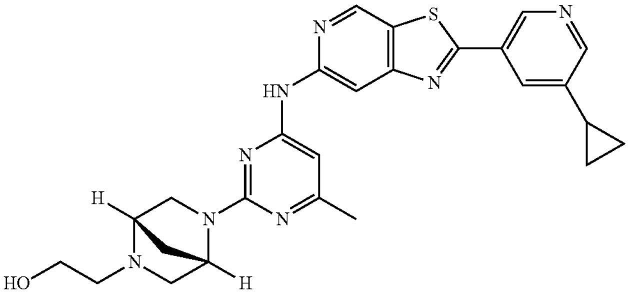 [SMILES: Cc1cc(Nc2cc3nc(-c4cncc(C5CC5)c4)sc3cn2)nc(N2C[C@@H]3C[C@H]2CN3CCO)n1] |
| 362 | 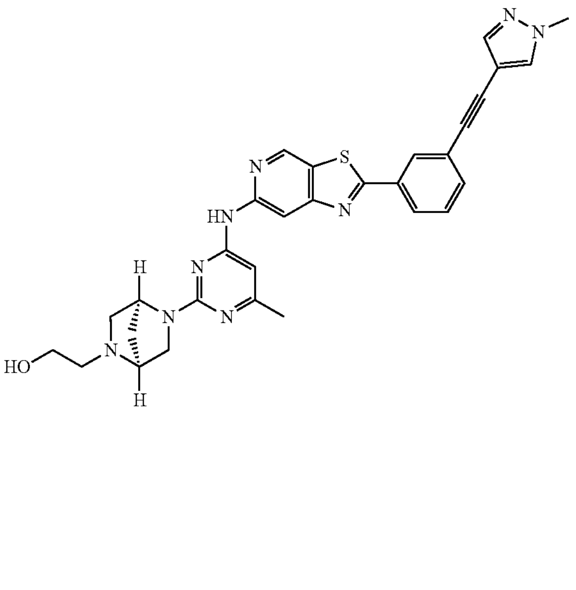 [SMILES: Cc1cc(Nc2cc3nc(-c4cccc(C#Cc5cnn(C)c5)c4)sc3cn2)nc(N2C[C@@H]3C[C@H]2CN3CCO)n1] |

TABLE 2-continued
| Ex. No. | Structure |
| --- | --- |
| 363 | 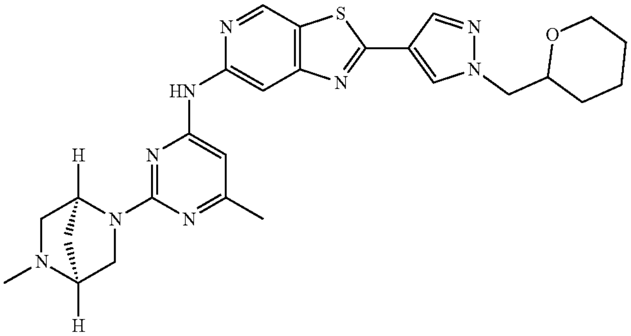 [SMILES: Cc1cc(Nc2cc3nc(-c4cnn(CC5CCCCO5)c4)sc3cn2)nc(N2C[C@@H]3C[C@H]2CN3C)n1] |
| 364 | 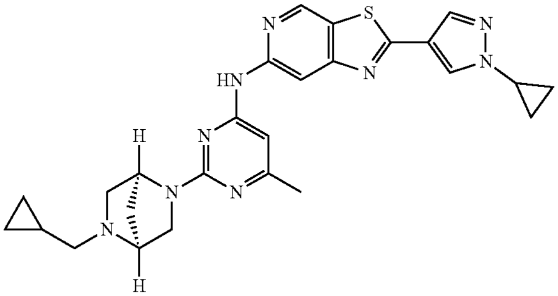 [SMILES: Cc1cc(Nc2cc3nc(-c4cnn(C5CC5)c4)sc3cn2)nc(N2C[C@@H]3C[C@H]2CN3CC2CC2)n1] |
| 365 | 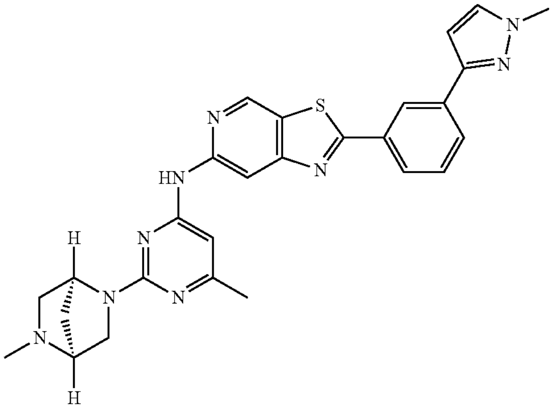 |
| 366 | 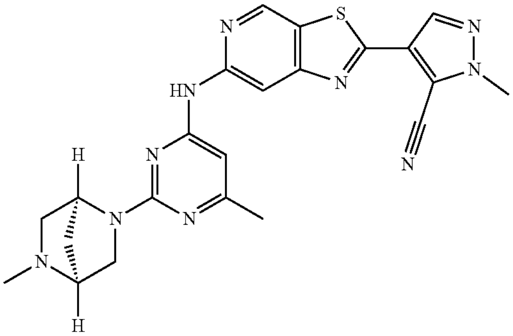 |

TABLE 2-continued
| Ex. No. | Structure |
|---|---|
| 367 | 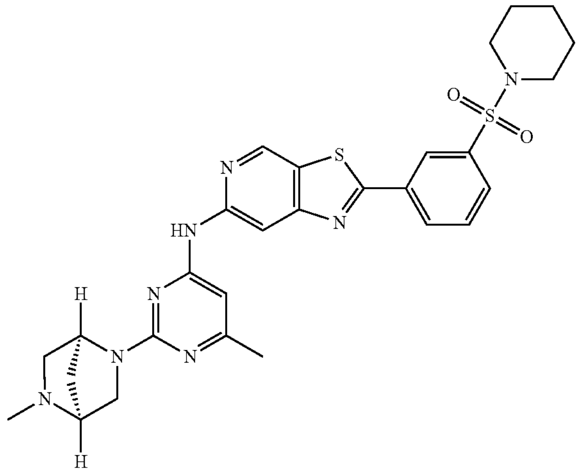 [SMILES: Cc1cc(Nc2cc3nc(-c4cccc(S(=O)(=O)N5CCCCC5)c4)sc3cn2)nc(N2C[C@@H]3C[C@H]2CN3C)n1] |
| 368 | 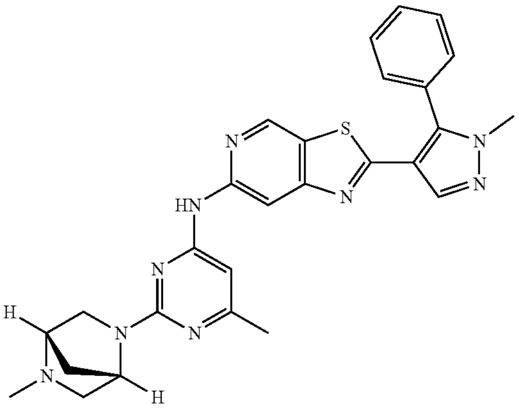 [SMILES: Cc1cc(Nc2cc3nc(-c4cnn(C)c4-c4ccccc4)sc3cn2)nc(N2C[C@@H]3C[C@H]2CN3C)n1] |
| 369 | 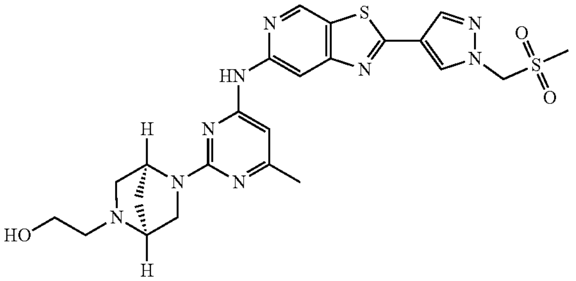 [SMILES: Cc1cc(Nc2cc3nc(-c4cnn(CS(C)(=O)=O)c4)sc3cn2)nc(N2C[C@@H]3C[C@H]2CN3CCO)n1] |
| 370 | 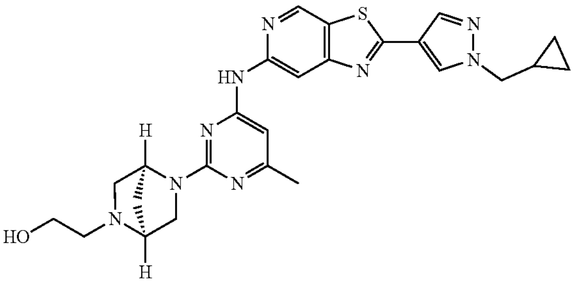 [SMILES: Cc1cc(Nc2cc3nc(-c4cnn(CC5CC5)c4)sc3cn2)nc(N2C[C@@H]3C[C@H]2CN3CCO)n1] |

TABLE 2-continued
| Ex. No. | Structure |
| --- | --- |
| 371 | 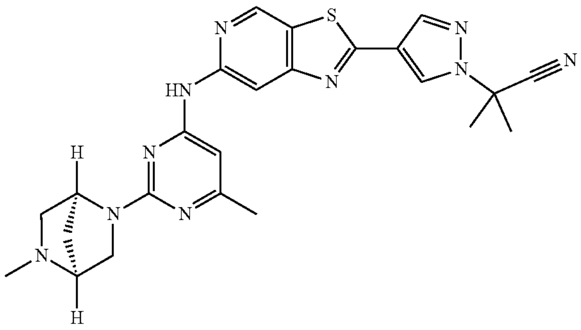 [SMILES: Cc1cc(Nc2cc3nc(-c4cnn(C(C)(C)C#N)c4)sc3cn2)nc(N2C[C@@H]3C[C@H]2CN3C)n1] |
| 372 | 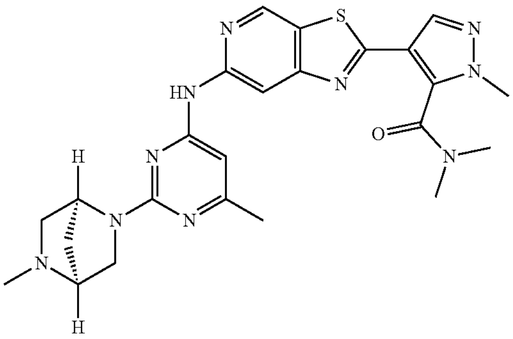 |
| 373 | 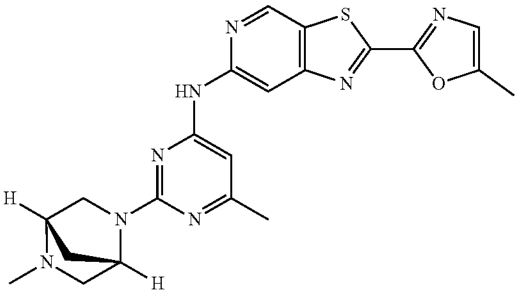 |
| 374 | 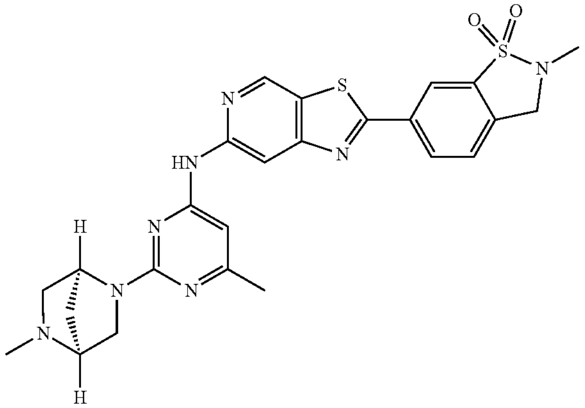 |

TABLE 2-continued
| Ex. No. | Structure |
| --- | --- |
| 375 | 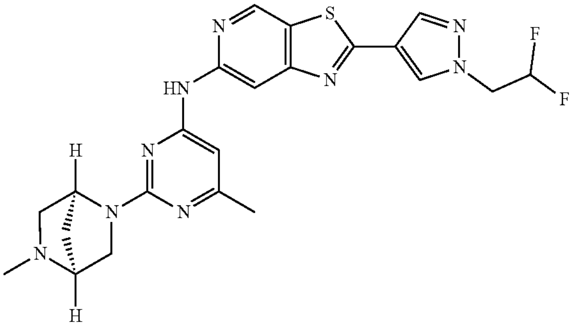 [SMILES: Cc1cc(Nc2cc3nc(-c4cnn(CC(F)F)c4)sc3cn2)nc(N2C[C@@H]3C[C@H]2CN3C)n1] |
| 376 | 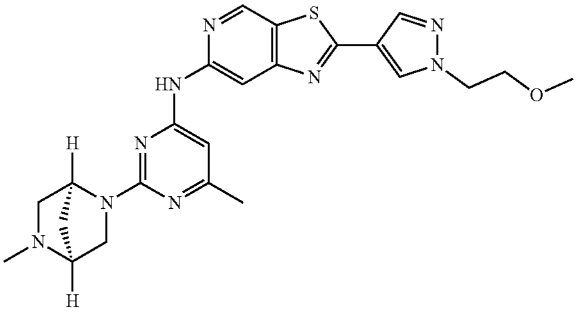 |
| 377 | 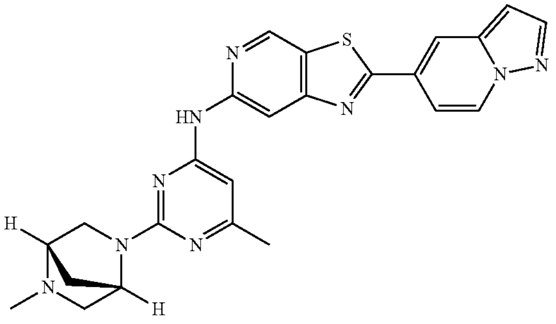 [SMILES: Cc1cc(Nc2cc3nc(-c4ccn5nccc5c4)sc3cn2)nc(N2C[C@@H]3C[C@H]2CN3C)n1] |
| 378 | 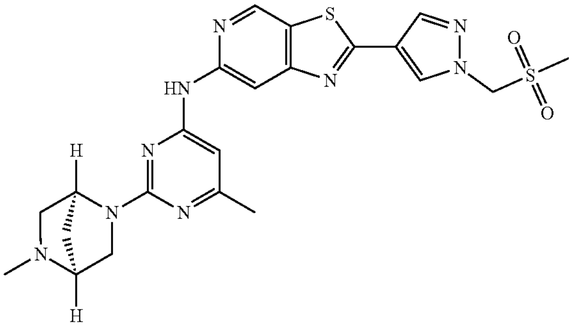 |

TABLE 2-continued
| Ex. No. | Structure |
|---|---|
| 379 | 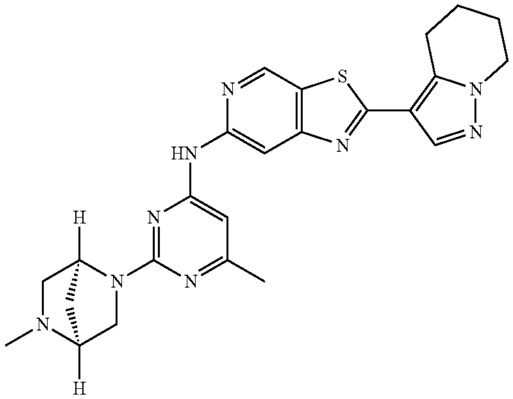 [SMILES: Cc1cc(Nc2cc3nc(-c4cnn5c4CCCC5)sc3cn2)nc(N2C[C@@H]3C[C@H]2CN3C)n1] |
| 380 | 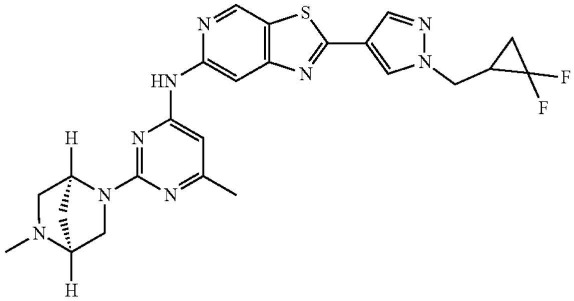 [SMILES: Cc1cc(Nc2cc3nc(-c4cnn(CC5CC5(F)F)c4)sc3cn2)nc(N2C[C@@H]3C[C@H]2CN3C)n1] |
| 381 | 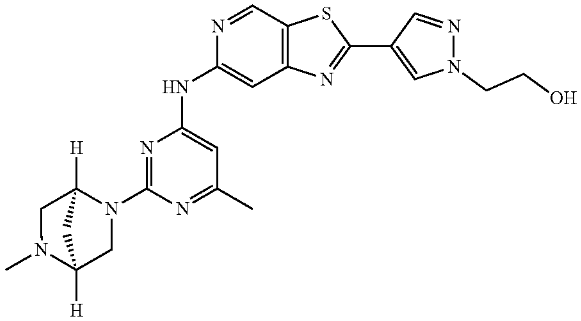 [SMILES: Cc1cc(Nc2cc3nc(-c4cnn(CCO)c4)sc3cn2)nc(N2C[C@@H]3C[C@H]2CN3C)n1] |
| 382 | 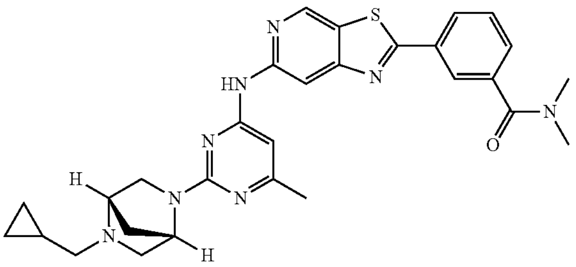 [SMILES: Cc1cc(Nc2cc3nc(-c4cccc(C(=O)N(C)C)c4)sc3cn2)nc(N2C[C@@H]3C[C@H]2CN3CC2CC2)n1] |

TABLE 2-continued
| Ex. No. | Structure |
|---|---|
| 383 | 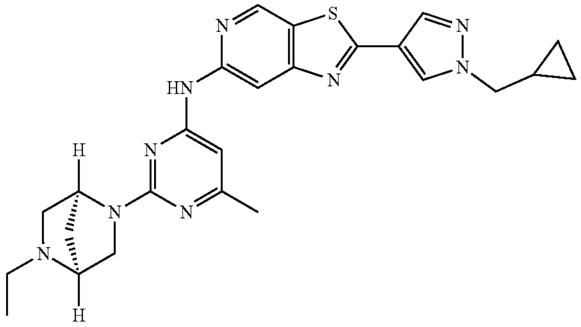 [SMILES: CCN1C[C@@H]2C[C@H]1CN2c1nc(C)cc(Nc2cc3nc(-c4cnn(CC5CC5)c4)sc3cn2)n1] |
| 384 | 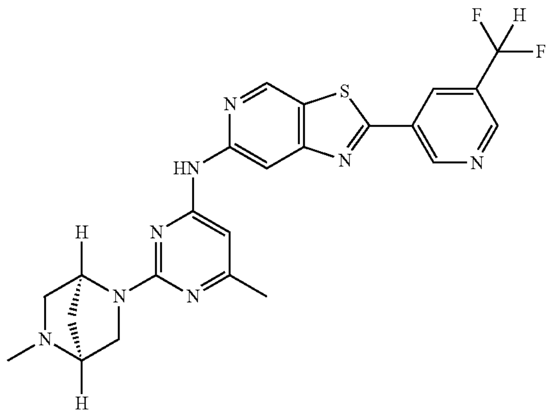 [SMILES: Cc1cc(Nc2cc3nc(-c4cncc(C(F)F)c4)sc3cn2)nc(N2C[C@@H]3C[C@H]2CN3C)n1] |
| 385 | 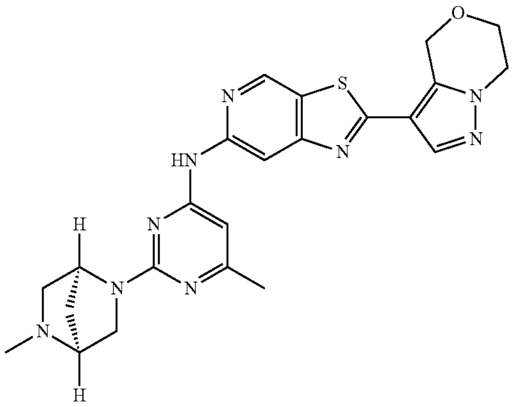 [SMILES: Cc1cc(Nc2cc3nc(-c4cnn5c4COCC5)sc3cn2)nc(N2C[C@@H]3C[C@H]2CN3C)n1] |
| 386 | 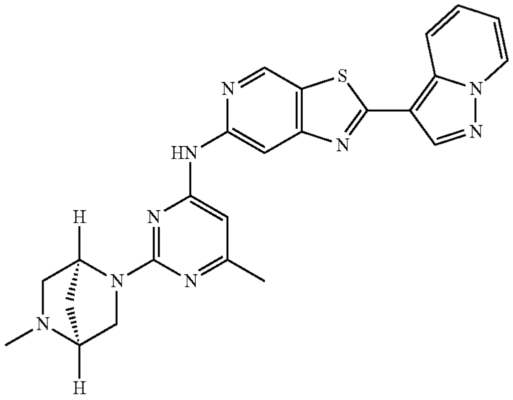 [SMILES: Cc1cc(Nc2cc3nc(-c4cnn5ccccc45)sc3cn2)nc(N2C[C@@H]3C[C@H]2CN3C)n1] |

TABLE 2-continued
| Ex. No. | Structure |
|---|---|
| 387 | 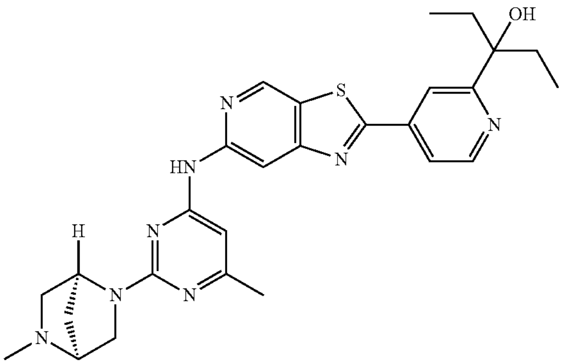 [SMILES: CCC(O)(CC)c1cc(-c2nc3cc(Nc4cc(C)nc(N5C[C@@H]6C[C@H]5CN6C)n4)ncc3s2)ccn1] |
| 388 | 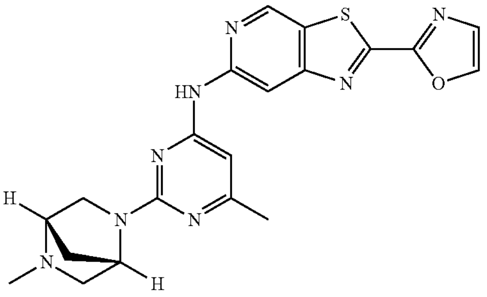 [SMILES: Cc1cc(Nc2cc3nc(-c4ncco4)sc3cn2)nc(N2C[C@@H]3C[C@H]2CN3C)n1] |
| 389 | 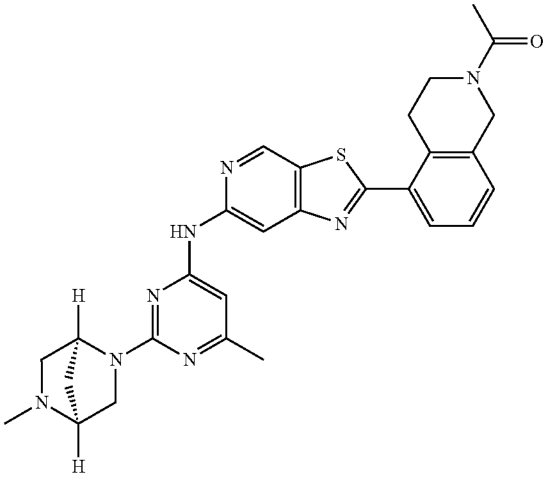 [SMILES: CC(=O)N1CCc2c(cccc2-c2nc3cc(Nc4cc(C)nc(N5C[C@@H]6C[C@H]5CN6C)n4)ncc3s2)C1] |
| 390 | 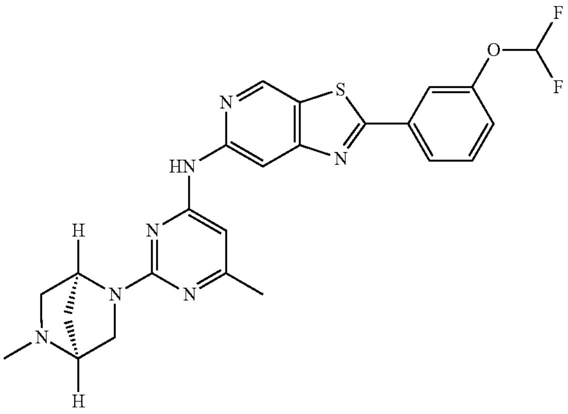 [SMILES: Cc1cc(Nc2cc3nc(-c4cccc(OC(F)F)c4)sc3cn2)nc(N2C[C@@H]3C[C@H]2CN3C)n1] |

TABLE 2-continued
| Ex. No. | Structure |
| --- | --- |
| 391 | 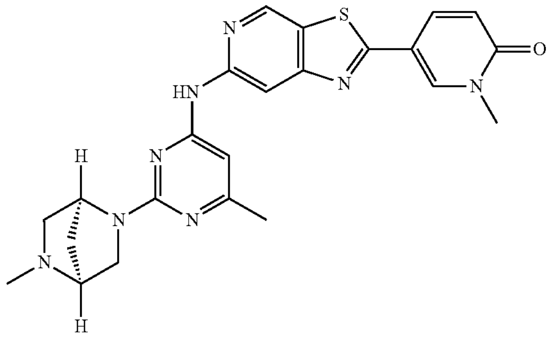 [SMILES: Cc1cc(Nc2cc3nc(-c4ccc(=O)n(C)c4)sc3cn2)nc(N2C[C@@H]3C[C@H]2CN3C)n1] |
| 392 | 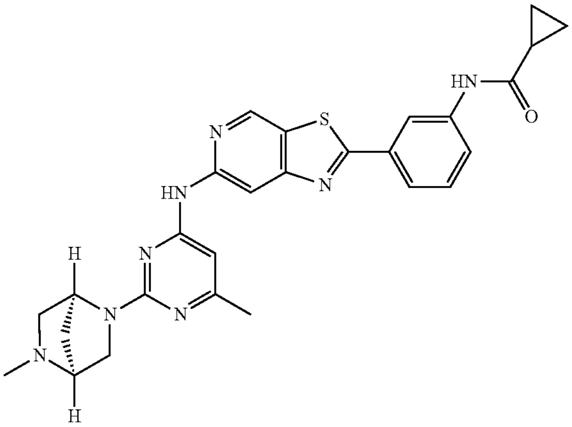 [SMILES: Cc1cc(Nc2cc3nc(-c4cccc(NC(=O)C5CC5)c4)sc3cn2)nc(N2C[C@@H]3C[C@H]2CN3C)n1] |
| 393 | 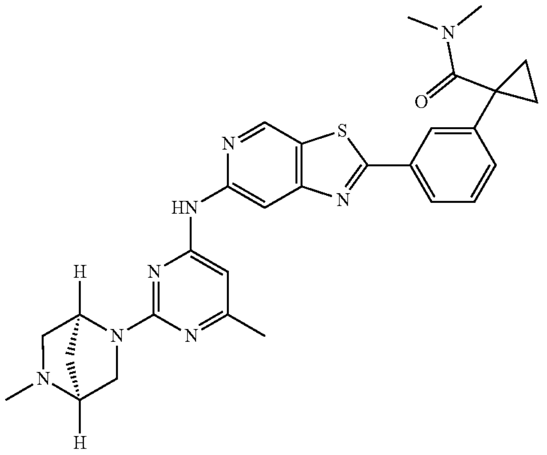 [SMILES: Cc1cc(Nc2cc3nc(-c4cccc(C5(C(=O)N(C)C)CC5)c4)sc3cn2)nc(N2C[C@@H]3C[C@H]2CN3C)n1] |

TABLE 2-continued
| Ex. No. | Structure |
| --- | --- |
| 394 | 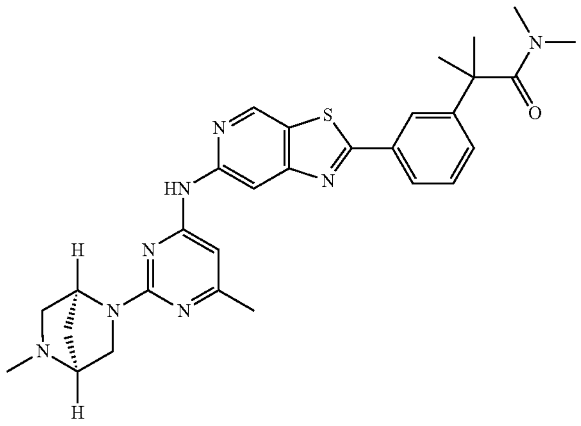 |
| 395 | 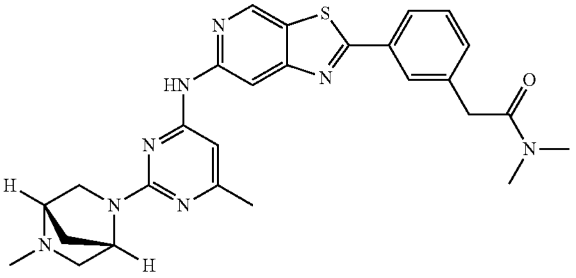 [SMILES: Cc1cc(Nc2cc3nc(-c4cccc(CC(=O)N(C)C)c4)sc3cn2)nc(N2C[C@@H]3C[C@H]2CN3C)n1] |
| 396 | 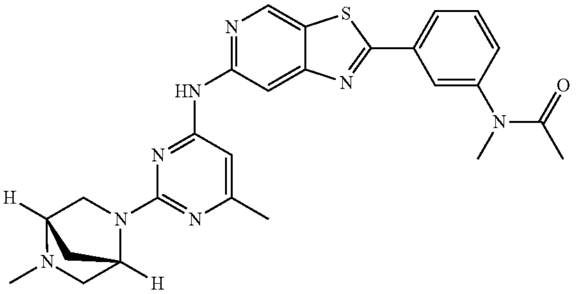 [SMILES: CC(=O)N(C)c1cccc(-c2nc3cc(Nc4cc(C)nc(N5C[C@@H]6C[C@H]5CN6C)n4)ncc3s2)c1] |
| 397 | 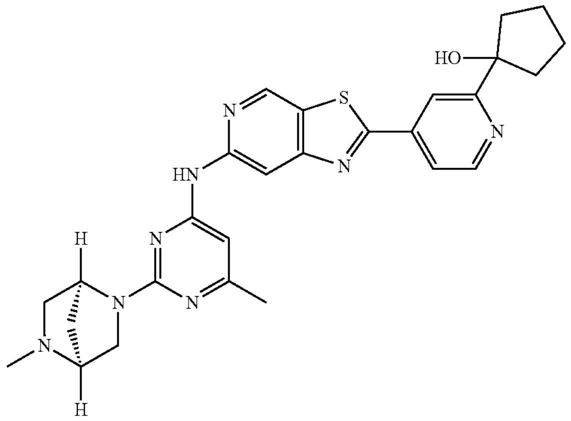 [SMILES: Cc1cc(Nc2cc3nc(-c4ccnc(C5(O)CCCC5)c4)sc3cn2)nc(N2C[C@@H]3C[C@H]2CN3C)n1] |

TABLE 2-continued
| Ex. No. | Structure |
|---|---|
| 398 | 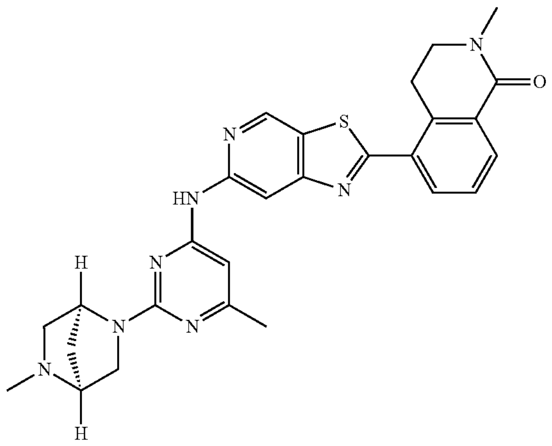 [SMILES: Cc1cc(Nc2cc3nc(-c4cccc5c4CCN(C)C5=O)sc3cn2)nc(N2C[C@@H]3C[C@H]2CN3C)n1] |
| 399 | 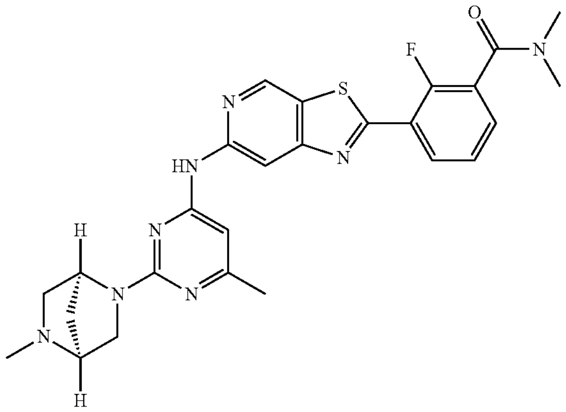 |
| 400 | 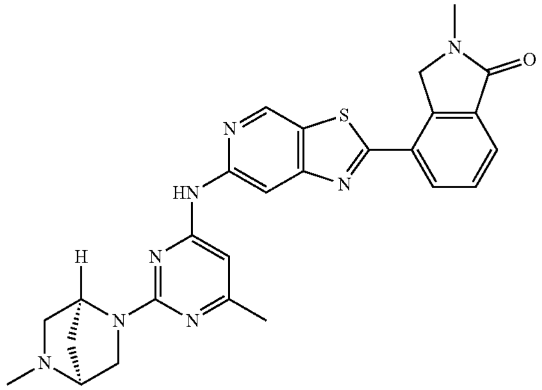 [SMILES: Cc1cc(Nc2cc3nc(-c4cccc5c4CN(C)C5=O)sc3cn2)nc(N2C[C@@H]3C[C@H]2CN3C)n1] |

TABLE 2-continued
| Ex. No. | Structure |
|---|---|
| 401 | 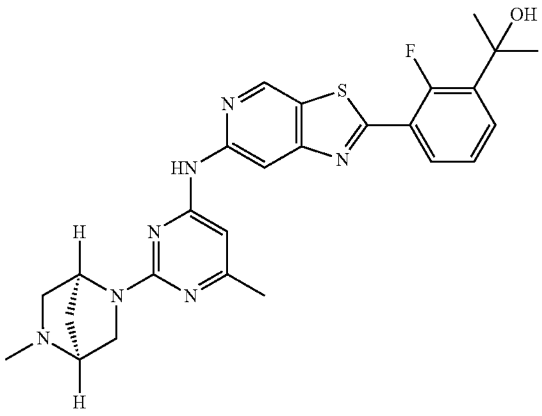 [SMILES: Cc1cc(Nc2cc3nc(-c4cccc(C(C)(C)O)c4F)sc3cn2)nc(N2C[C@@H]3C[C@H]2CN3C)n1] |
| 402 | 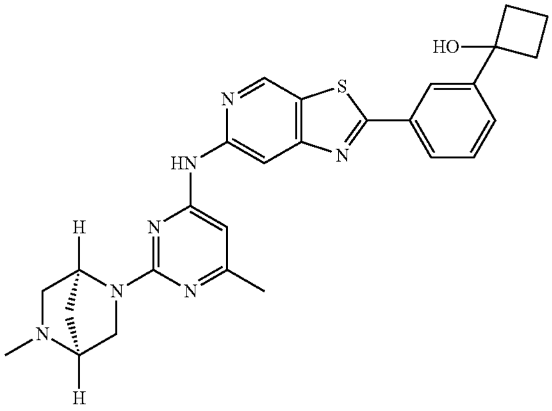 [SMILES: Cc1cc(Nc2cc3nc(-c4cccc(C5(O)CCC5)c4)sc3cn2)nc(N2C[C@@H]3C[C@H]2CN3C)n1] |
| 403 | 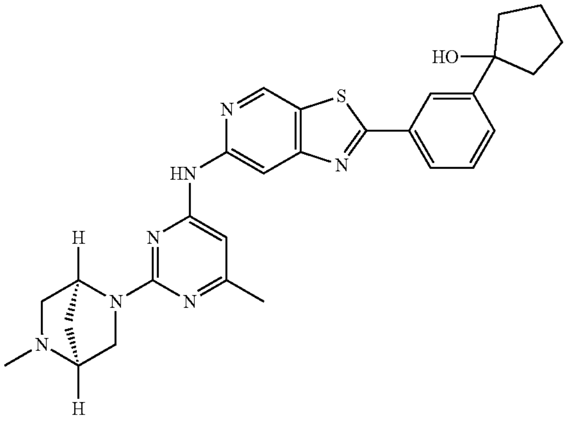 |

TABLE 2-continued
| Ex. No. | Structure |
|---|---|
| 404 | 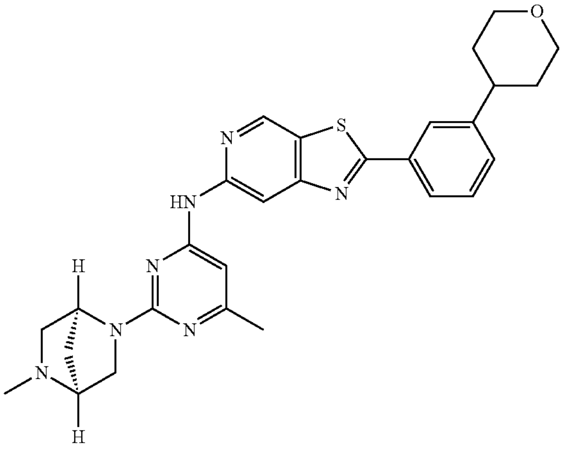 [SMILES: Cc1cc(Nc2cc3nc(-c4cccc(C5CCOCC5)c4)sc3cn2)nc(N2C[C@@H]3C[C@H]2CN3C)n1] |
| 405 | 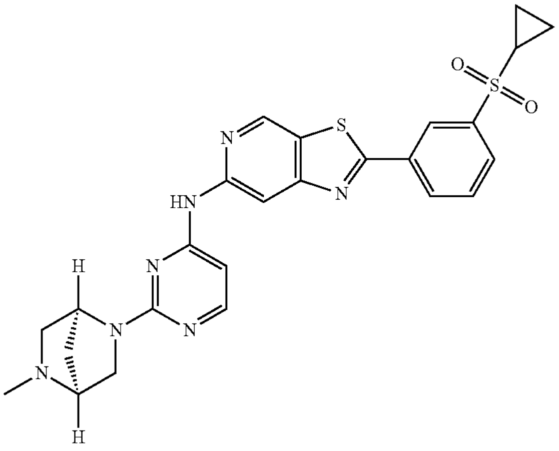 [SMILES: CN1C[C@@H]2C[C@H]1CN2c1nccc(Nc2cc3nc(-c4cccc(S(=O)(=O)C5CC5)c4)sc3cn2)n1] |
| 406 | 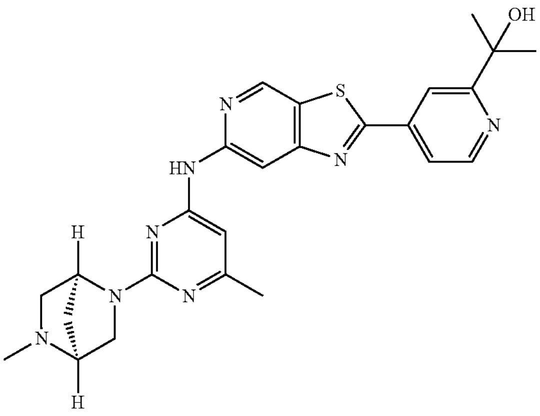 [SMILES: Cc1cc(Nc2cc3nc(-c4ccnc(C(C)(C)O)c4)sc3cn2)nc(N2C[C@@H]3C[C@H]2CN3C)n1] |

TABLE 2-continued
| Ex. No. | Structure |
| --- | --- |
| 407 | 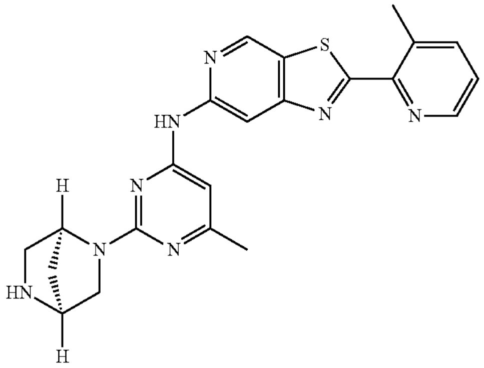 [SMILES: Cc1cc(Nc2cc3nc(-c4ncccc4C)sc3cn2)nc(N2C[C@@H]3C[C@H]2CN3)n1] |
| 408 | 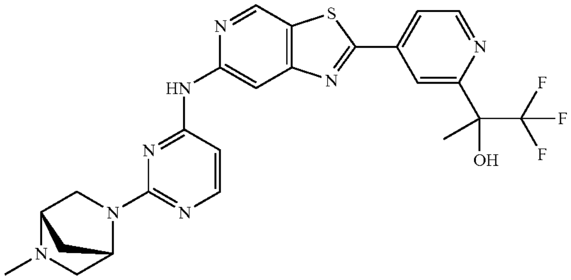 [SMILES: CN1C[C@@H]2C[C@H]1CN2c1nccc(Nc2cc3nc(-c4ccnc(C(C)(O)C(F)(F)F)c4)sc3cn2)n1] |
| 409 | 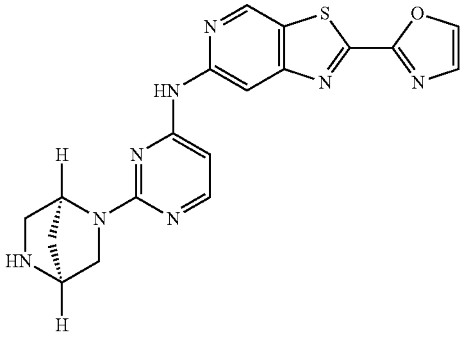 [SMILES: c1cc(Nc2cc3nc(-c4ncco4)sc3cn2)nc(N2C[C@@H]3C[C@H]2CN3)n1] |
| 410 | 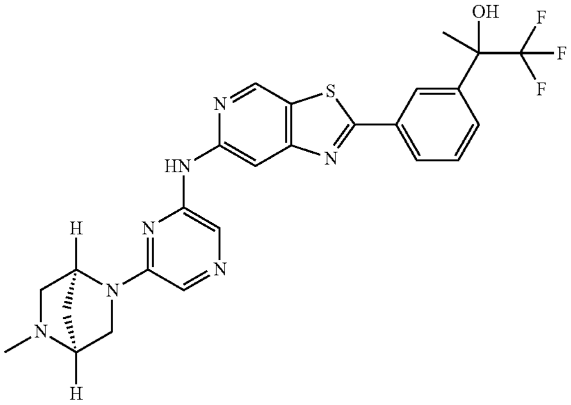 [SMILES: CN1C[C@@H]2C[C@H]1CN2c1cncc(Nc2cc3nc(-c4cccc(C(C)(O)C(F)(F)F)c4)sc3cn2)n1] |

TABLE 2-continued
| Ex. No. | Structure |
|---|---|
| 411 | 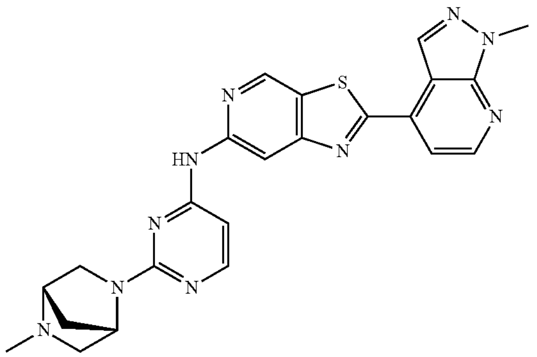 |
| 412 | 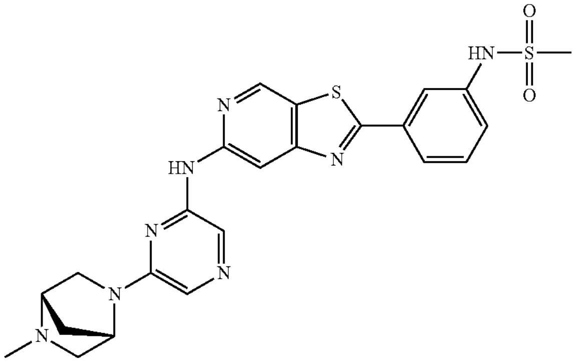 |
| 413 | 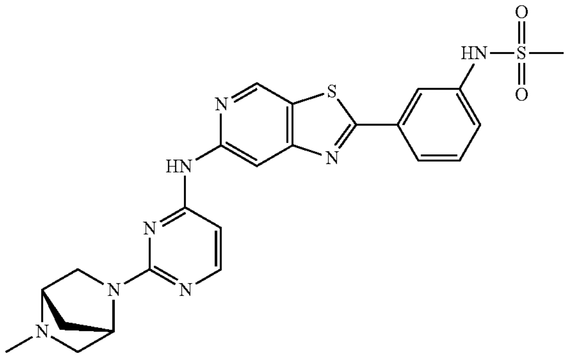 |
| 414 | 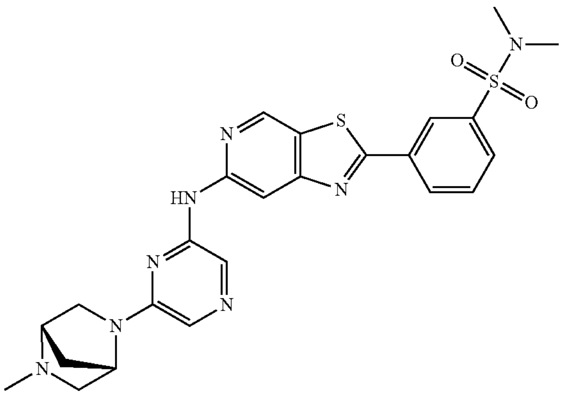 |

TABLE 2-continued
| Ex. No. | Structure |
|---|---|
| 415 | 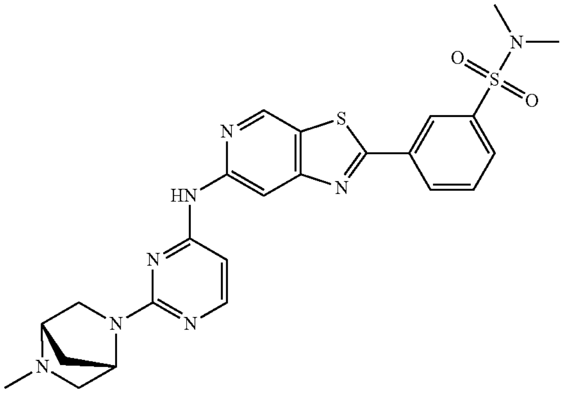 |
| 416 | 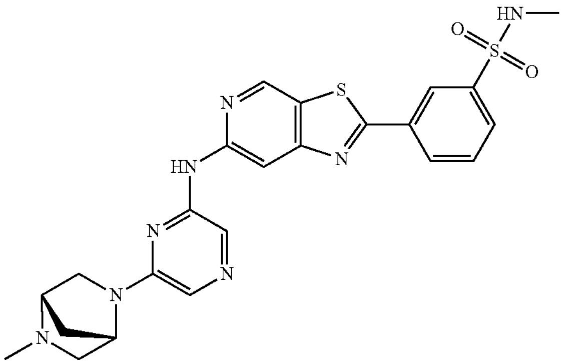 |
| 417 | 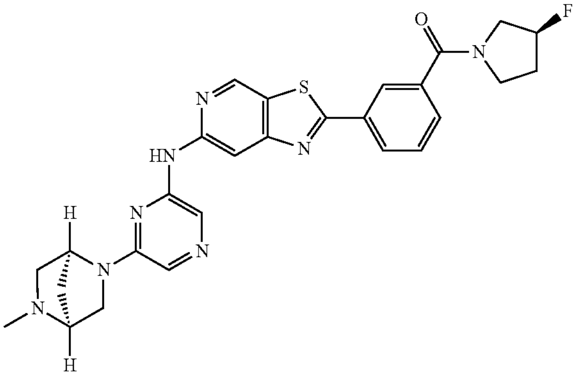 [SMILES: CN1C[C@@H]2C[C@H]1CN2c1cncc(Nc2cc3nc(-c4cccc(C(=O)N5CC[C@H](F)C5)c4)sc3cn2)n1] |
| 418 | 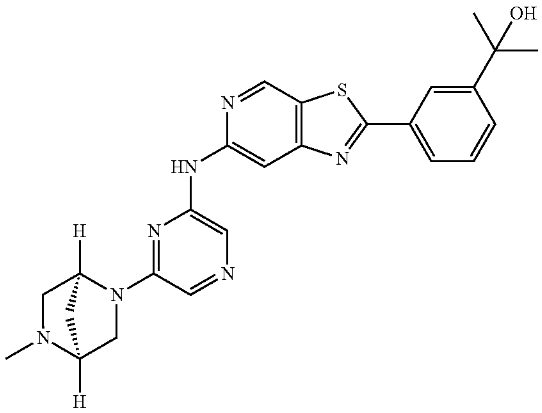 [SMILES: CN1C[C@@H]2C[C@H]1CN2c1cncc(Nc2cc3nc(-c4cccc(C(C)(C)O)c4)sc3cn2)n1] |

TABLE 2-continued
| Ex. No. | Structure |
|---|---|
| 419 | 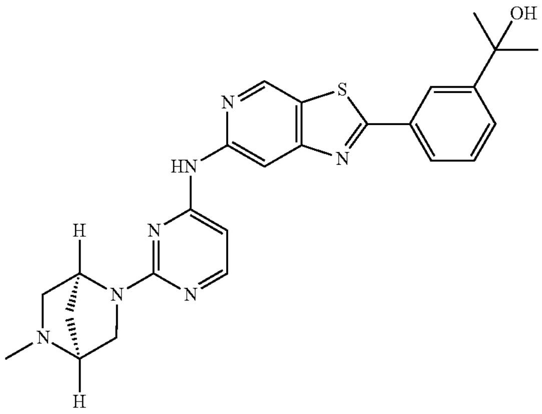 [SMILES: CN1C[C@@H]2C[C@H]1CN2c1nccc(Nc2cc3nc(-c4cccc(C(C)(C)O)c4)sc3cn2)n1] |
| 420 | 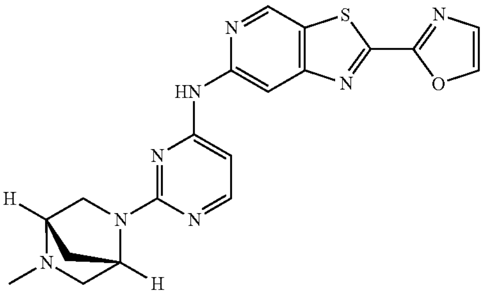 [SMILES: CN1C[C@@H]2C[C@H]1CN2c1nccc(Nc2cc3nc(-c4ncco4)sc3cn2)n1] |
| 421 | 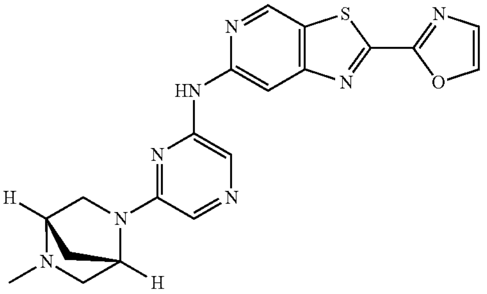 [SMILES: CN1C[C@@H]2C[C@H]1CN2c1cncc(Nc2cc3nc(-c4ncco4)sc3cn2)n1] |
| 422 | 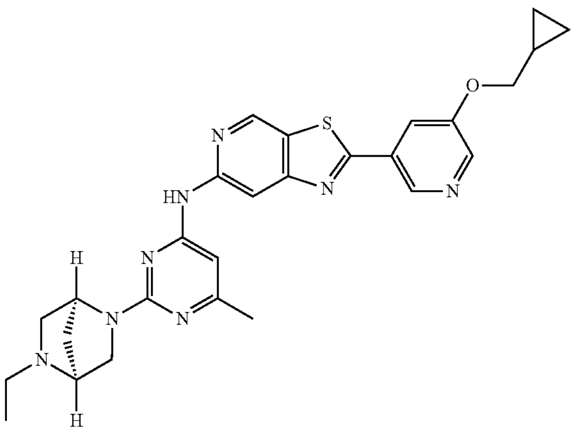 [SMILES: CCN1C[C@@H]2C[C@H]1CN2c1nc(C)cc(Nc2cc3nc(-c4cncc(OCC5CC5)c4)sc3cn2)n1] |

TABLE 2-continued
| Ex. No. | Structure |
|---|---|
| 423 | 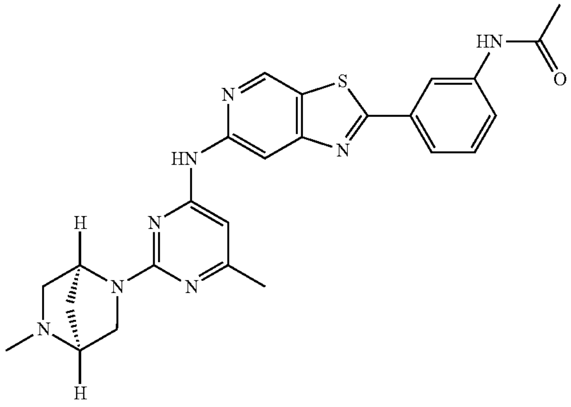 [SMILES: CC(=O)Nc1cccc(-c2nc3cc(Nc4cc(C)nc(N5C[C@@H]6C[C@H]5CN6C)n4)ncc3s2)c1] |
| 424 | 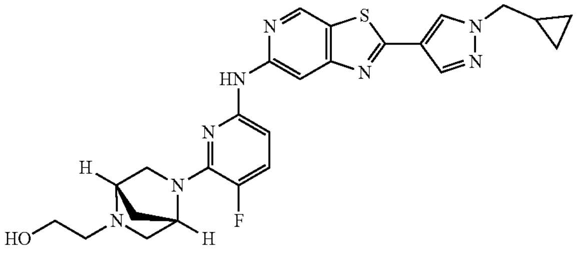 [SMILES: OCCN1C[C@@H]2C[C@H]1CN2c1nc(Nc2cc3nc(-c4cnn(CC5CC5)c4)sc3cn2)ccc1F] |
| 425 | 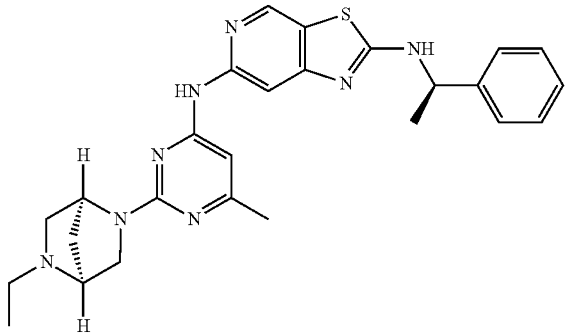 [SMILES: CCN1C[C@@H]2C[C@H]1CN2c1nc(C)cc(Nc2cc3nc(N[C@H](C)c4ccccc4)sc3cn2)n1] |
| 426 | 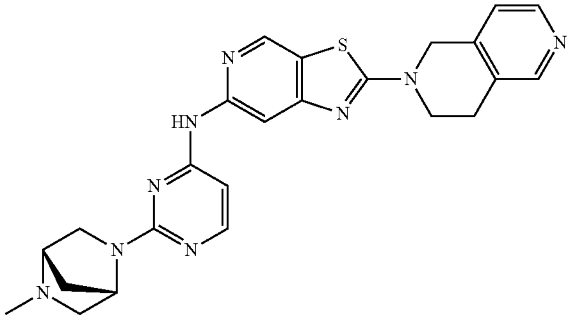 [SMILES: CN1C[C@@H]2C[C@H]1CN2c1nccc(Nc2cc3nc(N4CCc5cnccc5C4)sc3cn2)n1] |

TABLE 2-continued
| Ex. No. | Structure |
|---|---|
| 427 | 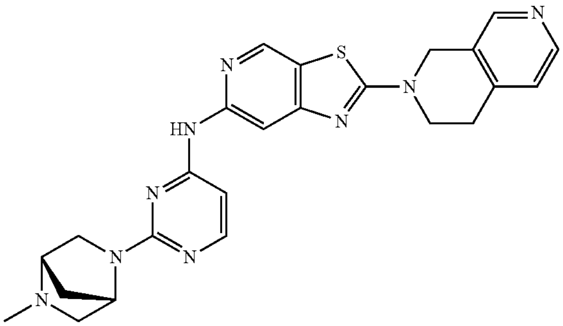 [SMILES: CN1C[C@@H]2C[C@H]1CN2c1nccc(Nc2cc3nc(N4CCc5ccncc5C4)sc3cn2)n1] |
| 428 | 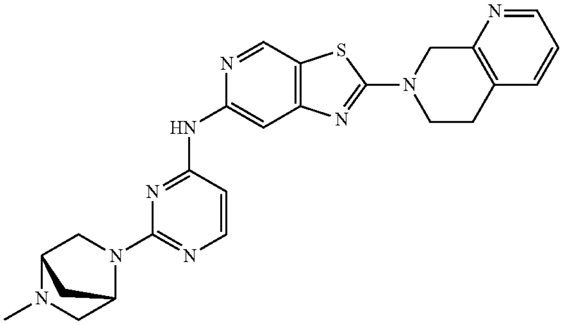 |
| 429 | 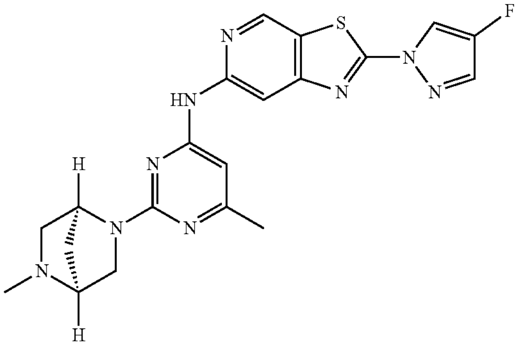 [SMILES: Cc1cc(Nc2cc3nc(-n4cc(F)cn4)sc3cn2)nc(N2C[C@@H]3C[C@H]2CN3C)n1] |
| 430 | 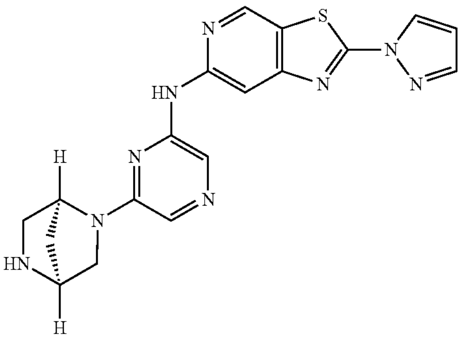 [SMILES: c1cnn(-c2nc3cc(Nc4cncc(N5C[C@@H]6C[C@H]5CN6)n4)ncc3s2)c1] |

TABLE 2-continued
| Ex. No. | Structure |
|---|---|
| 431 | 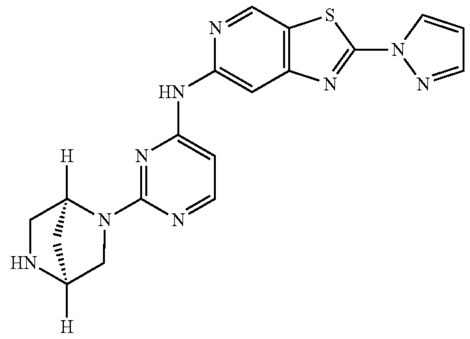 [SMILES: c1cnn(-c2nc3cc(Nc4ccnc(N5C[C@@H]6C[C@H]5CN6)n4)ncc3s2)c1] |
| 432 | 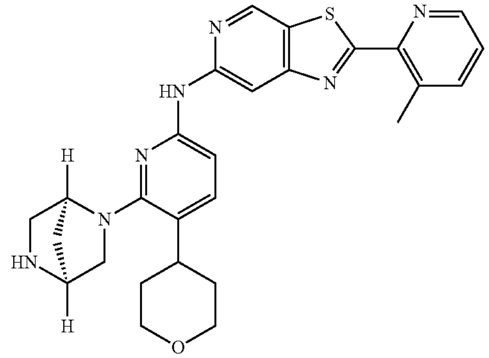 [SMILES: Cc1cccnc1-c1nc2cc(Nc3ccc(C4CCOCC4)c(N4C[C@@H]5C[C@H]4CN5)n3)ncc2s1] |
| 433 | 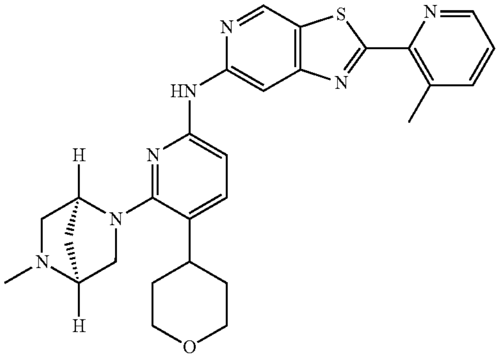 [SMILES: Cc1cccnc1-c1nc2cc(Nc3ccc(C4CCOCC4)c(N4C[C@@H]5C[C@H]4CN5C)n3)ncc2s1] |
| 434 | 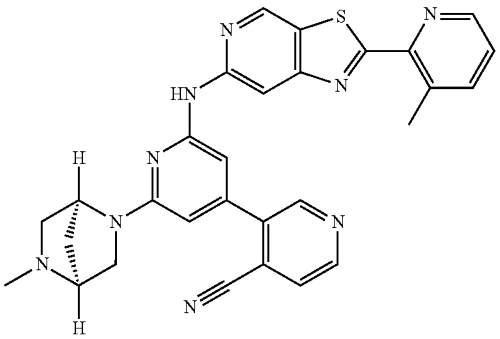 [SMILES: Cc1cccnc1-c1nc2cc(Nc3cc(-c4cnccc4C#N)cc(N4C[C@@H]5C[C@H]4CN5C)n3)ncc2s1] |

TABLE 2-continued
| Ex. No. | Structure |
|---|---|
| 435 | 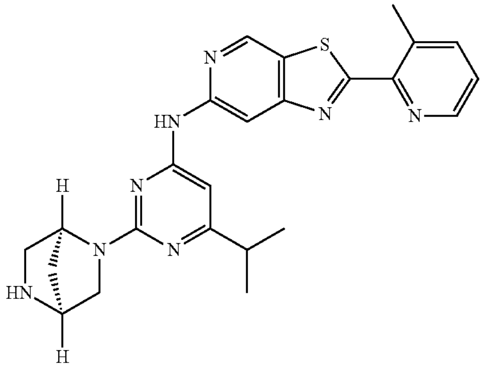 [SMILES: Cc1cccnc1-c1nc2cc(Nc3cc(C(C)C)nc(N4C[C@@H]5C[C@H]4CN5)n3)ncc2s1] |
| 436 | 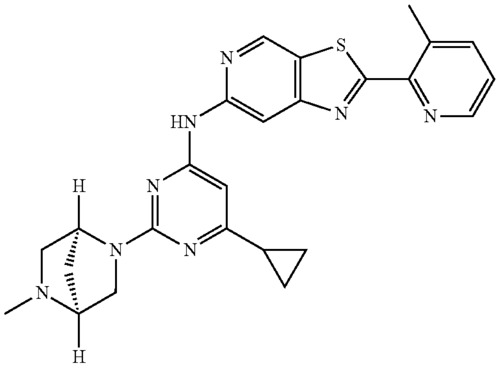 [SMILES: Cc1cccnc1-c1nc2cc(Nc3cc(C4CC4)nc(N4C[C@@H]5C[C@H]4CN5C)n3)ncc2s1] |
| 437 | 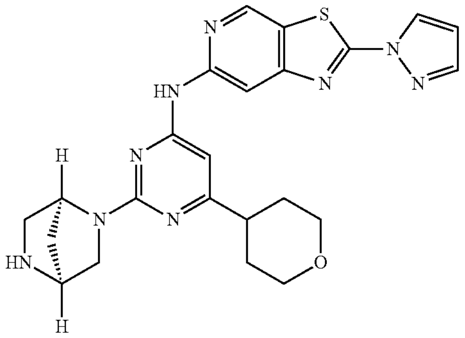 |
| 438 | 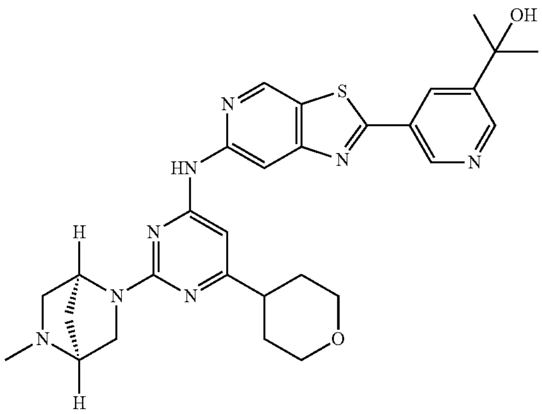 [SMILES: CN1C[C@@H]2C[C@H]1CN2c1nc(Nc2cc3nc(-c4cncc(C(C)(C)O)c4)sc3cn2)cc(C2CCOCC2)n1] |

TABLE 2-continued
| Ex. No. | Structure |
| --- | --- |
| 439 | 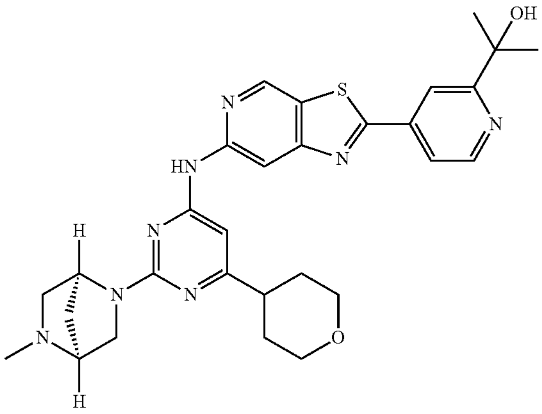 [SMILES: CN1C[C@@H]2C[C@H]1CN2c1nc(Nc2cc3nc(-c4ccnc(C(C)(C)O)c4)sc3cn2)cc(C2CCOCC2)n1] |
| 440 | 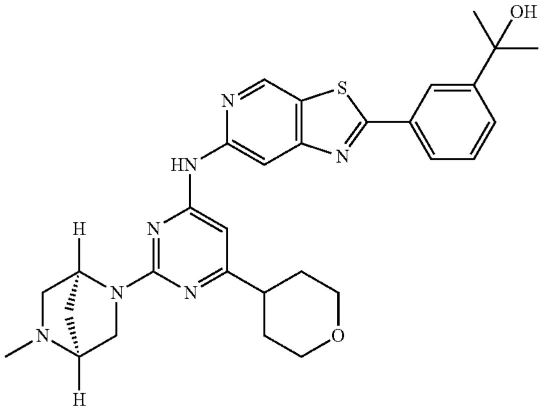 [SMILES: CN1C[C@@H]2C[C@H]1CN2c1nc(Nc2cc3nc(-c4cccc(C(C)(C)O)c4)sc3cn2)cc(C2CCOCC2)n1] |
| 441 | 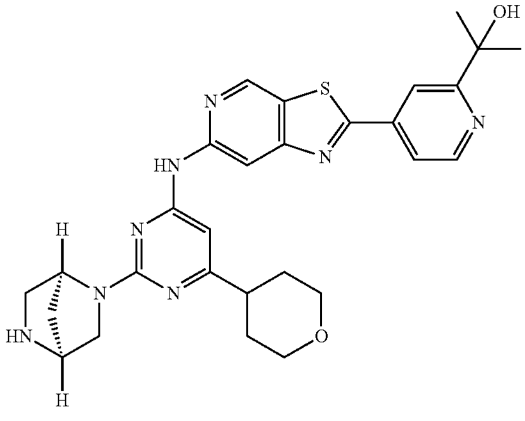 |

TABLE 2-continued
| Ex. No. | Structure |
| --- | --- |
| 442 | 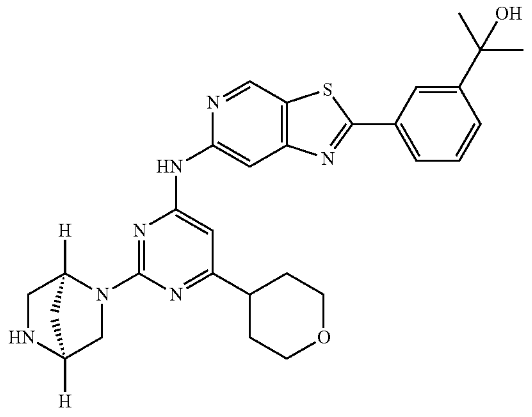 |
| 443 | 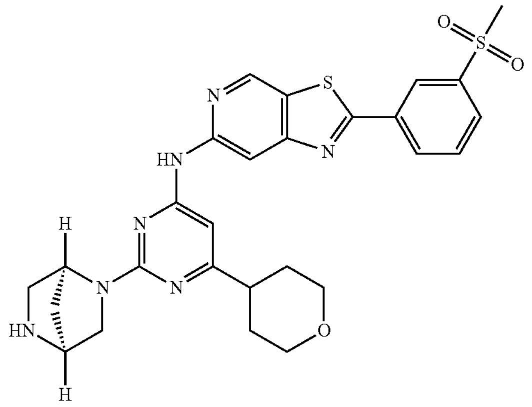 [SMILES: CS(=O)(=O)c1cccc(-c2nc3cc(Nc4cc(C5CCOCC5)nc(N5C[C@@H]6C[C@H]5CN6)n4)ncc3s2)c1] |
| 444 | 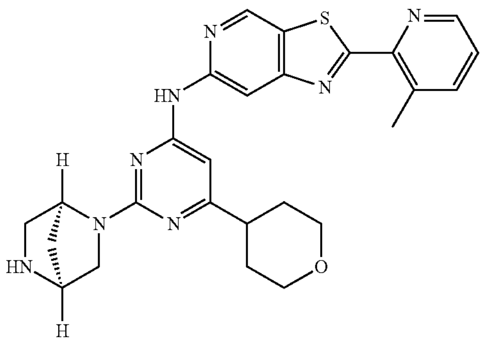 [SMILES: Cc1cccnc1-c1nc2cc(Nc3cc(C4CCOCC4)nc(N4C[C@@H]5C[C@H]4CN5)n3)ncc2s1] |

TABLE 2-continued
| Ex. No. | Structure |
| --- | --- |
| 445 | 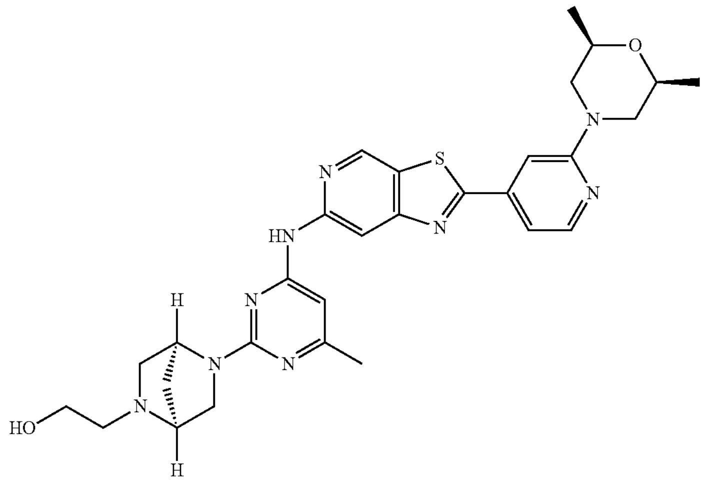 [SMILES: Cc1cc(Nc2cc3nc(-c4ccnc(N5C[C@@H](C)O[C@@H](C)C5)c4)sc3cn2)nc(N2C[C@@H]3C[C@H]2CN3CCO)n1] |
| 446 | 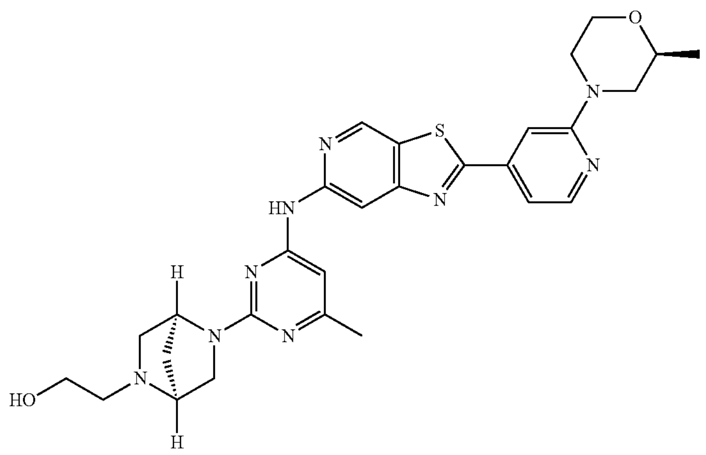 [SMILES: Cc1cc(Nc2cc3nc(-c4ccnc(N5CCO[C@@H](C)C5)c4)sc3cn2)nc(N2C[C@@H]3C[C@H]2CN3CCO)n1] |
| 447 | 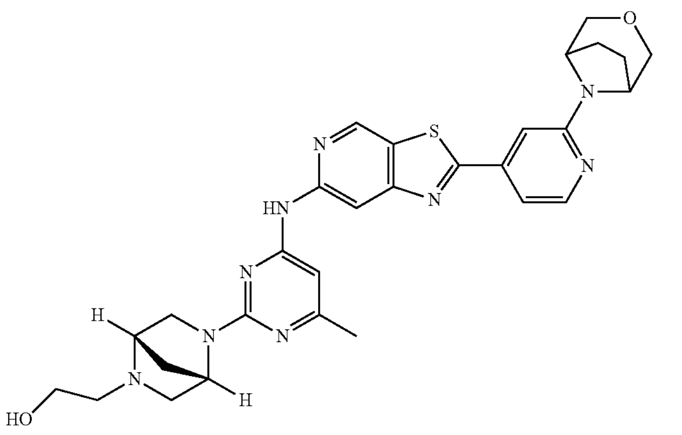 [SMILES: Cc1cc(Nc2cc3nc(-c4ccnc(N5C6CCC5COC6)c4)sc3cn2)nc(N2C[C@@H]3C[C@H]2CN3CCO)n1] |

TABLE 2-continued
| Ex. No. | Structure |
| --- | --- |
| 448 | 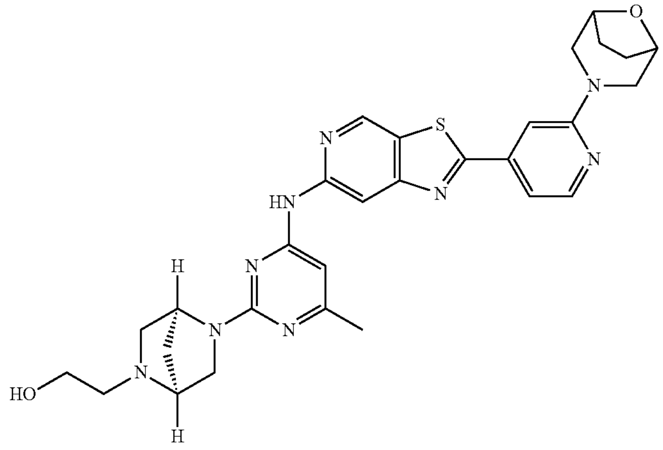 [SMILES: Cc1cc(Nc2cc3nc(-c4ccnc(N5CC6CCC(C5)O6)c4)sc3cn2)nc(N2C[C@@H]3C[C@H]2CN3CCO)n1] |
| 449 | 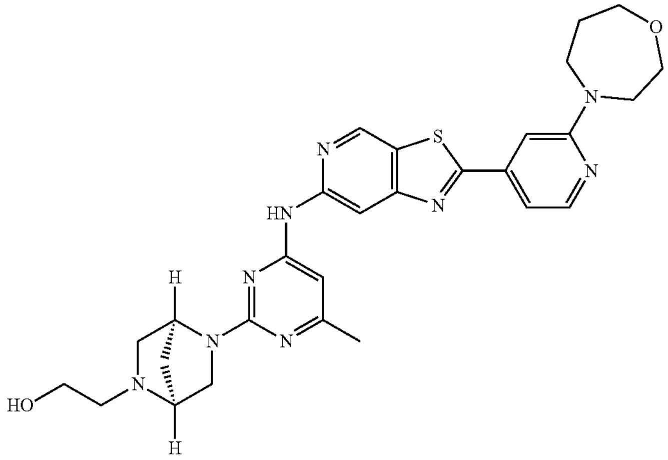 [SMILES: Cc1cc(Nc2cc3nc(-c4ccnc(N5CCCOCC5)c4)sc3cn2)nc(N2C[C@@H]3C[C@H]2CN3CCO)n1] |
| 450 | 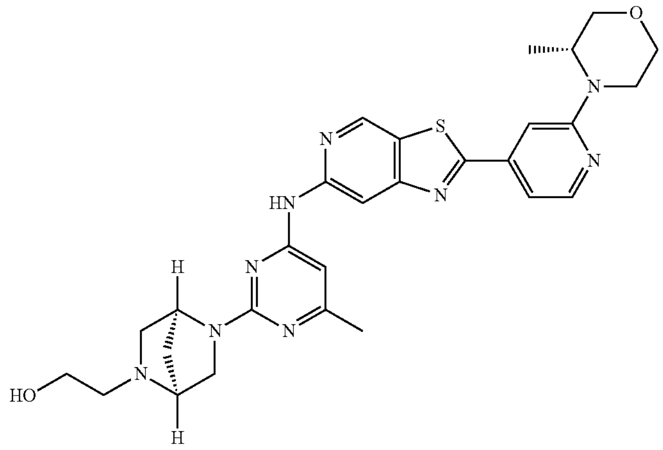 |

TABLE 2-continued
| Ex. No. | Structure |
| --- | --- |
| 451 | 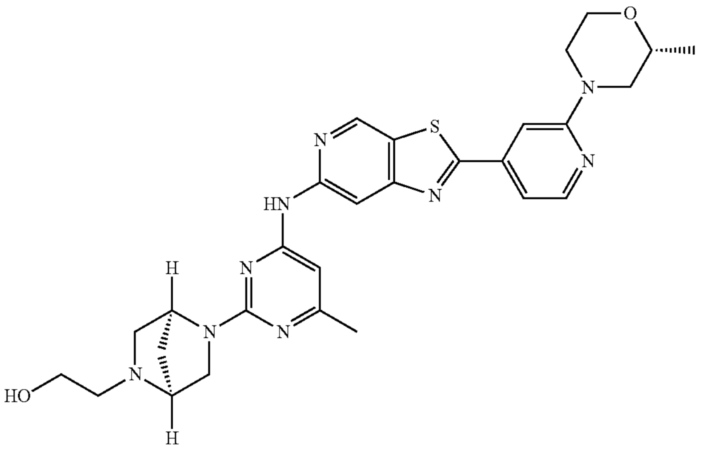 [SMILES: Cc1cc(Nc2cc3nc(-c4ccnc(N5CCO[C@H](C)C5)c4)sc3cn2)nc(N2C[C@@H]3C[C@H]2CN3CCO)n1] |
| 452 | 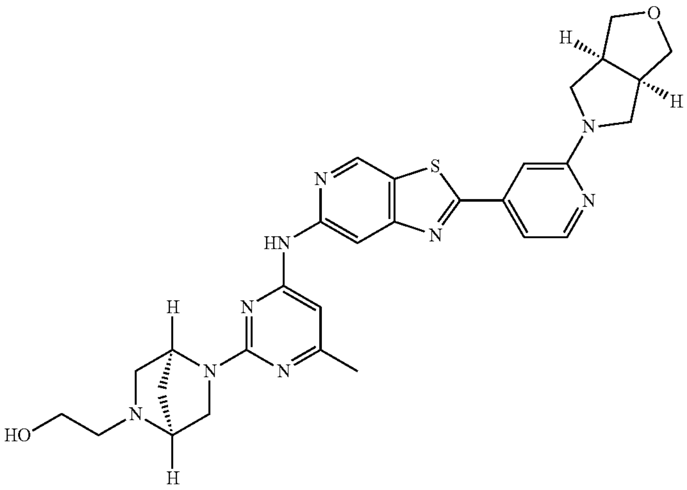 [SMILES: Cc1cc(Nc2cc3nc(-c4ccnc(N5C[C@H]6COC[C@H]6C5)c4)sc3cn2)nc(N2C[C@@H]3C[C@H]2CN3CCO)n1] |
| 453 | 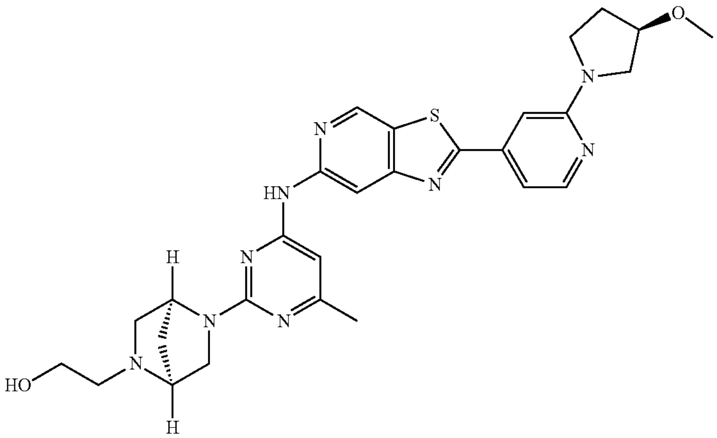 [SMILES: CO[C@@H]1CCN(c2cc(-c3nc4cc(Nc5cc(C)nc(N6C[C@@H]7C[C@H]6CN7CCO)n5)ncc4s3)ccn2)C1] |

TABLE 2-continued
| Ex. No. | Structure |
| --- | --- |
| 454 | 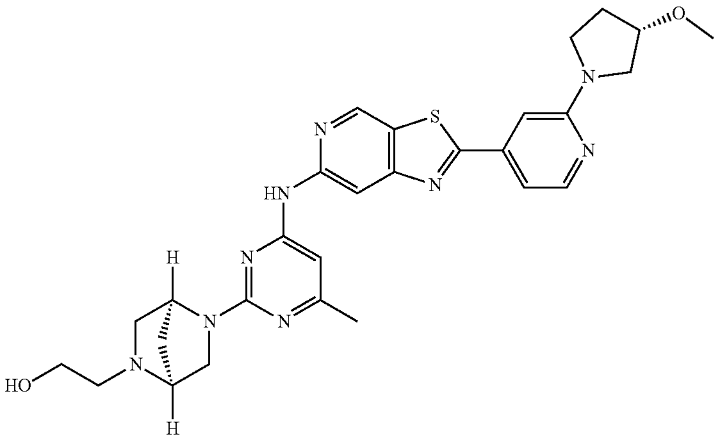 [SMILES: CO[C@H]1CCN(c2cc(-c3nc4cc(Nc5cc(C)nc(N6C[C@@H]7C[C@H]6CN7CCO)n5)ncc4s3)ccn2)C1] |
| 455 | 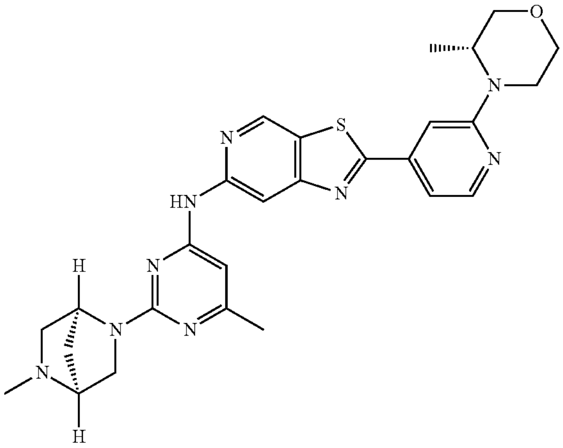 [SMILES: Cc1cc(Nc2cc3nc(-c4ccnc(N5CCOC[C@H]5C)c4)sc3cn2)nc(N2C[C@@H]3C[C@H]2CN3C)n1] |
| 456 | 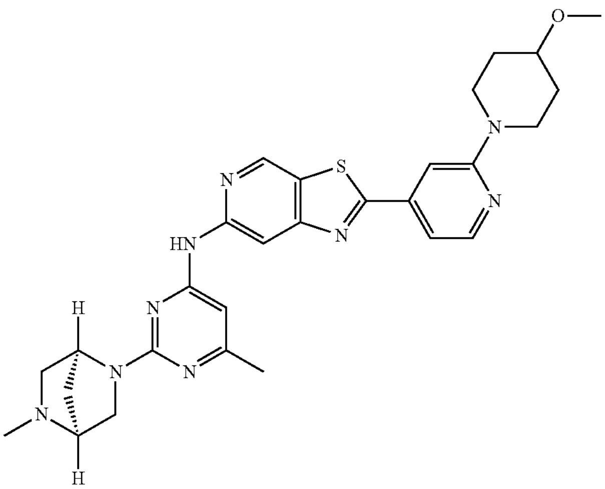 |

TABLE 2-continued
| Ex. No. | Structure |
|---|---|
| 457 | 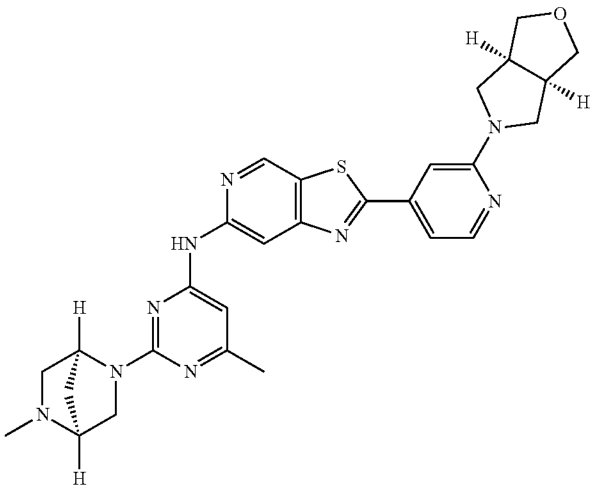 [SMILES: Cc1cc(Nc2cc3nc(-c4ccnc(N5C[C@H]6COC[C@H]6C5)c4)sc3cn2)nc(N2C[C@@H]3C[C@H]2CN3C)n1] |
| 458 | 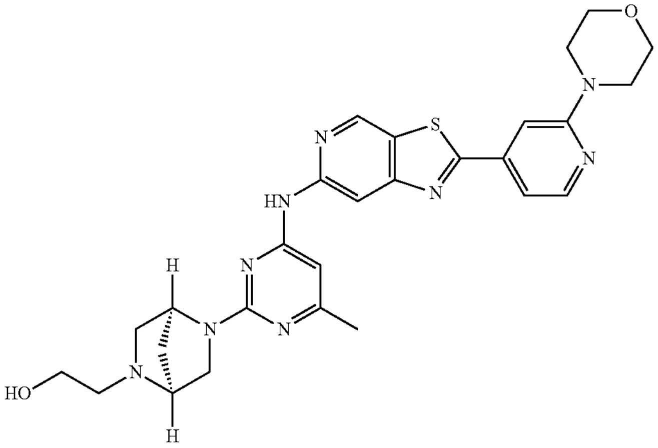 |
| 459 | 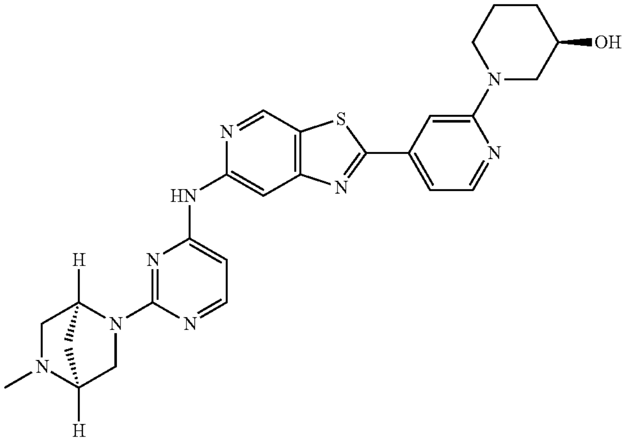 [SMILES: CN1C[C@@H]2C[C@H]1CN2c1nccc(Nc2cc3nc(-c4ccnc(N5CCC[C@@H](O)C5)c4)sc3cn2)n1] |

TABLE 2-continued
| Ex. No. | Structure |
| --- | --- |
| 460 | 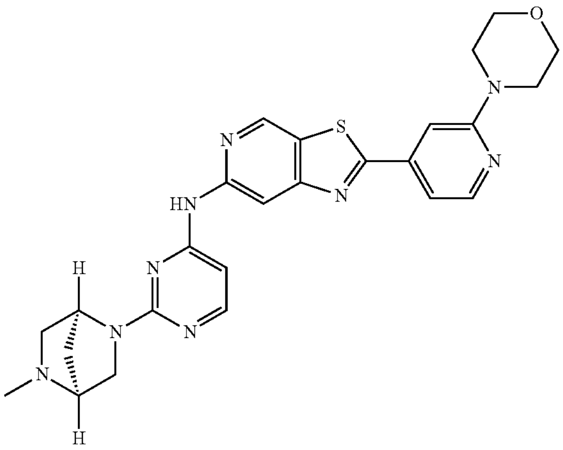 [SMILES: CN1C[C@@H]2C[C@H]1CN2c1nccc(Nc2cc3nc(-c4ccnc(N5CCOCC5)c4)sc3cn2)n1] |
| 461 | 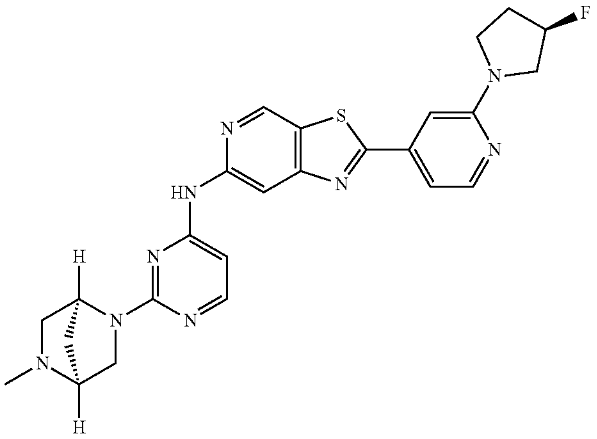 [SMILES: CN1C[C@@H]2C[C@H]1CN2c1nccc(Nc2cc3nc(-c4ccnc(N5CC[C@@H](F)C5)c4)sc3cn2)n1] |
| 462 | 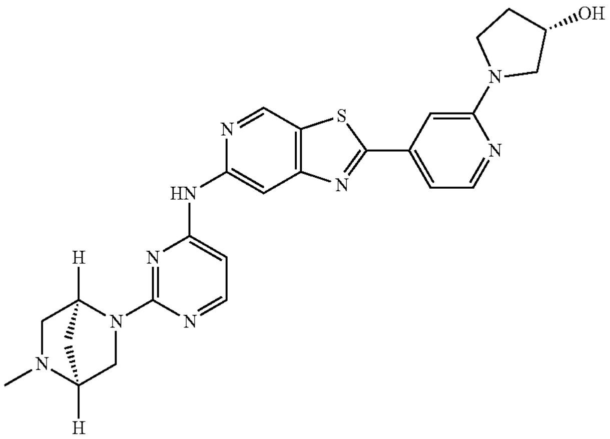 [SMILES: CN1C[C@@H]2C[C@H]1CN2c1nccc(Nc2cc3nc(-c4ccnc(N5CC[C@H](O)C5)c4)sc3cn2)n1] |

TABLE 2-continued
| Ex. No. | Structure |
| --- | --- |
| 463 | 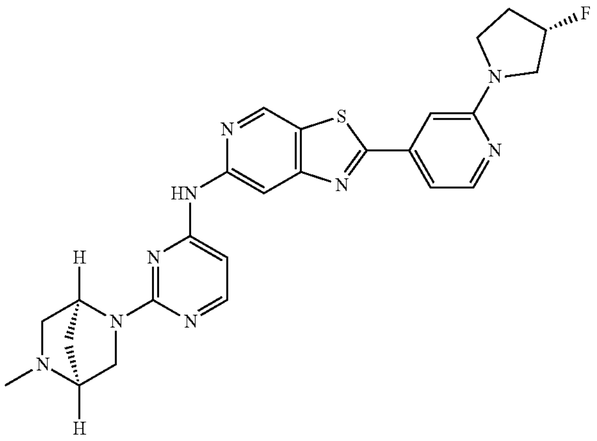 [SMILES: CN1C[C@@H]2C[C@H]1CN2c1nccc(Nc2cc3nc(-c4ccnc(N5CC[C@H](F)C5)c4)sc3cn2)n1] |
| 464 | 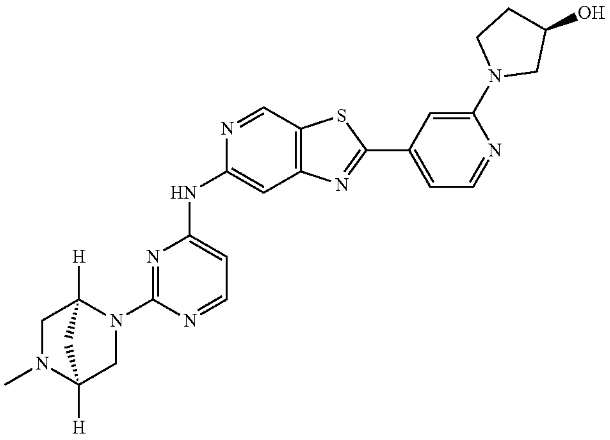 [SMILES: CN1C[C@@H]2C[C@H]1CN2c1nccc(Nc2cc3nc(-c4ccnc(N5CC[C@@H](O)C5)c4)sc3cn2)n1] |
| 465 | 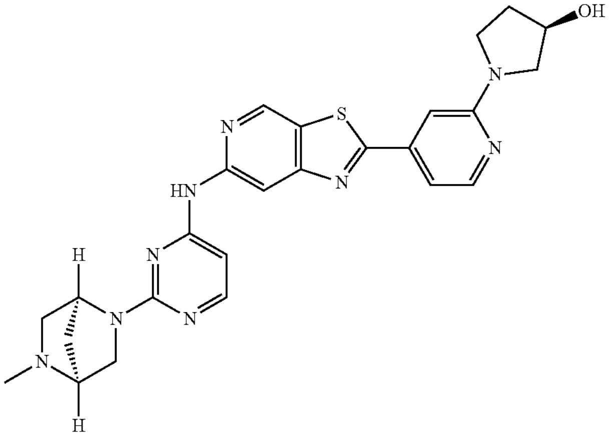 [SMILES: CN1C[C@@H]2C[C@H]1CN2c1nccc(Nc2cc3nc(-c4ccnc(N5CC[C@@H](O)C5)c4)sc3cn2)n1] |

TABLE 2-continued
| Ex. No. | Structure |
|---|---|
| 466 | 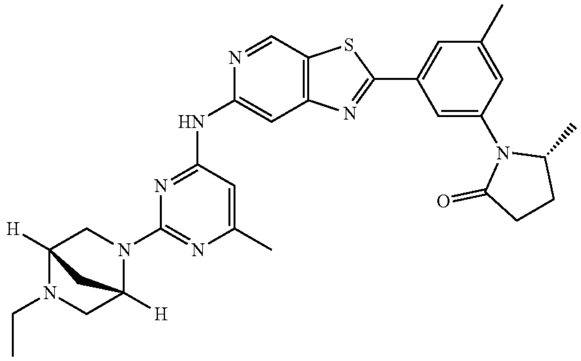 [SMILES: CCN1C[C@@H]2C[C@H]1CN2c1nc(C)cc(Nc2cc3nc(-c4cc(C)cc(N5C(=O)CC[C@H]5C)c4)sc3cn2)n1] |
| 467 | 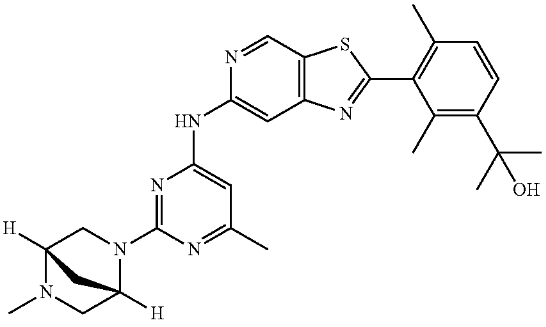 [SMILES: Cc1cc(Nc2cc3nc(-c4c(C)ccc(C(C)(C)O)c4C)sc3cn2)nc(N2C[C@@H]3C[C@H]2CN3C)n1] |
| 468 | 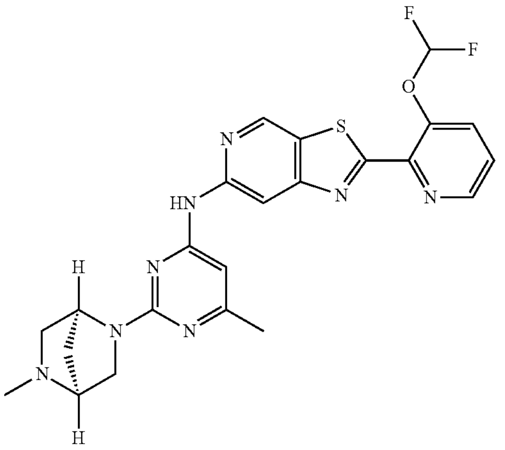 [SMILES: Cc1cc(Nc2cc3nc(-c4ncccc4OC(F)F)sc3cn2)nc(N2C[C@@H]3C[C@H]2CN3C)n1] |
| 469 | 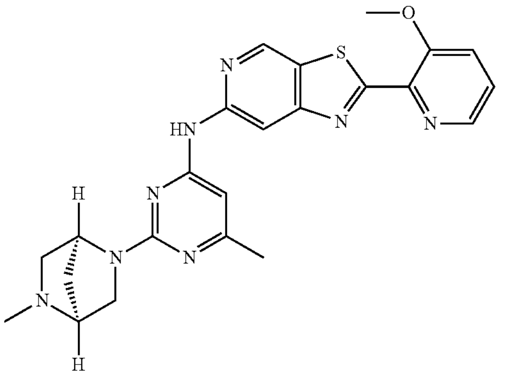 [SMILES: COc1cccnc1-c1nc2cc(Nc3cc(C)nc(N4C[C@@H]5C[C@H]4CN5C)n3)ncc2s1] |

TABLE 2-continued
| Ex. No. | Structure |
|---|---|
| 470 | 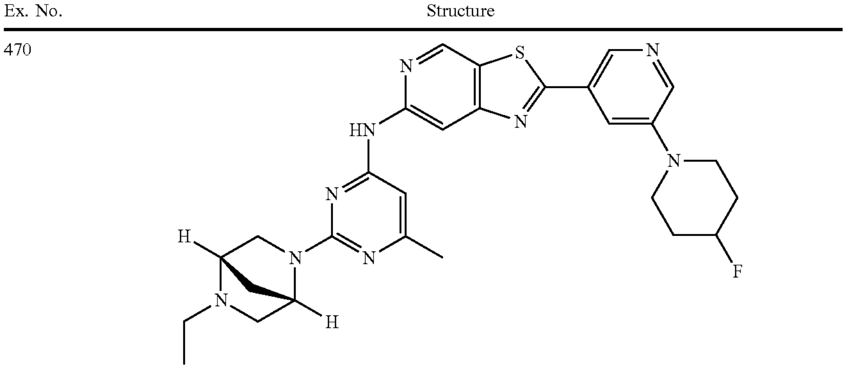 |
| 471 | 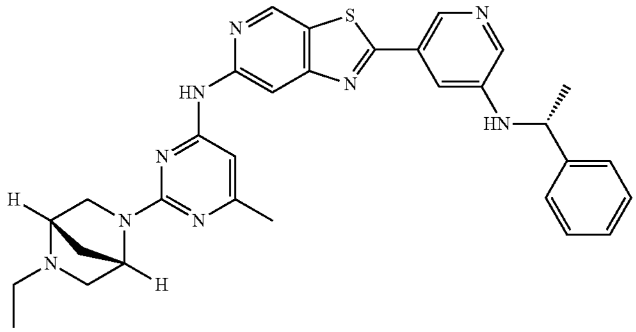 [SMILES: CCN1C[C@@H]2C[C@H]1CN2c1nc(C)cc(Nc2cc3nc(-c4cncc(N[C@H](C)c5ccccc5)c4)sc3cn2)n1] |
| 472 | 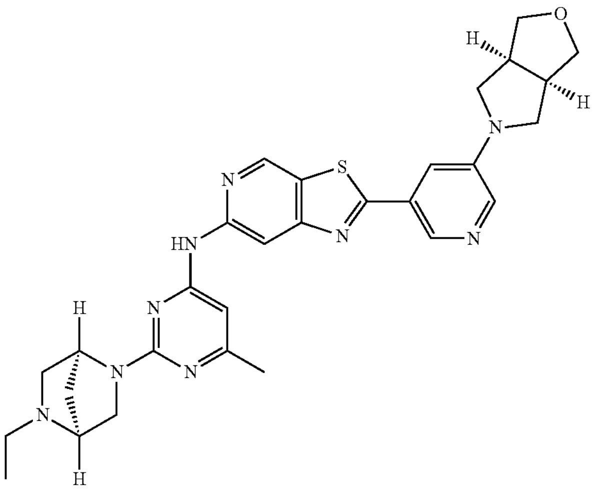 [SMILES: CCN1C[C@@H]2C[C@H]1CN2c1nc(C)cc(Nc2cc3nc(-c4cncc(N5C[C@H]6COC[C@H]6C5)c4)sc3cn2)n1] |
| 473 | 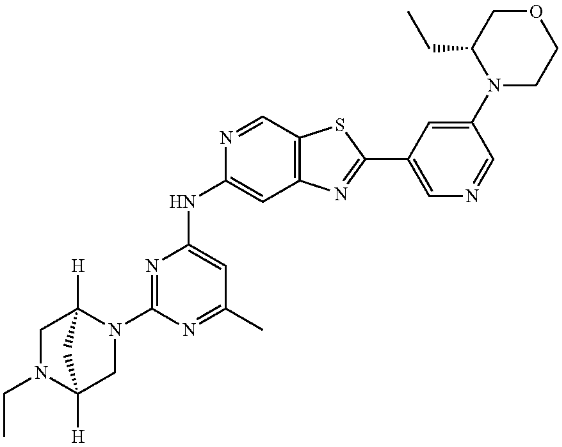 [SMILES: CC[C@@H]1COCCN1c1cncc(-c2nc3cc(Nc4cc(C)nc(N5C[C@@H]6C[C@H]5CN6CC)n4)ncc3s2)c1] |

TABLE 2-continued
| Ex. No. | Structure |
| --- | --- |
| 474 | 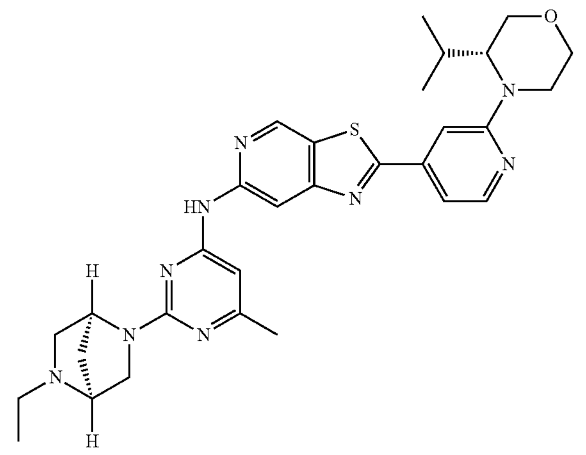 [SMILES: CCN1C[C@@H]2C[C@H]1CN2c1nc(C)cc(Nc2cc3nc(-c4ccnc(N5CCOC[C@H]5C(C)C)c4)sc3cn2)n1] |
| 475 | 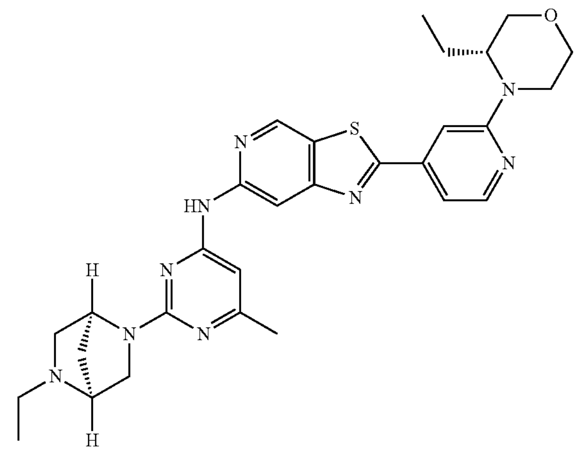 [SMILES: CC[C@@H]1COCCN1c1cc(-c2nc3cc(Nc4cc(C)nc(N5C[C@@H]6C[C@H]5CN6CC)n4)ncc3s2)ccn1] |
| 476 | 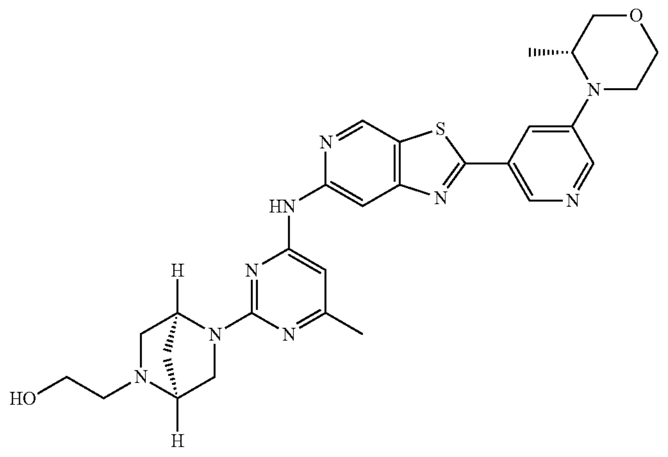 |

TABLE 2-continued
| Ex. No. | Structure |
| --- | --- |
| 477 | 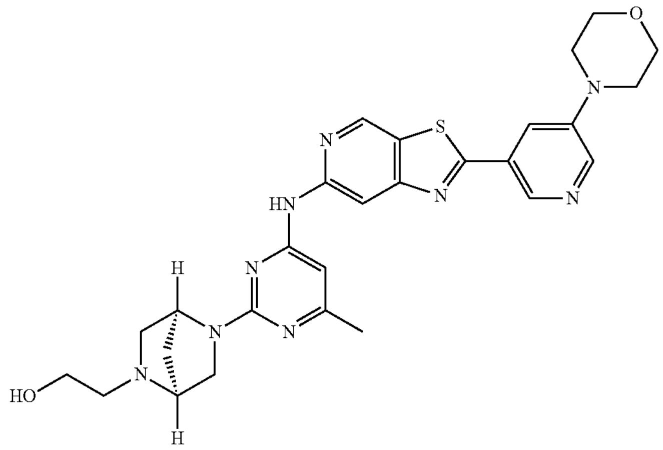 |
| 478 | 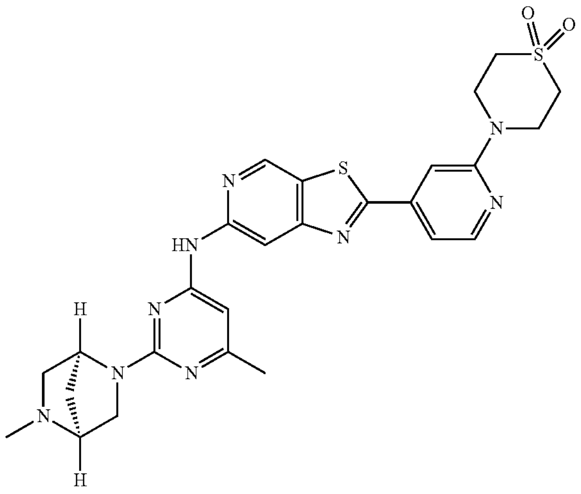 [SMILES: Cc1cc(Nc2cc3nc(-c4ccnc(N5CCS(=O)(=O)CC5)c4)sc3cn2)nc(N2C[C@@H]3C[C@H]2CN3C)n1] |
| 479 | 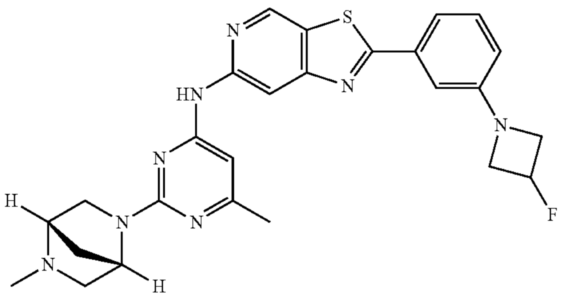 [SMILES: Cc1cc(Nc2cc3nc(-c4cccc(N5CC(F)C5)c4)sc3cn2)nc(N2C[C@@H]3C[C@H]2CN3C)n1] |

TABLE 2-continued
| Ex. No. | Structure |
|---|---|
| 480 | 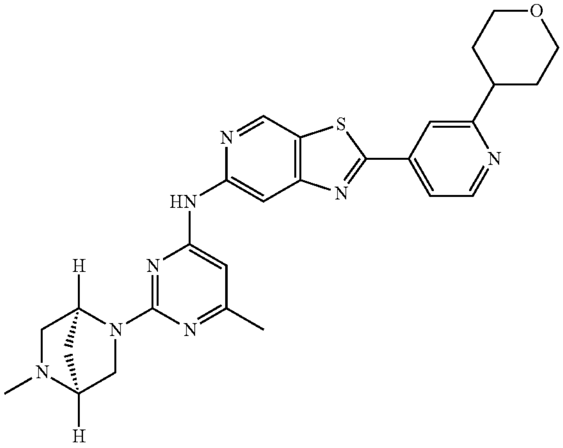 |
| 481 | 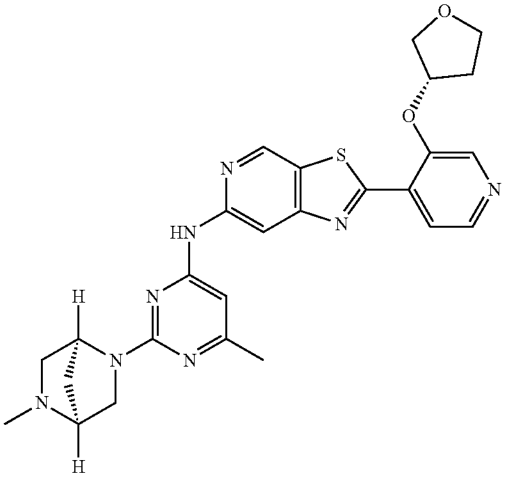 [SMILES: Cc1cc(Nc2cc3nc(-c4ccncc4O[C@H]4CCOC4)sc3cn2)nc(N2C[C@@H]3C[C@H]2CN3C)n1] |
| 482 | 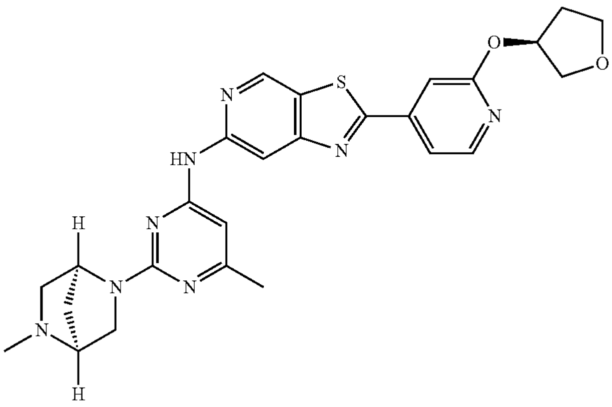 [SMILES: Cc1cc(Nc2cc3nc(-c4ccnc(O[C@H]5CCOC5)c4)sc3cn2)nc(N2C[C@@H]3C[C@H]2CN3C)n1] |

TABLE 2-continued
| Ex. No. | Structure |
|---|---|
| 483 | 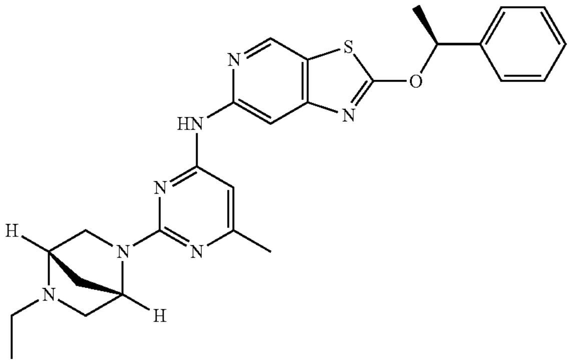 [SMILES: CCN1C[C@@H]2C[C@H]1CN2c1nc(C)cc(Nc2cc3nc(O[C@@H](C)c4ccccc4)sc3cn2)n1] |
| 484 | 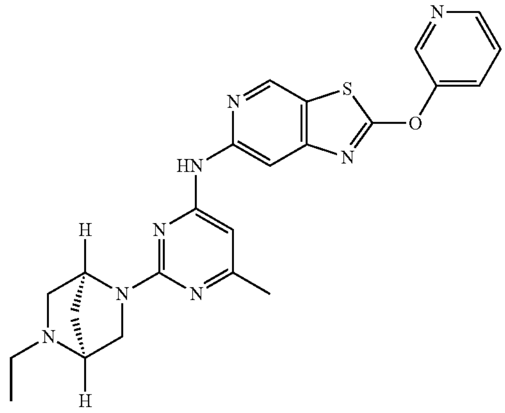 [SMILES: CCN1C[C@@H]2C[C@H]1CN2c1nc(C)cc(Nc2cc3nc(Oc4cccnc4)sc3cn2)n1] |
| 485 | 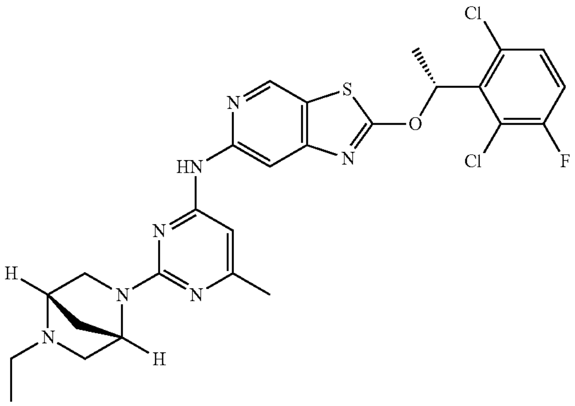 [SMILES: CCN1C[C@@H]2C[C@H]1CN2c1nc(C)cc(Nc2cc3nc(O[C@H](C)c4c(Cl)ccc(F)c4Cl)sc3cn2)n1] |
| 486 | 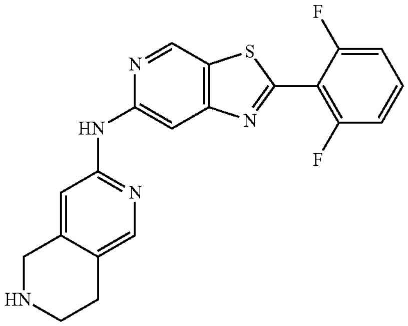 [SMILES: Fc1cccc(F)c1-c1nc2cc(Nc3cc4c(cn3)CCNC4)ncc2s1] |

TABLE 2-continued
| Ex. No. | Structure |
| --- | --- |
| 487 | 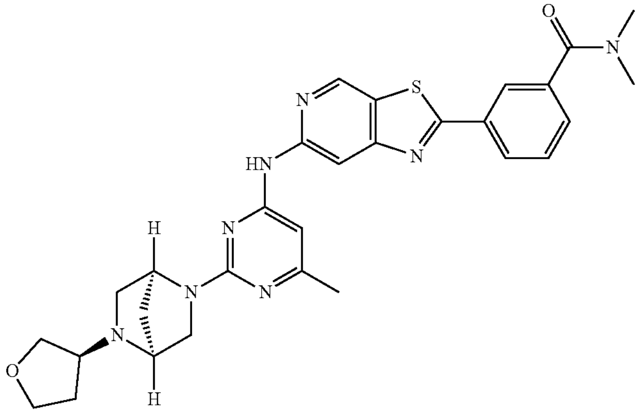 [SMILES: Cc1cc(Nc2cc3nc(-c4cccc(C(=O)N(C)C)c4)sc3cn2)nc(N2C[C@@H]3C[C@H]2CN3[C@H]2CCOC2)n1] |
| 488 | 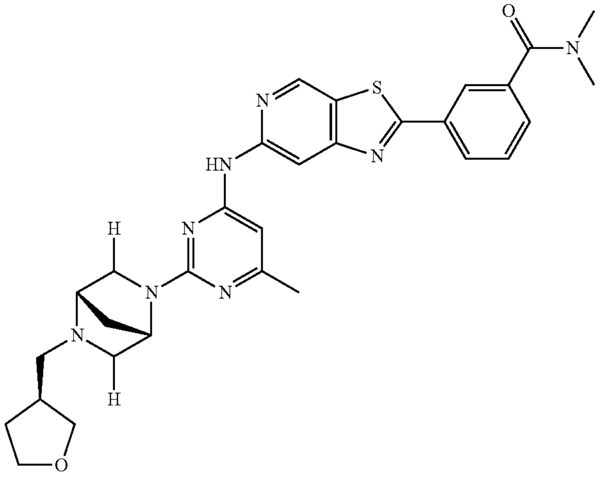 [SMILES: Cc1cc(Nc2cc3nc(-c4cccc(C(=O)N(C)C)c4)sc3cn2)nc(N2C[C@@H]3C[C@H]2CN3C[C@@H]2CCOC2)n1] |
| 489 | 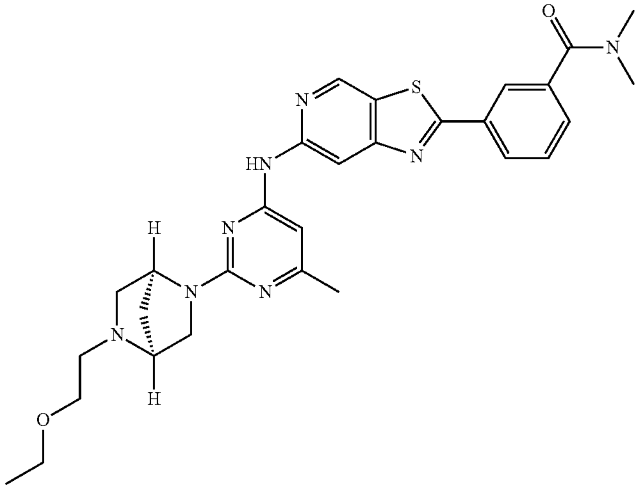 [SMILES: CCOCCN1C[C@@H]2C[C@H]1CN2c1nc(C)cc(Nc2cc3nc(-c4cccc(C(=O)N(C)C)c4)sc3cn2)n1] |

TABLE 2-continued
| Ex. No. | Structure |
|---|---|
| 490 | 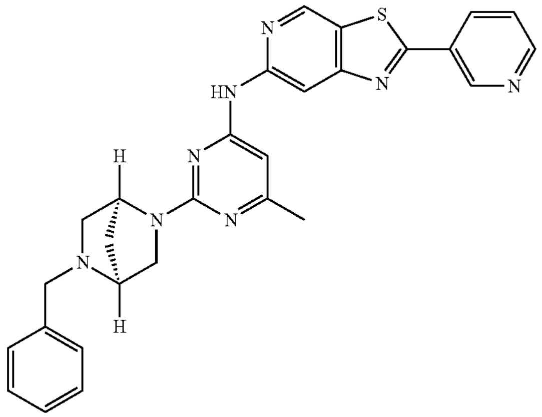 [SMILES: Cc1cc(Nc2cc3nc(-c4cccnc4)sc3cn2)nc(N2C[C@@H]3C[C@H]2CN3Cc2ccccc2)n1] |
| 491 | 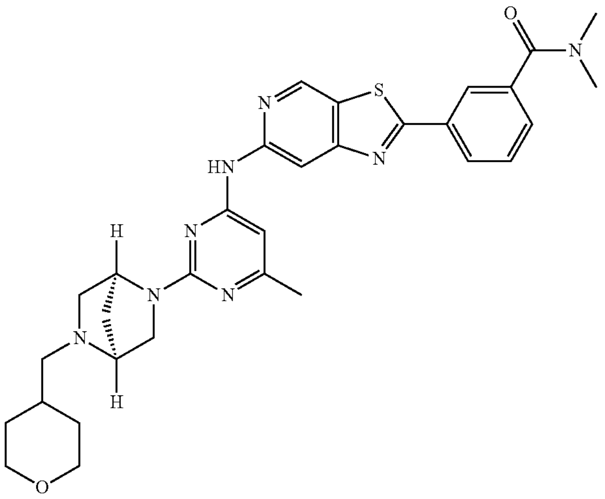 [SMILES: Cc1cc(Nc2cc3nc(-c4cccc(C(=O)N(C)C)c4)sc3cn2)nc(N2C[C@@H]3C[C@H]2CN3CC2CCOCC2)n1] |
| 492 | 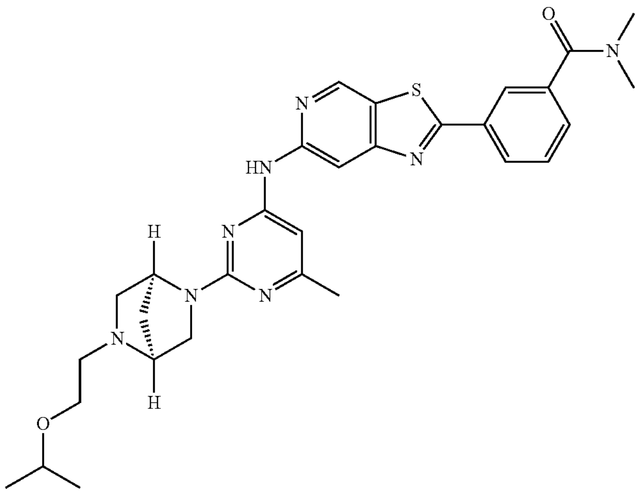 [SMILES: Cc1cc(Nc2cc3nc(-c4cccc(C(=O)N(C)C)c4)sc3cn2)nc(N2C[C@@H]3C[C@H]2CN3CCOC(C)C)n1] |

TABLE 2-continued
| Ex. No. | Structure |
|---|---|
| 493 | 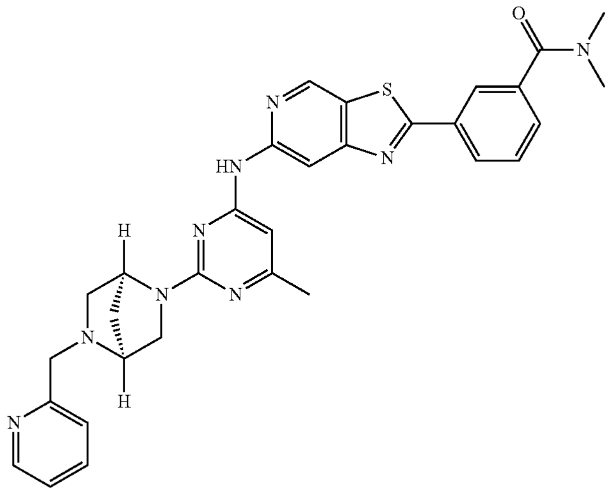 [SMILES: Cc1cc(Nc2cc3nc(-c4cccc(C(=O)N(C)C)c4)sc3cn2)nc(N2C[C@@H]3C[C@H]2CN3Cc2ccccn2)n1] |
| 494 | 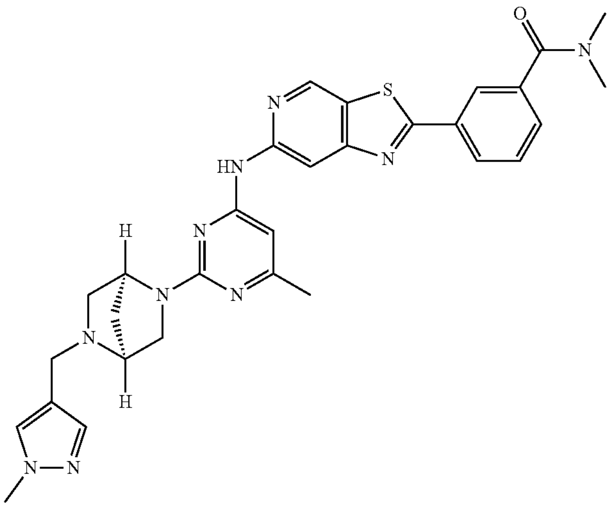 |
| 495 | 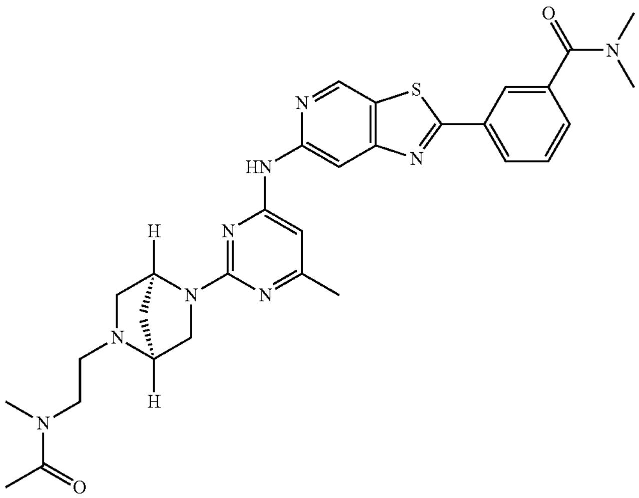 |

TABLE 2-continued
| Ex. No. | Structure |
|---|---|
| 496 | 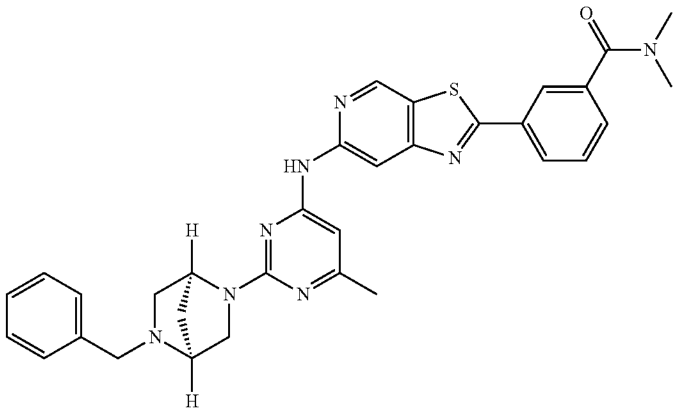 [SMILES: Cc1cc(Nc2cc3nc(-c4cccc(C(=O)N(C)C)c4)sc3cn2)nc(N2C[C@@H]3C[C@H]2CN3Cc2ccccc2)n1] |
| 497 | 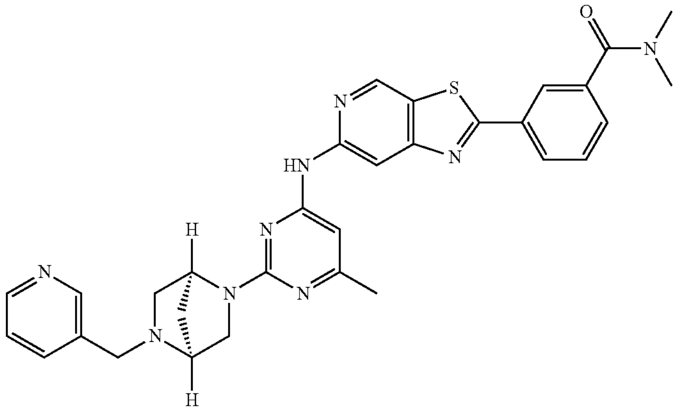 [SMILES: Cc1cc(Nc2cc3nc(-c4cccc(C(=O)N(C)C)c4)sc3cn2)nc(N2C[C@@H]3C[C@H]2CN3Cc2cccnc2)n1] |
| 498 | 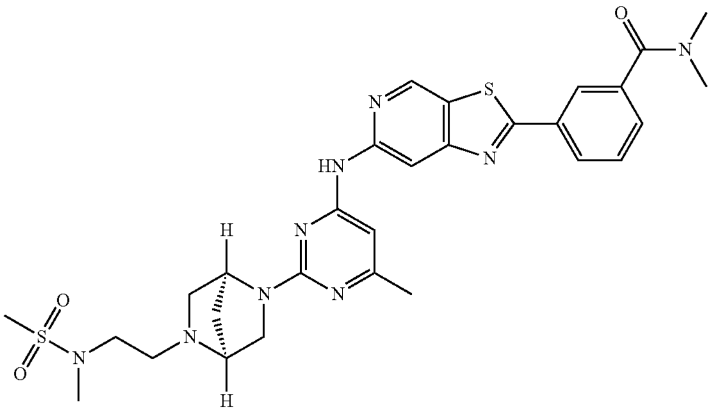 |
| 499 | 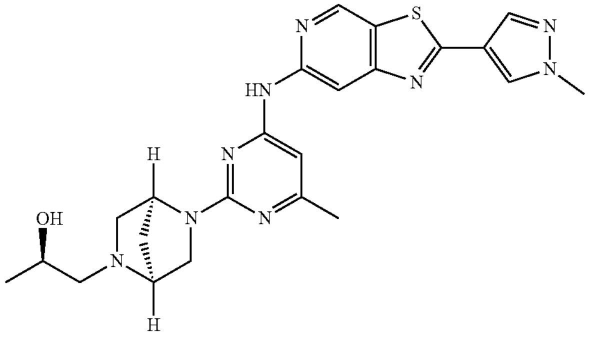 [SMILES: Cc1cc(Nc2cc3nc(-c4cnn(C)c4)sc3cn2)nc(N2C[C@@H]3C[C@H]2CN3C[C@@H](C)O)n1] |

TABLE 2-continued
| Ex. No. | Structure |
|---|---|
| 500 | 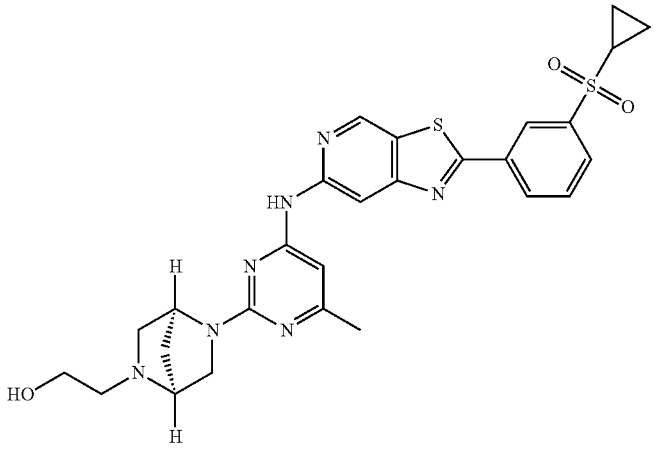 [SMILES: Cc1cc(Nc2cc3nc(-c4cccc(S(=O)(=O)C5CC5)c4)sc3cn2)nc(N2C[C@@H]3C[C@H]2CN3CCO)n1] |
| 501 | 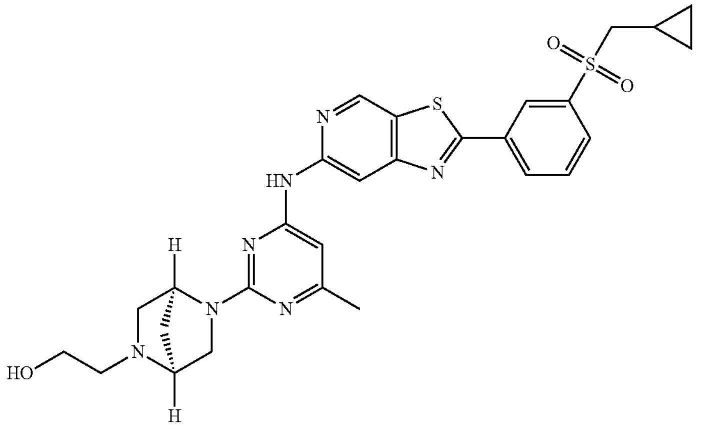 [SMILES: Cc1cc(Nc2cc3nc(-c4cccc(S(=O)(=O)CC5CC5)c4)sc3cn2)nc(N2C[C@@H]3C[C@H]2CN3CCO)n1] |
| 502 | 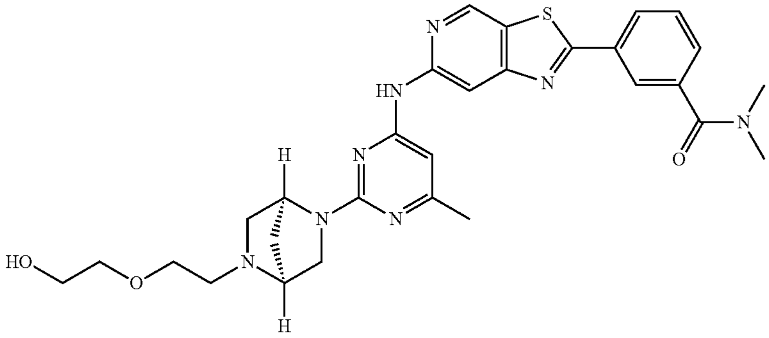 [SMILES: Cc1cc(Nc2cc3nc(-c4cccc(C(=O)N(C)C)c4)sc3cn2)nc(N2C[C@@H]3C[C@H]2CN3CCOCCO)n1] |
| 503 | 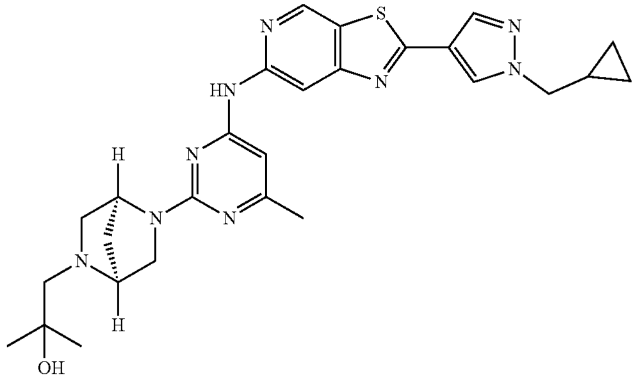 [SMILES: Cc1cc(Nc2cc3nc(-c4cnn(CC5CC5)c4)sc3cn2)nc(N2C[C@@H]3C[C@H]2CN3CC(C)(C)O)n1] |

TABLE 2-continued
| Ex. No. | Structure |
| --- | --- |
| 504 | 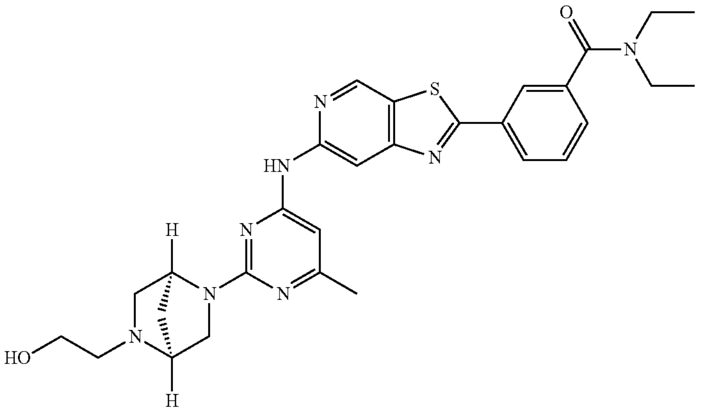 [SMILES: CCN(CC)C(=O)c1cccc(-c2nc3cc(Nc4cc(C)nc(N5C[C@@H]6C[C@H]5CN6CCO)n4)ncc3s2)c1] |
| 505 | 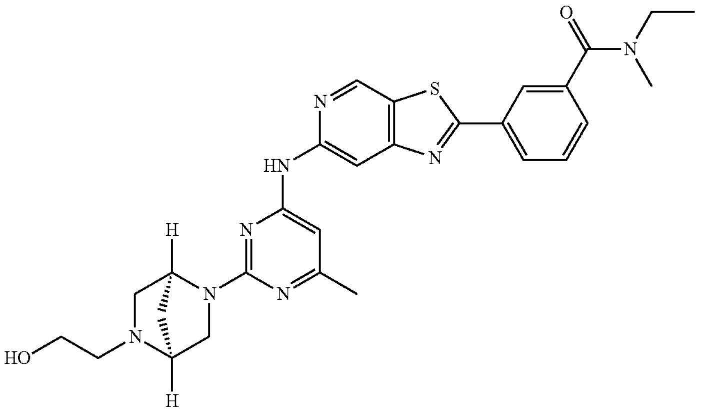 [SMILES: CCN(C)C(=O)c1cccc(-c2nc3cc(Nc4cc(C)nc(N5C[C@@H]6C[C@H]5CN6CCO)n4)ncc3s2)c1] |
| 506 | 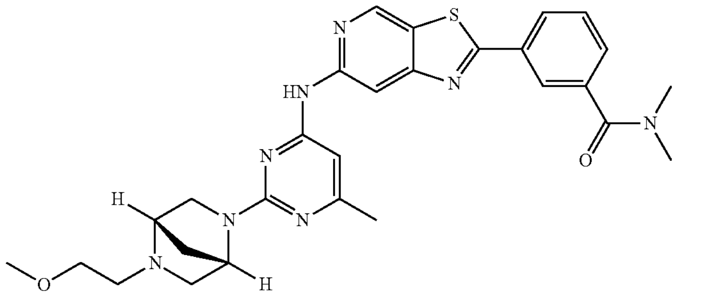 |
| 507 | 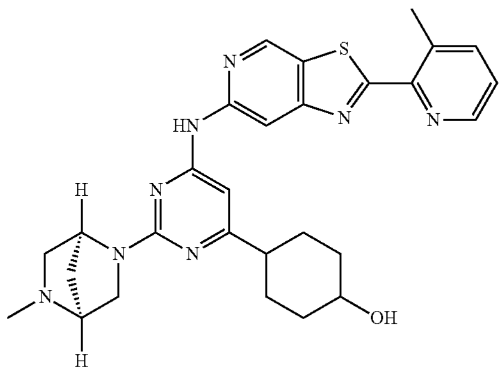 [SMILES: Cc1cccnc1-c1nc2cc(Nc3cc(C4CCC(O)CC4)nc(N4C[C@@H]5C[C@H]4CN5C)n3)ncc2s1] |

TABLE 2-continued
| Ex. No. | Structure |
|---|---|
| 508 | 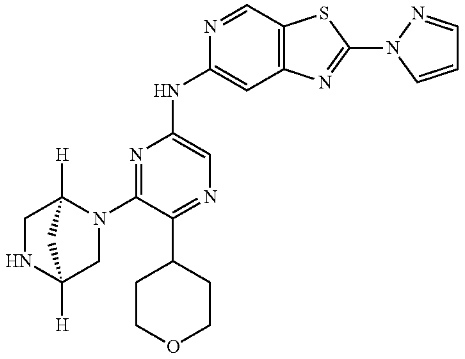 [SMILES: c1cnn(-c2nc3cc(Nc4cnc(C5CCOCC5)c(N5C[C@@H]6C[C@H]5CN6)n4)ncc3s2)c1] |
| 509 | 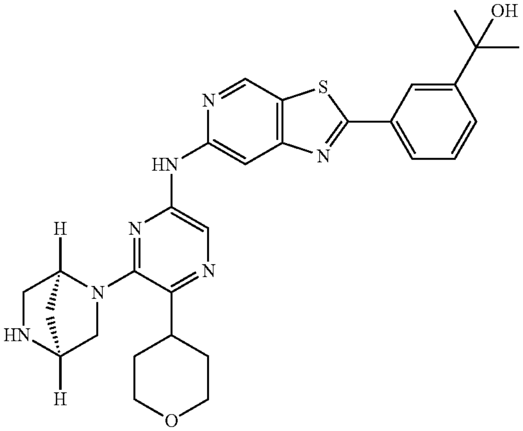 [SMILES: CC(C)(O)c1cccc(-c2nc3cc(Nc4cnc(C5CCOCC5)c(N5C[C@@H]6C[C@H]5CN6)n4)ncc3s2)c1] |
| 510 | 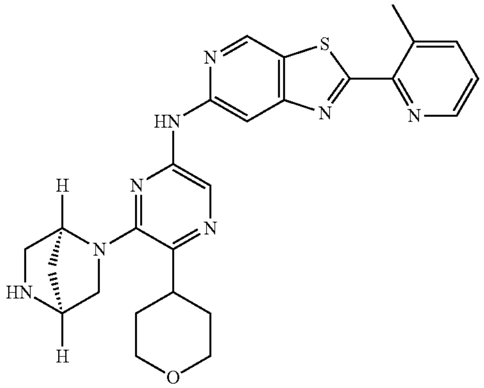 [SMILES: Cc1cccnc1-c1nc2cc(Nc3cnc(C4CCOCC4)c(N4C[C@@H]5C[C@H]4CN5)n3)ncc2s1] |
| 511 | 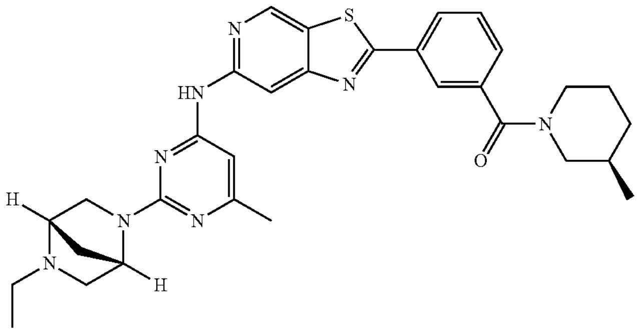 [SMILES: CCN1C[C@@H]2C[C@H]1CN2c1nc(C)cc(Nc2cc3nc(-c4cccc(C(=O)N5CCC[C@@H](C)C5)c4)sc3cn2)n1] |

TABLE 2-continued
| Ex. No. | Structure |
| --- | --- |
| 512 | 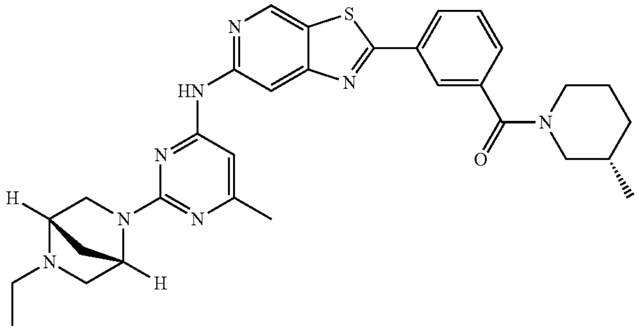 [SMILES: CCN1C[C@@H]2C[C@H]1CN2c1nc(C)cc(Nc2cc3nc(-c4cccc(C(=O)N5CCC[C@H](C)C5)c4)sc3cn2)n1] |
| 513 | 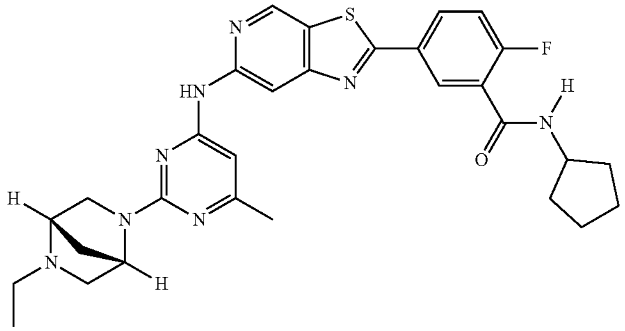 [SMILES: CCN1C[C@@H]2C[C@H]1CN2c1nc(C)cc(Nc2cc3nc(-c4ccc(F)c(C(=O)NC5CCCC5)c4)sc3cn2)n1] |
| 514 | 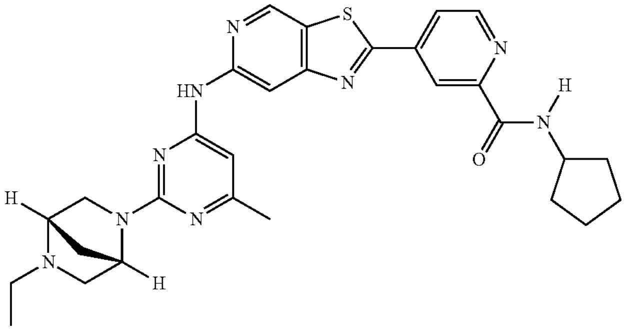 [SMILES: CCN1C[C@@H]2C[C@H]1CN2c1nc(C)cc(Nc2cc3nc(-c4ccnc(C(=O)NC5CCCC5)c4)sc3cn2)n1] |
| 515 | 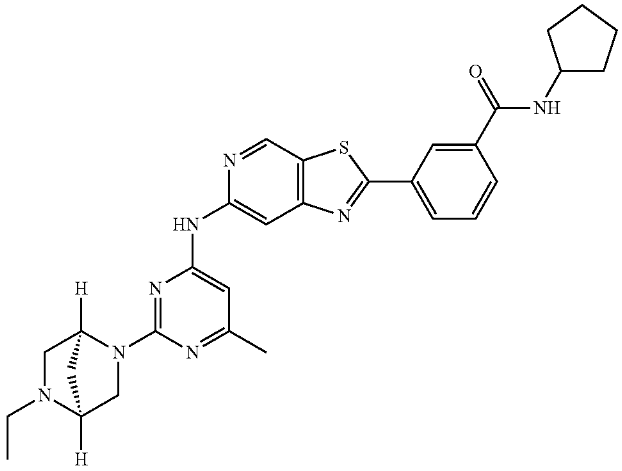 [SMILES: CCN1C[C@@H]2C[C@H]1CN2c1nc(C)cc(Nc2cc3nc(-c4cccc(C(=O)NC5CCCC5)c4)sc3cn2)n1] |

TABLE 2-continued
| Ex. No. | Structure |
| --- | --- |
| 516 | 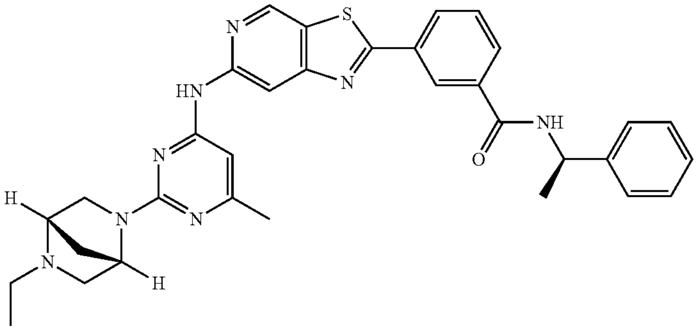 [SMILES: CCN1C[C@@H]2C[C@H]1CN2c1nc(C)cc(Nc2cc3nc(-c4cccc(C(=O)N[C@H](C)c5ccccc5)c4)sc3cn2)n1] |
| 517 | 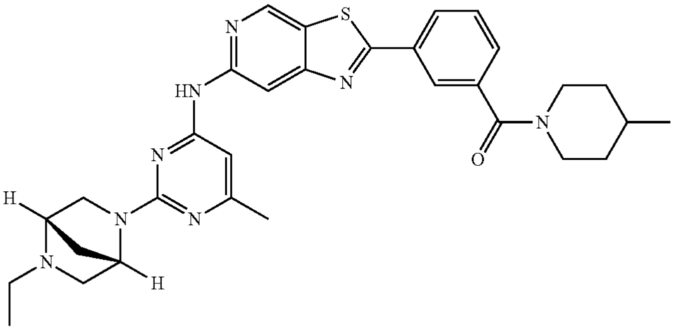 [SMILES: CCN1C[C@@H]2C[C@H]1CN2c1nc(C)cc(Nc2cc3nc(-c4cccc(C(=O)N5CCC(C)CC5)c4)sc3cn2)n1] |
| 518 | 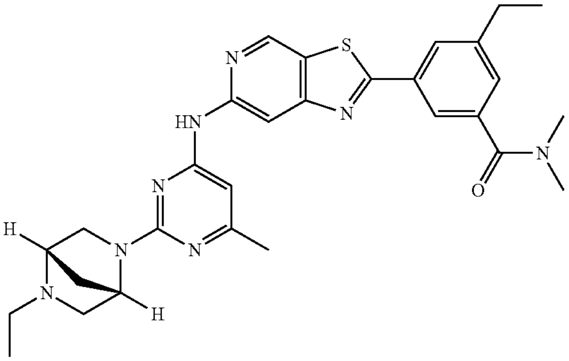 [SMILES: CCc1cc(C(=O)N(C)C)cc(-c2nc3cc(Nc4cc(C)nc(N5C[C@@H]6C[C@H]5CN6CC)n4)ncc3s2)c1] |
| 519 | 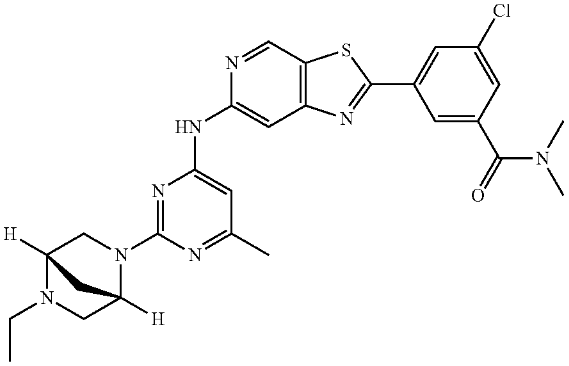 [SMILES: CCN1C[C@@H]2C[C@H]1CN2c1nc(C)cc(Nc2cc3nc(-c4cc(Cl)cc(C(=O)N(C)C)c4)sc3cn2)n1] |

TABLE 2-continued
| Ex. No. | Structure |
|---|---|
| 520 | 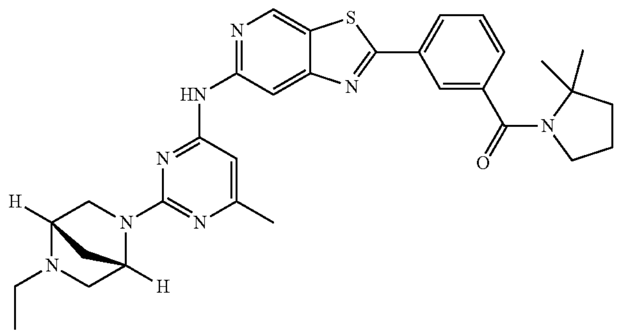 [SMILES: CCN1C[C@@H]2C[C@H]1CN2c1nc(C)cc(Nc2cc3nc(-c4cccc(C(=O)N5CCCC5(C)C)c4)sc3cn2)n1] |
| 521 | 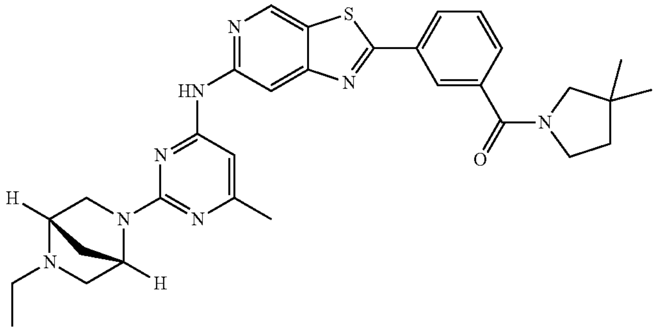 [SMILES: CCN1C[C@@H]2C[C@H]1CN2c1nc(C)cc(Nc2cc3nc(-c4cccc(C(=O)N5CCC(C)(C)C5)c4)sc3cn2)n1] |
| 522 | 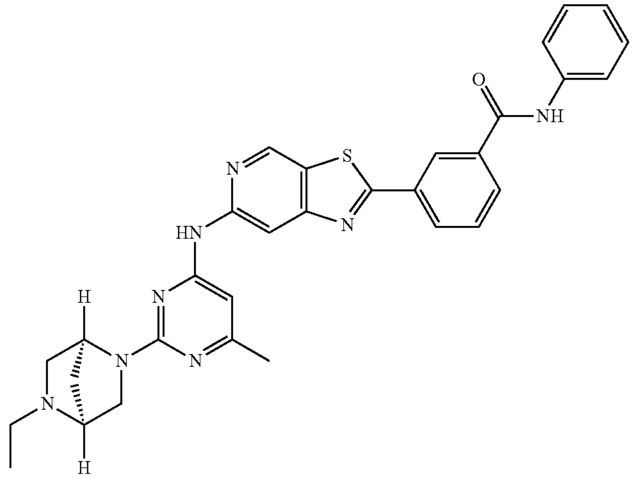 [SMILES: CCN1C[C@@H]2C[C@H]1CN2c1nc(C)cc(Nc2cc3nc(-c4cccc(C(=O)Nc5ccccc5)c4)sc3cn2)n1] |
| 523 | 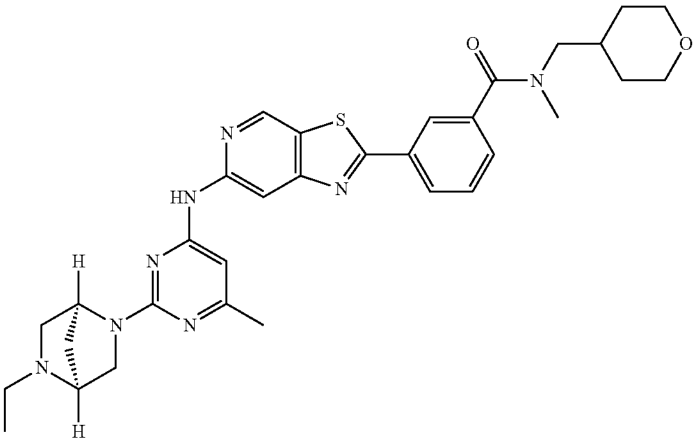 [SMILES: CCN1C[C@@H]2C[C@H]1CN2c1nc(C)cc(Nc2cc3nc(-c4cccc(C(=O)N(C)CC5CCOCC5)c4)sc3cn2)n1] |

TABLE 2-continued
| Ex. No. | Structure |
|---|---|
| 524 | 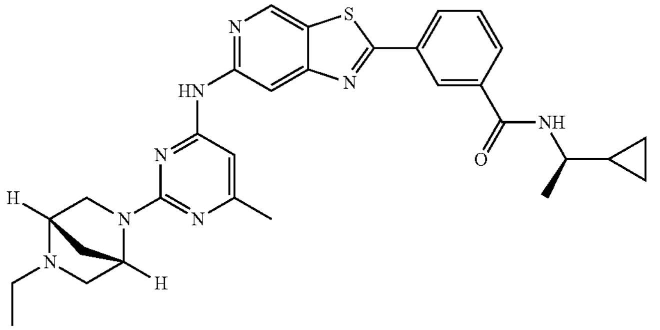 [SMILES: CCN1C[C@@H]2C[C@H]1CN2c1nc(C)cc(Nc2cc3nc(-c4cccc(C(=O)N[C@H](C)C5CC5)c4)sc3cn2)n1] |
| 525 | 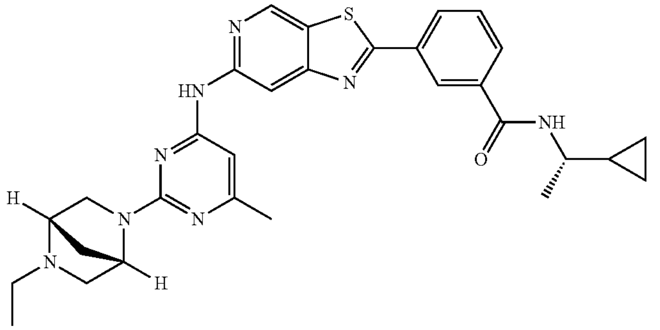 [SMILES: CCN1C[C@@H]2C[C@H]1CN2c1nc(C)cc(Nc2cc3nc(-c4cccc(C(=O)N[C@@H](C)C5CC5)c4)sc3cn2)n1] |
| 526 | 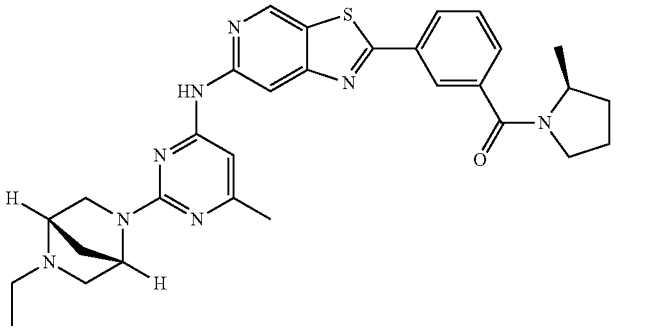 [SMILES: CCN1C[C@@H]2C[C@H]1CN2c1nc(C)cc(Nc2cc3nc(-c4cccc(C(=O)N5CCC[C@@H]5C)c4)sc3cn2)n1] |
| 527 | 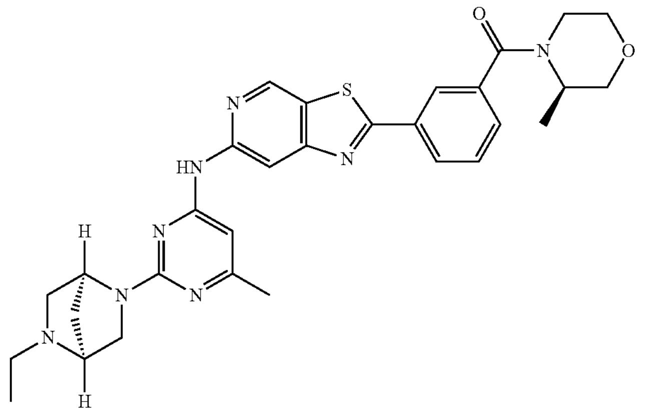 [SMILES: CCN1C[C@@H]2C[C@H]1CN2c1nc(C)cc(Nc2cc3nc(-c4cccc(C(=O)N5CCOC[C@H]5C)c4)sc3cn2)n1] |

TABLE 2-continued
| Ex. No. | Structure |
| --- | --- |
| 528 | 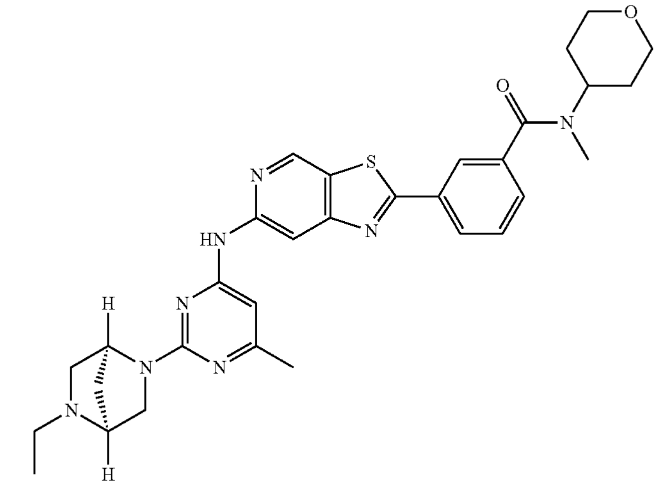 [SMILES: CCN1C[C@@H]2C[C@H]1CN2c1nc(C)cc(Nc2cc3nc(-c4cccc(C(=O)N(C)C5CCOCC5)c4)sc3cn2)n1] |
| 529 | 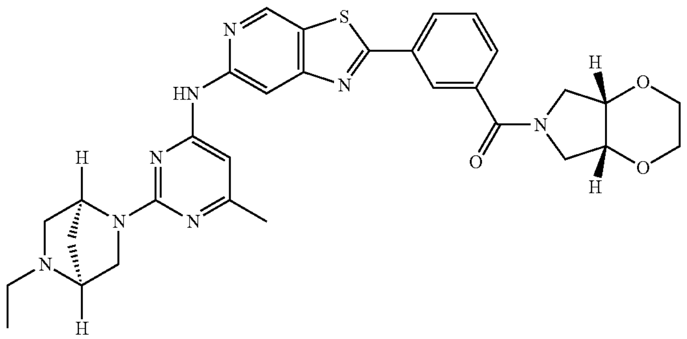 [SMILES: CCN1C[C@@H]2C[C@H]1CN2c1nc(C)cc(Nc2cc3nc(-c4cccc(C(=O)N5C[C@@H]6OCCO[C@@H]6C5)c4)sc3cn2)n1] |
| 530 | 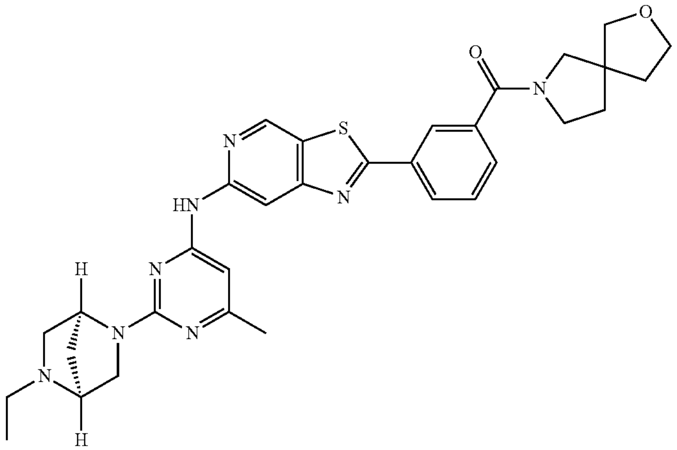 [SMILES: CCN1C[C@@H]2C[C@H]1CN2c1nc(C)cc(Nc2cc3nc(-c4cccc(C(=O)N5CCC6(CCOC6)C5)c4)sc3cn2)n1] |

TABLE 2-continued
| Ex. No. | Structure |
|---|---|
| 531 | 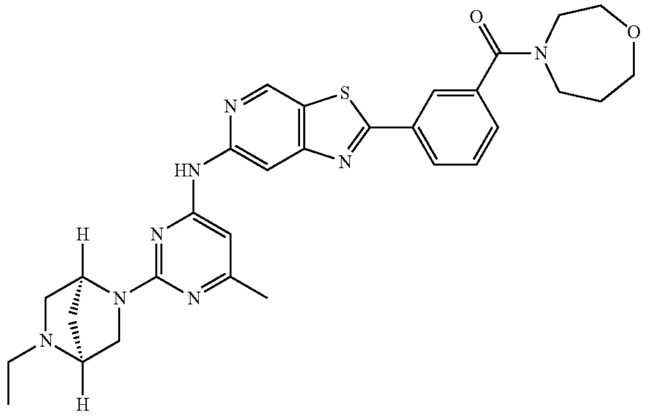 [SMILES: CCN1C[C@@H]2C[C@H]1CN2c1nc(C)cc(Nc2cc3nc(-c4cccc(C(=O)N5CCCOCC5)c4)sc3cn2)n1] |
| 532 | 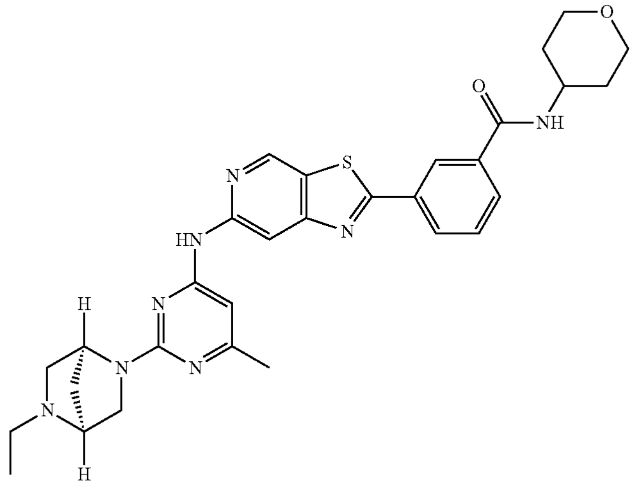 [SMILES: CCN1C[C@@H]2C[C@H]1CN2c1nc(C)cc(Nc2cc3nc(-c4cccc(C(=O)NC5CCOCC5)c4)sc3cn2)n1] |
| 533 | 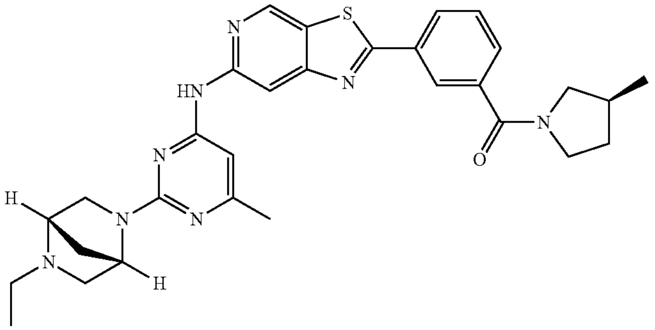 [SMILES: CCN1C[C@@H]2C[C@H]1CN2c1nc(C)cc(Nc2cc3nc(-c4cccc(C(=O)N5CC[C@H](C)C5)c4)sc3cn2)n1] |
| 534 | 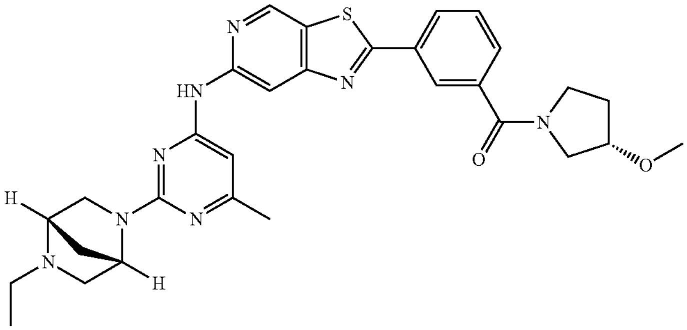 [SMILES: CCN1C[C@@H]2C[C@H]1CN2c1nc(C)cc(Nc2cc3nc(-c4cccc(C(=O)N5CC[C@H](OC)C5)c4)sc3cn2)n1] |

TABLE 2-continued
| Ex. No. | Structure |
|---|---|
| 535 | 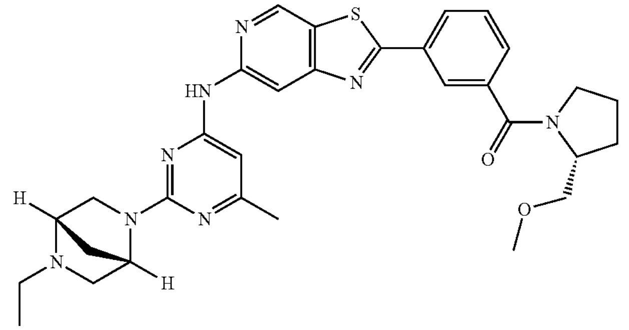 [SMILES: CCN1C[C@@H]2C[C@H]1CN2c1nc(C)cc(Nc2cc3nc(-c4cccc(C(=O)N5CCC[C@@H]5COC)c4)sc3cn2)n1] |
| 536 | 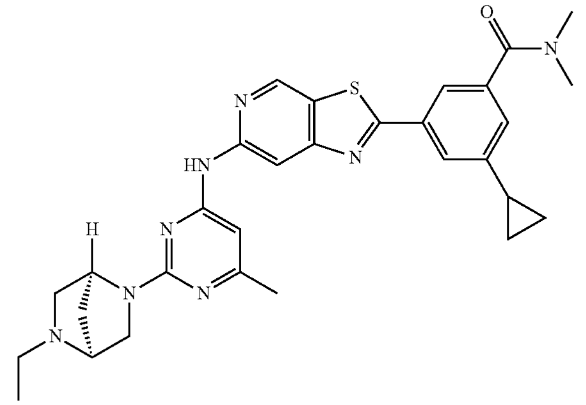 [SMILES: CCN1C[C@@H]2C[C@H]1CN2c1nc(C)cc(Nc2cc3nc(-c4cc(C(=O)N(C)C)cc(C5CC5)c4)sc3cn2)n1] |
| 537 | 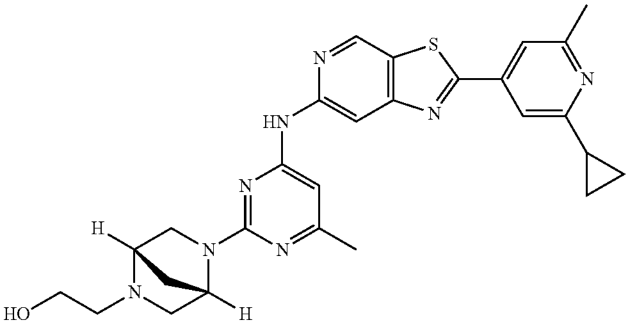 [SMILES: Cc1cc(-c2nc3cc(Nc4cc(C)nc(N5C[C@@H]6C[C@H]5CN6CCO)n4)ncc3s2)cc(C2CC2)n1] |
| 538 | 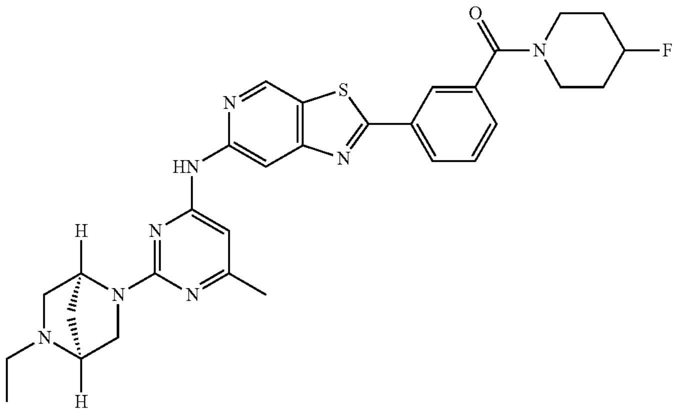 [SMILES: CCN1C[C@@H]2C[C@H]1CN2c1nc(C)cc(Nc2cc3nc(-c4cccc(C(=O)N5CCC(F)CC5)c4)sc3cn2)n1] |

TABLE 2-continued
| Ex. No. | Structure |
| --- | --- |
| 539 | 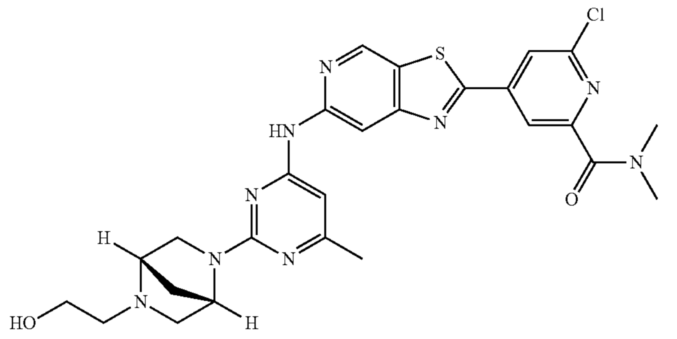 [SMILES: Cc1cc(Nc2cc3nc(-c4cc(Cl)nc(C(=O)N(C)C)c4)sc3cn2)nc(N2C[C@@H]3C[C@H]2CN3CCO)n1] |
| 540 | 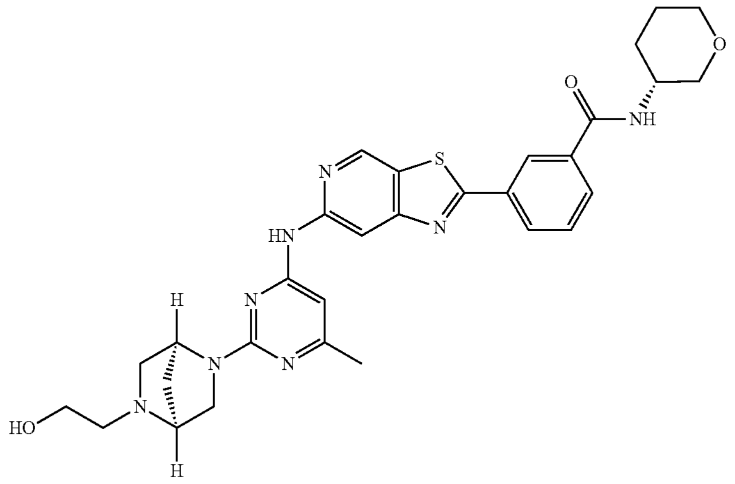 [SMILES: Cc1cc(Nc2cc3nc(-c4cccc(C(=O)N[C@@H]5CCCOC5)c4)sc3cn2)nc(N2C[C@@H]3C[C@H]2CN3CCO)n1] |
| 541 | 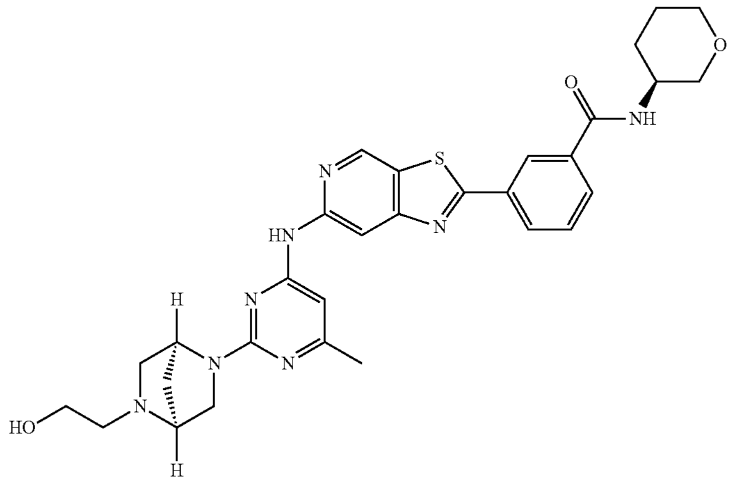 [SMILES: Cc1cc(Nc2cc3nc(-c4cccc(C(=O)N[C@H]5CCCOC5)c4)sc3cn2)nc(N2C[C@@H]3C[C@H]2CN3CCO)n1] |

TABLE 2-continued
| Ex. No. | Structure |
| --- | --- |
| 542 | 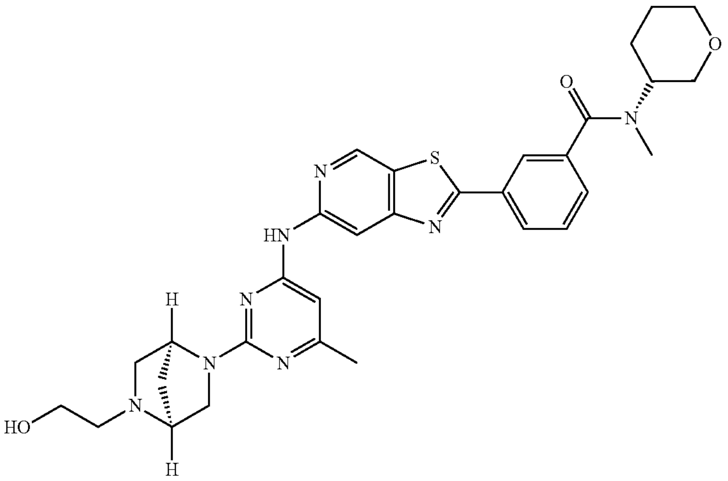 |
| 543 | 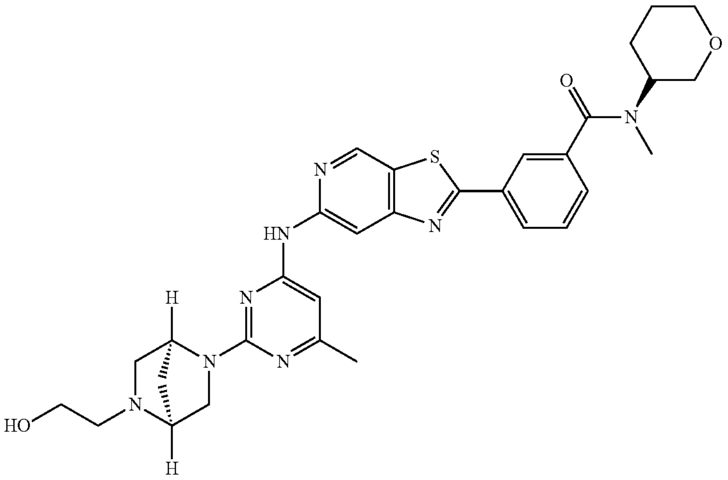 |
| 544 | 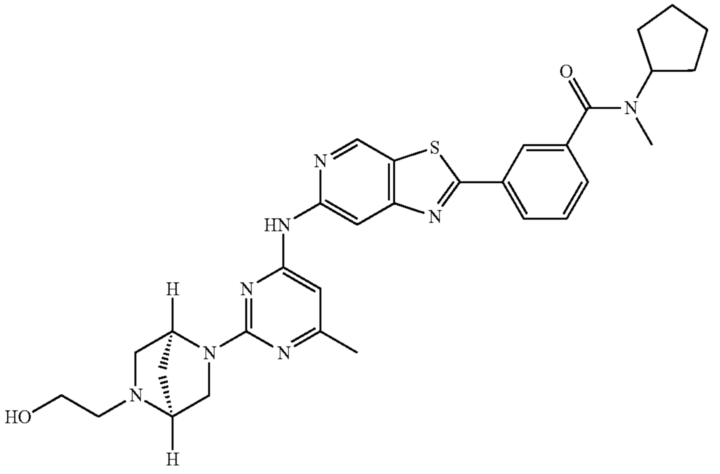 [SMILES: Cc1cc(Nc2cc3nc(-c4cccc(C(=O)N(C)C5CCCC5)c4)sc3cn2)nc(N2C[C@@H]3C[C@H]2CN3CCO)n1] |

TABLE 2-continued
| Ex. No. | Structure |
|---|---|
| 545 | 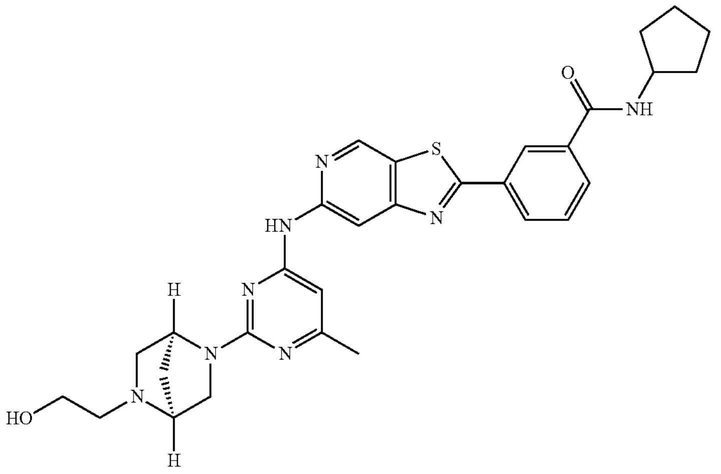 [SMILES: Cc1cc(Nc2cc3nc(-c4cccc(C(=O)NC5CCCC5)c4)sc3cn2)nc(N2C[C@@H]3C[C@H]2CN3CCO)n1] |
| 546 | 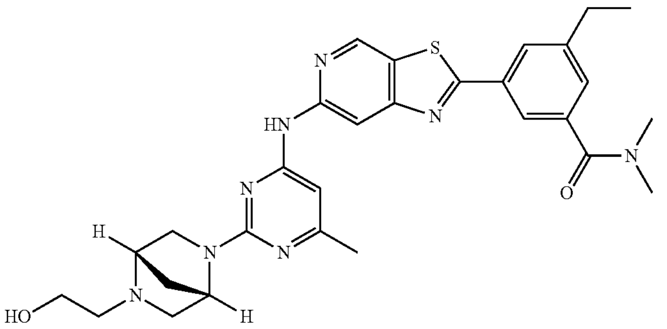 [SMILES: CCc1cc(C(=O)N(C)C)cc(-c2nc3cc(Nc4cc(C)nc(N5C[C@@H]6C[C@H]5CN6CCO)n4)ncc3s2)c1] |
| 547 | 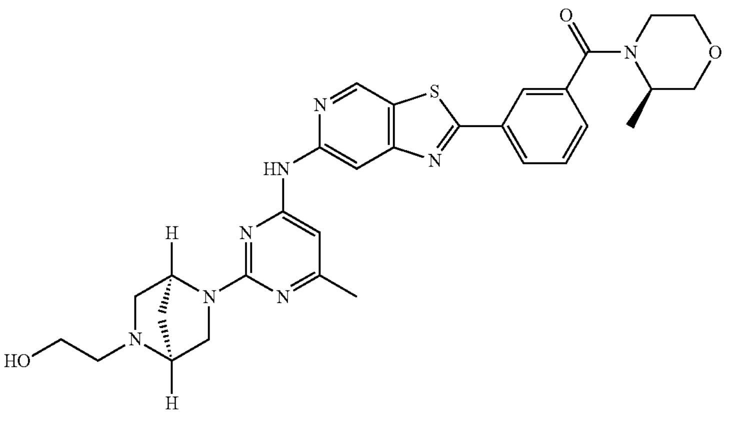 [SMILES: Cc1cc(Nc2cc3nc(-c4cccc(C(=O)N5CCOC[C@H]5C)c4)sc3cn2)nc(N2C[C@@H]3C[C@H]2CN3CCO)n1] |
| 548 | 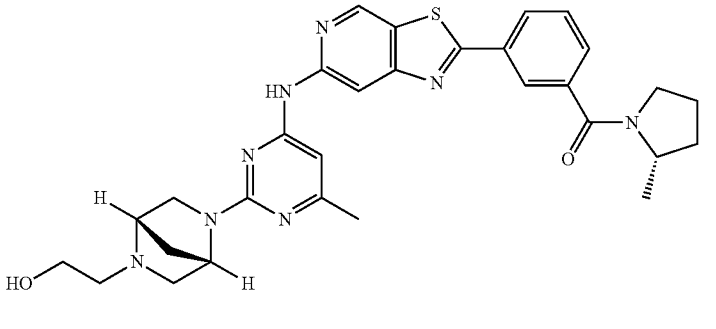 [SMILES: Cc1cc(Nc2cc3nc(-c4cccc(C(=O)N5CCC[C@@H]5C)c4)sc3cn2)nc(N2C[C@@H]3C[C@H]2CN3CCO)n1] |

TABLE 2-continued
| Ex. No. | Structure |
|---|---|
| 549 | 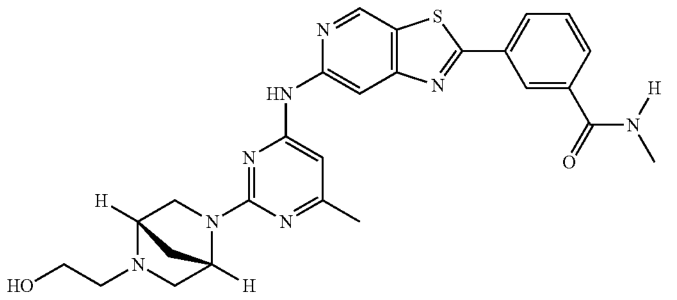 [SMILES: CNC(=O)c1cccc(-c2nc3cc(Nc4cc(C)nc(N5C[C@@H]6C[C@H]5CN6CCO)n4)ncc3s2)c1] |
| 550 | 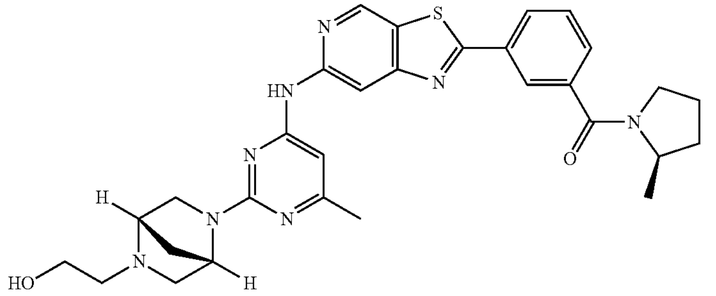 [SMILES: Cc1cc(Nc2cc3nc(-c4cccc(C(=O)N5CCC[C@H]5C)c4)sc3cn2)nc(N2C[C@@H]3C[C@H]2CN3CCO)n1] |
| 551 | 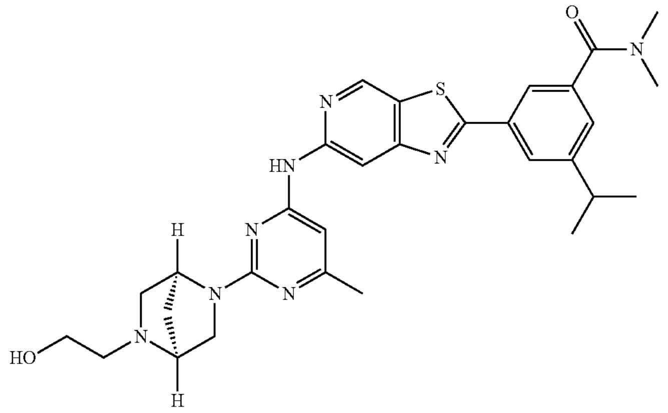 [SMILES: Cc1cc(Nc2cc3nc(-c4cc(C(=O)N(C)C)cc(C(C)C)c4)sc3cn2)nc(N2C[C@@H]3C[C@H]2CN3CCO)n1] |
| 552 | 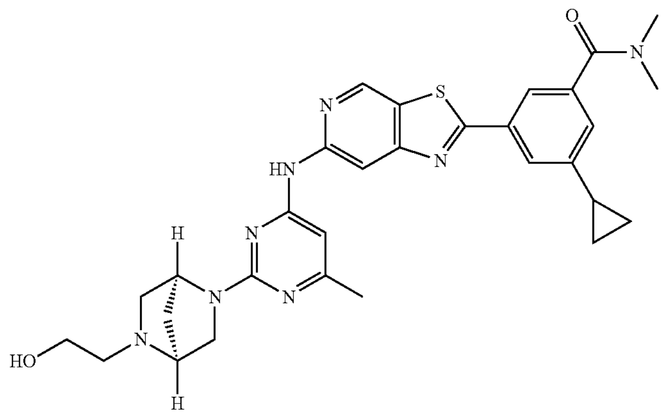 [SMILES: Cc1cc(Nc2cc3nc(-c4cc(C(=O)N(C)C)cc(C5CC5)c4)sc3cn2)nc(N2C[C@@H]3C[C@H]2CN3CCO)n1] |

TABLE 2-continued
| Ex. No. | Structure |
|---|---|
| 553 | 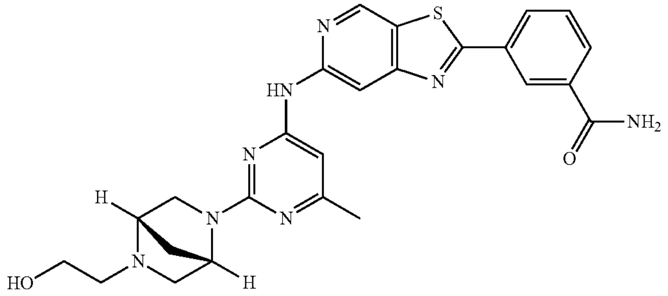 [SMILES: Cc1cc(Nc2cc3nc(-c4cccc(C(N)=O)c4)sc3cn2)nc(N2C[C@@H]3C[C@H]2CN3CCO)n1] |
| 554 | 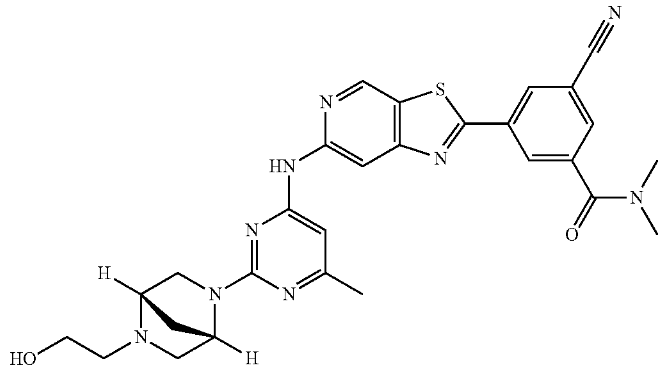 [SMILES: Cc1cc(Nc2cc3nc(-c4cc(C#N)cc(C(=O)N(C)C)c4)sc3cn2)nc(N2C[C@@H]3C[C@H]2CN3CCO)n1] |
| 555 | 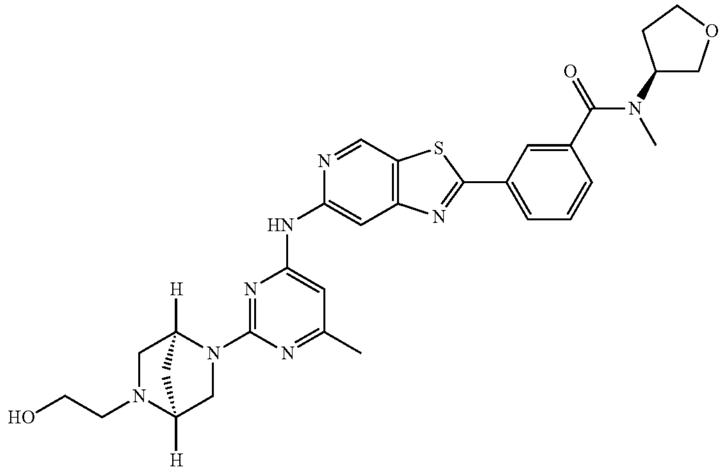 [SMILES: Cc1cc(Nc2cc3nc(-c4cccc(C(=O)N(C)[C@H]5CCOC5)c4)sc3cn2)nc(N2C[C@@H]3C[C@H]2CN3CCO)n1] |
| 556 | 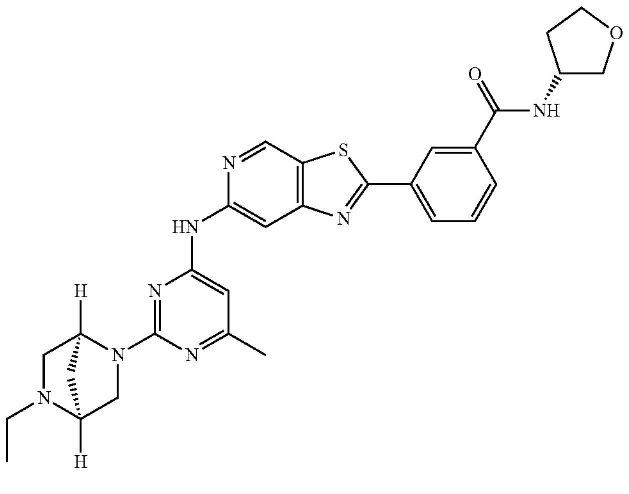 |

TABLE 2-continued
| Ex. No. | Structure |
| --- | --- |
| 557 | 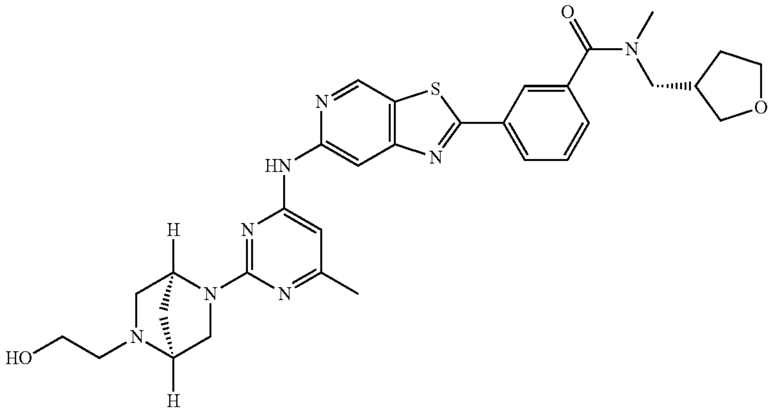 |
| 558 | 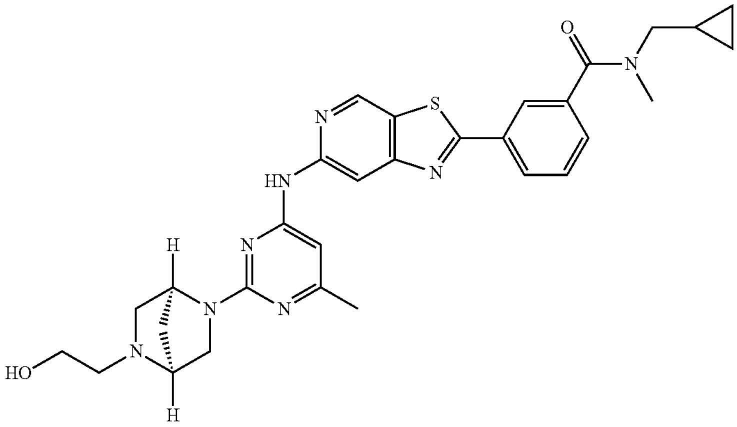 [SMILES: Cc1cc(Nc2cc3nc(-c4cccc(C(=O)N(C)CC5CC5)c4)sc3cn2)nc(N2C[C@@H]3C[C@H]2CN3CCO)n1] |
| 559 | 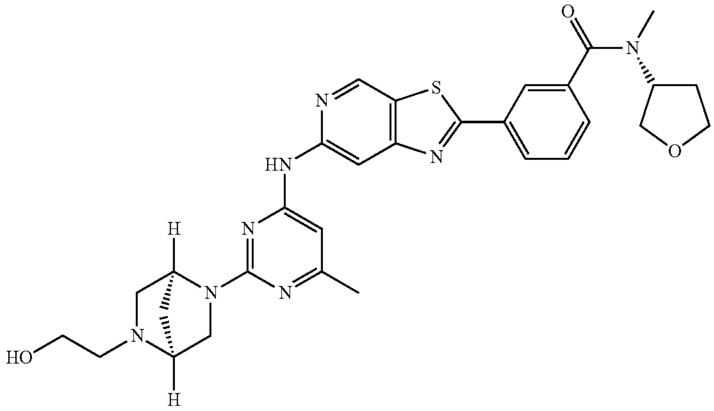 |

TABLE 2-continued
| Ex. No. | Structure |
|---|---|
| 560 | 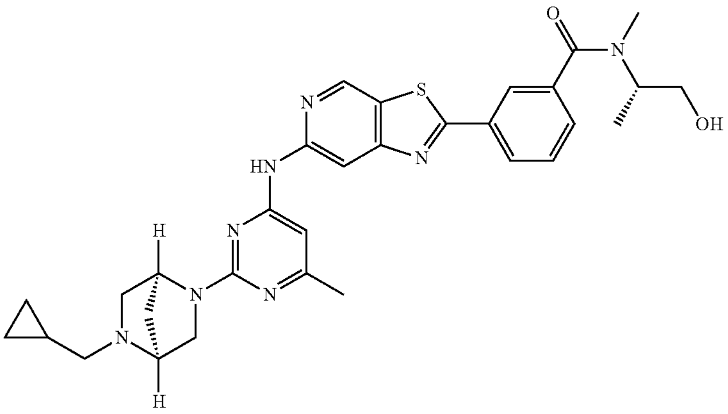 [SMILES: Cc1cc(Nc2cc3nc(-c4cccc(C(=O)N(C)[C@@H](C)CO)c4)sc3cn2)nc(N2C[C@@H]3C[C@H]2CN3CC2CC2)n1] |
| 561 | 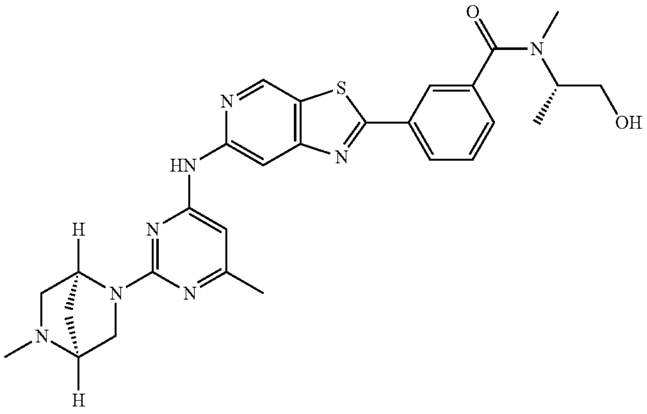 [SMILES: Cc1cc(Nc2cc3nc(-c4cccc(C(=O)N(C)[C@@H](C)CO)c4)sc3cn2)nc(N2C[C@@H]3C[C@H]2CN3C)n1] |
| 562 | 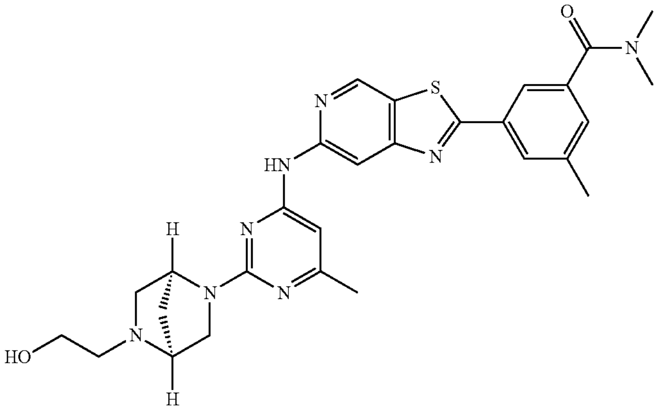 [SMILES: Cc1cc(C(=O)N(C)C)cc(-c2nc3cc(Nc4cc(C)nc(N5C[C@@H]6C[C@H]5CN6CCO)n4)ncc3s2)c1] |

TABLE 2-continued
| Ex. No. | Structure |
| --- | --- |
| 563 | 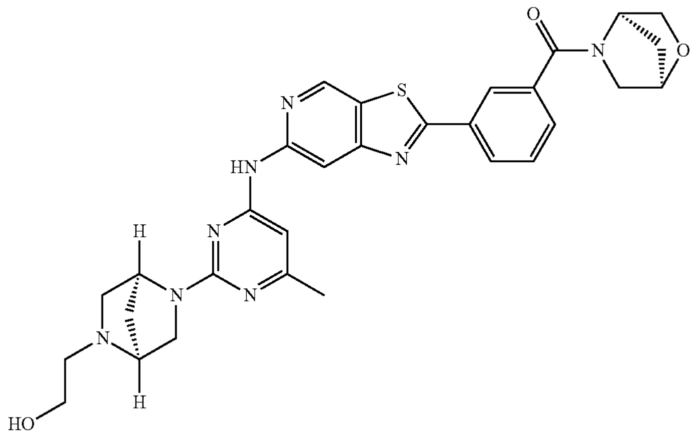 [SMILES: Cc1cc(Nc2cc3nc(-c4cccc(C(=O)N5C[C@H]6C[C@@H]5CO6)c4)sc3cn2)nc(N2C[C@@H]3C[C@H]2CN3CCO)n1] |
| 564 | 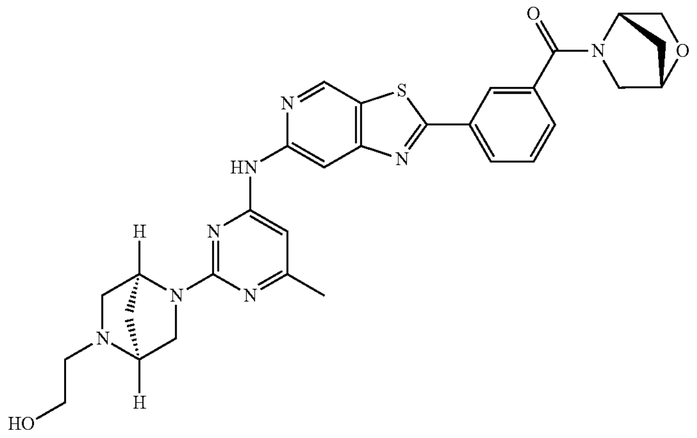 [SMILES: Cc1cc(Nc2cc3nc(-c4cccc(C(=O)N5C[C@@H]6C[C@H]5CO6)c4)sc3cn2)nc(N2C[C@@H]3C[C@H]2CN3CCO)n1] |
| 565 | 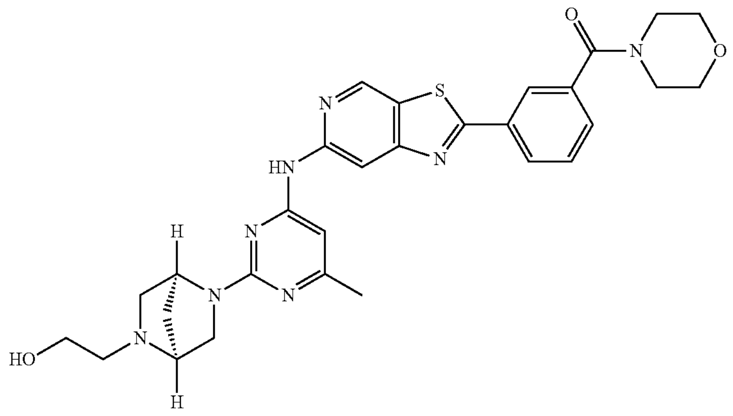 [SMILES: Cc1cc(Nc2cc3nc(-c4cccc(C(=O)N5CCOCC5)c4)sc3cn2)nc(N2C[C@@H]3C[C@H]2CN3CCO)n1] |

TABLE 2-continued
| Ex. No. | Structure |
| --- | --- |
| 566 | 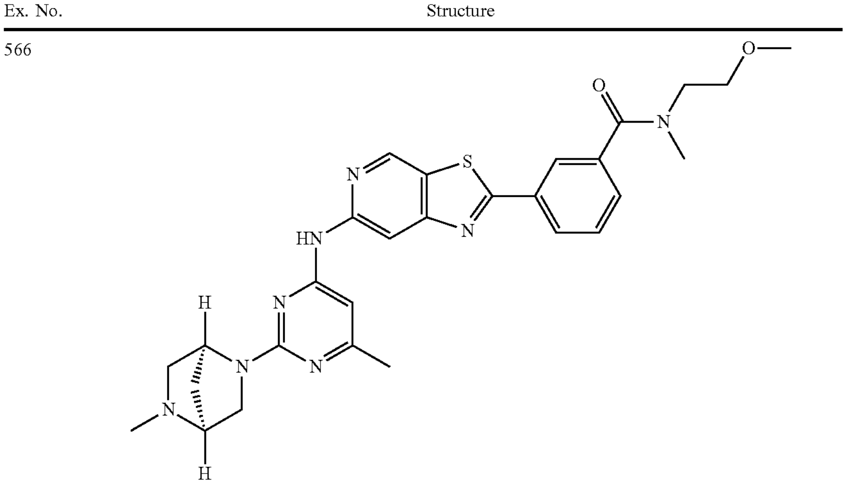 |
| 567 | 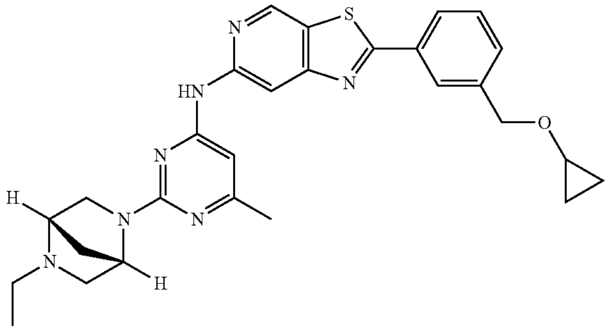 [SMILES: CCN1C[C@@H]2C[C@H]1CN2c1nc(C)cc(Nc2cc3nc(-c4cccc(COC5CC5)c4)sc3cn2)n1] |
| 568 | 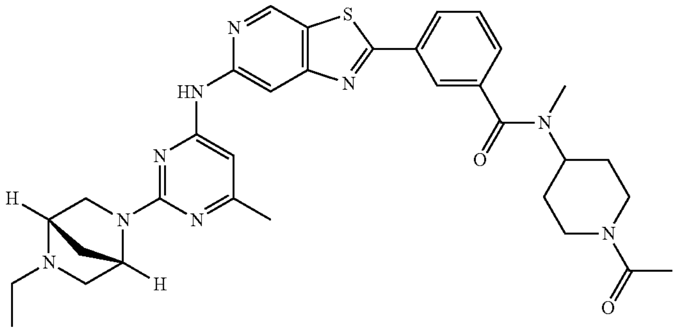 [SMILES: CCN1C[C@@H]2C[C@H]1CN2c1nc(C)cc(Nc2cc3nc(-c4cccc(C(=O)N(C)C5CCN(C(C)=O)CC5)c4)sc3cn2)n1] |
| 569 | 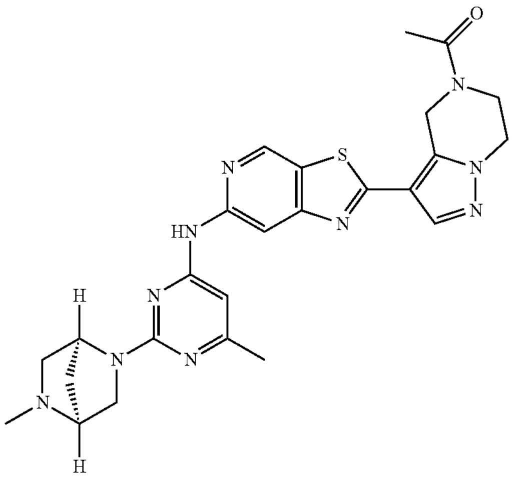 [SMILES: CC(=O)N1CCn2ncc(-c3nc4cc(Nc5cc(C)nc(N6C[C@@H]7C[C@H]6CN7C)n5)ncc4s3)c2C1] |

TABLE 2-continued
| Ex. No. | Structure |
| --- | --- |
| 570 | 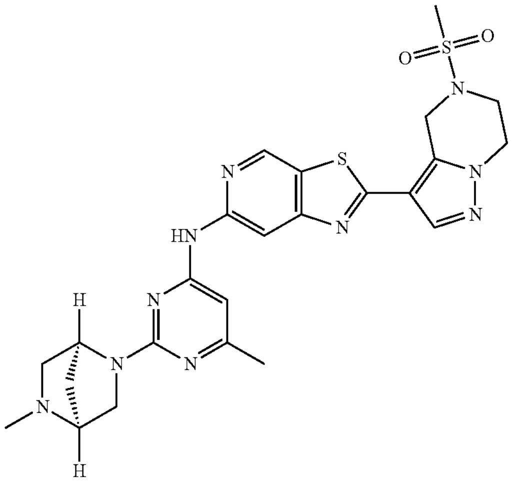 [SMILES: Cc1cc(Nc2cc3nc(-c4cnn5c4CN(S(C)(=O)=O)CC5)sc3cn2)nc(N2C[C@@H]3C[C@H]2CN3C)n1] |
| 571 | 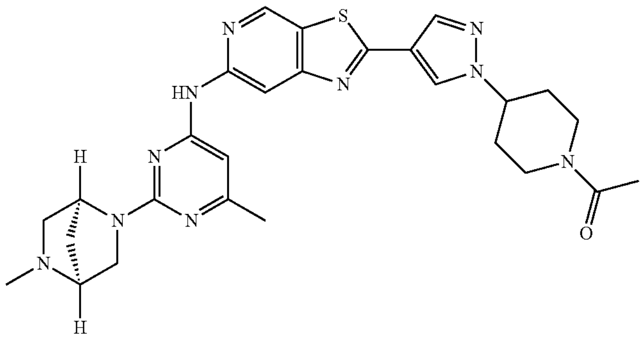 [SMILES: CC(=O)N1CCC(n2cc(-c3nc4cc(Nc5cc(C)nc(N6C[C@@H]7C[C@H]6CN7C)n5)ncc4s3)cn2)CC1] |
| 572 | 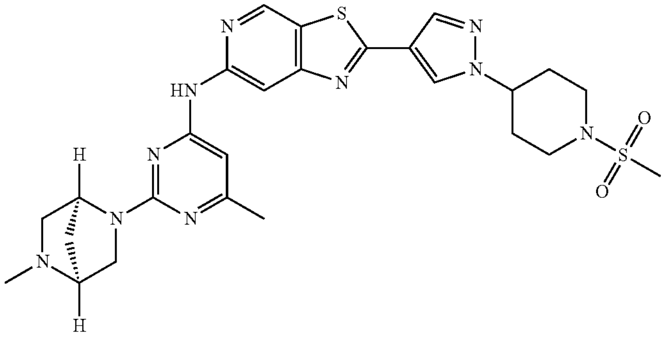 |
| 573 | 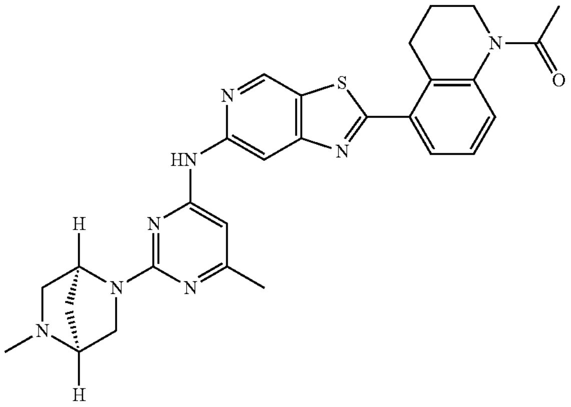 [SMILES: CC(=O)N1CCCc2c(-c3nc4cc(Nc5cc(C)nc(N6C[C@@H]7C[C@H]6CN7C)n5)ncc4s3)cccc21] |

TABLE 2-continued
| Ex. No. | Structure |
| --- | --- |
| 574 | 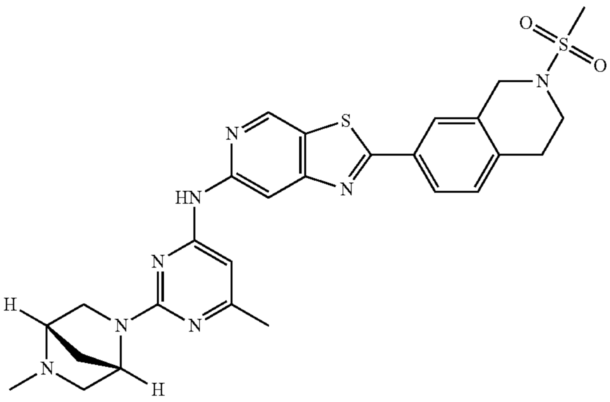 [SMILES: Cc1cc(Nc2cc3nc(-c4ccc5c(c4)CN(S(C)(=O)=O)CC5)sc3cn2)nc(N2C[C@@H]3C[C@H]2CN3C)n1] |
| 575 | 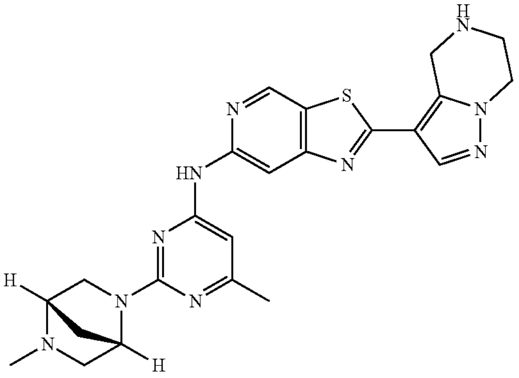 [SMILES: Cc1cc(Nc2cc3nc(-c4cnn5c4CNCC5)sc3cn2)nc(N2C[C@@H]3C[C@H]2CN3C)n1] |
| 576 | 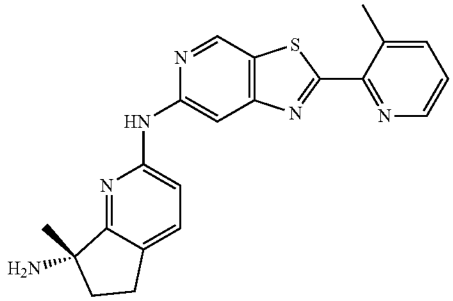 [SMILES: Cc1cccnc1-c1nc2cc(Nc3ccc4c(n3)[C@@](C)(N)CC4)ncc2s1] |
| 577 | 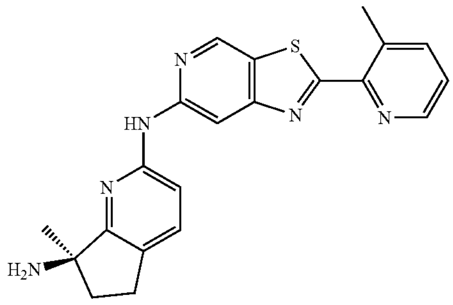 [SMILES: Cc1cccnc1-c1nc2cc(Nc3ccc4c(n3)[C@](C)(N)CC4)ncc2s1] |

TABLE 2-continued
| Ex. No. | Structure |
| --- | --- |
| 578 | 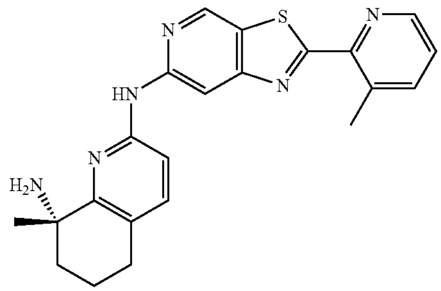 [SMILES: Cc1cccnc1-c1nc2cc(Nc3ccc4c(n3)[C@@](C)(N)CCC4)ncc2s1] |
| 579 | 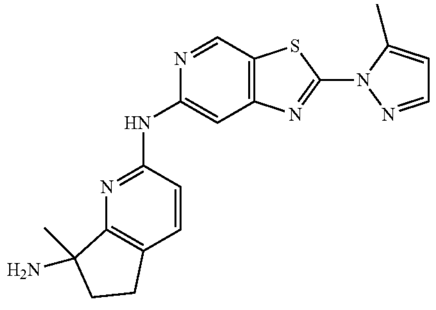 [SMILES: Cc1ccnn1-c1nc2cc(Nc3ccc4c(n3)C(C)(N)CC4)ncc2s1] |
| 580 | 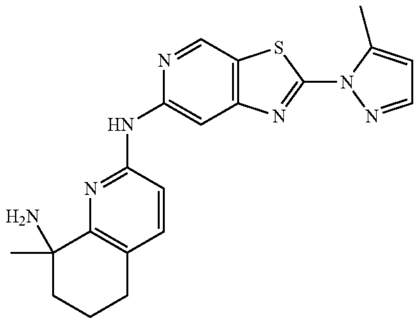 [SMILES: Cc1ccnn1-c1nc2cc(Nc3ccc4c(n3)C(C)(N)CCC4)ncc2s1] |
| 581 | 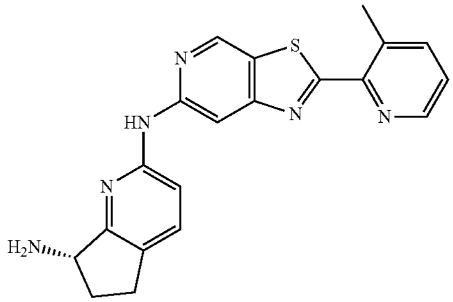 [SMILES: Cc1cccnc1-c1nc2cc(Nc3ccc4c(n3)[C@@H](N)CC4)ncc2s1] |
| 582 | 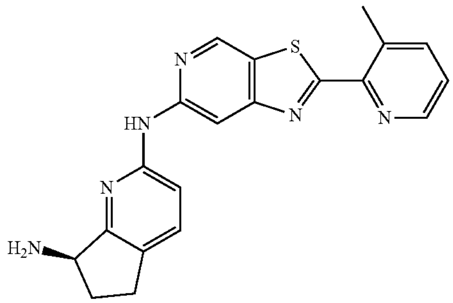 [SMILES: Cc1cccnc1-c1nc2cc(Nc3ccc4c(n3)[C@H](N)CC4)ncc2s1] |

TABLE 2-continued
| Ex. No. | Structure |
| --- | --- |
| 583 | 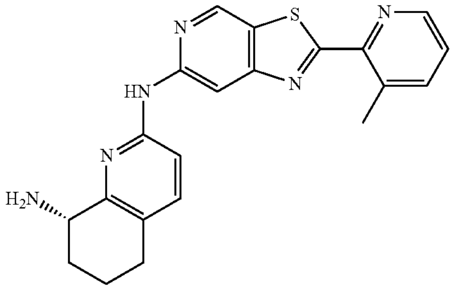 [SMILES: Cc1cccnc1-c1nc2cc(Nc3ccc4c(n3)[C@@H](N)CCC4)ncc2s1] |
| 584 | 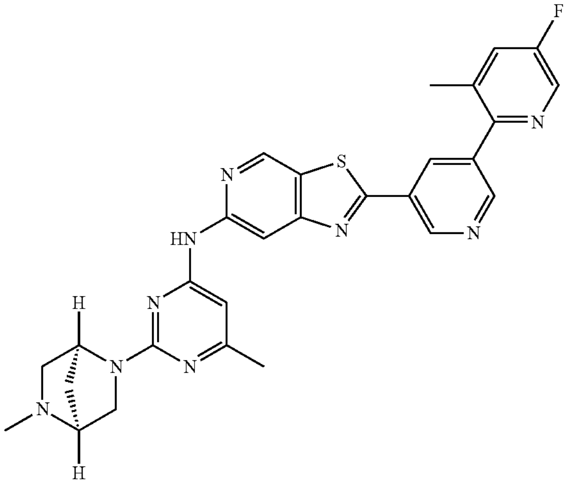 [SMILES: Cc1cc(Nc2cc3nc(-c4cncc(-c5ncc(F)cc5C)c4)sc3cn2)nc(N2C[C@@H]3C[C@H]2CN3C)n1] |
| 585 | 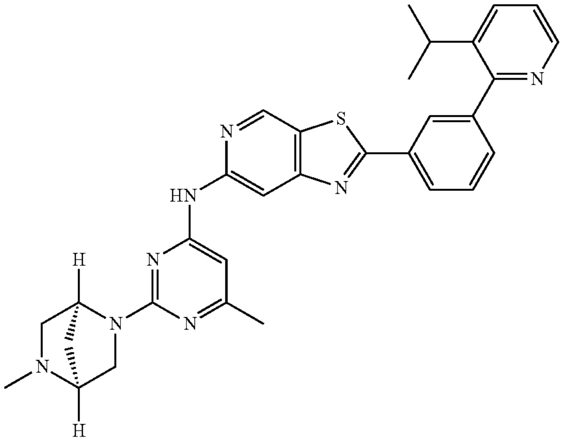 [SMILES: Cc1cc(Nc2cc3nc(-c4cccc(-c5ncccc5C(C)C)c4)sc3cn2)nc(N2C[C@@H]3C[C@H]2CN3C)n1] |

TABLE 2-continued

| Ex. No. | Structure |
|---|---|
| 586 | 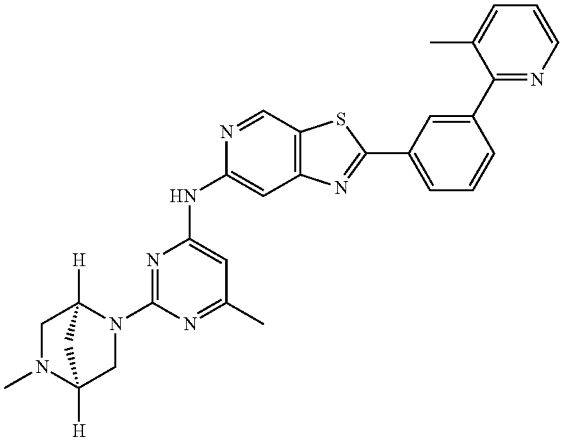 [SMILES: Cc1cc(Nc2cc3nc(-c4cccc(-c5ncccc5C)c4)sc3cn2)nc(N2C[C@@H]3C[C@H]2CN3C)n1] |

Therapeutic and Prophylactic Uses

The present disclosure provides methods for using compounds described herein in the preparation of a medicament for inhibiting HPK1. As used herein, the terms "inhibit", "inhibition" and the like refer to the ability of a compound to decrease the function or activity of a particular target, e.g., HPK1. The decrease is preferably at least 50% and may be, for example, at least about 55%, at least about 60%, at least about 65%, at least about 70%, at least about 75%, at least about 80%, at least about 85%, at least about 90%, or at least about 95%. The present disclosure also encompasses the use of the compounds described herein in the preparation of a medicament for the treatment or prevention of diseases, disorders, and/or conditions that would benefit from inhibition of HPK1. As one example, the present disclosure encompasses the use of the compounds described herein in the preparation of a medicament for the treatment of cancer. As one example, the present disclosure encompasses the use of the compounds described herein in the preparation of a medicament for the treatment of an infectious disease, optionally a viral infection. In some embodiments of the aforementioned methods, the compounds described herein are used in combination with at least one additional therapy, examples of which are set forth elsewhere herein.

HPK1 is a serine/threonine kinase and member of the MAP4K family. Through this activity, HPK1 functions, in one aspect, as a negative regulator of immune cell (e.g., T cell, B, cell, dendritic cell) activation. For example, activated HPK1, which is phosphorylated at residues Y381, S171, and T165, binds and phosphorylates adaptor proteins critical for T cell signaling, leading to destabilization of the T cell receptor (TCR) signaling complex and disruption of TCR signaling. In particular, activated HPK1 phosphorylates SLP76 and GADS leading to recruitment of 14-3-3 and ubiquitin mediated proteasomal degradation of intracellular signaling proteins. HPK1 is believed to negatively regulate B cell receptor signaling in an analogous way to T cells and may have a role in limiting dendritic cell activation through TLR4.

As demonstrated herein, the use of compounds described herein potently inhibit HPK1 activity, resulting in increased immune cell activity and anti-tumor immune responses. Diseases, disorders, and/or conditions that would benefit from HPK1 inhibition may include those where greater immune cell (e.g., T cell, NK cell, etc.) activation is desired; where there is limited immune cell stimulation, for example, due to low antigen density, poor quality neoantigen, high PD-L1 expression, T cell exhaustion, or combinations thereof; and/or where the tumor microenvironment is characterized by extracellular immunosuppressive molecules such as adenosine, TGF-beta, PGE2, or combinations thereof.

Accordingly, in some embodiments, the compounds described herein are administered to a subject in need thereof in an amount effective to inhibit HPK1 activity. HPK1 activity may be assessed using cells (e.g., T cells, B cells, dendritic cells, or precursors thereof) obtained from a peripheral blood sample or a tissue sample (e.g., a tumor sample) that was obtained from the subject. Activity may be determined, for example, by comparison to a previous sample obtained from the subject (i.e., prior to administration of the compound) or by comparison to a reference value for a control group (e.g., standard of care, a placebo, etc.). In some embodiments, a measure of HPK1 inhibition may be decreased phosphorylation of SLP76 at S376 and/or GADS in T cells. In another example, a measure of HPK1 inhibition may be increased MAP kinase pathway signaling and AP-1 transcription in T cells. In a further example, a measure of HPK1 inhibition may be decreased phosphorylation of BLNK Th-152 in B cells.

Alternatively or in addition, in some embodiments, the compounds described herein are administered to a subject in need thereof in an amount effective to increase immune cell activity, as compared to a suitable control (e.g., a subject receiving standard of care, a subject receiving no treatment or a placebo treatment, etc.). Immune cell activity may be assessed using cells (e.g., T cells, B cells, dendritic cells, or precursors thereof) obtained from a peripheral blood sample or a tissue sample (e.g., a tumor sample) that was obtained from the subject. Non-limiting examples of measures of increased immune cell activity may include increased expression, production and/or secretion of chemokines, pro-inflammatory cytokines and/or cytotoxic factors, increased cytotoxic activity, and increased gene expression and/or cell surface markers related to immune cell function and immune signaling. Examples of pro-inflammatory cytokines include, but are not limited to, IL-1a, IL-1b, IL-2, IL-6, IL-13, IL-17a, interferon gamma (INF-γ or INF-g), tumor necrosis factor-alpha (TNF-α or TNF-α), TNF-beta (TNF-β or TNF-b), fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of cytotoxic factors include, but are not limited to, granzyme A, granzyme B, soluble Fas ligand (sFasL), and perforin.

Alternatively or in addition, in some embodiments, the compounds described herein are administered to a subject in need thereof in an amount effective to increase immune cell proliferation. Immune cell numbers in tissue or blood may be quantified (absolute numbers or relative numbers) by immunophenotyping, i.e., a process of using antibodies (or other antigen-specific reagent) to detect and quantify cell-associated antigens. Lymphoid cell markers may include but are not limited to CD3, CD4, CD8, CD16, CD25, CD39, CD45, CD56, CD69, CD103, CD127, and FOXP3. CD4 and CD8 can distinguish T cell with different effector functions (e.g., CD4+ T cells and CD8+ T cells). Co-expression of different cell markers can further distinguish sub-groups. For example, co-expression of CD39 and CD103 can differentiate tumor-specific T cells (CD8+CD39+CD103+ T cells) from bystander T cells in the tumor microenvironment (TME). For dendritic cells, suitable markers may include but are not limited to CD11c, HLA-DR, CD141, and CLEC9A. For myeloid cells, suitable markers may include but are not limited to CD14, CD68, CD80, CD83, CD86, CD163, and CD206. Ki67 is a non-limiting example of a suitable marker of cell proliferation, such that an increase in Ki67 positive cells (e.g., CD8+ T cells, NK cells, etc.) as compared to a reference sample indicate cell proliferation.

In some embodiments, the compounds described herein are administered to a subject in need thereof in an amount effective to increase T cell activity. In certain embodiments, the T cells are CD8+ T cells, optionally tumor infiltrating CD8+ T cells and/or antigen experienced CD8+ T cells. Measures of increased T cell activity may be increased T cell expression, production or secretion of chemokines, pro-inflammatory cytokines (e.g., IFNγ, TNF-α, IL-2, etc.) and/or cytotoxic factors (e.g. perforin, Granzyme B, etc.); increased pro-inflammatory cytokine levels in the tumor microenvironment or periphery; increased expression of T cell surface markers of activation (e.g., CD69); increased T cell receptor (TCR) signaling; increased calcium flux in a T cell, increased glucose uptake by a T cell; increased glycolysis in a T cell; and increased killing of cancer cells by T cells.

In some embodiments, the compounds according to this disclosure are useful in the treatment of a viral infection. In some embodiments, the viral infection is a disease caused by hepatitis C virus (HCV), human papilloma virus (HPV), cytomegalovirus (CMV), herpes simplex virus (HSV), Epstin-Barr virus (EBV), varicella zoster virus, coxsackie virus, human immunodeficiency virus (HIV), or lymphocytic choriomeningitis virus (LCMV).

Alternatively or in addition, in some embodiments, the compounds described herein are administered to a subject in need thereof to treat and/or prevent cancer or a cancer-related disease, disorder or condition. In some embodiments, the compounds described herein are administered to a subject in need thereof to treat cancer, optionally in combination with at least one additional therapy, examples of which are set forth elsewhere herein.

Alternatively or in addition, in some embodiments, the compounds described herein are brought into contact with an immune cell or a plurality of immune cells, in vitro or ex vivo, in an amount effective to increase proliferation, activation or activity of the immune cell(s). In some embodiments, the immune cells may be T cells, B cells or dendritic cells. The immune cell(s) may be allogenic immune cell(s) collected from one or more subjects, or may be autologous immune cell(s) collected from a subject in need of treatment. In certain embodiments, the cells may be "(re)programmed" allogenic immune cells produced from immune precursor cells (e.g., lymphoid progenitor cells, myeloid progenitor cells, common dendritic cell precursor cells, stem cells, induced pluripotent stem cells, etc.). In various embodiments, the immune cells may be genetically modified to target the cells to a specific antigen and/or enhance the cells' anti-tumor effects (e.g., engineered T cell receptor (TCR) cellular therapies, chimeric antigen receptor (CAR) cellular therapies, etc.). In some embodiments, the in vitro or ex vivo treated immune cell(s) are then administered to a subject in need thereof to treat and/or prevent cancer or a cancer-related disease, disorder or condition. In some embodiments, the in vitro or ex vivo treated immune cells are administered to a subject in need thereof to treat cancer, optionally in combination with at least one additional therapy, examples of which are set forth elsewhere herein.

In one or more embodiments, the compounds described herein are useful in the treatment and/or prophylaxis of cancer (e.g., carcinomas, sarcomas, leukemias, lymphomas, myelomas, etc.). In certain embodiments, the cancer may be locally advanced and/or unresectable, metastatic, or at risk of becoming metastatic. Alternatively, or in addition, the cancer may be recurrent or no longer responding to a treatment, such as a standard of care treatment known to one of skill in the art. Exemplary types of cancer contemplated by this disclosure include cancer of the genitourinary tract (e.g., bladder, kidney, renal cell, penile, prostate, testicular, uterus, cervix, ovary, etc.), breast, gastrointestinal tract (e.g., esophagus, oropharynx, stomach, small or large intestines, colon, or rectum), bone, bone marrow, skin (e.g., melanoma), head and neck, liver, gall bladder, bile ducts, heart, lung, pancreas, salivary gland, adrenal gland, thyroid, brain (e.g., gliomas), ganglia, central nervous system (CNS), peripheral nervous system (PNS), the hematopoietic system (i.e., hematological malignancies), and the immune system (e.g., spleen or thymus), and cancers associated with Von Hippel-Lindau disease (VHL).

In some embodiments, the compounds according to this disclosure are useful in the treatment and/or prophylaxis of hematological malignancies. Exemplary types of cancer affecting the hematopoietic system include leukemias, lymphomas and myelomas, including acute myeloid leukemia, adult T-cell leukemia, T-cell large granular lymphocyte leukemia, acute lymphoblastic leukemia, chronic lymphocytic leukemia, chronic myelogenous leukemia, acute monocytic leukemia, Hodgkin's and Non-Hodgkin's lymphoma, Diffuse large B Cell lymphoma, and multiple myeloma. In a specific embodiment, the compounds according to this disclosure are useful in the treatment of Diffuse large B Cell lymphoma, optionally Diffuse large B Cell lymphoma with Richter transformation.

In another embodiment, the compounds according to this disclosure are useful in the treatment and/or prophylaxis of solid tumors. The solid tumor may be, for example, ovarian cancer, endometrial cancer, breast cancer, lung cancer (small cell or non-small cell), colon cancer, prostate cancer, cervical cancer, biliary cancer, pancreatic cancer, gastric cancer, esophageal cancer, liver cancer (hepatocellular carcinoma), kidney cancer (renal cell carcinoma), head-and-neck tumors, mesothelioma, melanoma, sarcomas, central nervous system (CNS) hemangioblastomas, and brain tumors (e.g., gliomas, such as astrocytoma, oligodendroglioma and glioblastomas).

In another embodiment, the compounds according to this disclosure are useful in the treatment and/or prophylaxis of breast cancer, genitourinary cancer, gastrointestinal cancer, lung cancer, skin cancer, neuroendocrine cancer, head and neck cancer, liver cancer, hematological cancer, or a combination thereof.

In some embodiments, the compounds according to this disclosure are useful in the treatment of breast cancer. In further embodiments, the breast cancer is hormone receptor positive (e.g., ERα-positive breast cancer, PR-positive breast cancer, ERα-positive and PR-positive breast cancer), HER2 positive breast cancer, HER2 over-expressing breast cancer, or any combination thereof. In still further embodiments, the breast cancer is triple negative breast cancer.

In some embodiments, the compounds according to this disclosure are useful in the treatment of genitourinary cancer. In further embodiments, the genitourinary cancer is gynecologic cancer. In still further embodiments, the gynecologic cancer is endometrial cancer, cervical cancer, ovarian cancer or fallopian tube carcinoma. In still further embodiments, the genitourinary cancer is urothelial cancer. In still further embodiments, the genitourinary cancer is prostate cancer, optionally castration-resistant prostate cancer.

In some embodiments, the compounds according to this disclosure are useful in the treatment of kidney cancer. In further embodiments, the kidney cancer is renal cell carcinoma. In still further embodiments, the renal cell carcinoma is clear cell renal carcinoma.

In some embodiments, the compounds according to this disclosure are useful in the treatment of liver cancer. In further embodiments, the liver cancer is hepatocellular carcinoma.

In some embodiments, the compounds according to this disclosure are useful in the treatment of head and neck cancer. In further embodiments, the head and neck cancer is head and neck squamous cell carcinoma.

In some embodiments, the compounds according to this disclosure are useful in the treatment of skin cancer. In further embodiments, the skin cancer is melanoma.

In some embodiments, the compounds according to this disclosure are useful in the treatment of lung cancer. In further embodiments, the lung cancer is mesothelioma, small cell lung cancer (SCLC) or non-small cell lung cancer (NSCLC). In still further embodiments, the NSCLC is lung squamous cell carcinoma or lung adenocarcinoma.

In some embodiments, the compounds according to this disclosure are useful in the treatment of gastrointestinal (GI) cancer. In some embodiments, the gastrointestinal cancer is upper GI cancer, such as esophageal or gastric cancer. In further embodiments, the upper GI cancer is an adenocarcinoma, a squamous cell carcinoma, or any combination thereof. In still further embodiments, the upper GI cancer is esophageal adenocarcinoma (EAC), esophageal squamous cell carcinoma (ESCC), gastroesophageal junction adenocarcinoma (GEJ), gastric adenocarcinoma (also referred to herein as "gastric cancer") or any combination thereof. In some embodiments, the gastrointestinal cancer is lower GI cancer. In further embodiments, the lower GI cancer is colorectal cancer.

In some embodiments, the compounds according to this disclosure are useful in the treatment of hematological cancer. In some embodiments, the hematological cancer is lymphoma. In some embodiments, the lymphoma is Hodgkin's lymphoma. In some embodiments, the hematological cancer is leukemia.

In some embodiments, the compounds according to this disclosure are useful in the treatment of a neuroendocrine tumor. In further embodiments, the neuroendocrine tumor is pancreatic neuroendocrine tumor, pheochromocytoma, paraganglioma, or a tumor of the adrenal gland.

In some embodiments, the compounds according to this disclosure are useful in the treatment of brain cancer. In further embodiments, the brain cancer is a glioma. In still further embodiments, the glioma is an astrocytoma, an oligodendroglioma, or a glioblastoma.

In some embodiments, the compounds according to this disclosure are useful in the treatment of pancreatic cancer. In further embodiments, the pancreatic cancer is pancreatic neuroendocrine tumor or pancreatic adenocarcinoma.

In the aforementioned embodiments, the methods of the present disclosure may be practiced in an adjuvant setting or neoadjuvant setting, optionally in the treatment of locally advanced, unresectable, or metastatic cancer. Alternatively or in addition, the methods described herein may be indicated as a first line treatment, optionally in the treatment of locally advanced, unresectable, or metastatic cancer. In some embodiments, the methods described herein may be indicated as a second line, third line, or greater line of treatment, optionally in the treatment of locally advanced, unresectable, or metastatic cancer. When indicated as a second line or greater treatment, in some embodiments an earlier line of therapy included a checkpoint inhibitor.

The present disclosure also provides methods of treating or preventing other cancer-related diseases, disorders or conditions. The use of the term(s) cancer-related diseases, disorders and conditions is meant to refer broadly to conditions that are associated, directly or indirectly, with cancer and non-cancerous proliferative disease, and includes, e.g., angiogenesis, precancerous conditions such as dysplasia, and non-cancerous proliferative diseases disorders or conditions, such as benign proliferative breast disease and papillomas. For clarity, the term(s) cancer-related disease, disorder and condition do not include cancer per se.

In general, the disclosed methods for treating or preventing cancer, or a cancer-related disease, disorder or condition, in a subject in need thereof comprise administering to the subject a compound disclosed herein, or a pharmaceutically acceptable salt thereof. In some embodiments, the present disclosure provides methods for treating or preventing cancer, or a cancer-related disease, disorder or condition with a compound disclosed herein, or a pharmaceutically acceptable salt thereof, and at least one additional therapy, examples of which are set forth elsewhere herein.

In particular embodiments of the present disclosure, the compounds are used to increase or enhance an immune response to an antigen by providing adjuvant activity. In a particular embodiment, at least one antigen or vaccine is administered to a subject in combination with at least one compound of the present disclosure to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one compound of the present disclosure.

In some instances, the methods according to this disclosure may be provided in selected patients, for example subjects identified as having in a relevant tissue or sample, e.g., detectable PD-L1 expression, microsatellite instability (MSI), deficient mismatch repair (dMMR), high tumor mutational burden, or any combination thereof. In some instances, the subject is identified as having an oncogene driven cancer that has a mutation in at least one gene associated with the cancer.

In some embodiments, patients are selected by assessing the expression of relevant biomarkers, e.g., PD-L1 expression, microsatellite instability markers, T-cell inflamed gene expression profile (GEP), etc., in a relevant sample, such as a peripheral blood sample or a tumor biopsy, using immunohistochemistry, immunophenotyping, PCR-based amplification, RNA sequencing, or other clinically validated assay. In one embodiment, the disclosure provides a method of treating cancer in a patient having (i) detectable PD-L1 expression, (ii) elevated PD-L1 expression, (iii) MSI-low, (iv) MSI-high, (v) elevated GEP expression, or (vi) any combination of (i) to (v) by administering a compound as described herein. In another embodiment, the disclosure provides a method of treating cancer in a patient having (i) detectable PD-L1 expression, (ii) elevated PD-L1 expression, (iii) MSI-low, (iv) MSI-high, (v) elevated GEP expression, or (vi) any combination of (i) to (v) by administering a therapeutically effective amount of a compound as described herein. In still another embodiment, the disclosure provides a method of administering a therapeutically effective amount of a compound as described herein to an individual for the treatment of cancer based on a determination of the relative amount of PD-L1 expression. In yet another embodiment, the disclosure provides a method of administering a therapeutically effective amount of a compound described herein to an individual for the treatment of cancer, the method comprising measuring PD-L1 expression and/or microsatellite instability (e.g., MSI-low or MSI-high) in a sample obtained from an individual, for example by immunohistochemistry, immunophenotyping, PCR-based amplification, or other clinically validated test, and administering a therapeutically effective amount of the compound to the individual whose sample contained detectable PD-L1 expression and/or microsatellite instability. In various embodiments of the disclosure, detectable PD-L1 expression may be a tumor proportion (TPS) score of ≥50%, as measured by a clinically validated PD-L1 IHC assay or FDA-approved test. In various embodiments of the disclosure, detectable PD-L1 expression may be TPS score of <50%, as measured by a clinically validated PD-L1 IHC assay or FDA-approved test.

Routes of Administration

In some embodiments, pharmaceutical compositions containing a compound according to this disclosure may be in a form suitable for oral administration. Oral administration may involve swallowing the formulation thereby allowing the compound to be absorbed into the bloodstream in the gastrointestinal tract. Alternatively, oral administration may involve buccal, lingual or sublingual administration, thereby allowing the compound to be absorbed into the blood stream through oral mucosa.

In another embodiment, the pharmaceutical compositions containing a compound according to this disclosure may be in a form suitable for parenteral administration. Forms of parenteral administration include, but are not limited to, intravenous, intraarterial, intramuscular, intradermal, intraperitoneal, intrathecal, intracisternal, intracerebral, intracerebroventricular, intraventricular, and subcutaneous. Pharmaceutical compositions suitable for parenteral administration may be formulated using suitable aqueous or non-aqueous carriers. Depot injections, which are generally administered subcutaneously or intramuscularly, may also be utilized to release the compounds disclosed herein over a defined period of time.

Other routes of administration are also contemplated by this disclosure, including, but not limited to, nasal, vaginal, intraocular, rectal, topical (e.g., transdermal), and inhalation.

Particular embodiments of the present disclosure contemplate oral administration or parenteral administration.

Pharmaceutical Compositions

The compounds of the present disclosure may be in the form of compositions suitable for administration to a subject. In general, such compositions are pharmaceutical compositions comprising a compound according to this disclosure or a pharmaceutically acceptable salt thereof and one or more pharmaceutically acceptable excipients. In certain embodiments, the compound may be present in an effective amount. The pharmaceutical compositions may be used in the methods of the present disclosure; thus, for example, the pharmaceutical compositions comprising a compound according to this disclosure can be administered to a subject in order to practice the therapeutic and prophylactic methods and uses described herein.

The pharmaceutical compositions of the present disclosure can be formulated to be compatible with the intended method or route of administration. Routes of administration may include those known in the art. Exemplary routes of administration are oral and parenteral. Furthermore, the pharmaceutical compositions may be used in combination with one or more other therapies described herein in order to treat or prevent the diseases, disorders and conditions as contemplated by the present disclosure. In one embodiment, one or more other therapeutic agents contemplated by this disclosure are included in the same pharmaceutical composition that comprises the compound according to this disclosure. In another embodiment, the one or more other therapeutical agents are in a composition that is separate from the pharmaceutical composition comprising the compound according to this disclosure.

In one aspect, the compounds described herein may be administered orally. Oral administration may be via, for example, capsule or tablets. In making the pharmaceutical compositions that include the compounds of the present disclosure (e.g., a compound of Formula (I)), or a pharmaceutically acceptable salt thereof, the tablet or capsule includes at least one pharmaceutically acceptable excipient. Non-limiting examples of pharmaceutically acceptable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, sterile water, syrup, and methyl cellulose. Additional pharmaceutically acceptable excipients include lubricating agents such as talc, magnesium stearate, and mineral oil; wetting agents; emulsifying and suspending agents; preserving agents such as methyl and propylhydroxy-benzoates.

In another aspect, the compounds of the present disclosure, or a pharmaceutically acceptable salt thereof, may be administered parenterally, for example by intravenous injection. A pharmaceutical composition appropriate for parenteral administration may be formulated in solution for injection or may be reconstituted for injection in an appropriate system such as a physiological solution. Such solutions may include sterile water for injection, salts, buffers, and tonicity excipients in amounts appropriate to achieve isotonicity with the appropriate physiology.

The pharmaceutical compositions described herein may be stored in an appropriate sterile container or containers. In some embodiments, the container is designed to maintain stability for the pharmaceutical composition over a given period of time.

Administering

In general, the disclosed methods comprise administering a compound described herein, or a composition thereof, in an effective amount to a subject in need thereof. An "effective amount" with reference to a HPK1 inhibitor of the present disclosure means an amount of the compound that is sufficient to engage the target (e.g., by inhibiting the target) at a level that is indicative of the potency of the compound. For HPK1, target engagement can be determined by one or more biochemical or cellular assays resulting in an EC50, ED50, EC90, IC50, or similar value which can be used as one assessment of the potency of the compound. Assays for determining target engagement include, but are not limited to, those described in the Examples. The effective amount may be administered as a single quantity or as multiple, smaller quantities (e.g., as one tablet with "x" amount, as two tablets each with "x/2" amount, etc.).

In some embodiments, the disclosed methods comprise administering a therapeutically effective amount of a compound described herein to a subject in need thereof. As used herein, the phrase "therapeutically effective amount" with reference to compound disclosed herein means a dose regimen (i.e., amount and interval) of the compound that provides the specific pharmacological effect for which the compound is administered to a subject in need of such treatment. For prophylactic use, a therapeutically effective amount may be effective to eliminate or reduce the risk, lessen the severity, or delay the onset of the disease, including biochemical, histological and/or behavioral signs or symptoms of the disease. For treatment, a therapeutically effective amount may be effective to reduce, ameliorate, or eliminate one or more signs or symptoms associated with a disease, delay disease progression, prolong survival, decrease the dose of other medication(s) required to treat the disease, or a combination thereof. With respect to cancer specifically, a therapeutically effective amount may, for example, result in the killing of cancer cells, reduce cancer cell counts, reduce tumor burden, eliminate tumors or metastasis, or reduce metastatic spread. A therapeutically effective amount may vary based on, for example, one or more of the following: the age and weight of the subject, the subject's overall health, the stage of the subject's disease, the route of administration, and prior or concomitant treatments.

Administration may comprise one or more (e.g., one, two, or three or more) dosing cycles.

In certain embodiments, the compounds contemplated by the present disclosure may be administered (e.g., orally, parenterally, etc.) at about 0.01 mg/kg to about 50 mg/kg, or about 1 mg/kg to about 25 mg/kg, of subject's body weight per day, one or more times a day, a week, or a month, to obtain the desired effect. In some embodiments, once daily or twice daily administration is contemplated. In some embodiments, a suitable weight-based dose of a compound contemplated by the present disclosure is used to determine a dose that is administered independent of a subject's body weight. In certain embodiments, the compounds of the present disclosure are administered (e.g., orally, parenterally, etc.) at fixed dosage levels of about 1 mg to about 1000 mg, particularly 1, 3, 5, 10, 15, 20, 25, 50, 75, 100, 150, 200, 250, 300, 400, 500, 600, 750, 800, 900, or 1000 mg, one or more times a day, a week, or a month, to obtain the desired effect.

In certain embodiments, the compound is contained in a "unit dosage form". The phrase "unit dosage form" refers to physically discrete units, each unit containing a predetermined amount of the compound, either alone or in combination with one or more additional agents, sufficient to produce the desired effect. It will be appreciated that the parameters of a unit dosage form will depend on the particular agent and the effect to be achieved.

Combination Therapy

The present disclosure contemplates the use of compounds disclosed herein alone or in combination with one or more additional therapy. Each additional therapy can be a therapeutic agent or another treatment modality. In embodiments comprising one or more additional therapeutic agents, each agent may target a different, but complementary, mechanism of action. The additional therapeutic agents can be small chemical molecules; macromolecules such as proteins, antibodies, peptibodies, peptides, DNA, RNA or fragments of such macromolecules; or cellular or gene therapies. Non-limiting examples of additional treatment modalities include surgical resection of a tumor, bone marrow transplant, radiation therapy, and photodynamic therapy. The use of a compound disclosed herein in combination with one or more additional therapies may have a synergistic therapeutic or prophylactic effect on the underlying disease, disorder, or condition. In addition to or alternatively, the combination therapy may allow for a dose reduction of one or more of the therapies, thereby ameliorating, reducing or eliminating adverse effects associated with one or more of the agents.

In embodiments comprising one or more additional treatment modality, the compound can be administered before, after or during treatment with the additional treatment modality. In embodiments comprising one or more additional therapeutic agents, the therapeutic agents used in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

Cancer Therapies

The present disclosure contemplates the use of the compounds described herein in combination with one or more additional therapies useful in the treatment of cancer.

In some embodiments, one or more of the additional therapies is an additional treatment modality. Exemplary treatment modalities include but are not limited to surgical resection of a tumor, bone marrow transplant, radiation therapy, and photodynamic therapy.

In some embodiments, one or more of the additional therapies is a therapeutic agent. Exemplary therapeutic agents include chemotherapeutic agents, radiation therapy, hormone therapies, epigenetic modulators, ATP-adenosine axis-targeting agents, targeted therapies, signal transduction inhibitors, RAS signaling inhibitors, PI3K inhibitors, arginase inhibitors, HIF inhibitors, AXL inhibitors, PAK4 inhibitors, immunotherapeutic agents, cellular therapies, gene therapies, immune checkpoint inhibitors, and agonists of stimulatory or co-stimulatory immune checkpoints.

In some embodiments, one or more of the additional therapeutic agents is a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, pomalidomide, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab paclitaxel, and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; proteasome inhibitors such as bortezomib, carfilzomib and ixazomib; topoisomerase inhibitors such as irinotecan, topotecan, etoposide, mitoxantrone, teniposide; difluoromethylornithine (DMFO); retinoic acid; esperamicins; capecitabine; anthracyclines and pharmaceutically acceptable salts, acids or derivatives of any of the above. In certain embodiments, combination therapy comprises a chemotherapy regimen that includes one or more chemotherapeutic agents. In one embodiment, combination therapy comprises a chemotherapeutic regimen comprising one or more of FOLFOX (folinic acid, fluorouracil, and oxaliplatin), FOLFIRI (e.g., folinic acid, fluorouracil, and irinotecan), FOLFIRINOX (folinic acid, fluorouracil, irinotecan, and oxaliplatin), a taxoid (e.g., docetaxel, paclitaxel, nab-paclitaxel, etc.), and/or gemcitabine.

In some embodiments, one or more of the additional therapeutic agents is a radiation therapy. Radiation therapy includes radiopharmaceuticals which are a form of internal radiation therapy in which a source of radiation (i.e., one or more radionuclide) is put inside a subject's body. The radiation source can be in solid or liquid form. Non-limiting examples of radiopharmaceuticals include sodium iodide I-131, radium-223 dichloride, lobenguane iodine-131, radioiodinated vesicles (e.g., saposin C-dioleoylphosphatidylserine (SapC-DOPS) nanovesicles), various forms of brachytherapy, and various forms of targeted radionuclides. Targeted radionuclides comprise a radionuclide associated (e.g., by covalent or ionic interactions) with a molecule ("a targeting agent") that specifically binds to a target on a cell, typically a cancer cell or an immune cell. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeting agent is an antibody and the target is a tumor-associated antigen (i.e., an antigen enriched but not specific to a cancer cell), a tumor-specific antigen (i.e., an antigen with minimal to no expression in normal tissue), or a neo-antigen (i.e., an antigen specific to the genome of a cancer cell generated by non-synonymous mutations in the tumor cell genome). Non-limiting examples of targeted radionuclides include radionuclides attached to: somatostatin or peptide analogs thereof (e.g., 177Lu-Dotatate, etc.); prostate specific membrane antigen or peptide analogs thereof (e.g., 177Lu-PSMA-617, 225Ac-PSMA-617, 177Lu-PSMA-I&T, 177Lu-MIP-1095, etc.); a receptor's cognate ligand, peptide derived from the ligand, or variants thereof (e.g., 188Re-labeled $VEGF_{125-136}$ or variants thereof with higher affinity to VEGF receptor, etc.); antibodies targeting tumor antigens (e.g., 131I-tositumomab, 90Y-ibritumomab tiuxetan, CAM-H2-I131 (Precirix NV), 1131-omburtamab, etc.).

In some embodiments, one or more of the additional therapeutic agents is a hormone therapy. Hormone therapies act to regulate or inhibit hormonal action on tumors. Examples of hormone therapies include, but are not limited to: selective estrogen receptor degraders such as fulvestrant, giredestrant, SAR439859, RG6171, AZD9833, rintodestrant, ZN-c5, LSZ102, D 0502, LY3484356, SHR9549; selective estrogen receptor modulators such as tamoxifen, raloxifene, 4-hydroxytamoxifen, trioxifene, keoxifene, toremifene; aromatase inhibitors such as anastrozole, exemestane, letrozole and other aromatase inhibiting 4(5)-imidazoles; gonadotropin-releasing hormone agonists such as nafarelin, triptorelin, goserelin; gonadotropin-releasing hormone antagonists such as degarelix; antiandrogens such as abiraterone, enzalutamide, apalutamide, darolutamide, flutamide, nilutamide, bicalutamide, leuprolide; 5α-reductase inhibitors such as finasteride, dutasteride; and the like. In certain embodiments, combination therapy comprises administration of a hormone or related hormonal agent. In one embodiment, combination therapy comprises administration of enzalutamide.

In some embodiments, one or more of the additional therapeutic agents is an epigenetic modulator. An epigenetic modulator alters an epigenetic mechanism controlling gene expression, and may be, for example, an inhibitor or activator of an epigenetic enzyme. Non-limiting examples of epigenetic modulators include DNA methyltransferase (DNMT) inhibitors, hypomethylating agents, and histone deacetylase (HDAC) inhibitors. In one or more embodiments, the compounds according to this disclosure are combined with DNA methyltransferase (DNMT) inhibitors or hypomethylating agents. Exemplary DNMT inhibitors include decitabine, zebularine and azacitadine. In one or more embodiments, combinations of the compounds according to this disclosure with a histone deacetylase (HDAC) inhibitor is also contemplated. Exemplary HDAC inhibitors include vorinostat, givinostat, abexinostat, panobinostat, belinostat and trichostatin A.

In some embodiments, one or more of the additional therapeutic agents is an ATP-adenosine axis-targeting agent. ATP-adenosine axis-targeting agents alter signaling mediated by adenine nucleosides and nucleotides (e.g., adenosine, AMP, ADP, ATP), for example by modulating the level of adenosine or targeting adenosine receptors. Adenosine and ATP, acting at different classes of receptors, often have opposite effects on inflammation, cell proliferation and cell death. For instance, ATP and other adenine nucleotides have antitumor effects via activation of the PS2Y1 receptor subtype, while accumulation of adenosine in the tumor microenvironment has been shown to inhibit the antitumor function of various immune cells and to augment the immunosuppressive activity of myeloid and regulatory T cells by binding to cell surface adenosine receptors. In certain embodiments, an ATP-adenosine axis-targeting agent is an inhibitor of an ectonucleotidase involved in the conversion of ATP to adenosine or an antagonist of adenosine receptor. Ectonucleotidases involved in the conversion of ATP to adenosine include the ectonucleoside triphosphate diphosphohydrolase 1 (ENTPD1, also known as CD39 or Cluster of Differentiation 39) and the ecto-5'-nucleotidase (NT5E or 5NT, also known as CD73 or Cluster of Differentiation 73). Exemplary small molecule CD73 inhibitors include CB-708 (ATG 037), ORIC-533, LY3475070 and quemliclustat. Exemplary anti-CD39 and anti-CD73 antibodies include ES002023, TTX-030, IPH-5201, SRF-617, CPI-006, oleclumab (MEDI9447), NZV930, IPH5301, GS-1423, uliledlimab (TJD5, TJ004309), AB598, and BMS-986179. In one embodiment, the present disclosure contemplates combination of the compounds described herein with a CD73 inhibitor such as those described in WO 2017/120508, WO 2018/067424, WO 2018/094148, and WO 2020/046813. In further embodiments, the CD73 inhibitor is quemliclustat (AB680). Adenosine can bind to and activate four different G-protein coupled receptors: $A_1R$, $A_{2A}R$, $A_{2B}R$, and $A_3R$. $A_2R$ antagonists include etrumadenant, inupadenant, taminadenant, caffeine citrate, NUV-1182, TT-702, DZD-2269, INCB-106385, EVOEXS-21546, AZD-4635, imaradenant, RVU-330, ciforadenant, PBF-509, PBF-999, PBF-1129, and CS-3005. In some embodiments, the present disclosure contemplates the combination of the compounds described herein with an $A_{2A}R$ antagonist, an $A_{2B}R$ antagonist, or an antagonist of $A_{2A}R$ and $A_{2B}R$. In some embodiments, the present disclosure contemplates the combination of the compounds described herein with the adenosine receptor antagonists described in WO 2018/136700, WO 2018/204661, WO 2018/213377, or WO 2020/023846. In one embodiment, the adenosine receptor antagonist is etrumadenant.

In some embodiments, one or more of the additional therapeutic agents is a targeted therapy. In one aspect, a targeted therapy may comprise a chemotherapeutic agent, a radionuclide, a hormone therapy, or another small molecule drug attached to a targeting agent. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeting agent is an antibody and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). Specific examples include but are not limited to patritumab deruxtecan and telisotuzumab vedotin. In other aspects, a targeted therapy may inhibit or interfere with a specific protein that helps a tumor grow and/or spread. Non-limiting examples of such targeted therapies include signal transduction inhibitors, RAS signaling inhibitors, inhibitors of oncogenic transcription factors, activators of oncogenic transcription factor repressors, angiogenesis inhibitors, immunotherapeutic agents, tyrosine kinase inhibitors, ATP-adenosine axis-targeting agents, AXL inhibitors, PARP inhibitors, PAK4 inhibitors, PI3K inhibitors, HIF-2α inhibitors, CD39 inhibitors, CD73 inhibitors, A2R antagonists, TIGIT antagonists, and PD-1 antagonists. ATP-adenosine axis-targeting agents are described above, while other agents are described in further detail below.

In some embodiments, one or more of the additional therapeutic agents is a signal transduction inhibitor. Signal transduction inhibitors are agents that selectively inhibit one or more steps in a signaling pathway. Signal transduction inhibitors (STIs) contemplated by the present disclosure include but are not limited to: (i) BCR-ABL kinase inhibitors (e.g., imatinib); (ii) epidermal growth factor receptor tyrosine kinase inhibitors (EGFR TKIs), including small molecule inhibitors (e.g., CLN-081, gefitinib, erlotinib, afatinib, icotinib, and osimertinib), and anti-EGFR antibodies; (iii) inhibitors of the human epidermal growth factor (HER) family of transmembrane tyrosine kinases, e.g., HER-2/neu receptor inhibitors (e.g., trastuzumab) and HER-3 receptor inhibitors; (iv) vascular endothelial growth factor receptor (VEGFR) inhibitors including small molecule inhibitors (e.g., axitinib, sunitinib and sorafenib), VEGF kinase inhibitors (e.g., lenvatinib, cabozantinib, pazopanib, tivozanib, XL092, etc.) and anti-VEGF antibodies (e.g., bevacizumab); (v) inhibitors of AKT family kinases or the AKT pathway (e.g., rapamycin); (vi) inhibitors of serine/threonine-protein kinase B-Raf (BRAF), such as, for example, vemurafenib, dabrafenib and encorafenib; (vii) inhibitors of rearranged during transfection (RET), including, for example, selpercatinib and pralsetinib; (viii) tyrosine-protein kinase Met (MET) inhibitors (e.g., tepotinib, tivantinib, cabozantinib and crizotinib); (ix) anaplastic lymphoma kinase (ALK) inhibitors (e.g., ensartinib, ceritinib, lorlatinib, crizotinib, and brigatinib); (x) inhibitors of the RAS signaling pathway (e.g., inhibitors of KRAS, HRAS, RAF, MEK, ERK) as described elsewhere herein; (xi) FLT-3 inhibitors (e.g., gilteritinib); (xii) inhibitors of Trop-2; (xiii) inhibitors of the JAK/STAT pathway, e.g., JAK inhibitors including tofacitinib and ruxolitinib, or STAT inhibitors such as napabucasin; (xiv) inhibitors of NF-kB; (xv) cell cycle kinase inhibitors (e.g., flavopiridol); (xvi) phosphatidyl inositol kinase (PI3K) inhibitors; (xix) protein kinase B (AKT) inhibitors (e.g., capivasertib, miransertib); (xx) platelet-derived growth factor receptor (PDGFR) inhibitors (e.g., imatinib, sunitinib, regorafenib, avapritinib, Lenvatinib, nintedanib, famitinib, ponatinib, axitinib, repretinib, etc.); (xxi) insulin-like growth factor receptor (IGFR) inhibitors (e.g., erlotinib, afatinib, gefitinib, osimertinib, dacomitinib); and (xxii) inhibitors of anexelekto (AXL) as described in further detail below. In one or more embodiments, the additional therapeutic agent comprises a tyrosine kinase inhibitor that inhibits one or more of AXL, EGFR, VEGFR, PDGFR, IGFR, HER-2, HER-3, BRAF, RET, MET, ALK, RAS (e.g., KRAS, MEK, ERK), FLT-3, JAK, STAT, NF-kB, PI3K, AKT, or any combinations thereof.

In some embodiments, one or more of the additional therapeutic agents is a RAS signaling inhibitor. Oncogenic mutations in the RAS family of genes, e.g., HRAS, KRAS, and NRAS, are associated with a variety of cancers. For example, mutations of G12C, G12D, G12V, G12A, G13D, Q61H, G13C and G12S, among others, in the KRAS family of genes have been observed in multiple tumor types. Direct and indirect inhibition strategies have been investigated for the inhibition of mutant RAS signaling. Indirect inhibitors target effectors other than RAS in the RAS signaling pathway, and include, but are not limited to, inhibitors of RAF, MEK, ERK, PI3K, PTEN, SOS (e.g., SOS1), mTORC1, SHP2 (PTPN11), and AKT. Non-limiting examples of indirect inhibitors under development include RMC-4630, RMC-5845, RMC-6291, RMC-6236, JAB-3068, JAB-3312, TNO155, RLY-1971, BI1701963. Direct inhibitors of RAS mutants have also been explored, and generally target the KRAS-GTP complex or the KRAS-GDP complex. Exemplary direct RAS inhibitors under development include, but are not limited to, sotorasib (AMG510), adagrasib (MRTX849), mRNA-5671 and ARS 1620. In some embodiments, the one or more RAS signaling inhibitors are selected from the group consisting of RAF inhibitors, MEK inhibitors, ERK inhibitors, PI3K inhibitors, PTEN inhibitors, SOS1 inhibitors, mTORC1 inhibitors, SHP2 inhibitors, and AKT inhibitors. In other embodiments the one or more RAS signaling inhibitors directly inhibit RAS mutants.

In some embodiments one or more of the additional therapeutic agents is an inhibitor of a phosphatidylinositol 3-kinase (PI3K), particularly an inhibitor of the PI3Kγ and/or the PI3K6 isoforms. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T cell responses thereby decreasing cancer development and spread. Exemplary PI3Kγ inhibitors include copanlisib, duvelisib, AT-104, ZX-101, tenalisib, eganelisib, SF-1126, AZD3458, and pictilisib. In some embodiments, the compounds according to this disclosure are combined with one or more PI3Kγ inhibitors described in WO 2020/0247496A1. Additionally, PI3Kδ is expressed on malignant B cells, and plays a role in promoting B-cell activation, differentiation, proliferation and survival. Exemplary PI3Kδ inhibitors include duvelisib, leniolisib, parsaclisib, copanlisib, umbralisib, zandelisib, eganelisib, linperlisib, pilaralisib, and tenalisib, In some embodiments, one or more of the additional therapeutic agents is an inhibitor of arginase. Arginase has been shown to be either responsible for or participate in inflammation-triggered immune dysfunction, tumor immune escape, immunosuppression and immunopathology of infectious disease. Exemplary arginase compounds include CB-1158 and OAT-1746. In some embodiments, the compounds according to this disclosure are combined with one or more arginase inhibitors described in WO/2019/173188 and WO 2020/102646.

In some embodiments, one or more of the additional therapeutic agents is an inhibitor of an oncogenic transcription factor or an activator of an oncogenic transcription factor repressor. Suitable agents may act at the expression level (e.g., RNAi, siRNA, etc.), through physical degradation, at the protein/protein level, at the protein/DNA level, or by binding in an activation/inhibition pocket. Non-limiting examples include inhibitors of one or more subunit of the MLL complex (e.g., HDAC, DOT1L, BRD4, Menin, LEDGF, WDR5, KDM4C (JMJD2C) and PRMT1), inhibitors of hypoxia-inducible factor (HIF) transcription factor, and the like.

In some embodiments, one or more of the additional therapeutic agents is an inhibitor of a hypoxia-inducible factor (HIF) transcription factor, particularly HIF-2a. Exemplary HIF-2α inhibitors include belzutifan, ARO-HIF2, PT-2385, AB521, and those described in WO 2021113436 and WO 2021188769. In some embodiments, the compounds according to this disclosure are combined with one or more HIF-2α inhibitors described in WO 2021188769. In some embodiments, the HIF-2α inhibitor is AB521.

In some embodiments, one or more of the additional therapeutic agents is an inhibitor of anexelekto (AXL). The AXL signaling pathway is associated with tumor growth and metastasis, and is believed to mediate resistance to a variety of cancer therapies. There are a variety of AXL inhibitors under development that also inhibit other kinases in the TAM family (i.e., TYRO3, MERTK), as well as other receptor tyrosine kinases including MET, FLT3, RON and AURORA, among others. Exemplary multikinase inhibitors include sitravatinib, rebastinib, glesatinib, gilteritinib, merestinib, cabozantinib, foretinib, BMS777607, LY2801653, S49076, and RXDX-106. AXL specific inhibitors have also been developed, e.g., small molecule inhibitors including DS-1205, SGI-7079, SLC-391, dubermatinib, bemcentinib, DP3975, and AB801; anti-AXL antibodies such as ADCT-601; and antibody drug conjugates (ADCs) such as BA3011. Another strategy to inhibit AXL signaling involves targeting AXL's ligand, GAS6. For example, batiraxcept is under development as is a Fc fusion protein that binds the GAS6 ligand thereby inhibiting AXL signaling. In some embodiments, the compounds according to this disclosure are combined with one or more AXL inhibitors described in WO2022246177 or WO2022246179. In some embodiments, the AXL inhibitor is AB801.

In some embodiments, one or more of the additional therapeutic agents is an inhibitor of p21-activated kinase 4 (PAK4). PAK4 overexpression has been shown across a variety of cancer types, notably including those resistant to PD-1 therapies.

In some embodiments, one or more of the additional therapeutic agents is (i) an agent that inhibits the enzyme poly (ADP-ribose) polymerase (e.g., olaparib, niraparib and rucaparib, etc.); (ii) an inhibitor of the Bcl-2 family of proteins (e.g., venetoclax, navitoclax, etc.); (iii) an inhibitor of MCL-1; (iv) an inhibitor of the CD47-SIRPα pathway (e.g., an anti-CD47 antibody); (v) an isocitrate dehydrogenase (IDH) inhibitor, e.g., IDH-1 or IDH-2 inhibitor (e.g., ivosidenib, enasidenib, etc.).

In some embodiments, one or more of the additional therapeutic agents is an immunotherapeutic agent. Immunotherapeutic agents treat a disease by stimulating or suppressing the immune system. Immunotherapeutic agents useful in the treatment of cancers typically elicit or amplify an immune response to cancer cells. Non-limiting examples of suitable immunotherapeutic agents include: immunomodulators; cellular immunotherapies; vaccines; gene therapies; ATP-adenosine axis-targeting agents; immune checkpoint modulators; and certain signal transduction inhibitors. ATP-adenosine axis-targeting agents and signal transduction inhibitors are described above. Immunomodulators, cellular immunotherapies, vaccines, gene therapies, and immune checkpoint modulatorsare described further below.

In some embodiments, one or more of the additional therapeutic agents is an immunotherapeutic agent, more specifically a cytokine or chemokine, such as, IL-1, IL-2, IL-12, IL-18, ELC/CCL19, SLC/CCL21, MCP-1, IL-4, TNF, IL-15, MDC, IFNa/b, M-CSF, IL-3, GM-CSF, IL-13, and anti-IL-10; bacterial lipopolysaccharides (LPS); an organic or inorganic adjuvant that activates antigen-presenting cells and promote the presentation of antigen epitopes on major histocompatibility complex molecules agonists including, but not limited to Toll-like receptor (TLR) agonists, antagonists of the mevalonate pathway, agonists of STING; indoleamine 2,3-dioxygenase 1 (IDO1) inhibitors and immune-stimulatory oligonucleotides, as well as other T cell adjuvants.

In some embodiments, one or more of the additional therapeutic agents is an immunotherapeutic agent, more specifically a cellular therapy. Cellular therapies are a form of treatment in which viable cells are administered to a subject. In certain embodiments, one or more of the additional therapeutic agents is a cellular immunotherapy that activates or suppresses the immune system. Cellular immunotherapies useful in the treatment of cancers typically elicit or amplify an immune response. The cells can be autologous or allogenic immune cells (e.g., monocytes, macrophages, dendritic cells, NK cells, T cells, etc.) collected from one or more subject. Alternatively, the cells can be “(re)programmed” allogenic immune cells produced from immune precursor cells (e.g., lymphoid progenitor cells, myeloid progenitor cells, common dendritic cell precursor cells, stem cells, induced pluripotent stem cells, etc.). In some embodiments, such cells may be an expanded subset of cells with distinct effector functions and/or maturation markers (e.g., adaptive memory NK cells, tumor infiltrating lymphocytes, immature dendritic cells, monocyte-derived dendritic cells, plasmacytoid dendritic cells, conventional dendritic cells (sometimes referred to as classical dendritic cells), M1 macrophages, M2 macrophages, etc.), may be genetically modified to target the cells to a specific antigen and/or enhance the cells’ anti-tumor effects (e.g., engineered T cell receptor (TCR) cellular therapies, chimeric antigen receptor (CAR) cellular therapies, lymph node homing of antigen-loaded dendritic cells, etc.), may be engineered to express of have increased expression of a tumor-associated antigen, or may be any combination thereof. Non-limiting types of cellular therapies include CAR-T cell therapy, CAR-NK cell therapy, TCR therapy, and dendritic cell vaccines. Exemplary cellular immunotherapies include sipuleucel-T, tisagenlecleucel, lisocabtagene maraleucel, and idecabtagene vicleucel, as well as CTX110, JCAR015, JCAR017, MB-CART19.1, MB-CART20.1, MB-CART2019.1, UniCAR02-T-CD123, BMCA-CAR-T, JNJ-68284528, BNT211, and NK-92/5.28.z.

In some embodiments, one or more of the additional therapeutic agents is an immunotherapeutic agent, more specifically a gene therapy. Gene therapies comprise recombinant nucleic acids administered to a subject or to a subject’s cells ex vivo in order to modify the expression of an endogenous gene or to result in heterologous expression of a protein (e.g., small interfering RNA (siRNA) agents, double-stranded RNA (dsRNA) agents, micro RNA (miRNA) agents, viral or bacterial gene delivery, etc.), as well as gene editing therapies that may or may not comprise a nucleic acid component (e.g., meganucleases, zinc finger nucleases, TAL nucleases, CRISPR/Cas nucleases, etc.), oncolytic viruses, and the like. Non-limiting examples of gene therapies that may be useful in cancer treatment include Gendicine® (rAd-p53), Oncorine® (rAD5-H101), talimogene laherparepvec, Mx-dnG1, ARO-HIF2 (Arrowhead), quaratusugene ozeplasmid (Immunogene), CTX110 (CRISPR Therapeutics), CTX120 (CRISPR Therapeutics), and CTX130 (CRISPR Therapeutics).

In some embodiments, one or more of the additional therapeutic agents is an immunotherapeutic agent, more specifically an agent that modulates an immune checkpoint. Immune checkpoints are a set of inhibitory and stimulatory pathways that directly affect the function of immune cells (e.g., B cells, T cells, NK cells, etc.). Immune checkpoints engage when proteins on the surface of immune cells recognize and bind to their cognate ligands. The present invention contemplates the use of compounds described herein in combination with agonists of stimulatory or co-stimulatory pathways and/or antagonists of inhibitory pathways. Agonists of stimulatory or co-stimulatory pathways and antagonists of inhibitory pathways may have utility as agents to overcome distinct immune suppressive pathways within the tumor microenvironment, inhibit T regulatory cells, reverse/prevent T cell anergy or exhaustion, trigger innate immune activation and/or inflammation at tumor sites, or combinations thereof.

In some embodiments, one or more of the additional therapeutic agents is an immune checkpoint inhibitor. As used herein, the term “immune checkpoint inhibitor” refers to an antagonist of an inhibitory or co-inhibitory immune checkpoint. The terms “immune checkpoint inhibitor”, “checkpoint inhibitor” and “CPP” may be used herein interchangeably. Immune checkpoint inhibitors may antagonize an inhibitory or co-inhibitory immune checkpoint by interfering with receptor-ligand binding and/or altering receptor signaling. Examples of immune checkpoints (ligands and receptors), some of which are selectively upregulated in various types of cancer cells, that can be antagonized include PD-1 (programmed cell death protein 1); PD-L1 (PD1 ligand); BTLA (B and T lymphocyte attenuator); CTLA-4 (cytotoxic T-lymphocyte associated antigen 4); TIM-3 (T cell immunoglobulin and mucin domain containing protein 3); LAG-3 (lymphocyte activation gene 3); TIGIT (T cell immunoreceptor with Ig and ITIM domains); CD276 (B7-H3), PD-L2, Galectin 9, CEACAM-1, CD69, Galectin-1, CD113, GPR56, VISTA, 2B4, CD48, GARP, PD1H, LAIR1, TIM-1, and TIM-4, and Killer Inhibitory Receptors, which can be divided into two classes based on their structural features: i) killer cell immunoglobulin-like receptors (KIRs), and ii) C-type lectin receptors (members of the type II transmembrane receptor family). Also contemplated are other less well-defined immune checkpoints that have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

In some embodiments, an immune checkpoint inhibitor is a CTLA-4 antagonist. In further embodiments, the CTLA-4 antagonist can be an antagonistic CTLA-4 antibody. Suitable antagonistic CTLA-4 antibodies include, for example, monospecific antibodies such as ipilimumab or tremelimumab, as well as bispecific antibodies such as MEDI5752 and KN046.

In some embodiments, an immune checkpoint inhibitor is a PD-1 antagonist. In further embodiments, the PD-1 antagonist can be an antagonistic PD-1 antibody, small molecule or peptide. Suitable antagonistic PD-1 antibodies include, for example, monospecific antibodies such as balstilimab, budigalimab, camrelizumab, cosibelimab, dostarlimab, cemiplimab, ezabenlimab, MEDI-0680 (AMP-514; WO2012/145493), nivolumab, pembrolizumab, pidilizumab (CT-011), pimivalimab, retifanlimab, sasanlimab, spartalizumab, sintilmab, tislelizumab, toripalimab, and zimberelimab; as well as bi-specific antibodies such as LY3434172. In still further embodiments, the PD-1 antagonist can be a recombinant protein composed of the extracellular domain of PD-L2 (B7-DC) fused to the Fc portion of IgGl (AMP-224). In certain embodiments, an immune checkpoint inhibitor is zimberelimab.

In some embodiments, an immune checkpoint inhibitor is a PD-L1 antagonist. In further embodiments, the PD-L1 antagonist can be an antagonistic PD-L1 antibody. Suitable antagonistic PD-L1 antibodies include, for example, monospecific antibodies such as avelumab, atezolizumab, durvalumab, BMS-936559, and envafolimab as well as bispecific antibodies such as LY3434172 and KN046.

In some embodiments, an immune checkpoint inhibitor is a TIGIT antagonist. In further embodiments, the TIGIT antagonist can be an antagonistic TIGIT antibody. Suitable antagonistic anti-TIGIT antibodies include monospecific antibodies such as AGEN1327, AB308 (WO2021247591), BMS 986207, COM902, domvanalimab, EOS-448, etigilimab, IBI-929, JS006, M6223, ociperlimab, SEA-TGT, tiragolumab, vibostolimab; as well as bi-specific antibodies such as AGEN1777 and AZD2936. In certain embodiments, an immune checkpoint inhibitor is an antagonistic anti-TIGIT antibody disclosed in WO2017152088 or WO2021247591. In certain embodiments, an immune checkpoint inhibitor is domvanalimab or AB308.

In some embodiments, an immune checkpoint inhibitor is a LAG-3 antagonist. In further embodiments, the LAG-3 antagonist can be an antagonistic LAG-3 antibody. Suitable antagonistic LAG-3 antibodies include, for example, BMS-986016 (WO10/19570, WO14/08218), or IMP-731 or IMP-321 (WO08/132601, WO09/44273).

In certain embodiments, an immune checkpoint inhibitor is a B7-H3 antagonist. In further embodiments, the B7-H3 antagonist is an antagonistic B7-H3 antibody. Suitable antagonist B7-H3 antibodies include, for example, enoblituzumab (WO11/109400), omburtumab, DS-7300a, ABBV-155, and SHR-A1811.

In some embodiments, one or more of the additional therapeutic agents activates a stimulatory or co-stimulatory immune checkpoint. Examples of stimulatory or co-stimulatory immune checkpoints (ligands and receptors) include B7-1, B7-2, CD28, 4-1BB (CD137), 4-1BBL, ICOS, ICOS-L, OX40, OX40L, GITR, GITRL, CD70, CD27, CD40, DR3 and CD2.

In some embodiments, an agent that activates a stimulatory or co-stimulatory immune checkpoint is a CD137 (4-1BB) agonist. In further embodiments, the CD137 agonist can be an agonistic CD137 antibody. Suitable CD137 antibodies include, for example, urelumab and utomilumab (WO12/32433). In some embodiments, an agent that activates a stimulatory or co-stimulatory immune checkpoint is a GITR agonist. In further embodiments, the GITR agonist can be an agonistic GITR antibody. Suitable GITR antibodies include, for example, BMS-986153, BMS-986156, TRX-518 (WO06/105021, WO09/009116) and MK-4166 (WO11/028683). In some embodiments, an agent that activates a stimulatory or co-stimulatory immune checkpoint is an OX40 agonist. In further embodiments, the OX40 agonist can be an agonistic OX40 antibody. Suitable OX40 antibodies include, for example, MEDI-6383, MEDI-6469, MEDI-0562, PF-04518600, GSK3174998, BMS-986178, and MOXR0916. In some embodiments, an agent that activates a stimulatory or co-stimulatory immune checkpoint is a CD40 agonist. In further embodiments, the CD40 agonist can be an agonistic CD40 antibody. In some embodiments, an agent that activates a stimulatory or co-stimulatory immune checkpoint is a CD27 agonist. In further embodiments, the CD27 agonist can be an agonistic CD27 antibody. Suitable CD27 antibodies include, for example, varlilumab.

In some embodiments, one or more of the additional therapeutic agents is an agent that inhibits or depletes immune-suppressive immune cells. For example, to inhibit or deplete immunosuppressive macrophages or monocytes the agent may be CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264).

In some embodiments, each additional therapeutic agent can independently be a chemotherapeutic agent, radiation therapy, a hormone therapy, an epigenetic modulator, a targeted agent, an immunotherapeutic agent, a cellular therapy, or a gene therapy. For example, in one embodiment, the present disclosure contemplates the use of the compounds described herein in combination with one or more chemotherapeutic agent and optionally one or more additional therapeutic agents, wherein each additional therapeutic agent is independently radiation therapy, a hormone therapy, a targeted agent, an immunotherapeutic agent, a cellular therapy, or a gene therapy. In another embodiment, the present disclosure contemplates the use of the compounds described herein in combination with one or more chemotherapeutic agent and optionally one or more additional therapeutic agents, wherein each additional therapeutic agent is independently a targeted agent, an immunotherapeutic agent, or a cellular therapy. In another embodiment, the present disclosure contemplates the use of the compounds described herein in combination with one or more immunotherapeutic agents and optionally one or more additional therapeutic agents, wherein each additional therapeutic agent is independently radiation therapy, a hormone therapy, a targeted agent, a chemotherapeutic agent, a cellular therapy, or a gene therapy. In another embodiment, the present disclosure contemplates the use of the compounds described herein in combination with one or more immunotherapeutic agents and optionally one or more additional therapeutic agents, wherein each additional therapeutic agent is independently a chemotherapeutic agent, a targeted agent, or a cellular therapy. In another embodiment, the present disclosure contemplates the use of the compounds described herein in combination with one or more immune checkpoint inhibitors and/or one or more ATP-adenosine axis-targeting agents, and optionally one or more additional therapeutic agents, wherein each additional therapeutic agent is independently a chemotherapeutic agent, a targeted agent, a tyrosine kinase inhibitor, an immunotherapeutic agent, or a cellular therapy. In further embodiments of the above (a) the targeted agent can be a PI3K inhibitor, an arginase inhibitor, a HIF-2α inhibitor, an AXL inhibitor, or a PAK4 inhibitor; (b) the immunotherapeutic agent is an ATP-adenosine axis-targeting agent or an immune checkpoint inhibitor; (c) the ATP-adenosine axis-targeting agent is an $A2_AR$ and/or $A2_BR$ antagonist, a CD73 inhibitor, or a CD39 inhibitor; (d) the ATP-adenosine axis-targeting agent is etrumadenant, quemliclustat, or AB598; (e) the tyrosine kinase inhibitor can inhibit one or more of AXL, EGFR, VEGF, HER-2, HER-3, BRAF, PDGFR, MET, MEK, ERK, ALK, RET, KIT, IGFR, TRK, and/or FGFR; (f) the tyrosine kinase inhibitor is AB801; (g) the immunotherapeutic agent is an anti-PD-1 antagonist antibody or an anti-TIGIT antagonist antibody; (h) the immunotherapeutic agent is zimberelimab, domvanalimab, or AB308; or (i) any combination thereof. In still further embodiments of the above, the present disclosure contemplates the use of the compounds described herein in combination with domvanalimab, etrumadenant, quemliclustat, zimberelimab, AB308, AB521, AB598, AB801, or any combination thereof.

Selection of the additional therapeutic agent(s) may be informed by current standard of care for a particular cancer and/or mutational status of a subject's cancer and/or stage of disease. Detailed standard of care guidelines are published, for example, by National Comprehensive Cancer Network (NCCN). See, for instance, NCCN Colon Cancer v3.2021, NCCN Hepatobiliary Cancer v5.2021, NCCN Kidney Cancer, v3.2022, NCCN NSCLC v7.2021, NCCN Pancreatic Adenocarcinoma v2.2021, NCCN Esophageal and Esophagogastric Junction Cancers v4.2021, NCCN Gastric Cancer v5.2021, Cervical Cancer v1.2022, Ovarian Cancer/Fallopian Tube Cancer/Primary Peritoneal Cancer v3.2021.

EXPERIMENTAL

The following examples are put forth so as to provide those of ordinary skill in the art with a complete disclosure and description of how to make and use the present disclosure, and are not intended to limit the scope of what the inventors regard as their invention. Additional compounds within the scope of this disclosure may be made using methods based on those illustrated in these examples, or based on other methods known in the art. Efforts have been made to ensure accuracy with respect to numbers used (e.g., amounts, temperature, etc.), but some experimental errors and deviations should be accounted for.

All reactions were performed using a Teflon-coated magnetic stir bar at the indicated temperature and were conducted under an inert atmosphere when stated. Purchased starting materials and reagents were generally used as received. Reactions were monitored by TLC (silica gel 60 with fluorescence F254, visualized with a short wave/long wave UV lamp) and/or LCMS (AGILENT® 1100 or 1200 series LCMS with UV detection at 254 or 280 nm using a binary solvent system [0.1% formic acid in MeCN/0.1% formic acid in $H_2O$] using one of the following columns: AGILENT® Eclipse Plus C18 [3.5 μm, 4.6 mm i.d.×100 mm], WATERS™ XSelect HSS C18 [3.5 μm, 2.1 mm i.d.×75 mm]). Flash chromatography was conducted on silica gel using an automated system (COMBIFLASH® RF+ manufactured by Teledyne ISCO), with detection wavelengths of 254 and 280 nm, and optionally equipped with an evaporative light scattering detector. Reverse phase preparative HPLC was conducted on an AGILENT® 1260 or 1290 Infinity series HPLC. Samples were eluted using a binary solvent system (MeCN/$H_2O$ with an acid modifier as needed—for example 0.1% TFA or 0.1% formic acid) with gradient elution on a Gemini C18 110 Å column (21.2 mm i.d.×250 mm) with variable wavelength detection. Final compounds obtained through preparative HPLC were concentrated through lyophilization. All assayed compounds were purified to ≥95% purity as determined by $^1H$ NMR or LCMS (AGILENT® 1100 or 1200 series LCMS with UV detection at 254 or 280 nm using a binary solvent system [0.1% formic acid in MeCN/0.1% formic acid in $H_2O$] using one of the following columns: AGILENT® Eclipse Plus C18 [3.5 μm, 4.6 mm i.d.×100 mm], WATERS™ XSelect HSS C18 [3.5 μm, 2.1 mm i.d.×75 mm]) $^1H$ NMR spectra were recorded on a Varian 400 MHz NMR spectrometer equipped with an Oxford AS400 magnet or a BRUKER® AVANCE NEO 400 MHz NMR. Chemical shifts (δ) are reported as parts per million (ppm) relative to residual undeuterated solvent as an internal reference. The abbreviations s, br s, d, t, q, dd, dt, ddd, and m stand for singlet, broad singlet, doublet, triplet, quartet, doublet of doublets, doublet of triplets, doublet of doublet of doublets, and multiplet, respectively.

Unless indicated otherwise, temperature is in degrees Celsius (° C.), and pressure is at or near atmospheric. Standard abbreviations are used, including the following: RT and r.t.=room temperature; min=minute(s); h or hr=hour(s); mg=milligram; g=gram; nl or nL=nanoliter; μL or μl=microliter; ml or mL=milliliter; 1 or L=liter; mM=millimolar; M=molar; N=normal; mol=mole; mmol=millimole; calcd=calculated; sat.=saturated; sol.=solution; aq.=aqueous; anhyd.=anhydrous; psi or psi=pounds per square inch; DCM and $CH_2Cl_2$=dichloromethane; $CDCl_3$=chloroform-d; THF=tetrahydrofuran; THP=tetrahydropyran; $Et_2O$=diethyl ether; EtOAc=ethyl acetate; MeCN, ACN, and $CH_3CN$=acetonitrile; AcOH=acetic acid; NMP=N-methyl-2-pyrrolidone; DMF=N,N-dimethylformamide; DMSO=dimethyl sulfoxide; DMSO-$d_6$=dimethyl sulfoxide-$d_6$; EtOH=ethanol; MeOH=methanol; $H_2$=hydrogen gas; $N_2$=nitrogen gas; MsCl=methanesulfonyl chloride; $HCO_2NH_4$=ammonium formate; nBuLi=n-butyl lithium; $TMSN_3$=trimethylsilyl azide; $InBr_3$=Indium (III) bromide; MeMgBr=methylmagnesium bromide; $Ti(OEt)_4$=Titanium (IV) ethoxide; $AlMe_3$=trimethylaluminum; Pd/C=palladium on carbon; $Pd_2(dba)_3$=Tris(dibenzylideneacetone)dipalladium(0); $Pd(PPh_3)_4$=Tetrakis(triphenylphosphine) palladium(0); $PdCl_2(dppf)$_[1,1'-Bis(diphenylphosphino)ferrocene] dichloropalladium(II); t-BuBrettPhos Pd G3=[(2-Di-tert-butylphosphino-3,6-dimethoxy-2',4',6'-triisopropyl-1,1'-biphenyl)-2-(2'-amino-1,1'-biphenyl)]palladium(II) methanesulfonate; t-BuXPhos-Pd-G3=[(2-Di-tert-butylphosphino-2',4',6'-triisopropyl-1,1'-biphenyl)-2-(2'-amino-1,1'-biphenyl)]palladium(II) methanesulfonate; RuPhos Pd G4=(SP-4-3)-[[2',6'-Bis(1-methylethoxy)[1,1'-biphenyl]-2-yl]dicyclohexylphosphine-κP](methanesulfonato-KO)[2'-(methylamino-κN)[1,1'-biphenyl]-2-yl-KC]palladium; Pd-PEPPSI-iPent=[1,3-Bis(2,6-Di-3-pentylphenyl)imidazol-2-ylidene](3-chloropyridyl) dichloropalladium(II); $PtO_2$=platinum dioxide; $Na_2SO_4$=sodium sulfate; $MgSO_4$=magnesium sulfate; $Cs_2CO_3$=cesium carbonate; $NaBH(OAc)_3$=sodium triacetoxyborohydride; NaH=sodium hydride; $NaHCO_3$=sodium bicarbonate; $NH_4Cl$=ammonium chloride; $Et_3N$=triethyl amine; DIPEA=N,N-diisopropyl ethyl amine; DMEDA=1,2-dim ethylethylenediamine, BINAP=2,2'-bis(diphenylphosphino)-1,1'-binaphthyl; NaOt-Bu=sodium tert-butoxide; NaOH=sodium hydroxide; $NaBH_4$=sodium borohydride; $NaBH(OAc)_3$=sodium triacetoxyborohydride;

KOAc=potassium acetate; K2CO$_3$=potassium carbonate; TFA=trifluoroacetic acid; $HCO_2NH_4$=ammonium formate; HATU=1-[bis(dimethylamino)methylene]-1H-1,2,3-triazolo[4,5-b]pyridinium 3-oxid hexafluorophosphate; CuCl=copper(I) chloride; Xantphos=4,5-Bis(diphenylphosphino)-9,9-dimethylxanthene; Brettphos=2-(Dicyclohexylphosphino)3,6-dimethoxy-2',4',6'-triisopropyl-1,1'-biphenyl; t-BuBrettPhos=2-(Di-tert-butylphosphino)-2',4',6'-triisopropyl-3,6-dimethoxy-1,1'-biphenyl; t-BuXPhos=2-Di-tert-butylphosphino-2',4',6'-triisopropylbipheny; Sphos=2-Dicyclohexylphosphino-2',6'-dimethoxybiphenyl; N-Boc (S)-3-hydroxypiperidine=(S)-tert-Butyl 3-hydroxypiperidine-1-carboxylate; MHz=megahertz; Hz=hertz; ppm=parts per million; ESI MS=electrospray ionization mass spectrometry; NMR=nuclear magnetic resonance; LCMS=liquid chromatography-mass spectrometry; HPLC=high pressure liquid chromatography; SFC=supercritical fluid chromatography.

Example 1: N-[2-(2,6-Difluorophenyl)-[1,3]thiazolo[5,4-c]pyridin-6-yl]-6-[(dimethylamino)methyl]-5-(morpholin-4-yl)pyridin-2-amine

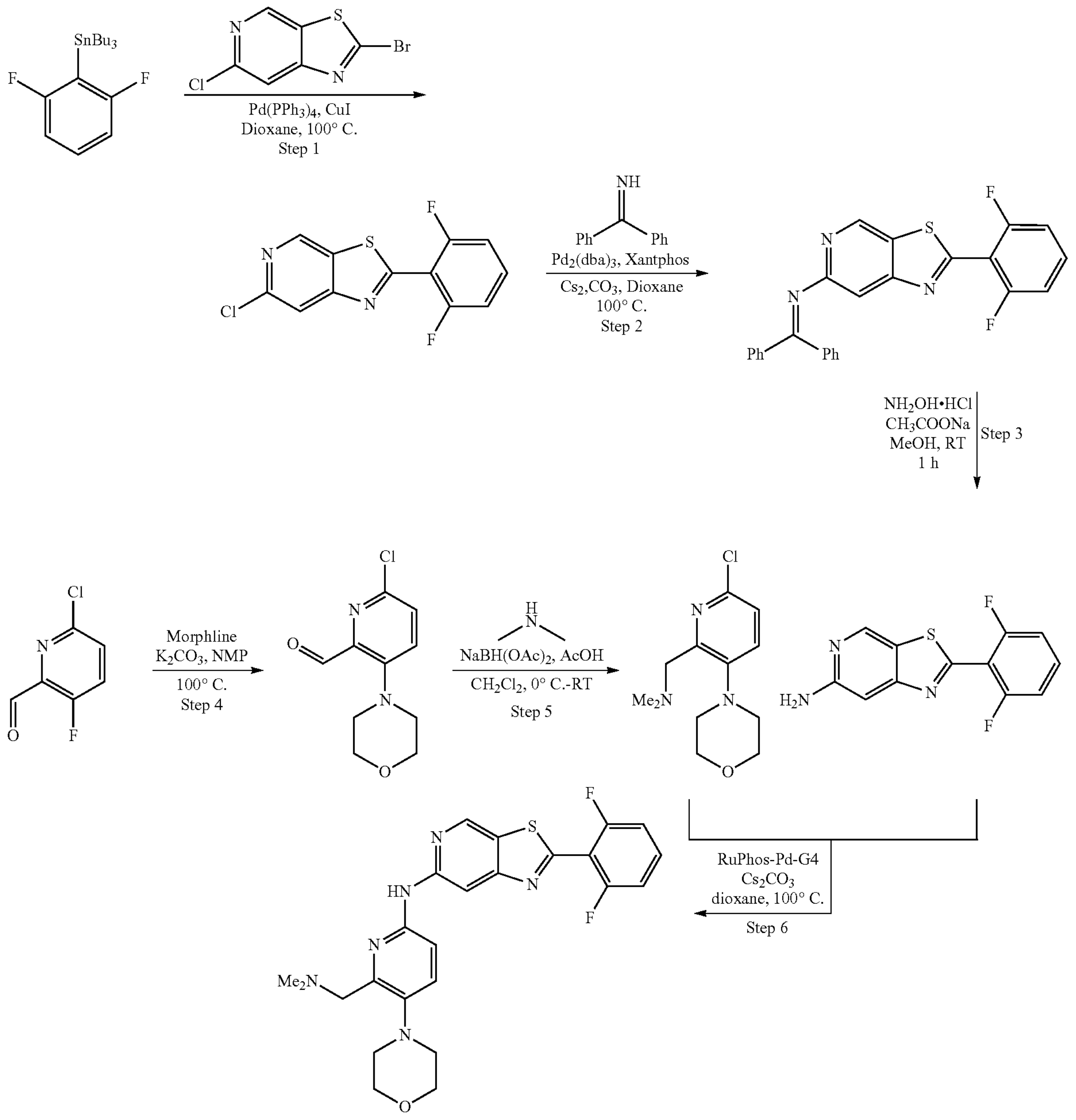

Step 1: To a solution of 2-Bromo-6-chloro[1,3]thiazolo[5,4-c]pyridine (2.02 g, 8.1 mmol) and Tributyl(2,6-difluorophenyl)stannane (3 g, 7.4 mmol) in Dioxane (80 mL) was added $Pd(PPh_3)_4$ (1.65 g, 1.48 mmol) and CuI (562 mg 2.96 mmol). After degassing for 25 min under Na atmosphere, the reaction mixture was heated to 100° C. and stirred for 5 h. The reaction mixture filtered through Celite® and concentrated under reduced pressure. The residue was purified by flash column chromatography (silica gel; gradient: 0% to 20% EtOAc in hexanes) to get the desired compound (2.7 g, 76%).

Step 2: To a stirred solution of azabenzathiazole derivative obtained from step 1 (1.67 g, 6.0 mmol) and Benzophenone imine (1.0 g, 6.0 mmol) in Dioxane (15 ml) was added $Pd_2(dba)_3$ (550 mg, 0.6 mmol), Xantphos (690 mg, 1.2 mmol) and $Cs_2CO_3$ (5.8 g, 18.0 mmol). The reaction mixture was heated to 100° C. and stirred for 12 h. The reaction mixture was poured into water and extracted twice with EtOAc. The organic layers were dried over $Na_2SO_4$ and concentrated in vacuo. The residue was purified by flash column chromatography (silica gel; gradient: 0% to 50% EtOAc in hexanes) to get the desired imine intermediate (1.6 g, 66%).

Step 3: To a stirred solution of imine intermediate obtained from step 2 (2.02 g, 4.74 mmol) in Methanol (50 ml) was added sodium acetate (625 mg, 7.6 mmol) and hydroxylamine hydrochloride (665 mg, 9.5 mmol). The reaction mixture was stirred at RT for 1 h. The reaction mixture was then filtered through sintered glass and the filtrate was concentrated in vacuo. The residue was purified by flash column chromatography (silica gel; gradient: 0% to 70% EtOAc in hexanes) to obtain the desired amine as a white solid (1.05 g, 85%).

Step 4: A round-bottom flask was charged with 3.2 g (20 mmol) of commercially available fluoropyridine derivative. To this flask was added 20 mL of dry NMP, morpholine (1.73 mL, 20 mmol) and $K2CO_3$ (2.8 g, 30 mmol) and heated at 100° C. for 1 h under $N_2$. After cooling to room temperature, 50 mL EtOAc was added. The organic mixture was washed with water (3×20 mL), dried over $Na_2SO_4$ and concentrated. The crude material thus obtained was taken to next step without further purification.

Step 5: To a solution of the pyridine-carbaldehyde derivative obtained from step 4 in $CH_2Cl_2$ (50 mL) at 0° C. was added a 2 M solution of dimethylamine in THE (10 mL, 20 mmol), $NaBH(OAc)_3$ (16.9 g, 80 mmol) and 5 mL AcOH. The reaction mixture was stirred at room temperature for 0.5 h under $N_2$. The reaction mixture was diluted with 50 mL $CH_2Cl_2$ and 20 mL of saturated aqueous Rochelle salt was added and stirred for 1 h at room temperature. The organic layer was washed with $H_2O$ (5×50 mL), dried over $Na_2SO_4$ and concentrated to obtain the desired product 2.6 g, (51% over two steps). This material was used in the next step without further purification.

Step 6: To a solution of 5-aminoazabenzothiazole obtained from step 3 (105 mg, 0.4 mmol) and the chloropyridine derivative obtained from step 5 (102 mg, 0.4 mmol) in Dioxane (5 mL) was added RuPhos PdG4 (34 mg, 0.04 mmol) and $Cs_2CO_3$ (390 mg 1.2 mmol). After degassing for 25 min under $N_2$ atmosphere, the reaction mixture was heated to 100° C. and stirred for 12 h. After cooling to RT, the reaction mixture filtered through Celite® and concentrated under reduced pressure. The resulting residue a was purified by flash column chromatography (silica gel; gradient: 0% to 30% MeOH in $CH_2Cl_2$) to get desired compound in (135 mg, 70%). $^1H$ NMR (400 MHz, Chloroform-d) δ 8.89 (d, J=0.9 Hz, 1H), 8.04 (d, J=0.9 Hz, 1H), 7.63 (d, J=8.7 Hz, 1H), 7.55-7.42 (m, 3H), 7.11 (t, J=8.5 Hz, 2H), 3.91-3.81 (m, 4H), 3.67 (s, 2H), 2.97-2.86 (m, 4H), 2.37 (s, 6H). ESI MS $[M+H]^+$ for $C_{24}H_{24}F_2N_6OS$, calcd 483.2, found 483.8.

Example 2: 2-(2-Methylpyridin-4-yl)-N-[4-(morpholin-4-yl)-3-[(pyrrolidin-1-yl)methyl]phenyl]-[1,3]thiazolo[5,4-c]pyridin-6-amine

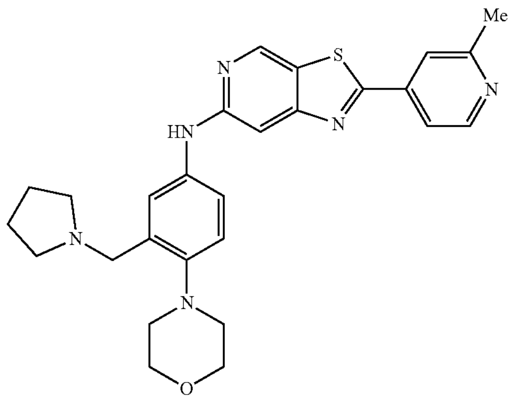 [SMILES: Cc1cc(-c2nc3cc(Nc4ccc(N5CCOCC5)c(CN5CCCC5)c4)ncc3s2)ccn1]

The title compound was synthesized in a similar fashion to example 1 from the appropriate starting materials. $^1H$ NMR (400 MHz, DMSO-$d_6$) δ 9.34 (s, 1H), 9.03 (s, 1H), 8.73 (d, J=5.5 Hz, 1H), 8.08 (d, J=1.7 Hz, 1H), 7.98 (dd, J=5.5, 1.7 Hz, 1H), 7.77 (d, J=2.6 Hz, 1H), 7.57 (dd, J=8.7, 2.6 Hz, 1H), 7.46 (s, 1H), 7.29 (d, J=8.7 Hz, 1H), 4.37 (d, J=5.4 Hz, 2H), 3.77-3.69 (m, 4H), 3.22-3.13 (m, 2H), 3.48-3.37 (m, 2H), 2.83-2.74 (m, 4H), 2.64 (s, 3H), 2.09-1.98 (m, 2H), 1.94-1.82 (m, 2H). ESI MS $[M+H]^+$ for $C_{27}H_{30}N_6OS$, calcd 487.2, found 487.2.

Example 3: 6-[(Dimethylamino)methyl]-N-[2-(4-methylpyridin-3-yl)-[1,3]thiazolo[5,4-c]pyridin-6-yl]-5-(morpholin-4-yl)pyridin-2-amine

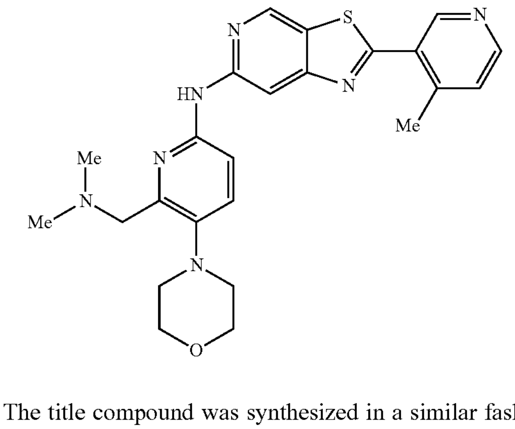

The title compound was synthesized in a similar fashion to example 1 from the appropriate starting materials. $^1H$ NMR (400 MHz, Chloroform-d) δ 8.97 (s, 1H), 8.83 (d, J=0.9 Hz, 1H), 8.56 (d, J=5.1 Hz, 1H), 8.10 (d, J=0.9 Hz, 1H), 7.53 (s, 1H), 7.50 (d, J=8.7 Hz, 1H), 7.44 (d, J=8.7 Hz, 1H), 7.27 (d, J=5.1 Hz, 1H), 3.86-3.81 (m, 4H), 3.64 (s, 2H), 2.94-2.90 (m, 4H), 2.69 (s Hz, 3H), 2.35 (s, 6H). ESI MS $[M+H]^+$ for $C_{24}H_{27}N_7OS$, calcd 462.2, found 462.1.

Example 4: 6-[(Dimethylamino)methyl]-N-[2-(3-fluoropyridin-4-yl)-[1,3]thiazolo[5,4-c]pyridin-6-yl]-5-(morpholin-4-yl)pyridin-2-amine

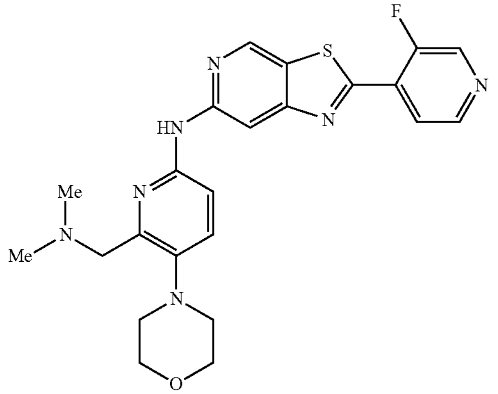 [SMILES: CN(C)Cc1nc(Nc2cc3nc(-c4ccncc4F)sc3cn2)ccc1N1CCOCC1]

The title compound was synthesized in a similar fashion to example 1 from the appropriate starting materials. $^1$H NMR (400 MHz, DMSO-$d_6$) δ 9.86 (s, 1H), 9.11 (d, J=0.9 Hz, 1H), 8.89 (d, J=2.5 Hz, 1H), 8.68-8.63 (m, 2H), 8.29 (dd, J=6.4, 5.0 Hz, 1H), 7.62 (d, J=8.8 Hz, 1H), 7.43 (d, J=8.8 Hz, 1H), 3.89 (s, 2H), 3.72 (t, J=4.5 Hz, 4H), 3.31 (s, 6H), 2.87 (t, J=4.5 Hz, 4H). ESI MS $[M+H]^+$ for $C_{23}H_{24}FN_7OS$, calcd 466.2, found 466.2.

Example 5: 6-[(Dimethylamino)methyl]-5-(morpholin-4-yl)-N-[2-(pyridin-4-yl)-[1,3]thiazolo[5,4-c]pyridin-6-yl]pyridin-2-amine

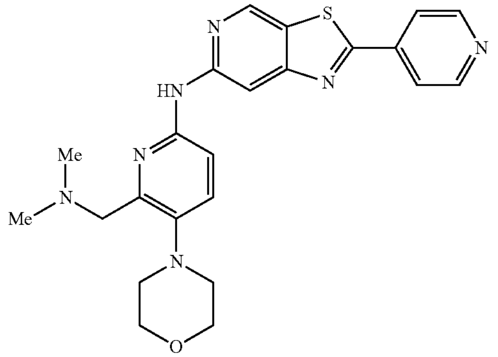 [SMILES: CN(C)Cc1nc(Nc2cc3nc(-c4ccncc4)sc3cn2)ccc1N1CCOCC1]

The title compound was synthesized in a similar fashion to example 1 from the appropriate starting materials. $^1$H NMR (400 MHz, DMSO-$d_6$) δ 9.91 (s, 1H), 9.11 (d, J=0.9 Hz, 1H), 8.84-8.79 (m, 2H), 8.44 (d, J=0.9 Hz, 1H), 8.07-8.03 (m, 2H), 7.78 (d, J=8.9 Hz, 1H), 7.56 (d, J=8.9 Hz, 1H), 4.48 (s, 2H), 3.77-3.70 (m, 4H), 2.93 (s, 6H), 2.80 (m, 4H). ESI MS $[M+H]^+$ for $C_{23}H_{25}N_7OS$, calcd 448.2, found 448.2.

Example 6: 6-[(Dimethylamino)methyl]-5-(morpholin-4-yl)-N-[2-(pyridin-3-yl)-[1,3]thiazolo[5,4-c]pyridin-6-yl]pyridin-2-amine

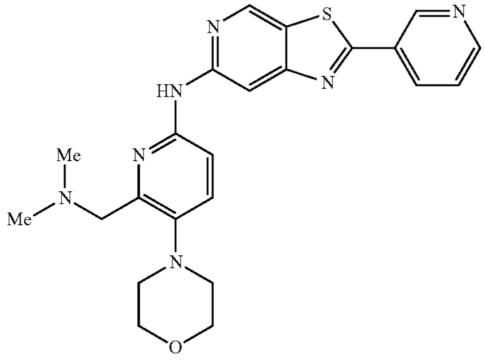 [SMILES: CN(C)Cc1nc(Nc2cc3nc(-c4cccnc4)sc3cn2)ccc1N1CCOCC1]

The title compound was synthesized in a similar fashion to example 1 from the appropriate starting materials. $^1$H NMR (400 MHz, DMSO-$d_6$) δ 10.06 (s, 1H), 9.31 (dd, J=2.3, 0.8 Hz, 1H), 9.10 (t, J=1.0 Hz, 1H), 8.80 (dd, J=4.8, 1.6 Hz, 1H), 8.49 (ddd, J=8.0, 2.4, 1.6 Hz, 1H), 8.36 (s, 1H), 7.78 (d, J=8.9 Hz, 1H), 7.64 (ddd, J=8.0, 4.8, 0.9 Hz, 1H), 7.57 (d, J=8.9 Hz, 1H), 4.48 (s, 2H), 3.77-3.71 (m, 4H), 2.93 (s, 6H), 2.84-2.77 (m, 4H). ESI MS $[M+H]^+$ for $C_{23}H_{25}N_7OS$, calcd 448.2, found 448.2.

Example 7: 5-(Morpholin-4-yl)-N-[2-(pyridin-2-yl)-[1,3]thiazolo[5,4-c]pyridin-6-yl]-6-[(pyrrolidin-1-yl)methyl]pyridin-2-amine

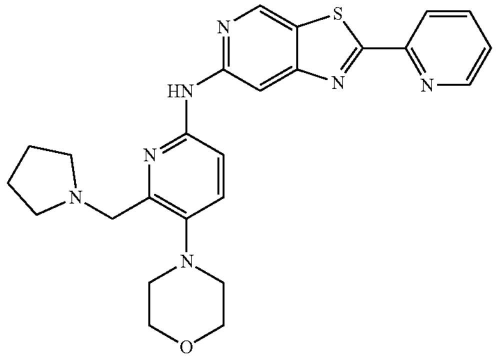 [SMILES: c1ccc(-c2nc3cc(Nc4ccc(N5CCOCC5)c(CN5CCCC5)n4)ncc3s2)nc1]

The title compound was synthesized in a similar fashion to example 1 from the appropriate starting materials. $^1$H NMR (400 MHz, Chloroform-d) δ 8.84 (s, 1H), 8.69 (ddd, J=3.3, 1.6, 0.8 Hz, 1H), 8.37 (dq, J=7.9, 1.0 Hz, 1H), 8.10 (s, 1H), 7.91-7.84 (m, 1H), 7.52 (s, 1H), 7.50-7.39 (m, 3H), 3.89 (s, 2H), 3.87-3.81 (m, 4H), 2.95-2.88 (m, 4H), 2.73 (d, J=6.1 Hz, 4H), 1.83 (p, J=3.2 Hz, 4H). ESI MS $[M+H]^+$ for $C_{25}H_{27}N_7OS$, calcd 474.6, found 474.5.

Example 8: N-[2-(3-Fluoropyridin-2-yl)-[1,3]thiazolo[5,4-c]pyridin-6-yl]-5-(morpholin-4-yl)-6-[(pyrrolidin-1-yl)methyl]pyridin-2-amine

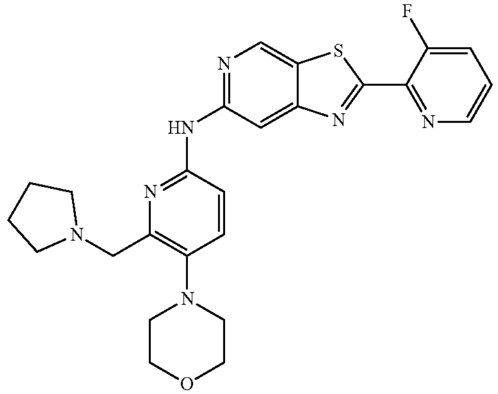 [SMILES: Fc1cccnc1-c1nc2cc(Nc3ccc(N4CCOCC4)c(CN4CCCC4)n3)ncc2s1]

The title compound was synthesized in a similar fashion to example 1 from the appropriate starting materials. $^1$H NMR (400 MHz, Chloroform-d) δ 8.87 (d, J=0.9 Hz, 1H), 8.56 (dt, J=4.5, 1.4 Hz, 1H), 8.11 (d, J=0.9 Hz, 1H), 7.64 (ddd, J=10.4, 8.4, 1.3 Hz, 1H), 7.54-7.45 (m, 3H), 7.42 (d, J=8.7 Hz, 1H), 3.87 (s, 2H), 3.86-3.81 (m, 4H), 2.96-2.89 (m, 4H), 2.77-2.66 (m, 4H), 1.86-1.77 (m, 4H). ESI MS $[M+H]^+$ for $C_{25}H_{26}FN_7OS$, calcd 492.2, found 491.8.

Example 9: 5-(3,3-Difluoropyrrolidin-1-yl)-N-[2-(3-methylpyridin-2-yl)-[1,3]thiazolo[5,4-c]pyridin-6-yl]-6-[(pyrrolidin-1-yl)methyl]pyridin-2-amine

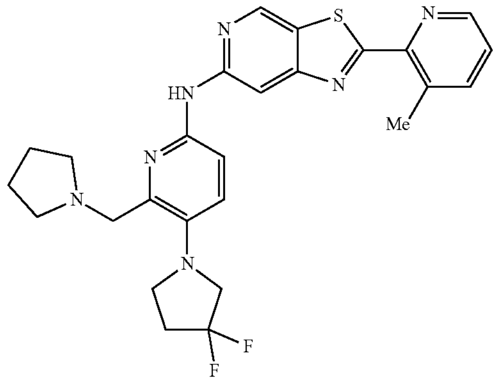 [SMILES: Cc1cccnc1-c1nc2cc(Nc3ccc(N4CCC(F)(F)C4)c(CN4CCCC4)n3)ncc2s1]

The title compound was synthesized in a similar fashion to example 1 from the appropriate starting materials. $^1$H NMR (400 MHz, DMSO-$d_6$) δ 9.69 (s, 1H), 8.96 (d, J=0.9 Hz, 1H), 8.85 (s, 1H), 8.58 (ddd, J=4.6, 1.6, 0.7 Hz, 1H), 7.88 (ddd, J=7.8, 1.6, 0.8 Hz, 1H), 7.52-7.48 (m, 2H), 7.24 (d, J=8.7 Hz, 1H), 3.71 (bs, 2H), 3.47 (t, J=13.1 Hz, 2H), 3.25 (t, J=6.9 Hz, 2H), 2.84 (s, 3H), 2.66 (bs, 4H), 2.39 (dt, J=14.9, 6.9 Hz, 2H), 1.74 (bs, 4H). ESI MS $[M+H]^+$ for $C_{26}H_{28}N_7SF_2$, calcd 508.2, found 508.2.

Example 10: 5-(3,3-Difluoropyrrolidin-1-yl)-N-[2-(2,6-dimethylphenyl)-[1,3]thiazolo[5,4-c]pyridin-6-yl]-6-[(pyrrolidin-1-yl)methyl]pyridin-2-amine

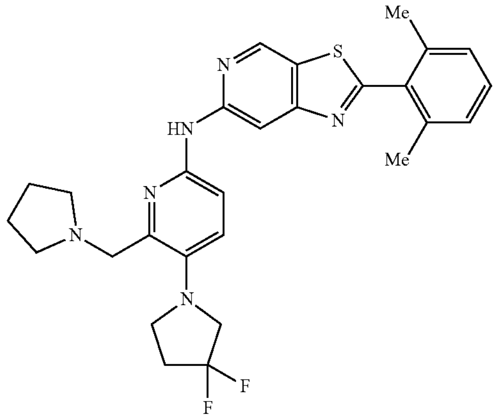 [SMILES: Cc1cccc(C)c1-c1nc2cc(Nc3ccc(N4CCC(F)(F)C4)c(CN4CCCC4)n3)ncc2s1]

The title compound was synthesized in a similar fashion to example 1 from the appropriate starting materials. $^1$H NMR (400 MHz, Chloroform-d) δ 8.81 (s, 1H), 8.15 (s, 1H), 7.66 (d, J=8.8 Hz, 1H), 7.42 (d, J=8.8 Hz, 1H), 7.32-7.25 (m, 2H), 7.14 (d, J=7.8 Hz, 3H), 4.06 (s, 2H), 3.42 (t, J=13.1 Hz, 2H), 3.24 (t, J=6.8 Hz, 2H), 3.01 (t, J=6.2 Hz, 4H), 2.43 (tt, J=14.4, 6.9 Hz, 2H), 2.21 (s, 6H), 1.94-1.87 (m, 4H). ESI MS $[M+H]^+$ for $C_{28}H_{30}F_2N_6S$, calcd 521.2, found 521.2.

Example 11: N-[2-(2,6-Difluorophenyl)-[1,3]thiazolo[5,4-c]pyridin-6-yl]-5-(3,3-difluoropyrrolidin-1-yl)-6-[(pyrrolidin-1-yl)methyl]pyridin-2-amine

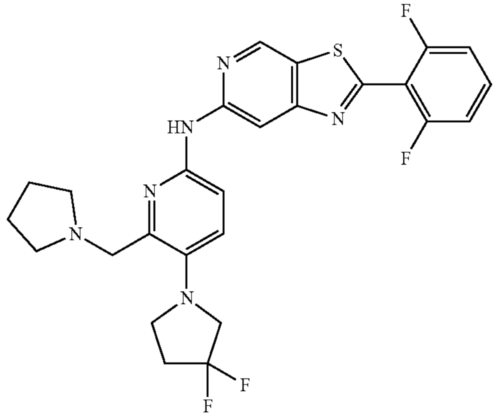 [SMILES: Fc1cccc(F)c1-c1nc2cc(Nc3ccc(N4CCC(F)(F)C4)c(CN4CCCC4)n3)ncc2s1]

The title compound was synthesized in a similar fashion to example 1 from the appropriate starting materials. $^1$H NMR (400 MHz, Chloroform-d) δ 8.88 (s, 1H), 8.15 (s, 1H), 7.58-7.45 (m, 3H), 7.39 (d, J=8.7 Hz, 1H), 7.11 (t, J=8.5 Hz, 2H), 3.84 (s, 2H), 3.47 (t, J=13.2 Hz, 2H), 3.28 (t, J=6.8 Hz, 2H), 2.73 (s, 4H), 2.43 (tt, J=14.4, 6.9 Hz, 2H), 1.83 (s, 4H). ESI MS $[M+H]^+$ for $C_{26}H_{24}F_4N_6S$, calcd 529.2, found 529.2.

Example 12: 1-(6-{[2-(2,6-Difluorophenyl)-[1,3]thiazolo[5,4-c]pyridin-6-yl]amino}-2-[(dimethylamino)methyl]pyridin-3-yl)piperidin-4-ol

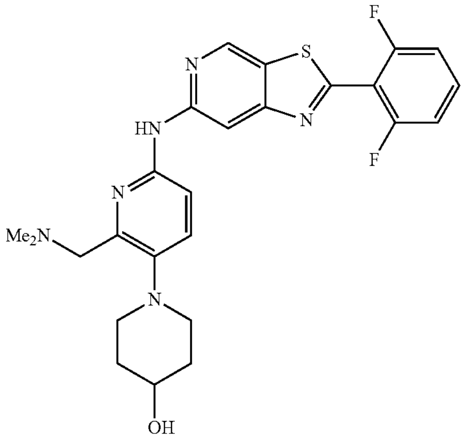 [SMILES: CN(C)Cc1nc(Nc2cc3nc(-c4c(F)cccc4F)sc3cn2)ccc1N1CCC(O)CC1]

The title compound was synthesized in a similar fashion to example 1 from the appropriate starting materials. $^1$H NMR (400 MHz, Chloroform-d) δ 8.88 (d, J=0.9 Hz, 1H), 7.99 (d, J=0.9 Hz, 1H), 7.61 (d, J=8.7 Hz, 1H), 7.53 (s, 1H), 7.52 (s, 1H), 7.45 (d, J=8.7 Hz, 1H), 7.11 (t, J=8.5 Hz, 2H), 3.85 (tt, J=8.6, 4.1 Hz, 1H), 3.64 (s, 2H), 3.09 (dt, J=10.2, 4.4 Hz, 2H), 2.75 (ddd, J=12.1, 9.6, 2.9 Hz, 2H), 2.36 (s, 6H), 2.04-2.02 (m, 1H), 1.75 (dtd, J=19.8, 10.8, 10.0, 5.4 Hz, 4H). ESI MS $[M+H]^+$ for $C_{25}H_{26}F_2N_6OS$, calcd 497.2, found 497.6.

Example 13: 6-[(Dimethylamino)methyl]-N-[2-(2,6-dimethylphenyl)-[1,3]thiazolo[5,4-c]pyridin-6-yl]-5-(morpholin-4-yl)pyridin-2-amine

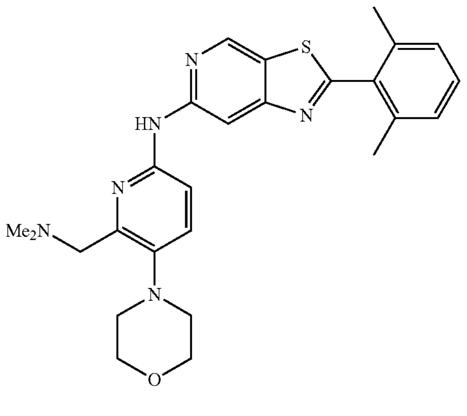 [SMILES: Cc1cccc(C)c1-c1nc2cc(Nc3ccc(N4CCOCC4)c(CN(C)C)n3)ncc2s1]

The title compound was synthesized in a similar fashion to example 1 from the appropriate starting materials. $^1$H NMR (400 MHz, Chloroform-d) δ 9.03 (d, J=0.7 Hz, 1H), 8.46 (d, J=0.8 Hz, 1H), 7.66 (d, J=8.9 Hz, 1H), 7.58 (d, J=8.9 Hz, 1H), 7.36-7.29 (m, 1H), 7.18-7.11 (m, 2H), 4.55 (s, 2H), 3.82 (dd, J=5.7, 3.3 Hz, 4H), 2.93 (s, 6H), 2.83-2.78 (m, 4H), 2.19 (s, 6H). ESI MS $[M+H]^+$ for $C_{26}H_{30}N_6OS$, calcd 475.2, found 475.8.

Example 14: 6-[(Dimethylamino)methyl]-N-[2-(2-fluoro-6-methylphenyl)-[1,3]thiazolo[5,4-c]pyridin-6-yl]-5-(morpholin-4-yl)pyridin-2-amine

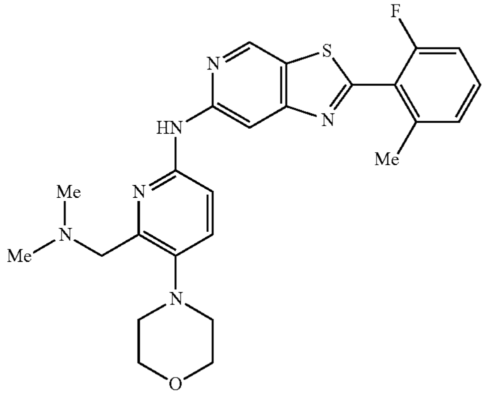 [SMILES: Cc1cccc(F)c1-c1nc2cc(Nc3ccc(N4CCOCC4)c(CN(C)C)n3)ncc2s1]

The title compound was synthesized in a similar fashion to example 1 from the appropriate starting materials. $^1$H NMR (400 MHz, DMSO-$d_6$) δ 9.53 (s, 1H), 9.08 (d, J=0.9 Hz, 1H), 8.44 (d, J=0.9 Hz, 1H), 7.77 (d, J=8.9 Hz, 1H), 7.60-7.47 (m, 2H), 7.31-7.21 (m, 2H), 4.47 (s, 2H), 3.78-3.69 (m, 4H), 2.91 (s, 6H), 2.83-2.75 (m, 4H), 2.33 (s, 3H). ESI MS $[M+H]^+$ for $C_{25}H_{27}FN_6OS$, calcd 479.2, found 479.3.

Example 15: 6-[(Dimethylamino)methyl]-N-{2-[2-fluoro-6-(trifluoromethyl)phenyl]-[1,3]thiazolo[5,4-c]pyridin-6-yl}-5-(morpholin-4-yl)pyridin-2-amine

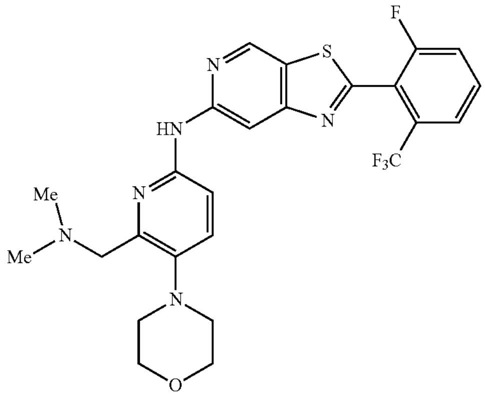 [SMILES: CN(C)Cc1nc(Nc2cc3nc(-c4c(F)cccc4C(F)(F)F)sc3cn2)ccc1N1CCOCC1]

The title compound was synthesized in a similar fashion to example 1 from the appropriate starting materials. $^1$H NMR (400 MHz, Chloroform-d) δ 8.88 (d, J=0.8 Hz, 1H), 8.15 (d, J=0.9 Hz, 1H), 7.66 (q, J=3.3 Hz, 2H), 7.58 (s, 1H), 7.52 (d, J=8.7 Hz, 1H), 7.49-7.39 (m, 2H), 3.89-3.82 (m, 4H), 3.66 (s, 2H), 2.97-2.90 (m, 4H), 2.36 (s, 6H). ESI MS $[M+H]^+$ for $C_{25}H_{24}F_4N_6OS$, calcd 533.2, found 533.2.

Example 16: N-[2-(2-Fluoro-6-methylphenyl)-[1,3]thiazolo[5,4-c]pyridin-6-yl]-5-(morpholin-4-yl)-6-[(pyrrolidin-1-yl)methyl]pyridin-2-amine

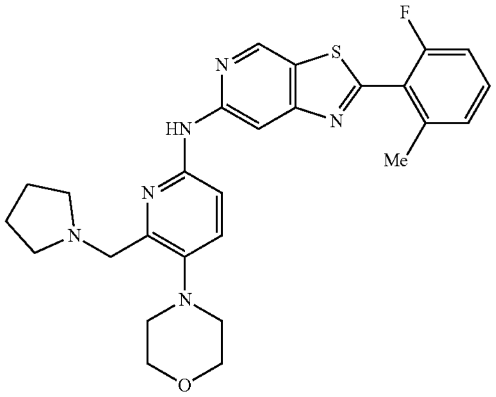 [SMILES: Cc1cccc(F)c1-c1nc2cc(Nc3ccc(N4CCOCC4)c(CN4CCCC4)n3)ncc2s1]

The title compound was synthesized in a similar fashion to example 1 from the appropriate starting materials. $^1$H NMR (400 MHz, Chloroform-d) δ 8.85 (d, J=0.8 Hz, 1H), 8.21 (s, 1H), 7.55 (s, 1H), 7.44 (s, 2H), 7.37 (td, J=8.0, 5.8 Hz, 1H), 7.14 (d, J=7.7 Hz, 1H), 7.06 (t, J=9.0 Hz, 1H), 3.86 (dd, J=9.4, 5.0 Hz, 6H), 2.99-2.90 (m, 4H), 2.72 (s, 4H), 2.44 (s, 3H), 1.85-1.74 (m, 4H). ESI MS $[M+H]^+$ for $C_{27}H_{29}FN_6OS$, calcd 505.2, found 505.3.

Example 17: N-[2-(2,6-Difluorophenyl)-[1,3]thiazolo[5,4-c]pyridin-6-yl]-5-(morpholin-4-yl)-6-[(pyrrolidin-1-yl)methyl]pyridin-2-amine

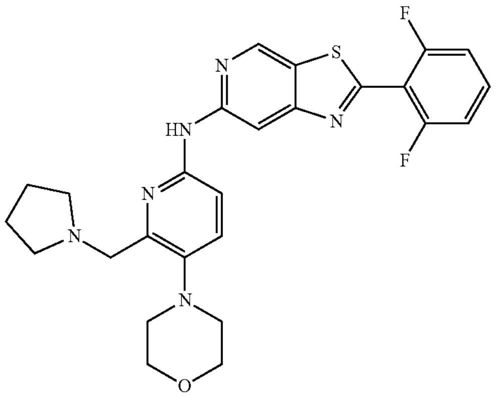 [SMILES: Fc1cccc(F)c1-c1nc2cc(Nc3ccc(N4CCOCC4)c(CN4CCCC4)n3)ncc2s1]

The title compound was synthesized in a similar fashion to example 1 from the appropriate starting materials. $^1$H NMR (400 MHz, Chloroform-d) δ 8.86 (d, J=0.9 Hz, 1H), 8.12 (d, J=0.9 Hz, 1H), 7.52-7.40 (m, 4H), 7.09 (t, J=8.5 Hz, 2H), 3.85-3.83 (m, 6H), 2.96-2.87 (m, 4H), 2.71-2.63 (m, 4H), 1.78 (p, J=3.3 Hz, 4H). ESI MS $[M+H]^+$ for $C_{26}H_{26}F_2N_6OS$, calcd 509.2, found 509.6.

Example 18: 1-{2-[(Dimethylamino)methyl]-6-{[2-(2-fluoro-6-methylphenyl)-[1,3]thiazolo[5,4-c]pyridin-6-yl]amino}pyridin-3-yl}piperidin-4-ol

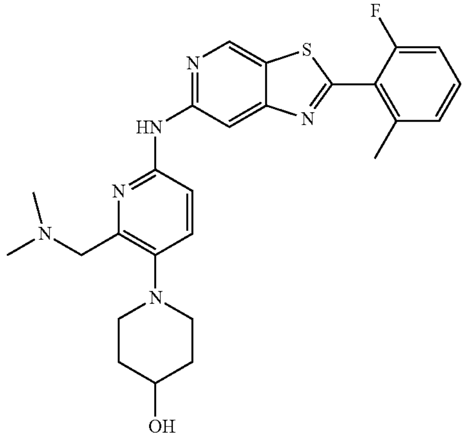 [SMILES: Cc1cccc(F)c1-c1nc2cc(Nc3ccc(N4CCC(O)CC4)c(CN(C)C)n3)ncc2s1]

The title compound was synthesized in a similar fashion to example 1 from the appropriate starting materials. $^1$H NMR (400 MHz, Chloroform-d) δ 8.84 (d, J=0.8 Hz, 1H), 8.04 (d, J=0.8 Hz, 1H), 7.52 (d, J=8.7 Hz, 1H), 7.43 (d, J=8.7 Hz, 1H), 7.36 (td, J=8.0, 5.7 Hz, 1H), 7.14-7.11 (m, 1H), 7.04 (dddd, J=10.2, 8.4, 1.2, 0.6 Hz, 1H), 3.83 (tt, J=8.6, 4.1 Hz, 1H), 3.65 (s, 2H), 3.15-3.03 (m, 2H), 2.75-2.69 (m, 2H), 2.41 (s, 3H), 2.36 (s, 6H), 2.02-1.98 (m, 2H), 1.93 (s, 1H), 1.78-1.69 (s, 2H). ESI MS $[M+H]^+$ for $C_{26}H_{29}FN_6OS$, calcd 493.2, found 493.9.

Example 19: N-(2-{6-Chloro-[1,3]thiazolo[5,4-c]pyridin-2-yl}-3-fluorophenyl)-6-[(dimethylamino)methyl]-5-(morpholin-4-yl)pyridin-2-amine

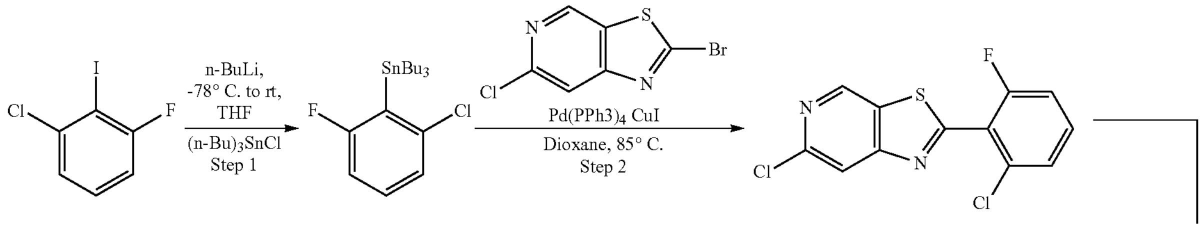

-continued

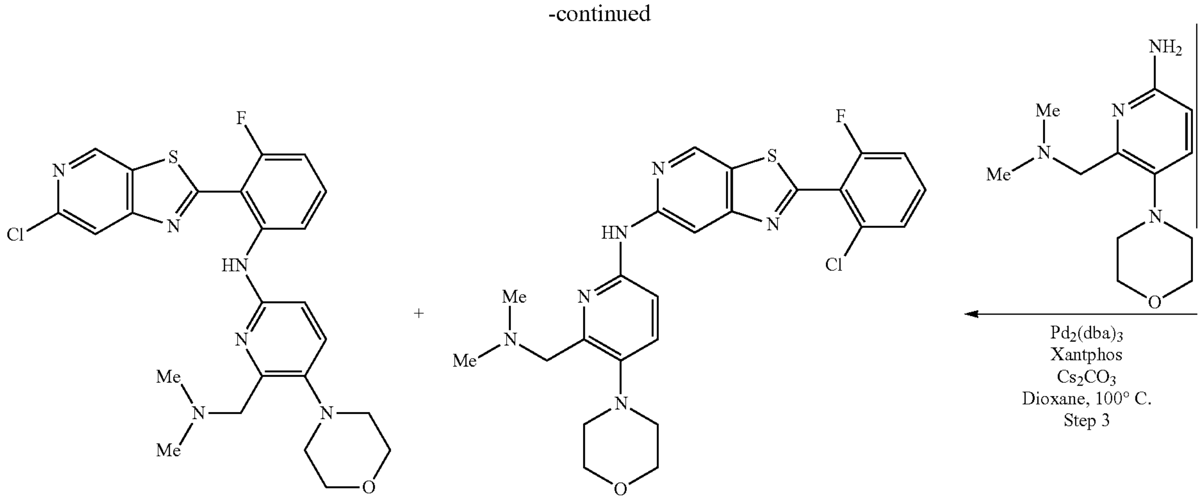

Example 19

Example 20

Step 1: To a dry screw cap reaction vial containing septum, was added 1-chloro-5-fluoro-2-iodobenzene (3.9 mmol, 1 g). The reaction vial was degassed and filled with nitrogen thrice and to this dry THF was added (15 mL) under nitrogen. This reaction mixture was then cooled to −78° C. using dry ice/acetone bath and n-butyl lithium (2.5 M sol., 4.29 mmol, 1.71 mL) was added under constant stirring. The reaction mixture was stirred at this temperature for half an hour and tri-n-butyltin chloride (4.68 mmol, 1.26 mL) was then added to the reaction mixture. The reaction mixture was then slowly brought to room temperature and stirred for 2 hours. After confirming the completion of the reaction by LCMS, the reaction was quenched using saturated $NH_4Cl$ solution and extracted with ethyl acetate (50 mL×2). The combined organic layers were dried using anhydrous sodium sulfate and concentrated. Crude product was purified using flash column chromatography to afford the stannane as an oily liquid (0.85 g, 52.1%).

Step 2: The stannane (0.84 g, 2.0 mmol) obtained in Step 2 was taken in a dry screw cap vial and to this was added commercially available azabenzothiazole derivative (0.5 g, 2 mmol) followed by $Pd(PPh_3)_4$ (463 mg, 0.4 mmol) and CuI (153 mg, 0.8 mmol) under nitrogen. To this reaction mixture, anhydrous dioxane (10 mL) was added and degassed using nitrogen for 5 min. The reaction mixture was subsequently stirred at 85° C. for 6 hours. After confirming the completion of the reaction by LCMS, the temperature of the reaction mixture was brought to room temperature and filtered through a small pad of Celite®. The solvent was evaporated under reduced pressure and the crude product was purified by flash column chromatography to afford the azabenzothiazole intermediate as an off white solid (300 mg, 50%).

Step 3: To a dry screw cap reaction vial containing septum, were added the amine (79 mg, 0.33 mmol) obtained via steps 1 and 2 of example 63, azabenzothiazole derivative (100 mg, 0.33 mmol) from Step 2, $Pd_2(dba)_3$ (31 mg, 0.033 mmol), Xantphos (39 mg, 0.066 mmol), $Cs_2CO_3$ (327 mg, 1.0 mmol) and Dioxane (4 mL). The reaction mixture was then degassed for 5 min using nitrogen and stirred at 100° C. overnight. After confirming the completion of the reaction using LCMS, the reaction mixture was cooled to room temperature and the crude reaction mixture was filtered through a small pad of Celite®. The solvent was evaporated under reduced pressure and the crude product was purified by flash column chromatography to afford the title compound 19 along with 20 as a 1:1 mixture. This mixture was separated by preparative HPLC to afford the title compound 19 (10 mg, 6%) and 20 (15 mg, 9%). 19: $^1H$ NMR (400 MHz, DMSO-$d_6$) δ 9.51 (s, 1H), 9.29 (d, J=0.8 Hz, 1H), 8.45 (d, J=0.8 Hz, 1H), 8.38 (d, J=8.7 Hz, 1H), 7.79 (d, J=8.8 Hz, 1H), 7.59 (td, J=8.4, 6.9 Hz, 1H), 7.38 (d, J=8.8 Hz, 1H), 7.04 (dd, J=12.8, 8.6 Hz, 1H), 4.52 (d, J=5.2 Hz, 2H), 3.82-3.71 (m, 4H), 2.93 (d, J=4.7 Hz, 6H), 2.88-2.78 (m, 4H). ESI MS $[M+H]^+$ for $C_{24}H_{24}C_1FN_6OS$, calcd 499.1, found 499.1.

Example 20: N-[2-(2-Chloro-6-fluorophenyl)-[1,3]thiazolo[5,4-c]pyridin-6-yl]-6-[(dimethylamino)methyl]-5-(morpholin-4-yl)pyridin-2-amine $^1H$ NMR (400 MHz, DMSO-$d_6$) δ 9.41 (s, 1H), 9.11 (d, J=0.9 Hz, 1H), 8.55 (d, J=0.9 Hz, 1H), 7.77 (d, J=8.9 Hz, 1H), 7.69 (td, J=8.3, 6.1 Hz, 1H), 7.58 (dd, J=8.2, 0.9 Hz, 1H), 7.54-7.44 (m, 2H), 4.51-4.43 (m, 3H), 3.79-3.67 (m, 4H), 2.90 (s, 6H), 2.83-2.73 (m, 4H). ESI MS $[M+H]^+$ for $C_{24}H_{24}ClFN_6OS$, calcd 499.1, found 499.1.

Example 21: 4-(6-{[5-(Morpholin-4-yl)-6-[(pyrrolidin-1-yl)methyl]pyridin-2-yl]amino}-[1,3]thiazolo[5,4-c]pyridin-2-yl)benzonitrile

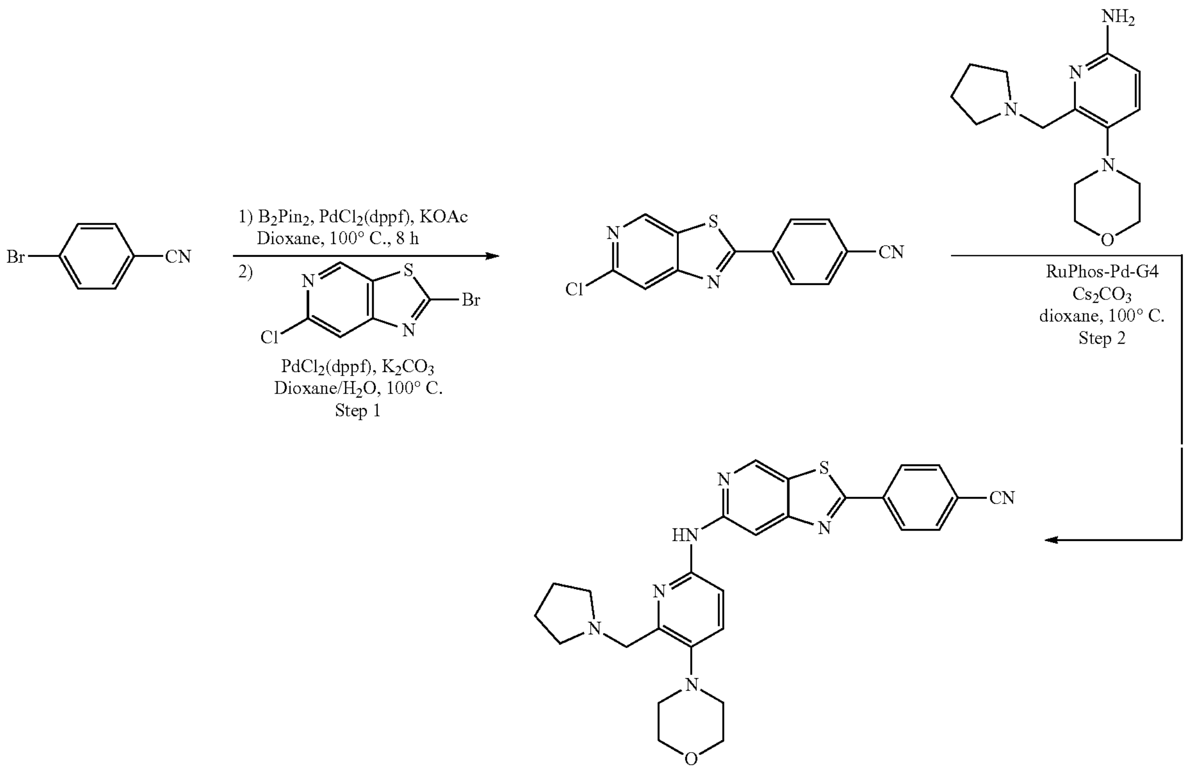 [SMILES: N#Cc1ccc(Br)cc1 ; Clc1cc2nc(Br)sc2cn1 ; N#Cc1ccc(-c2nc3cc(Cl)ncc3s2)cc1 ; Nc1ccc(N2CCOCC2)c(CN2CCCC2)n1 ; N#Cc1ccc(-c2nc3cc(Nc4ccc(N5CCOCC5)c(CN5CCCC5)n4)ncc3s2)cc1]

Step 1: This reaction was performed in a similar fashion to step 1 of example 120 from the appropriate starting materials.

Step 2: The title compound was synthesized in a similar fashion to step 6 of example 1. $^1H$ NMR (400 MHz, DMSO-$d_6$) δ 9.74 (s, 1H), 9.02 (d, J=0.9 Hz, 1H), 8.81 (d, J=0.9 Hz, 1H), 8.29-8.26 (m, 2H), 8.06-8.04 (m, 2H), 7.49 (d, J=8.8 Hz, 1H), 7.31 (d, J=8.7 Hz, 1H), 3.74 (s, 2H), 3.71 (t, J=4.5 Hz, 4H), 2.89 (t, J=4.5 Hz, 4H), 2.63 (d, J=5.3 Hz, 4H), 1.69 (s, 4H). ESI MS $[M+H]^+$ for $C_{27}H_{27}N_7SO$, calcd 498.2, found 498.3.

Example 22: N-[2-(4-Fluorophenyl)-[1,3]thiazolo[5,4-c]pyridin-6-yl]-5-(morpholin-4-yl)-6-[(pyrrolidin-1-yl)methyl]pyridin-2-amine

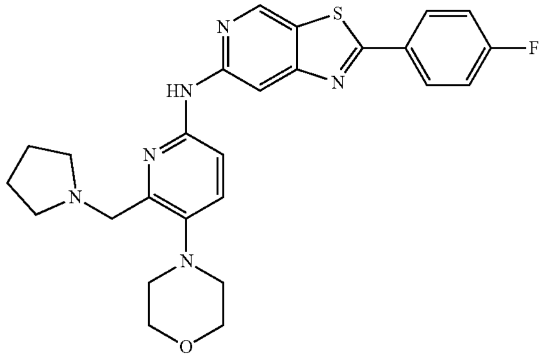 [SMILES: Fc1ccc(-c2nc3cc(Nc4ccc(N5CCOCC5)c(CN5CCCC5)n4)ncc3s2)cc1]

The title compound was synthesized in a similar fashion to example 21 from the appropriate starting materials. $^1H$ NMR (400 MHz, DMSO-$d_6$) δ 9.69 (s, 1H), 8.94 (d, J=0.9 Hz, 1H), 8.71 (s, 1H), 8.17 (dd, J=8.9, 5.3 Hz, 1H), 7.49 (d, J=8.8 Hz, 1H), 7.42 (t, J=8.8 Hz, 2H), 7.33 (d, J=8.8 Hz, 1H), 3.72 (dd, J=10.9, 6.6 Hz, 6H), 2.89 (t, J=4.5 Hz, 4H), 2.63 (s, 4H), 1.69 (s, 4H). ESI MS $[M+H]^+$ for $C_{26}H_{27}N_6SOF$, calcd 491.2, found 491.2.

Example 23: 5-(Morpholin-4-yl)-N-{2-[1-(propan-2-yl)-1H-pyrazol-4-yl]-[1,3]thiazolo[5,4-c]pyridin-6-yl}-6-[(pyrrolidin-1-yl)methyl]pyridin-2-amine

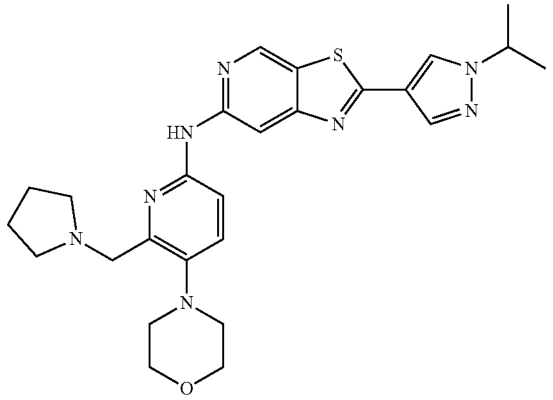 [SMILES: CC(C)n1cc(-c2nc3cc(Nc4ccc(N5CCOCC5)c(CN5CCCC5)n4)ncc3s2)cn1]

The title compound was synthesized in a similar fashion to example 21 from the appropriate starting materials. $^1$H NMR (400 MHz, Chloroform-d) δ 8.69 (s, 1H), 8.10 (s, 1H), 8.02 (s, 1H), 7.80 (s, 1H), 7.59 (d, J=8.7 Hz, 1H), 7.56 (s, 1H), 7.41 (d, J=8.7 Hz, 1H), 4.56 (p, J=6.7 Hz, 1H), 3.87 (s, 2H), 3.87-3.73 (m, 4H), 2.96-2.89 (m, 4H), 2.75-2.68 (m, 4H), 1.80 (m, 4H), 1.56 (d, J=6.7 Hz, 6H). ESI MS $[M+H]^+$ for $C_{26}H_{32}N_8OS$, calcd 505.7, found 505.8.

Example 24: N-[2-(1-Methyl-1H-pyrazol-4-yl)-[1,3]thiazolo[5,4-c]pyridin-6-yl]-5-(morpholin-4-yl)-6-[(pyrrolidin-1-yl)methyl]pyridin-2-amine

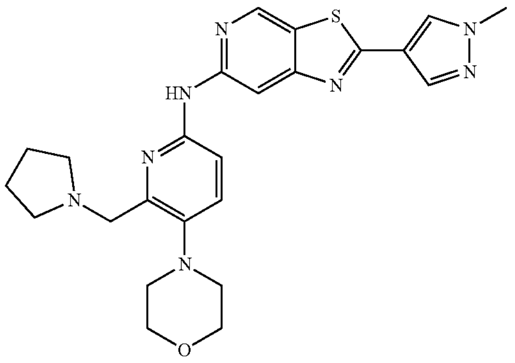 [SMILES: Cn1cc(-c2nc3cc(Nc4ccc(N5CCOCC5)c(CN5CCCC5)n4)ncc3s2)cn1]

The title compound was synthesized in a similar fashion to example 21 from the appropriate starting materials. $^1$H NMR (400 MHz, Chloroform-d) δ 8.67 (d, J=0.8 Hz, 1H), 8.00 (s, 2H), 7.89 (d, J=0.9 Hz, 1H), 7.64 (s, 1H), 7.49 (d, J=8.7 Hz, 1H), 7.38 (d, J=8.7 Hz, 1H), 3.95 (s, 2H), 3.84-3.79 (m, 4H), 2.93-2.87 (m, 4H), 2.67-2.61 (m, 4H), 1.97 (s, 3H), 1.79-1.75 (m, 4H). ESI MS $[M+H]^+$ for $C_{24}H_{28}N_8OS$, calcd 477.6, found 477.9.

Example 25: 5-(Morpholin-4-yl)-N-[2-(1H-pyrazol-4-yl)-[1,3]thiazolo[5,4-c]pyridin-6-yl]-6-[(pyrrolidin-1-yl)methyl]pyridin-2-amine

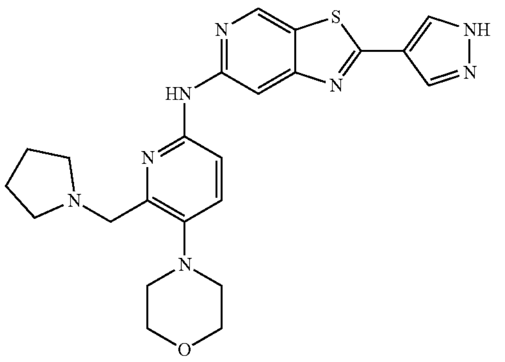 [SMILES: c1n[nH]cc1-c1nc2cc(Nc3ccc(N4CCOCC4)c(CN4CCCC4)n3)ncc2s1]

The title compound was synthesized in a similar fashion to example 21 from the appropriate starting materials. After step 2, the deprotection of THP-group was carried out using HCl in dioxane (3 mL) for a period of 3 h at room temperature followed by purification via reverse phase preparative HPLC. $^1$H NMR (400 MHz, Chloroform-d) δ 10.56 (s, 1H), 8.69 (d, J=0.8 Hz, 1H), 8.35 (s, 2H), 8.30 (d, J=8.8 Hz, 1H), 7.58 (d, J=0.8 Hz, 1H), 7.49 (d, J=8.9 Hz, 1H), 3.99 (s, 2H), 3.85 (dd, J=5.8, 3.2 Hz, 4H), 2.85 (dd, J=5.6, 3.4 Hz, 4H), 2.80-2.74 (m, 4H), 1.90 (q, J=3.9, 3.3 Hz, 4H). ESI MS $[M+H]^+$ for $C_{23}H_{26}N_8OS$, calcd 463.2, found 463.4.

Example 26: 6-[(Dimethylamino)methyl]-N-[2-(2-fluoro-6-methoxyphenyl)-[1,3]thiazolo[5,4-c]pyridin-6-yl]-5-(morpholin-4-yl)pyridin-2-amine

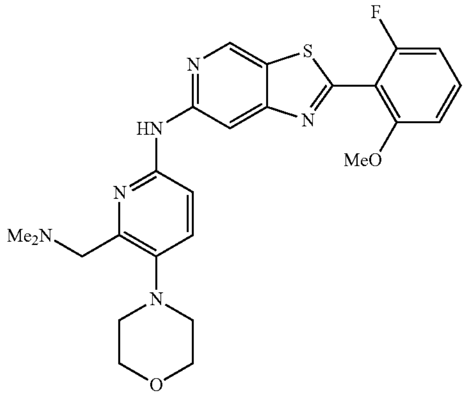 [SMILES: COc1cccc(F)c1-c1nc2cc(Nc3ccc(N4CCOCC4)c(CN(C)C)n3)ncc2s1]

The title compound was synthesized in a similar fashion to example 21 from the appropriate starting materials. $^1$H NMR (400 MHz, Chloroform-d) δ 8.84 (d, J=0.9 Hz, 1H), 7.94 (d, J=0.9 Hz, 1H), 7.91 (s, 1H), 7.75 (d, J=8.8 Hz, 1H), 7.48 (d, J=8.8 Hz, 1H), 7.43 (td, J=8.4, 6.3 Hz, 1H), 6.92-6.80 (m, 2H), 3.91 (s, 3H), 3.86 (s, 2H), 3.85-3.81 (m, 4H), 2.91-2.86 (m, 4H), 2.53 (s, 6H). ESI MS $[M+H]^+$ for $C_{25}H_{27}FN_6O_2S$, calcd 495.2, found 495.2.

Example 27: N-(2-{8-Methyl-1H,2H,3H-pyrido[2,3-b][1,4]oxazin-7-yl}-[1,3]thiazolo[5,4-c]pyridin-6-yl)-5-(morpholin-4-yl)-6-[(pyrrolidin-1-yl)methyl]pyridin-2-amine

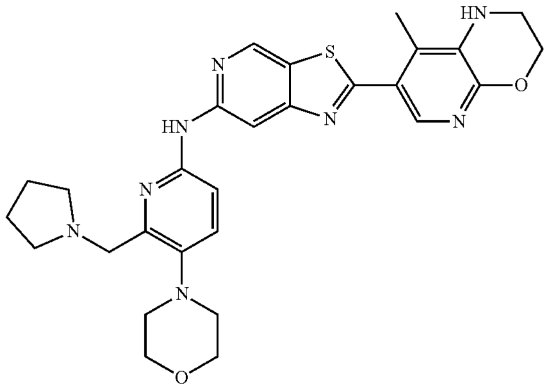 [SMILES: Cc1c(-c2nc3cc(Nc4ccc(N5CCOCC5)c(CN5CCCC5)n4)ncc3s2)cnc2c1NCCO2]

The title compound was synthesized in a similar fashion to example 21 from the appropriate starting materials. $^1$H NMR (400 MHz, Chloroform-d) δ 8.78 (d, J=0.9 Hz, 1H), 8.15 (d, J=0.9 Hz, 1H), 8.04 (s, 1H), 3.57-3.45 (m, 3H), 4.49-4.42 (m, 2H), 3.88-3.79 (m, 6H), 3.57-3.45 (m, 2H), 2.97-2.87 (m, 4H), 2.68 (d, J=5.7 Hz, 4H), 2.45 (s, 3H), 1.80 (h, J=3.4 Hz, 4H). ESI MS $[M+H]^+$ for $C_{28}H_{32}N_8O_2S$, calcd 545.2, found 545.7.

Example 28: 6-[(Dimethylamino)methyl]-N-(2-{8-methyl-1H,2H,3H-pyrido[2,3-b][1,4]oxazin-7-yl}-[1,3]thiazolo[5,4-c]pyridin-6-yl)-5-(morpholin-4-yl)pyridin-2-amine

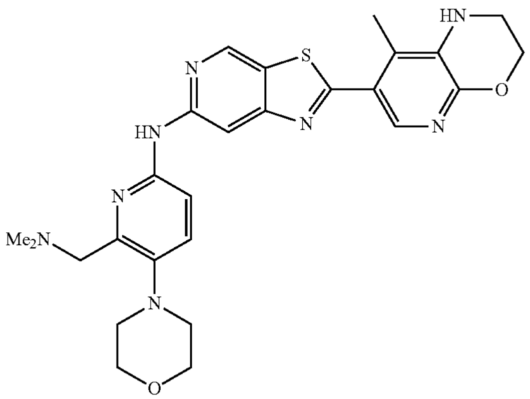 [SMILES: Cc1c(-c2nc3cc(Nc4ccc(N5CCOCC5)c(CN(C)C)n4)ncc3s2)cnc2c1NCCO2]

The title compound was synthesized in a similar fashion to example 21 from the appropriate starting materials. $^1H$ NMR (400 MHz, Methanol-$d_4$) δ 9.02 (d, J=0.9 Hz, 1H), 8.08 (d, J=0.9 Hz, 1H), 7.91 (s, 1H), 7.86 (d, J=9.0 Hz, 1H), 7.57 (d, J=9.0 Hz, 1H), 4.64 (s, 2H), 4.49-4.43 (m, 2H), 3.91-3.86 (m, 4H), 3.55-3.50 (m, 2H), 3.03 (s, 6H), 2.95-2.87 (m, 4H), 2.46 (s, 3H). ESI MS $[M+H]^+$ for $C_{26}H_{30}N_8O_2S$, calcd 519.2, found 519.3.

Example 29: N-[2-(5-Amino-4-methylpyridin-3-yl)-[1,3]thiazolo[5,4-c]pyridin-6-yl]-6-[(dimethylamino)methyl]-5-(morpholin-4-yl)pyridin-2-amine

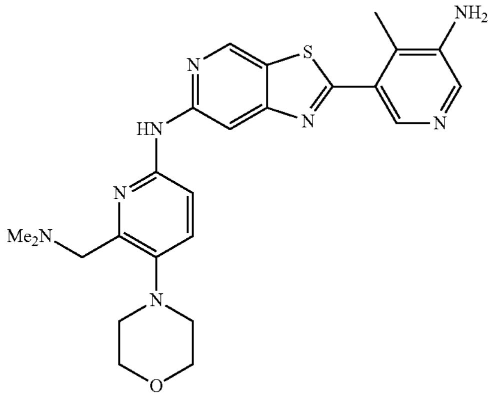 [SMILES: Cc1c(N)cncc1-c1nc2cc(Nc3ccc(N4CCOCC4)c(CN(C)C)n3)ncc2s1]

The title compound was synthesized in a similar fashion to example 21 from the appropriate starting materials. $^1H$ NMR (400 MHz, Methanol-$d_4$) δ 8.89 (d, J=0.9 Hz, 1H), 8.54 (d, J=0.9 Hz, 1H), 8.11-8.08 (m, 2H), 7.59 (d, J=8.8 Hz, 1H), 7.42 (d, J=8.8 Hz, 1H), 3.86-3.81 (m, 4H), 3.76 (s, 2H), 2.94-2.89 (m, 4H), 2.41 (s, 6H), 2.40 (s, 3H). ESI MS $[M+H]^+$ for $C_{24}H_{28}N_8OS$, calcd 477.2, found 477.3.

Example 30: 2-[(6-{[2-(2-Fluoro-6-methylphenyl)-[1,3]thiazolo[5,4-c]pyridin-6-yl]amino}-3-(morpholin-4-yl)pyridin-2-yl)methyl]-1λ$^6$,2-thiazolidine-1,1-dione

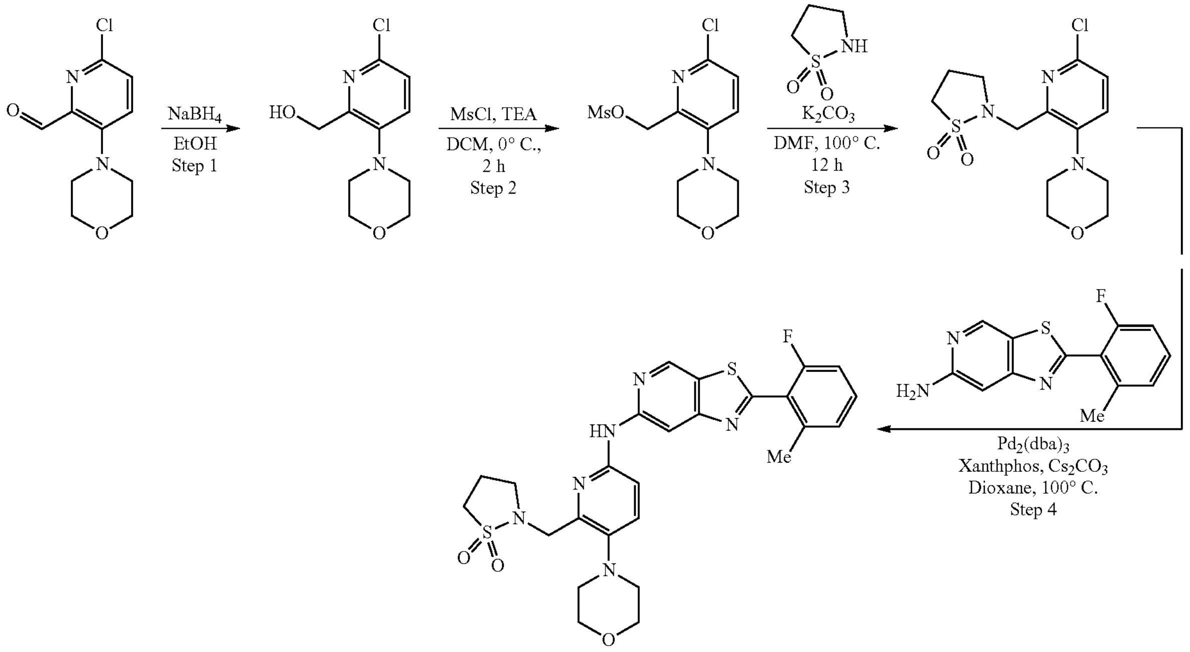

Step 1: To solution of the aldehyde (3.0 g, 13.3 mmol) in Ethanol (100 mL) was added $NaBH_4$ (1.0 g, 26.6 mmol) portion wise at 0° C. The reaction was then heated at 60° C. until complete consumption of the starting material as determined by LCMS. The solvent was removed and diluted with water and extracted with EtOAc. The combined organic layers were dried over $Na_2SO_4$ and concentrated in vacuo. The residue was purified by flash column chromatography (silica gel; gradient: 0% to 100% EtOAc in hexanes) to get alcohol intermediate (2.4 g, 79%) as the white solid.

Step 2: Methanesulfonyl chloride (1.8 g, 15.9 mmol) was added to the mixture of alcohol intermediate from step 1 (2.5 g, 10.5 mmol) and triethyl amine (2.1 g, 21.0 mmol) at 0° C. After 2 h at the same temperature, the reaction was diluted with water, $NaHCO_3$ (sat.) and extracted with $CH_2Cl_2$. The combined organic layers were dried over $Na_2SO_4$ and concentrated in vacuo. The residue was purified by flash column chromatography (silica gel; gradient: 0% to 100% EtOAc in hexanes) to get methanesulfonyl intermediate (2.0 g, 62%) as the brown oil.

Step 3: Commercially available Isothiazolidine, 1,1-dioxide (945 mg, 7.8 mmol) was added to the mixture of methanesulfonyl intermediate (2.0 g, 6.5 mmol) from step 2 and K2$CO_3$ (1.8 g, 13.0 mmol) in DMF and refluxed at 100° C. for 12 h. After cooling to RT, the reaction mixture was diluted with water and extracted with EtOAc. The combined organic layers were dried over $Na_2SO_4$ and concentrated in vacuo. The residue was purified by flash column chromatography (silica gel; gradient: 0% to 100% EtOAc in hexanes) to get 1,1-Dioxido-2-isothiazolidinyl intermediate (1.4 g, 42%) as the brown solid.

Step 4: To a dry screw cap reaction vial containing septum, were added the amine (128 mg, 0.385 mmol) from Step 3, benzothiazole derivative (100 mg, 0.385 mmol), $Pd_2(dba)_3$ (35.3 mg, 0.038 mmol), Xantphos (45 mg, 0.077 mmol), $Cs_2CO_3$ (377 mg, 1.15 mmol) and Dioxane (5 mL) and degassed for 5 min using nitrogen. Then this reaction mixture was stirred at 100° C. overnight. After confirming the completion of the reaction using LCMS, the reaction mixture was cooled to room temperature and the crude reaction mixture was filtered through a small pad of Celite®. Solvent was evaporated under reduced pressure and the crude product was purified by column chromatography (silica gel; gradient: 0% to 50% MeOH in $CH_2Cl_2$) to afford the title compound (47 mg, 22%). $^1$H NMR (400 MHz, Chloroform-d) δ 8.86 (d, J=0.8 Hz, 1H), 8.71 (d, J=0.8 Hz, 1H), 7.57 (s, 1H), 7.48 (d, J=8.7 Hz, 1H), 7.39 (td, J=8.0, 5.8 Hz, 1H), 7.18-7.02 (m, 3H), 4.45 (s, 2H), 3.87 (dd, J=5.3, 3.7 Hz, 4H), 3.55 (t, J=6.8 Hz, 2H), 3.29-3.20 (m, 2H), 2.90 (dd, J=5.3, 3.7 Hz, 4H), 2.44 (s, 3H), 2.36 (dt, J=14.3, 6.8 Hz, 2H). ESI MS $[M+H]^+$ for $C_{26}H_{27}FN_6O_3S_2$, calcd 555.2, found 555.2.

Example 31: N-[(6-{[2-(2,6-Difluorophenyl)-[1,3]thiazolo[5,4-c]pyridin-6-yl]amino}-3-(morpholin-4-yl)pyridin-2-yl)methyl]-N-methylmethanesulfonamide

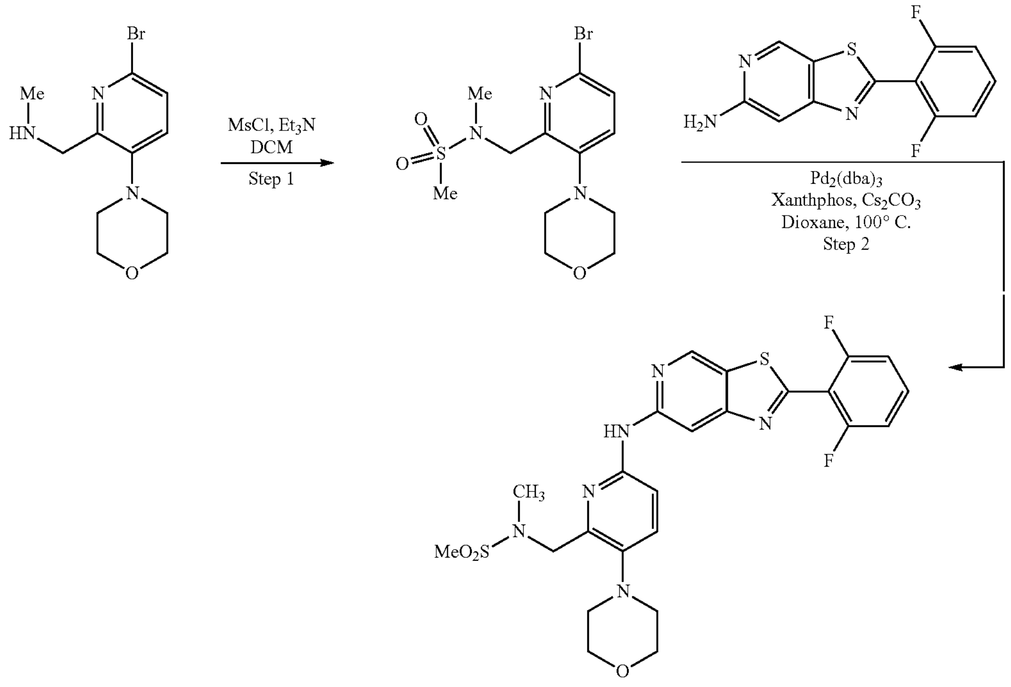

Step 1: Methanesulfonyl chloride (50 μL, 0.60 mmol) was added to the mixture of pyridine methylamine (114 mg, 0.40 mmol) obtained in a similar fashion by following steps 4 and 5 of example 1 and triethyl amine (110 μL, 0.80 mmol) in 4 mL $CH_2Cl_2$ at 0° C. After 20 minutes at room temperature, the reaction was diluted with water, $NaHCO_3$ (sat.) and extracted with $CH_2Cl_2$. The combined organic layers were dried over $Na_2SO_4$ and concentrated in vacuo. The crude material was used in the next step without further purification Step 2: This step was performed in a similar fashion to step 4 of example 30. $^1$H NMR (400 MHz, Chloroform-d) δ 8.88 (d, J=0.9 Hz, 1H), 8.46 (d, J=0.9 Hz, 1H), 7.53-7.45 (m, 2H), 7.35 (s, 1H), 7.27 (d, J=8.7 Hz, 1H), 7.10 (t, J=8.5 Hz, 2H), 4.66 (s, 2H), 3.97-3.73 (m, 4H), 3.00 (s, 3H), 2.99 (s, 3H), 2.91-2.80 (m, 4H). ESI MS $[M+H]^+$ for $C_{24}H_{24}F_2N_6O_3S_2$, calcd 547.1, found 547.8.

Example 32: N-[2-(4-Fluorophenyl)-[1,3]thiazolo[5,4-c]pyridin-6-yl]-5-methyl-6-[(pyrrolidin-1-yl)methyl]pyridin-2-amine

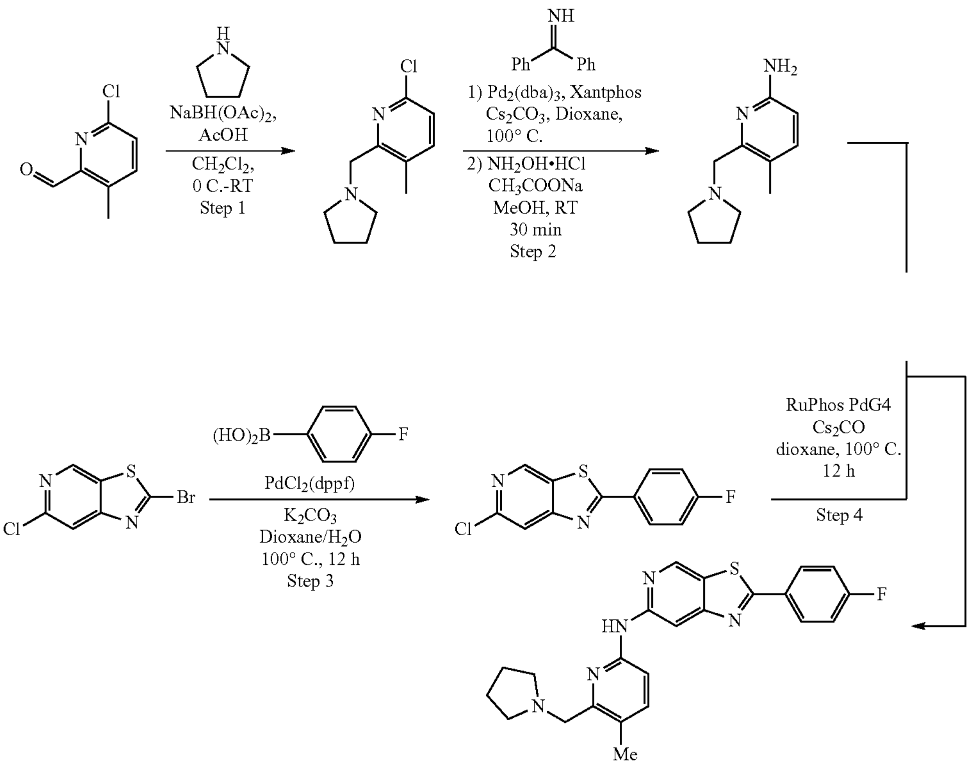

Step 1: A vial was charged with 6-Chloro-3-methylpicolinaldehyde (1.55 g, 10.0 mmol) in $CH_2Cl_2$ (40 mL) and was added pyrrolidine (850 mg, 12 mmol) in 5 mL of $CH_2Cl_2$. After stirring for 30 min at room temperature, acetic acid (0.5 mL) and sodium triacetoxyborohydride (3.4 g, 16 mmol) were added and stirred for 3 h at RT. The reaction mixture was then diluted with sodium bicarbonate solution (100 mL) and extracted with $CH_2Cl_2$ (3×50 mL). The combined organic extracts were washed with brine (60 mL), dried over $Na_2SO_4$, filtered, and concentrated under reduced pressure. The residue was purified by column chromatography (2% methanol gradient in $CH_2Cl_2$) to afford the desired product (1.38 g, 66%).

Step 2: This reaction was performed in a similar fashion to steps 2 and 3 of example 1 using the product of step 1.

Step 3: This reaction was performed in a similar fashion to step 1 of example 128 using the appropriate starting materials.

Step 4: The title compound was synthesized in a similar fashion to step 6 of example 1. $^1H$ NMR (400 MHz, DMSO-$d_6$) δ 9.68 (s, 1H), 8.95 (d, J=0.9 Hz, 1H), 8.68 (d, J=0.9 Hz, 1H), 8.20-8.15 (m, 2H), 7.44-7.39 (m, 3H), 7.29 (d, J=8.3 Hz, 1H), 3.65 (s, 2H), 2.52 (bs, 4H), 2.24 (s, 3H), 1.70 (t, J=3.6 Hz, 4H). ESI MS $[M+H]^+$ for $C_{23}H_{22}N_5SF$, calcd 420.2, found 420.2.

Example 33: N-[2-(3,5-Difluorophenyl)-[1,3]thiazolo[5,4-c]pyridin-6-yl]-5-methyl-6-[(pyrrolidin-1-yl)methyl]pyridin-2-amine

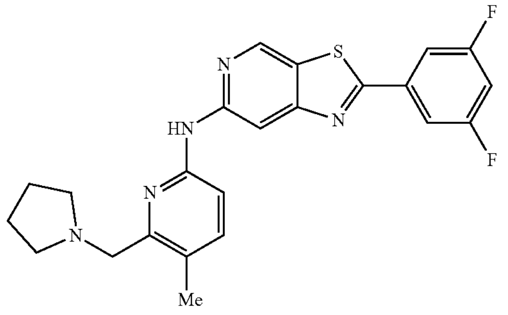 [SMILES: Cc1ccc(Nc2cc3nc(-c4cc(F)cc(F)c4)sc3cn2)nc1CN1CCCC1]

The title compound was synthesized in a similar fashion to example 32 using the appropriate starting materials. $^1H$ NMR (400 MHz, DMSO-$d_6$) δ 9.70 (s, 1H), 8.97 (d, J=0.8 Hz, 1H), 8.70 (d, J=0.9 Hz, 1H), 8.16 (ddd, J=11.2, 7.6, 2.2 Hz, 1H), 7.97 (ddd, J=7.2, 3.6, 1.8 Hz, 1H), 7.65 (dt, J=10.4, 8.4 Hz, 1H), 7.41 (s, 1H), 7.28 (d, J=8.3 Hz, 1H), 3.65 (s, 2H), 2.53-2.48 (m, 4H), 2.23 (s, 3H), 1.71-1.68 (m, 4H). ESI MS $[M+H]^+$ for $C_{23}H_{21}N_5SF_2$, calcd 438.2, found 438.2.

Example 34: 4-Methyl-N-[2-(3-methylpyridin-2-yl)-[1,3]thiazolo[5,4-c]pyridin-6-yl]-6-(piperidin-4-yloxy)pyridin-2-amine

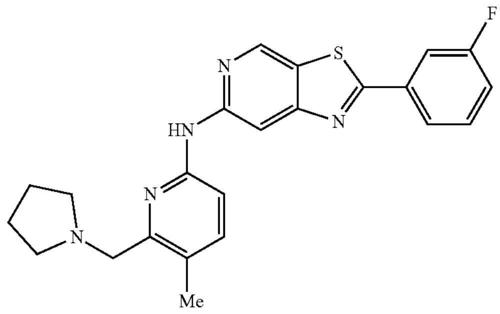 [SMILES: Cc1ccc(Nc2cc3nc(-c4cccc(F)c4)sc3cn2)nc1CN1CCCC1]

The title compound was synthesized in a similar fashion to example 32 using the appropriate starting materials. $^1H$ NMR (400 MHz, DMSO-$d_6$) δ 9.70 (s, 1H), 8.98 (d, J=0.9 Hz, 1H), 8.72 (d, J=0.9 Hz, 1H), 7.96-7.89 (m, 2H), 7.63 (td, J=8.0, 5.9 Hz, 1H), 7.47 (tdd, J=8.6, 2.7, 0.9 Hz, 1H), 7.41-7.39 (m, 1H), 7.28 (d, J=8.3 Hz, 1H), 3.65 (s, 2H), 2.53-2.50 (m, 4H), 2.23 (s, 3H), 1.73-1.69 (m, 4H). ESI MS $[M+H]^+$ for $C_{23}H_{22}N_5SF$, calcd 420.2, found 420.3.

Example 35: 5-Methyl-N-[2-(pyridin-4-yl)-[1,3]thiazolo[5,4-c]pyridin-6-yl]-6-[(pyrrolidin-1-yl)methyl]pyridin-2-amine

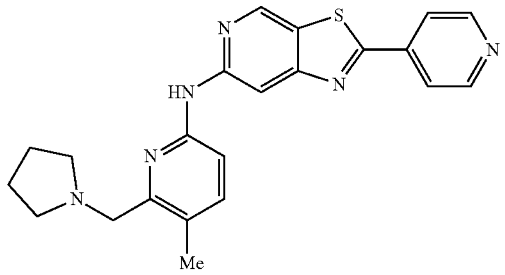 [SMILES: Cc1ccc(Nc2cc3nc(-c4ccncc4)sc3cn2)nc1CN1CCCC1]

The title compound was synthesized in a similar fashion to example 32 using the appropriate starting materials. $^1H$ NMR (400 MHz, DMSO-$d_6$) δ 0.75 (s, 1H), 9.04 (d, J=0.9 Hz, 1H), 8.80-8.79 (m, 3H), 8.04-8.02 (m, 2H), 7.41 (dd, J=8.2, 0.7 Hz, 1H), 7.26 (d, J=8.3 Hz, 1H), 3.66 (s, 2H), 2.54-2.51 (m, 4H), 2.24 (s, 3H), 1.72-1.70 (m, 4H). ESI MS $[M+H]^+$ for $C_{22}H_{22}N_6S$, calcd 403.2, found 403.2.

Example 36: 5-Methyl-6-[(pyrrolidin-1-yl)methyl]-N-{2-[1-(trifluoromethyl)-1H-pyrazol-4-yl]-[1,3]thiazolo[5,4-c]pyridin-6-yl}pyridin-2-amine

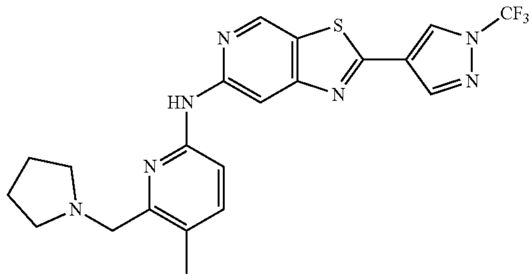 [SMILES: Cc1ccc(Nc2cc3nc(-c4cnn(C(F)(F)F)c4)sc3cn2)nc1CN1CCCC1]

The title compound was synthesized in a similar fashion to example 32 using the appropriate starting materials. $^1H$ NMR (400 MHz, Chloroform-d) δ 8.75 (d, J=0.9 Hz, 1H), 8.46 (s, 1H), 8.29 (t, J=0.9 Hz, 1H), 8.20 (d, J=0.9 Hz, 1H), 7.44 (s, 1H), 7.36 (dd, J=8.3, 0.7 Hz, 1H), 7.24 (dd, J=8.3, 0.7 Hz, 1H), 3.73 (s, 2H), 2.68-2.61 (m, 4H), 2.30 (s, 3H), 1.83-1.87 (m, 4H). ESI MS $[M+H]^+$ for $C_{21}H_{20}F_3N_7S$, calcd 460.2 found 460.7.

Example 37: 3-{4-[6-({5-Methyl-6-[(pyrrolidin-1-yl)methyl]pyridin-2-yl}amino)-[1,3]thiazolo[5,4-c]pyridin-2-yl]-1H-pyrazol-1-yl}propanamide

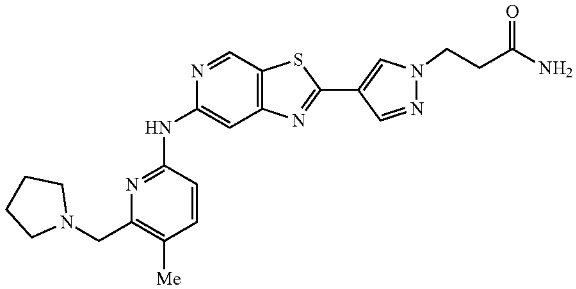 [SMILES: Cc1ccc(Nc2cc3nc(-c4cnn(CCC(N)=O)c4)sc3cn2)nc1CN1CCCC1]

The title compound was synthesized in a similar fashion to example 32 using the appropriate starting materials. $^1H$ NMR (400 MHz, DMSO-$d_6$) δ 9.81 (s, 1H), 8.92 (d, J=0.8 Hz, 1H), 8.51 (d, J=0.8 Hz, 1H), 8.10 (dd, J=4.8, 0.8 Hz, 2H), 7.56 (dd, J=8.4, 0.7 Hz, 1H), 7.47 (d, J=8.4 Hz, 1H), 6.92 (s, 1H), 4.53 (m, 3H), 4.38 (t, J=6.7 Hz, 2H), 3.51 (m, 5H), 2.71-2.63 (m, 2H), 2.19 (s, 3H), 2.04 (t, J=2.9 Hz, 4H). ESI MS $[M+H]^+$ for $C_{23}H_{26}N_8OS$, calcd 463.2, found 463.2.

Example 38: 5-Methyl-N-{2-[1-(oxolan-3-yl)-1H-pyrazol-4-yl]-[1,3]thiazolo[5,4-c]pyridin-6-yl}-6-[(pyrrolidin-1-yl)methyl]pyridin-2-amine

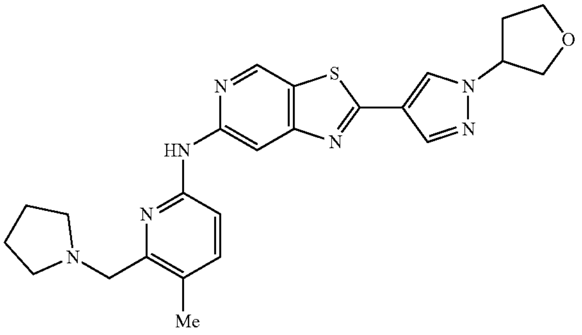 [SMILES: Cc1ccc(Nc2cc3nc(-c4cnn(C5CCOC5)c4)sc3cn2)nc1CN1CCCC1]

The title compound was synthesized in a similar fashion to example 32 using the appropriate starting materials. $^1$H NMR (400 MHz, DMSO-$d_6$) δ 11.21 (s, 1H), 9.36 (s, 1H), 8.81 (s, 1H), 8.27 (s, 1H), 7.99 (s, 1H), 7.70 (d, J=8.4 Hz, 1H), 7.31 (d, J=8.4 Hz, 1H), 5.13 (ddt, J=7.6, 5.5, 3.7 Hz, 1H), 4.60 (s, 2H), 4.05-3.90 (m, 4H), 3.82 (td, J=8.3, 5.4 Hz, 1H), 3.42 (m, 3H), 2.44-2.33 (m, 2H), 2.27 (s, 3H), 1.99 (p, J=3.5 Hz, 4H). ESI MS $[M+H]^+$ for $C_{24}H_{27}N_7OS$, calcd 462.2, found 462.2.

Example 39: 5-Methyl-N-{2-[1-(oxan-4-yl)-1H-pyrazol-4-yl]-[1,3]thiazolo[5,4-c]pyridin-6-yl}-6-[(pyrrolidin-1-yl)methyl]pyridin-2-amine

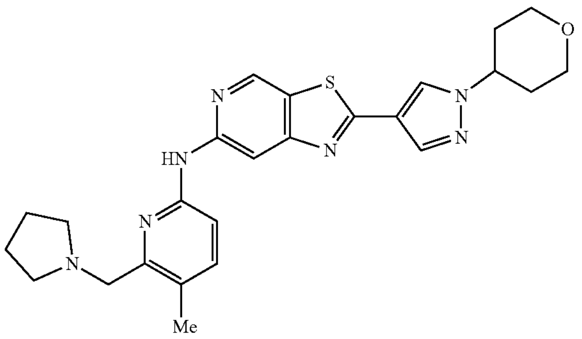 [SMILES: Cc1ccc(Nc2cc3nc(-c4cnn(C5CCOCC5)c4)sc3cn2)nc1CN1CCCC1]

The title compound was synthesized in a similar fashion to example 32 using the appropriate starting materials. $^1$H NMR (400 MHz, DMSO-$d_6$) δ 10.94 (s, 1H), 9.27 (s, 1H), 8.81 (s, 1H), 8.24 (s, 1H), 7.98 (s, 1H), 7.68 (d, J=8.4 Hz, 1H), 7.33 (d, J=8.4 Hz, 1H), 4.65-4.43 (m, 3H), 3.96 (dt, J=11.7, 3.3 Hz, 2H), 3.74-3.10 (m, 6H), 2.26 (s, 3H), 2.01 (q, J=3.5 Hz, 8H). ESI MS $[M+H]^+$ for $C_{25}H_{29}N_7OS$, calcd 476.2, found 476.2.

Example 40: 2-{4-[6-({5-Methyl-6-[(pyrrolidin-1-yl)methyl]pyridin-2-yl}amino)-[1,3]thiazolo[5,4-c]pyridin-2-yl]-1H-pyrazol-1-yl}ethan-1-ol

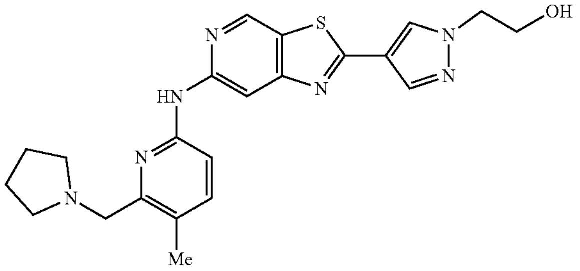 [SMILES: Cc1ccc(Nc2cc3nc(-c4cnn(CCO)c4)sc3cn2)nc1CN1CCCC1]

The title compound was synthesized in a similar fashion to example 32 using the appropriate starting materials. $^1$H NMR (400 MHz, DMSO-$d_6$) δ 11.12 (s, 1H), 9.34 (s, 1H), 8.71 (s, 1H), 8.24 (s, 1H), 7.96 (s, 1H), 7.71 (d, J=8.4 Hz, 1H), 7.29 (d, J=8.4 Hz, 1H), 4.59 (d, J=3.4 Hz, 2H), 4.24 (t, J=5.4 Hz, 2H), 3.77 (t, J=5.4 Hz, 2H), 3.41 (m, 4H), 2.28 (s, 3H), 1.99 (m, 4H). ESI MS $[M+H]^+$ for $C_{22}H_{25}N_7OS$, calcd 436.2, found 436.2.

Example 41: 5-Methyl-N-[2-(3-methylpyridin-2-yl)-[1,3]thiazolo[5,4-c]pyridin-6-yl]-6-[(pyrrolidin-1-yl)methyl]pyridin-2-amine

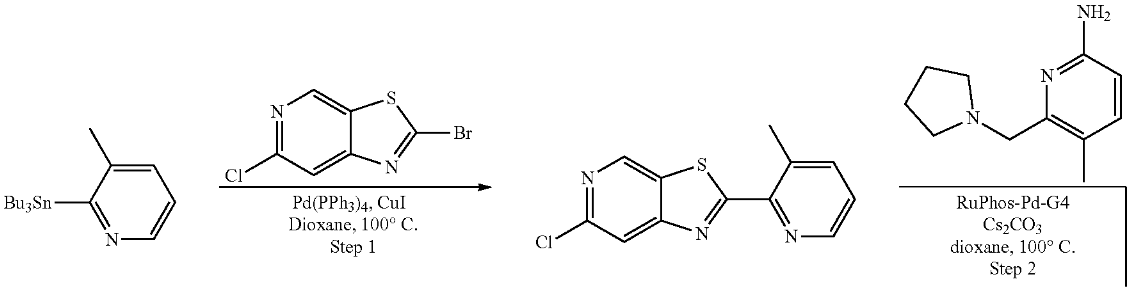

-continued

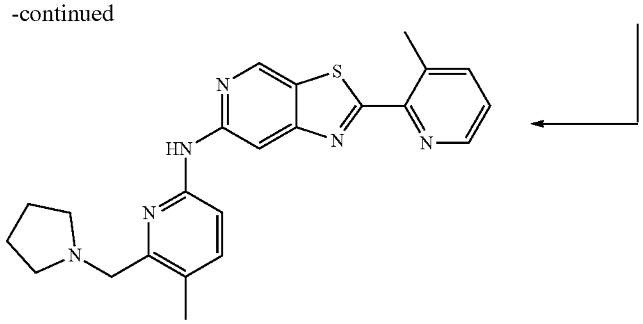

Step 1: The Stille coupling reaction was performed in a similar fashion to step 1 of example 1 using the appropriate starting materials.

Step 2: The title compound was synthesized in a similar fashion to step 6 of example 1, wherein the amino pyridine derivative used in step 2 was prepared substantially as described in steps 1 and 2 of example 32. $^{1}$H NMR (400 MHz, Chloroform-d) δ 8.83 (d, J=0.9 Hz, 1H), 8.57-8.48 (m, 1H), 8.37 (s, 1H), 7.72-7.64 (m, 1H), 7.36 (d, J=8.3 Hz, 1H), 7.34 (s, 1H), 7.31 (dd, J=7.7, 4.6 Hz, 1H), 7.17 (d, J=8.2 Hz, 1H), 3.75 (s, 2H), 2.72-2.75 (m, 4H), 2.70 (s, 3H), 2.29 (s, 3H), 1.87-1.83 (m, 4H). ESI MS [M+H]$^+$ for $C_{23}H_{24}N_6S$, calcd 417.2, found 417.7.

Example 42: 6-{[(3R)-3-Fluoropyrrolidin-1-yl]methyl}-5-methyl-N-[2-(3-methylpyridin-2-yl)-[1,3]thiazolo[5,4-c]pyridin-6-yl]pyridin-2-amine

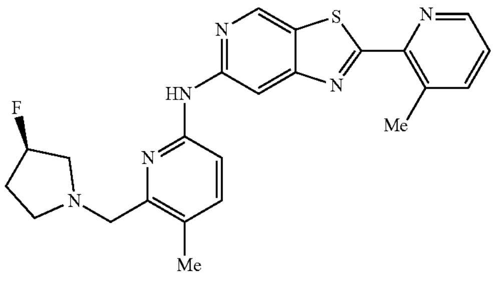 [SMILES: Cc1ccc(Nc2cc3nc(-c4ncccc4C)sc3cn2)nc1CN1CC[C@@H](F)C1]

The title compound was synthesized in a similar fashion to example 41 using the appropriate starting materials. $^{1}$H NMR (400 MHz, DMSO-d$_6$) δ 9.68 (s, 1H), 8.96 (d, J=0.9 Hz, 1H), 8.68 (d, J=0.9 Hz, 1H), 8.63-8.49 (m, 1H), 7.88 (ddd, J=7.8, 1.6, 0.8 Hz, 1H), 7.50 (dd, J=7.8, 4.6 Hz, 1H), 7.46-7.39 (m, 1H), 7.30 (d, J=8.3 Hz, 1H), 5.29-5.13 (m, 1H), 3.72 (d, J=12.9 Hz, 1H), 3.65 (d, J=13.0 Hz, 1H), 2.88-2.78 (m, 6H), 2.54-2.50 (m, 1H), 2.23 (s, 3H), 2.14 (dq, J=20.9, 6.9 Hz, 1H), 1.95-1.81 (m, 1H). ESI MS [M+H]$^+$ for $C_{23}H_{23}N_6SF$, calcd 435.2, found 435.2.

Example 43: 6-{[(3S)-3-Fluoropyrrolidin-1-yl]methyl}-5-methyl-N-[2-(3-methylpyridin-2-yl)-[1,3]thiazolo[5,4-c]pyridin-6-yl]pyridin-2-amine

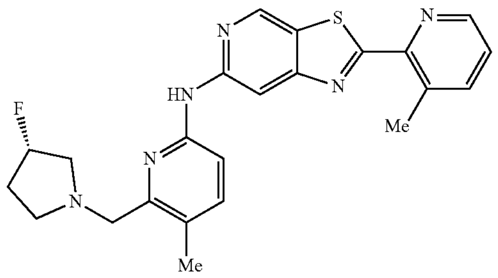 [SMILES: Cc1ccc(Nc2cc3nc(-c4ncccc4C)sc3cn2)nc1CN1CC[C@H](F)C1]

The title compound was synthesized in a similar fashion to example 41 from the appropriate starting materials. $^{1}$H NMR (400 MHz, DMSO-d$_6$) δ 9.68 (s, 1H), 8.96 (d, J=0.9 Hz, 1H), 8.68 (d, J=0.9 Hz, 1H), 8.63-8.49 (m, 1H), 7.88 (ddd, J=7.8, 1.6, 0.8 Hz, 1H), 7.50 (dd, J=7.8, 4.6 Hz, 1H), 7.46-7.39 (m, 1H), 7.30 (d, J=8.3 Hz, 1H), 5.35-5.15 (m, 1H), 3.72 (d, J=12.9 Hz, 1H), 3.65 (d, J=13.0 Hz, 1H), 2.88-2.79 (m, 6H), 2.54-2.48 (m, 1H), 2.23 (s, 3H), 2.14 (dq, J=20.9, 6.9 Hz, 1H), 1.94-1.83 (m, 1H). ESI MS [M+H]$^+$ for $C_{23}H_{23}N_6SF$, calcd 435.2, found 435.2.

Example 44: 5-Methyl-N-[2-(3-methylpyridin-2-yl)-[1,3]thiazolo[5,4-c]pyridin-6-yl]-6-{[(2R)-2-methylpyrrolidin-1-yl]methyl}pyridin-2-amine

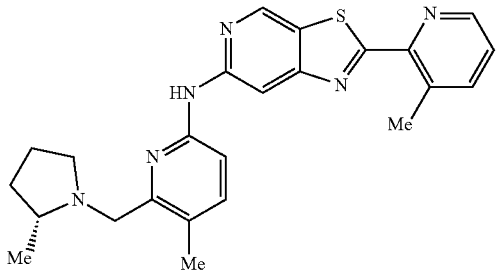 [SMILES: Cc1ccc(Nc2cc3nc(-c4ncccc4C)sc3cn2)nc1CN1CCC[C@H]1C]

The title compound was synthesized in a similar fashion to example 41 from the appropriate starting materials. $^{1}$H NMR (400 MHz, DMSO-d$_6$) δ 9.65 (s, 1H), 8.95 (d, J=0.9 Hz, 1H), 8.78 (d, J=1.0 Hz, 1H), 8.58 (ddd, J=4.7, 1.6, 0.7 Hz, 1H), 7.89-7.87 (m, 1H), 7.50 (dd, J=7.7, 4.6 Hz, 1H), 7.40-7.38 (m, 1H), 7.24 (d, J=8.2 Hz, 1H), 4.05 (d, J=12.5

Hz, 1H), 3.18 (d, J=12.5 Hz, 1H), 2.93-2.88 (m, 1H), 2.84 (s, 3H), 2.47 (m, 2H), 2.26-2.20 (s, 4H), 1.89 (ddd, J=12.4, 8.7, 5.1 Hz, 1H), 1.66-1.55 (m, 1H), 1.37-1.27 (m, 1H), 1.15 (d, J=5.9 Hz, 3H). ESI MS $[M+H]^+$ for $C_{24}H_{26}N_6S$, calcd 431.2, found 431.1.

Example 45: 5-Methyl-N-[2-(3-methylpyridin-2-yl)-[1,3]thiazolo[5,4-c]pyridin-6-yl]-6-{[(2S)-2-methylpyrrolidin-1-yl]methyl}pyridin-2-amine

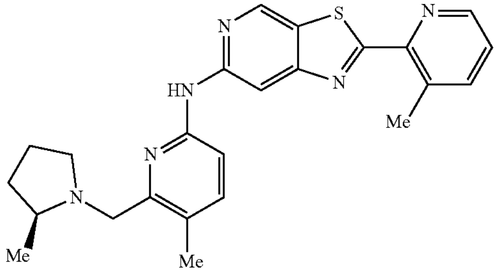 [SMILES: Cc1ccc(Nc2cc3nc(-c4ncccc4C)sc3cn2)nc1CN1CCC[C@@H]1C]

The title compound was synthesized in a similar fashion to example 41 from the appropriate starting materials. $^1H$ NMR (400 MHz, DMSO-$d_6$) δ 9.65 (s, 1H), 8.95 (d, J=0.9 Hz, 1H), 8.78 (d, J=0.9 Hz, 1H), 8.58 (ddd, J=4.6, 1.6, 0.7 Hz, 1H), 7.87 (ddd, J=7.8, 1.6, 0.8 Hz, 1H), 7.50 (dd, J=7.7, 4.6 Hz, 1H), 7.39 (dd, J=8.3, 0.7 Hz, 1H), 7.23 (d, J=8.3 Hz, 1H), 4.05 (d, J=12.5 Hz, 1H), 3.18 (d, J=12.5 Hz, 1H), 2.90 (ddd, J=9.5, 7.7, 2.6 Hz, 1H), 2.83 (s, 3H), 2.47 (m, 2H), 2.28-2.23 (s, 4H), 1.93-1.85 (m, 1H), 1.64-1.55 (m, 1H), 1.36-1.29 (m, 1H), 1.15 (d, J=6.0 Hz, 3H). ESI MS $[M+H]^+$ for $C_{24}H_{26}N_6S$, calcd 431.2, found 431.1.

Example 46: N-[2-(2,6-Difluorophenyl)-[1,3]thiazolo[5,4-c]pyridin-6-yl]-6-[(dimethylamino)methyl]-5-methylpyridin-2-amine

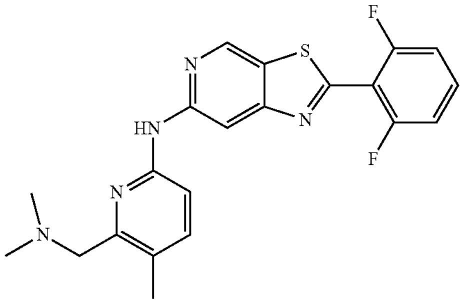 [SMILES: Cc1ccc(Nc2cc3nc(-c4c(F)cccc4F)sc3cn2)nc1CN(C)C]

The title compound was synthesized in a similar fashion to example 41 from the appropriate starting materials. $^1H$ NMR (400 MHz, Chloroform-d) δ 8.87 (d, J=0.9 Hz, 1H), 8.21 (d, J=1.0 Hz, 1H), 7.57-7.44 (m, 1H), 7.39 (d, J=0.7 Hz, 2H), 7.09 (t, J=8.5 Hz, 2H), 3.53 (s, 2H), 2.33 (s, 6H), 2.31 (s, 3H). ESI MS $[M+H]^+$ for $C_{21}H_{19}F_2N_5S$, calcd 412.2, found 412.6.

Example 47: 6-[(2,2-Dimethylpyrrolidin-1-yl)methyl]-5-methyl-N-[2-(3-methylpyridin-2-yl)-[1,3]thiazolo[5,4-c]pyridin-6-yl]pyridin-2-amine

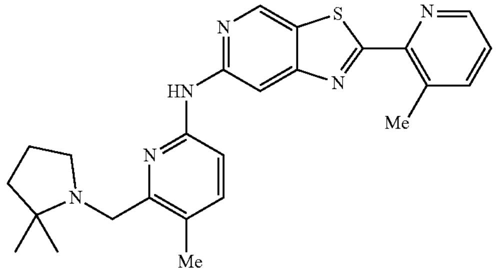 [SMILES: Cc1ccc(Nc2cc3nc(-c4ncccc4C)sc3cn2)nc1CN1CCCC1(C)C]

The title compound was synthesized in a similar fashion to example 41 from the appropriate starting materials. $^1H$ NMR (400 MHz, DMSO-$d_6$) δ 9.63 (s, 1H), 8.96 (s, 1H), 8.89 (s, 1H), 8.62-8.55 (m, 1H), 7.91-7.84 (m, 1H), 7.51 (dd, J=7.8, 4.6 Hz, 1H), 7.37 (d, J=8.3 Hz, 1H), 7.18 (d, J=8.2 Hz, 1H), 3.58 (m, 2H), 2.84 (s, 3H), 2.68 (m, 2H), 2.25 (s, 3H), 1.61 (m, 4H), 1.10 (s, 6H). ESI MS $[M+H]^+$ for $C_{25}H_{28}N_6S$, calcd 445.2, found 445.2.

Example 48: [(2S)-1-[(3-Methyl-6-{[2-(3-methylpyridin-2-yl)-[1,3]thiazolo[5,4-c]pyridin-6-yl]amino}pyridin-2-yl)methyl]pyrrolidin-2-yl]methanol

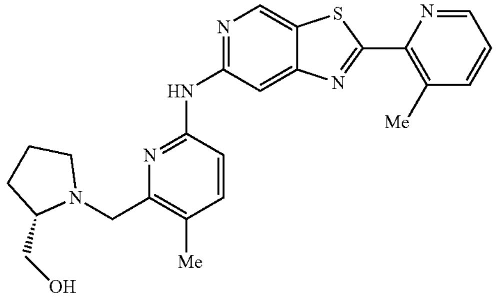 [SMILES: Cc1ccc(Nc2cc3nc(-c4ncccc4C)sc3cn2)nc1CN1CCC[C@H]1CO]

The title compound was synthesized in a similar fashion to example 41 from the appropriate starting materials. $^1H$ NMR (400 MHz, DMSO-$d_6$) δ 9.78 (s, 1H), 9.00 (s, 1H), 8.66-8.42 (m, 2H), 7.95-7.85 (m, 1H), 7.55-7.45 (m, 2H), 7.35 (s, 1H), 5.44 (m, 1H), 4.51 (m, 1H), 3.98-3.47 (m, 4H), 2.85 (s, 3H), 2.24 (s, 3H), 2.14-1.54 (m, 5H). ESI MS $[M+H]^+$ for $C_{24}H_{26}N_6OS$, calcd 447.2, found 447.2.

Example 49: [(2R)-1-[(3-Methyl-6-{[2-(3-methylpyridin-2-yl)-[1,3]thiazolo[5,4-c]pyridin-6-yl]amino}pyridin-2-yl)methyl]pyrrolidin-2-yl]methanol

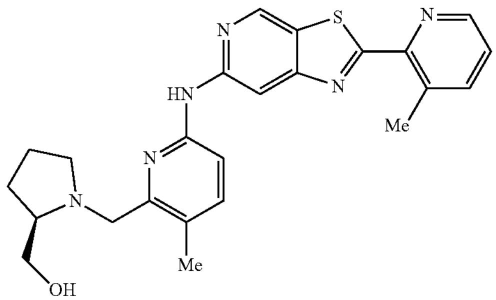 [SMILES: Cc1ccc(Nc2cc3nc(-c4ncccc4C)sc3cn2)nc1CN1CCC[C@@H]1CO]

The title compound was synthesized in a similar fashion to example 41 from the appropriate starting materials. $^1$H NMR (400 MHz, DMSO-$d_6$) δ 9.66 (s, 1H), 8.97 (s, 1H), 8.73 (s, 1H), 8.62-8.56 (m, 1H), 7.93-7.85 (m, 1H), 7.51 (dd, J=7.8, 4.6 Hz, 1H), 7.41 (s, 1H), 7.26 (d, J=8.2 Hz, 1H), 4.27 (d, J=83.6 Hz, 2H), 3.50 (m, 3H), 2.94 (m, 1H), 2.85 (s, 3H), 2.43-2.26 (m, 1H), 2.24 (s, 3H), 1.64 (m, 4H). ESI MS $[M+H]^+$ for $C_{24}H_{26}N_6OS$, calcd 447.2, found 447.2.

Example 50: 5-Methyl-N-{2-[3-(propan-2-yl)pyridin-2-yl]-[1,3]thiazolo[5,4-c]pyridin-6-yl}-6-[(pyrrolidin-1-yl)methyl]pyridin-2-amine

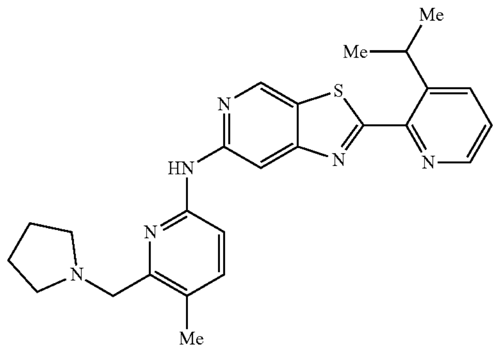 [SMILES: Cc1ccc(Nc2cc3nc(-c4ncccc4C(C)C)sc3cn2)nc1CN1CCCC1]

The title compound was synthesized in a similar fashion to example 41 from the appropriate starting materials. $^1$H NMR (400 MHz, DMSO-$d_6$) δ 9.82 (s, 1H), 9.01 (d, J=0.8 Hz, 1H), 8.58 (dd, J=4.5, 1.5 Hz, 1H), 8.54 (s, 1H), 8.07 (dd, J=8.1, 1.6 Hz, 1H), 7.68 (dd, J=8.1, 4.5 Hz, 1H 1H), 7.51 (d, J=8.4 Hz, 1H), 7.30 (d, J=8.4 Hz, 1H), 4.75 (p, J=6.8 Hz, 1H), 4.38 (s, 2H), 3.48-3.33 (m, 4H), 2.21 (s, 3H), 2.06-1.98 (m, 4H), 1.27 (d, J=6.8 Hz, 6H). ESI MS $[M+H]^+$ for $C_{25}H_{28}N_6S$, calcd 445.2, found 445.1.

Example 51: 5-Methyl-N-[2-(1-methyl-1H-pyrazol-4-yl)-[1,3]thiazolo[5,4-c]pyridin-6-yl]-6-[(pyrrolidin-1-yl)methyl]pyridin-2-amine

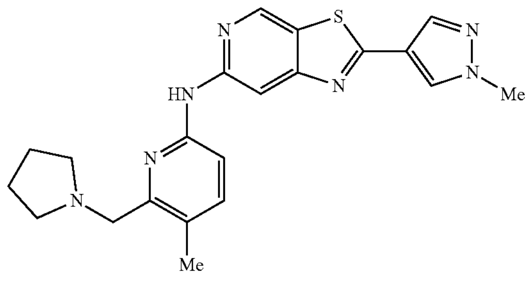 [SMILES: Cc1ccc(Nc2cc3nc(-c4cnn(C)c4)sc3cn2)nc1CN1CCCC1]

The title compound was synthesized in a similar fashion to example 41 from the appropriate starting materials. $^1$H NMR (400 MHz, DMSO-$d_6$) δ 9.69 (s, 1H), 8.88 (s, 1H), 8.56 (s, 1H), 8.19 (s, 1H), 8.09 (s, 1H), 7.53-7.45 (m, 2H), 4.37-4.25 (m, 2H), 3.91 (s, 3H), 3.28-3.15 (m, 4H), 2.19 (s, 3H), 1.95 (bs, 4H). ESI MS $[M+H]^+$ for $C_{21}H_{23}N_7S$, calcd 406.2, found 406.1.

Example 52: N-[2-(3-Methylpyridin-2-yl)-[1,3]thiazolo[5,4-c]pyridin-6-yl]-6-[(pyrrolidin-1-yl)methyl]pyridin-2-amine

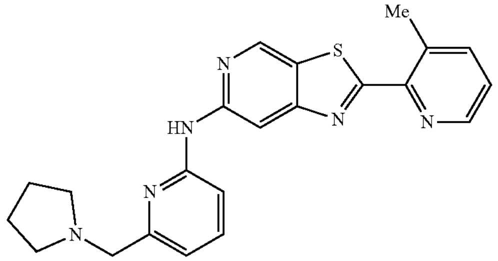 [SMILES: Cc1cccnc1-c1nc2cc(Nc3cccc(CN4CCCC4)n3)ncc2s1]

The title compound was synthesized in a similar fashion to example 41 from the appropriate starting materials. $^1$H NMR (400 MHz, Deuterium Oxide) δ 8.84 (s, 1H), 8.03 (m, 1H), 7.56-7.45 (m, 2H), 7.32 (s, 1H), 7.12 (dd, J=7.9, 4.6 Hz, 1H), 6.98 (d, J=7.4 Hz, 1H), 6.67 (d, J=8.5 Hz, 1H), 4.35 (s, 2H), 3.47-3.01 (m, 4H), 2.10-1.84 (m, 4H). ESI MS $[M+H]^+$ for $C_{22}H_{22}N_6S$, calcd 403.2, found 403.1.

Example 53: 5-Methyl-N-[2-(pyridin-3-yl)-[1,3]thiazolo[5,4-c]pyridin-6-yl]-6-[(pyrrolidin-1-yl)methyl]pyridin-2-amine

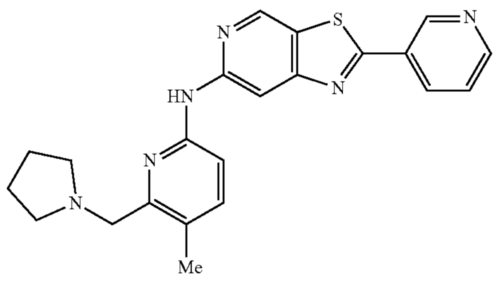 [SMILES: Cc1ccc(Nc2cc3nc(-c4cccnc4)sc3cn2)nc1CN1CCCC1]

The title compound was synthesized in a similar fashion to example 41 from the appropriate starting materials. $^1$H NMR (400 MHz, Chloroform-d) δ 9.33 (dd, J=2.3, 0.9 Hz, 1H), 8.82 (d, J=0.9 Hz, 1H), 8.77 (dd, J=4.8, 1.6 Hz, 1H), 8.40 (ddd, J=8.0, 2.3, 1.7 Hz, 1H), 8.33 (d, J=0.9 Hz, 1H), 7.47 (ddt, J=8.4, 4.4, 2.2 Hz, 2H), 7.39 (dd, J=8.2, 0.7 Hz, 1H), 7.30-7.22 (m, 1H), 3.76 (s, 2H), 2.69 (s, 4H), 2.32 (s, 3H), 1.85 (p, J=3.1 Hz, 4H). ESI MS $[M+H]^+$ for $C_{22}H_{22}N_6S$, calcd 403.2, found 403.2.

Example 54: 6 (3R)-1-[(3-Methyl-6-{[2-(3-methylpyridin-2-yl)-[1,3]thiazolo[5,4-c]pyridin-6-yl]amino}pyridin-2-yl)methyl]pyrrolidine-3-carbonitrile

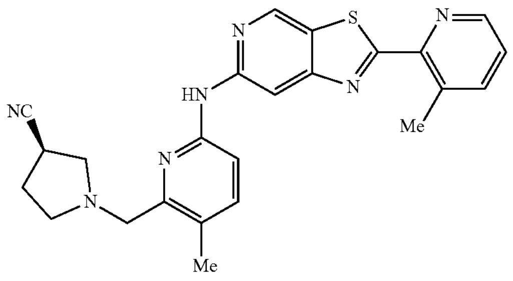 [SMILES: Cc1ccc(Nc2cc3nc(-c4ncccc4C)sc3cn2)nc1CN1CC[C@@H](C#N)C1]

The title compound was synthesized in a similar fashion to example 41 from the appropriate starting materials. $^1$H NMR (400 MHz, DMSO-$d_6$) δ 9.75 (s, 1H), 9.00 (d, J=0.9 Hz, 1H), 8.70 (d, J=0.9 Hz, 1H), 8.63-8.61 (m, 1H), 7.94-7.92 (m, 1H), 7.54 (dd, J=7.7, 4.6 Hz, 1H), 7.45 (d, J=8.3 Hz, 1H), 7.34 (d, J=8.3 Hz, 1H), 3.77 (d, J=13.1 Hz, 1H), 3.69 (d, J=13.2 Hz, 1H), 3.35-3.29 (dm, 2H), 3.02 (dd, J=9.3, 7.8 Hz, 1H), 2.76-2.70 (s, 3H), 2.78 (m, 3H), 2.26 (s, 3H), 2.04-1.97 (m, 1H). ESI MS $[M+H]^+$ for $C_{24}H_{23}N_7S$, calcd 442.2, found 442.1.

Example 55: 5-Methyl-N-[2-(pyrimidin-2-yl)-[1,3]thiazolo[5,4-c]pyridin-6-yl]-6-[(pyrrolidin-1-yl)methyl]pyridin-2-amine

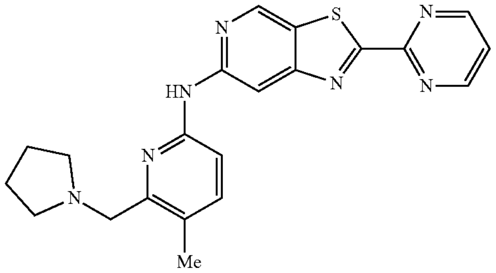 [SMILES: Cc1ccc(Nc2cc3nc(-c4ncccn4)sc3cn2)nc1CN1CCCC1]

The title compound was synthesized in a similar fashion to example 41 from the appropriate starting materials. $^1$H NMR (400 MHz, DMSO-$d_6$) δ 9.74 (s, 1H), 9.07-9.01 (m, 2H), 8.85 (s, 1H), 7.70 (t, J=4.9 Hz, 1H), 7.41 (d, J=8.2 Hz, 1H), 7.22 (d, J=8.3 Hz, 1H), 3.68 (s, 2H), 2.57-2.49 (m, 4H), 2.25 (s, 3H), 1.72-1.62 (m, 4H). ESI MS $[M+H]^+$ for $C_{21}H_{21}N_7S$, calcd 404.2, found 404.1.

Example 56: 5-Methyl-N-[2-(pyrazin-2-yl)-[1,3]thiazolo[5,4-c]pyridin-6-yl]-6-[(pyrrolidin-1-yl)methyl]pyridin-2-amine

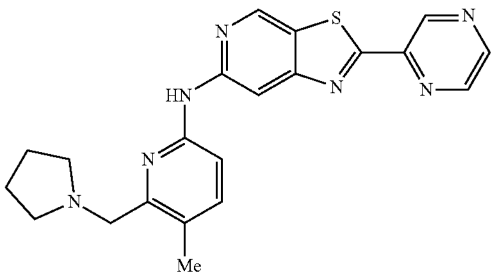 [SMILES: Cc1ccc(Nc2cc3nc(-c4cnccn4)sc3cn2)nc1CN1CCCC1]

The title compound was synthesized in a similar fashion to example 41 from the appropriate starting materials. $^1$H NMR (400 MHz, DMSO-$d_6$) δ 9.74 (s, 1H), 9.49 (d, J=1.5 Hz, 1H), 9.04 (d, J=0.9 Hz, 1H), 8.87 (d, J=2.5 Hz, 1H), 8.83 (dd, J=2.5, 1.5 Hz, 1H), 8.79 (d, J=0.9 Hz, 1H), 7.41 (d, J=8.3 Hz, 1H), 7.29 (d, J=8.3 Hz, 1H), 3.68 (s, 2H), 2.57-2.51 (m, 4H), 2.24 (s, 3H), 1.75-1.69 (m, 4H). ESI MS $[M+H]^+$ for $C_{21}H_{21}N_7S$, calcd 404.2, found 404.1.

Example 57: 5-Methyl-N-[2-(pyridazin-4-yl)-[1,3]thiazolo[5,4-c]pyridin-6-yl]-6-[(pyrrolidin-1-yl)methyl]pyridin-2-amine

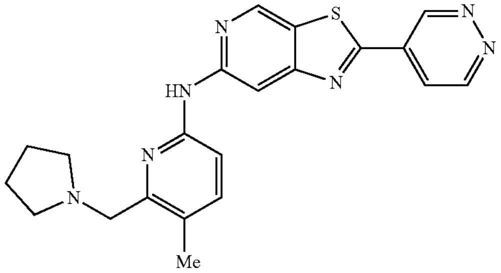 [SMILES: Cc1ccc(Nc2cc3nc(-c4ccnnc4)sc3cn2)nc1CN1CCCC1]

The title compound was synthesized in a similar fashion to example 41 from the appropriate starting materials. $^1$H NMR (400 MHz, DMSO-$d_6$) δ 9.85 (dd, J=2.4, 1.2 Hz, 1H), 9.81 (s, 1H), 9.48 (dd, J=5.4, 1.2 Hz, 1H), 9.11 (d, J=0.9 Hz, 1H), 8.76 (s, 1H), 8.30 (dd, J=5.4, 2.4 Hz, 1H), 7.45 (d, J=8.3 Hz, 1H), 7.29 (d, J=8.3 Hz, 1H), 3.85 (s, 2H), 2.74 (bs, 4H), 2.23 (s, 3H), 1.79 (bs, 4H). ESI MS $[M+H]^+$ for $C_{21}H_{21}N_7S$, calcd 404.2, found 404.2.

Example 58: 5-Methyl-N-[2-(pyrimidin-5-yl)-[1,3]thiazolo[5,4-c]pyridin-6-yl]-6-[(pyrrolidin-1-yl)methyl]pyridin-2-amine

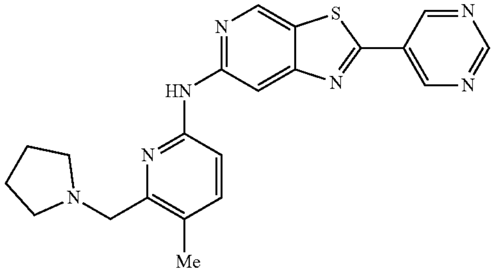 [SMILES: Cc1ccc(Nc2cc3nc(-c4cncnc4)sc3cn2)nc1CN1CCCC1]

The title compound was synthesized in a similar fashion to example 41 from the appropriate starting materials. $^1$H NMR (400 MHz, DMSO-$d_6$) δ 9.83 (s, 1H), 9.46 (s, 1H), 9.39 (s, 1H), 9.10 (d, J=0.9 Hz, 1H), 8.50 (s, 1H), 7.52 (d, J=8.4 Hz, 1H), 7.41 (d, J=8.4 Hz, 1H), 4.28 (s, 2H), 3.09 (bs, 4H), 2.21 (s, 3H), 1.95 (bs, 4H). ESI MS $[M+H]^+$ for $C_{21}H_{21}N_7S$, calcd 404.2, found 404.2.

Example 59: N-[2-(3-Methylpyridin-2-yl)-[1,3]thiazolo[5,4-c]pyridin-6-yl]-6-[(pyrrolidin-1-yl)methyl]-5-(trifluoromethyl)pyridin-2-amine

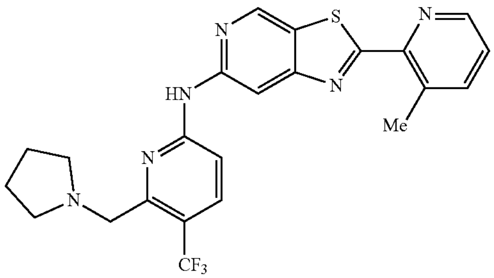 [SMILES: Cc1cccnc1-c1nc2cc(Nc3ccc(C(F)(F)F)c(CN4CCCC4)n3)ncc2s1]

The title compound was synthesized in a similar fashion to example 41 from the appropriate starting materials. $^1$H NMR (400 MHz, Chloroform-d) δ 8.89 (d, J=0.9 Hz, 1H), 8.58-8.50 (m, 1H), 8.33 (s, 1H), 7.80 (d, J=8.7 Hz, 1H), 7.71 (s, 1H), 7.68 (ddd, J=7.8, 1.7, 0.9 Hz, 1H), 7.43 (d, J=8.8 Hz, 1H), 7.32 (dd, J=7.8, 4.6 Hz, 1H), 3.93 (s, 2H), 2.92 (s, 3H), 2.75 (p, J=3.3 Hz, 4H), 1.89 (p, J=3.4 Hz, 4H). ESI MS $[M+H]^+$ for $C_{23}H_{21}F_3N_6S$, calcd 471.2, found 471.7.

Example 60: N-{5-Chloro-6-[(pyrrolidin-1-yl)methyl]pyridin-2-yl}-2-(3-methylpyridin-2-yl)-1,3-benzothiazol-5-amine

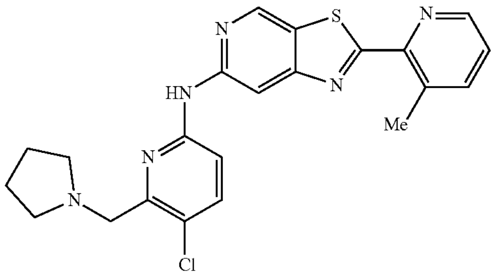 [SMILES: Cc1cccnc1-c1nc2cc(Nc3ccc(Cl)c(CN4CCCC4)n3)ncc2s1]

The title compound was synthesized in a similar fashion to example 41 from the appropriate starting materials. $^1H$ NMR (400 MHz, DMSO-$d_6$) δ 10.03 (s, 1H), 9.00 (d, J=0.9 Hz, 1H), 8.82 (d, J=0.9 Hz, 1H), 8.58 (ddd, J=4.7, 1.6, 0.7 Hz, 1H), 7.88 (ddd, J=7.7, 1.6, 0.8 Hz, 1H), 7.67 (d, J=8.8 Hz, 1H), 7.51 (dd, J=7.8, 4.6 Hz, 1H), 7.33 (d, J=8.8 Hz, 1H), 3.78 (bs, 2H), 2.84 (s, 3H) 2.64-2.62 (m, 4H), 1.78-1.75 (m, 4H). ESI MS $[M+H]^+$ for $C_{22}H_{21}N_6SCl$, calcd 437.1, found 437.2.

Example 61: 5-Fluoro-N-[2-(3-methylpyridin-2-yl)-[1,3]thiazolo[5,4-c]pyridin-6-yl]-6-[(pyrrolidin-1-yl)methyl]pyridin-2-amine

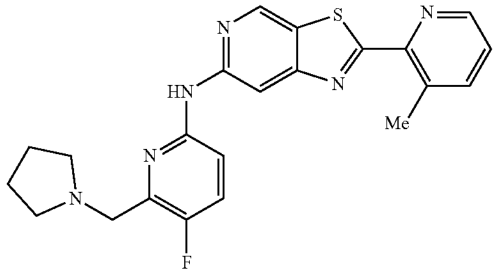 [SMILES: Cc1cccnc1-c1nc2cc(Nc3ccc(F)c(CN4CCCC4)n3)ncc2s1]

The title compound was synthesized in a similar fashion to example 41 from the appropriate starting materials. $^1H$ NMR (400 MHz, DMSO-$d_6$) δ 9.91 (s, 1H), 8.98 (d, J=0.9 Hz, 1H), 8.61 (d, J=0.9 Hz, 1H), 8.58 (ddd, J=4.7, 1.6, 0.7 Hz, 1H), 7.88 (ddd, J=7.8, 1.7, 0.8 Hz, 1H), 7.56 (t, J=9.1 Hz, 1H), 7.51 (dd, J=7.7, 4.6 Hz, 1H), 7.45 (dd, J=9.0, 3.2 Hz, 1H), 3.72 (s, 2H), 2.60 (s, 5H), 1.73-1.70 (m, 4H). ESI MS $[M+H]^+$ for $C_{22}H_{21}N_6SF$, calcd 421.2, found 421.2.

Example 62: 5-Methyl-N-[2-(3-methylpyridin-2-yl)-[1,3]thiazolo[5,4-c]pyridin-6-yl]-6-[2-(pyrrolidin-1-yl)ethyl]pyridin-2-amine

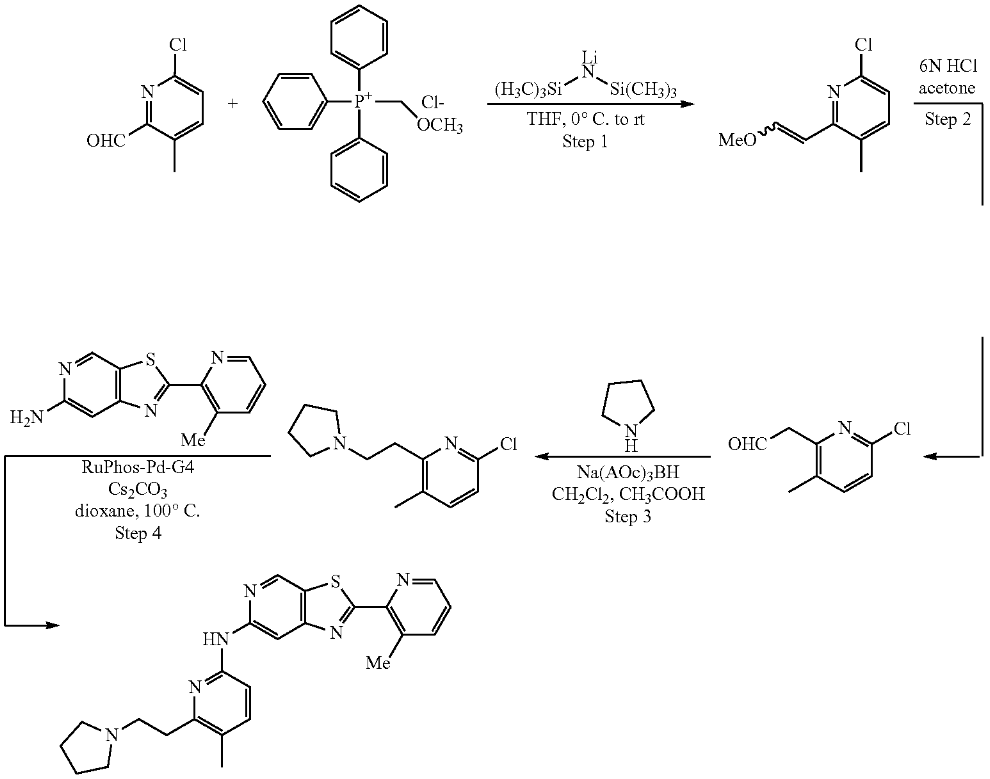

Step 1: Methoxymethyl-triphenylphosphonium chloride (2.77 g, 8.1 mmol) was suspended in tetrahydrofuran (20 mL) under a nitrogen atmosphere, and Lithium hexamethyldisilazane tetrahydrofuran solution (35 mL, 10.5 mmol) was added dropwise thereto at 0° C. and then the mixture was stirred for 10 min. A THE solution (3 mL) of the 6-Chloro-3-methylpicolinaldehyde (1.26 g, 8.1 mmol) was added dropwise to the suspension, and the mixture was warmed to room temperature and stirred for 10 h. Saturated aqueous ammonium chloride solution (3 mL) was added to the reaction mixture, followed by concentration under reduced pressure. The residue was diluted with water and ethyl acetate for separation into phases. The aqueous layer was extracted with ethyl acetate. The combined organic layers were dried over $Na_2SO_4$ and concentrated, and the residue was purified by silica gel column chromatography (gradient: 0% to 40% EtOAc in hexanes) to afford the desired compound (1.36 g, 92%).

Step 2: The product obtained from step 1 (1.2 g, 6.6 mmol) was dissolved in acetone (30 mL), and 15 mL of 6 N HCl was added thereto, followed by stirring at room temperature for 5 hr. To the reaction mixture was added saturated sodium hydrogen carbonate to adjust the pH to 4. Ethyl acetate was added thereto for separation into phases. The combined organic layer was filtered through a phase separator and then, the filtrate was concentrated, and the residue was purified by silica gel column chromatography (gradient: 0% to 30% EtOAc in hexanes) to afford the desired compound (110 mg, 10%).

Step 3: This step was performed in a similar fashion to step 5 of example 1 using the appropriate starting materials.

Step 4: This step was performed in a similar fashion to step 6 of example 1. $^1H$ NMR (400 MHz, Chloroform-d) δ 8.82 (d, J=0.9 Hz, 1H), 8.68 (d, J=0.9 Hz, 1H), 8.55 (ddd, J=4.6, 1.6, 0.7 Hz, 1H), 7.67 (ddd, J=7.7, 1.7, 0.8 Hz, 1H), 7.34-7.30 (m, 2H), 7.29 (s, 1H), 6.87 (d, J=8.2 Hz, 1H), 3.01 (s, 4H), 2.92 (s, 3H), 2.70-2.66 (m, 4H), 2.25 (s, 3H), 1.88-1.80 (m, 4H). ESI MS $[M+H]^+$ for $C_{24}H_{26}N_6S$, calcd 431.2, found 431.7.

Example 63: N-[2-(3-Methylpyridin-2-yl)-[1,3]thiazolo[5,4-c]pyridin-6-yl]-5-(morpholin-4-yl)-6-[(pyrrolidin-1-yl)methyl]pyridin-2-amine

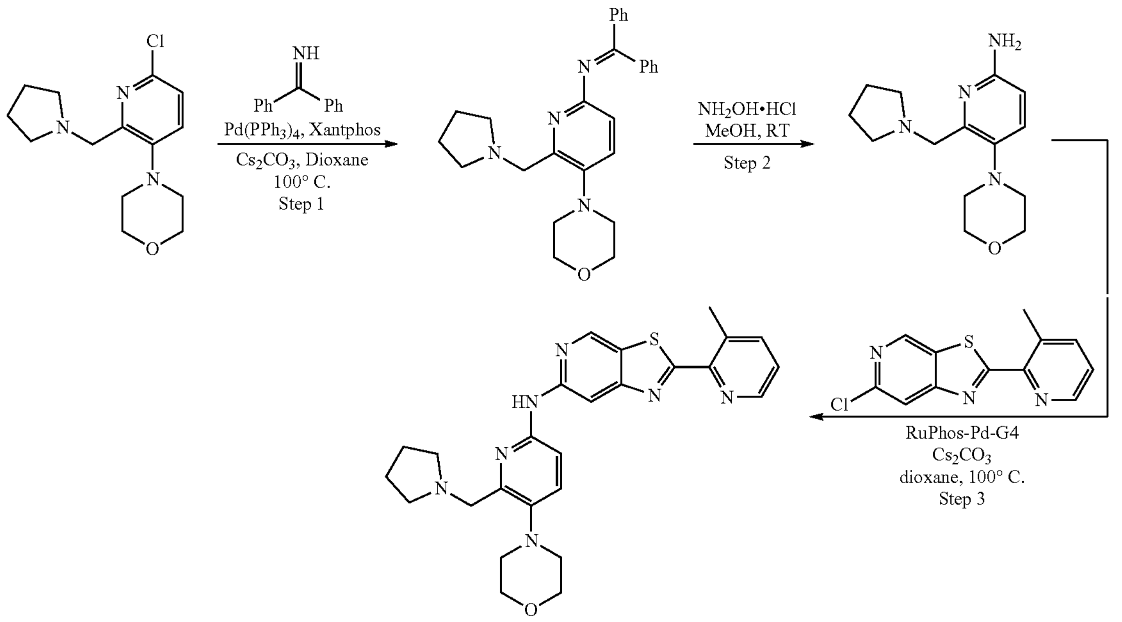 [SMILES: Clc1ccc(N2CCOCC2)c(CN2CCCC2)n1 ; N=C(c1ccccc1)c1ccccc1 ; c1ccc(C(=Nc2ccc(N3CCOCC3)c(CN3CCCC3)n2)c2ccccc2)cc1 ; Nc1ccc(N2CCOCC2)c(CN2CCCC2)n1 ; Cc1cccnc1-c1nc2cc(Nc3ccc(N4CCOCC4)c(CN4CCCC4)n3)ncc2s1 ; Cc1cccnc1-c1nc2cc(Cl)ncc2s1]

Step 1: To a stirred solution of pyridine derivative (700 mg, 2.48 mmol) (prepared in a manner similar to that described for steps 4 and 5 of example 1 using the appropriate starting materials) and benzophenone imine (497 mg, 2.75 mmol) in dioxane (9 ml) was added $Pd_2(dba)_3$ (250 mg, 0.275 mmol), Xantphos (320 mg, 0.55 mmol) and $Cs_2CO_3$ (2.68 g, 8.25 mmol). The reaction mixture was heated to 100° C. and stirred for 12 h. The reaction mixture was then filtered through sintered glass and the filtrate was concentrated in vacuo. The resulting residue a was purified by flash column chromatography (silica gel; gradient: 0% to 30% MeOH in $CH_2Cl_2$) to get desired compound (814 mg, 77%).

Step 2: To a stirred solution of imine intermediate from step 1 (800 mg, 1.9 mmol) in methanol (50 ml) were added sodium acetate (425 mg, 5 mmol) and hydroxylamine hydrochloride (280 mg, 4 mmol). The reaction mixture was stirred at room temperature for 1 h. The reaction mixture was then filtered through sintered glass and the filtrate was concentrated in vacuo. The resulting residue a was purified by flash column chromatography (silica gel; gradient: 0% to 30% MeOH in $CH_2Cl_2$) to get desired compound (430 mg, 86%).

Step 3: The target compound was synthesized in a similar fashion using step 6 of example 1. $^1H$ NMR (400 MHz, Chloroform-d) δ 8.83 (d, J=0.9 Hz, 1H), 8.54 (ddd, J=4.7, 1.6, 0.7 Hz, 1H), 8.28 (d, J=0.9 Hz, 1H), 7.66 (ddd, J=7.8, 1.7, 0.8 Hz, 1H), 7.41 (d, J=8.7 Hz, 1H), 7.32-7.39 (m, 2H), 3.87 (s, 2H), 3.86-3.81 (m, 4H), 2.94-2.89 (m, 4H), 2.90 (s, 3H), 2.74-2.68 (m, 4H), 1.82 (t, J=3.6 Hz, 4H). ESI MS $[M+H]^+$ for $C_{26}H_{29}N_7OS$, calcd 488.2, found 488.7.

Example 64: N-[2-(3-Methylpyridin-2-yl)-[1,3]thiazolo[5,4-c]pyridin-6-yl]-5-(morpholin-4-yl)-6-[(piperidin-1-yl)methyl]pyridin-2-amine

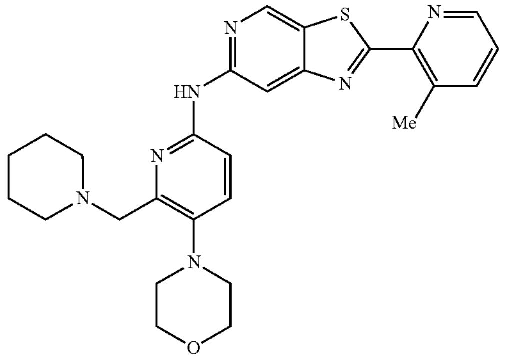 [SMILES: Cc1cccnc1-c1nc2cc(Nc3ccc(N4CCOCC4)c(CN4CCCCC4)n3)ncc2s1]

The title compound was synthesized in a similar fashion to example 63 from the appropriate starting materials. $^1H$ NMR (400 MHz, DMSO-$d_6$) δ 9.75 (s, 1H), 8.99 (d, J=0.9 Hz, 1H), 8.81 (d, J=0.9 Hz, 1H), 8.59 (dd, J=4.7, 1.5 Hz, 1H), 7.90-7.87 (m, 1H), 7.52 (s, 1H), 6.57 (s, 1H), 6.03 (d, J=1.1 Hz, 1H), 4.93 (dt, J=10.1, 5.6 Hz, 2H), 3.20 (d, J=11.8 Hz, 2H), 2.85-2.81 (m, 4H), 2.53 (d, J=10.9 Hz, 2H), 2.40-2.36 (m, 2H), 2.30-2.26 (m, 1H), 2.16 (s, 3H), 1.74 (d, J=18.7 Hz, 2H), 1.50-1.41 (m, 4H). ESI MS $[M+H]^+$ for $C_{27}H_{31}N_7SO$, calcd 502.2, found 502.2.

Example 65: [(2S,4S)-4-Amino-1-(3-methyl-6-{[2-(3-methylpyridin-2-yl)-[1,3]thiazolo[5,4-c]pyridin-6-yl]amino}pyridin-2-yl)pyrrolidin-2-yl]methanol Step 1: A heterogenous mixture of tert-Butyl (3S,5S)-5-(hydroxymethyl)-3-pyrrolidinylcarbamate (532 mg, 2 mmol), 6-Bromo-2-fluoro-3-methylpyridine (380 mg, 2 mmol), K2CO3 (552 mg, 4 mmol), and DMF (4 mL) was heated at 70° C. for 12 h. The reaction was cooled to room temperature, diluted with water, and extracted with EtOAc. The organic extract was concentrated, and the residue was purified by column chromatography (silica gel; gradient: 0% to 10% MeOH in $CH_2Cl_2$) to obtain the desired aminopyridine derivative (308 mg, 40%).

Step 2: To a solution of aminopyridine intermediate obtained from step 1 (154 mg, 0.4 mmol) and amino azabenzothiazole derivative (104 mg, 0.4 mmol) in Dioxane (5 mL) was added RuPhos PdG4 (34 mg, 0.04 mmol) and $Cs_2CO_3$ (390 mg 1.2 mmol). After degassing for 25 min under $N_2$ atmosphere, the reaction mixture was heated to 100° C. and stirred for 12 h. The reaction mixture filtered through Celite® and concentrated under reduced pressure. The resulting residue a was purified by flash column chromatography (silica gel; gradient: 0% to 30% MeOH in $CH_2Cl_2$) to get desired compound in (135 mg, 62%).

Step 3. To the intermediate obtained from step 2 (100 mg, 0.18 mmol) was added TFA (3 mL) dropwise at room temperature. The reaction was stirred for 1 h and then concentrated under reduced pressure. The crude material was purified by reverse phase preparative HPLC to afford the desired compound (71 mg, 89%). $^1H$ NMR (400 MHz, Chloroform-d) δ 8.80 (d, J=0.9 Hz, 1H), 8.64 (d, J=0.9 Hz, 1H), 8.54 (ddd, J=4.6, 1.6, 0.7 Hz, 1H), 7.66 (ddd, J=7.8, 1.7, 0.8 Hz, 1H), 7.31 (dd, J=7.7, 4.6 Hz, 1H), 7.24-4.23 (m, 1H), 7.17 (s, 1H), 6.41 (d, J=7.9 Hz, 1H), 4.84-4.71 (m, 1H), 3.94 (d, J=11.2 Hz, 1H), 3.76 (dd, J=11.2, 5.1 Hz, 1H), 3.66-3.29 (m, 4H), 2.87 (s, 3H), 2.47 (dd, J=12.6, 6.4 Hz, 1H), 2.33 ($s_{br}$, 2H), 2.22 (s, 3H), 1.80-1.72 (m, 1H). ESI MS $[M+H]^+$ for $C_{23}H_{25}N_7OS$, calcd 448.2, found 448.8.

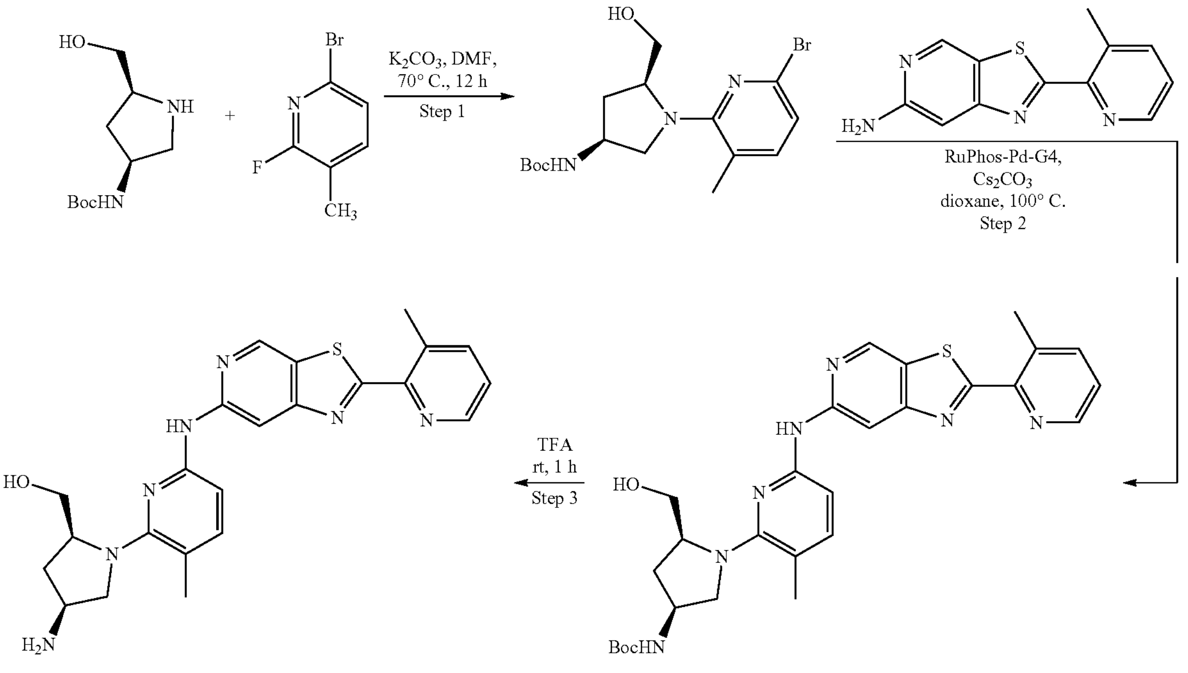

Example 66: [(2S,4S)-4-Amino-1-(6-{[2-(3-methylpyridin-2-yl)-[1,3]thiazolo[5,4-c]pyridin-6-yl]amino}pyridin-2-yl)pyrrolidin-2-yl]methanol

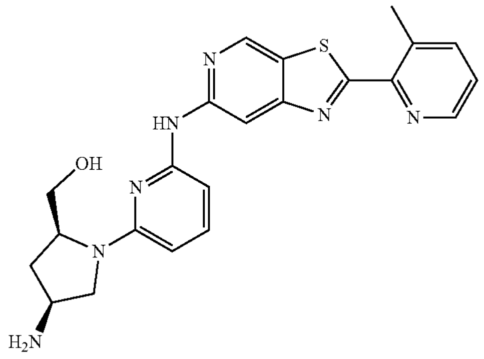 [SMILES: Cc1cccnc1-c1nc2cc(Nc3cccc(N4C[C@@H](N)C[C@H]4CO)n3)ncc2s1]

The title compound was synthesized in a similar fashion to example 65 from the appropriate starting materials. $^1$H NMR (400 MHz, Chloroform-d) δ 8.80 (d, J=0.9 Hz, 1H), 8.64 (d, J=0.9 Hz, 1H), 8.56-8.51 (m, 1H), 7.66 (ddd, J=7.6, 1.6, 0.8 Hz, 1H), 7.38 (d, J=7.9 Hz, 1H), 7.30 (dd, J=7.7, 4.6 Hz, 1H), 7.23 (s, 1H), 6.34 (d, J=7.8 Hz, 1H), 5.93 (d, J=8.1 Hz, 1H), 4.57-4.48 (m, 1H), 4.27 (dd, J=11.2, 3.5 Hz, 1H), 3.91-3.76 (m, 2H), 3.59 (dd, J=10.6, 5.6 Hz, 1H), 3.39 (d, J=10.6 Hz, 1H), 2.89 (s, 3H), 2.45 (ddd, J=13.4, 9.6, 5.7 Hz, 1H), 1.85 (d, J=13.3 Hz, 1H). ESI MS $[M+H]^+$ for $C_{22}H_{23}N_7OS$, calcd 434.2, found 434.3.

Example 67: [(2R,4R)-4-Amino-1-(3-methyl-6-{[2-(3-methylpyridin-2-yl)-[1,3]thiazolo[5,4-c]pyridin-6-yl]amino}pyridin-2-yl)pyrrolidin-2-yl]methanol

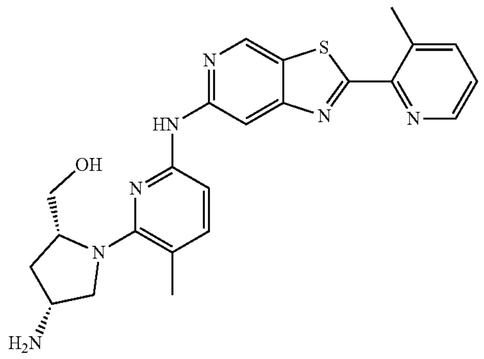 [SMILES: Cc1cccnc1-c1nc2cc(Nc3ccc(C)c(N4C[C@H](N)C[C@@H]4CO)n3)ncc2s1]

The title compound was synthesized in a similar fashion to example 65 from the appropriate starting materials. $^1$H NMR (400 MHz, Chloroform-d) δ 8.80 (d, J=0.9 Hz, 1H), 8.64 (d, J=0.9 Hz, 1H), 8.54 (ddd, J=4.6, 1.6, 0.7 Hz, 1H), 7.66 (ddd, J=7.8, 1.7, 0.8 Hz, 1H), 7.31 (dd, J=7.7, 4.6 Hz, 1H), 7.26 (d, J=7.7, 1H), 7.17 (s, 1H), 6.41 (d, J=7.9 Hz, 1H), 4.85-4.72 (m, 1H), 3.94 (d, J=11.1 Hz, 1H), 3.76 (dd, J=11.2, 5.1 Hz, 1H), 3.66-3.38 (m, 4H), 2.87 (s, 3H), 2.48 (dt, J=12.8, 6.6 Hz, 1H), 2.33 (d, J=37.0 Hz, 2H), 2.22 (s, 3H), 1.76 (dt, J=12.5, 7.8 Hz, 1H). ESI MS $[M+H]^+$ for $C_{23}H_{25}N_7OS$, calcd 448.2, found 448.5.

Example 68: [(4S)-4-Amino-1-(3-methyl-6-{[2-(3-methylpyridin-2-yl)-[1,3]thiazolo[5,4-c]pyridin-6-yl]amino}pyridin-2-yl)pyrrolidin-2-yl]methanol

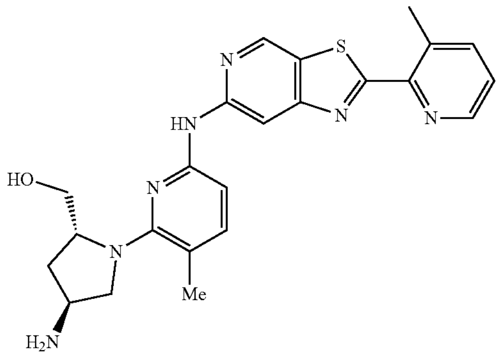 [SMILES: Cc1cccnc1-c1nc2cc(Nc3ccc(C)c(N4C[C@@H](N)C[C@@H]4CO)n3)ncc2s1]

The title compound was synthesized in a similar fashion to example 65 from the appropriate starting materials. $^1$H NMR (400 MHz, Chloroform-d) δ 8.80 (s, 1H), 8.71 (d, J=0.9 Hz, 1H), 8.54 (ddd, J=4.6, 1.7, 0.7 Hz, 1H), 7.66 (ddd, J=7.7, 1.7, 0.8 Hz, 1H), 7.36-7.29 (m, 1H), 7.25 (d, J=7.9 Hz, 1H), 7.19 (s, 1H), 6.40 (d, J=7.9 Hz, 1H), 4.90 (d, J=13.3 Hz, 1H), 4.05-3.91 (m, 2H), 3.71-3.52 (m, 2H), 3.10-3.01 (m, 1H), 2.87 (s, 3H), 2.22 (s, 3H), 2.17-2.05 (m, 1H), 2.04-1.97 (m, 1H). ESI MS $[M+H]^+$ for $C_{23}H_{25}N_7OS$, calcd 448.2, found 448.4.

Example 69: [(2S,4R)-4-Amino-1-(3-methyl-6-{[2-(3-methylpyridin-2-yl)-[1,3]thiazolo[5,4-c]pyridin-6-yl]amino}pyridin-2-yl)pyrrolidin-2-yl]methanol

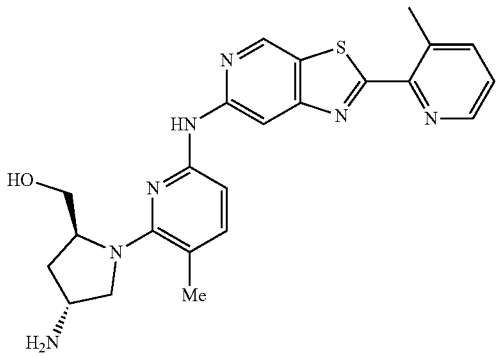 [SMILES: Cc1cccnc1-c1nc2cc(Nc3ccc(C)c(N4C[C@H](N)C[C@H]4CO)n3)ncc2s1]

The title compound was synthesized in a similar fashion to example 65 from the appropriate starting materials. $^1$H NMR (400 MHz, Chloroform-d) δ 8.79 (d, J=1.0 Hz, 1H), 8.69 (d, J=0.9 Hz, 1H), 8.54 (ddd, J=4.6, 1.7, 0.7 Hz, 1H), 7.66 (ddd, J=7.7, 1.7, 0.8 Hz, 1H), 7.31 (dd, J=7.7, 4.6 Hz, 1H), 7.24-7.18 (m, 2H), 6.41 (d, J=7.9 Hz, 1H), 4.87 (p, J=6.7 Hz, 1H), 4.01 (ddd, J=18.6, 10.6, 4.4 Hz, 2H), 3.69-3.59 (m, 2H), 3.07 (d, J=10.1 Hz, 1H), 2.86 (s, 3H), 2.21 (s, 3H), 2.19-1.97 (m, 2H). ESI MS $[M+H]^+$ for $C_{23}H_{25}N_7OS$, calcd 448.2, found 448.6.

Example 70: [(2S,4R)-4-Amino-1-(6-{[2-(3-methylpyridin-2-yl)-[1,3]thiazolo[5,4-c]pyridin-6-yl]amino}pyridin-2-yl)pyrrolidin-2-yl]methanol

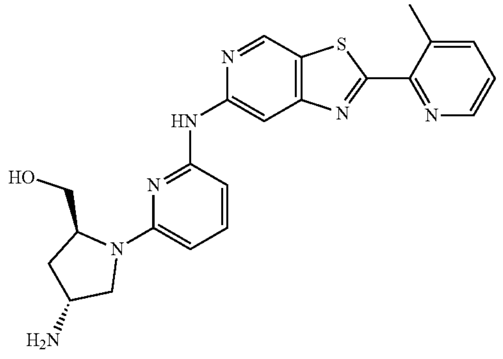 [SMILES: Cc1cccnc1-c1nc2cc(Nc3cccc(N4C[C@H](N)C[C@H]4CO)n3)ncc2s1]

The title compound was synthesized in a similar fashion to example 65 from the appropriate starting materials. $^1$H NMR (400 MHz, Chloroform-d) δ 8.82 (d, J=0.8 Hz, 1H), 8.68 (d, J=0.9 Hz, 1H), 8.57-8.50 (m, 1H), 7.69-7.62 (m, 1H), 7.39 (t, J=8.0 Hz, 1H), 7.30 (dd, J=7.8, 4.6 Hz, 1H), 7.26 (d, J=7.9 Hz, 1H), 6.41 (d, J=7.8 Hz, 1H), 5.92 (d, J=8.1 Hz, 1H), 4.50 (q, J=7.1 Hz, 1H), 4.05 (dd, J=11.0, 5.8 Hz, 1H), 3.82 (p, J=7.0 Hz, 1H), 3.68 (dd, J=9.2, 6.7 Hz, 1H), 3.58 (dt, J=11.0, 6.5 Hz, 1H), 2.96 (t, J=8.5 Hz, 1H), 2.86 (s, 3H), 2.24 (dd, J=12.3, 5.9 Hz, 1H), 1.85 (dt, J=12.4, 8.8 Hz, 1H). ESI MS $[M+H]^+$ for $C_{22}H_{23}N_7OS$, calcd 434.2, found 434.5.

Example 71: 6-[(3S)-3-Aminopiperidin-1-yl]-5-methyl-N-[2-(3-methylpyridin-2-yl)-[1,3]thiazolo[5,4-c]pyridin-6-yl]pyridin-2-amine

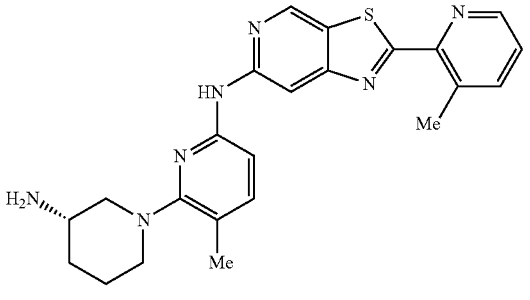 [SMILES: Cc1cccnc1-c1nc2cc(Nc3ccc(C)c(N4CCC[C@H](N)C4)n3)ncc2s1]

The title compound was synthesized in a similar fashion to example 65 from the appropriate starting materials. $^1$H NMR (400 MHz, DMSO-$d_6$) δ 8.78 (d, J=1.0 Hz, 1H), 8.57-8.53 (m, 2H), 7.66-7.61 (m, 1H), 7.53-7.56 (m, 1H), 7.30 (dd, J=7.7, 4.7 Hz, 1H), 7.24 (t, J=4.0 Hz, 2H), 6.75 (d, J=8.0 Hz, 1H), 3.57 (d, J=12.5 Hz, 1H), 3.36-3.31 (m, 1H), 3.24 (b s, 1H), 3.04-3.02 (m, 2H), 2.87 (s, 4H), 2.13 (s, 4H), 1.99-1.93 (d, J=5.2 Hz, OH), 1.86-1.81 (m, 1H), 1.66-1.61 (qd, J=9.0, 4.7 Hz, 1H). ESI MS $[M+H]^+$ for $C_{23}H_{25}N_7S$, calcd 432.2, found 432.1.

Example 72: 6-[(2S)-2-(Aminomethyl)pyrrolidin-1-yl]-5-methyl-N-[2-(3-methylpyridin-2-yl)-[1,3]thiazolo[5,4-c]pyridin-6-yl]pyridin-2-amine

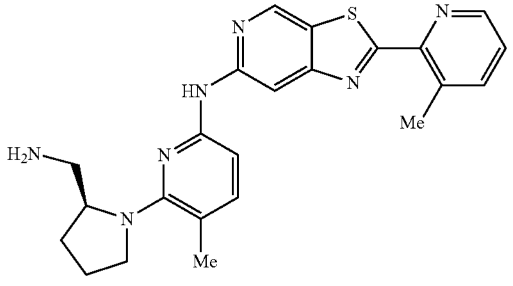 [SMILES: Cc1cccnc1-c1nc2cc(Nc3ccc(C)c(N4CCC[C@H]4CN)n3)ncc2s1]

The title compound was synthesized in a similar fashion to example 65 from the appropriate starting materials. $^1$H NMR (400 MHz, DMSO-$d_6$) δ 8.75 (d, J=0.9 Hz, 1H), 8.59 (s, 1H), 8.54 (dd, J=4.8, 1.6 Hz, 1H), 7.65 (ddd, J=7.7, 1.6, 0.8 Hz, 1H), 7.51 (s, 1H), 7.30 (dd, J=7.7, 4.6 Hz, 1H), 7.15 (d, J=7.9 Hz, 1H), 6.39 (d, J=7.9 Hz, 1H), 4.62-4.57 (t, J=6.3 Hz, 1H), 3.78-3.72 (m, 1H), 3.29-3.24 (m, 1H), 3.20 (dd, J=12.8, 4.4 Hz, 1H), 2.85 (s, 3H), 2.84-2.77 (m, 1H), 2.33 (bs, 2H), 2.27-2.23 (m, 1H), 2.02-1.92 (m, OH), 1.82-1.71 (m, 2H). ESI MS $[M+H]^+$ for $C_{23}H_{25}N_7S$, calcd 432.2, found 432.1.

Example 73: 6-(3-Amino-3-methylpyrrolidin-1-yl)-4-methyl-N-[2-(2-methylpyridin-4-yl)-[1,3]thiazolo[5,4-c]pyridin-6-yl]pyridin-2-amine

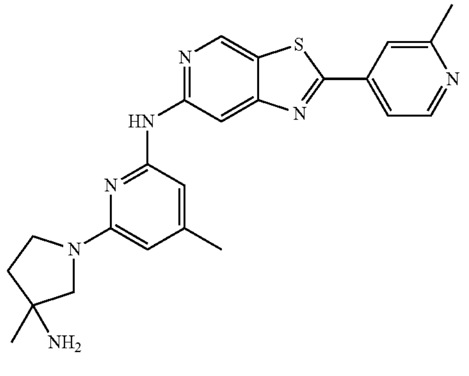 [SMILES: Cc1cc(Nc2cc3nc(-c4ccnc(C)c4)sc3cn2)nc(N2CCC(C)(N)C2)c1]

The title compound was synthesized in a similar fashion to example 65 from the appropriate starting materials. $^1$H NMR (400 MHz, Methanol-$d_4$) δ 8.80 (s, 1H), 8.73 (s, 1H), 8.53 (d, J=5.3 Hz, 1H), 7.85 (s, 1H), 7.80 (d, J=5.3 Hz, 1H), 6.11 (s, 1H), 5.73 (s, 1H), 3.81-3.53 (m, 4H), 2.61 (s, 3H), 2.20 (s, 3H), 1.99 (t, J=7.1 Hz, 2H), 1.38 (s, 3H). ESI MS $[M+H]^+$ for $C_{23}H_{25}N_7S$, calcd 432.2, found 432.2.

Example 74: 6-[(3R)-3-Aminopyrrolidin-1-yl]-5-methyl-N-[2-(3-methylpyridin-2-yl)-[1,3]thiazolo[5,4-c]pyridin-6-yl]pyridin-2-amine

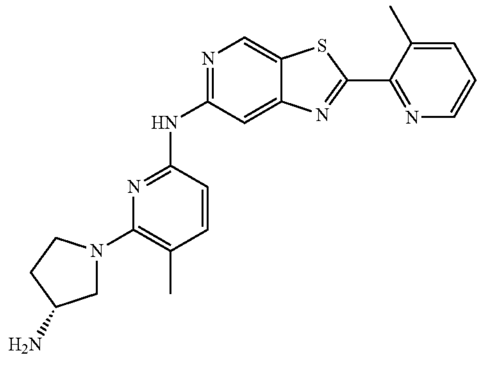 [SMILES: Cc1cccnc1-c1nc2cc(Nc3ccc(C)c(N4CC[C@@H](N)C4)n3)ncc2s1]

The title compound was synthesized in a similar fashion to example 65 from the appropriate starting materials. $^1$H NMR (400 MHz, Methanol-$d_4$) δ 8.83 (d, J=0.9 Hz, 1H), 8.81 (d, J=0.9 Hz, 1H), 8.53 (ddd, J=4.7, 1.6, 0.7 Hz, 1H), 7.82 (dd, J=7.8, 1.6, 0.7 Hz, 1H), 7.43 (dd, J=7.8, 4.7 Hz, 1H), 7.25 (dd, J=7.8, 0.7 Hz, 1H), 6.49 (d, J=7.8 Hz, 1H), 3.87-3.76 (m, 2H), 3.74-3.57 (m, 2H), 3.50-3.42 (m, 1H), 2.89 (s, 3H), 2.29 (s, 3H), 2.28-2.17 (m, 1H), 1.89-1.78 (m, 1H). ESI MS $[M+H]^+$ for $C_{22}H_{23}N_7S$, calcd 418.2, found 418.2.

Example 75: 6-[(3S)-3-Aminopyrrolidin-1-yl]-5-methyl-N-[2-(3-methylpyridin-2-yl)-[1,3]thiazolo[5,4-c]pyridin-6-yl]pyridin-2-amine

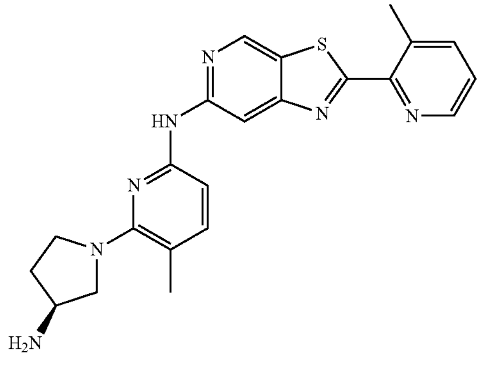 [SMILES: Cc1cccnc1-c1nc2cc(Nc3ccc(C)c(N4CC[C@H](N)C4)n3)ncc2s1]

The title compound was synthesized in a similar fashion to example 65 from the appropriate starting materials. $^1$H NMR (400 MHz, Methanol-$d_4$) δ 8.83 (d, J=0.9 Hz, 1H), 8.81 (d, J=0.9 Hz, 1H), 8.53 (ddd, J=4.7, 1.6, 0.7 Hz, 1H), 7.82 (dd, J=7.8, 1.6, 0.7 Hz, 1H), 7.43 (dd, J=7.8, 4.7 Hz, 1H), 7.25 (dd, J=7.8, 0.7 Hz, 1H), 6.49 (d, J=7.8 Hz, 1H), 3.87-3.76 (m, 2H), 3.74-3.57 (m, 2H), 3.50-3.42 (m, 1H), 2.89 (s, 3H), 2.29 (s, 3H), 2.28-2.17 (m, 1H), 1.89-1.78 (m, 1H). ESI MS $[M+H]^+$ for $C_{22}H_{23}N_7S$, calcd 418.2, found 418.2.

Example 76: 4-Methyl-N2-[(1-methyl-1H-imidazol-2-yl)methyl]-N6-[2-(2-methylpyridin-4-yl)-[1,3]thiazolo[5,4-c]pyridin-6-yl]pyridine-2,6-diamine

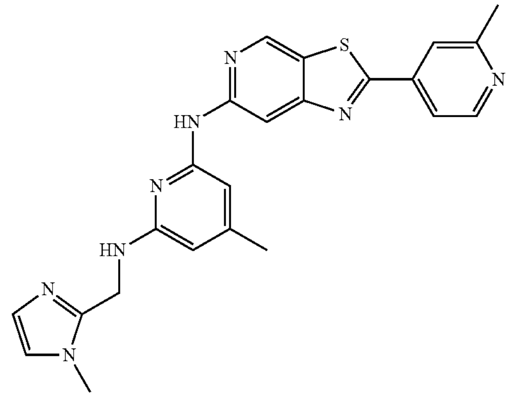 [SMILES: Cc1cc(NCc2nccn2C)nc(Nc2cc3nc(-c4ccnc(C)c4)sc3cn2)c1]

The title compound was synthesized in a similar fashion to example 65 from the appropriate starting materials. $^1$H NMR (400 MHz, Chloroform-d) δ 8.82 (d, J=0.9 Hz, 1H), 8.69 (d, J=0.9 Hz, 1H), 8.68 (d, J=5.2 Hz, 1H), 7.84-7.81 (m, 1H), 7.73 (ddd, J=5.2, 1.7, 0.7 Hz, 1H), 7.29 (s, 1H), 7.00 (d, J=1.3 Hz, 1H), 6.89 (d, J=1.3 Hz, 1H), 6.24 (s, 1H), 5.98 (s, 1H), 5.10 (t, J=5.2 Hz, 1H), 4.71 (d, J=5.2 Hz, 2H), 3.73 (s, 3H), 2.69 (s, 3H), 2.23 (s, 3H). ESI MS $[M+H]^+$ for $C_{23}H_{22}N_8S$, calcd 443.2, found 443.1.

Example 77: (3R,5S)-5-(Hydroxymethyl)-1-(3-methyl-6-{[2-(3-methylpyridin-2-yl)-[1,3]thiazolo[5,4-c]pyridin-6-yl]amino}pyridin-2-yl)pyrrolidin-3-ol

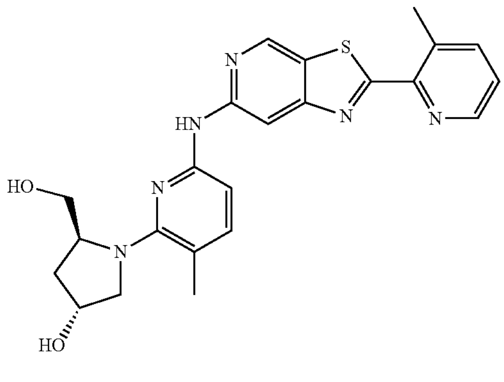 [SMILES: Cc1cccnc1-c1nc2cc(Nc3ccc(C)c(N4C[C@H](O)C[C@H]4CO)n3)ncc2s1]

The title compound was synthesized in a similar fashion to example 65 from the appropriate starting materials. $^1$H NMR (400 MHz, Methanol-$d_4$) δ 8.70 (s, 1H), 8.56 (s, 1H), 8.45-8.41 (m, 1H), 7.73-7.67 (m, 1H), 7.32 (dd, J=7.8, 4.6 Hz, 1H), 7.22 (dd, J=7.8, 0.7 Hz, 1H), 6.48 (d, J=7.8 Hz, 1H), 4.92-4.83 (m, 1H), 4.49-4.39 (m, 1H), 3.96 (dd, J=10.8, 3.9 Hz, 1H), 3.91-3.75 (m, 2H), 3.27 (d, J=10.8 Hz, 1H), 2.80 (s, 3H), 2.21 (s, 3H), 2.19-2.10 (m, 2H). ESI MS $[M+H]^+$ for $C_{23}H_{24}N_6O_2S$, calcd 449.2, found 449.2.

Example 78: 6-[(1S,4S)-2,5-Diazabicyclo[2.2.1]heptan-2-yl]-N-[2-(3-methylpyridin-2-yl)-[1,3]thiazolo[5,4-c]pyridin-6-yl]pyridin-2-amine

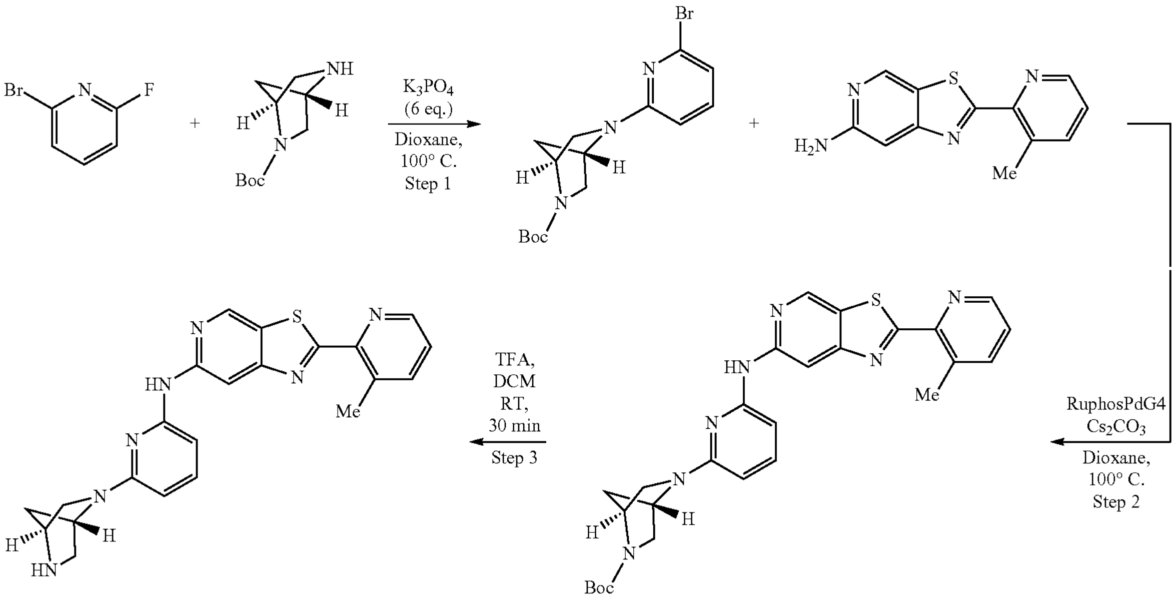

Step 1: To a dry screw cap reaction vial containing septum, was added commercially available 2-bromo-6-fluoro pyridine (1.0 g, 5.68 mmol) followed by (1S,4S)-2-boc-2,5-diazabicyclo[2.2.1]heptane (1.23 g, 6.25 mmol) and $K_3PO_4$ (6.03 g, 28.40 mmol). To this mixture, dioxane (15 mL) was added and stirred overnight at 100° C. After confirming the completion of the reaction by LCMS, the temperature of the reaction mixture was brought to room temperature and filtered through a small pad of Celite®. The solvent was evaporated under reduced pressure and the crude product was purified by flash column chromatography (silica gel; gradient: 0% to 50% MeOH in $CH_2Cl_2$) to afford the pyridine derivative as a viscous oily liquid (1.2 g, 60%).

Step 2: To a dry screw cap reaction vial containing septum, were added the azabenzothiazole derived amine (150 mg, 0.619 mmol) (prepared in a similar fashion to that described in steps 1-3 of example 1 using the appropriate starting materials), pyridine derivative from step 1 (219 mg, 0.619 mmol), Ruphos Pd G4 (105 mg, 0.123 mmol), $Cs_2CO_3$ (605 mg, 1.857 mmol) and Dioxane (8 mL) and degassed for 5 min using nitrogen. Then this reaction mixture was stirred at 100° C. overnight. After confirming the completion of the reaction using LCMS, the reaction mixture was cooled to room temperature and the crude reaction mixture was filtered through a small pad of Celite® and the volatiles were evaporated under reduced pressure.

Step 3: To the crude reaction mixture from step 2 in a screw cap vial was added $CH_2Cl_2$ (5 mL) and 1.5 mL of neat TFA and stirred for 30 min. After confirming the completion of the Boc deprotection by LCMS, reaction was stopped, and the volatiles were removed under reduced pressure. The crude product was purified by preparative HPLC. The pure fractions were combined, and the organic solvent was evaporated under reduced pressure. The pH of the aqueous layer was adjusted to 11 using $K_2CO_3$ and extracted with $CH_2Cl_2$. The combined organic layers were dried using anhydrous $Na_2SO_4$ and concentrated under reduced pressure to afford the title compound (20 mg, 8%). $^1H$ NMR (400 MHz, Chloroform-d) δ 8.82 (d, J=0.9 Hz, 1H), 8.73 (d, J=0.9 Hz, 1H), 8.55 (ddd, J=4.6, 1.6, 0.7 Hz, 1H), 7.67 (ddd, J=7.8, 1.6, 0.8 Hz, 1H), 7.41-7.29 (m, 3H), 6.28 (d, J=7.7 Hz, 1H), 5.90 (d, J=8.0 Hz, 1H), 4.80 (s, 1H), 3.85 (s, 1H), 3.70 (dd, J=9.4, 2.0 Hz, 1H), 3.32-3.21 (m, 2H), 3.16 (dd, J=9.9, 1.8 Hz, 1H), 2.89 (s, 3H), 1.95 (d, J=9.6 Hz, 1H), 1.88 (d, J=9.5 Hz, 1H), 1.78 (s, 1H). ESI MS $[M+H]^+$ for $C_{22}H_{21}N_7S$, calcd 416.2, found 416.1.

Example 79: N-[2-(2-Fluoro-6-methoxyphenyl)-[1,3]thiazolo[5,4-c]pyridin-6-yl]-6-{5-methyl-2,5-diazabicyclo[2.2.2]octan-2-yl}pyridin-2-amine

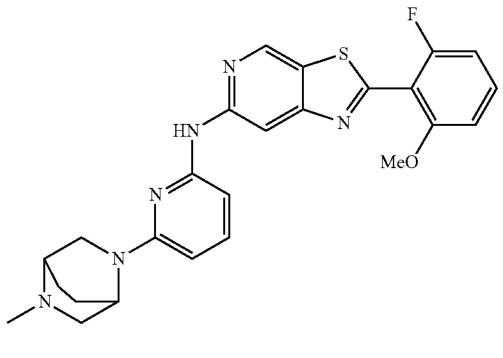 [SMILES: COc1cccc(F)c1-c1nc2cc(Nc3cccc(N4CC5CCC4CN5C)n3)ncc2s1]

The title compound was synthesized in a similar fashion to steps 1 and 2 of example 78 from the appropriate starting materials. $^{1}$H NMR (400 MHz, Methanol-$d_4$) δ 9.08 (s, 1H), 8.10 (s, 1H), 7.68 (t, J=8.2 Hz, 1H), 7.61 (td, J=8.5, 6.2 Hz, 1H), 7.10 (dt, J=8.6, 1.0 Hz, 1H), 6.97 (ddd, J=10.5, 8.4, 1.0 Hz, 1H), 6.54 (d, J=8.0 Hz, 1H), 6.51 (d, J=8.4 Hz, 1H), 4.18 (m, 4H), 4.01 (s, 3H), 3.60-3.44 (m, 2H), 2.94 (s, 3H), 2.38-2.34 (m, 2H), 2.18 (d, J=8.7 Hz, 2H). ESI MS $[M+H]^+$ for $C_{25}H_{25}FN_6OS$, calcd 477.2, found 477.3.

Example 80: N-[2-(2-Fluoro-6-methoxyphenyl)-[1,3]thiazolo[5,4-c]pyridin-6-yl]-6-[(1S,4S)-5-methyl-2,5-diazabicyclo[2.2.1]heptan-2-yl]pyridin-2-amine

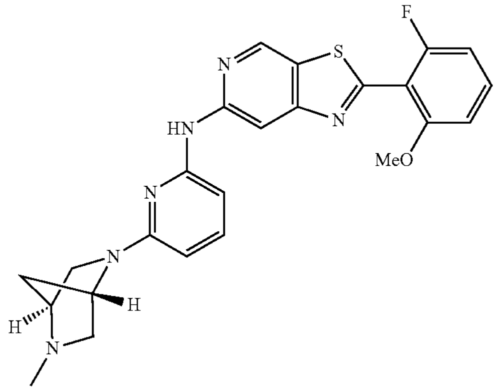 [SMILES: COc1cccc(F)c1-c1nc2cc(Nc3cccc(N4C[C@@H]5C[C@H]4CN5C)n3)ncc2s1]

The title compound was synthesized in a similar fashion to steps 1 and 2 of example 78 from the appropriate starting materials. $^{1}$H NMR (400 MHz, Methanol-$d_4$) δ 9.08 (s, 1H), 7.89 (m, 1H), 7.70 (t, J=8.2 Hz, 1H), 7.60 (td, J=8.5, 6.2 Hz, 1H), 7.09 (dt, J=8.6, 0.9 Hz, 1H), 6.97 (ddd, J=10.6, 8.4, 0.9 Hz, 1H), 6.2 (d, J=8.4 Hz, 1H), 6.36 (d, J=8.4 Hz, 1H), 5.00 (s, 1H), 4.56 (s, 1H), 4.02 (s, 3H), 4.00-3.86 (m, 3H), 3.03 (s, 3H), 2.61-2.32 (m, 3H). ESI MS $[M+H]^+$ for $C_{24}H_{23}FN_6OS$, calcd 463.2, found 463.3.

Example 81: N-[2-(2-Fluoro-6-methoxyphenyl)-[1,3]thiazolo[5,4-c]pyridin-6-yl]-6-(4-methylpiperazin-1-yl)pyridin-2-amine

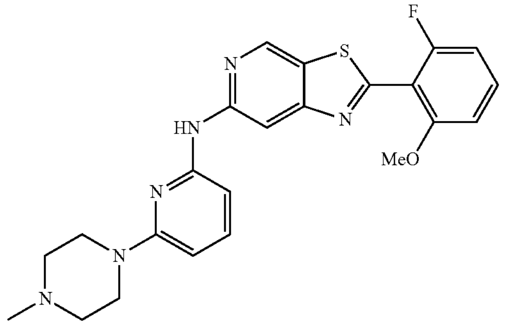 [SMILES: COc1cccc(F)c1-c1nc2cc(Nc3cccc(N4CCN(C)CC4)n3)ncc2s1]

The title compound was synthesized in a similar fashion to steps 1 and 2 of example 78 from the appropriate starting materials. $^{1}$H NMR (400 MHz, Chloroform-d) δ 8.83 (d, J=0.9 Hz, 1H), 8.31 (d, J=0.9 Hz, 1H), 7.48-7.38 (m, 2H), 7.22 (s, 1H), 6.93-6.80 (m, 2H), 6.60 (d, J=7.8 Hz, 1H), 6.20 (d, J=8.2 Hz, 1H), 3.91 (s, 3H), 3.63-3.53 (m, 4H), 2.55-2.47 (m, 4H), 2.33 (s, 3H). ESI MS $[M+H]^+$ for $C_{23}H_{23}FN_6OS$, calcd 451.2, found 451.3.

Example 82: 6-[(1S,4S)-2,5-Diazabicyclo[2.2.1]heptan-2-yl]-N-[2-(1H-pyrazol-1-yl)-[1,3]thiazolo[5,4-c]pyridin-6-yl]pyridin-2-amine

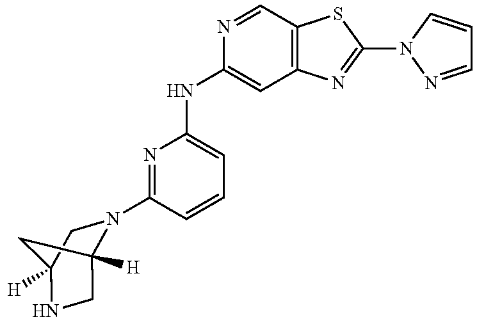 [SMILES: c1cc(Nc2cc3nc(-n4cccn4)sc3cn2)nc(N2C[C@@H]3C[C@H]2CN3)c1]

The title compound was synthesized in a similar fashion to example 78 from the appropriate starting materials. $^{1}$H NMR (400 MHz, Chloroform-d) δ 8.66 (d, J=0.8 Hz, 1H), 8.54-8.48 (m, 2H), 7.80 (dd, J=1.7, 0.6 Hz, 1H), 7.40-7.32 (m, 2H), 6.55 (dd, J=2.7, 1.6 Hz, 1H), 6.28 (dd, J=7.8, 0.5 Hz, 1H), 5.92 (dd, J=8.1, 0.5 Hz, 1H), 4.72 (s, 1H), 3.85 (d, J=2.1 Hz, 1H), 3.71 (dd, J=9.5, 2.0 Hz, 1H), 3.31 (d, J=9.5 Hz, 1H), 3.21-3.10 (m, 2H), 1.98-1.92 (m, 1H), 1.90-1.85 (m, 1H), 1.69 (s, 1H). ESI MS $[M+H]^+$ for $C_{19}H_{18}N_8S$, calcd 391.1, found 391.2.

Example 83: 6-[(1S,4S)-2,5-Diazabicyclo[2.2.1]heptan-2-yl]-5-fluoro-N-[2-(3-methylpyridin-2-yl)-[1,3]thiazolo[5,4-c]pyridin-6-yl]pyridin-2-amine

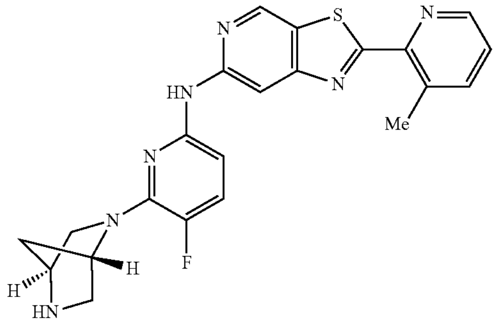 [SMILES: Cc1cccnc1-c1nc2cc(Nc3ccc(F)c(N4C[C@@H]5C[C@H]4CN5)n3)ncc2s1]

The title compound was synthesized in a similar fashion to example 78 from the appropriate starting materials. $^{1}$H NMR (400 MHz, Chloroform-d) δ 8.81 (d, J=0.9 Hz, 1H), 8.57-8.51 (m, 2H), 7.66 (ddd, J=7.7, 1.7, 0.8 Hz, 1H), 7.36 (s, 1H), 7.30 (dd, J=7.7, 4.6 Hz, 1H), 7.13 (dd, J=12.4, 8.3 Hz, 1H), 6.26 (dd, J=8.3, 1.7 Hz, 1H), 4.88 (s, 1H), 3.87 (ddd, J=10.0, 3.0, 2.1 Hz, 1H), 3.80 (s, 1H), 3.48 (ddd, J=10.0, 4.0, 1.5 Hz, 1H), 3.34 (dd, J=10.0, 1.3 Hz, 1H), 3.18 (dd, J=10.0, 1.9 Hz, 1H), 2.88 (s, 3H), 1.98-1.89 (m, 1H), 1.87-1.81 (m, 1H), 1.60 (s, 1H). ESI MS $[M+H]^+$ for $C_{22}H_{20}FN_7S$, calcd 434.2, found 434.1.

Example 84: 6-[(1S,4S)-2,5-Diazabicyclo[2.2.1]heptan-2-yl]-5-methyl-N-[2-(3-methylpyridin-2-yl)-[1,3]thiazolo[5,4-c]pyridin-6-yl]pyridin-2-amine

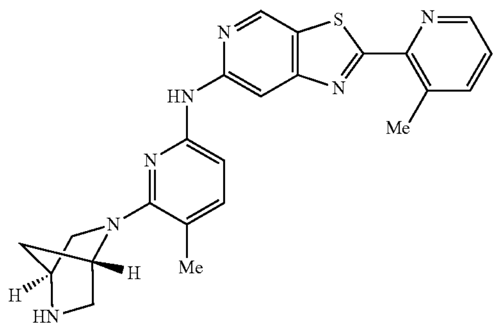 [SMILES: Cc1cccnc1-c1nc2cc(Nc3ccc(C)c(N4C[C@@H]5C[C@H]4CN5)n3)ncc2s1]

The title compound was synthesized in a similar fashion to example 78 from the appropriate starting materials. $^1$H NMR (400 MHz, Chloroform-d) δ 8.81 (d, J=0.9 Hz, 1H), 8.74 (d, J=0.9 Hz, 1H), 8.56 (ddd, J=4.6, 1.7, 0.7 Hz, 1H), 7.68 (ddd, J=7.7, 1.7, 0.8 Hz, 1H), 7.31 (dd, J=7.7, 4.6 Hz, 1H), 7.23-7.17 (m, 2H), 6.31 (d, J=7.8 Hz, 1H), 4.83 (s, 1H), 3.87 (dd, J=8.9, 2.3 Hz, 1H), 3.78 (s, 1H), 3.59 (dd, J=10.1, 1.3 Hz, 1H), 3.30-3.22 (m, 2H), 2.90 (s, 3H), 2.20 (s, 3H), 1.99-1.92 (m, 1H), 1.84 (ddt, J=9.6, 2.5, 1.3 Hz, 1H), 1.66 (s, 1H). ESI MS $[M+H]^+$ for $C_{23}H_{23}N_7S$, calcd 430.2, found 430.1.

Example 85: N-[2-(2-Methylpyridin-4-yl)-[1,3]thiazolo[5,4-c]pyridin-6-yl]-6-(piperazin-1-yl)pyridin-2-amine

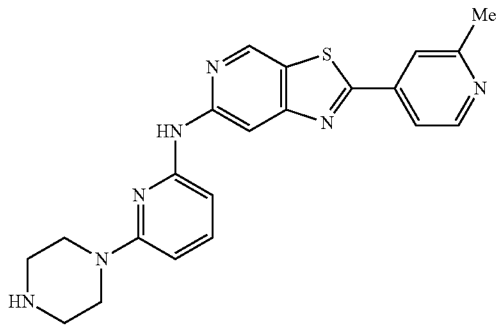 [SMILES: Cc1cc(-c2nc3cc(Nc4cccc(N5CCNCC5)n4)ncc3s2)ccn1]

The title compound was synthesized in a similar fashion to example 78 from the appropriate starting materials. $^1$H NMR (400 MHz, Chloroform-d) δ 8.83 (s, 1H), 8.67 (d, J=5.2 Hz, 1H), 8.46 (s, 1H), 7.82 (s, 1H), 7.74 (dd, J=5.2, 1.5 Hz, 1H), 7.44 (t, J=8.0 Hz, 1H), 7.38 (s, 1H), 6.50 (d, J=7.8 Hz, 1H), 6.23 (d, J=8.2 Hz, 1H), 3.61-3.54 (m, 4H), 3.08-3.00 (m, 4H), 2.69 (s, 3H), 1.84 (s, 1H). ESI MS $[M+H]^+$ for $C_{21}H_{21}N_7S$, calcd 404.2, found 404.2.

Example 86: 4-[(1S,4S)-2,5-Diazabicyclo[2.2.1]heptan-2-yl]-N-[2-(3-methylpyridin-2-yl)-[1,3]thiazolo[5,4-c]pyridin-6-yl]pyridin-2-amine

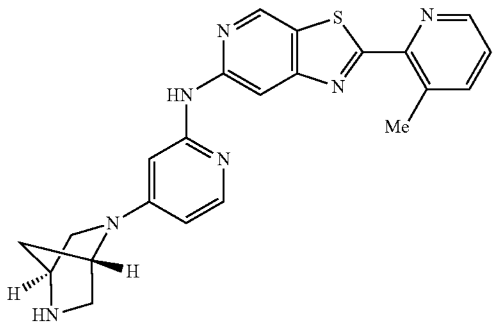 [SMILES: Cc1cccnc1-c1nc2cc(Nc3cc(N4C[C@@H]5C[C@H]4CN5)ccn3)ncc2s1]

The title compound was synthesized in a similar fashion to example 78 from the appropriate starting materials. $^1$H NMR (400 MHz, DMSO-$d_6$) δ 11.36 (s, 1H), 9.29 (s, 1H), 9.18 (d, J=0.8 Hz, 1H), 8.80 (s, 1H), 8.68-8.58 (m, 1H), 8.04-7.88 (m, 2H), 7.66-7.49 (m, 2H), 5.02 (m, 1H), 4.58 (m, 1H), 3.27 (m, 5H), 2.85 (s, 3H), 2.17 (d, J=11.9 Hz, 1H), 2.00 (d, J=11.4 Hz, 1H). ESI MS $[M+H]^+$ for $C_{23}H_{21}N_7S$, calcd 416.2, found 416.2.

Example 87: 6-{2,5-Diazabicyclo[4.1.0]heptan-2-yl}-N-[2-(3-methylpyridin-2-yl)-[1,3]thiazolo[5,4-c]pyridin-6-yl]pyridin-2-amine

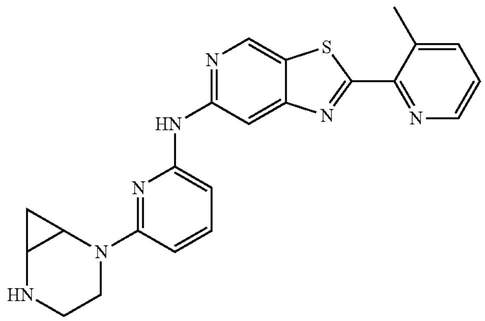 [SMILES: Cc1cccnc1-c1nc2cc(Nc3cccc(N4CCNC5CC54)n3)ncc2s1]

The title compound was synthesized in a similar fashion to example 78 from the appropriate starting materials. $^1$H NMR (400 MHz, Chloroform-d) δ 8.92 (s, 1H), 8.81 (d, J=0.9 Hz, 1H), 8.54 (ddd, J=4.6, 1.6, 0.6 Hz, 1H), 7.66 (ddd, J=7.8, 1.6, 0.8 Hz, 1H), 7.43 (t, J=8.0 Hz, 1H), 7.32-7.26 (m, 2H), 6.29 (dd, J=8.0, 4.2 Hz, 2H), 3.84 (dd, J=12.1, 6.3 Hz, 1H), 3.27 (ddd, J=12.1, 5.8, 4.0 Hz, 1H), 3.09-2.96 (m, 2H), 2.87 (m, 4H), 2.73 (td, J=6.7, 3.8 Hz, 1H), 1.14 (q, J=6.3 Hz, 1H), 0.50 (ddd, J=6.0, 4.9, 3.9 Hz, 1H). ESI MS $[M+H]^+$ for $C_{22}H_{21}N_7S$, calcd 416.2, found 416.3.

Example 88: N-[2-(3-Methylpyridin-2-yl)-[1,3]thiazolo[4,5-c]pyridin-6-yl]-6-{octahydropyrrolo[3,2-b]pyrrol-1-yl}pyridin-2-amine

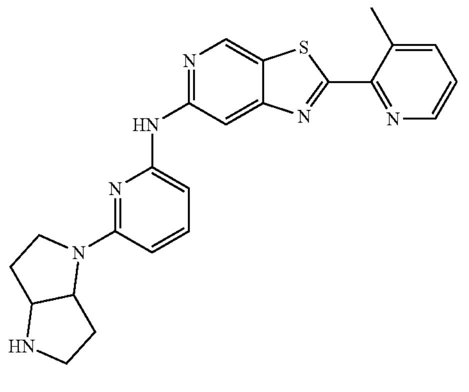 [SMILES: Cc1cccnc1-c1nc2cc(Nc3cccc(N4CCC5NCCC54)n3)ncc2s1]

The title compound was synthesized in a similar fashion to example 78 from the appropriate starting materials. $^1$H NMR (400 MHz, Chloroform-d) δ 8.99 (d, J=0.9 Hz, 1H), 8.81 (d, J=0.9 Hz, 1H), 8.55 (ddd, J=4.7, 1.7, 0.7 Hz, 1H), 7.67 (ddd, J=7.7, 1.7, 0.8 Hz, 1H), 7.37 (t, J=7.9 Hz, 1H), 7.30 (dd, J=7.7, 4.6 Hz, 1H), 7.24 (s, 1H), 6.19 (d, J=7.7 Hz, 1H), 5.96 (d, J=8.1 Hz, 1H), 4.51 (td, J=6.7, 2.4 Hz, 1H), 4.00 (td, J=6.7, 3.5 Hz, 1H), 3.61 (dt, J=8.1, 5.5 Hz, 2H), 2.99 (dd, J=7.6, 5.7 Hz, 2H), 2.89 (s, 3H), 2.29 (dq, J=14.7, 7.5 Hz, 1H), 2.19-2.03 (m, 2H), 2.00-1.91 (m, 1H). ESI MS $[M+H]^+$ for $C_{23}H_{23}N_7S$, calcd 430.2, found 430.2.

Example 89: 6-[(1S,4S)-5-Methyl-2,5-diazabicyclo[2.2.1]heptan-2-yl]-N-[2-(pyridin-3-yl)-[1,3]thiazolo[5,4-c]pyridin-6-yl]pyridin-2-amine Step 1: To a dry screw cap reaction vial containing septum, was added commercially available 2-bromo-6-fluoro pyridine (1.54 g, 8.76 mmol) followed by (1S,4S)-2-methyl-2,5-diazabicyclo[2.2.1]heptane dihydrobromide (2 g, 7.29 mmol) and $K_3PO_4$ (9.3 g, 43.79 mmol). To this mixture, dioxane (37 mL) was added and stirred overnight at 100° C. After confirming the completion of the reaction by LCMS, the temperature of the reaction mixture was brought to room temperature and filtered through a small pad of Celite®. The solvent was evaporated under reduced pressure and the crude product was purified by flash column chromatography (silica gel; gradient: 0% to 50% MeOH in $CH_2Cl_2$) to afford the pyridine derivative as a viscous oily liquid (1.88 g, 96%).

Step 2: To a dry screw cap reaction vial containing septum, were added bromopyridine derivative (1.88 g, 7.01 mmol) from step 1, Boc carbamate (16.4 g, 140.2 mmol), $Pd_2(dba)_3$ (1.28 g, 1.40 mmol), Brettphos (1.5 g, 2.80 mmol), $Cs_2CO_3$ (7 g, 21.03 mmol) and Dioxane (47 mL) under $N_2$ and degassed this reaction mixture for 5 min using nitrogen. Then this reaction mixture was stirred at 100° C. overnight. After confirming the completion of the reaction using LCMS, the reaction mixture was cooled to room temperature and the crude reaction mixture was filtered using a small pad of Celite®. The crude reaction mixture was purified by flash column chromatography (silica gel; gradient: 0% to 50% MeOH in $CH_2Cl_2$) to obtain the Boc protected amine (1.9 g, 89%).

Step 3: The Boc protected pyridine amine derivative (1.9 g, 6.24 mmol) obtained from Step 2 was taken in a screw cap vial with septum and to this HCl in dioxane was added in excess and stirred overnight. After confirming the complete deprotection of Boc group, volatiles were evaporated under reduced pressure. The crude reaction mixture was dissolved in water and extracted with $CH_2Cl_2$ to remove any impurities. Then

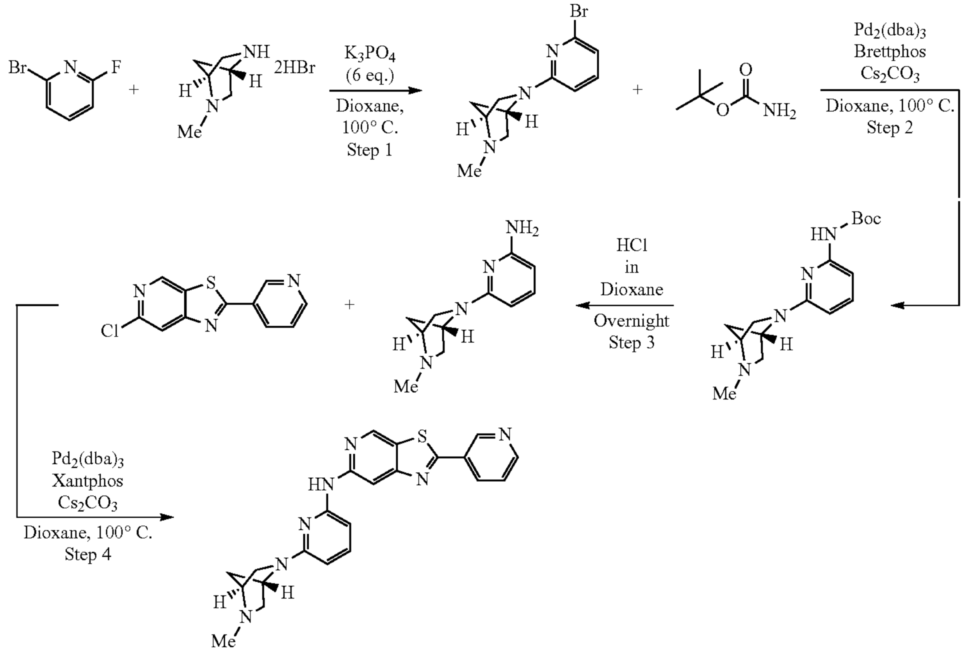

the pH of the aqueous layer was brought to 11 using $K_2CO_3$ and the aqueous layer was extracted using $CH_2Cl_2$ thrice. The combined organic layers were dried over anhydrous $Na_2SO_4$ and concentrated to afford the amine (747 mg, 59%).

Step 4: To a dry screw cap reaction vial containing septum, were added the amine (83 mg, 0.4 mmol) from step 3, benzothiazole derivative (100 mg, 0.4 mmol) obtained in a similar fashion to step 1 of example 1, $Pd_2(dba)_3$ (37 mg, 0.04 mmol), Xantphos (47 mg, 0.08 mmol), $Cs_2CO_3$ (395 mg, 1.21 mmol) and Dioxane (5 mL) and degassed for 5 min using nitrogen. Then this reaction mixture was stirred at 100° C. overnight. After confirming the completion of the reaction using LCMS, the reaction mixture was cooled to room temperature and the crude reaction mixture was filtered through a small pad of Celite®. Solvent was evaporated under reduced pressure and the crude product was purified by column chromatography (silica gel; gradient: 0% to 50% EtOAc in Hexanes) to afford the title compound (15 mg, 9%). $^1H$ NMR (400 MHz, Chloroform-d) δ 9.33 (d, J=2.2 Hz, 1H), 8.80 (d, J=0.8 Hz, 1H), 8.76 (dd, J=4.8, 1.6 Hz, 1H), 8.70-8.67 (m, 1H), 8.41 (dt, J=8.0, 2.0 Hz, 1H), 7.49-7.44 (m, 1H), 7.37 (t, J=7.9 Hz, 1H), 7.33 (s, 1H), 6.30 (d, J=7.7 Hz, 1H), 5.94 (d, J=8.1 Hz, 1H), 4.69 (s, 1H), 3.65 (d, J=9.4 Hz, 1H), 3.57 (s, 1H), 3.46 (dd, J=9.7, 2.0 Hz, 1H), 3.08 (dd, J=9.6, 2.0 Hz, 1H), 2.76 (d, J=9.1 Hz, 1H), 2.44 (s, 3H), 2.04 (d, J=9.5 Hz, 1H), 1.91 (d, J=9.6 Hz, 1H). ESI MS $[M+H]^+$ for $C_{22}H_{21}N_7S$, calcd 415.2, found 416.2.

Example 90: 6-[(1S,4S)-5-Methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

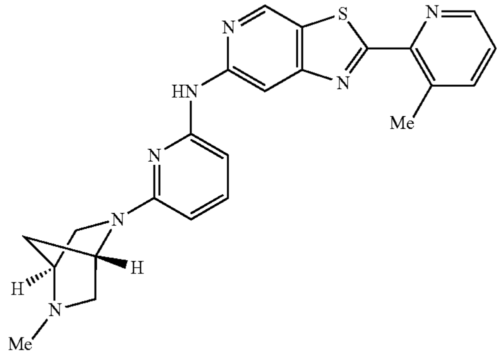 [SMILES: Cc1cccnc1-c1nc2cc(Nc3cccc(N4C[C@@H]5C[C@H]4CN5C)n3)ncc2s1]

The title compound was synthesized in a similar fashion to example 89 from the appropriate starting materials. $^1H$ NMR (400 MHz, Chloroform-d) δ 8.83 (d, J=0.8 Hz, 1H), 8.71 (d, J=0.9 Hz, 1H), 8.56 (dd, J=4.6, 1.1 Hz, 1H), 7.71-7.65 (m, 1H), 7.38 (t, J=7.9 Hz, 1H), 7.31 (dd, J=7.7, 4.6 Hz, 2H), 6.29 (d, J=7.7 Hz, 1H), 5.92 (d, J=8.0 Hz, 1H), 4.73 (s, 1H), 3.64 (d, J=9.7 Hz, 1H), 3.57 (s, 1H), 3.43 (dd, J=9.6, 2.1 Hz, 1H), 3.12 (dd, J=9.5, 2.1 Hz, 1H), 2.90 (s, 3H), 2.78 (d, J=10.3 Hz, 1H), 2.44 (s, 3H), 2.03 (d, J=9.5 Hz, 1H), 1.92 (d, J=9.5 Hz, 1H). ESI MS $[M+H]^+$ for $C_{23}H_{23}N_7S$, calcd 430.2, found 430.2.

Example 91: 6-[(1R,4R)-5-Methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

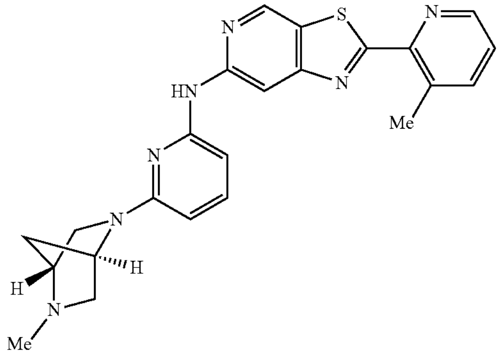 [SMILES: Cc1cccnc1-c1nc2cc(Nc3cccc(N4C[C@H]5C[C@@H]4CN5C)n3)ncc2s1]

The title compound was synthesized in a similar fashion to example 89 from the appropriate starting materials. $^1H$ NMR (400 MHz, Chloroform-d) δ 8.82 (d, J=0.9 Hz, 1H), 8.71 (d, J=0.9 Hz, 1H), 8.54 (ddd, J=4.7, 1.6, 0.7 Hz, 1H), 7.66 (ddd, J=7.7, 1.6, 0.8 Hz, 1H), 7.48 (s, 1H), 7.36 (t, J=7.9 Hz, 1H), 7.30 (dd, J=7.7, 4.6 Hz, 1H), 6.27 (d, J=7.7 Hz, 1H), 5.91 (d, J=8.0 Hz, 1H), 4.72 (s, 1H), 3.62 (d, J=9.6 Hz, 1H), 3.55 (s, 1H), 3.41 (dd, J=9.6, 2.2 Hz, 1H), 3.10 (dd, J=9.5, 2.1 Hz, 1H), 2.89 (s, 3H), 2.76 (dd, J=9.5, 1.4 Hz, 1H), 2.43 (s, 3H), 2.02 (ddt, J=9.5, 2.4, 1.2 Hz, 1H), 1.90 (ddt, J=9.5, 2.3, 1.1 Hz, 1H). ESI MS $[M+H]^+$ for $C_{23}H_{23}N_7S$, calcd 430.2, found 430.2.

Example 92: 6-[(1S,4S)-5-Methyl-2,5-diazabicyclo[2.2.1]heptan-2-yl]-N-{2-[3-(trifluoromethyl)pyridin-2-yl]-[1,3]thiazolo[5,4-c]pyridin-6-yl}pyridin-2-amine

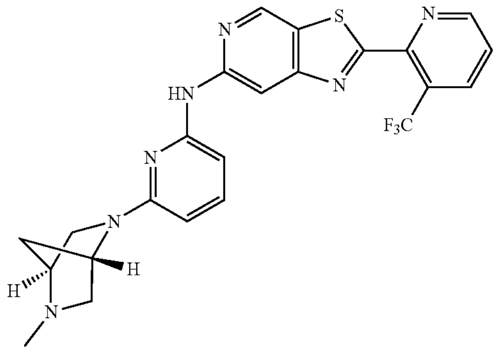 [SMILES: CN1C[C@@H]2C[C@H]1CN2c1cccc(Nc2cc3nc(-c4ncccc4C(F)(F)F)sc3cn2)n1]

The title compound was synthesized in a similar fashion to example 89 from the appropriate starting materials. $^1H$ NMR (400 MHz, DMSO-$d_6$) δ 9.58 (s, 1H), 9.02 (d, J=0.8 Hz, 1H), 9.00 (dd, J=4.8, 1.5 Hz, 1H), 8.93 (d, J=0.9 Hz, 1H), 8.46 (dd, J=8.1, 1.5 Hz, 1H), 7.84 (dd, J=8.1, 4.8 Hz, 1H), 7.34 (t, J=7.9 Hz, 1H), 6.43 (d, J=7.8 Hz, 1H), 5.93 (d, J=8.0 Hz, 1H), 4.59 (s, 1H), 3.45 (d, J=7.8 Hz, 2H), 3.32 (d, J=2.2 Hz, 1H), 2.89 (dd, J=9.4, 2.1 Hz, 1H), 2.57 (d, J=9.3 Hz, 1H), 2.27 (s, 3H), 1.85 (d, J=9.4 Hz, 1H), 1.78 (d, J=9.3 Hz, 1H). ESI MS $[M+H]^+$ for $C_{23}H_{20}F_3N_7S$, calcd 484.2, found 484.1.

Example 93: 6-[(1S,4S)-5-Methyl-2,5-diazabicyclo[2.2.1]heptan-2-yl]-N-{2-[3-(propan-2-yl)pyridin-2-yl]-[1,3]thiazolo[5,4-c]pyridin-6-yl}pyridin-2-amine

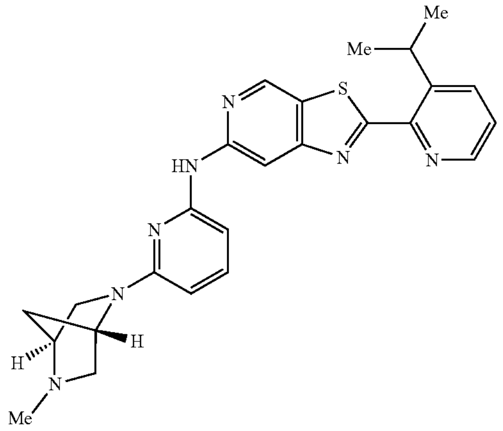 [SMILES: CC(C)c1cccnc1-c1nc2cc(Nc3cccc(N4C[C@@H]5C[C@H]4CN5C)n3)ncc2s1]

The title compound was synthesized in a similar fashion to example 89 from the appropriate starting materials. $^1H$ NMR (400 MHz, DMSO-$d_6$) δ 9.88 (s, 1H), 8.99 (d, J=0.8 Hz, 1H), 8.61-8.54 (m, 2H), 8.06 (dd, J=8.1, 1.6 Hz, 1H), 7.58 (dd, J=8.0, 4.5 Hz, 1H), 7.46 (m, 1H), 6.72 (d, J=7.9 Hz, 1H), 6.10 (d, J=8.0 Hz, 1H), 4.81 (s, 1H), 4.58 (p, J=6.7 Hz, 1H), 4.37 (s, 1H), 3.74-3.64 (m, 2H), 3.07 (d, J=11.4 Hz, 1H), 2.87 (d, J=4.7 Hz, 3H), 2.79 (d, J=4.3 Hz, 1H), 2.39 (d, J=11.5 Hz, 1H), 2.21 (d, J=11.4 Hz, 1H), 1.30 (dd, J=6.7, 6.4 Hz, 6H). ESI MS $[M+H]^+$ for $C_{25}H_{27}N_7S$, calcd 458.2, found 458.1.

Example 94: 6-[(3S)-3,4-Dimethylpiperazin-1-yl]-N-[2-(3-methylpyridin-2-yl)-[1,3]thiazolo[5,4-c]pyridin-6-yl]pyridin-2-amine

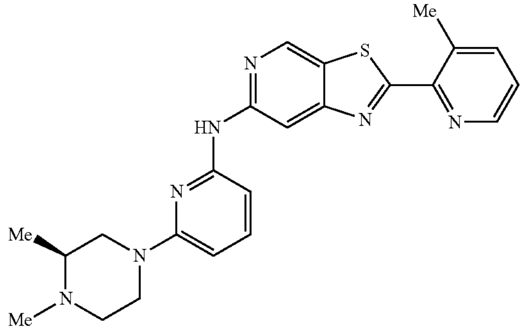 [SMILES: Cc1cccnc1-c1nc2cc(Nc3cccc(N4CCN(C)[C@@H](C)C4)n3)ncc2s1]

The title compound was synthesized in a similar fashion to example 89 from the appropriate starting materials. $^1H$ NMR (400 MHz, DMSO-$d_6$) δ 10.27 (s, 1H), 9.75 (s, 1H), 9.00 (d, J=0.8 Hz, 1H), 8.59 (d, J=4.7 Hz, 1H), 8.53 (s, 1H), 7.91-7.87 (m, 1H), 7.53-7.44 (m, 2H), 6.70 (d, J=7.9 Hz, 1H), 6.42 (d, J=8.2 Hz, 1H), 4.53 (d, J=13.8 Hz, 1H), 4.28 (d, J=13.8 Hz, 1H), 3.52 (d, J=11.8 Hz, 1H), 3.34 (m, 1H), 3.27 (t, J=12.7 Hz, 1H), 3.15 (m, 1H), 3.03 (dd, J=14.2, 11.1 Hz, 1H), 2.85-2.77 (m, 5H), 1.42 (d, J=6.4 Hz, 3H). ESI MS $[M+H]^+$ for $C_{23}H_{25}N_7S$, calcd 432.2, found 432.1.

Example 95: 6-[(2S)-2,4-Dimethylpiperazin-1-yl]-N-[2-(3-methylpyridin-2-yl)-[1,3]thiazolo[5,4-c]pyridin-6-yl]pyridin-2-amine

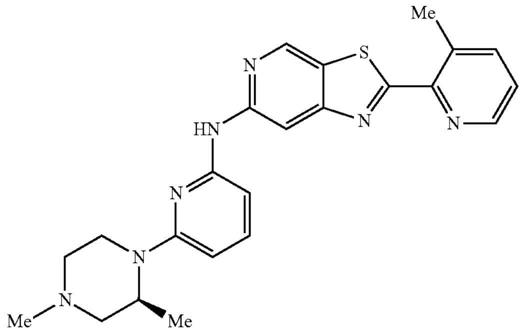 [SMILES: Cc1cccnc1-c1nc2cc(Nc3cccc(N4CCN(C)C[C@@H]4C)n3)ncc2s1]

The title compound was synthesized in a similar fashion to example 89 from the appropriate starting materials. $^1H$ NMR (400 MHz, DMSO-$d_6$) δ 9.96 (s, 1H), 9.65 (s, 1H), 8.99 (d, J=0.8 Hz, 1H), 8.59 (dd, J=4.8, 1.6 Hz, 1H), 8.47 (d, J=0.9 Hz, 1H), 7.91-7.86 (m, 1H), 7.54-7.45 (m, 2H), 6.74 (d, J=7.9 Hz, 1H), 6.32 (d, J=8.2 Hz, 1H), 4.88-4.82 (m, 1H), 4.24 (d, J=14.3 Hz, 1H), 3.52-3.44 (m, 2H), 3.30-3.19 (m, 2H), 3.06 (m, 1H), 2.84 (d, J=4.7 Hz, 5H), 1.32 (d, J=7.0 Hz, 3H). ESI MS $[M+H]^+$ for $C_{23}H_{25}N_7S$, calcd 432.2, found 432.1.

Example 96: 6-[(1S,4S)-5-Methyl-2,5-diazabicyclo[2.2.1]heptan-2-yl]-N-[2-(2-methylpyridin-4-yl)-[1,3]thiazolo[5,4-c]pyridin-6-yl]pyridin-2-amine

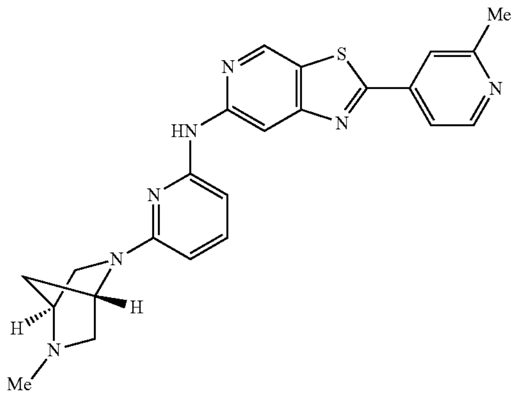 [SMILES: Cc1cc(-c2nc3cc(Nc4cccc(N5C[C@@H]6C[C@H]5CN6C)n4)ncc3s2)ccn1]

The title compound was synthesized in a similar fashion to example 89 from the appropriate starting materials. $^1H$ NMR (400 MHz, Chloroform-d) δ 8.81 (d, J=0.8 Hz, 1H), 8.69-8.65 (m, 2H), 7.82 (s, 1H), 7.74 (ddd, J=5.2, 1.7, 0.7 Hz, 1H), 7.40 (s, 1H), 7.37 (t, J=7.9 Hz, 1H), 6.29 (d, J=7.7 Hz, 1H), 5.93 (d, J=8.1 Hz, 1H), 4.68 (s, 1H), 3.65 (d, J=9.7 Hz, 1H), 3.57 (s, 1H), 3.45 (dd, J=9.7, 2.2 Hz, 1H), 3.09 (dd, J=9.6, 2.1 Hz, 1H), 2.75 (dd, J=9.6, 1.3 Hz, 1H), 2.69 (s, 3H), 2.44 (s, 3H), 2.04 (d, J=9.5 Hz, 1H), 1.91 (d, J=9.5 Hz, 1H). ESI MS $[M+H]^+$ for $C_{23}H_{23}N_7S$, calcd 430.2, found 430.1.

Example 97: 6-{5-Methyl-2,5-diazabicyclo[2.2.2]octan-2-yl}-N-[2-(3-methylpyridin-2-yl)-[1,3]thiazolo[5,4-c]pyridin-6-yl]pyridin-2-amine

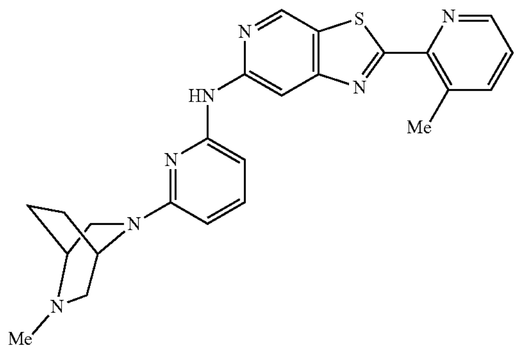 [SMILES: Cc1cccnc1-c1nc2cc(Nc3cccc(N4CC5CCC4CN5C)n3)ncc2s1]

The title compound was synthesized in a similar fashion to example 89 from the appropriate starting materials. $^1$H NMR (400 MHz, Chloroform-d) δ 8.83 (d, J=0.9 Hz, 1H), 8.67 (d, J=0.9 Hz, 1H), 8.56 (ddd, J=4.6, 1.6, 0.7 Hz, 1H), 7.68 (ddd, J=7.7, 1.7, 0.8 Hz, 1H), 7.41 (t, J=7.9 Hz, 1H), 7.31 (dd, J=7.7, 4.6 Hz, 1H), 7.27 (s, 1H), 6.29 (d, J=7.7 Hz, 1H), 5.95 (d, J=8.1 Hz, 1H), 4.66 (s, 1H), 3.91 (dt, J=10.5, 2.5 Hz, 1H), 3.36 (dd, J=10.5, 2.2 Hz, 1H), 3.17 (dd, J=10.4, 2.5 Hz, 1H), 2.94 (t, J=2.5 Hz, 1H), 2.91 (t, J=2.6 Hz, 1H), 2.90 (s, 3H), 2.88 (dt, J=4.5, 2.2 Hz, 1H), 2.48 (s, 3H), 2.23-2.03 (m, 2H), 1.96-1.84 (m, 1H), 1.72 (dddd, J=12.8, 10.8, 5.2, 2.0 Hz, 1H). ESI MS $[M+H]^+$ for $C_{24}H_{25}N_7S$, calcd 444.2, found 444.1.

Example 98: 6-{6-Methyl-3,6-diazabicyclo[3.1.1]heptan-3-yl}-N-[2-(3-methylpyridin-2-yl)-[1,3]thiazolo[5,4-c]pyridin-6-yl]pyridin-2-amine

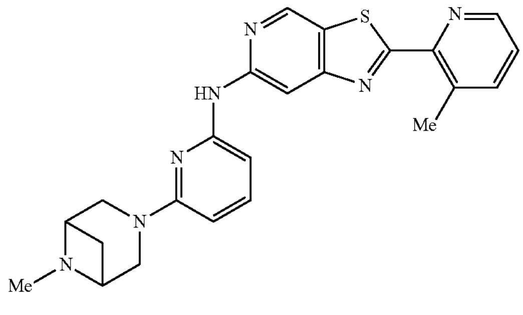 [SMILES: Cc1cccnc1-c1nc2cc(Nc3cccc(N4CC5CC(C4)N5C)n3)ncc2s1]

The title compound was synthesized in a similar fashion to example 89 from the appropriate starting materials. $^1$H NMR (400 MHz, Chloroform-d) δ 8.88 (d, J=1.0 Hz, 1H), 8.84 (d, J=0.9 Hz, 1H), 8.57 (ddd, J=4.6, 1.6, 0.6 Hz, 1H), 7.69 (ddd, J=7.7, 1.6, 0.8 Hz, 1H), 7.46 (t, J=8.0 Hz, 1H), 7.33 (dd, J=7.7, 4.6 Hz, 1H), 7.28 (s, 1H), 6.36 (d, J=7.7 Hz, 1H), 6.09 (d, J=8.1 Hz, 1H), 3.82 (dd, J=21.8, 9.0 Hz, 4H), 3.65 (d, J=12.0 Hz, 2H), 2.90 (s, 3H), 2.75-2.67 (m, 1H), 2.25 (s, 3H), 1.69 (d, J=8.7 Hz, 1H). ESI MS $[M+H]^+$ for $C_{23}H_{23}N_7S$, calcd 430.2, found 430.1.

Example 99: 6-{3-Methyl-3,6-diazabicyclo[3.1.1]heptan-6-yl}-N-[2-(3-methylpyridin-2-yl)-[1,3]thiazolo[5,4-c]pyridin-6-yl]pyridin-2-amine

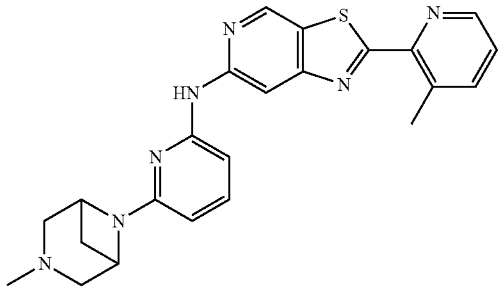 [SMILES: Cc1cccnc1-c1nc2cc(Nc3cccc(N4C5CC4CN(C)C5)n3)ncc2s1]

The title compound was synthesized in a similar fashion to example 89 from the appropriate starting materials. $^1$H NMR (400 MHz, DMSO-$d_6$) δ 9.55 (s, 1H), 8.95 (d, J=0.9 Hz, 1H), 8.73 (d, J=0.9 Hz, 1H), 8.62 (m, 1H), 7.88 (d, J=7.4 Hz, 1H), 7.50 (dd, J=7.7, 4.6 Hz, 1H), 7.35 (t, J=7.9 Hz, 1H), 6.62-6.59 (m, 1H), 5.90-5.88 (m, 1H), 4.31 (d, J=5.6 Hz, 2H), 3.28 (bs, 1H), 3.09 (d, J=10.7 Hz, 2H), 2.82 (s, 3H), 2.76 (d, J=10.9 Hz, 2H), 2.10 (s, 3H), 1.95-1.92 (m, 1H). ESI MS $[M+H]^+$ for $C_{23}H_{23}N_7S$, calcd 430.2, found 430.2.

Example 100: N-[2-(3-Methylpyridin-2-yl)-[1,3]thiazolo[5,4-c]pyridin-6-yl]-6-[(3R,5S)-3,4,5-trimethylpiperazin-1-yl]pyridin-2-amine

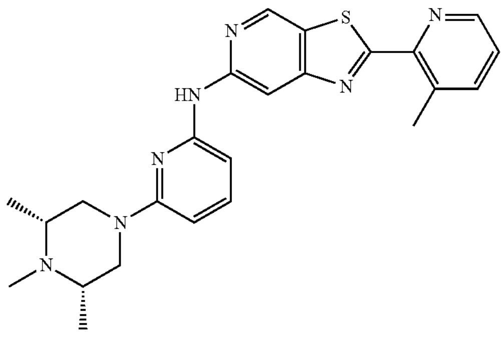 [SMILES: Cc1cccnc1-c1nc2cc(Nc3cccc(N4C[C@@H](C)N(C)[C@@H](C)C4)n3)ncc2s1]

The title compound was synthesized in a similar fashion to example 89 from the appropriate starting materials. $^1$H NMR (400 MHz, DMSO-$d_6$) δ 9.58 (s, 1H), 8.96 (d, J=0.8 Hz, 1H), 8.81 (d, J=0.9 Hz, 1H), 8.58-8.57 (m, 1H), 7.88-7.86 (m, 1H), 7.50 (dd, J=7.7, 4.6 Hz, 1H), 7.37 (t, J=8.0 Hz, 1H), 6.48 (d, J=7.8 Hz, 1H), 6.26 (d, J=8.2 Hz, 1H), 4.12 (d, J=12.5 Hz, 2H), 2.82 (s, 3H), 2.59 (dd, J=12.7, 10.8 Hz, 2H), 2.17 (s, 3H), 1.12 (d, J=6.2 Hz, 6H). ESI MS $[M+H]^+$ for $C_{24}H_{27}N_7S$, calcd 446.2, found 446.1.

Example 101: 5-Methyl-6-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

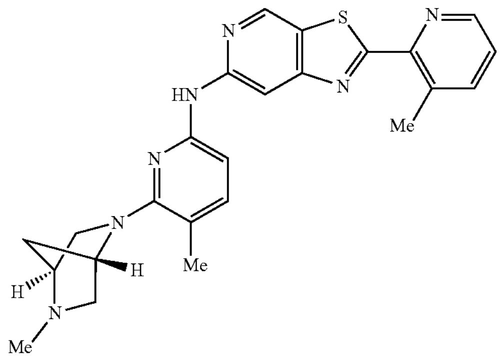

The title compound was synthesized in a similar fashion to example 89 from the appropriate starting materials. $^1$H NMR (400 MHz, Chloroform-d) δ 8.81 (d, J=0.9 Hz, 1H), 8.74 (d, J=0.9 Hz, 1H), 8.55 (ddd, J=4.6, 1.6, 0.7 Hz, 1H), 7.67 (ddd, J=7.7, 1.7, 0.8 Hz, 1H), 7.31 (dd, J=7.7, 4.6 Hz, 1H), 7.24-7.16 (m, 2H), 6.31 (d, J=7.8 Hz, 1H), 4.74 (s, 1H), 3.67-3.55 (m, 2H), 3.49 (s, 1H), 3.17 (s, 2H), 2.91 (s, 3H), 2.44 (s, 3H), 2.21 (s, 3H), 2.00 (d, J=9.5 Hz, 1H), 1.91 (d, J=9.5 Hz, 1H). ESI MS $[M+H]^+$ for $C_{24}H_{25}N_7S$, calcd 444.4, found 444.1.

Example 102: N-[2-(3-Methylpyridin-2-yl)-[1,3]thiazolo[5,4-c]pyridin-6-yl]-6-[(3S,5S)-3,4,5-trimethylpiperazin-1-yl]pyridin-2-amine

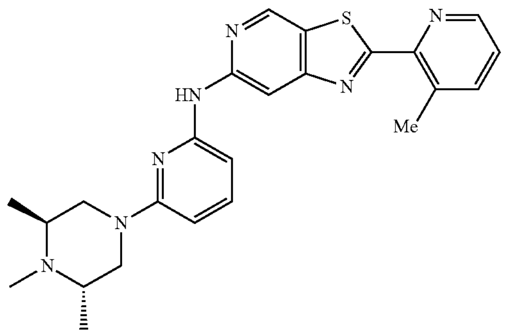 [SMILES: Cc1cccnc1-c1nc2cc(Nc3cccc(N4C[C@H](C)N(C)[C@@H](C)C4)n3)ncc2s1]

The title compound was synthesized in a similar fashion to example 89 from the appropriate starting materials. $^1$H NMR (400 MHz, Chloroform-d) δ 8.81 (d, J=0.9 Hz, 1H), 8.74 (d, J=0.9 Hz, 1H), 8.54 (ddd, J=4.6, 1.6, 0.7 Hz, 1H), 7.69-7.62 (m, 1H), 7.43-7.35 (m, 1H), 7.32-7.27 (m, 2H), 6.26 (d, J=7.7 Hz, 1H), 6.15 (d, J=8.2 Hz, 1H), 3.74 (dd, J=12.4, 3.3 Hz, 2H), 3.35 (dd, J=12.4, 6.4 Hz, 2H), 2.95 (td, J=6.4, 3.4 Hz, 2H), 2.89 (s, 3H), 2.37 (s, 3H), 1.13 (d, J=6.4 Hz, 6H). ESI MS $[M+H]^+$ for $C_{24}H_{27}N_7S$, calcd 446.2 found 446.7.

Example 103: 6-[(2R)-2,4-Dimethylpiperazin-1-yl]-N-[2-(3-methylpyridin-2-yl)-[1,3]thiazolo[5,4-c]pyridin-6-yl]pyridin-2-amine

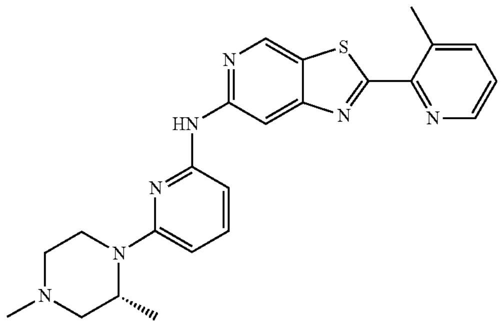 [SMILES: Cc1cccnc1-c1nc2cc(Nc3cccc(N4CCN(C)C[C@H]4C)n3)ncc2s1]

The title compound was synthesized in a similar fashion to example 89 from the appropriate starting materials. $^1$H NMR (400 MHz, Methanol-$d_4$) δ 8.73 (d, J=0.9 Hz, 1H), 8.64 (d, J=0.9 Hz, 1H), 8.47-8.44 (m, 1H), 7.77-7.68 (m, 1H), 7.47-7.26 (m, 2H), 6.39 (d, J=7.7 Hz, 1H), 6.19 (d, J=8.2 Hz, 1H), 4.69-4.55 (m, 1H), 3.97 (d, J=12.5 Hz, 1H), 3.19 (td, J=12.5, 3.2 Hz, 1H), 2.95-2.88 (m, 1H), 2.85-2.77 (m, 4H), 2.38-2.26 (m, 4H), 2.13 (td, J=11.5, 3.6 Hz, 1H), 1.31 (d, J=6.7 Hz, 3H). ESI MS $[M+H]^+$ for $C_{23}H_{25}N_7S$, calcd 432.2, found 432.2.

Example 104: 6-[(3R)-3,4-Dimethylpiperazin-1-yl]-N-[2-(3-methylpyridin-2-yl)-[1,3]thiazolo[5,4-c]pyridin-6-yl]pyridin-2-amine

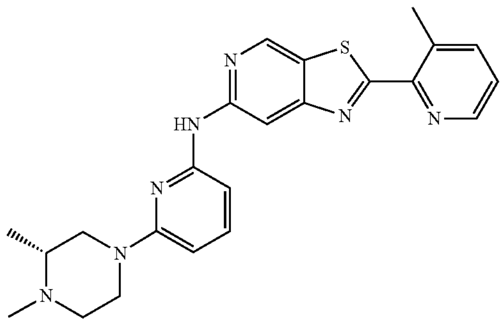 [SMILES: Cc1cccnc1-c1nc2cc(Nc3cccc(N4CCN(C)[C@H](C)C4)n3)ncc2s1]

The title compound was synthesized in a similar fashion to example 89 from the appropriate starting materials. $^1$H NMR (400 MHz, Methanol-$d_4$) δ 8.74 (d, J=0.9 Hz, 1H), 8.69 (d, J=0.9 Hz, 1H), 8.48-8.44 (m, 1H), 7.74-7.70 (m, 1H), 7.40 (t, J=8.0 Hz, 1H), 7.35 (dd, J=7.8, 4.6 Hz, 1H), 6.40 (d, J=7.8 Hz, 1H), 6.25 (d, J=8.0 Hz, 1H), 4.34-4.25 (m, 1H), 4.08-3.99 (m, 1H), 3.05 (td, J=12.3, 3.0 Hz, 1H), 2.91 (dt, J=11.7, 2.8 Hz, 1H), 2.81 (s, 3H), 2.68 (dd, J=12.9, 10.5 Hz, 1H), 2.42-2.32 (s, 4H), 2.31-2.20 (m, 1H), 1.22 (d, J=6.3 Hz, 3H). ESI MS $[M+H]^+$ for $C_{23}H_{25}N_7S$, calcd 432.2, found 432.2.

Example 105: (1R,5S,8R)-3-(6-{[2-(3-Methylpyridin-2-yl)-[1,3]thiazolo[5,4-c]pyridin-6-yl]amino}pyridin-2-yl)-3-azabicyclo[3.2.1]octan-8-ol

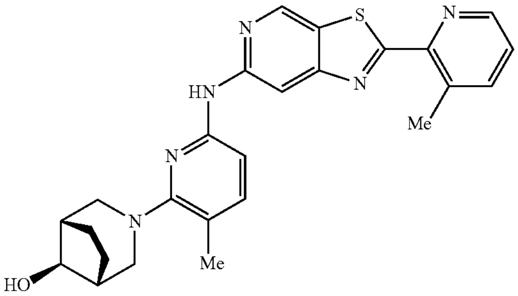

The title compound was synthesized in a similar fashion to example 89 from the appropriate starting materials. $^1$H NMR (400 MHz, DMSO-$d_6$) δ 9.47 (s, 1H), 8.94 (d, J=0.8 Hz, 1H), 8.71 (d, J=1.0 Hz, 1H), 8.57 (ddd, J=4.6, 1.7, 0.7 Hz, 1H), 7.86 (ddd, J=7.8, 1.7, 0.8 Hz, 1H), 7.48 (dd, J=7.8, 4.6 Hz, 1H), 7.34 (t, J=8.0 Hz, 1H), 6.57 (d, J=7.8 Hz, 1H), 6.11 (d, J=8.2 Hz, 1H), 4.73 (d, J=2.6 Hz, 1H), 3.96 (dd, J=12.2, 3.4 Hz, 2H), 3.85 (d, J=2.6 Hz, 1H), 2.92 (dd, J=11.6, 1.6 Hz, 2H), 2.82 (s, 3H), 2.13 (s, 2H), 1.83 (dt, J=6.7, 2.6 Hz, 2H), 1.43 (t, J=6.7 Hz, 2H). ESI MS [M+H]$^+$ for $C_{25}H_{26}N_6OS$, calcd 459.2, found 459.2.

Example 106: (1R,5S,8S)-3-(3-Methyl-6-{[2-(3-methylpyridin-2-yl)-[1,3]thiazolo[5,4-c]pyridin-6-yl]amino}pyridin-2-yl)-3-azabicyclo[3.2.1]octan-8-ol

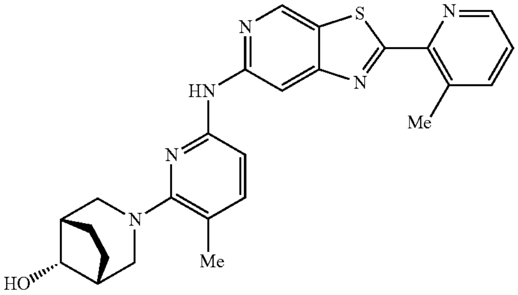

The title compound was synthesized in a similar fashion to example 89 from the appropriate starting materials. $^1$H NMR (400 MHz, DMSO-$d_6$) δ 9.81 (s, 1H), 8.99 (d, J=0.9 Hz, 1H), 8.82 (s, 1H), 8.67 (d, J=0.9 Hz, 1H), 8.64-8.56 (m, 1H), 8.38 (s, 1H), 7.91 (ddd, J=7.8, 1.6, 0.8 Hz, 1H), 7.52 (dd, J=7.8, 4.6 Hz, 1H), 7.46 (dd, J=7.9, 0.8 Hz, 1H), 6.75 (d, J=7.9 Hz, 1H), 5.19 (t, J=5.1 Hz, 1H), 3.67 (m, 2H), 3.25 (t, J=11.4 Hz, 2H), 3.04 (d, J=12.5 Hz, 2H), 2.85 (s, 3H), 2.63 (d, J=5.2 Hz, 2H), 2.21-2.10 (m, 4H), 1.86 (d, J=8.4 Hz, 2H). ESI MS [M+H]$^+$ for $C_{25}H_{26}N_6OS$, calcd 459.2, found 459.2.

Example 107: 6-{8-Methyl-3,8-diazabicyclo[3.2.1]octan-3-yl}-N-[2-(3-methylpyridin-2-yl)-[1,3]thiazolo[5,4-c]pyridin-6-yl]pyridin-2-amine

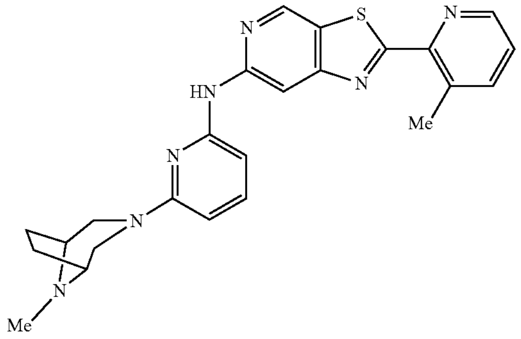 [SMILES: Cc1cccnc1-c1nc2cc(Nc3cccc(N4CC5CCC(C4)N5C)n3)ncc2s1]

The title compound was synthesized in a similar fashion to example 89 from the appropriate starting materials. $^1$H NMR (400 MHz, Chloroform-d) δ 8.82 (s, 1H), 8.57 (s, 1H), 8.56-8.53 (m, 1H), 7.72-7.64 (m, 1H), 7.39 (td, J=8.1, 0.8 Hz, 1H), 7.34-7.28 (m, 1H), 7.17 (s, 1H), 6.39 (d, J=7.8 Hz, 1H), 6.08 (d, J=8.2 Hz, 1H), 3.95-3.84 (m, 2H), 3.28-3.18 (m, 4H), 2.90 (s, 3H), 2.38 (s, 3H), 2.05-1.99 (m, 4H). ESI MS [M+H]$^+$ for $C_{24}H_{25}N_7S$, calcd 444.2 found 444.2.

Example 108: N-[2-(1-Methyl-1H-imidazol-2-yl)-[1,3]thiazolo[5,4-c]pyridin-6-yl]-6-[(1S,4S)-5-methyl-2,5-diazabicyclo[2.2.1]heptan-2-yl]pyridin-2-amine

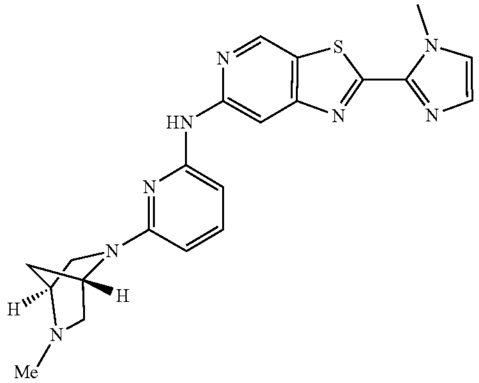 [SMILES: CN1C[C@@H]2C[C@H]1CN2c1cccc(Nc2cc3nc(-c4nccn4C)sc3cn2)n1]

The title compound was synthesized in a similar fashion to example 89 from the appropriate starting materials. $^1$H NMR (400 MHz, Chloroform-d) δ 8.69 (d, J=0.9 Hz, 1H), 8.57 (d, J=0.9 Hz, 1H), 7.72 (d, J=0.9 Hz, 1H), 7.61 (t, J=0.8 Hz, 1H), 7.36 (t, J=7.9 Hz, 1H), 7.21 (s, 1H), 6.28 (dd, J=7.8, 0.6 Hz, 1H), 5.92 (dd, J=8.1, 0.6 Hz, 1H), 4.68 (s, 1H), 4.11 (s, 3H), 3.61 (d, J=9.6 Hz, 1H), 3.53 (s, 1H), 3.40 (dd, J=9.6, 2.2 Hz, 1H), 3.06 (dd, J=9.5, 2.1 Hz, 1H), 2.73 (dd, J=9.5, 1.4 Hz, 1H), 2.41 (s, 3H), 1.99 (d, J=1.8 Hz, 1H), 1.88 (d, J=1.9 Hz, 1H). ESI MS [M+H]$^+$ for $C_{21}H_{22}N_8S$, calcd 419.2, found 419.7.

Example 109: 3-Fluoro-6-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

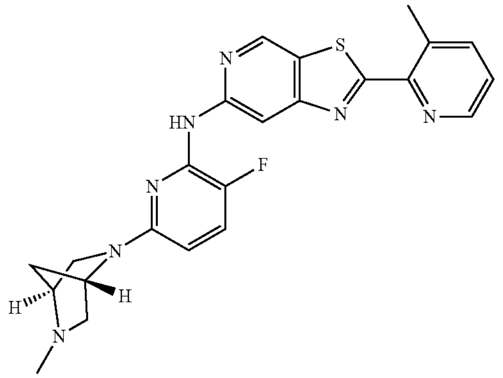 [SMILES: Cc1cccnc1-c1nc2cc(Nc3nc(N4C[C@@H]5C[C@H]4CN5C)ccc3F)ncc2s1]

The title compound was synthesized in a similar fashion to example 89 from the appropriate starting materials. $^1$H NMR (400 MHz, Methanol-$d_4$) δ 8.95 (s, 1H), 8.84 (s, 1H), 8.54-8.48 (m, 1H), 7.84-7.77 (m, 1H), 7.42 (dd, J=7.8, 4.6 Hz, 1H), 7.30 (dd, J=10.6, 8.7 Hz, 1H), 5.95 (dd, J=8.7, 2.0 Hz, 1H), 4.67 (s, 1H), 3.60 (d, J=10.6 Hz, 2H), 3.49 (dd, J=9.9, 2.1 Hz, 1H), 2.96 (dd, J=9.9, 2.1 Hz, 1H), 2.92-2.85 (m, 4H), 2.43 (s, 3H), 2.04 (d, J=9.9 Hz, 1H), 1.98 (d, J=9.9 Hz, 1H). ESI MS $[M+H]^+$ for $C_{23}H_{22}FN_7S$, calcd 448.2, found 448.2.

Example 110: 5-Chloro-6-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

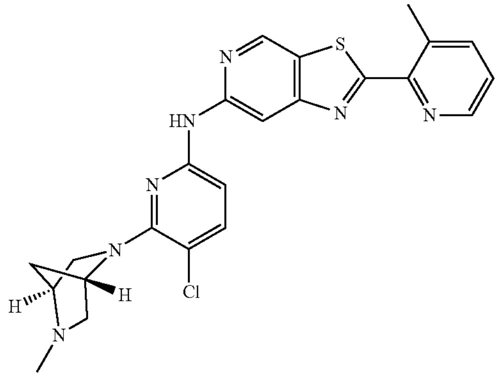 [SMILES: Cc1cccnc1-c1nc2cc(Nc3ccc(Cl)c(N4C[C@@H]5C[C@H]4CN5C)n3)ncc2s1]

The title compound was synthesized in a similar fashion to example 89 from the appropriate starting materials. $^1$H NMR (400 MHz, Methanol-$d_4$) δ 8.85 (d, J=0.9 Hz, 1H), 8.73 (s, 1H), 8.54 (d, J=4.6 Hz, 1H), 7.83 (d, J=7.8 Hz, 1H), 7.49-7.37 (m, 2H), 6.54 (d, J=8.4 Hz, 1H), 4.85 (s, 1H), 3.93 (dd, J=10.1, 2.3 Hz, 1H), 3.71 (dd, J=10.1, 1.4 Hz, 1H), 3.58 (s, 1H), 3.31-3.24 (m, 1H), 3.06 (dd, J=10.1, 2.3 Hz, 1H), 2.90 (s, 3H), 2.45 (s, 3H), 2.03 (d, J=10.1 Hz, 1H), 1.95 (d, J=10.1 Hz, 1H). ESI MS $[M+H]^+$ for $C_{23}H_{22}C_1N_7S$, calcd 464.1, found 464.1.

Example 111: 6-[(3aS,6aS)-1-Methyl-octahydropyrrolo[3,4-b]pyrrol-5-yl]-N-[2-(3-methylpyridin-2-yl)-[1,3]thiazolo[5,4-c]pyridin-6-yl]pyridin-2-amine

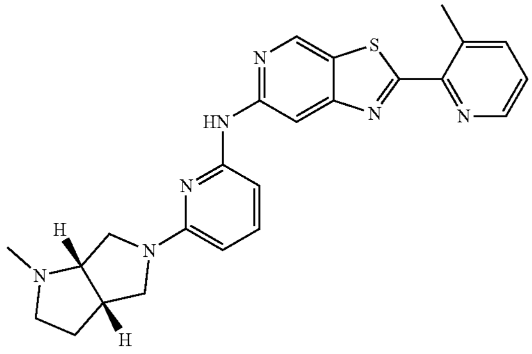 [SMILES: Cc1cccnc1-c1nc2cc(Nc3cccc(N4C[C@@H]5CCN(C)[C@@H]5C4)n3)ncc2s1]

The title compound was synthesized in a similar fashion to example 89 from the appropriate starting materials. $^1$H NMR (400 MHz, Chloroform-d) δ 8.91 (d, J=0.9 Hz, 1H), 8.80 (d, J=0.9 Hz, 1H), 8.54 (ddd, J=4.6, 1.7, 0.7 Hz, 1H), 7.65 (ddd, J=7.7, 1.7, 0.8 Hz, 1H), 7.35 (d, J=7.9 Hz, 1H), 7.33-7.27 (m, 1H), 7.23 (s, 1H), 6.21 (d, J=7.7 Hz, 1H), 5.93 (d, J=8.0 Hz, 1H), 3.84 (d, J=11.2 Hz, 1H), 3.68 (dd, J=10.0, 8.4 Hz, 1H), 3.45 (ddd, J=15.9, 10.6, 4.8 Hz, 2H), 3.16 (ddd, J=9.4, 7.6, 1.9 Hz, 1H), 3.00-2.82 (m, 5H), 2.42 (s, 3H), 2.35 (td, J=9.5, 7.6 Hz, 1H), 2.14 (dddd, J=12.7, 9.1, 7.6, 1.9 Hz, 1H), 1.80 (tdd, J=8.2, 6.6, 4.0 Hz, 1H). ESI MS $[M+H]^+$ for $C_{24}H_{25}N_7S$, calcd 444.2, found 444.6.

Example 112: 6-[(3aS,6aS)-1-Methyl-octahydropyrrolo[3,4-b]pyrrol-5-yl]-5-methyl-N-[2-(3-methylpyridin-2-yl)-[1,3]thiazolo[5,4-c]pyridin-6-yl]pyridin-2-amine

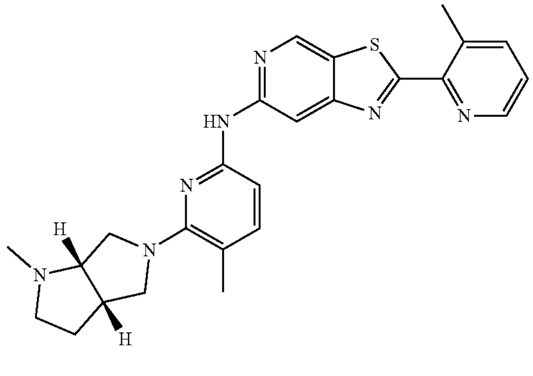 [SMILES: Cc1cccnc1-c1nc2cc(Nc3ccc(C)c(N4C[C@@H]5CCN(C)[C@@H]5C4)n3)ncc2s1]

The title compound was synthesized in a similar fashion to example 89 from the appropriate starting materials. $^1$H NMR (400 MHz, Chloroform-d) δ 8.81-8.78 (m, 2H), 8.55 (ddd, J=4.7, 1.6, 0.7 Hz, 1H), 7.66 (ddd, J=7.7, 1.6, 0.8 Hz, 1H), 7.30 (dd, J=7.7, 4.6 Hz, 1H), 7.20 (dd, J=7.8, 0.8 Hz, 1H), 7.15 (s, 1H), 6.38 (d, J=7.8 Hz, 1H), 3.71 (dd, J=11.0, 1.1 Hz, 1H), 3.63 (dd, J=10.0, 4.1 Hz, 1H), 3.52 (dd, J=11.1, 5.3 Hz, 1H), 3.38 (dd, J=10.0, 7.8 Hz, 1H), 3.11 (ddd, J=9.0, 7.0, 1.9 Hz, 1H), 2.97-2.80 (m, 5H), 2.43 (s, 3H), 2.37-2.31 (m, 1H), 2.27 (d, J=0.6 Hz, 3H), 2.12 (dddd, J=12.2, 8.7, 6.7, 1.9 Hz, 1H), 1.82 (ddt, J=12.7, 10.2, 6.8 Hz, 1H). ESI MS $[M+H]^+$ for $C_{25}H_{27}N_7S$, calcd 458.2, found 458.4.

Example 113: 6-[(8aS)—Octahydropyrrolo[1,2-a]pyrazin-2-yl]-N-[2-(3-methylpyridin-2-yl)-[1,3]thiazolo[5,4-c]pyridin-6-yl]pyridin-2-amine

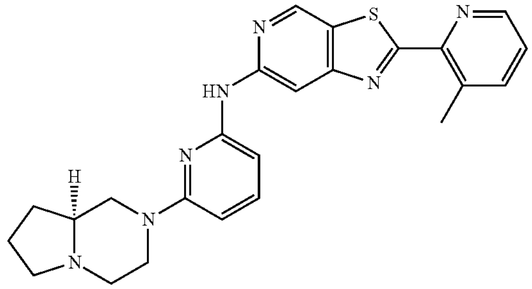 [SMILES: Cc1cccnc1-c1nc2cc(Nc3cccc(N4CCN5CCC[C@H]5C4)n3)ncc2s1]

The title compound was synthesized in a similar fashion to example 89 from the appropriate starting materials. $^1$H NMR (400 MHz, DMSO-$d_6$) δ 9.56 (s, 1H), 8.96 (d, J=0.8 Hz, 1H), 8.72 (d, J=1.0 Hz, 1H), 8.57 (ddd, J=4.6, 1.6, 0.7 Hz, 1H), 7.88 (ddd, J=7.7, 1.6, 0.8 Hz, 1H), 7.51 (dd, J=7.7, 4.6 Hz, 1H), 7.39 (t, J=8.0 Hz, 1H), 6.58 (d, J=7.8 Hz, 1H), 6.27 (d, J=8.2 Hz, 1H), 4.52 (d, J=11.8 Hz, 1H), 4.05 (d, J=12.2 Hz, 1H), 3.05-2.99 (m, 2H), 2.93-2.87 (m, 1H), 2.84 (s, 3H), 2.56 (t, J=11.1 Hz, 1H), 2.13 (d, J=11.1 Hz, 1H), 2.08-1.98 (m, 2H), 1.88-1.84 (m, 1H), 1.75-1.67 (m, 2H), 1.45-1.38 (m, 1H). ESI MS [M+H]$^+$ for $C_{24}H_{22}N_7S$, calcd 444.2, found 444.1.

Example 114: 6-[(8aR)—Octahydropyrrolo[1,2-a]pyrazin-2-yl]-N-[2-(3-methylpyridin-2-yl)-[1,3]thiazolo[5,4-c]pyridin-6-yl]pyridin-2-amine

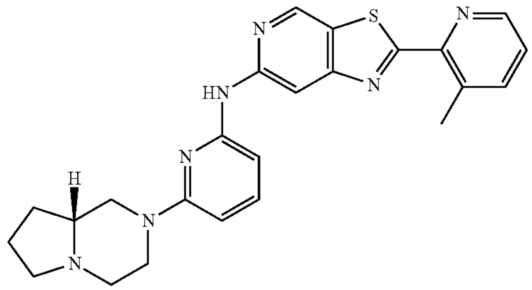 [SMILES: Cc1cccnc1-c1nc2cc(Nc3cccc(N4CCN5CCC[C@@H]5C4)n3)ncc2s1]

The title compound was synthesized in a similar fashion to example 89 from the appropriate starting materials. $^1$H NMR (400 MHz, DMSO-$d_6$) δ 9.57 (s, 1H), 8.96 (d, J=0.8 Hz, 1H), 8.72 (d, J=1.0 Hz, 1H), 8.58 (ddd, J=4.6, 1.6, 0.7 Hz, 1H), 7.89 (ddd, J=7.7, 1.6, 0.8 Hz, 1H), 7.51 (dd, J=7.7, 4.6 Hz, 1H), 7.39 (t, J=8.0 Hz, 1H), 6.58 (d, J=7.8 Hz, 1H), 6.27 (d, J=8.2 Hz, 1H), 4.52 (d, J=11.8 Hz, 1H), 4.07 (d, J=12.2 Hz, 1H), 3.05-2.99 (m, 2H), 2.93-2.87 (m, 1H), 2.84 (s, 3H), 2.56 (t, J=11.1 Hz, 1H), 2.17 (d, J=11.1 Hz, 1H), 2.06-1.95 (m, 2H), 1.90-1.86 (m, 1H), 1.75-1.67 (m, 2H), 1.42-1.38 (m, 1H). ESI MS [M+H]$^+$ for $C_{24}H_{25}N_7S$, calcd 444.2, found 444.1.

Example 115: 6-(1-Methylpiperidin-4-yl)-N-[2-(3-methylpyridin-2-yl)-[1,3]thiazolo[5,4-c]pyridin-6-yl]pyridin-2-amine

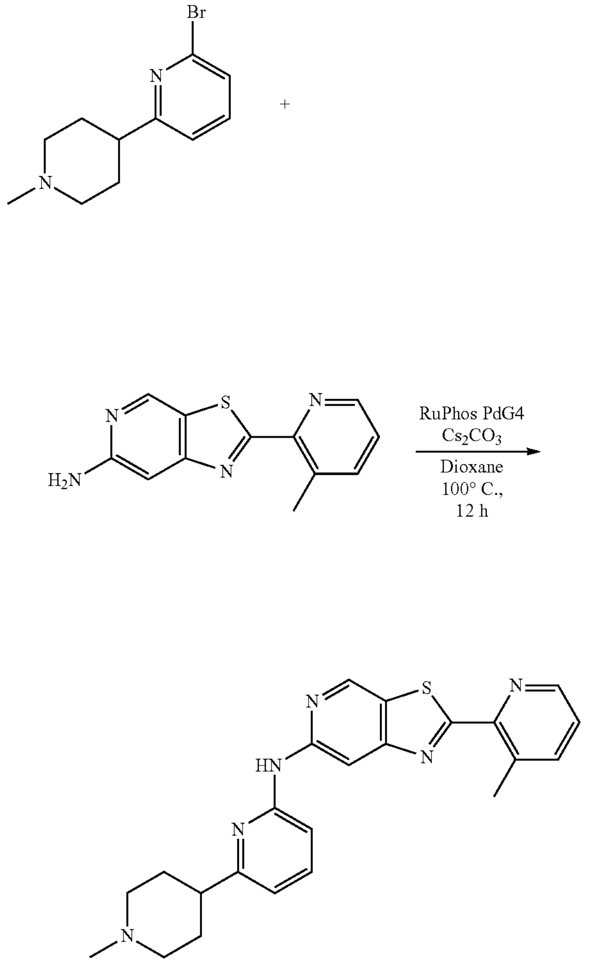

To a stirred solution of commercially available piperidinyl derivative (101 mg, 0.4 mmol) and 5-aminoazabenzothiazole derivative (97 mg, 0.4 mmol) (synthesized in a fashion similar to that described for steps 1-3 of example 1 from the appropriate starting materials) in Dioxane (5 ml) was added RuPhos PdG4 (34 mg, 0.04 mmol) and $Cs_2CO_3$ (390 mg 1.2 mmol). After degassing for 10 min under $N_2$ atmosphere, the reaction mixture was heated to 100° C. and stirred for 12 h. The reaction mixture filtered through Celite® and concentrated under reduced pressure. The resulting residue a was purified by flash column chromatography (silica gel; gradient: 0% to 30% MeOH in $CH_2Cl_2$) to get the desired compound. $^1$H NMR (400 MHz, DMSO-$d_6$) δ 9.75 (s, 1H), 8.99 (d, J=0.9 Hz, 1H), 8.70 (d, J=0.9 Hz, 1H), 8.59-8.58 (m, 1H), 7.90-7.87 (m, 1H), 7.57-7.49 (m, 2H), 7.29 (d, J=8.3 Hz, 1H), 6.74-6.72 (m, 1H), 2.84 (s, 5H), 2.59-2.50 (m, 1H), 2.18 (s, 3H), 1.97 (td, J=11.4, 2.9 Hz, 2H), 1.88-1.76 (m, 4H). ESI MS [M+H]$^+$ for $C_{23}H_{24}N_6S$, calcd 417.2, found 417.2.

Example 116: N-[2-(3-Methylpyridin-2-yl)-[1,3]thiazolo[5,4-c]pyridin-6-yl]-6-[(1S,4S)-5-(propan-2-yl)-2,5-diazabicyclo[2.2.1]heptan-2-yl]pyridin-2-amine

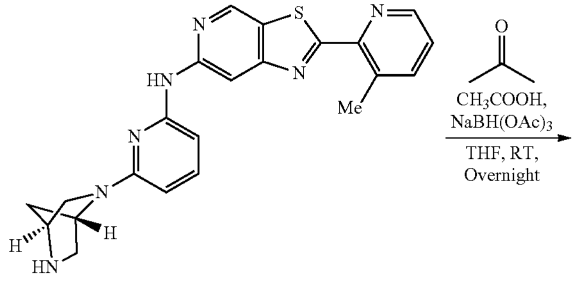

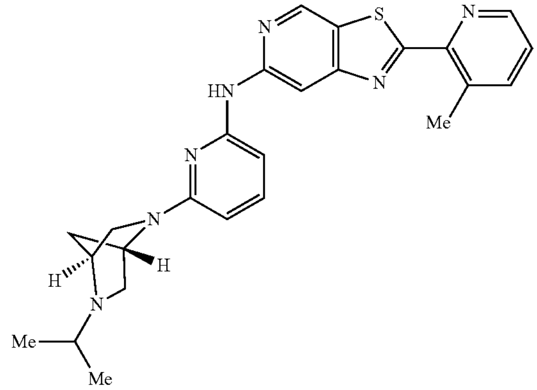

To a dry screw cap reaction vial containing septum, were added example 78 (120 mg, 0.288 mmol) and an excess of acetone (~4 mL) followed by acetic acid (0.132 mL, 2.309 mmol) and THF (5 mL). The reaction mixture was stirred at room temperature for 1 hour. After this, $NaBH(OAc)_3$ (122 mg, 0.577 mmol) was added and stirred overnight at room temperature. After confirming the complete conversion of starting material by LCMS, the reaction mixture was purified by preparative HPLC to afford the title compound (29 mg, 22%). $^1H$ NMR (400 MHz, Chloroform-d) δ 8.80 (dd, J=21.2, 0.9 Hz, 2H), 8.55 (ddd, J=4.6, 1.6, 0.7 Hz, 1H), 7.67 (ddd, J=7.7, 1.7, 0.8 Hz, 1H), 7.37 (t, J=7.9 Hz, 1H), 7.34-7.29 (m, 2H), 6.26 (d, J=7.7 Hz, 1H), 5.92 (d, J=8.0 Hz, 1H), 4.70 (s, 1H), 3.87 (s, 1H), 3.66 (d, J=9.8 Hz, 1H), 3.42 (dd, J=9.7, 2.1 Hz, 1H), 3.33 (dd, J=9.6, 2.2 Hz, 1H), 2.89 (s, 3H), 2.68-2.57 (m, 2H), 2.06 (d, J=9.4 Hz, 1H), 1.95 (d, J=9.2 Hz, 1H), 1.11 (d, J=6.2 Hz, 3H), 1.06 (d, J=6.1 Hz, 3H). ESI MS $[M+H]^+$ for $C_{25}H_{27}N_7S$, calcd 458.2, found 458.2.

Example 117: N-[2-(3-Methylpyridin-2-yl)-[1,3]thiazolo[5,4-c]pyridin-6-yl]-6-[(1S,4S)-5-(oxan-4-yl)-2,5-diazabicyclo[2.2.1]heptan-2-yl]pyridin-2-amine

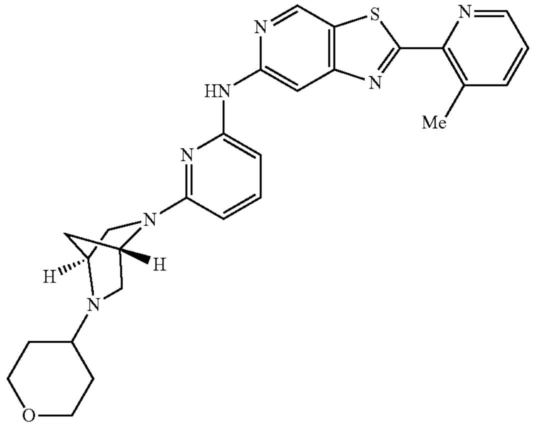 [SMILES: Cc1cccnc1-c1nc2cc(Nc3cccc(N4C[C@@H]5C[C@H]4CN5C4CCOCC4)n3)ncc2s1]

The title compound was synthesized in a similar fashion to example 116 from the appropriate starting materials. $^1H$ NMR (400 MHz, DMSO-$d_6$) δ δ 9.49 (s, 1H), 8.95 (d, J=0.9 Hz, 1H), 8.80 (d, J=0.9 Hz, 1H), 8.58 (ddd, J=4.6, 1.6, 0.6 Hz, 1H), 7.88 (ddd, J=7.8, 1.6, 0.8 Hz, 1H), 7.50 (dd, J=7.7, 4.6 Hz, 1H), 7.33 (t, J=7.9 Hz, 1H), 6.49 (d, J=7.8 Hz, 1H), 5.94 (d, J=8.0 Hz, 1H), 4.58 (s, 1H), 3.74 (d, J=25.2 Hz, 3H), 3.49 (m, 1H), 3.33 (m, 1H), 3.33-3.22 (m, 2H), 3.10 (d, J=9.1 Hz, 1H), 2.39 (m, 1H), 1.80 (s, 2H), 1.67 (t, J=14.0 Hz, 2H), 1.38-1.20 (m, 3H). ESI MS $[M+H]^+$ for $C_{27}H_{29}N_7SO$, calcd 500.2, found 500.1.

Example 118: 3-Methoxy-6-[(1S,4S)-5-methyl-2,5-diazabicyclo[2.2.1]heptan-2 yl]-N-[2-(3-methylpyridin-2-yl)-[1,3]thiazolo[5,4-c]pyridin-6-yl]pyridin-2-amine

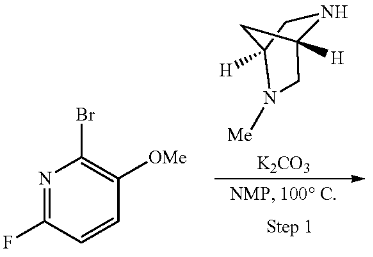

-continued

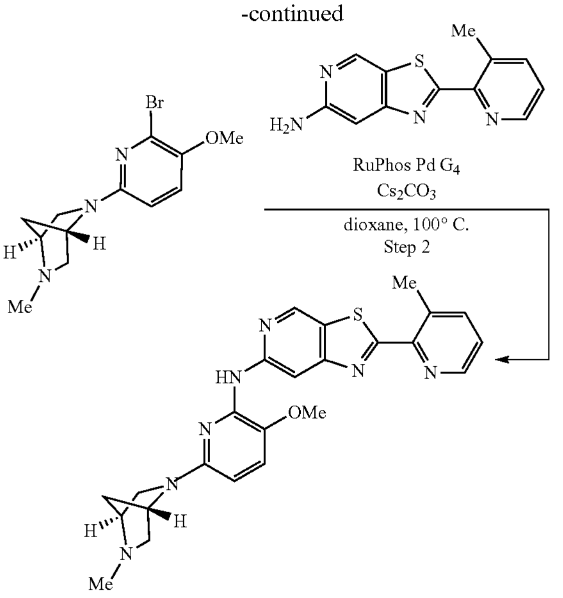

Step 1: A round-bottom flask was charged with 2-Bromo-6-fluoro-3-methoxypyridine (400 mg, 1.94 mmol), 2,5=Diazabicyclo[2.2.1]heptane, 2-methyl-, hydrobromide (1:2), (1S,4S) (532 mg, 1.94 mmol), $K_2CO_3$ (1.07 g, 7.76 mmol) and 3.9 mL of NMP and was stirred for 45 min at 100° C. The reaction mixture was then diluted with water and extracted with EtOAc. The combined organic extract was washed with a saturated solution of NaCl and the solvent was evaporated. The residue was purified using column chromatography on silica gel ($CH_2Cl_2$/MeOH 0%→10%) to afford the product (123 mg, 21%).

Step 2: The title compound was synthesized in a similar fashion to step 6 of example 1 wherein the aminoazabenzothiazole derivative was prepared in a similar fashion to that described in steps 1-3 of example 1 from the appropriate starting materials. $^1H$ NMR (400 MHz, DMSO-$d_6$) δ 8.96 (d, J=2.4, 2H), 8.57 (d, J=4.4 Hz, 1H), 7.90-7.84 (m, 2H), 7.49 (dd, J=7.8, 4.6 Hz, 1H), 7.23 (d, J=8.6 Hz, 1H), 5.96 (d, J=8.5 Hz, 1H), 4.51 (s, 1H), 3.79 (s, 3H), 3.54 (s, 1H), 3.48-3.44 (m, 1H), 3.37 (dd, J=9.6, 2.2 Hz, 1H), 2.90 (dd, J=9.6, 2.0 Hz, 1H), 2.82 (s, 3H), 2.71 (d, J=9.6 Hz, 1H), 2.31 (s, 3H), 1.92 (d, J=9.5 Hz, 1H), 1.84 (d, J=9.7 Hz, 1H). ESI MS $[M+H]^+$ for $C_{24}H_{25}N_7OS$, calcd 460.2, found 460.1.

Example 119: 4-Fluoro-6-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

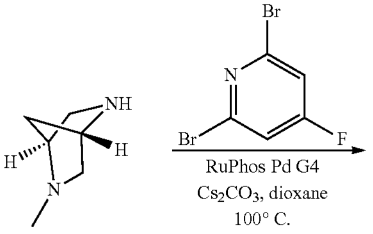

-continued

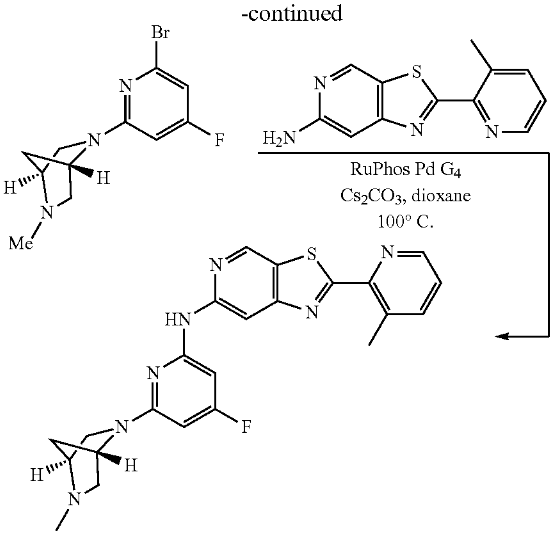

Step 1: To a mixture of (1S,4S)-2-methyl-2,5-diazabicyclo[2.2.1]heptane.2HBr (328 mg, 1.20 mmol) and 2,6-dibromo-4-fluoropyridine (508 mg, 2 mmol) in dioxane (10 mL) was added RuPhos Pd G4 (200 mg, 0.24 mmol) and $Cs_2CO_3$ (1.17 g 3.6 mmol). After degassing for 10 min under $N_2$ atmosphere, the reaction mixture was heated at 100° C. for 15 h. The reaction mixture was filtered through a pad of Celite® and the filtrate was concentrated under reduced pressure. The resulting residue was purified by column chromatography (silica gel; gradient: 0-30% MeOH/$CH_2Cl_2$) to obtain the desired intermediate (84 mg, 24%).

Step 2: To a stirred solution of intermediate obtained from step 1 (84 mg, 0.3 mmol) and aminoazabenzothiazole derivative (63 mg, 0.26 mmol) (obtained in a fashion similar to that described in steps 1-3 of example 1 from the appropriate starting materials) in dioxane (3 mL) was added RuPhos Pd G4 (37 mg, 0.05 mmol) and $Cs_2CO_3$ (224 mg 0.7 mmol). After degassing for 10 min under $N_2$ atmosphere, the reaction mixture was heated at 100° C. for 15 h. The reaction mixture was filtered through a pad of Celite® and the filtrate was concentrated under reduced pressure. The resulting residue a was purified by column chromatography (silica gel; gradient: 0-20% MeOH/$CH_2Cl_2$) to obtain the desired compound (74 mg, 64%). $^1H$ NMR (400 MHz, Methanol-$d_4$) δ 8.87 (d, J=0.9 Hz, 1H), 8.64 (d, J=0.9 Hz, 1H), 8.56-8.52 (m, 1H), 7.85-7.81 (m, 1H), 7.44 (dd, J=7.8, 4.6 Hz, 1H), 6.35 (dd, J=11.2, 1.8 Hz, 1H), 5.76 (dd, J=11.2, 1.8 Hz, 1H), 4.75 (s, 1H), 3.64-3.56 (m, 2H), 3.50-3.42 (m, 1H), 2.96 (dd, J=10.0, 2.1 Hz, 1H), 2.92-2.84 (m, 4H), 2.45 (s, 3H), 2.05 (d, J=9.9 Hz, 1H), 1.96 (d, J=9.9 Hz, 1H). ESI MS $[M+H]^+$ for $C_{23}H_{22}FN_7S$, calcd 448.2, found 448.2.

Example 120: 2-{4-[6-({2-[(1S,4S)-2,5-Diazabicyclo[2.2.1]heptan-2-yl]pyrimidin-4-yl}amino)-[1,3]thiazolo[5,4-c]pyridin-2-yl]pyridin-2-yl}propan-2-ol

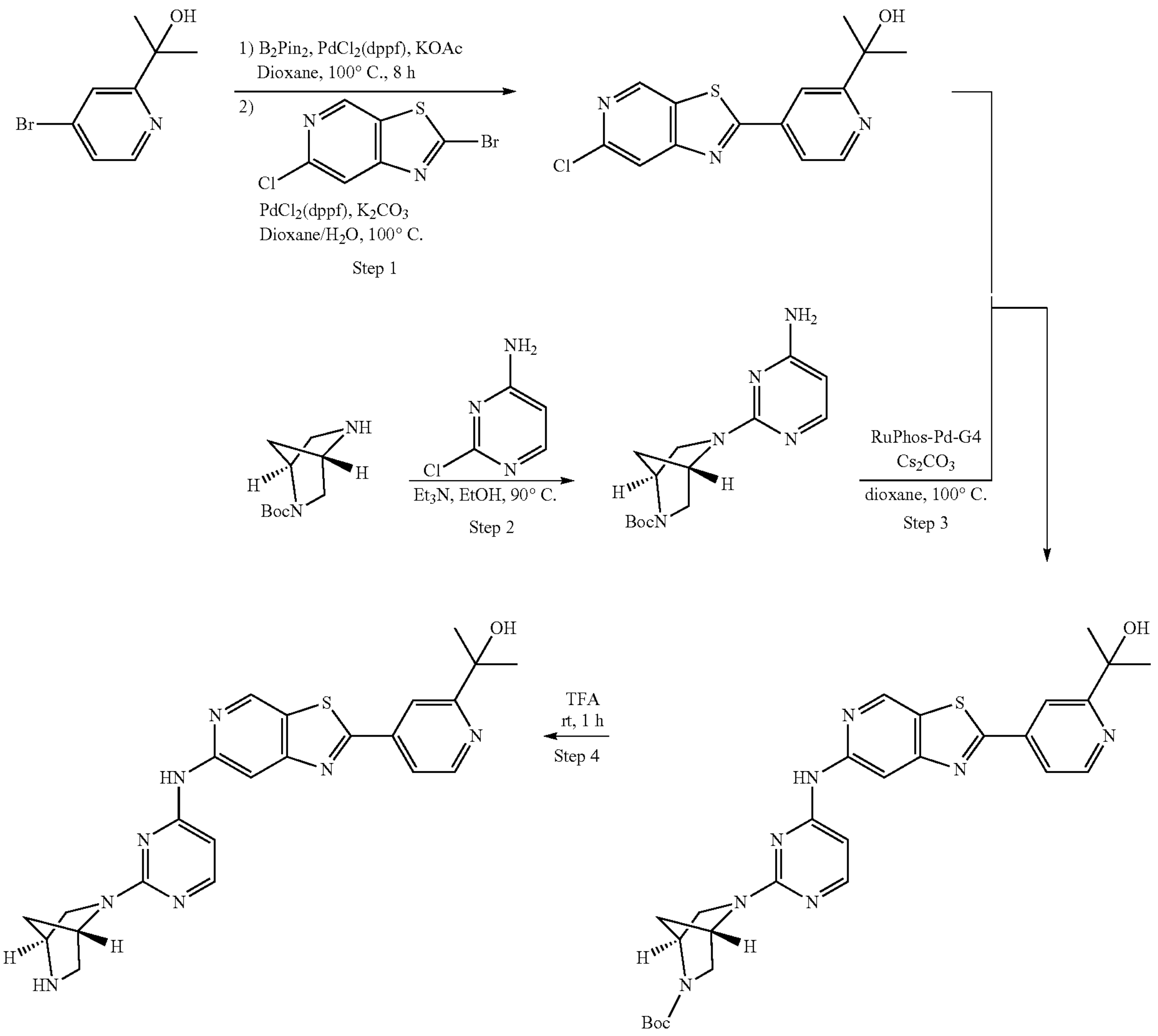

Step 1: To a solution of 2-(4-Bromopyridin-2-yl)propan-2-ol (1.08 g, 5 mmol) and Bis(pinacolato)diboron (1.34 g, 5.2 mmol) in Dioxane (15 mL) was added $PdCl_2$(dppf) (366 mg, 0.5 mmol) and KOAc (980 mg, 10.0 mmol). After degassing for 25 min with $N_2$, the reaction mixture was heated to 100° C. and stirred for 8 h. The reaction mixture was cooled down to RT, filtered and concentrated in vacuo. To this crude reaction mixture, 2-bromo-6-chloro[1,3]thiazolo[5,4-c]pyridine (1.25 g, 5.0 mmol), $PdCl_2$(dppf) (366 mg, 0.5 mmol) and $K_2CO_3$ (1.38 g, 1.0 mmol) and Dioxane (12 mL)/$H_2O$ (3 mL) was added. After degassing for 25 min with $N_2$, the reaction mixture was heated to 100° C. and stirred for 4 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 70% EtOAc in hexanes) to get the desired derivative (890 mg, 59%) as off-white solid.

Step 2: To a stirred suspension of (1S,4S)-2-Boc-2,5-diazabicyclo[2.2.1]heptane (297 mg, 1.5 mmol), 4-amino-2-chloropyrimidine (194 mg, 1.50 mmol) in EtOH (3 mL) was added triethylamine (0.42 mL, 3.00 mmol) dropwise. The reaction was stirred at 90° C. for 20 h. The reaction was cooled to room temperature, diluted with $CH_2Cl_2$, washed with saturated brine, dried over anhydrous $Na_2SO_4$, and concentrated under reduced pressure to obtain desired intermediate in quantitative yield.

Step 3 and Step 4: These transformations were performed in a similar fashion to step 2 and step 3 protocol respectively for the synthesis of example 78. $^1H$ NMR (400 MHz, Methanol-$d_4$) δ 8.86 (s, 1H), 8.76 (s, 1H), 8.64 (d, J=0.8 Hz, 1H), 8.32 (dd, J=1.8, 0.8 Hz, 1H), 7.88-7.79 (m, 2H), 6.30 (s, 1H), 4.87 ($s_{br}$, 1H), 3.83 (s, 1H), 3.60 (s, 2H), 3.03 (s, 2H), 1.92 (d, J=9.4 Hz, 1H), 1.82 (d, J=9.9 Hz, 1H), 1.59 (s, 6H). ESI MS [M+H]$^+$ for $C_{23}H_{24}N_8OS$, calcd 461.2, found 461.2.

Example 121: 2-{4-[6-({2-[(1S,4S)-5-Methyl-2,5-diazabicyclo[2.2.1]heptan-2-yl]pyrimidin-4-yl}amino)-[1,3]thiazolo[5,4-c]pyridin-2-yl]pyridin-2-yl}propan-2-ol

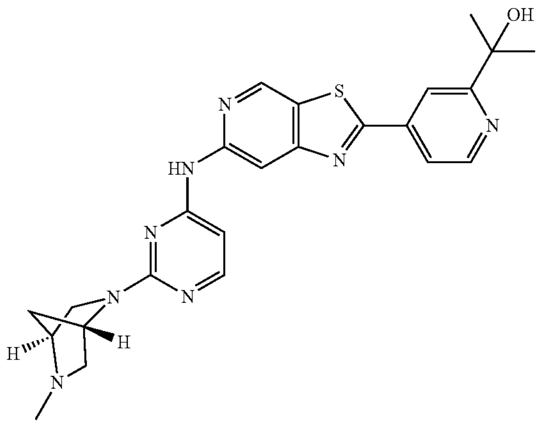 [SMILES: CN1C[C@@H]2C[C@H]1CN2c1nccc(Nc2cc3nc(-c4ccnc(C(C)(C)O)c4)sc3cn2)n1]

The title compound was synthesized in a similar fashion to steps 1, 2, and 3 of example 120 from the appropriate starting materials. $^1$H NMR (400 MHz, Chloroform-d) δ 8.88 (s, 1H), 8.69 (dd, J=5.1, 0.8 Hz, 1H), 8.13 (s, 1H), 8.07-8.02 (m, 1H), 7.84 (dd, J=5.1, 1.6 Hz, 1H), 7.64 (s, 1H), 6.19 (s, 1H), 5.80-5.35 (m, 1H), 4.83 ($s_{br}$, 1H), 4.64 ($s_{br}$, 1H), 3.86 ($s_{br}$, 1H), 3.56 ($s_{br}$, 1H), 3.10-2.95 (m, 1H), 2.73 (d, J=9.6 Hz, 1H), 2.45 (s, 3H), 1.99-1.78 (d, 2H), 1.64 (s, 6H). ESI MS $[M+H]^+$ for $C_{24}H_{26}N_8OS$, calcd 475.2, found 475.4.

Example 122: 2-{3-[6-({2-[(1S,4S)-5-Methyl-2,5-diazabicyclo[2.2.1]heptan-2-yl]pyrimidin-4-yl}amino)-[1,3]thiazolo[5,4-c]pyridin-2-yl]phenyl}propan-2-ol

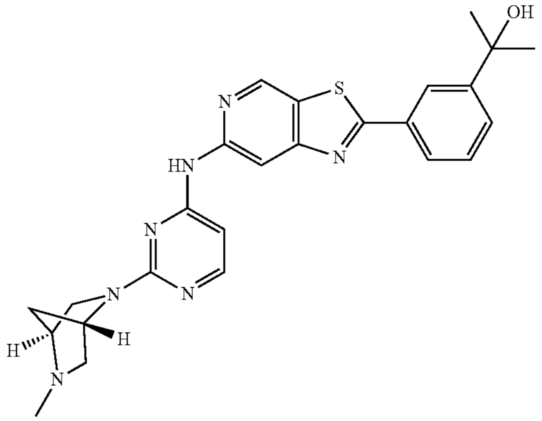 [SMILES: CN1C[C@@H]2C[C@H]1CN2c1nccc(Nc2cc3nc(-c4cccc(C(C)(C)O)c4)sc3cn2)n1]

The title compound was synthesized in a similar fashion to steps 1, 2, and 3 of example 120 from the appropriate starting materials. $^1$H NMR (400 MHz, Chloroform-d) δ 8.79 (t, J=0.8 Hz, 1H), 8.61 (d, J=36.7 Hz, 1H), 8.28 (t, J=1.9 Hz, 1H), 8.04 (d, J=5.7 Hz, 1H), 8.01-7.97 (m, 1H), 7.66 (ddt, J=7.9, 1.8, 0.8 Hz, 1H), 7.51-7.43 (m, 2H), 6.22 (s, 1H), 4.84 (s, 1H), 3.88 (s, 1H), 3.59 (s, 1H), 3.08 (s, 1H), 2.71 (dd, J=9.7, 1.3 Hz, 1H), 2.46 (s, 3H), 2.03 (d, J=10.8 Hz, 3H), 1.88 (d, J=9.8 Hz, 1H), 1.65 (s, 6H). ESI MS $[M+H]^+$ for $C_{25}H_{27}N_7OS$, calcd 474.2, found 474.4.

Example 123: (3S)-1-{3-[6-({2-[(1S,4S)-5-Methyl-2,5-diazabicyclo[2.2.1]heptan-2-yl]pyrimidin-4-yl}amino)-[1,3]thiazolo[5,4-c]pyridin-2-yl]phenyl}pyrrolidin-3-ol

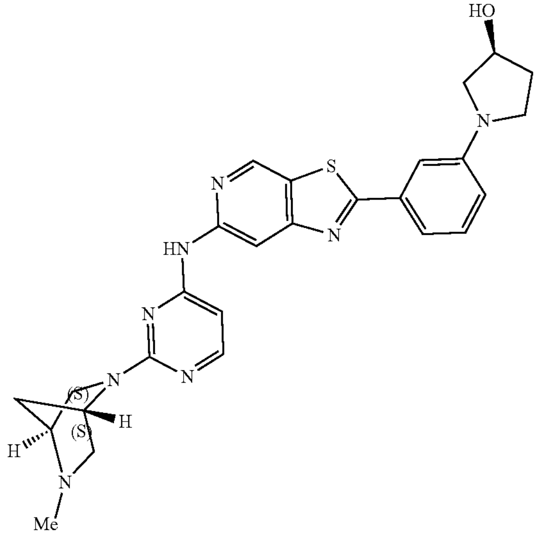

The title compound was synthesized in a similar fashion to steps 1, 2, and 3 of example 120 from the appropriate starting materials. $^1$H NMR (400 MHz, Methanol-$d_4$) δ 8.75 (d, J=0.9 Hz, 1H), 8.64 ($s_{br}$, 1H), 7.92-7.89 (m, 1H), 7.42 (d, J=1.2 Hz, 1H), 7.33-7.28 (m, 2H), 7.20 (dd, J=2.7, 1.4 Hz, 1H), 6.77-6.68 (m, 1H), 6.33 (d, J=5.8 Hz, 1H), 4.80-4.73 (m, 1H), 4.54 (dq, J=5.1, 2.7 Hz, 1H), 3.80 (s, 1H), 3.59-3.50 (m, 4H), 3.41 (td, J=8.7, 3.6 Hz, 1H), 2.99 (s, 1H), 2.68 (d, J=9.9 Hz, 1H), 2.40 (s, 3H), 2.14 (ddd, J=13.3, 8.9, 4.9 Hz, 1H), 2.10-2.02 (m, 1H), 2.02-1.94 (m, 1H), 1.93-1.86 (m, 1H). ESI MS $[M+H]^+$ for $C_{26}H_{28}N_8OS$, calcd 501.2, found 501.8.

Example 124: N-(2-{4-[(3S)-3-Fluoropyrrolidin-1-yl]pyridin-2-yl}-[1,3]thiazolo[5,4-c]pyridin-6-yl)-6-[(1S,4S)-5-methyl-2,5-diazabicyclo[2.2.1]heptan-2-yl]pyrazin-2-amine

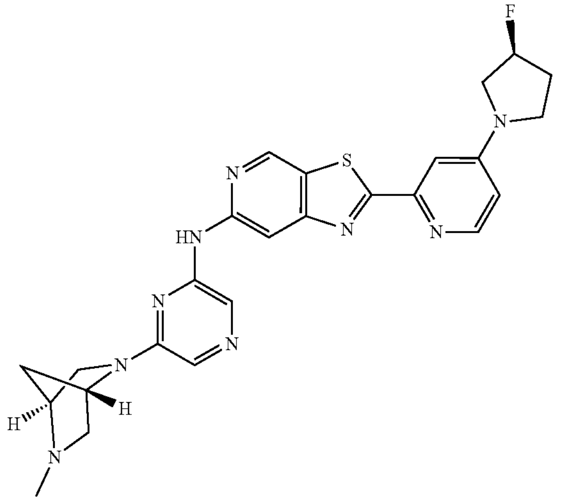 [SMILES: CN1C[C@@H]2C[C@H]1CN2c1cncc(Nc2cc3nc(-c4cc(N5CC[C@H](F)C5)ccn4)sc3cn2)n1]

The title compound was synthesized in a similar fashion to steps 1, 2, and 3 of example 120 from the appropriate starting materials. $^1$H NMR (400 MHz, $CDCl_3$) δ 8.85 (d, J=0.9 Hz, 1H), 8.70 (s, 1H), 8.33 (dd, J=5.2, 0.8 Hz, 1H), 8.07 (d, J=5.7 Hz, 1H), 7.56 (s, 1H), 7.18 (dd, J=5.3, 1.5 Hz, 1H), 7.08 (dd, J=1.5, 0.8 Hz, 1H), 6.28 (d, J=5.7 Hz, 1H), 5.51-5.48 (m, 1H), 5.36-5.31 (m, 1H), 4.90 (s, 1H), 3.97-3.91 (m, 2H), 3.84-3.79 (m, 1H), 3.74-3.68 (m, 2H), 2.83 (d, J=10.0 Hz, 1H), 2.55 (s, 4H), 2.51-2.41 (m, 1H), 2.31-2.25 (m, 1H), 2.18-2.13 (m, 2H), 2.02 (s, 2H), 1.97 (d, J=10.1 Hz, 1H). ESI MS $[M+H]^+$ for $C_{25}H_{26}N_9SF$, calcd 504.2, found 504.1.

Example 125: N-(2-{4-[(3R)-3-Dluoropyrrolidin-1-yl]pyridin-2-yl}-[1,3]thiazolo[5,4-c]pyridin-6-yl)-6-[(1S,4S)-5-methyl-2,5-diazabicyclo[2.2.1]heptan-2-yl]pyrazin-2-amine

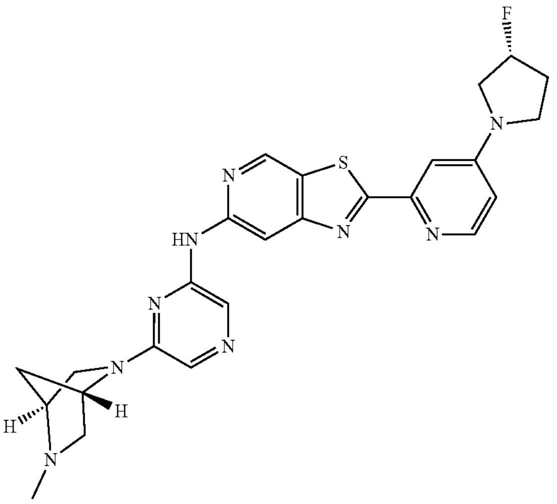 [SMILES: CN1C[C@@H]2C[C@H]1CN2c1cncc(Nc2cc3nc(-c4cc(N5CC[C@@H](F)C5)ccn4)sc3cn2)n1]

The title compound was synthesized in a similar fashion to steps 1, 2, and 3 of example 120 from the appropriate starting materials. $^1$H NMR (400 MHz, DMSO-$d_6$) δ 9.74 (s, 1H), 9.00 (d, J=0.9 Hz, 1H), 8.37 (d, J=0.9 Hz, 1H), 8.24 (d, J=5.8 Hz, 1H), 8.06 (s, 1H), 7.43 (s, 1H), 7.41 (d, J=2.5 Hz, 1H), 5.48 (d, J=53.3 Hz, 1H), 4.64 (s, 1H), 3.74-3.72 (m, 1H), 3.61 (d, J=10.6 Hz, 2H), 3.50 (q, J=10.0 Hz, 3H), 3.39 (d, J=2.2 Hz, 1H), 2.87 (dd, J=9.5, 2.0 Hz, 1H), 2.52 (d, J=9.5 Hz, 1H), 2.30-2.24 (m, 4H), 2.16-2.14 (m, 1H), 1.90 (d, J=9.4 Hz, 1H), 1.78 (d, J=9.3 Hz, 1H). ESI MS $[M+H]^+$ for $C_{25}H_{26}N_9SF$, calcd 504.2, found 504.1.

Example 126: 2-[(1S,4S)-5-Methyl-2,5-diazabicyclo[2.2.1]heptan-2-yl]-N-{2-[3-(pyrrolidine-1-carbonyl)phenyl]-[1,3]thiazolo[5,4-c]pyridin-6-yl}pyrimidin-4-amine

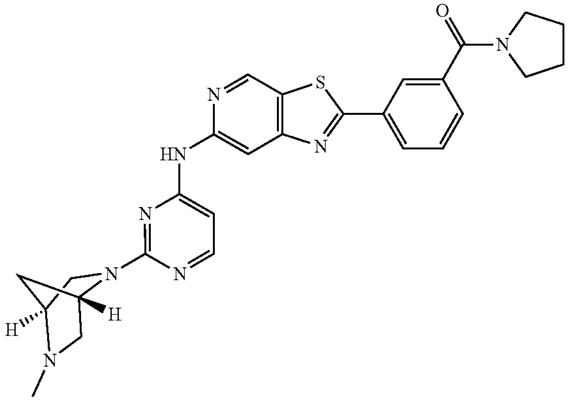 [SMILES: CN1C[C@@H]2C[C@H]1CN2c1nccc(Nc2cc3nc(-c4cccc(C(=O)N5CCCC5)c4)sc3cn2)n1]

The title compound was synthesized in a similar fashion to steps 1, 2, and 3 of example 120 from the appropriate starting materials. $^1$H NMR (400 MHz, Chloroform-d) δ 8.90-8.53 (m, 2H), 8.31 (s, 1H), 8.18 (ddd, J=7.7, 1.9, 1.2 Hz, 1H), 8.06 (d, J=5.6 Hz, 1H), 7.69 (dt, J=7.7, 1.5 Hz, 1H), 7.57 (td, J=7.7, 0.5 Hz, 1H), 7.49 (s, 1H), 6.20 (br s, 1H), 4.85 (br s, 1H), 3.89 (br s, 1H), 3.70 (t, J=7.0 Hz, 2H), 3.64-3.36 (m, 4H), 3.23-2.90 (m, 1H), 2.72 (d, J=9.9 Hz, 1H), 2.47 (s, 3H), 2.10-1.86 (m, 6H). ESI MS $[M+H]^+$ for $C_{27}H_{28}N_8OS$, calcd 513.2, found 513.2.

Example 127: N,N-Dimethyl-4-[6-({2-[(1S,4S)-5-methyl-2,5-diazabicyclo[2.2.1]heptan-2-yl]pyrimidin-4-yl}amino)-[1,3]thiazolo[5,4-c]pyridin-2-yl]pyridine-2-carboxamide

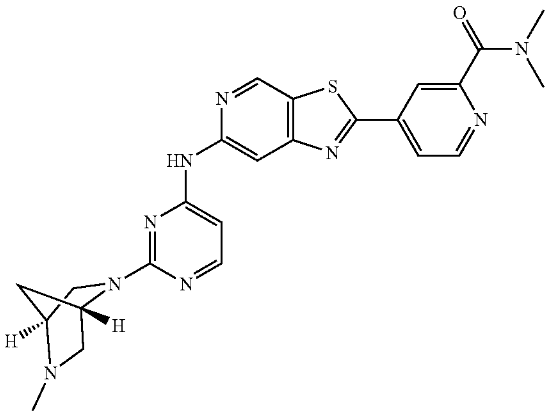 [SMILES: CN(C)C(=O)c1cc(-c2nc3cc(Nc4ccnc(N5C[C@@H]6C[C@H]5CN6C)n4)ncc3s2)ccn1]

The title compound was synthesized in a similar fashion to steps 1, 2, and 3 of example 120 from the appropriate starting materials. $^1$H NMR (400 MHz, DMSO-$d_6$) δ 10.05 (s, 1H), 9.14 (d, J=0.9 Hz, 1H), 8.93-8.85 (m, 1H), 8.79 (dd, J=5.1, 0.9 Hz, 1H), 8.71 (s, 1H), 8.21-8.08 (m, 2H), 7.97 (d, J=5.5 Hz, 1H), 6.47 (bs, 1H), 4.66 (bs, 1H), 3.64 (bs, 1H), 3.44 (d, J=8.9 Hz, 2H), 3.03 (s, 3H), 2.96 (s, 3H), 2.79 (bs, 1H), 2.51 (bs, 1H), 2.28 (s, 3H), 1.85 (bs, 1H), 1.76 (bs, 1H). ESI MS $[M+H]^+$ for $C_{24}H_{25}N_9SO$, calcd 488.2, found 488.1.

Example 128: 3-[6-({6-[(1S,4S)-5-Methyl-2,5-diazabicyclo[2.2.1]heptan-2-yl]pyridin-2-yl}amino)-[1,3]thiazolo[5,4-c]pyridin-2-yl]benzamide

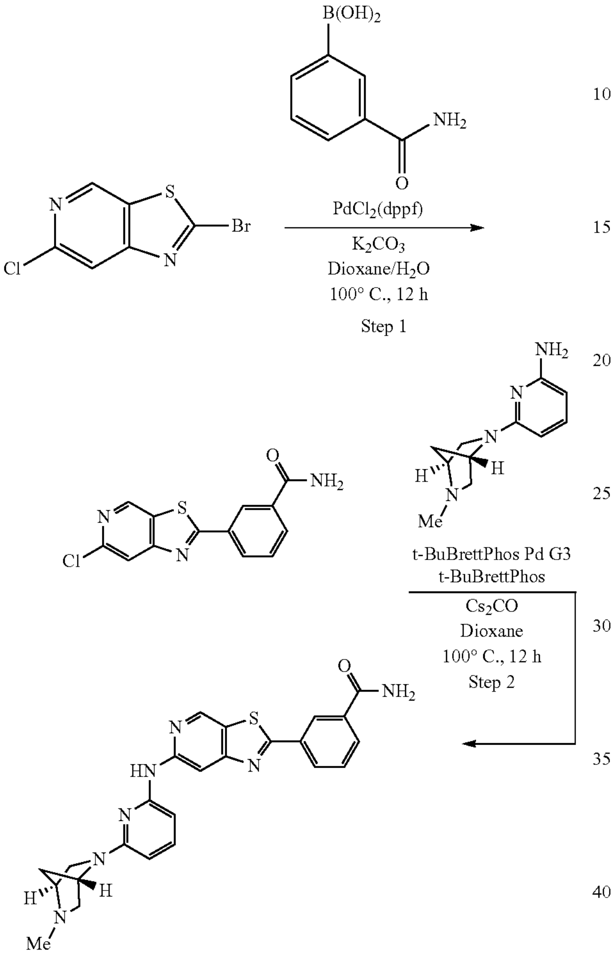

Step 1: To a solution of Azabenzothiozole (1.0 g, 4.0 mmol) and Boronic acid (560 mg, 4.0 mmol) in Dioxane (20 mL)/$H_2O$ (5 mL) was added $PdCl_2$(dppf) (292 mg, 0.4 mmol) and $K_2CO_3$ (1.10 g, 8.0 mmol). After degassing for 10 min with $N_2$, the reaction mixture was heated to 100° C. and stirred for 4 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 100% EtOAc in hexanes) to get imine intermediate (508 mg, 44%) as a white solid.

Step 2: To a stirred solution of Chloro azabenzothiozole intermediate from step 1 (114 mg, 0.4 mmol) and amine (82 mg, 0.4 mmol) (prepared in a fashion similar to that described in step 2 of example 120 using the appropriate starting materials) in Dioxane (5 mL) was added t-BuBrettPhos Pd G3 (34 mg, 0.04 mmol) t-BuBrettPhos (39 mg, 0.08 mmol) and $Cs_2CO_3$ (390 mg 1.2 mmol). After degassing for 10 min under $N_2$ atmosphere, the reaction mixture was heated to 100° C. and stirred for 12 h. The reaction mixture filtered through Celite® and concentrated under reduced pressure. The resulting residue a was purified by flash column chromatography (silica gel; gradient: 0% to 30% MeOH in $CH_2Cl_2$) to get the desired compound. $^1H$ NMR (400 MHz, DMSO-$d_6$) δ 9.49 (s, 1H), 8.98 (d, J=0.8 Hz, 1H), 8.83 (m, 1H), 8.52 (t, J=1.8 Hz, 1H), 8.27-8.24 (m, 2H), 8.09-8.07 (m, 1H), 7.66 (t, J=7.8 Hz, 1H), 7.58 (s, 1H), 7.33 (t, J=7.9 Hz, 1H), 6.55 (d, J=7.8 Hz, 1H), 5.94 (d, J=8.0 Hz, 1H), 4.55 (s, 1H), 3.47 (d, J=14.9 Hz, 2H), 3.34 (dd, J=9.6, 2.2 Hz, 1H), 2.84 (dd, J=9.5, 2.0 Hz, 1H), 2.53 (d, J=9.3 Hz, 1H), 2.26 (s, 3H), 1.88 (d, J=9.3 Hz, 1H), 1.95-1.76 (m, 1H). ESI MS $[M+H]^+$ for $C_{24}H_{23}N_7SO$, calcd 458.2, found 458.1.

Example 129: N-[2-(2,6-Dimethylpyridin-3-yl)-[1,3]thiazolo[5,4-c]pyridin-6-yl]-6-[(1S,4S)-5-methyl-2,5-diazabicyclo[2.2.1]heptan-2-yl]pyridin-2-amine

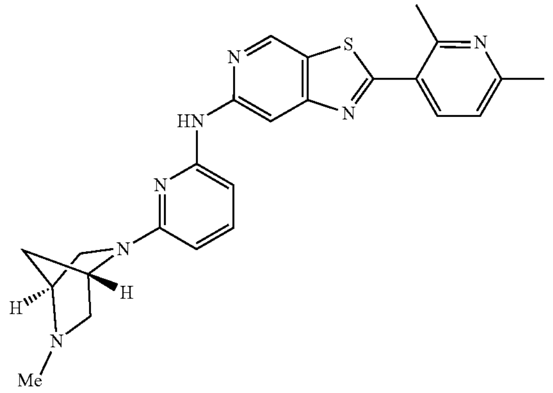 [SMILES: Cc1ccc(-c2nc3cc(Nc4cccc(N5C[C@@H]6C[C@H]5CN6C)n4)ncc3s2)c(C)n1]

The title compound was synthesized in a similar fashion to example 128 from the appropriate starting materials. $^1H$ NMR (400 MHz, DMSO-$d_6$) δ 9.50 (s, 1H), 8.97 (d, J=0.8 Hz, 1H), 8.75 (d, J=0.9 Hz, 1H), 8.10 (d, J=8.0 Hz, 1H), 7.35-7.28 (m, 2H), 6.51 (d, J=7.8 Hz, 1H), 5.93 (d, J=8.0 Hz, 1H), 4.55 (s, 1H), 3.45 (d, J=14.3 Hz, 2H), 3.33 (d, J=2.2 Hz, 1H), 2.83 (dd, J=9.3, 2.0 Hz, 1H), 2.76 (s, 3H), 2.55-2.52 (m, 1H), 2.50 (s, 3H), 2.25 (s, 3H), 1.85 (d, J=9.3 Hz, 1H), 1.75 (d, J=9.2 Hz, 1H). ESI MS $[M+H]^+$ for $C_{24}H_{25}N_7S$, calcd 444.2, found 444.1.

Example 130: 6-[(1S,4S)-5-Methyl-2,5-diazabicyclo[2.2.1]heptan-2-yl]-N-{2-[3-(pyrrolidine-1-carbonyl)phenyl]-[1,3]thiazolo[5,4-c]pyridin-6-yl}pyridin-2-amine

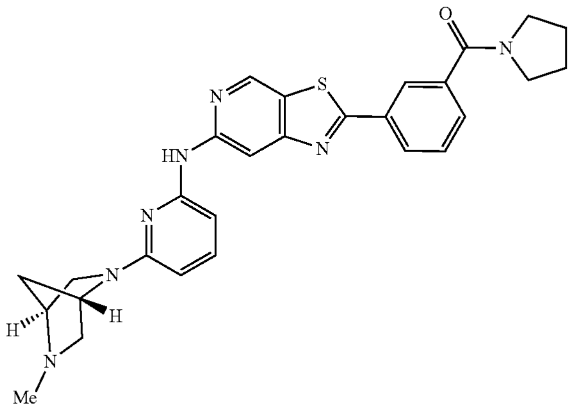 [SMILES: CN1C[C@@H]2C[C@H]1CN2c1cccc(Nc2cc3nc(-c4cccc(C(=O)N5CCCC5)c4)sc3cn2)n1]

The title compound was synthesized in a similar fashion to example 128 from the appropriate starting materials. $^1H$ NMR (400 MHz, DMSO-$d_6$) δ 9.49 (s, 1H), 8.96 (d, J=0.8 Hz, 1H), 8.68 (d, J=0.9 Hz, 1H), 8.16 (dd, J=2.3, 1.4 Hz, 2H), 7.74 (dt, J=7.7, 1.4 Hz, 1H), 7.63 (dd, J=8.4, 7.7 Hz, 1H), 7.33 (t, J=7.9 Hz, 1H), 6.53 (d, J=7.8 Hz, 1H), 5.93 (d, J=8.0 Hz, 1H), 4.54 (s, 1H), 3.47 (dd, J=13.0, 6.0 Hz, 4H), 3.41 (t, J=6.4 Hz, 2H), 3.37 (m, 1H), 2.84 (dd, J=9.4, 2.0 Hz, 1H), 2.53 (d, J=9.3 Hz, 1H), 1.88-1.75 (m, 6H). ESI MS $[M+H]^+$ for $C_{28}H_{29}N_7SO$, calcd 512.2, found 512.3.

Example 131: N-[2-(5-Methanesulfonylpyridin-3-yl)-[1,3]thiazolo[5,4-c]pyridin-6-yl]-6-[(1S,4S)-5-methyl-2,5-diazabicyclo[2.2.1]heptan-2-yl]pyridin-2-amine

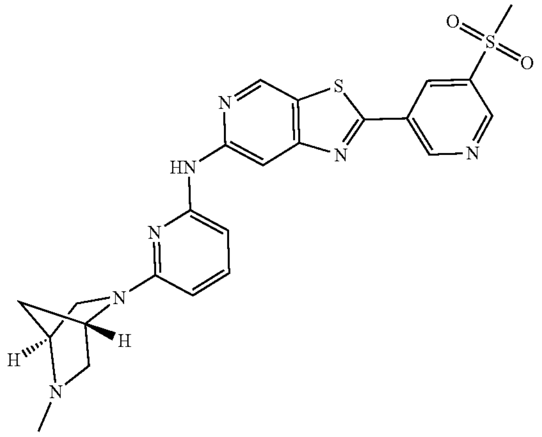 [SMILES: CN1C[C@@H]2C[C@H]1CN2c1cccc(Nc2cc3nc(-c4cncc(S(C)(=O)=O)c4)sc3cn2)n1]

The title compound was synthesized in a similar fashion to example 128 from the appropriate starting materials. $^1H$ NMR (400 MHz, DMSO-$d_6$) δ 9.63-9.50 (m, 2H), 9.25 (d, J=2.1 Hz, 1H), 9.06 (d, J=0.9 Hz, 1H), 8.83 (t, J=2.2 Hz, 1H), 8.74 (d, J=0.9 Hz, 1H), 7.34 (t, J=8.0 Hz, 1H), 6.54 (d, J=7.8 Hz, 1H), 5.95 (d, J=8.1 Hz, 1H), 4.54 (s, 1H), 3.49 (m, 1H), 3.35 (dd, J=9.4, 2.1 Hz, 1H), 3.32-3.30 (m, 4H), 2.86-2.83 (m, 1H), 2.54-2.46 (m, 1H), 2.26 (s, 3H), 1.88 (d, J=9.2 Hz, 1H), 1.77 (d, J=9.2 Hz, 1H). ESI MS $[M+H]^+$ for $C_{23}H_{23}N_7S_2O_2$, calcd 494.2, found 494.2.

Example 132: 2-{3-[6-({6-[(1S,4S)-5-Methyl-2,5-diazabicyclo[2.2.1]heptan-2-yl]pyridin-2-yl}amino)-[1,3]thiazolo[5,4-c]pyridin-2-yl]phenyl}propan-2-ol

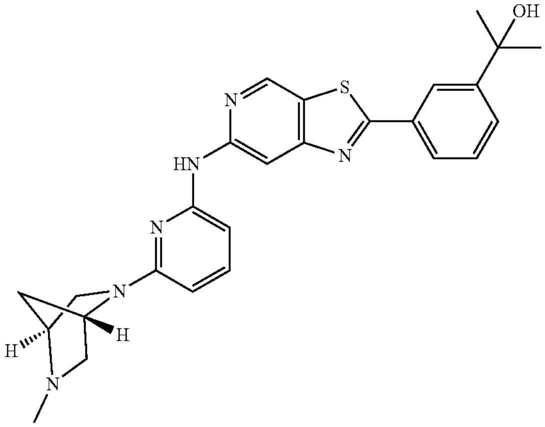 [SMILES: CN1C[C@@H]2C[C@H]1CN2c1cccc(Nc2cc3nc(-c4cccc(C(C)(C)O)c4)sc3cn2)n1]

The title compound was synthesized in a similar fashion to example 128 from the appropriate starting materials. $^1H$ NMR (400 MHz, Chloroform-d) δ 8.69 (d, J=0.9 Hz, 1H), 8.54 (d, J=0.9 Hz, 1H), 8.23 (t, J=1.8 Hz, 1H), 7.91 (ddd, J=7.7, 1.9, 1.1 Hz, 1H), 7.61 (ddd, J=7.9, 1.9, 1.1 Hz, 1H), 7.54 (s, 1H), 7.41 (t, J=7.8 Hz, 1H), 7.33 (d, J=7.9 Hz, 1H), 6.31 (d, J=7.7 Hz, 1H), δ 5.87 (d, J=8.2 Hz, 1H), 4.63 (s, 1H), 3.59 (d, J=9.7 Hz, 1H), 3.49 (d, J=2.1 Hz, 1H), 3.43-3.36 (m, 1H), 3.01 (dd, J=9.6, 2.1 Hz, 1H), 2.68 (dd, J=9.6, 1.4 Hz, 1H), 2.37 (s, 3H), 1.99-1.97 (m, 3H), 1.96 (s, 6H). ESI MS $[M+H]^+$ for $C_{26}H_{28}N_6OS$, calcd 473.2, found 473.4.

Example 133: 3-[6-({6-[(1S,4S)-5-Methyl-2,5-diazabicyclo[2.2.1]heptan-2-yl]pyridin-2-yl}amino)-[1,3]thiazolo[5,4-c]pyridin-2-yl]benzonitrile

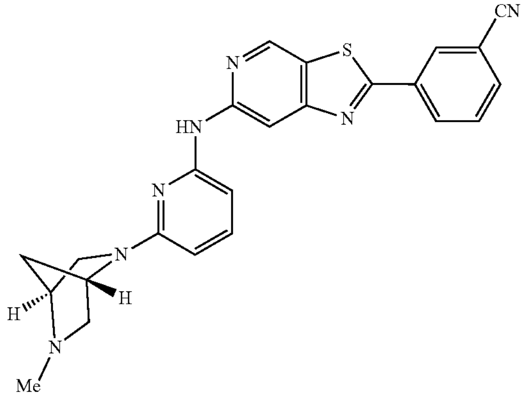 [SMILES: CN1C[C@@H]2C[C@H]1CN2c1cccc(Nc2cc3nc(-c4cccc(C#N)c4)sc3cn2)n1]

The title compound was synthesized in a similar fashion to example 128 from the appropriate starting materials. $^1H$ NMR (400 MHz, Chloroform-d) δ 8.79 (d, J=0.8 Hz, 1H), 8.70 (d, J=0.9 Hz, 1H), 8.43 (t, J=1.7 Hz, 1H), 8.30 (dt, J=8.0, 1.5 Hz, 1H), 7.80 (dt, J=7.8, 1.4 Hz, 1H), 7.63 (t, J=7.8 Hz, 1H), 7.36 (t, J=7.9 Hz, 1H), 7.26 (s, 1H), 6.25 (d, J=7.7 Hz, 1H), 5.93 (d, J=8.1 Hz, 1H), 4.66 (s, 1H), 3.64 (d, J=9.7 Hz, 1H), 3.56 (s, 1H), 3.46 (dd, J=9.6, 2.2 Hz, 1H), 3.06 (dd, J=9.5, 2.1 Hz, 1H), 2.78-2.70 (m, 1H), 2.43 (s, 3H), 2.10-2.02 (m, 1H), 1.96-1.85 (m, 1H). ESI MS $[M+H]^+$ for $C_{24}H_{21}N_7S$, calcd 440.2, found 440.1.

Example 134: N-(2-{8-Methyl-1H,2H,3H-pyrido[2,3-b][1,4]oxazin-7-yl}-[1,3]thiazolo[5,4-c]pyridin-6-yl)-6-[(1S,4S)-5-methyl-2,5-diazabicyclo[2.2.1]heptan-2-yl]pyridin-2-amine

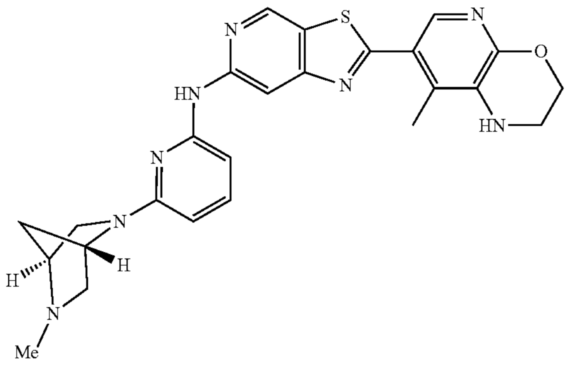 [SMILES: Cc1c(-c2nc3cc(Nc4cccc(N5C[C@@H]6C[C@H]5CN6C)n4)ncc3s2)cnc2c1NCCO2]

The title compound was synthesized in a similar fashion to example 128 from the appropriate starting materials. $^1$H NMR (400 MHz, DMSO-$d_6$) δ 9.47 (s, 1H), 8.92 (d, J=0.8 Hz, 1H), 8.72 (d, J=0.9 Hz, 1H), 7.80 (s, 1H), 7.32 (t, J=7.9 Hz, 1H), 6.51 (d, J=7.8 Hz, 1H), 5.92 (d, J=7.9 Hz, 12H), 4.55 (s, 1H), 4.36 (m, 2H), 3.44 (m, 2H), 3.39 (m, 2H), 3.30 (m, 2H), 3.13 (s, 1H), 2.81 (dd, J=9.3, 2.1 Hz, 1H), 2.53 (d, J=9.4 Hz, 1H), 2.33 (s, 3H), 2.25 (s, 3H), 1.84 (d, J=9.3 Hz, 1H), 1.85-1.74 (m, 1H). ESI MS $[M+H]^+$ for $C_{25}H_{26}N_8SO$, calcd 487.2, found 487.2.

Example 135: N-Methyl-3-[6-({6-[(1S,4S)-5-methyl-2,5-diazabicyclo[2.2.1]heptan-2-yl]pyridin-2-yl}amino)-[1,3]thiazolo[5,4-c]pyridin-2-yl]benzamide

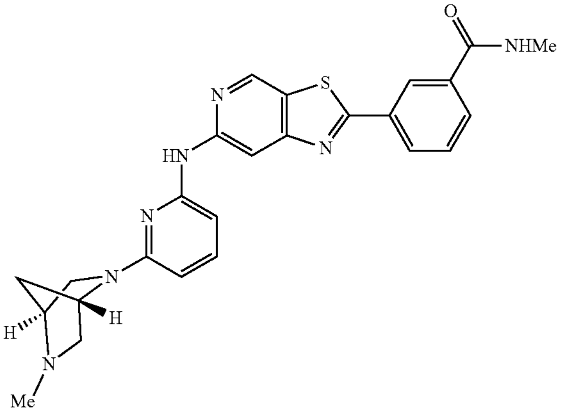 [SMILES: CNC(=O)c1cccc(-c2nc3cc(Nc4cccc(N5C[C@@H]6C[C@H]5CN6C)n4)ncc3s2)c1]

The title compound was synthesized in a similar fashion to example 128 from the appropriate starting materials. $^1$H NMR (400 MHz, DMSO-$d_6$) δ 9.50 (s, 1H), 8.98 (d, J=0.8 Hz, 1H), 8.75 (q, J=4.3 Hz, 1H), 8.66 (d, J=0.9 Hz, 1H), 8.50 (t, J=1.8 Hz, 1H), 8.24 (ddd, J=7.8, 1.9, 1.1 Hz, 1H), 8.05-8.03 (m, 1H), 7.67 (t, J=7.8 Hz, 1H), 7.33 (t, J=7.9 Hz, 1H), 6.55 (d, J=7.8 Hz, 1H), 5.94 (d, J=8.0 Hz, 1H), 4.55 (s, 1H), 3.46 (s, 2H), 3.34 (dd, J=9.4, 2.1 Hz, 1H), 2.86-2.80 (m, 4H), 2.58 (m, 1H), 2.26 (s, 3H), 1.88 (d, J=9.3 Hz, 1H), 1.79-1.76 (m, 1H). ESI MS $[M+H]^+$ for $C_{25}H_{25}N_7SO$, calcd 472.2, found 472.2.

Example 136: N-[2-(3-Methanesulfonylphenyl)-[1,3]thiazolo[5,4-c]pyridin-6-yl]-6-[(1S,4S)-5-methyl-2,5-diazabicyclo[2.2.1]heptan-2-yl]pyridin-2-amine

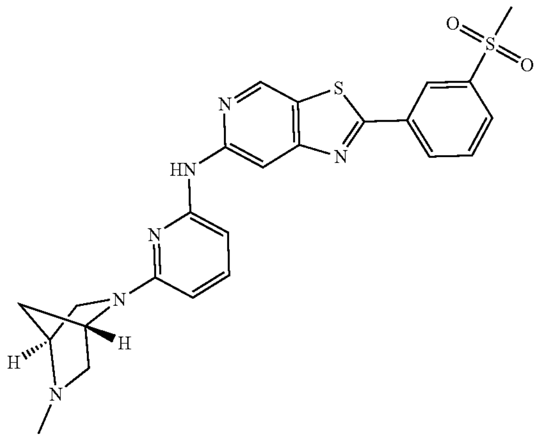 [SMILES: CN1C[C@@H]2C[C@H]1CN2c1cccc(Nc2cc3nc(-c4cccc(S(C)(=O)=O)c4)sc3cn2)n1]

The title compound was synthesized in a similar fashion to example 128 from the appropriate starting materials. $^1$H NMR (400 MHz, DMSO-$d_6$) δ 8.81 (d, J=0.9 Hz, 1H), 8.68 (td, J=1.8, 0.5 Hz, 1H), 8.57 (d, J=0.9 Hz, 1H), 8.39 (ddd, J=7.8, 1.8, 1.1 Hz, 1H), 8.10 (ddd, J=7.9, 1.8, 1.1 Hz, 1H), 7.75 (td, J=7.8, 0.5 Hz, 1H), 7.41 (t, J=8.0 Hz, 1H), 7.28 (s, 1H), 6.37 (d, J=7.8 Hz, 1H), 6.10 (m, 1H), 4.81 (s, 1H), 3.93 (s, 1H), 3.83 (d, J=10.6 Hz, 1H), 3.69 (m, 1H), 3.37 (s, 1H), 3.15 (s, 4H), 3.02 (s, 1H), 2.64 (s, 4H), 2.31 (d, J=10.7 Hz, 1H), 2.12 (d, J=10.5 Hz, 1H). ESI MS $[M+H]^+$ for $C_{24}H_{24}N_6S_2O_2$, calcd 493.1, found 493.1.

Example 137: N,N-Dimethyl-3-[6-({6-[(1S,4S)-5-methyl-2,5-diazabicyclo[2.2.1]heptan-2-yl]pyridin-2-yl}amino)-[1,3]thiazolo[5,4-c]pyridin-2-yl]benzamide

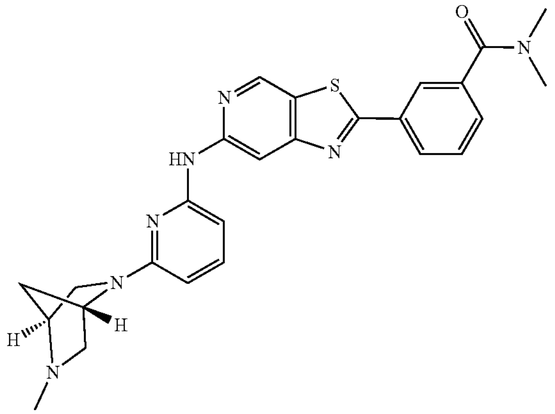 [SMILES: CN(C)C(=O)c1cccc(-c2nc3cc(Nc4cccc(N5C[C@@H]6C[C@H]5CN6C)n4)ncc3s2)c1]

The title compound was synthesized in a similar fashion to example 128 from the appropriate starting materials. $^1$H NMR (400 MHz, DMSO-$d_6$) δ 9.49 (s, 1H), 8.97 (d, J=0.8 Hz, 1H), 8.67 (d, J=0.9 Hz, 1H), 8.16 (ddd, J=5.6, 3.4, 1.9 Hz, 1H), 8.06 (dt, J=2.0, 0.9 Hz, 1H), 7.65-7.63 (m, 2H), 7.33 (t, J=7.9 Hz, 1H), 6.54 (d, J=7.8 Hz, 1H), 5.94 (d, J=8.0 Hz, 1H), 4.54 (s, 1H), 3.47 (d, J=13.1 Hz, 2H), 3.41 (m, 1H), 3.00 (s, 3H), 2.93 (s, 3H), 2.84 (dd, J=9.2, 2.0 Hz, 1H), 2.53 (d, J=9.3 Hz, 1H), 1.88 (d, J=9.2 Hz, 1H), 1.77 (d, J=9.2 Hz, 1H). ESI MS $[M+H]^+$ for $C_{26}H_{27}N_7S$, calcd 486.2, found 486.1.

Example 138: 6-[(1S,4S)-5-Methyl-2,5-diazabicyclo[2.2.1]heptan-2-yl]-N-[2-(2-methylpyridin-3-yl)-[1,3]thiazolo[5,4-c]pyridin-6-yl]pyridin-2-amine

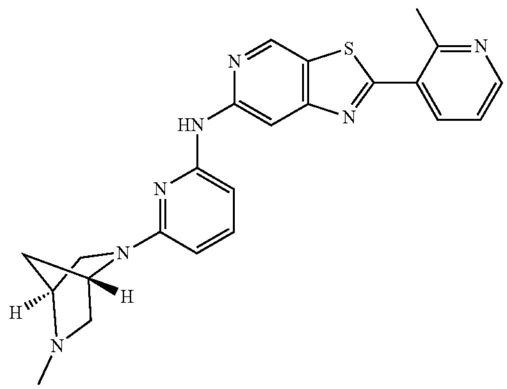 [SMILES: Cc1ncccc1-c1nc2cc(Nc3cccc(N4C[C@@H]5C[C@H]4CN5C)n3)ncc2s1]

The title compound was synthesized in a similar fashion to example 128 from the appropriate starting materials. $^1$H NMR (400 MHz, DMSO-$d_6$) δ 9.53 (s, 1H), 9.00 (d, J=0.9 Hz, 1H), 8.79 (d, J=0.9 Hz, 1H), 8.62 (dd, J=4.8, 1.7 Hz, 1H), 8.20 (dd, J=7.9, 1.7 Hz, 1H), 7.44 (ddd, J=7.9, 4.8, 0.7 Hz, 1H), 7.33 (t, J=7.9 Hz, 1H), 6.50 (d, J=7.8 Hz, 1H), 5.93 (d, J=8.0 Hz, 1H), 4.55 (s, 1H), 3.45-3.43 (m, 2H), 3.33 (d, J=2.2 Hz, 1H), 2.83 (dd, J=9.3, 2.1 Hz, 1H), 2.79 (s, 3H), 2.54 (d, J=9.3 Hz, 1H), 2.25 (s, 3H), 1.85 (d, J=9.1 Hz, 1H), 1.77-1.74 (m, 1H). ESI MS $[M+H]^+$ for $C_{23}H_{23}N_7S$, calcd 430.2, found 430.1.

Example 139: 6-[(1S,4S)-5-Methyl-2,5-diazabicyclo[2.2.1]heptan-2-yl]-N-[2-(4-methylpyridin-3-yl)-[1,3]thiazolo[5,4-c]pyridin-6-yl]pyridin-2-amine

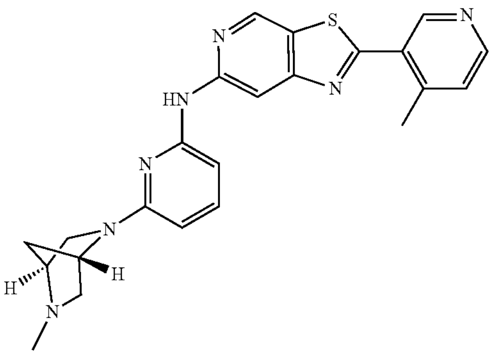 [SMILES: Cc1ccncc1-c1nc2cc(Nc3cccc(N4C[C@@H]5C[C@H]4CN5C)n3)ncc2s1]

The title compound was synthesized in a similar fashion to example 128 from the appropriate starting materials. $^1$H NMR (400 MHz, $CDCl_3$) δ 8.81 (d, J=0.9 Hz, 1H), 8.64-8.61 (m, 2H), 8.09 (dd, J=7.8, 1.7 Hz, 1H), 7.39 (t, J=7.9 Hz, 1H), 7.32-7.28 (m, 2H), 6.35 (d, J=7.8 Hz, 1H), 5.94 (dd, J=8.1, 0.5 Hz, 1H), 4.76 (s, 1H), 3.75 (m, 2H), 3.52 (dd, J=10.3, 2.2 Hz, 1H), 3.24 (d, J=9.8 Hz, 1H), 2.89 (m, 4H), 2.55 (s, 3H), 2.18 (d, J=10.1 Hz, 1H), 2.02 (d, J=10.1 Hz, 1H). ESI MS $[M+H]^+$ for $C_{23}H_{23}N_7S$, calcd 430.2, found 430.1.

Example 140: 3-[6-({6-[(1S,4S)-2,5-Diazabicyclo[2.2.1]heptan-2-yl]pyridin-2-yl}amino)-[1,3]thiazolo[5,4-c]pyridin-2-yl]-N,N-dimethylbenzamide

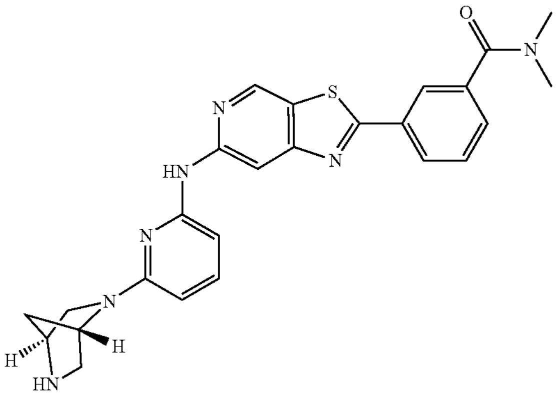 [SMILES: CN(C)C(=O)c1cccc(-c2nc3cc(Nc4cccc(N5C[C@@H]6C[C@H]5CN6)n4)ncc3s2)c1]

The title compound was synthesized in a similar fashion to example 78 using the appropriate starting materials. $^1$H NMR (400 MHz, DMSO-$d_6$) δ 9.48 (d, J=3.9 Hz, 1H), 8.96 (d, J=0.9 Hz, 1H), 8.73 (d, J=5.9 Hz, 1H), 8.16 (td, J=3.8, 1.8 Hz, 1H), 8.06 (dt, J=2.1, 1.0 Hz, 1H), 7.73-7.55 (m, 2H), 7.45-7.26 (m, 1H), 6.48 (dd, J=13.0, 7.8 Hz, 1H), 5.92 (d, J=8.1 Hz, 1H), 4.57 (s, 1H), 3.65 (s, 1H), 3.52 (m, 2H), 3.38 (m, 1H), 3.00 (s, 3H), 2.92 (s, 3H), 2.86 (d, J=7.8 Hz, 1H), 1.79 (bs, 1H), 1.66 (d, J=9.2 Hz, 1H). ESI MS $[M+H]^+$ for $C_{25}H_{25}N_7SO$, calcd 472.2, found 472.1.

Example 141: 6-[(1S,4S)-2,5-Diazabicyclo[2.2.1]heptan-2-yl]-N-[2-(3-methanesulfonylphenyl)-[1,3]thiazolo[5,4-c]pyridin-6-yl]pyridin-2-amine

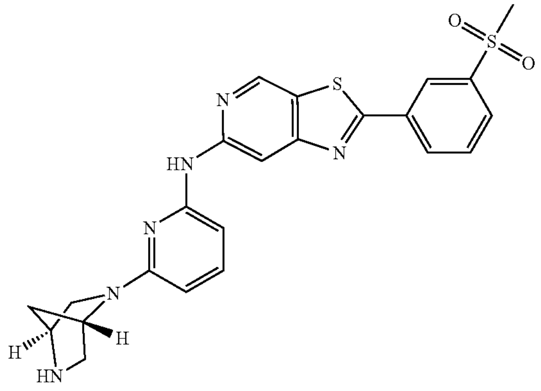 [SMILES: CS(=O)(=O)c1cccc(-c2nc3cc(Nc4cccc(N5C[C@@H]6C[C@H]5CN6)n4)ncc3s2)c1]

The title compound was synthesized in a similar fashion to example 78 using the appropriate starting materials. $^1$H NMR (400 MHz, DMSO-$d_6$) δ 9.51 (d, J=4.1 Hz, 1H), 9.00 (d, J=0.8 Hz, 1H), 8.78 (s, 1H), 8.54 (d, J=1.9 Hz, 1H), 8.43 (dd, J=8.0, 1.6 Hz, 1H), 8.16 (s, 1H), 8.15-8.08 (m, 1H), 7.86 (t, J=7.8 Hz, 1H), 7.30 (t, J=7.9 Hz, 1H), 6.46 (d, J=7.8 Hz, 1H), 5.90 (d, J=8.5 Hz, 1H), 4.57 (s, 1H), 4.24 (s, 1H), 3.46 (d, J=8.6 Hz, 1H), 3.00 (s, 3H), 3.27 (m, 2H), 2.85 (s, 1H), 1.79 (m, 2H). ESI MS $[M+H]^+$ for $C_{23}H_{22}N_6S_2O_2$, calcd 479.2, found 479.1.

Example 142: 6-[(1S,4S)-2,5-Diazabicyclo[2.2.1]heptan-2-yl]-N-{2-[3-(1,3,4-oxadiazol-2-yl)phenyl]-[1,3]thiazolo[5,4-c]pyridin-6-yl}pyridin-2-amine

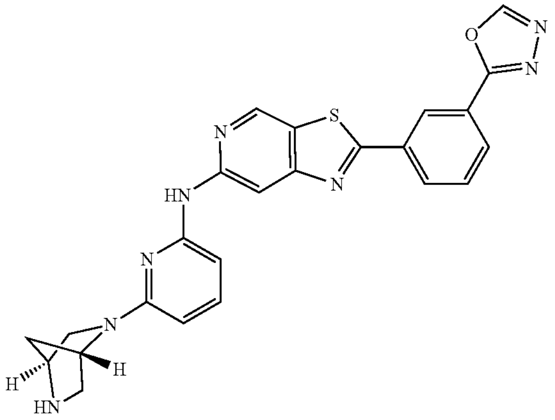 [SMILES: c1cc(-c2nnco2)cc(-c2nc3cc(Nc4cccc(N5C[C@@H]6C[C@H]5CN6)n4)ncc3s2)c1]

The title compound was synthesized in a similar fashion to example 78 using the appropriate starting materials. $^1$H NMR (400 MHz, Chloroform-d) δ 8.80 (s, 1H), 8.78 (s, 1H), 8.67 (s, 1H), 8.33-8.19 (m, 2H), 7.77-7.59 (m, 2H), 7.36 (t, J=8.0 Hz, 1H), 7.00-6.90 (m, 1H), 6.27 (d, J=7.8 Hz, 1H), 5.92 (d, J=8.1 Hz, 1H), 4.74 (s, 1H), 3.90 (s, 1H), 3.72 (d, J=9.4 Hz, 1H), 3.35 (d, J=9.5 Hz, 1H), 3.25-3.14 (m, 2H), 2.02-1.87 (m, 2H). ESI MS $[M+H]^+$ for $C_{24}H_{20}N_8OS$, calcd 469.2 found 469.4.

Example 143: 1-{3-[6-({6-[(1S,4S)-5-Methyl-2,5-diazabicyclo[2.2.1]heptan-2-yl]pyrazin-2-yl}amino)-[1,3]thiazolo[5,4-c]pyridin-2-yl]phenyl}pyrrolidin-2-one

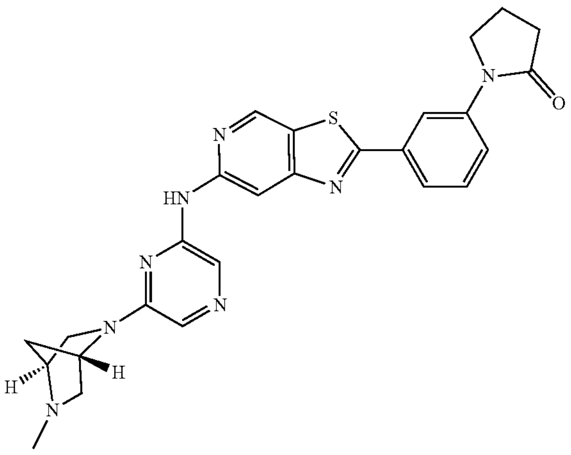 [SMILES: CN1C[C@@H]2C[C@H]1CN2c1cncc(Nc2cc3nc(-c4cccc(N5CCCC5=O)c4)sc3cn2)n1]

The title compound was synthesized in a similar fashion to example 128 and step 1 of example 148 from the appropriate starting materials. $^1H$ NMR (400 MHz, DMSO-$d_6$) δ 9.80 (s, 1H), 9.01 (d, J=0.9 Hz, 1H), 8.56 (t, J=1.9 Hz, 1H), 8.47 (d, J=0.9 Hz, 1H), 7.98 (s, 1H), 7.86 (ddd, J=7.7, 1.8, 1.0 Hz, 1H), 7.74 (ddd, J=8.3, 2.3, 1.0 Hz, 1H), 7.57 (t, J=8.0 Hz, 1H), 7.42 (s, 1H), 4.60 (s, 1H), 3.90 (t, J=7.0 Hz, 2H), 3.56-3.44 (m, 2H), 3.37 (dd, J=9.7, 2.2 Hz, 1H), 2.85 (dd, J=9.5, 2.0 Hz, 1H), 2.59-2.49 (m, 3H), 2.28 (s, 3H), 2.17-2.01 (m, 2H), 1.90 (d, J=9.3 Hz, 1H), 1.85-1.76 (m, 1H). ESI MS $[M+H]^+$ for $C_{26}H_{26}N_8SO$, calcd 499.2, found 499.1.

Example 144: 6-[(1S,4S)-2,5-Diazabicyclo[2.2.1]heptan-2-yl]-N-[2-(3-methylpyridin-2-yl)-[1,3]thiazolo[5,4-c]pyridin-6-yl]pyrazin-2-amine

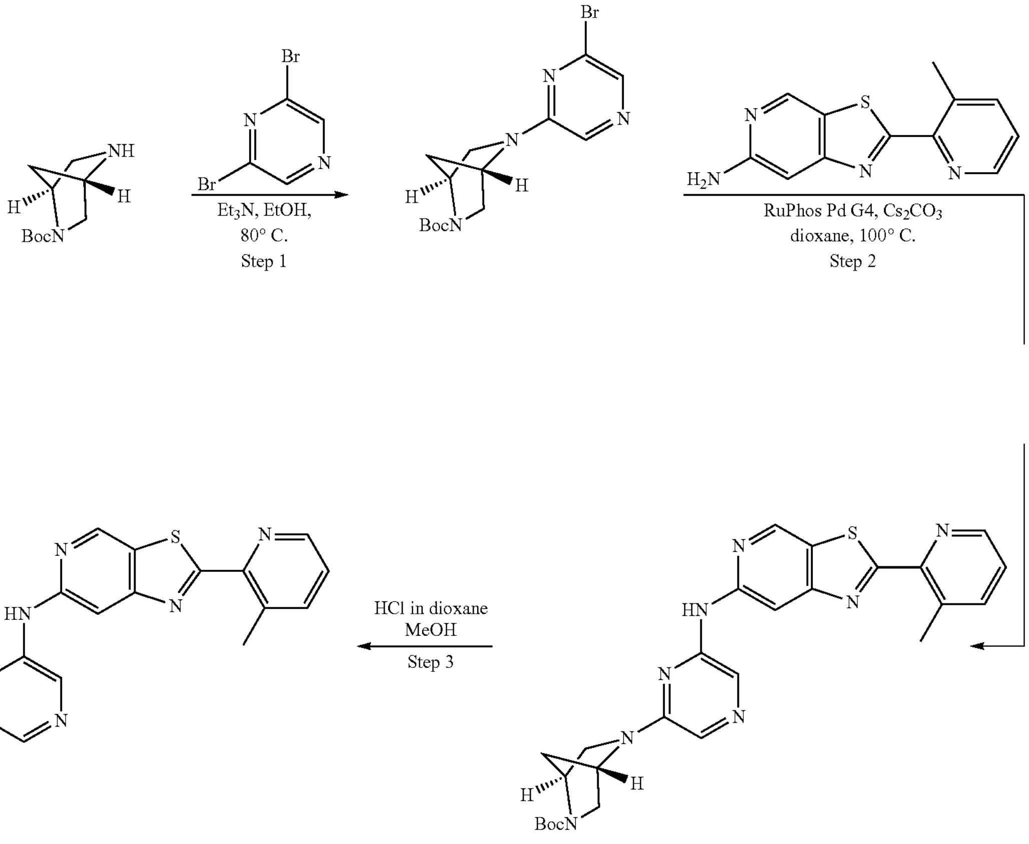

Step 1: To a stirred suspension of (1S,4S)-2-Boc-2,5-diazabicyclo[2.2.1]heptane (595 mg, 3 mmol), 2,6-dibromopyrazine (714 mg, 3 mmol) in EtOH (6 mL) was added triethylamine (0.84 mL, 6.00 mmol) dropwise. The reaction was stirred at 80° C. for 2 h. The reaction was cooled to room temperature, diluted with $CH_2Cl_2$, washed with sat. $NH_4Cl$, dried over anhydrous $Na_2SO_4$, and concentrated under reduced pressure to obtain the desired intermediate in quantitative yield.

Step 2: To a stirred solution of intermediate from step 1 (117 mg, 0.33 mmol) and aminoazabenzothiazole derivative (73 mg, 0.3 mmol) in dioxane (3 mL) (prepared in a similar fashion to that described for steps 1-3 of example 1 using the appropriate starting materials) were added RuPhos Pd G4 (50 mg, 0.06 mmol) and $Cs_2CO_3$ (292 mg 0.9 mmol). After degassing for 10 min under $N_2$ atmosphere, the reaction mixture was heated at 100° C. for 15 h. The reaction mixture was filtered through a pad of Celite® and the filtrate was concentrated under reduced pressure. The resulting residue was purified by column chromatography (silica gel; gradient: 0% to 100% EtOAc in hexanes) to obtain the desired intermediate (103 mg, 66%).

Step 3: To a stirred suspension of intermediate from step 2 (103 mg, 0.20 mmol) in MeOH (1.5 mL) was added 4 M HCl solution in Dioxane (3 mL) dropwise. The reaction was stirred at room temperature for 1 h and then concentrated under reduced pressure. The resultant was purified by reverse phase preparative HPLC to afford the desired compound (47 mg, 57%). $^1$H NMR (400 MHz, Methanol-$d_4$) δ 8.92-8.88 (m, 1H), 8.65-8.62 (m, 1H), 8.53 (dd, J=4.7, 1.4 Hz, 1H), 7.86-7.77 (m, 2H), 7.44 (dd, J=7.8, 4.7 Hz, 1H), 7.34 (s, 1H), 4.84 (s, 1H), 3.88 (s, 1H), 3.68 (dd, J=9.6, 2.2 Hz, 1H), 3.43 (d, J=9.6 Hz, 1H), 3.16-3.04 (m, 2H), 2.89 (s, 3H), 2.06-1.98 (m, 1H), 1.93-1.84 (m, 1H). ESI MS $[M+H]^+$ for $C_{21}H_{20}N_8S$, calcd 417.2, found 417.2.

Example 145: 6-[(1S,4S)-5-Methyl-2,5-diazabicyclo[2.2.1]heptan-2-yl]-N-[2-(3-methylpyridin-2-yl)-[1,3]thiazolo[5,4-c]pyridin-6-yl]pyrazin-2-amine

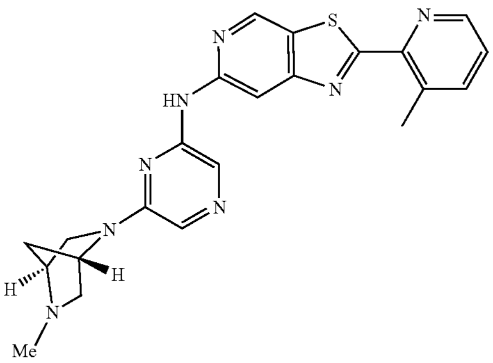 [SMILES: Cc1cccnc1-c1nc2cc(Nc3cncc(N4C[C@@H]5C[C@H]4CN5C)n3)ncc2s1]

The title compound was synthesized in a similar fashion to steps 1 and 2 of example 144 from the appropriate starting materials. $^1$H NMR (400 MHz, Methanol-$d_4$) δ 8.91 (d, J=0.9 Hz, 1H), 8.61 (d, J=0.9 Hz, 1H), 8.54 (ddd, J=4.7, 1.6, 0.7 Hz, 1H), 7.86 (s, 1H), 7.84 (ddd, J=7.7, 1.6, 0.7 Hz, 1H), 7.45 (dd, J=7.7, 4.7 Hz, 1H), 7.36 (s, 1H), 4.80-4.76 (m, 1H), 3.75-3.65 (d, J=11.4 Hz, 2H), 3.54 (dd, J=10.0, 2.1 Hz, 1H), 2.96 (dd, J=10.0, 2.1 Hz, 1H), 2.90 (s, 3H), 2.86 (d, J=10.0

Hz, 1H), 2.46 (s, 3H), 2.09 (d, J=10.1 Hz, 1H), 1.98 (d, J=10.1 Hz, 1H). ESI MS $[M+H]^+$ for $C_{22}H_{22}N_8S$, calcd 431.2, found 431.1.

Example 146: 6-[(1S,4S)-5-Methyl-2,5-diazabicyclo[2.2.1]heptan-2-yl]-N-[2-(pyridin-4-yl)-[1,3]thiazolo[5,4-c]pyridin-6-yl]pyrazin-2-amine

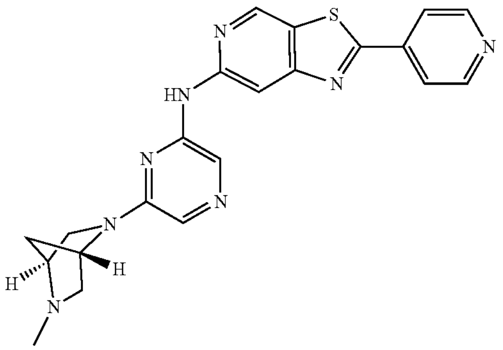 [SMILES: CN1C[C@@H]2C[C@H]1CN2c1cncc(Nc2cc3nc(-c4ccncc4)sc3cn2)n1]

The title compound was synthesized in a similar fashion to steps 1 and 2 of example 144 from the appropriate starting materials. $^1$H NMR (400 MHz, Methanol-$d_4$) δ 9.05 (d, J=0.9 Hz, 1H), 8.88-8.78 (m, 2H), 8.56 (d, J=0.9 Hz, 1H), 8.27-8.19 (m, 2H), 8.06 (s, 1H), 7.52 (s, 1H), 5.10 (s, 1H), 4.51 (s, 1H), 3.97-3.70 (m, 3H), 3.41-3.30 (m, 1H), 3.04 (s, 3H), 2.62-2.29 (m, 2H). ESI MS $[M+H]^+$ for $C_{21}H_{20}N_8S$, calcd 417.2, found 417.2.

Example 147: 6-[(1S,4S)-5-Methyl-2,5-diazabicyclo[2.2.1]heptan-2-yl]-N-{2-[3-(pyrrolidine-1-carbonyl)phenyl]-[1,3]thiazolo[5,4-c]pyridin-6-yl}pyrazin-2-amine

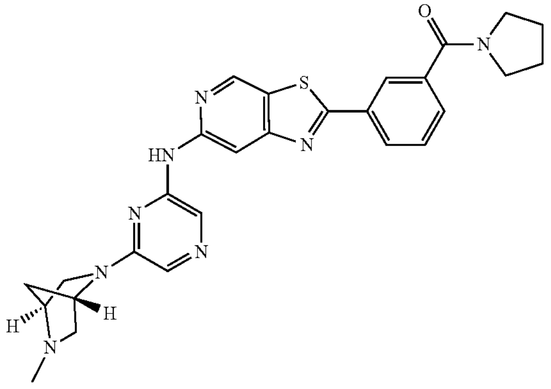 [SMILES: CN1C[C@@H]2C[C@H]1CN2c1cncc(Nc2cc3nc(-c4cccc(C(=O)N5CCCC5)c4)sc3cn2)n1]

The title compound was synthesized in a similar fashion to steps 1 and 2 of example 144 from the appropriate starting materials. $^1$H NMR (400 MHz, Chloroform-d) δ 8.82 (d, J=0.9 Hz, 1H), 8.60 (d, J=0.9 Hz, 1H), 8.31 (td, J=1.8, 0.6 Hz, 1H), 8.18 (ddd, J=7.8, 1.8, 1.2 Hz, 1H), 7.72 (s, 1H), 7.69 (ddd, J=7.8, 1.6, 1.2 Hz, 1H), 7.57 (td, J=7.8, 0.6 Hz, 1H), 7.41 (s, 1H), 7.31 (s, 1H), 4.69 (s, 1H), 3.70 (t, J=6.8 Hz, 3H), 3.61 (s, 1H), 3.54-3.43 (m, 3H), 3.07 (dd, J=9.7, 2.1 Hz, 1H), 2.79-2.69 (m, 1H), 2.45 (s, 3H), 2.16-1.86 (m, 6H). ESI MS $[M+H]^+$ for $C_{27}H_{28}N_8OS$, calcd 513.2, found 513.2.

Example 148: 6-[(1S,4S)-2,5-Diazabicyclo[2.2.1]heptan-2-yl]-5-methyl-N-[2-(3-methylpyridin-2-yl)-[1,3]thiazolo[5,4-c]pyridin-6-yl]pyrazin-2-amine

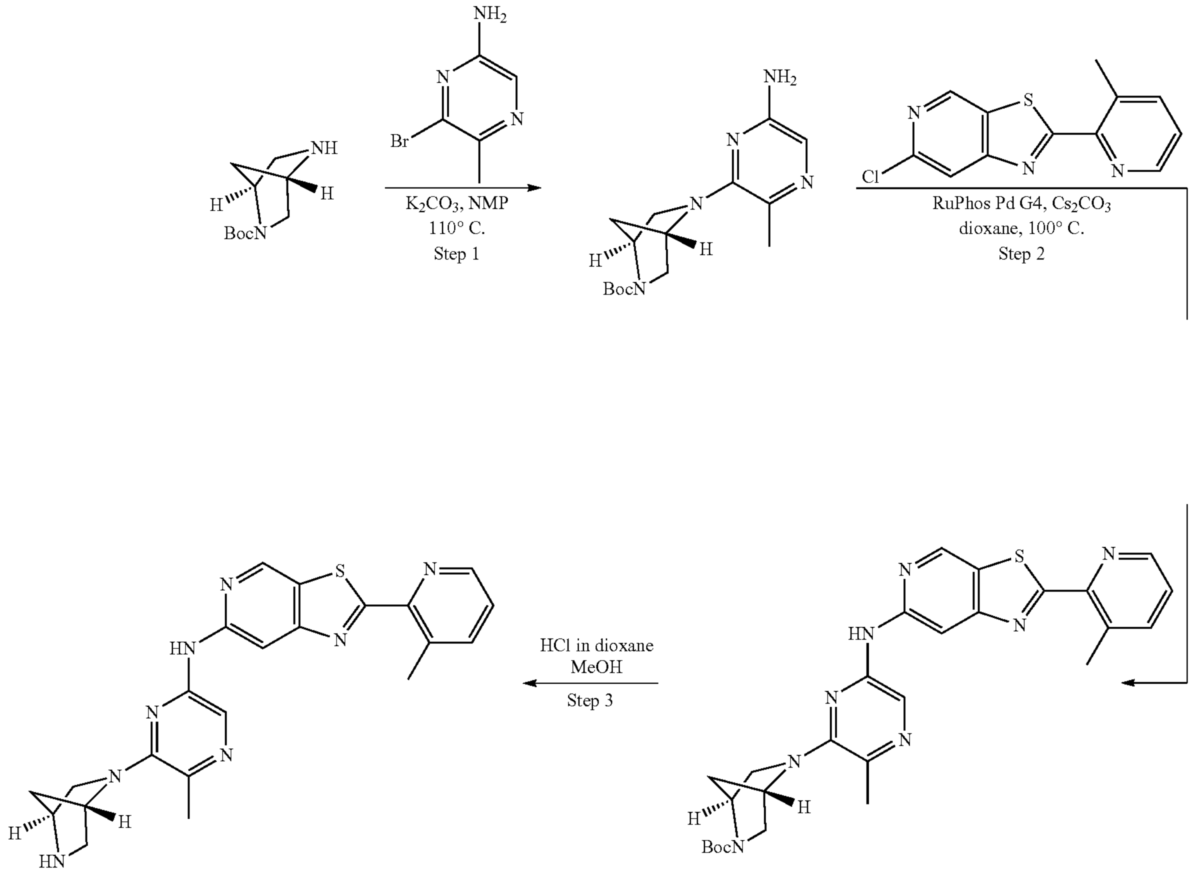

Step 1: A heterogenous mixture of (1S,4S)-2-Boc-2,5-diazabicyclo[2.2.1]heptane (198 mg, 1.00 mmol), 6-bromo-5-methyl-2-pyrazinamine (188 mg, 1.00 mmol), $K_2CO_3$ (276 mg, 2.00 mmol), and NMP (2 mL) was heated at 110° C. for 15 h. The reaction was cooled to room temperature, diluted with water, and extracted with EtOAc. The organic extract was concentrated, and the residue was purified by column chromatography (silica gel; gradient: 0-10% MeOH/$CH_2Cl_2$) to obtain the desired aminopyrazine derivative (178 mg, 58%).

Step 2: This reaction was performed in a similar fashion to step 2 of example 144.

Step 3: The title compound was synthesized in a similar fashion to step 3 of example 144. $^1$H NMR (400 MHz, Methanol-$d_4$) δ 8.87 (s, 1H), 8.58 (s, 1H), 8.52 (d, J=4.6 Hz, 1H), 7.85 (s, 1H), 7.82 (d, J=7.9 Hz, 1H), 7.43 (dd, J=7.9, 4.6 Hz, 1H), 4.80 (s, 1H), 3.91 (dd, J=9.1, 2.4 Hz, 1H), 3.82 (s, 1H), 3.50-3.37 (m, 2H), 3.17 (dd, J=10.3, 2.1 Hz, 1H), 2.88 (s, 3H), 2.43 (s, 3H), 2.02 (d, J=9.9 Hz, 1H), 1.85 (d, J=9.9 Hz, 1H). ESI MS $[M+H]^+$ for $C_{22}H_{22}N_8S$, calcd 431.2, found 431.2.

Example 149: 2-[(1S,4S)-2,5-Diazabicyclo[2.2.1]heptan-2-yl]-N-[2-(3-methylpyridin-2-yl)-[1,3]thiazolo[5,4-c]pyridin-6-yl]pyrimidin-4-amine

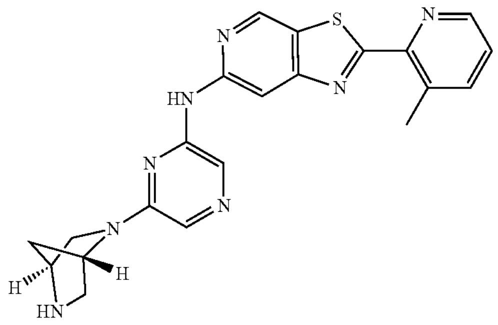 [SMILES: Cc1cccnc1-c1nc2cc(Nc3cncc(N4C[C@@H]5C[C@H]4CN5)n3)ncc2s1]

The title compound was synthesized in a similar fashion to example 148 from the appropriate starting materials. $^1$H NMR (400 MHz, Methanol-$d_4$) δ 8.94 (d, J=0.7 Hz, 1H), 8.83 (s, 1H), 8.56-8.53 (m, 1H), 7.95 (d, J=5.9 Hz, 1H), 7.86-7.82 (m, 1H), 7.45 (dd, J=7.8, 4.6 Hz, 1H), 6.45 (d, J=5.9 Hz, 1H), 4.98-4.88 (m, 1H), 3.85 (s, 1H), 3.78-3.48

(m, 2H), 3.16-3.01 (m, 2H), 2.90 (s, 3H), 2.05-1.92 (m, 1H), 1.88-1.79 (m, 1H). ESI MS $[M+H]^+$ for $C_{21}H_{20}N_8S$, calcd 417.2, found 417.2.

Example 150: [(2S,4S)-4-Amino-1-(6-{[2-(3-methylpyridin-2-yl)-[1,3]thiazolo[5,4-c]pyridin-6-yl]amino}pyrazin-2-yl)pyrrolidin-2-yl]methanol

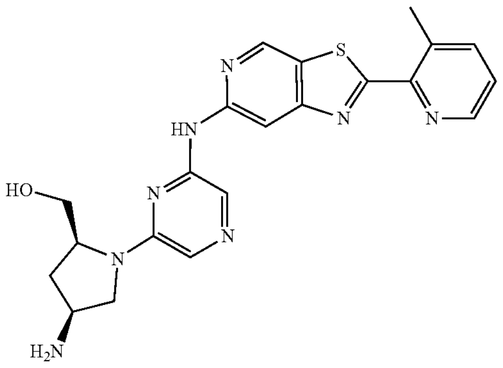 [SMILES: Cc1cccnc1-c1nc2cc(Nc3cncc(N4C[C@@H](N)C[C@H]4CO)n3)ncc2s1]

The title compound was synthesized in a similar fashion to example 148 from the appropriate starting materials. $^1$H NMR (400 MHz, Chloroform-d) δ 8.84 (d, J=0.8 Hz, 1H), 8.65 (d, J=1.0 Hz, 1H), 8.55 (ddd, J=4.6, 1.7, 0.7 Hz, 1H), 7.72 (s, 1H), 7.70-7.65 (m, 1H), 7.41 (s, 1H), 7.36 (s, 1H), 7.31 (dd, J=7.7, 4.6 Hz, 1H), 4.54 (d, J=9.8 Hz, 1H), 4.38 (dd, J=11.4, 3.5 Hz, 1H), 3.95 (t, J=5.4 Hz, 1H), 3.78 (dd, J=11.5, 1.9 Hz, 1H), 3.64 (dd, J=10.8, 5.5 Hz, 1H), 3.46 (d, J=10.7 Hz, 1H), 2.89 (s, 3H), 2.48 (ddd, J=13.5, 9.8, 5.5 Hz, 1H), 1.91 (d, J=13.5 Hz, 1H). ESI MS $[M+H]^+$ for $C_{21}H_{22}N_8OS$, calcd 435.2, found 435.3.

Example 151: 2-{4-[6-({6-[(1S,4S)-5-Methyl-2,5-diazabicyclo[2.2.1]heptan-2-yl]pyrazin-2-yl}amino)-[1,3]thiazolo[5,4-c]pyridin-2-yl]pyridin-2-yl}propan-2-ol

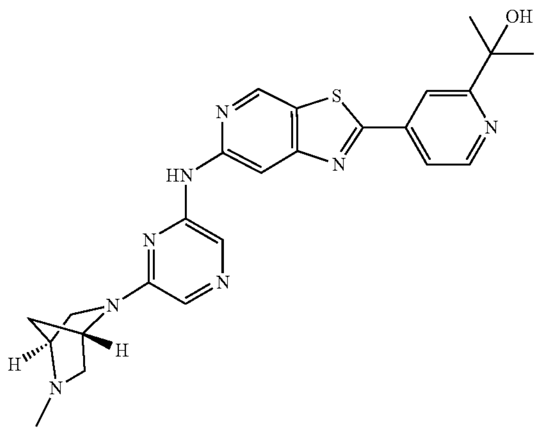 [SMILES: CN1C[C@@H]2C[C@H]1CN2c1cncc(Nc2cc3nc(-c4ccnc(C(C)(C)O)c4)sc3cn2)n1]

The title compound was synthesized in a similar fashion to steps 1 and 2 of example 148 from the appropriate starting materials. $^1$H NMR (400 MHz, Chloroform-d) δ 8.86 (d, J=0.9 Hz, 1H), 8.69 (dd, J=5.2, 0.9 Hz, 1H), 8.64 (d, J=0.9 Hz, 1H), 8.08 (dd, J=1.6, 0.9 Hz, 1H), 7.84 (dd, J=5.1, 1.6 Hz, 1H), 7.72 (s, 1H), 7.41 (s, 2H), 4.64 (d, J=20.0 Hz, 2H), 3.69 (d, J=9.8 Hz, 1H), 3.49 (dd, J=9.6, 2.1 Hz, 1H), 3.04 (dd, J=9.7, 2.1 Hz, 1H), 2.73 (dd, J=9.8, 1.3 Hz, 1H), 2.43 (s, 3H), 2.06 (d, J=9.9 Hz, 1H), 1.93-1.87 (m, 1H), 1.64 (s, 6H). ESI MS $[M+H]^+$ for $C_{24}H_{26}N_8OS$, calcd 475.2, found 475.7.

Example 152: 2-{3-[6-({6-[(1S,4S)-5-Methyl-2,5-diazabicyclo[2.2.1]heptan-2-yl]pyrazin-2-yl}amino)-[1,3]thiazolo[5,4-c]pyridin-2-yl]phenyl}propan-2-ol

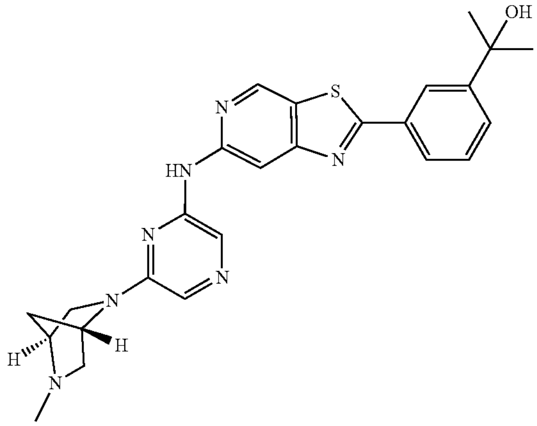 [SMILES: CN1C[C@@H]2C[C@H]1CN2c1cncc(Nc2cc3nc(-c4cccc(C(C)(C)O)c4)sc3cn2)n1]

The title compound was synthesized in a similar fashion to steps 1 and 2 of example 148 from the appropriate starting materials. $^1$H NMR (400 MHz, Chloroform-d) δ 8.75 (d, J=0.8 Hz, 1H), 8.52 (d, J=0.9 Hz, 1H), 8.27 (t, J=1.8 Hz, 1H), 7.98-7.93 (m, 1H), 7.71 (s, 1H), 7.64 (ddd, J=7.9, 1.9, 1.1 Hz, 1H), 7.57 (s, 1H), 7.45 (t, J=7.8 Hz, 1H), 7.34 (s, 1H), 4.65 (s, 1H), 3.65 (d, J=9.8 Hz, 1H), 3.55 (s, 1H), 3.45 (dd, J=9.9, 2.2 Hz, 1H), 3.02 (dd, J=9.7, 2.1 Hz, 1H), 2.78-2.65 (m, 1H), 2.40 (s, 3H), 2.03 (d, J=8.8 Hz, 1H), 1.89-1.84 (m, 1H), 1.64 (s, 6H). ESI MS $[M+H]^+$ for $C_{25}H_{27}N_7OS$, calcd 474.2, found 474.5.

Example 153: 2-{5-[6-({2-[(1S,4S)-5-Methyl-2,5-diazabicyclo[2.2.1]heptan-2-yl]pyrimidin-4-yl}amino)-[1,3]thiazolo[5,4-c]pyridin-2-yl]pyridin-3-yl}propan-2-ol

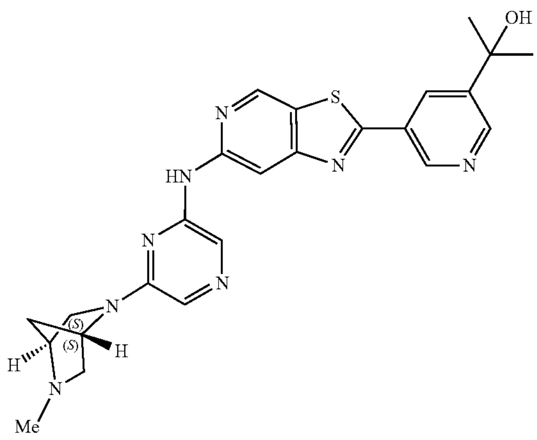

The title compound was synthesized in a similar fashion to steps 1 and 2 of example 148 from the appropriate starting materials. $^1$H NMR (400 MHz, Methanol-$d_4$) δ 9.14 (d, J=2.1 Hz, 1H), 8.93 (d, J=0.8 Hz, 1H), 8.86 (d, J=2.2 Hz, 1H), 8.84-8.71 (m, 1H), 8.61 (t, J=2.2 Hz, 1H), 7.92 (d, J=5.9 Hz, 1H), 6.39 (s, 1H), 4.83-4.64 (m, 2H), 3.80 ($s_{br}$, 1H), 3.64 ($s_{br}$, 1H), 2.93 ($s_{br}$, 1H), 2.80 (d, J=9.8 Hz, 1H), 2.44 (s, 3H), 2.05 (d, J=10.1 Hz, 1H), 1.94 (d, J=10.0 Hz, 1H), 1.63 (s, 6H). ESI MS $[M+H]^+$ for $C_{24}H_{26}N_8OS$, calcd 475.2, found 475.5.

Example 154: 5-Methyl-6-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyrazin-2-amine

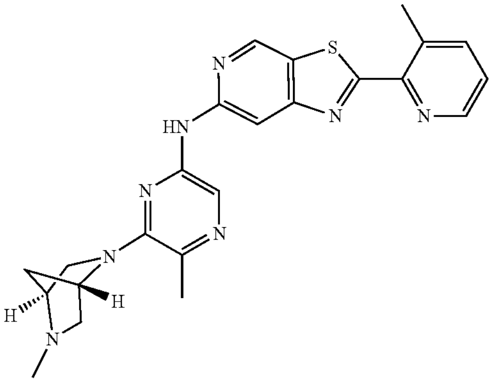 [SMILES: Cc1cccnc1-c1nc2cc(Nc3cnc(C)c(N4C[C@@H]5C[C@H]4CN5C)n3)ncc2s1]

The title compound was synthesized in a similar fashion to steps 1 and 2 of example 148 from the appropriate starting materials. $^1$H NMR (400 MHz, Chloroform-d) δ 8.84 (d, J=0.9 Hz, 1H), 8.64 (d, J=0.9 Hz, 1H), 8.58-8.50 (m, 1H), 7.72 (s, 1H), 7.70-7.66 (m, 1H), 7.40 (s, 1H), 7.32 (dd, J=7.7, 4.6 Hz, 1H), 4.71 (s, 1H), 3.66 (s, 2H), 3.51 (s, 1H), 3.19-3.04 (m, 2H), 2.90 (s, 3H), 2.48 (s, 3H), 2.42 (s, 3H), 2.07-1.99 (m, 1H), 1.94-1.88 (m, 1H). ESI MS $[M+H]^+$ for $C_{23}H_{22}N_8S$, calcd 445.2, found 445.2.

Example 155: [(2S,4S)-4-Mmino-1-(4-{[2-(3-methylpyridin-2-yl)-[1,3]thiazolo[5,4-c]pyridin-6-yl]amino}pyrimidin-2-yl)pyrrolidin-2-yl]methanol

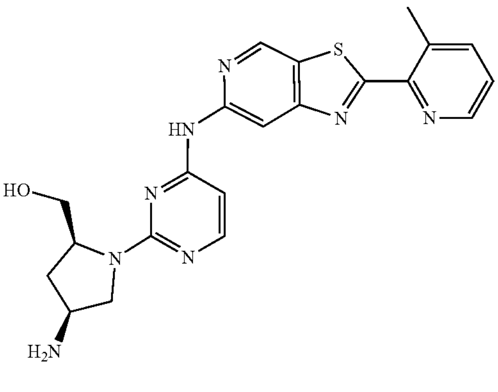 [SMILES: Cc1cccnc1-c1nc2cc(Nc3ccnc(N4C[C@@H](N)C[C@H]4CO)n3)ncc2s1]

The title compound was synthesized in a similar fashion to example 148 from the appropriate starting materials.

2-Chloro-4-pyrimidinamine was used as starting material instead of 6-Bromo-5-methyl-2-pyrazinamine for step 1. The minor isomer isolated was the desired starting material for step 2. $^1$H NMR (400 MHz, Methanol-$d_4$) δ 8.87 (s, 1H), 8.71 (s, 1H), 8.51-8.40 (m, 1H), 7.90 (dd, J=5.9, 0.4 Hz, 1H), 7.81-7.75 (m, 1H), 7.38 (dd, J=7.8, 4.6 Hz, 1H), 6.39 (d, J=5.9 Hz, 1H), 4.40-3.51 (m, 3H), 3.75-3.51 (m, 2H), 3.38 (dd, J=11.3, 3.9 Hz, 1H), 2.83 (s, 3H), 2.54-2.37 (m, 1H), 1.83 (s, 1H). ESI MS $[M+H]^+$ for $C_{21}H_{22}N_8OS$, calcd 435.5, found 435.3.

Example 156: 6-[(1S,4S)-5-Methyl-2,5-diazabicyclo[2.2.1]heptan-2-yl]-N-[2-(1,3-oxazol-2-yl)-[1,3]thiazolo[5,4-c]pyridin-6-yl]pyrazin-2-amine

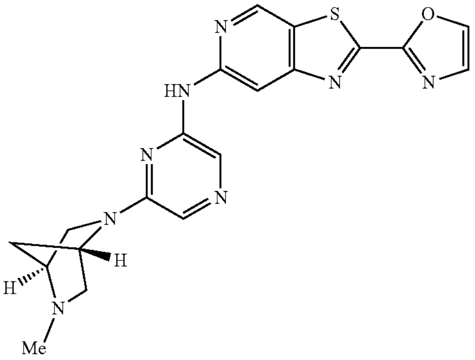 [SMILES: CN1C[C@@H]2C[C@H]1CN2c1cncc(Nc2cc3nc(-c4ncco4)sc3cn2)n1]

The title compound was synthesized in a similar fashion to steps 1 and 2 of example 148 from the appropriate starting materials. $^1$H NMR (400 MHz, Methanol-$d_4$) δ 8.97 (d, J=0.8 Hz, 1H), 8.78 (d, J=0.7 Hz, 1H), 8.26 (d, J=0.6 Hz, 1H), 7.72 (s, 1H), 7.52 (d, J=0.6 Hz, 1H), 7.35 (s, 1H), 4.81 (s, 1H), 3.70 (d, J=14.5 Hz, 2H), 3.56 (dd, J=10.2, 2.0 Hz, 1H), 2.99 (dd, J=10.0, 2.0 Hz, 1H), 2.82 (d, J=10.0 Hz, 1H), 2.47 (s, 3H), 2.11 (d, J=9.6 Hz, 1H), 1.99 (d, J=10.5 Hz, 1H). ESI MS $[M+H]^+$ for $C_{19}H_{18}N_8OS$, calcd 407.1, found 407.2.

Example 157: 2-[(1S,4S)-5-Methyl-2,5-diazabicyclo[2.2.1]heptan-2-yl]-N-[2-(1,3-oxazol-2-yl)-[1,3]thiazolo[5,4-c]pyridin-6-yl]pyrimidin-4-amine

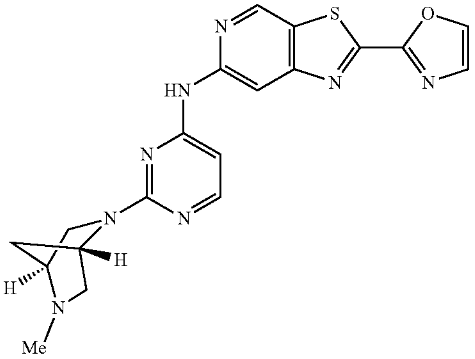 [SMILES: CN1C[C@@H]2C[C@H]1CN2c1nccc(Nc2cc3nc(-c4ncco4)sc3cn2)n1]

The title compound was synthesized in a similar fashion to steps 1, 2 of example 148 from the appropriate starting materials. $^1$H NMR (400 MHz, Methanol-$d_4$) δ 8.96 (d, J=0.8 Hz, 1H), 8.91 (s, 1H), 8.25 (d, J=0.7 Hz, 1H), 7.92 (d, J=5.9 Hz, 1H), 7.51 (d, J=0.7 Hz, 1H), 6.35 (d, J=5.4 Hz, 1H), 4.77 (s, 1H), 3.82 (s, 1H), 3.68 (s, 1H), 3.54 (s, 1H), 3.00 (s, 1H), 2.84 (d, J=7.1 Hz, 1H), 2.49 (s, 3H), 2.09 (d, J=9.6 Hz, 1H), 1.99 (d, J=10.1 Hz, 1H). ESI MS $[M+H]^+$ for $C_{19}H_{18}N_8OS$, calcd 407.1, found 407.1.

Example 158: 2-[(1S,4S)-5-Methyl-2,5-diazabicyclo[2.2.1]heptan-2-yl]-N-[2-(3-methylpyridin-2-yl)-[1,3]thiazolo[5,4-c]pyridin-6-yl]pyrimidin-4-amine

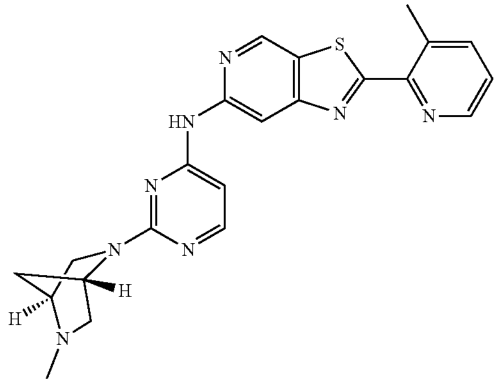 [SMILES: Cc1cccnc1-c1nc2cc(Nc3ccnc(N4C[C@@H]5C[C@H]4CN5C)n3)ncc2s1]

The title compound was synthesized in a similar fashion to steps 1 and 2 of example 148 from the appropriate starting materials. $^1$H NMR (400 MHz, Chloroform-d) δ 8.88 (d, J=0.9 Hz, 1H), 8.75 (s, 1H), 8.57 (dd, J=4.7, 1.4 Hz, 1H), 8.08 (d, J=5.7 Hz, 1H), 7.70 (ddd, J=7.7, 1.4, 0.8 Hz, 1H), 7.41 (s, 1H), 7.34 (dd, J=7.7, 4.7 Hz, 1H), 6.23 (d, J=5.7 Hz, 1H), 4.85 (s, 1H), 3.89 (d, J=10.4 Hz, 1H), 3.63-3.36 (m, 2H), 3.27-2.96 (m, 1H), 2.92 (s, 3H), 2.74 (d, J=9.6 Hz, 1H), 2.46 (s, 3H), 2.02 (d, J=9.6 Hz, 1H), 1.90 (d, J=9.6 Hz, 1H). ESI MS $[M+H]^+$ for $C_{22}H_{22}N_8S$, calcd 431.2, found 431.2.

Example 159: 2-[(1S,4S)-5-Methyl-2,5-diazabicyclo[2.2.1]heptan-2-yl]-N-[2-(pyridin-4-yl)-[1,3]thiazolo[5,4-c]pyridin-6-yl]pyrimidin-4-amine

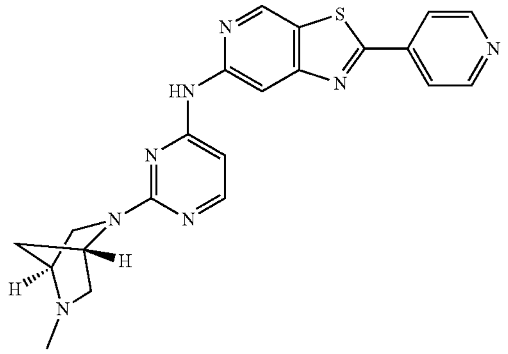 [SMILES: CN1C[C@@H]2C[C@H]1CN2c1nccc(Nc2cc3nc(-c4ccncc4)sc3cn2)n1]

The title compound was synthesized in a similar fashion to steps 1 and 2 of example 148 from the appropriate starting materials. $^1$H NMR (400 MHz, Methanol-d$_4$) δ 9.19 (d, J=0.9 Hz, 1H), 8.91-8.77 (m, 2H), 8.67 (br s, 1H), 8.33-8.16 (m, 2H), 7.99 (d, J=7.1 Hz, 1H), 6.93 (br s, 1H), 5.21 (br s, 1H), 4.62 (s, 1H), 4.26-3.35 (m, 4H), 3.07 (s, 3H), 2.66-2.32 (m, 2H). ESI MS $[M+H]^+$ for $C_{21}H_{22}N_8S$, calcd 417.2, found 417.2.

Example 160: 6-Methyl-2-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyrimidin-4-amine

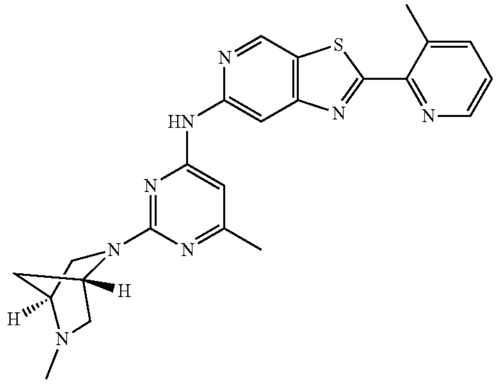 [SMILES: Cc1cc(Nc2cc3nc(-c4ncccc4C)sc3cn2)nc(N2C[C@@H]3C[C@H]2CN3C)n1]

The title compound was synthesized in a similar fashion to steps 1 and 2 of example 148 from the appropriate starting materials. $^1$H NMR (400 MHz, Chloroform-d) δ 8.86 (d, J=0.9 Hz, 1H), 8.74 (s, 1H), 8.57-8.54 (m, 1H), 7.71-7.64 (m, 1H), 7.46 (s, 1H), 7.32 (dd, J=7.7, 4.6 Hz, 1H), 6.10 (s, 1H) 4.88 (s, 1H), 3.89 (d, J=10.6 Hz, 1H), 3.58-3.42 (m, 2H), 3.21-3.00 (m, 1H), 2.90 (s, 3H), 2.72 (d, J=9.6 Hz, 1H), 2.45 (s, 3H), 2.29 (s, 3H), 2.03-1.80 (m, 2H). ESI MS $[M+H]^+$ for $C_{23}H_{24}N_8S$, calcd 445.2, found 445.1.

Example 161: 4-Methyl-N-[2-(3-methylpyridin-2-yl)-[1,3]thiazolo[5,4-c]pyridin-6-yl]-6-[(3S)-piperidin-3-yloxy]pyridin-2-amine

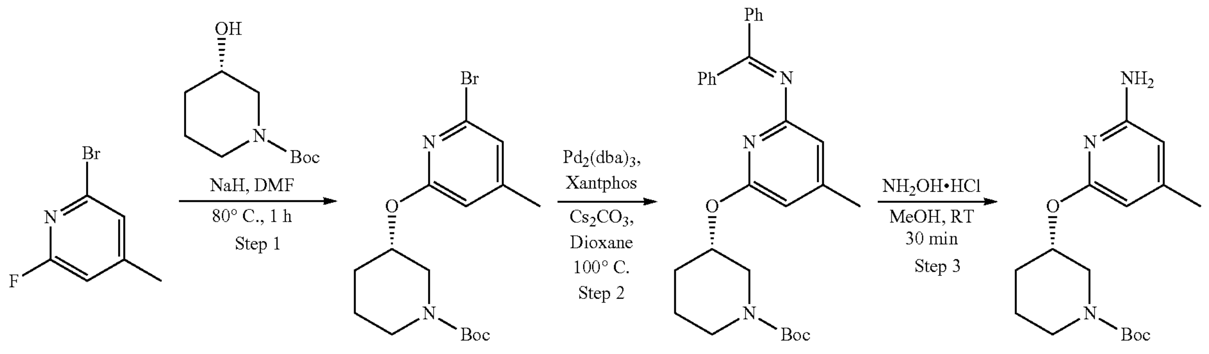

-continued

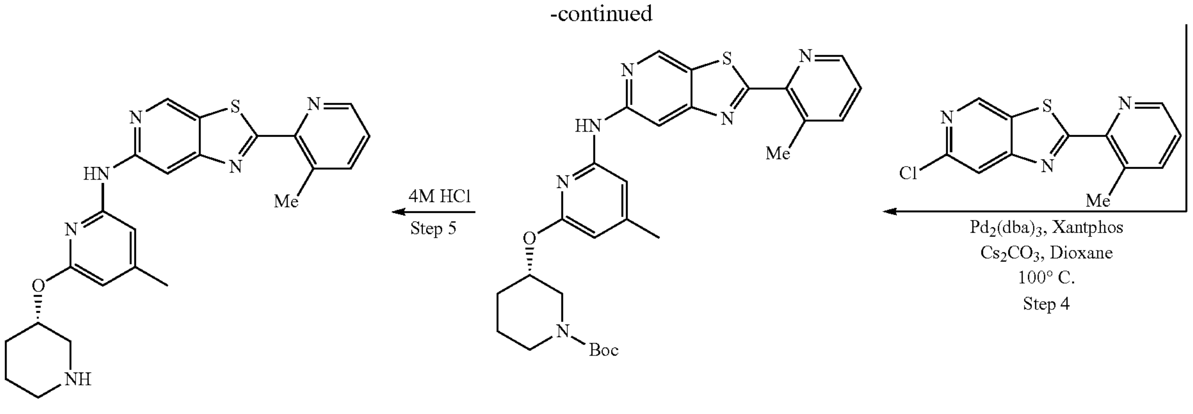

Step 1: A round-bottom flask was charged with commercially available N-Boc (S)-3-hydroxypiperidine (1.0 g, 5 mmol) in DMF (10 mL). To this flask was added NaH (270 mg, 6.5 mmol) at ° C. After 10 minutes, commercially available pyridine derivative was added at same temperature. Then the resulting reaction heated at 80° C. for 1 h. After cooling to ambient temperature, the reaction mixture was diluted with water and washed with EtOAc and combined organic layers were dried over $Na_2SO_4$ and concentrated. The crude material was purified by column chromatography (silica gel; gradient: 0% to 70% EtOAc in hexanes) to obtain the desired pyridyl ether derivative (2.4 g, 65%).

Step 2: To a stirred solution of pyridyl ether derivative from step 1 (2.2 g, 6 mmol) and benzophenone imine (1 g, 6 mmol) in Dioxane (20 ml) was added $Pd_2(dba)_3$ (550 mg, 0.6 mmol), Xantphos (690 mg, 1.2 mmol) and $Cs_2CO_3$ (5.8 g, 18.0 mmol). The reaction mixture was heated to 100° C. and stirred for 12 h. The reaction mixture was poured into water and extracted twice with EtOAc. The organic layers were dried over $Na_2SO_4$ and concentrated in vacuo. The residue was purified by flash column chromatography (silica gel; gradient: 0% to 50% EtOAc in hexanes) to get imine intermediate (2.23 g, 79%) as a yellow viscous oil.

Step 3: To a stirred solution of imine intermediate from step 2 (2.23 g, 4.74 mmol) in methanol (50 ml) were added sodium acetate (625 mg, 7.6 mmol) and hydroxylamine hydrochloride (665 mg, 9.5 mmol). The reaction mixture was stirred at RT for 1 h. The reaction mixture was then filtered through sintered glass and the filtrate was concentrated in vacuo. The residue was purified by flash column chromatography (silica gel; gradient: 0% to 100% EtOAc in hexanes) to obtain the desired amine as a white solid (1.2 g, 82%).

Step 4: To a stirred solution of Azabenzothiazole derivative prepared by step 1 of example 41 (104 mg, 0.4 mmol) and amine from step 3 (131 mg, 0.4 mmol) in Dioxane (5 mL) was added $Pd_2(dba)_3$ (36 mg, 0.04 mmol), Xantphos (46 mg, 0.08 mmol) and $Cs_2CO_3$ (390 mg, 1.2 mmol). The reaction mixture was heated to 100° C. and stirred for 12 h. The reaction mixture was filtered through Celite® and purified by flash column chromatography (silica gel; gradient: 0% to 100% EtOAc in hexanes) to get Azabenzothiazole-ether derivative.

Step 5: To a stirred solution of Boc protected derivative from step 4 (65 mg, 0.12 mmol) in $CH_2Cl_2$ (5 mL) was added TFA and stirred at RT until complete consumption of starting material. The reaction mixture was concentrated in vacuo and purified by reverse phase preparative HPLC (10-90% Water/ACN) to obtain the desired product. $^1$H NMR (400 MHz, DMSO-$d_6$) δ 9.74 (s, 1H), 8.99 (d, J=0.9 Hz, 1H), 8.81 (d, J=0.9 Hz, 1H), 8.59 (dd, J=4.8, 1.5 Hz, 1H), 7.87-7.90 (m, 1H), 7.51 (dd, J=7.8, 4.6 Hz, 1H), 6.57 (d, J=1.2 Hz, 1H), 6.03 (d, J=0.9 Hz, 1H), 4.93 (dt, J=10.0, 5.4 Hz, 1H), 3.20 (d, J=11.6 Hz, 1H), 2.85 (s, 4H), 2.54-2.47 (m, 1H), 2.30 (s, 1H), 2.16 (s, 3H), 1.74 (d, J=16.6 Hz, 3H), 1.46 (dd, J=10.9, 4.8 Hz, 1H). ESI MS $[M+H]^+$ for $C_{23}H_{24}N_6SO$, calcd 433.2, found 433.3.

Example 162: 5-Methyl-N-[2-(3-methylpyridin-2-yl)-[1,3]thiazolo[5,4-c]pyridin-6-yl]-6-(pyrrolidin-3-yloxy)pyridin-2-amine

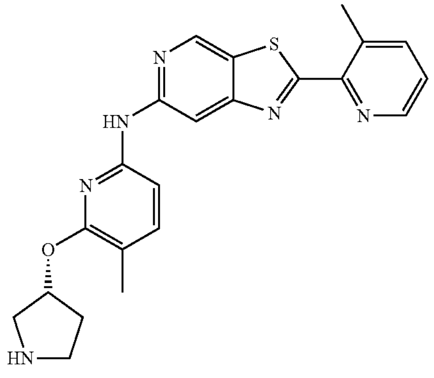

The title compound was synthesized in a similar fashion to example 161 from the appropriate starting materials. $^1$H NMR (400 MHz, DMSO-$d_6$) δ 9.64 (s, 1H), 8.96 (s, 1H), 8.76 (s, 1H), 8.58 (dd, J=4.3, 1.1 Hz, 1H), 7.88 (dd, J=7.8, 0.8 Hz, 1H), 7.50 (dd, J=7.8, 4.6 Hz, 1H), 7.43-7.32 (m, 1H), 6.78 (d, J=7.8 Hz, 1H), 5.45 (td, J=5.7, 2.6 Hz, 1H), 3.24 (dd, J=12.3, 5.6 Hz, 1H), 3.08-2.97 (m, 2H), 2.91-2.83 (m, 1H), 2.81 (s, 3H), 2.23 (dq, J=14.3, 7.3 Hz, 1H), 2.3 (s, 3H), 1.90 (ddd, J=13.6, 8.3, 5.7 Hz, 1H). ESI MS $[M+H]^+$ for $C_{22}H_{22}N_6OS$, calcd 419.2, found 419.6.

Example 163: 4-Methyl-N-[2-(6-methylpyridin-2-yl)-[1,3]thiazolo[5,4-c]pyridin-6-yl]-6-[(3S)-pyrrolidin-3-yloxy]pyridin-2-amine

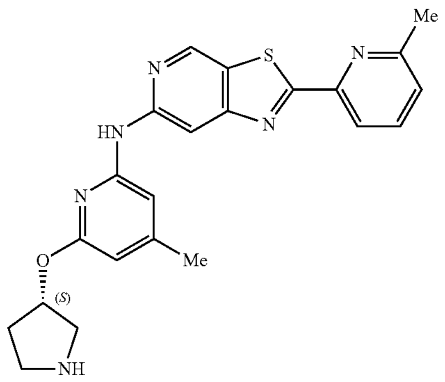

The title compound was synthesized in a similar fashion to example 161 from the appropriate starting materials. $^1H$ NMR (400 MHz, Chloroform-d) δ 8.84 (s, 1H), 8.52 (s, 1H), 8.19 (d, J=7.7 Hz, 1H), 7.75 (t, J=7.7 Hz, 1H), 7.29 (d, J=7.2 Hz, 2H), 6.50 (s, 1H), 6.12 (s, 1H), 5.53 (ddt, J=6.2, 4.1, 1.8 Hz, 1H), 3.26-3.17 (m, 3H), 3.03-2.93 (m, 1H), 2.66 (s, 3H), 2.31-2.20 (m, 4H), 2.10-1.95 (m, 2H). ESI MS $[M+H]^+$ for $C_{22}H_{22}N_6OS$, calcd 419.2, found 419.1.

Example 164: 4-Methyl-N-[2-(3-methylpyridin-2-yl)-[1,3]thiazolo[5,4-c]pyridin-6-yl]-6-[(3S)-pyrrolidin-3-yloxy]pyridin-2-amine

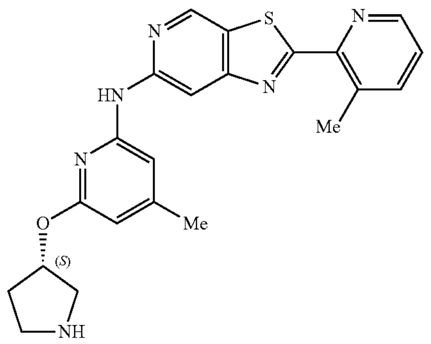

The title compound was synthesized in a similar fashion to example 161 from the appropriate starting materials. $^1H$ NMR (400 MHz, Chloroform-d) δ 8.83 (d, J=0.9 Hz, 1H), 8.68 (d, J=0.9 Hz, 1H), 8.57-8.51 (m, 1H), 7.65 (ddd, J=7.8, 1.6, 0.7 Hz, 1H), 7.47 (s, 1H), 7.30 (dd, J=7.7, 4.6 Hz, 1H), 6.44-6.39 (m, 1H), 6.12-6.07 (m, 1H), 5.52 (ddt, J=6.6, 4.3, 2.0 Hz, 1H), 3.32-3.10 (m, 3H), 2.93 (ddd, J=10.6, 8.2, 5.5 Hz, 1H), 2.88 (s, 3H), 2.25 (s, 4H), 2.05 (p, J=6.7 Hz, 2H). ESI MS $[M+H]^+$ for $C_{22}H_{22}N_6OS$, calcd 419.2, found 419.1.

Example 165 N-{3-Methyl-5-[(3S)-pyrrolidin-3-yloxy]phenyl}-2-(2-methylpyridin-4-yl)-[1,3]thiazolo[5,4-c]pyridin-6-amine

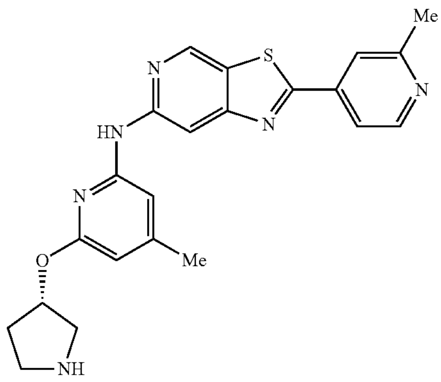 [SMILES: Cc1cc(Nc2cc3nc(-c4ccnc(C)c4)sc3cn2)nc(O[C@H]2CCNC2)c1]

The title compound was synthesized in a similar fashion to example 161 from the appropriate starting materials. $^1H$ NMR (400 MHz, DMSO-$d_6$) δ 9.14 (s, 1H), 9.05 (s, 1H), 8.68 (d, J=5.3 Hz, 1H), 7.93 (s, 1H), 7.84 (dd, J=5.2, 1.7 Hz, 1H), 7.44 (s, 1H), 7.18 (d, J=2.2 Hz, 1H), 6.92 (s, 1H), 6.32 (s, 1H), 4.85 (m, 1H), 3.14 (dd, J=12.3, 5.2 Hz, 1H), 3.04-2.94 (m, 2H), 2.89 (m, 1H), 2.61 (s, 3H), 2.26 (s, 3H), 2.05 (m, 1H), 1.85 (m, 1H). ESI MS $[M+H]^+$ for $C_{22}H_{22}N_6OS$, calcd 419.2, found 419.1.

Example 166: 4-Methyl-N-[2-(pyridin-4-yl)-[1,3]thiazolo[5,4-c]pyridin-6-yl]-6-[(3S)-pyrrolidin-3-yloxy]pyridin-2-amine

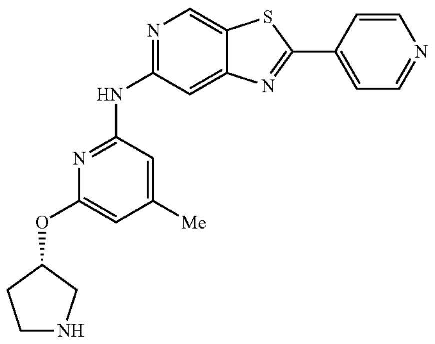 [SMILES: Cc1cc(Nc2cc3nc(-c4ccncc4)sc3cn2)nc(O[C@H]2CCNC2)c1]

The title compound was synthesized in a similar fashion to example 161 from the appropriate starting materials. $^1H$ NMR (400 MHz, DMSO-$d_6$) δ 9.83 (s, 1H), 9.09 (s, 1H), 8.84-8.77 (m, 2H), 8.57 (s, 1H), 8.09-8.03 (m, 2H), 6.81 (s, 1H), 6.13 (s, 1H), 5.52 (m, 1H), 3.52 (dd, J=12.9, 5.0 Hz, 1H), 3.37 (s, 1H), 3.34-3.18 (m, 2H), 2.31 (m, 1H), 2.23-2.11 (m, 4H). ESI MS $[M+H]^+$ for $C_{21}H_{20}N_6OS$, calcd 405.1, found 405.1.

Example 167: 4-Methyl-N-[2-(pyridin-3-yl)-[1,3]thiazolo[5,4-c]pyridin-6-yl]-6-[(3S)-pyrrolidin-3-yloxy]pyridin-2-amine

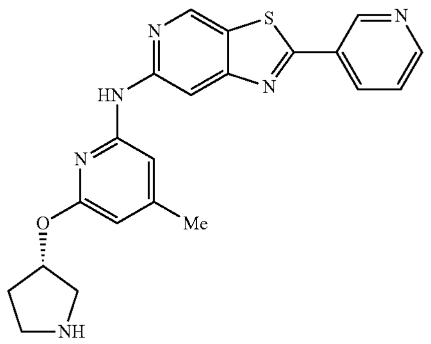 [SMILES: Cc1cc(Nc2cc3nc(-c4cccnc4)sc3cn2)nc(O[C@H]2CCNC2)c1]

The title compound was synthesized in a similar fashion to example 161 from the appropriate starting materials. $^1$H NMR (400 MHz, DMSO-$d_6$) δ 9.83 (s, 1H), 9.32 (d, J=2.3 Hz, 1H), 9.05 (d, J=0.9 Hz, 1H), 8.78 (dd, J=4.8, 1.6 Hz, 1H), 8.51 (d, J=0.9 Hz, 1H), 8.48 (ddd, J=8.0, 2.3, 1.6 Hz, 1H), 7.63-7.59 (m, 1H), 6.83 (s, 1H), 6.13 (s, 1H), 5.55 (m, 1H), 3.61 (m, 1H), 3.49 (m, 1H), 3.38 (m, 1H), 3.30 (m, 1H), 2.35 (m, 1H), 2.25 (m, 1H), 2.21 (s, 3H). ESI MS [M+H]$^+$ for $C_{21}H_{20}N_6OS$, calcd 405.1, found 405.1.

Example 168: 4-Methyl-N-[2-(2-methylpyridin-4-yl)-[1,3]thiazolo[5,4-c]pyridin-6-yl]-6-[(3S)-pyrrolidin-3-yloxy]pyridin-2-amine

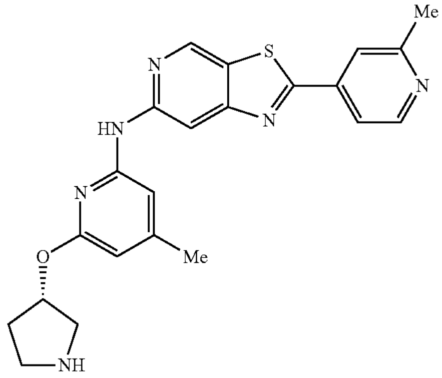 [SMILES: Cc1cc(Nc2cc3nc(-c4ccnc(C)c4)sc3cn2)nc(O[C@H]2CCNC2)c1]

The title compound was synthesized in a similar fashion to example 161 from the appropriate starting materials. $^1$H NMR (400 MHz, DMSO-$d_6$) δ 9.80 (s, 1H), 9.07 (s, 1H), 8.65 (d, J=5.2 Hz, 1H), 8.53 (s, 1H), 7.90 (s, 1H), 7.84 (d, J=5.1 Hz, 1H), 6.81 (s, 1H), 6.11 (s, 1H), 5.50 (m, 1H), 3.48 (dd, J=12.8, 5.1 Hz, 1H), 3.33 (m, 1H), 3.25-3.17 (m, 2H), 2.58 (s, 3H), 2.28 (m, 1H), 2.20 (s, 3H), 2.14 (m, 1H). ESI MS [M+H]$^+$ for $C_{22}H_{22}N_6OS$, calcd 419.2, found 419.1.

Example 169: 4-Methyl-N-[2-(3-methylpyridin-4-yl)-[1,3]thiazolo[5,4-c]pyridin-6-yl]-6-[(3S)-pyrrolidin-3-yloxy]pyridin-2-amine

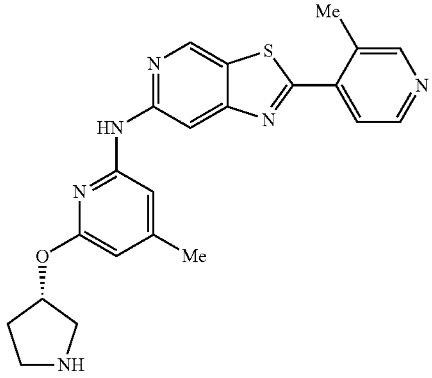 [SMILES: Cc1cc(Nc2cc3nc(-c4ccncc4C)sc3cn2)nc(O[C@H]2CCNC2)c1]

The title compound was synthesized in a similar fashion to example 161 from the appropriate starting materials. $^1$H NMR (400 MHz, DMSO-$d_6$) δ 9.86 (s, 1H), 9.11 (d, J=0.9 Hz, 1H), 8.71 (s, 1H), 8.63 (d, J=5.2 Hz, 1H), 8.56 (d, J=0.9 Hz, 1H), 7.88 (d, J=5.2 Hz, 1H), 6.83 (s, 1H), 6.13 (s, 1H), 5.55 (m, 1H), 3.59-3.42 (m, 2H), 3.34-3.28 (m, 2H), 2.62 (s, 3H), 2.38-2.22 (m, 2H), 2.21 (s, 3H). ESI MS [M+H]$^+$ for $C_{22}H_{22}N_6OS$, calcd 419.2, found 419.1.

Example 170: N-[2-(2-Aminopyridin-4-yl)-[1,3]thiazolo[5,4-c]pyridin-6-yl]-4-methyl-6-[(3S)-pyrrolidin-3-yloxy]pyridin-2-amine

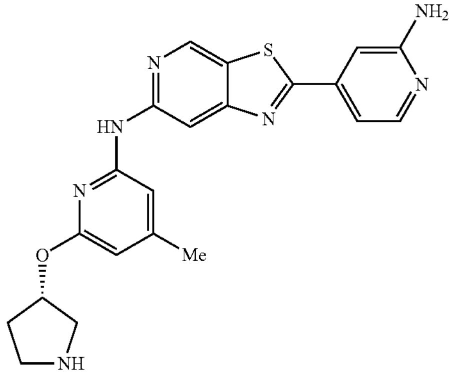 [SMILES: Cc1cc(Nc2cc3nc(-c4ccnc(N)c4)sc3cn2)nc(O[C@H]2CCNC2)c1]

The title compound was synthesized in a similar fashion to example 161 from the appropriate starting materials. $^1$H NMR (400 MHz, DMSO-$d_6$) δ 9.73 (s, 1H), 9.02 (d, J=0.9 Hz, 1H), 8.61 (d, J=0.9 Hz, 1H), 8.08 (d, J=5.2 Hz, 1H), 7.13-7.04 (m, 2H), 6.74 (s, 1H), 6.35 (s, 2H), 6.08 (s, 1H), 5.35 (m, 1H), 3.19 (dd, J=12.3, 5.4 Hz, 1H), 3.01-2.91 (m, 2H), 2.91-2.80 (m, 1H), 2.19 (s, 3H), 2.13 (m, 1H), 1.87 (m, 1H). ESI MS [M+H]$^+$ for $C_{21}H_{21}N_7OS$, calcd 420.2, found 420.1.

Example 171: 6-[(4,4-Difluoropyrrolidin-3-yl)oxy]-4-methyl-N-[2-(2-methylpyridin-4-yl)-[1,3]thiazolo[5,4-c]pyridin-6-yl]pyridin-2-amine

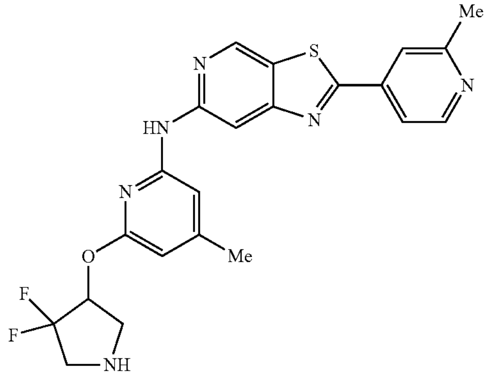 [SMILES: Cc1cc(Nc2cc3nc(-c4ccnc(C)c4)sc3cn2)nc(OC2CNCC2(F)F)c1]

The title compound was synthesized in a similar fashion to example 161 from the appropriate starting materials. $^1$H NMR (400 MHz, DMSO-$d_6$) δ 9.86 (s, 1H), 9.11 (s, 1H), 8.69 (d, J=5.6 Hz, 1H), 8.33 (s, 1H), 7.97 (s, 1H), 7.97 (d, J=5.6 Hz, 1H), 7.02 (s, 1H), 6.22 (s, 1H), 5.80 (m, 1H), 3.98-3.76 (m, 3H), 3.70 (dt, J=13.4, 2.5 Hz, 1H), 2.61 (s, 3H), 2.24 (s, 3H). ESI MS [M+H]$^+$ for $C_{22}H_2O\ F_2N_6OS$, calcd 455.1, found 455.1.

Example 172: 5-Methyl-N-[2-(2-methylpyridin-4-yl)-[1,3]thiazolo[5,4-c]pyridin-6-yl]-6-[(3S)-pyrrolidin-3-yloxy]pyridin-2-amine

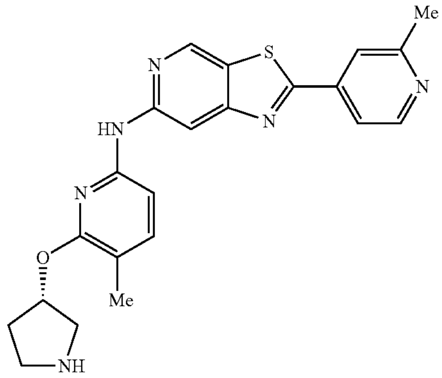 [SMILES: Cc1cc(-c2nc3cc(Nc4ccc(C)c(O[C@H]5CCNC5)n4)ncc3s2)ccn1]

The title compound was synthesized in a similar fashion to example 161 from the appropriate starting materials. $^1$H NMR (400 MHz, DMSO-$d_6$) δ 9.76 (s, 1H), 9.09 (s, 1H), 8.68 (d, J=5.2 Hz, 1H), 8.48 (s, 1H), 7.93 (s, 1H), 7.88 (d, J=5.2 Hz, 1H), 7.48 (d, J=7.9 Hz, 1H), 7.00 (d, J=7.9 Hz, 1H), 5.62 (t, J=4.9 Hz, 1H), 3.61 (dd, J=12.9, 4.9 Hz, 1H), 3.47 (d, J=12.9 Hz, 1H), 3.42-3.29 (m, 2H), 2.62 (s, 3H), 2.38 (m, 1H), 2.25 (m, 1H), 2.09 (s, 3H). ESI MS [M+H]$^+$ for $C_{22}H_{22}N_6OS$, calcd 419.2, found 419.2.

Example 173: 5-Methyl-N-[2-(4-methylpyridin-3-yl)-[1,3]thiazolo[5,4-c]pyridin-6-yl]-6-[(3S)-pyrrolidin-3-yloxy]pyridin-2-amine

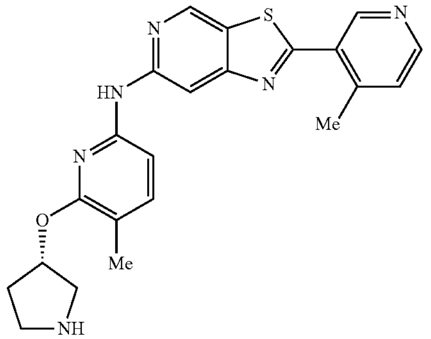 [SMILES: Cc1ccncc1-c1nc2cc(Nc3ccc(C)c(O[C@H]4CCNC4)n3)ncc2s1]

The title compound was synthesized in a similar fashion to example 161 from the appropriate starting materials. $^1$H NMR (400 MHz, DMSO-$d_6$) δ 9.69 (s, 1H), 9.02 (s, 1H), 8.97 (s, 1H), 8.67 (s, 1H), 8.58 (d, J=5.1 Hz, 1H), 7.46 (d, J=5.1 Hz, 1H), 7.38 (d, J=7.9 Hz, 1H), 6.82 (d, J=7.9 Hz, 1H), 5.51-5.43 (m, 1H), 3.31 (dd, J=12.5, 5.3 Hz, 1H), 3.15-3.00 (m, 2H), 3.00-2.92 (m, 1H), 2.63 (s, 3H), 2.21 (tt, J=14.2, 7.1 Hz, 1H), 2.03 (s, 3H), 2.01 (m, 1H). ESI MS [M+H]$^+$ for $C_{22}H_{22}N_6OS$, calcd 419.2, found 419.2.

Example 174: 4-Methyl-N-[2-(3-methylpyridin-2-yl)-[1,3]thiazolo[5,4-c]pyridin-6-yl]-6-(piperidin-4-yloxy)pyridin-2-amine

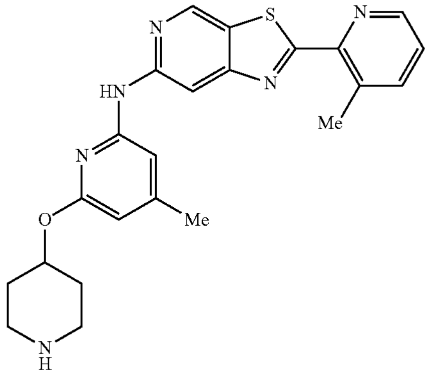 [SMILES: Cc1cc(Nc2cc3nc(-c4ncccc4C)sc3cn2)nc(OC2CCNCC2)c1]

The title compound was synthesized in a similar fashion to example 161 from the appropriate starting materials. $^1$H NMR (400 MHz, DMSO-$d_6$) δ 9.74 (s, 1H), 8.99 (d, J=0.9 Hz, 1H), 8.81 (d, J=0.9 Hz, 1H), 8.59 (dd, J=4.8, 1.5 Hz, 1H), 7.87-7.90 (m, 1H), 7.51 (dd, J=7.8, 4.6 Hz, 1H), 6.57 (d, J=1.2 Hz, 1H), 6.03 (d, J=0.9 Hz, 1H), 4.93 (dt, J=10.0, 5.4 Hz, 1H), 3.20 (d, J=11.6 Hz, 1H), 2.85 (s, 4H), 2.54-2.47 (m, 1H), 2.30 (s, 1H), 2.16 (s, 3H), 1.74 (d, J=16.6 Hz, 3H), 1.46 (dd, J=10.9, 4.8 Hz, 1H). ESI MS [M+H]+ for $C_{23}H_{24}N_6SO$, calcd 433.2, found 433.3.

Example 175: N-[2-(2,6-Difluorophenyl)-[1,3]thiazolo[5,4-c]pyridin-6-yl]-4-methyl-6-[(3S)-pyrrolidin-3-yloxy]pyridin-2-amine

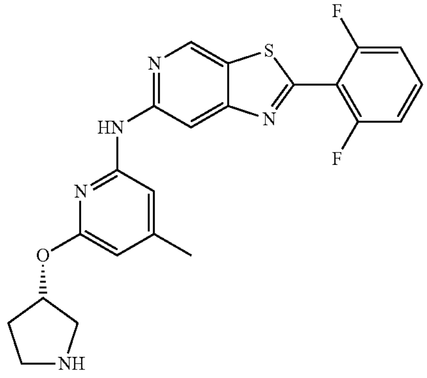

The title compound was synthesized in a similar fashion to example 161 from the appropriate starting materials. $^1H$ NMR (400 MHz, Methanol-$d_4$) δ 9.02 (d, J=0.9 Hz, 1H), 8.66 (d, J=0.9 Hz, 1H), 7.77-7.64 (m, 1H), 7.35-7.19 (m, 2H), 6.67 (dd, J=1.1, 0.7 Hz, 1H), 6.25 (dd, J=1.1, 0.7 Hz, 1H), 5.85-5.80 (m, 1H), 3.64 (d, J=2.9 Hz, 2H), 3.55-3.44 (m, 2H), 2.50-2.36 (m, 2H), 2.31 (s, 3H). ESI MS $[M+H]^+$ for $C_{22}H_{19}F_2N_5OS$, calcd 440.1, found 440.1.

Example 176: 4-Methyl-3-(6-{[4-methyl-6-((3S)-pyrrolidin-3-yloxy)pyridin-2-yl]amino}-[1,3]thiazolo[5,4-c]pyridin-2-yl)benzonitrile

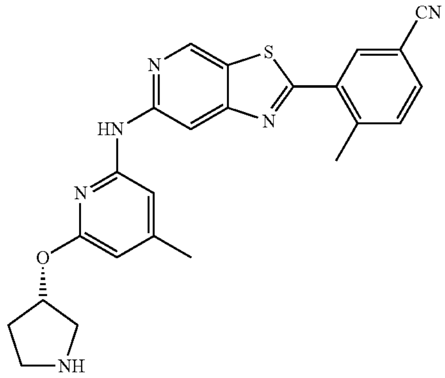

The title compound was synthesized in a similar fashion to example 161 from the appropriate starting materials. $^1H$ NMR (400 MHz, DMSO-$d_6$) δ 9.78 (s, 1H), 9.08 (d, J=0.8 Hz, 1H), 8.79 (d, J=0.8 Hz, 1H), 8.29 (d, J=1.8 Hz, 1H), 7.97 (d, J=8.0 Hz, 1H), 7.68 (d, J=8.0 Hz, 1H), 6.71 (s, 1H), 6.10 (s, 1H), 5.42-5.33 (m, 2H), 3.22-3.12 (m, 1H), 2.99-2.87 (m, 2H), 2.84-2.72 (m, 1H), 2.68 (s, 3H), 2.21 (s, 3H), 2.19-2.08 (m, 1H), 1.90-1.80 (m, 1H). ESI MS $[M+H]^+$ for $C_{24}H_{22}N_6OS$, calcd 443.2, found 443.1.

Example 177: N-[2-(2,6-Difluorophenyl)-[1,3]thiazolo[5,4-c]pyridin-6-yl]-6-[(3S)-pyrrolidin-3-yloxy]pyridin-2-amine

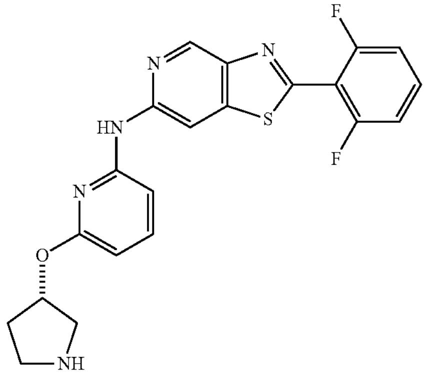

The title compound was synthesized in a similar fashion to example 161 from the appropriate starting materials. $^1H$ NMR (400 MHz, DMSO-$d_6$) δ 9.14 (d, J=0.8 Hz, 1H), 8.59-8.55 (m, 1H), 7.75 (tt, J=8.4, 6.4 Hz, 1H), 7.64 (t, J=7.9 Hz, 1H), 7.40 (t, J=8.7 Hz, 2H), 7.28-7.11 (m, 1H), 7.06 (d, J=7.8 Hz, 1H), 6.31 (d, J=7.8 Hz, 1H), 5.60 (dt, J=4.5, 2.5 Hz, 1H), 3.61-3.48 (m, 2H), 3.35 (ddp, J=18.1, 11.7, 6.2, 5.3 Hz, 2H), 2.41-2.28 (m, 3H). ESI MS $[M+H]^+$ for $C_{21}H_{17}F_2N_5OS$, calcd 426.1, found 426.1.

Example 178: N-[2-(2-Fluoro-6-methylphenyl)-[1,3]thiazolo[5,4-c]pyridin-6-yl]-4-methyl-6-[(3S)-pyrrolidin-3-yloxy]pyridin-2-amine

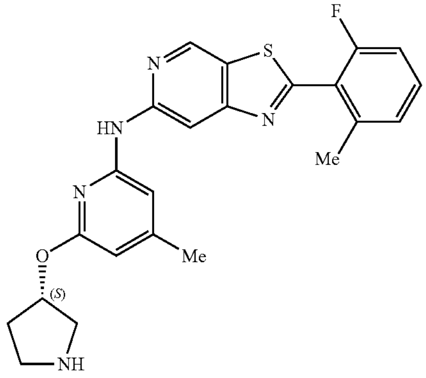

The title compound was synthesized in a similar fashion to example 161 from the appropriate starting materials. $^1H$ NMR (400 MHz, Chloroform-d) δ 8.85 (d, J=0.9 Hz, 1H), 8.62 (d, J=0.9 Hz, 1H), 7.38 (td, J=8.1, 5.8 Hz, 2H), 7.14 (d, J=7.7 Hz, 1H), 7.06 (t, J=9.1 Hz, 1H), 6.49 (s, 1H), 6.12 (s, 1H), 5.49 (ddt, J=6.5, 4.2, 1.9 Hz, 1H), 3.28-3.11 (m, 3H), 2.94 (ddd, J=11.2, 8.6, 5.4 Hz, 1H), 2.44 (s, 3H), 2.37 (s, 1H), 2.26 (s, 3H), 2.25-2.15 (m, 1H), 2.03 (dt, J=13.3, 6.3 Hz, 1H). ESI MS $[M+H]^+$ for $C_{23}H_{22}FN_5OS$, calcd 436.2, found 436.2.

Example 179: 4-Methyl-N-[2-(2-methylpyridin-3-yl)-[1,3]thiazolo[5,4-c]pyridin-6-yl]-6-[(3S)-pyrrolidin-3-yloxy]pyridin-2-amine

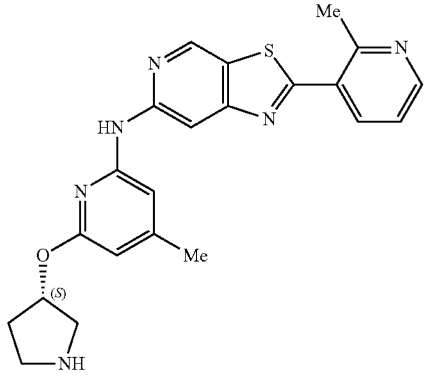

The title compound was synthesized in a similar fashion to example 161 from the appropriate starting materials. $^1$H NMR (400 MHz, Chloroform-d) δ 8.84-8.80 (m, 1H), 8.66-8.60 (m, 2H), 8.09 (dd, J=7.8, 1.7 Hz, 1H), 7.54 (s, 1H), 7.28 (dd, J=7.9, 4.9 Hz, 1H), 6.46 (s, 1H), 6.11 (s, 1H), 5.49 (td, J=4.7, 2.5 Hz, 1H), 3.28-3.11 (m, 3H), 2.90 (s, 4H), 2.28-2.17 (m, 4H), 2.13 (s, 1H), 2.02 (dt, J=14.1, 6.7 Hz, 1H). ESI MS [M+H]$^+$ for $C_{22}H_{22}N_6OS$, calcd 419.2, found 419.1.

Example 180: 6-[(2R)-2-Amino-3,3-dimethylbutoxy]-5-methyl-N-[2-(3-methylpyridin-2-yl)-[1,3]thiazolo[5,4-c]pyridin-6-yl]pyridin-2-amine

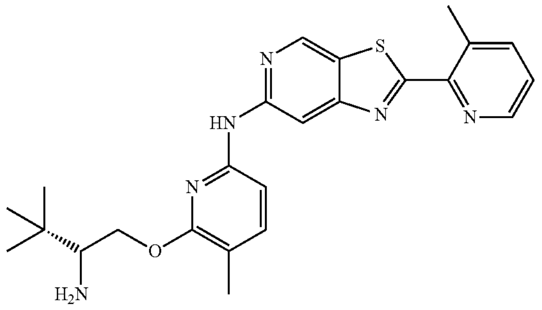

The title compound was synthesized in a similar fashion to example 161 from the appropriate starting materials. $^1$H NMR (400 MHz, Chloroform-d) δ 8.81 (d, J=0.9 Hz, 1H), 8.69 (d, J=1.0 Hz, 1H), 8.55 (ddd, J=4.6, 1.6, 0.7 Hz, 1H), 7.66 (ddd, J=7.8, 1.7, 0.9 Hz, 1H), 7.32-7.28 (m, 2H), 7.20 (s, 1H), 6.45 (d, J=7.7 Hz, 1H), 4.68 (dd, J=10.2, 3.0 Hz, 1H), 4.20 (dd, J=10.2, 9.6 Hz, 1H), 3.00 (dd, J=9.6, 3.0 Hz, 1H), 2.89 (s, 3H), 2.15 (s, 3H), 1.06 (s, 9H). ESI MS [M+H]$^+$ for $C_{24}H_{28}N_6OS$, calcd 449.2, found 449.4.

Example 181: 4-Methyl-N-[2-(1-methyl-1H-pyrazol-5-yl)-[1,3]thiazolo[5,4-c]pyridin-6-yl]-6-[(3S)-pyrrolidin-3-yloxy]pyridin-2-amine

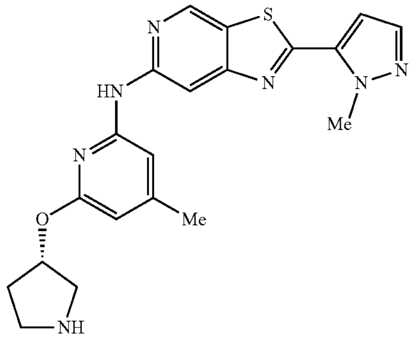 [SMILES: Cc1cc(Nc2cc3nc(-c4ccnn4C)sc3cn2)nc(O[C@H]2CCNC2)c1]

The title compound was synthesized in a similar fashion to example 161 from the appropriate starting materials. $^1$H NMR (400 MHz, DMSO-$d_6$) δ 9.80 (s, 1H), 9.00 (d, J=0.9 Hz, 1H), 8.55 (d, J=0.9 Hz, 1H), 7.60 (d, J=2.1 Hz, 1H), 7.08 (d, J=2.1 Hz, 1H), 6.79 (s, 1H), 6.10 (s, 1H), 5.49 (m, 1H), 4.26 (s, 3H), 3.46 (dd, J=12.8, 5.1 Hz, 1H), 3.35 (d, J=12.8 Hz, 1H), 3.21 (dd, J=8.8, 5.8 Hz, 2H), 2.27 (m, 1H), 2.21-2.10 (m, 4H). ESI MS [M+H]$^+$ for $C_{20}H_{21}N_7OS$, calcd 408.2, found 408.1.

Example 182: 5-Methyl-N-[2-(1-methyl-1H-pyrazol-5-yl)-[1,3]thiazolo[5,4-c]pyridin-6-yl]-6-[(3S)-pyrrolidin-3-yloxy]pyridin-2-amine

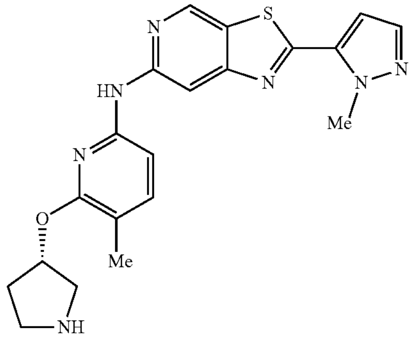 [SMILES: Cc1ccc(Nc2cc3nc(-c4ccnn4C)sc3cn2)nc1O[C@H]1CCNC1]

The title compound was synthesized in a similar fashion to example 161 from the appropriate starting materials. $^1$H NMR (400 MHz, DMSO-$d_6$) δ 9.70 (s, 1H), 8.97 (s, 1H), 8.62 (s, 1H), 7.59 (d, J=2.1 Hz, 1H), 7.39 (d, J=7.9 Hz 1H), 7.07 (d, J=2.1 Hz, 1H), 6.84 (d, J=7.9 Hz, 1H), 5.49 (m, 1H), 4.26 (s, 3H), 3.35 (dd, J=12.5, 5.4 Hz, 1H), 3.18-2.97 (m, 4H), 2.23 (td, J=14.2, 8.2 Hz, 1H), 2.03 (s, 3H), 2.01 (m, 1H). ESI MS [M+H]$^+$ for $C_{20}H_{21}N_7OS$, calcd 408.1, found 408.1.

Example 183: 4-Methyl-N-[2-(1-methyl-1H-imidazol-2-yl)-[1,3]thiazolo[5,4-c]pyridin-6-yl]-6-[(3S)-pyrrolidin-3-yloxy]pyridin-2-amine

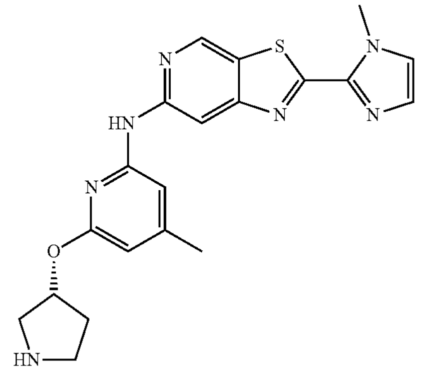

The title compound was synthesized in a similar fashion to example 161 from the appropriate starting materials. $^1$H NMR (400 MHz, Chloroform-d) δ 8.69 (d, J=0.9 Hz, 1H), 8.50 (d, J=0.9 Hz, 1H), 7.70 (d, J=1.0 Hz, 1H), 7.61 (s, 1H), 6.46 (t, J=0.9 Hz, 1H), 6.09 (t, J=0.9 Hz, 1H), 5.47 (ddt, J=6.6, 4.5, 1.9 Hz, 1H), 4.09 (s, 3H), 3.26-3.12 (m, 2H), 3.09 (dd, J=12.8, 4.8 Hz, 1H), 2.88 (ddd, J=11.3, 8.6, 5.5 Hz, 1H), 2.24 (s, 3H), 2.23-2.14 (m, 1H), 2.09-1.97 (m, 1H). ESI MS [M+H]$^+$ for $C_{20}H_{21}N_7OS$, calcd 408.2, found 408.4.

Example 184: 4-Methyl-N-[2-(oxan-4-yl)-[1,3]thiazolo[5,4-c]pyridin-6-yl]-6-[(3S)-pyrrolidin-3-yloxy]pyridin-2-amine Step 1: To a solution of 2-bromo 5-chloro azabenzothiozole derivative (1.0 g, 4 mmol) and Boronic acid (820 mg, 4.0 mmol) in Dioxane (20 mL)/$H_2O$ (5 mL) was added $PdCl_2$(dppf) (292 mg, 0.4 mmol) and $K_2CO_3$ (1.10 g, 8 mmol). After degassing for 10 min with $N_2$, the reaction mixture was heated to 100° C. and stirred for 4 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 50% EtOAc in hexanes) to get imine intermediate (760 mg, 75%) as a white solid.

Step 2: In a Parr hydrogenator, a solution of unsaturated THP derivative from step 1 (760 mg, 3.0 mmol) in methanol (20 mL) was added Pd/C (20%). After stirring at 40 psi $H_2$ atmosphere for 24 h, the reaction mixture was filtered through Celite®. The filtrate was concentrated under reduced pressure to obtain the desired intermediate as the while solid (760 mg, 96%) and used in the next step without purification.

Step 3: This step was performed in a similar fashion to step 4 of example 161 wherein the amine intermediate was prepared in a similar fashion to that described for steps 1-3 of example 161 from the appropriate starting materials.

Step 4: This step was performed in a similar fashion to step 5 of example 161. $^1$H NMR (400 MHz, DMSO-$d_6$) δ 9.61 (s, 1H), 8.89 (d, J=0.8 Hz, 1H), 8.50 (d, J=0.8 Hz, 1H), 6.73 (t, J=0.9 Hz, 1H), 6.04 (d, J=0.9 Hz, 1H), 5.32-5.29 (m, 1H), 3.92 (ddd, J=11.6, 4.5, 2.0 Hz, 2H), 3.46 (td, J=11.8, 2.3 Hz, 2H), 3.39 (td, J=7.6, 3.8 Hz, 1H), 3.12 (dd, J=12.3, 5.5 Hz, 1H), 2.93-2.86 (m, 2H), 2.76 (ddd, J=10.6, 8.0, 4.9 Hz, 1H), 2.17 (s, 3H), 2.07-1.99 (m, 3H), 1.78 (dtd, J=13.1, 11.6, 4.5 Hz, 3H). ESI MS [M+H]$^+$ for $C_{22}H_{22}N_6SO$, calcd 419.2, found 419.1.

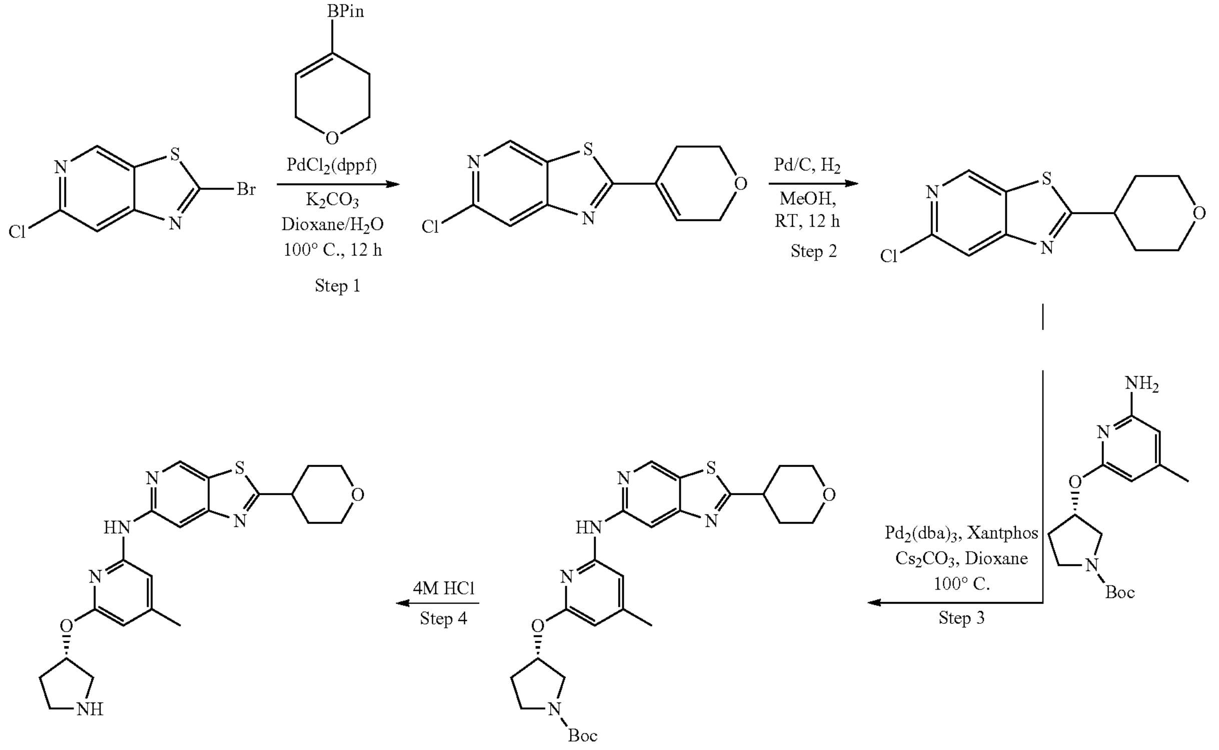

Example 185: 2-(6-{[4-Methyl-6-((3S)-pyrrolidin-3-yloxy)pyridin-2-yl]amino}-[1,3]thiazolo[5,4-c]pyridin-2-yl)-6-(propan-2-yl)-4H,5H,6H,7H,8H-pyrazolo[1,5-d][1,4]diazepin-7-one

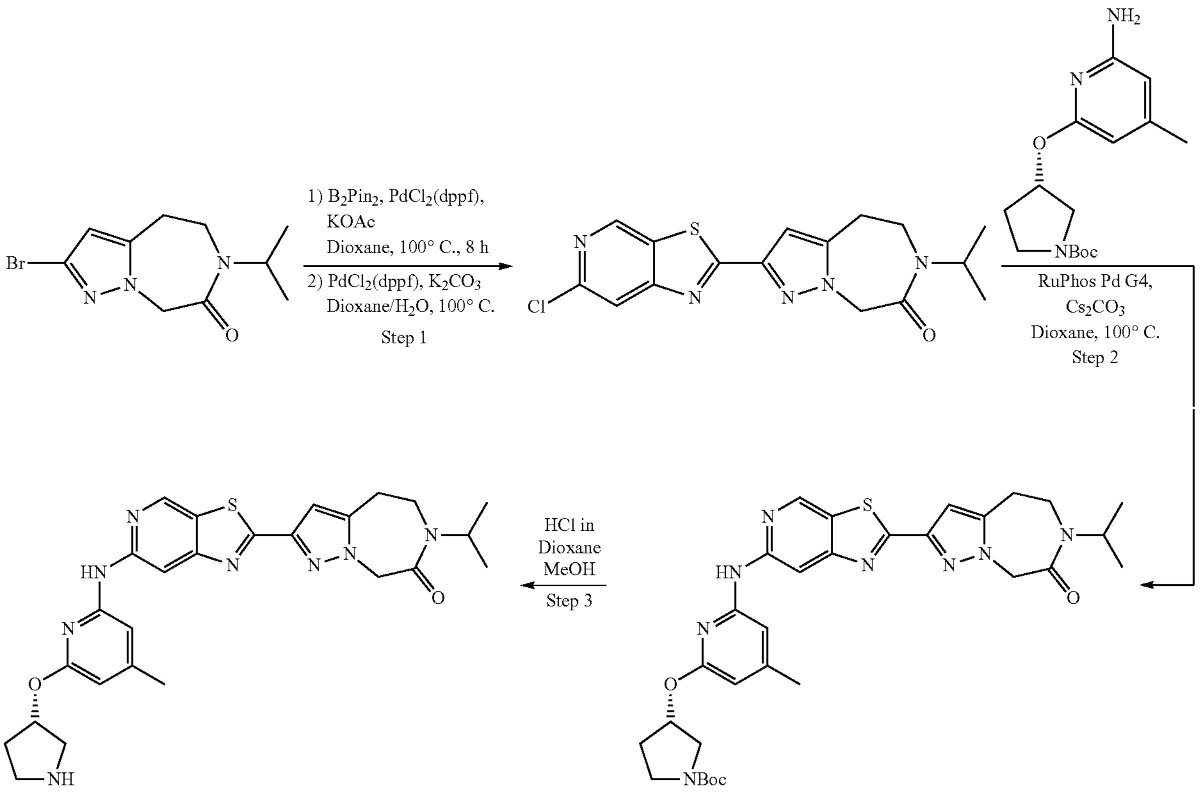

Step 1: The reaction was performed in a similar fashion to step 1 of example 120 from the appropriate starting materials.

Step 2: To a stirred solution of chloroazabenzothiozole (72 mg, 0.2 mmol) and aminopyridine derivative obtained in a similar manner to steps 1, 2, and 3 of example 161 (59 mg, 0.2 mmol) in dioxane (3 mL) was added RuPhos Pd G4 (25 mg, 0.03 mmol) and $Cs_2CO_3$ (195 mg 0.6 mmol). After degassing for 10 min under $N_2$ atmosphere, the reaction mixture was heated at 100° C. for 15 h. The reaction mixture was filtered through a pad of Celite® and concentrated under reduced pressure. The resulting residue a was purified by flash column chromatography (silica gel; gradient: 50% to 100% EtOAc in hexanes) to get the desired compound (71 mg, 57%).

Step 3. To a stirred suspension of intermediate from step 2 (71 mg, 0.11 mmol) in MeOH (1.5 mL) was added 4M HCl solution in Dioxane (3 mL) dropwise. The reaction was stirred at room temperature for 1 h and then concentrated under reduced pressure. The resultant was purified by reverse phase preparative HPLC to afford the desired compound (64 mg, trifluoroacetate salt). $^1$H NMR (400 MHz, Methanol-$d_4$) δ 8.95 (d, J=0.8 Hz, 1H), 8.25 (d, J=0.8 Hz, 1H), 6.91 (s, 1H), 6.67 (s, 1H), 6.34 (s, 1H), 5.88-5.69 (m, 1H), 5.26 (s, 2H), 4.82-4.67 (m, 1H), 4.02-3.82 (m, 2H), 3.65 (d, J=2.9 Hz, 2H), 3.57-3.46 (m, 2H), 3.27-3.18 (m, 2H), 2.55-2.37 (m, 2H), 2.33 (s, 3H), 1.24 (d, J=6.8 Hz, 6H). ESI MS $[M+H]^+$ for $C_{26}H_{30}N_8O_2S$, calcd 519.2, found 519.2.

Example 186: 5 N-[2-(4-Methanesulfonylphenyl)-[1,3]thiazolo[5,4-c]pyridin-6-yl]-4-methyl-6-[(3S)-pyrrolidin-3-yloxy]pyridin-2-amine

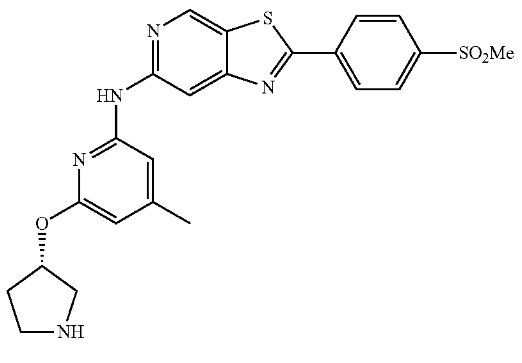 [SMILES: Cc1cc(Nc2cc3nc(-c4ccc(S(C)(=O)=O)cc4)sc3cn2)nc(O[C@H]2CCNC2)c1]

The title compound was synthesized in a similar fashion to example 185 from the appropriate starting materials. $^1$H NMR (400 MHz, DMSO-$d_6$) δ 9.74 (s, 1H), 9.05 (d, J=0.8 Hz, 1H), 8.69 (s, 1H), 8.28 (d, J=8.4 Hz, 2H), 8.04 (d, J=8.4 Hz, 2H), 6.71 (s, 1H), 6.07 (s, 1H), 5.41-5.34 (m, 1H), 3.62

(s, OH), 3.46 (s, OH), 3.22-3.09 (m, 1H), 2.92-2.85 (m, 2H), 2.81-2.75 (m, 1H), 2.18 (s, 3H), 2.10 (dd, J=13.9, 6.9 Hz, 1H), 1.85-1.81 (m, 1H). ESI MS $[M+H]^+$ for $C_{23}H_{23}N_5S_2O_3$, calcd 482.1, found 482.2.

Example 187: 4-(6-{[4-Methyl-6-(pyrrolidin-3-yloxy)pyridin-2-yl]amino}-[1,3]thiazolo[5,4-c]pyridin-2-yl)benzonitrile

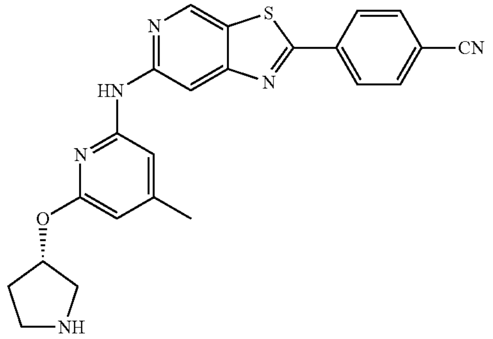 [SMILES: Cc1cc(Nc2cc3nc(-c4ccc(C#N)cc4)sc3cn2)nc(O[C@H]2CCNC2)c1]

The title compound was synthesized in a similar fashion to example 185 from the appropriate starting materials. $^1H$ NMR (400 MHz, DMSO-$d_6$) δ 9.74 (s, 1H), 9.05 (d, J=0.8 Hz, 1H), 8.69 (s, 1H), 8.28 (d, J=8.4 Hz, 2H), 8.04 (d, J=8.4 Hz, 2H), 6.71 (s, 1H), 6.07 (s, 1H), 5.34 (s, 1H), 3.62 (m, 1H), 3.46 (m, 1H), 3.16 (m, 1H), 2.91 (m, 2H), 2.80 (m, 1H), 2.18 (s, 3H), 2.10 (dd, J=13.9, 6.9 Hz, 1H), 1.83 (m, 1H). ESI MS $[M+H]^+$ for $C_{22}H_{20}N_5SOF$, calcd 429.1, found 429.2.

Example 188: N-[2-(4-Fluorophenyl)-[1,3]thiazolo[5,4-c]pyridin-6-yl]-4-methyl-6-[(3S)-pyrrolidin-3-yloxy]pyridin-2-amine

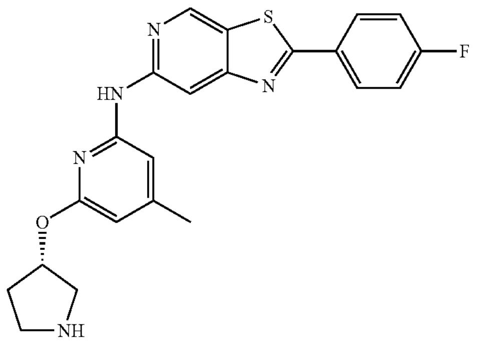 [SMILES: Cc1cc(Nc2cc3nc(-c4ccc(F)cc4)sc3cn2)nc(O[C@H]2CCNC2)c1]

The title compound was synthesized in a similar fashion to example 185 from the appropriate starting materials. $^1H$ NMR (400 MHz, DMSO-$d_6$) δ 9.70 (d, J=3.7 Hz, 1H), 8.98 (d, J=0.9 Hz, 1H), 8.62-8.58 (m, 1H), 8.20-8.16 (m, 2H), 7.42 (t, J=8.8 Hz, 2H), 6.74 (d, J=5.2 Hz, 1H), 6.07 (d, J=2.6 Hz, 1H), 5.39-5.33 (m, 1H), 3.58 (dd, J=12.0, 4.9 Hz, 1H), 3.40 (d, J=12.4 Hz, 1H), 3.16 (dd, J=12.3, 5.5 Hz, 1H), 2.92-2.88 (m, 1H), 2.79 (ddd, J=10.7, 8.1, 4.9 Hz, 1H), 2.18 (s, 3H), 2.11 (dt, J=14.1, 7.4 Hz, 1H), 1.83 (t, J=6.8 Hz, 1H). ESI MS $[M+H]^+$ for $C_{22}H_{20}N_5SOF$, calcd 422.1, found 422.2.

Example 189: 1-(6-{[4-Methyl-6-((3S)-pyrrolidin-3-yloxy)pyridin-2-yl]amino}-[1,3]thiazolo[5,4-c]pyridin-2-yl)piperidin-4-ol

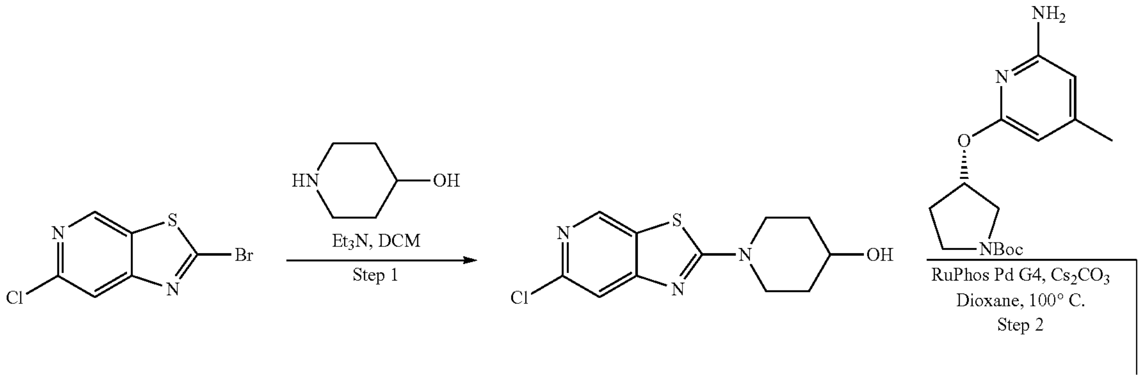

-continued

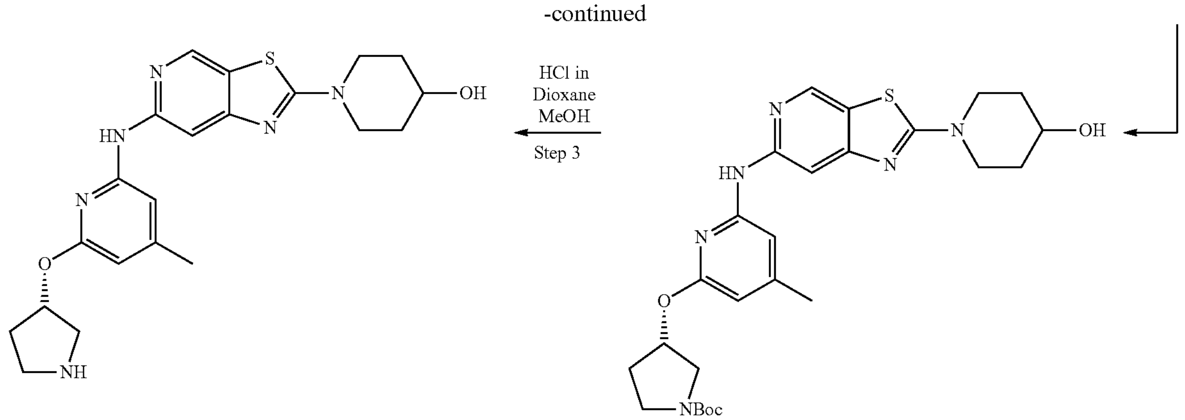

Step 1: To a stirred solution of azabenzothiazole derivative (250 mg, 1 mmol) and 4-hydroxypiperidine (101 mg, 1 mmol) in $CH_2Cl_2$ (2 mL) was added triethylamine (0.42 mL, 3 mmol), and the reaction mixture was allowed to stir for 3 h at ambient temperature. The mixture was quenched by addition of sat. $NH_4Cl$ and extracted with $CH_2Cl_2$. The organic extract was dried over anhydrous $Na_2SO_4$ and then concentrated under reduced pressure to afford the desired compound in quantitative yield.

Step 2: This reaction was performed in a similar fashion as step 2 of example 185.

Step 3: This reaction was performed in a similar fashion as step 3 of example 185. $^1$H NMR (400 MHz, DMSO-$d_6$) δ 9.30 (s, 1H), 8.45 (d, J=0.8 Hz, 1H), 7.87 (d, J=0.8 Hz, 1H), 6.88 (d, J=1.1 Hz, 1H), 6.03 (d, J=1.1 Hz, 1H), 5.34-5.24 (m, 1H), 4.88 (d, J=4.1 Hz, 1H), 3.93-3.73 (m, 3H), 3.48-3.36 (m, 3H), 3.20-3.09 (m, 1H), 2.98-2.74 (m, 3H), 2.18 (s, 3H), 2.14-2.01 (m, 1H), 1.91-1.76 (m, 3H), 1.53-1.39 (m, 2H). ESI MS $[M+H]^+$ for $C_{21}H_{26}N_6O_2S$, calcd 427.2, found 427.2.

Example 190: N-[2-(4-Methoxypiperidin-1-yl)-[1,3]thiazolo[5,4-c]pyridin-6-yl]-4-methyl-6-((3S)-pyrrolidin-3-yloxy)pyridin-2-amine

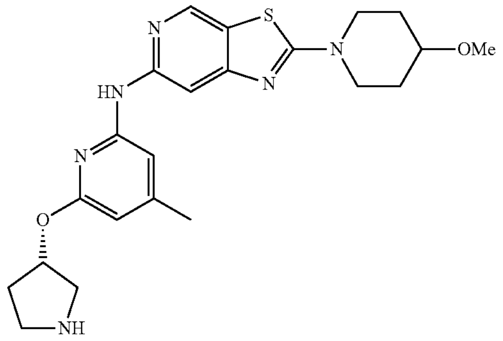

The title compound was synthesized in a similar fashion to example 189 from the appropriate starting materials. $^1$H NMR (400 MHz, Methanol-$d_4$) δ 8.31 (d, J=0.8 Hz, 1H), 7.97 (d, J=0.8 Hz, 1H), 6.60 (dd, J=1.1, 0.7 Hz, 1H), 6.08 (dd, J=1.1, 0.7 Hz, 1H), 5.56-5.50 (m, 1H), 3.92-3.82 (m, 2H), 3.56-3.47 (m, 3H), 3.38 (s, 3H), 3.22 (dd, J=12.7, 5.2 Hz, 1H), 3.13-3.04 (m, 2H), 3.0-2.90 (m, 1H), 2.27-2.12 (m, 4H), 2.06-1.93 (m, 3H), 1.74-1.62 (m, 2H). ESI MS $[M+H]^+$ for $C_{22}H_{28}N_6O_2S$, calcd 441.2, found 441.2.

Example 191: 4-Methyl-N-[2-(morpholin-4-yl)-[1,3]thiazolo[5,4-c]pyridin-6-yl]-6-((3S)-pyrrolidin-3-yloxy)pyridin-2-amine

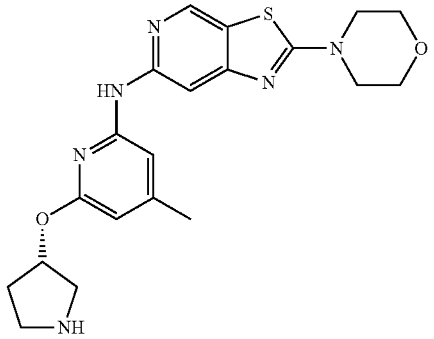

The title compound was synthesized in a similar fashion to example 189 from the appropriate starting materials. $^1$H NMR (400 MHz, DMSO-$d_6$) δ 9.36 (s, 1H), 8.51 (d, J=0.7 Hz, 1H), 7.94 (d, J=0.7 Hz, 1H), 6.86 (t, J=0.9 Hz, 1H), 6.04 (t, J=0.9 Hz, 1H), 5.38-5.28 (m, 1H), 3.75-3.59 (m, 10H), 3.53-3.43 (m, 1H), 3.17 (dd, J=12.3, 5.5 Hz, 1H), 2.99-2.89 (m, 2H), 2.83 (ddd, J=10.7, 8.1, 4.8 Hz, 1H), 2.19 (d, J=0.6 Hz, 3H), 2.09 (dtd, J=14.3, 7.9, 6.6 Hz, 1H), 1.89-1.77 (m, 1H). ESI MS $[M+H]^+$ for $C_{20}H_{24}N_6O_2S$, calcd 413.2, found 413.1.

Example 192: (3S)-1-(6-{[4-Methyl-6-((3S)-pyrrolidin-3-yloxy)pyridin-2-yl]amino}-[1,3]thiazolo[5,4-c]pyridin-2-yl)piperidin-3-ol

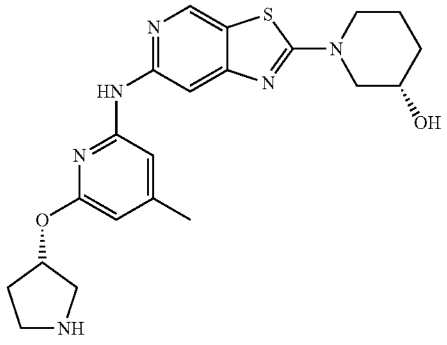

The title compound was synthesized in a similar fashion to example 189 from the appropriate starting materials. $^1H$ NMR (400 MHz, Methanol-$d_4$) δ 8.35-8.29 (m, 1H), 8.01-7.95 (m, 1H), 6.67-6.56 (m, 1H), 6.13-6.05 (m, 1H), 5.63-5.45 (m, 1H), 4.09-3.90 (m, 1H), 3.85-3.70 (m, 2H), 3.62-3.33 (m, 2H), 3.21 (m, 1H), 3.13-3.02 (m, 2H), 2.98-2.88 (m, 1H), 2.30-2.09 (m, 4H), 2.06-1.88 (m, 3H), 1.65 (m, 2H). ESI MS $[M+H]^+$ for $C_{21}H_{27}N_6O_2S$, calcd 427.2, found 427.2. ESI MS $[M+H]^+$ for $C_{21}H_{26}N_6O_2S$, calcd 427.2, found 427.2.

Example 193: (3R)-1-(6-{[4-Methyl-6-((3S)-pyrrolidin-3-yloxy)pyridin-2-yl]amino}-[1,3]thiazolo[5,4-c]pyridin-2-yl)piperidin-3-ol

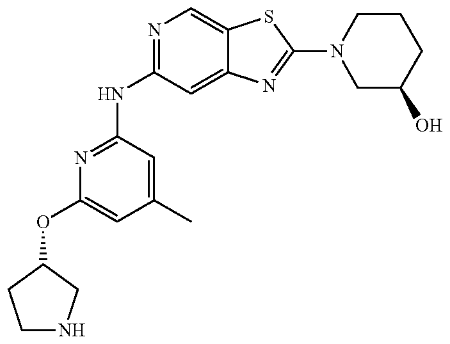

The title compound was synthesized in a similar fashion to example 189 from the appropriate starting materials. $^1H$ NMR (400 MHz, Methanol-$d_4$) δ 8.35-8.29 (m, 1H), 8.01-7.95 (m, 1H), 6.67-6.56 (m, 1H), 6.13-6.05 (m, 1H), 5.63-5.45 (m, 1H), 4.09-3.90 (m, 1H), 3.85-3.70 (m, 2H), 3.62-3.33 (m, 2H), 3.21 (m, 1H), 3.13-3.02 (m, 2H), 2.98-2.88 (m, 1H), 2.30-2.09 (m, 4H), 2.06-1.88 (m, 3H), 1.65 (m, 2H). ESI MS $[M+H]^+$ for $C_{21}H_{26}N_6O_2S$, calcd 427.2, found 427.2.

Example 194: N-[2-(5-Methyl-1H-pyrazol-1-yl)-[1,3]thiazolo[5,4-c]pyridin-6-yl]-5-(morpholin-4-yl)-6-[(pyrrolidin-1-yl)methyl]pyridin-2-amine

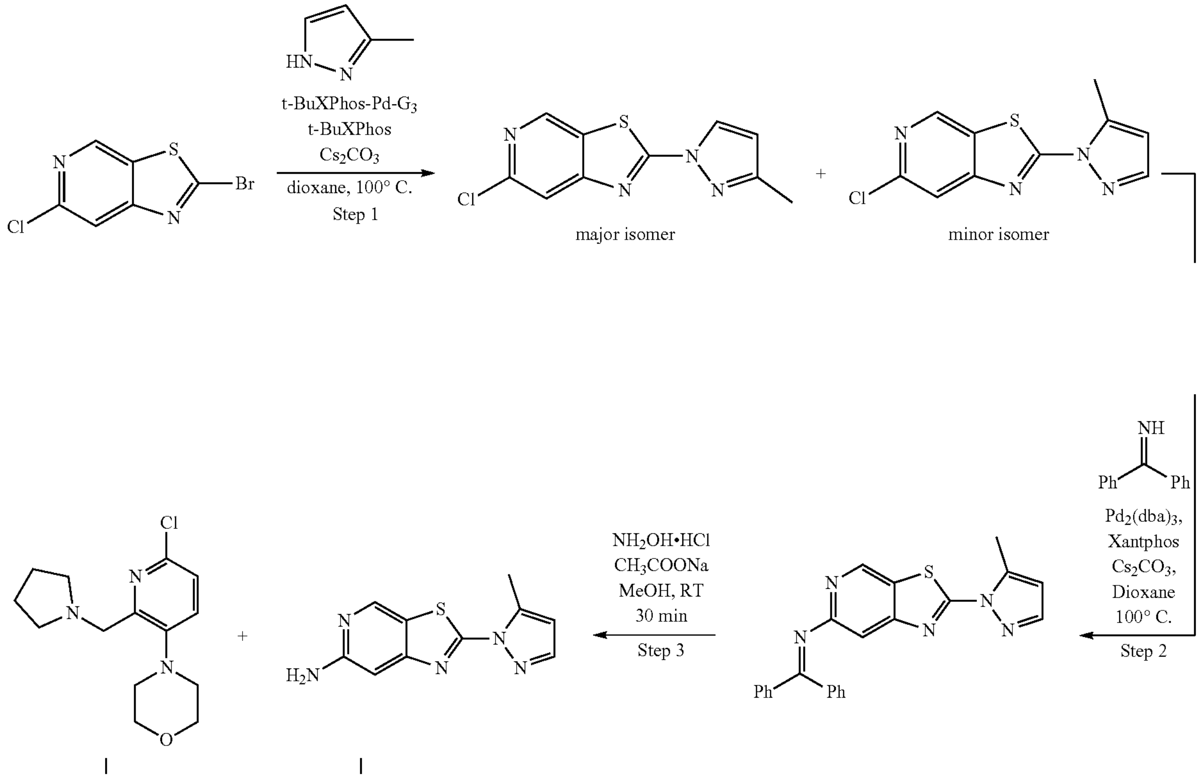

-continued

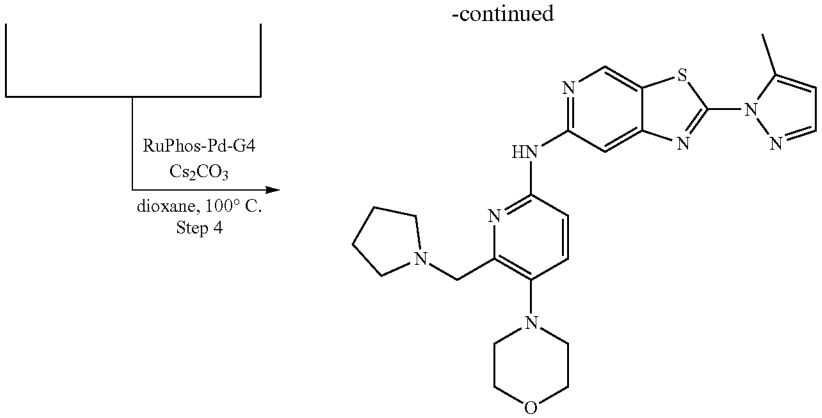

Step 1: To a solution of 2-Bromo-6-chloro[1,3]thiazolo[5,4-c]pyridine (1.1 g, 4.4 mmol) and 5-Methyl-1H-pyrazole (330 Mg, 4.0 mmol) in Dioxane (10 mL) was added t-BuXPhos-Pd-G3 (310 mg, 0.4 mmol), t-BuX-Phos (340 mg, 0.8 mmol), and $Cs_2CO_3$ (3.92 g 2.96 mmol). After degassing for 25 min under $N_2$ atmosphere, the reaction mixture was heated to 75° C. and stirred for 15 h. The reaction mixture was filtered through Celite® and concentrated under reduced pressure. The major isomer was obtained by precipitating the crude reaction mixture in EtOAc (725 mg, 52%). The minor isomer was purified by column chromatography (silica gel; gradient: 0% to 50% EtOAc in hexanes) of the remaining filtrate (350 mg, 35%).

Step 2: This reaction was performed in a similar fashion to step 2 of example 1.

Step 3: This reaction was performed in a similar fashion to step 3 of example 1.

Step 4: This reaction was performed in a similar fashion using step 6 of example 1 using a chloropyridine derivative obtained in a fashion similar to that described for steps 4 and 5 of example 1 using the appropriate starting materials. $^1$H NMR (400 MHz, Chloroform-d) δ 8.65 (s, 1H), 8.07 (s, 1H), 7.64 (s, 1H), 7.45 (s, 1H), 7.42 (d, J=8.7 Hz, 1H), 7.35 (d, J=8.7 Hz, 1H), 6.25 (dd, J=1.6, 0.9 Hz, 1H), 3.88 (s, 2H), 3.86-3.80 (m, 4H), 2.92-2.89 (m, 4H), 2.81 (s, 3H), 2.75-2.72 (m, 4H), 1.87-1.77 (m, 4H). ESI MS $[M+H]^+$ for $C_{24}H_{28}N_8OS$, calcd 477.2, found 477.7.

Example 195: N-[2-(3-Methyl-1H-pyrazol-1-yl)-[1,3]thiazolo[5,4-c]pyridin-6-yl]-5-(morpholin-4-yl)-6-[(pyrrolidin-1-yl)methyl]pyridin-2-amine

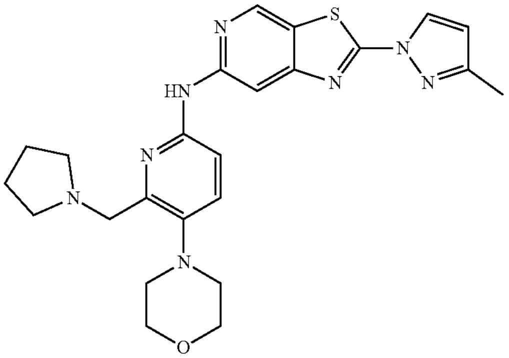 [SMILES: Cc1ccn(-c2nc3cc(Nc4ccc(N5CCOCC5)c(CN5CCCC5)n4)ncc3s2)n1]

The title compound was synthesized in a similar fashion to example 194 using the major isomer formed from step 1. $^1$H NMR (400 MHz, Chloroform-d) δ 8.64 (s, 1H), 8.33 (s, 1H), 7.86 (d, J=0.8 Hz, 1H), 7.48 (d, J=8.7 Hz, 1H), 7.41 (d, J=8.7 Hz, 1H), 6.34 (d, J=2.6 Hz, 1H), 3.85 (s, 2H), 3.84-3.82 (m, 4H), 2.95-2.86 (m, 4H), 2.70-2.67 (m, 4H), 2.38 (s, 3H), 1.82-1.79 (m, 4H). ESI MS $[M+H]^+$ for $C_{24}H_{28}N_8OS$, calcd 477.2, found 477.8.

Example 196: N-[2-(3,5-Dimethyl-1H-pyrazol-1-yl)-[1,3]thiazolo[5,4-c]pyridin-6-yl]-5-(morpholin-4-yl)-6-[(pyrrolidin-1-yl)methyl]pyridin-2-amine

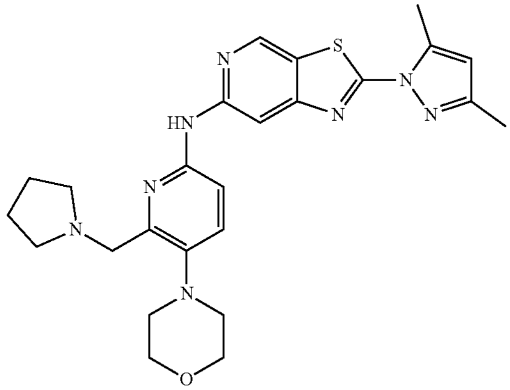 [SMILES: Cc1cc(C)n(-c2nc3cc(Nc4ccc(N5CCOCC5)c(CN5CCCC5)n4)ncc3s2)n1]

The title compound was synthesized in a similar fashion to example 194 from the appropriate starting materials. $^1$H NMR (400 MHz, Chloroform-d) δ 8.62 (d, J=0.8 Hz, 1H), 8.01 (d, J=0.8 Hz, 1H), 7.41 (d, J=8.7 Hz, 1H), 7.36 (s, 1H), 7.34 (d, J=8.7 Hz, 1H), 6.05 (d, J=1.1 Hz, 1H), 3.85 (s, 2H), 3.84-3.79 (m, 4H), 2.94-2.87 (m, 4H), 2.75 (s, 3H), 2.72-2.66 (m, 4H), 2.29 (s, 3H), 1.85-1.77 (m, 4H). ESI MS $[M+H]^+$ for $C_{25}H_{30}N_8OS$, calcd 491.2, found 491.5.

Example 197: 5-Methyl-N-[2-(5-methyl-1H-pyrazol-1-yl)-[1,3]thiazolo[5,4-c]pyridin-6-yl]-6-[(pyrrolidin-1-yl)methyl]pyridin-2-amine

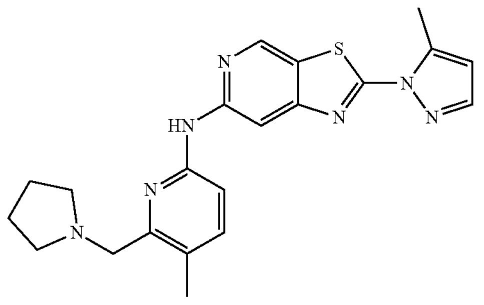 [SMILES: Cc1ccc(Nc2cc3nc(-n4nccc4C)sc3cn2)nc1CN1CCCC1]

The title compound was synthesized in a similar fashion to example 194 from the appropriate starting materials. $^1$H NMR (400 MHz, Chloroform-d) δ 8.65 (d, J=0.8 Hz, 1H), 8.19 (d, J=0.8 Hz, 1H), 7.63 (d, J=1.6 Hz, 1H), 7.36 (d, J=8.3 Hz, 1H), 7.33 (s, 1H), 7.17 (d, J=8.2 Hz, 1H), 6.25 (dd, J=1.7, 1.0 Hz, 1H), 3.73 (s, 2H), 2.82 (s, 3H), 2.68 (p, J=4.1 Hz, 4H), 2.28 (s, 3H), 1.84 (p, J=3.2 Hz, 4H). ESI MS $[M+H]^+$ for $C_{21}H_{23}N_7S$, calcd 406.22, found 406.4.

Example 198: 5-Methyl-N-[2-(5-methyl-1H-pyrazol-1-yl)-[1,3]thiazolo[5,4-c]pyridin-6-yl]-6-({[(3S)-oxolan-3-yl]amino}methyl)pyridin-2-amine

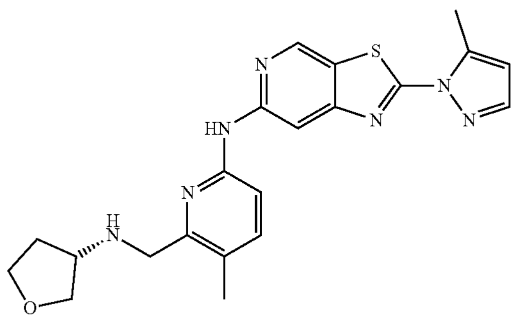

The title compound was synthesized in a similar fashion to example 194 from the appropriate starting materials. $^1$H NMR (400 MHz, Chloroform-d) δ 8.65 (d, J=0.9 Hz, 1H), 8.31 (d, J=0.9 Hz, 1H), 7.70-7.54 (m, 1H), 7.39-7.33 (m, 2H), 6.96 (d, J=8.2 Hz, 1H), 6.24 (dd, J=1.7, 0.9 Hz, 1H), 4.01-3.93 (m, 2H), 3.86 (s, 2H), 3.82 (td, J=8.2, 5.5 Hz, 1H), 3.75 (dd, J=8.8, 4.1 Hz, 1H), 3.56 (ddt, J=7.0, 5.6, 4.1 Hz, 1H), 2.82 (s, 3H), 2.22 (s, 3H), 2.19-2.10 (m, 1H), 1.93 (dddd, J=12.6, 7.5, 5.5, 4.0 Hz, 1H). ESI MS $[M+H]^+$ for $C_{21}H_{23}N_7OS$, calcd 422.2, found 422.7.

Example 199: 5-Methyl-N-[2-(5-methyl-1H-pyrazol-1-yl)-[1,3]thiazolo[5,4-c]pyridin-6-yl]-6-({[(3R)-oxolan-3-yl]amino}methyl)pyridin-2-amine

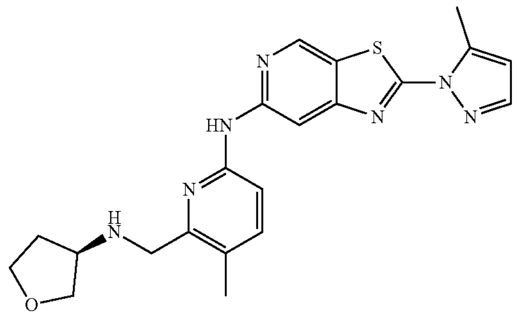 [SMILES: Cc1ccc(Nc2cc3nc(-n4nccc4C)sc3cn2)nc1CN[C@@H]1CCOC1]

The title compound was synthesized in a similar fashion to example 194 from the appropriate starting materials. $^1$H NMR (400 MHz, Chloroform-d) δ 8.66 (d, J=0.9 Hz, 1H), 8.32 (d, J=0.8 Hz, 1H), 7.64 (dd, J=1.6, 0.5 Hz, 1H), 7.36 (dd, J=8.2, 0.7 Hz, 1H), 7.31 (s, 1H), 6.97 (d, J=8.1 Hz, 1H), 6.25 (dq, J=1.9, 0.9 Hz, 1H), 5.32 (s, 1H), 4.03-3.93 (m, 2H), 3.86 (s, 2H), 3.84-3.78 (m, 1H), 3.76 (dd, J=8.8, 4.1 Hz, 1H), 3.56 (ddt, J=7.8, 5.8, 4.1 Hz, 1H), 2.82 (dd, J=1.0, 0.5 Hz, 3H), 2.22 (s, 3H), 2.20-2.07 (m, 1H), 1.93 (dddd, J=12.6, 7.5, 5.4, 4.0 Hz, 1H). ESI MS $[M+H]^+$ for $C_{21}H_{23}N_7OS$, calcd 422.2, found 422.7.

Example 200: 5-Methyl-N-[2-(1H-pyrazol-1-yl)-[1,3]thiazolo[5,4-c]pyridin-6-yl]-6-[(pyrrolidin-1-yl)methyl]pyridin-2-amine

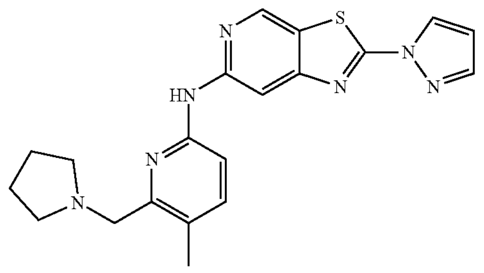 [SMILES: Cc1ccc(Nc2cc3nc(-n4cccn4)sc3cn2)nc1CN1CCCC1]

The title compound was synthesized in a similar fashion to example 194 from the appropriate starting materials. $^1$H NMR (400 MHz, Chloroform-d) δ 8.67 (d, J=0.9 Hz, 1H), 8.47 (dd, J=2.7, 0.6 Hz, 1H), 8.09 (d, J=0.9 Hz, 1H), 7.79 (dd, J=1.6, 0.6 Hz, 1H), 7.43 (s, 1H), 7.37 (dd, J=8.3, 0.7 Hz, 1H), 7.28 (d, J=8.2 Hz, 1H), 6.55 (dd, J=2.7, 1.6 Hz, 1H), 3.74 (s, 2H), 2.67 (qd, J=4.2, 2.8, 1.9 Hz, 4H), 2.30 (s, 3H), 1.83 (td, J=5.8, 4.9, 3.2 Hz, 4H). ESI MS $[M+H]^+$ for $C_{20}H_{21}N_7S$, calcd 392.2, found 392.5.

Example 201: [(2S,4S)-4-Amino-1-(3-methyl-6-{[2-(5-methyl-1H-pyrazol-1-yl)-[1,3]thiazolo[5,4-c]pyridin-6-yl]amino}pyridin-2-yl)pyrrolidin-2-yl]methanol

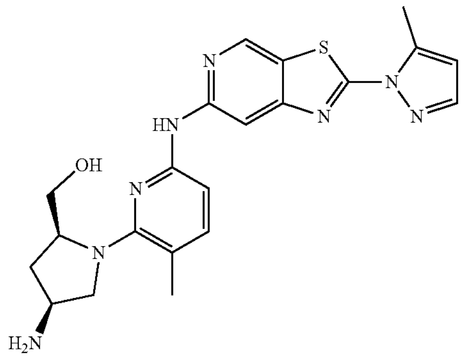 [SMILES: Cc1ccc(Nc2cc3nc(-n4nccc4C)sc3cn2)nc1N1C[C@@H](N)C[C@H]1CO]

The title compound was synthesized in a similar fashion to example 65 using azabenzothiazole derivative obtained in step 1 of example 194. $^{1}$H NMR (400 MHz, Methanol-$d_4$) δ 8.52 (d, J=0.8 Hz, 1H), 8.32 (d, J=0.9 Hz, 1H), 7.59 (dd, J=1.6, 0.5 Hz, 1H), 7.20 (dd, J=7.9, 0.8 Hz, 1H), 6.52 (d, J=7.9 Hz, 1H), 6.27 (dd, J=1.7, 0.9 Hz, 1H), 4.65-4.57 (m, 1H), 3.72 (d, J=4.0 Hz, 2H), 3.45-3.39 (m, 2H), 3.29 (p, J=1.6 Hz, 1H), 2.71 (s, 3H), 2.39-2.30 (m, 1H), 2.17 (s, 3H), 1.83-1.71 (m, 1H). ESI MS $[M+H]^+$ for $C_{21}H_{24}N_8OS$, calcd 437.2, found 437.6.

Example 202: (3S)-1-(3-Methyl-6-{[2-(5-methyl-1H-pyrazol-1-yl)-[1,3]thiazolo[5,4-c]pyridin-6-yl]amino}pyridin-2-yl)pyrrolidin-3-ol

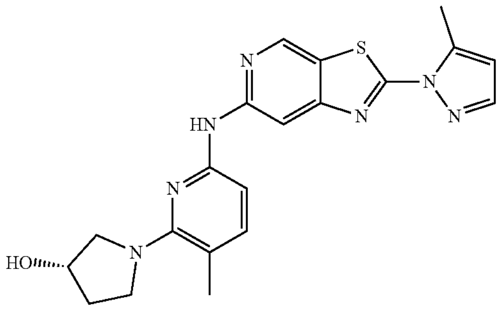 [SMILES: Cc1ccc(Nc2cc3nc(-n4nccc4C)sc3cn2)nc1N1CC[C@H](O)C1]

The title compound was synthesized in a similar fashion to example 65 using the appropriate starting materials, and the azabenzothiazole derivative obtained in step 1 of example 194. $^{1}$H NMR (400 MHz, Chloroform-d) δ 8.60 (d, J=0.8 Hz, 1H), 8.45-8.35 (m, 1H), 7.62 (d, J=1.6 Hz, 1H), 7.22-7.17 (m, 1H), 7.15 (s, 1H), 6.42 (dd, J=7.8, 1.3 Hz, 1H), 6.24 (dd, J=1.7, 1.0 Hz, 1H), 4.53 (tt, J=4.8, 2.5 Hz, 1H), 3.92-3.74 (m, 2H), 3.64-3.57 (m, 2H), 2.79 (s, 3H), 2.37-2.28 (m, 1H), 2.26 (s, 3H), 2.17-2.05 (m, 1H), 2.06-1.95 (m, 1H). ESI MS $[M+H]^+$ for $C_{20}H_{21}N_7OS$, calcd 408.2, found 408.5.

Example 203: 2-[4-(3-Methyl-6-{[2-(5-methyl-1H-pyrazol-1-yl)-[1,3]thiazolo[5,4-c]pyridin-6-yl]amino}pyridin-2-yl)piperazin-1-yl]ethan-1-ol

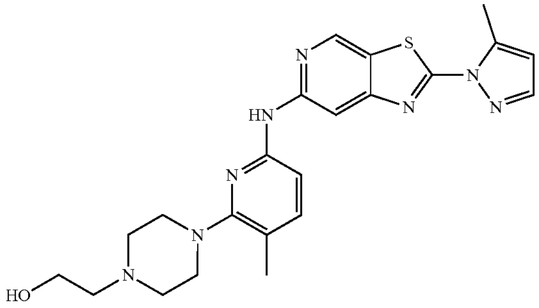 [SMILES: Cc1ccc(Nc2cc3nc(-n4nccc4C)sc3cn2)nc1N1CCN(CCO)CC1]

The title compound was synthesized in a similar fashion to example 65 using the appropriate starting materials, and the azabenzothiazole derivative obtained in step 1 of example 194. $^{1}$H NMR (400 MHz, Chloroform-d) δ 8.61 (s, 1H), 8.49 (s, 1H), 7.62 (d, J=1.6 Hz, 1H), 7.47 (s, 1H), 7.35-7.26 (m, 1H), 6.64 (d, J=7.9 Hz, 1H), 6.23 (d, J=0.8 Hz, 1H), 3.71-3.58 (m, 2H), 3.48-3.43 (m, 1H), 3.29-3.26 (m, 4H), 2.80 (s, 3H), 2.69-2.65 (m, 4H), 2.63-2.59 (m, 2H), 2.18 (s, 3H). ESI MS $[M+H]^+$ for $C_{22}H_{26}N_8OS$, calcd 451.2, found 451.7.

Example 204: 5-Methyl-N-[2-(5-methyl-1H-pyrazol-1-yl)-[1,3]thiazolo[5,4-c]pyridin-6-yl]-6-(piperazin-1-yl)pyridin-2-amine

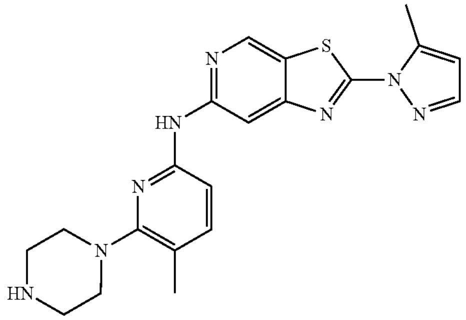 [SMILES: Cc1ccc(Nc2cc3nc(-n4nccc4C)sc3cn2)nc1N1CCNCC1]

The title compound was synthesized in a similar fashion to example 194 from the appropriate starting materials. $^{1}$H NMR (400 MHz, Chloroform-d) δ 8.63 (d, J=0.8 Hz, 1H), 8.48 (d, J=0.8 Hz, 1H), 7.62 (d, J=1.6 Hz, 1H), 7.32-7.28 (m, 3H), 6.62 (d, J=7.9 Hz, 1H), 6.24 (dd, J=1.7, 1.0 Hz, 1H), 3.28-3.18 (m, 4H), 3.07-3.00 (m, 4H), 2.81 (s, 3H), 2.20 (s, 3H). ESI MS $[M+H]^+$ for $C_{20}H_{22}N_8S$, calcd 407.52, found 407.3.

Example 205: N-[2-(5-Methyl-1H-pyrazol-1-yl)-[1,3]thiazolo[5,4-c]pyridin-6-yl]-6-[(1S,4S)-5-methyl-2,5-diazabicyclo[2.2.1]heptan-2-yl]pyridin-2-amine

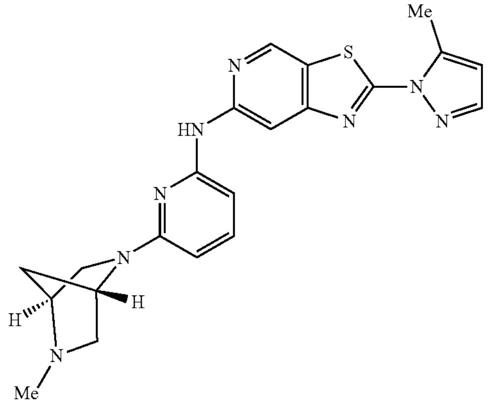 [SMILES: Cc1ccnn1-c1nc2cc(Nc3cccc(N4C[C@@H]5C[C@H]4CN5C)n3)ncc2s1]

The title compound was synthesized in a similar fashion to example 89 using azabenzothiazole derivative obtained in step 1, example 194. $^{1}$H NMR (400 MHz, Chloroform-d) δ 8.66 (d, J=0.9 Hz, 1H), 8.52 (d, J=0.9 Hz, 1H), 7.65 (d, J=1.6 Hz, 1H), 7.38 (t, J=7.9 Hz, 1H), 7.19 (s, 1H), 6.32-6.25 (m, 2H), 5.95-5.91 (m, 1H), 4.70 (s, 1H), 3.63 (d, J=9.7 Hz, 1H), 3.57 (s, 1H), 3.42 (dd, J=9.7, 2.2 Hz, 1H), 3.10 (dd, J=9.6, 2.1 Hz, 1H), 2.82 (t, J=0.6 Hz, 3H), 2.80-2.72 (m, 1H), 2.44 (s, 3H), 2.11-1.99 (m, 2H), 1.92 (d, J=9.5 Hz, 1H). ESI MS $[M+H]^+$ for $C_{21}H_{22}N_8S$, calcd 419.2, found 419.2.

Example 206: 6-[(1S,4S)-5-Methyl-2,5-diazabicyclo[2.2.1]heptan-2-yl]-N-[2-(1H-pyrazol-1-yl)-[1,3]thiazolo[5,4-c]pyridin-6-yl]pyridin-2-amine

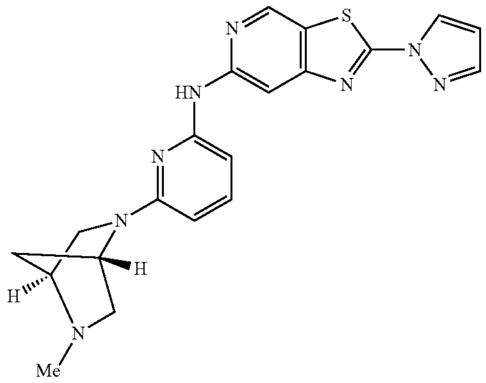 [SMILES: CN1C[C@@H]2C[C@H]1CN2c1cccc(Nc2cc3nc(-n4cccn4)sc3cn2)n1]

The title compound was synthesized in a similar fashion to example 89 using azabenzothiazole derivative obtained in a similar manner to step 1, example 194 from the appropriate starting materials. $^{1}$H NMR (400 MHz, Chloroform-d) δ 8.66 (d, J=0.8 Hz, 1H), 8.52 (dd, J=2.7, 0.6 Hz, 1H), 8.49 (d, J=0.9 Hz, 1H), 7.80 (dd, J=1.7, 0.6 Hz, 1H), 7.37 (t, J=7.9 Hz, 1H), 7.27 (s, 1H), 6.56 (dd, J=2.7, 1.6 Hz, 1H), 6.29 (d, J=7.7 Hz, 1H), 5.93 (dd, J=8.1, 0.5 Hz, 1H), 4.66 (s, 1H), 3.64 (d, J=9.7 Hz, 1H), 3.55 (s, 1H), 3.44 (dd, J=9.6, 2.2 Hz, 1H), 3.07 (dd, J=9.5, 2.1 Hz, 1H), 2.73 (dd, J=9.5, 1.4 Hz, 1H), 2.43 (s, 3H), 2.09-1.99 (m, 1H), 1.94-1.83 (m, 2H). ESI MS $[M+H]^+$ for $C_{20}H_{20}N_8S$, calcd 405.2, found 405.2.

Example 207: (5R)-5-Methyl-1-(6-{[5-(oxan-4-yl)-6-[(pyrrolidin-1-yl)methyl]pyridin-2-yl]amino}-[1,3]thiazolo[5,4-c]pyridin-2-yl)pyrrolidin-2-one

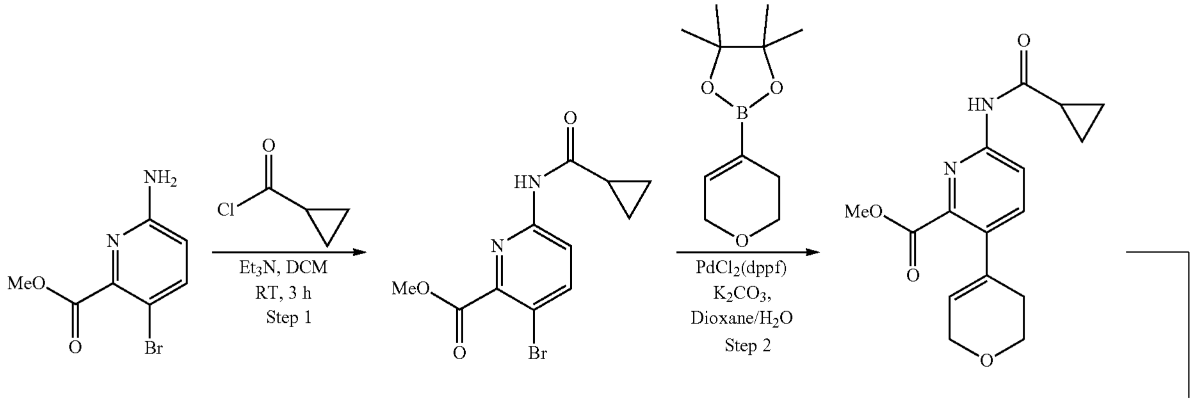

-continued

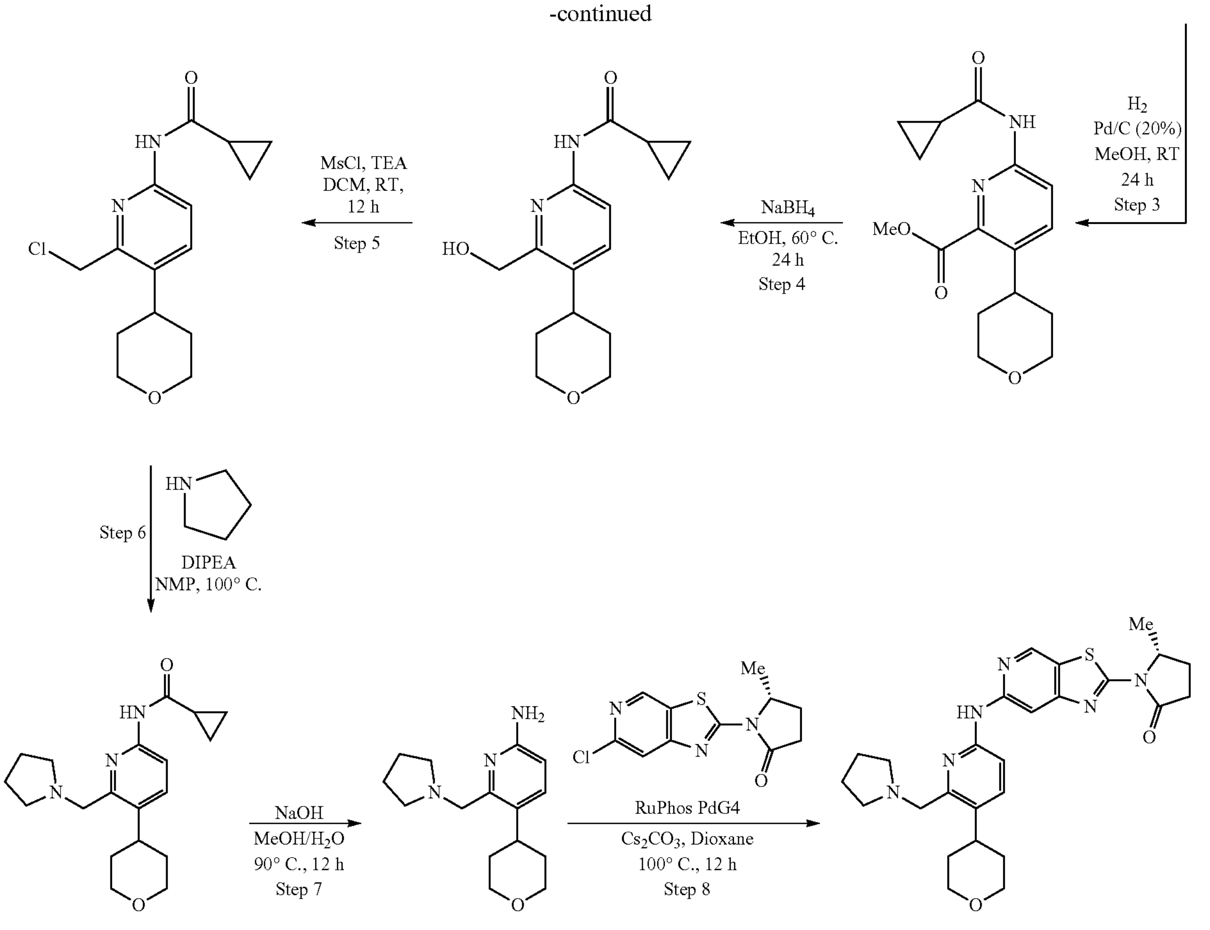

Step 1: To a solution of commercially available Aniline derivative (10 g, 43.7 mmol) in $CH_2Cl_2$ (150 mL) was added triethyl amine (13.3 g, 131 mmol) followed by cyclopropane carbonyl chloride (9 g, 87.4 mmol) at 0° C. After complete consumption of starting material, the reaction mixture was quenched with water and extracted with $CH_2Cl_2$. The combined organic layers were dried over $Na_2SO_4$ and concentrated. The residue was used in the next step without purification.

Step 2: To a solution of amide derivative from step 1 (9.5 g, 33 mmol) and boronic ester (7.7 g, 36 mmol) in Dioxane (100 mL)/$H_2O$ (20 mL) was added $PdCl_2$ (dppf) (2.6 g, 3.3 mmol) and $K_2CO_3$ (10 g, 66 mmol). After degassing for 10 min with $N_2$, the reaction mixture was heated to 100° C. and stirred for 4 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 50% EtOAc in hexanes) to get imine intermediate (9.6 g, 87%) as the white solid.

Step 3: In a Parr hydrogenator, a solution of unsaturated THP derivative from step 2 (9.6 g, 32 mmol) in methanol (100 mL) was added Pd/C (20%). After stirring at 40 psi $H_2$ atmosphere for 24 h, the reaction mixture was filtered through Celite®. The filtrate was concentrated under reduced pressure to obtain the desired intermediate as the while solid (8.7 g, 90%) and used in the next step without purification.

Step 4: To solution of saturated THP derivative from step 3 (8.7 g, 28.0 mmol) in Ethanol (100 mL) was added $NaBH_4$ (3.5 g, 85 mmol) portion wise at 0° C. Then the reaction was heated at 60° C. until completed consumption of starting material as determined by LCMS. The solvent was removed and diluted with water and extracted with EtOAc. The combined organic layers were dried over $Na_2SO_4$ and concentrated in vacuo. The residue was purified by flash column chromatography (silica gel; gradient: 0% to 100% EtOAc in hexanes) to get alcohol intermediate (5.1 g, 62%) as the white solid.

Step 5: Methanesulfonyl chloride (3.2 g, 28 mmol) was added to the mixture of alcohol intermediate from step 4 (5.1 g, 18.5 mmol) and DIPEA (7.2 g, 55.0 mmol) at 0° C. After 16 h at RT, the reaction was diluted with water, $NaHCO_3$ (sat.) and extracted with $CH_2Cl_2$. The combined organic layers were dried over $Na_2SO_4$ and concentrated in vacuo. The residue was purified by flash column chromatography (silica gel; gradient: 0% to 100% EtOAc in hexanes) to get chloride intermediate (5.15 g, 95%) as the brown solid.

Step 6: A mixture of chloromethylpyridyl intermediate from step 5 (2 g, 6.8 mmol), pyrrolidine (482 mg, 6.8 mmol) and $K_2CO_3$ (2.8 g, 21 mmol) in NMP (5 mL) was heated at 100° C. for 12 h. After cooling to RT, the reaction mixture was diluted with water and extracted with EtOAc. The combined organic layers were dried over $Na_2SO_4$ and concentrated in vacuo. The residue was purified by flash column chromatography (silica gel; gradient: 0% to 100% EtOAc in hexanes) to get chloride intermediate (1.8 g, 78%) as the brown solid.

Step 7: A mixture of amide intermediate from step 6 (2 g, 6 mmol) and NaOH (1.0 g, 60 mmol) in MeOH (20 mL)/$H_2O$ (6 mL) was heated at 100° C. for 12 h. After cooling to RT, the reaction mixture was diluted with water and extracted with $CH_2Cl_2$ (10% MeOH). The combined organic layers were dried over $Na_2SO_4$ and concentrated in vacuo to afford amine intermediate (1.25 g, 79%).

Step 8: To a stirred solution of Chloro azabenzothiozole intermediate prepared in a similar fashion to step 1 of example 194 from the appropriate starting materials (106 mg, 0.4 mmol) and amine from step 7 (104 mg, 0.4 mmol) in Dioxane (5 mL) was added RuPhos PdG4 (34 mg, 0.04 mmol) and $Cs_2CO_3$ (390 mg 1.2 mmol). After degassing for 10 min under $N_2$ atmosphere, the reaction mixture was heated to 100° C. and stirred for 12 h. The reaction mixture was then filtered through Celite® and concentrated under reduced pressure. The resulting residue a was purified by flash column chromatography (silica gel; gradient: 0% to 30% MeOH in $CH_2Cl_2$) to get desired compound. $^1$H NMR (400 MHz, DMSO-$d_6$) δ 9.73 (s, 1H), 8.81 (s, 1H), 8.01 (s, 1H), 7.69 (d, J=8.7 Hz, 1H), 7.53 (d, J=8.7 Hz, 1H), 4.72 (tt, J=6.7, 5.0 Hz, 1H), 4.64 (s, 2H), 3.93 (dd, J=10.7, 3.6 Hz, 2H), 3.51-3.41 (m, 6H), 2.95-2.80 (m, 2H), 2.57 (ddd, J=17.7, 9.5, 2.3 Hz, 1H), 2.43-2.33 (m, 1H), 2.05-2.02 (m, 4H), 1.88-1.81 (m, 1H), 1.70-1.58 (m, 4H), 1.45 (d, J=6.4 Hz, 3H). ESI MS $[M+H]^+$ for $C_{26}H_{32}N_6SO_2$, calcd 493.2, found 493.2.

Example 208: (5S)-5-Methyl-1-(6-{[5-(oxan-4-yl)-6-[(pyrrolidin-1-yl)methyl]pyridin-2-yl]amino}-[1,3]thiazolo[5,4-c]pyridin-2-yl)pyrrolidin-2-one

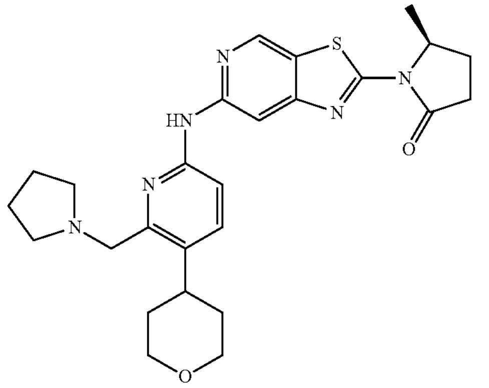 [SMILES: C[C@H]1CCC(=O)N1c1nc2cc(Nc3ccc(C4CCOCC4)c(CN4CCCC4)n3)ncc2s1]

The title compound was synthesized in a similar fashion to example 207 from the appropriate starting materials. $^1$H NMR (400 MHz, DMSO-$d_6$) δ 9.67 (s, 1H), 8.81 (s, 1H), 8.01 (s, 1H), 7.69 (d, J=8.7 Hz, 1H), 7.53 (d, J=8.7 Hz, 1H), 4.73-4.62 (m, 3H), 3.92 (dd, J=10.7, 3.6 Hz, 2H), 3.46-3.33 (m, 6H), 2.95-2.85 (m, 2H), 2.60-2.53 (m, 1H), 2.43-2.35 (m, 1H), 2.05-2.02 (m, 4H), 1.87-1.82 (m, 1H), 1.67-1.57 (m, 4H), 1.45 (d, J=6.4 Hz, 3H). ESI MS $[M+H]^+$ for $C_{26}H_{32}N_6S_{02}$, calcd 493.2, found 493.2.

Example 209: N-[2-(5-Methyl-1H-pyrazol-1-yl)-[1,3]thiazolo[5,4-c]pyridin-6-yl]-5-(oxan-4-yl)-6-({[(3S)-oxolan-3-yl]amino}methyl)pyridin-2-amine

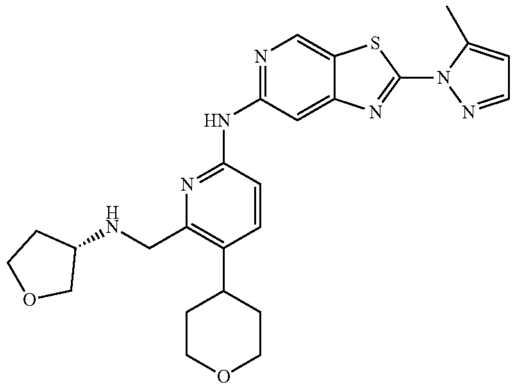 [SMILES: Cc1ccnn1-c1nc2cc(Nc3ccc(C4CCOCC4)c(CN[C@H]4CCOC4)n3)ncc2s1]

The title compound was synthesized in a similar fashion to example 207 from the appropriate starting materials. $^1$H NMR (400 MHz, DMSO-$d_6$) δ 9.75 (s, 1H), 8.88 (d, J=0.8 Hz, 1H), 8.49 (d, J=0.9 Hz, 1H), 7.85 (d, J=1.6 Hz, 1H), 7.62 (d, J=8.4 Hz, 1H), 7.33 (d, J=8.6 Hz, 1H), 6.51 (dd, J=1.7, 1.0 Hz, 1H), 3.97-3.93 (m, 4H), 3.84-3.79 (m, 2H), 3.71-3.66 (m, 1H), 3.62 (m, 1H), 3.50-3.44 (t, J=11.4 Hz, 4H), 3.04-2.98 (t, J=11.6 Hz, 1H), 2.78 (m, 3H), 2.07-2.04 (m, 1H), 1.85 (bs, 1H), 1.70-1.59 (m, 4H). ESI MS $[M+H]^+$ for $C_{25}H_{29}N_7S_{02}$, calcd 492.2, found 492.1.

Example 210: 5-(Oxan-4-yl)-N-[2-(1H-pyrazol-1-yl)-[1,3]thiazolo[5,4-c]pyridin-6-yl]-6-[(pyrrolidin-1-yl)methyl]pyridin-2-amine

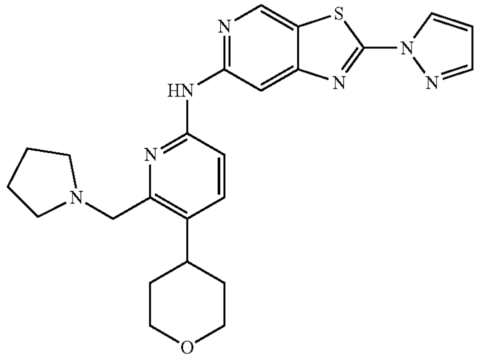 [SMILES: c1cnn(-c2nc3cc(Nc4ccc(C5CCOCC5)c(CN5CCCC5)n4)ncc3s2)c1]

The title compound was synthesized in a similar fashion to example 207 from the appropriate starting materials. $^1$H NMR (400 MHz, Chloroform-d) δ 8.67 (d, J=0.8 Hz, 1H), 8.48 (dd, J=2.8, 0.6 Hz, 1H), 8.04 (s, 1H), 7.80 (dd, J=1.8, 0.6 Hz, 1H), 7.53 (d, J=8.5 Hz, 1H), 7.49-7.45 (m, 2H), 6.55 (dd, J=2.7, 1.7 Hz, 1H), 4.08 (dd, J=11.3, 4.2 Hz, 2H), 3.90 (s, 3H), 3.53 (td, J=11.7, 2.1 Hz, 2H), 3.12-3.05 (m, 1H), 2.76 ($s_{br}$, 4H), 1.85 ($s_{br}$, 4H), 1.76 (td, J=12.3, 4.2 Hz, 1H), 1.70-1.61 (m, 2H). ESI MS $[M+H]^+$ for $C_{24}H_{26}N_7OS$, calcd 462.59, found 462.6.

Example 211: N-{5-Chloro-6-[(pyrrolidin-1-yl) methyl]pyridin-2-yl}-2-(3-methylpyridin-2-yl)-1,3-benzothiazol-5-amine

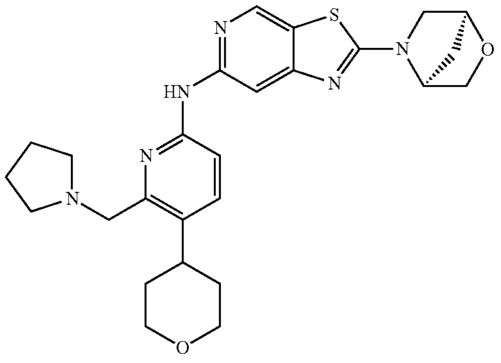 [SMILES: c1cc(C2CCOCC2)c(CN2CCCC2)nc1Nc1cc2nc(N3C[C@@H]4C[C@H]3CO4)sc2cn1]

The title compound was synthesized in a similar fashion to example 207, and where the Chloro azabenzothiozole intermediate in step 8 was prepared in a similar fashion to step 1 of Example 189 from the appropriate starting materials. $^1$H NMR (400 MHz, DMSO-$d_6$) δ 9.35 (s, 1H), 8.42 (d, J=0.7 Hz, 1H), 7.83 (d, J=0.7 Hz, 1H), 7.53 (s, 2H), 4.72 (bs, 2H), 3.91 (dd, J=10.7, 3.9 Hz, 2H), 3.81-3.76 (m, 2H), 3.69 (d, J=1.3 Hz, 2H), 3.59-3.57 (m, 1H), 3.41-3.35 (m, 2H), 3.14-3.08 (m, 1H), 2.01 (dd, J=10.1, 2.4 Hz, 1H), 1.91 (d, J=10.1 Hz, 1H), 1.65-1.54 (m, 7H). ESI MS [M+H]$^+$ for $C_{26}H_{32}N_6SO_2$, calcd 493.2, found 493.3.

Example 212: N-[2-(3-Methylpyridin-2-yl)-[1,3] thiazolo[5,4-c]pyridin-6-yl]-5-(oxan-4-yl)-6-[(pyrrolidin-1-yl)methyl]pyridin-2-amine

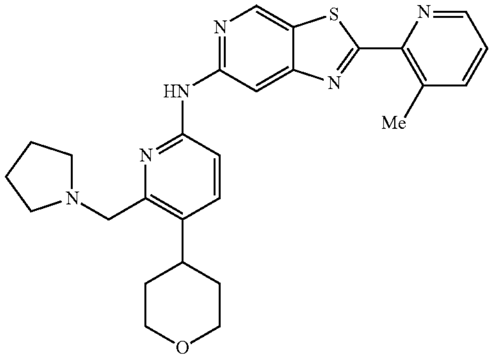 [SMILES: Cc1cccnc1-c1nc2cc(Nc3ccc(C4CCOCC4)c(CN4CCCC4)n3)ncc2s1]

The title compound was synthesized in a similar fashion to example 207, and where the Chloro azabenzothiozole intermediate in step 8 was prepared in a similar fashion to step 1 of example 1 from the appropriate starting materials. $^1$H NMR (400 MHz, DMSO-$d_6$) δ 9.68 (s, 1H), 8.96 (d, J=0.9 Hz, 1H), 8.72 (d, J=0.9 Hz, 1H), 8.58 (ddd, J=4.7, 1.7, 0.7 Hz, 1H), 7.88 (ddd, J=7.8, 1.6, 0.8 Hz, 1H), 7.57 (d, J=8.6 Hz, 1H), 7.50 (dd, J=7.8, 4.6 Hz, 1H), 7.35 (d, J=8.5 Hz, 1H), 3.92 (dd, J=10.9, 3.8 Hz, 2H), 3.75 (s, 2H), 3.41 (td, J=11.5, 2.4 Hz, 2H), 3.13-3.05 (m, 1H), 2.84 (s, 3H), 2.55 (td, J=5.1, 4.1, 2.2 Hz, 4H), 1.69 (t, J=3.5 Hz, 4H), 1.61 (dt, J=15.5, 10.0 Hz, 4H). ESI MS [M+H]$^+$ for $C_{27}H_{30}N_6SO$, calcd 487.2, found 487.1.

Example 213: 6-{[(3R)-3-Fluoropyrrolidin-1-yl] methyl}-N-[2-(3-methylpyridin-2-yl)-[1,3]thiazolo [5,4-c]pyridin-6-yl]-5-(oxan-4-yl)pyridin-2-amine

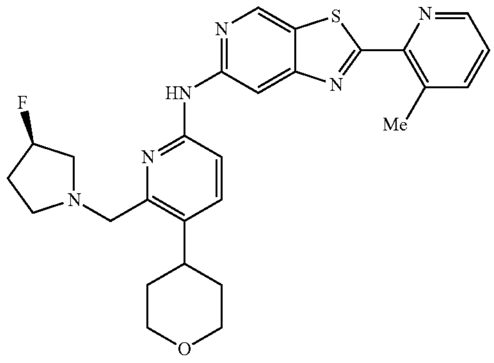 [SMILES: Cc1cccnc1-c1nc2cc(Nc3ccc(C4CCOCC4)c(CN4CC[C@@H](F)C4)n3)ncc2s1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, DMSO-$d_6$) δ 9.72 (s, 1H), 8.96 (d, J=0.9 Hz, 1H), 8.64 (d, J=0.9 Hz, 1H), 8.58 (ddd, J=4.6, 1.6, 0.7 Hz, 1H), 7.88 (ddd, J=7.8, 1.6, 0.8 Hz, 1H), 7.59 (d, J=8.6 Hz, 1H), 7.50 (dd, J=7.7, 4.6 Hz, 1H), 7.40 (d, J=8.6 Hz, 1H), 5.25-5.10 (m, 1H), 3.91 (dd, J=10.3, 3.6 Hz, 2H), 3.82-3.74 (m, 2H), 3.41 (td, J=11.3, 2.6 Hz, 2H), 3.12-3.08 (m, 1H), 2.85-2.75 (m, 1H), 2.83 (s, 3H), 2.12 (ddq, J=27.8, 14.0, 6.9 Hz, 1H), 1.86 (ddd, J=31.4, 14.1, 7.1 Hz, 1H), 1.67-1.57 (m, 4H). ESI MS [M+H]$^+$ for $C_{27}H_{29}N_6SOF$, calcd 505.2, found 505.3.

Example 214: 6-{[(3S)-3-Fluoropyrrolidin-1-yl] methyl}-N-[2-(3-methylpyridin-2-yl)-[1,3]thiazolo [5,4-c]pyridin-6-yl]-5-(oxan-4-yl)pyridin-2-amine

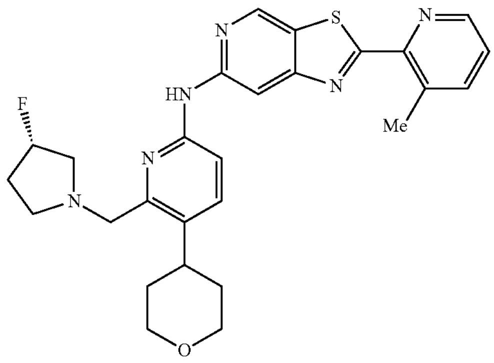 [SMILES: Cc1cccnc1-c1nc2cc(Nc3ccc(C4CCOCC4)c(CN4CC[C@H](F)C4)n3)ncc2s1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, DMSO-$d_6$) δ 9.72 (s, 1H), 8.97 (d, J=0.9 Hz, 1H), 8.64 (d, J=0.9 Hz, 1H), 8.58 (ddd, J=4.7, 1.6, 0.7 Hz, 1H), 7.88 (ddd, J=7.8, 1.7, 0.8 Hz, 1H), 7.59 (d, J=8.6 Hz, 1H), 7.50 (dd, J=7.8, 4.6 Hz, 1H), 7.40 (d, J=8.6 Hz, 1H), 5.05 (m, 1H), 3.91 (m, 2H), 3.75 (m, 2H), 3.41 (m, 2H), 3.09 (m, 1H), 2.84

(s, 3H), 2.74 (m, 1H), 2.13 (ddq, J=27.7, 13.8, 6.9 Hz, 1H), 1.86 (m, 1H), 1.63 (dt, J=23.8, 8.4 Hz, 4H). ESI MS $[M+H]^+$ for $C_{27}H_{29}N_6SOF$, calcd 505.2, found 505.3.

Example 215: N-[2-(3-Methylpyridin-2-yl)-[1,3]thiazolo[5,4-c]pyridin-6-yl]-5-(oxan-4-yl)-6-({[(3R)-oxolan-3-yl]amino}methyl)pyridin-2-amine

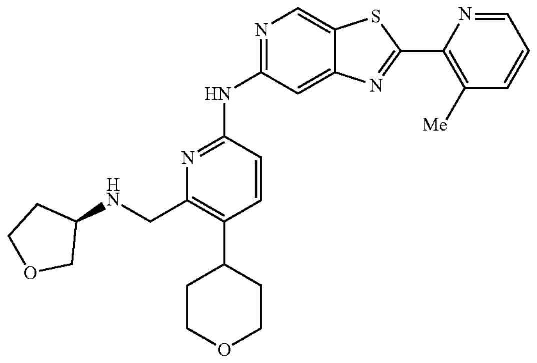 [SMILES: Cc1cccnc1-c1nc2cc(Nc3ccc(C4CCOCC4)c(CN[C@@H]4CCOC4)n3)ncc2s1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, DMSO-$d_6$) δ 9.84 (s, 1H), 9.09 (d, J=0.9 Hz, 1H), 8.73 (d, J=0.9 Hz, 1H), 8.69 (dd, J=5.2, 0.8 Hz, 1H), 7.96-7.94 (m, 1H), 7.87-7.85 (m, 1H), 7.62 (d, J=8.6 Hz, 1H), 7.35 (d, J=8.6 Hz, 1H), 3.97-3.94 (m, 2H), 3.90 (bs, 2H), 3.87-3.77 (m, 2H), 3.72 (td, J=8.0, 5.1 Hz, 1H), 3.59 (dd, J=8.7, 3.8 Hz, 1H), 3.49-3.44 (m, 4H), 3.08-3.03 (m, 1H), 2.03 (dq, J=12.3, 7.4 Hz, 1H), 1.87-1.80 (m, 1H), 1.74-1.60 (m, 4H). ESI MS $[M+H]^+$ for $C_{27}H_{30}N_6SO_2$, calcd 503.2, found 503.1.

Example 216: 5-(Oxan-4-yl)-N-[2-(pyridin-4-yl)-[1,3]thiazolo[5,4-c]pyridin-6-yl]-6-[(pyrrolidin-1-yl)methyl]pyridin-2-amine

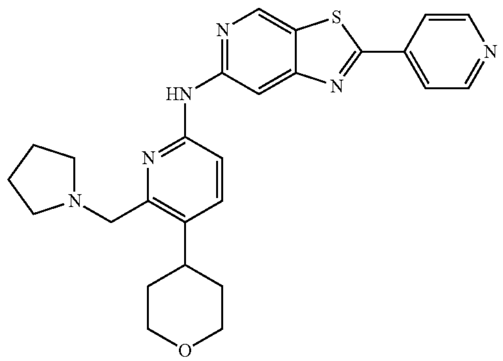 [SMILES: c1cc(-c2nc3cc(Nc4ccc(C5CCOCC5)c(CN5CCCC5)n4)ncc3s2)ccn1]

The title compound was synthesized in a similar fashion to example 207, and where the Chloro azabenzothiozole intermediate in step 8 was prepared in a similar fashion to step 1 of Example 1 from the appropriate starting materials. $^1$H NMR (400 MHz, DMSO-$d_6$) δ 9.78 (s, 1H), 9.04 (d, J=0.8 Hz, 1H), 8.80-8.79 (m, 3H), 8.04-8.02 (m, 2H), 7.58 (d, J=8.6 Hz, 1H), 7.34 (d, J=8.5 Hz, 1H), 3.94-3.90 (m, 2H), 3.75 (s, 2H), 3.40 (td, J=11.5, 2.4 Hz, 2H), 3.15-3.09 (m, 1H), 2.53-2.46 (m, 4H), 1.70-1.65 (m, 4H), 1.63-1.55 (m, 4H). ESI MS $[M+H]^+$ for $C_{26}H_{28}N_6SO$, calcd 473.2, found 473.2.

Example 217: N-[2-(1-Methyl-1H-imidazol-2-yl)-[1,3]thiazolo[5,4-c]pyridin-6-yl]-5-(oxan-4-yl)-6-[(pyrrolidin-1-yl)methyl]pyridin-2-amine

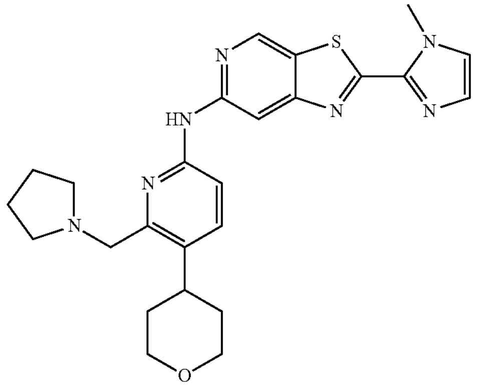 [SMILES: Cn1ccnc1-c1nc2cc(Nc3ccc(C4CCOCC4)c(CN4CCCC4)n3)ncc2s1]

The title compound was synthesized in a similar fashion to example 207, and where the Chloro azabenzothiozole intermediate in step 8 was prepared in a similar fashion to step 1 of Example 1 from the appropriate starting materials. $^1$H NMR (400 MHz, Chloroform-d) δ 8.72 (d, J=0.9 Hz, 1H), 8.20 (s, 1H), 7.73 (d, J=1.0 Hz, 1H), 7.61 (s, 1H), 7.52 (d, J=8.6 Hz, 1H), 7.34 (d, J=8.5 Hz, 1H), 4.13 (s, 3H), 4.10-4.03 (m, 2H), 3.84 (s, 2H), 3.53 (td, J=11.7, 2.2 Hz, 2H), 3.17-3.07 (m, 1H), 2.67 (d, J=6.7 Hz, 4H), 1.87-1.60 (m, 8H). ESI MS $[M+H]^+$ for $C_{25}H_{29}N_7OS$, calcd 476.2, found 476.6.

Example 218: 6-[(3,3-Difluoropyrrolidin-1-yl)methyl]-5-(oxan-4-yl)-N-[2-(pyridin-4-yl)-[1,3]thiazolo[5,4-c]pyridin-6-yl]pyridin-2-amine

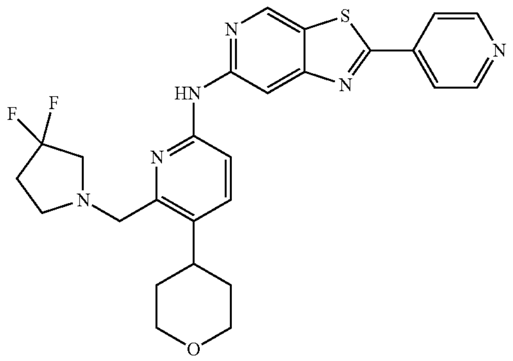 [SMILES: FC1(F)CCN(Cc2nc(Nc3cc4nc(-c5ccncc5)sc4cn3)ccc2C2CCOCC2)C1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, DMSO-$d_6$) δ 9.82 (s, 1H), 9.05 (d, J=0.8 Hz, 1H), 8.81-8.79

(m, 2H), 8.75 (d, J=0.9 Hz, 1H), 8.04-8.03 (m, 2H), 7.62 (d, J=8.6 Hz, 1H), 7.37 (d, J=8.5 Hz, 1H), 3.92 (dd, J=11.3, 3.7 Hz, 2H), 3.81 (s, 2H), 3.42 (td, J=11.6, 2.2 Hz, 2H), 3.10-3.04 (m, 1H), 2.97 (t, J=13.2 Hz, 2H), 2.78 (t, J=6.9 Hz, 2H), 2.25 (tt, J=15.0, 6.9 Hz, 2H), 1.70-1.55 (m, 4H). ESI MS $[M+H]^+$ for $C_{26}H_{26}N_6SOF_2$, calcd 509.2, found 509.2.

Example 219: 6-[(Morpholin-4-yl)methyl]-5-(oxan-4-yl)-N-[2-(pyridin-4-yl)-[1,3]thiazolo[5,4-c]pyridin-6-yl]pyridin-2-amine

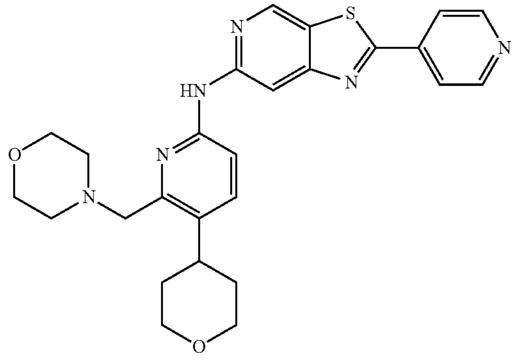 [SMILES: c1cc(-c2nc3cc(Nc4ccc(C5CCOCC5)c(CN5CCOCC5)n4)ncc3s2)ccn1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, DMSO-$d_6$) δ 9.81 (s, 1H), 9.05 (d, J=0.9 Hz, 1H), 8.80 (ddd, J=4.3, 1.8, 0.8 Hz, 2H), 8.74 (s, 1H), 8.05 (ddd, J=4.4, 1.8, 0.8 Hz, 2H), 7.62 (d, J=8.5 Hz, 1H), 7.40 (d, J=8.5 Hz, 1H), 3.94 (d, J=11.3 Hz, 2H), 3.64 (bs, 2H), 3.56 (d, J=5.1 Hz, 4H), 3.42 (t, J=10.7 Hz, 2H), 3.16-3.14 (m, 1H), 2.43 (bs, 4H), 1.64 (m, 4H). ESI MS $[M+H]^+$ for $C_{26}H_{28}N_6SO_2$, calcd 489.2, found 489.1.

Example 220: 6-[(3,3-Difluoropyrrolidin-1-yl)methyl]-N-[2-(2-methylpyridin-4-yl)-[1,3]thiazolo[5,4-c]pyridin-6-yl]-5-(oxan-4-yl)pyridin-2-amine

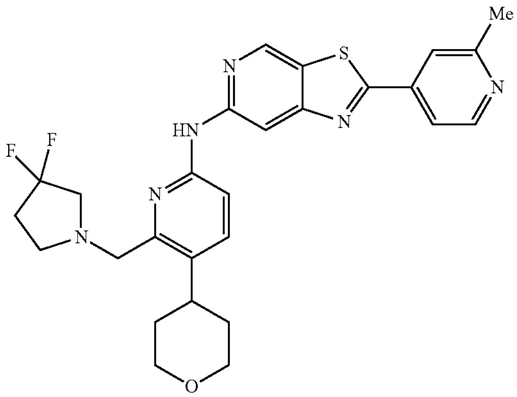 [SMILES: Cc1cc(-c2nc3cc(Nc4ccc(C5CCOCC5)c(CN5CCC(F)(F)C5)n4)ncc3s2)ccn1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, DMSO-$d_6$) δ 9.81 (s, 1H), 9.05 (d, J=0.8 Hz, 1H), 8.74 (d, J=0.9 Hz, 1H), 8.65 (dd, J=5.2, 0.8 Hz, 1H), 7.92-7.90 (m, 1H), 7.83 (dd, J=5.2, 1.7 Hz, 1H), 7.61 (d, J=8.6 Hz, 1H), 7.38 (d, J=8.6 Hz, 1H), 3.92 (dd, J=11.1, 3.7 Hz, 2H), 3.81 (s, 2H), 3.42 (td, J=11.5, 2.2 Hz, 2H), 3.08-3.04 (m, 1H), 2.97 (t, J=13.2 Hz, 2H), 2.77 (t, J=6.9 Hz, 2H), 2.58 (s, 3H), 2.25 (tt, J=15.0, 6.9 Hz, 2H), 1.67-1.55 (m, 4H). ESI MS $[M+H]^+$ for $C_{27}H_{28}N_6SOF_2$, calcd 523.2, found 523.2.

Example 221: N-[2-(2-Methylpyridin-4-yl)-[1,3]thiazolo[5,4-c]pyridin-6-yl]-5-(oxan-4-yl)-6-({[(3S)-oxolan-3-yl]amino}methyl)pyridin-2-amine

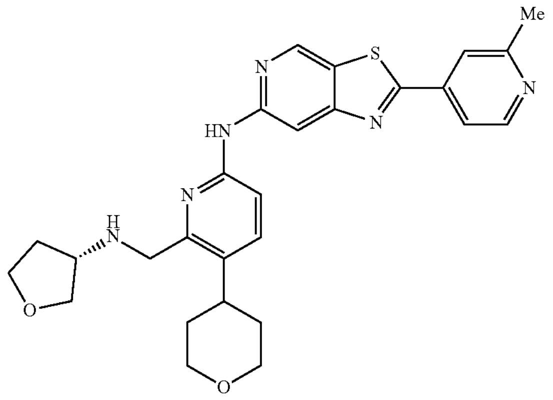 [SMILES: Cc1cc(-c2nc3cc(Nc4ccc(C5CCOCC5)c(CN[C@H]5CCOC5)n4)ncc3s2)ccn1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, DMSO-$d_6$) δ 9.80 (s, 1H), 9.05 (d, J=0.9 Hz, 1H), 8.70 (d, J=0.9 Hz, 1H), 8.67-8.65 (m, 1H), 7.92 (d, J=1.5 Hz, 1H), 7.84-7.81 (m, 1H), 7.59 (d, J=8.6 Hz, 1H), 7.31 (d, J=8.5 Hz, 1H), 3.92 (d, J=10.4 Hz, 2H), 3.86 (bs, 2H), 3.84-3.74 (m, 2H), 3.68 (td, J=8.0, 5.1 Hz, 1H), 3.55 (dd, J=8.7, 3.9 Hz, 1H), 3.43 (t, J=11.1 Hz, 2H), 3.01 (d, J=11.6 Hz, 1H), 2.58 (s, 3H), 2.00 (dq, J=12.2, 7.4 Hz, 1H), 1.84-1.76 (m, 1H), 1.67-1.57 (q, J=13.4, 12.3 Hz, 4H). ESI MS $[M+H]^+$ for $C_{27}H_{30}N_6SO_2$, calcd 503.2, found 503.1.

Example 222: N-[2-(6-Methylpyridin-3-yl)-[1,3]thiazolo[5,4-c]291yridine-6-yl]-5-(oxan-4-yl)-6-[(291yridine291ne-1-yl)methyl]291yridine-2-amine

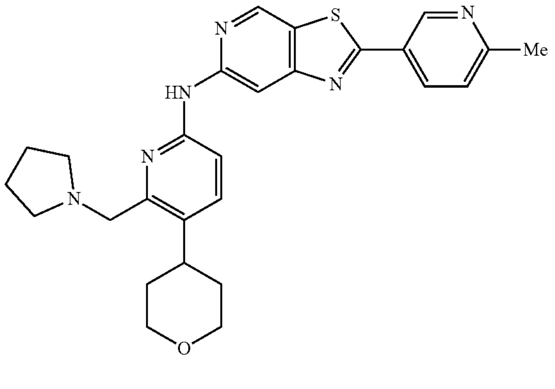 [SMILES: Cc1ccc(-c2nc3cc(Nc4ccc(C5CCOCC5)c(CN5CCCC5)n4)ncc3s2)cn1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1$H NMR (400 MHz, Chloroform-d) δ 9.20 (dd, J=2.4, 0.8 Hz, 1H), 8.80 (d, J=0.9 Hz, 1H), 8.33-8.24 (m, 2H), 7.53 (d, J=8.5 Hz, 2H), 7.39-7.28 (m, 2H), 4.14-4.04 (m, 2H), 3.84 (s, 2H), 3.54 (td, J=11.7, 2.3 Hz, 2H), 3.18 (tt, J=11.8, 3.9 Hz, 1H), 2.66 (s, 3H), 2.63 (s, 3H), 1.88-1.64 (m, 9H). ESI MS [M+H]$^+$ for $C_{27}H_{30}N_6OS$, calcd 487.2, found 487.2.

Example 223: 4-Methyl-N-[2-(3-methylpyridin-2-yl)-[1,3]thiazolo[5,4-c]pyridin-6-yl]-6-(piperidin-4-yloxy)pyridin-2-amine

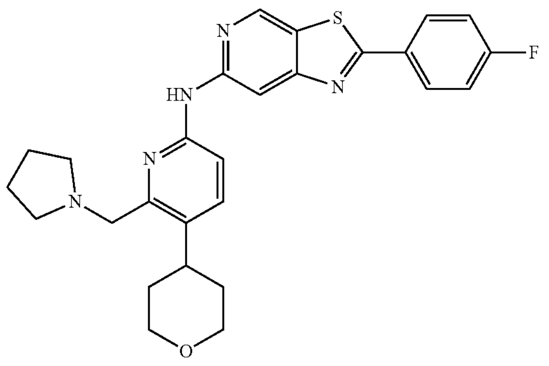

The title compound was synthesized in a similar fashion to example 207, and where the Chloro azabenzothiozole intermediate in step 8 was prepared in a similar fashion to step 1 of Example 128 from the appropriate starting materials. $^1$H NMR (400 MHz, DMSO-$d_6$) δ 9.72 (s, 1H), 8.96 (d, J=0.9 Hz, 1H), 8.67 (s, 1H), 8.20-8.16 (m, 2H), 7.59 (d, J=8.5 Hz, 1H), 7.44-7.36 (m, 3H), 3.92 (dd, J=10.8, 3.9 Hz, 2H), 3.75 (s, 2H), 3.43-3.40 (m, 2H), 3.11 (s, 1H), 2.52 (bs, 4H), 1.68-1.56 (m, 8H). ESI MS [M+H]$^+$ for $C_{27}H_{28}N_5SF$, calcd 490.2, found 490.2.

Example 224: N-{2-[1-(Difluoromethyl)-1H-pyrazol-4-yl]-[1,3]thiazolo[5,4-c]pyridin-6-yl}-5-(oxan-4-yl)-6-[(pyrrolidin-1-yl)methyl]pyridin-2-amine

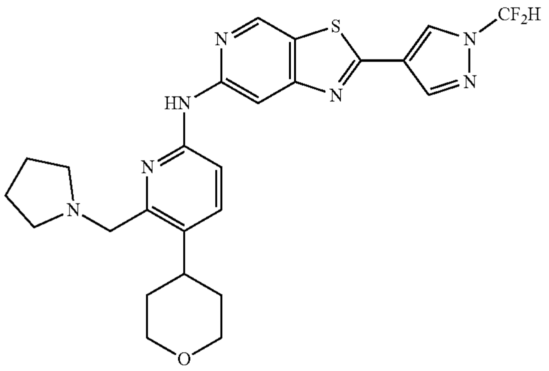 [SMILES: FC(F)n1cc(-c2nc3cc(Nc4ccc(C5CCOCC5)c(CN5CCCC5)n4)ncc3s2)cn1]

The title compound was synthesized in a similar fashion to example 207, and where the Chloro azabenzothiozole intermediate in step 8 was prepared in a similar fashion to step 1 of Example 128 from the appropriate starting materials. $^1$H NMR (400 MHz, Chloroform-d) δ 8.75 (d, J=0.9 Hz, 1H), 8.46 (d, J=0.6 Hz, 1H), 8.21-8.19 (m, 2H), 7.51 (d, J=8.5 Hz, 1H), 7.37 (dd, J=15.6, 8.7 Hz, 2H), 7.25-7.22 (m, 1H), 4.08 (dd, J=11.3, 4.1 Hz, 2H), 3.81 (s, 2H), 3.53 (td, J=11.7, 2.4 Hz, 2H), 3.18 (tt, J=11.7, 4.0 Hz, 1H), 2.59 (d, J=5.8 Hz, 4H), 1.82-1.60 (m, 8H). ESI MS [M+H]$^+$ for $C_{25}H_{27}F_2N_7OS$, calcd 512.2, found 512.8.

Example 225: 5-(Oxan-4-yl)-N-[2-(pyridin-3-yl)-[1,3]thiazolo[5,4-c]pyridin-6-yl]-6-[(pyrrolidin-1-yl)methyl]pyridin-2-amine

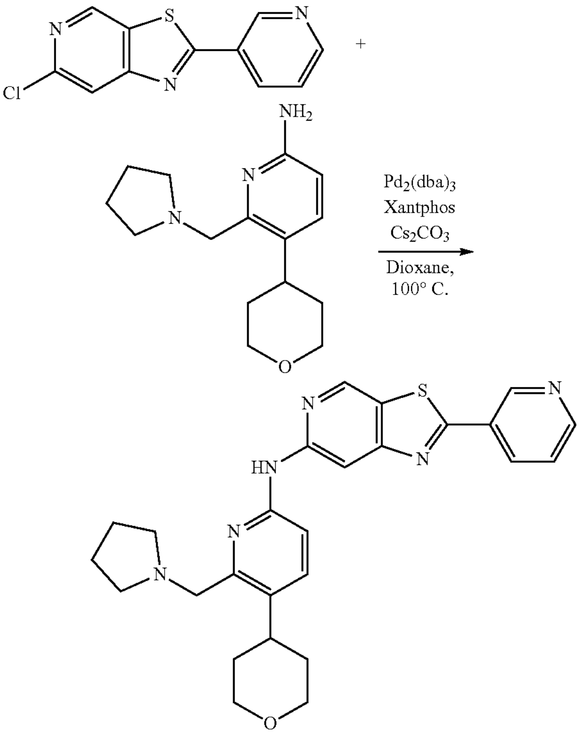

To a dry screw cap reaction vial containing septum, were added the amine (0.4 mmol, 106 mg) obtained from step 7 of example 207, benzothiazole derivative (0.4 mmol, 100 mg) prepared in a similar fashion to step 1 of example 1 from the appropriate starting materials, $Pd_2(dba)_3$ (0.08 mmol, 74 mg), Xantphos (0.16 mmol, 94 mg), $Cs_2CO_3$ (1.21 mmol, 395 mg) and Dioxane (5 mL). The reaction mixture was degassed for 5 min using nitrogen, then stirred at 100° C. overnight. After confirming the completion of the reaction using LCMS, the reaction mixture was cooled to room temperature and the crude reaction mixture was filtered through a small pad of Celite®. Solvent was evaporated under reduced pressure and the crude product was purified by column chromatography (silica gel; gradient: 0% to 50% EtOAc in Hexanes) to afford the title compound (87 mg, 46%). $^1$H NMR (400 MHz, Chloroform-d) δ 9.31 (d, J=2.0 Hz, 1H), 8.82 (s, 1H), 8.75 (dd, J=4.8, 1.6 Hz, 1H), 8.41-8.35 (m, 2H), 7.64 (s, 1H), 7.52 (d, J=8.5 Hz, 1H), 7.45 (dd, J=8.0, 4.8 Hz, 1H), 7.30 (d, J=8.5 Hz, 1H), 4.08 (dd, J=11.1, 3.5 Hz, 2H), 3.83 (s, 2H), 3.54 (td, J=11.6, 2.1 Hz, 2H), 3.18 (tt, J=11.6, 3.8 Hz, 1H), 2.62 (s, 4H), 1.79 (q, J=8.5, 7.3 Hz, 6H), 1.71 (dt, J=12.6, 7.6 Hz, 2H). ESI MS $[M+H]^+$ for $C_{26}H_{28}N_6OS$, calcd 473.2, found 473.2.

Example 226: N-[2-(3-Methylpyridin-2-yl)-[1,3]thiazolo[5,4-c]pyridin-6-yl]-5-(propan-2-yl)-6-[(pyrrolidin-1-yl)methyl]pyridin-2-amine

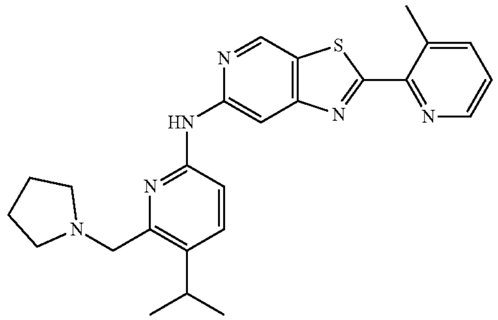 [SMILES: Cc1cccnc1-c1nc2cc(Nc3ccc(C(C)C)c(CN4CCCC4)n3)ncc2s1]

The title compound was synthesized in a similar fashion to example 207 from the appropriate starting materials, and where the Chloro azabenzothiozole intermediate in step 8 was prepared in a similar fashion to step 1 of Example 1 from the appropriate starting materials. $^1H$ NMR (400 MHz, Chloroform-d) δ 8.83 (d, J=0.9 Hz, 1H), 8.59-8.53 (m, 1H), 8.35 (d, J=0.9 Hz, 1H), 7.67 (ddd, J=7.7, 1.6, 0.8 Hz, 1H), 7.52 (d, J=8.5 Hz, 1H), 7.34 (d, J=2.4 Hz, 1H), 7.31 (dd, J=7.7, 4.6 Hz, 1H), 7.25 (d, J=8.4 Hz, 1H), 3.82 (s, 2H), 3.28 (p, J=6.8 Hz, 1H), 2.91 (s, 3H), 2.68-2.65 (m, 4H), 1.86-1.75 (m, 4H), 1.21 (d, J=6.9 Hz, 6H). ESI MS $[M+H]^+$ for $C_{25}H_{28}N_6S$, calcd 445.2, found 445.6.

Example 227: N-[2-(1-Methyl-1H-pyrazol-4-yl)-[1,3]thiazolo[5,4-c]pyridin-6-yl]-5-(propan-2-yl)-6-[(pyrrolidin-1-yl)methyl]pyridin-2-amine

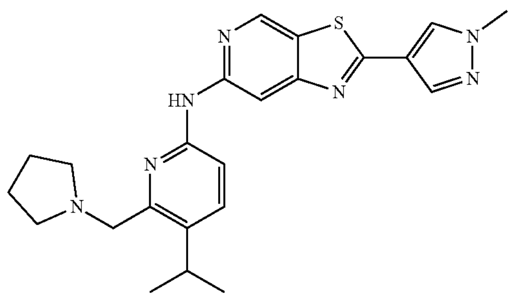 [SMILES: CC(C)c1ccc(Nc2cc3nc(-c4cnn(C)c4)sc3cn2)nc1CN1CCCC1]

The title compound was synthesized in a similar fashion to example 207 from the appropriate starting materials, and where the Chloro azabenzothiozole intermediate in step 8 was prepared in a similar fashion to step 1 of Example 128 from the appropriate starting materials. $^1H$ NMR (400 MHz, Chloroform-d) δ 8.69 (s, 1H), 8.03 (s, 2H), 8.01 (s, 1H), 7.52 (d, J=8.5 Hz, 1H), 7.41 (d, J=8.5 Hz, 1H), 7.35 (s, 1H), 3.98 (s, 3H), 3.78 (s, 2H), 3.32 (p, J=6.9 Hz, 1H), 2.59 (td, J=5.5, 4.2, 2.8 Hz, 4H), 1.78 (p, J=3.1 Hz, 4H), 1.20 (d, J=6.8 Hz, 6H). ESI MS $[M+H]^+$ for $C_{23}H_{27}N_7S$, calcd 434.2, found 434.9.

Example 228: 5-(Propan-2-yl)-N-[2-(1H-pyrazol-1-yl)-[1,3]thiazolo[5,4-c]pyridin-6-yl]-6-[(pyrrolidin-1-yl)methyl]pyridin-2-amine

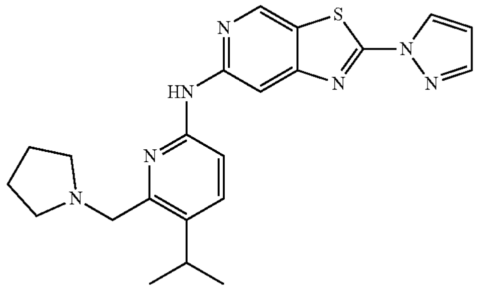 [SMILES: CC(C)c1ccc(Nc2cc3nc(-n4cccn4)sc3cn2)nc1CN1CCCC1]

The title compound was synthesized in a similar fashion to example 207 from the appropriate starting materials, and where the Chloro azabenzothiozole intermediate in step 8 was prepared in a similar fashion to step 1 of Example 194 from the appropriate starting materials. $^1H$ NMR (400 MHz, Chloroform-d) δ 8.99 (s, 1H), 8.47 (dd, J=2.8, 0.7 Hz, 1H), 8.08 (s, 1H), 7.92 (d, J=8.8 Hz, 1H), 7.81 (d, J=1.8 Hz, 1H), 7.65 (d, J=8.8 Hz, 1H), 7.26 (s, 1H), 6.58 (dd, J=2.8, 1.7 Hz, 1H), 4.40 (s, 2H), 3.39 (p, J=3.4 Hz, 4H), 2.99 (q, J=6.8 Hz, 1H), 2.17 (p, J=3.5 Hz, 4H), 1.23 (d, J=6.8 Hz, 6H). ESI MS $[M+H]^+$ for $C_{22}H_{25}N_7S$, calcd 420.2, found 420.5.

Example 229: N-{2-[(2R)-2-Methylpyrrolidin-1-yl]-[1,3]thiazolo[5,4-c]pyridin-6-yl}-5-(oxan-4-yl)-6-[(pyrrolidin-1-yl)methyl]pyridin-2-amine

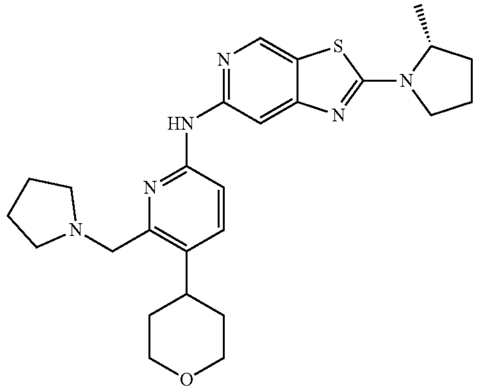 [SMILES: C[C@@H]1CCCN1c1nc2cc(Nc3ccc(C4CCOCC4)c(CN4CCCC4)n3)ncc2s1]

The title compound was synthesized in a similar fashion to example 207, where the Chloro azabenzothiozole intermediate in step 8 was prepared in a similar fashion to step 1 of Example 189 from the appropriate starting materials. $^1H$ NMR (400 MHz, Methanol-$d_4$) δ 8.58 (d, J=0.6 Hz, 1H), 7.98 (d, J=8.8 Hz, 1H), 7.17 (d, J=8.7 Hz, 1H), 7.14 (s, 1H), 4.78 (s, 2H), 4.15-3.36 (m, 11H), 3.21-3.08 (m, 1H), 2.40-2.03 (m, 7H), 1.98-1.78 (m, 3H), 1.74-1.65 (m, 2H), 1.42 (d, J=6.4 Hz, 3H). ESI MS $[M+H]^+$ for $C_{26}H_{34}N_6OS$, calcd 479.3, found 479.2.

Example 230: N-{2-[(2S)-2-Methylpyrrolidin-1-yl]-[1,3]thiazolo[5,4-c]pyridin-6-yl}-5-(oxan-4-yl)-6-[(pyrrolidin-1-yl)methyl]pyridin-2-amine

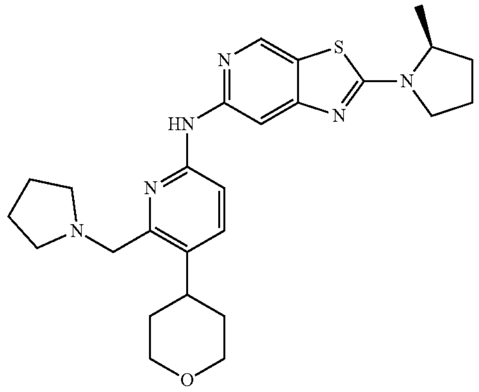 [SMILES: C[C@H]1CCCN1c1nc2cc(Nc3ccc(C4CCOCC4)c(CN4CCCC4)n3)ncc2s1]

The title compound was synthesized in a similar fashion to example 207, where the Chloro azabenzothiozole intermediate in step 8 was prepared in a similar fashion to step 1 of Example 189 from the appropriate starting materials. $^1$H NMR (400 MHz, Methanol-$d_4$) δ 8.58 (d, J=0.6 Hz, 1H), 7.98 (d, J=8.8 Hz, 1H), 7.17 (d, J=8.7 Hz, 1H), 7.14 (s, 1H), 4.78 (s, 2H), 4.15-3.36 (m, 11H), 3.21-3.08 (m, 1H), 2.40-2.03 (m, 7H), 1.98-1.78 (m, 3H), 1.74-1.65 (m, 2H), 1.42 (d, J=6.4 Hz, 3H). ESI MS $[M+H]^+$ for $C_{26}H_{34}N_6OS$, calcd 479.3, found 479.3.

Example 231: 5-(Oxan-4-yl)-N-[2-(pyrrolidin-1-yl)-[1,3]thiazolo[5,4-c]pyridin-6-yl]-6-[(pyrrolidin-1-yl)methyl]pyridin-2-amine

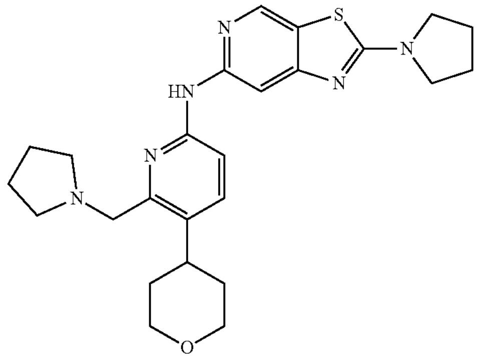 [SMILES: c1cc(C2CCOCC2)c(CN2CCCC2)nc1Nc1cc2nc(N3CCCC3)sc2cn1]

The title compound was synthesized in a similar fashion to example 207, where the Chloro azabenzothiozole intermediate in step 8 was prepared in a similar fashion to step 1 of Example 189 from the appropriate starting materials. $^1$H NMR (400 MHz, Methanol-$d_4$) δ 8.59 (s, 1H), 7.98 (d, J=8.7 Hz, 1H), 7.17 (d, J=8.7 Hz, 1H), 7.12 (s, 1H), 4.79 (s, 2H), 4.07 (dd, J=11.0, 3.7 Hz, 2H), 3.87 (t, J=6.6 Hz, 2H), 3.70-3.38 (m, 8H), 3.23-3.09 (m, 1H), 2.27-2.07 (m, 8H), 1.95-1.79 (m, 2H), 1.75-1.63 (m, 2H). ESI MS $[M+H]^+$ for $C_{25}H_{32}N_6OS$, calcd 465.2, found 465.3.

Example 232: 5-(Oxan-4-yl)-N-[2-(piperidin-1-yl)-[1,3]thiazolo[5,4-c]pyridin-6-yl]-6-[(pyrrolidin-1-yl)methyl]pyridin-2-amine

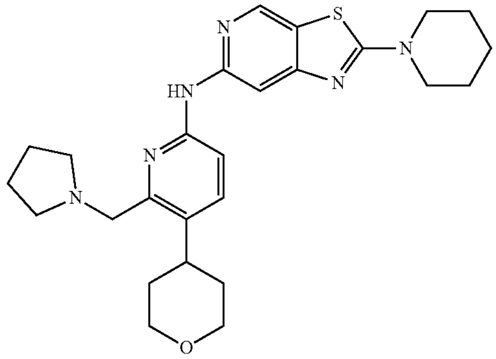 [SMILES: c1cc(C2CCOCC2)c(CN2CCCC2)nc1Nc1cc2nc(N3CCCCC3)sc2cn1]

The title compound was synthesized in a similar fashion to example 207, where the Chloro azabenzothiozole intermediate in step 8 was prepared in a similar fashion to step 1 of Example 189 from the appropriate starting materials. $^1$H NMR (400 MHz, Methanol-$d_4$) δ 8.54 (s, 1H), 7.98 (d, J=8.7 Hz, 1H), 7.16 (d, J=8.7 Hz, 1H), 7.07 (s, 1H), 4.78 (s, 2H), 4.16-3.36 (m, 12H), 3.21-3.05 (m, 1H), 2.16 (s, 4H), 1.99-1.61 (m, 10H). ESI MS $[M+H]^+$ for $C_{26}H_{34}N_6OS$, calcd 479.3, found 479.3.

Example 233: (3S)-1-(6-{[5-(Oxan-4-yl)-6-[(pyrrolidin-1-yl)methyl]pyridin-2-yl]amino}-[1,3]thiazolo[5,4-c]pyridin-2-yl)pyrrolidin-3-ol

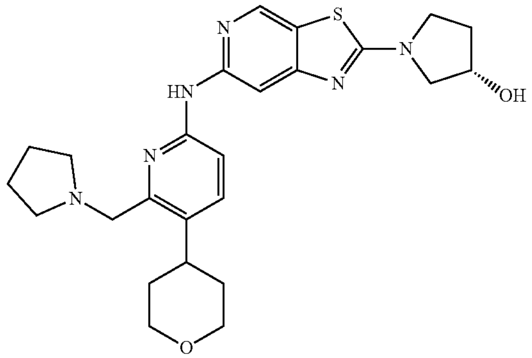 [SMILES: O[C@H]1CCN(c2nc3cc(Nc4ccc(C5CCOCC5)c(CN5CCCC5)n4)ncc3s2)C1]

The title compound was synthesized in a similar fashion to example 207, where the Chloro azabenzothiozole intermediate in step 8 was prepared in a similar fashion to step 1 of Example 189 from the appropriate starting materials. $^1$H NMR (400 MHz, Methanol-$d_4$) δ 8.61 (d, J=1.4 Hz, 1H), 7.98 (d, J=8.7 Hz, 1H), 7.22-7.06 (m, 2H), 4.79 (s, 2H), 4.68-4.56 (m, 1H), 4.14-3.38 (m, 12H), 3.24-3.06 (m, 1H), 2.39-2.06 (m, 6H), 1.94-1.78 (m, 2H), 1.75-1.63 (m, 2H). ESI MS $[M+H]^+$ for $C_{25}H_{32}N_6O_2S$, calcd 481.2, found 481.3.

Example 234: (3R)-1-(6-{[5-(Oxan-4-yl)-6-[(pyrrolidin-1-yl)methyl]pyridin-2-yl]amino}-[1,3]thiazolo[5,4-c]pyridin-2-yl)pyrrolidin-3-ol

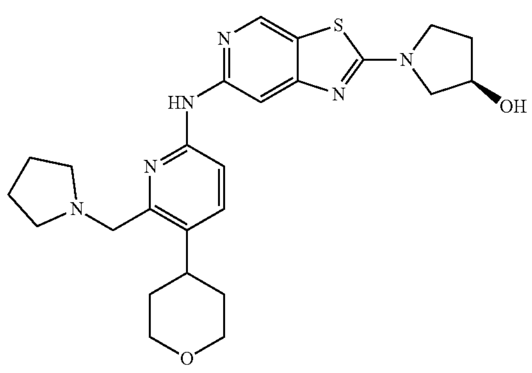 [SMILES: O[C@@H]1CCN(c2nc3cc(Nc4ccc(C5CCOCC5)c(CN5CCCC5)n4)ncc3s2)C1]

The title compound was synthesized in a similar fashion to example 207, where the Chloro azabenzothiozole intermediate in step 8 was prepared in a similar fashion to step 1 of Example 189 from the appropriate starting materials. $^1H$ NMR (400 MHz, Methanol-$d_4$) δ 8.61 (d, J=1.4 Hz, 1H), 7.98 (d, J=8.7 Hz, 1H), 7.22-7.06 (m, 2H), 4.79 (s, 2H), 4.68-4.56 (m, 1H), 4.14-3.38 (m, 12H), 3.24-3.06 (m, 1H), 2.39-2.06 (m, 6H), 1.94-1.78 (m, 2H), 1.75-1.63 (m, 2H). ESI MS $[M+H]^+$ for $C_{25}H_{32}N_6O_2S$, calcd 481.2, found 481.2.

Example 235: N-{2-[(3S)-3-Methylmorpholin-4-yl]-[1,3]thiazolo[5,4-c]pyridin-6-yl}-5-(oxan-4-yl)-6-[(pyrrolidin-1-yl)methyl]pyridin-2-amine

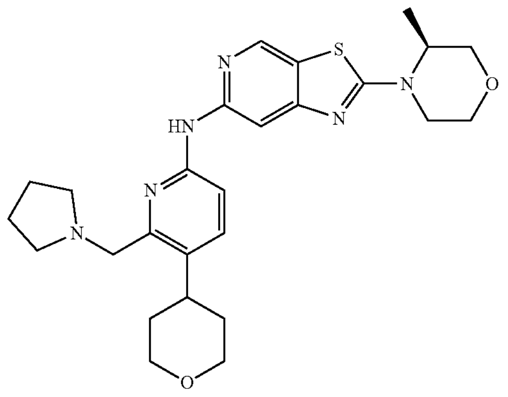 [SMILES: C[C@H]1COCCN1c1nc2cc(Nc3ccc(C4CCOCC4)c(CN4CCCC4)n3)ncc2s1]

The title compound was synthesized in a similar fashion to example 207, where the Chloro azabenzothiozole intermediate in step 8 was prepared in a similar fashion to step 1 of example 189 from the appropriate starting materials. $^1H$ NMR (400 MHz, Methanol-$d_4$) δ 8.61 (d, J=0.5 Hz, 1H), 7.99 (d, J=8.8 Hz, 1H), 7.17 (d, J=8.8 Hz, 1H), 7.13 (d, J=0.5 Hz, 1H), 4.79 (s, 2H), 4.13-3.99 (m, 3H), 3.88-3.27 (m, 12H), 3.23-3.07 (m, 1H), 2.16 (s, 4H), 1.97-1.78 (m, 2H), 1.76-1.64 (m, 2H), 1.49 (d, J=6.8 Hz, 3H). ESI MS $[M+H]^+$ for $C_{26}H_{34}N_6O_2S$, calcd 495.3, found 495.3.

Example 236: N-{2-[(2S)-2-Methylpiperidin-1-yl]-[1,3]thiazolo[5,4-c]pyridin-6-yl}-5-(oxan-4-yl)-6-[(pyrrolidin-1-yl)methyl]pyridin-2-amine

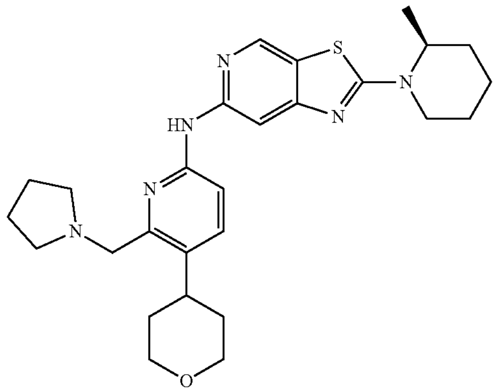 [SMILES: C[C@H]1CCCCN1c1nc2cc(Nc3ccc(C4CCOCC4)c(CN4CCCC4)n3)ncc2s1]

The title compound was synthesized in a similar fashion to example 207, where the Chloro azabenzothiozole intermediate in step 8 was prepared in a similar fashion to step 1 of example 189 from the appropriate starting materials. $^1H$ NMR (400 MHz, Methanol-$d_4$) δ 8.33 (d, J=0.5 Hz, 1H), 7.77 (d, J=8.8 Hz, 1H), 6.95 (d, J=8.8 Hz, 1H), 6.86 (d, J=0.5 Hz, 1H), 4.57 (s, 2H), 3.92-3.76 (m, 2H), 3.56-3.07 (m, 9H), 3.00-2.87 (m, 1H), 1.95 (s, 4H), 1.75-1.31 (m, 10H), 1.20 (d, J=6.9 Hz, 3H). ESI MS $[M+H]^+$ for $C_{27}H_{36}N_6OS$, calcd 493.3, found 493.3.

Example 237: N-(2-{3-Oxa-6-azabicyclo[3.1.1]heptan-6-yl}-[1,3]thiazolo[5,4-c]pyridin-6-yl)-5-(oxan-4-yl)-6-[(pyrrolidin-1-yl)methyl]pyridin-2-amine

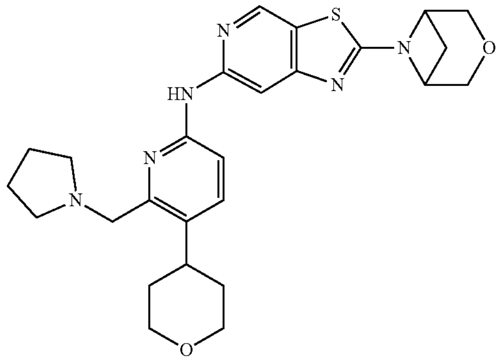 [SMILES: c1cc(C2CCOCC2)c(CN2CCCC2)nc1Nc1cc2nc(N3C4COCC3C4)sc2cn1]

The title compound was synthesized in a similar fashion to example 207, where the Chloro azabenzothiozole intermediate in step 8 was prepared in a similar fashion to step 1 of example 189 from the appropriate starting materials. $^1H$ NMR (400 MHz, Chloroform-d) δ 8.39 (d, J=0.8 Hz, 1H), 7.57 (d, J=8.5 Hz, 1H), 7.48 (d, J=8.5 Hz, 1H), 7.43 (d, J=0.8 Hz, 1H), 7.34 (s, 1H), 4.47 (dd, J=17.5, 8.6 Hz, 4H), 4.08-4.01 (m, 2H), 3.87-3.81 (m, 2H), 3.74 (s, 2H), 3.50 (td, J=11.8, 2.2 Hz, 2H), 3.20-3.05 (m, 1H), 2.91 (q, J=6.7 Hz, 1H), 2.54 (q, J=3.4 Hz, 4H), 2.10-2.18 (m, 1H), 1.81-1.60 (m, 8H). ESI MS $[M+H]^+$ for $C_{26}H_{32}N_6O_2S$, calcd 493.2 found 493.6.

Example 238: N-{2-[(1R,4R)-2-Oxa-5-azabicyclo[2.2.1]heptan-5-yl]-[1,3]thiazolo[5,4-c]pyridin-6-yl}-5-(oxan-4-yl)-6-[(pyrrolidin-1-yl)methyl]pyridin-2-amine

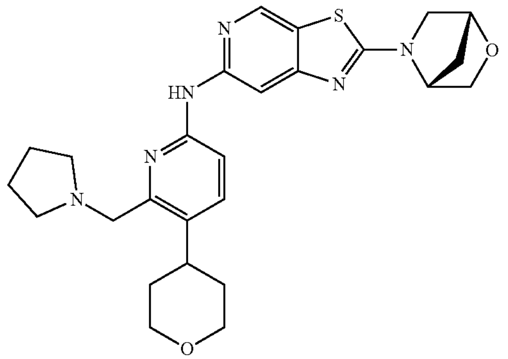 [SMILES: c1cc(C2CCOCC2)c(CN2CCCC2)nc1Nc1cc2nc(N3C[C@H]4C[C@@H]3CO4)sc2cn1]

The title compound was synthesized in a similar fashion to example 207, where the Chloro azabenzothiozole intermediate in step 8 was prepared in a similar fashion to step 1 of example 189 from the appropriate starting materials. $^1$H NMR (400 MHz, Chloroform-d) δ 8.36 (t, J=0.6 Hz, 1H), 7.60 (d, J=8.5 Hz, 1H), 7.48 (d, J=8.6 Hz, 1H), 7.35 (d, J=0.7 Hz, 1H), 7.23 (s, 1H), 4.77 ($s_{br}$, 1H), 4.75 (s, 1H), 4.12-3.95 (m, 3H), 3.91 (dd, J=7.9, 1.5 Hz, 1H), 3.75 (s, 2H), 3.65-3.40 (m, 4H), 3.19-3.11 (m, 1H), 2.54 (d, J=6.1 Hz, 4H), 2.08-1.90 (m, 3H), 1.82-1.55 (m, 7H). ESI MS $[M+H]^+$ for $C_{26}H_{32}N_6O_2S$, calcd 493.2, found 493.5.

Example 239: N-[2-(2-Methyl-1H-imidazol-1-yl)-[1,3]thiazolo[5,4-c]pyridin-6-yl]-5-(oxan-4-yl)-6-[(pyrrolidin-1-yl)methyl]pyridin-2-amine

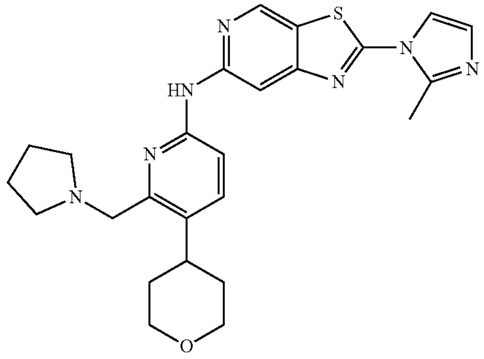 [SMILES: Cc1nccn1-c1nc2cc(Nc3ccc(C4CCOCC4)c(CN4CCCC4)n3)ncc2s1]

The title compound was synthesized in a similar fashion to example 207, where the Chloro azabenzothiozole intermediate in step 8 was prepared in a similar fashion to step 1 of example 189 from the appropriate starting materials. $^1$H NMR (400 MHz, Chloroform-d) δ 8.68 (d, J=0.8 Hz, 1H), 8.24 (s, 1H), 7.53 (d, J=8.5 Hz, 1H), 7.47 (d, J=1.7 Hz, 1H), 7.34 (d, J=8.4 Hz, 1H), 7.04 (d, J=1.7 Hz, 1H), 4.11-4.04 (m, 2H), 3.88 (s, 2H), 3.53 (td, J=11.7, 2.2 Hz, 2H), 3.11 (t, J=12.2 Hz, 1H), 2.83 (s, 3H), 2.73 ($s_{br}$, 4H), 1.84 ($s_{br}$, 4H), 1.80-1.62 (m, 4H). ESI MS $[M+H]^+$ for $C_{25}H_{29}N_7OS$, calcd 476.2, found 476.6.

Example 240: 4-[(1S,4S)-2,5-Diazabicyclo[2.2.1]heptan-2-yl]-N-[2-(3-methylpyridin-2-yl)-[1,3]thiazolo[5,4-c]pyridin-6-yl]pyrimidin-2-amine

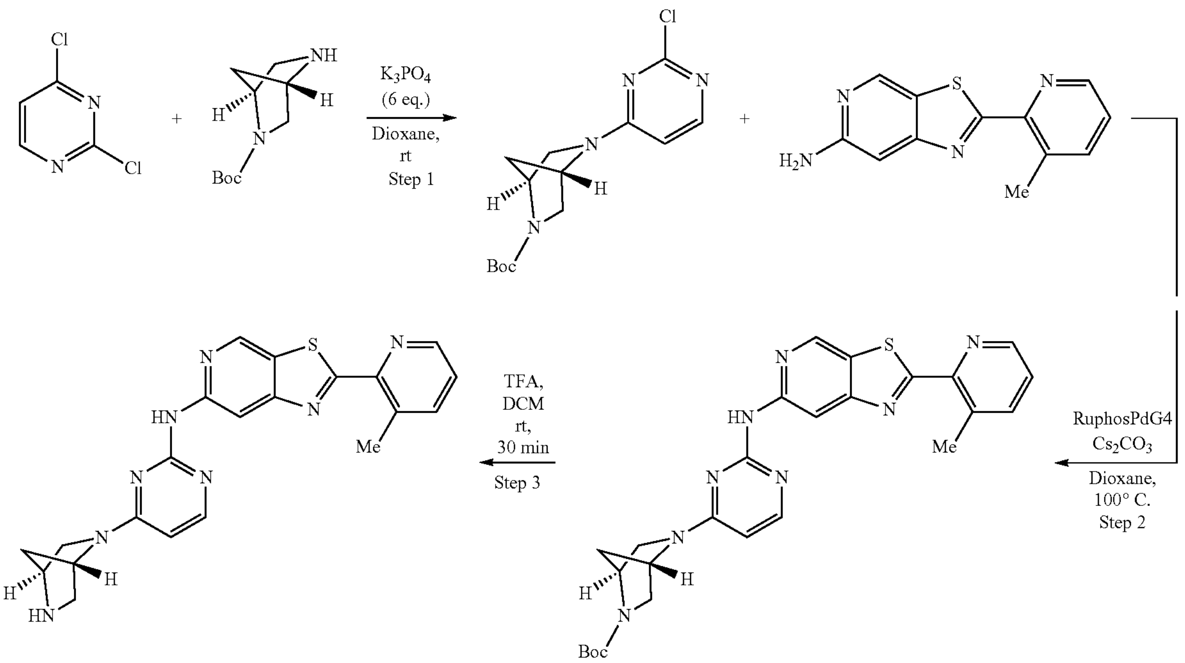

Step 1: To a dry screw cap reaction vial containing septum, was added commercially available 2,4-dichloro pyrimidine (0.5 g, 2.69 mmol) followed by (1S,4S)-2-boc-2,5-diazabicyclo[2.2.1]heptane (3.23 mmol, 0.64 g) and $K_3PO_4$ (3.4 g, 16.17 mmol). To this mixture, dioxane (10 mL) was added and stirred for 2 hours at room temperature. After confirming the completion of the reaction by LCMS, the crude reaction mixture was filtered through a small pad of Celite®. The solvent was evaporated under reduced pressure and the crude product was purified by flash column chromatography to afford the pyrimidine derivative (250 mg, 30%).

Step 2: To a dry screw cap reaction vial containing septum, were added the benzothiazole derived amine (100 mg, 0.412 mmol) prepared in a similar fashion to that described for steps 1-3 of example 1, pyrimidine derivative from step 1 (128 mg, 0.412 mmol), Ruphos Pd G4 (70 mg, 0.082 mmol), $Cs_2CO_3$ (403 mg, 1.238 mmol) and Dioxane (5 mL) and degassed for 5 min using nitrogen. Then this reaction mixture was stirred at 100° C. overnight. After confirming the completion of the reaction using LCMS, the reaction mixture was cooled to room temperature and the crude reaction mixture was filtered through a small pad of Celite® and the volatiles were evaporated under reduced pressure.

Step 3: To the crude reaction mixture from step 2 in a screw cap vial was added $CH_2Cl_2$ (5 mL) and 1.5 mL of neat TFA and stirred for 30 min. After confirming the completion of the Boc deprotection by LCMS, reaction was stopped, and the volatiles were removed under reduced pressure. The crude product was purified by preparative HPLC. The pure fractions were passed through bicarbonate cartridges to neutralized. The neutralized fractions were then combined, frozen at −78° C., and lyophilized to afford the title compound (40 mg, 23%). $^1H$ NMR (400 MHz, DMSO-$d_6$) δ 9.18 (d, J=25.9 Hz, 1H), 9.03 (s, 1H), 9.00 (s, 1H), 8.64-8.60 (m, 1H), 8.03 (d, J=4.8 Hz, 1H), 7.95-7.90 (m, 1H), 7.54 (dd, J=7.7, 4.6 Hz, 1H), 6.27 (d, J=4.3 Hz, 1H), 5.96 (d, J=4.3 Hz, 1H), 4.95 (s, 1H), 4.54 (s, 1H), 3.79-3.64 (m, 1H), 3.61-3.40 (m, 2H), 3.13 (d, J=9.2 Hz, 1H), 2.99-2.90 (m, 1H), 2.87 (s, 3H), 1.79 (dd, J=23.1, 9.4 Hz, 1H), 1.70 (d, J=8.6 Hz, 1H). ESI MS $[M+H]^+$ for $C_{21}H_{20}N_8S$, calcd 417.2, found 417.1.

Example 241: 4-[(1S,4S)-2,5-Diazabicyclo[2.2.1]heptan-2-yl]-N-[2-(pyridin-4-yl)-[1,3]thiazolo[5,4-c]pyridin-6-yl]pyrimidin-2-amine

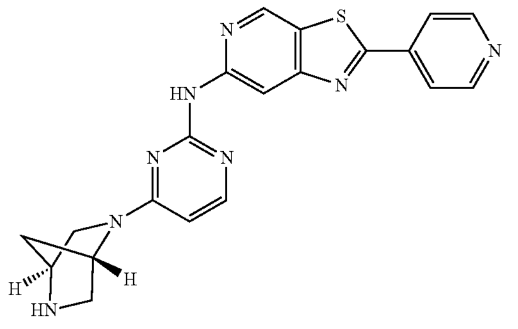 [SMILES: c1cc(-c2nc3cc(Nc4nccc(N5C[C@@H]6C[C@H]5CN6)n4)ncc3s2)ccn1]

The title compound was synthesized in a similar fashion to example 240 from the appropriate starting materials. $^1H$ NMR (400 MHz, DMSO-$d_6$) δ 9.29 (s, 1H), 9.12 (s, 1H), 9.01 (d, J=16.9 Hz, 1H), 8.86-8.80 (m, 2H), 8.11-8.06 (m, 2H), 8.02 (d, J=9.3 Hz, 1H), 6.27 (s, 1H), 5.98 (s, 1H), 4.95 (s, 1H), 4.55 (s, 1H), 3.74 (s, 1H), 3.67-3.50 (m, 1H), 3.05-2.74 (m, 2H), 1.88-1.76 (m, 1H), 1.76-1.68 (m, 1H). ESI MS $[M+H]^+$ for $C_{20}H_{18}N_8S$, calcd 403.1, found 403.1.

Example 242: [(2S,4S)-4-amino-1-(2-{[2-(3-Methylpyridin-2-yl)-[1,3]thiazolo[5,4-c]pyridin-6-yl]amino}pyrimidin-4-yl)pyrrolidin-2-yl]methanol

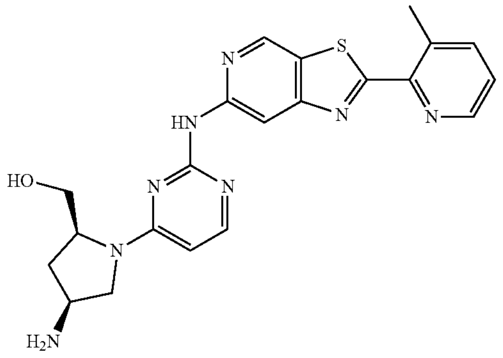 [SMILES: Cc1cccnc1-c1nc2cc(Nc3nccc(N4C[C@@H](N)C[C@H]4CO)n3)ncc2s1]

The title compound was synthesized in a similar fashion to example 240 from the appropriate starting materials. $^1H$ NMR (400 MHz, Chloroform-d) δ 9.01 (d, J=0.9 Hz, 1H), 8.85 (d, J=0.9 Hz, 1H), 8.54 (ddd, J=4.6, 1.7, 0.7 Hz, 1H), 8.06 (d, J=6.0 Hz, 1H), 7.84 ($s_{br}$, 1H), 7.66 (ddd, J=7.8, 1.7, 0.8 Hz, 1H), 7.31 (dd, J=7.7, 4.6 Hz, 1H), 5.92 ($s_{br}$, 1H), 4.63 ($s_{br}$, 1H), 4.33 ($s_{br}$, 1H), 3.90 (t, J=5.7 Hz, 1H), 3.92-3.61 (m, 2H), 3.19 ($s_{br}$, 1H), 2.90 (s, 3H), 2.48 (ddd, J=14.6, 9.6, 5.7 Hz, 1H), 1.85 (d, J=13.6 Hz, 1H). ESI MS $[M+H]^+$ for $C_{21}H_{22}N_8OS$, calcd 435.2, found 435.1.

Example 243: N,N-Dimethyl-3-[6-({4-[(1S,4S)-5-methyl-2,5-diazabicyclo[2.2.1]heptan-2-yl]pyrimidin-2-yl}amino)-[1,3]thiazolo[5,4-c]pyridin-2-yl]benzamide

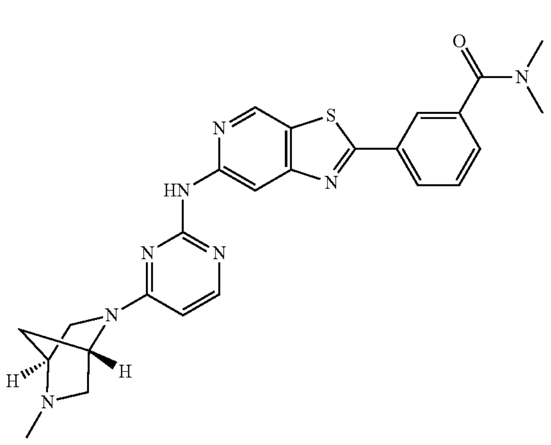 [SMILES: CN(C)C(=O)c1cccc(-c2nc3cc(Nc4nccc(N5C[C@@H]6C[C@H]5CN6C)n4)ncc3s2)c1]

The title compound was synthesized in a similar fashion to example 240 from the appropriate starting materials. $^1H$ NMR (400 MHz, DMSO-$d_6$) δ 8.99 (s, 1H), 8.82 (d, J=0.9 Hz, 1H), 8.19 (t, J=1.1 Hz, 1H), 8.18-8.11 (m, 1H), 8.03 (d, J=5.9 Hz, 1H), 7.92 (s, 1H), 7.71-7.50 (m, 2H), 5.89 (d, J=6.0 Hz, 1H), 3.70 (bs, 1H), 3.55-3.32 (m, 2H), 3.15-3.12 (m, 4H), 3.03 (s, 3H), 2.80 (bs, 2H), 2.51 (s, 3H), 2.15-2.12 (m, 1H), 1.95-1.91 (m, 1H). ESI MS [M+H]+ for $C_{25}H_{26}N_8SO$, calcd 487.2, found 487.2.

Example 244: N-[2-(3-Methanesulfonylphenyl)-[1,3]thiazolo[5,4-c]pyridin-6-yl]-4-[(1S,4S)-5-methyl-2,5-diazabicyclo[2.2.1]heptan-2-yl]pyrimidin-2-amine

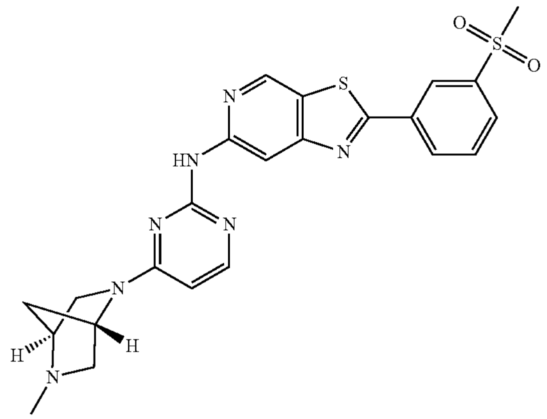 [SMILES: CN1C[C@@H]2C[C@H]1CN2c1ccnc(Nc2cc3nc(-c4cccc(S(C)(=O)=O)c4)sc3cn2)n1]

The title compound was synthesized in a similar fashion to example 240 from the appropriate starting materials. $^1H$ NMR (400 MHz, DMSO-$d_6$) δ 9.27 (s, 1H), 9.09 (d, J=0.9 Hz, 1H), 8.97 (s, 1H), 8.60 (t, J=1.8 Hz, 1H), 8.48 (ddd, J=7.8, 1.8, 1.0 Hz, 1H), 8.19 (ddd, J=7.9, 1.9, 1.1 Hz, 1H), 8.04 (s, 1H), 7.98-7.82 (m, 1H), 6.27 (bs, 1H), 6.02 (bs, 1H), 4.89 (bs, 1H), 4.50 (bs, 1H), 3.73 (m, 1H), 3.52 (bs, 1H), 3.37 (s, 3H), 2.86 (m, 1H), 2.32 (s, 3H), 1.92 (d, J=9.5 Hz, 1H), 1.77 (m, 1H). ESI MS $[M+H]^+$ for $C_{23}H_{23}N_7S_2O_2$, calcd 494.1, found 494.2.

Example 245: 4-[(1S,4S)-5-Methyl-2,5-diazabicyclo[2.2.1]heptan-2-yl]-N-{2-[3-(pyrrolidine-1-carbonyl)phenyl]-[1,3]thiazolo[5,4-c]pyridin-6-yl}pyrimidin-2-amine

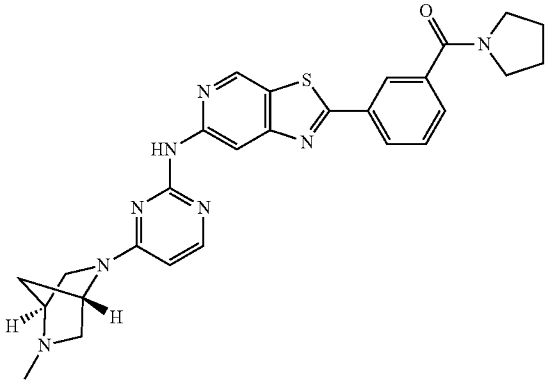 [SMILES: CN1C[C@@H]2C[C@H]1CN2c1ccnc(Nc2cc3nc(-c4cccc(C(=O)N5CCCC5)c4)sc3cn2)n1]

The title compound was synthesized in a similar fashion to example 240 from the appropriate starting materials. $^1H$ NMR (400 MHz, $CDCl_3$) δ 9.14-8.96 (m, 1H), 8.83 (d, J=0.9 Hz, 1H), 8.28 (t, J=1.7 Hz, 1H), 8.15 (ddd, J=7.8, 1.9, 1.2 Hz, 1H), 8.03 (d, J=5.8 Hz, 2H), 7.66 (dt, J=7.7, 1.4 Hz, 1H), 7.54 (td, J=7.8, 0.6 Hz, 1H), 5.88 (s, 1H), 3.67 (q, J=8.1, 7.5 Hz, 3H), 3.47 (t, J=6.6 Hz, 3H), 3.08 (dd, J=9.8, 2.1 Hz, 1H), 2.76 (bs, 1H), 2.30 (bs, 2H), 2.09 (d, J=9.9 Hz, 1H), 2.03-1.94 (m, 2H), 1.95-1.80 (m, 3H). ESI MS $[M+H]^+$ for $C_{27}H_{28}N_8SO$, calcd 513.2, found 513.3.

Example 246: 6-[(1S,4S)-2,5-Diazabicyclo[2.2.1]heptan-2-yl]-N-[2-(3-methylpyridin-2-yl)-[1,3]thiazolo[5,4-c]pyridin-6-yl]-5-(oxan-4-yl)pyridin-2-amine

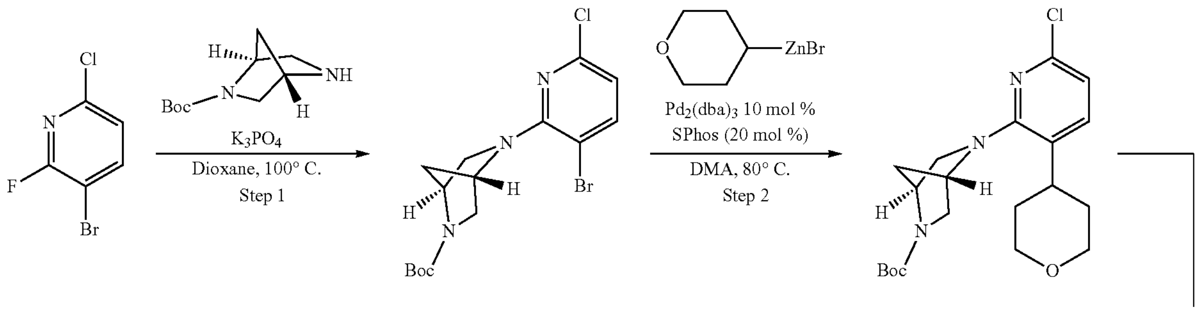

-continued

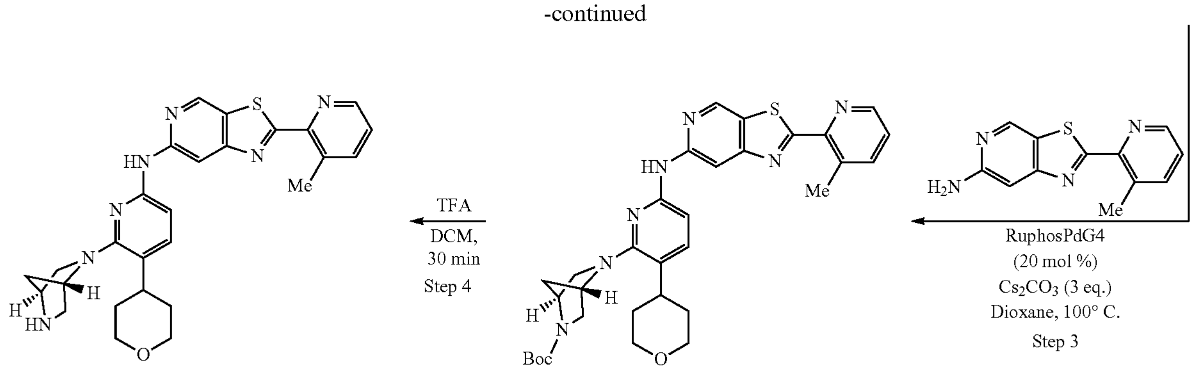

Step 1: To a dry screw cap reaction vial containing septum, was added commercially available 3-bromo-6-chloro-2-fluoro pyridine (0.5 g, 2.38 mmol) followed by (1S,4S)-2-boc-2,5-diazabicyclo[2.2.1]heptane (0.47 g, 2.37 mmol) and $K_3PO_4$ (2.52 g, 11.88 mmol). To this mixture, dioxane (10 mL) was added and stirred for 3 hours at 100° C. After confirming the completion of the reaction by LCMS, the temperature of the reaction mixture was brought to room temperature and filtered through a small pad of Celite®. The solvent was evaporated under reduced pressure and the crude product was purified by flash column chromatography (silica gel; gradient: 0% to 50% MeOH in $CH_2Cl_2$) to afford the pyridine derivative in quantitative yield.

Step 2: To a dry screw cap reaction vial containing septum, was added the pyridine derivative from Step 1 (452 mg, 1.16 mmol), followed by the addition of $Pd_2(dba)_3$ (106 mg, 0.12 mmol) and Sphos ligand (95 mg, 0.232 mmol) under inert conditions. To this mixture, dry N, N-dimethylacetamide (8 mL) was added and the reaction mixture degassed using nitrogen. To this degassed reaction mixture, 0.5 M solution of THP zinc bromide solution (2.32 mL, 1.16 mmol) was added at room temperature and heated at 80° C. under constant stirring overnight. After confirming the completion of the reaction by LCMS, the temperature of the reaction mixture was brought to room temperature and quenched with saturated ammonium chloride. This reaction mixture was diluted with water and extracted with ethyl acetate twice. The combined organic layers were dried over anhydrous $Na_2SO_4$ and concentrated. The crude product was purified by column chromatography (silica gel; gradient: 0% to 50% MeOH in $CH_2Cl_2$) to afford the THP containing intermediate (200 mg, 44%).

Step 3: To a dry screw cap reaction vial containing septum, were added the benzothiazole derived amine (100 mg, 0.41 mmol) prepared in a similar fashion to that described for steps 1-3 of example 1 from the appropriate starting materials, pyridine derivative from step 2 (163 mg, 0.41 mmol), RuPhos Pd G4 (70 mg, 0.08 mmol), $Cs_2CO_3$ (403 mg, 1.24 mmol) and Dioxane (5 mL) and degassed for 5 min using nitrogen. Then this reaction mixture was stirred at 100° C. overnight. After confirming the completion of the reaction using LCMS, the reaction mixture was cooled to room temperature and the crude reaction mixture was filtered through a small pad of Celite® and the volatiles were evaporated under reduced pressure.

Step 4: To the crude reaction mixture from step 3 in a screw cap vial was added $CH_2Cl_2$ (5 mL) and 1.5 mL of neat TFA and stirred for 30 min. After confirming the completion of the Boc deprotection by LCMS, the reaction was stopped, and the volatiles were removed under reduced pressure. The crude product was purified by preparative HPLC. The pure fractions were passed through bicarbonate cartridges to be neutralized. The neutralized fractions were combined, frozen at −78° C., and lyophilized to afford the title compound (42 mg, 20%). $^1H$ NMR (400 MHz, Chloroform-d) δ 8.81 (d, J=0.8 Hz, 1H), 8.72 (d, J=0.8 Hz, 1H), 8.55 (dd, J=4.6, 1.1 Hz, 1H), 7.70-7.64 (m, 1H), 7.39-7.28 (m, 3H), 6.45 (d, J=8.1 Hz, 1H), 4.77 (s, 1H), 4.15-4.00 (m, 2H), 3.83-3.75 (m, 2H), 3.59 (d, J=9.9 Hz, 1H), 3.56-3.48 (m, 2H), 3.27-3.15 (m, 2H), 2.89 (s, 4H), 2.00-1.93 (m, 1H), 1.88-1.77 (m, 4H), 1.77-1.67 (m, 1H), 1.60 (dtd, J=13.4, 11.9, 4.3 Hz, 1H). ESI MS $[M+H]^+$ for $C_{27}H_{29}N_7OS$, calcd 500.2, found 500.3.

Example 247: 6-[(1S,4S)-5-Methyl-2,5-diazabicyclo[2.2.1]heptan-2-yl]-N-[2-(3-methylpyridin-2-yl)-[1,3]thiazolo[5,4-c]pyridin-6-yl]-5-(oxan-4-yl)pyridin-2-amine

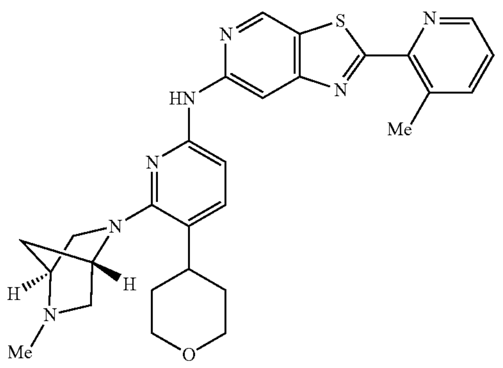 [SMILES: Cc1cccnc1-c1nc2cc(Nc3ccc(C4CCOCC4)c(N4C[C@@H]5C[C@H]4CN5C)n3)ncc2s1]

The title compound was synthesized in a similar fashion to steps 1, 2 and 3 of example 246 from the appropriate starting materials. $^1H$ NMR (400 MHz, Chloroform-d) δ 8.82 (d, J=0.8 Hz, 1H), 8.73 (d, J=0.8 Hz, 1H), 8.56 (dd, J=4.4, 1.3 Hz, 1H), 7.69 (ddd, J=7.8, 1.5, 0.7 Hz, 1H), 7.39-7.29 (m, 2H), 7.24 (s, 1H), 6.46 (d, J=8.1 Hz, 1H), 4.71 (s, 1H), 4.17-4.01 (m, 2H), 3.58-3.47 (m, 5H), 3.21 (d, J=9.8 Hz, 1H), 3.12 (dd, J=9.8, 2.3 Hz, 1H), 2.92 (s, 4H), 2.45 (s, 3H), 2.01 (d, J=9.5 Hz, 1H), 1.92 (d, J=9.5 Hz, 1H), 1.83 (td, J=10.3, 9.4, 3.8 Hz, 2H), 1.77-1.69 (m, 1H), 1.69-1.56 (m, 1H). ESI MS $[M+H]^+$ for $C_{28}H_{31}N_7OS$, calcd 514.2, found 514.2.

Example 248: 6-[(3aS,6aS)-1-Methyl-octahydropyrrolo[3,4-b]pyrrol-5-yl]-N-[2-(2-methylpyridin-4-yl)-[1,3]thiazolo[5,4-c]pyridin-6-yl]-5-(oxan-4-yl)pyridin-2-amine

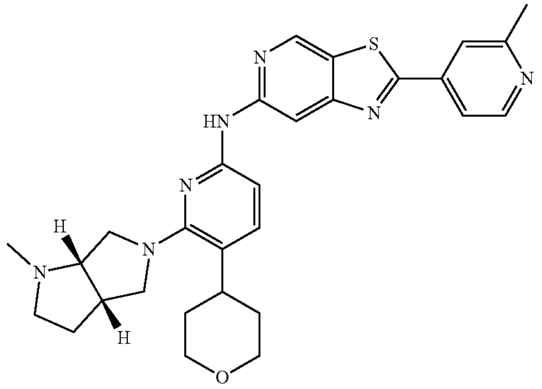

The title compound was synthesized in a similar fashion to steps 1, 2 and 3 of example 246 from the appropriate starting materials. $^1H$ NMR (400 MHz, Chloroform-d) δ 8.81 (d, J=0.9 Hz, 1H), 8.67 (dd, J=5.2, 0.8 Hz, 1H), 8.60 (d, J=0.9 Hz, 1H), 7.82 (dt, J=1.5, 0.7 Hz, 1H), 7.74 (ddd, J=5.2, 1.7, 0.7 Hz, 1H), 7.40 (s, 1H), 7.22 (s, 1H), 6.67 (d, J=8.1 Hz, 1H), 4.08 (t, J=11.0 Hz, 2H), 3.56-3.37 (m, 6H), 3.32 (dd, J=9.8, 7.4 Hz, 1H), 3.06 (dt, J=21.7, 6.6 Hz, 3H), 2.92-2.88 (m, 1H), 2.68 (s, 3H), 2.46 (s, 3H), 2.40 (td, J=9.5, 6.6 Hz, 1H), 2.14 (dtd, J=12.8, 6.6, 3.3 Hz, 1H), 1.88-1.67 (m, 4H). ESI MS $[M+H]^+$ for $C_{29}H_{33}N_7OS$, calcd 528.3, found 528.7.

Example 249: 2-[(1S,4S)-5-Methyl-2,5-diazabicyclo[2.2.1]heptan-2-yl]-N-[2-(3-methylpyridin-2-yl)-[1,3]thiazolo[5,4-c]pyridin-6-yl]-6-(oxan-4-yl)pyrimidin-4-amine

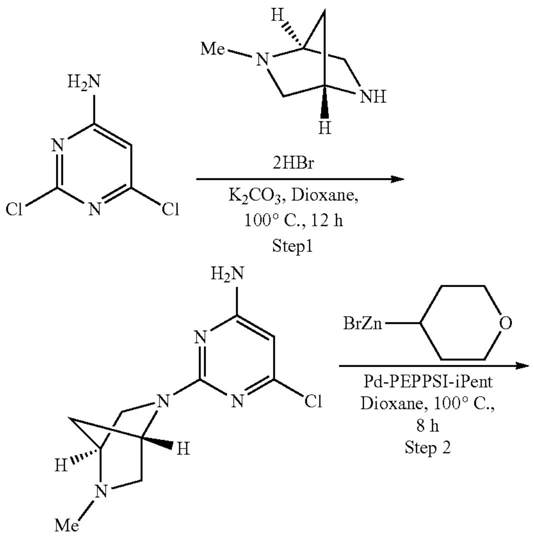

-continued

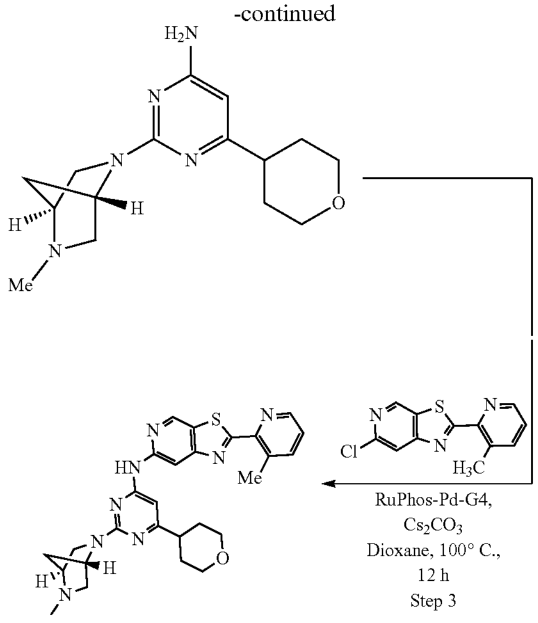

Step 1: To a stirred suspension of (1S,4S)-2-methyl-2,5-diazabicyclo[2.2.1]heptane dihydrobromide (1.67 g, 6.1 mmol), 2-bromo-6-chloropyrazine (1 g, 6.1 mmol) in dioxane (12 mL) was added $K_2CO_3$ (4.2 g, 30.50 mmol). The reaction was stirred at 100° C. for 16 h. The reaction mixture was then filtered through Celite® and concentrated under reduced pressure. The resulting residue a was purified by flash column chromatography (silica gel; gradient: 0% to 30% MeOH in $CH_2Cl_2$) to get desired compound in (1.02 g, 70%).

Step 2: To a dry screw cap reaction vial containing septum, was added the pyrimidine derivative from step 1 (239 mg, 1.0 mmol), followed by the addition of Pd-PEPPSI-iPent (80 mg, 0.1 mmol), under inert conditions. To this mixture, dry dioxane (6 mL) was added and the resulting mixture degassed using nitrogen. To this degassed reaction mixture, 0.5 M solution of THP zinc bromide (4 mL, 2.0 mmol) was added at room temperature and then heated at 100° C. for 8 h. The reaction mixture was then filtered through Celite® and concentrated under reduced pressure. The resulting residue a was purified by flash column chromatography (silica gel; gradient: 0% to 30% MeOH in $CH_2Cl_2$) to get desired compound in (1.02 g, 70%).

Step 3: This step was performed in a similar fashion to step 6 of example 1, wherein the chloro azabenzothiazole intermediate was prepared in a similar manner to that described in step 1 of example 1 from the appropriate starting materials. $^1H$ NMR (400 MHz, Chloroform-d) δ 8.85 (d, J=0.9 Hz, 1H), 8.73 (s, 1H), 8.55 (ddd, J=4.6, 1.6, 0.6 Hz, 1H), 7.68 (ddd, J=7.8, 1.7, 0.8 Hz, 1H), 7.35 (s, 1H), 7.32 (dd, J=7.7, 4.6 Hz, 1H), 6.09 (s, 1H), 4.87 (s, 1H), 4.17-4.01 (m, 2H), 3.88 (d, J=10.7 Hz, 1H), 3.61-3.37 (m, 4H), 3.06 (s, 1H), 2.90 (s, 3H), 2.75 (d, J=9.1 Hz, 1H), 2.71-2.61 (m, 1H), 2.46 (s, 3H), 2.01 (d, J=9.7 Hz, 1H), 1.93-1.79 (m, 4H). ESI MS $[M+H]^+$ for $C_{27}H_{30}N_8OS$, calcd 515.2, found 515.8.

Example 250: 2-[(1S,4S)-2,5-Diazabicyclo[2.2.1]heptan-2-yl]-N-[2-(3-methylpyridin-2-yl)-[1,3]thiazolo[5,4-c]pyridin-6-yl]-6-(oxan-4-yl)pyrimidin-4-amine

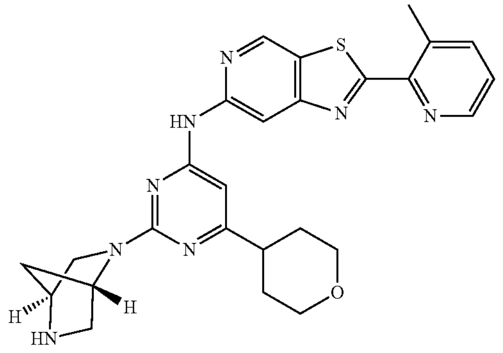 [SMILES: Cc1cccnc1-c1nc2cc(Nc3cc(C4CCOCC4)nc(N4C[C@@H]5C[C@H]4CN5)n3)ncc2s1]

The title compound was synthesized in a similar fashion to example 249 from the appropriate starting materials. After step 3, the deprotection of Boc-group was carried out in a similar fashion to step 3 of example 78. $^1$H NMR (400 MHz, Methanol-$d_4$) δ 8.83 (s, 1H), 8.79 (s, 1H), 8.48 (d, J=4.3 Hz, 1H), 7.76 (d, J=7.8 Hz, 1H), 7.38 (dd, J=7.8, 4.6 Hz, 1H), 6.26 (s, 1H), 4.91 (s, 1H), 4.07-3.98 (m, 2H), 3.81 (s, 1H), 3.66 (d, J=10.3 Hz, 1H), 3.52 (dq, J=13.5, 9.2, 8.6 Hz, 3H), 3.04 (t, J=10.2 Hz, 2H), 2.83 (s, 3H), 2.74-2.59 (m, 1H), 1.95 (d, J=10.0 Hz, 1H), 1.82 (ddp, J=10.1, 6.6, 3.7, 3.3 Hz, 5H). ESI MS [M+H]$^+$ for $C_{26}H_{28}N_8OS$, calcd 501.63, found 501.9.

Example 251: $N_2$-[(1-Methyl-1H-imidazol-2-yl)methyl]-$N_6$-[2-(3-methylpyridin-2-yl)-[1,3]thiazolo[5,4-c]pyridin-6-yl]-3-(oxan-4-yl)pyridine-2,6-diamine

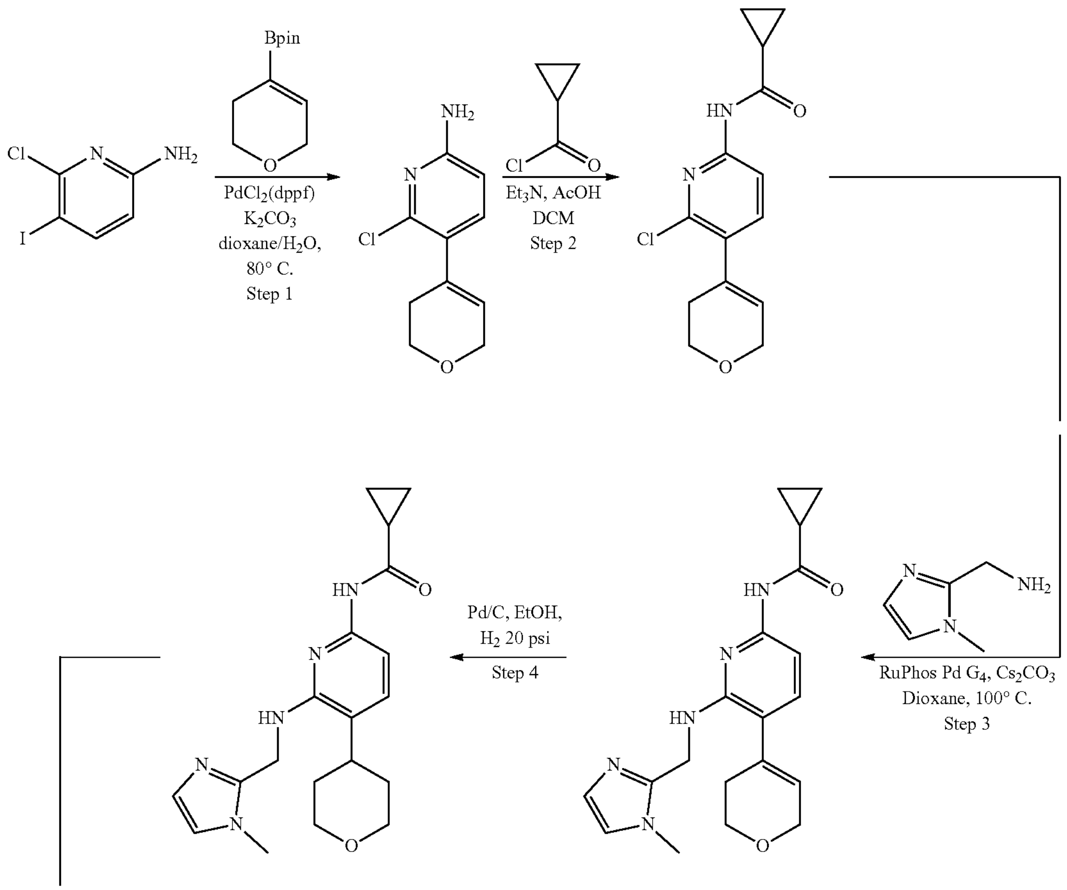

-continued

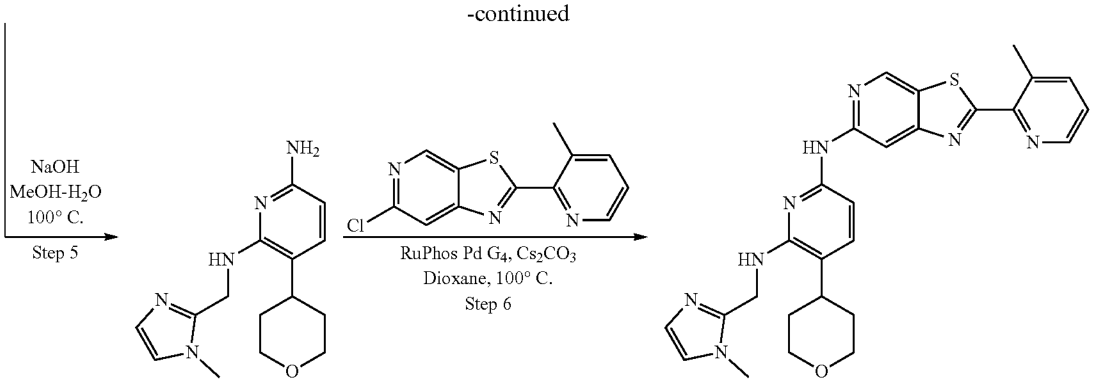

Step 1: To a solution of 6-Chloro-5-iodopyridin-2-amine (762 mg, 3.0 mmol) and 3,6-Dihydro-4-(4,4,5,5-tetramethyl-1,3,2-dioxaborolan-2-yl)-2H-pyran (630 mg, 3.0 mmol) in Dioxane (12 mL)/$H_2O$ (3 mL) was added $PdCl_2$(dppf) (260 mg, 0.33 mmol) and $K_2CO_3$ (1.0 g, 6.6 mmol). After degassing for 25 min with $N_2$, the reaction mixture was heated to 80° C. and stirred for 2 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 50% EtOAc in hexanes) to get imine intermediate (580 mg, 92%) as the white solid.

Step 2: To a stirred suspension of 2-aminopyridine derivative obtained from step 1 (1.57 g, 7.45 mmol) in $CH_2Cl_2$ (20 mL) was added $Et_3N$ (3.1 mL, 22.35 mmol) slowly at 0° C. After stirring for 5 min, cyclopropanecarbonyl chloride (2.70 mL, 29.80 mmol) was added dropwise over 15 min and the reaction was stirred at room temperature for 2 h. The reaction was concentrated under reduced pressure and the residue was dissolved in $CH_2Cl_2$, then washed with sat. $NaHCO_3$ followed by brine. The organic layer was dried over anhydrous $Na_2SO_4$, and then concentrated under reduced pressure to afford the desired amide in 96% (2.0 g) yield.

Step 3: To a stirred solution of amide intermediate from step 2 (278 mg, 1.0 mmol), N-Methyl-1H-imidazol-2-amine (222 mg, 2 mmol) in dioxane (3 mL) was added RuPhos Pd G4 (170 mg, 0.20 mmol) and $Cs_2CO_3$ (977 mg 3 mmol). After degassing for 10 min with $N_2$, the reaction mixture was heated at 100° C. for 15 h. The reaction mixture was then filtered through a pad of Celite® and concentrated under reduced pressure. The resulting residue was purified by column chromatography (silica gel; gradient: 0-10% MeOH/$CH_2Cl_2$) to obtain the desired imidazole intermediate (106 mg, 30%).

Step 4: A suspension of imidazole intermediate from step 3 (106 mg, 0.3 mmol) and Pd/C (20 wt. %, 200 mg) in ethanol (20 mL) was shaken in a Parr hydrogenator at 20 psi of $H_2$ atmosphere for 3 h. The reaction mixture was filtered through a pad of Celite®, and the filtrate was concentrated under reduced pressure to give the desired intermediate (99 mg, 93%).

Step 5: The intermediate from step 4 (99 mg, 0.28 mm), NaOH (120 mg, 3 mmol), MeOH (4 mL), $H_2O$ (1 mL) were combined and heated at 100° C. overnight. After cooling to room temperature, the organic solvent was evaporated, and the resultant was purified by column chromatography (silica gel; gradient: 0-60% MeOH/$CH_2Cl_2$) to obtain desired amine in 88% (71 mg) yield.

Step 6: The title compound was synthesized in a similar fashion to step 6 of example 1, wherein the chloro azabenzothiazole intermediate was prepared in a similar manner to that described for step 1 of example 1 from the appropriate starting materials. $^1H$ NMR (400 MHz, Chloroform-d) δ 8.85 (d, J=0.9 Hz, 1H), 8.60 (d, J=0.9 Hz, 1H), 8.59-8.56 (m, 1H), 7.72-7.65 (m, 1H), 7.36-7.28 (m, 2H), 7.23 (s, 1H), 7.02 (d, J=1.2 Hz, 1H), 6.89 (d, J=1.2 Hz, 1H), 6.47 (d, J=8.0 Hz, 1H), 5.42 (t, J=4.8 Hz, 1H), 4.85 (d, J=4.8 Hz, 2H), 4.10 (dd, J=11.7, 3.9 Hz, 2H), 3.72 (s, 3H), 3.61 (td, J=11.7, 2.5 Hz, 2H), 2.89 (s, 3H), 2.70 (tt, J=11.4, 4.0 Hz, 1H), 1.89-1.62 (m, 4H). ESI MS $[M+H]^+$ for $C_{27}H_{28}N_8OS$, calcd 513.2, found 513.2.

Example 252: N-[2-(3-Methylpyridin-2-yl)-[1,3]thiazolo[5,4-c]pyridin-6-yl]-5-(oxolan-3-yl)-6-[(pyrrolidin-1-yl)methyl]pyridin-2-amine
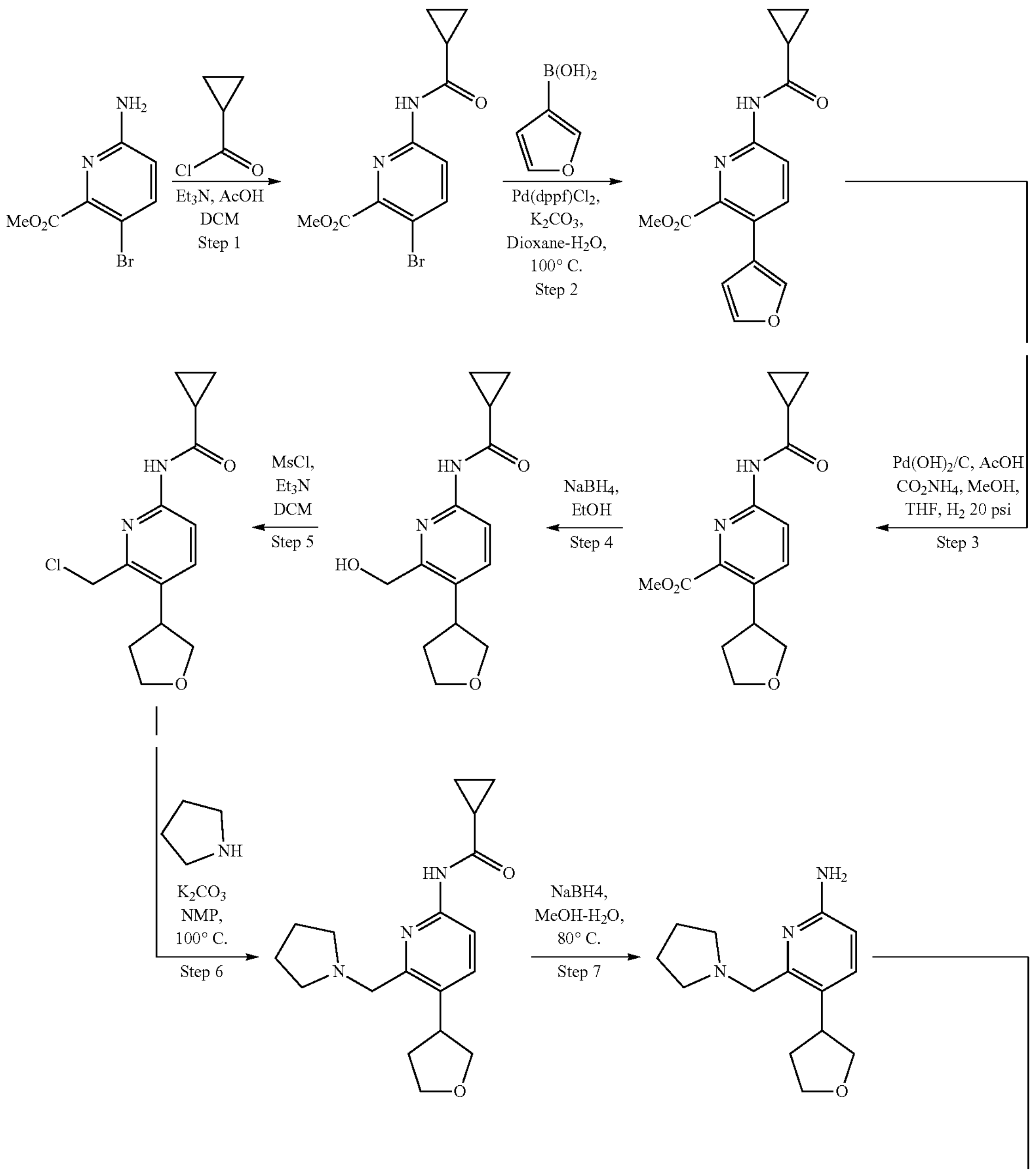

-continued

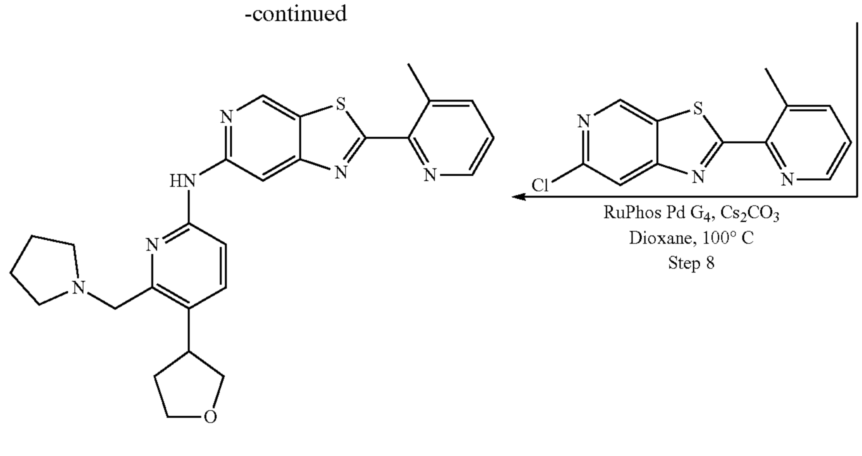

Step 1: To a stirred suspension of methyl 6-amino-3-bromopyridine-2-carboxylate (11.55 g, 50 mmol) in $CH_2Cl_2$ (120 mL) was added $Et_3N$ (13.9 mL, 100 mmol) slowly at 0° C. After stirring for 5 min, cyclopropanecarbonyl chloride (5.23 g, 50 mmol) was added dropwise over 15 min and the reaction was stirred at room temperature for 15 h. The reaction was concentrated under reduced pressure and the resultant residue was dissolved in $CH_2Cl_2$, then washed with sat. $NaHCO_3$ followed by brine. The organic layer was dried over $Na_2SO_4$, concentrated under reduced pressure, and purified by column chromatography (silica gel; gradient: 0% to 30% EtOAc in hexanes) to isolate amide intermediate in 34% (5.10 g) yield.

Step 2: Amide intermediate from step 1 (5.0 g, 16.7 mmol), boronic acid (2.3 g, 20.1 mmol), $Pd(dppf)Cl_2$ (1.16 g, 1.7 mmol), $K_3PO_4$ (10.6 g, 50.1 mmol), Dioxane (60 mL), and $H_2O$ (10 mL) were combined and degassed by bubbling $N_2$ for 10 min. The mixture was stirred at 105° C. under inert atmosphere for 3 h and then cooled to room temperature. The reaction was filtered through a pad of Celite® and the filtrate was concentrated under reduced pressure. The residue was purified by column chromatography (silica gel; gradient: 0% to 70% EtOAc in hexanes) to get the desired compound (4.37 g, 91%).

Step 3: To a solution of intermediate from step 2 (4.0 g, 13.9 mmol) in the mixture of methanol (40 mL) and THE (30 mL) was added $Pd(OH)_2/C$ (2.5 g, 20 wt. %), $HCO_2NH_4$ (1.7 g, 27 mmol), and acetic acid (3.4 mL). The resultant heterogenous mixture was shaken in a Parr hydrogenator for 15 h at 20 psi of $H_2$ atmosphere. The reaction mixture was filtered through a pad of Celite®, and the filtrate was concentrated under reduced pressure. Then the residue was dissolved in $CH_2Cl_2$, washed with sat. $NaHCO_3$, dried over $Na_2SO_4$, and concentrated to obtain the desired intermediate (3.73 g, 92%).

Step 4: To a solution of intermediate from step 3 (3.73 g, 12.9 mmol) in ethanol (40 mL) was added $NaBH_4$ (2.0 g, 52.9 mmol) portion wise at 0° C. Then the reaction was stirred at room temperature for 15 h. At 0° C., the reaction was quenched with water and extracted with $CH_2Cl_2$. The organic layer was washed with brine, dried over anhydrous $Na_2SO_4$, and concentrated to afford desired intermediate (3.34 g, 99%).

Step 5: Methanesulfonyl chloride (3.2 g, 28 mmol) was added to a solution of alcohol intermediate from step 4 (3.34 g, 12.7 mmol) and triethylamine (4.37 mL, 30 mmol) in $CH_2Cl_2$ (40 mL) at 0° C. After stirring at room temperature for 15 h, the reaction was quenched with sat. $NaHCO_3$ and then extracted with $CH_2Cl_2$. The extracted organic layer was dried over anhydrous $Na_2SO_4$ and concentrated under reduced pressure to afford desired chloromethyl intermediate (3.56 g, 96%).

Step 6: A heterogenous mixture of chloromethyl intermediate from step 5 (3.56 g, 12.7 mmol), pyrrolidine (1.08 g, 15.2 mmol), $K_2CO_3$ (3.8 g, 27.5 mmol), and NMP (20 mL) was heated at 100° C. for 1 h. After cooling to room temperature, the reaction mixture was diluted with water and then extracted with EtOAc. The organic layer was washed with water followed by with brine, dried over anhydrous $Na_2SO_4$, and concentrated under reduced pressure to afford crude intermediate, which was used in the next reaction without further purification.

Step 7: A mixture of crude intermediate from step 6, NaOH (4.0 g, 120 mmol), MeOH (40 mL), and $H_2O$ (10 mL) was heated at 80° C. for 20 h. After cooling to room temperature, the organic solvent was evaporated, and the resultant was extracted with $CH_2Cl_2$. The organic extract was concentrated under reduced pressure and purified by column chromatography (silica gel; gradient: 0% to 80% $MeOH/CH_2Cl_2$) to obtain desired aminopyridine (1.85 g, 59%) as a racemic mixture.

Step 8: To a stirred solution of chloroazabenzothiazole derivative prepared in a similar manner to that described for step 1 of example 1 from the appropriate starting materials (79 mg, 0.3 mmol), and aminopyridine (racemic) from step 7 (49 mg, 0.2 mmol) in dioxane (3 mL) was added RuPhos Pd G4 (25 mg, 0.03 mmol) and $Cs_2CO_3$ (195 mg 0.6 mmol). After degassing for 10 min under $N_2$ atmosphere, the reaction mixture was heated at 100° C. for 15 h. The reaction mixture was filtered through a pad of Celite® and concentrated under reduced pressure. The resulting residue was purified by reverse phase preparative HPLC to obtain the title compound (18 mg, 19%). $^1H$ NMR (400 MHz, Methanol-$d_4$) δ 8.86-8.84 (m, 1H), 8.69 (s, 1H), 8.56-8.50 (m, 1H), 7.84-7.79 (m, 1H), 7.64 (d, J=8.6 Hz, 1H), 7.43 (dd, J=7.8, 4.6 Hz, 1H), 7.25 (d, J=8.6 Hz, 1H), 4.14-4.03 (m, 2H), 3.99-3.83 (m, 3H), 3.83-3.73 (m, 1H), 3.69 (dd, J=8.2, 6.6 Hz, 1H), 2.90 (s, 3H), 2.85-2.74 (m, 4H), 2.45-2.34 (m, 1H), 2.04-1.92 (m, 1H), 1.92-1.84 (m, 4H). ESI MS $[M+H]^+$ for $C_{26}H_{28}N_6OS$, calcd 473.2, found 473.2.

Example 253: N-[2-(2-Methylpyridin-4-yl)-[1,3]thiazolo[5,4-c]pyridin-6-yl]-5-(oxolan-3-yl)-6-[(pyrrolidin-1-yl)methyl]pyridin-2-amine

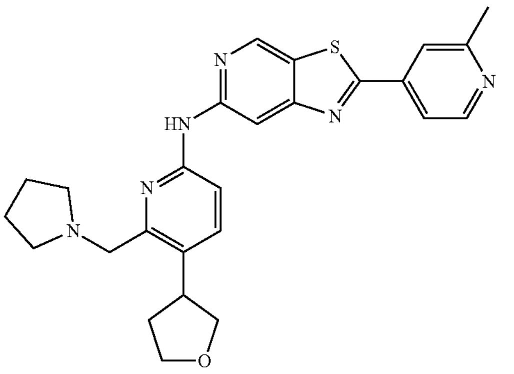 [SMILES: Cc1cc(-c2nc3cc(Nc4ccc(C5CCOC5)c(CN5CCCC5)n4)ncc3s2)ccn1]

The title compound was synthesized in a similar fashion to example 252 from the appropriate starting materials. $^1H$ NMR (400 MHz, Methanol-$d_4$) δ 8.92 (s, 1H), 8.80 (s, 1H), 8.62 (d, J=5.3 Hz, 1H), 8.01 (s, 1H), 7.93 (d, J=5.3 Hz, 1H), 7.65 (d, J=8.6 Hz, 1H), 7.26 (d, J=8.6 Hz, 1H), 4.14-4.05 (m, 2H), 4.03-3.78 (m, 4H), 3.69 (dd, J=8.4, 6.6 Hz, 1H), 2.77 (s, 4H), 2.67 (s, 3H), 2.47-2.35 (m, 1H), 2.05-1.92 (m, 1H), 1.88 (s, 4H). ESI MS $[M+H]^+$ for $C_{26}H_{28}N_6OS$, calcd 473.2, found 473.3.

Example 254: 5-(Oxolan-3-yl)-N-[2-(pyridin-3-yl)-[1,3]thiazolo[5,4-c]pyridin-6-yl]-6-[(pyrrolidin-1-yl)methyl]pyridin-2-amine

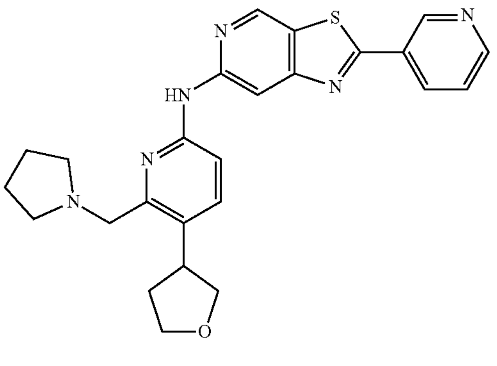 [SMILES: c1cncc(-c2nc3cc(Nc4ccc(C5CCOC5)c(CN5CCCC5)n4)ncc3s2)c1]

The title compound was synthesized in a similar fashion to example 252 from the appropriate starting materials. $^1H$ NMR (400 MHz, Chloroform-d) δ 9.34-9.31 (m, 1H), 8.83 (d, J=0.7 Hz, 1H), 8.77 (dd, J=4.8, 1.6 Hz, 1H), 8.40 (dt, J=8.0, 1.9 Hz, 1H), 8.38 (s, 1H), 7.58 (d, J=8.5 Hz, 1H), 7.53 (s, 1H), 7.47 (ddd, J=8.0, 4.8, 0.7 Hz, 1H), 7.31 (d, J=8.5 Hz, 1H), 4.14-4.03 (m, 2H), 3.98-3.75 (m, 4H), 3.73-3.66 (m, 1H), 2.67-2.54 (m, 4H), 2.42-2.30 (m, 1H), 1.93 (dq, J=12.4, 7.5 Hz, 1H), 1.80 (s, 4H). ESI MS $[M+H]^+$ for $C_{25}H_{26}N_6OS$, calcd 459.2, found 459.2.

Example 255: 6-[(Dimethylamino)methyl]-N-[2-(2-fluoro-6-methylphenyl)-[1,3]thiazolo[5,4-c]pyridin-6-yl]-5-(oxolan-3-yl)pyridin-2-amine

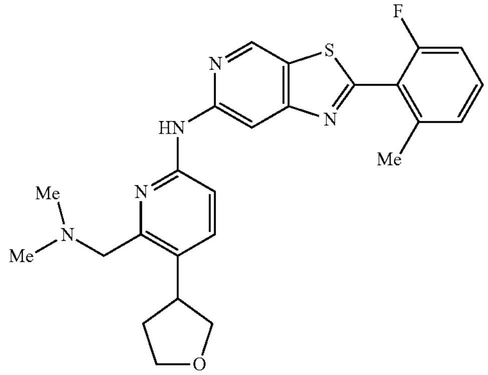 [SMILES: Cc1cccc(F)c1-c1nc2cc(Nc3ccc(C4CCOC4)c(CN(C)C)n3)ncc2s1]

The title compound was synthesized in a similar fashion to example 252 from the appropriate starting materials. $^1H$ NMR (400 MHz, DMSO-$d_6$) δ 9.13 (d, J=0.8 Hz, 1H), 8.46 (d, J=0.7 Hz, 1H), 7.78 (d, J=8.8 Hz, 1H), 7.61-7.52 (m, 2H), 7.31 (d, J=8.0 Hz, 2H), 7.28-7.21 (m, 1H), 4.56 (s, 2H), 4.05-3.94 (m, 2H), 3.82 (q, J=7.5 Hz, 1H), 3.59-3.50 (m, 2H), 2.95 (s, 6H), 2.36 (s, 3H), 2.29 (s, 1H), 1.95-1.84 (m, 1H). ESI MS $[M+H]^+$ for $C_{25}H_{26}FN_5OS$, calcd 464.2, found 464.2.

Example 256: N-[2-(5-Methyl-1H-pyrazol-1-yl)-[1,3]thiazolo[5,4-c]pyridin-6-yl]-5-(oxolan-3-yl)-6-[(pyrrolidin-1-yl)methyl]pyridin-2-amine

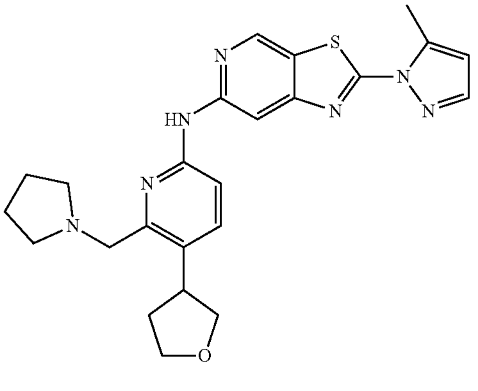 [SMILES: Cc1ccnn1-c1nc2cc(Nc3ccc(C4CCOC4)c(CN4CCCC4)n3)ncc2s1]

The title compound was synthesized in a similar fashion to example 252 from the appropriate starting materials. $^1H$ NMR (400 MHz, Methanol-$d_4$) δ 8.67 (d, J=0.8 Hz, 1H), 8.45 (d, J=0.8 Hz, 1H), 7.66 (d, J=1.6 Hz, 1H), 7.61 (d, J=8.6 Hz, 1H), 7.25 (d, J=8.6 Hz, 1H), 6.36-6.34 (m, 1H), 4.17-4.00 (m, 2H), 3.97-3.86 (m, 2H), 3.85-3.61 (m, 3H), 2.89-2.61 (m, 7H), 2.48-2.26 (m, 1H), 2.01-1.91 (m, 1H), 1.90-1.79 (m, 4H). ESI MS $[M+H]^+$ for $C_{24}H_{27}N_7OS$, calcd 462.2, found 462.2.

Example 257: N-[2-(2,6-Difluorophenyl)-[1,3]thiazolo[5,4-c]pyridin-6-yl]-6-[(dimethylamino)methyl]-5-(oxolan-3-yl)pyridin-2-amine

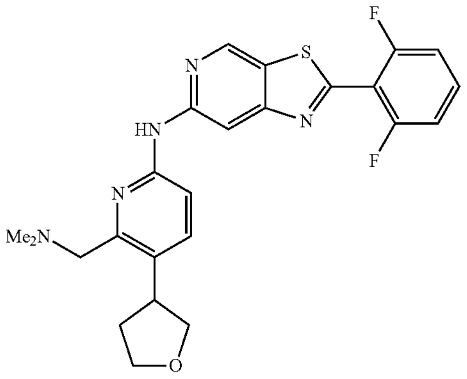 [SMILES: CN(C)Cc1nc(Nc2cc3nc(-c4c(F)cccc4F)sc3cn2)ccc1C1CCOC1]

The title compound was synthesized in a similar fashion to example 252 from the appropriate starting materials. $^1$H NMR (400 MHz, Chloroform-d) δ 8.89 (d, J=0.9 Hz, 1H), 8.30 (d, J=0.9 Hz, 1H), 7.61 (d, J=8.5 Hz, 1H), 7.50 (tt, J=8.4, 6.2 Hz, 1H), 7.43 (d, J=8.8 Hz, 2H), 7.11 (t, J=8.5 Hz, 2H), 4.15-4.04 (m, 2H), 3.97-3.83 (m, 2H), 3.72-3.66 (m, 1H), 3.64 (s, 1H), 3.58 (s, 1H), 2.43-2.31 (m, 1H), 2.29 (s, 6H), 1.93 (dq, J=12.4, 7.6 Hz, 1H). ESI MS $[M+H]^+$ for $C_{24}H_{23}F_2N_5OS$, calcd 468.2, found 468.5.

Example 258: N-[2-(3-Methylpyridin-2-yl)-[1,3]thiazolo[5,4-c]pyridin-6-yl]-5-[(3R or 3S)-oxolan-3-yl]-6-[(pyrrolidin-1-yl)methyl]pyridin-2-amine

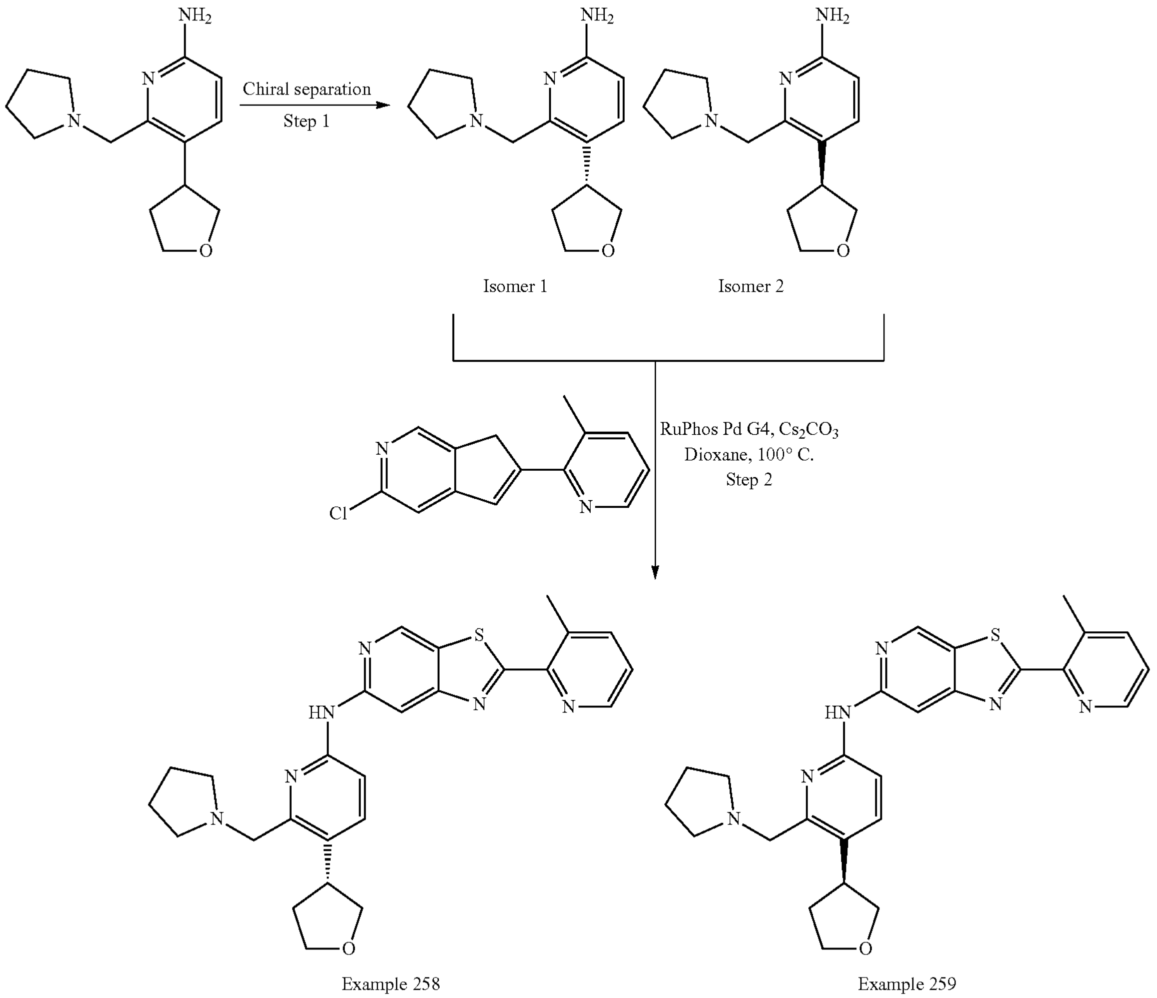

Step 1: The product from step 7 of example 252 was subjected to chiral SFC separation to obtain pure enantiomers, which were assigned isomer 1 and isomer 2 arbitrarily. Column: 2.1×25.0 cm Chiralcel OX-H from Chiral Technologies (West Chester, PA). Method: 43% Co-solvent at 84 g/min at 25° C. and 125 barr. $CO_2$ Co-solvent: Methanol/Acetonitrile (1:3) with 1% Isopropylamine.

Step 2: This step was performed in a similar fashion to step 8 of example 252 wherein the chloro azabenzothiazole intermediate was prepared in a similar manner to that described for step 1 of example 1 from the appropriate starting materials. $^1$H NMR (400 MHz, Methanol-$d_4$) δ 8.77 (d, J=0.8 Hz, 1H), 8.60 (d, J=0.8 Hz, 1H), 8.49-8.44 (m, 1H), 7.76-7.71 (m, 1H), 7.59 (d, J=8.6 Hz, 1H), 7.36 (dd, J=7.7, 4.6 Hz, 1H), 7.20 (d, J=8.6 Hz, 1H), 4.13-4.00 (m, 2H), 3.95-3.85 (m, 2H), 3.84-3.70 (m, 2H), 3.67 (dd, J=8.2, 6.6 Hz, 1H), 2.84 (s, 3H), 2.81-2.70 (m, 4H), 2.44-2.31 (m, 1H), 2.02-1.90 (m, 1H), 1.89-1.79 (m, 4H). ESI MS $[M+H]^+$ for $C_{26}H_{28}N_6OS$, calcd 473.2, found 473.3.

Example 259: N-[2-(3-Methylpyridin-2-yl)-[1,3]thiazolo[5,4-c]pyridin-6-yl]-5-[(3R or 3S)-oxolan-3-yl]-6-[(pyrrolidin-1-yl)methyl]pyridin-2-amine The title compound was synthesized in a similar fashion to example 258. $^1$H NMR (400 MHz, Methanol-$d_4$) δ 8.81 (d, J=0.8 Hz, 1H), 8.66 (d, J=0.8 Hz, 1H), 8.49-8.44 (m, 1H), 7.76-7.71 (m, 1H), 7.61 (d, J=8.6 Hz, 1H), 7.39 (dd, J=7.7, 4.6 Hz, 1H), 7.22 (d, J=8.6 Hz, 1H), 4.13-4.00 (m, 2H), 3.95-3.85 (m, 2H), 3.84-3.70 (m, 2H), 3.68 (dd, J=8.2, 6.6 Hz, 1H), 2.87 (s, 3H), 2.81-2.70 (m, 4H), 2.44-2.31 (m, 1H), 2.02-1.90 (m, 1H), 1.89-1.79 (m, 4H). ESI MS $[M+H]^+$ for $C_{26}H_{28}N_6OS$, calcd 473.2, found 473.2.

Example 260: 5-[(3R or 3S)—Oxolan-3-yl]-N-[2-(pyridin-3-yl)-[1,3]thiazolo[5,4-c]pyridin-6-yl]-6-[(pyrrolidin-1-yl)methyl]pyridin-2-amine

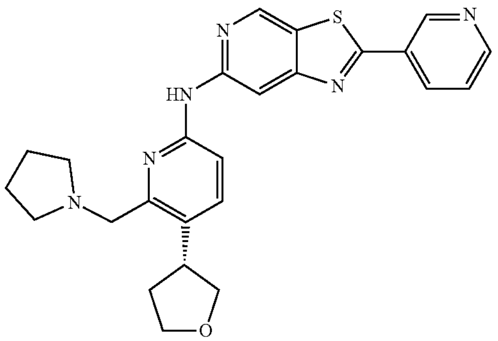 [SMILES: c1cncc(-c2nc3cc(Nc4ccc([C@H]5CCOC5)c(CN5CCCC5)n4)ncc3s2)c1]

The title compound was synthesized in a similar fashion to example 258 using isomer 1. $^1$H NMR (400 MHz, Methanol-$d_4$) δ 9.17 (s, 1H), 8.74 (s, 1H), 8.68-8.54 (m, 2H), 8.38 (d, J=7.8 Hz, 1H), 7.60-7.48 (m, 2H), 7.17 (d, J=7.8 Hz, 1H), 4.15-3.97 (m, 2H), 3.97-3.82 (m, 2H), 3.82-3.68 (m, 2H), 3.64 (t, J=7.3 Hz, 1H), 2.76-2.56 (m, 4H), 2.41-2.30 (m, 1H), 2.00-1.87 (m, 1H), 1.86-1.71 (m, 4H). ESI MS $[M+H]^+$ for $C_{25}H_{26}N_6OS$, calcd 459.2, found 459.2.

Example 261: 5-[(3R or 3S)—Oxolan-3-yl]-N-[2-(pyridin-3-yl)-[1,3]thiazolo[5,4-c]pyridin-6-yl]-6-[(pyrrolidin-1-yl)methyl]pyridin-2-amine

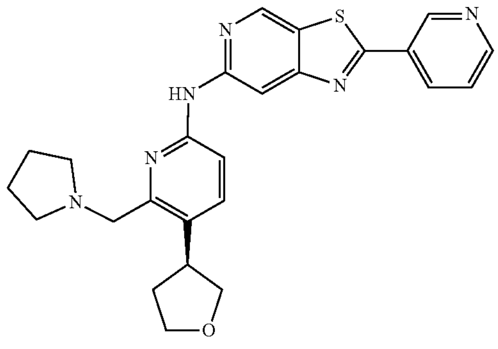 [SMILES: c1cncc(-c2nc3cc(Nc4ccc([C@@H]5CCOC5)c(CN5CCCC5)n4)ncc3s2)c1]

The title compound was synthesized in a similar fashion to example 258 using isomer 2. $^1$H NMR (400 MHz, Methanol-$d_4$) δ 9.27 (dd, J=2.3, 0.9 Hz, 1H), 8.84 (d, J=0.9 Hz, 1H), 8.74-8.69 (m, 2H), 8.50 (ddd, J=8.0, 2.3, 1.6 Hz, 1H), 7.66-7.55 (m, 2H), 7.23 (d, J=8.6 Hz, 1H), 4.15-4.02 (m, 2H), 3.98-3.87 (m, 2H), 3.87-3.75 (m, 2H), 3.68 (dd, J=8.3, 6.6 Hz, 1H), 2.80-2.66 (m, 4H), 2.45-2.33 (m, 1H), 2.02-1.91 (m, 1H), 1.90-1.78 (m, 4H). ESI MS $[M+H]^+$ for $C_{25}H_{26}N_6OS$, calcd 459.2, found 459.2.

Example 262: 5-Cyclopropyl-N-[2-(3-methylpyridin-2-yl)-[1,3]thiazolo[5,4-c]pyridin-6-yl]-6-[(pyrrolidin-1-yl)methyl]pyridin-2-amine

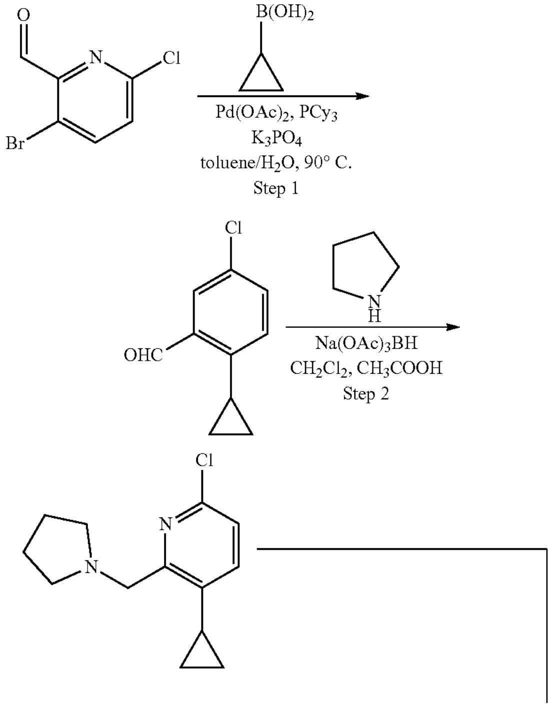

-continued

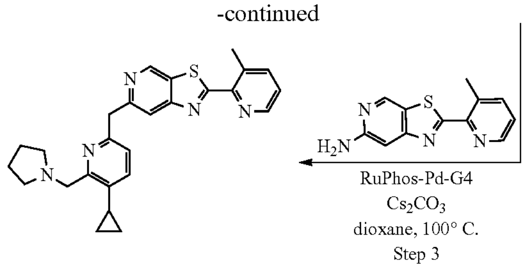

Step 1: To a solution of 3-Bromo-6-chloro-2-pyridinecarbaldehyde (1.07 g, 4.85 mmol) and Cyclopropylboronic acid (438 mg, 5.1 mmol) in Toluene (10 mL)/$H_2O$ (0.5 mL) was added $Pd(OAc)_2$ (160 mg, 0.72 mmol), Tricyclohexylphosphine (420 mg, 1.4 mmol), and $K_3PO_4$ (2.05 g, 14.5 mmol). After degassing for 25 min with $N_2$, the reaction mixture was heated to 100° C. and stirred for 3 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 20% EtOAc in hexanes) to get the desired compound (157 mg, 18%).

Step 2: This step was performed in a similar fashion to step 5 of example 1.

Step 3: This step was performed in a similar fashion to step 6 of example 1, wherein the azabenzothiazole amine intermediate was prepared in a similar fashion to that described in step 1-3 of example 1 from the appropriate starting materials. $^1H$ NMR (400 MHz, Chloroform-d) δ 8.82 (d, J=0.8 Hz, 1H), 8.55 (dd, J=4.7, 1.6 Hz, 1H), 8.36 (d, J=0.9 Hz, 1H), 7.66 (ddd, J=7.7, 1.7, 0.9 Hz, 1H), 7.37 (s, 1H), 7.30 (dd, J=7.8, 4.6 Hz, 1H), 7.26-7.23 (d, J=8.4 Hz, 1H), 7.16 (d, J=8.4 Hz, 1H), 3.96 (s, 2H), 2.91 (s, 3H), 2.74 (p, J=3.6 Hz, 4H), 2.00 (tt, J=8.4, 5.4 Hz, 1H), 1.87 (p, J=3.1 Hz, 4H), 0.96-0.90 (m, 2H), 0.61-0.55 (m, 2H). ESI MS $[M+H]^+$ for $C_{25}H_{26}N_6S$, calcd 443.2, found 443.7.

Example 263: (3R)-1-{4-[6-({6-[(1S,4S)-5-Methyl-2,5-diazabicyclo[2.2.1]heptan-2-yl]pyrazin-2-yl}amino)-[1,3]thiazolo[5,4-c]pyridin-2-yl]pyridin-2-yl}pyrrolidin-3-ol

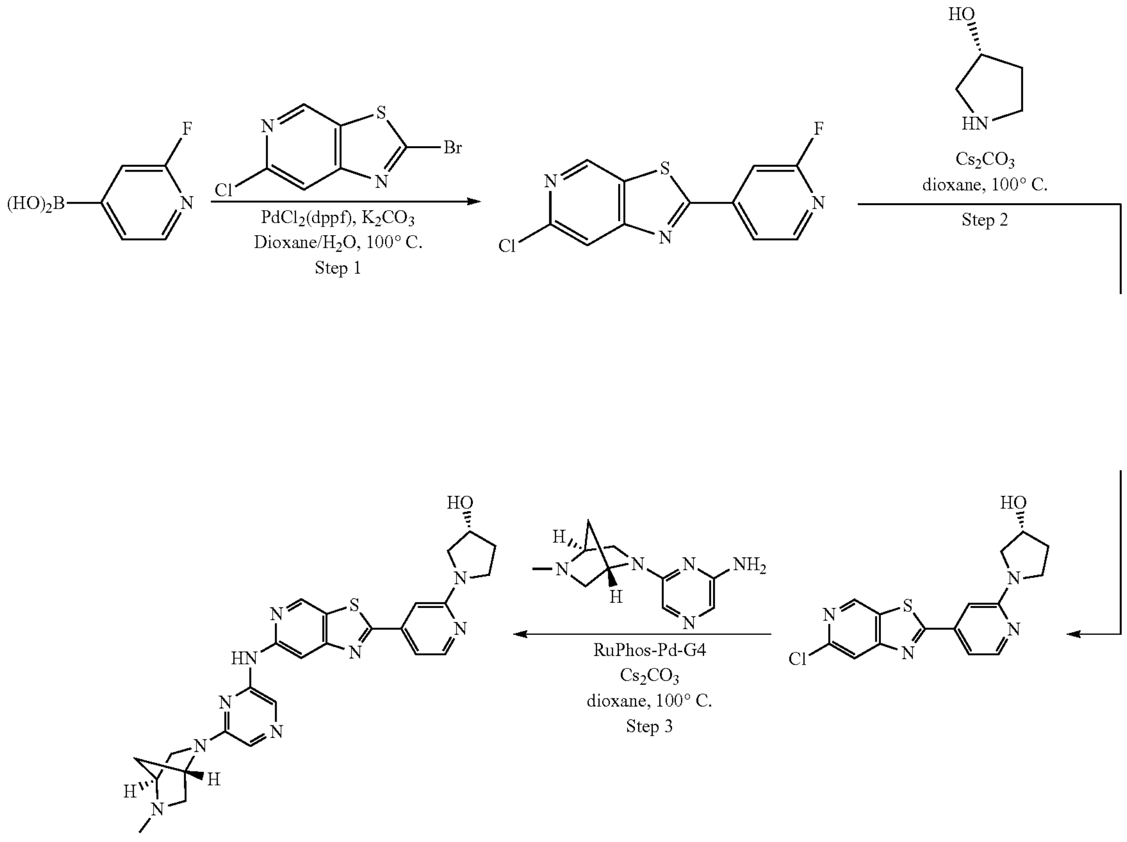

Step 1: To a solution of 2-Fluoro-4-pyridinylboronic acid (1.41 g, 10 mmol) and 2-Bromo-6-chloro[1,3]thiazolo[5,4-c]pyridine (2.49 g, 10 mmol) in Dioxane (12 mL)/$H_2O$ (3 mL) was added $PdCl_2$(dppf) (733 mg, 1.0 mmol) and $K_2CO_3$ (2.76 g, 20 mmol). After degassing for 25 min with $N_2$, the reaction mixture was heated to 100° C. and stirred for 3 h. The reaction mixture was cooled down to RT, filtered and concentrated in vacuo. The residue was purified by flash column chromatography (silica gel; gradient: 0% to 50% EtOAc in hexanes) to get the desired derivative (1.91 g, 72%) as an off-white solid.

Step 2: A heterogenous mixture of azabenzathiazole intermediate obtained from step 1 (265 mg, 1 mmol), (3R)-pyrrolidin-3-ol (105 mg, 1.2 mmol), $Cs_2CO_3$ (652 mg, 2 mmol), and dioxane (4 mL) was heated at 100° C. for 12 h. The reaction was cooled to room temperature, filtered, and concentrated in vacuo. The residue was purified by flash column chromatography (silica gel; gradient: 0% to 80% EtOAc in hexanes) to get the desired derivative (160 mg, 48%).

Step 3: This step was performed in a similar fashion to step 6 of example 1, where the amino pyrazine intermediate was prepared in a manner similar to that described in step 2 of example 120 from the appropriate starting materials. $^1$H NMR (400 MHz, Chloroform-d) δ 8.79 (d, J=0.9 Hz, 1H), 8.53 (d, J=0.9 Hz, 1H), 8.27 (dd, J=5.2, 0.8 Hz, 1H), 7.72 (s, 1H), 7.37 (d, J=8.2 Hz, 2H), 7.13 (dd, J=5.3, 1.4 Hz, 1H), 6.99 (dd, J=1.5, 0.8 Hz, 1H), 4.80-4.65 (m, 2H), 3.77-3.55 (m, 7H), 3.47 (dd, J=9.9, 2.2 Hz, 1H), 3.04 (dd, J=9.7, 2.1 Hz, 1H), 2.76-2.67 (m, 1H), 2.43 (s, 3H), 2.22-2.11 (m, 2H), 2.05 (d, J=9.7 Hz, 1H), 1.92-1.87 (m, 1H). ESI MS $[M+H]^+$ for $C_{25}H_{27}N_9OS$, calcd 502.2, found 502.8.

Example 264: (3R)-1-{4-[6-({2-[(1S,4S)-5-Methyl-2,5-diazabicyclo[2.2.1]heptan-2-yl]pyrimidin-4-yl}amino)-[1,3]thiazolo[5,4-c]pyridin-2-yl]pyridin-2-yl}pyrrolidin-3-ol

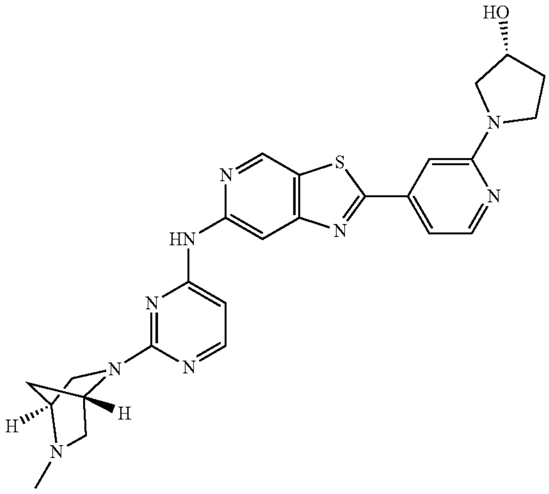 [SMILES: CN1C[C@@H]2C[C@H]1CN2c1nccc(Nc2cc3nc(-c4ccnc(N5CC[C@@H](O)C5)c4)sc3cn2)n1]

The title compound was synthesized in a similar fashion to example 263 from the appropriate starting materials. $^1$H NMR (400 MHz, Chloroform-d) δ 8.78 (d, J=0.8 Hz, 1H), 8.68 (s, 1H), 8.26 (dd, J=5.3, 0.8 Hz, 1H), 8.04 (d, J=5.5 Hz, 1H), 7.49 (s, 1H), 7.11 (d, J=1.5 Hz, 1H), 6.98 (dd, J=1.4, 0.8 Hz, 1H), 6.20 (s, 1H), 4.83 (s, 1H), 4.64 (dd, J=4.6, 2.4 Hz, 1H), 3.87 (d, J=10.5 Hz, 1H), 3.78-3.40 (m, 6H), 3.14 (m, 1H), 2.73 (d, J=9.7 Hz, 1H), 2.45 (s, 3H), 2.38-2.02 (m, 2H), 2.02 (d, J=9.6 Hz, 1H), 1.87 (d, J=9.8 Hz, 1H). ESI MS $[M+H]^+$ for $C_{25}H_{27}N_9OS$, calcd 502.2, found 502.5.

Example 265: N-(2-{2-[(3S)-3-Fluoropyrrolidin-1-yl]pyridin-4-yl}-[1,3]thiazolo[5,4-c]pyridin-6-yl)-2-[(1S,4S)-5-methyl-2,5-diazabicyclo[2.2.1]heptan-2-yl]pyrimidin-4-amine

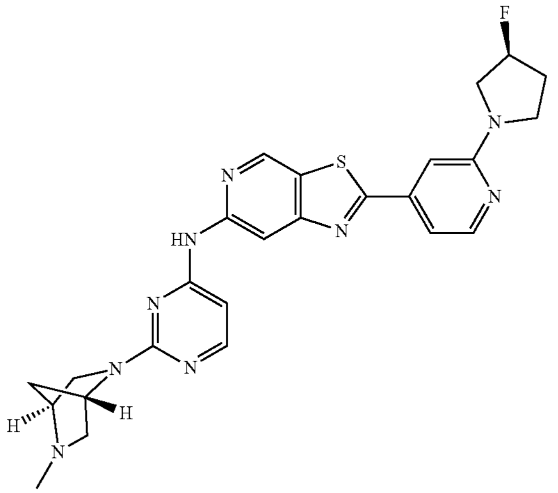 [SMILES: CN1C[C@@H]2C[C@H]1CN2c1nccc(Nc2cc3nc(-c4ccnc(N5CC[C@H](F)C5)c4)sc3cn2)n1]

The title compound was synthesized in a similar fashion to example 263 from the appropriate starting materials. $^1$H NMR (400 MHz, Chloroform-d) δ 8.84 (d, J=0.9 Hz, 1H), 8.77 ($s_{br}$, 1H), 8.31 (dd, J=5.2, 0.8 Hz, 1H), 8.06 (d, J=5.6 Hz, 1H), 7.42 (s, 1H), 7.17 (dd, J=5.2, 1.5 Hz, 1H), 7.07 (dd, J=1.5, 0.8 Hz, 1H), 6.21 ($s_{br}$, 1H), 5.42 (dt, J=52.4, 3.6 Hz, 1H), 4.84 ($s_{br}$, 1H), 4.00-3.60 (m, 6H), 3.56 (s, 1H), 3.17-2.99 (m, 1H), 2.72 (d, J=9.6 Hz, 1H), 2.45 (m, 4H), 2.35-2.07 (m, 1H), 2.01 (d, J=9.6 Hz, 1H), 1.87 (d, J=10.6 Hz, 1H). ESI MS $[M+H]^+$ for $C_{25}H_{26}FN_9S$, calcd 504.2, found 504.6.

Example 266: (3S)-1-{4-[6-({2-[(1S,4S)-5-Methyl-2,5-diazabicyclo[2.2.1]heptan-2-yl]pyrimidin-4-yl}amino)-[1,3]thiazolo[5,4-c]pyridin-2-yl]pyridin-2-yl}pyrrolidin-3-ol

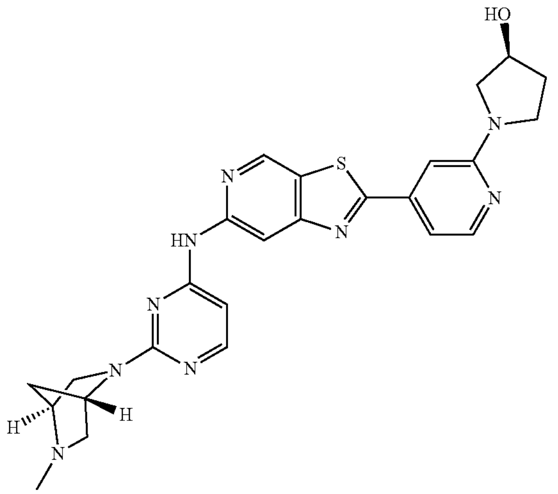 [SMILES: CN1C[C@@H]2C[C@H]1CN2c1nccc(Nc2cc3nc(-c4ccnc(N5CC[C@H](O)C5)c4)sc3cn2)n1]

The title compound was synthesized in a similar fashion to example 263 from the appropriate starting materials. $^1$H NMR (400 MHz, Chloroform-d) δ 8.77 (s, 1H), 8.65 ($s_{br}$, 1H), 8.26 (dd, J=5.2, 0.7 Hz, 1H), 8.03 (d, J=5.7 Hz, 1H), 7.51 (s, 1H), 7.10 (dd, J=5.2, 1.5 Hz, 1H), 6.97 (dd, J=1.5, 0.8 Hz, 1H), 6.19 ($s_{br}$, 1H), 4.83 (s, 1H), 4.71-4.56 (m, 1H), 3.86 (d, J=10.5 Hz, 1H), 3.76-3.32 (m, 6H), 2.97 (m, 1H), 2.74 (d, J=9.7 Hz, 1H), 2.45 (s, 3H), 2.23-2.09 (m, 2H), 2.06-1.78 (m, 2H). ESI MS $[M+H]^+$ for $C_{25}H_{27}N_9OS$, calcd 502.2, found 502.6.

Example 267: N-(2-{2-[(3R)-3-Fluoropyrrolidin-1-yl]pyridin-4-yl}-[1,3]thiazolo[5,4-c]pyridin-6-yl)-2-[(1S,4S)-5-methyl-2,5-diazabicyclo[2.2.1]heptan-2-yl]pyrimidin-4-amine

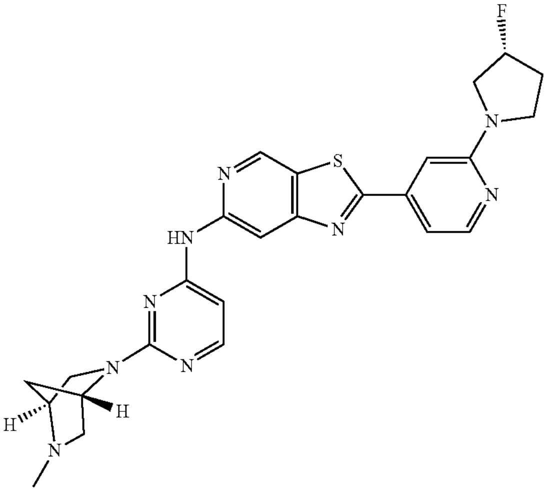 [SMILES: CN1C[C@@H]2C[C@H]1CN2c1nccc(Nc2cc3nc(-c4ccnc(N5CC[C@@H](F)C5)c4)sc3cn2)n1]

The title compound was synthesized in a similar fashion to example 263 from the appropriate starting materials. $^1$H NMR (400 MHz, Chloroform-d) δ 8.84 (d, J=0.9 Hz, 1H), 8.63 (m, J=99.9 Hz, 1H), 8.31 (dd, J=5.2, 0.8 Hz, 1H), 8.06 (d, J=5.7 Hz, 1H), 7.39 (s, 1H), 7.17 (dd, J=5.2, 1.5 Hz, 1H), 7.08 (d, J=1.1 Hz, 1H), 6.21 ($s_{br}$, 1H), 5.41 (dt, J=52.8, 3.6 Hz, 1H), 4.84 ($s_{br}$, 1H), 4.01-3.63 (m, 6H), 3.57 (s, 1H), 3.12-3.0 (m, 1H), 2.72 (d, J=9.6 Hz, 1H), 2.46 (m, 4H), 2.33-1.87 (m, 1H), 2.01 (d, J=0.5 Hz, 1H), 1.88 (d, J=9.7 Hz, 1H). ESI MS $[M+H]^+$ for $C_{25}H_{26}FN_9S$, calcd 504.2, found 504.3.

Example 268: 2-[(1S,4S)-5-Methyl-2,5-diazabicyclo[2.2.1]heptan-2-yl]-N-{2-[2-(morpholin-4-yl)pyridin-4-yl]-[1,3]thiazolo[5,4-c]pyridin-6-yl}pyrimidin-4-amine

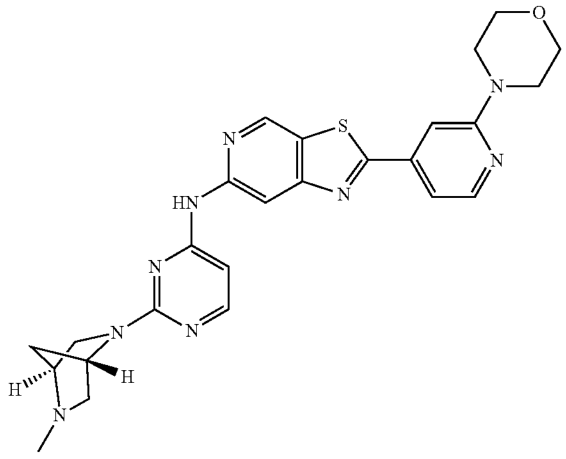 [SMILES: CN1C[C@@H]2C[C@H]1CN2c1nccc(Nc2cc3nc(-c4ccnc(N5CCOCC5)c4)sc3cn2)n1]

The title compound was synthesized in a similar fashion to example 263 from the appropriate starting materials. $^1$H NMR (400 MHz, Chloroform-d) δ 8.84 (d, J=0.9 Hz, 1H), 8.63 (m, 1H), 8.34 (dt, J=5.1, 0.8 Hz, 1H), 8.06 (d, J=5.4 Hz, 1H), 7.36 (d, J=16.6 Hz, 2H), 7.23-7.21 (m, 1H), 6.21 (s, 2H), 4.84 (s, 1H), 3.87-3.85 (m, 5H), 3.75-3.34 (m, 6H), 3.12-2.98 (m, 1H), 2.75-2.70 (m, 1H), 2.46 (s, 3H), 2.02 (d, J=8.7 Hz, 1H), 1.88-1.80 (m, 1H). ESI MS $[M+H]^+$ for $C_{25}H_{27}N_9OS$, calcd 502.2, found 502.4.

Example 269: 6-(2-Aminopropan-2-yl)-N-[2-(2,6-difluorophenyl)-[1,3]thiazolo[5,4-c]pyridin-6-yl]-5-(morpholin-4-yl)pyridin-2-amine

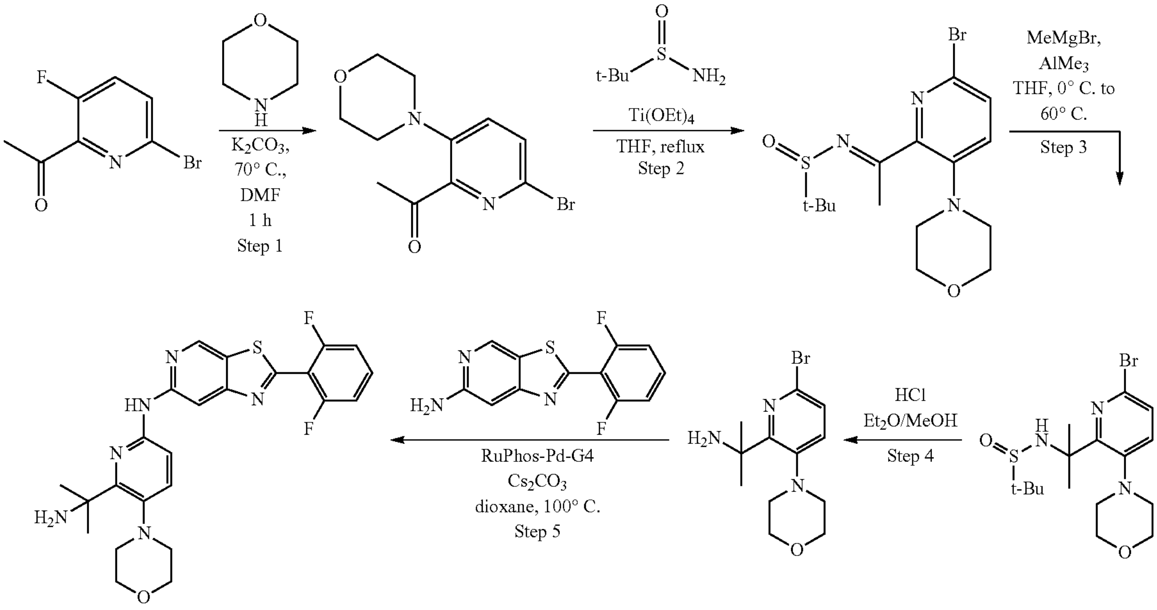

Step 1: A mixture of 1-(6-Bromo-3-fluoro-2-pyridinyl) ethanone (2.18 g, 10 mmol), Morpholine (871 mg, 10.00 mmol), $K_2CO_3$ (2.76 mg, 20 mmol), and DMF (12 mL) was heated at 70° C. for 1 h. The reaction was cooled to room temperature, diluted with water, and extracted with EtOAc. The organic extract was concentrated under reduced pressure, and the residue was purified by column chromatography (silica gel; gradient: 0% to 50% EtOAc in hexanes) to obtain the desired pyridine derivative (1.76 g, 62%).

Step 2: A vial was charged with product from step 1 (1.17 g, 4.12 mmol), 2-Methylpropane-2-sulfinamide (750 mg, 6.2 mmol) and 22 mL of THF. After addition of $Ti(OEt)_4$ (1.3 ml, 6.2 mmol) the mixture was stirred at reflux for 24 h. The reaction mixture was then quenched with a saturated solution of $NH_4Cl$ and extracted with EtOAc. The combined organic extract was washed with a saturated solution of NaCl and the solvent was evaporated. The residue was purified using column chromatography on silica gel (Hex/EtOAc—0%→50%) to afford the product (750 mg, 47%).

Step 3: A vial was charged with product from step 2 (725 mg, 1.56 mmol) and 8 mL of toluene. $AlMe_3$ (1.9 mL, 3.75 mmol) was then added at 0° C. and the mixture was stirred for 10 min before addition of MeMgBr (1.9 ml, 5.62 mmol). The reaction mixture was allowed to warm up to room temperature and stirred for 30 h before being quenched by sat. $NH_4Cl$ and extracted with EtOAc. The combined organic extract was washed with sat. sol. NaCl and the solvent was evaporated. The residue was purified using column chromatography on silica gel (Hex/EtOAc—0%→90%) to afford the product (430 mg, 69%).

Step 4: A vial was charged with product obtained from step 3 (430 mg, 1.43 mmol) and 10 mL of MeOH. HCl (1M in $Et_2O$, 4.3 ml, 3.0 mmol) was then added and the mixture was stirred for 30 min at room temp. The mixture was quenched with $NaHCO_3$ sat. and extracted with $CH_2Cl_2$. The combined organic extract was washed with sat. sol. NaCl and the solvent was evaporated. The residue was purified using column chromatography on silica gel ($CH_2Cl_2$/MeOH—0%→20%) to afford the product (393 mg, 92%).

Step 5: This step was performed in a similar fashion to step 6 of example 1 suing the azabenzothiazole amine intermediate prepared in step 3 of example 1. $^1$H NMR (400 MHz, Chloroform-d) δ 8.88 (d, J=0.9 Hz, 1H), 8.44 (d, J=0.9 Hz, 1H), 7.63 (d, J=8.6 Hz, 1H), 7.53 (s, 1H), 7.52-7.45 (m, 1H), 7.25 (d, J=8.6 Hz, 1H), 7.10 (t, J=8.4 Hz, 2H), 3.94 (d, J=11.7 Hz, 2H), 3.82-3.72 (m, 2H), 3.09-2.96 (m, 2H), 2.75 (d, J=11.6 Hz, 2H), 2.19 (s, 2H), 1.63 (s, 6H). ESI MS $[M+H]^+$ for $C_{24}H_{24}F_2N_6OS$, calcd 483.2, found 483.6.

Example 270: 6-(2-Aminopropan-2-yl)-N-[2-(5-methyl-1H-pyrazol-1-yl)-[1,3]thiazolo[5,4-c]pyridin-6-yl]-5-(morpholin-4-yl)pyridin-2-amine

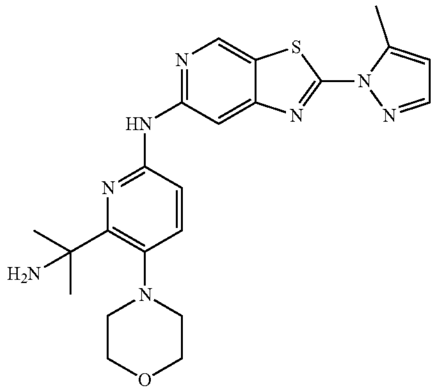 [SMILES: Cc1ccnn1-c1nc2cc(Nc3ccc(N4CCOCC4)c(C(C)(C)N)n3)ncc2s1]

The title compound was synthesized in a similar fashion to example 269 from the appropriate starting materials. $^1$H NMR (400 MHz, Chloroform-d) δ 8.66 (d, J=0.8 Hz, 1H), 8.33 (d, J=0.8 Hz, 1H), 7.63 (d, J=1.6 Hz, 1H), 7.60 (s, 1H), 7.42 (s, 1H), 7.12 (d, J=8.6 Hz, 1H), 6.24 (d, J=0.7 Hz, 1H), 3.92 (dd, J=11.3, 2.7 Hz, 2H), 3.80-3.61 (m, 2H), 3.08-2.91 (m, 2H), 2.81 (s, 3H), 2.74 (d, J=11.6 Hz, 2H), 2.35 (s, 2H), 1.62 (s, 6H). ESI MS $[M+H]^+$ for $C_{22}H_{26}N_8OS$, calcd 451.2, found 451.6.

Example 271: 6-(2-Aminopropan-2-yl)-N-[2-(2,6-difluorophenyl)-[1,3]thiazolo[5,4-c]pyridin-6-yl]-5-(3,3-difluoropyrrolidin-1-yl)pyridin-2-amine

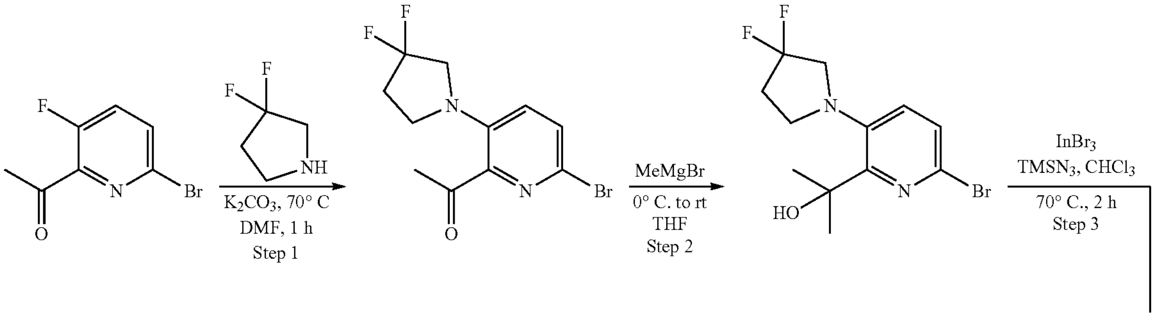

-continued

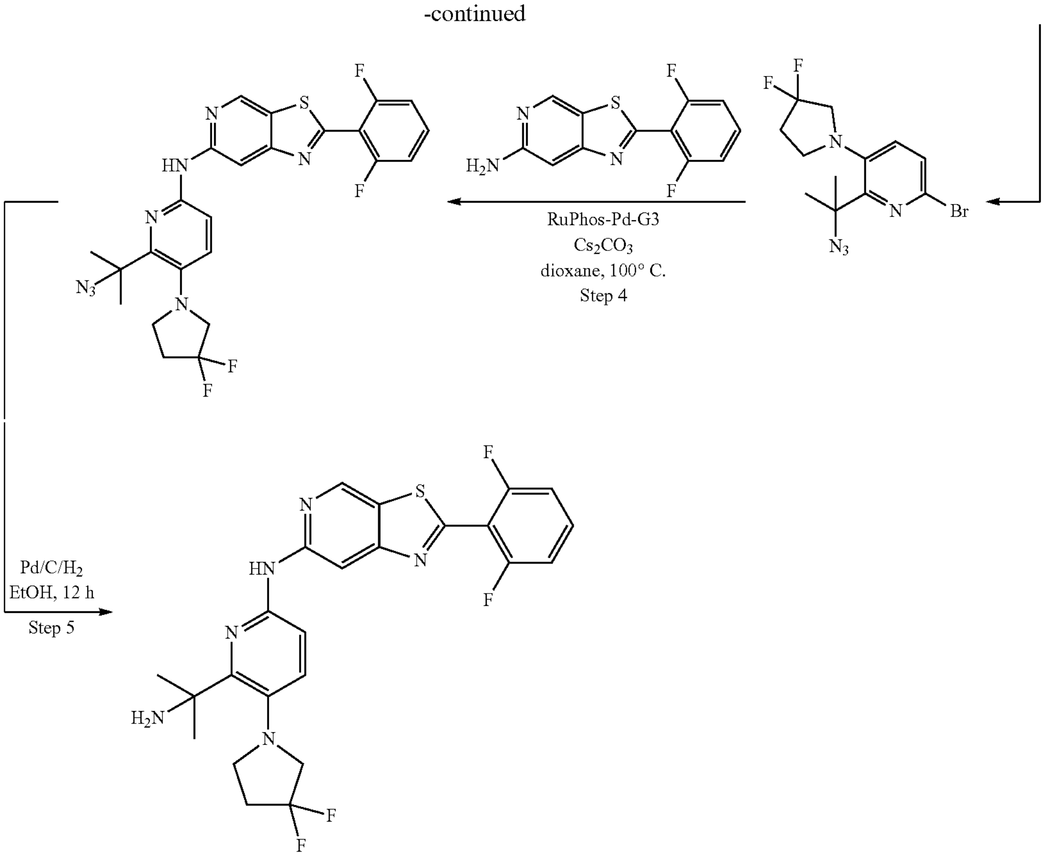

Step 1: This step was performed in a similar fashion to step 1 of example 269 using the appropriate starting materials.

Step 2: A vial was charged with product from step 1 (1.52 g, 5 mmol) and 30 mL of THF. MeMgBr (5 ml, 15 mmol) was then added at 0° C. and the mixture was allowed to warm up to room temperature and stirred for 12 h. The reaction was then quenched with a saturated solution of $NH_4Cl$ and extracted with EtOAc. The combined organic extract was washed with brine and the organic solvent was evaporated under reduced pressure. The residue was purified using column chromatography on silica gel (Hex/EtOAc—0%→60%) to afford the product (1.45 g, 92%).

Step 3: A vial was charged with product from step 2. (750 mg, 2.3 mmol), $InBr_3$ (325 mg, 0.9 mmol) and 15 mL of $CHCl_3$. After addition of $TMSN_3$ (1.2 ml, 9.2 mmol) the mixture was stirred at 70° C. for 2 h. The reaction mixture was then quenched with sat. $NH_4Cl$ and extracted with $CH_2Cl_2$. The combined organic extract was washed with sat. sol. NaCl and the solvent was evaporated under reduced pressure. The residue was purified using column chromatography on silica gel (Hex/EtOAc—0%→20%) to afford the product (350 mg, 44%).

Step 4: This step was performed in a similar fashion to step 6 example 1 using the product of step 3, and the product of step 3, example 1.

Step 5: In a Parr hydrogenator, a solution of product from step 4 (75 mg, 0.14 mmol) in ethanol (8 mL) was added Pd/C (20%). After stirring at 20 psi $H_2$ atmosphere for 12 h, the reaction mixture was filtered through Celite®. The filtrate was concentrated under reduced pressure and the residue was purified using column chromatography on silica gel (gradient: 0% to 30% MeOH in $CH_2Cl_2$) to afford the product (48 mg, 68%). $^1H$ NMR (400 MHz, Chloroform-d) δ 8.89 (d, J=0.9 Hz, 1H), 8.39 (d, J=0.9 Hz, 1H), 7.64 (d, J=8.6 Hz, 1H), 7.54-7.42 (m, 2H), 7.29 (d, J=8.6 Hz, 1H), 7.11 (t, J=8.4 Hz, 2H), 3.38 (t, J=13.1 Hz, 2H), 3.22 (t, J=6.9 Hz, 2H), 2.44 (tt, J=14.3, 6.9 Hz, 2H), 2.11 ($s_{br}$, 2H), 1.62 (s, 6H). ESI MS $[M+H]^+$ for $C_{24}H_{22}F_4N_6S$, calcd 503.2, found 503.6.

Example 272: 6-(2-Aminopropan-2-yl)-5-(3,3-difluoropyrrolidin-1-yl)-N-[2-(3-methylpyridin-2-yl)-[1,3]thiazolo[5,4-c]pyridin-6-yl]pyridin-2-amine

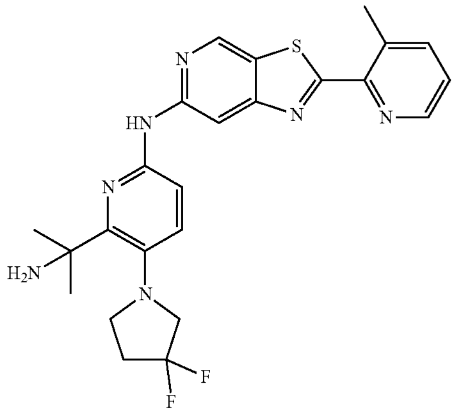 [SMILES: Cc1cccnc1-c1nc2cc(Nc3ccc(N4CCC(F)(F)C4)c(C(C)(C)N)n3)ncc2s1]

The title compound was synthesized in a similar fashion to example 271 using the appropriate starting materials. $^1H$ NMR (400 MHz, DMSO-$d_6$) δ 9.94 (s, 1H), 9.03 (s, 1H), 8.62-8.57 (m, 1H), 8.56 (s, 1H), 7.99 (d, J=8.8 Hz, 1H), 7.92-7.85 (m, 1H), 7.52 (dd, J=7.8, 4.6 Hz, 1H), 7.44 (d, J=8.8 Hz, 1H), 3.43-3.23 (m, 6H), 3.16 (t, J=6.9 Hz, 2H), 2.86 (s, 3H), 1.69 (s, 6H). ESI MS $[M+H]^+$ for $C_{24}H_{25}F_2N_7S$, calcd 482.2, found 482.7.

Example 273: 6-(2-Aminopropan-2-yl)-5-(3,3-difluoropyrrolidin-1-yl)-N-[2-(5-methyl-1H-pyrazol-1-yl)-[1,3]thiazolo[5,4-c]pyridin-6-yl]pyridin-2-amine

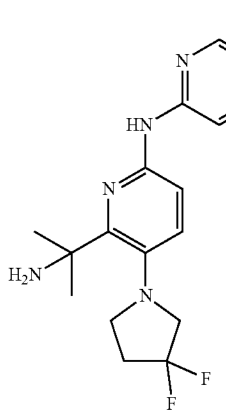

The title compound was synthesized in a similar fashion to example 271 using the appropriate starting materials. $^1H$ NMR (400 MHz, Chloroform-d) δ 8.67 (d, J=0.8 Hz, 1H), 8.29 (s, 1H), 7.64 (s, 1H), 7.62 (d, J=8.7 Hz, 1H), 7.33 (s, 1H), 7.17 (d, J=8.6 Hz, 1H), 6.26 (d, J=1.4 Hz, 1H), 3.36 (t, J=13.1 Hz, 2H), 3.20 (t, J=6.9 Hz, 2H), 2.82 (s, 3H), 2.43 (tt, J=13.9, 6.7 Hz, 2H), 2.18 ($s_{br}$, 2H)1.62 (s, 6H). ESI MS $[M+H]^+$ for $C_{22}H_{24}F_2N_8S$, calcd 471.2, found 471.5.

Example 274: 6-(1-Aminocyclopropyl)-N-[2-(2,6-difluorophenyl)-[1,3]thiazolo[5,4-c]pyridin-6-yl]-5-(3,3-difluoropyrrolidin-1-yl)pyridin-2-amine

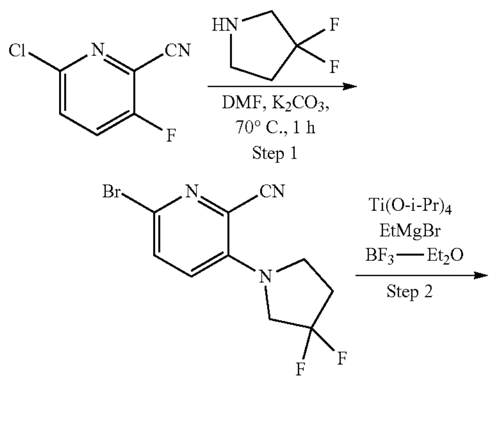

-continued

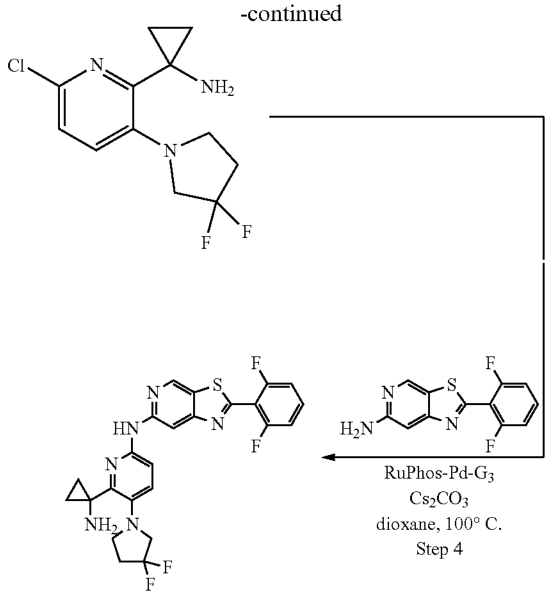

Step 1: This step was performed in a similar fashion to step 1 of example 269 using the appropriate starting materials.

Step 2: A vial was charged with product from step 1 (1 g, 3.4 mmol), and dry THF under Argon atmosphere. To this mixture was added slowly Titanium isopropoxide (1.9 g, 4.08 mmol) at ambient temperature. The reaction mixture was stirred for 15 min at RT. Ethyl Magnesium Bromide (1 M solution) in THF (8.5 ml, 8.5 mmol) was then added via syringe slowly at room temperature. Then the reaction mixture was stirred for 1 hr and boron trifluoride diethyl etherate (1.05 ml, 8.5 mmol) was added slowly at 0° C. After the completion of addition process, the reaction mixture was allowed to attain ambient temperature and the stirring continued overnight. Finally, 20 ml of water was added, and the reaction mixture was filtered through Celite®. The filtrate was basified with 10% NaOH solution (pH=9) then extracted with $CH_2Cl_2$ and washed with brine solution. The product (170 mg, 22%) was purified by silica gel column chromatography (gradient: 0% to 30% MeOH in $CH_2Cl_2$).

Step 3: This step was performed in a similar fashion to step 6 of example 1 using the product of step 2, and the product obtained from step 3, example 1. $^1H$ NMR (400 MHz, Chloroform-d) δ 8.86 (d, J=0.9 Hz, 1H), 8.19 (d, J=1.0 Hz, 1H), 7.48 (tt, J=8.4, 6.1 Hz, 1H), 7.36 (d, J=8.7 Hz, 1H), 7.32 (d, J=8.6 Hz, 1H), 7.29 (s, 1H), 7.09 (t, J=8.5 Hz, 2H), 3.56 (t, J=13.0 Hz, 2H), 3.39 (t, J=6.9 Hz, 2H), 2.47 (tt, J=14.2, 6.9 Hz, 2H), 1.58 (s, 2H), 1.37-1.31 (m, 2H), 1.10-1.03 (m, 2H). ESI MS $[M+H]^+$ for $C_{24}H_{20}F_4N_6S$, calcd 501.2, found 501.9.

Example 275: N-[2-(2,6-Difluorophenyl)-[1,3]thiazolo[5,4-c]pyridin-6-yl]-6-[(dimethylamino)methyl]-4-(morpholin-4-yl)pyridin-2-amine

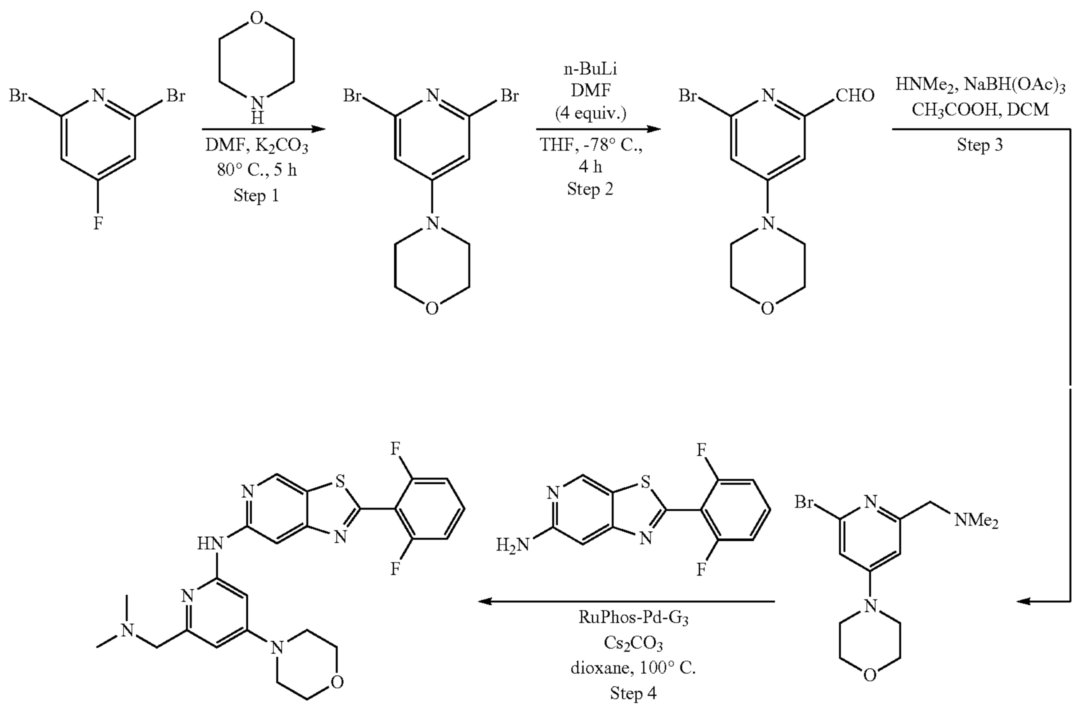

Step 1: This step was performed in a similar fashion to step 1 example 269 using the appropriate starting materials.

Step 2: A vial was charged with product from step 1 (1.04 g, 3.25 mmol) and 20 mL of THF. n-BuLi (1.36 ml, 3.42 mmol) was then added at −78° C. and the reaction mixture stirred for 2 h. After 1 h, DMF (1.05 ml, 13 mmol) was then added at −78° C. and stirred it for additional 4 h. The reaction mixture was quenched by sat. $NH_4Cl$ and extracted with EtOAc. The combined organic extract was washed with sat. sol. NaCl and the solvent was evaporated under reduced pressure. The residue was purified using column chromatography on silica gel (Hex/EtOAc—0%→50%) to afford the product (450 mg, 52%).

Step 3: A vial was charged with product from step 2 (450 mg, 1.6 mmol) in $CH_2Cl_2$ (6 mL) and dimethylamine solution (2M in THF) (1.17 mL, 2.4 mmol) was added. After stirring for 30 min at room temperature, acetic acid (0.1 mL) and sodium triacetoxyborohydride (680 mg, 3.20 mmol) were added and stirred for 2 h at RT. The reaction mixture was then diluted with sodium bicarbonate solution (30 mL) and extracted with $CH_2Cl_2$ (3×30 mL). The combined organic extracts were washed with brine (30 mL), dried over $Na_2SO_4$, filtered, and concentrated under reduced pressure. The residue was purified by column chromatography (2% methanol gradient in $CH_2Cl_2$) to afford the desired product (280 mg, 59%).

Step 4: This step was performed in a similar fashion to step 6 of example 1 using the product of step 3, and the product obtained from step 3, example 1. $^1H$ NMR (400 MHz, Chloroform-d) δ 8.88 (d, J=0.9 Hz, 1H), 8.24 (d, J=0.9 Hz, 1H), 7.55 (s, 1H), 7.48 (tt, J=8.4, 6.1 Hz, 1H), 7.09 (t, J=8.4 Hz, 2H), 6.88 (d, J=2.1 Hz, 1H), 6.50 (d, J=2.1 Hz, 1H), 3.87-3.79 (m, 4H), 3.45 (s, 2H), 3.35-3.27 (m, 4H), 2.31 (s, 6H). ESI MS $[M+H]^+$ for $C_{24}H_{24}F_2N_6OS$, calcd 483.2, found 483.8.

Example 276: N-[2-(2,6-Difluorophenyl)-[1,3]thiazolo[5,4-c]pyridin-6-yl]-6-[(dimethylamino)methyl]-3-(morpholin-4-yl)pyridin-2-amine

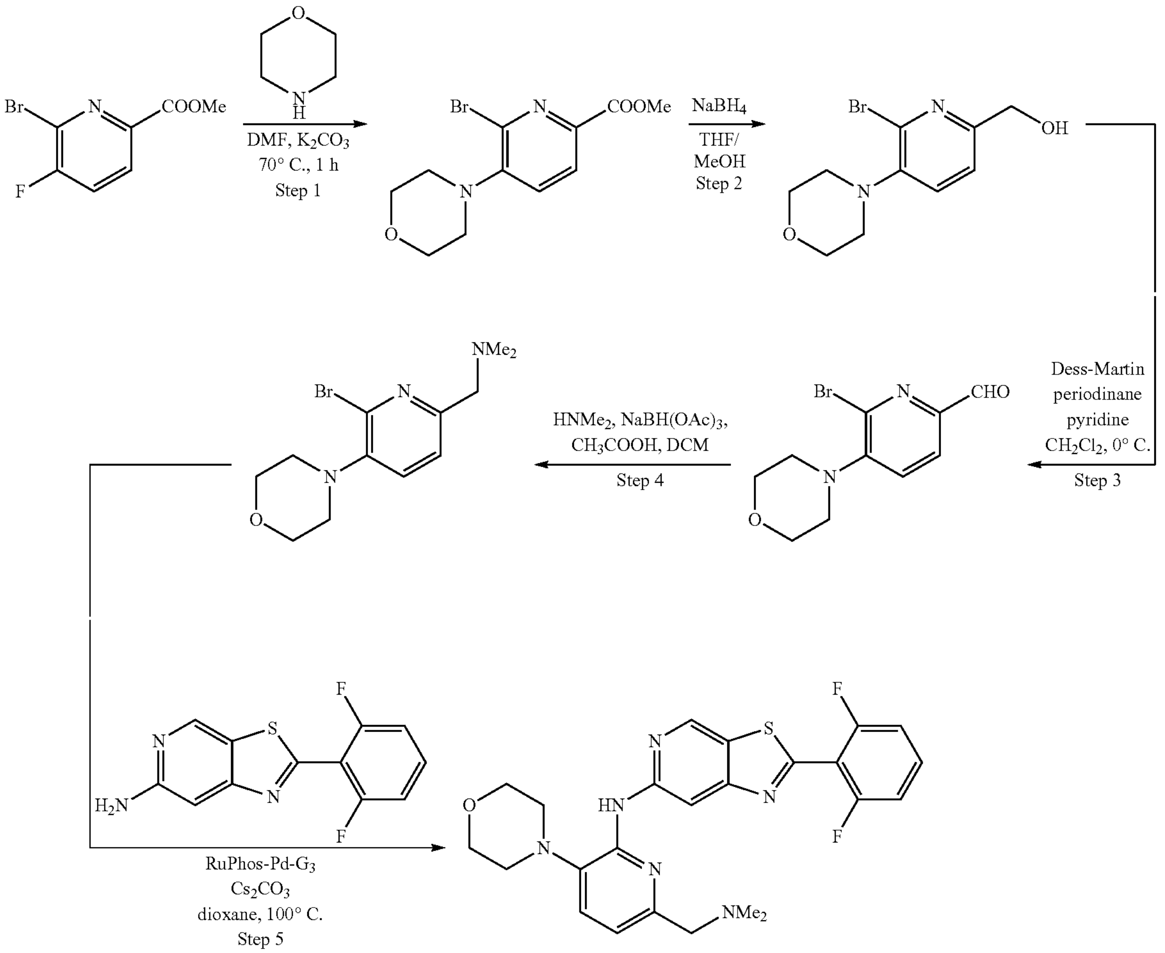

Step 1: This step was performed in a similar fashion to step 1 of example 269 using the appropriate starting materials.

Step 2: To a vial charged with product from step 1 (1.5 g, 5 mmol) in Ethanol (20 mL) was added $NaBH_4$ (370 mg, 5 mmol) portion wise at 0° C. Then the reaction was stirred at room temperature for 3 h. The solvent was removed under reduced pressure and the residue was diluted with water and extracted with EtOAc. The combined organic layers were dried over $Na_2SO_4$ and concentrated in vacuo. The residue was purified by flash column chromatography (silica gel; gradient: 0% to 100% EtOAc in hexanes) to get alcohol intermediate (1.25 g, 92%) as the white solid.

Step 3: To a vial charged with product from step 2 (1.25 g, 4.5 mmol) and pyridine (0.44 mL, 5.4 mmol) in $CH_2Cl_2$ (20 mL) was added Dess-Martin periodinane (2.9 g, 4.95 mmol) portion wise at 0° C. The reaction mixture was then stirred at room temperature for 2 h. The solvent was removed and diluted with water and extracted with EtOAc. The combined organic layers were dried over $Na_2SO_4$ and concentrated in vacuo. The residue was purified by flash column chromatography (silica gel; gradient: 0% to 100% EtOAc in hexanes) to get alcohol intermediate (1.25 g, 92%) as the white solid.

Step 4: This step was performed in a similar fashion to step 5 of example 1 using the product of step 3.

Step 5: This step was performed in a similar fashion to step 6 of example 1 using the product of step 4, and the product obtained from step 3, example 1. $^1H$ NMR (400 MHz, Chloroform-d) δ 9.32 (d, J=0.9 Hz, 1H), 8.86 (d, J=0.9 Hz, 1H), 8.49 (s, 1H), 7.47 (tt, J=8.4, 6.2 Hz, 1H), 7.36 (d, J=7.9 Hz, 1H), 7.08 (t, J=8.3 Hz, 2H), 6.96 (d, J=7.9 Hz, 1H), 3.96-3.89 (m, 4H), 3.61 (s, 2H), 2.97-2.87 (m, 4H), 2.33 (s, 6H). ESI MS $[M+H]^+$ for $C_{24}H_{24}F_2N_6OS$, calcd 483.2, found 483.6.

Example 277: N-[2-(2,6-Difluorophenyl)-[1,3]thiazolo[5,4-c]pyridin-6-yl]-6-[1-(dimethylamino)ethyl]-5-(morpholin-4-yl)pyridin-2-amine

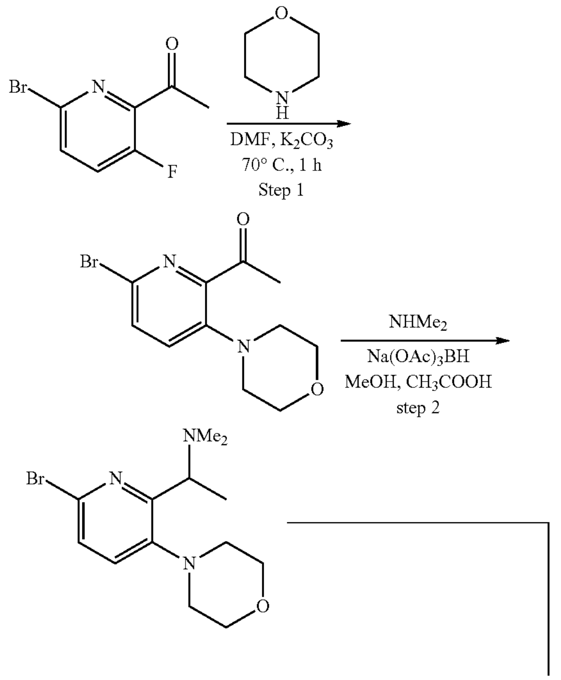

-continued

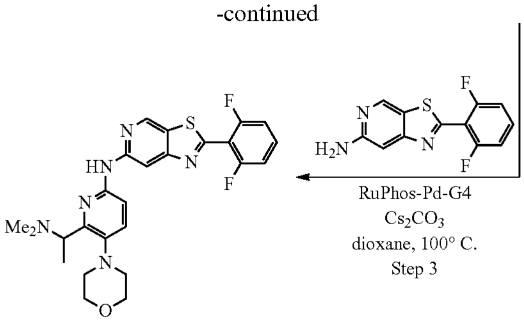

Step 1: This step was performed in a similar fashion to step 1 of example 269 using the appropriate starting materials.

Step 2: This step was performed in a similar fashion to step 5 of example 1 using the product of step 1.

Step 3: This step was performed in a similar fashion to step 6 of example 1 using the product of step 2, and the product obtained from step 3, example 1. $^{1}$H NMR (400 MHz, Chloroform-d) δ 8.87 (s, 1H), 8.01 (s, 1H), 7.58 (dd, J=8.7, 0.7 Hz, 1H), 7.54-7.42 (m, 3H), 7.15-7.06 (t, J 8.5 Hz, 2H), 4.29-4.18 (m, 1H), 3.88-3.76 (m, 4H), 2.96-2.78 (m, 4H), 2.27 (d, J=0.7 Hz, 6H), 1.39 (dd, J=6.7, 0.7 Hz, 3H). ESI MS $[M+H]^+$ for $C_{25}H_{26}F_2N_6OS$, calcd 497.2, found 497.7.

Example 278: N-[2-(2,6-Difluorophenyl)-[1,3]thiazolo[5,4-c]pyridin-6-yl]-6-[1-(ethylamino)ethyl]-5-(morpholin-4-yl)pyridin-2-amine

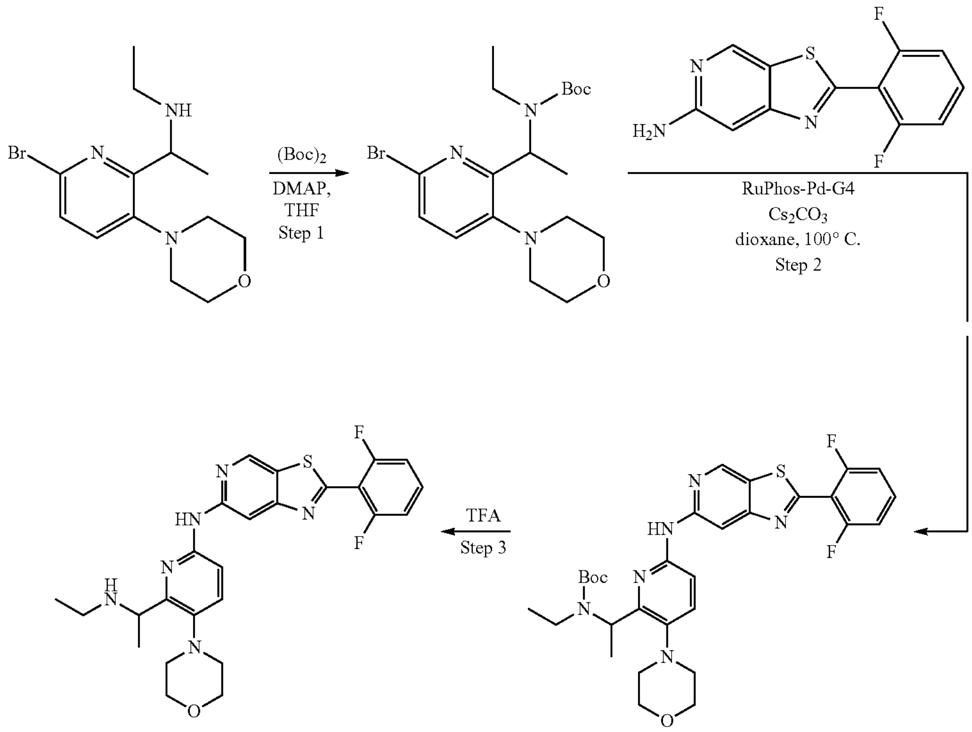

Step 1: A vial was charged with pyridine derivative obtained in a similar fashion to steps 1 and 2 of example 277 from the appropriate starting materials (314 mg, 1 mmol) and 4-Dimethylaminopyridine (50 mg, 0.4 mmol) in THE (5 mL). To this mixture was added di-tert-Butyl dicarbonate (327 mg, 1.5 mmol) at 0° C. portion wise. The reaction mixture was then stirred at room temperature for 2 h. The solvent was evaporated and the crude material was diluted with water and extracted with EtOAc. The combined organic layers were dried over $Na_2SO_4$ and concentrated in vacuo. The residue was purified by flash column chromatography (silica gel; gradient: 0% to 50% EtOAc in hexanes) to get the desired intermediate (340 mg, 82%) as the white solid.

Step 2: This step was performed in a similar fashion to step 6 of example 1 using the product of step 1, and the product obtained from step 3, example 1.

Step 3: This step was performed in a similar fashion to step 3 of example 65 using the product of step 2. $^1H$ NMR (400 MHz, Chloroform-d) δ 8.87 (d, J=0.9 Hz, 1H), 8.23 (d, J=0.9 Hz, 1H), 7.85 (s, 1H), 7.53-7.44 (m, 2H), 7.38 (d, J=8.6 Hz, 1H), 7.09 (t, J=8.4 Hz, 2H), 4.51 (q, J=6.7 Hz, 1H), 3.84 (td, J=4.2, 2.8 Hz, 4H), 2.84 (t, J=4.5 Hz, 4H), 2.47 (qq, J=11.2, 7.1 Hz, 2H), 1.40 (d, J=6.7 Hz, 3H), 1.09 (t, J=7.1 Hz, 3H). ESI MS $[M+H]^+$ for $C_{25}H_{26}F_2N_6OS$, calcd 497.2, found 497.8.

Example 279: 5-(3,3-Difluoropyrrolidin-1-yl)-6-[(ethylamino)methyl]-N-[2-(2-fluoro-6-methylphenyl)-[1,3]thiazolo[5,4-c]pyridin-6-yl]pyridin-2-amine

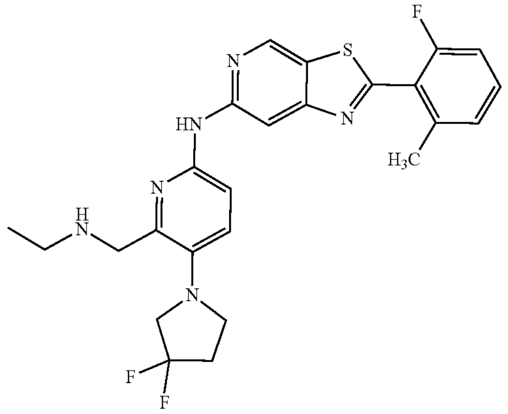 [SMILES: CCNCc1nc(Nc2cc3nc(-c4c(C)cccc4F)sc3cn2)ccc1N1CCC(F)(F)C1]

The title compound was prepared in a similar fashion to example 278, wherein the bromo pyridine derivative used in step 2 was obtained in a similar fashion to that described for step 1 of example 278 from the appropriate starting materials, and the azabenzothiazole amine derivative used in step 2 was prepared in a similar fashion to that described in step 3, example 1 using the appropriate starting materials. $^1H$ NMR (400 MHz, Chloroform-d) δ 8.83 (s, 1H), 8.14 (s, 1H), 7.71 (s, 1H), 7.46-7.30 (m, 3H), 7.17-7.10 (m, 1H), 7.05 (t, J=9.1 Hz, 1H), 4.00 (s, 2H), 3.36 (t, J=13.1 Hz, 2H), 3.20 (t, J=6.8 Hz, 2H), 2.84 (q, J=7.1 Hz, 2H), 2.49-2.30 (m, 6H), 1.25 (t, J=7.2 Hz, 3H). ESI MS $[M+H]^+$ for $C_{25}H_{25}F_3N_6S$, calcd 499.2, found 499.2.

Example 280: 5-(3,3-Difluoropyrrolidin-1-yl)-N-[2-(3-methylpyridin-2-yl)-[1,3]thiazolo[5,4-c]pyridin-6-yl]-6-(pyrrolidin-1-yl)pyridin-2-amine

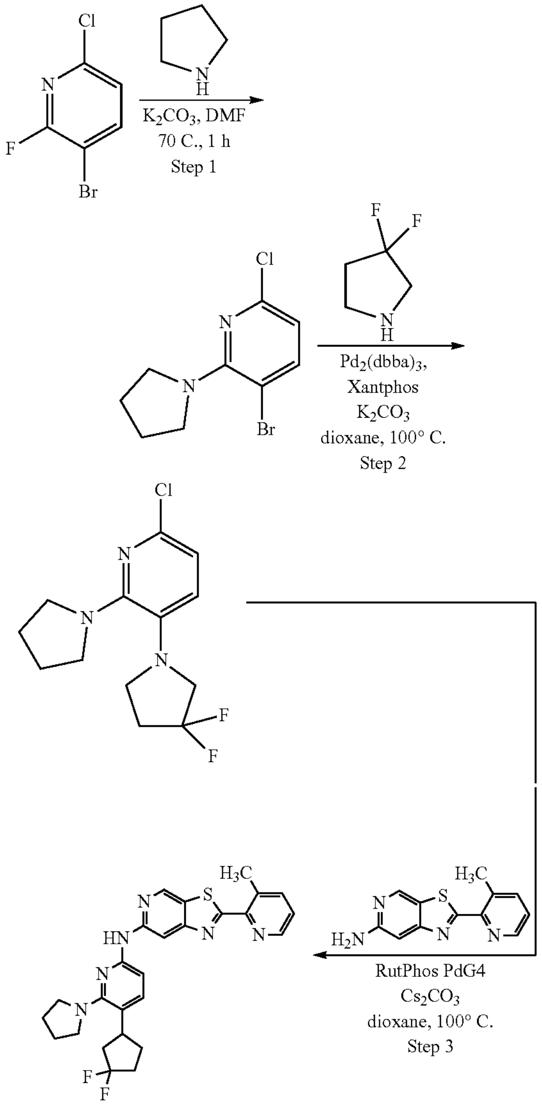

Step 1: This step was performed in a similar fashion to step 1 of example 269 using the appropriate starting materials.

Step 2: To a solution of pyridine intermediate obtained from step 1 (522 mg, 2 mmol) and 3,3-Difluoropyrrolidine (268 mg, 2.5 mmol) in Dioxane (8 mL) was added $Pd_2(dbba)_3$ (180 mg, 0.2 mmol), Xantphos (230 mg, 0.4 mmol) and $Cs_2CO_3$ (1.95 g, 6 mmol). After degassing for 25 min under $N_2$ atmosphere, the reaction mixture was heated to 100° C. and stirred for 12 h. The reaction mixture was then filtered through Celite® and concentrated under reduced pressure. The resulting residue a was purified by flash column chromatography (silica gel; gradient: 0% to 40% EtOAc in hexanes) to get desired compound (115 mg, 22%).

Step 3: This step was performed in a similar fashion to step 6 of example 1, wherein the azabenzothiazole amine derivative was obtained in a fashion similar to that described for step 3, example 1 using the appropriate starting materials. $^1$H NMR (400 MHz, Chloroform-d) δ 8.80 (d, J=0.9 Hz, 1H), 8.62 (d, J=0.9 Hz, 1H), 8.59-8.50 (m, 1H), 7.77-7.62 (m, 1H), 7.30 (dd, J=7.7, 4.6 Hz, 1H), 7.17 (d, J=8.2 Hz, 1H), 6.42 (d, J=8.2 Hz, 1H), 3.60 (td, J=6.7, 5.5, 3.1 Hz, 4H), 3.28 (t, J=13.1 Hz, 2H), 3.15 (t, J=6.9 Hz, 2H), 2.90 (s, 3H), 2.38 (tt, J=14.5, 6.9 Hz, 2H), 1.97-1.89 (m, 4H). ESI MS $[M+H]^+$ for $C_{25}H_{25}F_2N_7S$, calcd 494.2, found 494.7.

Example 281: 5-(3,3-Difluoropyrrolidin-1-yl)-6-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

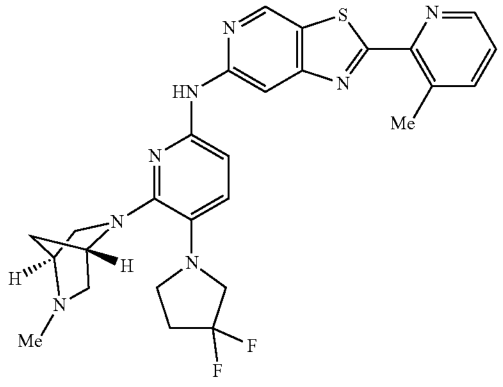 [SMILES: Cc1cccnc1-c1nc2cc(Nc3ccc(N4CCC(F)(F)C4)c(N4C[C@@H]5C[C@H]4CN5C)n3)ncc2s1]

The title compound was synthesized in a similar fashion to example 280 using the appropriate starting materials. $^1$H NMR (400 MHz, Chloroform-d) δ 8.81 (d, J=0.8 Hz, 1H), 8.64 (d, J=0.8 Hz, 1H), 8.56 (dd, J=4.6, 1.5 Hz, 1H), 7.68 (ddd, J=7.7, 1.6, 0.8 Hz, 1H), 7.31 (dd, J=7.7, 4.6 Hz, 1H), 7.26 (d, J=2.9 Hz, 1H), 7.17 (d, J=8.2 Hz, 1H), 6.39 (d, J=8.2 Hz, 1H), 4.84 (s, 1H), 3.63 (dd, J=10.2, 1.5 Hz, 1H), 3.53-3.45 (m, 2H), 3.39 (td, J=12.7, 11.0 Hz, 1H), 3.30-3.19 (m, 1H), 3.19-2.99 (m, 4H), 2.91 (s, 3H), 2.46-2.32 (m, 5H), 1.99 (dq, J=9.6, 1.5 Hz, 1H), 1.89-1.82 (m, 1H). ESI MS $[M+H]^+$ for $C_{27}H_{28}F_2N_8S$, calcd 535.2, found 535.1.

Example 282: N-[6-({6-[(Dimethylamino)methyl]-5-(morpholin-4-yl)pyridin-2-yl}amino)-[1,3]thiazolo[5,4-c]pyridin-2-yl]-2,6-difluorobenzamide

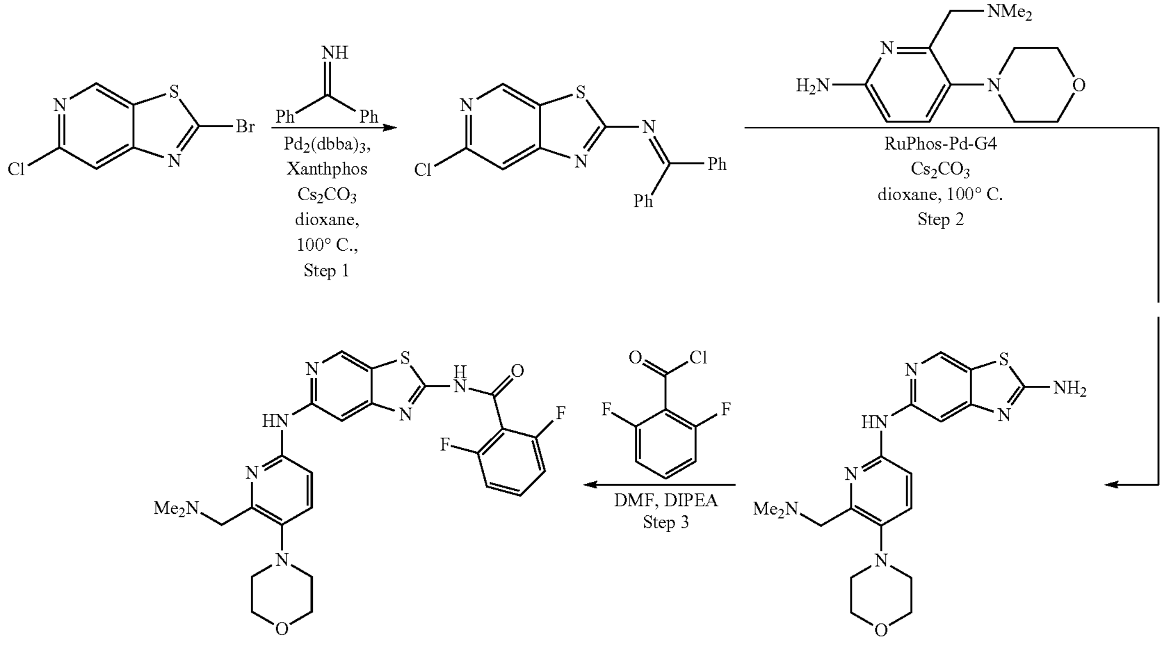

Step 1: This step was performed in a similar fashion to step 2 of example 1 using the appropriate starting materials.

Step 2: To a solution of iminopyridine intermediate obtained from step 1 (250 mg, 0.72 mmol) and pyridine-morpholine derivative obtained in a similar fashion to steps 1 and 2 of example 63 using the appropriate starting materials (170 mg, 0.72 mmol) in Dioxane (3 mL) was added RuPhos PdG4 (12 mg, 0.15 mmol) and $Cs_2CO_3$ (700 mg 2.16 mmol). After degassing for 25 min under $N_2$ atmosphere, the reaction mixture was heated to 100° C. and stirred for 5 h. The reaction mixture was next filtered through Celite® and concentrated under reduced pressure. The resulting residue was purified by flash column chromatography (silica gel; gradient: 0% to 30% MeOH in $CH_2Cl_2$) to get desired the compound (60 mg, 22%).

Step 3: To a stirred solution of product obtained from step 2 (60 mg, 0.15 mmol) and DIPEA (30 mg, 0.22 mmol) in DMF (3 mL) was added 2,6-Difluorobenzoyl chloride (27 mg, 0.15 mmol). The reaction mixture was stirred at room temperature for 6 h. The reaction mixture was diluted with water and ethyl acetate for separation into phases. The aqueous layer was extracted with ethyl acetate. The combined organic layer was filtered through a phase separator and then, the resulting filtrate concentrated, and the residue purified by silica gel column chromatography (silica gel; gradient: 0% to 40% MeOH in $CH_2Cl_2$) to get the desired compound (7 mg, 9%). $^1$H NMR (400 MHz, Methanol-$d_4$) δ 8.40 ($s_{br}$, 1H), 8.00-7.37 (m, 2H), 7.39-7.25 (m, 1H), 7.25-6.95 (m, 1H), 6.87 (t, J=8.1 Hz, 2H), 3.88-3.69 (m, 4H), 3.55 ($s_{br}$, 2H), 3.01-2.79 (m, 4H), 2.12 (s, 6H). ESI MS $[M+H]^+$ for $C_{25}H_{25}F_2N_7O_2S$, calcd 526.2, found 526.1.

Example 283: N-[2-(3-Methylpyridin-2-yl)-[1,3]thiazolo[5,4-c]pyridin-6-yl]-5-(oxan-4-yl)-6-(pyrrolidin-3-yl)pyridin-2-amine Step 1: To a solution of pyridine intermediate from step 1 of example 251 (580 mg, 2.76 mmol) and tert-Butyl 3-(4,4,5,5-tetramethyl-1,3,2-dioxaborolan-2-yl)-2,5-dihydro-1H-pyrrole-1-carboxylate (895 mg, 3.03 mmol) in Dioxane (12 mL)/$H_2O$ (3 mL) was added $PdCl_2$(dppf) (202 mg, 0.27 mmol) and $K_2CO_3$ (760 g, 5.52 mmol). After degassing for 25 min with $N_2$, the reaction mixture was heated to 100° C. and stirred for 4 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 50% EtOAc in hexanes) to get imine intermediate (760 mg, 81%) as the white solid.

Step 2: In a Parr hydrogenator, a solution of intermediate from step 1 (700 mg, 2.05 mmol) in methanol (100 mL) was added $PtO_2$ (20%) and 2 equivalents of HCl in methanol. After stirring at 50 psi $H_2$ atmosphere for 48 h, the reaction mixture was filtered through Celite®. The filtrate was concentrated, and the residue was purified by flash column chromatography (silica gel; gradient: 0% to 70% EtOAc in hexanes) to get the desired compound (340 mg, 42%) as a white solid.

Step 3: This step was performed in a similar fashion to step 6 of example 1, wherein the azabenzothiazole intermediate was obtained in a similar fashion to that described in step 1 of example 1 using the appropriate starting materials.

Step 4: This step was performed in a similar fashion to step 3 of example 65. $^1$H NMR (400 MHz, Methanol-$d_4$) δ 8.84 (d, J=0.9 Hz, 1H), 8.51 (ddd, J=4.6, 1.7, 0.7 Hz, 1H), 8.48 (s, 1H), 7.81 (ddd, J=7.8, 1.6, 0.8 Hz, 1H), 7.53 (d, J=8.6 Hz, 1H), 7.42 (dd, J=7.8, 4.6 Hz, 1H), 7.06 (d, J=8.6 Hz, 1H), 4.04 (dd, J=11.5, 4.3 Hz, 2H), 3.89-3.78 (m, 1H), 3.60 (td, J=11.8, 2.1 Hz, 2H), 3.47-3.38 (m, 1H), 3.24-3.20 (m, 2H), 3.17-3.05 (m, 2H), 2.90 (s, 3H), 2.37-2.27 (m, 1H), 2.26-2.14 (m,

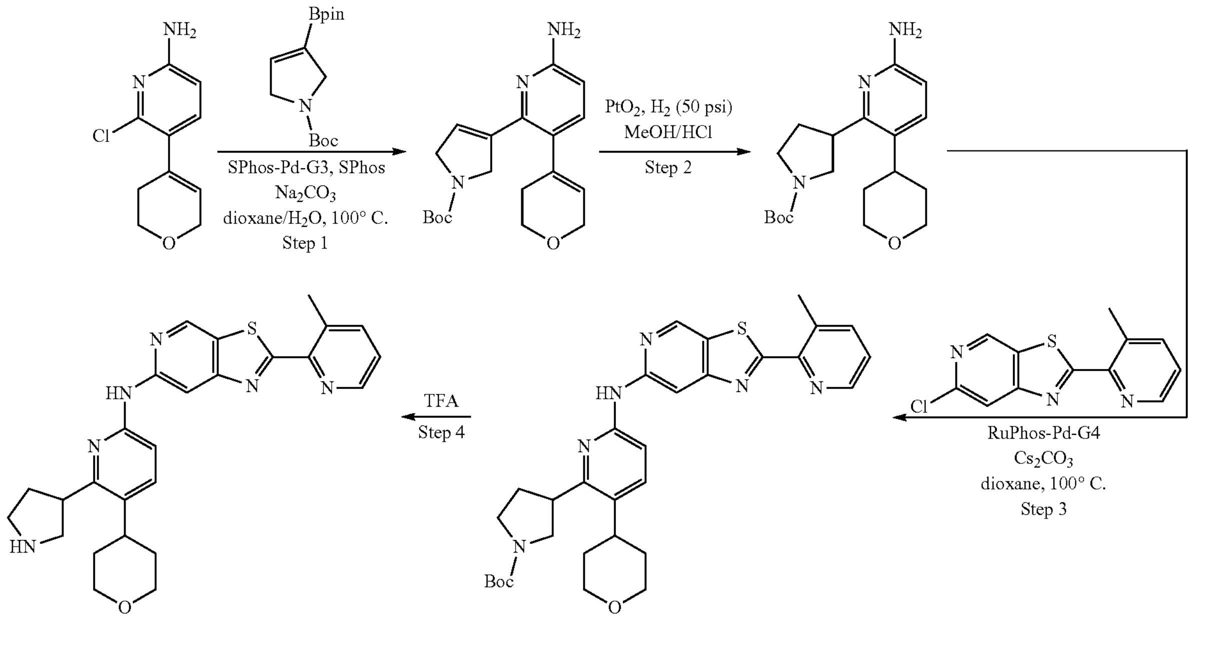

1H), 1.89-1.74 (m, 2H), 1.67 (d, J=10.0 Hz, 2H). ESI MS [M+H]+ for $C_{26}H_{28}N_6OS$, calcd 473.2, found 473.7.

Example 284: 3-methyl-6-[(1S,4S)-5-methyl-2,5-diazabicyclo[2.2.1]heptan-2-yl]-N-[2-(3-methylpyridin-2-yl)-[1,3]thiazolo[5,4-c]pyridin-6-yl]pyridin-2-amine

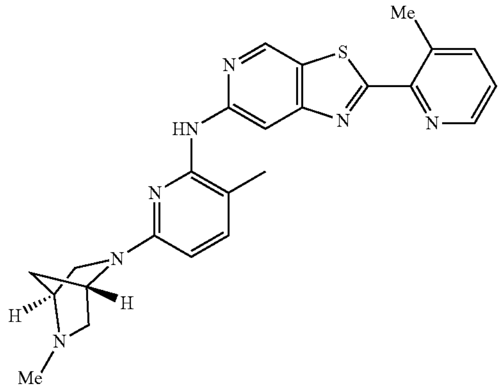 [SMILES: Cc1ccc(N2C[C@@H]3C[C@H]2CN3C)nc1Nc1cc2nc(-c3ncccc3C)sc2cn1]

The title compound was synthesized example 118 from the appropriate starting materials. $^1$H NMR (400 MHz, Chloroform-d) δ 9.10 (d, J=0.9 Hz, 1H), 8.80 (d, J=0.9 Hz, 1H), 8.55 (ddd, J=4.7, 1.7, 0.7 Hz, 1H), 7.67 (ddd, J=7.8, 1.6, 0.8 Hz, 1H), 7.30 (dd, J=7.7, 4.6 Hz, 1H), 7.21 (dd, J=8.0, 0.8 Hz, 1H), 7.08 (s, 1H), 5.88 (d, J=8.0 Hz, 1H), 4.70 (s, 1H), 3.61 (dd, J=9.6, 1.4 Hz, 1H), 3.54 (s, 1H), 3.43 (dd, J=9.5, 2.2 Hz, 1H), 3.14 (dd, J=9.5, 2.1 Hz, 1H), 2.89 (s, 3H), 2.78 (dd, J=9.5, 1.3 Hz, 1H), 2.42 (s, 3H), 2.20 (s, 2H), 2.04-1.97 (m, 1H), 1.96-1.86 (m, 1H). ESI MS [M+H]+ for $C_{24}H_{25}N_7S$, calcd 444.5, found 444.4.

Example 285: N-{3-[6-({6-[(1S,4S)-5-methyl-2,5-diazabicyclo[2.2.1]heptan-2-yl]pyrazin-2-yl}amino)-[1,3]thiazolo[5,4-c]pyridin-2-yl]phenyl}methanesulfonamide

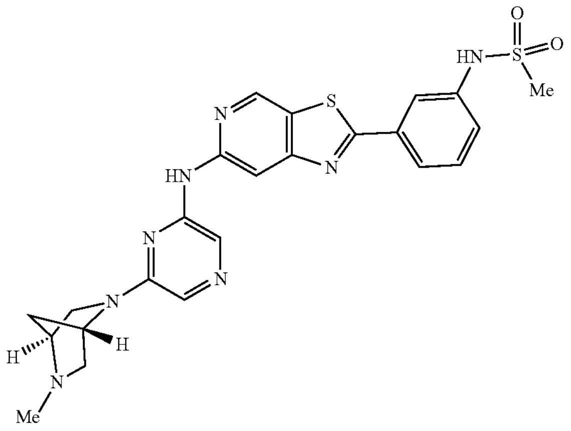 [SMILES: CN1C[C@@H]2C[C@H]1CN2c1cncc(Nc2cc3nc(-c4cccc(NS(C)(=O)=O)c4)sc3cn2)n1]

The title compound was synthesized in a similar fashion to example 89 from the appropriate starting materials. $^1$H NMR (400 MHz, DMSO-$d_6$) δ 9.82 (s, 1H), 9.02 (d, J=0.8 Hz, 1H), 8.50 (d, J=0.9 Hz, 1H), 8.19 (s, 1H), 7.98-793 (m, 2H), 7.81 (m, 1H), 7.54 (t, J=7.9 Hz, 1H), 7.43 (m, 1H), 4.61 (s, 1H), 3.52 (s, 2H), 3.39 (m, 1H), 3.05 (s, 3H), 2.86 (d, J=8.8 Hz, 1H), 2.55 (d, J=9.5 Hz, 1H), 2.29 (s, 3H), 1.92 (d, J=9.3 Hz, 1H), 1.80 (d, J=9.5 Hz, 1H). ESI MS [M+H]+ for $C_{23}H_{24}N_8O_2S_2$, calcd 509.2, found 509.1.

Example 286: N-{3-[6-({2-[(1S,4S)-5-methyl-2,5-diazabicyclo[2.2.1]heptan-2-yl]pyrimidin-4-yl}amino)-[1,3]thiazolo[5,4-c]pyridin-2-yl]phenyl}methanesulfonamide

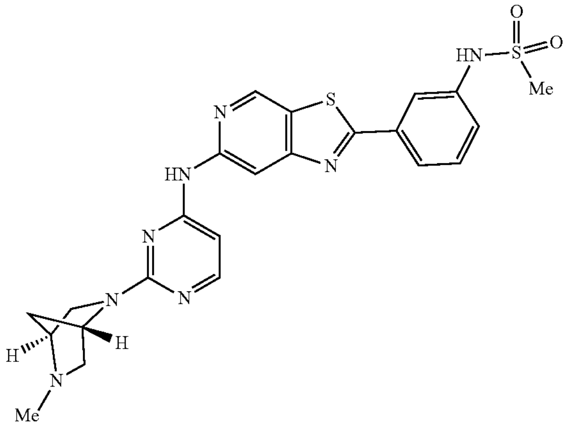 [SMILES: CN1C[C@@H]2C[C@H]1CN2c1nccc(Nc2cc3nc(-c4cccc(NS(C)(=O)=O)c4)sc3cn2)n1]

The title compound was synthesized in a similar fashion to example 89 from the appropriate starting materials. $^1$H NMR (400 MHz, DMSO-$d_6$) $^1$H NMR (400 MHz, DMSO-$d_6$) δ 10.12 (s, 1H), 10.06 (s, 1H), 9.07 (d, J=0.9 Hz, 1H), 8.62 (s, 1H), 8.07-7.99 (m, 1H), 7.96 (t, J=2.0 Hz, 1H), 7.87-7.80 (m, 1H), 7.55 (t, J=8.0 Hz, 1H), 7.48-7.42 (m, 1H), 6.67 (s, 1H), 4.85 (s, 1H), 4.25 (bs, 1H), 3.82 (bs, 1H), 3.65 (bs, 1H), 3.18 (m, 1H), 3.06 (s, 3H), 2.77 (s, 3H), 2.23 (m, 1H), 2.11 (d, J=10.9 Hz, 1H). ESI MS [M+H]+ for $C_{23}H_{24}N_8O_2S_2$, calcd 509.2, found 509.1.

Example 287: N-{3-[6-({6-[(1S,4S)-2,5-diazabicyclo[2.2.1]heptan-2-yl]pyridin-2-yl}amino)-[1,3]thiazolo[5,4-c]pyridin-2-yl]phenyl}methanesulfonamide

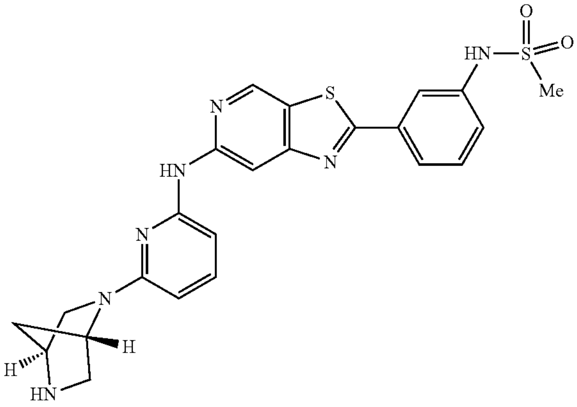 [SMILES: CS(=O)(=O)Nc1cccc(-c2nc3cc(Nc4cccc(N5C[C@@H]6C[C@H]5CN6)n4)ncc3s2)c1]

The title compound was synthesized in a similar fashion to example 78 from the appropriate starting materials. $^1$H NMR (400 MHz, DMSO-$d_6$) δ 9.51 (s, 1H), 8.95 (d, J=0.8 Hz, 1H), 8.67 (d, J=0.9 Hz, 1H), 7.94 (t, J=1.9 Hz, 1H), 7.79 (m, 1H), 7.52 (t, J=7.9 Hz, 1H), 7.43 (m, 1H), 7.35 (t, J=8.0 Hz, 1H), 6.56 (d, J=7.8 Hz, 1H), 5.96 (d, J=8.0 Hz, 1H), 4.64 (s, 1H), 3.88 (s, 1H), 3.56 (d, J=8.7 Hz, 2H), 3.03 (s, 3H), 3.02-2.96 (m, 2H), 1.90 (d, J=9.4 Hz, 1H), 1.75 (d, J=9.5 Hz, 1H). ESI MS $[M+H]^+$ for $C_{23}H_{23}N_7O_2S_2$, calcd 494.1, found 494.1.

Example 288: N,N-dimethyl-3-[6-({6-[(1S,4S)-5-methyl-2,5-diazabicyclo[2.2.1]heptan-2-yl]pyrazin-2-yl}amino)-[1,3]thiazolo[5,4-c]pyridin-2-yl]benzene-1-sulfonamide

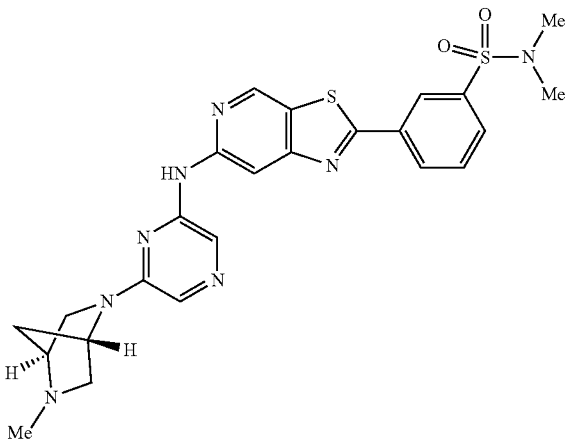 [SMILES: CN1C[C@@H]2C[C@H]1CN2c1cncc(Nc2cc3nc(-c4cccc(S(=O)(=O)N(C)C)c4)sc3cn2)n1]

The title compound was synthesized in a similar fashion to example 89 from the appropriate starting materials. $^1$H NMR (400 MHz, DMSO-$d_6$) δ 9.84 (s, 1H), 9.06 (d, J=0.9 Hz, 1H), 8.50 (d, J=0.9 Hz, 1H), 8.41 (m, 1H), 8.33 (t, J=1.8 Hz, 1H), 7.99 (s, 1H), 7.89-7.84 (m, 1H), 7.44 (s, 1H), 4.61 (s, 1H), 3.51 (s, 2H), 3.38 (dd, J=9.7, 2.1 Hz, 1H), 2.84 (dd, J=9.5, 2.0 Hz, 1H), 2.66 (s, 6H), 2.55 (d, J=9.7 Hz, 1H), 2.29 (s, 3H), 1.91 (d, J=9.5 Hz, 1H), 1.79 (d, J=9.5 Hz, 1H). ESI MS $[M+H]^+$ for $C_{24}H_{26}N_8O_2S_2$, calcd 523.2, found 523.2.

Example 289: N,N-dimethyl-3-[6-({2-[(1S,4S)-5-methyl-2,5-diazabicyclo[2.2.1]heptan-2-yl]pyrimidin-4-yl}amino)-[1,3]thiazolo[5,4-c]pyridin-2-yl]benzene-1-sulfonamide

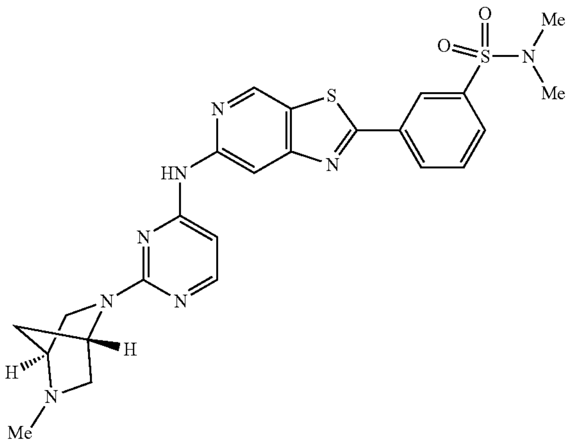 [SMILES: CN1C[C@@H]2C[C@H]1CN2c1nccc(Nc2cc3nc(-c4cccc(S(=O)(=O)N(C)C)c4)sc3cn2)n1]

The title compound was synthesized in a similar fashion to example 89 from the appropriate starting materials. $^1$H NMR (400 MHz, DMSO-$d_6$) δ 10.02 (s, 1H), 9.09 (d, J=0.9 Hz, 1H), 8.76 (s, 1H), 8.42 (m, 1H), 8.34 (t, J=1.8 Hz, 1H), 8.00-7.95 (m, 2H), 7.89-7.84 (m, 1H), 6.56 (s, 1H), 4.68 (s, 1H), 3.65 (s, 2H), 2.84 (bs, 2H), 2.67 (s, 6H), 2.57 (bs, 1H), 2.31 (s, 3H), 1.88 (d, J=9.4 Hz, 1H), 1.77 (d, J=9.5 Hz, 1H). ESI MS $[M+H]^+$ for $C_{24}H_{26}N_8O_2S_2$, calcd 523.2, found 523.2.

Example 290: N-methyl-3-[6-({6-[(1S,4S)-5-methyl-2,5-diazabicyclo[2.2.1]heptan-2-yl]pyrazin-2-yl}amino)-[1,3]thiazolo[5,4-c]pyridin-2-yl]benzene-1-sulfonamide

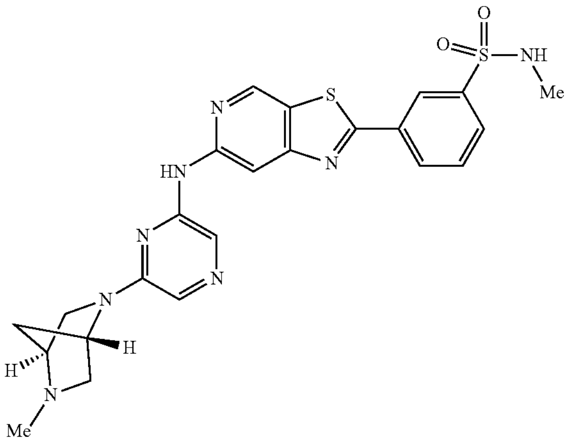 [SMILES: CNS(=O)(=O)c1cccc(-c2nc3cc(Nc4cncc(N5C[C@@H]6C[C@H]5CN6C)n4)ncc3s2)c1]

The title compound was synthesized in a similar fashion to example 89 from the appropriate starting materials. $^1$H NMR (400 MHz, DMSO-$d_6$) δ 9.85 (s, 1H), 9.07 (d, J=0.9 Hz, 1H), 8.51 (s, 1H), 8.45 (t, J=1.7 Hz, 1H), 8.36 (m, 1H), 7.98 (d, J=1.8 Hz, 1H), 7.82 (t, J=7.8 Hz, 1H), 7.43 (m, 1H), 4.61 (s, 1H), 3.52 (s, 2H), 3.39 (m, 1H), 2.85 (dd, J=9.4, 2.0 Hz, 1H), 2.57-2.53 (m, 1H), 2.44 (d, J=4.9 Hz, 3H), 2.29 (s, 3H), 1.94-1.89 (m, 1H), 1.80 (d, J=9.3 Hz, 1H). ESI MS $[M+H]^+$ for $C_{23}H_{24}N_8O_2S_2$, calcd 509.2, found 509.2.

Example 291: N-methyl-3-[6-({2-[(1S,4S)-5-methyl-2,5-diazabicyclo[2.2.1]heptan-2-yl]pyrimidin-4-yl}amino)-[1,3]thiazolo[5,4-c]pyridin-2-yl]benzene-1-sulfonamide

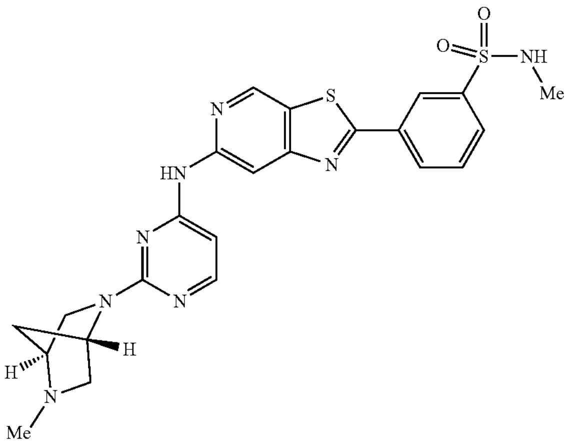 [SMILES: CNS(=O)(=O)c1cccc(-c2nc3cc(Nc4ccnc(N5C[C@@H]6C[C@H]5CN6C)n4)ncc3s2)c1]

The title compound was synthesized in a similar fashion to example 89 from the appropriate starting materials. $^1$H NMR (400 MHz, DMSO-$d_6$) δ 9.18 (s, 1H), 8.47 (s, 1H), 8.37 (d, J=7.9 Hz, 1H), 8.06 (d, J=6.1 Hz, 1H), 8.01 (m, 1H), 7.85 (t, J=7.8 Hz, 1H), 7.74 (q, J=5.0 Hz, 1H), 6.72 (s, 1H), 4.94 (s, 1H), 4.45 (s, 1H), 3.96-3.76 (m, 3H), 3.19 (m, 1H), 2.89 (d, J=4.8 Hz, 3H), 2.45 (d, J=5.0 Hz, 3H), 2.40 (m, 1H), 2.19 (d, J=11.5 Hz, 1H). ESI MS $[M+H]^+$ for $C_{23}H_{24}N_8O_2S_2$, calcd 509.2, found 509.2.

Example 292: 3-[6-({6-[(1S,4S)-2,5-diazabicyclo[2.2.1]heptan-2-yl]pyridin-2-yl}amino)-[1,3]thiazolo[5,4-c]pyridin-2-yl]-N-methylbenzene-1-sulfonamide

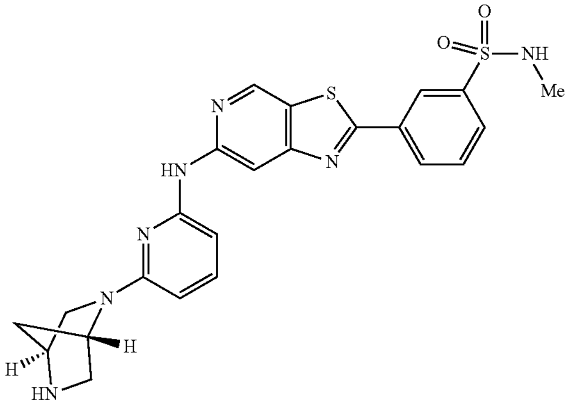 [SMILES: CNS(=O)(=O)c1cccc(-c2nc3cc(Nc4cccc(N5C[C@@H]6C[C@H]5CN6)n4)ncc3s2)c1]

The title compound was synthesized in a similar fashion to example 78 from the appropriate starting materials. $^1$H NMR (400 MHz, DMSO-$d_6$) δ 9.53 (s, 1H), 9.01 (d, J=0.8 Hz, 1H), 8.69 (d, J=0.9 Hz, 1H), 8.44 (t, J=1.8 Hz, 1H), 8.35 (ddd, J=7.8, 1.9, 1.1 Hz, 1H), 7.98 (ddd, J=7.8, 1.9, 1.1 Hz, 1H), 7.82 (t, J=7.8 Hz, 1H), 7.72 (s, 1H), 7.35 (t, J=7.9 Hz, 1H), 6.56 (d, J=7.8 Hz, 1H), 5.97 (d, J=8.1 Hz, 1H), 4.63 (s, 1H), 3.84 (s, 1H), 3.58-3.53 (m, 1H), 3.02-2.92 (m, 2H), 2.44 (s, 3H), 1.88 (d, J=9.6 Hz, 1H), 1.73 (d, J=9.3 Hz, 1H). ESI MS $[M+H]^+$ for $C_{23}H_{23}N_7O_2S_2$, calcd 494.1, found 494.1.

Example 293: 3-[6-({6-[(1S,4S)-2,5-diazabicyclo[2.2.1]heptan-2-yl]pyridin-2-yl}amino)-[1,3]thiazolo[5,4-c]pyridin-2-yl]-N-methylbenzene-1-sulfonamide

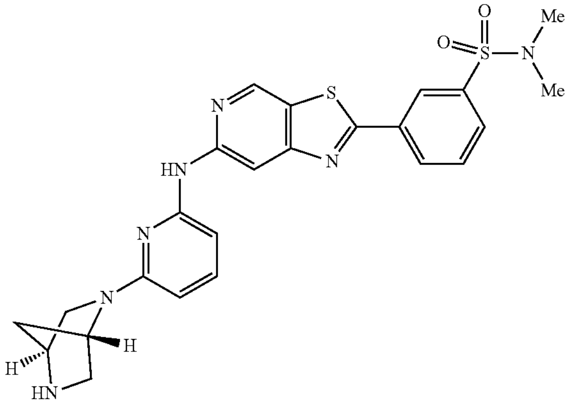 [SMILES: CN(C)S(=O)(=O)c1cccc(-c2nc3cc(Nc4cccc(N5C[C@@H]6C[C@H]5CN6)n4)ncc3s2)c1]

The title compound was synthesized in a similar fashion to example 78 from the appropriate starting materials. $^1$H NMR (400 MHz, DMSO-$d_6$) δ 9.81 (s, 1H), 9.24 (s, 1H), 9.06 (d, J=0.8 Hz, 1H), 8.70 (s, 1H), 8.52 (s, 1H), 8.41 (m, 1H), 8.35 (t, J=1.8 Hz, 1H), 7.99 (m, 1H), 7.91-7.84 (m, 1H), 7.46 (m, 1H), 6.70 (d, J=7.9 Hz, 1H), 6.12 (d, J=8.1 Hz, 1H), 4.80 (s, 1H), 4.50 (s, 1H), 3.67 (s, 2H), 3.26 (s, 2H), 2.67 (s, 6H), 2.19 (d, J=10.7 Hz, 1H), 1.95 (d, J=11.1 Hz, 1H). ESI MS $[M+H]^+$ for $C_{24}H_{25}N_7O_2S_2$, calcd 508.2, found 508.1.

Example 294: N-(2-{1-methyl-1H-pyrazolo[3,4-b]pyridin-4-yl}-[1,3]thiazolo[5,4-c]pyridin-6-yl)-2-[(1S,4S)-5-methyl-2,5-diazabicyclo[2.2.1]heptan-2-yl]pyrimidin-4-amine

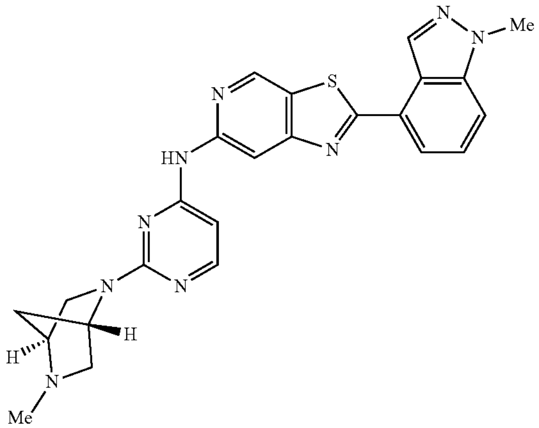 [SMILES: CN1C[C@@H]2C[C@H]1CN2c1nccc(Nc2cc3nc(-c4cccc5c4cnn5C)sc3cn2)n1]

The title compound was synthesized in a similar fashion to example 263 from the appropriate starting materials. $^1$H NMR (400 MHz, DMSO-$d_6$) δ 10.08 (s, 1H), 9.16 (d, J=0.8 Hz, 1H), 8.77 (d, J=4.7 Hz, 1H), 8.65 (s, 1H), 8.22 (s, 1H), 7.98 (d, J=5.7 Hz, 1H), 7.92 (d, J=4.8 Hz, 1H), 6.50 (s, 1H), 4.70 (s, 1H), 4.13 (s, 3H), 3.78-3.12 (m, 5H), 2.32 (s, 3H), 1.89 (m, 1H), 1.80 (m, 1H). ESI MS $[M+H]^+$ for $C_{23}H_{22}N_{10}S$, calcd 471.2, found 471.1.

Example 295: (4R)-3-{5-[6-({2-[(1S,4S)-5-ethyl-2,5-diazabicyclo[2.2.1]heptan-2-yl]-6-methylpyrimidin-4-yl}amino)-[1,3]thiazolo[5,4-c]pyridin-2-yl]pyridin-3-yl}-4-methyl-1,3-oxazolidin-2-one

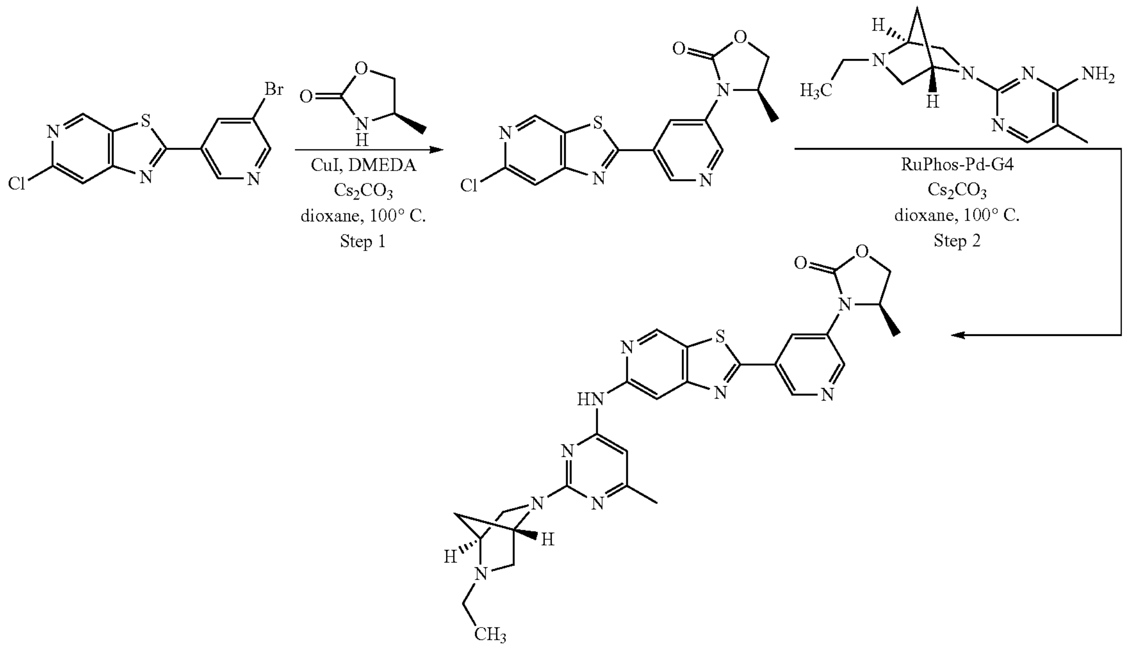

Step 1: A heterogenous mixture of azabenzathiazole intermediate (340 mg, 1.03 mmol), (R)-4-methyloxazolidin-2-one (105 mg, 1.03 mmol), CuI (20 mg, 0.103 mmol), DMEDA (18 mg, 0.206 mmol), $Cs_2CO_3$ (1 g, 3.1 mmol), and dioxane (8 mL) was degassed for 20 min using nitrogen. Then the reaction mixture was stirred at 100° C. overnight. After confirming the completion of the reaction using LCMS, the reaction mixture was cooled to room temperature and the crude reaction mixture was filtered through a small pad of Celite®. Solvent was evaporated under reduced pressure and the crude product was purified by column chromatography (silica gel; gradient: 0% to 2% MeOH in $CH_2Cl_2$) to afford the desired compound (90 mg, 25%).

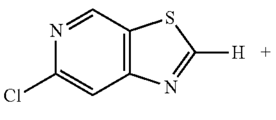

Step 2: The title compound was synthesized in a similar fashion to step 6 of example 1. $^1H$ NMR (400 MHz, Chloroform-d) δ 9.09 (d, J=1.9 Hz, 1H), 8.83 (s, 1H), 8.81 (d, J=2.6 Hz, 1H), 8.73 (s, 2H), 8.67 (t, J=2.3 Hz, 1H), 6.08 (s, 1H), 4.88 (s, 1H), 4.79-4.49 (m, 2H), 4.23-4.04 (m, 1H), 3.86 (d, J=10.2 Hz, 1H), 3.67 (s, 1H), 3.04 (d, J=9.6 Hz, 1H), 2.74-2.53 (m, 3H), 2.28 (s, 3H), 2.03-1.67 (m, 3H), 1.45 (d, J=5.9 Hz, 3H), 1.07 (t, J=7.2 Hz, 3H). ESI MS $[M+H]^+$ for $C_{27}H_{29}N_9O_2S$, calcd 544.2, found 544.1.

Example 296: N-[2-(6-amino-3-methylpyridin-2-yl)-[1,3]thiazolo[5,4-c]pyridin-6-yl]-2-[(1S,4S)-5-ethyl-2,5-diazabicyclo[2.2.1]heptan-2-yl]-6-methylpyrimidin-4-amine -continued

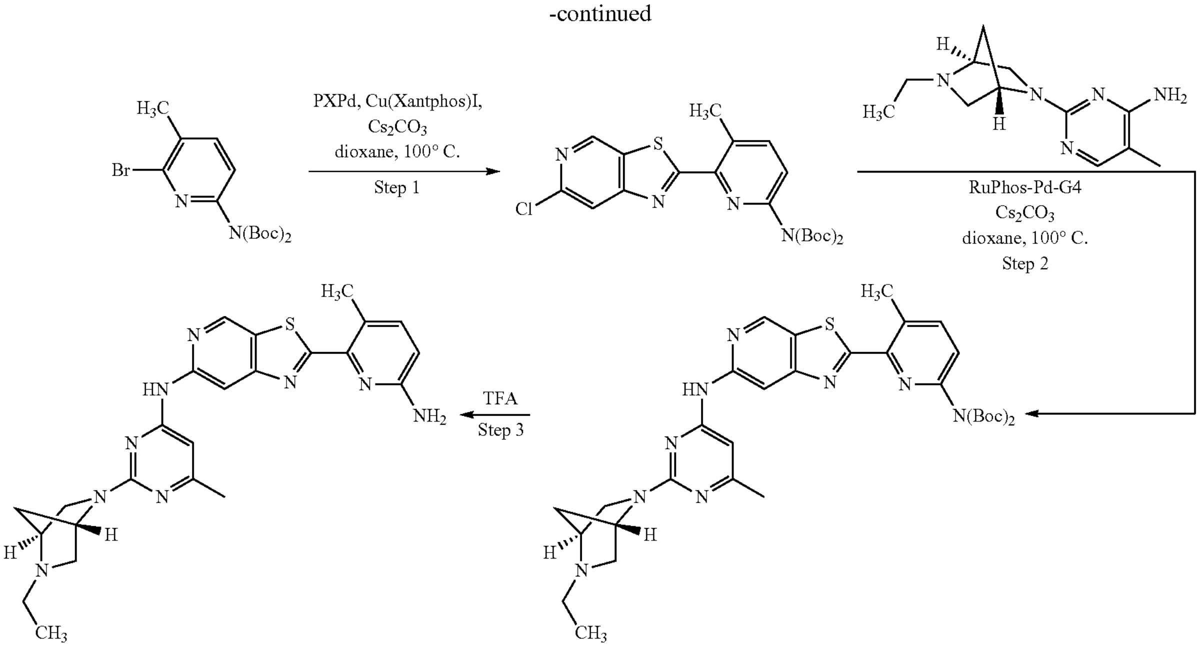

Step 1: A heterogenous mixture of 6-chlorothiazolo[5,4-c]pyridine (170 mg, 1 mmol), imidodicarbonic acid, 2-(6-bromo-5-methyl-2-pyridinyl)-, 1,3-bis(1,1-dimethylethyl) ester (774 mg, 2 mmol), dichlorobis(chloro-di-tert-butylphosphine)palladium (PXPd) (54 mg, 0.1 mmol), Cu(Xantphos)I (154 mg, 0.2 mmol), $Cs_2CO_3$ (815 mg, 2.5 mmol), and toluene (8 mL) was degassed for 20 min using nitrogen. Then the reaction mixture was stirred at 100° C. overnight. After confirming the completion of the reaction using LCMS, the reaction mixture was cooled to room temperature and the crude reaction mixture was filtered through a small pad of Celite®. Solvent was evaporated under reduced pressure and the crude product was purified by column chromatography (silica gel; gradient: 0% to 50% EtOAc in hexanes) to afford the desired compound (90 mg, 25%).

Step 2: This reaction was performed in a similar fashion to step 6 of example 1.

Step 3: The title compound was synthesized in a similar fashion to step 3 of example 78. $^1H$ NMR (400 MHz, Chloroform-d) δ 8.81 (s, 1H), 8.70 (s, 1H), 7.41 (d, J=8.3 Hz, 1H), 7.27 (s, 1H), 6.56 (d, J=8.3 Hz, 1H), 6.08 (s, 1H), 4.86 (s, 1H), 4.47 (s, 2H), 3.87 (d, J=10.6 Hz, 1H), 3.66 (s, 1H), 3.46 (d, J=10.5 Hz, 1H), 3.15 (s, 1H), 2.73 (s, 3H), 2.65-2.55 (m, 3H), 2.28 (s, 3H), 2.06-1.76 (m, 2H), 1.07 (t, J=7.2 Hz, 3H). ESI MS $[M+H]^+$ for $C_{24}H_{27}N_9S$, calcd 474.2, found 474.6.

Example 297: 2-[(1S,4S)-5-ethyl-2,5-diazabicyclo[2.2.1]heptan-2-yl]-6-methyl-N-(2-{5-[(3R)-3-methylmorpholin-4-yl]pyridin-3-yl}-[1,3]thiazolo[5,4-c]pyridin-6-yl)pyrimidin-4-amine

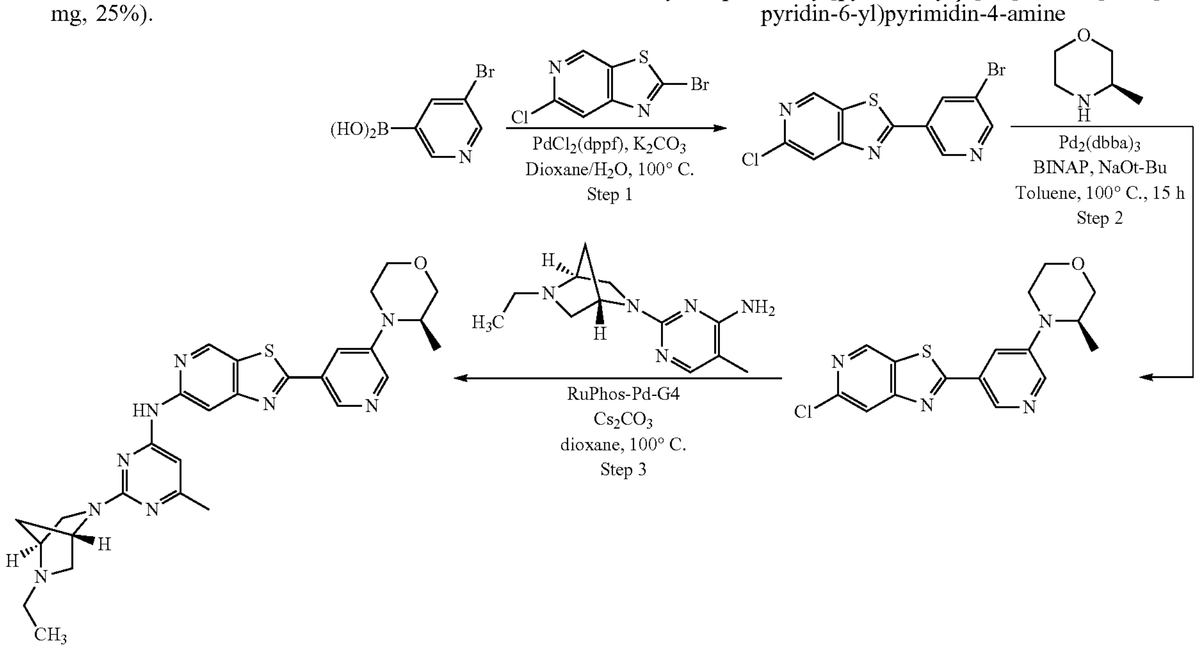

Step 1: To a solution of (3-bromopyridin-5-yl)boronic acid (2.01 g, 10 mmol) and 2-bromo-6-chloro[1,3]thiazolo[5,4-c]pyridine (2.49 g, 10 mmol) in dioxane (16 mL)/$H_2O$ (4 mL) was added $PdCl_2$(dppf) (733 mg, 1.0 mmol) and $K_2CO_3$ (2.76 g, 20 mmol). After degassing for 25 min with $N_2$, the reaction mixture was heated to 100° C. and stirred for 5 h. The reaction mixture was cooled down to RT, filtered and concentrated in vacuo. The residue was purified by flash column chromatography (silica gel; gradient: 0% to 80% EtOAc in hexanes) to get the desired derivative (1.91 g, 72%).

Step 2: A heterogenous mixture of azabenzathiazole intermediate obtained from step 1 (340 mg, 1.03 mmol), (R)-3-methylmorpholine (105 mg, 1.03 mmol), $Pd_2(dba)_3$ (95 mg, 0.103 mmol), BINAP (128 mg, 0.206 mmol), NaOt-Bu (150 Mg, 1.54 mmol), and toluene (8 mL) was degassed for 20 min using nitrogen. The reaction mixture was then stirred at 100° C. overnight. After confirming the completion of the reaction using LCMS, the reaction mixture was cooled to room temperature and the crude reaction mixture was filtered through a small pad of Celite®. Solvent was evaporated under reduced pressure and the crude product was purified by column chromatography (silica gel; gradient: 0% to 2% MeOH in $CH_2Cl_2$) to afford the desired compound (90 mg, 25%).

Step 3: The title compound was synthesized in a similar fashion to step 6 of example 1. $^1H$ NMR (400 MHz, Chloroform-d) δ 8.94-8.78 (m, 1H), 8.69 (d, J=1.8 Hz, 1H), 8.39 (d, J=2.9 Hz, 1H), 7.83 (dd, J=2.9, 1.8 Hz, 1H), 7.40 (s, 1H), 6.11 (s, 1H), 4.88 (s, 1H), 4.12-4.00 (m, 1H), 3.95-3.62 (m, 6H), 3.50 (s, 1H), 3.34-3.23 (m, 2H), 3.16-3.02 (m, 1H), 2.62 (ddd, J=18.9, 12.7, 8.3 Hz, 3H), 2.27 (s, 3H), 1.99 (s, 1H), 1.86 (s, 1H), 1.20 (d, J=6.6 Hz, 3H), 1.08 (t, J=7.1 Hz, 3H). ESI MS $[M+H]^+$ for $C_{28}H_{33}N_9OS$, calcd 544.3, found 544.1.

Example 298: 2-[(1S,4S)-5-ethyl-2,5-diazabicyclo[2.2.1]heptan-2-yl]-6-methyl-N-{2-[(1R)-1-phenylethoxy]-[1,3]thiazolo[5,4-c]pyridin-6-yl}pyrimidin-4-amine

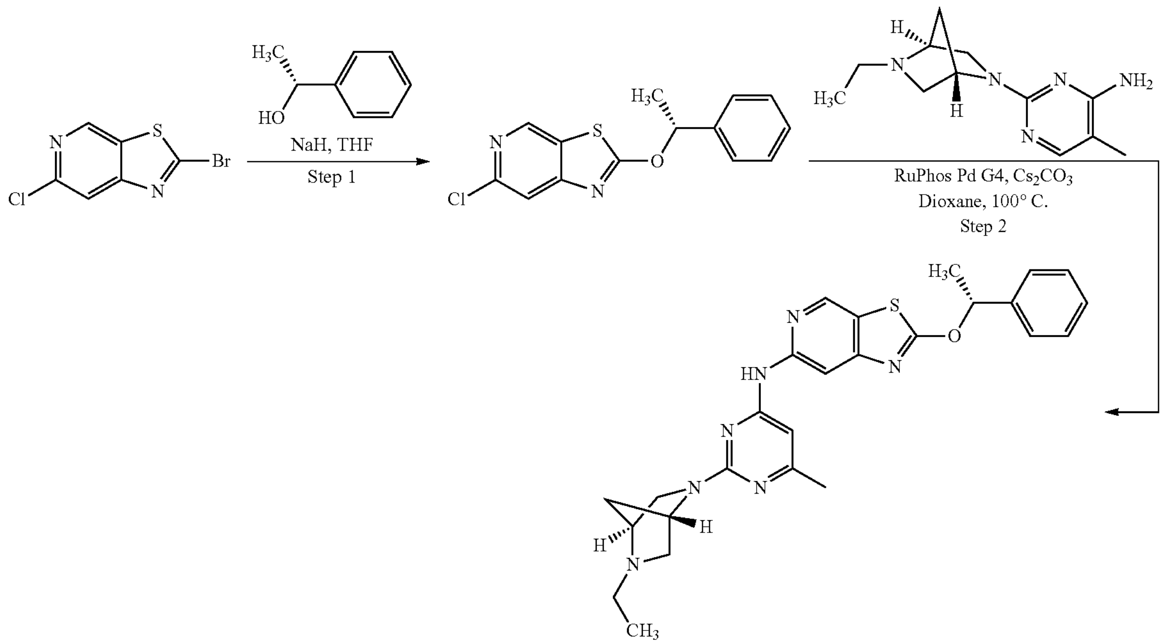

Step 1: To a stirred solution of phenylethanol (1 g, 8.1 mmol) in THE (20 mL) was added 60% NaH (310 mg, 8.1 mmol), and the reaction mixture was allowed to stir for 1 h at ambient temperature. After this, azabenzothiazole derivative (2.01 g, 8.1 mmol) was added and the reaction mixture was allowed to stir for 3 h at ambient temperature. The mixture was quenched by addition of sat. $NH_4Cl$ and extracted with $CH_2Cl_2$. Solvent was evaporated under reduced pressure and the crude product was purified by column chromatography (silica gel; gradient: 0% to 50% EtOAc in hexanes) to afford the desired compound (1.2 g, 52%).

Step 2: This reaction was performed in a similar fashion to step 2 of example 185. $^1H$ NMR (400 MHz, Chloroform-d) δ 8.43 (d, J=0.7 Hz, 1H), 8.24 (s, 1H), 7.50-7.43 (m, 2H), 7.40-7.29 (m, 4H), 6.27 (q, J=6.5 Hz, 1H), 6.09 (s, 1H), 4.82 (s, 1H), 3.83 (dd, J=10.6, 1.5 Hz, 1H), 3.65 (s, 1H), 3.42 (s, 1H), 3.10 (s, 1H), 2.69-2.53 (m, 3H), 2.25 (s, 3H), 2.00-1.83 (m, 2H), 1.76 (d, J=6.6 Hz, 3H), 1.08 (t, J=7.2 Hz, 3H). ESI MS $[M+H]^+$ for $C_{26}H_{29}N_7OS$, calcd 488.2, found 488.3.

Example 299: 2-[(1S,4S)-5-(4-methyl-6-{[2-(4-methyl-4H-1,2,4-triazol-3-yl)-[1,3]thiazolo[5,4-c]pyridin-6-yl]amino}pyrimidin-2-yl)-2,5-diazabicyclo[2.2.1]heptan-2-yl]ethan-1-ol

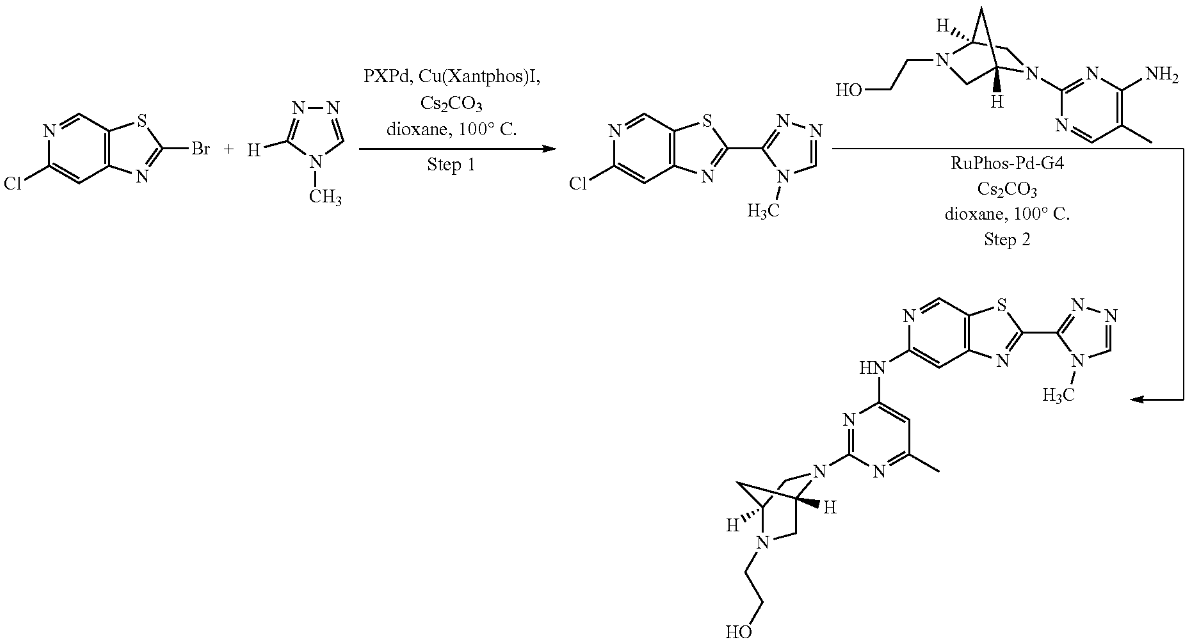

-

Step 1: A heterogenous mixture of azabenzathiazole intermediate (375 mg, 1.5 mmol), 4-methyl-4H-1,2,4-triazole (83.1 mg, 1 mmol), dichlorobis(chloro-di-tert-butylphosphine)palladium (PXPd) (54 mg, 0.1 mmol), Cu(Xantphos)I (154 mg, 0.2 mmol), $Cs_2CO_3$ (815 mg, 2.5 mmol), and toluene (6 mL) was degassed for 20 min using nitrogen. Then this reaction mixture was stirred at 100° C. overnight. After confirming the completion of the reaction using LCMS, the reaction mixture was cooled to room temperature and the crude reaction mixture was filtered through a small pad of Celite®. Solvent was evaporated under reduced pressure and the crude product was purified by column chromatography (silica gel; gradient: 0% to 50% EtOAc in hexanes) to afford the desired compound (35 mg, 14%).

Step 2: The title compound was synthesized in a similar fashion to step 6 of example 1. $^1H$ NMR (400 MHz, Chloroform-d) δ 8.87 (s, 1H), 8.73 (s, 1H), 8.30 (s, 1H), 7.36 (s, 1H), 6.10 (s, 1H), 4.90 (s, 1H), 4.23 (s, 3H), 3.79 (dd, J=10.5, 1.5 Hz, 1H), 3.62 (s, 1H), 3.55 (t, J=5.3 Hz, 3H), 3.06 (s, 1H), 2.84-2.68 (m, 3H), 2.29 (s, 3H), 2.00-1.84 (m, 2H). ESI MS $[M+H]^+$ for $C_{21}H_{24}N_{10}OS$, calcd 465.2, found 465.3.

Example 300: N-[2-(3-methylpyridin-2-yl)-[1,3]thiazolo[5,4-c]pyridin-6-yl]-5,6,7,8-tetrahydro-1,7-naphthyridin-2-amine

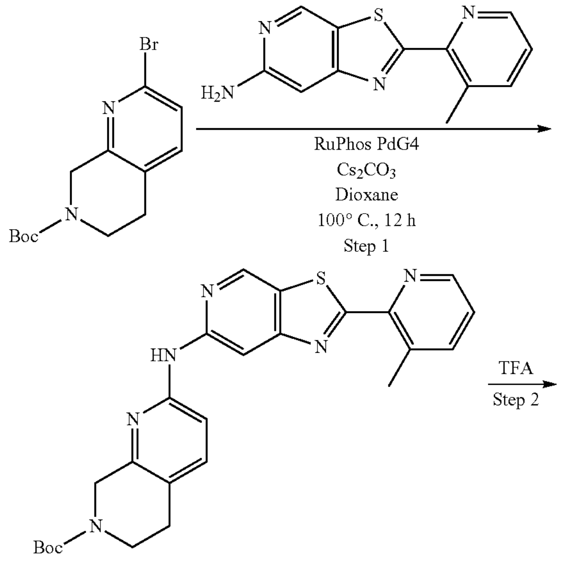

-continued

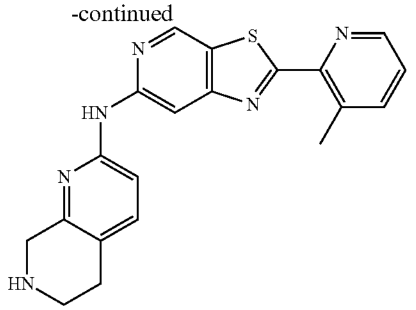

Step 1: This reaction was performed in a similar fashion to step 2 of example 185.

Step 2: This reaction was performed in a similar fashion as step 3 of example 78. $^1$H NMR (400 MHz, Chloroform-d) δ 8.84 (d, J=0.9 Hz, 1H), 8.55-8.54 (m, 1H), 8.36 (d, J=0.9 Hz, 1H), 7.76-7.63 (m, 1H), 7.38-7.27 (m, 3H), 7.10 (d, J=8.4 Hz, 1H), 4.07 (s, 2H), 3.14 (t, J=5.9 Hz, 2H), 2.91 (s, 3H), 2.73 (t, J=5.9 Hz, 2H), 1.74 (s, 2H). ESI MS $[M+H]^+$ for $C_{20}H_{18}N_6S$, calcd 375.1, found 375.2.

Example 301: 2-[(1S,4S)-5-(4-Methyl-6-{[2-(1-methyl-1H-pyrazol-4-yl)-[1,3]thiazolo[5,4-c]pyridin-6-yl]amino}pyrimidin-2-yl)-2,5-diazabicyclo[2.2.1]heptan-2-yl]ethan-1-ol

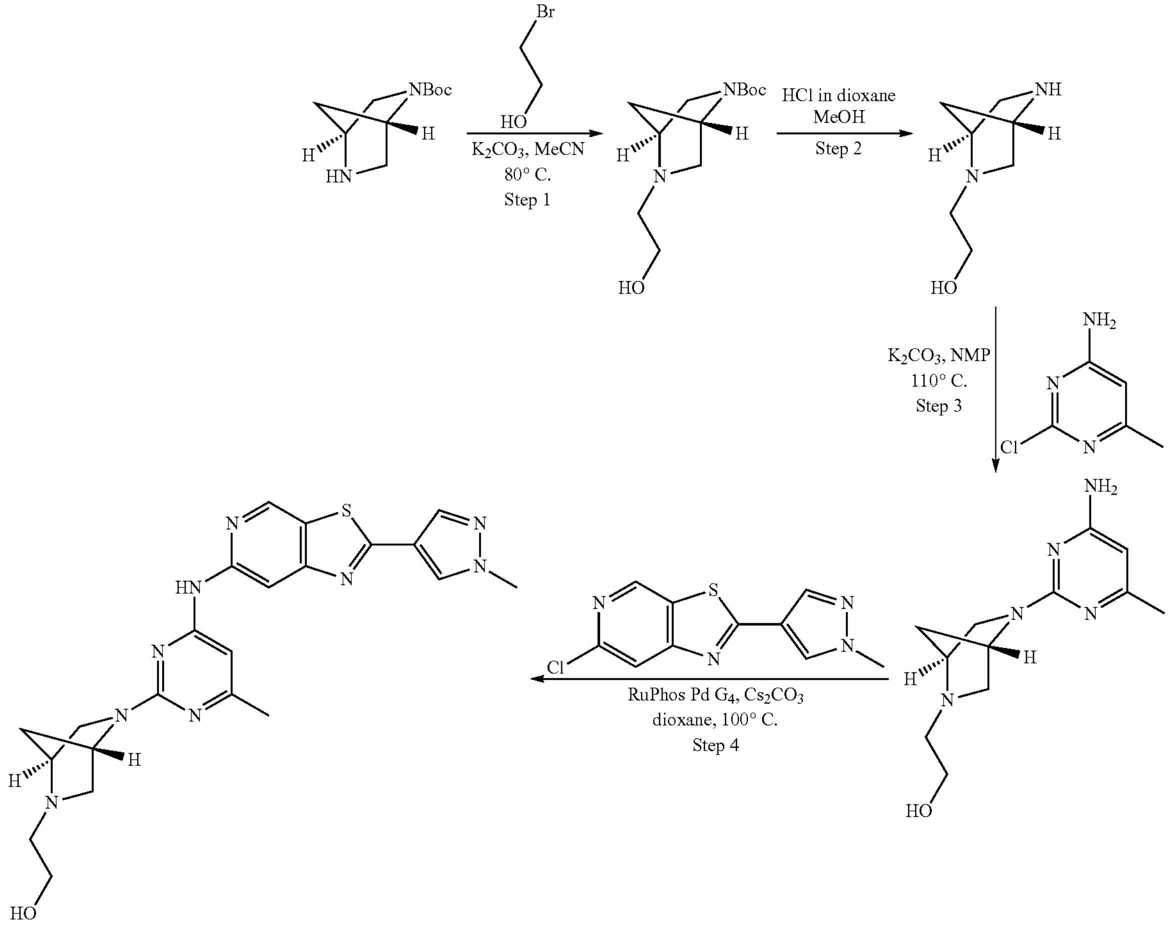

Step 1: A heterogenous mixture of (1S,4S)-2-Boc-2,5-diazabicyclo[2.2.1]heptane (396 mg, 2.00 mmol), 2-bromoethanol (500 mg, 4.00 mmol), $K_2CO_3$ (690 mg, 5.00 mmol), and MeCN (3 mL) was heated at 80° C. for 15 h. The reaction was cooled to room temperature, filtered through a pad of Celite®, concentrated, and used for next reaction without further purification.

Step 2: To a stirred suspension of crude intermediate from step 1 in MeOH (4.0 mL) was added 4M HCl solution in dioxane (8 mL) dropwise. The reaction was stirred at room temperature for 1 h and then concentrated under reduced pressure. The resultant was forwarded to next step without further purification.

Step 3: A heterogenous mixture of crude intermediate from step 2, 2-chloro-6-methyl-4-pyrimidinamine (430 mg, 3.00 mmol), $K_2CO_3$ (1.38 g, 10.00 mmol), and NMP (6 mL) was heated at 110° C. for 15 h. The filtered through a pad of Celite® and the filtrate was concentrated under reduced pressure. The resulting residue was purified by reverse phase HPLC to obtain the desired product. $^1H$ NMR (400 MHz, Methanol-$d_4$) δ 8.76 (d, J=0.8 Hz, 1H), 8.70 (s, 1H), 8.41-8.31 (m, 1H), 8.10 (d, J=0.8 Hz, 1H), 6.23 (s, 1H), 4.91-4.85 (m, 1H), 3.97 (s, 3H), 3.93-3.80 (m, 1H), 3.75 (br s, 1H), 3.62 (td, J=6.1, 1.0 Hz, 2H), 3.58-3.47 (m, 1H), 3.16-3.04 (m, 1H), 2.81-2.71 (m, 3H), 2.24 (s, 3H), 2.02 (d, J=9.8 Hz, 1H), 1.91 (d, J=9.8 Hz, 1H). ESI MS $[M+H]^+$ for $C_{22}H_{26}N_9OS$, calcd 417.2, found 464.2.

Example 302: 4-{2-[(1S,4S)-2,5-diazabicyclo[2.2.1]heptan-2-yl]-6-{[2-(3-methylpyridin-2-yl)-[1,3]thiazolo[5,4-c]pyridin-6-yl]amino}pyrimidin-4-yl}cyclohexan-1-ol

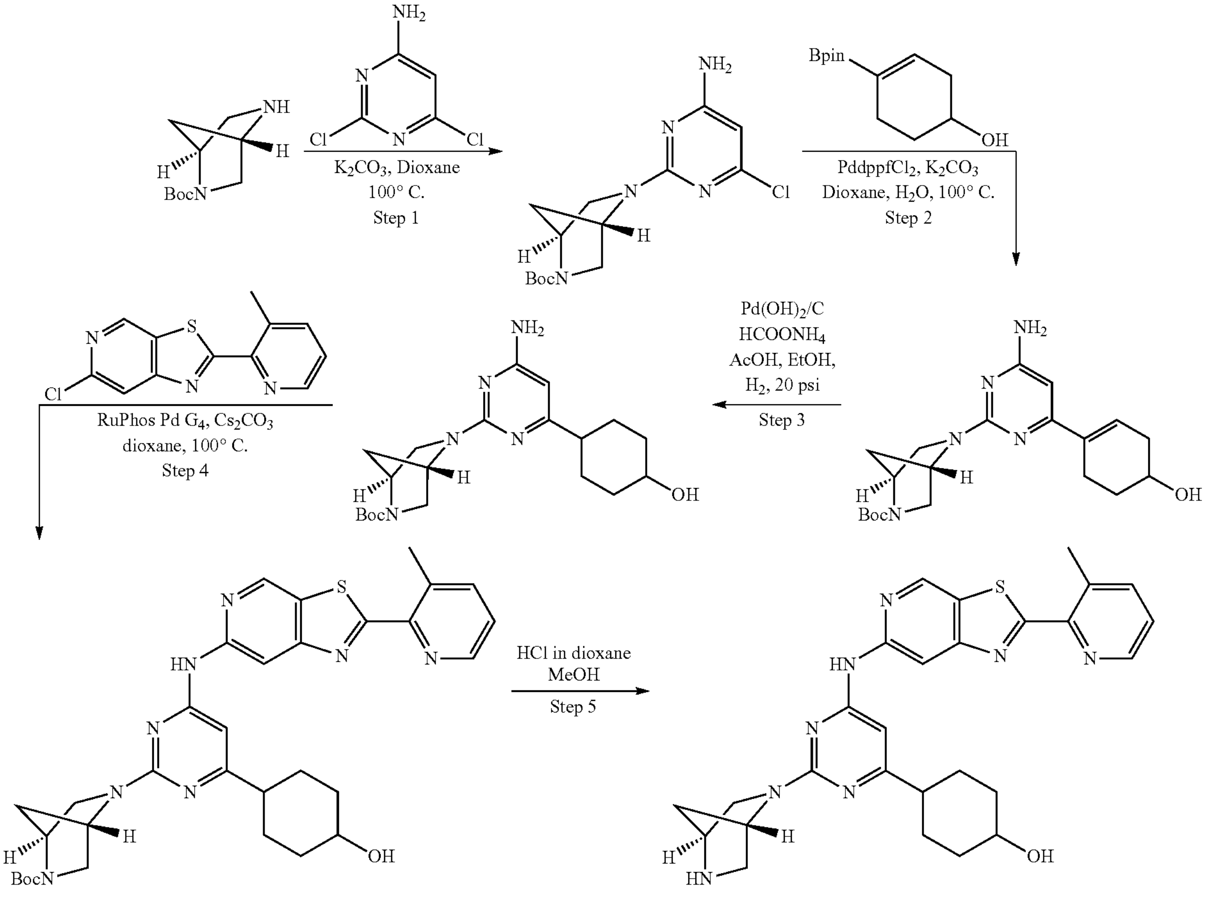

reaction was cooled to room temperature, loaded into silica gel column and eluted with 0-80% MeOH/DCM to obtain the desired aminopyrimidine derivative (245 mg, 49% in 3-steps).

Step 4: To a stirred solution of intermediate from step 3 (50 mg, 0.2 mmol) and azabenzothiazole derivative (synthesized separately using protocol similar to example 263, step 1) (50 mg, 0.20 mmol) in dioxane (3 mL) were added RuPhos Pd G4 (33 mg, 0.04 mmol) and $Cs_2CO_3$ (195 mg 0.60 mmol). After degassing for 10 min under $N_2$ atmosphere, the reaction mixture was heated at 100° C. for 15 h. The reaction mixture was Step 1: The nucleophilic aromatic substitution (SNAr) reaction was performed following protocol from example 301, step 1.

Step 2: The amino pyrimidine intermediate from step 1 (486 mg, 1.50 mmol), boronate (336 mg, 1.50 mmol), $Pd(dppf)Cl_2$ (220 mg, 0.30 mmol), $K_2CO_3$ (414 mg, 3.0 mmol), dioxane (9 mL), and $H_2O$ (3 mL) were combined and degassed by bubbling $N_2$ for 10 min. The mixture was stirred at 100° C. under inert atmosphere for 3 h and then cooled to room temperature. The reaction was filtered through a pad of Celite® and the filtrate was concentrated under reduced pressure. The residue was purified by column chromatography on silica gel (0-80% MeOH/DCM) to get the desired compound in quantitative yield.

Step 3: To a solution of intermediate from step 2 (580 mg, 1.50 mmol) in ethanol (60 mL) and was added $Pd(OH)_2/C$ (870 mg, 20 wt. %), $HCO_2NH_4$ (282 mg, 4.50 mmol), and acetic acid (0.36 mL). The resultant heterogenous mixture was shaken in Parr hydrogenator for 20 h at 20 psi of $H_2$ atmosphere. The reaction mixture was filtered through a pad of Celite®, and the filtrate was concentrated under reduced pressure to get the desired product in quantitative yield.

Step 4: The coupling reaction was performed following the protocol from example 301, step 4.

Step 5: To a stirred suspension of intermediate from step 4 (103 mg, 0.17 mmol) in MeOH (1.5 mL) was added 4M HCl solution in dioxane (3 mL) dropwise. The reaction was stirred at room temperature for 1 h and then concentrated under reduced pressure. The resultant was purified by reverse phase preparative HPLC to afford the desired compound. $^1H$ NMR (400 MHz, Methanol-$d_4$) δ 8.95-8.85 (m, 1H), 8.81-8.67 (m, 1H), 8.58-8.44 (m, 1H), 7.84-7.73 (m, 1H), 7.48-7.37 (m, 1H), 6.43-6.29 (m, 1H), 5.10-4.96 (m, 1H), 4.24-4.11 (m, 1H), 4.04-3.48 (m, 3H), 3.29-3.15 (m, 2H), 2.86 (s, 3H), 2.53-2.29 (m, 1H), 2.22-1.78 (m, 6H), 1.75-1.25 (m, 4H). ESI MS $[M+H]^+$ for $C_{27}H_{31}N_8OS$, calcd 515.2, found 515.3.

Example 303: 2-{4-[6-({6-[(1S,4S)-2,5-diazabicyclo[2.2.1]heptan-2-yl]-5-(oxan-4-yl)pyrazin-2-yl}amino)-[1,3]thiazolo[5,4-c]pyridin-2-yl]pyridin-2-yl}propan-2-ol

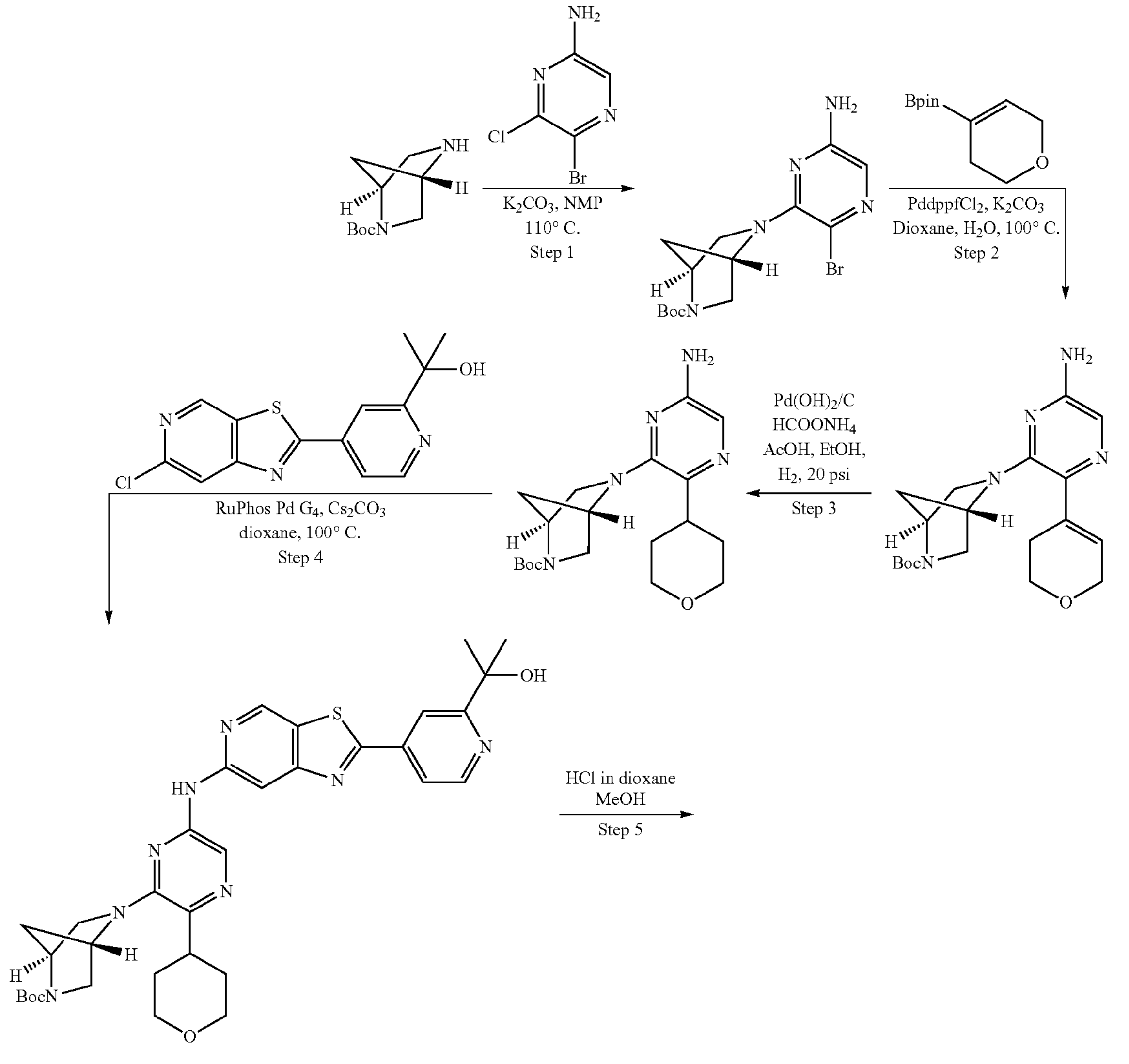

-continued

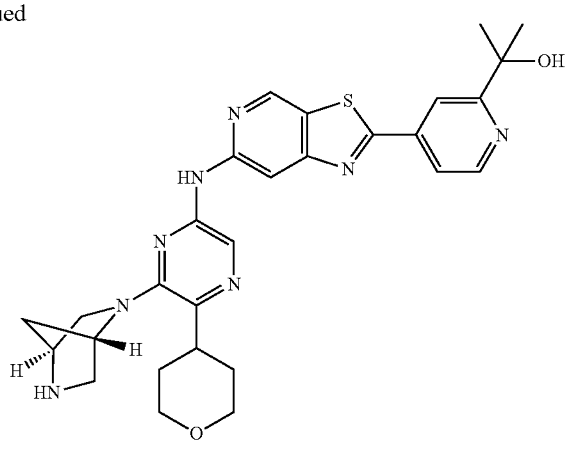

Step 1: The SNAr reaction was performed following protocol from example 301, step 3.

Step 2: The Suzuki reaction was performed following the protocol from example 302, step 2.

Step 3: The hydrogenation reaction was performed following the protocol from example 302, step 3.

Step 4: The coupling reaction was performed following the protocol from example 301, step 4.

Step 5: The deprotection reaction was performed following the protocol from example 302, step 5. Using intermediate from step 4 (105 mg, 0.17 mmol), 30 mg (33% yield) of final compound was obtained. $^1$H NMR (400 MHz, Chloroform-d) δ 8.81 (d, J=0.9 Hz, 1H), 8.66 (dd, J=5.1, 0.9 Hz, 1H), 8.39 (d, J=0.9 Hz, 1H), 8.04 (dd, J=1.6, 0.9 Hz, 1H), 7.93 (s, 1H), 7.79 (dd, J=5.1, 1.6 Hz, 1H), 7.35 (s, 1H), 4.77 (s, 1H), 4.15-3.95 (m, 3H), 3.84 (dd, J=9.5, 2.5 Hz, 1H), 3.66 (d, J=10.6 Hz, 1H), 3.55-3.33 (m, 4H), 2.96-2.85 (m, 1H), 2.24-1.96 (m, 3H), 1.90-1.70 (m, 2H), 1.67-1.54 (m, 7H). ESI MS [M+H]$^+$ for $C_{28}H_{33}N_8O_2S$, calcd 545.2, found 545.3.

Example 304: 2-{2-[(1S,4S)-5-methyl-2,5-diazabicyclo[2.2.1]heptan-2-yl]-6-{[2-(3-methylpyridin-2-yl)-[1,3]thiazolo[5,4-c]pyridin-6-yl]amino}pyrimidin-4-yl}propan-2-ol

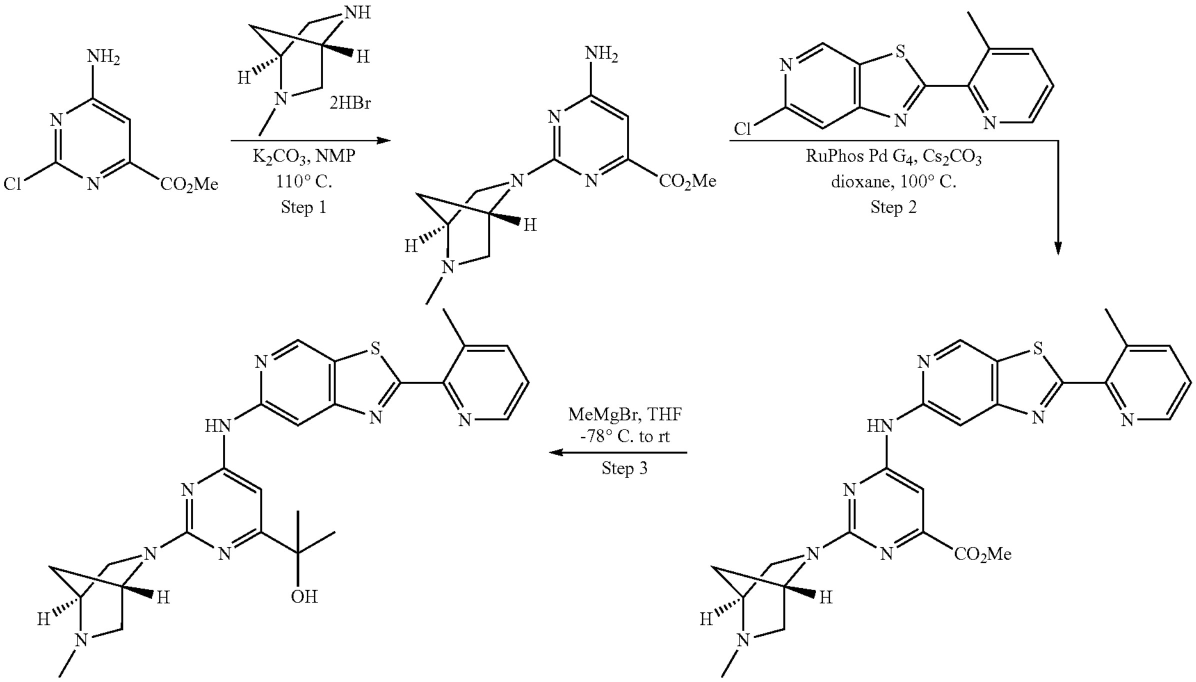

Step 1: The SNAr reaction was performed following protocol from example 301, step 3.

Step 2: The coupling reaction was performed following the protocol from example 301, step 4.

Step 3: A solution of MeMgBr in ether (0.05 mL of 3 M in ether, 0.16 mmol) was added dropwise to a chilled solution of intermediate from step 2 (20 mg, 0.04 mmol) at −78° C. The reaction was then stirred at room temperature for 2 h and quenched with sat. $NH_4Cl$. Organic residue was evaporated under reduced pressure and extracted with 10% MeOH/DCM. The combined extract was concentrated and purified via reverse phase HPLC to obtain final product. $^1H$ NMR (400 MHz, Chloroform-d) δ 8.87 (d, J=0.9 Hz, 1H), 8.72 (br s, 1H), 8.56 (ddd, J=4.6, 1.6, 0.9 Hz, 1H), 7.69 (ddd, J=7.8, 1.6, 0.9 Hz, 1H), 7.43-7.27 (m, 2H), 6.21 (s, 1H), 5.26-4.94 (m, 1H) 4.89 (s, 1H), 3.91 (br s, 1H), 3.70-3.39 (m, 2H), 3.28-3.00 (m, 1H), 2.91 (s, 3H), 2.85-2.70 (m, 1H), 2.50 (s, 3H), 2.15-1.88 (m, 2H), 1.47 (s, 6H). ESI MS $[M+H]^+$ for $C_{25}H_{29}N_8OS$, calcd 489.2, found 489.2.

Example 305: ([(R)-3-methyl-1-pyrrolidinyl]{m-[6-(2-{(1S,4S)-5-ethyl-2,5-diazabicyclo[2.2.1]hept-2-yl}-6-methyl-4-pyrimidinylamino)-3-thia-1,5-diaza-2-indenyl]phenyl}methanone)

overnight at room temperature. The next day, after confirming the complete consumption of the starting material, reaction mixture was filtered through a small pad of Celite®, and the crude reaction mixture was purified by flash column chromatography to afford the desired intermediate in almost quantitative yield.

Step-2: This transformation was performed in a similar fashion to step 1 protocol for the synthesis of example 128.

Step-3: To a solution of (1S,4S)-2-Boc-2,5-diazabicyclo [2.2.1]heptane (2 g, 10.08 mmol) in $CH_3CN$ (24 mL), were added ethyl iodide (1.57 g, 10.08 mmol), $K_2CO_3$ (4.19 g, 30.25 mmol). The mixture was stirred at 80° C. overnight. The next day, after confirming the completion of the reaction, the reaction mixture was filtered through a pad of Celite®, and the solvent was evaporated under reduced pressure to obtain the crude product. This crude product was taken in MeOH (10 mL) and added HCl in dioxane solution (excess, ~5 mL) and the reaction mixture was stirred at 60° C. for 6 hours.

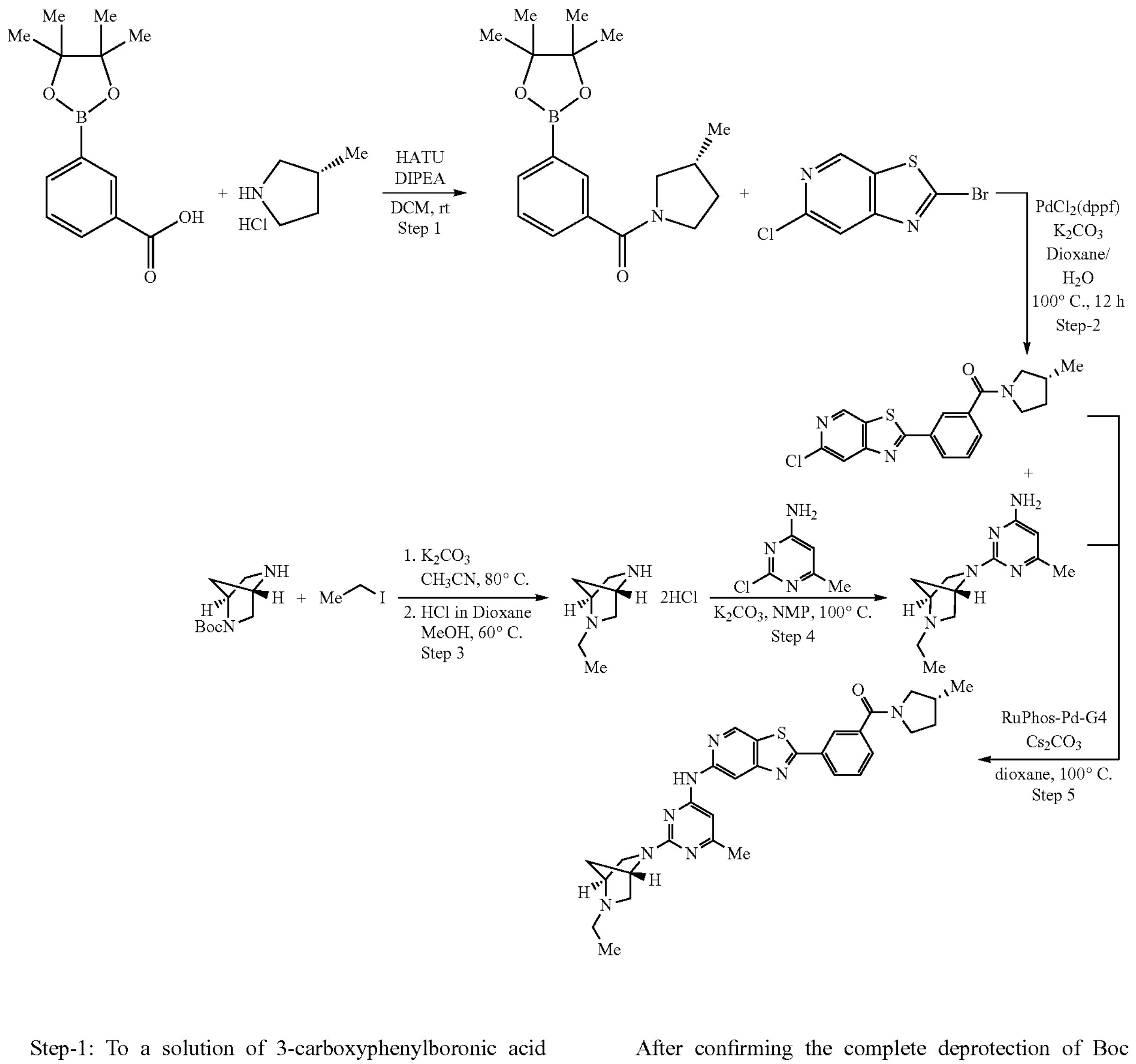

Step-1: To a solution of 3-carboxyphenylboronic acid pinacol ester (1 g, 4.01 mmol) in DCM (15 mL), were added (3R)-3-methylpyrrolidine hydrochloride (0.76 g, 6.02 mmol), HATU (3.05 g, 8.03 mmol), DIPEA (2.1 mL, 12.05 mmol) and stirred the reaction mixture After confirming the complete deprotection of Boc group, reaction mixture was brought to room temperature and the volatiles were evaporated under reduced pressure to afford the crude (1S,4S)-2-ethyl-2,5-diazabicyclo[2.2.1]heptane as a hydrochloride salt in quantitative yield. This material was taken to the next step without further purification.

Step 4 and Step 5: These transformations were performed in a similar fashion to step 2 and step 3 protocol respectively for the synthesis of example 120 to obtain the desired product $^1$H NMR (400 MHz, Chloroform-d) δ 8.81 (d, J=0.8 Hz, 1H), 8.62 (s, 1H), 8.26 (t, J=1.7 Hz, 1H), 8.15 (ddt, J=7.9, 3.0, 1.3 Hz, 1H), 7.66 (dt, J=7.4, 1.3 Hz, 2H), 7.54 (td, J=7.7, 2.0 Hz, 1H), 6.15 (s, 1H), 4.94 (s, 1H), 3.95 (dd, J=8.7, 3.2 Hz, 2H), 3.90-3.73 (m, 1H), 3.70-3.45 (m, 3H), 3.36 (d, J=10.1 Hz, 1H), 3.20 (DD, J=12.1, 8.5 Hz, 1H), 3.05 (dd, J=10.4, 8.4 Hz, 1H), 2.91-2.72 (m, 3H), 2.44-2.29 (m, 1H), 2.21 (d, J=10.8 Hz, 1H), 2.12 (ddd, J=17.2, 8.3, 5.3 Hz, 1H), 2.06-1.95 (m, 2H), 1.69-1.43 (m, 2H), 1.25-0.99 (m, 6H).

Example 306 (6-[8-(1-amino-1-methylethyl)-2-quinolylamino]-2-(3-methyl-2-pyridyl)-3-thia-1,5-diazaindene)

was quenched with saturated $NH_4Cl$. The reaction mixture was brought to room temperature, diluted with brine and extracted with EtOAc thrice. The combined organic layers were dried over anhydrous $Na_2SO_4$, and the volatiles were evaporated under reduced pressure. The crude product was purified by flash column chromatography to afford the desired intermediate (1.16 g, 69%).

Step-2: The intermediate from step 1 (1.16 g, 5.64 mmol) was taken in a dry screw capped reaction vial with septum, and to this, dry THE (17 mL) followed by t-butyl sulfinamide (1.02 g, 8.46 mmol), and $Ti(OEt)_4$ (1.8 mL, 8.46 mmol) were added under constant stirring at room temperature. Then this reaction mixture was heated to reflux. The progress of the reaction was monitored periodically by TLC and after confirming the complete consumption of the starting material, the reaction mixture was brought to room temperature and filtered through a pad of Celite®. The volatiles were evaporated under reduced pressure and the crude prod-

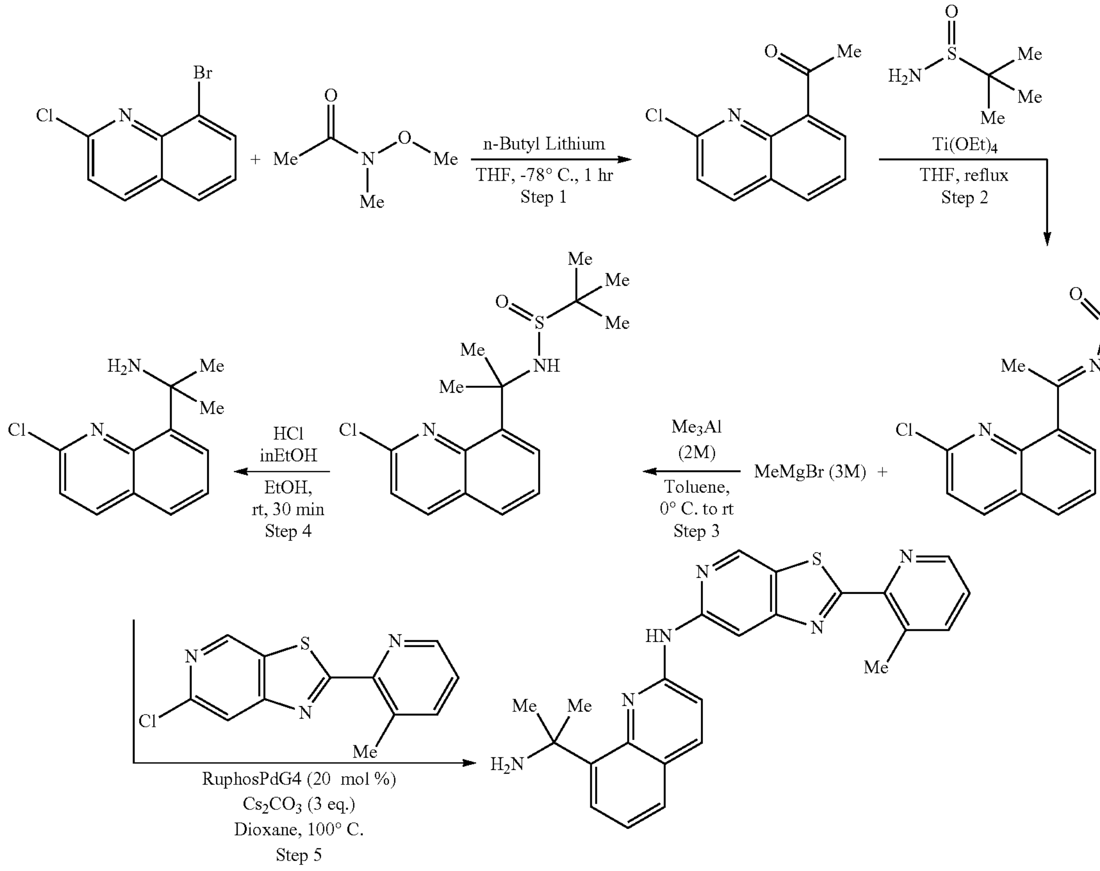

Step-1: In a dry round bottom flask, 8-bromo-2-chloroquinoline (2 g, 8.24 mmol) was taken in dry THF (30 mL) under nitrogen atmosphere, and cooled to −78° C. To the cooled mixture n-butyl lithium was added under constant stirring. After stirring the reaction mixture at this temperature for 30 min, N-methoxy-N-methylacetamide (0.88 mL, 8.24 mmol) was added to the reaction mixture and stirred at −78° C. for 1 hour. After confirming the completion of the reaction, the reaction uct was purified by flash column chromatography to afford the sulfinimine (0.74 g, 43%).

Step-3: The intermediate from step 2 (0.742 g, 2.40 mmol) was taken in a dry screw capped reaction vial with septum, and to this, dry toluene (12 mL) was added, and the reaction mixture cooled to 0° C. Then $AlMe_3$ (2M sol., 2.4 mL, 4.80 mmol) was added to the reaction mixture and stirred for 30 minutes. Then MeMgBr (3M sol., 2.4 mL, 7.20 mmol) was added and the temperature of the reaction mixture was brought to room temperature and stirred. The progress of the reaction was monitored periodically by TLC and after confirming the complete consumption of the starting material, the reaction was quenched using saturated $NH_4Cl$. The reaction mixture was diluted with brine and extracted with EtOAc thrice. The combined organic layers were dried over anhydrous $Na_2SO_4$, and the volatiles were evaporated under reduced pressure. The crude product was purified by flash column chromatography to afford the intermediate (0.57 g, 73%).

Step-4: The intermediate from step 3 (0.57 g, 1.75 mmol), was taken in EtOH (5 mL) in a dry screw capped reaction vial with septum, and to this, HCl in EtOH solution (1.25 M sol., 2.8 mL, 3.50 mmol) was added and stirred at room temperature. The progress of the reaction was monitored using LCMS and after confirming the complete deprotection of the auxiliary, the reaction was stopped, and the volatiles were evaporated under reduced pressure. This amine HCl salt was dissolved in minimum amount of water (5 mL) and the pH of this aqueous layer adjusted to 11 using $K_2CO_3$. Then this aqueous layer was extracted with DCM thrice. The combined organic layers were dried over anhydrous $Na_2SO_4$, and the volatiles were evaporated under reduced pressure to afford the intermediate amine (0.3 g, 77%). The resulting material was used in the next step without further purification.

Step-5: This transformation was performed in a similar fashion to step 3 for the synthesis of example 120 to obtain the desired final product. $^1H$ NMR (400 MHz, Chloroform-d) δ 8.88 (s, 1H), 8.82 (s, 1H), 8.55 (dd, J=4.6, 1.5 Hz, 1H), 7.98 (d, J=8.8 Hz, 1H), 7.67 (t, J=7.4 Hz, 2H), 7.56 (d, J=7.9 Hz, 1H), 7.35-7.20 (m, 4H), 2.95 (s, 3H), 2.82 (s, 2H), 1.87 (s, 6H).

Example 307: 2-[(1S,4S)-5-(4-{2-[2-(cyclopropylhydroxymethyl)-4-pyridyl]-3-thia-1,5-diaza-6-indenylamino}-6-methyl-2-pyrimidinyl)-2,5-diazabicyclo[2.2.1]hept-2-yl]ethanol

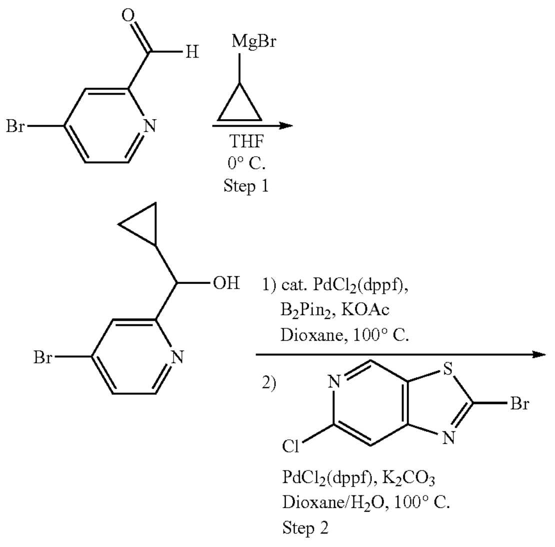

-continued

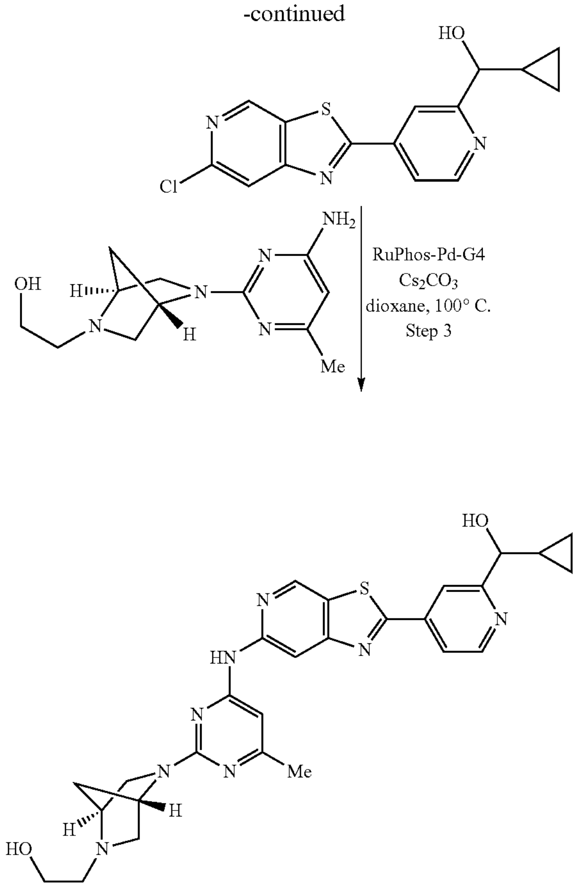

Step 1: 4-Bromopyridin-2-carboxaldehyde (1.30 g, 7 mmol, 1.0 equiv) was suspended in THF (22 mL, 0.3 M) and cooled to 0° C. Cyclopropylmagnesium bromide (0.5 M in THF) was added dropwise (15 mL, 7.7 mmol, 1.1 equiv) and the reaction was warmed to room temperature. When the starting aldehyde was fully consumed, the reaction was quenched with sat. $NH_4Cl$ (aq) and extracted thrice with EtOAc. The combined organic extracts were dried over $MgSO_4$, filtered, and concentrated in vacuo. The crude residue was purified by flash chromatography using a 0-40% EtOAc/hexanes gradient to afford the intermediate alcohol (1.09 g, 4.8 mmol, 68%).

Step 2: These transformations were performed in a similar fashion to step 1 example 120.

Step 3: This transformation was performed in a similar fashion to step 4 of example 301 to obtain the desired product. $^1H$ NMR (400 MHz, Chloroform-d) δ 8.86 (d, J=0.9 Hz, 1H), 8.79 (s, 1H), 8.73 (dd, J=5.2, 0.8 Hz, 1H), 8.12-8.04 (m, 1H), 7.90 (dd, J=5.2, 1.6 Hz, 1H), 7.31 (s, 1H), 6.08 (s, 1H), 4.92 (s, 2H), 4.27 (d, J=7.9 Hz, 1H), 4.12 (s, 1H), 3.81 (d, J=10.5 Hz, 1H), 3.63 (s, 2H), 3.55 (t, J=5.3 Hz, 2H), 3.07 (s, 1H), 2.82-2.74 (m, 3H), 2.29 (s, 3H), 1.98 (s, 1H), 1.90 (d, J=9.1 Hz, 1H), 1.22 (d, J=8.6 Hz, 1H), 0.68-0.58 (m, 4H).

Example 308: 2-[(1S,4S)-5-(4-{2-[2-(cyclopropylmethyl)-4-pyridyl]-3-thia-1,5-diaza-6-indenylamino}-6-methyl-2-pyrimidinyl)-2,5-diazabicyclo[2.2.1]hept-2-yl]ethanol

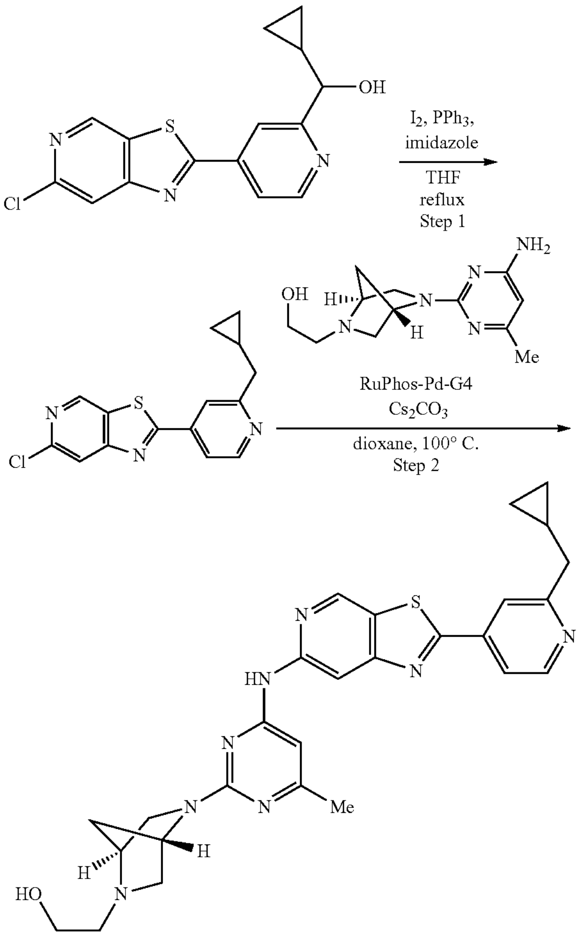

Step 1: The product of step 2, example 307 (261 mg, 0.82 mmol, 1.0 equiv) was dissolved in THF (5 mL, 0.16 M) prior to the sequential addition of $PPh_3$ (258 mg, 0.99 mmol, 1.2 equiv), imidazole (84 mg, 1.2 mmol, 1.5 equiv), and $I_2$ (250 mg, 0.99 mmol, 1.2 equiv). The solution was stirred at reflux (70° C.) for 16 h before cooling the solution to room temperature. The mixture was diluted with $H_2O$ and extracted twice with EtOAc. The combined organic extracts were dried over $MgSO_4$, filtered, and concentrated in vacuo. The crude residue was purified by flash chromatography using a 0-50% EtOAc/hexanes gradient to afford the deoxygenated intermediate (26 mg, 0.09 mmol, 10%).

Step 2: This transformation was performed in a similar fashion to step 4, example 301 to obtain the desired product. $^1H$ NMR (400 MHz, Chloroform-d) δ 8.86 (d, J=0.9 Hz, 1H), 8.72 (dd, J=5.2, 0.8 Hz, 1H), 8.66 (s, 1H), 8.49 (s, 1H), 7.92 (dd, J=1.8, 0.8 Hz, 1H), 7.79 (dd, J=5.1, 1.7 Hz, 1H), 7.46 (s, 1H), 6.20 (s, 1H), 5.01 (s, 1H), 4.15 (s, 1H), 3.99 (d, J=11.9 Hz, 1H), 3.87-3.64 (m, 3H), 3.50 (d, J=10.5 Hz, 1H), 3.13-2.96 (m, 3H), 2.84 (d, J=7.0 Hz, 2H), 2.29 (s, 3H), 2.21 (d, J=10.6 Hz, 1H), 2.09 (d, J=10.4 Hz, 1H), 1.20 (dddd, J=15.1, 10.1, 5.1, 2.4 Hz, 1H), 0.67-0.53 (m, 2H), 0.31 (dt, J=5.9, 4.5 Hz, 2H).

Example 309: 2-{4-[6-(2-{(1S,4S)-5-methyl-2,5-diazabicyclo[2.2.1]hept-2-yl}-6-methyl-4-pyrimidinylamino)-3-thia-1,5-diaza-2-indenyl]-1-methyl-5-pyrazolyl}-2-propanol

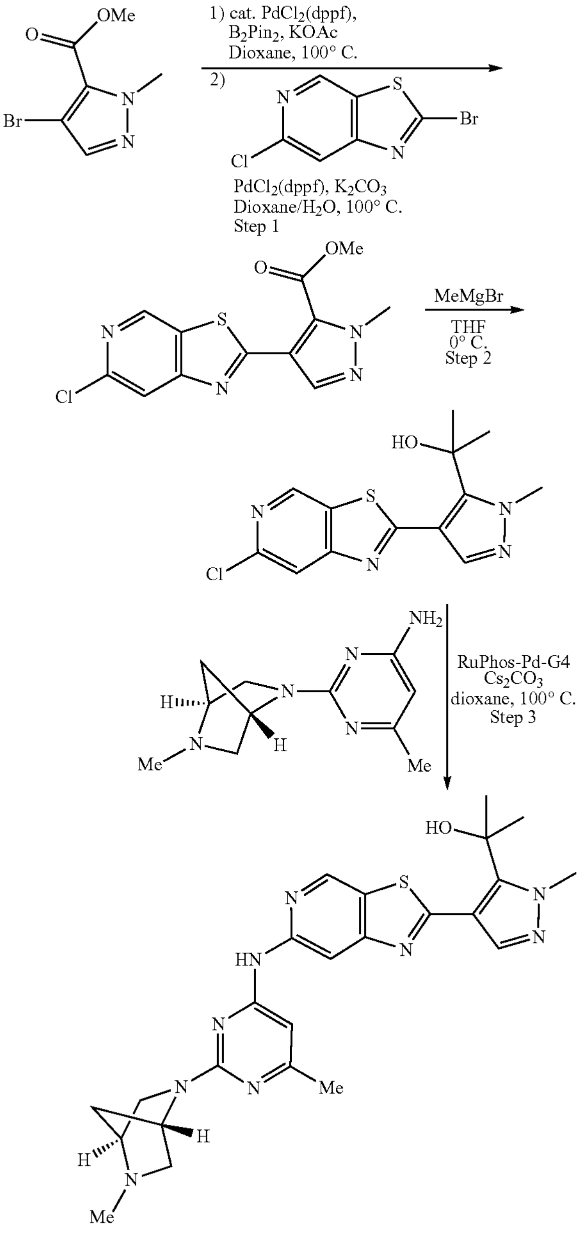

Step 1: These transformations were performed using methyl-4-bromo-1-methyl-1H-pyrazole-5-carboxylate in a similar fashion to step 1, example 120.

Step 2: The intermediate ester from step 1 (0.648 g, 2.1 mmol, 1.0 equiv) was dissolved in THE (10 mL, 0.2 M) and cooled to 0° C. Methylmagnesium bromide solution (3 M in $Et_2O$) was added (2.4 mL, 7.3 mmol, 3.5 equiv) before warming the reaction to room temperature. After the starting ester was fully consumed, the reaction was quenched with sat. $NH_4Cl$ (aq) and extracted twice with EtOAc. The combined organic extracts were dried over $MgSO_4$, filtered, and concentrated in vacuo. The crude residue was purified by flash chromatography using a 0-70% EtOAc/hexanes gradient to afford the dimethylcarbinol intermediate (100 mg, 0.32 mmol, 15% yield).

Step 3: This transformation was performed in a similar fashion to step 4, example 301 to obtain the desired product. $^1H$ NMR (400 MHz, Chloroform-d) δ 8.70 (t, J=0.9 Hz, 1H), 8.65 (d, J=1.0 Hz, 1H), 8.12 (s, 1H), 7.89 (s, 1H), 7.26-7.25 (s, 1H), 6.07 (s, 1H), 4.83 (s, 1H), 4.07 (s, 3H), 3.86 (d, J=10.6 Hz, 1H), 3.55 (s, 1H), 3.47 (d, J=10.6 Hz, 1H), 3.12 (s, 1H), 2.72-2.64 (m, 1H), 2.45 (s, 3H), 2.28 (s, 3H), 2.00 (d, J=9.7 Hz, 1H), 1.87 (d, J=9.8 Hz, 1H), 1.74 (d, J=1.3 Hz, 6H).

Example 310: (2-{(1S,4S)-5-ethyl-2,5-diazabicyclo[2.2.1]hept-2-yl}-6-methyl-4-pyrimidinyl)(2-{m-[(2-oxo-1,3-oxazolidin-3-yl)methyl]phenyl}-3-thia-1,5-diaza-6-indenyl)amine

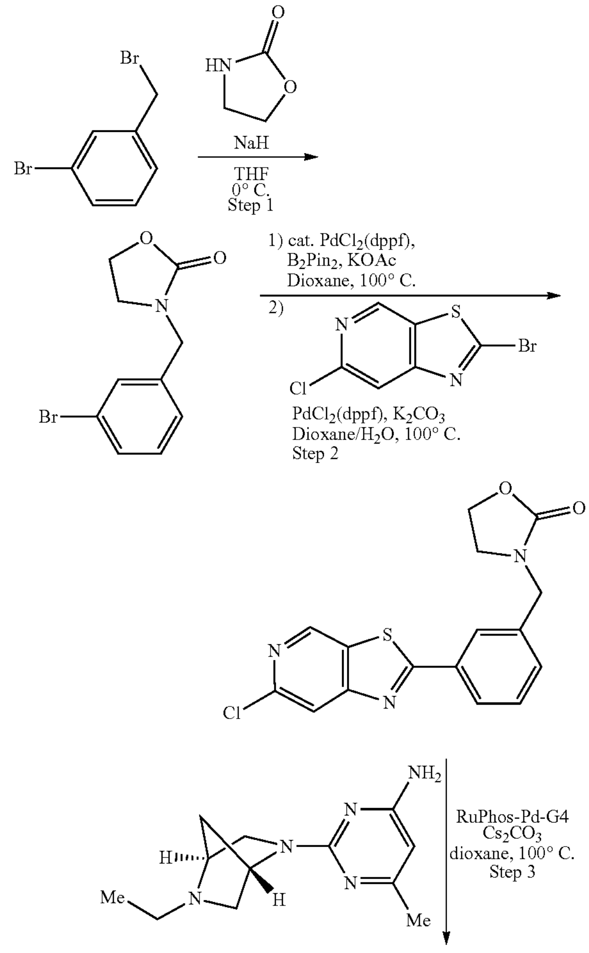

-continued

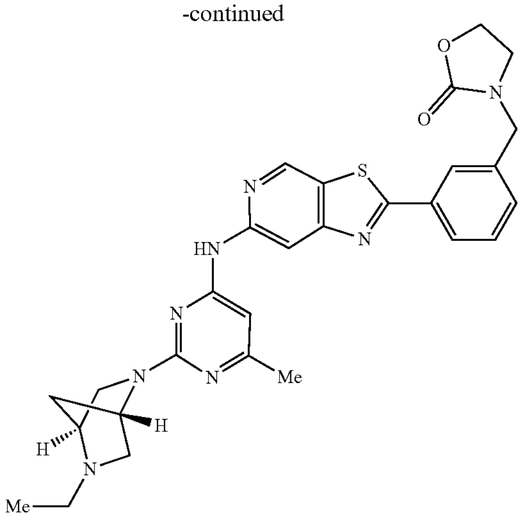

Step 1: Sodium hydride (0.21 g, 5.25 mmol, 1.05 equiv) was suspended in THF (25 mL, 0.2 M) and cooled to 0° C. prior to adding 2-oxazolidinone (0.44 g, 5.0 mmol, 1.0 equiv). After gas stopped evolving, 3-bromobenzyl bromide (1.31 g, 5.25 mmol, 1.05 equiv) was added in a single portion and warmed to room temperature. The reaction was quenched with sat. $NH_4Cl$ (aq) and the mixture was extracted with $CH_2Cl_2$ thrice. The combined organic extracts were dried over $MgSO_4$, filtered, and concentrated in vacuo. The crude residue was purified by flash chromatography using a 0-50% EtOAc/hexanes gradient to afford the alkylated oxazolidinone intermediate as a colorless oil (1.13 g, 4.4 mmol, 84% yield).

Step 2: These transformations were performed using the intermediate from step 1 in a similar fashion to step 1 of example 120.

Step 3: This transformation was performed in a similar fashion to step 4, example 301 to obtain the desired product. $^1H$ NMR (400 MHz, Chloroform-d) δ 8.79 (s, 1H), 8.58 (s, 1H), 8.01 (m, 2H), 7.70 (s, 1H), 7.53-7.41 (m, 2H), 6.17 (s, 1H), 4.93 (s, 1H), 4.52 (s, 2H), 4.43-4.24 (m, 2H), 4.02-3.88 (m, 2H), 3.57 (d, J=11.4 Hz, 1H), 3.53-3.39 (m, 2H), 3.36 (s, 1H), 2.92-2.69 (m, 3H), 2.25 (s, 3H), 2.14 (d, J=10.3 Hz, 1H), 1.96 (d, J=10.2 Hz, 1H), 1.24-1.12 (m, 3H).

Example 311: N-(1-mesyl-4-piperidyl)-N-methylm-[6-(2-{(1S,4S)-5-ethyl-2,5-diazabicyclo[2.2.1]hept-2-yl}-6-methyl-4-pyrimidinylamino)-3-thia-1,5-diaza-2-indenyl]benzamide

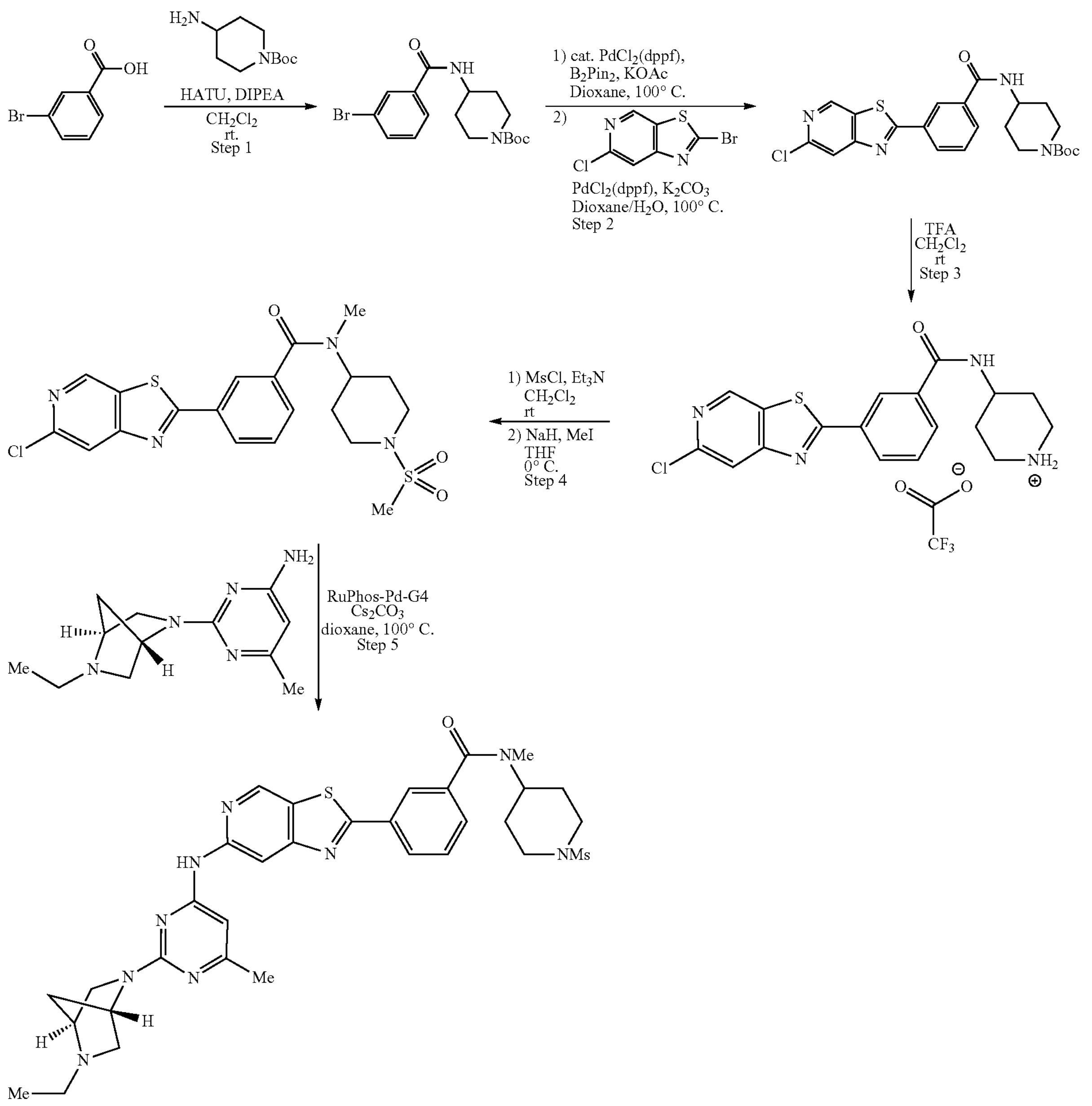

Step 1: This transformation was performed in a similar fashion to step 1, example 305 using appropriate starting materials.

Step 2: This transformation was performed in a similar fashion to step 1, example 120, using intermediate from step 1.

Step 3: Boc-amine product from step 2 (250 mg, 0.53 mmol, 1 equiv) was suspended in $CH_2Cl_2$ before adding TFA (4 mL:1 mL $CH_2Cl_2$:TFA, 0.1 M). The reaction was concentrated under reduced pressure when complete consumption of starting material was observed. Excess TFA was further removed by co-evaporation with $CH_2Cl_2$. The crude residue containing ammonium TFA salt was used in step 4.

Step 4: The crude ammonium salt from step 3 (0.53 mmol, 1 equiv) was dissolved in $CH_2Cl_2$ (11 mL, 0.05 M) before the sequential addition of $Et_3N$ (0.15 mL, 1.1 mmol, 2.0 equiv) and MsCl (0.05 mL, 0.6 mmol, 1.1 equiv). After complete reaction, the solution was concentrated in vacuo. The crude residue was purified by flash chromatography using a 0-15% MeOH/$CH_2Cl_2$ gradient to afford N-mesylated product (227 mg, 0.50 mmol, 95% yield over two steps). This product was redissolved in THE (3 mL, 0.2 M) and cooled to 0° C.

prior to the careful addition of NaH (60% by weight in mineral oil, 23 mg, 0.50 mmol, 1 equiv). After gas stopped evolving, MeI was added before the reaction warmed to room temperature. The reaction was quenched with sat. $NH_4Cl$(aq) and the mixture was extracted with $CH_2Cl_2$ thrice. The combined organic extracts were dried over $MgSO_4$, filtered, and concentrated in vacuo. The crude residue was purified by flash chromatography using a 0-5% MeOH/$CH_2Cl_2$ gradient to afford the N-methylated benzamide intermediate (149 mg, 0.34 mmol, 61% yield).

Step 5: This transformation was performed in a similar fashion to step 5, example 305 using intermediate from step 4. $^1H$ NMR (400 MHz, Chloroform-d) δ 8.81 (s, 1H), 8.62 (s, 1H), 8.15 (s, 2H), 7.55 (dt, J=14.2, 7.8 Hz, 2H), 7.38 (s, 1H), 6.11 (s, 1H), 4.91 (s, 1H), 4.69 (s, 1H), 3.90 (dd, J=26.6, 15.6 Hz, 4H), 3.55 (s, 1H), 3.26 (s, 1H), 3.01 (s, 1H), 2.85 (m, 6H), 2.80-2.42 (m, 4H), 2.27 (s, 3H), 2.08 (d, J=10.5 Hz, 1H), 1.93 (m, 5H), 1.13 (t, J=7.1 Hz, 3H).

Example 312: N-[2-(1-methanesulfonyl-1,2,3,4-tetrahydroquinolin-5-yl)-[1,3]thiazolo[5,4-c]pyridin-6-yl]-6-methyl-2-[(1S,4S)-5-methyl-2,5-diazabicyclo[2.2.1]heptan-2-yl]pyrimidin-4-amine

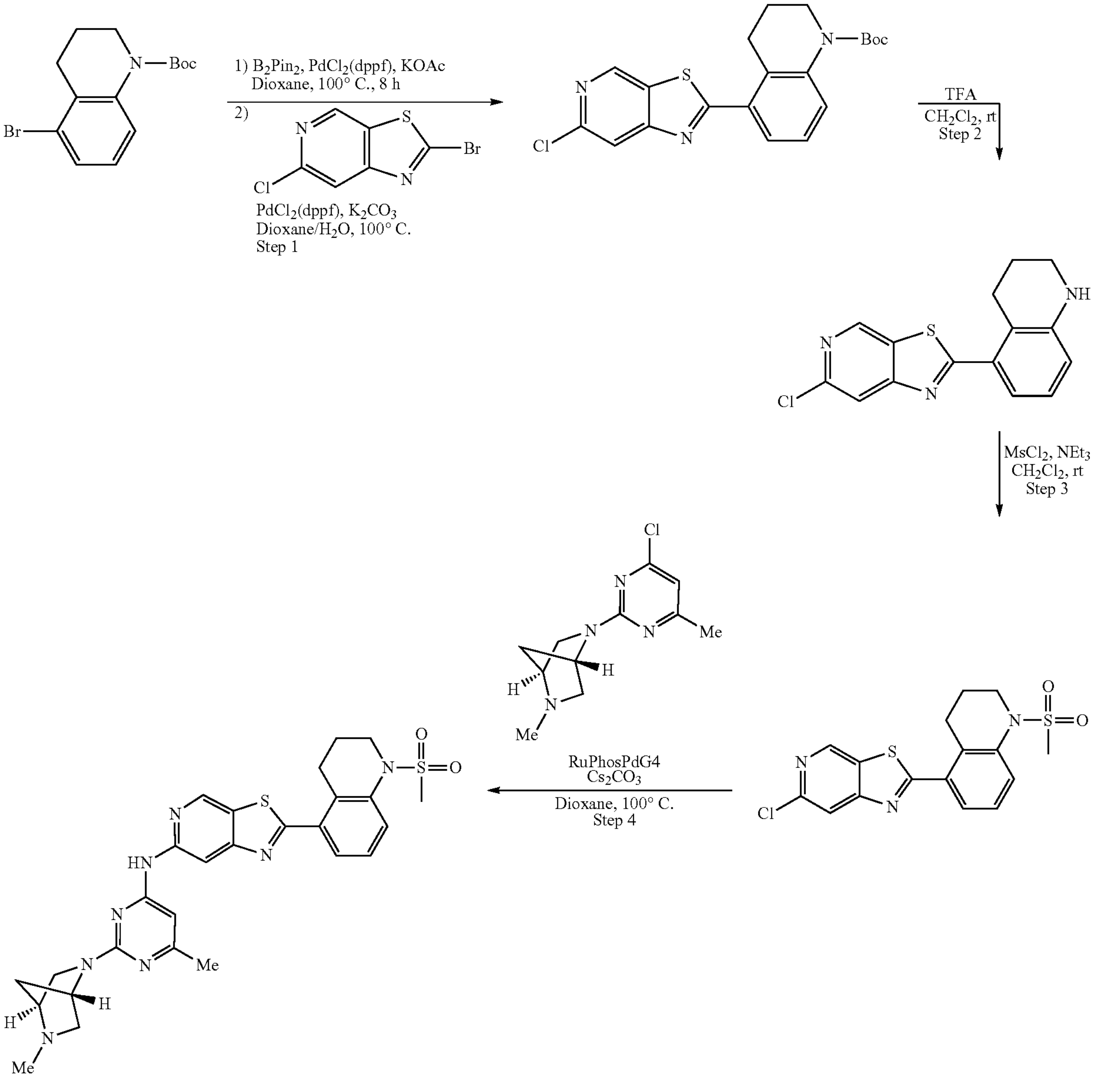

Step 1: This reaction was performed in a similar fashion to step 1 of example 120 from the appropriate starting materials.

Step 2: To a solution of the product of step 1 (168 mg, 0.418 mmol) in $CH_2Cl_2$ (2.1 mL) was added TFA (2.1 mL). The reaction mixture was stirred at r.t. for 2 h and then concentrated. The residue was dissolved in $CH_2Cl_2$ and minimal MeOH then washed with sat. aq. $NaHCO_3$. The aqueous layer was extracted with $CH_2Cl_2$ (2x5 mL), then combined organic layers were washed with brine, dried over anhyd. $Na_2SO_4$, and concentrated to afford the desired product (94 mg; 75%).

Step 3: To a solution of the product of step 2 (50 mg, 0.167 mmol) in $CH_2Cl_2$ (3.3 mL) was added $NEt_3$ (70 μL, 0.498 mmol), followed by dropwise addition of methanesulfonyl chloride (20 μL, 0.249 mmol). The reaction was stirred for 16 h then carefully quenched with sat. aq. $NaHCO_3$. The layers were separated, then the aqueous layer was extracted with $CH_2Cl_2$ (2×10 mL). The combined organic layers were washed with brine, dried over anhyd. $Na_2SO_4$, filtered, and concentrated. The residue was purified by silica gel chromatography (100% hexanes to 50% EtOAc in hexanes to 100% EtOAc) to afford the desired product (36 mg; 57%).

Step 4: This step was performed in a similar fashion to step 6 of example 1, where the amino pyrimidine intermediate was prepared in a manner similar to that described in step 2 of example 120 from the appropriate starting materials. $^1H$ NMR (400 MHz, Chloroform-d) δ 8.85 (t, J=0.7 Hz, 1H), 8.78 (s, 1H), 7.92 (ddd, J=8.4, 1.2, 0.6 Hz, 1H), 7.53-7.45 (m, 1H), 7.38-7.30 (m, 1H), 7.29-7.27 (m, 1H), 6.08 (s, 1H), 4.88 (s, 1H), 3.92-3.81 (m, 3H), 3.57-3.43 (m, 2H), 3.16 (t, J=6.6 Hz, 2H), 3.10-2.99 (m, 1H), 2.97 (s, 3H), 2.70 (d, J=9.5 Hz, 1H), 2.45 (s, 3H), 2.30 (s, 3H), 2.07-1.95 (m, 3H), 1.89-1.81 (m, 1H). ESI MS $[M+H]^+$ for $C_{27}H_{31}N_8O_2S_2$, calcd 563.2, found 563.2.

Example 313: 6-methyl-2-[(1S,4S)-5-methyl-2,5-diazabicyclo[2.2.1]heptan-2-yl]-N-[2-(1,2,3,4-tetrahydroquinolin-5-yl)-[1,3]thiazolo[5,4-c]pyridin-6-yl]pyrimidin-4-amine

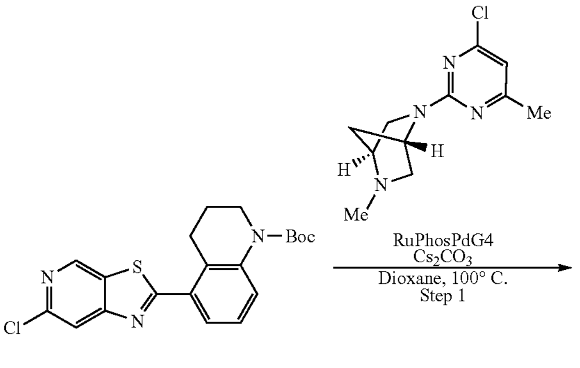

-continued

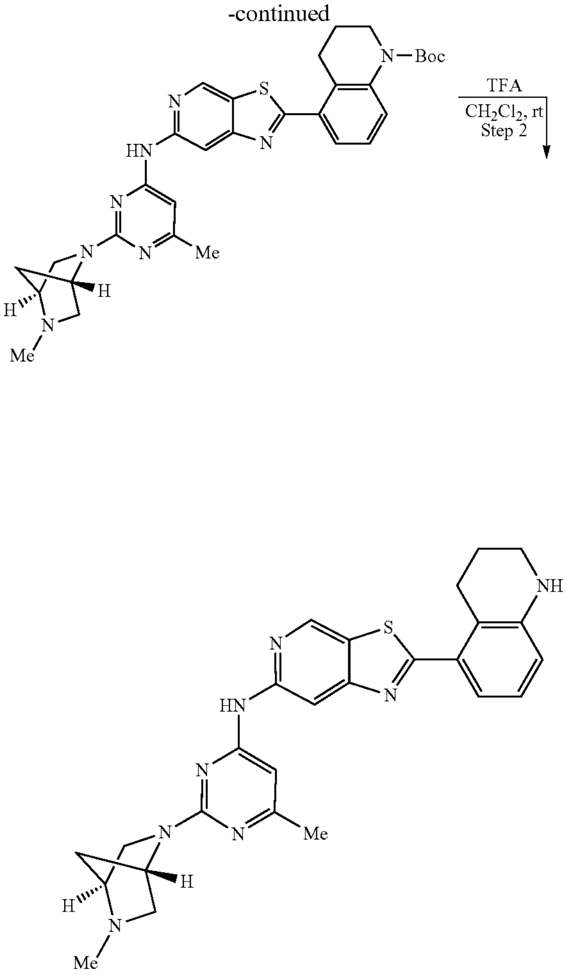

Step 1: This step was performed in a similar fashion to step 6 of example 1, where the amino pyrimidine intermediate was prepared in a manner similar to that described in step 2 of example 120 from the appropriate starting materials.

Step 2: To a solution of the crude product of step 1 (0.127 mmol) in $CH_2Cl_2$ (2.1 mL) was added TFA (2.1 mL). The reaction stirred for 2 h at r.t. and then was concentrated. Purification by reverse phase HPLC (10-90% ACN in $H_2O$, 0.1% TFA), neutralization by passing through a bicarbonate cartridge, and lyophilization provided the title compound. $^1H$ NMR (400 MHz, Chloroform-d) δ 8.82 (d, J=0.9 Hz, 1H), 8.73 (s, 1H), 7.25 (s, 1H), 7.08 (t, J=7.8 Hz, 1H), 7.00 (dd, J=7.6, 1.3 Hz, 1H), 6.63 (dd, J=8.0, 1.3 Hz, 1H), 6.10 (s, 1H), 4.88 (d, J=2.3 Hz, 1H), 4.08 (s, 1H), 3.89 (d, J=10.5 Hz, 1H), 3.53 (s, 1H), 3.39-3.30 (m, 2H), 3.12-2.99 (m, 3H), 2.68 (d, J=9.5 Hz, 1H), 2.44 (s, 3H), 2.30 (s, 3H), 2.01-1.89 (m, 3H), 1.85 (d, J=9.5 Hz, 1H). ESI MS $[M+H]^+$ for $C_{26}H_{29}N_8S$, calcd 485.2, found 485.2.

Example 314: 5-{6-[2-(3-methyl-2-pyridyl)-3-thia-1,5-diaza-6-indenylamino]-2-pyridyl}-2-azabicyclo[2.2.1]heptan-5-ol and Example 315: {6-(5-fluoro-2-azabicyclo[2.2.1]hept-5-yl)-2-pyridyl}[2-(3-methyl-2-pyridyl)-3-thia-1,5-diaza-6-indenyl]amine

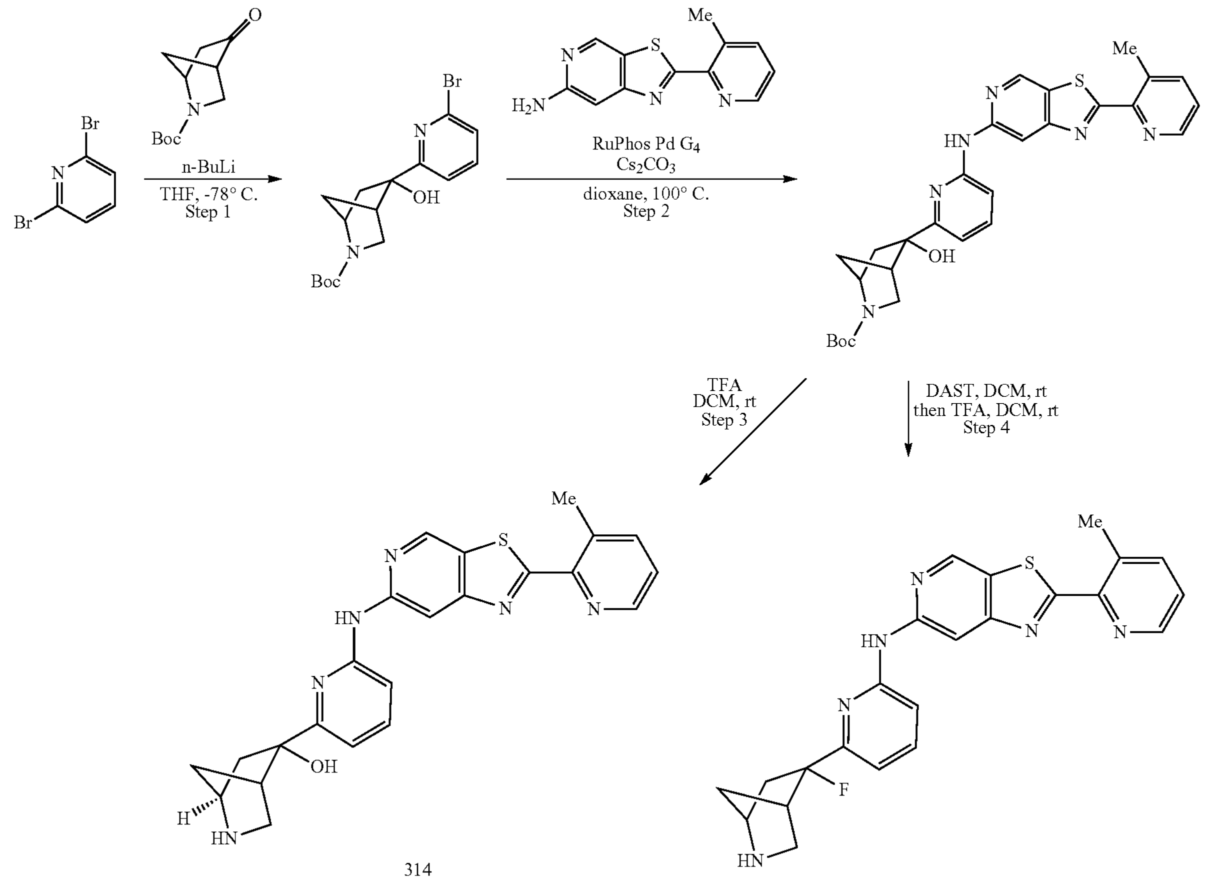

314

315

Step 1: A round-bottom flask was charged with 2,6-dibromopyridine (355 mg, 1.50 mmol) and 8 mL of THF. After cooling to −78° C., nBuLi (0.60 mL, 1.50 mmol) was added and the reaction was stirred for 15 min at −78° C. before addition of a solution of 1,1-dimethylethyl-5-oxo-2-azabicyclo[2.2.1]heptane-2-carboxylate (211 mg, 1.0 mmol) in 2 mL of THF. The reaction mixture was then stirred at −78° C. for an additional 30 minutes. The reaction was quenched with sat. $NH_4C_1$ and extracted with EtOAc. The combined organic extract was washed with sat. sol. NaCl and the solvent was evaporated. The residue was purified using column chromatography on silica gel (Hex/EtOAc—10%→40%) to afford the desired product.

Step 2: This step was performed similar to step 6, example 1 using intermediate obtained from the above step.

Step 3: A round-bottom flask was charged with product from step 2 (55 mg, 0.104 mmol) and 1 mL of DCM. TFA (0.2 mL) was then added, and the mixture was stirred at r.t. for 1 hour. The reaction was quenched with sat. sol. $NaHCO_3$ and extracted with DCM. The combined organic extract was washed with sat. sol. NaCl and the solvent was evaporated. The residue was purified by reversed phase HPLC to afford the desired product (Example 314). $^1$H NMR (400 MHz, DMSO-$d_6$) δ 8.96 (d, J=2.4, 2H), 8.57 (d, J=4.4 Hz, 1H), 7.90-7.84 (m, 2H), 7.49 (dd, J=7.8, 4.6 Hz, 1H), 7.23 (d, J=8.6 Hz, 1H), 5.96 (d, J=8.5 Hz, 1H), 4.51 (s, 1H), 3.79 (s, 3H), 3.54 (s, 1H), 3.48-3.44 (m, 1H), 3.37 (dd, J=9.6, 2.2 Hz, 1H), 2.90 (dd, J=9.6, 2.0 Hz, 1H), 2.82 (s, 3H), 2.71 (d, J=9.6 Hz, 1H), 2.31 (s, 3H), 1.92 (d, J=9.5 Hz, 1H), 1.84 (d, J=9.7 Hz, 1H). ESI MS $[M+H]^+$ for $C_{24}H_{25}N_7OS$, calcd 460.2, found 460.1.

Step 4: A round-bottom flask was charged with product from step 2 (26 mg, 0.049 mmol) and 1 mL of DCM. At 0° C., DAST (31.6 mg, 0.196 mmol) was added and the reaction was stirred for 2 hours at the same temperature. The reaction was quenched with sat. sol. $NaHCO_3$ and extracted with DCM. The combined organic extract was washed with sat. sol. NaCl and the solvent was evaporated. The crude material was dissolved in 1 mL of DCM and TFA (0.2 mL) was then added, and the mixture was stirred at r.t. for 1 hour. The reaction was quenched with sat. sol. $NaHCO_3$ and extracted with DCM. The combined organic extract was washed with sat. sol. NaCl and the solvent was evaporated. The residue was purified by reversed phase HPLC to afford the desired product (Example 315). $^{1}$H NMR (400 MHz, DMSO-$d_6$) δ 10.05 (s, 1H), 9.03 (d, J=0.8 Hz, 1H), 8.62-8.57 (m, 1H), 8.53-8.47 (m, 1H), 8.34 (s, 1H), 7.91-7.87 (m, 1H), 7.73 (d, J=7.8 Hz, 1H), 7.57 (d, J=8.4 Hz, 1H), 7.51 (dd, J=7.7, 4.6 Hz, 1H), 7.11 (d, J=7.4 Hz, 1H), 3.93 (s, 1H), 3.06 (s, 1H), 2.85 (s, 5H), 2.66 (d, J=11.3 Hz, 1H), 2.22-2.07 (m, 2H), 1.78 (d, J=10.2 Hz, 1H).

Example 316: (8R)-8-methyl-$N_2$-[2-(3-methylpyridin-2-yl)-[1,3]thiazolo[5,4-c]pyridin-6-yl]-5,6,7,8-tetrahydroquinoline-2,8-diamine

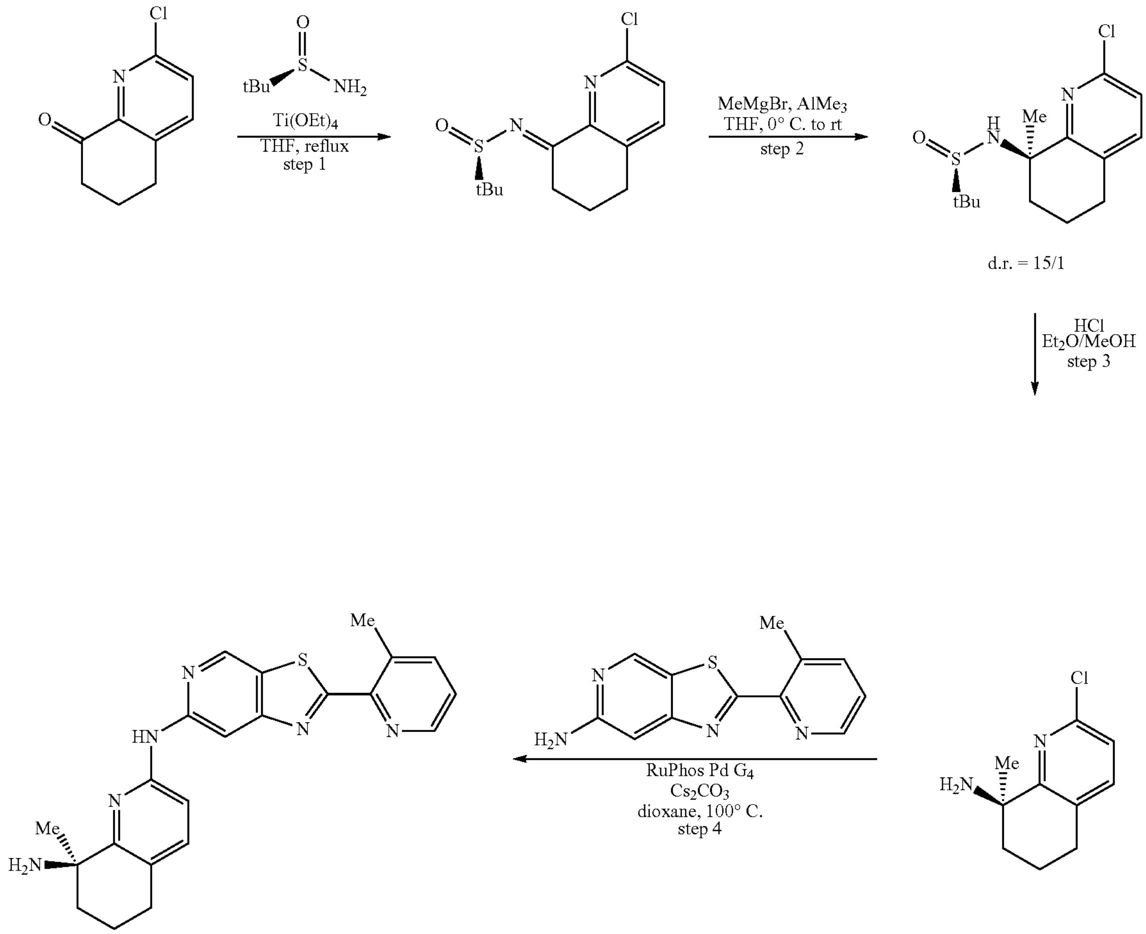

Step 1: A vial was charged with 2-chloro-6,7-dihydro-8(5H)-quinolinone (500 mg, 2.75 mmol), (R)-2-methyl-propane-2-sulfinamide (500 mg, 4.13 mmol) and 14 mL of THF. After addition of $Ti(OEt)_4$ (0.87 ml, 4.13 mmol) the mixture was stirred at reflux for 45 min. The reaction mixture was then quenched with $NH_4Cl$ sat. and extracted with EtOAc. The combined organic extract was washed with sat. sol. NaCl and the solvent was evaporated. The residue was purified using column chromatography on silica gel (Hex/EtOAc—20%→50%) to afford the product (392 mg, 50%).

Step 2: A vial was charged with product from step 1 (445 mg, 1.56 mmol) and 8 mL of toluene. $AlMe_3$ (1.6 ml, 3.12 mmol) was then added at 0° C. and the mixture was stirred for 10 min before addition of MeMgBr (1.6 ml, 4.68 mmol). The reaction mixture was allowed to warm up to room temp. overnight before being quenched by $NH_4Cl$ sat. and extracted with EtOAc. The combined organic extract was washed with sat. sol. NaCl and the solvent was evaporated. The residue was purified using column chromatography on silica gel (Hex/EtOAc—20%→70%) to afford the product (341 mg, 73%).

Step 3: A vial was charged with product from step 2 (341 mg, 1.14 mmol) and 10 mL of MeOH. HCl (1M in $Et_2O$, 3 ml, 3.0 mmol) was then added and the mixture was stirred for 30 min at room temperature. The mixture was quenched with sat. sol. $NaHCO_3$ and extracted with DCM. The combined organic extract was washed with sat. sol. NaCl and the solvent was evaporated. The residue was purified using column chromatography on silica gel (DCM/MeOH—0%→10%) to afford the product (189 mg, 85%).

Step 4: The title compound was synthesized in a similar fashion to step 3, example 120. $^{1}$H NMR (400 MHz, DMSO-$d_6$) δ 9.76 (s, 1H), 8.99 (d, J=0.9 Hz, 1H), 8.62-8.57 (m, 2H), 8.35 (s, 1H), 7.89 (ddd, J=7.7, 1.6, 0.8 Hz, 1H), 7.51 (dd, J=7.8, 4.6 Hz, 1H), 7.36 (m, d, J=8.4 Hz, 1H), 7.27 (d, J=8.4 Hz, 1H), 2.85 (s, 3H), 2.66-2.60 (m, 2H), 1.91-1.81 (m, 3H), 1.73 (m, 1H), 1.49 (s, 3H). ESI MS $[M+H]^+$ for $C_{22}H_{22}N_6S$, calcd 403.2, found 403.1.

Example 317: (8R)-N2-[2-(3-methylpyridin-2-yl)-[1,3]thiazolo[5,4-c]pyridin-6-yl]-5,6,7,8-tetrahydro-quinoline-2,8-diamine

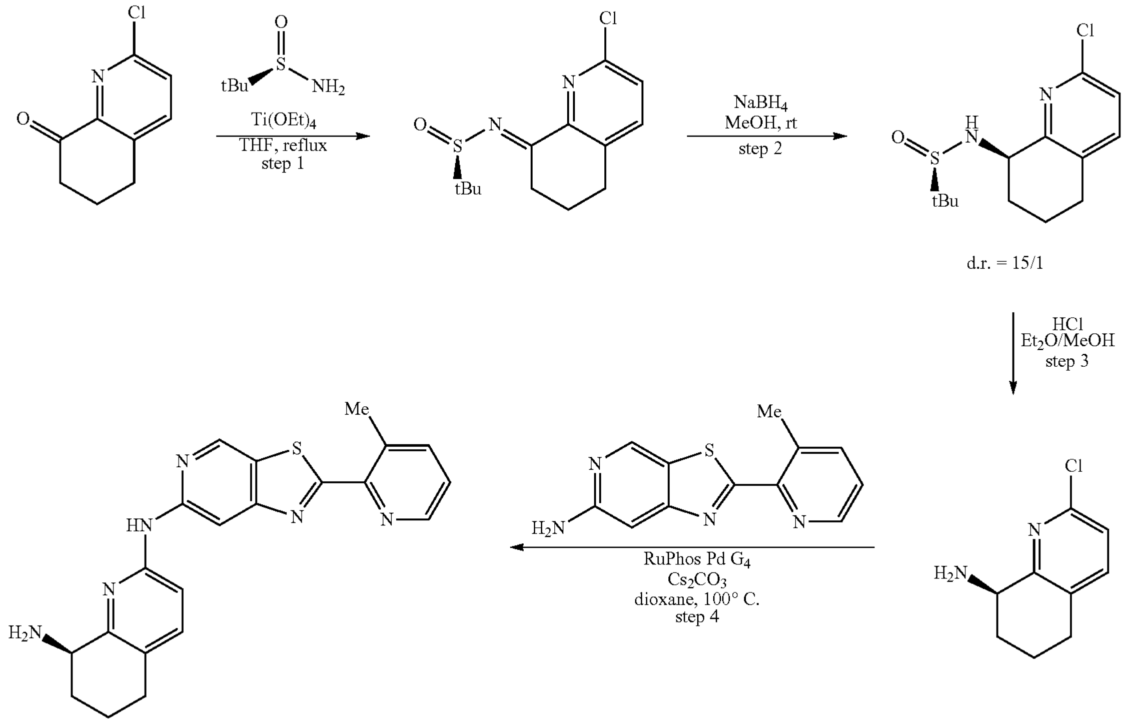

Step 1: A vial was charged with 2-chloro-6,7-dihydro-8(5H)-quinolinone (500 mg, 2.75 mmol), (R)-2-methyl-propane-2-sulfinamide (500 mg, 4.13 mmol) and 14 mL of THF. After addition of $Ti(OEt)_4$ (0.87 ml, 4.13 mmol) the mixture was stirred at reflux for 45 min. The reaction mixture was then quenched with sat. sol. $NH_4Cl$ and extracted with EtOAc. The combined organic extract was washed with sat. sol. NaCl and the solvent was evaporated. The residue was purified using column chromatography on silica gel (Hex/EtOAc—20%→50%) to afford the product (392 mg, 50%).

Step 2: A vial was charged with product from step 1 (254 mg, 0.89 mmol) and 9 mL of MeOH. $NaBH_4$ (34 mg, 0.89 mmol) was then added, and the mixture was stirred for 30 min at room temperature. The reaction was quenched with sat. sol. $NH_4Cl$ and extracted with EtOAc. The combined organic extract was washed with sat. sol. NaCl and the solvent was evaporated. The residue was purified using column chromatography on silica gel (Hex/EtOAc—20%→60%) to afford the product (204 mg, 80%).

Step 3: A vial was charged with product from step 2 (204 mg, 0.71 mmol) and 10 mL of MeOH. HCl (1M in $Et_2O$, 3 ml, 3.0 mmol) was then added and the mixture was stirred for 30 min at room temperature. The mixture was quenched with sat. sol. $NaHCO_3$ and extracted with DCM. The combined organic extract was washed with sat. sol. NaCl and the solvent was evaporated. The residue was purified using column chromatography on silica gel (DCM/MeOH—0%→10%) to afford the product (113 mg, 87%).

Step 4: The title compound was synthesized in a similar fashion to step 3, example 120. $^1H$ NMR (400 MHz, DMSO-$d_6$) δ 9.71 (s, 1H), 8.98 (d, J=0.9 Hz, 1H), 8.60-8.56 (m, 1H), 8.49 (d, J=0.9 Hz, 1H), 7.89 (ddd, J=7.8, 1.7, 0.8 Hz, 1H), 7.51 (dd, J=7.8, 4.6 Hz, 1H), 7.38-7.30 (m, 2H), 3.83 (t, J=6.3 Hz, 1H), 2.84 (s, 3H), 2.66-2.59 (m, 2H), 2.01 (m, 1H), 1.88 (m, 1H), 1.68-1.54 (m, 2H). ESI MS $[M+H]^+$ for $C_{21}H_{20}N_6S$, calcd 389.2, found 389.2.

Example 318: 2-[(1S,4S)-5-{6-methyl-4-[2-(3-methyl-2,3'-bipyridyl-5'-yl)-3-thia-1,5-diaza-6-indenylamino]-2-pyrimidinyl}-2,5-diazabicyclo[2.2.1]hept-2-yl]ethanol

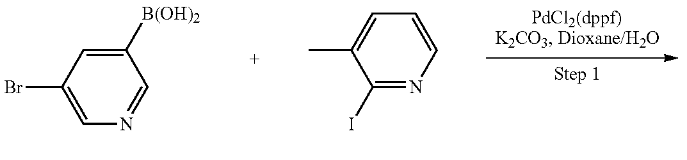

-continued

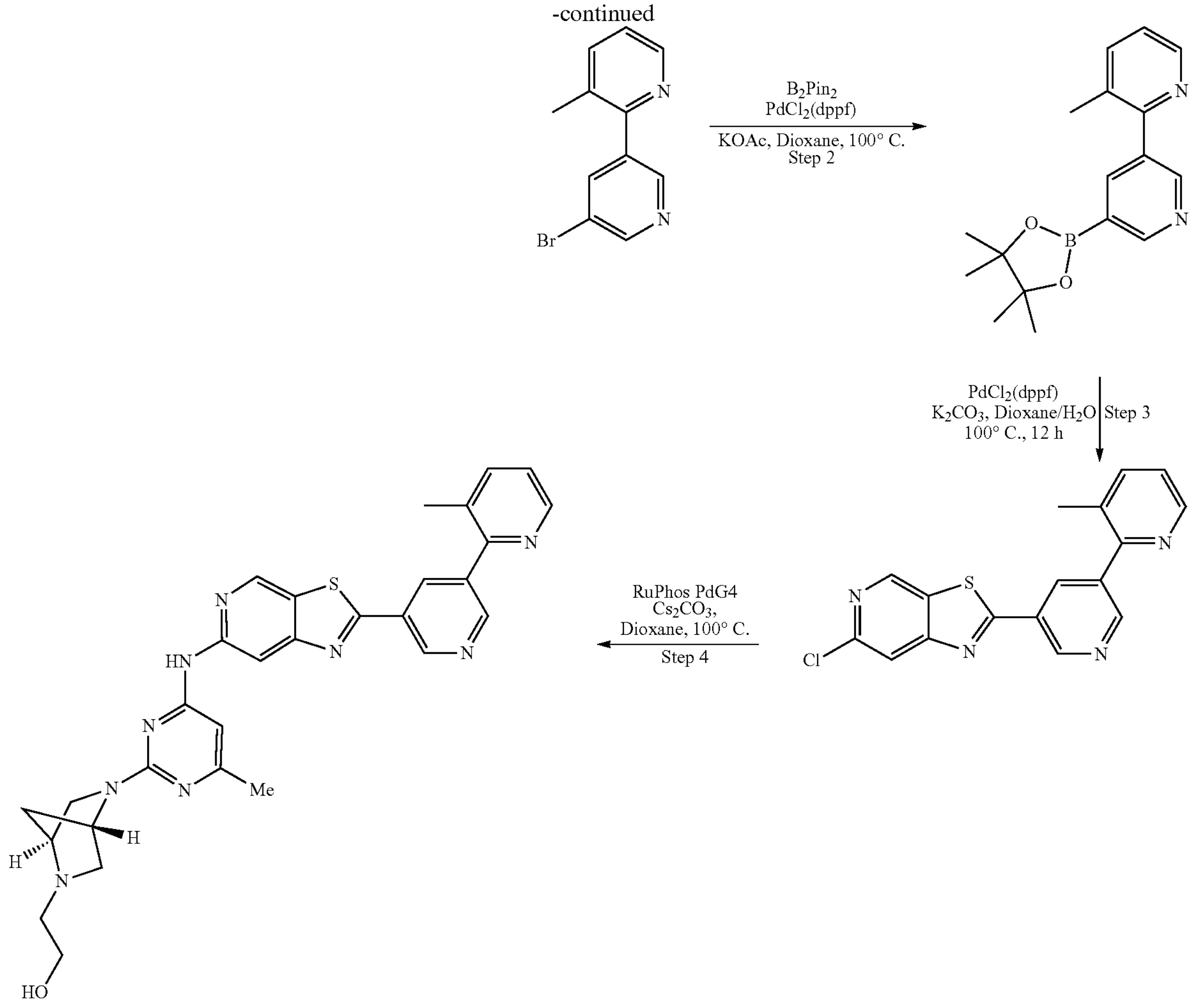

Step 1: To a solution of iodo intermediate (1.1 g, 5.0 mmol) and boronic acid (1.0 g, 5.0 mmol) in dioxane (20 mL)/$H_2O$ (5 mL) was added $PdCl_2$(dppf) (731 mg, 1 mmol) and $K_2CO_3$ (1.4 g, 10 mmol). After degassing for 10 min with $N_2$, the reaction mixture was heated to 100° C. and stirred for 4 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 50% EtOAc in hexanes) to afford the imine intermediate (0.8 g, 62%). Steps 2-4 were performed in a similar manner to steps 1-3 of example 120.

Example 319: [2-(3,3-difluoro-1-pyrrolidinyl)-6-(3-pyrrolidinyl)-4-pyrimidinyl][2-(3-methyl-2-pyridyl)-3-thia-1,5-diaza-6-indenyl]amine

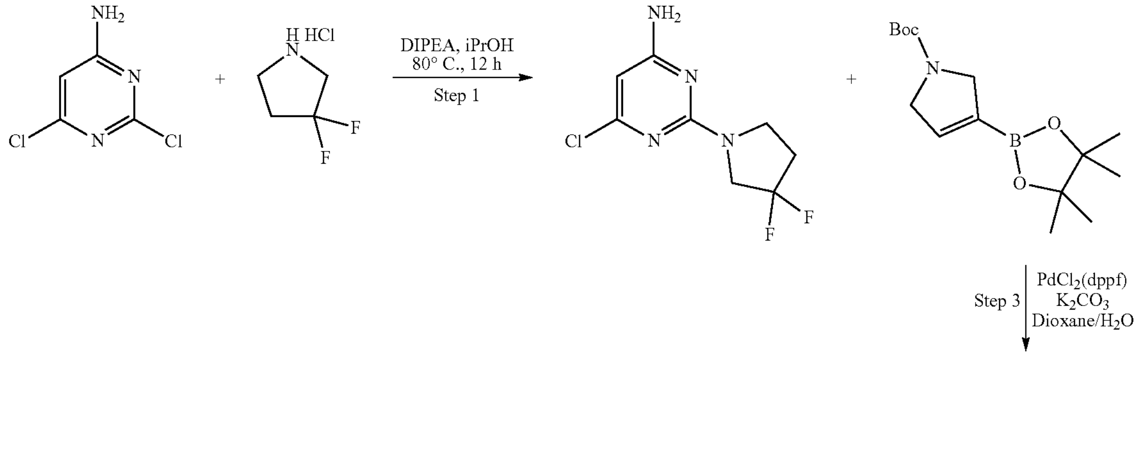

-continued

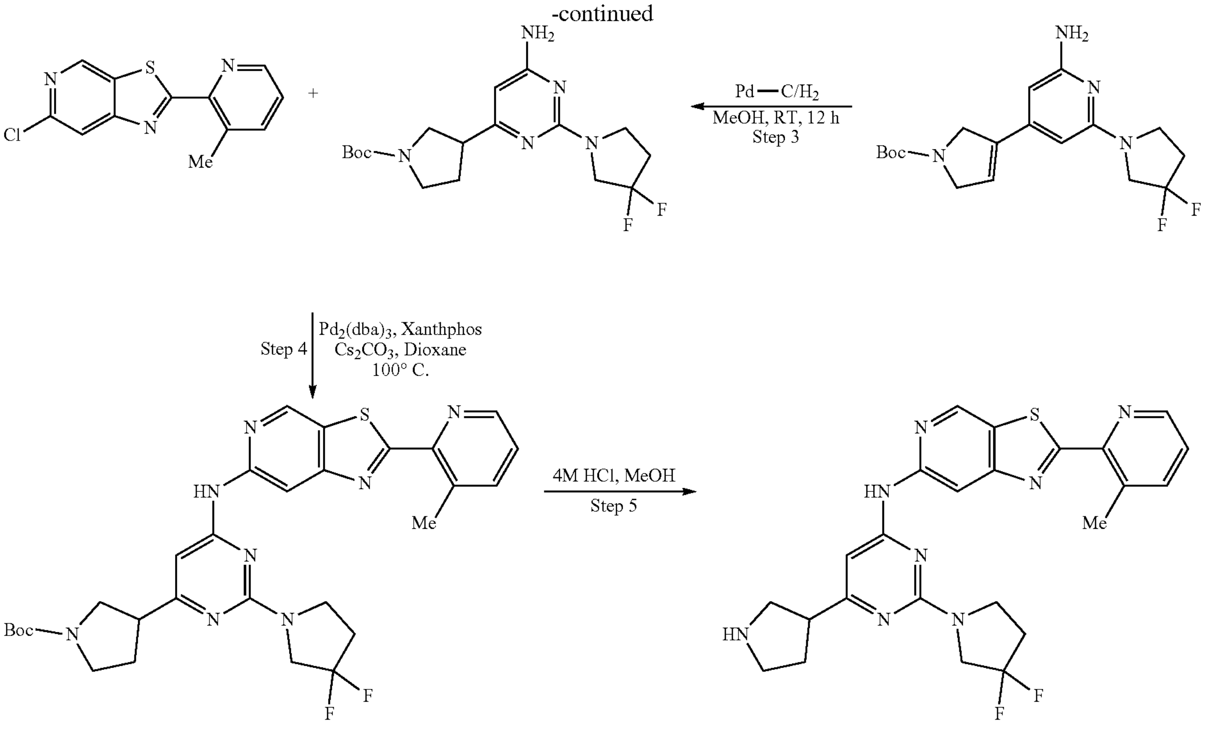

Step 1: To a solution of 4-amino-2,6-dichloropyrimidine (1.63 g, 10 mmol) in anhydrous 2-propanol (100 mL) was added N,N'-diisopropylethylamine (8.6 mL, 50 mmol) and secondary amine derivative (1.74 g, 12.2 mmol). The solution was heated to 80° C. and stirred for 12 hours. The reaction mixture was allowed to cool to room temperature before dilution with water (100 mL) and subsequent extraction with ethyl acetate (100 mL). The organic extract was washed with water (100 mL×2) and brine (100 mL), dried over anhydrous sodium sulfate, and filtered. The resulting filtrate was concentrated in vacuo to obtain the crude product which was next purified by flash chromatography (0-100% ethyl acetate in hexanes over 10 column volumes) to obtain the desired intermediate (1.85 g, 79%).

Step 2: To a stirred solution of pyridyl ether derivative from step 1 (1.8 g, 7.4 mmol) and boronic ester (2.4 g, 8.2 mmol) in dioxane (30 mL)/$H_2O$ (8 mL) was added $PdCl_2$(dppf) (1.1 g, 1.48 mmol) and $K_2CO_3$ (2.0 g, 15 mmol). After degassing for 10 min with $N_2$, the reaction mixture was heated to 100° C. and stirred for 4 h. The reaction mixture was cooled down to RT, diluted with water and extracted with EtOAc. The combined organic layers were dried over $Na_2SO_4$ and concentrated in vacuo. The residue was purified by flash column chromatography (silica gel; gradient: 0% to 50% EtOAc in hexanes) to get imine intermediate (2.4 g, 67%).

Step 3: In a Parr hydrogenator, a solution of unsaturated derivative from step 2 (2.3 g, 6.3 mmol) in methanol (100 mL) was added Pd/C (20%). After stirring at 40 psi $H_2$ atmosphere for 24 h, the reaction mixture was filtered through Celite®. The filtrate was concentrated under reduced pressure to obtain the desired intermediate (2.0 g, 87%) and used in the next step without purification.

Step 4: To a stirred solution of azabenzothiazole derivative (104 mg, 0.4 mmol) and amine from step 3 (146 mg, 0.4 mmol) in dioxane (5 ml) was added $Pd_2(dba)_3$ (36 mg, 0.04 mmol), Xanthphos (46 mg, 0.08 mmol) and $Cs_2CO_3$ (390 mg, 1.2 mmol). The reaction mixture was heated to 100° C. and stirred for 12 h. The reaction mixture was filtered through Celite® and purified by flash column chromatography (silica gel; gradient: 0% to 100% EtOAc in hexanes) to get the desired azabenzothiazole-ether derivative.

Step 5: To a stirred solution of Boc protected derivative from step 4 (65 mg) in MeOH (5 ml) was added 4M HCl (in dioxane) and stirred at RT until complete consumption of starting material. The reaction mixture was concentrated in vacuo and purified by HPLC to obtain the desired product. $^1H$ NMR (400 MHz, DMSO-$d_6$) δ 10.04 (s, 1H), 9.02 (s, 1H), 8.73 (s, 1H), 8.62-8.51 (m, 1H), 7.97-7.81 (m, 1H), 7.49 (dd, J=7.8, 4.6 Hz, 1H), 6.57 (s, 1H), 3.91 (t, J=13.2 Hz, 2H), 3.75 (t, J=7.2 Hz, 2H), 3.56 (t, J=9.0 Hz, 1H), 3.38 (m, 3H), 3.31 (m, 1H), 3.07 (t, J=7.9 Hz, 1H), 2.82 (s, 3H), 2.54 (dt, J=14.4, 7.2 Hz, 1H), 2.13 (m, 2H). ESI MS $[M+H]^+$ for $C_{24}H_{24}F_2N_8S$, calcd 494.18, found 494.2.

Examples 320-586 were prepared in an analogous manner as in procedures described above, and as indicated in Table 3 below, from the appropriate starting materials.
TABLE 3
| Example No. | Chemical Structure | [M + H] Calcd. | [M + H] Found | Analogous Procedure Example No. |
|---|---|---|---|---|
| 320 | 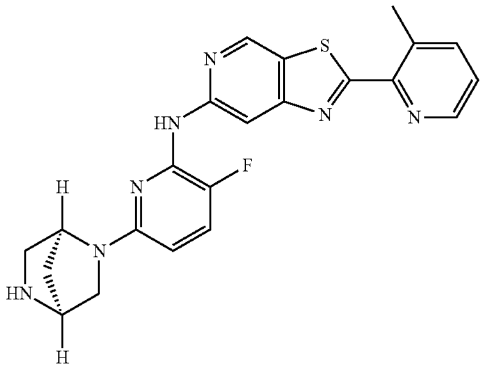 [SMILES: Cc1cccnc1-c1nc2cc(Nc3nc(N4C[C@@H]5C[C@H]4CN5)ccc3F)ncc2s1] | 434.1 | 434.1 | 65 |
| 321 | 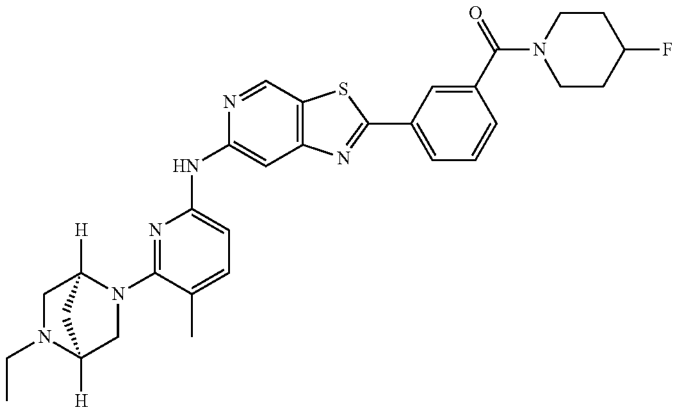 [SMILES: CCN1C[C@@H]2C[C@H]1CN2c1nc(Nc2cc3nc(-c4cccc(C(=O)N5CCC(F)CC5)c4)sc3cn2)ccc1C] | 572.3 | 572.3 | 89 |
| 322 | 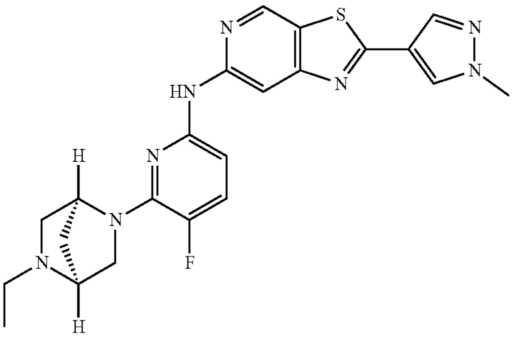 [SMILES: CCN1C[C@@H]2C[C@H]1CN2c1nc(Nc2cc3nc(-c4cnn(C)c4)sc3cn2)ccc1F] | 451.2 | 451.2 | 89 |

TABLE 3-continued
| Example No. | Chemical Structure | [M + H] Calcd. | [M + H] Found | Analogous Procedure Example No. |
|---|---|---|---|---|
| 323 | 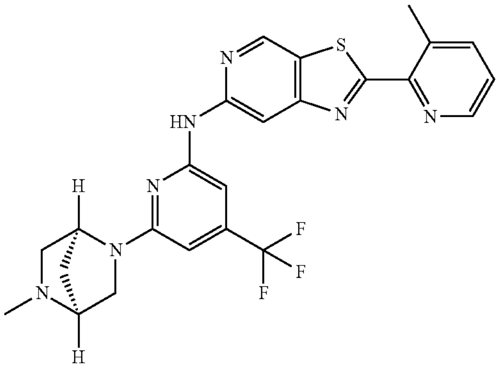 [SMILES: Cc1cccnc1-c1nc2cc(Nc3cc(C(F)(F)F)cc(N4C[C@@H]5C[C@H]4CN5C)n3)ncc2s1] | 498.2 | 498.2 | 89 |
| 324 | 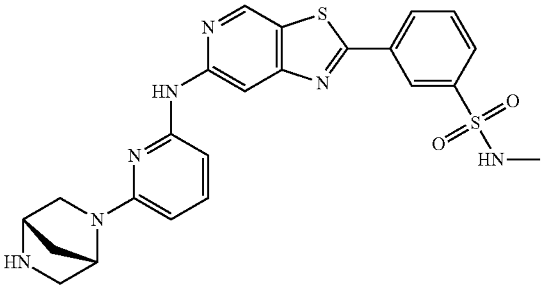 | 494.1 | 494.1 | 89 |
| 325 | 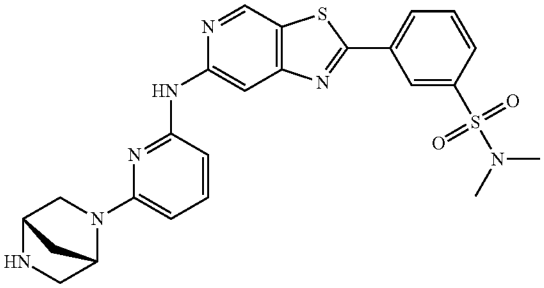 | 508.2 | 508.2 | 89 |
| 326 | 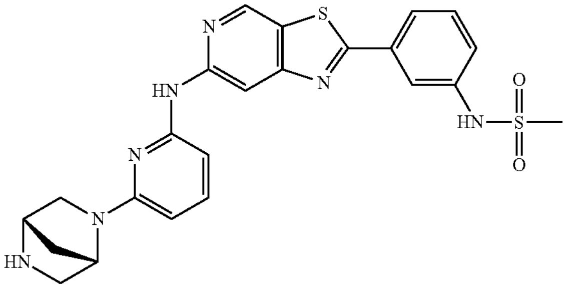 [SMILES: CS(=O)(=O)Nc1cccc(-c2nc3cc(Nc4cccc(N5C[C@@H]6C[C@H]5CN6)n4)ncc3s2)c1] | 494.1 | 494.1 | 89 |

TABLE 3-continued
| Example No. | Chemical Structure | [M + H] Calcd. | [M + H] Found | Analogous Procedure Example No. |
|---|---|---|---|---|
| 327 | 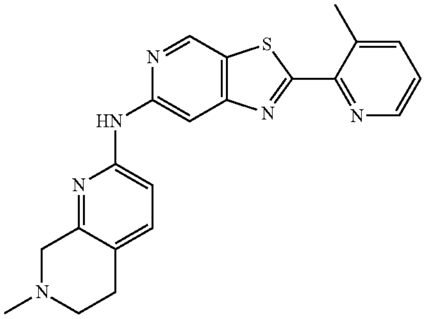 [SMILES: Cc1cccnc1-c1nc2cc(Nc3ccc4c(n3)CN(C)CC4)ncc2s1] | 389.1 | 389.2 | 115 |
| 328 | 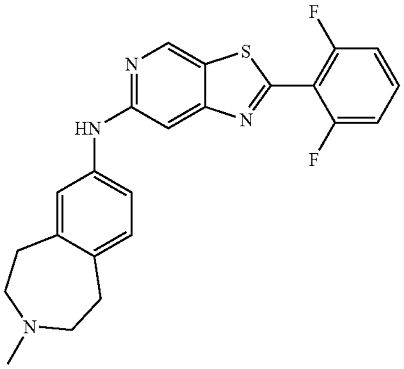 [SMILES: CN1CCc2ccc(Nc3cc4nc(-c5c(F)cccc5F)sc4cn3)cc2CC1] | 423.1 | 423.2 | 115 |
| 329 | 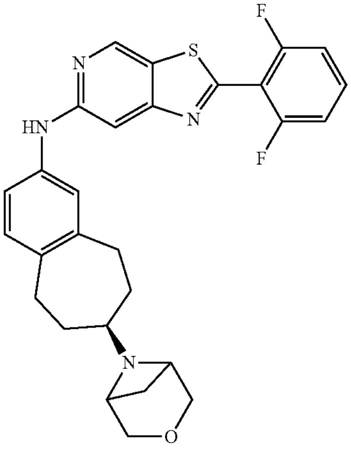 [SMILES: Fc1cccc(F)c1-c1nc2cc(Nc3ccc4c(c3)CC[C@@H](N3C5COCC3C5)CC4)ncc2s1] | 505.2 | 505.3 | 115 |
| 330 | 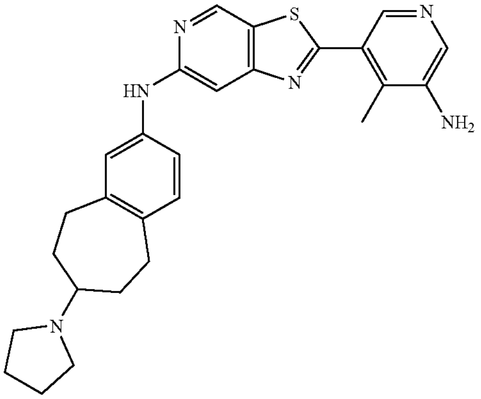 [SMILES: Cc1c(N)cncc1-c1nc2cc(Nc3ccc4c(c3)CCC(N3CCCC3)CC4)ncc2s1] | 471.2 | 471.2 | 115 |

TABLE 3-continued
| Example No. | Chemical Structure | [M + H] Calcd. | [M + H] Found | Analogous Procedure Example No. |
|---|---|---|---|---|
| 331 | 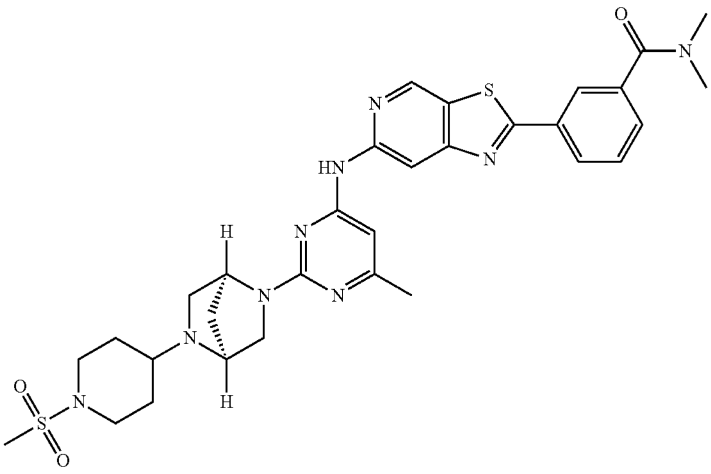 | 648.2 | 648.3 | 116 |
| 332 | 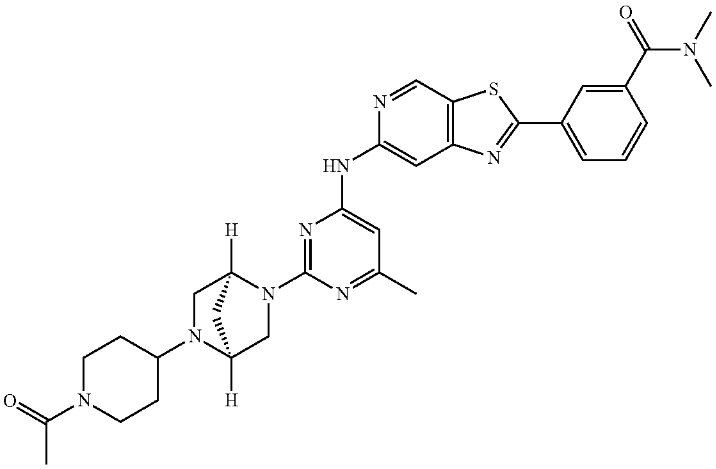 [SMILES: CC(=O)N1CCC(N2C[C@@H]3C[C@H]2CN3c2nc(C)cc(Nc3cc4nc(-c5cccc(C(=O)N(C)C)c5)sc4cn3)n2)CC1] | 612.3 | 612.3 | 116 |
| 333 | 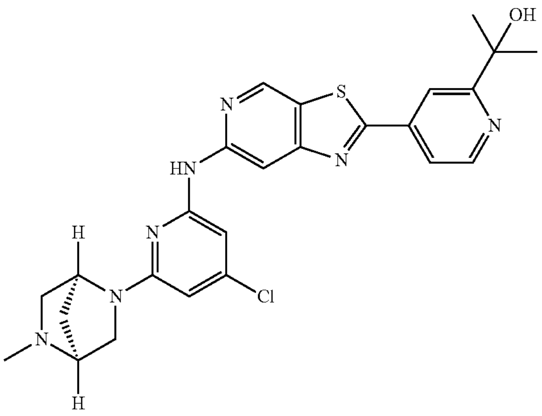 [SMILES: CN1C[C@@H]2C[C@H]1CN2c1cc(Cl)cc(Nc2cc3nc(-c4ccnc(C(C)(C)O)c4)sc3cn2)n1] | 508.2 | 508.2 | 119 |

TABLE 3-continued
| Example No. | Chemical Structure | [M + H] Calcd. | [M + H] Found | Analogous Procedure Example No. |
|---|---|---|---|---|
| 334 | 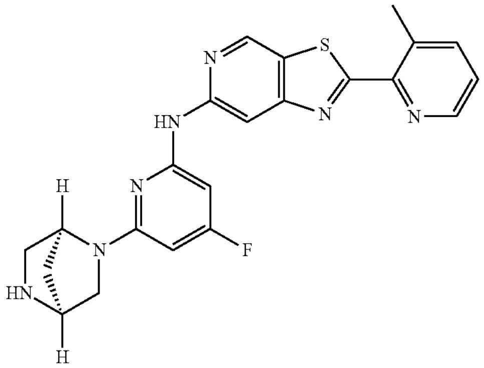 | 434.1 | 434.1 | 119 |
| 335 | 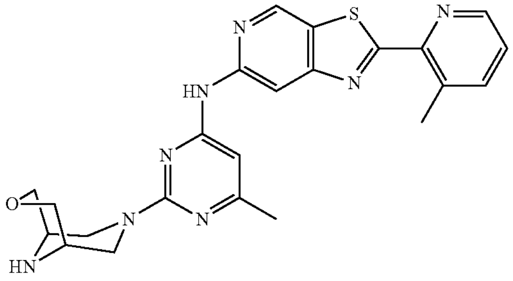 [SMILES: Cc1cc(Nc2cc3nc(-c4ncccc4C)sc3cn2)nc(N2CC3COCC(C2)N3)n1] | 434.1 | 434.1 | 120 |
| 336 | 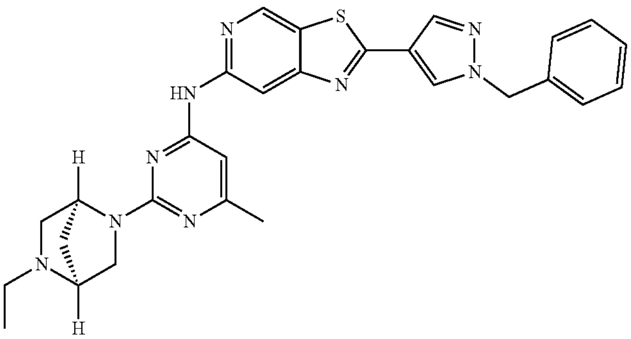 [SMILES: CCN1C[C@@H]2C[C@H]1CN2c1nc(C)cc(Nc2cc3nc(-c4cnn(Cc5ccccc5)c4)sc3cn2)n1] | 524.2 | 524.2 | 121 |
| 337 | 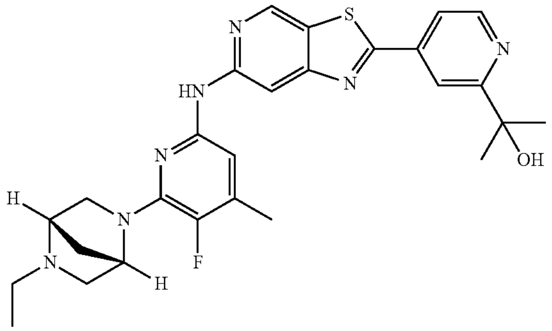 [SMILES: CCN1C[C@@H]2C[C@H]1CN2c1nc(Nc2cc3nc(-c4ccnc(C(C)(C)O)c4)sc3cn2)cc(C)c1F] | 520.2 | 520.1 | 121 |

TABLE 3-continued
| Example No. | Chemical Structure | [M + H] Calcd. | [M + H] Found | Analogous Procedure Example No. |
|---|---|---|---|---|
| 338 | 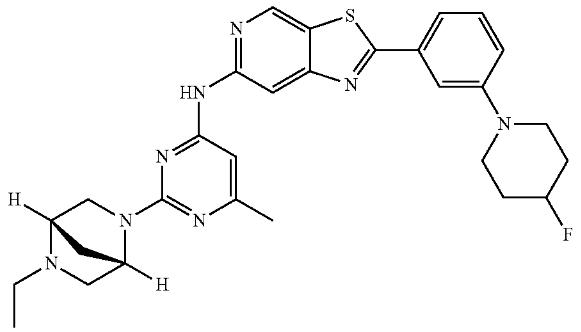 [SMILES: CCN1C[C@@H]2C[C@H]1CN2c1nc(C)cc(Nc2cc3nc(-c4cccc(N5CCC(F)CC5)c4)sc3cn2)n1] | 545.3 | 545.2 | 121 |
| 339 | 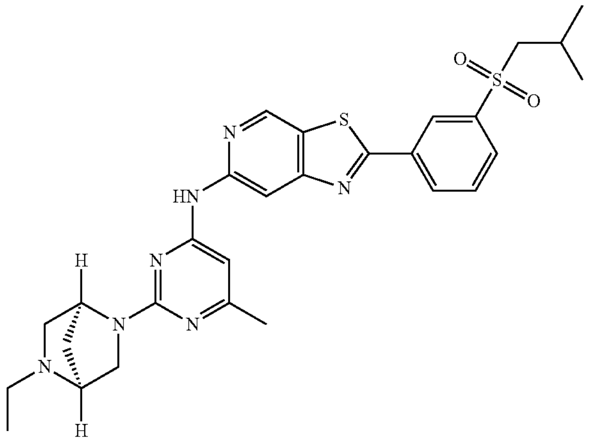 [SMILES: CCN1C[C@@H]2C[C@H]1CN2c1nc(C)cc(Nc2cc3nc(-c4cccc(S(=O)(=O)CC(C)C)c4)sc3cn2)n1] | 564.2 | 564.2 | 121 |
| 340 | 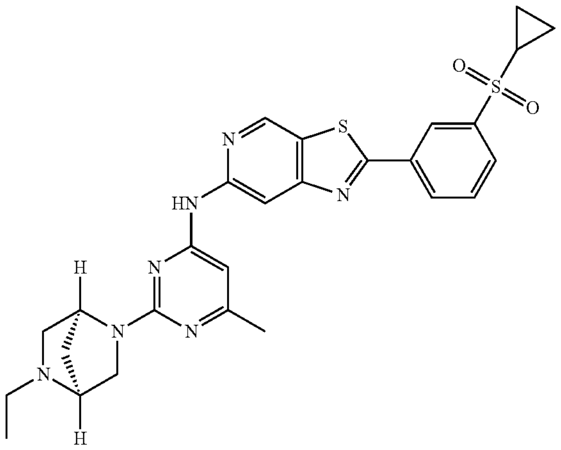 [SMILES: CCN1C[C@@H]2C[C@H]1CN2c1nc(C)cc(Nc2cc3nc(-c4cccc(S(=O)(=O)C5CC5)c4)sc3cn2)n1] | 548.2 | 548.2 | 121 |

TABLE 3-continued
| Example No. | Chemical Structure | [M + H] Calcd. | [M + H] Found | Analogous Procedure Example No. |
|---|---|---|---|---|
| 341 | 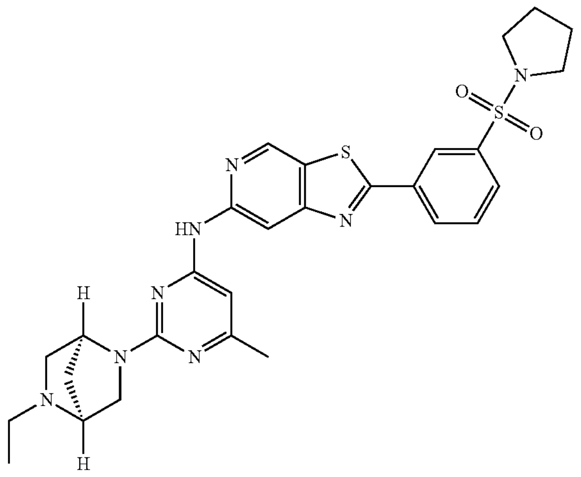 [SMILES: CCN1C[C@@H]2C[C@H]1CN2c1nc(C)cc(Nc2cc3nc(-c4cccc(S(=O)(=O)N5CCCC5)c4)sc3cn2)n1] | 577.2 | 577.1 | 121 |
| 342 | 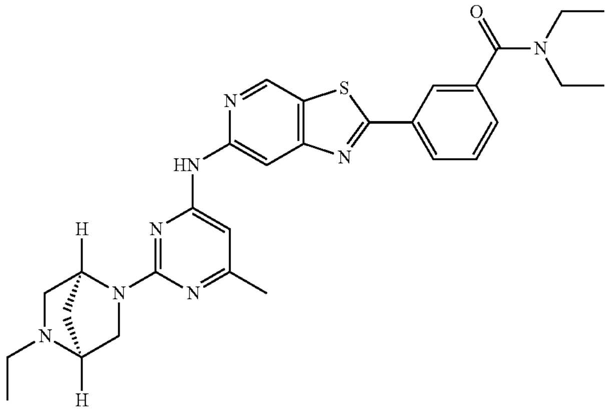 [SMILES: CCN(CC)C(=O)c1cccc(-c2nc3cc(Nc4cc(C)nc(N5C[C@@H]6C[C@H]5CN6CC)n4)ncc3s2)c1] | 543.3 | 543.2 | 121 |
| 343 | 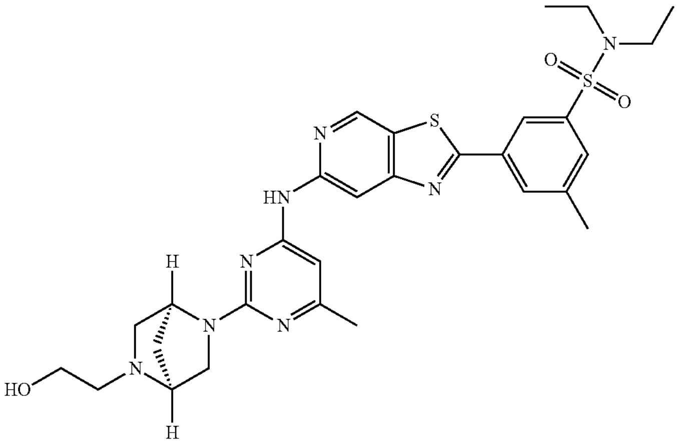 [SMILES: CCN(CC)S(=O)(=O)c1cc(C)cc(-c2nc3cc(Nc4cc(C)nc(N5C[C@@H]6C[C@H]5CN6CCO)n4)ncc3s2)c1] | 609.2 | 609.3 | 121 |

TABLE 3-continued
| Example No. | Chemical Structure | [M + H] Calcd. | [M + H] Found | Analogous Procedure Example No. |
|---|---|---|---|---|
| 344 | 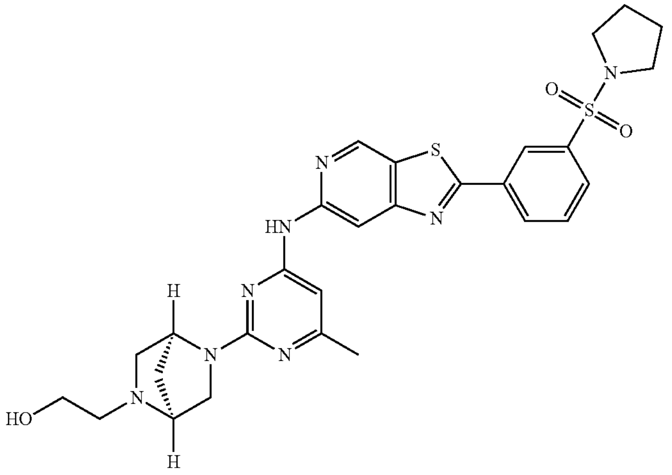 [SMILES: Cc1cc(Nc2cc3nc(-c4cccc(S(=O)(=O)N5CCCC5)c4)sc3cn2)nc(N2C[C@@H]3C[C@H]2CN3CCO)n1] | 593.2 | 593.3 | 121 |
| 345 | 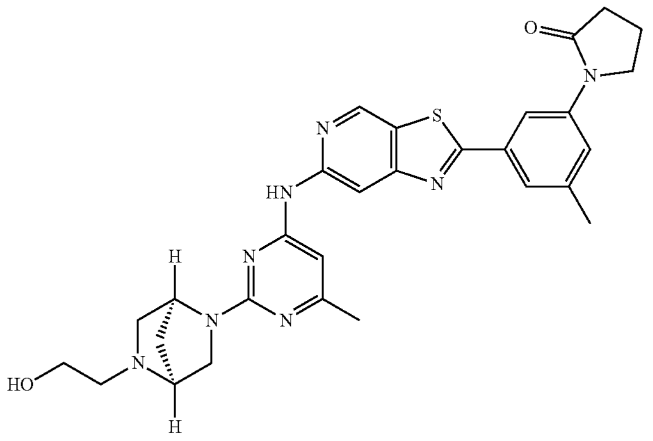 [SMILES: Cc1cc(-c2nc3cc(Nc4cc(C)nc(N5C[C@@H]6C[C@H]5CN6CCO)n4)ncc3s2)cc(N2CCCC2=O)c1] | 557.2 | 557.3 | 121 |
| 346 | 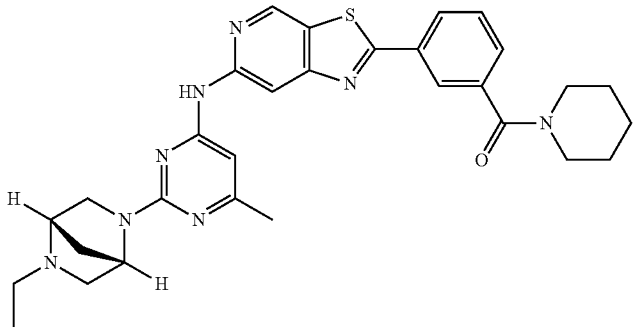 | 555.3 | 555.2 | 121 |

TABLE 3-continued
| Example No. | Chemical Structure | [M + H] Calcd. | [M + H] Found | Analogous Procedure Example No. |
|---|---|---|---|---|
| 347 | 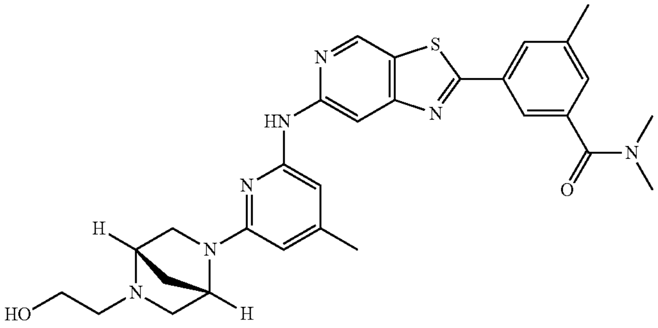 [SMILES: Cc1cc(C(=O)N(C)C)cc(-c2nc3cc(Nc4cc(C)cc(N5C[C@@H]6C[C@H]5CN6CCO)n4)ncc3s2)c1] | 544.2 | 544.2 | 121 |
| 348 | 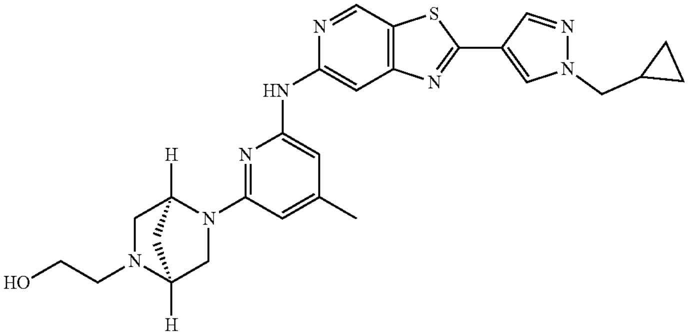 [SMILES: Cc1cc(Nc2cc3nc(-c4cnn(CC5CC5)c4)sc3cn2)nc(N2C[C@@H]3C[C@H]2CN3CCO)c1] | 503.2 | 503.1 | 121 |
| 349 | 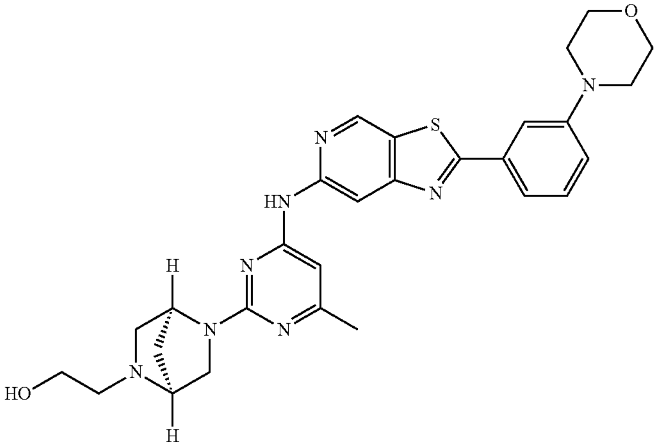 [SMILES: Cc1cc(Nc2cc3nc(-c4cccc(N5CCOCC5)c4)sc3cn2)nc(N2C[C@@H]3C[C@H]2CN3CCO)n1] | 545.2 | 545.3 | 121 |
| 350 | 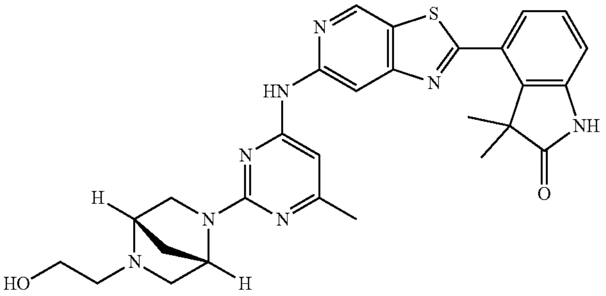 [SMILES: Cc1cc(Nc2cc3nc(-c4cccc5c4C(C)(C)C(=O)N5)sc3cn2)nc(N2C[C@@H]3C[C@H]2CN3CCO)n1] | 543.2 | 543.3 | 121 |

TABLE 3-continued
| Example No. | Chemical Structure | [M + H] Calcd. | [M + H] Found | Analogous Procedure Example No. |
|---|---|---|---|---|
| 351 | 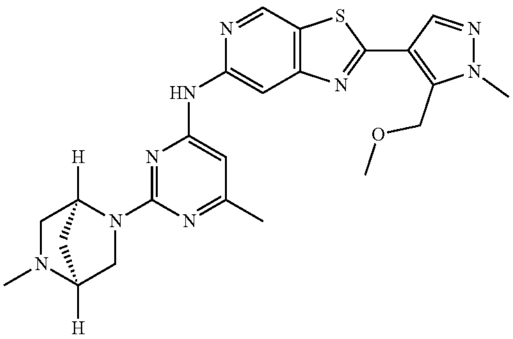 | 478.2 | 478.1 | 121 |
| 352 | 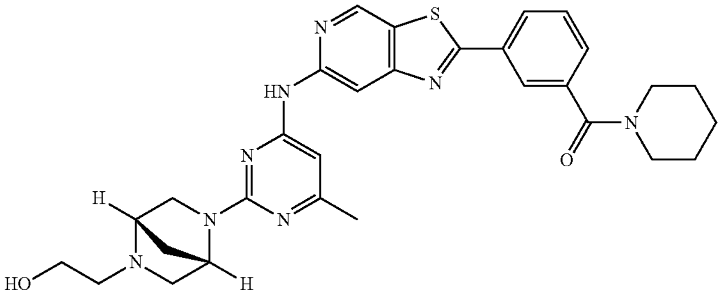 [SMILES: Cc1cc(Nc2cc3nc(-c4cccc(C(=O)N5CCCCC5)c4)sc3cn2)nc(N2C[C@@H]3C[C@H]2CN3CCO)n1] | 571.3 | 571.3 | 121 |
| 353 | 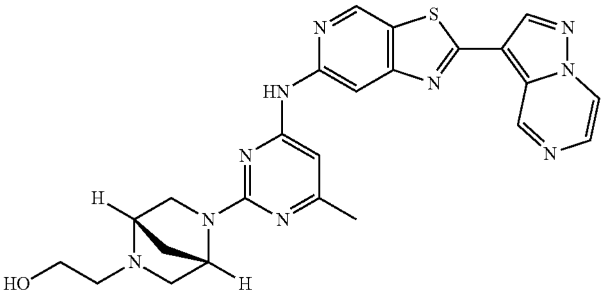 | 501.2 | 501.2 | 121 |
| 354 | 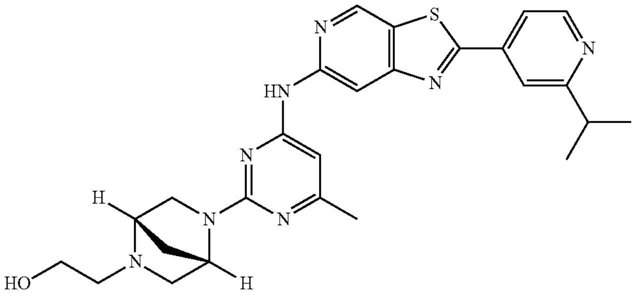 [SMILES: Cc1cc(Nc2cc3nc(-c4ccnc(C(C)C)c4)sc3cn2)nc(N2C[C@@H]3C[C@H]2CN3CCO)n1] | 503.2 | 503.2 | 121 |

TABLE 3-continued
| Example No. | Chemical Structure | [M + H] Calcd. | [M + H] Found | Analogous Procedure Example No. |
| --- | --- | --- | --- | --- |
| 355 | 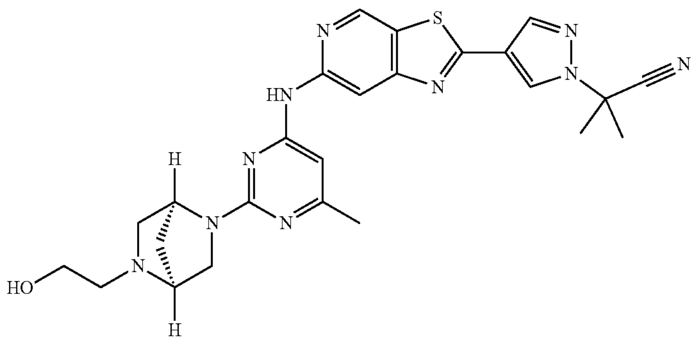 [SMILES: Cc1cc(Nc2cc3nc(-c4cnn(C(C)(C)C#N)c4)sc3cn2)nc(N2C[C@@H]3C[C@H]2CN3CCO)n1] | 517.2 | 517.2 | 121 |
| 356 | 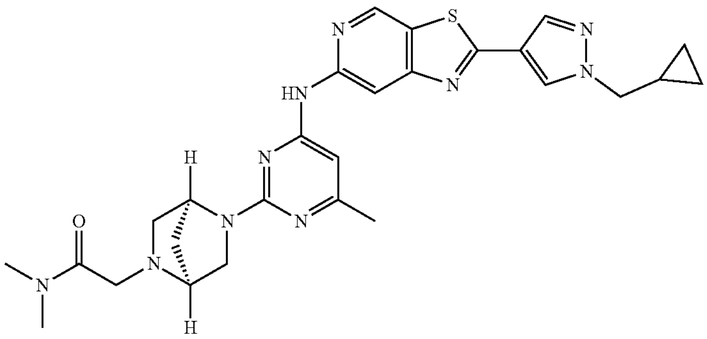 [SMILES: Cc1cc(Nc2cc3nc(-c4cnn(CC5CC5)c4)sc3cn2)nc(N2C[C@@H]3C[C@H]2CN3CC(=O)N(C)C)n1] | 545.2 | 545.1 | 121 |
| 357 | 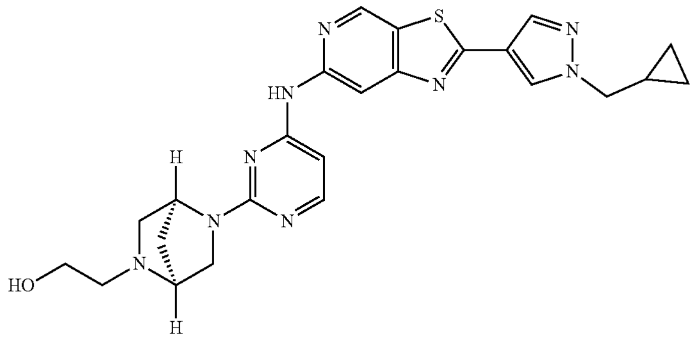 [SMILES: OCCN1C[C@@H]2C[C@H]1CN2c1nccc(Nc2cc3nc(-c4cnn(CC5CC5)c4)sc3cn2)n1] | 490.2 | 490.1 | 121 |
| 358 | 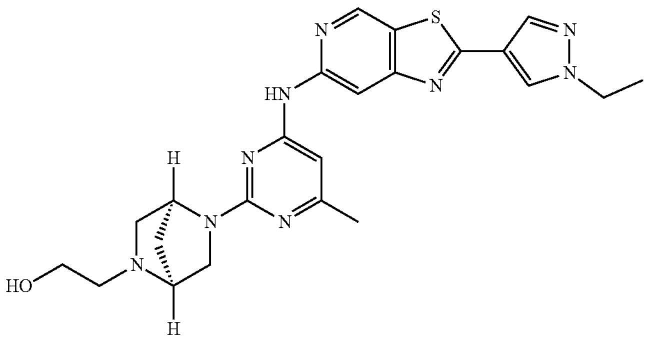 [SMILES: CCn1cc(-c2nc3cc(Nc4cc(C)nc(N5C[C@@H]6C[C@H]5CN6CCO)n4)ncc3s2)cn1] | 478.2 | 478.2 | 121 |

TABLE 3-continued
| Example No. | Chemical Structure | [M + H] Calcd. | [M + H] Found | Analogous Procedure Example No. |
|---|---|---|---|---|
| 359 | 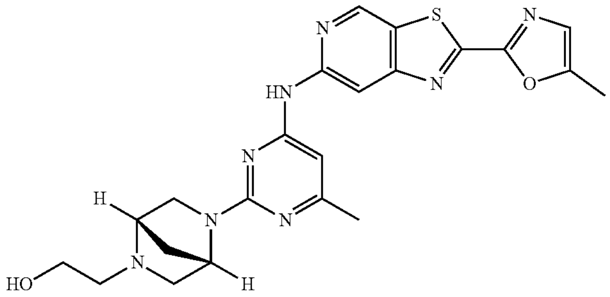 [SMILES: Cc1cc(Nc2cc3nc(-c4ncc(C)o4)sc3cn2)nc(N2C[C@@H]3C[C@H]2CN3CCO)n1] | 465.2 | 465.3 | 121 |
| 360 | 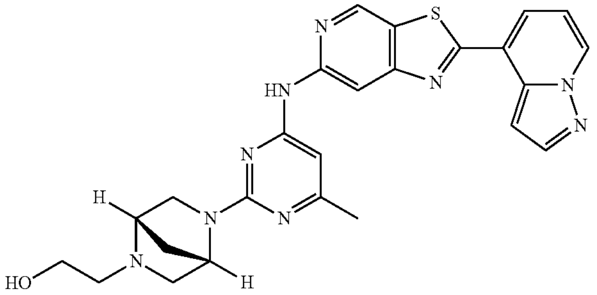 [SMILES: Cc1cc(Nc2cc3nc(-c4cccn5nccc45)sc3cn2)nc(N2C[C@@H]3C[C@H]2CN3CCO)n1] | 500.2 | 500.2 | 121 |
| 361 | 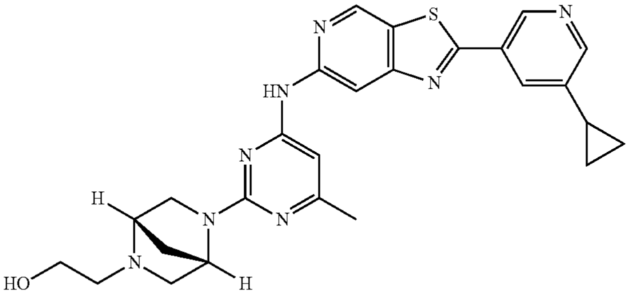 [SMILES: Cc1cc(Nc2cc3nc(-c4cncc(C5CC5)c4)sc3cn2)nc(N2C[C@@H]3C[C@H]2CN3CCO)n1] | 501.2 | 501.3 | 121 |
| 362 | 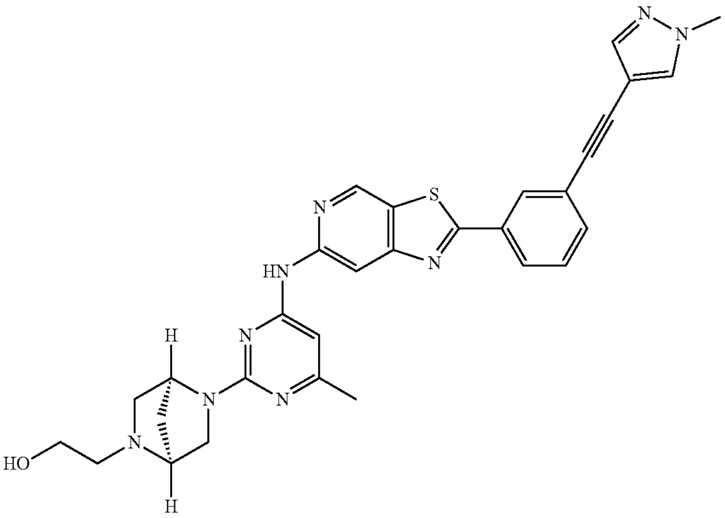 [SMILES: Cc1cc(Nc2cc3nc(-c4cccc(C#Cc5cnn(C)c5)c4)sc3cn2)nc(N2C[C@@H]3C[C@H]2CN3CCO)n1] | 564.2 | 564.2 | 121 |

TABLE 3-continued
| Example No. | Chemical Structure | [M + H] Calcd. | [M + H] Found | Analogous Procedure Example No. |
|---|---|---|---|---|
| 363 | 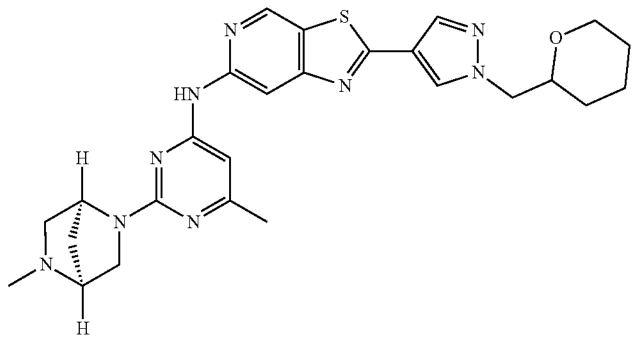 [SMILES: Cc1cc(Nc2cc3nc(-c4cnn(CC5CCCCO5)c4)sc3cn2)nc(N2C[C@@H]3C[C@H]2CN3C)n1] | 518.2 | 518.3 | 121 |
| 364 | 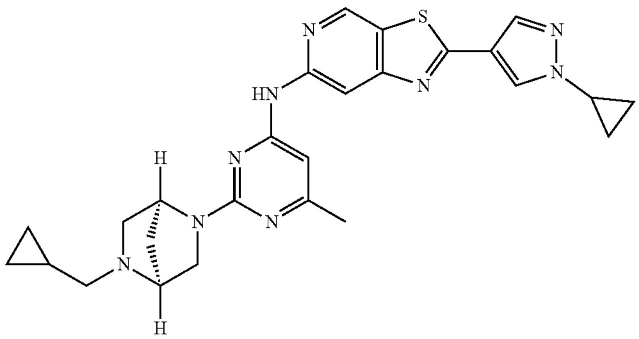 [SMILES: Cc1cc(Nc2cc3nc(-c4cnn(C5CC5)c4)sc3cn2)nc(N2C[C@@H]3C[C@H]2CN3CC2CC2)n1] | 500.2 | 500.2 | 121 |
| 365 | 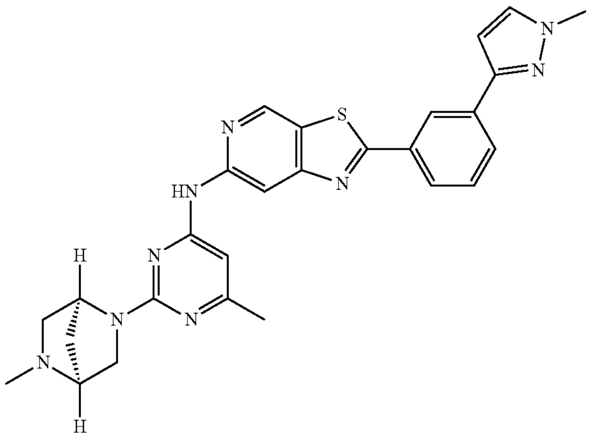 | 510.2 | 510.1 | 121 |
| 366 | 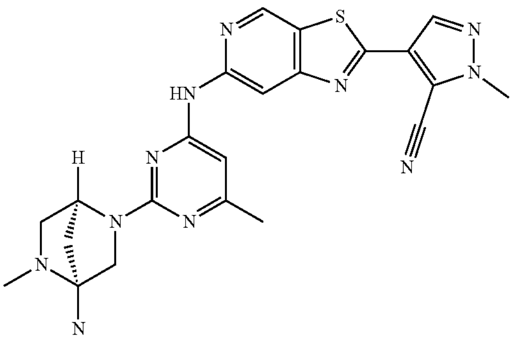 | 459.2 | 459.2 | 121 |

TABLE 3-continued
| Example No. | Chemical Structure | [M + H] Calcd. | [M + H] Found | Analogous Procedure Example No. |
|---|---|---|---|---|
| 367 | 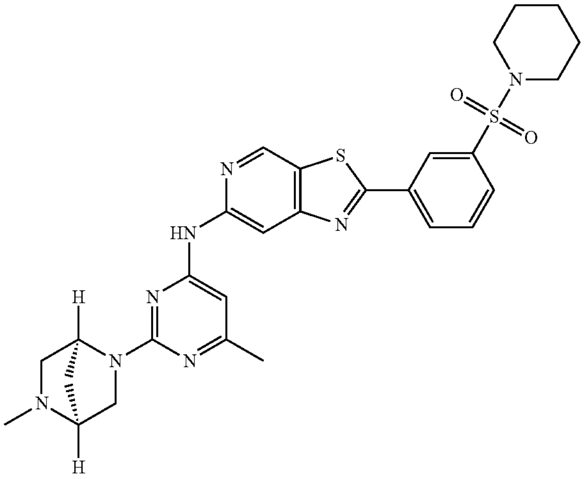 [SMILES: Cc1cc(Nc2cc3nc(-c4cccc(S(=O)(=O)N5CCCCC5)c4)sc3cn2)nc(N2C[C@@H]3C[C@H]2CN3C)n1] | 577.2 | 577.2 | 121 |
| 368 | 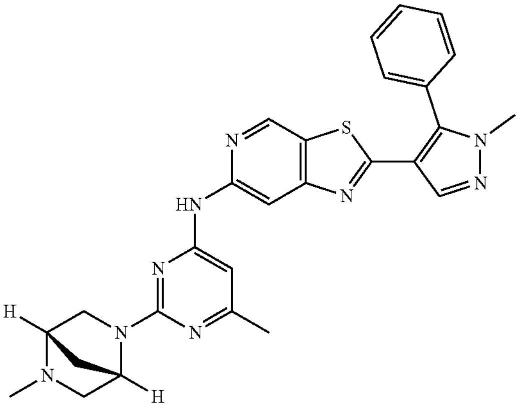 [SMILES: Cc1cc(Nc2cc3nc(-c4cnn(C)c4-c4ccccc4)sc3cn2)nc(N2C[C@@H]3C[C@H]2CN3C)n1] | 510.2 | 510.2 | 121 |
| 369 | 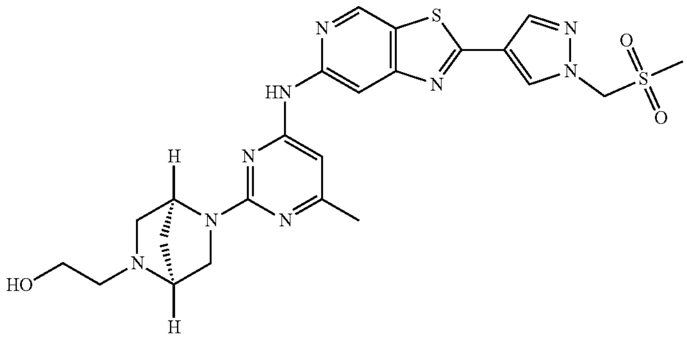 [SMILES: Cc1cc(Nc2cc3nc(-c4cnn(CS(C)(=O)=O)c4)sc3cn2)nc(N2C[C@@H]3C[C@H]2CN3CCO)n1] | 542.2 | 542.1 | 121 |

TABLE 3-continued
| Example No. | Chemical Structure | [M + H] Calcd. | [M + H] Found | Analogous Procedure Example No. |
|---|---|---|---|---|
| 370 | 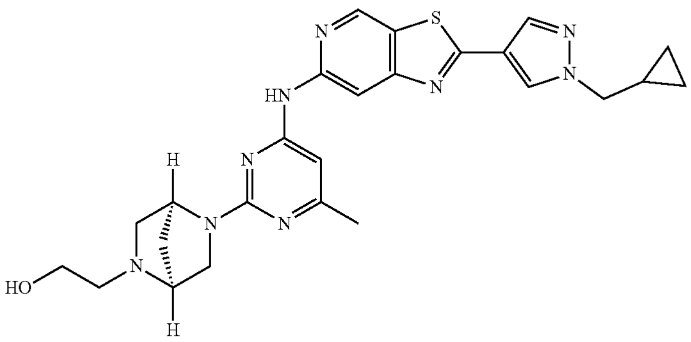 | 504.2 | 504.1 | 121 |
| 371 | 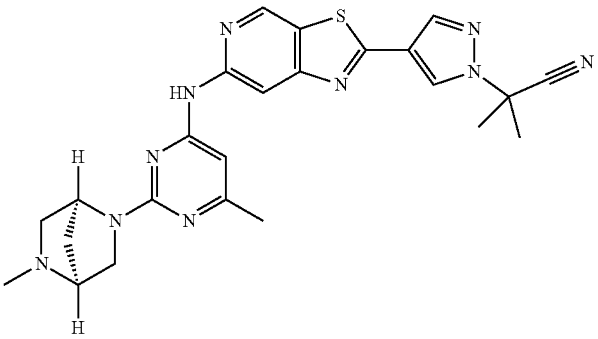 [SMILES: Cc1cc(Nc2cc3nc(-c4cnn(C(C)(C)C#N)c4)sc3cn2)nc(N2C[C@@H]3C[C@H]2CN3C)n1] | 487.2 | 487.1 | 121 |
| 372 | 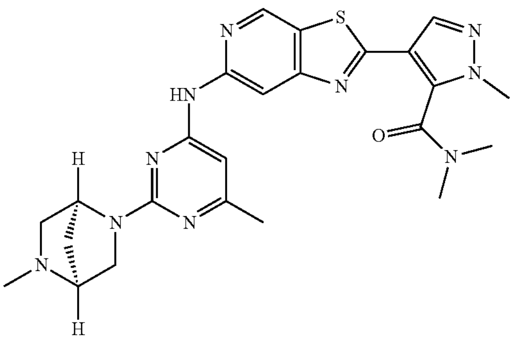 | 505.2 | 505.2 | 121 |
| 373 | 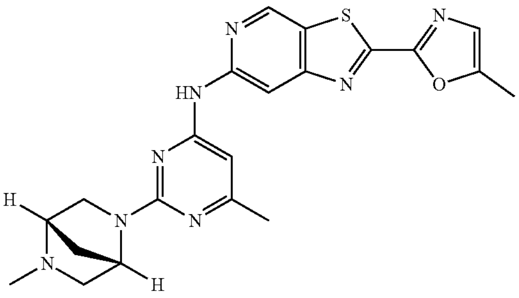 [SMILES: Cc1cc(Nc2cc3nc(-c4ncc(C)o4)sc3cn2)nc(N2C[C@@H]3C[C@H]2CN3C)n1] | 435.2 | 435.1 | 121 |

TABLE 3-continued
| Example No. | Chemical Structure | [M + H] Calcd. | [M + H] Found | Analogous Procedure Example No. |
|---|---|---|---|---|
| 374 | 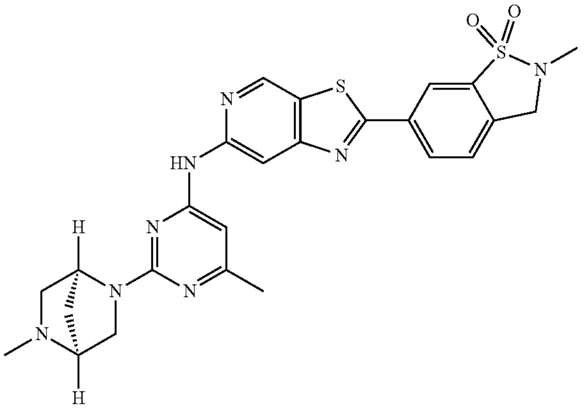 | 535.2 | 535.2 | 121 |
| 375 | 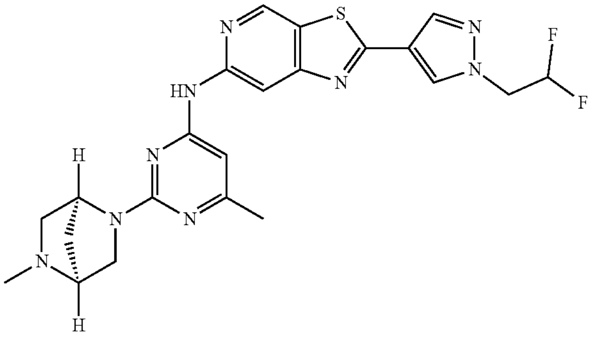 [SMILES: Cc1cc(Nc2cc3nc(-c4cnn(CC(F)F)c4)sc3cn2)nc(N2C[C@@H]3C[C@H]2CN3C)n1] | 484.2 | 484.1 | 121 |
| 376 | 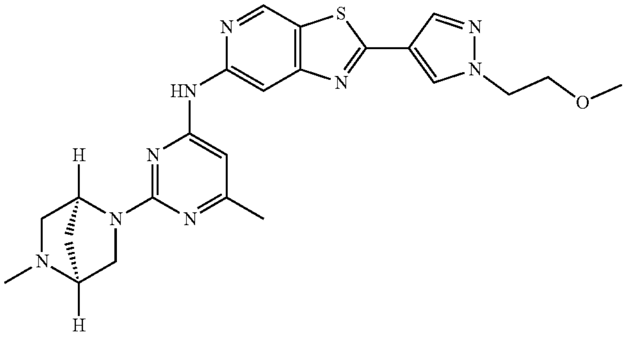 | 478.2 | 478.1 | 121 |
| 377 | 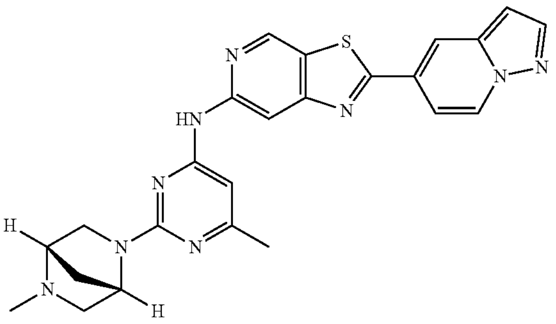 [SMILES: Cc1cc(Nc2cc3nc(-c4ccn5nccc5c4)sc3cn2)nc(N2C[C@@H]3C[C@H]2CN3C)n1] | 470.2 | 470.2 | 121 |

TABLE 3-continued
| Example No. | Chemical Structure | [M + H] Calcd. | [M + H] Found | Analogous Procedure Example No. |
|---|---|---|---|---|
| 378 | 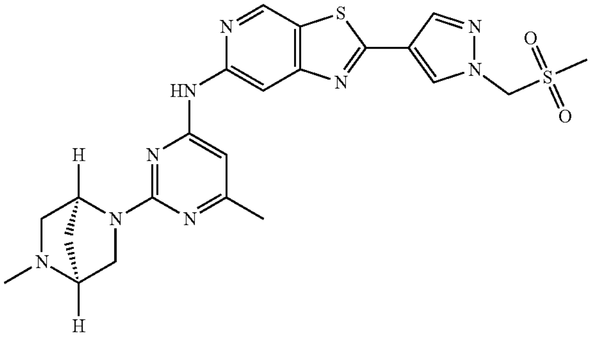 | 512.2 | 512.1 | 121 |
| 379 | 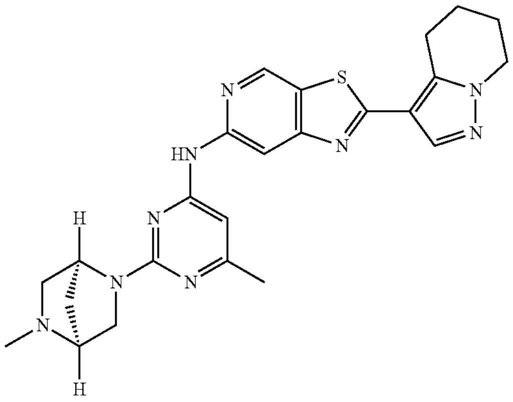 [SMILES: Cc1cc(Nc2cc3nc(-c4cnn5c4CCCC5)sc3cn2)nc(N2C[C@@H]3C[C@H]2CN3C)n1] | 474.2 | 474.2 | 121 |
| 380 | 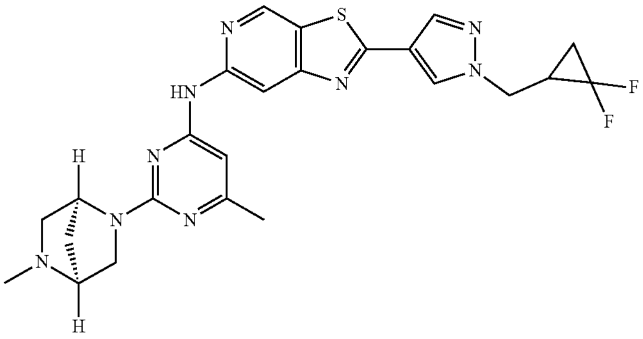 [SMILES: Cc1cc(Nc2cc3nc(-c4cnn(CC5CC5(F)F)c4)sc3cn2)nc(N2C[C@@H]3C[C@H]2CN3C)n1] | 510.2 | 510.1 | 121 |
| 381 | 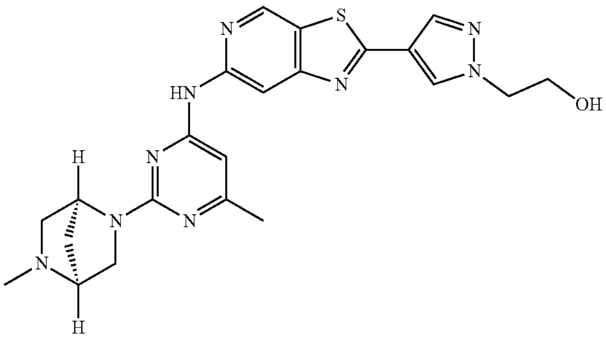 [SMILES: Cc1cc(Nc2cc3nc(-c4cnn(CCO)c4)sc3cn2)nc(N2C[C@@H]3C[C@H]2CN3C)n1] | 464.2 | 464.2 | 121 |

TABLE 3-continued
| Example No. | Chemical Structure | [M + H] Calcd. | [M + H] Found | Analogous Procedure Example No. |
|---|---|---|---|---|
| 382 | 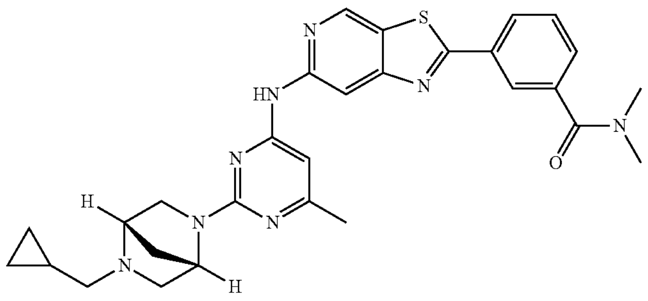 [SMILES: Cc1cc(Nc2cc3nc(-c4cccc(C(=O)N(C)C)c4)sc3cn2)nc(N2C[C@@H]3C[C@H]2CN3CC2CC2)n1] | 541.2 | 541.2 | 121 |
| 383 | 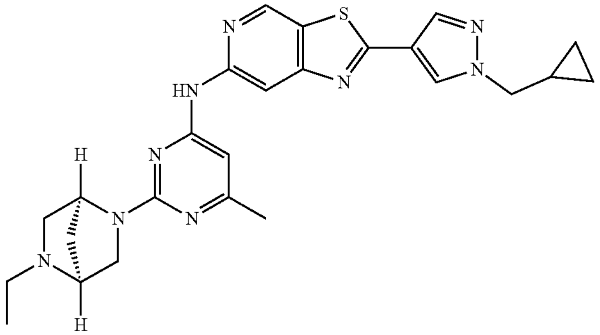 [SMILES: CCN1C[C@@H]2C[C@H]1CN2c1nc(C)cc(Nc2cc3nc(-c4cnn(CC5CC5)c4)sc3cn2)n1] | 488.2 | 488.2 | 121 |
| 384 | 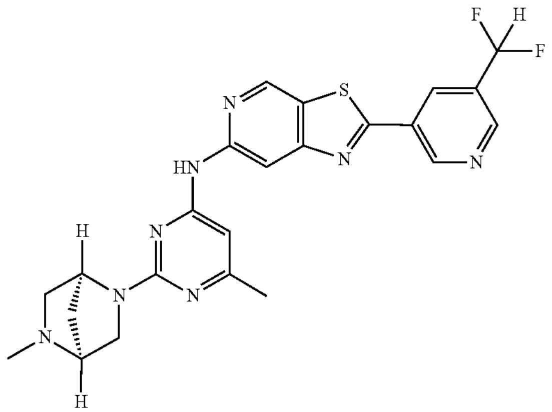 [SMILES: Cc1cc(Nc2cc3nc(-c4cncc(C(F)F)c4)sc3cn2)nc(N2C[C@@H]3C[C@H]2CN3C)n1] | 481.2 | 481.4 | 121 |
| 385 | 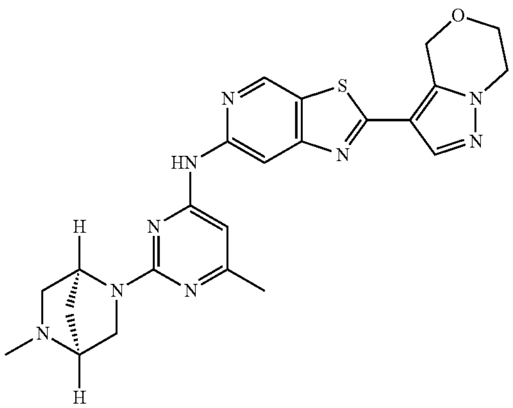 [SMILES: Cc1cc(Nc2cc3nc(-c4cnn5c4COCC5)sc3cn2)nc(N2C[C@@H]3C[C@H]2CN3C)n1] | 476.2 | 476.1 | 121 |

TABLE 3-continued
| Example No. | Chemical Structure | [M + H] Calcd. | [M + H] Found | Analogous Procedure Example No. |
|---|---|---|---|---|
| 386 | 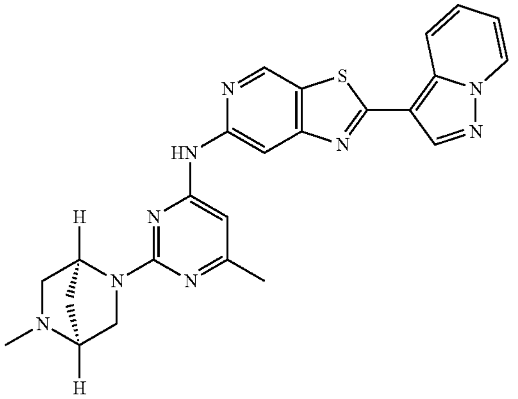 [SMILES: Cc1cc(Nc2cc3nc(-c4cnn5ccccc45)sc3cn2)nc(N2C[C@@H]3C[C@H]2CN3C)n1] | 470.2 | 470.4 | 121 |
| 387 | 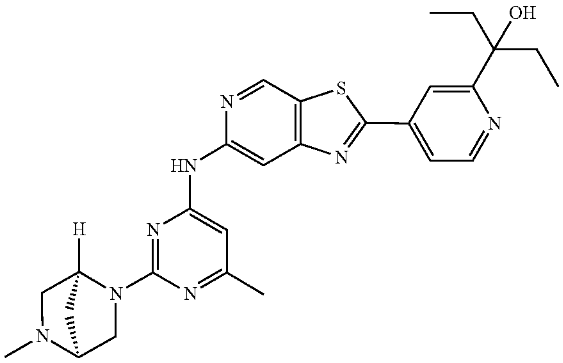 [SMILES: CCC(O)(CC)c1cc(-c2nc3cc(Nc4cc(C)nc(N5C[C@@H]6C[C@H]5CN6C)n4)ncc3s2)ccn1] | 517.2 | 517.2 | 121 |
| 388 | 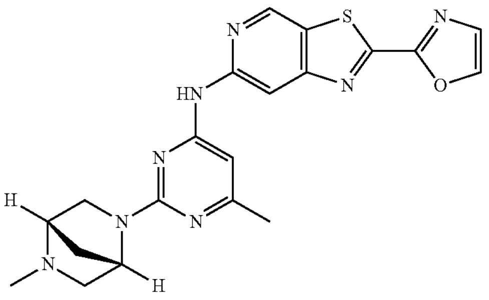 [SMILES: Cc1cc(Nc2cc3nc(-c4ncco4)sc3cn2)nc(N2C[C@@H]3C[C@H]2CN3C)n1] | 421.1 | 421.1 | 121 |
| 389 | 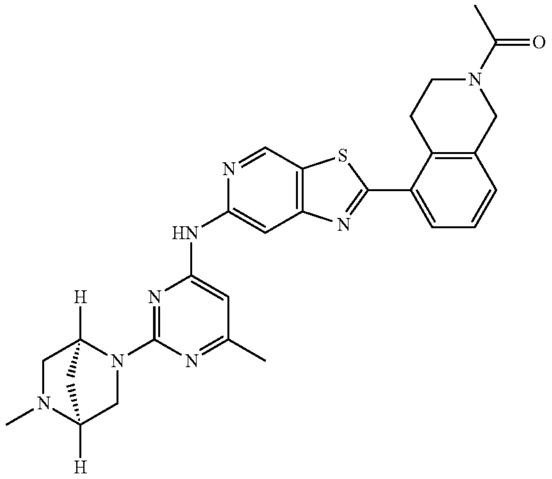 [SMILES: CC(=O)N1CCc2c(cccc2-c2nc3cc(Nc4cc(C)nc(N5C[C@@H]6C[C@H]5CN6C)n4)ncc3s2)C1] | 527.2 | 527.2 | 121 |

TABLE 3-continued
| Example No. | Chemical Structure | [M + H] Calcd. | [M + H] Found | Analogous Procedure Example No. |
|---|---|---|---|---|
| 390 | 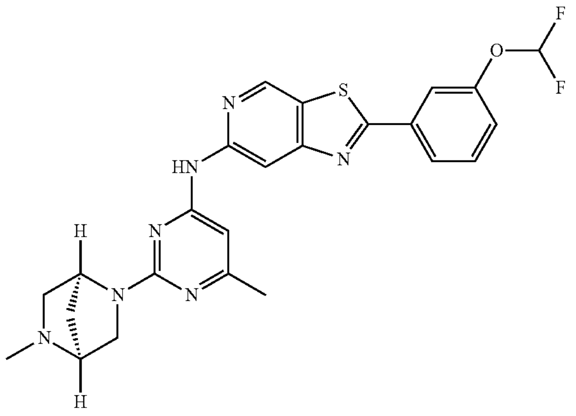 [SMILES: Cc1cc(Nc2cc3nc(-c4cccc(OC(F)F)c4)sc3cn2)nc(N2C[C@@H]3C[C@H]2CN3C)n1] | 496.2 | 496.3 | 121 |
| 391 | 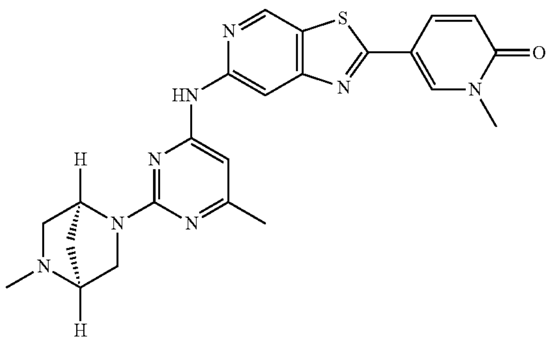 [SMILES: Cc1cc(Nc2cc3nc(-c4ccc(=O)n(C)c4)sc3cn2)nc(N2C[C@@H]3C[C@H]2CN3C)n1] | 461.2 | 461.2 | 121 |
| 392 | 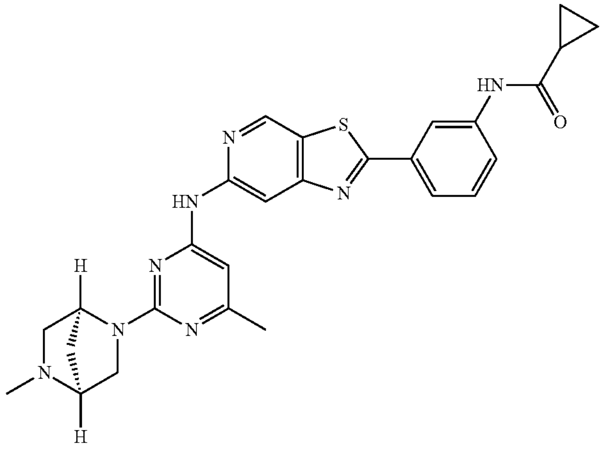 [SMILES: Cc1cc(Nc2cc3nc(-c4cccc(NC(=O)C5CC5)c4)sc3cn2)nc(N2C[C@@H]3C[C@H]2CN3C)n1] | 513.2 | 513.1 | 121 |

TABLE 3-continued
| Example No. | Chemical Structure | [M + H] Calcd. | [M + H] Found | Analogous Procedure Example No. |
|---|---|---|---|---|
| 393 | 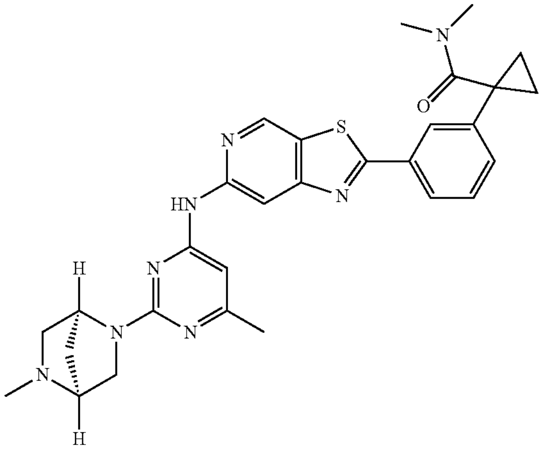 [SMILES: Cc1cc(Nc2cc3nc(-c4cccc(C5(C(=O)N(C)C)CC5)c4)sc3cn2)nc(N2C[C@@H]3C[C@H]2CN3C)n1] | 541.2 | 541.2 | 121 |
| 394 | 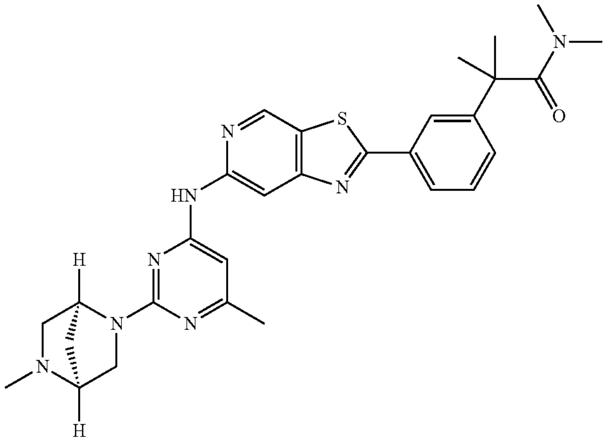 | 543.3 | 543.2 | 121 |
| 395 | 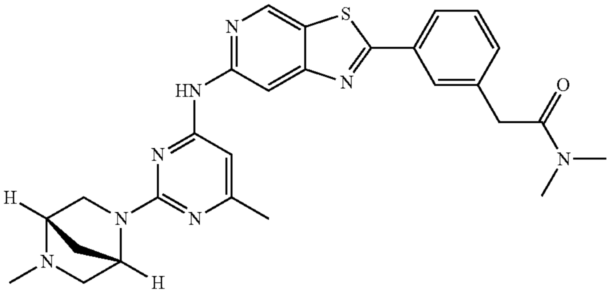 [SMILES: Cc1cc(Nc2cc3nc(-c4cccc(CC(=O)N(C)C)c4)sc3cn2)nc(N2C[C@@H]3C[C@H]2CN3C)n1] | 515.2 | 515.1 | 121 |
| 396 | 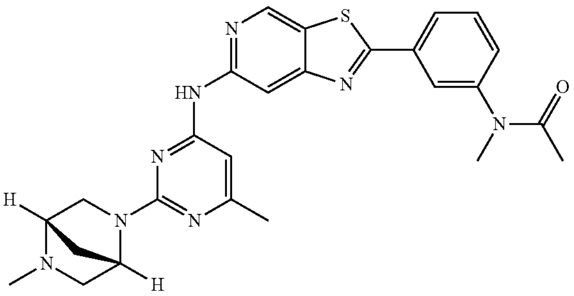 [SMILES: CC(=O)N(C)c1cccc(-c2nc3cc(Nc4cc(C)nc(N5C[C@@H]6C[C@H]5CN6C)n4)ncc3s2)c1] | 501.2 | 501.2 | 121 |

TABLE 3-continued
| Example No. | Chemical Structure | [M + H] Calcd. | [M + H] Found | Analogous Procedure Example No. |
|---|---|---|---|---|
| 397 | 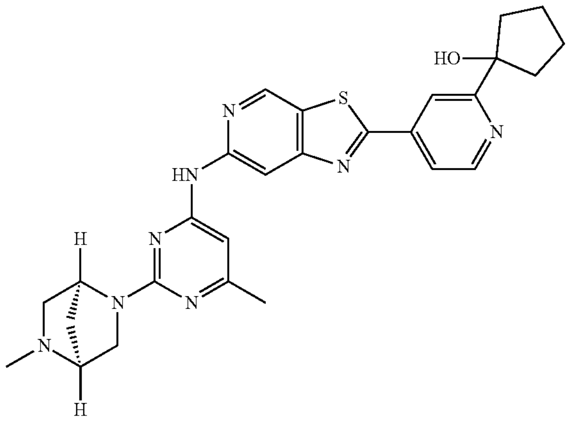 [SMILES: Cc1cc(Nc2cc3nc(-c4ccnc(C5(O)CCCC5)c4)sc3cn2)nc(N2C[C@@H]3C[C@H]2CN3C)n1] | 515.2 | 515.2 | 121 |
| 398 | 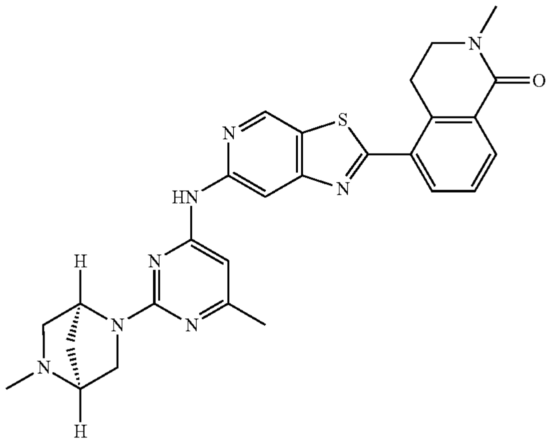 [SMILES: Cc1cc(Nc2cc3nc(-c4cccc5c4CCN(C)C5=O)sc3cn2)nc(N2C[C@@H]3C[C@H]2CN3C)n1] | 513.2 | 513.2 | 121 |
| 399 | 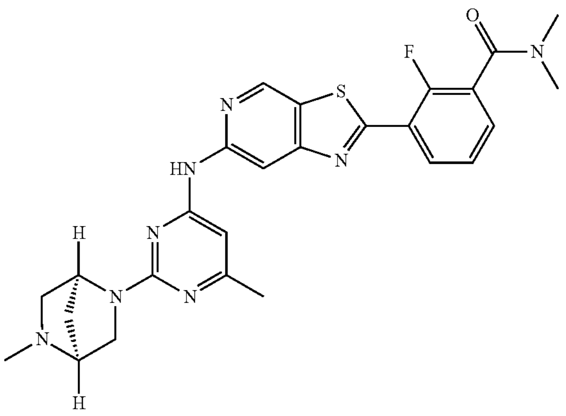 | 519.2 | 519.1 | 121 |

TABLE 3-continued
| Example No. | Chemical Structure | [M + H] Calcd. | [M + H] Found | Analogous Procedure Example No. |
|---|---|---|---|---|
| 400 | 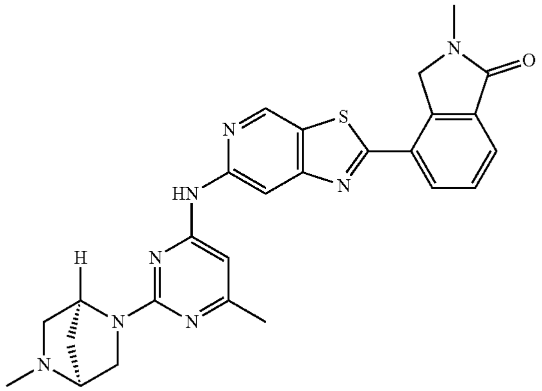 [SMILES: Cc1cc(Nc2cc3nc(-c4cccc5c4CN(C)C5=O)sc3cn2)nc(N2C[C@@H]3C[C@H]2CN3C)n1] | 499.2 | 499.3 | 121 |
| 401 | 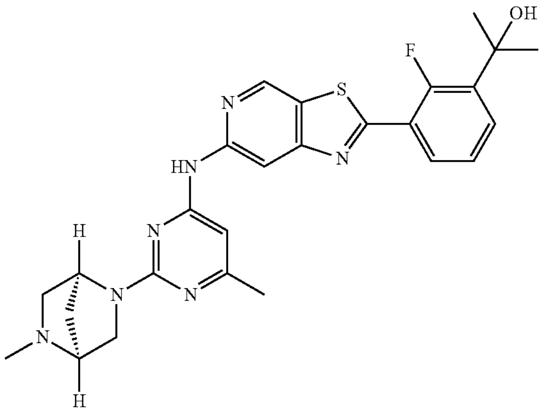 [SMILES: Cc1cc(Nc2cc3nc(-c4cccc(C(C)(C)O)c4F)sc3cn2)nc(N2C[C@@H]3C[C@H]2CN3C)n1] | 506.2 | 506.2 | 121 |
| 402 | 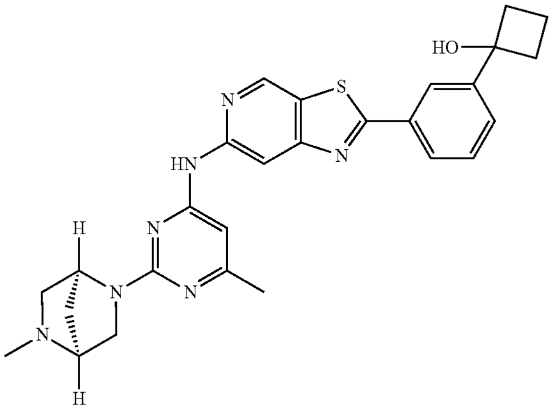 [SMILES: Cc1cc(Nc2cc3nc(-c4cccc(C5(O)CCC5)c4)sc3cn2)nc(N2C[C@@H]3C[C@H]2CN3C)n1] | 500.2 | 500.2 | 121 |

TABLE 3-continued
| Example No. | Chemical Structure | [M + H] Calcd. | [M + H] Found | Analogous Procedure Example No. |
|---|---|---|---|---|
| 403 | 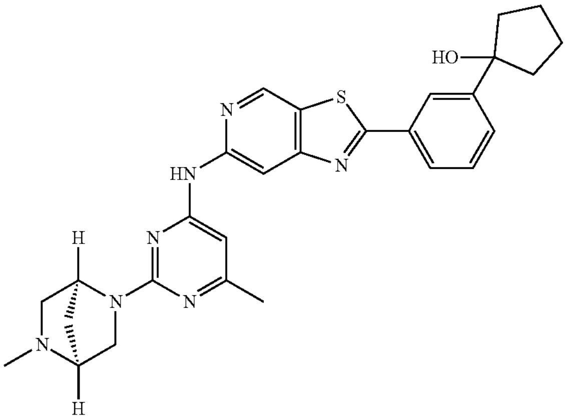 [SMILES: Cc1cc(Nc2cc3nc(-c4cccc(C5(O)CCCC5)c4)sc3cn2)nc(N2C[C@@H]3C[C@H]2CN3C)n1] | 514.2 | 514.3 | 121 |
| 404 | 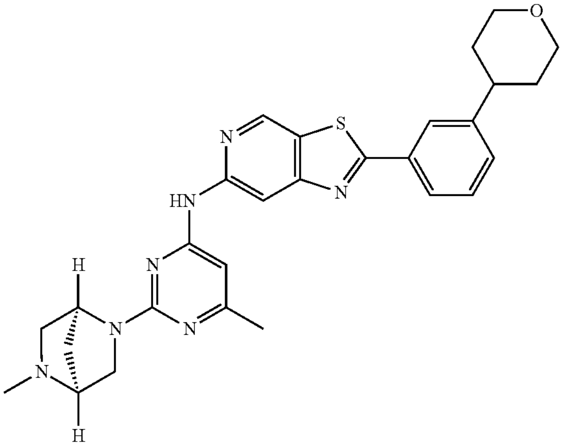 [SMILES: Cc1cc(Nc2cc3nc(-c4cccc(C5CCOCC5)c4)sc3cn2)nc(N2C[C@@H]3C[C@H]2CN3C)n1] | 514.2 | 514.2 | 121 |
| 405 | 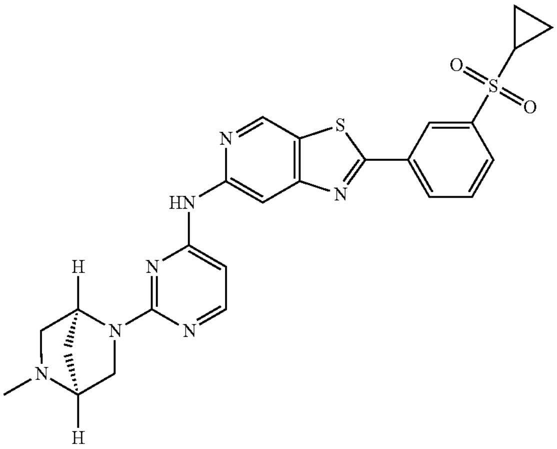 [SMILES: CN1C[C@@H]2C[C@H]1CN2c1nccc(Nc2cc3nc(-c4cccc(S(=O)(=O)C5CC5)c4)sc3cn2)n1] | 520.2 | 520.1 | 121 |

TABLE 3-continued
| Example No. | Chemical Structure | [M + H] Calcd. | [M + H] Found | Analogous Procedure Example No. |
|---|---|---|---|---|
| 406 | 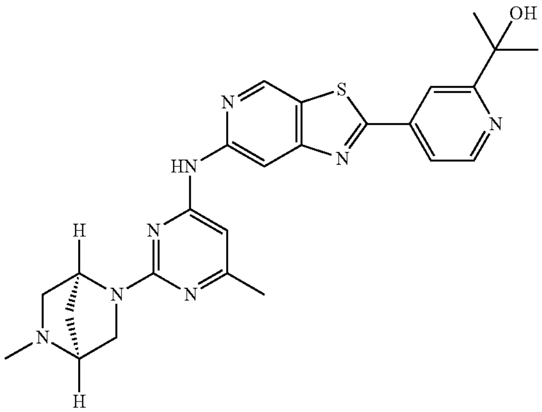 [SMILES: Cc1cc(Nc2cc3nc(-c4ccnc(C(C)(C)O)c4)sc3cn2)nc(N2C[C@@H]3C[C@H]2CN3C)n1] | 489.2 | 489.2 | 121 |
| 407 | 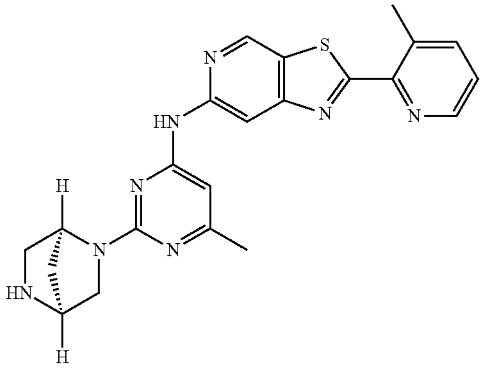 | 431.2 | 431.1 | 121 |
| 408 | 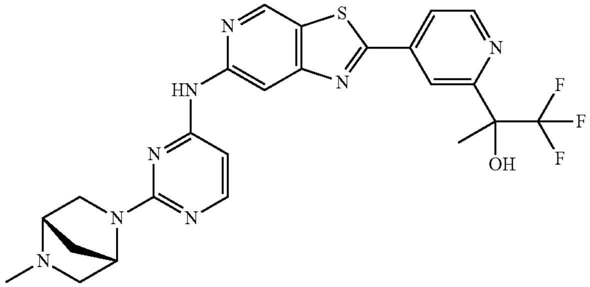 [SMILES: CN1C[C@@H]2C[C@H]1CN2c1nccc(Nc2cc3nc(-c4ccnc(C(C)(O)C(F)(F)F)c4)sc3cn2)n1] | 529.2 | 529.2 | 121 |
| 409 | 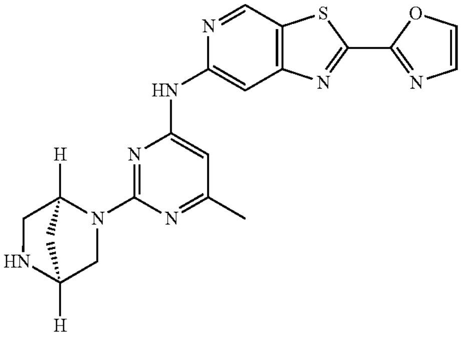 | 393.1 | 393.1 | 121 |

TABLE 3-continued
| Example No. | Chemical Structure | [M + H] Calcd. | [M + H] Found | Analogous Procedure Example No. |
|---|---|---|---|---|
| 410 | 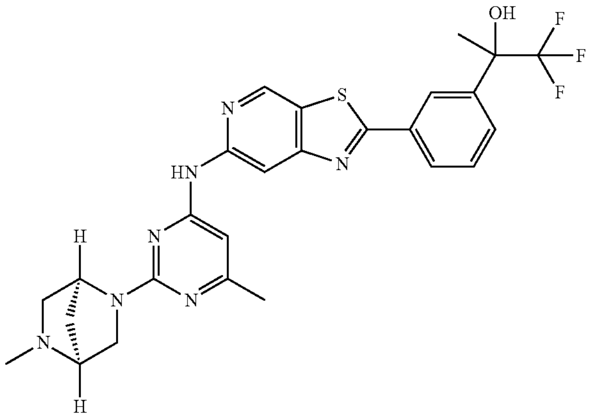 [SMILES: Cc1cc(Nc2cc3nc(-c4cccc(C(C)(O)C(F)(F)F)c4)sc3cn2)nc(N2C[C@@H]3C[C@H]2CN3C)n1] | 528.2 | 528.2 | 121 |
| 411 | 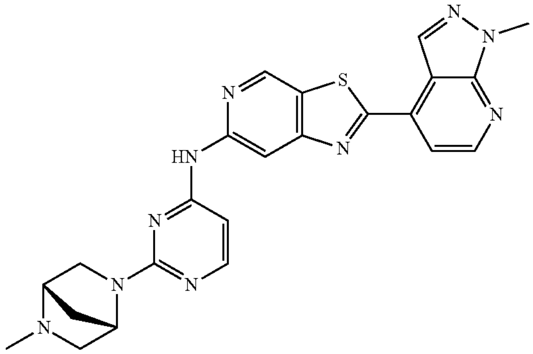 | 471.2 | 471.2 | 121 |
| 412 | 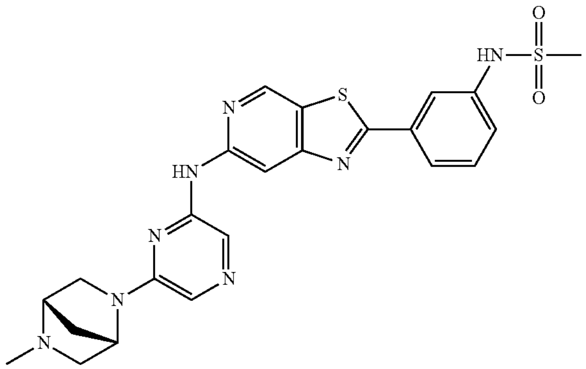 | 509.1 | 509.1 | 121 |
| 413 | 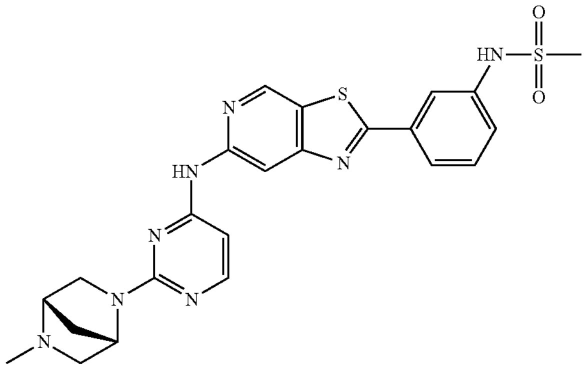 | 509.1 | 509.1 | 121 |

TABLE 3-continued
| Example No. | Chemical Structure | [M + H] Calcd. | [M + H] Found | Analogous Procedure Example No. |
|---|---|---|---|---|
| 414 | 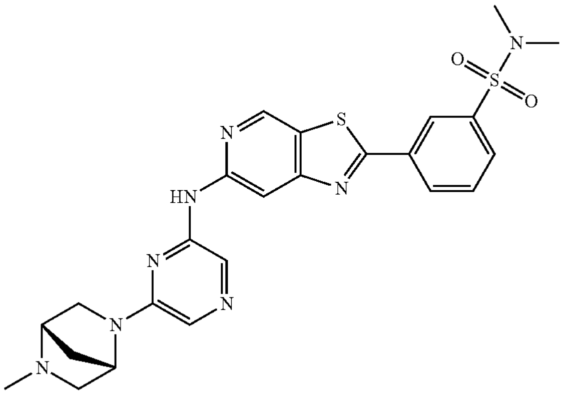 | 523.2 | 523.2 | 121 |
| 415 | 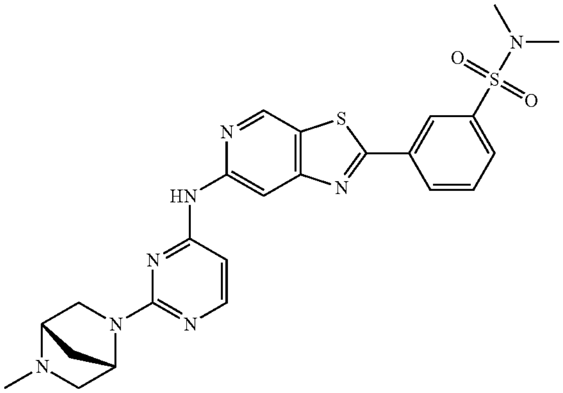 | 523.2 | 523.2 | 121 |
| 416 | 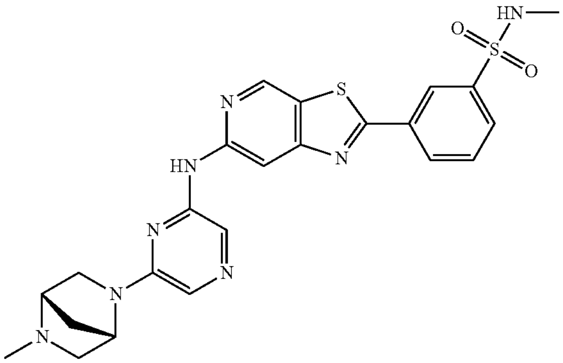 | 509.1 | 509.1 | 121 |

TABLE 3-continued
| Example No. | Chemical Structure | [M + H] Calcd. | [M + H] Found | Analogous Procedure Example No. |
|---|---|---|---|---|
| 417 | 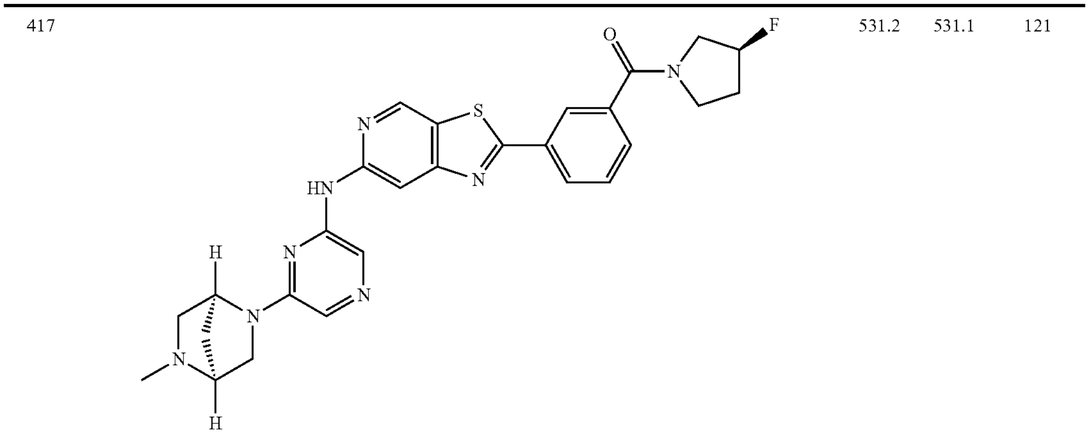 | 531.2 | 531.1 | 121 |
| 418 | 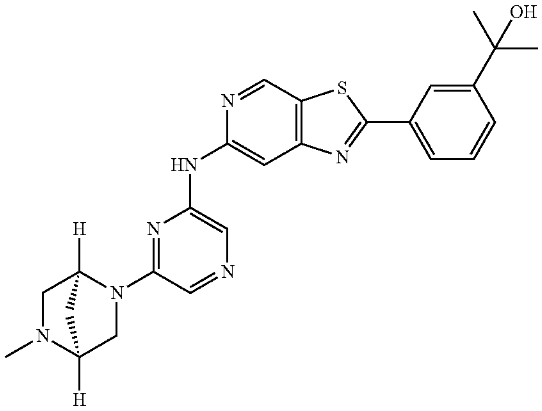 [SMILES: CN1C[C@@H]2C[C@H]1CN2c1cncc(Nc2cc3nc(-c4cccc(C(C)(C)O)c4)sc3cn2)n1] | 474.2 | 474.5 | 121 |
| 419 | 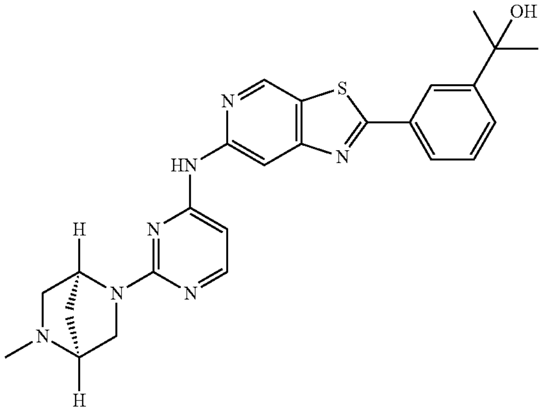 [SMILES: CN1C[C@@H]2C[C@H]1CN2c1nccc(Nc2cc3nc(-c4cccc(C(C)(C)O)c4)sc3cn2)n1] | 474.2 | 474.4 | 121 |
| 420 | 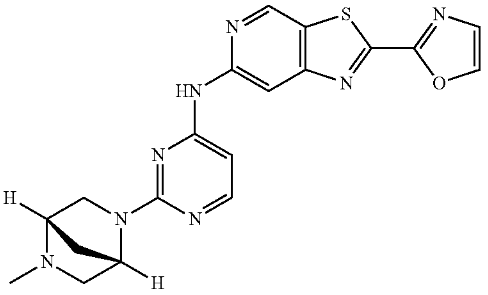 [SMILES: CN1C[C@@H]2C[C@H]1CN2c1nccc(Nc2cc3nc(-c4ncco4)sc3cn2)n1] | 407.1 | 407.1 | 121 |

TABLE 3-continued
| Example No. | Chemical Structure | [M + H] Calcd. | [M + H] Found | Analogous Procedure Example No. |
|---|---|---|---|---|
| 421 | 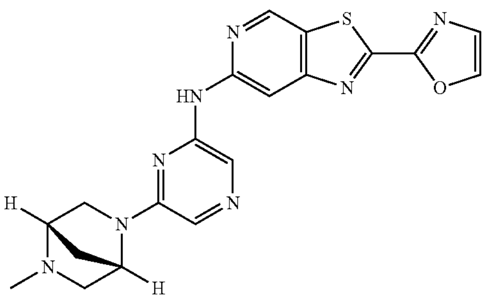 [SMILES: CN1C[C@@H]2C[C@H]1CN2c1cncc(Nc2cc3nc(-c4ncco4)sc3cn2)n1] | 407.1 | 407.2 | 121 |
| 422 | 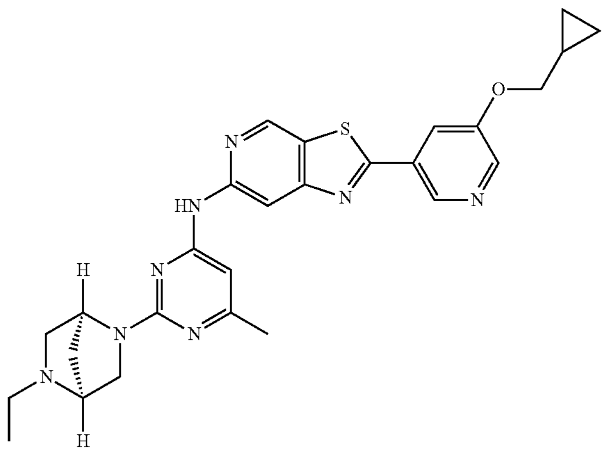 [SMILES: CCN1C[C@@H]2C[C@H]1CN2c1nc(C)cc(Nc2cc3nc(-c4cncc(OCC5CC5)c4)sc3cn2)n1] | 515.6 | 515.6 | 121 |
| 423 | 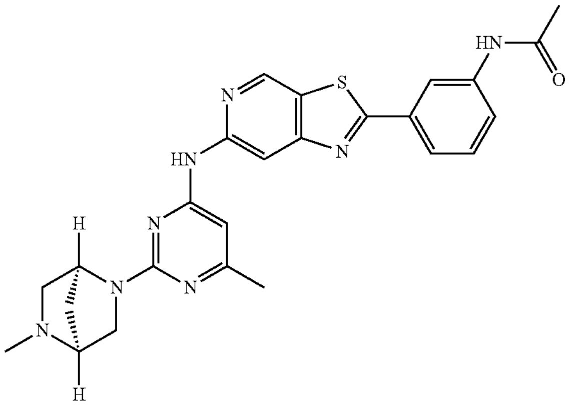 [SMILES: CC(=O)Nc1cccc(-c2nc3cc(Nc4cc(C)nc(N5C[C@@H]6C[C@H]5CN6C)n4)ncc3s2)c1] | 487.2 | 487.2 | 121 |
| 424 | 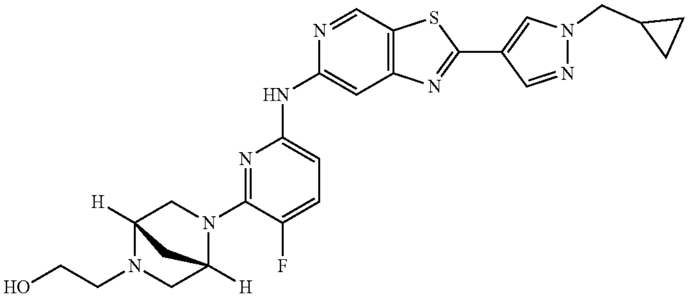 [SMILES: OCCN1C[C@@H]2C[C@H]1CN2c1nc(Nc2cc3nc(-c4cnn(CC5CC5)c4)sc3cn2)ccc1F] | 507.2 | 507.3 | 128 |

TABLE 3-continued
| Example No. | Chemical Structure | [M + H] Calcd. | [M + H] Found | Analogous Procedure Example No. |
|---|---|---|---|---|
| 425 | 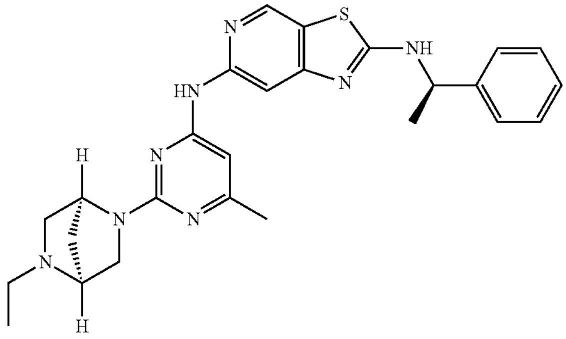 [SMILES: CCN1C[C@@H]2C[C@H]1CN2c1nc(C)cc(Nc2cc3nc(N[C@H](C)c4ccccc4)sc3cn2)n1] | 487.2 | 487.1 | 189 |
| 426 | 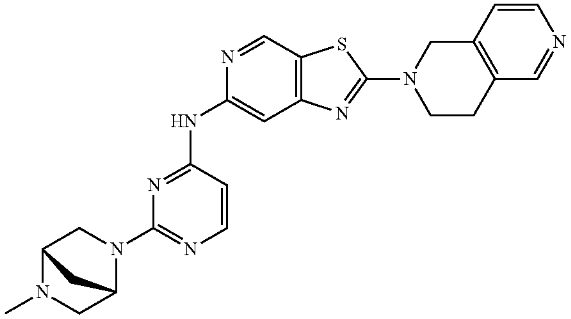 [SMILES: CN1C[C@@H]2C[C@H]1CN2c1nccc(Nc2cc3nc(N4CCc5cnccc5C4)sc3cn2)n1] | 472.2 | 472.2 | 194 |
| 427 | 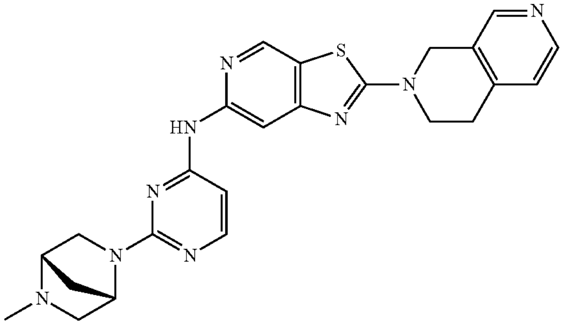 [SMILES: CN1C[C@@H]2C[C@H]1CN2c1nccc(Nc2cc3nc(N4CCc5ccncc5C4)sc3cn2)n1] | 472.2 | 472.2 | 194 |
| 428 | 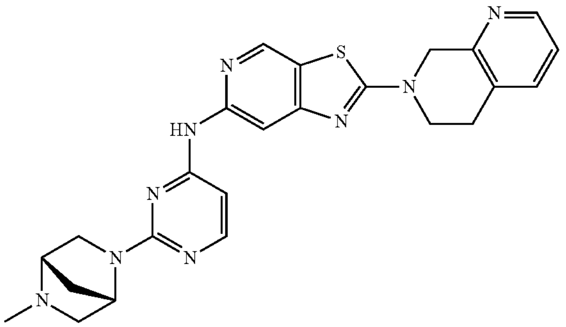 [SMILES: CN1C[C@@H]2C[C@H]1CN2c1nccc(Nc2cc3nc(N4CCc5cccnc5C4)sc3cn2)n1] | 472.2 | 472.2 | 194 |

TABLE 3-continued
| Example No. | Chemical Structure | [M + H] Calcd. | [M + H] Found | Analogous Procedure Example No. |
|---|---|---|---|---|
| 429 | 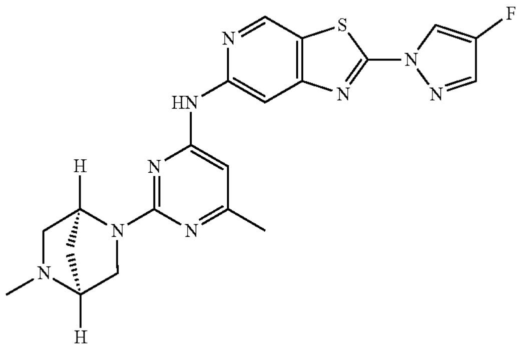 [SMILES: Cc1cc(Nc2cc3nc(-n4cc(F)cn4)sc3cn2)nc(N2C[C@@H]3C[C@H]2CN3C)n1] | 438.2 | 438.1 | 206 |
| 430 | 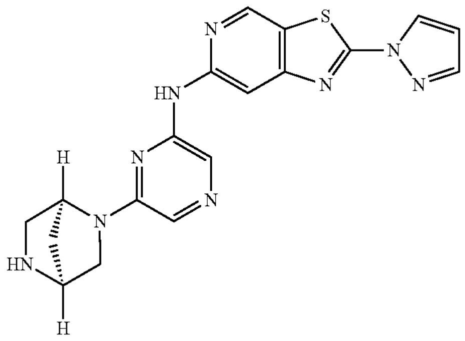 [SMILES: c1cnn(-c2nc3cc(Nc4cncc(N5C[C@@H]6C[C@H]5CN6)n4)ncc3s2)c1] | 392.1 | 392.1 | 206 |
| 431 | 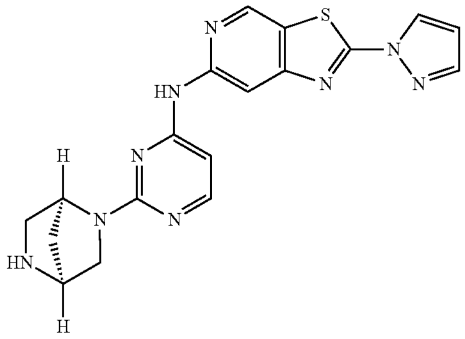 [SMILES: c1cnn(-c2nc3cc(Nc4ccnc(N5C[C@@H]6C[C@H]5CN6)n4)ncc3s2)c1] | 392.1 | 392.1 | 206 |
| 432 | 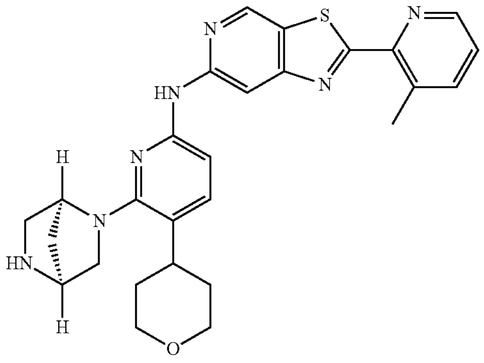 [SMILES: Cc1cccnc1-c1nc2cc(Nc3ccc(C4CCOCC4)c(N4C[C@@H]5C[C@H]4CN5)n3)ncc2s1] | 500.2 | 500.3 | 246 |

TABLE 3-continued
| Example No. | Chemical Structure | [M + H] Calcd. | [M + H] Found | Analogous Procedure Example No. |
|---|---|---|---|---|
| 433 | 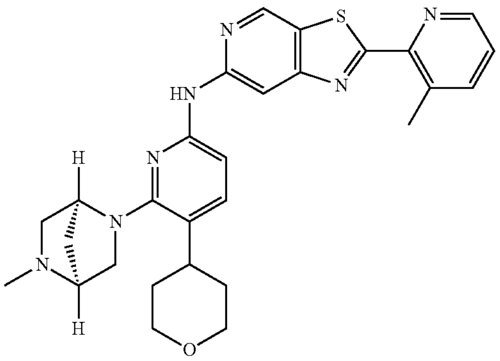 [SMILES: Cc1cccnc1-c1nc2cc(Nc3ccc(C4CCOCC4)c(N4C[C@@H]5C[C@H]4CN5C)n3)ncc2s1] | 514.2 | 514.2 | 246 |
| 434 | 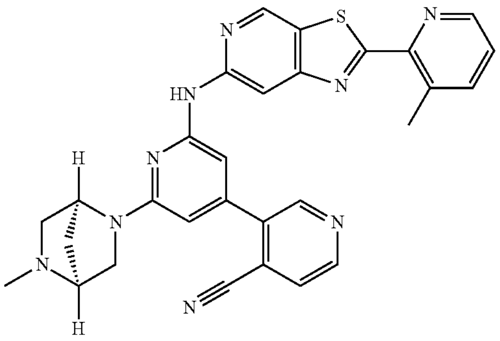 [SMILES: Cc1cccnc1-c1nc2cc(Nc3cc(-c4cnccc4C#N)cc(N4C[C@@H]5C[C@H]4CN5C)n3)ncc2s1] | 532.2 | 532.2 | 249 |
| 435 | 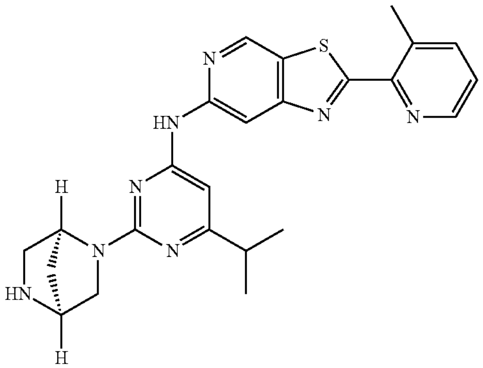 | 459.2 | 459.2 | 249 |
| 436 | 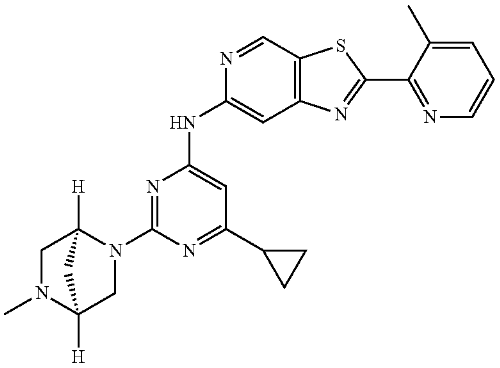 [SMILES: Cc1cccnc1-c1nc2cc(Nc3cc(C4CC4)nc(N4C[C@@H]5C[C@H]4CN5C)n3)ncc2s1] | 471.2 | 471.2 | 249 |

TABLE 3-continued
| Example No. | Chemical Structure | [M + H] Calcd. | [M + H] Found | Analogous Procedure Example No. |
|---|---|---|---|---|
| 437 | 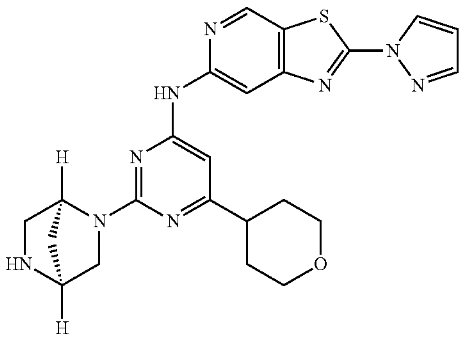 | 476.2 | 476.1 | 249 |
| 438 | 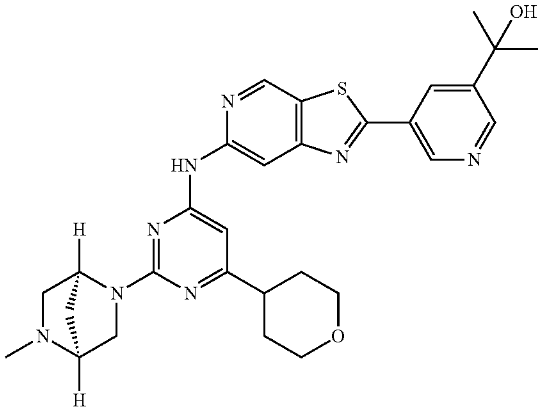 [SMILES: CN1C[C@@H]2C[C@H]1CN2c1nc(Nc2cc3nc(-c4cncc(C(C)(C)O)c4)sc3cn2)cc(C2CCOCC2)n1] | 559.3 | 559.4 | 249 |
| 439 | 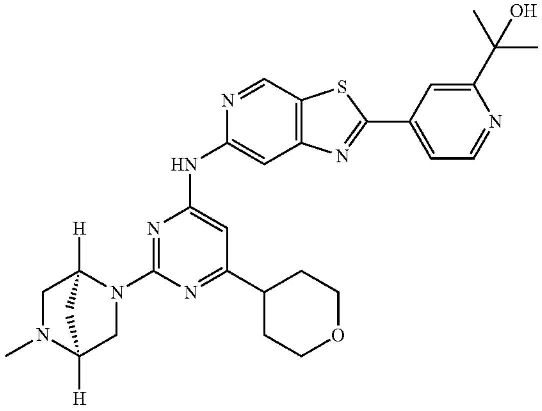 [SMILES: CN1C[C@@H]2C[C@H]1CN2c1nc(Nc2cc3nc(-c4ccnc(C(C)(C)O)c4)sc3cn2)cc(C2CCOCC2)n1] | 559.3 | 559.4 | 249 |

TABLE 3-continued
| Example No. | Chemical Structure | [M + H] Calcd. | [M + H] Found | Analogous Procedure Example No. |
|---|---|---|---|---|
| 440 | 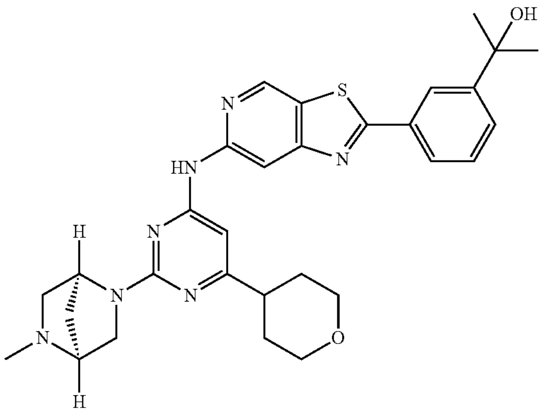 [SMILES: CN1C[C@@H]2C[C@H]1CN2c1nc(Nc2cc3nc(-c4cccc(C(C)(C)O)c4)sc3cn2)cc(C2CCOCC2)n1] | 558.3 | 558.1 | 249 |
| 441 | 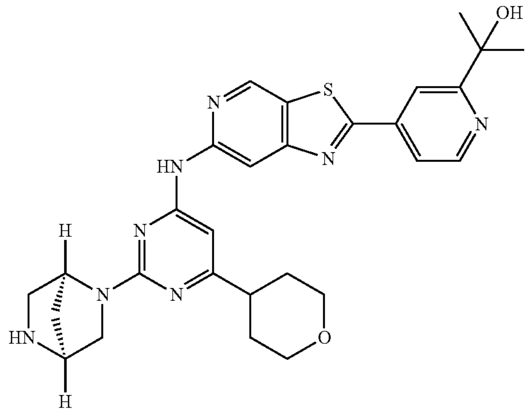 [SMILES: CC(C)(O)c1cc(-c2nc3cc(Nc4cc(C5CCOCC5)nc(N5C[C@@H]6C[C@H]5CN6)n4)ncc3s2)ccn1] | 545.2 | 545.1 | 250 |
| 442 | 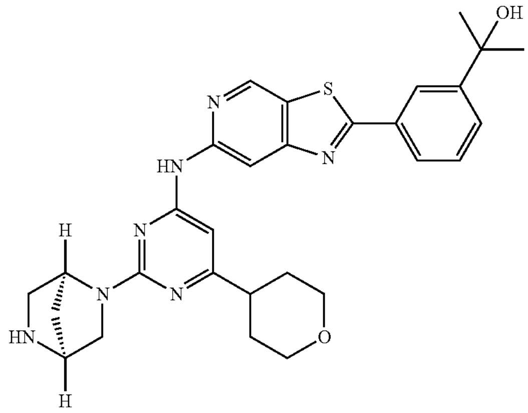 [SMILES: CC(C)(O)c1cccc(-c2nc3cc(Nc4cc(C5CCOCC5)nc(N5C[C@@H]6C[C@H]5CN6)n4)ncc3s2)c1] | 544.2 | 544.3 | 250 |

TABLE 3-continued
| Example No. | Chemical Structure | [M + H] Calcd. | [M + H] Found | Analogous Procedure Example No. |
|---|---|---|---|---|
| 443 | 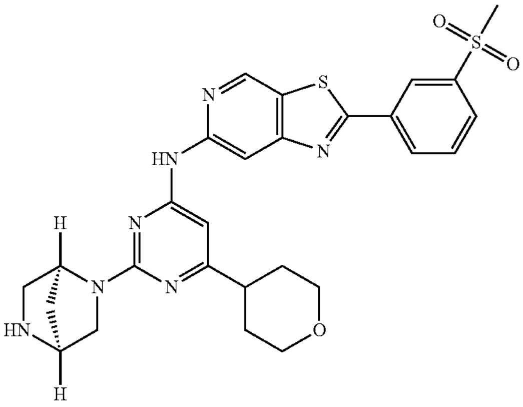 [SMILES: CS(=O)(=O)c1cccc(-c2nc3cc(Nc4cc(C5CCOCC5)nc(N5C[C@@H]6C[C@H]5CN6)n4)ncc3s2)c1] | 564.2 | 564.2 | 250 |
| 444 | 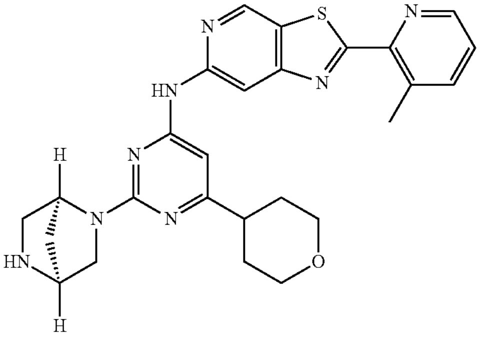 [SMILES: Cc1cccnc1-c1nc2cc(Nc3cc(C4CCOCC4)nc(N4C[C@@H]5C[C@H]4CN5)n3)ncc2s1] | 501.2 | 501.3 | 250 |
| 445 | 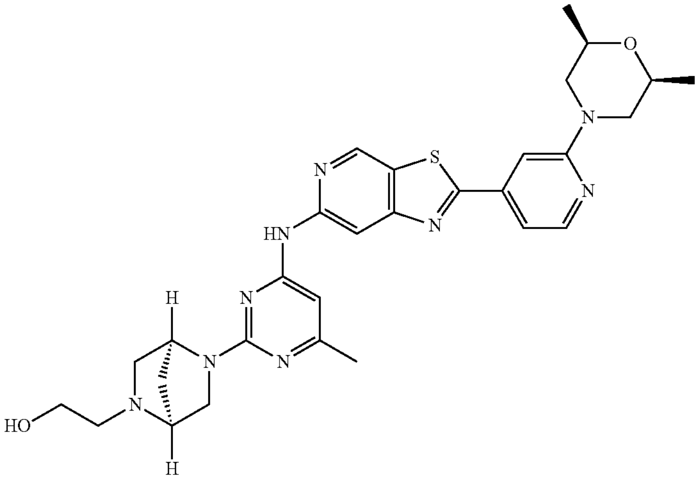 [SMILES: Cc1cc(Nc2cc3nc(-c4ccnc(N5C[C@@H](C)O[C@@H](C)C5)c4)sc3cn2)nc(N2C[C@@H]3C[C@H]2CN3CCO)n1] | 574.3 | 574.3 | 263 |

TABLE 3-continued
| Example No. | Chemical Structure | [M + H] Calcd. | [M + H] Found | Analogous Procedure Example No. |
|---|---|---|---|---|
| 446 | 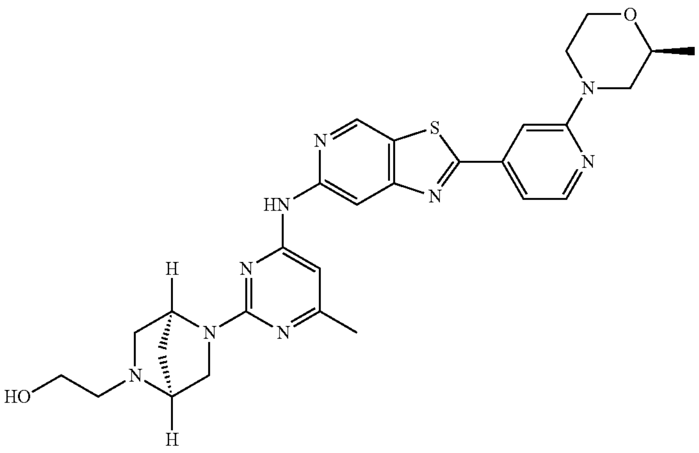 [SMILES: Cc1cc(Nc2cc3nc(-c4ccnc(N5CCO[C@@H](C)C5)c4)sc3cn2)nc(N2C[C@@H]3C[C@H]2CN3CCO)n1] | 560.2 | 560.3 | 263 |
| 447 | 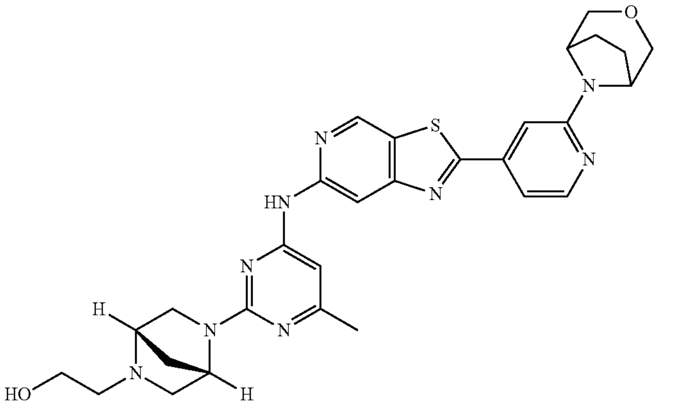 [SMILES: Cc1cc(Nc2cc3nc(-c4ccnc(N5C6CCC5COC6)c4)sc3cn2)nc(N2C[C@@H]3C[C@H]2CN3CCO)n1] | 572.2 | 572.3 | 263 |
| 448 | 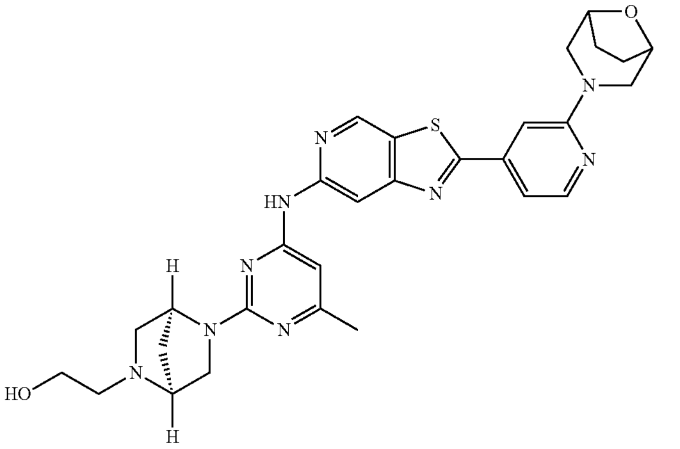 [SMILES: Cc1cc(Nc2cc3nc(-c4ccnc(N5CC6CCC(C5)O6)c4)sc3cn2)nc(N2C[C@@H]3C[C@H]2CN3CCO)n1] | 572.2 | 572.3 | 263 |

TABLE 3-continued
| Example No. | Chemical Structure | [M + H] Calcd. | [M + H] Found | Analogous Procedure Example No. |
|---|---|---|---|---|
| 449 | 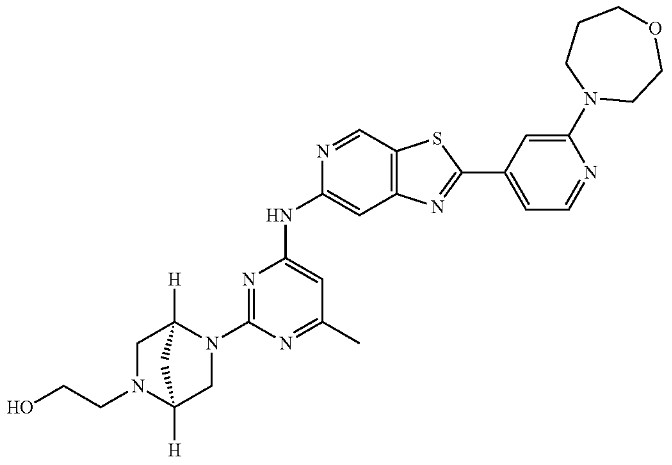 [SMILES: Cc1cc(Nc2cc3nc(-c4ccnc(N5CCCOCC5)c4)sc3cn2)nc(N2C[C@@H]3C[C@H]2CN3CCO)n1] | 560.2 | 560.3 | 263 |
| 450 | 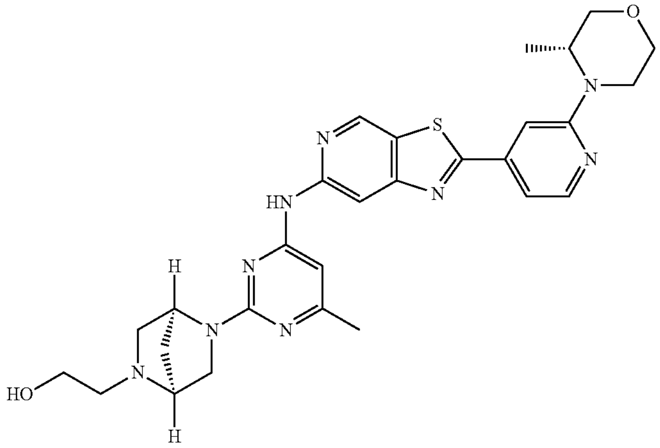 [SMILES: Cc1cc(Nc2cc3nc(-c4ccnc(N5CCOC[C@H]5C)c4)sc3cn2)nc(N2C[C@@H]3C[C@H]2CN3CCO)n1] | 560.2 | 560.3 | 263 |
| 451 | 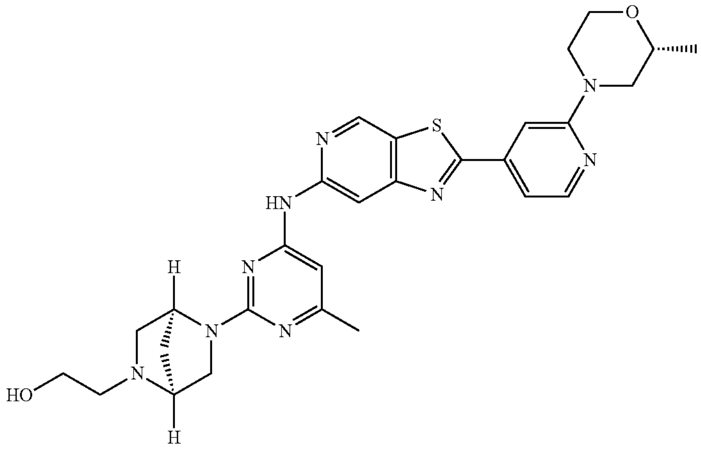 [SMILES: Cc1cc(Nc2cc3nc(-c4ccnc(N5CCO[C@H](C)C5)c4)sc3cn2)nc(N2C[C@@H]3C[C@H]2CN3CCO)n1] | 560.2 | 560.3 | 263 |

TABLE 3-continued
| Example No. | Chemical Structure | [M + H] Calcd. | [M + H] Found | Analogous Procedure Example No. |
|---|---|---|---|---|
| 452 | 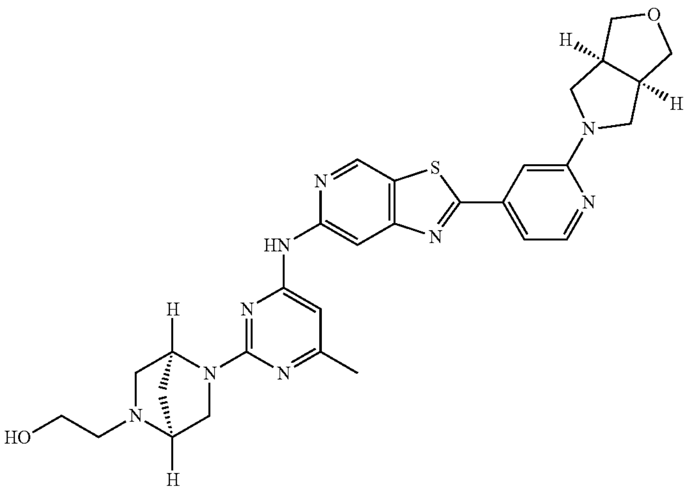 [SMILES: Cc1cc(Nc2cc3nc(-c4ccnc(N5C[C@H]6COC[C@H]6C5)c4)sc3cn2)nc(N2C[C@@H]3C[C@H]2CN3CCO)n1] | 572.2 | 572.2 | 263 |
| 453 | 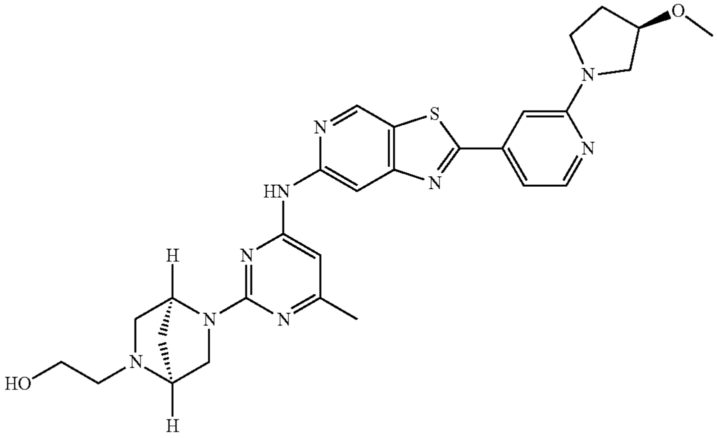 [SMILES: CO[C@@H]1CCN(c2cc(-c3nc4cc(Nc5cc(C)nc(N6C[C@@H]7C[C@H]6CN7CCO)n5)ncc4s3)ccn2)C1] | 560.2 | 560.3 | 263 |
| 454 | 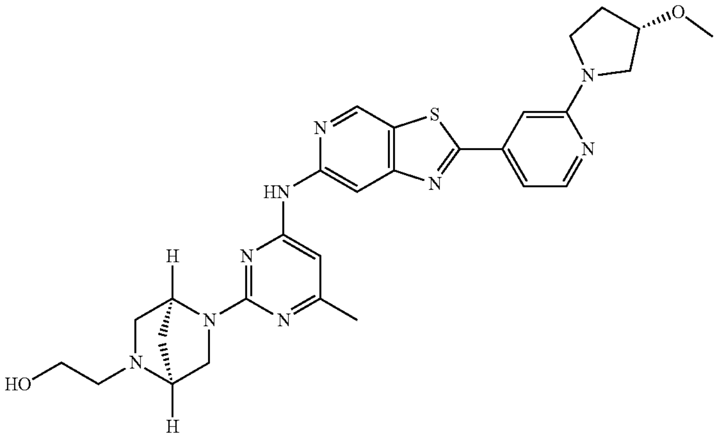 [SMILES: CO[C@H]1CCN(c2cc(-c3nc4cc(Nc5cc(C)nc(N6C[C@@H]7C[C@H]6CN7CCO)n5)ncc4s3)ccn2)C1] | 560.2 | 560.3 | 263 |

TABLE 3-continued
| Example No. | Chemical Structure | [M + H] Calcd. | [M + H] Found | Analogous Procedure Example No. |
|---|---|---|---|---|
| 455 | 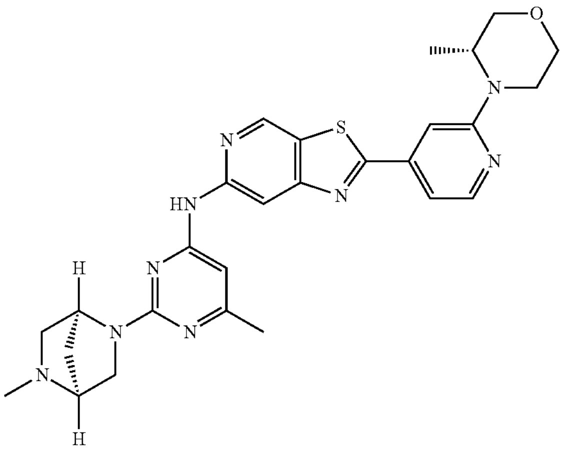 [SMILES: Cc1cc(Nc2cc3nc(-c4ccnc(N5CCOC[C@H]5C)c4)sc3cn2)nc(N2C[C@@H]3C[C@H]2CN3C)n1] | 530.2 | 530.3 | 263 |
| 456 | 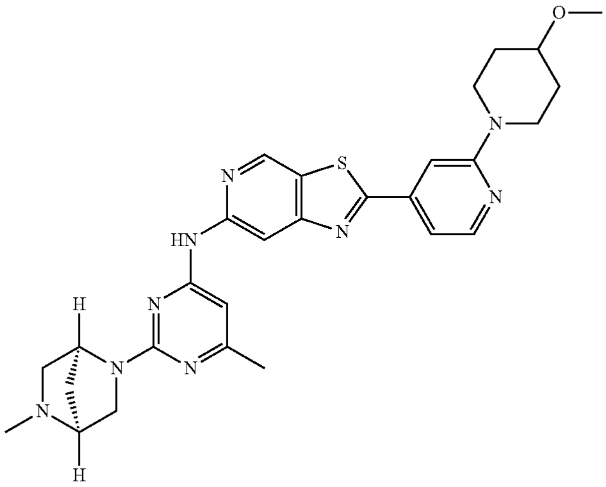 | 544.3 | 544.3 | 263 |
| 457 | 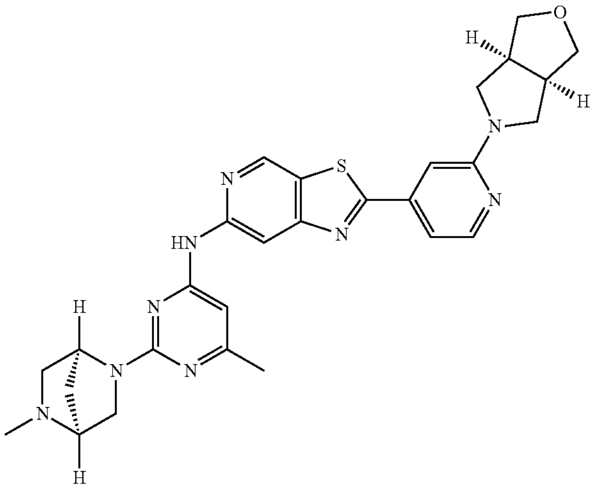 [SMILES: Cc1cc(Nc2cc3nc(-c4ccnc(N5C[C@H]6COC[C@H]6C5)c4)sc3cn2)nc(N2C[C@@H]3C[C@H]2CN3C)n1] | 542.2 | 542.3 | 263 |

TABLE 3-continued
| Example No. | Chemical Structure | [M + H] Calcd. | [M + H] Found | Analogous Procedure Example No. |
|---|---|---|---|---|
| 458 | 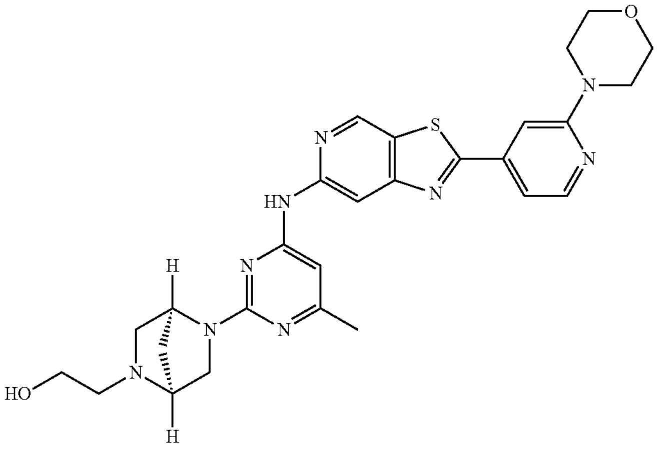 [SMILES: Cc1cc(Nc2cc3nc(-c4ccnc(N5CCOCC5)c4)sc3cn2)nc(N2C[C@@H]3C[C@H]2CN3CCO)n1] | 546.2 | 546.3 | 263 |
| 459 | 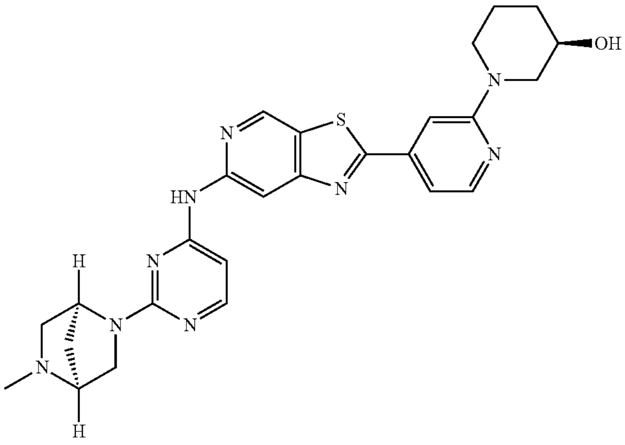 [SMILES: CN1C[C@@H]2C[C@H]1CN2c1nccc(Nc2cc3nc(-c4ccnc(N5CCC[C@@H](O)C5)c4)sc3cn2)n1] | 516.2 | 516.3 | 263 |
| 460 | 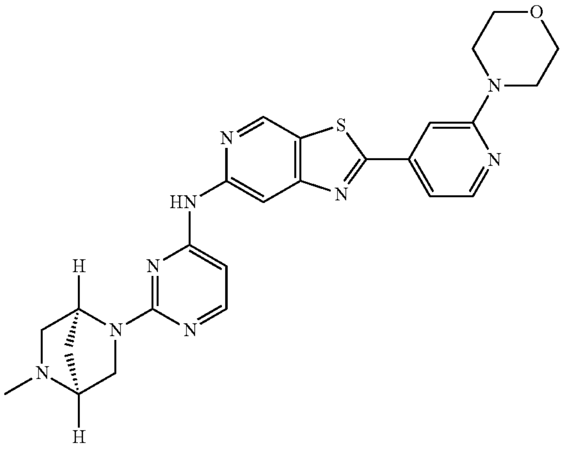 [SMILES: CN1C[C@@H]2C[C@H]1CN2c1nccc(Nc2cc3nc(-c4ccnc(N5CCOCC5)c4)sc3cn2)n1] | 502.2 | 502.1 | 263 |

TABLE 3-continued
| Example No. | Chemical Structure | [M + H] Calcd. | [M + H] Found | Analogous Procedure Example No. |
|---|---|---|---|---|
| 461 | 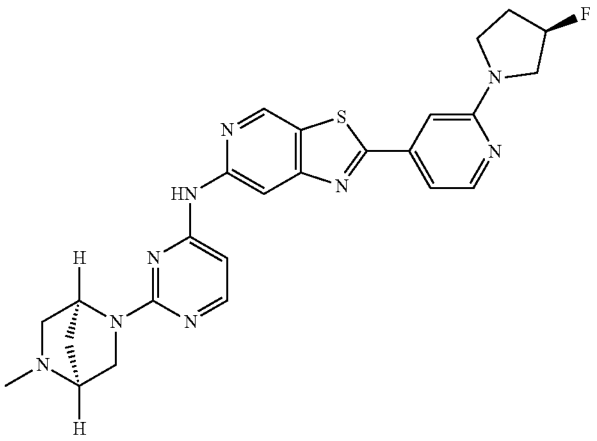 [SMILES: CN1C[C@@H]2C[C@H]1CN2c1nccc(Nc2cc3nc(-c4ccnc(N5CC[C@@H](F)C5)c4)sc3cn2)n1] | 504.2 | 504.3 | 263 |
| 462 | 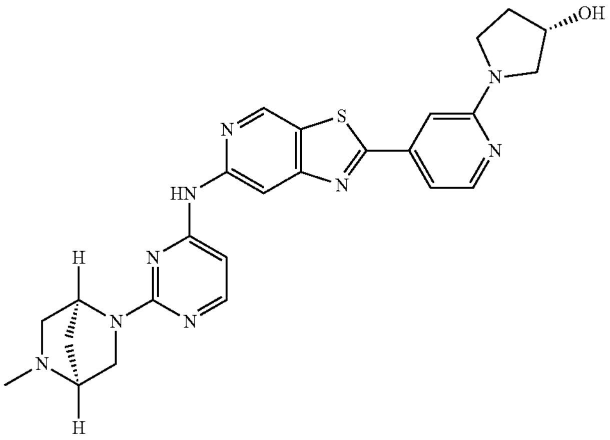 [SMILES: CN1C[C@@H]2C[C@H]1CN2c1nccc(Nc2cc3nc(-c4ccnc(N5CC[C@H](O)C5)c4)sc3cn2)n1] | 502.2 | 502.2 | 263 |
| 463 | 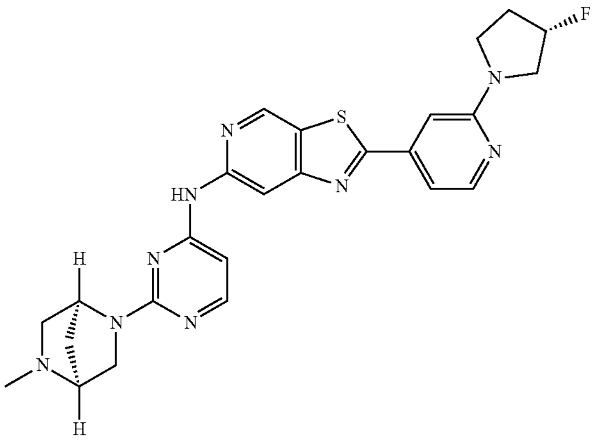 [SMILES: CN1C[C@@H]2C[C@H]1CN2c1nccc(Nc2cc3nc(-c4ccnc(N5CC[C@H](F)C5)c4)sc3cn2)n1] | 504.2 | 504.3 | 263 |

TABLE 3-continued
| Example No. | Chemical Structure | [M + H] Calcd. | [M + H] Found | Analogous Procedure Example No. |
|---|---|---|---|---|
| 464 | 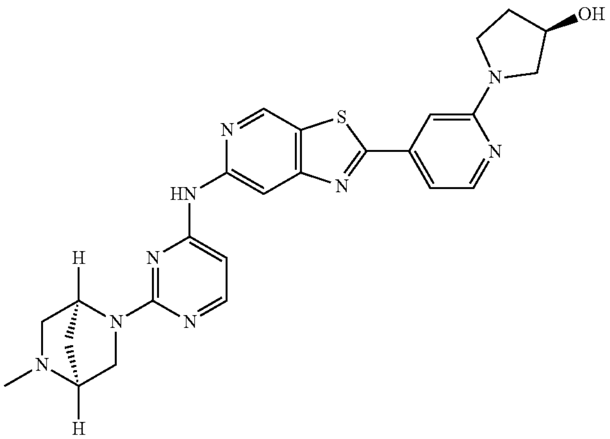 [SMILES: CN1C[C@@H]2C[C@H]1CN2c1nccc(Nc2cc3nc(-c4ccnc(N5CC[C@@H](O)C5)c4)sc3cn2)n1] | 502.2 | 502.1 | 263 |
| 465 | 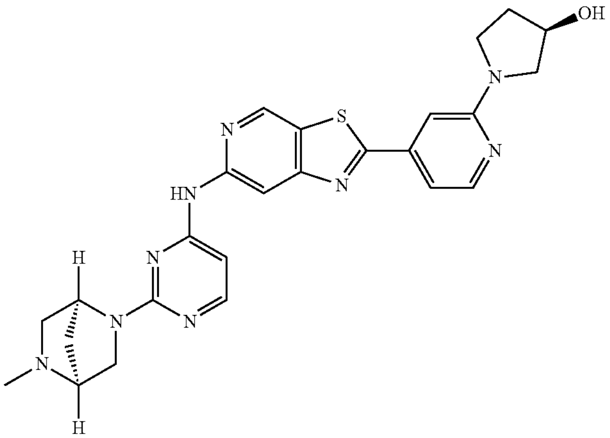 [SMILES: CN1C[C@@H]2C[C@H]1CN2c1nccc(Nc2cc3nc(-c4ccnc(N5CC[C@@H](O)C5)c4)sc3cn2)n1] | 502.2 | 502.3 | 263 |
| 466 | 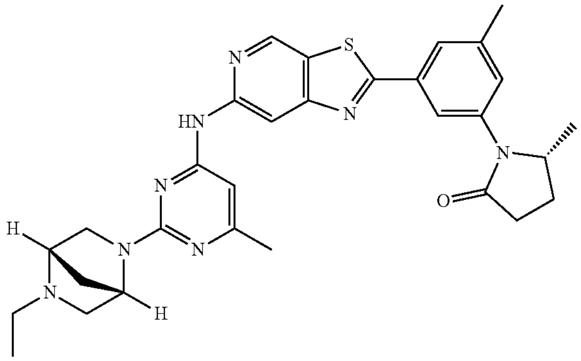 [SMILES: CCN1C[C@@H]2C[C@H]1CN2c1nc(C)cc(Nc2cc3nc(-c4cc(C)cc(N5C(=O)CC[C@H]5C)c4)sc3cn2)n1] | 555.3 | 555.1 | 295 |

TABLE 3-continued
| Example No. | Chemical Structure | [M + H] Calcd. | [M + H] Found | Analogous Procedure Example No. |
|---|---|---|---|---|
| 467 | 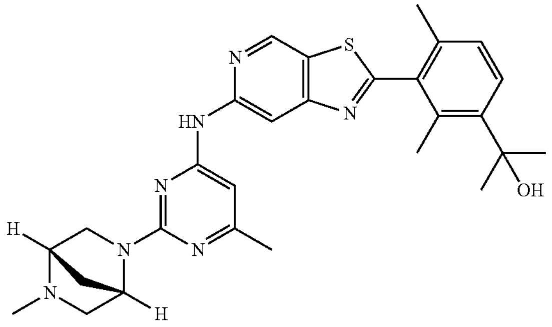 [SMILES: Cc1cc(Nc2cc3nc(-c4c(C)ccc(C(C)(C)O)c4C)sc3cn2)nc(N2C[C@@H]3C[C@H]2CN3C)n1] | 516.2 | 516.3 | 296 |
| 468 | 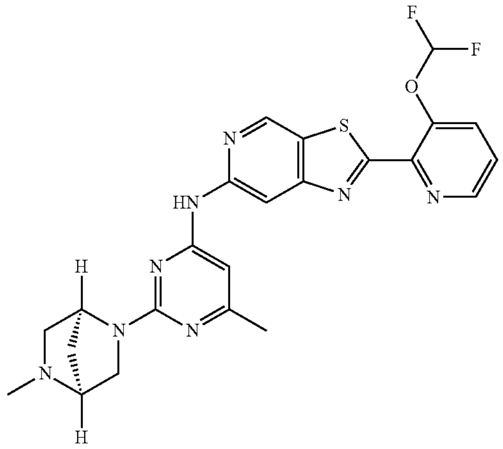 [SMILES: Cc1cc(Nc2cc3nc(-c4ncccc4OC(F)F)sc3cn2)nc(N2C[C@@H]3C[C@H]2CN3C)n1] | 497.2 | 487.3 | 296 |
| 469 | 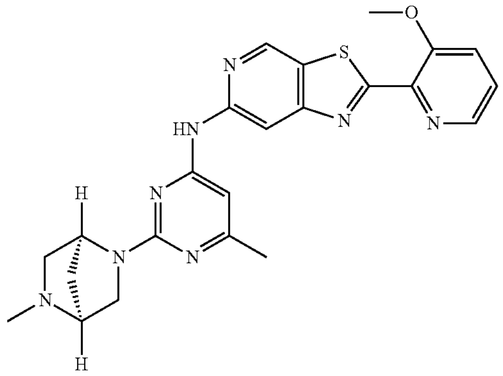 [SMILES: COc1cccnc1-c1nc2cc(Nc3cc(C)nc(N4C[C@@H]5C[C@H]4CN5C)n3)ncc2s1] | 461.2 | 461.1 | 296 |
| 470 | 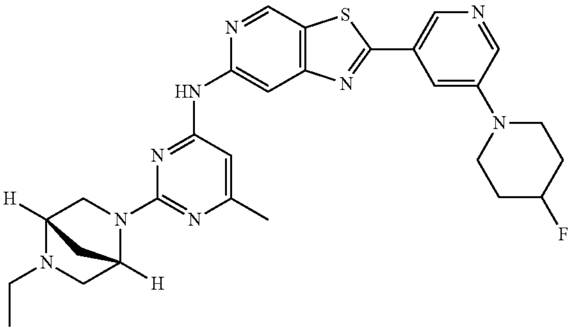 [SMILES: CCN1C[C@@H]2C[C@H]1CN2c1nc(C)cc(Nc2cc3nc(-c4cncc(N5CCC(F)CC5)c4)sc3cn2)n1] | 546.2 | 546.1 | 297 |

TABLE 3-continued
| Example No. | Chemical Structure | [M + H] Calcd. | [M + H] Found | Analogous Procedure Example No. |
|---|---|---|---|---|
| 471 | 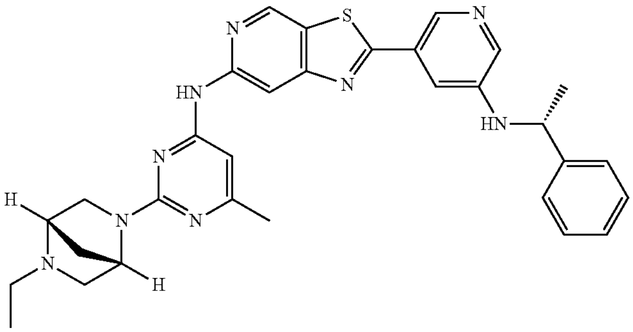 [SMILES: CCN1C[C@@H]2C[C@H]1CN2c1nc(C)cc(Nc2cc3nc(-c4cncc(N[C@H](C)c5ccccc5)c4)sc3cn2)n1] | 564.3 | 564.1 | 297 |
| 472 | 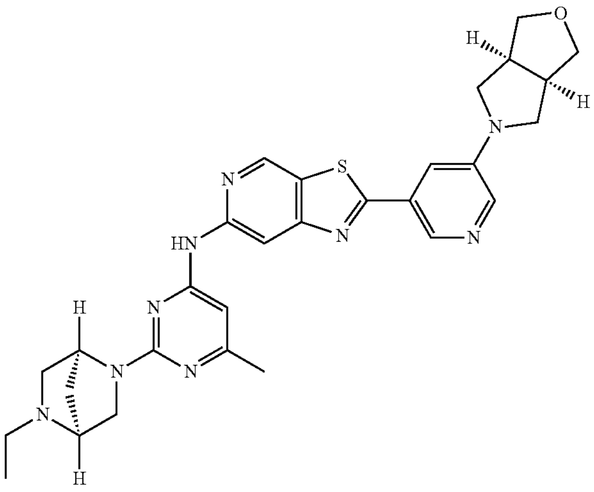 [SMILES: CCN1C[C@@H]2C[C@H]1CN2c1nc(C)cc(Nc2cc3nc(-c4cncc(N5C[C@H]6COC[C@H]6C5)c4)sc3cn2)n1] | 556.3 | 556.1 | 297 |
| 473 | 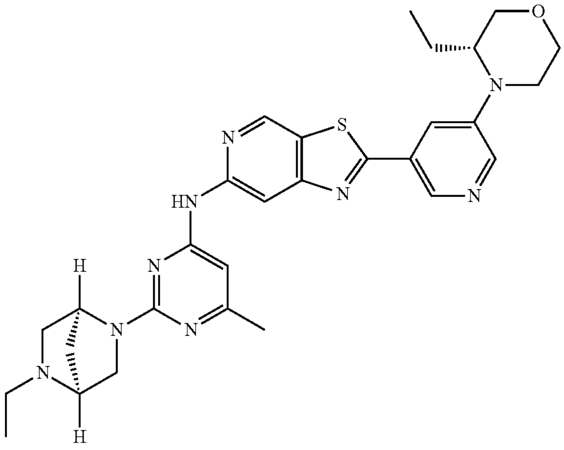 [SMILES: CC[C@@H]1COCCN1c1cncc(-c2nc3cc(Nc4cc(C)nc(N5C[C@@H]6C[C@H]5CN6CC)n4)ncc3s2)c1] | 558.3 | 558.1 | 297 |

TABLE 3-continued
| Example No. | Chemical Structure | [M + H] Calcd. | [M + H] Found | Analogous Procedure Example No. |
|---|---|---|---|---|
| 474 | 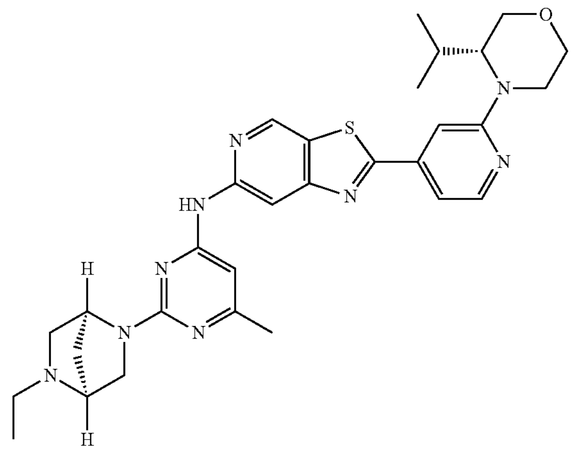 [SMILES: CCN1C[C@@H]2C[C@H]1CN2c1nc(C)cc(Nc2cc3nc(-c4ccnc(N5CCOC[C@H]5C(C)C)c4)sc3cn2)n1] | 572.3 | 572.3 | 297 |
| 475 | 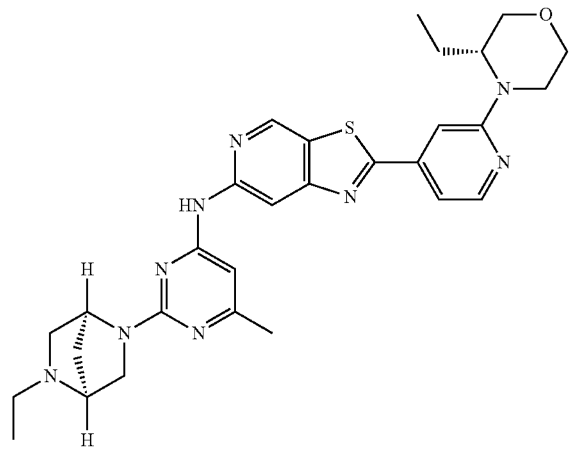 [SMILES: CC[C@@H]1COCCN1c1cc(-c2nc3cc(Nc4cc(C)nc(N5C[C@@H]6C[C@H]5CN6CC)n4)ncc3s2)ccn1] | 558.3 | 558.3 | 297 |
| 476 | 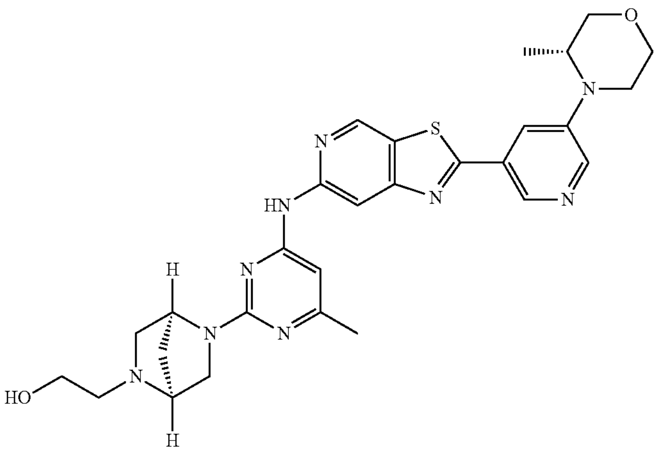 [SMILES: Cc1cc(Nc2cc3nc(-c4cncc(N5CCOC[C@H]5C)c4)sc3cn2)nc(N2C[C@@H]3C[C@H]2CN3CCO)n1] | 560.2 | 560.2 | 297 |

TABLE 3-continued
| Example No. | Chemical Structure | [M + H] Calcd. | [M + H] Found | Analogous Procedure Example No. |
|---|---|---|---|---|
| 477 | 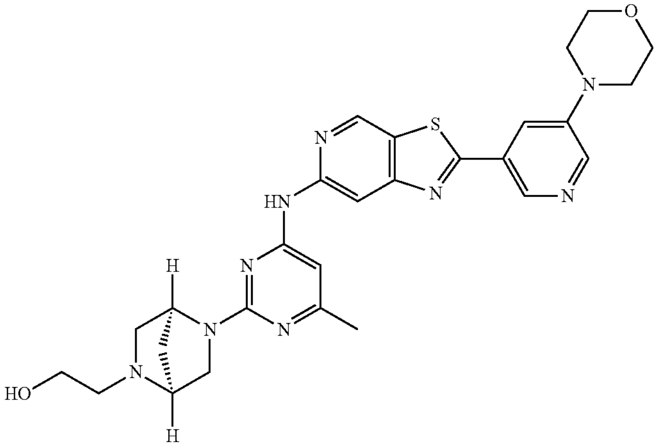 [SMILES: Cc1cc(Nc2cc3nc(-c4cncc(N5CCOCC5)c4)sc3cn2)nc(N2C[C@@H]3C[C@H]2CN3CCO)n1] | 546.2 | 546.3 | 297 |
| 478 | 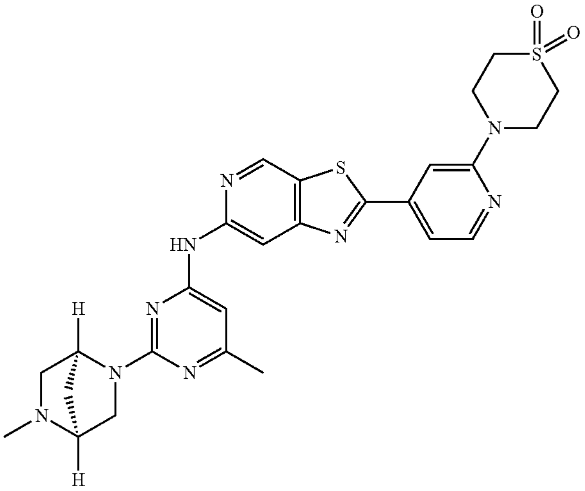 [SMILES: Cc1cc(Nc2cc3nc(-c4ccnc(N5CCS(=O)(=O)CC5)c4)sc3cn2)nc(N2C[C@@H]3C[C@H]2CN3C)n1] | 564.2 | 564.2 | 297 |
| 479 | 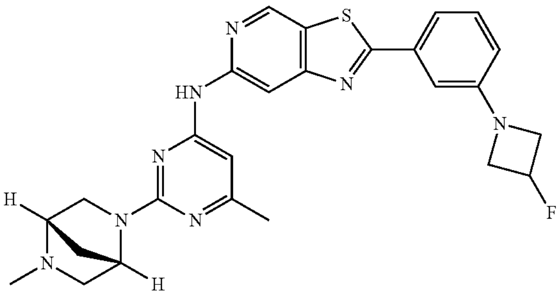 [SMILES: Cc1cc(Nc2cc3nc(-c4cccc(N5CC(F)C5)c4)sc3cn2)nc(N2C[C@@H]3C[C@H]2CN3C)n1] | 503.2 | 503.2 | 297 |

TABLE 3-continued
| Example No. | Chemical Structure | [M + H] Calcd. | [M + H] Found | Analogous Procedure Example No. |
|---|---|---|---|---|
| 480 | 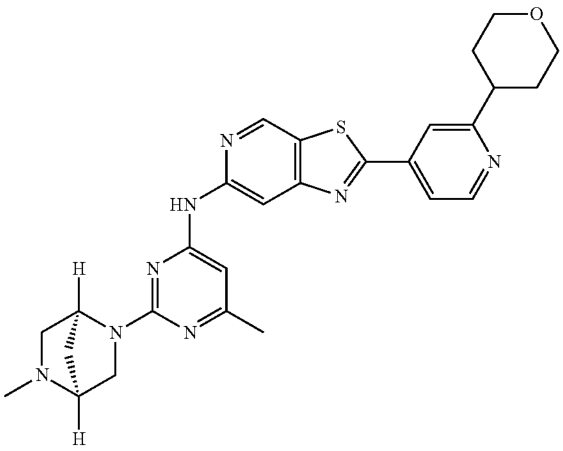 | 515.2 | 515.2 | 297 |
| 481 | 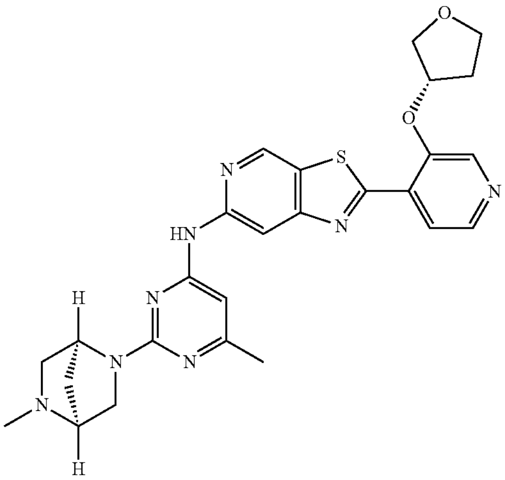 [SMILES: Cc1cc(Nc2cc3nc(-c4ccncc4O[C@H]4CCOC4)sc3cn2)nc(N2C[C@@H]3C[C@H]2CN3C)n1] | 517.2 | 517.1 | 297 |
| 482 | 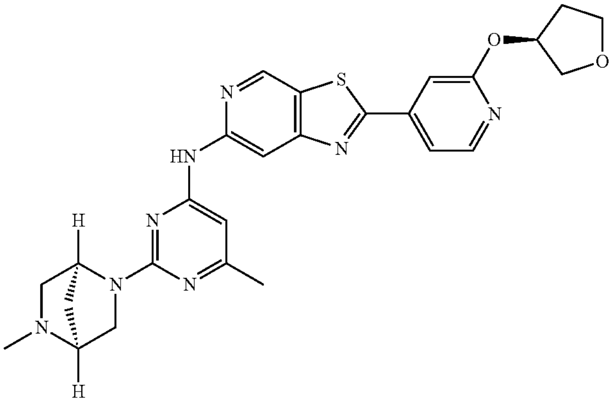 [SMILES: Cc1cc(Nc2cc3nc(-c4ccnc(O[C@H]5CCOC5)c4)sc3cn2)nc(N2C[C@@H]3C[C@H]2CN3C)n1] | 517.2 | 517.1 | 297 |

TABLE 3-continued
| Example No. | Chemical Structure | [M + H] Calcd. | [M + H] Found | Analogous Procedure Example No. |
|---|---|---|---|---|
| 483 | 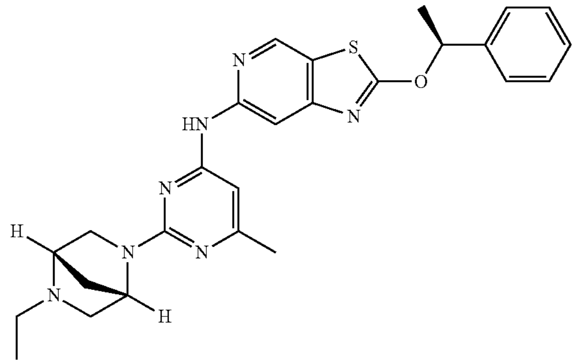 [SMILES: CCN1C[C@@H]2C[C@H]1CN2c1nc(C)cc(Nc2cc3nc(O[C@@H](C)c4ccccc4)sc3cn2)n1] | 488.2 | 488.1 | 298 |
| 484 | 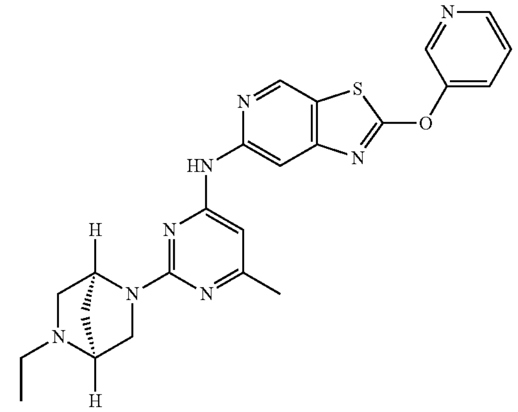 [SMILES: CCN1C[C@@H]2C[C@H]1CN2c1nc(C)cc(Nc2cc3nc(Oc4cccnc4)sc3cn2)n1] | 461.2 | 461.1 | 298 |
| 485 | 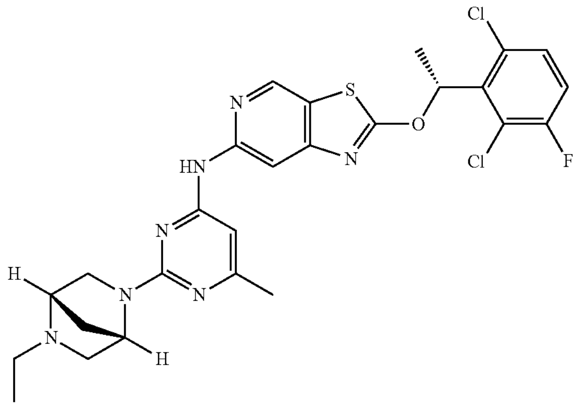 [SMILES: CCN1C[C@@H]2C[C@H]1CN2c1nc(C)cc(Nc2cc3nc(O[C@H](C)c4c(Cl)ccc(F)c4Cl)sc3cn2)n1] | 574.1 | 574.2 | 298 |
| 486 | 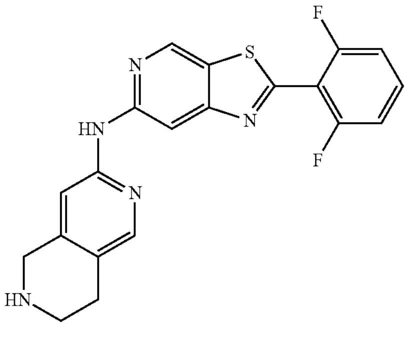 [SMILES: Fc1cccc(F)c1-c1nc2cc(Nc3cc4c(cn3)CCNC4)ncc2s1] | 396.1 | 396 | 300 |

TABLE 3-continued
| Example No. | Chemical Structure | [M + H] Calcd. | [M + H] Found | Analogous Procedure Example No. |
|---|---|---|---|---|
| 487 | 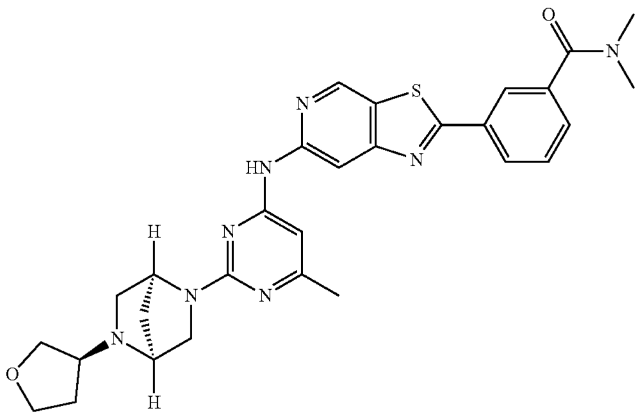 [SMILES: Cc1cc(Nc2cc3nc(-c4cccc(C(=O)N(C)C)c4)sc3cn2)nc(N2C[C@@H]3C[C@H]2CN3[C@H]2CCOC2)n1] | 557.2 | 557.2 | 301 |
| 488 | 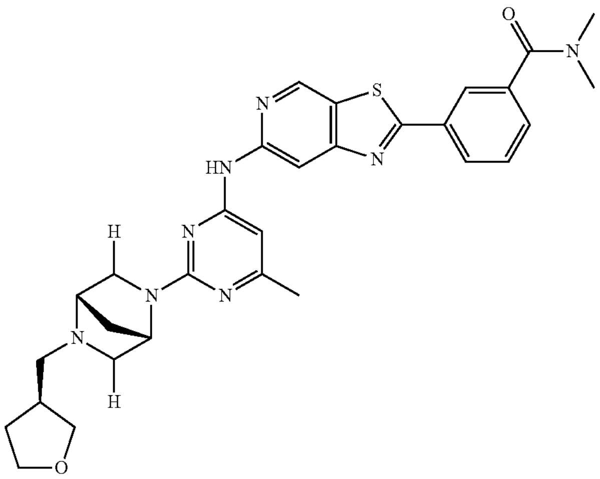 [SMILES: Cc1cc(Nc2cc3nc(-c4cccc(C(=O)N(C)C)c4)sc3cn2)nc(N2C[C@@H]3C[C@H]2CN3C[C@@H]2CCOC2)n1] | 571.3 | 571.3 | 301 |
| 489 | 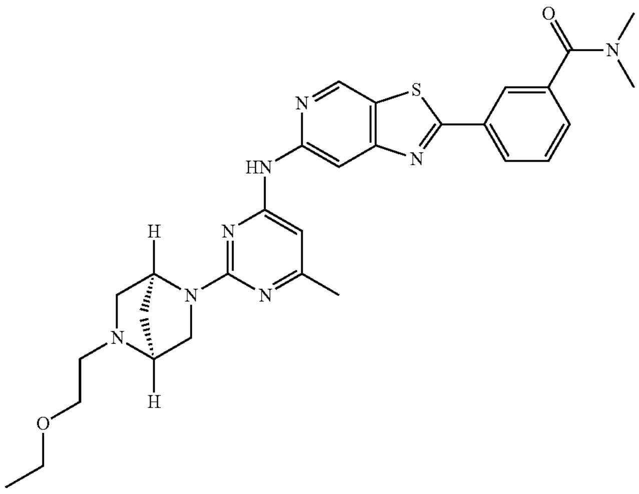 [SMILES: CCOCCN1C[C@@H]2C[C@H]1CN2c1nc(C)cc(Nc2cc3nc(-c4cccc(C(=O)N(C)C)c4)sc3cn2)n1] | 559.3 | 599.3 | 301 |

TABLE 3-continued
| Example No. | Chemical Structure | [M + H] Calcd. | [M + H] Found | Analogous Procedure Example No. |
| --- | --- | --- | --- | --- |
| 490 | 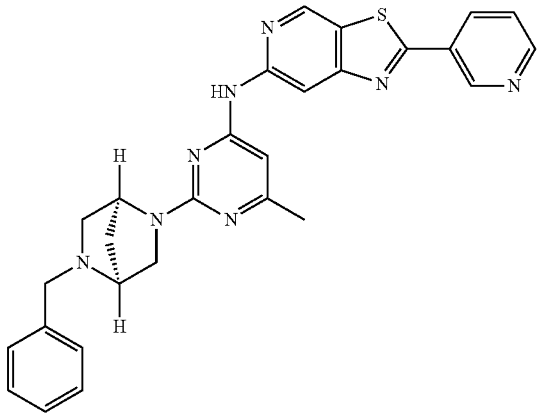 [SMILES: Cc1cc(Nc2cc3nc(-c4cccnc4)sc3cn2)nc(N2C[C@@H]3C[C@H]2CN3Cc2ccccc2)n1] | 507.2 | 507 | 301 |
| 491 | 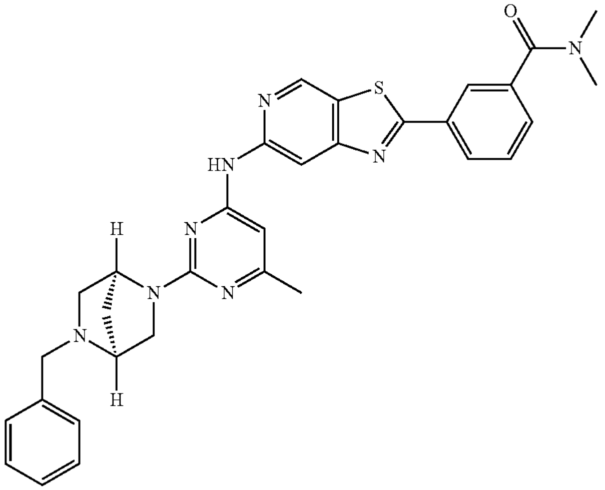 [SMILES: Cc1cc(Nc2cc3nc(-c4cccc(C(=O)N(C)C)c4)sc3cn2)nc(N2C[C@@H]3C[C@H]2CN3Cc2ccccc2)n1] | 585.3 | 585.3 | 301 |
| 492 | 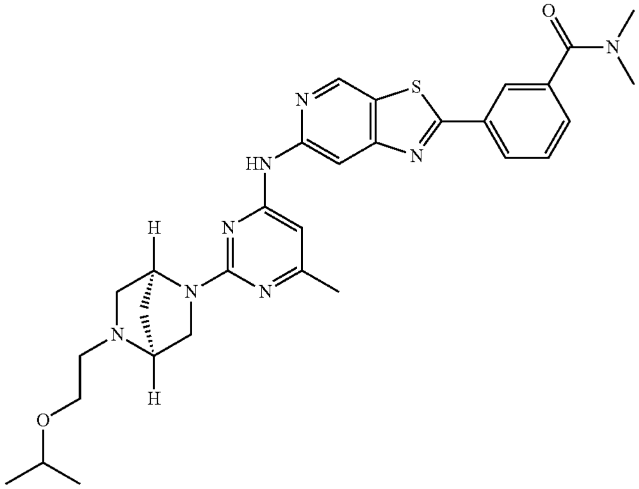 [SMILES: Cc1cc(Nc2cc3nc(-c4cccc(C(=O)N(C)C)c4)sc3cn2)nc(N2C[C@@H]3C[C@H]2CN3CCOC(C)C)n1] | 573.3 | 573.3 | 301 |

TABLE 3-continued
| Example No. | Chemical Structure | [M + H] Calcd. | [M + H] Found | Analogous Procedure Example No. |
|---|---|---|---|---|
| 493 | 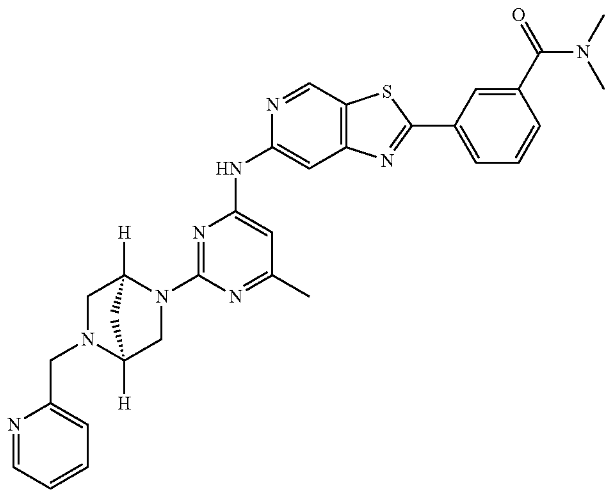 [SMILES: Cc1cc(Nc2cc3nc(-c4cccc(C(=O)N(C)C)c4)sc3cn2)nc(N2C[C@@H]3C[C@H]2CN3Cc2ccccn2)n1] | 578.2 | 578.1 | 301 |
| 494 | 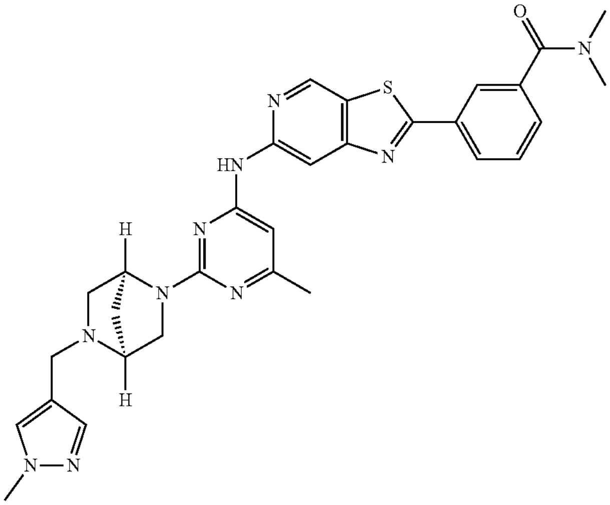 | 581.2 | 581.1 | 301 |
| 495 | 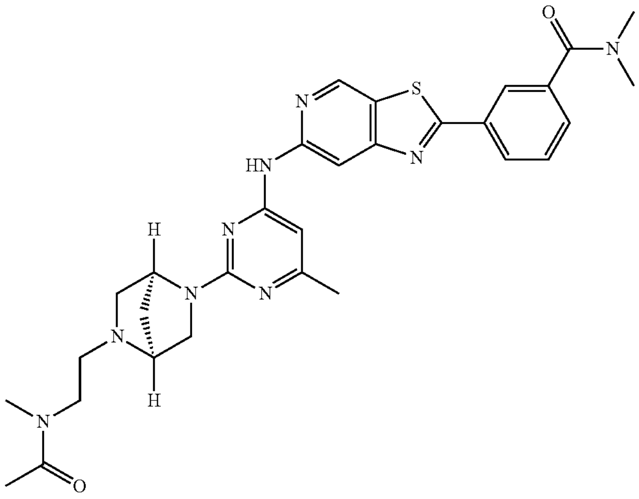 [SMILES: CC(=O)N(C)CCN1C[C@@H]2C[C@H]1CN2c1nc(C)cc(Nc2cc3nc(-c4cccc(C(=O)N(C)C)c4)sc3cn2)n1] | 586.3 | 586.2 | 301 |

TABLE 3-continued
| Example No. | Chemical Structure | [M + H] Calcd. | [M + H] Found | Analogous Procedure Example No. |
|---|---|---|---|---|
| 496 | 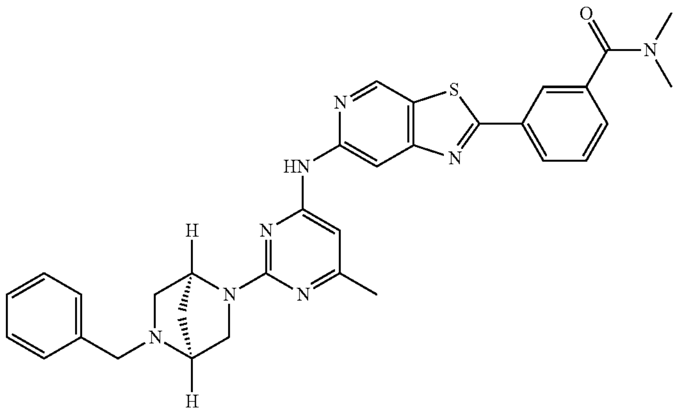 [SMILES: Cc1cc(Nc2cc3nc(-c4cccc(C(=O)N(C)C)c4)sc3cn2)nc(N2C[C@@H]3C[C@H]2CN3Cc2ccccc2)n1] | 577.2 | 577 | 301 |
| 497 | 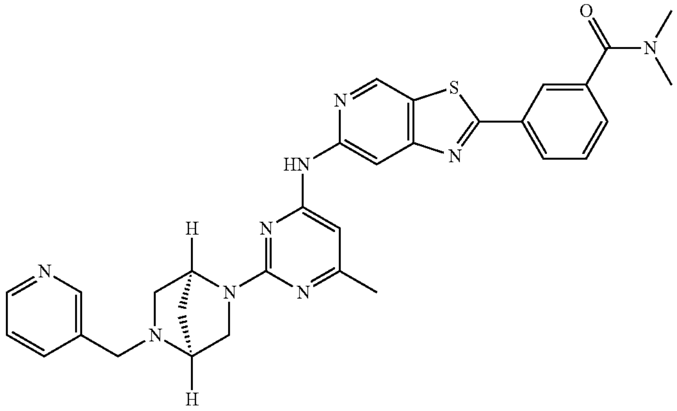 [SMILES: Cc1cc(Nc2cc3nc(-c4cccc(C(=O)N(C)C)c4)sc3cn2)nc(N2C[C@@H]3C[C@H]2CN3Cc2cccnc2)n1] | 578.2 | 578.3 | 301 |
| 498 | 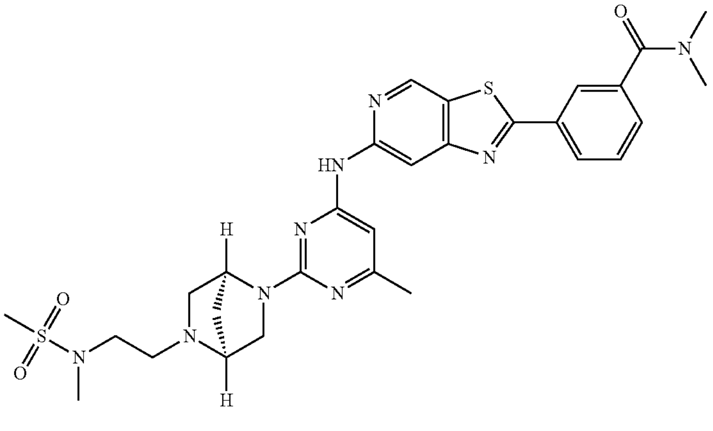 | 622.2 | 622.2 | 301 |

TABLE 3-continued
| Example No. | Chemical Structure | [M + H] Calcd. | [M + H] Found | Analogous Procedure Example No. |
|---|---|---|---|---|
| 499 | 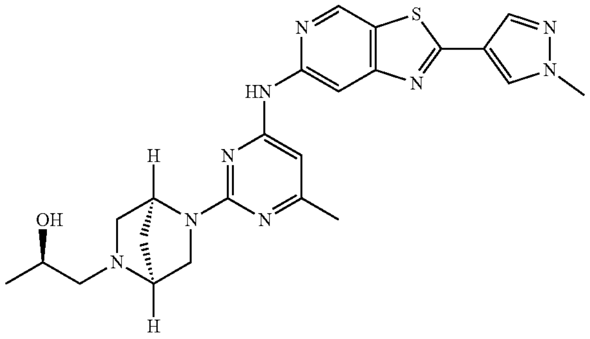 [SMILES: Cc1cc(Nc2cc3nc(-c4cnn(C)c4)sc3cn2)nc(N2C[C@@H]3C[C@H]2CN3C[C@@H](C)O)n1] | 478.2 | 478.2 | 301 |
| 500 | 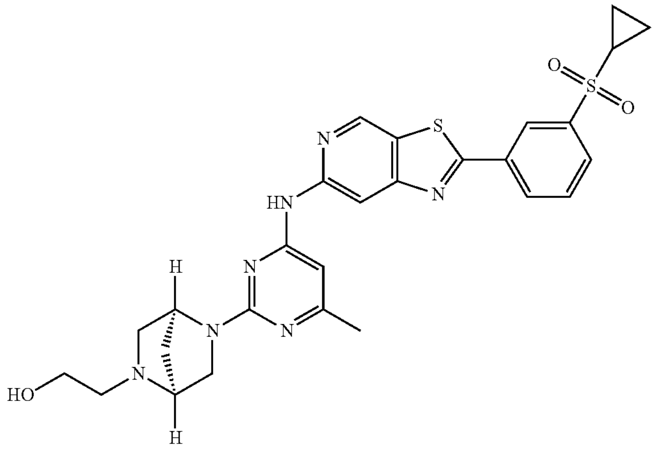 [SMILES: Cc1cc(Nc2cc3nc(-c4cccc(S(=O)(=O)C5CC5)c4)sc3cn2)nc(N2C[C@@H]3C[C@H]2CN3CCO)n1] | 564.2 | 564.2 | 301 |
| 501 | 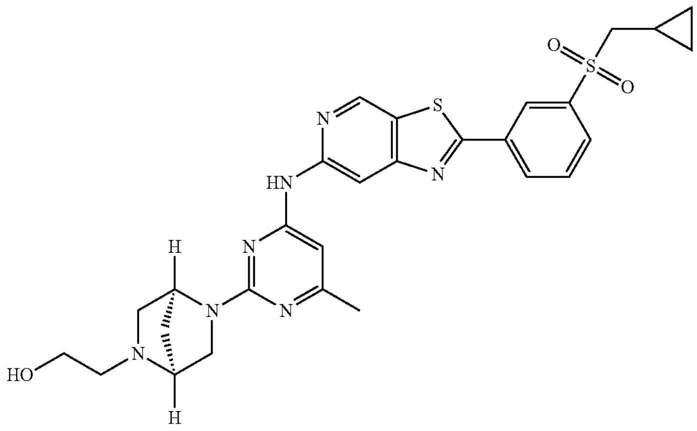 [SMILES: Cc1cc(Nc2cc3nc(-c4cccc(S(=O)(=O)CC5CC5)c4)sc3cn2)nc(N2C[C@@H]3C[C@H]2CN3CCO)n1] | 578.2 | 578.2 | 301 |

TABLE 3-continued
| Example No. | Chemical Structure | [M + H] Calcd. | [M + H] Found | Analogous Procedure Example No. |
|---|---|---|---|---|
| 502 | 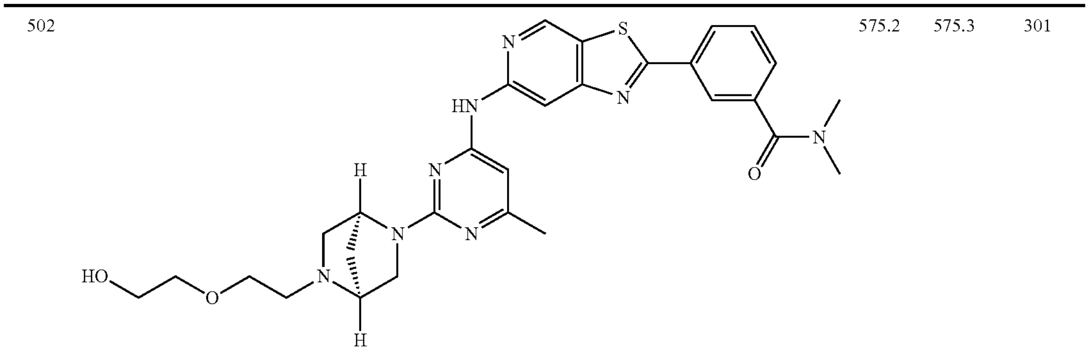 | 575.2 | 575.3 | 301 |
| 503 | 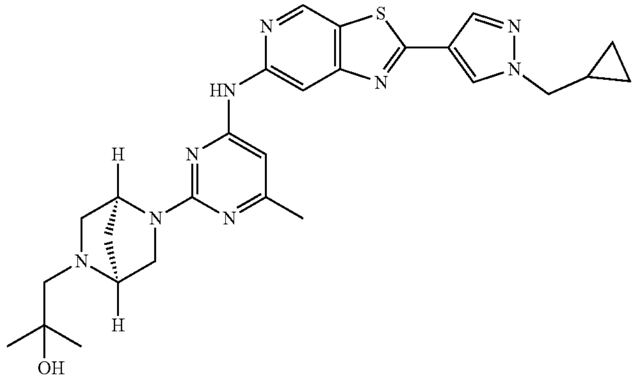 [SMILES: Cc1cc(Nc2cc3nc(-c4cnn(CC5CC5)c4)sc3cn2)nc(N2C[C@@H]3C[C@H]2CN3CC(C)(C)O)n1] | 532.3 | 532.1 | 301 |
| 504 | 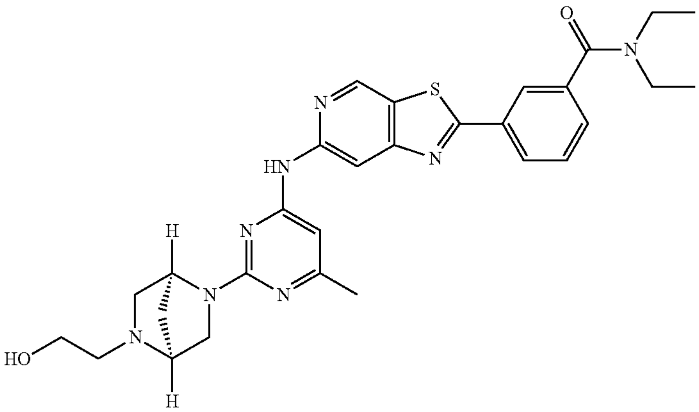 [SMILES: CCN(CC)C(=O)c1cccc(-c2nc3cc(Nc4cc(C)nc(N5C[C@@H]6C[C@H]5CN6CCO)n4)ncc3s2)c1] | 559.3 | 559.2 | 301 |
| 505 | 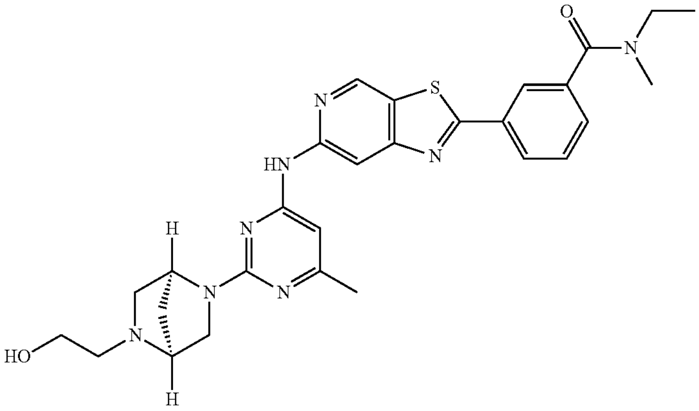 [SMILES: CCN(C)C(=O)c1cccc(-c2nc3cc(Nc4cc(C)nc(N5C[C@@H]6C[C@H]5CN6CCO)n4)ncc3s2)c1] | 545.2 | 545.4 | 301 |

TABLE 3-continued
| Example No. | Chemical Structure | [M + H] Calcd. | [M + H] Found | Analogous Procedure Example No. |
|---|---|---|---|---|
| 506 | 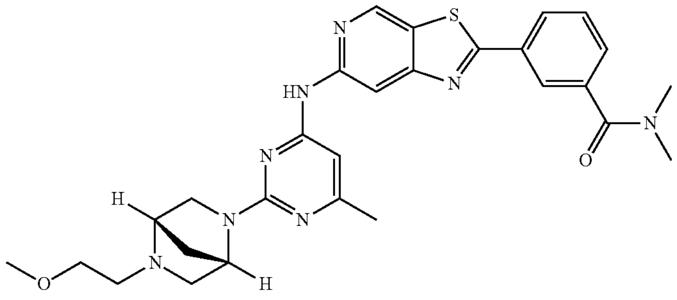 | 545.2 | 545.2 | 301 |
| 507 | 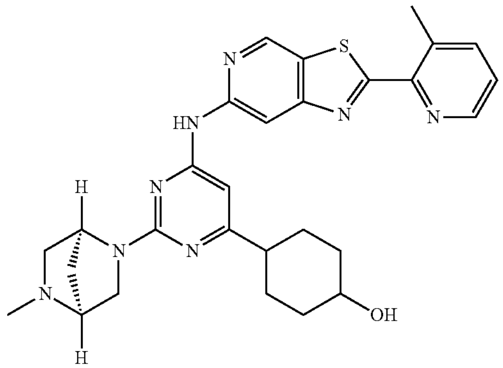 [SMILES: Cc1cccnc1-c1nc2cc(Nc3cc(C4CCC(O)CC4)nc(N4C[C@@H]5C[C@H]4CN5C)n3)ncc2s1] | 529.2 | 529.3 | 302 |
| 508 | 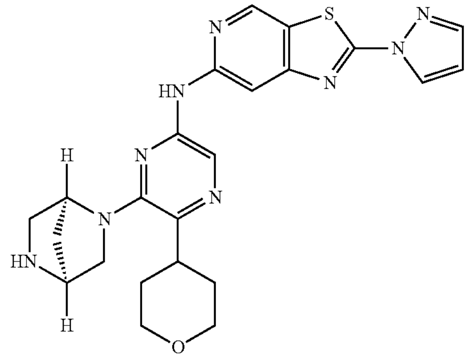 [SMILES: c1cnn(-c2nc3cc(Nc4cnc(C5CCOCC5)c(N5C[C@@H]6C[C@H]5CN6)n4)ncc3s2)c1] | 476.2 | 476.1 | 303 |
| 509 | 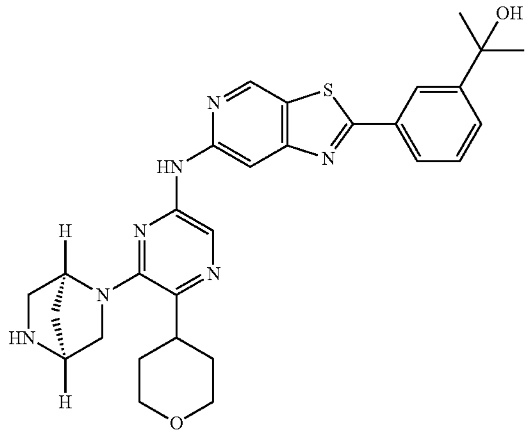 [SMILES: CC(C)(O)c1cccc(-c2nc3cc(Nc4cnc(C5CCOCC5)c(N5C[C@@H]6C[C@H]5CN6)n4)ncc3s2)c1] | 544.2 | 544.2 | 303 |

TABLE 3-continued
| Example No. | Chemical Structure | [M + H] Calcd. | [M + H] Found | Analogous Procedure Example No. |
|---|---|---|---|---|
| 510 | 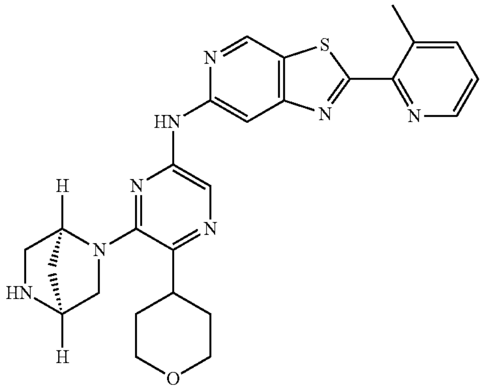 [SMILES: Cc1cccnc1-c1nc2cc(Nc3cnc(C4CCOCC4)c(N4C[C@@H]5C[C@H]4CN5)n3)ncc2s1] | 501.2 | 501.2 | 303 |
| 511 | 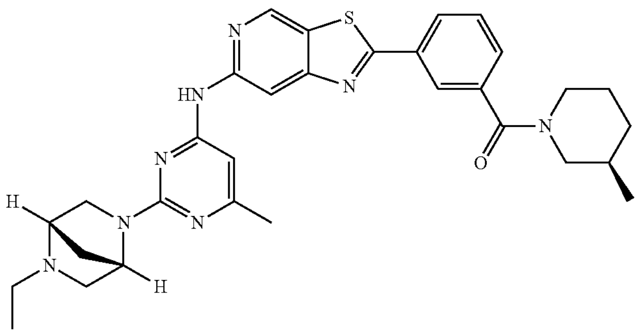 [SMILES: CCN1C[C@@H]2C[C@H]1CN2c1nc(C)cc(Nc2cc3nc(-c4cccc(C(=O)N5CCC[C@@H](C)C5)c4)sc3cn2)n1] | 569.3 | 569.3 | 305 |
| 512 | 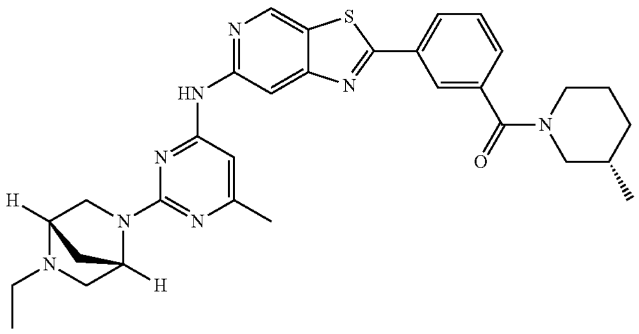 [SMILES: CCN1C[C@@H]2C[C@H]1CN2c1nc(C)cc(Nc2cc3nc(-c4cccc(C(=O)N5CCC[C@H](C)C5)c4)sc3cn2)n1] | 569.3 | 569.3 | 305 |
| 513 | 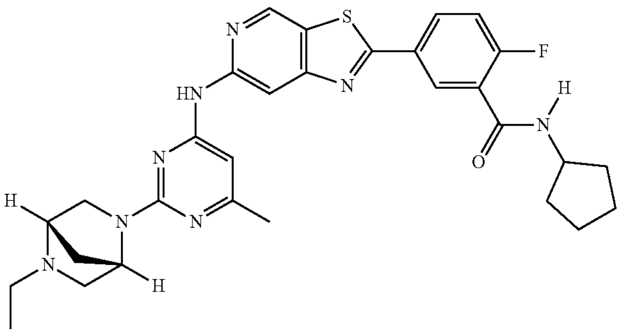 [SMILES: CCN1C[C@@H]2C[C@H]1CN2c1nc(C)cc(Nc2cc3nc(-c4ccc(F)c(C(=O)NC5CCCC5)c4)sc3cn2)n1] | 573.2 | 573.3 | 305 |

TABLE 3-continued
| Example No. | Chemical Structure | [M + H] Calcd. | [M + H] Found | Analogous Procedure Example No. |
| --- | --- | --- | --- | --- |
| 514 | 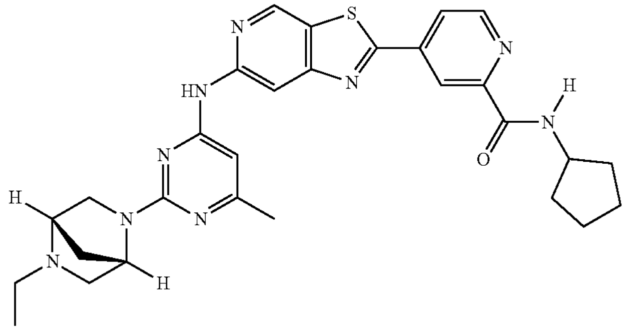 [SMILES: CCN1C[C@@H]2C[C@H]1CN2c1nc(C)cc(Nc2cc3nc(-c4ccnc(C(=O)NC5CCCC5)c4)sc3cn2)n1] | 556.3 | 556.3 | 305 |
| 515 | 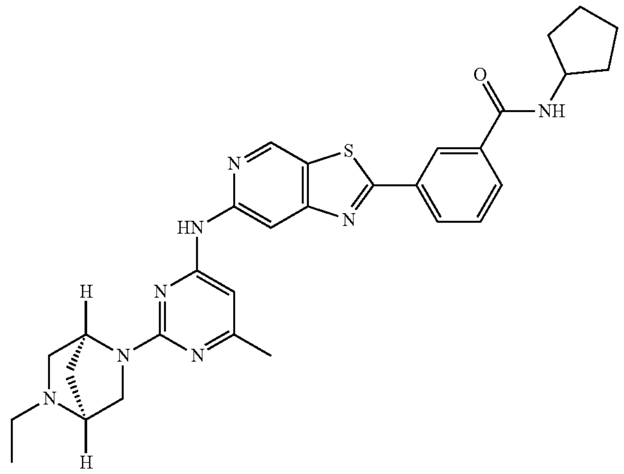 [SMILES: CCN1C[C@@H]2C[C@H]1CN2c1nc(C)cc(Nc2cc3nc(-c4cccc(C(=O)NC5CCCC5)c4)sc3cn2)n1] | 555.3 | 555.3 | 305 |
| 516 | 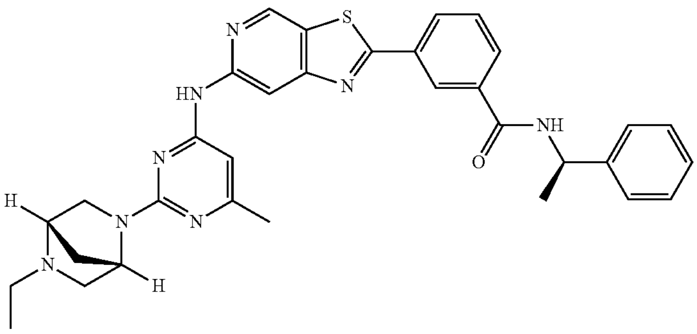 [SMILES: CCN1C[C@@H]2C[C@H]1CN2c1nc(C)cc(Nc2cc3nc(-c4cccc(C(=O)N[C@H](C)c5ccccc5)c4)sc3cn2)n1] | 591.3 | 591 | 305 |
| 517 | 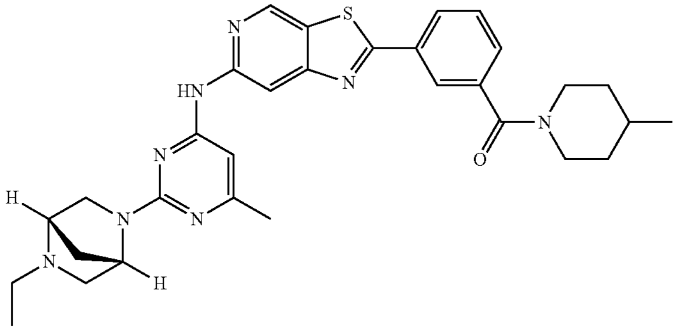 [SMILES: CCN1C[C@@H]2C[C@H]1CN2c1nc(C)cc(Nc2cc3nc(-c4cccc(C(=O)N5CCC(C)CC5)c4)sc3cn2)n1] | 569.3 | 569.2 | 305 |

TABLE 3-continued
| Example No. | Chemical Structure | [M + H] Calcd. | [M + H] Found | Analogous Procedure Example No. |
|---|---|---|---|---|
| 518 | 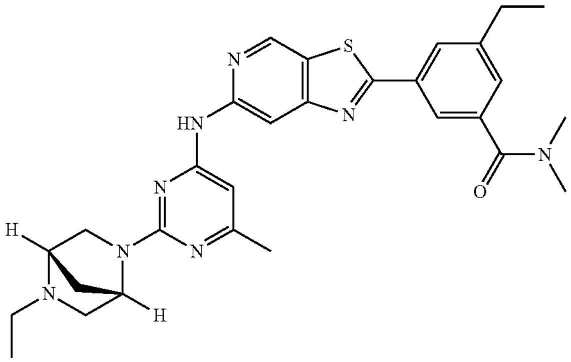 [SMILES: CCc1cc(C(=O)N(C)C)cc(-c2nc3cc(Nc4cc(C)nc(N5C[C@@H]6C[C@H]5CN6CC)n4)ncc3s2)c1] | 543.3 | 543.3 | 305 |
| 519 | 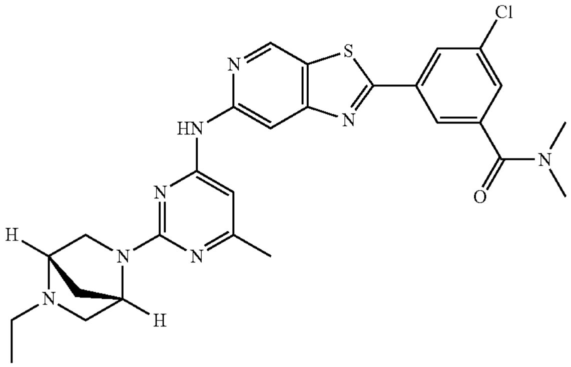 [SMILES: CCN1C[C@@H]2C[C@H]1CN2c1nc(C)cc(Nc2cc3nc(-c4cc(Cl)cc(C(=O)N(C)C)c4)sc3cn2)n1] | 549.2 | 549.2 | 305 |
| 520 | 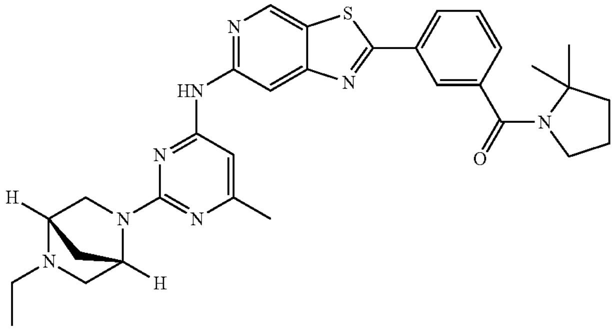 [SMILES: CCN1C[C@@H]2C[C@H]1CN2c1nc(C)cc(Nc2cc3nc(-c4cccc(C(=O)N5CCCC5(C)C)c4)sc3cn2)n1] | 569.3 | 569.1 | 305 |
| 521 | 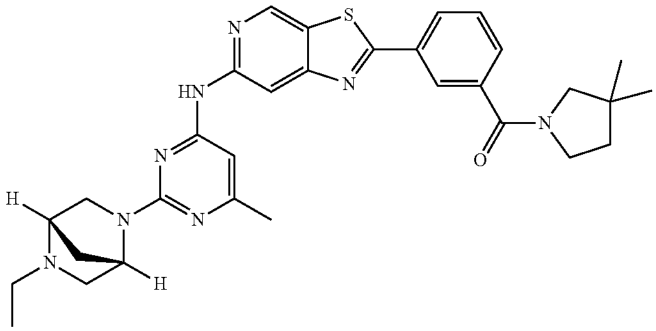 [SMILES: CCN1C[C@@H]2C[C@H]1CN2c1nc(C)cc(Nc2cc3nc(-c4cccc(C(=O)N5CCC(C)(C)C5)c4)sc3cn2)n1] | 569.3 | 569.1 | 305 |

TABLE 3-continued
| Example No. | Chemical Structure | [M + H] Calcd. | [M + H] Found | Analogous Procedure Example No. |
|---|---|---|---|---|
| 522 | 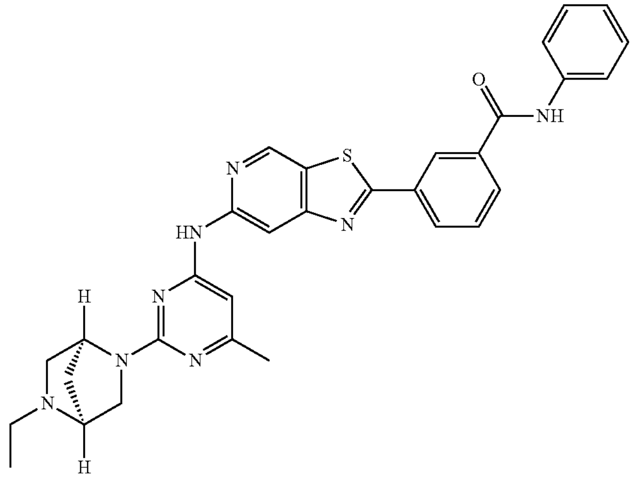 [SMILES: CCN1C[C@@H]2C[C@H]1CN2c1nc(C)cc(Nc2cc3nc(-c4cccc(C(=O)Nc5ccccc5)c4)sc3cn2)n1] | 563.2 | 563.3 | 305 |
| 523 | 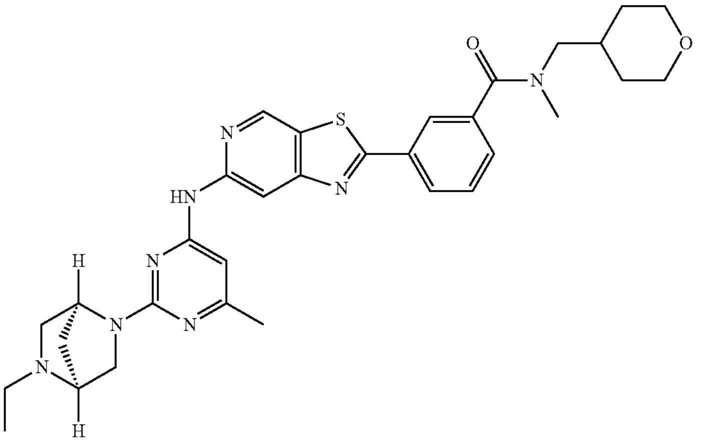 [SMILES: CCN1C[C@@H]2C[C@H]1CN2c1nc(C)cc(Nc2cc3nc(-c4cccc(C(=O)N(C)CC5CCOCC5)c4)sc3cn2)n1] | 599.3 | 599.3 | 305 |
| 524 | 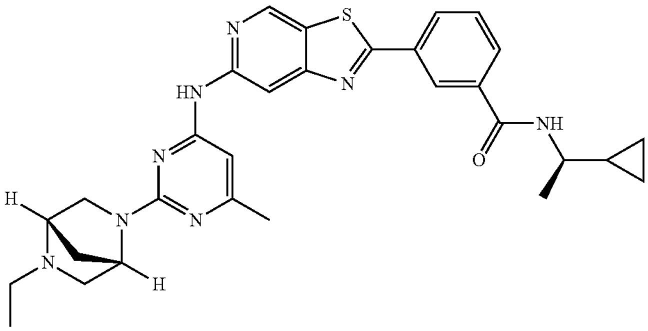 [SMILES: CCN1C[C@@H]2C[C@H]1CN2c1nc(C)cc(Nc2cc3nc(-c4cccc(C(=O)N[C@H](C)C5CC5)c4)sc3cn2)n1] | 555.3 | 555.2 | 305 |

TABLE 3-continued
| Example No. | Chemical Structure | [M + H] Calcd. | [M + H] Found | Analogous Procedure Example No. |
|---|---|---|---|---|
| 525 | 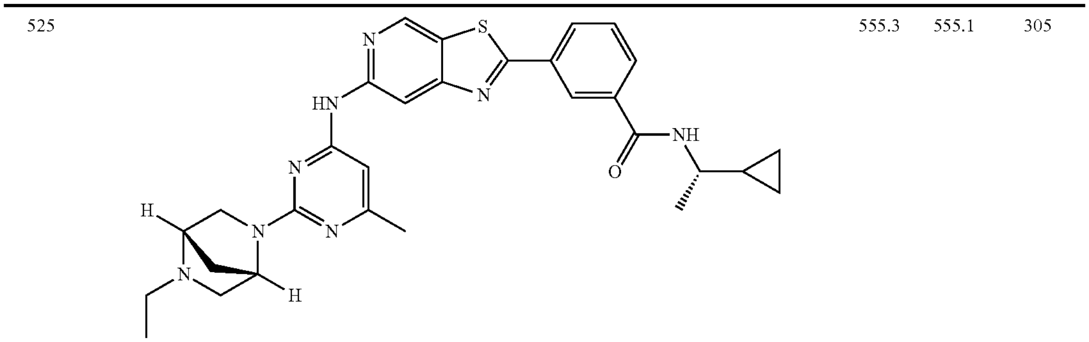 | 555.3 | 555.1 | 305 |
| 526 | 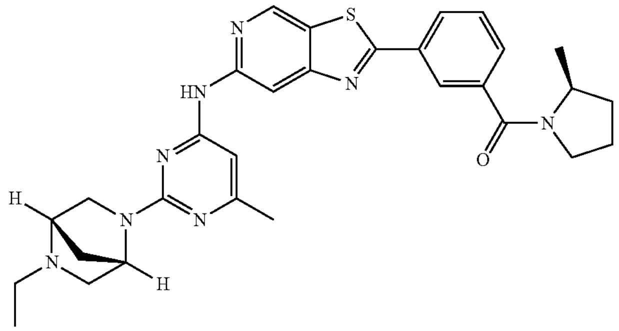 [SMILES: CCN1C[C@@H]2C[C@H]1CN2c1nc(C)cc(Nc2cc3nc(-c4cccc(C(=O)N5CCC[C@@H]5C)c4)sc3cn2)n1] | 555.3 | 555.1 | 305 |
| 527 | 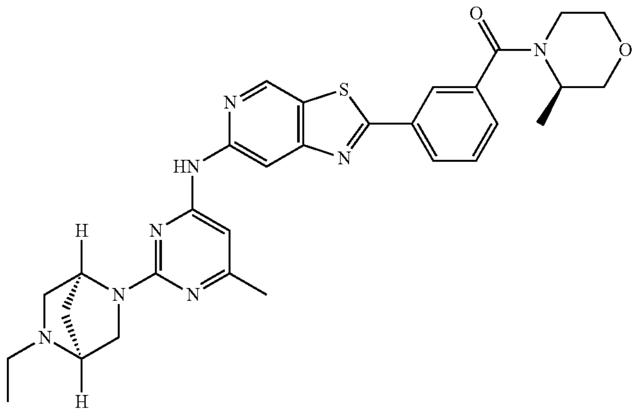 [SMILES: CCN1C[C@@H]2C[C@H]1CN2c1nc(C)cc(Nc2cc3nc(-c4cccc(C(=O)N5CCOC[C@H]5C)c4)sc3cn2)n1] | 571.3 | 571.1 | 305 |
| 528 | 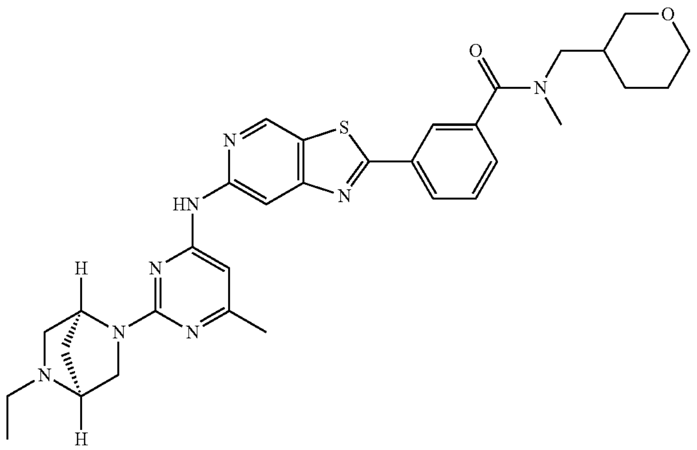 [SMILES: CCN1C[C@@H]2C[C@H]1CN2c1nc(C)cc(Nc2cc3nc(-c4cccc(C(=O)N(C)CC5CCCOC5)c4)sc3cn2)n1] | 585.3 | 585.3 | 305 |

TABLE 3-continued
| Example No. | Chemical Structure | [M + H] Calcd. | [M + H] Found | Analogous Procedure Example No. |
|---|---|---|---|---|
| 529 | 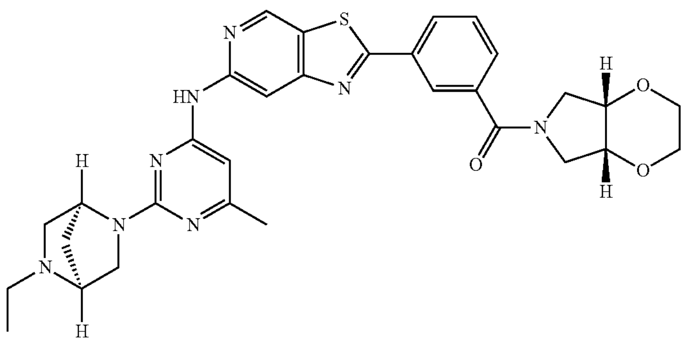 [SMILES: CCN1C[C@@H]2C[C@H]1CN2c1nc(C)cc(Nc2cc3nc(-c4cccc(C(=O)N5C[C@@H]6OCCO[C@@H]6C5)c4)sc3cn2)n1] | 599.2 | 599.3 | 305 |
| 530 | 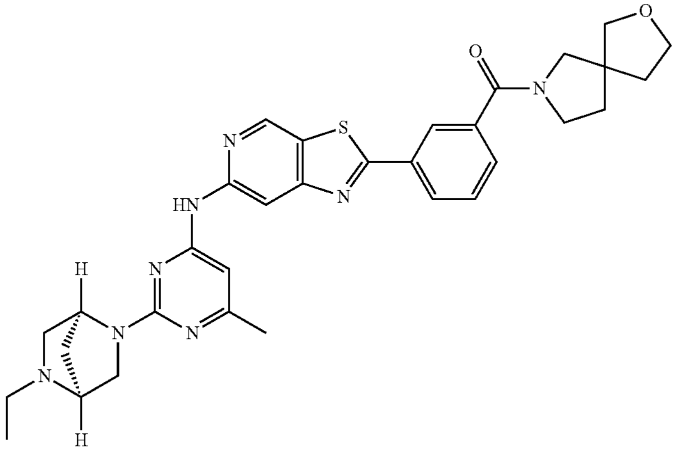 [SMILES: CCN1C[C@@H]2C[C@H]1CN2c1nc(C)cc(Nc2cc3nc(-c4cccc(C(=O)N5CCC6(CCOC6)C5)c4)sc3cn2)n1] | 597.3 | 597.3 | 305 |
| 531 | 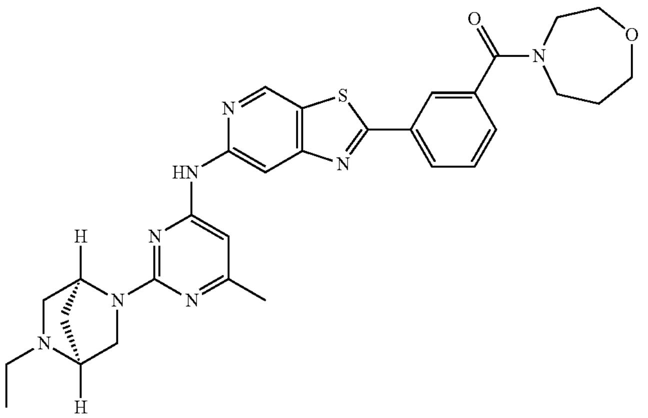 [SMILES: CCN1C[C@@H]2C[C@H]1CN2c1nc(C)cc(Nc2cc3nc(-c4cccc(C(=O)N5CCCOCC5)c4)sc3cn2)n1] | 571.3 | 571.3 | 305 |

TABLE 3-continued
| Example No. | Chemical Structure | [M + H] Calcd. | [M + H] Found | Analogous Procedure Example No. |
|---|---|---|---|---|
| 532 | 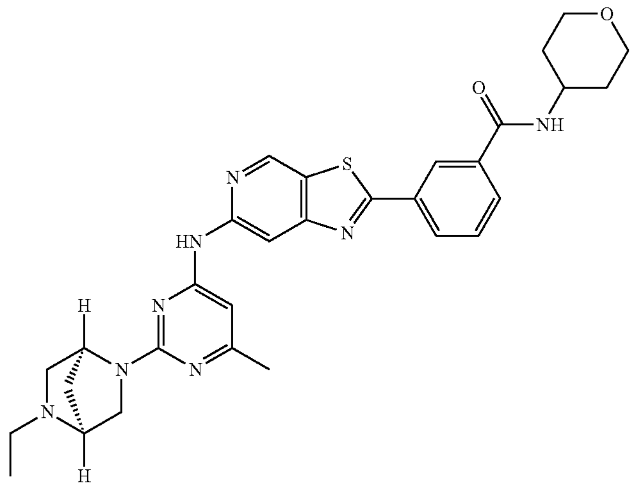 [SMILES: CCN1C[C@@H]2C[C@H]1CN2c1nc(C)cc(Nc2cc3nc(-c4cccc(C(=O)NC5CCOCC5)c4)sc3cn2)n1] | 571.3 | 571.3 | 305 |
| 533 | 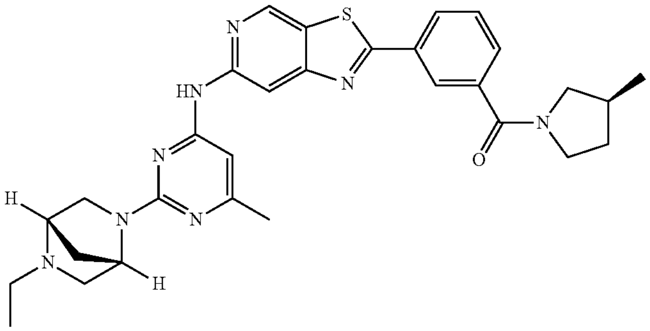 [SMILES: CCN1C[C@@H]2C[C@H]1CN2c1nc(C)cc(Nc2cc3nc(-c4cccc(C(=O)N5CC[C@H](C)C5)c4)sc3cn2)n1] | 555.3 | 555.3 | 305 |
| 534 | 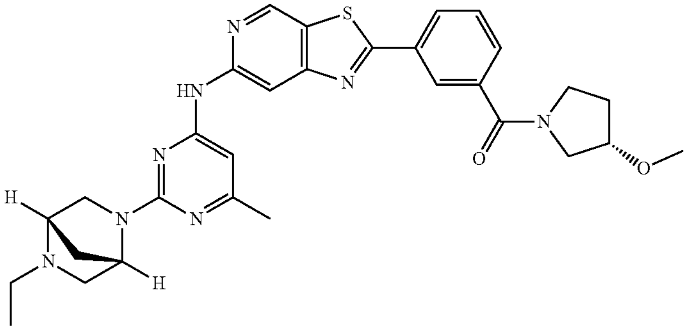 [SMILES: CCN1C[C@@H]2C[C@H]1CN2c1nc(C)cc(Nc2cc3nc(-c4cccc(C(=O)N5CC[C@H](OC)C5)c4)sc3cn2)n1] | 571.3 | 571.3 | 305 |
| 535 | 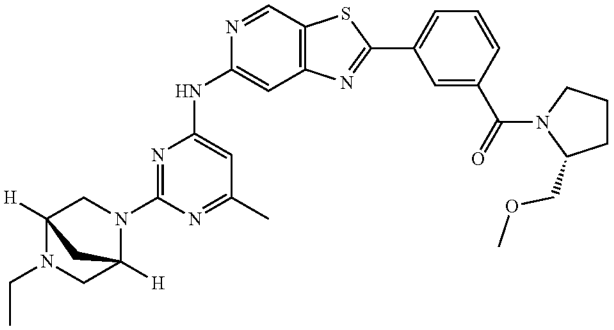 [SMILES: CCN1C[C@@H]2C[C@H]1CN2c1nc(C)cc(Nc2cc3nc(-c4cccc(C(=O)N5CCC[C@@H]5COC)c4)sc3cn2)n1] | 585.3 | 585.3 | 305 |

TABLE 3-continued
| Example No. | Chemical Structure | [M + H] Calcd. | [M + H] Found | Analogous Procedure Example No. |
|---|---|---|---|---|
| 536 | 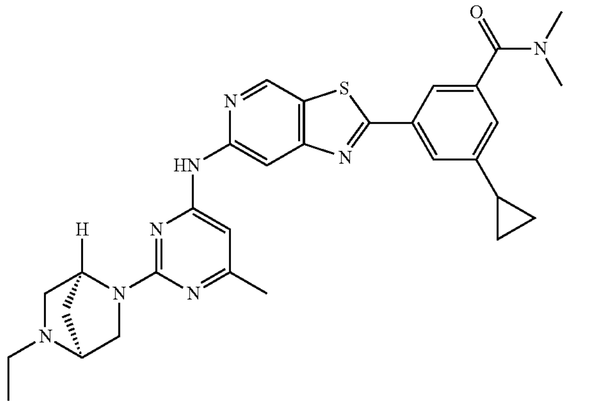 [SMILES: CCN1C[C@@H]2C[C@H]1CN2c1nc(C)cc(Nc2cc3nc(-c4cc(C(=O)N(C)C)cc(C5CC5)c4)sc3cn2)n1] | 555.3 | 555.3 | 305 |
| 537 | 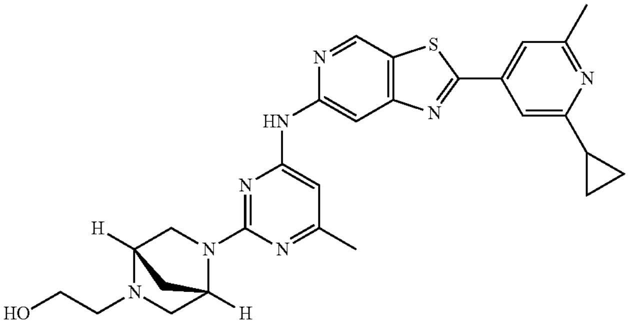 [SMILES: Cc1cc(-c2nc3cc(Nc4cc(C)nc(N5C[C@@H]6C[C@H]5CN6CCO)n4)ncc3s2)cc(C2CC2)n1] | 515.2 | 515.2 | 305 |
| 538 | 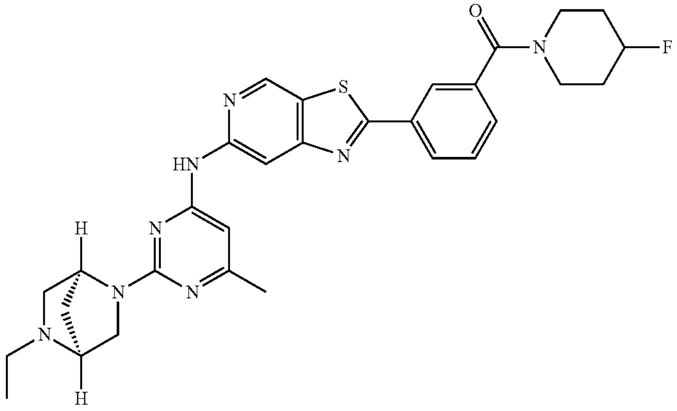 [SMILES: CCN1C[C@@H]2C[C@H]1CN2c1nc(C)cc(Nc2cc3nc(-c4cccc(C(=O)N5CCC(F)CC5)c4)sc3cn2)n1] | 573.2 | 573.2 | 305 |
| 539 | 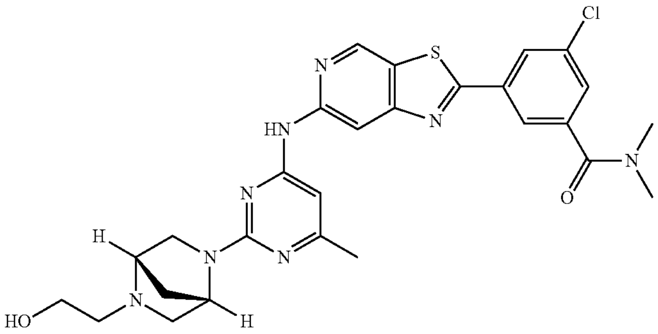 [SMILES: Cc1cc(Nc2cc3nc(-c4cc(Cl)cc(C(=O)N(C)C)c4)sc3cn2)nc(N2C[C@@H]3C[C@H]2CN3CCO)n1] | 565.2 | 565.2 | 305 |

TABLE 3-continued
| Example No. | Chemical Structure | [M + H] Calcd. | [M + H] Found | Analogous Procedure Example No. |
|---|---|---|---|---|
| 540 | 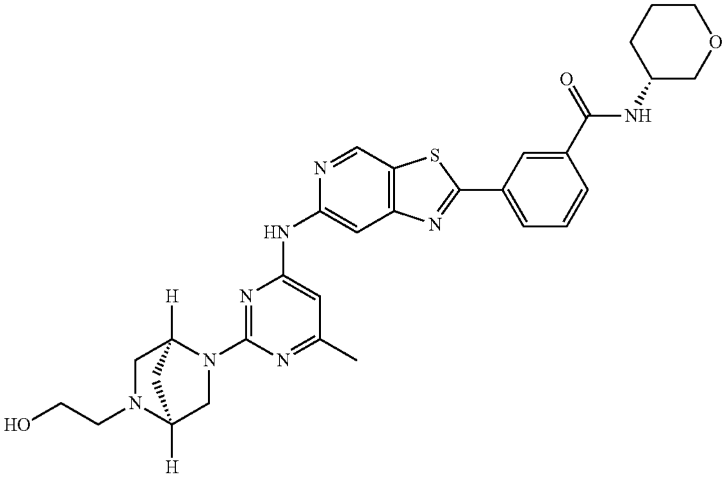 [SMILES: Cc1cc(Nc2cc3nc(-c4cccc(C(=O)N[C@@H]5CCCOC5)c4)sc3cn2)nc(N2C[C@@H]3C[C@H]2CN3CCO)n1] | 587.2 | 587.3 | 305 |
| 541 | 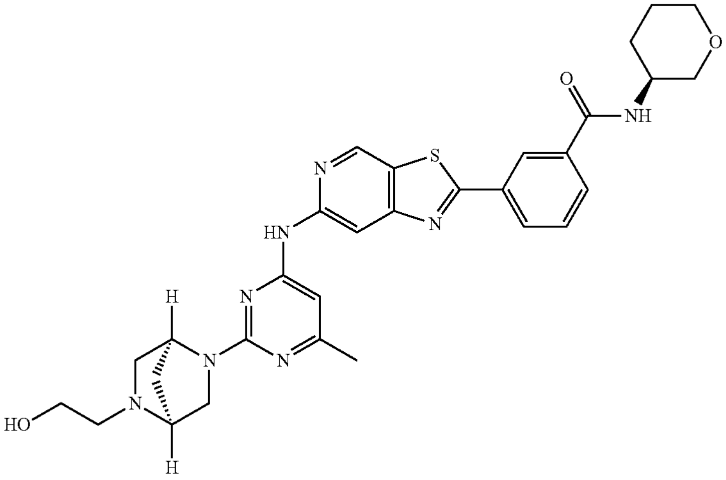 [SMILES: Cc1cc(Nc2cc3nc(-c4cccc(C(=O)N[C@H]5CCCOC5)c4)sc3cn2)nc(N2C[C@@H]3C[C@H]2CN3CCO)n1] | 587.2 | 587.3 | 305 |
| 542 | 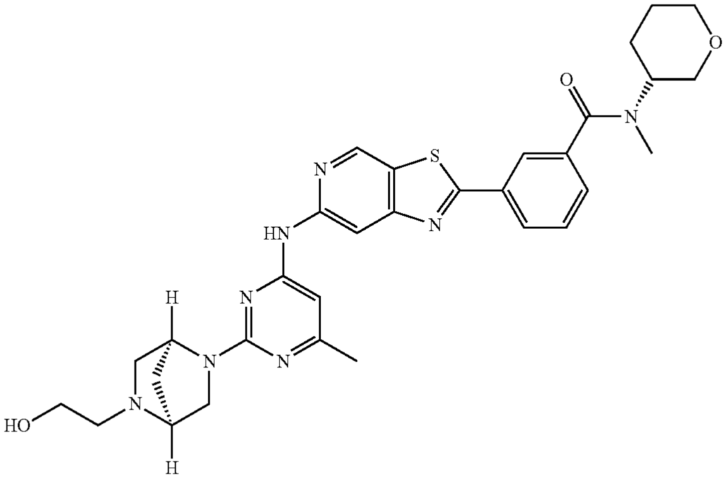 | 601.3 | 601.3 | 305 |

TABLE 3-continued
| Example No. | Chemical Structure | [M + H] Calcd. | [M + H] Found | Analogous Procedure Example No. |
|---|---|---|---|---|
| 543 | 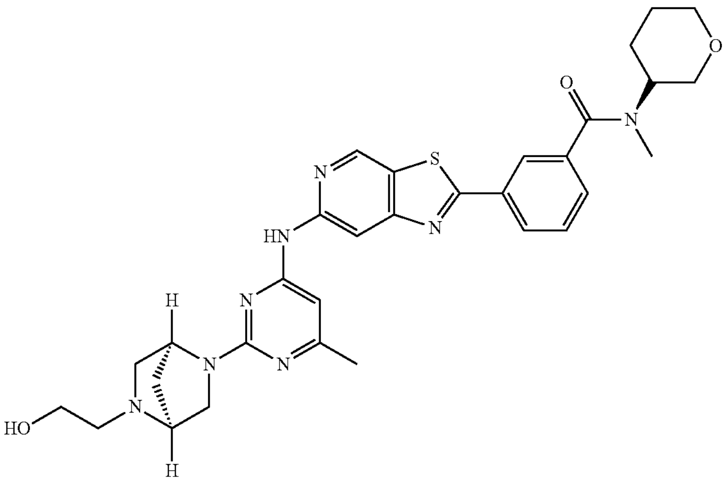 | 601.3 | 601.3 | 305 |
| 544 | 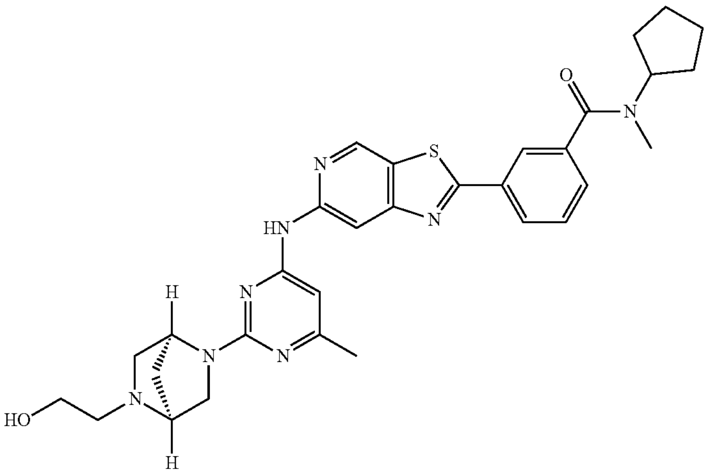 [SMILES: Cc1cc(Nc2cc3nc(-c4cccc(C(=O)N(C)C5CCCC5)c4)sc3cn2)nc(N2C[C@@H]3C[C@H]2CN3CCO)n1] | 585.3 | 585.3 | 305 |
| 545 | 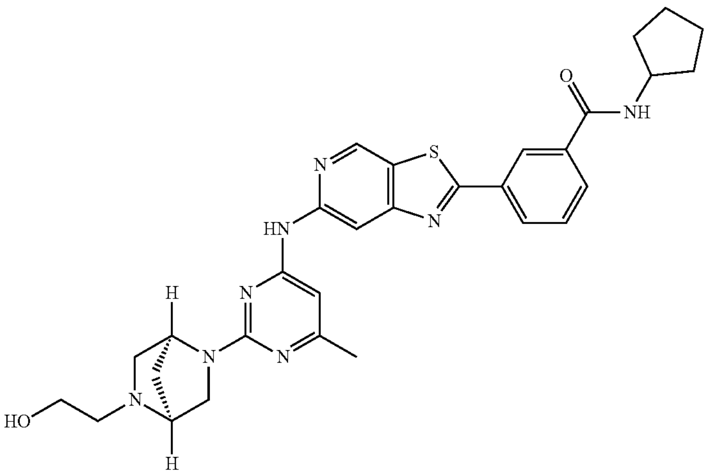 [SMILES: Cc1cc(Nc2cc3nc(-c4cccc(C(=O)NC5CCCC5)c4)sc3cn2)nc(N2C[C@@H]3C[C@H]2CN3CCO)n1] | 571.3 | 571.3 | 305 |

TABLE 3-continued
| Example No. | Chemical Structure | [M + H] Calcd. | [M + H] Found | Analogous Procedure Example No. |
|---|---|---|---|---|
| 546 | 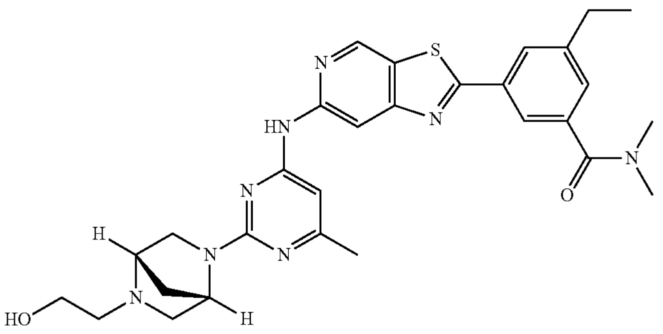 [SMILES: CCc1cc(C(=O)N(C)C)cc(-c2nc3cc(Nc4cc(C)nc(N5C[C@@H]6C[C@H]5CN6CCO)n4)ncc3s2)c1] | 559.3 | 559.2 | 305 |
| 547 | 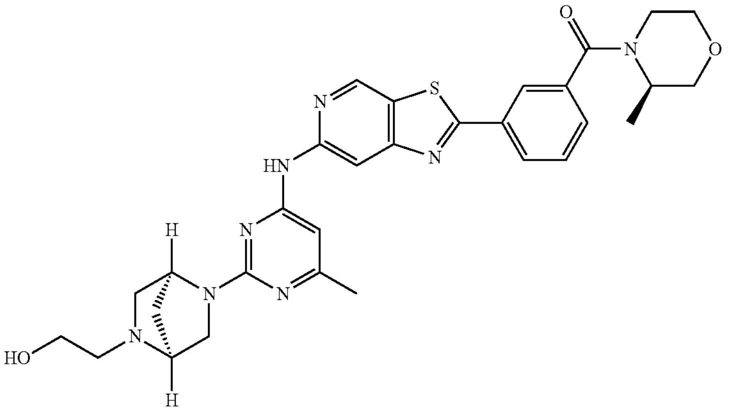 [SMILES: Cc1cc(Nc2cc3nc(-c4cccc(C(=O)N5CCOC[C@H]5C)c4)sc3cn2)nc(N2C[C@@H]3C[C@H]2CN3CCO)n1] | 587.2 | 587.3 | 305 |
| 548 | 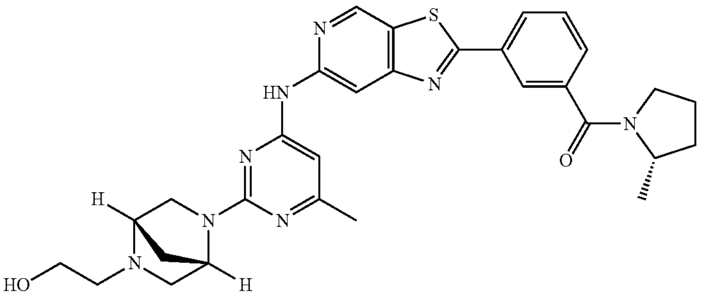 [SMILES: Cc1cc(Nc2cc3nc(-c4cccc(C(=O)N5CCC[C@@H]5C)c4)sc3cn2)nc(N2C[C@@H]3C[C@H]2CN3CCO)n1] | 571.3 | 571.2 | 305 |
| 549 | 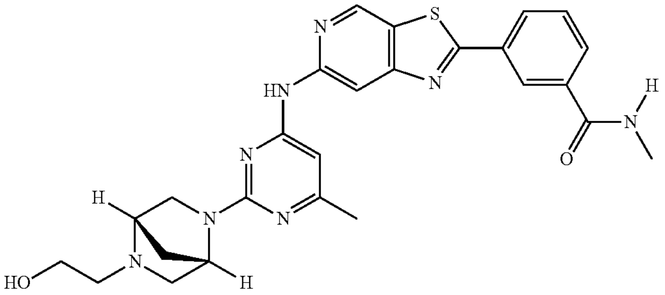 [SMILES: CNC(=O)c1cccc(-c2nc3cc(Nc4cc(C)nc(N5C[C@@H]6C[C@H]5CN6CCO)n4)ncc3s2)c1] | 517.2 | 517.2 | 305 |

TABLE 3-continued
| Example No. | Chemical Structure | [M + H] Calcd. | [M + H] Found | Analogous Procedure Example No. |
|---|---|---|---|---|
| 550 | 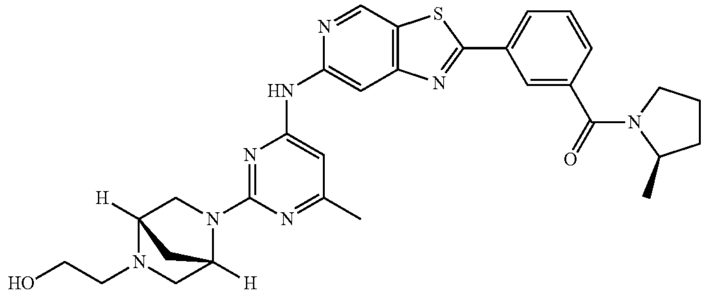 [SMILES: Cc1cc(Nc2cc3nc(-c4cccc(C(=O)N5CCC[C@H]5C)c4)sc3cn2)nc(N2C[C@@H]3C[C@H]2CN3CCO)n1] | 571.3 | 571.1 | 305 |
| 551 | 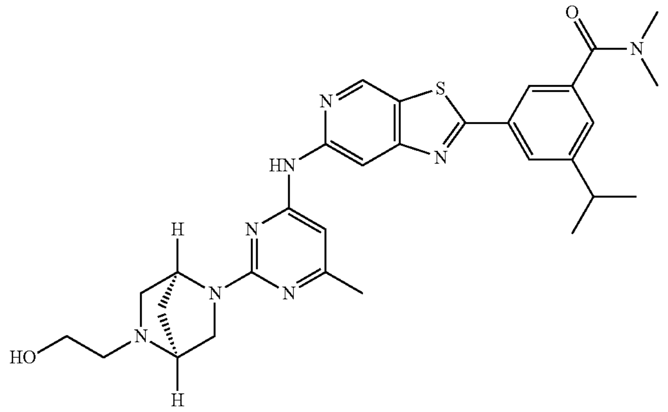 [SMILES: Cc1cc(Nc2cc3nc(-c4cc(C(=O)N(C)C)cc(C(C)C)c4)sc3cn2)nc(N2C[C@@H]3C[C@H]2CN3CCO)n1] | 573.3 | 573.3 | 305 |
| 552 | 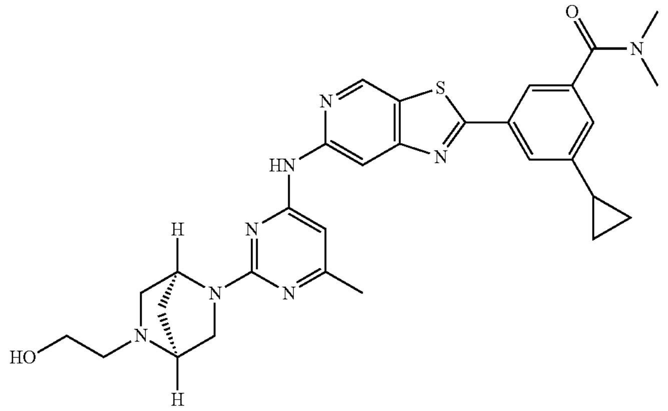 [SMILES: Cc1cc(Nc2cc3nc(-c4cc(C(=O)N(C)C)cc(C5CC5)c4)sc3cn2)nc(N2C[C@@H]3C[C@H]2CN3CCO)n1] | 571.3 | 571.2 | 305 |
| 553 | 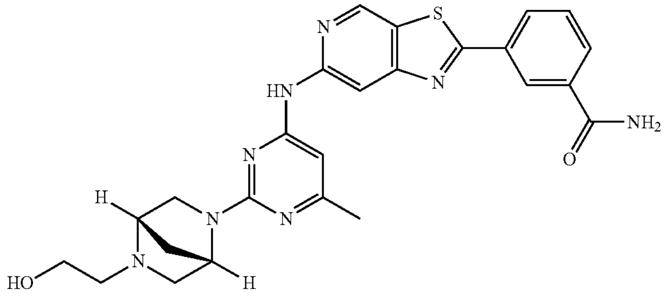 [SMILES: Cc1cc(Nc2cc3nc(-c4cccc(C(N)=O)c4)sc3cn2)nc(N2C[C@@H]3C[C@H]2CN3CCO)n1] | 503.2 | 503.2 | 305 |

TABLE 3-continued
| Example No. | Chemical Structure | [M + H] Calcd. | [M + H] Found | Analogous Procedure Example No. |
|---|---|---|---|---|
| 554 | 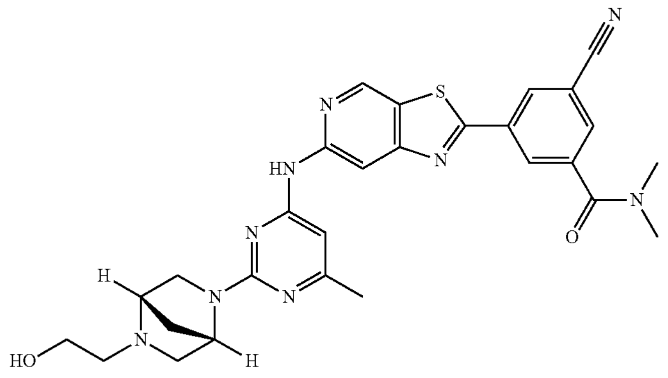 [SMILES: Cc1cc(Nc2cc3nc(-c4cc(C#N)cc(C(=O)N(C)C)c4)sc3cn2)nc(N2C[C@@H]3C[C@H]2CN3CCO)n1] | 556.2 | 556.3 | 305 |
| 555 | 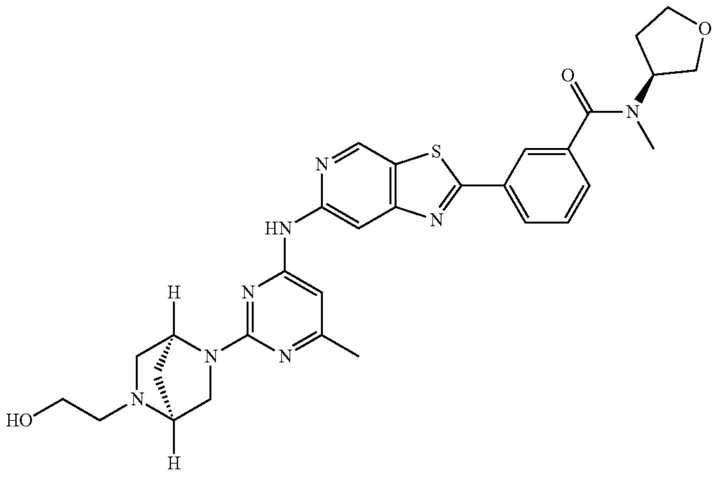 [SMILES: Cc1cc(Nc2cc3nc(-c4cccc(C(=O)N(C)[C@H]5CCOC5)c4)sc3cn2)nc(N2C[C@@H]3C[C@H]2CN3CCO)n1] | 587.2 | 587.3 | 305 |
| 556 | 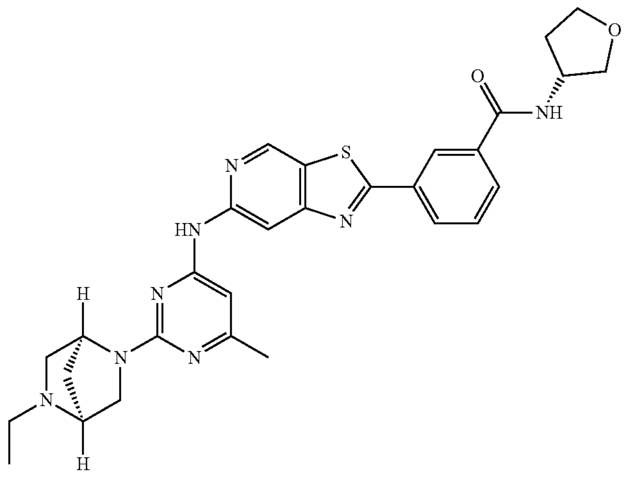 | 557.2 | 557.3 | 305 |

TABLE 3-continued
| Example No. | Chemical Structure | [M + H] Calcd. | [M + H] Found | Analogous Procedure Example No. |
|---|---|---|---|---|
| 557 | 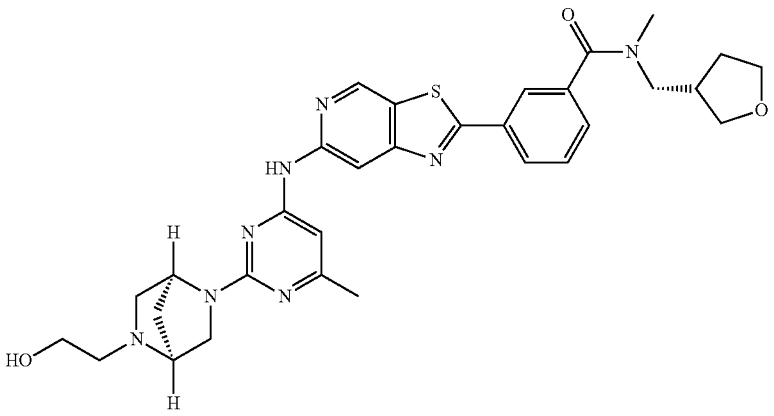 | 601.3 | 601.3 | 305 |
| 558 | 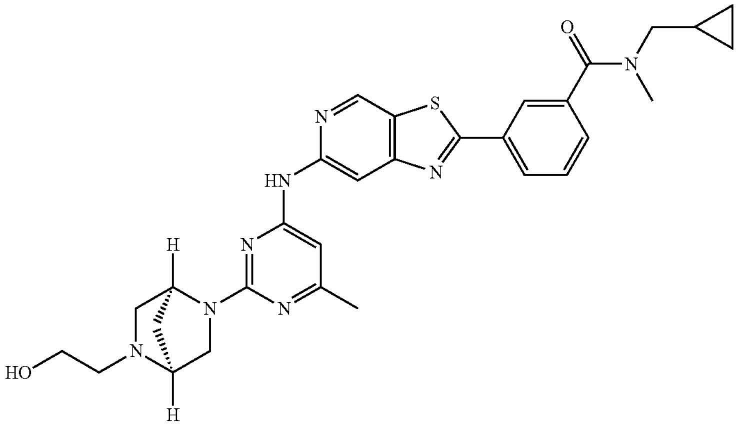 [SMILES: Cc1cc(Nc2cc3nc(-c4cccc(C(=O)N(C)CC5CC5)c4)sc3cn2)nc(N2C[C@@H]3C[C@H]2CN3CCO)n1] | 571.3 | 571.3 | 305 |
| 559 | 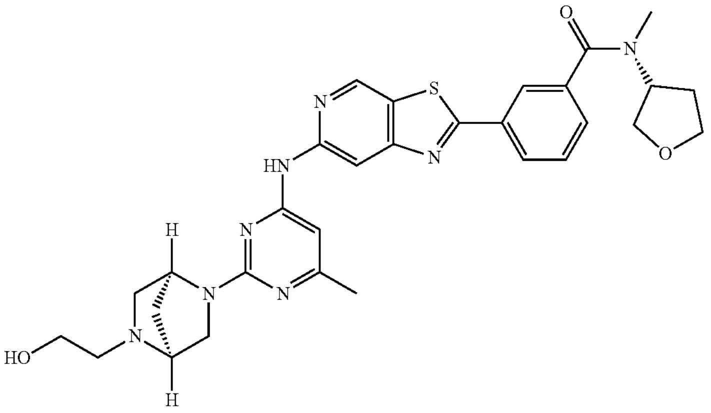 | 587.2 | 587.3 | 305 |

TABLE 3-continued
| Example No. | Chemical Structure | [M + H] Calcd. | [M + H] Found | Analogous Procedure Example No. |
|---|---|---|---|---|
| 560 | 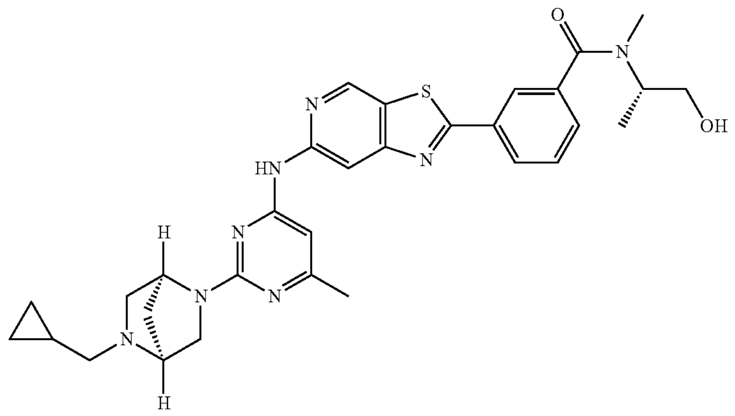 [SMILES: Cc1cc(Nc2cc3nc(-c4cccc(C(=O)N(C)[C@@H](C)CO)c4)sc3cn2)nc(N2C[C@@H]3C[C@H]2CN3CC2CC2)n1] | 585.3 | 585.2 | 305 |
| 561 | 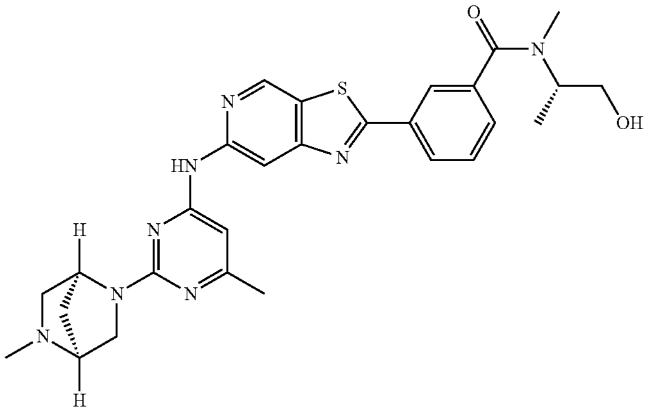 [SMILES: Cc1cc(Nc2cc3nc(-c4cccc(C(=O)N(C)[C@@H](C)CO)c4)sc3cn2)nc(N2C[C@@H]3C[C@H]2CN3C)n1] | 545.2 | 545.2 | 305 |
| 562 | 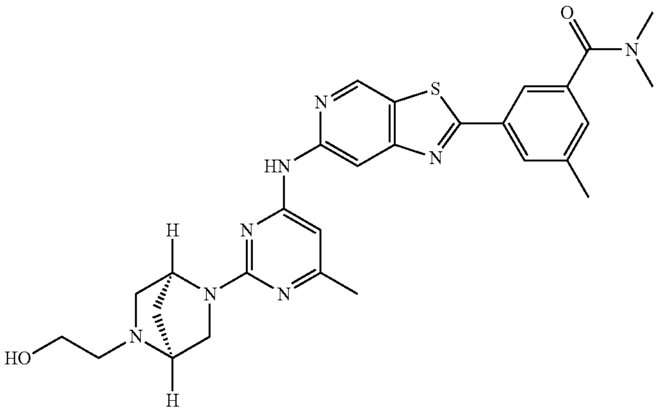 [SMILES: Cc1cc(C(=O)N(C)C)cc(-c2nc3cc(Nc4cc(C)nc(N5C[C@@H]6C[C@H]5CN6CCO)n4)ncc3s2)c1] | 545.2 | 545.1 | 305 |

TABLE 3-continued
| Example No. | Chemical Structure | [M + H] Calcd. | [M + H] Found | Analogous Procedure Example No. |
|---|---|---|---|---|
| 563 | 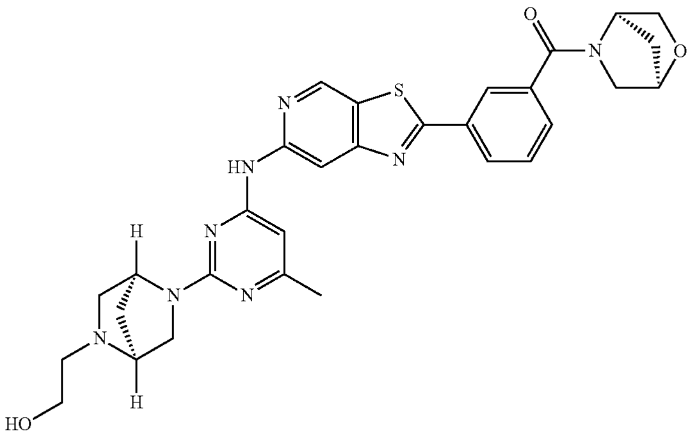 [SMILES: Cc1cc(Nc2cc3nc(-c4cccc(C(=O)N5C[C@H]6C[C@@H]5CO6)c4)sc3cn2)nc(N2C[C@@H]3C[C@H]2CN3CCO)n1] | 585.2 | 585.1 | 305 |
| 564 | 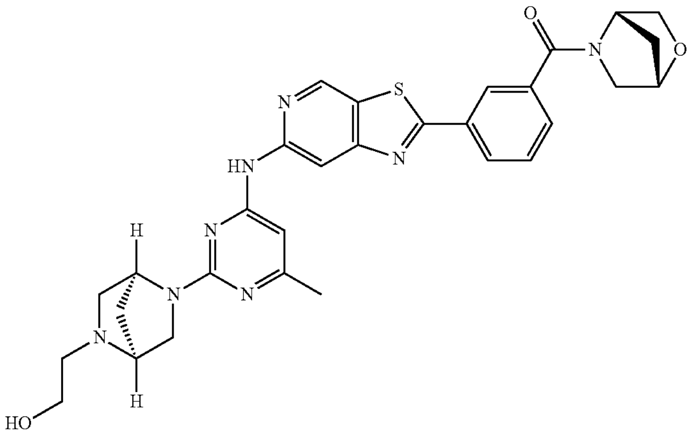 [SMILES: Cc1cc(Nc2cc3nc(-c4cccc(C(=O)N5C[C@@H]6C[C@H]5CO6)c4)sc3cn2)nc(N2C[C@@H]3C[C@H]2CN3CCO)n1] | 585.2 | 585.1 | 305 |
| 565 | 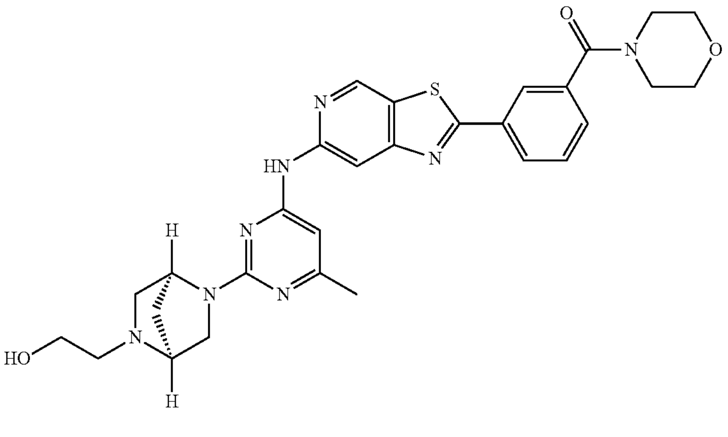 [SMILES: Cc1cc(Nc2cc3nc(-c4cccc(C(=O)N5CCOCC5)c4)sc3cn2)nc(N2C[C@@H]3C[C@H]2CN3CCO)n1] | 573.2 | 573.2 | 305 |

TABLE 3-continued
| Example No. | Chemical Structure | [M + H] Calcd. | [M + H] Found | Analogous Procedure Example No. |
|---|---|---|---|---|
| 566 | 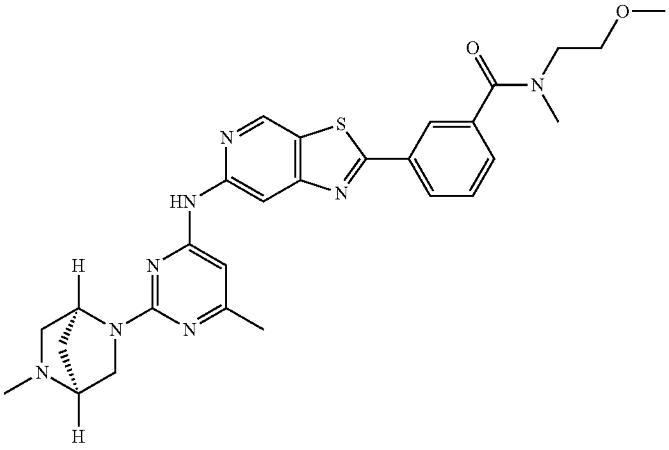 | 545.2 | 545.3 | 305 |
| 567 | 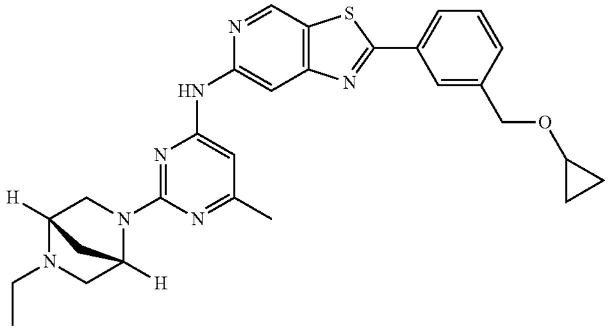 [SMILES: CCN1C[C@@H]2C[C@H]1CN2c1nc(C)cc(Nc2cc3nc(-c4cccc(COC5CC5)c4)sc3cn2)n1] | 514.2 | 514.1 | 310 |
| 568 | 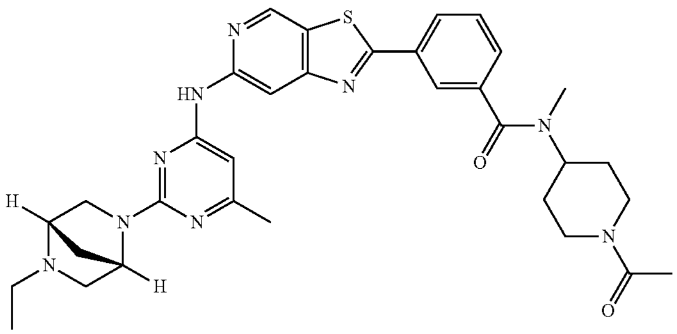 [SMILES: CCN1C[C@@H]2C[C@H]1CN2c1nc(C)cc(Nc2cc3nc(-c4cccc(C(=O)N(C)C5CCN(C(C)=O)CC5)c4)sc3cn2)n1] | 626.3 | 626.2 | 311 |

TABLE 3-continued
| Example No. | Chemical Structure | [M + H] Calcd. | [M + H] Found | Analogous Procedure Example No. |
|---|---|---|---|---|
| 569 | 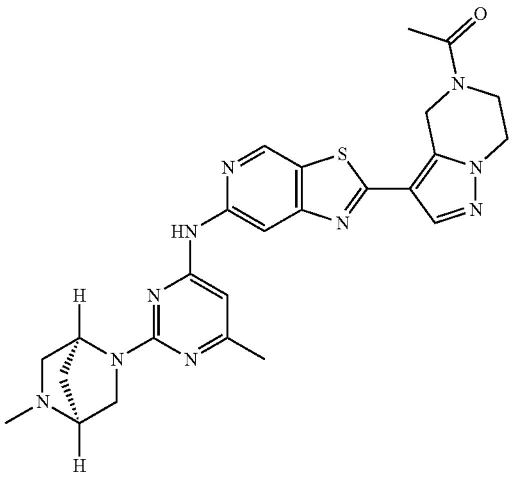 [SMILES: CC(=O)N1CCn2ncc(-c3nc4cc(Nc5cc(C)nc(N6C[C@@H]7C[C@H]6CN7C)n5)ncc4s3)c2C1] | 517.2 | 517.3 | 312 |
| 570 | 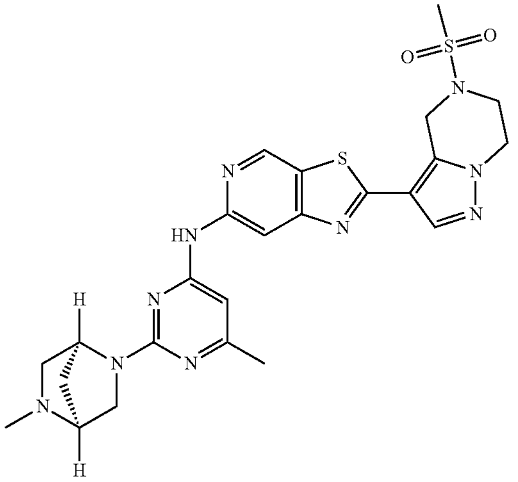 [SMILES: Cc1cc(Nc2cc3nc(-c4cnn5c4CN(S(C)(=O)=O)CC5)sc3cn2)nc(N2C[C@@H]3C[C@H]2CN3C)n1] | 553.2 | 553.3 | 312 |
| 571 | 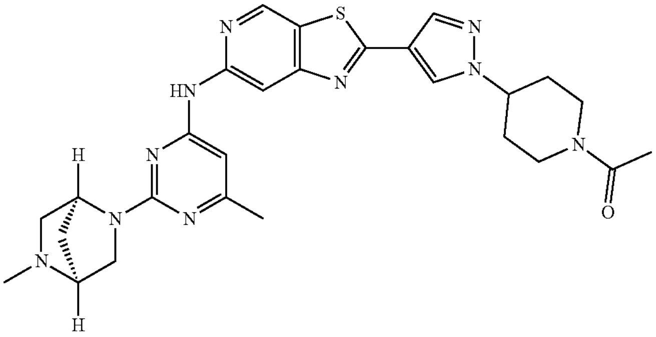 [SMILES: CC(=O)N1CCC(n2cc(-c3nc4cc(Nc5cc(C)nc(N6C[C@@H]7C[C@H]6CN7C)n5)ncc4s3)cn2)CC1] | 545.2 | 545.3 | 312 |

TABLE 3-continued
| Example No. | Chemical Structure | [M + H] Calcd. | [M + H] Found | Analogous Procedure Example No. |
|---|---|---|---|---|
| 572 | 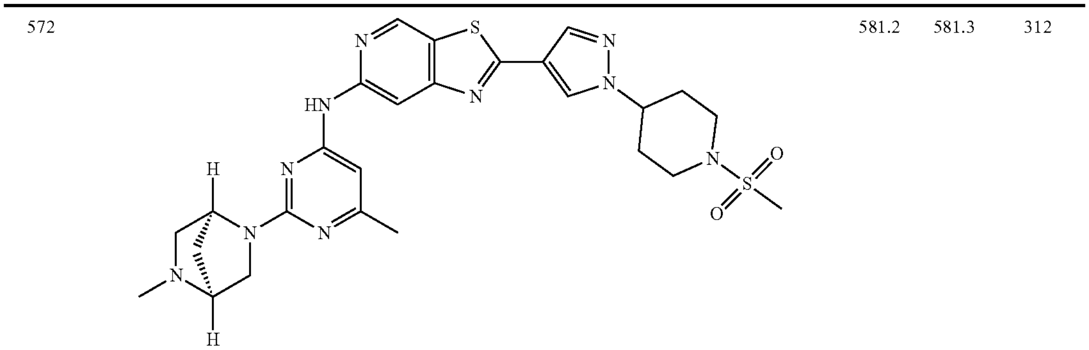 | 581.2 | 581.3 | 312 |
| 573 | 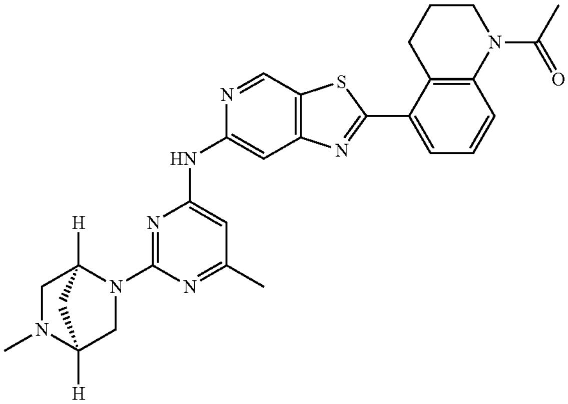 [SMILES: CC(=O)N1CCCc2c(-c3nc4cc(Nc5cc(C)nc(N6C[C@@H]7C[C@H]6CN7C)n5)ncc4s3)cccc21] | 527.2 | 527.2 | 312 |
| 574 | 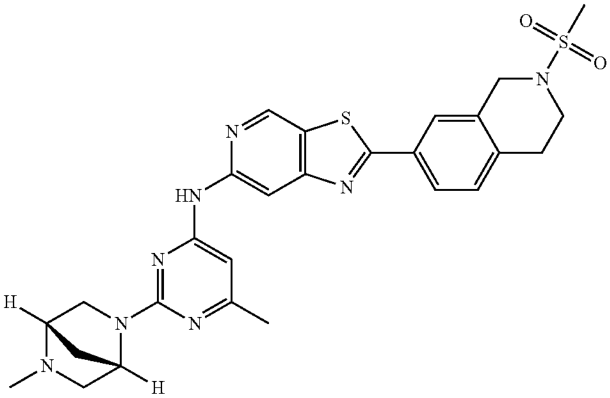 [SMILES: Cc1cc(Nc2cc3nc(-c4ccc5c(c4)CN(S(C)(=O)=O)CC5)sc3cn2)nc(N2C[C@@H]3C[C@H]2CN3C)n1] | 563.2 | 563.2 | 312 |
| 575 | 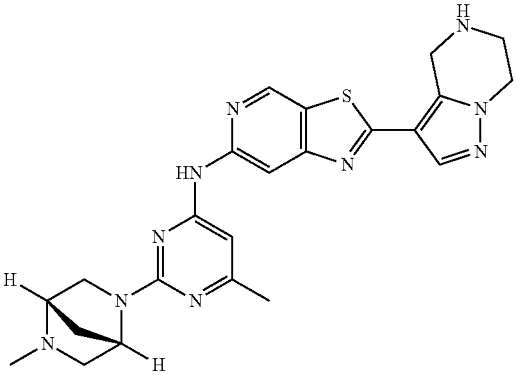 [SMILES: Cc1cc(Nc2cc3nc(-c4cnn5c4CNCC5)sc3cn2)nc(N2C[C@@H]3C[C@H]2CN3C)n1] | 475.2 | 475.3 | 313 |

TABLE 3-continued
| Example No. | Chemical Structure | [M + H] Calcd. | [M + H] Found | Analogous Procedure Example No. |
|---|---|---|---|---|
| 576 | 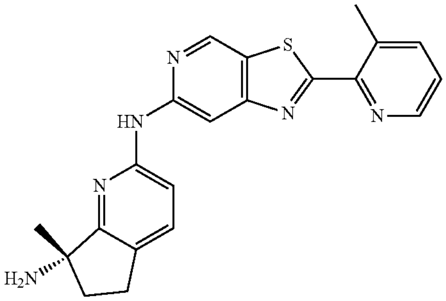 [SMILES: Cc1cccnc1-c1nc2cc(Nc3ccc4c(n3)[C@@](C)(N)CC4)ncc2s1] | 389.1 | 389.3 | 316 |
| 577 | 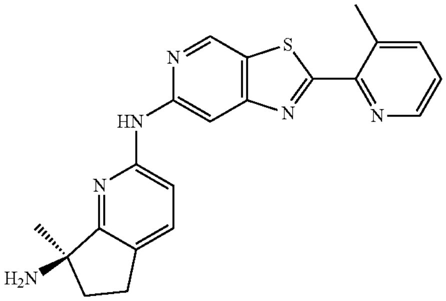 [SMILES: Cc1cccnc1-c1nc2cc(Nc3ccc4c(n3)[C@](C)(N)CC4)ncc2s1] | 389.1 | 389.2 | 316 |
| 578 | 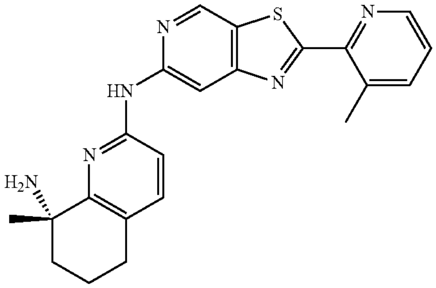 [SMILES: Cc1cccnc1-c1nc2cc(Nc3ccc4c(n3)[C@@](C)(N)CCC4)ncc2s1] | 403.2 | 403.2 | 316 |
| 579 | 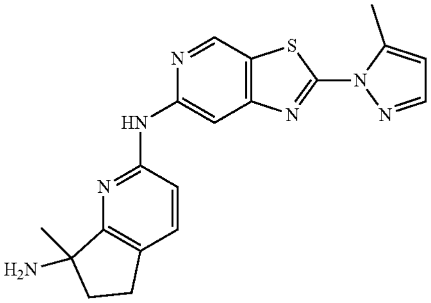 [SMILES: Cc1ccnn1-c1nc2cc(Nc3ccc4c(n3)C(C)(N)CC4)ncc2s1] | 378.1 | 378.3 | 316 |
| 580 | 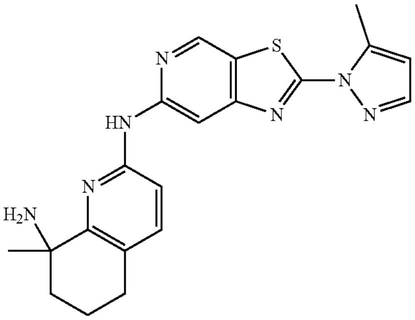 [SMILES: Cc1ccnn1-c1nc2cc(Nc3ccc4c(n3)C(C)(N)CCC4)ncc2s1] | 392.2 | 392.2 | 316 |

TABLE 3-continued
| Example No. | Chemical Structure | [M + H] Calcd. | [M + H] Found | Analogous Procedure Example No. |
|---|---|---|---|---|
| 581 | 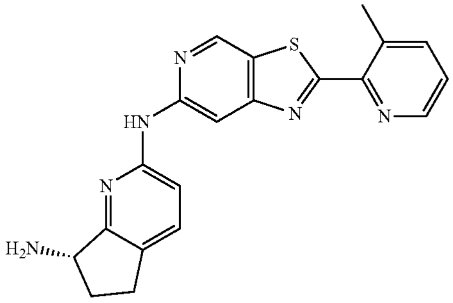 [SMILES: Cc1cccnc1-c1nc2cc(Nc3ccc4c(n3)[C@@H](N)CC4)ncc2s1] | 375.1 | 375 | 317 |
| 582 | 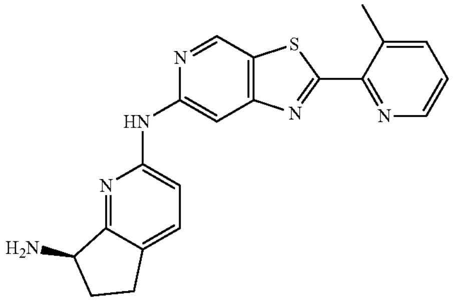 [SMILES: Cc1cccnc1-c1nc2cc(Nc3ccc4c(n3)[C@H](N)CC4)ncc2s1] | 375.1 | 375.2 | 317 |
| 583 | 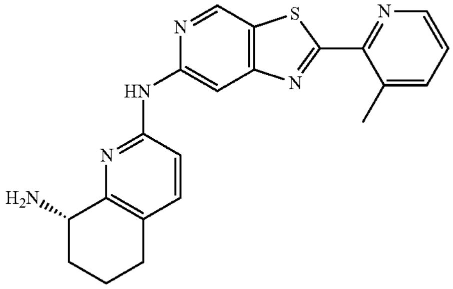 [SMILES: Cc1cccnc1-c1nc2cc(Nc3ccc4c(n3)[C@@H](N)CCC4)ncc2s1] | 389.1 | 389.2 | 317 |
| 584 | 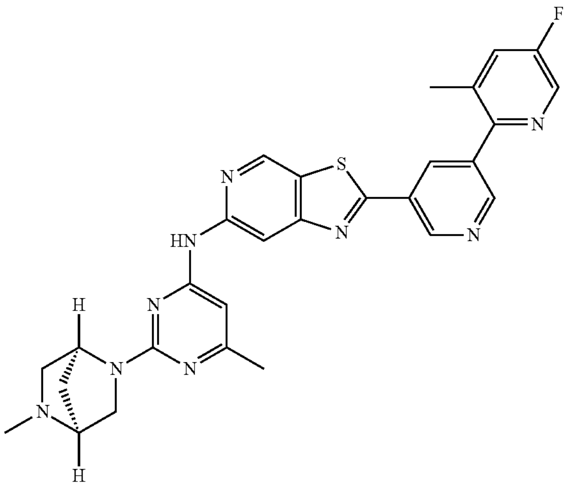 [SMILES: Cc1cc(Nc2cc3nc(-c4cncc(-c5ncc(F)cc5C)c4)sc3cn2)nc(N2C[C@@H]3C[C@H]2CN3C)n1] | 540.2 | 540.1 | 318 |

TABLE 3-continued

| Example No. | Chemical Structure | [M + H] Calcd. | [M + H] Found | Analogous Procedure Example No. |
|---|---|---|---|---|
| 585 | 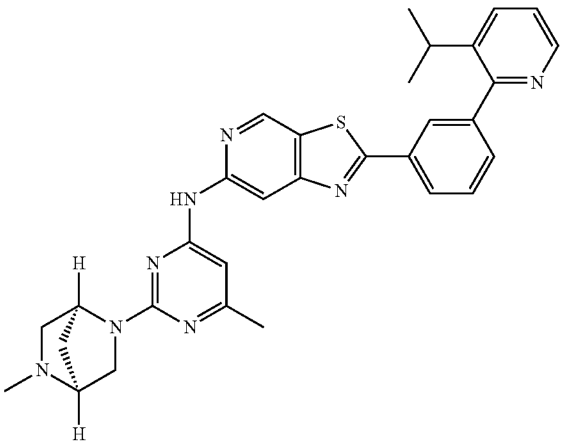 [SMILES: Cc1cc(Nc2cc3nc(-c4cccc(-c5ncccc5C(C)C)c4)sc3cn2)nc(N2C[C@@H]3C[C@H]2CN3C)n1] | 549.2 | 549.1 | 318 |
| 586 | 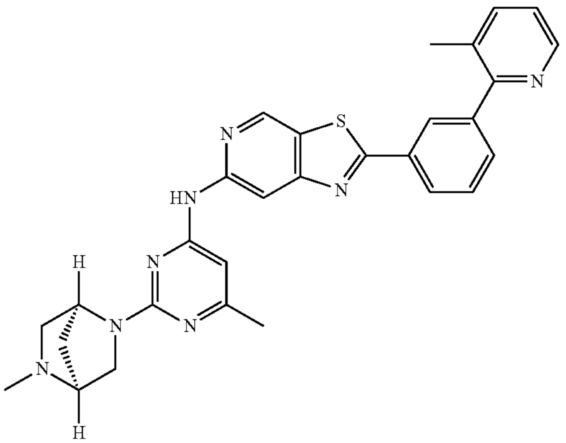 [SMILES: Cc1cc(Nc2cc3nc(-c4cccc(-c5ncccc5C)c4)sc3cn2)nc(N2C[C@@H]3C[C@H]2CN3C)n1] | 521.2 | 521.4 | 318 |

Biological Activity Assay Examples

HPK1 Biochemical Assay

Dose-response assays were performed in Corning® Low Volume 384-well assay plates containing 100 nL of 22 serial 2-fold compound dilutions. Wells containing DMSO alone were used as negative control. A kinase mixture (5 μL) containing 2 nM HPK1 (or 5 nM for high ATP assay assay) in assay buffer (50 mM Hepes pH 7.4, 10 mM $MgCl_2$, 0.01% Brij-15, 0.01% bovine serum albumin, and 1 mM dithiothreitol) was added to the assay plates and incubated at 25° C. for 1 hour. Wells without HPK1 were used as positive control. A 5 mixture of 10 μM ATP (or 200 μM for high ATP) and 0.2 μg/μL myelin binding protein was then added to the wells, resulting in a 10 μL total reaction volume. Following incubation of the assay plates at 25° C. for 1 hour, 10 μL of ADP-Glo reagent was added to the wells and the plates were incubated at 25° C. for a further 40 minutes (or 1 hour for high ATP assay). Finally, 20 μL of Kinase Detection Reagent was added, and the plates were incubated for another 30 minutes at 25° C. An Envision plate reader was then used to detect the luminescence signals. IC50 values were determined by fitting the data to a standard 4-parameter logistic equation. The results are summarized in the Biochemical Potency columns of Tables 4 and 5 below (Biochemical Potency (high ATP); Biochemical Potency (low ATP)).

pSLP76 Cellular Assay pSLP76 cellular assay was performed using Jurkat cells and the AlphaLISA SureFire Ultra p-SLP-76 (Ser376) Assay Kit (PerkinElmer). Dose-response assays were performed in Greiner® Low Volume 384-well assay plates containing 200 nL of 22 serial 2-fold compound dilutions using Bravo and Echo. Jurkat cells were grown in RPMI-1640 supplemented with 10% FBS and PSG. The day prior to the assay, the cells were collected, and serum starved overnight in Opti-MEM. The day of the assay, the cells were collected and resuspended in HBSS. 100,000 cells/well were added to the compound plates and after a short spin, the plates were incubated at 37° C. for 1 h. The cells were activated by adding 10 μL of 0.025 mg/ml anti-CD3. Plates were then incubated at 37° C. for 45 min. Stimulation was terminated by adding 8 of lysis buffer, followed by a brief centrifugation and 60 min of shaking at 300 rpm. Cell lysates (10 μL) were transferred to 384-well White Opti-plates and the samples were processed according to the manufacturer's directions. The fluorescence signal from pSLP76 was measured at 570 nm using Envision plate reader. IC50 values were determined by fitting the data to a standard 4-parameter logistic equation. The results are summarized in the Cellular Potency columns in Tables 4 and 5 below (Cellular Potency).

TABLE 4

Biochemical and cellular potency of specific examples ($IC_{50}$: + means >5 μM; ++ means >1 μM to 5 μM, +++ means 100 nM to 1 μM, ++++ means <100 nM)

| Ex. # | Biochemical Potency (low ATP) | Biochemical Potency (high ATP) | Cellular Potency | Ex. # | Biochemical Potency (low ATP) | Biochemical Potency (high ATP) | Cellular Potency |
|---|---|---|---|---|---|---|---|
| 1 | ++++ | | + | 2 | +++ | | |
| 3 | ++++ | | +++ | 4 | ++++ | | +++ |
| 5 | ++++ | | ++++ | 6 | ++++ | | +++ |
| 7 | ++++ | | ++ | 8 | ++++ | | |
| 9 | ++++ | | +++ | 10 | ++++ | | |
| 11 | +++ | | | 12 | ++++ | | ++ |
| 13 | ++++ | | +++ | 14 | ++++ | | +++ |
| 15 | ++++ | | +++ | 16 | ++++ | | ++ |
| 17 | ++++ | | ++ | 18 | ++++ | | +++ |
| 19 | + | | + | 20 | ++++ | | +++ |
| 21 | ++++ | | | 22 | ++++ | | |
| 23 | ++++ | | + | 24 | ++++ | | +++ |
| 25 | ++++ | | | 26 | ++++ | | +++ |
| 27 | ++++ | | +++ | 28 | ++++ | | +++ |
| 29 | ++++ | | +++ | 30 | ++++ | | +++ |
| 31 | ++ | | + | 32 | ++++ | | |
| 33 | +++ | | | 34 | ++++ | | |
| 35 | ++++ | | | 36 | +++ | | |
| 37 | ++++ | | +++ | 38 | ++++ | | |
| 39 | ++++ | | | 40 | ++++ | | |
| 41 | ++++ | | ++ | 42 | ++++ | | |
| 43 | ++++ | | + | 44 | ++++ | | + |
| 45 | ++++ | | | 46 | ++++ | | ++ |
| 47 | ++++ | | | 48 | ++++ | | |
| 49 | ++++ | | ++ | 50 | ++++ | | |
| 51 | ++++ | | | 52 | ++++ | | |
| 53 | ++++ | | | 54 | ++++ | | + |
| 55 | +++ | | | 56 | +++ | | |
| 57 | ++++ | | ++ | 58 | +++ | | |
| 59 | +++ | | | 60 | ++++ | | + |
| 61 | ++++ | | | 62 | +++ | | |
| 63 | ++++ | | +++ | 64 | ++++ | | |
| 65 | ++++ | | +++ | 66 | ++++ | | ++ |
| 67 | ++++ | | | 68 | ++++ | | |
| 69 | ++++ | | + | 70 | ++++ | | +++ |
| 71 | ++++ | | ++ | 72 | ++++ | | |
| 73 | ++++ | | | 74 | ++++ | | + |
| 75 | ++++ | | | 76 | ++++ | | ++ |
| 77 | ++++ | | | 78 | ++++ | | +++ |
| 79 | ++++ | | ++ | 80 | ++++ | | +++ |
| 81 | ++++ | | +++ | 82 | ++++ | | ++++ |
| 83 | ++++ | | +++ | 84 | ++++ | | +++ |
| 85 | ++++ | | ++ | 86 | + | | |
| 87 | ++++ | | ++ | 88 | ++++ | | + |
| 89 | ++++ | | +++ | 90 | ++++ | | +++ |
| 91 | ++++ | | | 92 | ++++ | | +++ |
| 93 | ++++ | | +++ | 94 | ++++ | | |
| 95 | ++ | | | 96 | ++++ | ++++ | +++ |
| 97 | ++++ | | ++ | 98 | ++++ | | |
| 99 | ++ | | | 100 | ++++ | | + |
| 101 | ++++ | | +++ | 102 | +++ | | |
| 103 | +++ | | | 104 | ++++ | | |
| 105 | ++ | | | 106 | ++++ | | |
| 107 | ++++ | | | 108 | ++++ | | ++++ |
| 109 | ++++ | | ++ | 110 | ++++ | | +++ |
| 111 | ++++ | | | 112 | ++++ | | + |
| 113 | ++++ | | | 114 | ++++ | | + |
| 115 | ++++ | | + | 116 | ++++ | | ++ |
| 117 | ++++ | | | 118 | ++++ | | |
| 119 | ++++ | | +++ | 120 | ++++ | | +++ |
| 121 | ++++ | | | 122 | ++++ | | |
| 123 | ++++ | ++++ | ++ | 124 | ++++ | | |
| 125 | ++++ | | | 126 | ++++ | | |
| 127 | ++++ | | | 128 | ++++ | | +++ |
| 129 | ++++ | | + | 130 | ++++ | | +++ |
| 131 | ++++ | | ++ | 132 | ++++ | | ++++ |
| 133 | ++++ | | + | 134 | ++++ | | ++ |
| 135 | ++++ | | ++ | 136 | ++++ | | +++ |
| 137 | ++++ | | +++ | 138 | ++++ | | |
| 139 | ++++ | | +++ | 140 | ++++ | | +++ |

TABLE 4-continued

Biochemical and cellular potency of specific examples ($IC_{50}$: + means >5 μM; ++ means >1 μM to 5 μM, +++ means 100 nM to 1 μM, ++++ means <100 nM)

| Ex. # | Biochemical Potency (low ATP) | Biochemical Potency (high ATP) | Cellular Potency | Ex. # | Biochemical Potency (low ATP) | Biochemical Potency (high ATP) | Cellular Potency |
|---|---|---|---|---|---|---|---|
| 141 | ++++ | | +++ | 142 | ++++ | | ++ |
| 143 | ++++ | | | 144 | ++++ | | +++ |
| 145 | ++++ | | +++ | 146 | ++++ | | |
| 147 | ++++ | | | 148 | ++++ | | ++++ |
| 149 | ++++ | | | 150 | ++++ | | |
| 151 | ++++ | | | 152 | ++++ | | |
| 153 | ++++ | ++++ | +++ | 154 | ++++ | | |
| 155 | ++++ | | +++ | 156 | ++++ | | |
| 157 | ++++ | | | 158 | ++++ | | |
| 159 | ++++ | | +++ | 160 | ++++ | | ++++ |
| 161 | ++++ | | | 162 | ++++ | | |
| 163 | ++++ | | | 164 | ++++ | | +++ |
| 165 | +++ | | | 166 | ++++ | | |
| 167 | ++++ | | ++++ | 168 | ++++ | | |
| 169 | ++++ | | | 170 | ++++ | | |
| 171 | ++++ | | | 172 | ++++ | | ++++ |
| 173 | ++++ | | | 174 | ++++ | | |
| 175 | ++++ | | +++ | 176 | ++++ | | |
| 177 | ++++ | | ++ | 178 | ++++ | | +++ |
| 179 | ++++ | | | 180 | | | + |
| 181 | ++++ | | | 182 | ++++ | | +++ |
| 183 | ++++ | | | 184 | ++++ | | |
| 185 | +++ | | | 186 | ++++ | | |
| 187 | ++++ | | | 188 | ++++ | | |
| 189 | ++++ | | | 190 | ++++ | | |
| 191 | ++++ | | | 192 | ++++ | | |
| 193 | ++++ | | | 194 | ++++ | | ++++ |
| 195 | ++++ | | | 196 | ++++ | | |
| 197 | ++++ | | +++ | 198 | ++++ | | + |
| 199 | ++++ | | | 200 | ++++ | | ++ |
| 201 | ++++ | | | 202 | +++ | | |
| 203 | +++ | | | 204 | ++++ | | |
| 205 | ++++ | ++++ | +++ | 206 | ++++ | | +++ |
| 207 | +++ | | | 208 | ++++ | | |
| 209 | ++++ | | ++ | 210 | ++++ | | +++ |
| 211 | +++ | | | 212 | ++++ | | ++++ |
| 213 | ++++ | | | 214 | ++++ | | +++ |
| 215 | ++++ | | | 216 | ++++ | | ++++ |
| 217 | ++++ | | ++++ | 218 | ++++ | | |
| 219 | ++++ | | | 220 | ++++ | | +++ |
| 221 | ++++ | | +++ | 222 | ++++ | | |
| 223 | ++++ | | | 224 | ++++ | | ++ |
| 225 | ++++ | | +++ | 226 | ++++ | | |
| 227 | ++++ | | +++ | 228 | ++++ | | |
| 229 | +++ | | | 230 | ++++ | | |
| 231 | +++ | | | 232 | ++++ | | |
| 233 | +++ | | | 234 | +++ | | |
| 235 | ++++ | | ++ | 136 | ++++ | | |
| 237 | ++++ | | | 238 | +++ | | |
| 239 | ++++ | | | 240 | +++ | | |
| 241 | ++++ | | | 242 | +++ | | |
| 243 | +++ | | | 244 | +++ | | |
| 245 | +++ | | | 246 | ++++ | | |
| 247 | ++++ | | | 248 | ++++ | ++++ | ++++ |
| 249 | ++++ | ++++ | +++ | 250 | ++++ | | |
| 251 | ++++ | | | 252 | ++++ | | +++ |
| 253 | ++++ | | +++ | 254 | ++++ | | +++ |
| 255 | ++++ | | +++ | 256 | ++++ | | ++++ |
| 257 | ++++ | | ++ | 258 | ++++ | | +++ |
| 259 | ++++ | | +++ | 260 | ++++ | | +++ |
| 261 | ++++ | | +++ | 262 | ++++ | | ++ |
| 263 | ++++ | | | 264 | ++++ | | +++ |
| 265 | ++++ | | | 266 | ++++ | | |
| 267 | ++++ | | | 268 | ++++ | | +++ |
| 269 | ++++ | | ++ | 270 | ++++ | | +++ |
| 271 | ++++ | | ++ | 272 | ++++ | | |
| 273 | ++++ | | +++ | 274 | ++++ | | + |
| 275 | ++++ | | + | 276 | + | | + |
| 277 | ++++ | | ++ | 278 | ++++ | | + |
| 279 | ++++ | | | 280 | ++ | | |
| 281 | ++++ | | | 282 | ++++ | | |
| 283 | ++++ | | | 284 | +++ | | |
| 285 | ++++ | ++++ | +++ | 286 | ++++ | ++++ | ++ |

TABLE 4-continued

Biochemical and cellular potency of specific examples ($IC_{50}$: + means >5 μM; ++ means >1 μM to 5 μM, +++ means 100 nM to 1 μM, ++++ means <100 nM)

| Ex. # | Biochemical Potency (low ATP) | Biochemical Potency (high ATP) | Cellular Potency | Ex. # | Biochemical Potency (low ATP) | Biochemical Potency (high ATP) | Cellular Potency |
|---|---|---|---|---|---|---|---|
| 287 | ++++ | | | 288 | +++ | | ++ |
| 289 | ++++ | | +++ | 290 | ++++ | | +++ |
| 291 | ++++ | | +++ | 292 | ++++ | | |
| 293 | ++++ | | | 294 | ++++ | | |

TABLE 5

Biochemical and Cellular potency of specific examples ($IC_{50}$: + means >5 μM-25 μM; ++ means >1 μM-5 μM, +++ means 100 nM to 1 μM, ++++ means <100 nM)

| Ex. # | Biochemical Potency (low ATP) | Biochemical Potency (high ATP) | Cellular Potency | Ex. # | Biochemical Potency (low ATP) | Biochemical Potency (high ATP) | Cellular Potency |
|---|---|---|---|---|---|---|---|
| 295 | | ++++ | +++ | 296 | | ++++ | ++++ |
| 297 | | ++++ | +++ | 298 | | ++++ | ++++ |
| 299 | | ++++ | +++ | 300 | ++++ | | ++ |
| 301 | | ++++ | ++++ | 302 | | ++++ | ++++ |
| 303 | ++++ | | | 304 | | ++++ | +++ |
| 305 | | ++++ | ++++ | 306 | ++++ | | |
| 307 | | ++++ | ++++ | 308 | | ++++ | ++++ |
| 309 | | ++++ | ++++ | 310 | | ++++ | +++ |
| 311 | | ++++ | +++ | 312 | | +++ | ++ |
| 313 | | ++++ | ++++ | 314 | ++++ | | |
| 315 | ++++ | ++++ | ++ | 316 | ++ | | ++ |
| 317 | ++++ | | ++ | 318 | | ++++ | ++++ |
| 319 | +++ | | | 320 | ++++ | ++++ | +++ |
| 321 | | ++++ | +++ | 322 | | ++++ | +++ |
| 323 | ++++ | ++++ | +++ | 324 | ++++ | | |
| 325 | ++++ | | | 326 | ++++ | | |
| 327 | ++++ | | +++ | 328 | +++ | | + |
| 329 | +++ | | + | 330 | ++++ | | + |
| 331 | | +++ | ++ | 332 | | ++++ | ++ |
| 333 | | ++++ | +++ | 334 | ++++ | | ++++ |
| 335 | | ++++ | +++ | 336 | | ++++ | +++ |
| 337 | | ++++ | +++ | 338 | | ++++ | ++ |
| 339 | | ++++ | +++ | 340 | | ++++ | ++++ |
| 341 | | ++++ | +++ | 342 | | ++++ | +++ |
| 343 | | ++++ | ++ | 344 | | ++++ | ++++ |
| 345 | | ++++ | ++++ | 346 | | ++++ | ++++ |
| 347 | | ++++ | ++++ | 348 | | ++++ | ++++ |
| 349 | | ++++ | +++ | 350 | | ++++ | ++++ |
| 351 | | ++++ | ++++ | 352 | | ++++ | ++++ |
| 353 | | ++++ | +++ | 354 | | ++++ | ++++ |
| 355 | | ++++ | +++ | 356 | | +++ | ++ |
| 357 | | ++++ | +++ | 358 | | ++++ | ++++ |
| 359 | | ++++ | ++++ | 360 | | ++++ | ++ |
| 361 | | ++++ | +++ | 362 | | ++++ | ++ |
| 363 | | ++++ | +++ | 364 | | ++++ | ++++ |
| 365 | | ++++ | + | 366 | | ++++ | +++ |
| 367 | | ++++ | ++ | 368 | | ++++ | +++ |
| 369 | | ++++ | +++ | 370 | | ++++ | ++++ |
| 371 | | ++++ | +++ | 372 | | ++++ | +++ |
| 373 | | ++++ | +++ | 374 | | +++ | + |
| 375 | | ++++ | +++ | 376 | | ++++ | +++ |
| 377 | | ++++ | + | 378 | | ++++ | +++ |
| 379 | | ++++ | ++ | 380 | | ++++ | ++ |
| 381 | | ++++ | +++ | 382 | | ++++ | +++ |
| 383 | | ++++ | ++++ | 384 | | ++++ | +++ |
| 385 | | ++++ | +++ | 386 | | ++++ | ++ |
| 387 | | ++++ | +++ | 388 | | ++++ | +++ |
| 389 | | +++ | ++ | 390 | | ++++ | +++ |
| 391 | | +++ | ++ | 392 | | ++++ | +++ |
| 393 | | ++++ | +++ | 394 | | ++++ | +++ |
| 395 | | +++ | +++ | 396 | | ++++ | +++ |
| 397 | | ++++ | ++++ | 398 | | +++ | ++ |
| 399 | | ++++ | +++ | 400 | | ++++ | + |
| 401 | | ++++ | +++ | 402 | | ++++ | +++ |
| 403 | | ++++ | +++ | 404 | | ++++ | ++ |

TABLE 5-continued

Biochemical and Cellular potency of specific examples ($IC_{50}$: + means >5 μM-25 μM; ++ means >1 μM-5 μM, +++ means 100 nM to 1 μM, ++++ means <100 nM)

| Ex. # | Biochemical Potency (low ATP) | Biochemical Potency (high ATP) | Cellular Potency | Ex. # | Biochemical Potency (low ATP) | Biochemical Potency (high ATP) | Cellular Potency |
|---|---|---|---|---|---|---|---|
| 405 | | ++++ | +++ | 406 | ++++ | ++++ | +++ |
| 407 | ++++ | ++++ | ++++ | 408 | ++++ | ++++ | +++ |
| 409 | ++++ | ++++ | +++ | 410 | ++++ | ++++ | +++ |
| 411 | ++++ | | | 412 | ++++ | ++++ | +++ |
| 413 | ++++ | ++++ | ++ | 414 | ++++ | | ++ |
| 415 | ++++ | | +++ | 416 | ++++ | | +++ |
| 417 | ++++ | | | 418 | ++++ | | |
| 419 | ++++ | | | 420 | ++++ | | |
| 421 | ++++ | | | 422 | | ++++ | +++ |
| 423 | | ++++ | +++ | 424 | | ++++ | +++ |
| 425 | | ++++ | ++ | 426 | +++ | | |
| 427 | +++ | | | 428 | +++ | | |
| 429 | | ++++ | +++ | 430 | ++++ | ++++ | +++ |
| 431 | ++++ | ++++ | +++ | 432 | ++++ | | ++++ |
| 433 | ++++ | | ++++ | 434 | | ++++ | +++ |
| 435 | | ++++ | +++ | 436 | | ++++ | +++ |
| 437 | ++++ | | | 438 | ++++ | | +++ |
| 439 | ++++ | | | 440 | ++++ | ++++ | ++++ |
| 441 | ++++ | | | 442 | ++++ | | |
| 443 | ++++ | ++++ | ++++ | 444 | ++++ | | ++++ |
| 445 | | ++++ | +++ | 446 | | ++++ | +++ |
| 447 | | ++++ | ++++ | 448 | | ++++ | +++ |
| 449 | | ++++ | +++ | 450 | | ++++ | ++++ |
| 451 | | ++++ | +++ | 452 | | ++++ | +++ |
| 453 | | ++++ | +++ | 454 | | ++++ | +++ |
| 455 | | ++++ | +++ | 456 | | ++++ | ++ |
| 457 | | ++++ | +++ | 458 | | ++++ | +++ |
| 459 | ++++ | | | 460 | ++++ | | +++ |
| 461 | ++++ | | | 462 | ++++ | | |
| 463 | ++++ | | | 464 | ++++ | | +++ |
| 465 | ++++ | | | 466 | | ++++ | +++ |
| 467 | | ++++ | ++++ | 468 | | ++++ | +++ |
| 469 | | ++++ | +++ | 470 | | ++++ | +++ |
| 471 | | ++++ | +++ | 472 | | ++++ | +++ |
| 473 | | ++++ | | 474 | | ++++ | ++++ |
| 475 | | ++++ | ++++ | 476 | | ++++ | ++++ |
| 477 | | ++++ | +++ | 478 | | ++++ | +++ |
| 479 | | ++++ | +++ | 480 | | ++++ | +++ |
| 481 | | ++++ | ++ | 482 | | ++++ | ++ |
| 483 | | ++++ | +++ | 484 | | ++++ | ++++ |
| 485 | | ++++ | +++ | 486 | +++ | | + |
| 487 | | ++++ | ++++ | 488 | | ++++ | +++ |
| 489 | | ++++ | +++ | 490 | | ++++ | +++ |
| 491 | | ++++ | ++ | 492 | | ++++ | +++ |
| 493 | | ++++ | +++ | 494 | | ++++ | +++ |
| 495 | | ++++ | +++ | 496 | | ++++ | ++++ |
| 497 | | ++++ | +++ | 498 | | +++ | ++ |
| 499 | | ++++ | ++++ | 500 | | ++++ | ++++ |
| 501 | | ++++ | ++++ | 502 | | ++++ | +++ |
| 503 | | ++++ | +++ | 504 | | ++++ | ++++ |
| 505 | | ++++ | ++++ | 506 | | ++++ | +++ |
| 507 | | ++++ | +++ | 508 | | ++++ | ++++ |
| 509 | ++++ | ++++ | ++++ | 510 | ++++ | ++++ | ++++ |
| 511 | | ++++ | +++ | 512 | | ++++ | ++++ |
| 513 | | ++++ | ++++ | 514 | | ++++ | +++ |
| 515 | | ++++ | ++++ | 516 | | ++++ | +++ |
| 517 | | ++++ | ++++ | 518 | | ++++ | ++++ |
| 519 | | ++++ | +++ | 520 | | ++++ | ++++ |
| 521 | | ++++ | +++ | 522 | | ++++ | +++ |
| 523 | | ++++ | +++ | 524 | | ++++ | ++++ |
| 525 | | ++++ | ++++ | 526 | | ++++ | ++++ |
| 527 | | ++++ | +++ | 528 | | ++++ | +++ |
| 529 | | ++++ | ++++ | 530 | | ++++ | +++ |
| 531 | | ++++ | +++ | 532 | | ++++ | +++ |
| 533 | | ++++ | ++++ | 534 | | ++++ | +++ |
| 535 | | ++++ | ++++ | 536 | | ++++ | ++++ |
| 537 | | ++++ | +++ | 538 | | ++++ | ++++ |
| 539 | | ++++ | ++++ | 540 | | ++++ | ++++ |
| 541 | | ++++ | +++ | 542 | | ++++ | ++++ |
| 543 | | ++++ | ++++ | 544 | | ++++ | ++++ |
| 545 | | ++++ | ++++ | 546 | | ++++ | ++++ |
| 547 | | ++++ | +++ | 548 | | ++++ | ++++ |

TABLE 5-continued

Biochemical and Cellular potency of specific examples ($IC_{50}$: + means >5 μM-25 μM; ++ means >1 μM-5 μM, +++ means 100 nM to 1 μM, ++++ means <100 nM)

| Ex. # | Biochemical Potency (low ATP) | Biochemical Potency (high ATP) | Cellular Potency | Ex. # | Biochemical Potency (low ATP) | Biochemical Potency (high ATP) | Cellular Potency |
|---|---|---|---|---|---|---|---|
| 549 | | ++++ | +++ | 550 | | ++++ | +++ |
| 551 | | ++++ | ++++ | 552 | | ++++ | ++++ |
| 553 | | ++++ | ++ | 554 | | ++++ | +++ |
| 555 | | ++++ | ++++ | 556 | | ++++ | ++++ |
| 557 | | ++++ | +++ | 558 | | ++++ | ++++ |
| 559 | | ++++ | +++ | 560 | | ++++ | ++++ |
| 561 | | ++++ | +++ | 562 | | ++++ | ++++ |
| 563 | | ++++ | +++ | 564 | | ++++ | +++ |
| 565 | | ++++ | +++ | 566 | | ++++ | +++ |
| 567 | | ++++ | +++ | 568 | | +++ | ++ |
| 569 | | ++++ | +++ | 570 | | ++++ | ++++ |
| 571 | | +++ | ++ | 572 | | ++++ | ++ |
| 573 | | +++ | ++ | 574 | | ++++ | + |
| 575 | | ++++ | +++ | 576 | ++++ | | ++ |
| 577 | ++++ | | ++ | 578 | ++++ | | |
| 579 | ++++ | | | 580 | ++++ | | |
| 581 | ++++ | | +++ | 582 | ++++ | | |
| 583 | ++++ | | | 584 | | ++++ | +++ |
| 585 | | ++++ | +++ | 586 | | ++++ | +++ |

Particular embodiments of this disclosure are described herein, including the best mode known to the inventors for carrying out the disclosure. Upon reading the foregoing, description, variations of the disclosed embodiments may become apparent to individuals working in the art, and it is expected that those skilled artisans may employ such variations as appropriate. Accordingly, it is intended that the disclosure be practiced otherwise than as specifically described herein, and that the disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All publications, patent applications, accession numbers, and other references cited in this specification are herein incorporated by reference for the purpose described herein.

The invention claimed is:

1. A compound having a structure of Formula I:

(Formula I)

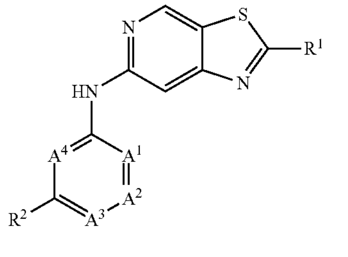

or a pharmaceutically acceptable salt thereof, wherein:

$R^1$ is-NH—C(O)-phenyl, —NH—($C_1$-$C_3$-alkylene)-phenyl, —O—($C_1$-$C_3$-alkylene)-phenyl, —O-(5- to 10-membered heteroaryl), phenyl, 5- to 10-membered heteroaryl, or 5- to 8-membered heterocycloalkyl; wherein said 5- to 10-membered heteroaryl and 5- to 8-membered heterocycloalkyl have from 1-3 ring heteroatoms independently selected from N, O, and S; and wherein said —NH—C(O)-phenyl, phenyl, —O—($C_1$-$C_3$-alkylene)-phenyl, 5- to 10-membered heteroaryl and 5- to 8-membered heterocycloalkyl are substituted with 0-3 $R^{1a}$;

each $R^{1a}$, when present, is independently selected from:

a) halo, oxo, —CN, —OH, —$C_1$-$C_6$-alkyl, —O—$C_1$-$C_6$-alkyl, —O—$C_1$-$C_6$-haloalkyl, —O—($C_1$-$C_3$-alkylene)-($C_3$-$C_6$-cycloalkyl), —$S(O)_2$—$R^{1b}$, —$S(O)_2NR^aR^b$, —$NR^aS(O)_2$—($C_1$-$C_6$-alkyl), —$NR^aR^b$, —C(O)$NR^aR^b$, and phenyl;

b) —$C_1$-$C_6$-alkyl substituted with 1-4 substituents independently selected from —OH, halo, —CN, —O—$C_1$-$C_3$-alkyl, —$C_3$-$C_6$-cycloalkyl, —O—($C_3$-$C_6$-cycloalkyl), —S(O) 2-($C_1$-$C_3$-alkyl), —C(O) $NR^aR^b$, phenyl, and -5- to 6-membered heterocycloalkyl; wherein said 5- to 6-membered heterocycloalkyl has 1-3 ring heteroatoms independently selected from N, O, and S; wherein said 5- to 6-membered heterocycloalkyl is substituted with 0-1 oxo; and wherein said $C_3$-$C_6$-cycloalkyl is substituted with 0-2 substituents independently selected from halo;

c) —$C_3$-$C_7$-cycloalkyl substituted with 0-3 substituents independently selected from the group consisting of halo, —OH, —$C_1$-$C_6$-alkoxy, and —C(O)$NR^aR^b$;

d) 4- to 8-membered heterocycloalkyl and —O-(4- to 8-membered heterocycloalkyl); wherein said 4- to 8-membered heterocycloalkyl has 1-3 ring heteroatoms independently selected from N, O, and S; and said 4- to 8-membered heterocycloalkyl is substituted with 0-3 substituents independently selected from the group consisting of oxo, —OH, halo, —$C_1$-$C_6$ alkyl, —$C_1$-$C_3$-alkoxy, —C(O)($C_1$-$C_3$-alkyl), and —$S(O)_2$($C_1$-$C_3$-alkyl);

e) 5- to 6-membered heteroaryl, —O-(5- to 6-membered heteroaryl), and —C≡C-(5- to 6-membered heteroaryl), wherein said 5- to 6-membered heteroaryl has 1-3 ring heteroatoms independently selected from N, O, and S; and wherein said 5- to 6-membered heteroaryl is substituted with 0-2 substituents independently selected from —OH, halo, and —$C_1$-$C_6$-alkyl; and f) two adjacent $R^{1a}$ are taken together with the atoms to which they are attached to form a 5- to 7-membered heterocycloalkyl, or a 5- to 6-membered heteroaryl; wherein said 5- to 7-membered heterocycloalkyl and 5- to 6-membered heteroaryl each have 1-2 ring heteroatoms independently selected from N, O, and S; and wherein said 5- to 7-membered heterocycloalkyl is substituted with 0-3 substituents independently selected from oxo, —$C_1$-$C_6$-alkyl, —C(O)($C_1$-$C_3$-alkyl), and —$S(O)_2$($C_1$-$C_3$-alkyl);

$R^{1b}$ is —$C_1$-$C_6$-alkyl, —$C_3$-$C_6$-cycloalkyl, or —($C_1$-$C_3$-alkylene)-($C_3$-$C_6$-cycloalkyl);

each $R^a$ and $R^b$, when present, are independently selected from —H; —$C_1$-$C_6$-alkyl; —$C_3$-$C_7$-cycloalkyl; —$C_1$-$C_6$-hydroxyalkyl; —C(O)($C_1$-$C_3$-alkyl); —C(O)($C_3$-$C_6$-cycloalkyl); phenyl; 5- to 10-membered heterocycloalkyl; and $C_1$-$C_3$-alkyl substituted with —$C_3$-$C_6$-cycloalkyl, —O—$C_1$-$C_3$-alkyl, phenyl, or 5- to 6-membered heterocycloalkyl having 1-3 ring heteroatoms independently selected from N, O, and S; wherein each 5- to 10-membered heterocycloalkyl has 1-3 ring heteroatoms independently selected from N, O, and S; and said 5- to 10-membered heterocycloalkyl is substituted with 0-1 substituents selected from —$S(O)_2$($C_1$-$C_3$ alkyl), and —C(O)($C_1$-$C_3$-alkyl); or $R^a$ and $R^b$ are taken together with the N atom to which they are attached to form a 5- to 10-membered heterocycloalkyl having 0-2 additional ring heteroatoms independently selected from N, O, and S; and said 5- to 10-membered heterocycloalkyl is substituted with 0-2 substituents independently selected from the group consisting of halo, —OH, —$C_1$-$C_3$-alkyl, —$C_1$-$C_3$-alkoxy, and —$C_1$-$C_3$-alkylene-O—($C_1$-$C_3$-alkyl);

$A^1$ is N, or $CR^{A1}$;

$A^2$ is N, or $CR^{A2}$;

$A^3$ is N, or $CR^{A3}$;

$A^4$ is N, or CH;

$R^2$ is —$X^1$—$NR^{2a}R^{2b}$, or —$X^1$-(5- to 10-membered heterocycloalkyl) having 1-4 ring heteroatom or heteroatom groups independently selected from N, O, S(O), and $S(O)_2$; wherein said 5- to 10-membered heterocycloalkyl is substituted with 0-3 substituents independently selected from the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—O—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl); wherein:

$X^1$ is —O—, —$(CR^oR^o)_n$—, or —O—$C_1$-$C_6$-alkylene-;

n is 0, 1 or 2;

each $R^o$ is independently —H or —$C_1$-$C_6$-alkyl; or two $R^o$ attached to the same C atom taken together form —$C_3$-$C_5$-cycloalkyl;

$R^{2a}$ and $R^{2b}$ are independently selected from the group consisting of —H, —$C_1$-$C_6$-alkyl, —$S(O)_2$($C_1$-$C_6$-alkyl), —$C_1$-$C_2$-alkylene-(5- to 6-membered heteroaryl), and 5- to 6-membered heterocycloalkyl; wherein said 5- to 6-membered heteroaryl and 5- to 6-membered heterocycloalkyl have 1-2 ring heteroatoms independently selected from N, O, and S; and wherein said 5- to 6-membered heteroaryl is optionally substituted with one-$C_1$-$C_3$-alkyl;

$Y^1$ is —$C_1$-$C_3$-alkylene; and $R^{2c}$ and $R^{2d}$ are independently —H, —$C_1$-$C_3$-alkyl, —C(O)($C_1$-$C_3$-alkyl), or —$S(O)_2$($C_1$-$C_3$-alkyl);

$R^{A1}$ is selected from —H, -halo, —$C_1$-$C_6$-alkyl, —O—$C_1$-$C_6$-alkyl, and 5- to 6-membered heterocycloalkyl having 1-2 ring heteroatoms independently selected from N and O;

$R^{A2}$ is selected from —H, -halo, —$C_1$-$C_6$-alkyl, —$C_1$-$C_6$-haloalkyl, —$C_1$-$C_6$-hydroxyalkyl, —O—$C_1$-$C_6$-alkyl, —$C_3$-$C_6$-cycloalkyl, 5- to 6-membered heterocycloalkyl, and 5- to 6-membered heteroaryl; wherein said 5- to 6-membered heterocycloalkyl and 5- to 6-membered heteroaryl have 1-2 ring heteroatoms independently selected from N and O; and wherein said —$C_3$-$C_6$-cycloalkyl, 5- to 6-membered heterocycloalkyl, and 5- to 6-membered heteroaryl are each substituted with 0-2 substituents independently selected from halo, —CN, and —OH; and $R^{A3}$ is —H, -halo, —$C_1$-$C_6$-alkyl, —$C_1$-$C_6$-haloalkyl, —$C_3$-$C_6$-cycloalkyl, or 5- to 6-membered heterocycloalkyl having 1-2 ring heteroatoms independently selected from N, O, and S; wherein said 5- to 6-membered heterocycloalkyl is optionally substituted with 1-2 substituents independently selected from -halo and —OH; or $R^2$ and $R^{A3}$ taken together with the atoms to which they are attached to form phenyl, —$C_5$-$C_7$-cycloalkyl, or 5- to 8-membered heterocycloalkyl having 1-3 ring heteroatoms selected from N, O, and S; wherein said phenyl, —$C_5$-$C_7$-cycloalkyl and 5- to 8-membered heterocycloalkyl are substituted with 0-3 substituents independently selected from —$C_1$-$C_3$-alkyl, —$NH_2$, —$C_1$-$C_3$-alkylene-$NH_2$, and 5- to 8-membered heterocycloalkyl having 1-2 ring heteroatoms independently selected from N and O.

2. The compound of claim 1, or a pharmaceutically acceptable salt thereof, wherein:

$R^2$ is —$X^1$-(5- to 10-membered heterocycloalkyl) having 1-4 ring heteroatoms independently selected from N, O and S, wherein said 5- to 10-membered heterocycloalkyl is substituted with 0-3 substituents independently selected from the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—O—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl);

$X^1$ is —$(CR^oR^o)_n$—;

n is 0; and $Y^1$ is —$C_1$-$C_3$-alkylene.

3. The compound of claim 1, or a pharmaceutically acceptable salt thereof, wherein $R^2$ is selected from the group consisting of

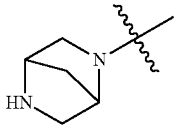, 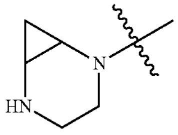,

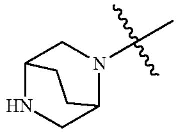, 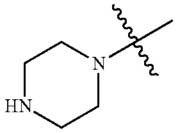,

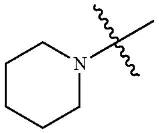, 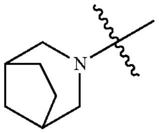,

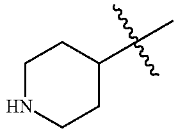, 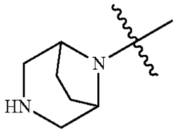,

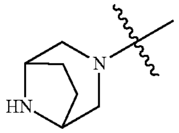, 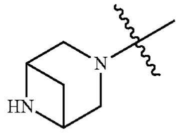,

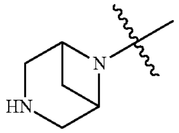, 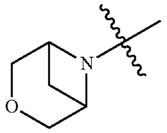,

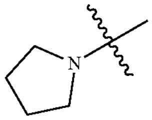, 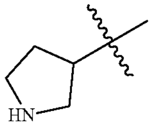,

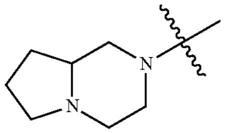, 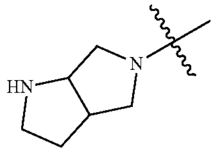,

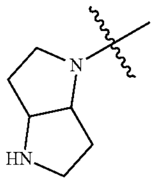, 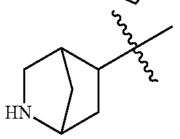, and

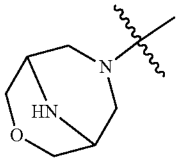, each of which is substituted with 0-3 substituents independently selected from the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—O—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl).

4. The compound of claim 1, or a pharmaceutically acceptable salt thereof, wherein $R^2$ is

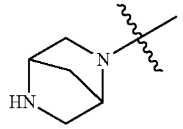 [SMILES: *N1CC2CC1CN2]

which is substituted with 0-3 substituents independently selected from the group consisting of halo, —OH, —CN, —$NH_2$, —$C_1$-$C_6$-alkyl, —$C_1$-$C_6$-haloalkyl, —$C_1$-$C_6$-hydroxyalkyl, —$Y^1$—$NR^{2c}R^{2d}$, —$Y^1$—O—($C_1$-$C_3$-alkyl), —$Y^1$—C(O)$NR^{2c}R^{2d}$, —$Y^1$—O—($C_1$-$C_3$-hydroxyalkyl), —$Y^1$—($C_3$-$C_6$-cycloalkyl), —$Y^1$-phenyl, —$Y^1$-(5- to 6-membered heteroaryl), 5- to 6-membered heterocycloalkyl, and —$Y^1$-(5- to 6-membered heterocycloalkyl); wherein said 5- to 6-membered heteroaryl, and 5- to 6-membered heterocycloalkyl each have 1-3 ring heteroatoms independently selected from N, O, and S; said 5- to 6-membered heteroaryl is unsubstituted or substituted with —$C_1$-$C_3$-alkyl; and said 5- to 6-membered heterocycloalkyl is unsubstituted or substituted with —$S(O)_2$($C_1$-$C_3$ alkyl), or —C(O)($C_1$-$C_3$ alkyl).

5. The compound of claim 1, or a pharmaceutically acceptable salt thereof, wherein $R^2$ is substituted with 0-2 substituents independently selected from the group consisting of —F, —$CH_3$, —$CH_2CH_3$, —$CH(CH_3)_2$, —OH, —$NH_2$, —$CH_2OH$, —$CH_2NH_2$, —$(CH_2)_2$—OH, —$(CH_2)_2$—O—$CH_3$, —$(CH_2)_2$—O—$CH_2CH_3$, —$(CH_2)_2$—O—$(CH_2)_2$—OH, —$(CH_2)_2$—O—$CH(CH_3)_2$, —$(CH_2)_2$—$NH_2$,

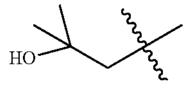 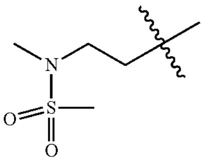,

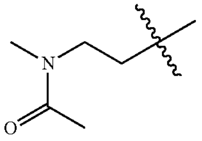, 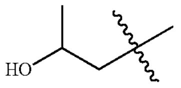,

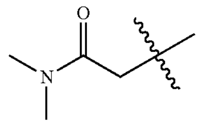, 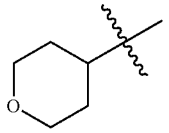,

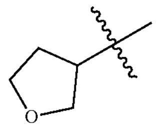, 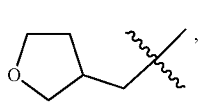,

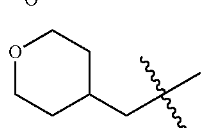, 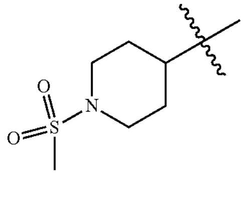,

-continued

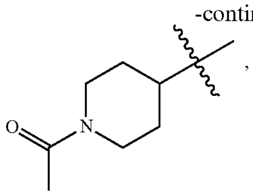, 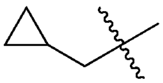,

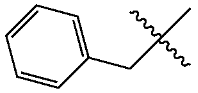, 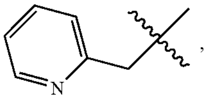,

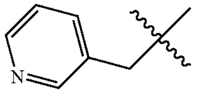, and 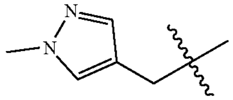.

6. The compound of claim 1, or a pharmaceutically acceptable salt thereof, wherein $R^2$ and $R^{43}$ taken together with the atoms to which they are attached form phenyl, —$C_5$-$C_7$-cycloalkyl, or 5- to 8-membered heterocycloalkyl having 1-3 ring heteroatoms selected from N, O, and S; wherein said phenyl, —$C_5$-$C_7$-cycloalkyl and 5- to 8-membered heterocycloalkyl are substituted with 0-3 substituents independently selected from —$C_1$-$C_3$-alkyl, —$NH_2$, —$C_1$-$C_3$-alkylene-$NH_2$, and 5- to 8-membered heterocycloalkyl having 1-2 ring heteroatoms independently selected from N and O.

7. The compound of claim 1, or a pharmaceutically acceptable salt thereof, wherein $R^1$ is pyridyl, pyridinonyl, phenyl, pyrazolyl, imidazolyl, oxazolyl, 1,2,4-triazolyl, pyrazinyl, pyridazinyl, pyrimidinyl, 6-oxa-3-azabicyclo[3.1.1]heptanyl, 2-oxa-5-azabicyclo[2.2.1]heptanyl, piperidinyl, morpholinyl, pyrrolidinyl, pyrrolidonyl, tetrahydropyranyl, tetrahydrofuranyl, pyrazolo[3,4-b]pyridinyl, pyrazolo[1,5-a]pyrazinyl, pyrazolo[1,5-a]pyridinyl, —NH—C(O)-phenyl, —NH—$CH(CH_3)$-phenyl, —O—$CH(CH_3)$-phenyl, or —O-pyridyl, each of which is substituted with 0-3 $R^{1a}$.

8. The compound of claim 1, or a pharmaceutically acceptable salt thereof, wherein, when present, at least one $R^{1a}$ is selected from halo, oxo, —CN, —OH, —$C_1$-$C_6$-alkyl, —O—$C_1$-$C_6$-alkyl, —O—$C_1$-$C_6$-haloalkyl, —O—($C_1$-$C_3$-alkylene)-($C_3$-$C_6$-cycloalkyl), —$S(O)_2$—$R^{1b}$, —$S(O)_2NR^aR^b$, —$NR^aS(O)_2$—($C_1$-$C_6$-alkyl), —$NR^aR^b$, —$C(O)NR^aR^b$, and phenyl.

9. The compound of claim 1, or a pharmaceutically acceptable salt thereof, wherein, when present, at least one $R^{1a}$ is-$C_1$-$C_6$-alkyl substituted with 1-4 substituents independently selected from —OH, halo, —CN, —O—$C_1$-$C_3$-alkyl, —$C_3$-$C_6$-cycloalkyl, —O—($C_3$-$C_6$-cycloalkyl), —$S(O)_2$—($C_1$-$C_3$-alkyl), —$C(O)NR^aR^b$, phenyl, and -5- to 6-membered heterocycloalkyl; wherein said 5- to 6-membered heterocycloalkyl has 1-3 ring heteroatoms independently selected from N, O, and S; wherein said 5- to 6-membered heterocycloalkyl is substituted with 0-1 oxo; and wherein said —$C_3$-$C_6$-cycloalkyl is substituted with 0-2 substituents independently selected from halo.

10. The compound of claim 1, or a pharmaceutically acceptable salt thereof, wherein, when present, at least one $R^{1a}$ is —$C_3$-$C_7$-cycloalkyl substituted with 0-3 substituents independently selected from the group consisting of halo, —OH, —$C_1$-$C_6$-alkoxy, and —$C(O)NR^aR^b$.

11. The compound of claim 10, or a pharmaceutically acceptable salt thereof, wherein at least one $R^{1a}$ is

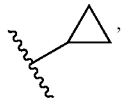, 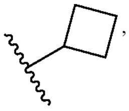, or 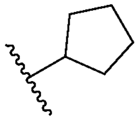, each of which is unsubstituted or substituted with a substituent selected from —OH and —$C(O)NR^aR^b$.

12. The compound of claim 1, or a pharmaceutically acceptable salt thereof, wherein, when present, at least one $R^{1a}$ is 4- to 8-membered heterocycloalkyl or —O-(4- to 8-membered heterocycloalkyl); wherein said 4- to 8-membered heterocycloalkyl has 1-3 ring heteroatoms independently selected from N, O, and S; and said 4- to 8-membered heterocycloalkyl is substituted with 0-3 substituents independently selected from the group consisting of oxo, —OH, halo, —$C_1$-$C_6$ alkyl, —$C_1$-$C_3$-alkoxy, —C(O)($C_1$-$C_3$-alkyl), and —$S(O)_2$($C_1$-$C_3$-alkyl).

13. The compound of claim 12, or a pharmaceutically acceptable salt thereof, wherein at least one $R^{1a}$ is

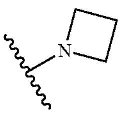, 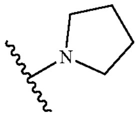, 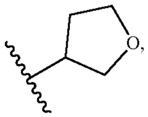

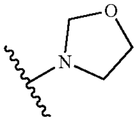, 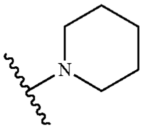, 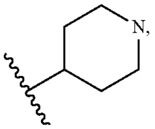

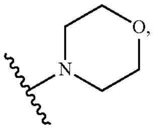 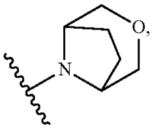 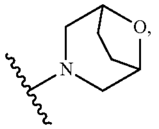

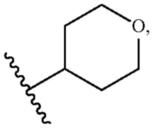 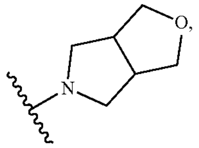

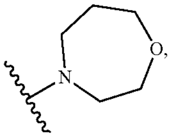 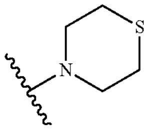, or

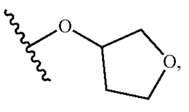

each of which is substituted with 0-2 substituents independently selected from oxo, —OH, halo, —$C_1$-$C_3$ alkyl, —$C_1$-$C_3$-alkoxy, —$C(O)CH_3$, and —$S(O)_2CH_3$.

14. The compound of claim 1, or a pharmaceutically acceptable salt thereof, wherein, when present, at least one $R^{1a}$ is 5- to 6-membered heteroaryl, —O-(5- to 6-membered heteroaryl), or —C≡C-(5- to 6-membered heteroaryl), wherein said 5- to 6-membered heteroaryl has 1-3 ring heteroatoms independently selected from N, O, and S; and wherein said 5- to 6-membered heteroaryl is substituted with 0-2 substituents independently selected from —OH, halo, and —$C_1$-$C_6$-alkyl.

15. The compound of claim 14, or a pharmaceutically acceptable salt thereof, wherein at least one $R^{1a}$ is

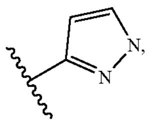
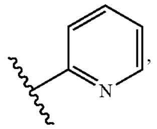
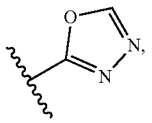
or
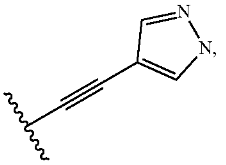

each of which is substituted with 0-2 substituents independently selected from halo and $C_1$-$C_3$-alkyl.

16. The compound of claim 1, or a pharmaceutically acceptable salt thereof, wherein, two adjacent $R^{1a}$ are taken together with the atoms to which they are attached to form a 5- to 7-membered heterocycloalkyl, or a 5- to 6-membered heteroaryl; wherein said 5- to 7-membered heterocycloalkyl and 5- to 6-membered heteroaryl each have 1-2 ring heteroatoms independently selected from N, O, and S; and wherein said 5- to 7-membered heterocycloalkyl is substituted with 0-3 substituents independently selected from oxo, —$C_1$-$C_6$-alkyl, —C(O)($C_1$-$C_3$-alkyl), and —$S(O)_2$($C_1$-$C_3$-alkyl).

17. The compound of claim 16, or a pharmaceutically acceptable salt thereof, wherein $R^1$ is:

a)

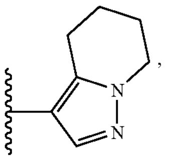
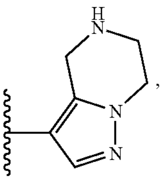
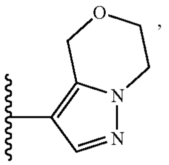
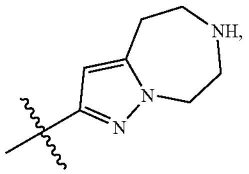
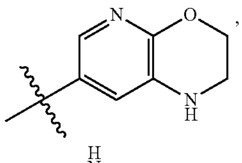
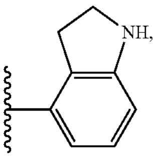
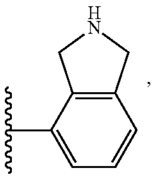
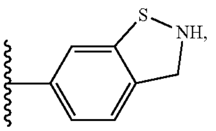
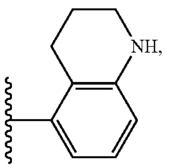
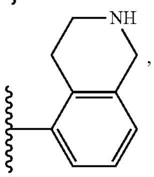
or -continued

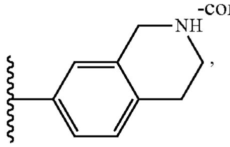

each of which is substituted with 0-3 substituents independently selected from oxo, —$C_1$-$C_6$-alkyl, —C(O)($C_1$-$C_3$-alkyl), and —$S(O)_2$($C_1$-$C_3$-alkyl); or b)

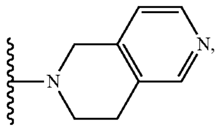
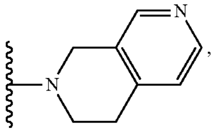
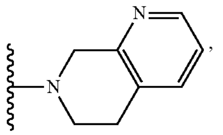
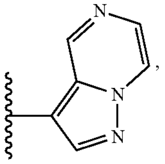
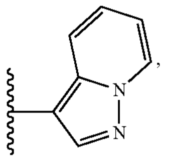
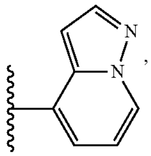
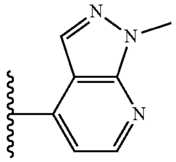
or
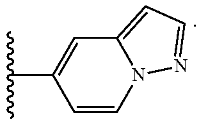

18. The compound of claim 1, or a pharmaceutically acceptable salt thereof, wherein:

$R^2$ is —$X^1$-(5- to 6-membered heterocycloalkyl) having 1-3 ring heteroatoms or heteroatom groups selected from N, O, and $S(O)_2$, wherein said 5- to 6-membered heterocycloalkyl is optionally substituted with 1-3 substituents independently selected from the group consisting of halo, —OH, —CN, —$NH_2$, —$C_1$-$C_6$-alkyl, —$C_1$-$C_6$-hydroxyalkyl, —$C_1$-$C_2$-alkylene-$NH_2$, and 5- to 6-membered heterocycloalkyl having 1-2 ring heteroatoms selected from N and O;

$X^1$ is —$(CR^oR^o)_n$—;

each $R^o$ is —H; and n is 1 or 2.

19. The compound of claim 18, or a pharmaceutically acceptable salt thereof, wherein $R^2$ is selected from the group consisting of:

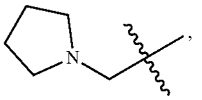
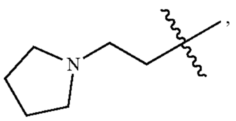

-continued

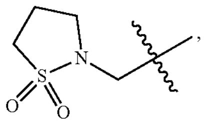, 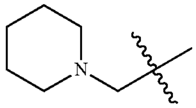, and 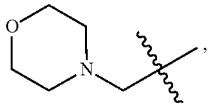, each 5- to 6-membered heterocycloalkyl of which is optionally substituted with 1-3 substituents independently selected from the group consisting of halo, —OH, —CN, —$NH_2$, —$C_1$-$C_6$-alkyl, —$C_1$-$C_6$-hydroxyalkyl, —$C_1$-$C_2$-alkylene-$NH_2$, and 5- to 6-membered heterocycloalkyl having 1-2 ring heteroatoms selected from N and O.

20. The compound of claim 1, or a pharmaceutically acceptable salt thereof, wherein:

$R^2$ is —$X^1$—$NR^{2a}R^{2b}$, $X^1$ is —$(CR^oR^o)_n$—, n is 0 or 1;

each $R^o$ is independently H or —$C_1$-$C_6$-alkyl; or two $R^o$attached to the same C atom taken together form —$C_3$-$C_5$-cycloalkyl; and $R^{2a}$ and $R^{2b}$ are independently selected from the group consisting of —H, $C_1$-$C_6$-alkyl, —$S(O)_2(C_1$-$C_6$-alkyl), —$C_1$-$C_2$-alkylene-(5- to 6-membered heteroaryl), and 5- to 6-membered heterocycloalkyl, wherein said 5- to 6-membered heteroaryl and 5- to 6-membered heterocycloalkyl have from 1-2 ring heteroatoms selected from N and O, and wherein said 5- to 6-membered heteroaryl is optionally substituted with one $C_1$-$C_3$-alkyl.

21. The compound of claim 20, or a pharmaceutically acceptable salt thereof, wherein $R^2$ is

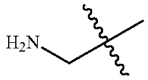, 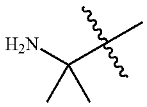, 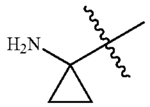,

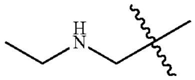, 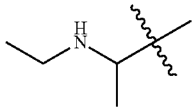,

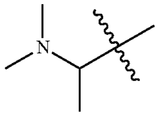, 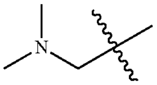,

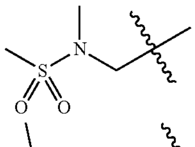, 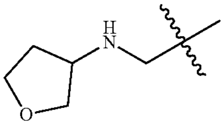, or

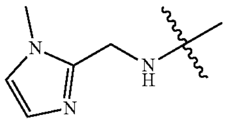.

22. The compound of claim 1, or a pharmaceutically acceptable salt thereof, wherein:

$R^2$ is —$X^1$-(5- to 6-membered heterocycloalkyl) having one ring N heteroatom, wherein said 5- to 6-membered heterocycloalkyl is optionally substituted with 1-2 substituents independently selected from halo, and $C_1$-$C_3$-alkyl; and $X^1$ is —O—.

23. The compound of claim 22, or a pharmaceutically acceptable salt thereof, wherein $R^2$ is —O-piperidine, or —O-pyrrolidine, each of which is optionally substituted with 1-2 halo.

24. The compound of claim 1, or a pharmaceutically acceptable salt thereof, wherein $R^{A1}$, when present, is —H, halo, $C_1$-$C_6$-alkyl, —O—$C_1$-$C_6$-alkyl, or 5- to 6-membered heterocycloalkyl having 1-2 ring heteroatoms independently selected from N and O;

$R^{A2}$, when present, is —H, halo, $C_1$-$C_6$-alkyl, or 5- to 6-membered heterocycloalkyl having 1-2 ring heteroatoms independently selected from N and O; and $R^{A3}$, when present, is —H, halo, $C_1$-$C_6$-alkyl, $C_1$-$C_6$-haloalkyl, $C_3$-$C_6$-cycloalkyl, or 5- to 6-membered heterocycloalkyl having 1-2 ring heteroatoms independently selected from N and O, wherein said 5- to 6-membered heterocycloalkyl is optionally substituted with 1-2 substituents independently selected from halo and —OH.

25. The compound of claim 1, or a pharmaceutically acceptable salt thereof, wherein:

$R^{A1}$, when present, is —H, —F, —$CH_3$, —$OCH_3$, or morpholinyl;

$R^{A2}$, when present, is H, —F, —$CH_3$, tetrahydropyranyl, or morpholiny; and $R^{A3}$, when present, is H, -halo, —$C_1$-$C_3$-alkyl, —$C_1$-haloalkyl, cyclopropyl, tetrahydrofuranyl, tetrahydropyranyl, morpholinyl, pyrrolidinyl, or piperidinyl, wherein said tetrahydrofuranyl, tetrahydropyranyl, morpholinyl, pyrrolidinyl, and piperidinyl are optionally substituted with 1-2 substituents independently selected from —F and —OH.

26. The compound of claim 25, or a pharmaceutically acceptable salt thereof, wherein $R^{A3}$, when present, is —H, —Cl, —F, —$CH_3$, $CF_3$, —$NH_2$,

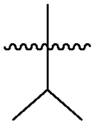, 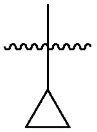, 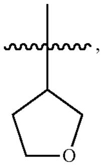, 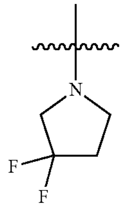,

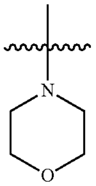, 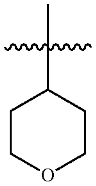, or 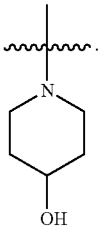.

27. A compound selected from the compounds in Table 1 and Table 2, or a pharmaceutically acceptable salt thereof.

28. A pharmaceutical composition comprising a compound of claim 1, or a pharmaceutically acceptable salt thereof, and a pharmaceutically acceptable excipient.

* * * * *